US011447465B2

(12) United States Patent
Wiles et al.

(10) Patent No.: US 11,447,465 B2
(45) Date of Patent: Sep. 20, 2022

(54) PHARMACEUTICAL COMPOUNDS FOR TREATMENT OF MEDICAL DISORDERS

(71) Applicant: Achillion Pharmaceuticals, Inc., New Haven, CT (US)

(72) Inventors: Jason Allan Wiles, Madison, CT (US); Avinash S. Phadke, Branford, CT (US); Milind Deshpande, Madison, CT (US); Atul Agarwal, Hamden, CT (US); Dawei Chen, Guilford, CT (US); Venkat Rao Gadhachanda, Hamden, CT (US); Akihiro Hashimoto, Branford, CT (US); Godwin Pais, Hamden, CT (US); Qiuping Wang, Bethany, CT (US); Xiangzhu Wang, Branford, CT (US); Joel Charles Barrish, Richboro, CT (US); William Greenlee, New Haven, CT (US); Kyle J. Eastman, New Haven, CT (US)

(73) Assignee: Achillion Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 16/555,946

(22) Filed: Aug. 29, 2019

(65) Prior Publication Data

US 2019/0382376 A1 Dec. 19, 2019

Related U.S. Application Data

(63) Continuation of application No. PCT/US2018/020530, filed on Mar. 1, 2018.

(60) Provisional application No. 62/465,754, filed on Mar. 1, 2017, provisional application No. 62/465,799, filed on Mar. 1, 2017, provisional application No. 62/466,308, filed on Mar. 2, 2017, provisional application No. 62/466,290, filed on Mar. 2, 2017.

(51) Int. Cl.

| | |
|---|---|
| *C07D 401/14* | (2006.01) |
| *C07D 403/06* | (2006.01) |
| *C07D 403/10* | (2006.01) |
| *C07D 405/14* | (2006.01) |
| *C07D 409/14* | (2006.01) |
| *C07D 417/14* | (2006.01) |
| *C07D 471/04* | (2006.01) |
| *C07D 493/04* | (2006.01) |
| *C07D 495/04* | (2006.01) |
| *C07D 513/04* | (2006.01) |
| *C07F 9/6558* | (2006.01) |

(52) U.S. Cl.

CPC ......... *C07D 401/14* (2013.01); *C07D 403/06* (2013.01); *C07D 403/10* (2013.01); *C07D 405/14* (2013.01); *C07D 409/14* (2013.01); *C07D 417/14* (2013.01); *C07D 471/04* (2013.01); *C07D 493/04* (2013.01); *C07D 495/04* (2013.01); *C07D 513/04* (2013.01); *C07F 9/65583* (2013.01)

(58) Field of Classification Search

CPC .. C07D 401/14; C07D 403/16; C07D 403/10; C07D 405/14; C07D 409/14; C07D 417/14; C07D 471/04; C07D 493/04; C07D 495/04; C07D 513/04

See application file for complete search history.

(56) References Cited

U.S. PATENT DOCUMENTS

| | | | |
|---|---|---|---|
| 5,628,984 | A | 5/1997 | Boucher, Jr. |
| 6,319,897 | B1 | 11/2001 | Lambris et al. |
| 6,489,476 | B1 | 12/2002 | Dang et al. |
| 6,653,340 | B1 | 11/2003 | Babu et al. |
| 7,629,340 | B2 | 12/2009 | Schmitz et al. |
| 7,888,323 | B2 | 2/2011 | Lambris et al. |
| 7,989,589 | B2 | 8/2011 | Lambris |
| 7,999,081 | B2 | 8/2011 | Tedesco et al. |
| 8,168,584 | B2 | 5/2012 | Deschatelets et al. |
| 8,241,628 | B2 | 8/2012 | Diefenbach-Streiber et al. |
| 8,524,716 | B2 | 9/2013 | Raboisson et al. |
| 8,580,735 | B2 | 11/2013 | Francois et al. |
| 8,883,158 | B2 | 11/2014 | Diefenbach-Streiber et al. |
| 8,946,145 | B2 | 2/2015 | Lambris et al. |
| 9,056,076 | B2 | 6/2015 | Deschatelets et al. |
| 9,085,555 | B2 * | 7/2015 | Altmann ................ A61P 19/02 |
| 9,169,307 | B2 | 10/2015 | Lambris et al. |

(Continued)

FOREIGN PATENT DOCUMENTS

| | | | |
|---|---|---|---|
| CN | 103402996 | A | 11/2013 |
| EA | 201890594 | A1 | 8/2018 |

(Continued)

OTHER PUBLICATIONS

"Are There Any Treatments for ALS?" WebMD, <https://www.webmd.com/brain/understanding-als-treatment#1>, retrieved on May 3, 2019 (8 pages).

"Arteriosclerosis/atherosclerosis," Mayo Clinic, <https://www.mayoclinic.org/diseases-conditions/arteriosclerosis-atherosclerosis/diagnosis-treatment/drc-20350575>, retrieved on Apr. 24, 2018 (10 pages).

"Cancer," MedLine Plus, <http://www.nlm.nih.gov/medlineplus/cancer.html>, retrieved Jul. 6, 2007 (10 pages).

(Continued)

*Primary Examiner* — Rebecca L Anderson

(74) *Attorney, Agent, or Firm* — Clark & Elbing LLP

(57) ABSTRACT

Complement Factor D inhibitors, pharmaceutical compositions, and uses thereof, as well as processes for their manufacture are provided. The compounds provided include Formula I, Formula II, Formula III, and Formula IV or a pharmaceutically acceptable salt, prodrug, isotopic analog, N-oxide, or isolated isomer thereof, optionally in a pharmaceutically acceptable composition. The inhibitors described herein target Factor D and inhibit or regulate the complement cascade.

8 Claims, 16 Drawing Sheets

(56) References Cited

U.S. PATENT DOCUMENTS

| | | | |
|---|---|---|---|
| 9,291,622 | B2 | 3/2016 | Zhang et al. |
| 9,371,365 | B2 | 6/2016 | Lambris et al. |
| 9,421,240 | B2 | 8/2016 | Francois et al. |
| 9,598,446 | B2 | 3/2017 | Gadhachanda et al. |
| 9,643,986 | B2 | 5/2017 | Wiles et al. |
| 9,663,543 | B2 | 5/2017 | Wiles et al. |
| 9,695,205 | B2 | 7/2017 | Wiles et al. |
| 9,732,103 | B2 | 8/2017 | Wiles et al. |
| 9,732,104 | B2 | 8/2017 | Gadhachanda et al. |
| 9,758,537 | B2 | 9/2017 | Wiles et al. |
| 9,796,741 | B2 | 10/2017 | Gadhachanda et al. |
| 9,828,396 | B2 | 11/2017 | Wiles et al. |
| 10,000,516 | B2 | 6/2018 | Wiles et al. |
| 10,005,802 | B2 | 6/2018 | Wiles et al. |
| 10,011,612 | B2 | 7/2018 | Wiles et al. |
| 10,081,645 | B2 | 9/2018 | Wiles et al. |
| 10,087,203 | B2 | 10/2018 | Wiles et al. |
| 10,092,547 | B2 | 10/2018 | Wiles et al. |
| 10,092,584 | B2 | 10/2018 | Wiles et al. |
| 10,100,072 | B2 | 10/2018 | Wiles et al. |
| 10,106,563 | B2 | 10/2018 | Wiles et al. |
| 10,138,225 | B2 | 11/2018 | Wiles et al. |
| 10,189,869 | B2 | 1/2019 | Gadhachanda et al. |
| 10,253,053 | B2 | 4/2019 | Wiles et al. |
| 10,287,301 | B2 | 5/2019 | Wiles et al. |
| 10,301,336 | B2 | 5/2019 | Wiles et al. |
| 10,370,394 | B2 | 8/2019 | Wiles et al. |
| 10,385,097 | B2 * | 8/2019 | Wiles ........................ A61P 1/16 |
| 10,428,094 | B2 | 10/2019 | Wiles et al. |
| 10,428,095 | B2 | 10/2019 | Wiles et al. |
| 10,464,956 | B2 | 11/2019 | Wiles et al. |
| 10,550,140 | B2 | 2/2020 | Wiles et al. |
| 10,660,876 | B2 | 5/2020 | Wiles et al. |
| 10,662,175 | B2 | 5/2020 | Wiles et al. |
| 10,807,952 | B2 | 10/2020 | Wiles et al. |
| 10,822,352 | B2 | 11/2020 | Wiles et al. |
| 10,906,887 | B2 | 2/2021 | Wiles et al. |
| 10,919,884 | B2 | 2/2021 | Wiles et al. |
| 11,084,800 | B2 * | 8/2021 | Wiles .................. C07F 9/65583 |
| 2002/0133004 | A1 | 9/2002 | Sekiyama et al. |
| 2005/0228000 | A1 | 10/2005 | Smallheer et al. |
| 2005/0267108 | A1 | 12/2005 | Hsieh et al. |
| 2006/0004000 | A1 | 1/2006 | D'Orchymont et al. |
| 2007/0155712 | A1 | 7/2007 | Zahn et al. |
| 2008/0075720 | A1 | 3/2008 | Holers et al. |
| 2008/0075728 | A1 | 3/2008 | Newman |
| 2008/0108691 | A1 | 5/2008 | Hamann et al. |
| 2010/0041628 | A1 | 2/2010 | Enomoto et al. |
| 2011/0280808 | A1 | 11/2011 | Kroth et al. |
| 2012/0231471 | A1 | 9/2012 | Sato et al. |
| 2012/0237515 | A1 | 9/2012 | Bell et al. |
| 2012/0295884 | A1 | 11/2012 | Altmann et al. |
| 2013/0029912 | A1 | 1/2013 | Holers et al. |
| 2013/0035392 | A1 | 2/2013 | McGeer et al. |
| 2013/0296377 | A1 | 11/2013 | Adams et al. |
| 2013/0324482 | A1 | 12/2013 | Francois et al. |
| 2013/0344073 | A1 | 12/2013 | Schwaeble et al. |
| 2014/0050739 | A1 | 2/2014 | Francois et al. |
| 2014/0323407 | A1 | 10/2014 | Francois et al. |
| 2014/0371133 | A1 | 12/2014 | Francois et al. |
| 2015/0141455 | A1 | 5/2015 | Altmann et al. |
| 2015/0148374 | A1 | 5/2015 | Hommel et al. |
| 2015/0158915 | A1 | 6/2015 | Lambris et al. |
| 2015/0191462 | A1 | 7/2015 | Hommel et al. |
| 2015/0239837 | A1 | 8/2015 | Wiles et al. |
| 2015/0239838 | A1 | 8/2015 | Phadke et al. |
| 2015/0239868 | A1 | 8/2015 | Pais et al. |
| 2015/0239893 | A1 | 8/2015 | Wang et al. |
| 2015/0239894 | A1 | 8/2015 | Gadhachanda et al. |
| 2015/0239895 | A1 | 8/2015 | Gadhachanda et al. |
| 2015/0239919 | A1 | 8/2015 | Gadhachanda et al. |
| 2015/0239920 | A1 | 8/2015 | Gadhachanda et al. |
| 2015/0239921 | A1 | 8/2015 | Wiles et al. |
| 2015/0269868 | A1 | 9/2015 | Carney et al. |
| 2015/0322060 | A1 | 11/2015 | Flohr et al. |
| 2015/0368271 | A1 | 12/2015 | Su et al. |
| 2016/0015810 | A1 | 1/2016 | Deschatelets et al. |
| 2016/0024079 | A1 | 1/2016 | Adams et al. |
| 2016/0060297 | A1 | 3/2016 | Deschatelets et al. |
| 2016/0194359 | A1 | 7/2016 | Francois et al. |
| 2016/0215020 | A1 | 7/2016 | Francois et al. |
| 2016/0215022 | A1 | 7/2016 | Francois et al. |
| 2016/0361329 | A1 | 12/2016 | Wiles et al. |
| 2016/0362398 | A1 | 12/2016 | Wiles et al. |
| 2016/0362399 | A1 | 12/2016 | Wiles et al. |
| 2016/0362432 | A1 | 12/2016 | Wiles et al. |
| 2016/0362433 | A1 | 12/2016 | Wiles et al. |
| 2017/0056428 | A1 | 3/2017 | Wiles et al. |
| 2017/0057950 | A1 | 3/2017 | Wiles et al. |
| 2017/0057983 | A1 | 3/2017 | Wiles et al. |
| 2017/0057993 | A1 | 3/2017 | Wiles et al. |
| 2017/0066783 | A1 | 3/2017 | Wiles et al. |
| 2017/0189410 | A1 | 7/2017 | Gadhachanda et al. |
| 2017/0202821 | A1 | 7/2017 | Bekker |
| 2017/0202935 | A1 | 7/2017 | Lambris et al. |
| 2017/0226142 | A1 | 8/2017 | Wiles et al. |
| 2017/0260219 | A1 | 9/2017 | Wiles et al. |
| 2017/0298084 | A1 | 10/2017 | Wiles et al. |
| 2017/0298085 | A1 | 10/2017 | Wiles et al. |
| 2018/0022766 | A1 | 1/2018 | Wiles et al. |
| 2018/0022767 | A1 | 1/2018 | Wiles et al. |
| 2018/0030075 | A1 | 2/2018 | Wiles et al. |
| 2018/0072762 | A1 | 3/2018 | Wiles et al. |
| 2018/0177761 | A1 | 6/2018 | Wiles et al. |
| 2018/0179185 | A1 | 6/2018 | Wiles et al. |
| 2018/0179186 | A1 | 6/2018 | Wiles et al. |
| 2018/0179236 | A1 | 6/2018 | Wiles et al. |
| 2018/0186782 | A1 | 7/2018 | Wiles et al. |
| 2018/0201580 | A1 | 7/2018 | Wiles et al. |
| 2018/0305375 | A1 | 10/2018 | Wiles et al. |
| 2019/0023729 | A1 | 1/2019 | Wiles et al. |
| 2019/0031692 | A1 | 1/2019 | Wiles et al. |
| 2019/0038623 | A1 | 2/2019 | Huang et al. |
| 2019/0048033 | A1 | 2/2019 | Wiles et al. |
| 2019/0085005 | A1 | 3/2019 | Wiles et al. |
| 2019/0144473 | A1 | 5/2019 | Gadhachanda et al. |
| 2019/0211033 | A1 | 7/2019 | Wiles et al. |
| 2019/0359645 | A1 | 11/2019 | Birkus et al. |
| 2019/0382376 | A1 | 12/2019 | Wiles et al. |
| 2020/0002347 | A1 | 1/2020 | Wiles et al. |
| 2020/0062790 | A1 | 2/2020 | Wiles et al. |
| 2020/0071301 | A1 | 3/2020 | Wiles et al. |
| 2020/0262818 | A1 | 8/2020 | Wiles et al. |

FOREIGN PATENT DOCUMENTS

| | | | |
|---|---|---|---|
| JP | 2014-506877 | A | 3/2014 |
| JP | 2015-522005 | A | 8/2015 |
| JP | 2015-522006 | A | 8/2015 |
| JP | 2015-522007 | A | 8/2015 |
| JP | 6400738 | B2 | 10/2018 |
| JP | 6537532 | B2 | 7/2019 |
| JP | 6688352 | B2 | 4/2020 |
| WO | WO-1993/020099 | A2 | 10/1993 |
| WO | WO-1995/029697 | A1 | 11/1995 |
| WO | WO-1999/048492 | A1 | 9/1999 |
| WO | WO-2004/007501 | A1 | 1/2004 |
| WO | WO-2004/045518 | A2 | 6/2004 |
| WO | WO-2004/111041 | A1 | 12/2004 |
| WO | WO-2008/047831 | A1 | 4/2008 |
| WO | WO-2009/091826 | A2 | 7/2009 |
| WO | WO-2012/093101 | A1 | 7/2012 |
| WO | WO-2012/177782 | A1 | 12/2012 |
| WO | WO-2013/166436 | A1 | 11/2013 |
| WO | WO-2013/192345 | A1 | 12/2013 |
| WO | WO-2014/002051 | A2 | 1/2014 |
| WO | WO-2014/002052 | A1 | 1/2014 |
| WO | WO-2014/002053 | A1 | 1/2014 |
| WO | WO-2014/002054 | A1 | 1/2014 |
| WO | WO-2014/002057 | A1 | 1/2014 |
| WO | WO-2014/002058 | A2 | 1/2014 |
| WO | WO-2014/002059 | A1 | 1/2014 |
| WO | WO-2014/002067 | A2 | 1/2014 |
| WO | WO-2014/005150 | A1 | 1/2014 |

(56) References Cited

FOREIGN PATENT DOCUMENTS

| | | | |
|---|---|---|---|
| WO | WO-2014/009833 | A2 | 1/2014 |
| WO | WO-2014/037480 | A1 | 3/2014 |
| WO | WO-2014/116880 | A1 | 7/2014 |
| WO | WO-2015/008861 | A1 | 1/2015 |
| WO | WO-2015/021166 | A2 | 2/2015 |
| WO | WO-2015/054569 | A1 | 4/2015 |
| WO | WO-2015/130784 | A1 | 9/2015 |
| WO | WO-2015/130795 | A1 | 9/2015 |
| WO | WO-2015/130806 | A1 | 9/2015 |
| WO | WO-2015/130830 | A1 | 9/2015 |
| WO | WO-2015/130838 | A1 | 9/2015 |
| WO | WO-2015/130842 | A2 | 9/2015 |
| WO | WO-2015/130845 | A1 | 9/2015 |
| WO | WO-2015/130854 | A1 | 9/2015 |
| WO | WO-2017/035348 | A1 | 3/2017 |
| WO | WO-2017/035349 | A1 | 3/2017 |
| WO | WO-2017/035351 | A1 | 3/2017 |
| WO | WO-2017/035352 | A1 | 3/2017 |
| WO | WO-2017/035353 | A1 | 3/2017 |
| WO | WO-2017/035355 | A1 | 3/2017 |
| WO | WO-2017/035357 | A1 | 3/2017 |
| WO | WO-2017/035360 | A1 | 3/2017 |
| WO | WO-2017/035361 | A1 | 3/2017 |
| WO | WO-2017/035362 | A1 | 3/2017 |
| WO | WO-2017/035401 | A1 | 3/2017 |
| WO | WO-2017/035405 | A1 | 3/2017 |
| WO | WO-2017/035408 | A1 | 3/2017 |
| WO | WO-2017/035409 | A1 | 3/2017 |
| WO | WO-2017/035411 | A1 | 3/2017 |
| WO | WO-2017/035413 | A2 | 3/2017 |
| WO | WO-2017/035415 | A1 | 3/2017 |
| WO | WO-2017/035417 | A1 | 3/2017 |
| WO | WO-2017/035418 | A1 | 3/2017 |
| WO | WO-2017/098328 | A2 | 6/2017 |
| WO | WO-2017/127761 | A1 | 7/2017 |
| WO | WO-2017/136395 | A1 | 8/2017 |
| WO | WO-2018/005552 | A1 | 1/2018 |
| WO | WO-2018/026722 | A1 | 2/2018 |
| WO | WO-2018/160889 | A1 | 9/2018 |
| WO | WO-2018/160891 | A1 | 9/2018 |
| WO | WO-2018/160892 | A1 | 9/2018 |
| WO | WO-2019/070714 | A1 | 4/2019 |

OTHER PUBLICATIONS

"Dermatomyositis," Mayo Clinic, <https://www.mayoclinic.org/diseases-conditions/dermatomyositis/diagnosis-treatment/drc-20353192>, retrieved on Aug. 1, 2017 (7 pages).
"Reperfusion injury," Wikipedia, <https://en.wikipedia.org/wiki/Reperfusion_injury>, retrieved Apr. 30, 2020 (8 pages).
"Treatment for Multiple Sclerosis," WebMD, <https://www.webmd.com/multiple-sclerosis/ms-treatment#1>, retrieved on May 3, 2019 (24 pages).
"What Are the Treatments for Cirrhosis?," WebMD, <https://www.webmd.com/digestive-disorders/understanding-cirrhosis-treatment#1>, retrieved May 3, 2019 (15 pages).
"What is Cardiovascular Disease?" American Heart Association, <https://www.heart.org/en/health-topics/consumer-healthcare/what-is-cardiovascular-disease>, dated May 31, 2017 (4 pages).
Airey et al., "A Convenient Preparation of Thieno[3,2-c]pyrazole," Synthesis. 46: 96-100 (2014).
Armand, "Fatty liver disease: What it is and what to do about it," Harvard Health Publishing, <https://www.health.harvard.edu/blog/fatty-liver-disease-what-it-is-and-what-to-do-about-it-2019011015746>, dated Jan. 10, 2019, retrieved May 2, 2019 (3 pages).
Babiker et al., "Transfer of prostasomal CD59 to CD59-deficient red blood cells results in protection against complement-mediated hemolysis," Am J Reprod Immunol. 47(3): 183-92 2002 (Abstract Only).
Barraclough et al., "Two separate and distinct syntheses of stereospecifically deuteriated samples of (2S)-proline," Org Biomol Chem. 4(8):1483-1491 (2006).
Barraclough et al., "Synthesis of (2S,3R)- and (2S,3S)-[3-$^2H_1$]-proline via highly selective hydrolysis of a silyl enol ether," Tetrahedron Letters. 46(1): 4653-4655 (2005).
Borowitz et al., "Guidelines for the Diagnosis and Monitoring of Paroxysmal Nocturnal Hemoglobinuria and Related Disorders by Flow Cytometry," Cytometry B Clin Cytom. 78B(4): 211-230 (2010).
Brodsky, "Eculizumab: another breakthrough," Blood. 129(8):922-3 (2017).
Carter, "Complement Activation: An Emerging Player in the Pathogenesis of Cardiovascular Disease," Scientifica. 2012(1):1-14 (2012).
CAS RN 1236228-05-9, dated Aug. 16, 2010 (1 page).
CAS RN 1236251-51-6, dated Aug. 17, 2010 (2 pages).
CAS RN 1270608-88-2, dated 2019 (1 page).
CAS RN 1277041-86-7, dated Apr. 8, 2011 (2 pages).
Cofiell et al., "Eculizumab reduces complement activation, inflammation, endothelial damage, thrombosis, and renal injury markers in aHUS," Blood. 125(21):3253-62 (2015).
Cole et al. "Structure of 3,4-Dichloroisocoumarin-Inhibited Factor D," Acta Crystallogr D Biol Crystallogr. 54(Pt 5): 711-717 (1998).
Compound Summary for CID 1129904, PubChem. <https://pubchem.ncbi.nlm.nih.gov/compound/1129904>, entered Jul. 10, 2005 (10 pages).
Compound Summary for CID 118324207, PubChem, <https://pubchem.ncbi.nlm.nih.gov/compound/118324207>, dated Feb. 23, 2016, retrieved on Jul. 14, 2020 (8 pages).
Compound Summary for CID 123543544, PubChem, <https://pubchem.ncbi.nlm.nih.gov/compound/123543544>, created on Jan. 25, 2019, retrieved on Jul. 13, 2020 (8 pages).
Compound Summary for CID 134222466, PubChem, <https://pubchem.ncbi.nlm.nih.gov/compound/134222466>, created on Jun. 23, 2018, retrieved on Jul. 14, 2020 (11 pages).
Compound Summary for CID 59912842, PubChem, <https://pubchem.ncbi.nlm.nih.gov/compound/59912842>, entered Aug. 20, 2012 (9 pages).
Damasio, "Alzheimer's disease and related dementias," Cecil Textbook of Medicine, 20th Edition, vol. 2. Bennet and Plum, Jun. 1992 (1996).
Database Registry Chemical Abstracts Service, Columbus, Ohio, Accession No. RN1236248-20-6, Entered STN: Aug. 16, 2010 (1 page).
Database Registry Chemical Abstracts Service, Columbus, Ohio, Accession No. RN1380849-41-1, Entered STN: Jul. 3, 2012 (2 pages).
De Luca et al. "HIV-1 integrase strand-transfer inhibitors: Design, synthesis and molecular modeling investigation" Eur J Med Chem. 46(2): 756-764 (2011).
DeZern et al., "Paroxysmal nocturnal hemoglobinuria: a complement-mediated hemolytic anemia," Hematol Oncol Clin North Am. 29(3):479-94 (2015).
Donthiri et al., "Copper-Catalyzed C—H Functionalization of Pyridines and Isoquinolines with Vinyl Azides: Synthesis of Imidazo Heterocycles," J Org Chem, 79(22): 11277-11284 (2014).
Dormoy et al., "Synthesis of N-t-Butoxycarbonyl-4,4-dideuterio-L-proline," Synthesis, 1: 81-82 (1986).
Gadhachanda et al., CAplus Database Summary Sheet for Document No. 164:507515, Acession No. 2016:627420, CAplus on STN. (2016) (6 pages).
Gavrillaki et al., "275 Small Molecule Factor D Inhibitors Block Complement Activation in Paroxysmal Nocturnal Hemoglobinuria and Atypical Hemolytic Uremic Syndrome," ASH 57th Annual Meeting & Exposition, Session: 101. Dec. 6, 2015 (2 pages).
Golub et al., "Molecular classification of cancer: class discovery and class prediction by gene expression monitoring," Science. 286(5439):531-537 (1999) (8 pages).
Gura, "Systems for identifying new drugs are often faulty," Science. 278(5340):1041-2 (1997).
Haddrill, "Stargardt's Disease (Fundus Flavimaculatus)," All About Vision, <https://www.allaboutvision.com/conditions/stargardts.htm#article-section-2>, retrieved May 3, 2019 (5 pages).
Harder et al., "Incomplete inhibition by eculizumab: mechanistic evidence for residual C5 activity during strong complement activation," Blood.129(8):970-80 (2017).

(56) References Cited

OTHER PUBLICATIONS

Hartmann et al., "Diagnostic Specificity of Sucrose Hemolysis Test for Paroxysmal Nocturnal Hemoglobinuria," Blood. 35(4):462-475 (1970).
Hecker et al., "Liver-Targeted Prodrugs of 2'-C-Methyladenosine for Therapy of Hepatitis C Virus Infection," J Med Chem. 50(16): 3891-3896 (2007).
Hruby et al., "$^{13}$C Nuclear Magnetic Resonance Studies of the Peptide Hormones Oxytocin, Arginine Vasopressin, Isotocin, Mesotocin, Glumitocin, Aspartocin, Related Analogues, and Diastereoisomers. Use of Specifically Deuterated Hormone Derivatives for Assignments and Effects of Structural Changes on $^{13}$C NMR Chemical Shifts in Peptides," J Am Chem Soc. 101(1): 202-212 (1979).
International Search Report and Written Opinion for PCT/US2015/017523 dated May 14, 2015.
International Search Report and Written Opinion for PCT/US2015/017538 dated May 14, 2015.
International Search Report and Written Opinion for PCT/US2015/017554 dated May 14, 2015.
International Search Report and Written Opinion for PCT/US2015/017583 dated May 27, 2015.
International Search Report and Written Opinion for PCT/US2015/017593 dated Jun. 16, 2015.
International Search Report and Written Opinion for PCT/US2015/017597 dated Jan. 29, 2016.
International Search Report and Written Opinion for PCT/US2015/017609 dated May 29, 2015.
International Search Report and Written Opinion for PCT/US2015/17600 dated May 27, 2015.
International Search Report and Written Opinion for PCT/US2016/048688 dated Dec. 28, 2016.
International Search Report and Written Opinion for PCT/US2016/048690 dated Dec. 28, 2016.
International Search Report and Written Opinion for PCT/US2016/048693 dated Jan. 13, 2017.
International Search Report and Written Opinion for PCT/US2016/048695 dated Dec. 30, 2016.
International Search Report and Written Opinion for PCT/US2016/048696 dated Jan. 5, 2017.
International Search Report and Written Opinion for PCT/US2016/048701 dated Jan. 10, 2017.
International Search Report and Written Opinion for PCT/US2016/048704 dated Dec. 27, 2016.
International Search Report and Written Opinion for PCT/US2016/048707 dated Jan. 5, 2017.
International Search Report and Written Opinion for PCT/US2016/048709 dated Jan. 17, 2017.
International Search Report and Written Opinion for PCT/US2016/048710 dated Jan. 5, 2017.
International Search Report and Written Opinion for PCT/US2016/048779 dated Dec. 27, 2016.
International Search Report and Written Opinion for PCT/US2016/048783 dated Feb. 3, 2017.
International Search Report and Written Opinion for PCT/US2016/048787 dated Jan. 5, 2017.
International Search Report and Written Opinion for PCT/US2016/048788 dated Jan. 5, 2017.
International Search Report and Written Opinion for PCT/US2016/048793 dated Dec. 28, 2016.
International Search Report and Written Opinion for PCT/US2016/048795 dated Feb. 17, 2017.
International Search Report and Written Opinion for PCT/US2016/048797 dated Jan. 5, 2017.
International Search Report and Written Opinion for PCT/US2016/048799 dated Nov. 15, 2016.
International Search Report and Written Opinion for PCT/US2016/048800 dated Jan. 5, 2017.
International Search Report for International Application No. PCT/US18/20530, dated Jun. 25, 2018 (3 pages).
International Search Report for International Application No. PCT/US2018/020528, dated Apr. 24, 2018 (3 pages).
International Search Report for International Application No. PCT/US2018/045057, dated Nov. 15, 2018 (5 pages).
International Search Report for International Application No. PCT/US2018/20531, dated May 15, 2018 (3 pages).
International Search Report for International Application No. PCT/US2019/034210, dated Sep. 13, 2019 (4 pages).
International Search Report for International Application No. PCT/US2019/047252, dated Dec. 17, 2019 (4 pages).
International Search Report for International Application No. PCT/US2019/050065, dated Feb. 25, 2020 (4 pages).
International Search Report for International Application No. PCT/US2019/050073, dated Nov. 21, 2019 (3 pages).
International Search Report for International Application No. PCT/US2019/053012, dated Jan. 28, 2020 (4 pages).
International Search Report for International Application No. PCT/US2019/066999, dated Feb. 12, 2020 (3 pages).
Johnson et al., "Relationships between drug activity in NCI preclinical in vitro and in vivo models and early clinical trials," Br J Cancer. 84(10):1424-31 (2001).
Józsi, "Anti-Complement Autoantibodies in Membranoproliferative Glomerulonephritis and Dense Deposit Disease", *An Update on Glomerulopathies—Etiology and Pathogenesis*. Prof. Sharma Prabhakar, 31-46 (2011) (18 pages).
Kathuria, "Membranoproliferative Glomerulonephritis Medication," Medscape, <https://emedicine.medscape.com/article/240056-medication>, dated Jun. 23, 2016, retrieved May 3, 2019, (1 page).
Kinman, "COPD Drugs: A List of Medications to Help Relieve Your Symptoms," Healthline, <https://www.healthline.com/health/copd/drugs>, retrieved on May 3, 2019 (12 pages).
Kobayashi et al., "Carboxylation of alkynylsilanes with carbon dioxide mediated by cesium fluoride in DMSO," Org Biomol Chem. 11:3773-3775 (2013).
Komiya et al., CAplus Database Summary Sheet for Document No. 162:229476, Acession No. 2015:126147, CAplus on STN. (2015) (2 pages).
Krauss, "Laboratory Diagnosis of Paroxysmal Nocturnal Hemoglobinuria," Annals of Clinical & Laboratory Science. 33(4): 401-406(2003).
Kuang et al., "Synthesis of (Z)-1-bromo-1-alkenes and terminal alkynes from anti-2,3-dibromoalkanoic acids by microwave-induced reaction," Tetrahedron. 61(16):4043-4052 (2005).
Lala et al., "Role of nitric oxide in tumor progression: lessons from experimental tumors," Cancer Metastasis Rev. 17(1):91-106 (1998).
Lassmann, "What drives disease in multiple sclerosis: Inflammation or neurodegeneration?" Clinical and Experimental Neuroimmunology. 1:2-11 (2010).
Layzer, "Degenerative Diseases of the Nervous System", Cecil Textbook of Medicine, 20th Edition, Vo. 2, pp. 2050-2057 (1996).
Le et al., "A mechanistic pharmacokinetic/pharmacodynamic model of factor D inhibition in cynomolgus monkeys by lampalizumab for the treatment of geographic atrophy," J Pharmacol Exp Ther. 355(2):288-96 (2015).
MacKay et al., "Rapid Synthesis of the N-Methylwelwitindolinone Skeleton," Org Lett. 7(16):3421-4 (2005).
Mastellos et al., "Complement in paroxysmal nocturnal hemoglobinuria: exploiting our current knowledge to improve the treatment landscape," Expert Rev Hematol. 7(5):583-98 (2014).
NCT03472885—A Treatment Study of ACH-0144471 in Patients With Paroxysmal Nocturnal Hemoglobinuria (PNH) With Inadequate Response to Eculizumab (PNH), First Posted Mar. 15, 2018, available at: https://clinicaltrials.gov/ct2/show/NCT03472885.
Noris et al., "Overview of Complement Activation and Regulation," Semin Nephrol. 33:479-492 (2013).
Office Action issued for Eurasian Patent Application No. 201992005, dated Oct. 23, 2020 (6 pages).
Okutani et al., "Conversion of Bromoalkenes into Alkynes by Wet Tetra-n-butylammonium Fluoride," J Org Chem. 74(1):442-444 (2009).
Oseini et al. "Therapies in Non-Alcoholic Steatohepatitis (NASH)," available in PMC Jan. 1, 2018, published in final edited form as: Liver Int. 37(Suppl 1):97-103 (2017) (15 pages).

(56) References Cited

OTHER PUBLICATIONS

Pandya et al., "Complement System in Lung Disease," Am J Respir Cell Mol Biol. 51(4):467-473 (2014).
Parker, "Update on the diagnosis and management of paroxysmal nocturnal hemoglobinuria," Hematology Am Soc Hemtol Educ Program. 2016(1):208-16 (2016).
Partial Supplementary European Search Report for European Application No. 18761960.6, dated Nov. 27, 2020 (12 pages).
Patel et al., "In Vitro Combination Studies of ACH-4471 with Eculizumab to Assess a Potential 'Switch' Treatment Approach for Paroxysmal Nocturnal Hemoglobinuria" Poster, 2017.
Pearce et al., "Failure modes in anticancer drug discovery and development," Cancer Drug Design and Discovery Edited by Stephen Neidle, Chapter 18, pp. 424-435 (2008).
Peifer et al., "Design, Synthesis, and Biological Evaluation of Novel 3-Aryl-4-(1 H-indole-3yl)-1,5-dihydro-2H-pyrrole-2-ones as Vascular Endothelial Growth Factor Receptor (VEGF-R) Inhibitors," J Med Chem. 51(13):3814-3824 (2008).
Pugsley et al., "Inhibitors of the complement system currently in development for cardiovascular disease," Cardiovasc Toxicol. 3(1):43-69 (2003).
Qu et al., "Recent Developments in Low Molecular Weight Complement Inhibitors," Mol Immunol. 47(2-3):185-195 (2009).
Quesada et al., "One-pot conversion of activated alcohols into terminal alkynes using manganese dioxide in combination with the Bestmann-Ohira reagent," Tetrahedron Letters. 46:6473-6476 (2005).
Ricklin et al., "Complement in immune and inflammatory disorders: pathophysiological mechanisms," J Immunol. 190(8):3831-3838 (2013).
Risitano et al., "Complement fraction 3 binding on erythrocytes as additional mechanism of disease in paroxysmal nocturnal hemoglobinuria patients treated by eculizumab," Blood. 113(17):4094-4100 (2009) (25 pages).
Risitano et al., "Peptide inhibitors of C3 activation as a novel strategy of complement inhibition for the treatment of paroxysmal nocturnal hemoglobinuria," Blood. 123(13):2094-101 (2014).
Risitano et al., "Safety and Pharmacokinetics of the Complement Inhibitor TT30 in a Phase I Trial for Untreated PNH Patients" Blood. 126(23): 2137 (2015).
Risitano et al., "Toward complement inhibition 2.0: Next generation anticomplement agents for paroxysmal nocturnal hemoglobinuria," Am J Hematol. 93(4):564-77 (2018).
Risitano, "Anti-Complement Treatment in Paroxysmal Nocturnal Hemoglobinuria: Where we Stand and Where we are Going," Transl Med UniSa. 8:43-52 (2014).
Risitano, "Paroxysmal nocturnal hemoglobinuria in the era of complement inhibition," Am J Hematol. 91(4):359-60 (2016).
Rohrer et al., "Eliminating complement factor D reduces photoreceptor susceptibility to light-induced damage," Invest Ophthalmol Vis Sci. 48(11):5282-9 (2007).
Roth et al., "Further Improvements of the Synthesis of Alkynes from Aldehydes," Synthesis. 1:59-62 (2004).
Ruiz-Gómez et al. "Structure-Activity Relationships for Substrate-Based Inhibitors of Human Complement Factor B," J Med Chem. 52(19):6042-6052 (2009).
Salifu, "Chronic Glomerulonephritis Medication," Medscape, <https://emedicine.medscape.com/article/239392-medication>, dated Feb. 1, 2017, retrieved on May 2, 2019 (1 page).
Segers et al., "Complement Alternative Pathway Activation in Human Nonalcoholic Steatohepatitis," Plos One. 9(10):e110053 (2014) (9 pages).
Sica et al., "Eculizumab treatment: stochastic occurrence of C3 binding to individual PNH erythrocytes," J Hematol Oncol. 10(1):126 (2017).
Simone, "Oncology: Introduction," Cecil Textbook of Medicine, 20th Edition, vol. 1, pp. 1004-1010, (1996).
Stanton et al., "Complement Factor D in Age-Related Macular Degeneration," Invest Ophthalmol Vis Sci. 52(12):8828-8834 (2011) (15 pages).
Strobel et al., "Anti-factor B autoantibody in dense deposit disease," Mol Immunol. 47:1476-1483 (2010).
Tandon et al., "Substrate specificity of human prolyl-4-hydroxylase," Bioorg Med Chem Lett. 8(10):1139-1144 (1998).
Tang et al., "Palladium-Catalyzed Carbonylative Sonogashira Coupling of Aryl Bromides via tert-Butyl Isocyanide Insertion," J Org Chem. 78(7):3170-3175 (2013).
Wehling et al., "Monitoring of complement activation biomarkers and eculizumab in complement-mediated renal disorders," Clin Exp Immunol. 187(2):304-15 (2017).
What is Dementia?[online] retrieved from the internet on Sep. 4, 2018. URL; https://www.alz.org/alzheimers-dementia/what-is-dementia.
Written Opinion for International Application No. PCT/US18/20528, dated Apr. 24, 2018 (6 pages).
Written Opinion for International Application No. PCT/US18/20530, dated Jun. 25, 2018 (6 pages).
Written Opinion for International Application No. PCT/US18/20531, dated May 15, 2018 (7 pages).
Written Opinion for International Application No. PCT/US19/047252, dated Dec. 17, 2019 (6 pages).
Written Opinion for International Application No. PCT/US19/50065, dated Feb. 25, 2020 (7 pages).
Written Opinion for International Application No. PCT/US19/53012, dated Jan. 28, 2020 (5 pages).
Written Opinion for International Application No. PCT/US19/66999, dated Feb. 12, 2020 (7 pages).
Written Opinion for International Application No. PCT/US2018/045057, dated Nov. 15, 2018 (7 pages).
Written Opinion for International Application No. PCT/US2019/034210, dated Sep. 13, 2019 (17 pages).
Written Opinion for International Application No. PCT/US2019/050073, dated Nov. 21, 2019 (4 pages).
Yuan et al., "Small-molecule Factor D Inhibitors Selectively Block the Alternative Pathway of Complement in Paroxysmal Nocturnal Hemoglobinuria and Atypical Hemolytic Uremic Syndrome," Haematologica. 102(3):466-75 (2017).
"History of Changes for Study: NCT03053102—A Treatment Study of ACH-0144471 in Patients With Paroxysmal Nocturnal Hemoglobinuria (PNH)," U.S. National Library of Medicine, available at: <https://clinicaltrials.gov/ct2/history/NCT03053102?V_4=View#StudyPageTop>, submitted Jun. 6, 2017, retrieved Mar. 9, 2021 (3 pages).
Ellis-Pegler et al., "An Orally Administered Small Molecule Factor D Inhibitor (ACH-4471) For Treatment of PNH and Complement Diseases: Preliminary Phase 1 Results In Healthy Volunteers," European Hematology Association. Abstract LB2250, available <https://library.ehaweb.org/eha/2016/21 st/135361/roderick.b.ellis-pegler.an.orally.administered.small.molecule.factor.d.html> (2016) (2 pages).
Ellis-Pegler et al., "An Orally Administered Small Molecule Factor D Inhibitor (ACH-4471) For Treatment of PNH, C3G and Complement—Mediated Diseases: Interim Phase 1 Results In Healthy Volunteers," European Hematology Association, Copenhagen 21st Congress, Jun. 9-12, Abstract ID: EHA-4145 (2016).

* cited by examiner 1 2 3

Rxn#1: 2.4 g from 2.5 g of 1

PHARMACEUTICAL COMPOUNDS FOR TREATMENT OF MEDICAL DISORDERS

CROSS-REFERENCE TO RELATED APPLICATIONS

This application is a continuation of International Application No. PCT/US2018/020530, filed Mar. 1, 2018, which claims the benefit of priority to U.S. Application No. 62/465,799, filed Mar. 1, 2017; U.S. Application No. 62/465,754, filed Mar. 1, 2017; U.S. Application No. 62/466,308, filed Mar. 2, 2017; and U.S. Application No. 62/466,290, filed Mar. 2, 2017; each of which is incorporated by reference herein for all purposes.

FIELD OF THE INVENTION

This invention provides pharmaceutical compounds to treat medical disorders, such as complement-mediated disorders.

BACKGROUND OF THE INVENTION

The complement system is a part of the innate immune system which does not adapt to changes over the course of the host's life, but is recruited and used by the adaptive immune system. For example, it assists, or complements, the ability of antibodies and phagocytic cells to clear pathogens. This sophisticated regulatory pathway allows rapid reaction to pathogenic organisms while protecting host cells from destruction. Over thirty proteins and protein fragments make up the complement system. These proteins act through opsonization (enhancing phagocytosis of antigens), chemotaxis (attracting macrophages and neutrophils), cell lysis (rupturing membranes of foreign cells), and agglutination (clustering and binding of pathogens together).

The complement system has three pathways: classical, alternative, and lectin. Complement Factor D plays an early and central role in activation of the alternative pathway of the complement cascade. Activation of the alternative complement pathway is initiated by spontaneous hydrolysis of a thioester bond within C3 to produce $C3(H_2O)$, which associates with Factor B to form the $C3(H_2O)B$ complex. Complement Factor D acts to cleave Factor B within the $C3(H_2O)B$ complex to form Ba and Bb. The Bb fragment remains associated with $C3(H_2O)$ to form the alternative pathway C3 convertase $C3(H_2O)Bb$. Additionally, C3b generated by any of the C3 convertases also associates with Factor B to form C3bB, which Factor D cleaves to generate the later stage alternative pathway C3 convertase C3bBb. This latter form of the alternative pathway C3 convertase may provide important downstream amplification within all three of the defined complement pathways, leading ultimately to the recruitment and assembly of additional factors in the complement cascade pathway, including the cleavage of C5 to C5a and C5b. C5b acts in the assembly of factors C6, C7, C8, and C9 into the membrane attack complex, which can destroy pathogenic cells by lysing the cell.

The dysfunction of or excessive activation of complement has been linked to certain autoimmune, inflammatory, and neurodegenerative diseases, as well as ischemia-reperfusion injury and cancer. For example, activation of the alternative pathway of the complement cascade contributes to the production of C3a and C5a, both potent anaphylatoxins, which also have roles in a number of inflammatory disorders. Therefore, in some instances, it is desirable to decrease the response of the complement pathway, including the alternative complement pathway. Some examples of disorders mediated by the complement pathway include age-related macular degeneration (AMD), paroxysmal nocturnal hemoglobinuria (PNH), multiple sclerosis, and rheumatoid arthritis.

Age-related macular degeneration (AMD) is a leading cause of vision loss in industrialized countries. Based on a number of genetic studies, there is evidence of the link between the complement cascade and macular degeneration. Individuals with mutations in the gene encoding complement Factor H have a fivefold increased risk of macular degeneration and individuals with mutations in other complement factor genes also have an increased risk of AMD. Individuals with mutant Factor H also have increased levels of C-reactive protein, a marker of inflammation. Without adequate functioning Factor H, the alternative pathway of the complement cascade is overly activated leading to cellular damage.

Paroxysmal nocturnal hemoglobinuria (PNH) is a non-malignant, hematological disorder characterized by the expansion of hematopoietic stem cells and progeny mature blood cells that are deficient in some surface proteins. PNH erythrocytes are not capable of modulating their surface complement activation, which leads to the typical hallmark of PNH—the chronic activation of complement mediated intravascular anemia. Currently, only one product, the anti-C5 monoclonal antibody eculizumab, has been approved in the U.S. for treatment of PNH. However, many of the patients treated with eculizumab remain anemic, and many patients continue to require blood transfusions. In addition, treatment with eculizumab requires life-long intravenous injections.

Additional complement-mediated disorders include those classified under component 3 glomerulopathy (C3G). C3G is a recently defined entity comprised of dense deposit disease (DDD) and C3 glomerulonephritis (C3GN) which encompasses a population of chronic kidney diseases wherein elevated activity of the alternative complement pathway and terminal complement pathway results in glomerular deposits made solely of complement C3 and no immunoglobulin (Ig).

Immune-complex membranoproliferative glomerulonephritis (IC-MPGN) is a renal disease which shares many clinical, pathologic, genetic and laboratory features with C3G, and therefore can be considered a sister disease of C3G. In the majority of patients with IC-MPGN, an underlying disease or disorder-most commonly infections, autoimmune diseases, or monoclonal gammopathies—are identified to which the renal disease is secondary. Patients with idiopathic IC-MPGN can have low C3 and normal C4 levels, similar to those observed in C3G, as well as many of the same genetic or acquired factors that are associated with abnormal alternative pathway activity. Although there are current hypotheses suggesting that the majority of IC-MPGN is attributable to over activity of the classical pathway, those patients with a low C3 and a normal C4 are likely to have significant overactivity of the alternative pathway. IC-MPGN patients with a low C3 and a normal C4 may benefit from alternative pathway inhibition.

Other disorders that have been linked to the complement cascade include atypical hemolytic uremic syndrome (aHUS), hemolytic uremic syndrome (HUS), abdominal aortic aneurysm, hemodialysis complications, hemolytic anemia, or hemodialysis, neuromylitis (NMO), myasthenia gravis (MG), fatty liver, nonalcoholic steatohepatitis (NASH), liver inflammation, cirrhosis, liver failure, dermatomyositis, and amyotrophic lateral sclerosis.

Factor D is an attractive target for inhibition or regulation of the complement cascade due to its early and essential role in the alternative complement pathway, and for its potential role in signal amplification within the classical and lectin complement pathways. Inhibition of Factor D effectively interrupts the pathway and attenuates the formation of the membrane attack complex.

While initial attempts have been made to develop inhibitors of Factor D, there are currently no clinically approved small molecule Factor D inhibitors. Examples of Factor D inhibitor compounds are described in the following disclosures.

Biocryst Pharmaceuticals U.S. Pat. No. 6,653,340 titled "Compounds useful in the complement, coagulate and kallikrein pathways and method for their preparation" describes fused bicyclic ring compounds that are potent inhibitors of Factor D. Development of the Factor D inhibitor BCX1470 was discontinued due to lack of specificity and short half-life of the compound.

Novartis PCT patent publication WO2012/093101 titled "Indole compounds or analogues thereof useful for the treatment of age-related macular degeneration" describes certain Factor D inhibitors. Additional Factor D inhibitors are described in Novartis PCT patent publications WO2013/164802, WO2013/192345, WO2014/002051, WO2014/002052, WO2014/002053, WO2014/002054, WO2014/002057, WO2014/002058, WO2014/002059, WO2014/005150, WO2014/009833, WO2014/143638, WO2015/009616, WO2015/009977, and WO2015/066241.

A paper published by Novartis titled "Structure-Based Library Design and Fragment Screening for the Identification of Reversible Complement Factor D Protease Inhibitors" (Vulpetti et al., J. Med. Chem. 10.1021/acs.jmedchem.6b01684) describes an in silico active site mapping for regions that contribute to a large fraction of binding energy using the Factor D crystal structure and NMR-based screening (structure-based drug design (SBDD) and fragment-based screening (FBD)). Another Novartis paper titled "Small-molecule factor D inhibitors targeting the alternative complement pathway" (Maibaum et al., Nat. Chem. Bio. 2016; 12; 1105) discloses small-molecule inhibitors designed by use of a structure-based design approach in combination with fragment-based screening.

Lifesci Pharmaceuticals PCT patent publication WO2017/098328 titled "Therapeutic Inhibitory Compounds" describes various Factor D inhibitors with variations in the central core ring heterocycle ring. PCT patent publication WO2018/015818 is also titled "Therapeutic Inhibitory Compounds" and describes Factor D inhibitors without cyclic central core.

Bristol-Myers Squibb PCT patent publication WO2004/045518 titled "Open chain prolyl urea-related modulators of androgen receptor function" describes open chain prolyl urea and thiourea related compounds for the treatment of androgen receptor-associated conditions, such as age-related diseases, for example, sarcopenia.

Japan Tobacco Inc. PCT patent publication WO1999/048492 titled "Amide derivatives and nociceptin antagonists" describes compounds with a proline-like core and aromatic substituents connected to the proline core through amide linkages useful for the treatment of pain.

Ferring B. V. and Yamanouchi Pharmaceutical Co. ITD. PCT patent publication WO1993/020099 titled "CCK and/or gastrin receptor ligands" describes compounds with a proline-like core and heterocyclic substituents connected to the proline core through amide linkages for the treatment of, for example, gastric disorders or pain.

Alexion Pharmaceuticals PCT patent publication WO1995/029697 titled "Methods and compositions for the treatment of glomerulonephritis and other inflammatory diseases" discloses antibodies directed to C5 of the complement pathway for the treatment of glomerulonephritis and inflammatory conditions involving pathologic activation of the complement system. Alexion Pharmaceutical's anti-C5 antibody eculizumab (Soliris®) is currently the only complement-specific antibody on the market, and is the first and only approved treatment for paroxysmal nocturnal hemoglobinuria (PNH).

On Feb. 25, 2015, Achillion Pharmaceuticals filed PCT Patent Application No. PCT/US2015/017523 and U.S. patent application Ser. No. 14/631,090 titled "Alkyne Compounds for Treatment of Complement Mediated Disorders"; PCT Patent Application No. PCT/US2015/017538 and U.S. patent application Ser. No. 14/631,233 titled "Amide Compounds for Treatment of Complement Mediated Disorders"; PCT Patent Application No. PCT/US2015/017554 and U.S. patent application Ser. No. 14/631,312 titled "Amino Compounds for Treatment of Complement Mediated Disorders"; PCT Patent Application No. PCT/US2015/017583 and U.S. patent application Ser. No. 14/631,440 titled "Carbamate, Ester, and Ketone Compounds for Treatment of Complement Mediated Disorders"; PCT Patent Application No. PCT/US2015/017593 and U.S. patent application Ser. No. 14/631,625 titled "Aryl, Heteroaryl, and Heterocyclic Compounds for Treatment of Complement Mediated Disorders"; PCT Patent Application No. PCT/US2015/017597 and U.S. patent application Ser. No. 14/631,683 titled "Ether Compounds for Treatment of Complement Mediated Disorders"; PCT Patent Application No. PCT/US2015/017600 and U.S. patent application Ser. No. 14/631,785 titled "Phosphonate Compounds for Treatment of Complement Mediated Disorders"; and PCT Patent Application No. PCT/US2015/017609 and U.S. patent application Ser. No. 14/631,828 titled "Compounds for Treatment of Complement Mediated Disorders" and U.S. patent application Ser. No. 14/630,959 titled "Factor D Inhibitors Useful for Treating Infectious Disorders."

Additional complement factor D inhibitors are described in U.S. Pat. Nos. 9,828,396; 9,695,205; 9,598,446; 9,732,103; 9,796,741; 9,732,104; 9,663,543; 9,758,537; and 9,643,986; International Publication Nos. WO 2015/130784; WO 2015/130795; WO 2015/130806; WO 2015/130830; WO 2015/130838; WO 2015/130842; WO 2015/130845; and WO 2015/130854; and U.S. Patent Publication Nos. US 2017-0298084; US 2016-0362398; US 2017-0189410; US 2017-0298085; US 2018-0030075; US 2016-0362399; US 2018-0022766; US 2016-0362433; US 2017-0260219; US 2016-0362432; US 2018-0022767; US 2016-0361329; and US 2017-0226142; all owned by Achillion Pharmaceuticals, Inc.

Given the wide variety of medical disorders that are caused by detrimental immune or inflammatory responses, new compounds are needed for medical treatment.

SUMMARY

This invention includes a compound of Formula I, Formula II, Formula III, or Formula IV or a pharmaceutically acceptable salt, prodrug, isotopic analog, isolated isomer, or N-oxide thereof, optionally in a pharmaceutically acceptable composition for the treatment of a disorder which is an inflammatory or immune condition, a disorder mediated by the complement cascade (including a dysfunctional cascade for example of Complement D), a disorder or abnormality of a cell that adversely affects the ability of the cell to engage in or respond to normal complement activity including the alternative complement pathway, or an undesired complement-mediated response to a medical treatment, such as surgery or other medical procedure or a pharmaceutical or biopharmaceutical drug administration, a blood transfusion, or other allogenic tissue or fluid administration.

In certain aspects of the invention, the compound presented herein has one or more of the following:

a. An A ring of the formula:

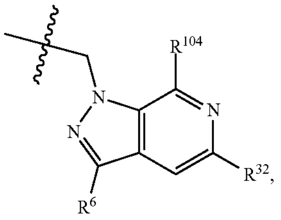
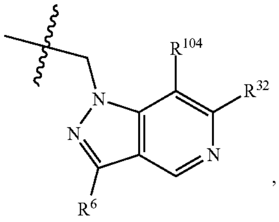
,
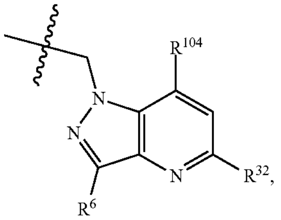
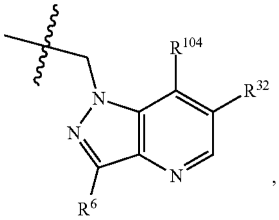
,
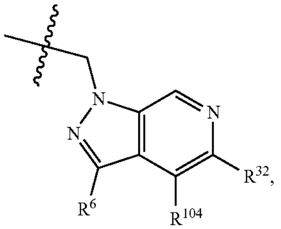
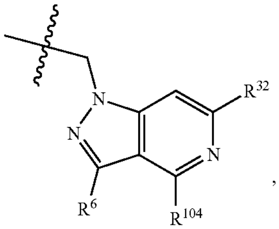
,
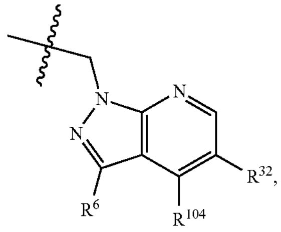
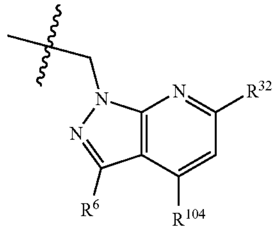
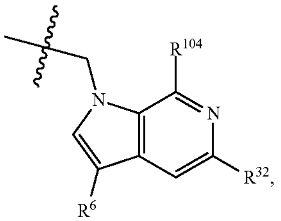
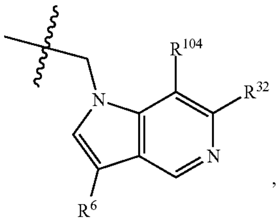
,
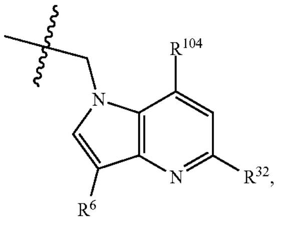
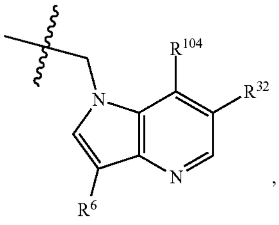
, -continued

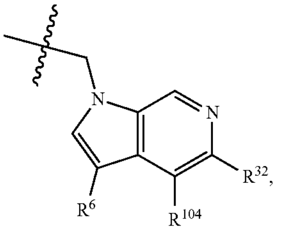
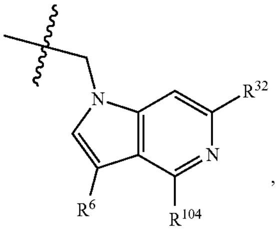
,
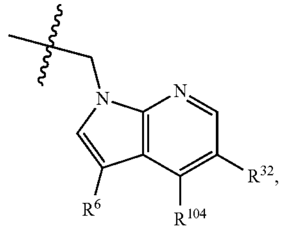
or
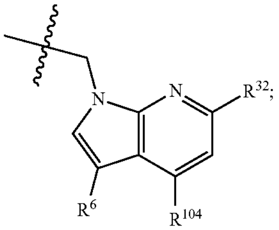

b. An A ring of the formula:

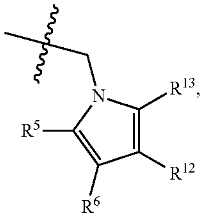
or
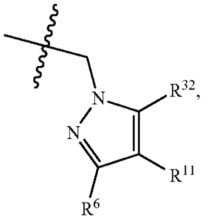
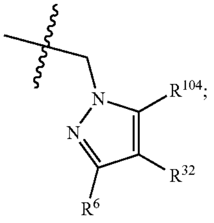

c. An A ring of the formula:

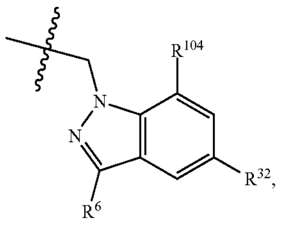
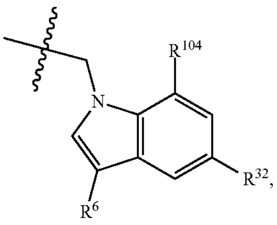

-continued

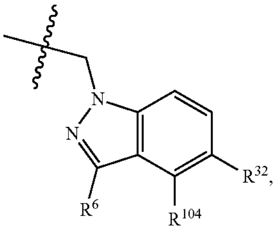

, or

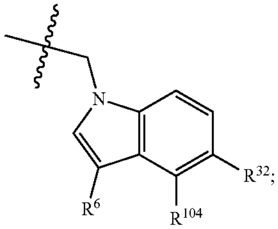

;

d. A B ring of the formula:

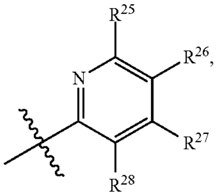

,

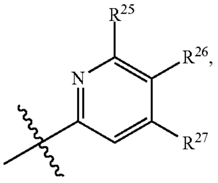

,

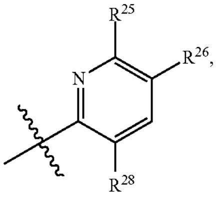

,

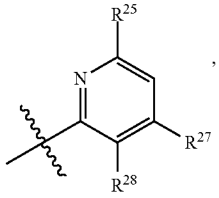

, or

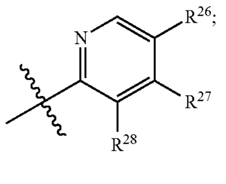

;

e. A C ring selected from:

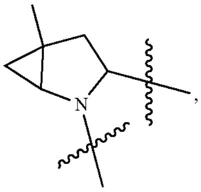

,

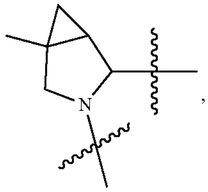

,

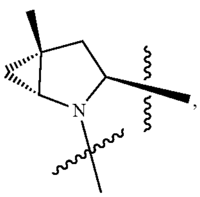

,

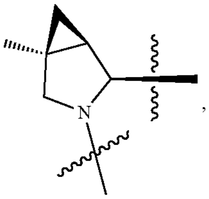

, and

-continued

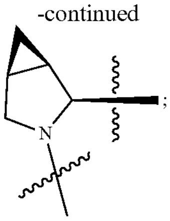

;

f. A C ring of formula:

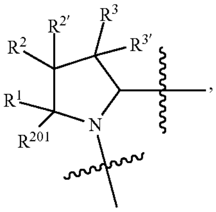

,

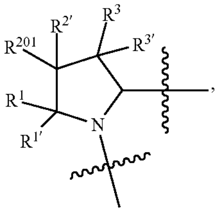

,

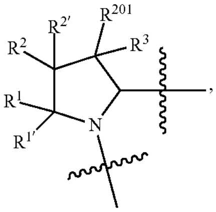

,

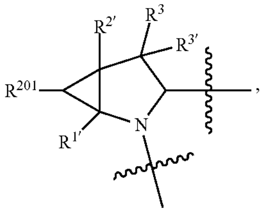

, or

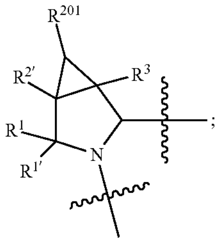

;

g. A C ring selected from a proline spirocycle (such as those described in the paper published by Litter et al. titled "Development of a Manufacturing Process for an HCV Protease Inhibitor Candidate Molecule" (Organic Process Research & Development 2015, 19, 270-283);

h. An $R^{32}$ selected from a cyclic sulfonimidamide (such as those described in the paper published by Pemberton et al. titled "Synthesis and Functionalization of Cyclic Sulfonimidamides: A Novel Chiral Heterocyclic Carboxylic Acid Biostere" (ACS Med, Chem Letters 2012, 3, 574-578);

i. A compound of the invention with at least one $R^{201}$ substituent selected from aminoalkyl-, alkylaminoalkyl-, heterocycloalkyl-, and hydroxyalkyl; -alkyl-O-alkyl including —$CH_2OCH_3$, -alkyl-S-alkyl, -alkyl-N(alkyl)-alkyl, -alkyl-NH-alkyl, -aliphatic-O-aliphatic, -aliphatic-S-aliphatic, -aliphatic-N(aliphatic)-aliphatic, -aliphatic-NH-aliphatic, -aliphatic-O-heterocycle, -aliphatic-S-heterocycle, -aliphatic-N(aliphatic)-heterocycle, -aliphatic-NH-heterocycle, -alkyl-NHC(O)haloalkyl, -alkyl-$NR^9C$(O)haloalkyl, -alkyl-C(O)NHhaloalkyl, -alkyl-C(O)$NR^9$haloalkyl, -alkyl-NHC(O)haloalkyl, -alkyl-$NR^9C$(O)aliphatic, -alkyl-C(O)NHaliphatic, -alkyl-$NR^9C$(O)aliphatic, -alkyl-NHC(O)aliphatic, -substituted alkyl-N($R^9$)-substituted alkyl, alkyl-heteroaryl, heteroaryl, heterocycle, alkyl-heterocycle, -alkyl-O-haloalkyl, —N(aliphatic)$_2$; and wherein each $R^{201}$ can be optionally substituted as defined in the Terminology section below, and wherein each $R^{201}$ can be optionally substituted with $R^{301}$, which can be directly linked to $R^{201}$ or can be linked to $R^{201}$ through an amino, hydroxyl, thio, carboxyl acid, phosphate, phosphonate or sulfonate linkage as desired and appropriate;

j. A compound with at least one $R^{201}$ substituent on the A ring;

k. A compound with at least one $R^{201}$ substituent on the B ring;

l. A compound with at least one $R^{201}$ substituent on the C ring;

m. Certain stable acylated embodiments and acyl prodrugs of the present invention, that include an $R^{301}$ substituent, as further described below.

These compounds can be used to treat medical conditions in a host in need thereof, typically a human. The active compound may act as an inhibitor of the Complement Factor D cascade. In one embodiment, a method for the treatment of such a disorder is provided that includes the administration of an effective amount of a compound of Formula I, Formula II, Formula III, or Formula IV or a pharmaceutically acceptable salt, prodrug, isotopic analog, or isolated isomer thereof, optionally in a pharmaceutically acceptable composition, as described in more detail below.

In certain embodiments, compounds are provided that have minimal effect on BSEP (bile salt export pump protein) (e.g., with an $IC_{50}$ of greater than about 20, 30, 40, 50, 60, 75 or 100 μM or greater), or with a therapeutic index of BSEP relative to complement D inhibition (e.g., $IC_{50}$ inhibition of BSEP/$IC_{50}$ inhibition of complement D inhibitor), of about at least 50, 100, 200, 300, 400, 500, 750, 1000 or greater). BSEP inhibition correlates with cholestatic drug-induced liver injury. Certain compounds of the present invention with low BSEP inhibition have at least one $R^{201}$.

In some embodiments, the compounds of the present invention exhibit minimal hydrolysis of the amide bond between the C ring and the B ring in vivo, for example, by including a proline that has a cis-substituent relative to the proline-carbonyl bond directed toward the B-ring. In certain embodiments, the cis-substituent is in the Q3 position or the Q2 position or is a group that bridges Q3 and Q2.

It has also been discovered that including a B-ring substituent in the position ortho to the amide (for example 2-(L1)-3-methyl-6-substituted-pyridine or 2-(L1)-3-cyclopropyl-6-substituted-pyridine) decreases the potential for formation of reactive metabolites.

In one aspect of the invention, an $R^{301}$ acylated embodiment of an active compound of the invention is provided that exhibits extended half-life or other advantageous pharmacokinetic properties, which may be achieved by albumin stabilization in vivo. In certain embodiments, the acylated analogue can include several linking moieties in linear, branched or cyclic manner. In certain embodiments, either one or a series of amino acids is used as a linker to a terminal fatty acid. In one non-limiting example, a non-natural amino acid is used, for example 8-amino-3,6-dioxaoctanoic acid (one or several in sequence) is covalently bound to the selected complement D inhibitor of the present invention through a functional group such as a carboxylic acid, sulfonyl, hydroxyl or amino group. See generally Lau, et al., "Discovery of the Once-Weekly Glucagon-Like Peptide-1 (GLP-1) Analogue Semiglutide", *J. Med. Chem.*, 2015, 58, 7370-7380. In this embodiment, the 8-amino-3,6-dioxaoctanoic acid or similar molecule is covalently linked to an aliphatic acid, including but not limited to a $C_{16}$, $C_{18}$, $C_{20}$ aliphatic acid, or a dicarboxylic acid, including but not limited to a $C_8$, $C_{10}$, $C_{12}$, $C_{14}$, $C_{16}$, $C_{18}$ or $C_{20}$ diacid. One or more amino acids can also be used in the selected configuration to add length or functionality. More generally, nonlimiting embodiments include the use of a divalent linker moiety such as a dicarboxylic acid, amino acid, diamine, hydroxycarboxylic acid, hydroxyamine, di-hydroxy compound, or other compound that has at least two functional groups that can link the parent molecule with another linking moiety, and which may be albumin stabilized in vivo. In some embodiments, 2, 3, 4 or 5 linking moieties are covalently bound in sequence, branched or cyclic fashion to the parent compound. In some embodiments, an $R^{301}$ acyl group is located in a position of the active compound that does not significantly adversely affect the complement D inhibition of the molecule, for example, as (i) a substituent on the $R^{32}$ group or (ii) a substituent on a C-ring, such as proline, or as a substituent on a substituent on the C-ring, such as on an $R^1$, $R^2$ or $R^3$ substituent, including for example, on a bridged moiety such as a fused cyclopropyl on the proline ring. In certain embodiments, the acyl group has an aliphatic or heteroaliphatic carbon range of $C_{12}$, $C_{14}$, $C_{16}$, $C_{18}$, $C_{20}$, $C_{22}$ or $C_{24}$.

In one embodiment, the disorder is associated with the alternative complement cascade pathway. In yet another embodiment, the disorder is associated with the complement classical pathway. In a further embodiment, the disorder is associated with the complement lectin pathway. Alternatively, the active compound or its salt or prodrug may act through a different mechanism of action than the complement cascade, or in particular as a Complement Factor D inhibitor, to treat the disorder described herein.

In one embodiment, a method for the treatment of C3 glomerulonephritis (C3G) is provided that includes the administration of an effective amount of a compound to a host of Formula I, Formula II, Formula III, or Formula IV or a pharmaceutically acceptable salt, prodrug, isotopic analog, or isolated isomer thereof, optionally in a pharmaceutically acceptable composition. In one embodiment, a method for the treatment of paroxysmal nocturnal hemoglobinuria (PNH) is provided that includes the administration of an effective amount of a compound to a host of Formula I, Formula II, Formula III, or Formula IV or a pharmaceutically acceptable salt, prodrug, isotopic analog, or isolated isomer thereof, optionally in a pharmaceutically acceptable composition. In another embodiment, a method for the treatment of wet or dry age-related macular degeneration (AMD) in a host is provided that includes the administration of an effective amount of a compound of Formula I, Formula II, Formula III, or Formula IV, or a pharmaceutically acceptable salt, prodrug, isotopic analog, or isolated isomer thereof, optionally in a pharmaceutically acceptable composition. In another embodiment, a method for the treatment of rheumatoid arthritis in a host is provided that includes the administration of an effective amount of a compound of Formula I, Formula II, Formula III, or Formula IV or a pharmaceutically acceptable salt, prodrug, isotopic analog, or isolated isomer thereof, optionally in a pharmaceutically acceptable composition. In another embodiment, a method for the treatment of multiple sclerosis in a host is provided that includes the administration of an effective amount of a compound of Formula I, Formula II, Formula III, or Formula IV or a pharmaceutically acceptable salt, prodrug, isotopic analog, or isolated isomer thereof, optionally in a pharmaceutically acceptable composition.

In other embodiments, an active compound or its salt or prodrug as described herein can be used to treat fatty liver and conditions stemming from fatty liver, nonalcoholic steatohepatitis (NASH), liver inflammation, cirrhosis, and liver failure, dermatomyocitis, or amyotrophic lateral sclerosis.

The active compound or its pharmaceutically acceptable salt, prodrug, isotopic analog, or isolated isomer thereof, optionally in a pharmaceutically acceptable composition, as disclosed herein is also useful for administration in combination (in the same or a different dosage form) or alternation with a second pharmaceutical agent for use in ameliorating or reducing a side effect of the second pharmaceutical agent. For example, in one embodiment, the active compound may be used in combination with an adoptive cell transfer therapy to reduce an inflammatory response associated with such therapy, for example, a cytokine mediated response such as cytokine response syndrome. In one embodiment, the adoptive cell transfer therapy is a chimeric antigen receptor T-Cell (CAR T) or a dendritic cell used to treat a hematologic or solid tumor, for example, a B-cell related hematologic cancer. In one embodiment, the hematologic or solid tumor is acute lymphoblastic leukemia (ALL), acute myeloid leukemia (AML), non-Hodgkin's lymphoma, chronic lymphocytic leukemia (CLL), pancreatic cancer, glioblastoma, or a cancer that expresses CD19. In one embodiment, the associated inflammatory response is a cytokine mediated response.

Another embodiment is provided that includes the administration of an effective amount of an active compound or a pharmaceutically acceptable salt, prodrug, isotopic analog, or isolated isomer thereof, optionally in a pharmaceutically acceptable composition to a host to treat an ocular, pulmonary, gastrointestinal, or other disorder that can benefit from topical or local delivery.

Any of the compounds described herein (e.g. Formula I, Formula II, Formula III, or Formula IV) can be administered to the eye in any desired form of administration, including via intravitreal, intrastromal, intracameral, sub-tenon, sub-retinal, retro-bulbar, peribulbar, suprachorodial, choroidal, subchoroidal, conjunctival, subconjunctival, episcleral, posterior juxtascleralscleral, circumcorneal, and tear duct injections, or through a mucus, mucin, or a mucosal barrier, in an immediate or controlled release fashion. In certain embodiments, the active compound includes a lipophilic group, such as a lipophilic acyl group, which is delivered to the eye in a polymeric drug delivery system such as polylactic acid, polylactide-co-glycolide, polyglycolide or other erodible polymer, or a combination thereof, or in another type of lipophilic material for ocular delivery. In some embodiments, the lipophilic active molecule is more soluble in the polymeric or other form of delivery system than in ocular fluid.

In other embodiments of the invention, an active compound provided herein can be used to treat or prevent a disorder in a host mediated by Complement Factor D, or by an excessive or detrimental amount of the complement-C3 amplification loop of the complement pathway. As examples, the invention includes methods to treat or prevent complement associated disorders that are induced by antibody-antigen interactions, a component of an immune or autoimmune disorder or by ischemic injury. The invention also provides methods to decrease inflammation or an immune response, including an autoimmune response, where mediated or affected by factor D.

In another embodiment, a method is provided for treating a host, typically a human, with a disorder mediated by the complement system, that includes administration of a prophylactic antibiotic or vaccine to reduce the possibility of a bacterial infection during the treatment using one of the compounds described herein. In certain embodiments, the host, typically a human, is given a prophylactic vaccine prior to, during or after treatment with one of the compounds described herein. In certain embodiments, the host, typically a human, is given a prophylactic antibiotic prior to, during or after treatment with one of the compounds described herein. In some embodiments, the infection is a meningococcal infection (e.g., septicemia and/or meningitis), an *Aspergillus* infection, or an infection due to an encapsulated organism, for example, *Streptococcus pneumoniae* or *Haemophilus* influenza type b (Hib), especially in children. In other embodiments, the vaccine or antibiotic is administered to the patient after contracting an infection due to, or concommitent with inhibition of the complement system.

The disclosure provides a compound of Formula I, Formula II, or Formula III:

(I)

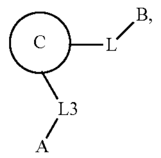

(II)

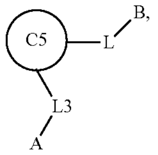

or (III)

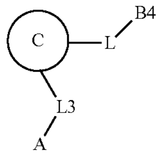

or a pharmaceutically acceptable salt, isotopic analog, prodrug, N-oxide, or isolated isomer thereof optionally in pharmaceutically acceptable carrier;

wherein:

A is selected from A1, A2, and A3;

B is selected from B1, B2, and B3;

B4 is separately defined below;

C is selected from C1, C2, C3, and C4;

C5 is separately defined below;

L is selected from L1 and L2;

L3 is —C(O)—, —C(S)—, —P(O)OH—, —S(O)—, $—S(O)_2—$, or $—C(R^{52})_2—$;

and wherein for compounds of Formula I, A is A3, B is B3, or C is C4;

C1 is

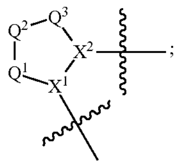

$Q^1$ is $N(R^1)$, $C(R^1R^{1'})$, $C(R^1R^{1'})C(R^1R^{1'})$, $C(R^1R^{1'})C(R^1R^{1'})C(R^1R^{1'})$, S or O;

$Q^2$ is $C(R^2R^{2'})$, $C(R^2R^{2'})C(R^2R^{2'})$, $C(R^2R^{2'})C(R^2R^{2'})C(R^2R^{2'})$, $N(R^2)$, S, O, or $C(R^2R^{2'})O$;

$Q^3$ is $N(R^3)$, S, O, $C(R^3R^{3'})$, $C(R^3R^{3'})C(R^3R^{3'})$, or $C(R^3R^{3'})C(R^3R^{3'})C(R^3R^{3'})$;

$X^1$ and $X^2$ are independently N, CH, or CZ;

or $X^1$ and $X^2$ together are C═C;

wherein $X^1$ is directly bound to L3 and $X^2$ is directly bound to L;

wherein $Q^1$, $Q^2$, $Q^3$, $X^1$, and $X^2$ are selected such that a stable compound results;

Z is F, Cl, $NH_2$, $CH_3$, $CH_2D$, $CHD_2$, or $CD_3$;

$R^1$, $R^{1'}$, $R^2$, $R^{2'}$, $R^3$, and $R^{3'}$ are independently selected at each occurrence, as appropriate, and only where a stable compound results, from hydrogen, $R^{201}$, $R^{301}$, halogen (and specifically fluoro, chloro, bromo), hydroxyl, nitro, cyano, amino, alkyl including $C_1$-$C_6$alkyl; alkenyl including $C_2$-$C_6$alkenyl; alkynyl including $C_2$-$C_6$alkynyl; alkoxy, including $C_1$-$C_6$alkoxy; alkanoyl including $C_2$-$C_6$alkanoyl; thioalkyl, including $C_1$-$C_6$alkylthio; hydroxy$C_1$-$C_6$alkyl; amino$C_1$-$C_6$alkyl; —$C_0$-$C_4$alkyl$NR^9R^{10}$; —C(O)$OR^9$; —OR', —NR'R'', —OC(O)$R^9$; —$NR^9$C(O)$R^{10}$; —C(O)$NR^9R^{10}$; —OC(O)$NR^9R^{10}$; —$NR^9$C(O)$OR^{10}$, haloalkyl including $C_1$-$C_6$haloalkyl, and $C_1$-$C_6$haloalkoxy;

or in an alternative embodiment, $R^1$, $R^{1'}$, $R^2$, $R^{2'}$, $R^3$, or $R^{3'}$ is $R^{202}$;

or $R^1$ and $R^{1'}$ are taken together to form a 3- to 6-membered carbocyclic spiro ring or a 3- to 6-membered heterocyclic spiro ring containing 1 or 2 heteroatoms independently selected from N, O, or S;

or $R^3$ and $R^{3'}$ are taken together to form a 3- to 6-membered carbocyclic spiro ring or a 3- to 6-membered heterocyclic spiro ring containing 1 or 2 heteroatoms independently selected from N, O, or S;

or $R^2$ and $R^{2'}$ are taken together to form a 3- to 6-membered carbocyclic spiro ring or a 3- to 6-membered heterocyclic spiro ring;

wherein, each of the above spiro rings may be optionally substituted with 1 or more substituents independently selected from $R^{201}$, halogen (and in particular F), hydroxyl, cyano, —COOH; alkyl, including $C_1$-$C_4$alkyl (including in particular methyl); alkenyl, including $C_2$-$C_4$alkenyl; alkynyl, including $C_2$-$C_4$alkynyl; alkoxy including $C_1$-$C_6$alkoxy; alkanoyl, including $C_2$-$C_4$alkanoyl; hydroxy$C_1$-$C_4$alkyl, (mono- and di-alkylamino)$C_1$-$C_4$alkyl, —$C_0$-$C_4$alkyl($C_3$-$C_7$cycloalkyl), —O-alkyl($C_3$-$C_7$cycloalkyl), haloalkyl including $C_1$-$C_6$haloalkyl, and haloalkoxy including $C_1$-$C_6$haloalkoxy;

or $R^1$ and $R^2$ are taken together to form a 3-membered carbocyclic ring, a 4- to 6-membered carbocyclic or aryl ring, or a 4- to 6-membered heterocyclic or heteroaryl ring containing 1 or 2 heteroatoms independently selected from N, O, and S;

or $R^2$ and $R^3$, are taken together to form a 3- to 6-membered carbocyclic or aryl ring or a 3- to 6-membered heterocyclic or heteroaryl ring;

wherein each of which fused $R^1$ and $R^2$ or $R^2$ and $R^3$ rings or generally $R^1$, $R^2$, $R^3$, $R^{1'}$, $R^{2'}$, or $R^{3'}$, are optionally substituted with 1 or more substituents independently selected from $R^{201}$, halogen (and in particular F), hydroxyl, cyano, —COOH; alkyl, including $C_1$-$C_4$alkyl (including in particular methyl); alkenyl, including $C_2$-$C_4$alkenyl; alkynyl, including $C_2$-$C_4$alkynyl; alkoxy, including $C_1$-$C_4$alkoxy; alkanoyl, including $C_2$-$C_4$alkanoyl, hydroxy$C_1$-$C_4$alkyl, (mono- and di-alkylamino)$C_0$-$C_4$alkyl; alkyl($C_3$-$C_7$cycloalkyl), including —$C_1$-$C_4$alkyl($C_3$-$C_7$cycloalkyl); —O—($C_3$-$C_7$cycloalkyl), haloalkyl including $C_1$-$C_6$haloalkyl, and haloalkoxy including $C_1$-$C_6$haloalkoxy;

or $R^1$ and $R^{1'}$ are taken together to form a carbonyl group;

or $R^2$ and $R^{2'}$ are taken together to form a carbonyl group;

or $R^3$ and $R^{3'}$ are taken together to form a carbonyl group;

or $R^1$ and $R^2$ are taken together to form a carbon-carbon double bond;

or $R^2$ and $R^3$ are taken together to form a carbon-carbon double bond;

R and R' are independently selected from H, $R^{201}$, alkyl, cycloalkyl, cycloalkylalkyl, heterocycle, heterocycloalkyl, aryl, arylalkyl, heteroaryl, and heteroarylalkyl;

or in an alternative embodiment, R, R', and R'' are independently selected from $R^{301}$, heteroalkyl, H, $R^{201}$, alkyl, cycloalkyl, cycloalkylalkyl, heterocycle, heterocycloalkyl, aryl, arylalkyl, heteroaryl, and heteroarylalkyl, and heteroaliphatic;

$R^9$ and $R^{10}$ are independently selected from hydrogen, alkyl including $C_1$-$C_6$alkyl, ($C_3$-$C_7$cycloalkyl)$C_0$-$C_4$alkyl, —$C_0$-$C_4$alkyl($C_3$-$C_7$cycloalkyl), and —O—$C_0$-$C_4$alkyl($C_3$-$C_7$cycloalkyl);

C2 is selected from:

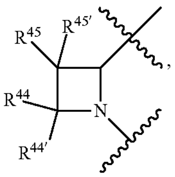,
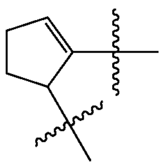,
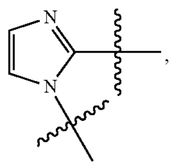,
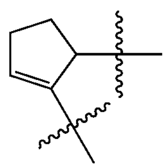
and
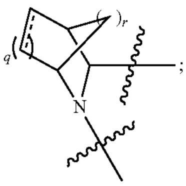;

q is 0, 1, 2 or 3;

r is 1, 2 or 3;

$R^{44}$, $R^{44'}$, $R^{45}$, $R^{45'}$ are independently selected at each occurrence, as appropriate, and only where a stable compound results, from hydrogen, $R^{201}$, halogen (and specifically fluoro, chloro, bromo), hydroxyl, nitro, cyano, amino, alkyl, including $C_1$-$C_6$alkyl; alkenyl, including $C_2$-$C_6$alkenyl; alkynyl, including $C_2$-$C_6$alkynyl; alkoxy, including $C_1$-$C_6$alkoxy; alkanoyl, including $C_2$-$C_6$alkanoyl; thioalkyl, including $C_1$-$C_6$alkylthio; hydroxy$C_1$-$C_6$alkyl; amino$C_1$-$C_6$alkyl; —$C_0$-$C_4$alkyl$NR^9R^{10}$; —C(O)$OR^9$; —OC(O)$R^9$; —$NR^9$C(O)$R^{10}$; —C(O)$NR^9R^{10}$; —OC(O)$NR^9R^{10}$; —$NR^9$C(O)$OR^{10}$, haloalkyl including $C_1$-$C_6$haloalkyl, and $C_1$-$C_6$haloalkoxy;

or $R^{44}$ and $R^{44'}$, $R^{45}$ and $R^{45'}$, or two $R^{47}$ groups are taken together to form a carbonyl group;

or $R^{44}$ and $R^{44'}$, $R^{45}$ and $R^{45'}$, or $R^{46}$ and $R^{46'}$ are taken together to form an optionally substituted 3- to 6-membered carbocyclic spiro ring or a 3- to 6-membered heterocyclic spiro ring containing 1 or 2 heteroatoms independently selected from N, O, or S;

wherein, each of the above spiro rings may be optionally substituted with 1 or more substituents independently selected from $R^{201}$, halogen (and in particular F), hydroxyl, cyano, —COOH; alkyl, including $C_1$-$C_4$alkyl (including in particular methyl); alkenyl, including $C_2$-$C_4$alkenyl; alkynyl, including $C_2$-$C_4$alkynyl; alkoxy, including alkoxy including $C_1$-$C_6$alkoxy; alkanoyl, including $C_2$-$C_4$alkanoyl; hydroxy$C_1$-$C_4$alkyl, (mono- and di-alkylamino)$C_1$-$C_4$alkyl, —$C_0$-$C_4$alkyl($C_3$-$C_7$cycloalkyl), —O-alkyl($C_3$-$C_7$cycloalkyl), haloalkyl including $C_1$-$C_6$haloalkyl, and haloalkoxy including $C_1$-$C_6$haloalkoxy;

or $R^{44}$ and $R^{45}$ or $R^{44'}$ and $R^{45'}$ are taken together to form a 4- to 6-membered carbocyclic or aryl ring or a 4- to 6-membered heterocyclic or heteroaryl ring; each of which ring may be optionally substituted with 1 or more substituents;

each of which fused rings or generally $R^{44}$, $R^{44'}$, $R^{45}$, or $R^{45'}$ are optionally substituted with 1 or more substituents independently selected from $R^{201}$, halogen (and in particular F), hydroxyl, cyano, —COOH; alkyl, including $C_1$-$C_4$alkyl (including in particular methyl); alkenyl, including $C_2$-$C_4$alkenyl; alkynyl, including $C_2$-$C_4$alkynyl; alkoxy, including $C_1$-$C_4$alkoxy; alkanoyl, including $C_2$-$C_4$alkanoyl, hydroxy$C_1$-$C_4$alkyl, (mono- and di-alkylamino)$C_0$-$C_4$alkyl; alkyl($C_3$-$C_7$cycloalkyl), including —$C_1$-$C_4$alkyl($C_3$-$C_7$cycloalkyl); —O—($C_3$-$C_7$cycloalkyl), haloalkyl including $C_1$-$C_6$haloalkyl, and haloalkoxy including $C_1$-$C_6$haloalkoxy;

C3 is selected from:

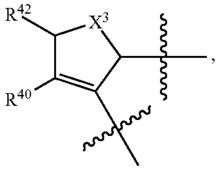,
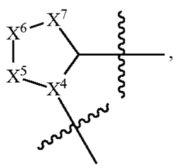,
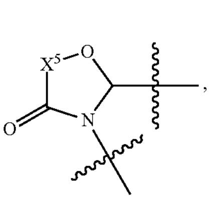,
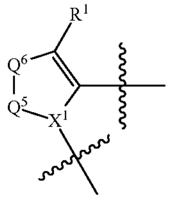,
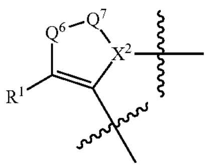,
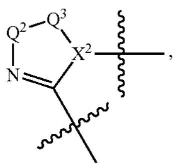,
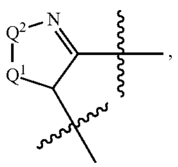,
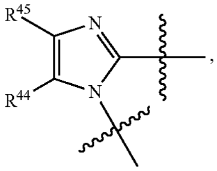,
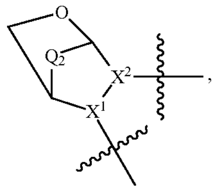,
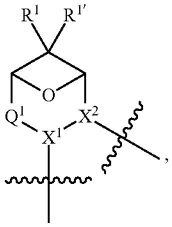,
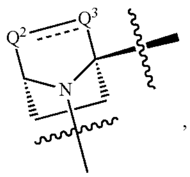,
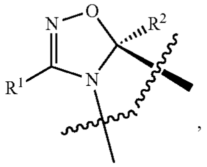, -continued

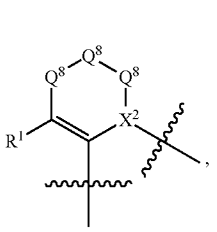,
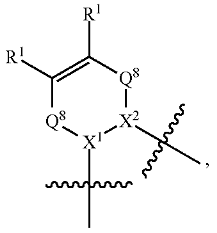,
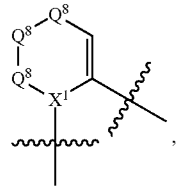,
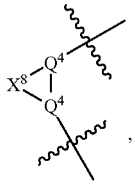,
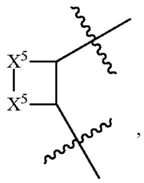,
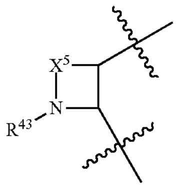,
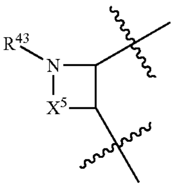,
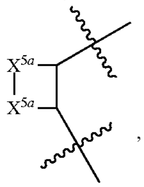,
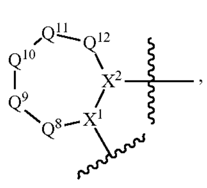,
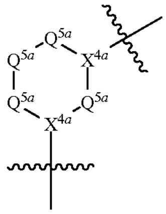
and
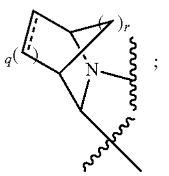;

$X^3$ is C($R^1R^{1'}$);
$X^4$ is N or CH;
$X^4$a is N, CH or CZ;
$X^5$ and $X^6$ are C($R^1R^{1'}$);
or $X^4$ and $X^5$ or $X^5$ and $X^6$ together are C═C;
$X^7$ is SO or $SO_2$;
$X^8$ is C($R^1R^{1'}$) or N($R^{43}$);
$X^5$a is C($R^1R^{1'}$) or O;
$Q^4$ is N or CH;
$Q^5$ is N($R^{47}$) or C($R^{46}R^{46'}$);
$Q^5$a is C($R^{47}R^{47}$), N($R^{47}$), O, S, SO, or $SO_2$;
$Q^6$ is N($R^{47}$), C($R^{46}R^{46'}$), S, or O;
$Q^7$ is C($R^{46}R^{46'}$), S or N($R^{47}$);
$Q^8$, $Q^9$, $Q^{10}$, $Q^{11}$ and $Q^{12}$ are each independently C($R^2R^{2'}$), S, SO, $SO_2$, O, N($R^2$), B($R^{50}$), or Si($R^{49}$)$_2$;

$R^{40}$ is hydrogen, alkyl, cycloalkyl, cycloalkylalkyl, heterocycle, heterocycloalkyl, aryl, arylalkyl, heteroaryl, or heteroarylalkyl wherein each group can be optionally substituted;

$R^{42}$ is halo, hydroxy, alkoxy including $C_1$-$C_6$alkoxy, haloalkoxy including $C_1$-$C_6$haloalkoxy, —SH, or —S($C_1$-$C_6$alkyl);

$R^{43}$ is hydrogen, acyl, alkyl, cycloalkyl, cycloalkylalkyl, heterocycle, heterocycloalkyl, aryl, arylalkyl, heteroaryl, or heteroarylalkyl wherein each group can be optionally substituted;

$R^{46}$ and $R^{46'}$ are independently hydrogen, alkyl, cycloalkyl, cycloalkylalkyl, heterocycle, heterocycloalkyl, aryl, arylalkyl, heteroaryl, or heteroarylalkyl wherein each group can be optionally substituted;

$R^{47}$ is hydrogen, acyl, alkyl, cycloalkyl, cycloalkylalkyl, heterocycle, heterocycloalkyl, aryl, arylalkyl, heteroaryl, or heteroarylalkyl wherein each group can be optionally substituted;

$R^{49}$ is halo, hydrogen, alkyl, cycloalkyl, cycloalkylalkyl, heterocycle, heterocycloalkyl, aryl, arylalkyl, heteroaryl, or heteroarylalkyl wherein each group can be optionally substituted or two $R^{49}$ groups are taken together to form a double bond that can be optionally substituted;

$R^{50}$ is hydroxy or $C_1$-$C_6$alkyoxy;

or $X^1$ and $Q^8$ or $Q^8$ and $Q^9$ or $Q^9$ and $Q^{10}$ or $Q^{10}$ and $Q^{11}$ or $Q^{11}$ and $Q^{12}$ or $Q^{12}$ and $X^2$ can form a carbon-carbon double bond;

or two $Q^{5a}$ groups or a $X^4$a and a $Q^{5a}$ group can form a carbon-carbon double bond; and where any of these groups may be further optionally substituted as that term is defined in the Terminology Section below, if desired to achieve the target effect, results in a stable compound that makes chemical sense to the skilled artisan, and the group is not redundant (i.e., as known in the art, alkyl substituted with alkyl is redundant; however, for example, alkoxy substituted with alkoxy is not redundant);

or the central core moiety, C3, is a small mimetic of a beta-turn such as a benzodiazepine, a Friedinger lactam, a 2-oxo-1,3-oxazolidine-4-caroxylate or a β-D-glucose scaffold. See, De Marco, R. et al., "In-peptide synthesis of di-oxazolidinone and dehydroamino acid-oxazolidinone motifs as β-turn inducers", J. Org. Biomol. Chem., 2013, 11, 4316-4326, Hirschmann, R. F. et al., The β-D-Glucose Scaffold as a β-Turn Mimetic, Accounts Chem. Res., 2009, 42, 1511-1520 and Smith, A. B, et al., Accounts of Chem. Res., 2011, 44, 180-193. In another embodiment, the central core moiety, C, can comprise a reverse turn mimetic that can include, but is not limited to; a non-peptidic residue, a metal chelation based mimic, or a foldamer. See, Nair, R. V. et al., "Synthetic turn mimetics and hairpin nucleators: Quo Vadimus?", Chem. Comm., 2014, 50, 13874-13884. In some embodiments, the central core moiety, C, can comprise a conformationally constrained cyclic amino acid including but not limited to a (S)- or (R)-α-trifluoromethyl pyroglutamic acid derivative. See, Chaume, G. et al., "Concise access to enantiopure (S)- or (R)-α-trifluoromethyl pyroglutamic acids from ethyl trifluoropyruvate-base chiral CF3-oxazolidines (Fox)", J. Fluor. Chem., 2008, 129, 1104-1109 and Andre, C. et al., "(S)-ABOC: A Rigid Bicyclic β-Amino Acid as Turn Inducer", Org. Lett., 2012, 14, 960-963. In some embodiments, the central core moiety, C, can comprise a monomeric unit of a foldamer such as, but not limited to an oxazolidin-2-one. See, Tomasii, C., Angelicim G. and Castellucci, N., "Foldamers Based on Oxazolidin-2-ones", Eur. J. Org. Chem., 2011, 3648-3669;

C4 is selected from:

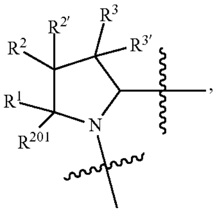,
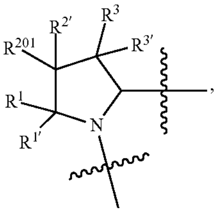,
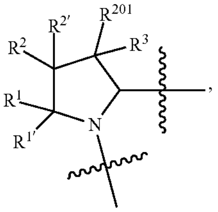,
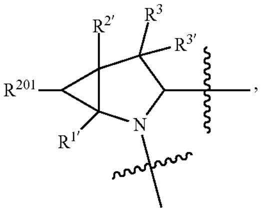, and

-continued

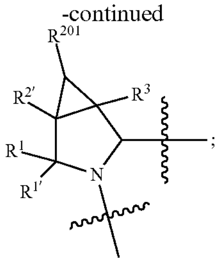;

or C4 is selected from:

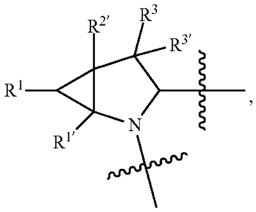,
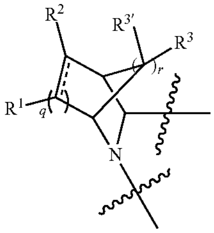, and
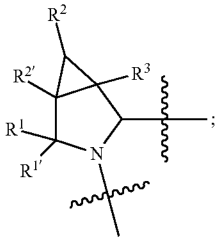;

or C4 is selected from:

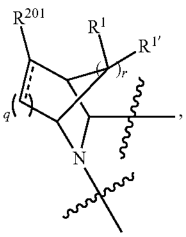,
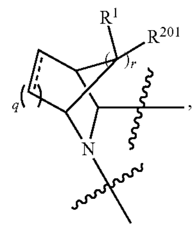, and
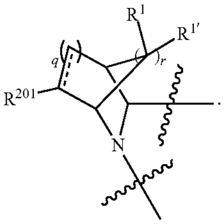.

C5 is selected from:

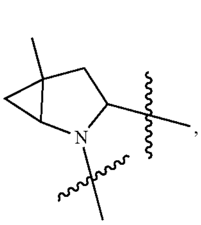,
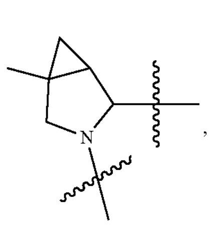,

-continued
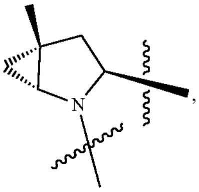
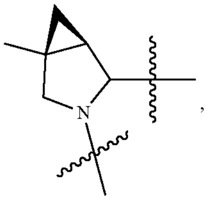
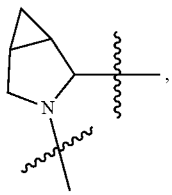
and
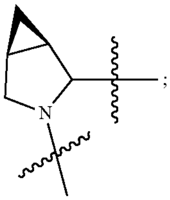
A1 is selected from:
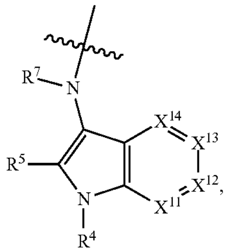
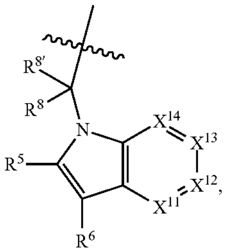
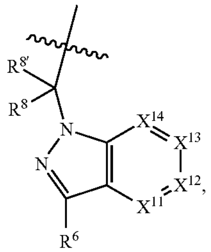
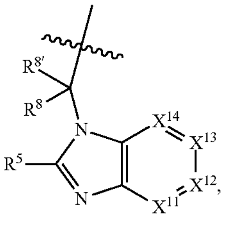
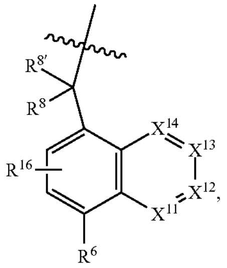
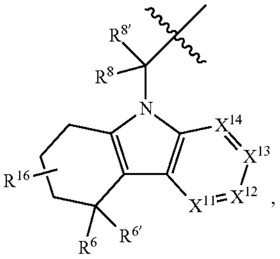
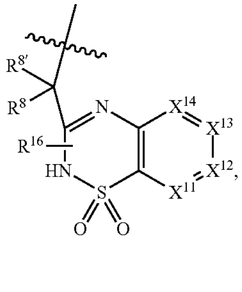
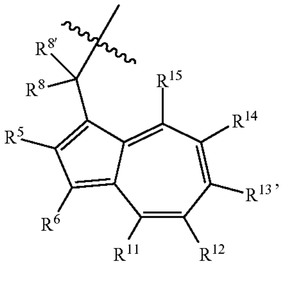
-continued
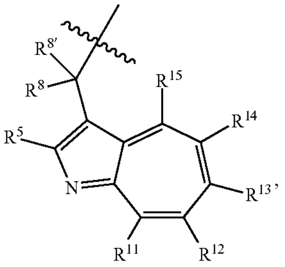
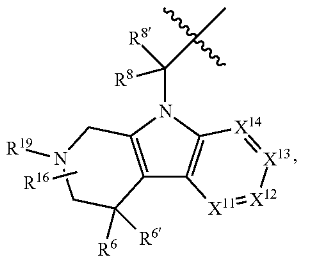
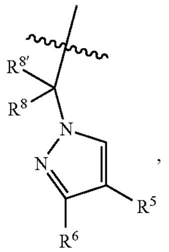
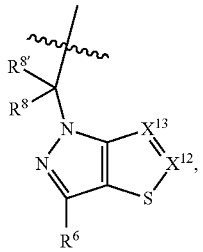
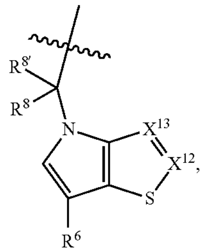
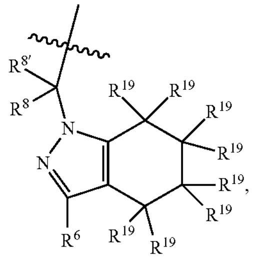
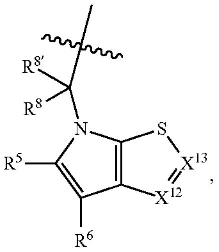
and
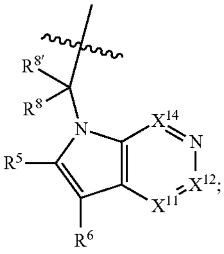
or A1 is selected from:
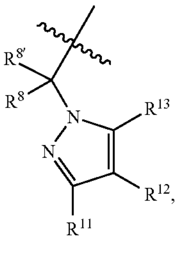
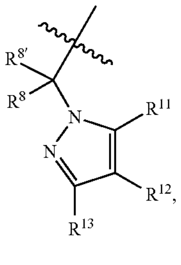
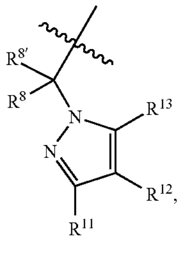

-continued
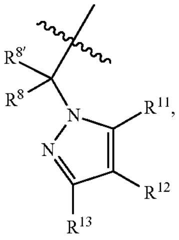
and
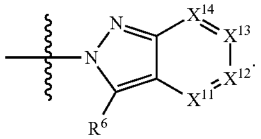
A2 is selected from:
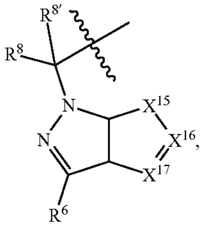
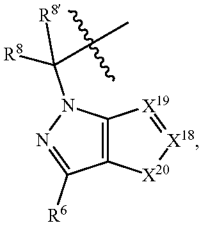
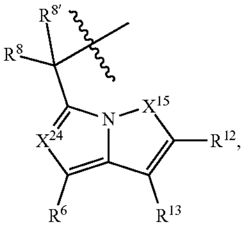
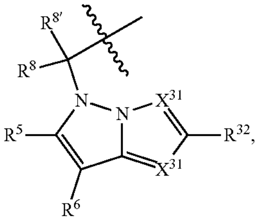
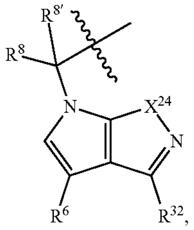
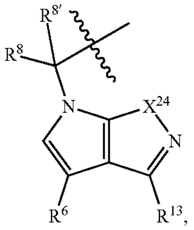
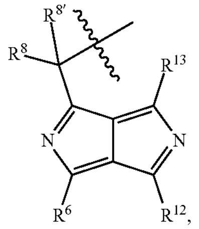
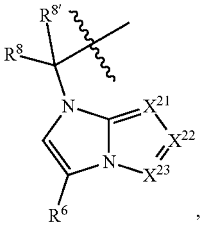
,
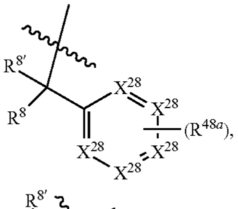
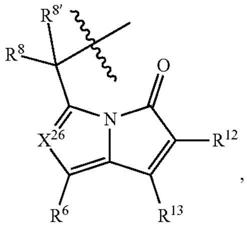
,
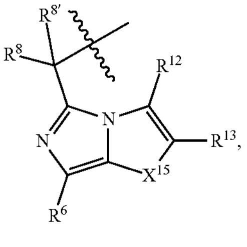
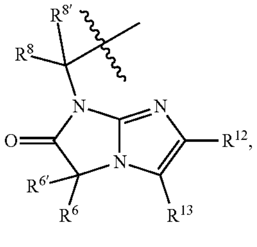
-continued
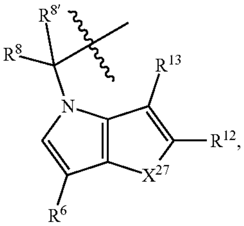
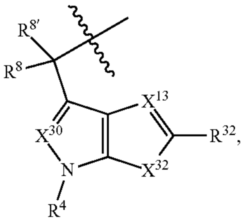
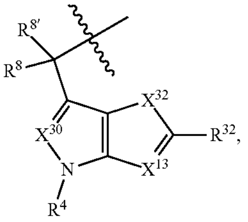
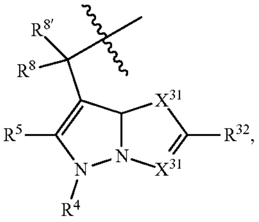
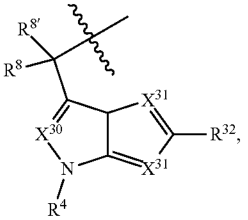
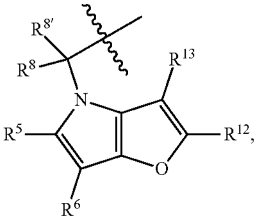
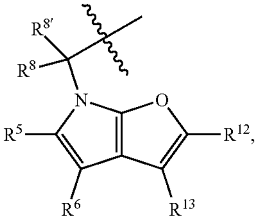
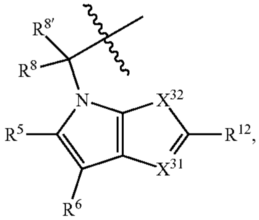
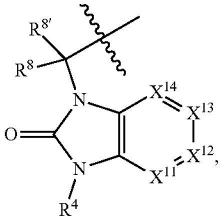
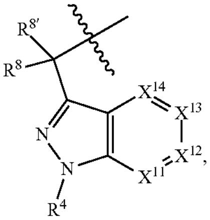
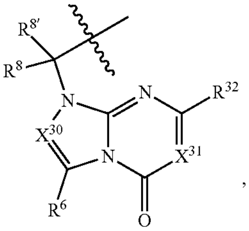
,
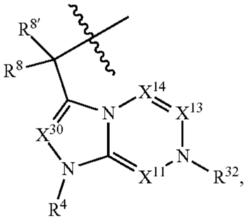
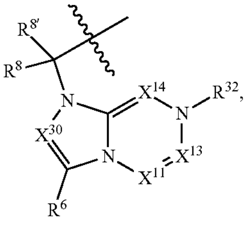
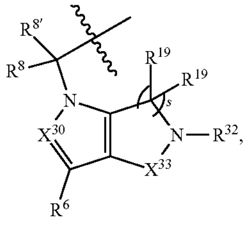

-continued
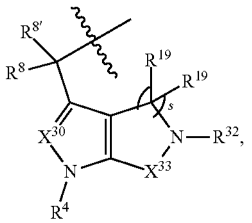
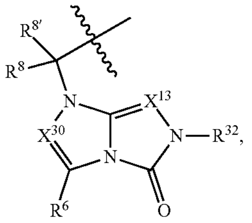
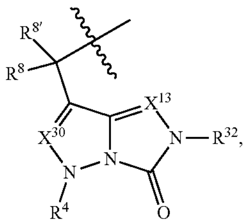
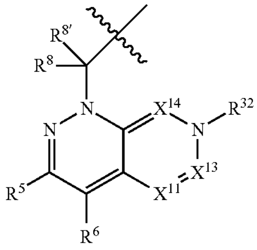
,
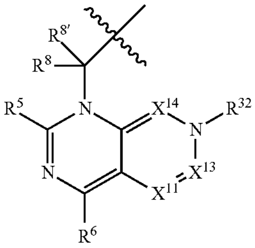
,
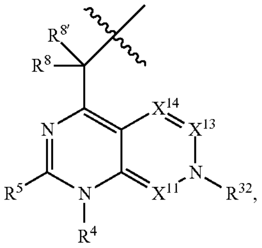
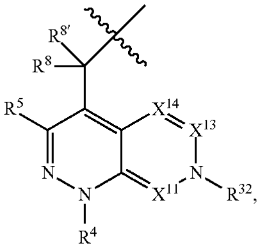
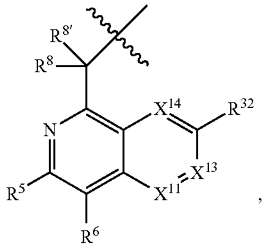
,
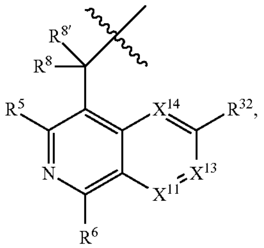
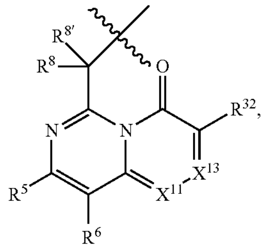
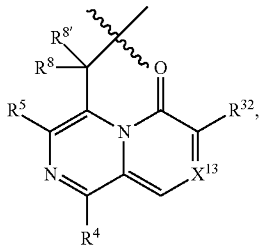
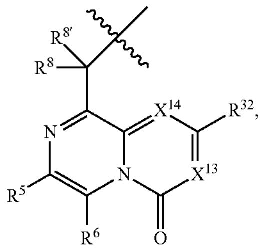
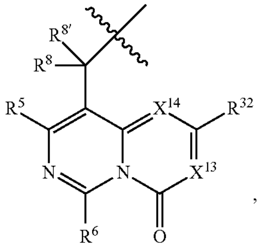
,
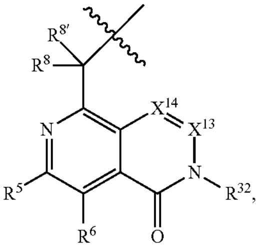
-continued
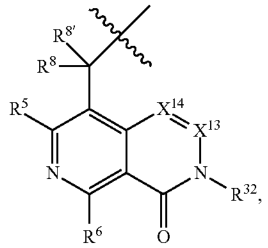
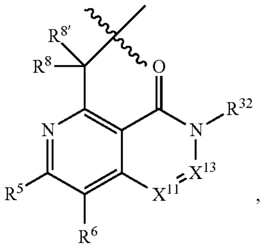
,
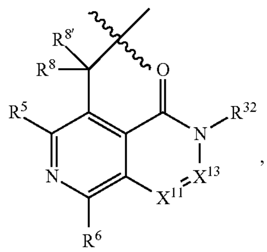
,
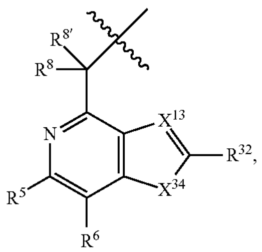
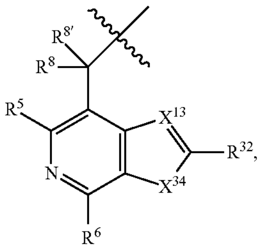
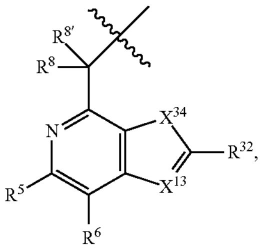
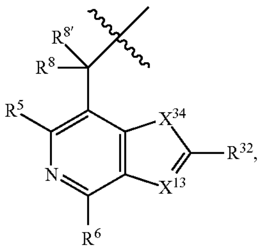
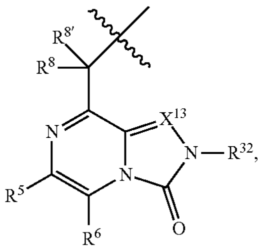
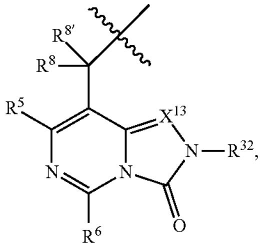
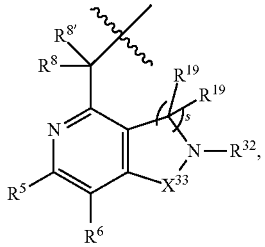
and
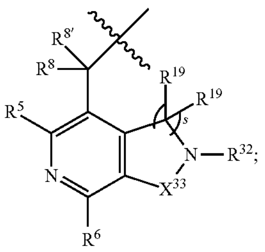

A3 is selected from:
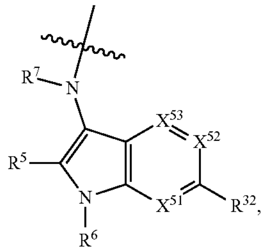
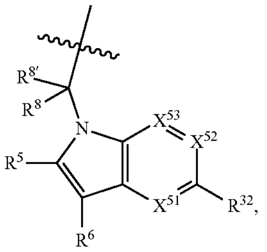
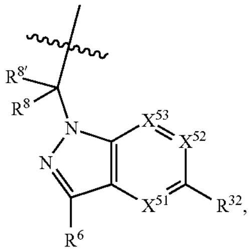
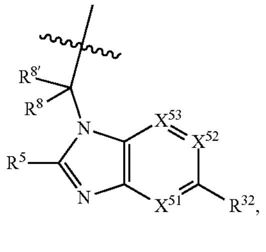
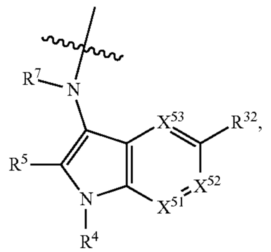
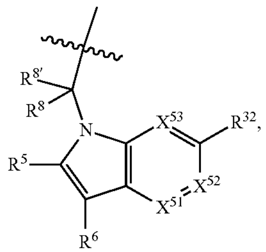
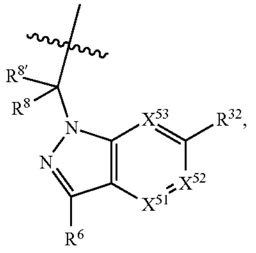
and
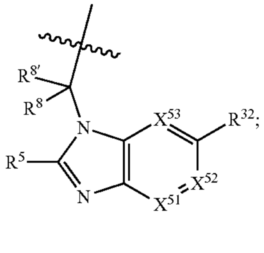
A3 is selected from:
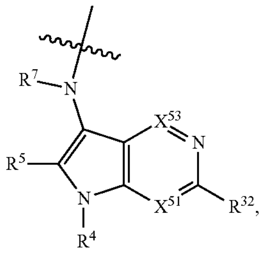
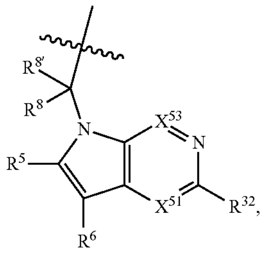
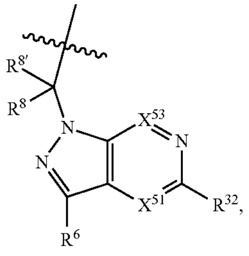
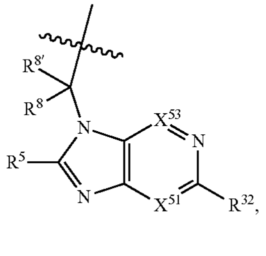
-continued
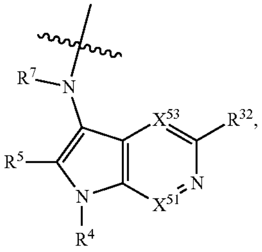
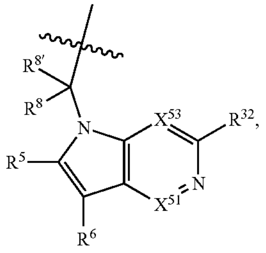
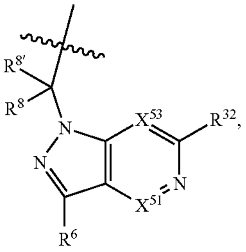
and
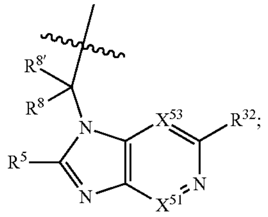
or A3 is selected from:
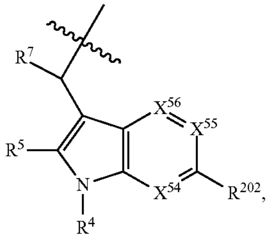
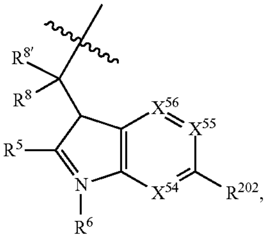
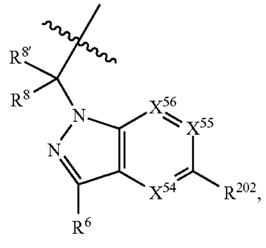
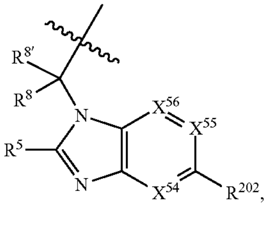
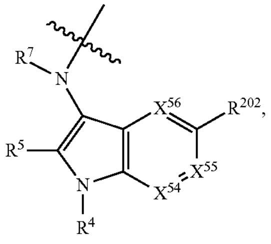
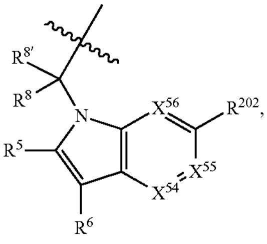

-continued
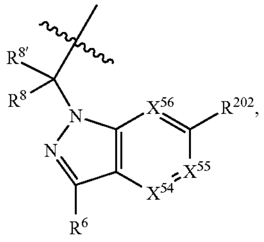
and
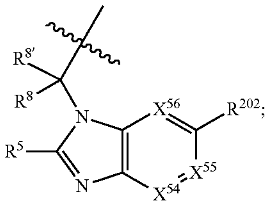
or A3 is selected from:
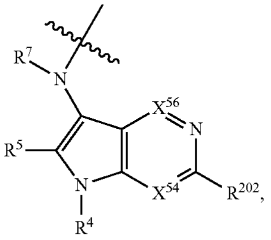
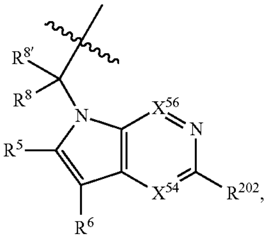
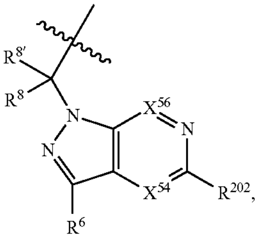
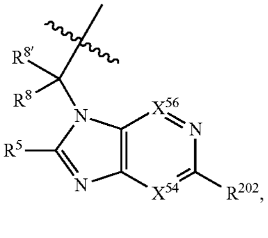
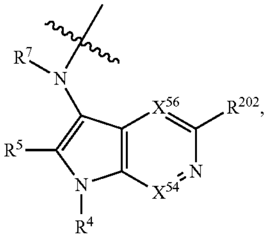
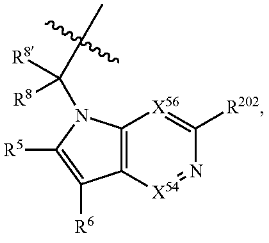
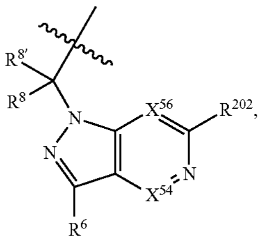
and
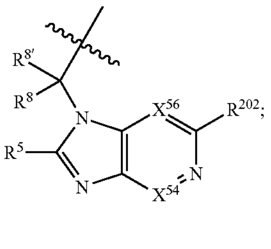
or A3 is selected from:
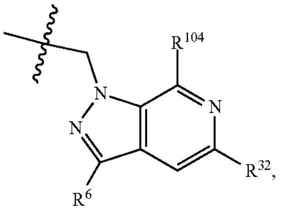
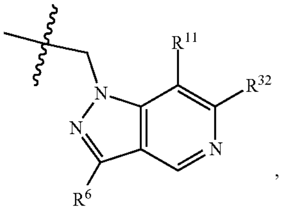
,
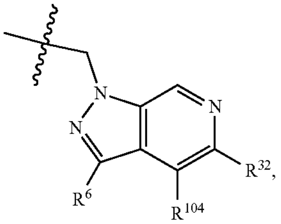
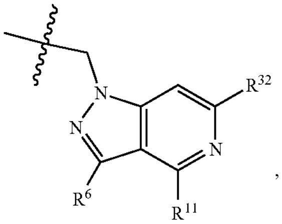
,
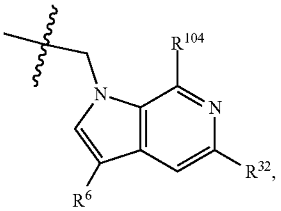
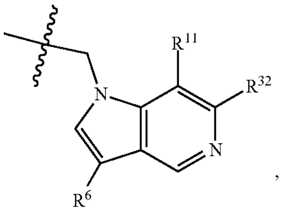
,
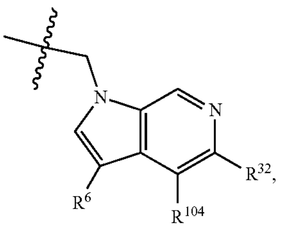
and
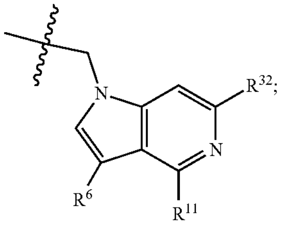
or A3 is selected from:
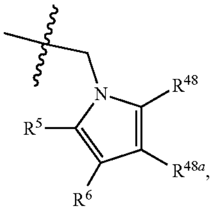
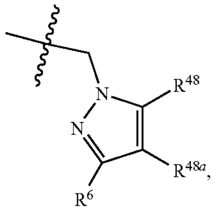
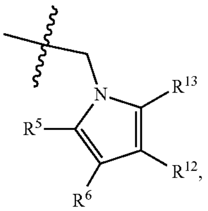
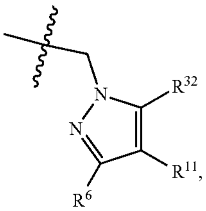
and -continued

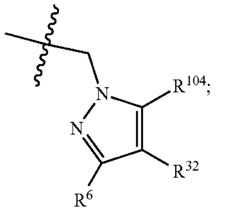

or A3 is selected from:

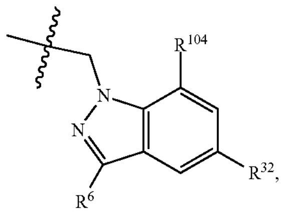

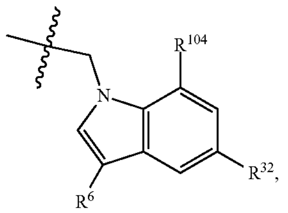

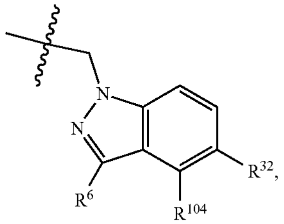

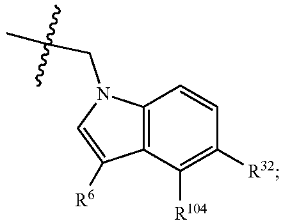

$X^{51}$, $X^{52}$, and $X^{53}$ are independently selected from N, $CR^{31}$, and $CR^{201}$;

wherein at least one of $X^{51}$, $X^{52}$, and $X^{53}$ is selected from $CR^{201}$;

$X^{54}$, $X^{55}$, and $X^{56}$ are independently selected from N, $CR^{31}$, and $CR^{201}$;

$R^{104}$ is selected from $R^{201}$, $C_1$-$C_4$ alkyl, $C_3$-$C_6$ cycloalkyl, $C_1$-$C_4$ haloalkyl, deuterium, —$CO_2H$, $CO_2R^9$, heteroaryl, F, Cl, Br, and cyano;

$R^{201}$ is selected from aminoalkyl-, alkylaminoalkyl-, heterocycloalkyl-, and hydroxyalkyl; -alkyl-O-alkyl including —$CH_2OCH_3$, -alkyl-S-alkyl, -alkyl-N(alkyl)-alkyl, -alkyl-NH-alkyl, -aliphatic-O-aliphatic, -aliphatic-S-aliphatic, -aliphatic-N(aliphatic)-aliphatic, -aliphatic-NH-aliphatic, -aliphatic-O-heterocycle, -aliphatic-S-heterocycle, -aliphatic-N(aliphatic)-heterocycle, -aliphatic-NH-heterocycle, -alkyl-NHC(O)haloalkyl, -alkyl-$NR^9$C(O)haloalkyl, -alkyl-C(O)NHhaloalkyl, -alkyl-C(O)$NR^9$haloalkyl, -alkyl-NHC(O)haloalkyl, -alkyl-$NR^9$C(O)aliphatic, -alkyl-C(O)NHaliphatic, -alkyl-$NR^9$C(O)aliphatic, -alkyl-NHC(O)aliphatic, -substituted alkyl-N($R^9$)-substituted alkyl, alkyl-heteroaryl, heteroaryl, heterocycle, alkyl-heterocycle, -alkyl-O-haloalkyl, —N(aliphatic)$_2$; and wherein each $R^{201}$ can be optionally substituted as defined in the Terminology section below, and wherein each $R^{201}$ can be optionally substituted with $R^{301}$, which can be directly linked to $R^{201}$ or can be linked to $R^{201}$ through an amino, hydroxyl, thio, carboxyl acid, phosphate, phosphonate or sulfonate linkage as desired and appropriate; and wherein $R^{201}$ can be optionally substituted with $R^{301}$, which can be directly linked to $R^{201}$ or can be linked to $R^{201}$ through an amino, hydroxyl, thio, carboxyl acid, phosphate, phosphonate or sulfonate linkage;

$R^{202}$ is $R^{32}$ with at least one $R^{201}$ substituent;

$R^{301}$ is selected from the following:

a. The residue of a fatty acid. Examples are short chain fatty acids with 3, 4, or 5 aliphatic carbons, medium-chain fatty acids with aliphatic tails of 6, 7, 8, 9, 10, 11 or 12 carbons, long chain fatty acids, which have aliphatic tails of 13, 14, 15, 16, 17, 18, 19, 20, 21 or 22 carbons, or a very long fatty acid, which has 22, 23, 24, 25, 26 27, or 28 or more aliphatic carbons. The aliphatic chain can be saturated, mono-unsaturated, di-unsaturated, tri-unsaturated, polyunsaturated, or alkynyl. Unsaturated fatty acids can be used in a cis or trans configuration, and include, but are not limited to oleic acid, ω6 fatty acid such as linoleic acid, ω3 fatty acid such as α-linolenic acid, docosahexaenoic acid, stearidonic acid, eicosapentaenoic acid, docosapentaenoic acid, eicosatetraenoic acid, myristoleic acid, palmitoleic acid, sapienic acid, elaidic acid, vaccenic acid, gadoleic acid, eicosenoic acid, nervonic acid, eicosadienoic acid, docasadienoic acid, linolenic acid, t-linolenic acid, pinolenic acid, eleosteric acid, β-eleostearic acid, mead acid, eicosatrienoic acid, linoleic acid, linoelaidic acid, α-linolenic acid, arachidonic acid, erucic acid and docosahexaenoic acid. Nonlimiting examples of saturated fatty acids that can be used to provide the prodrugs of the present invention are caprylic acid, capric acid, lauric acid, myristic acid, palmitic, stearic acid, arachidic acid, behenic acid, lignoceric acid and cerotic acid.

b. The residue of an amino acid that is naturally occurring or synthetic, and includes for example, α, β γ or δ amino acids. Naturally occurring amino acids include those found in proteins, e.g., glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In some embodiments, the amino acid is in the L-configuration. Alternatively, the amino acid can be used in the D-configuration or in a mixture of L- and D-. Alternatively, the amino acid can be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. Additional amino acids include selenocysteine, pyrrolysine, N-formylmethionine, γ-aminobutyric acid (GABA), δ-aminolevulinic acid, aminobenzoic acid (including 4-aminobenzoic acid), aminoisobutyric acid, dehydroalanine, cystathionine, lanthionine, djenkolic acid, diaminopimelic acid, norvaline, alloisoleucine, t-leucine, α-amino-heptanoic acid, pipecolic acid, α,β-diaminopropionic acid, α,γ-diaminobutyric acid, ornithine, glutamic acid, allothreonine, homocysteine, β-aminobutyric acid, α-aminoisobutyric acid, isovaline, sarcosine, N-ethylglycine, N-propylglycine, N-isopropyl glycine, N-methyl alanine, N-ethyl alanine, N-methyl-β-alanine, isoserine, norleucine, homoserine, O-methyl-homoserine, O-ethyl-homoserine, homonorleucine, carboxyglutamic acid, hydroxyproline, hypusine, pyroglutamic acid, and α-hydroxy-γ-aminobutyric acid.

c. The residue of a non-naturally occurring amino acid with an extended length between the amino group and the carboxylic acid, which can be used either alone or as a linker to another prodrug moiety. Examples include amino acids wherein the amino and carboxylic acid are separated by an aliphatic or heteroaliphatic moiety (nonlimiting example is 8-amino-3,6-dioxaoctanoic acid), for example an alkyl, alkenyl, alkynyl, ethylene glycol, propylene glycol, alkylene glycol, or the like, moiety, e.g., with 3, 4, 5, 6, 7, 8, 9, 10, 11 or 12 or more straight, branched or cyclic atoms or moieties (e.g., alkylene glycol moieties), as appropriate to provide the desired properties. In some embodiments, the amino acid has one or more internal amine, carbonyl, carboxy, oxo, thio, phosphate or phosphonate moieties in the heteroaliphatic chain.

d. The residue of one or a series of amino acids linked to a terminal fatty acid or to an endcap like hydrogen or alkyl. In one non-limiting example, 8-amino-3,6-dioxaoctanoic acid (one or several in sequence) is covalently bound to the selected complement D inhibitor of the present invention through a functional group such as a carboxylic acid, sulfonyl, hydroxyl or amino group. See generally Lau, et al., "Discovery of the Once-Weekly Glucagon-Like Peptide-1 (GLP-1) Analogue Semiglutide", *J. Med. Chem.,* 2015, 58, 7370-7380. The 8-amino-3,6-dioxaoctanoic acid is covalently linked to an aliphatic acid, including but not limited to a C16, C18, C20 aliphatic acid, or a dicarboxylic acid, including but not limited to a C8, C10, C12, C14, C16, C18 or C20 diacid. One or more amino acids can also be used in the selected configuration to add length or functionality.

$R^4$, $R^5$, and $R^6$ are selected from hydrogen, -JCHO, -JC(O)$NH_2$, -$JC_2$-$C_6$alkanoyl, -JC(O)NH($CH_3$), -J-COOH, -JP(O)($OR^9$)$_2$, -JOC(O)$R^9$, -JC(O)$OR^9$, -JC(O)N($CH_2CH_2R^9$)($R^{10}$), -$JNR^9$C(O)$R^{10}$, -$JSO_2NH_2$, -JS(O)$NH_2$, -JC($CH_2$)$_2$F, -JCH($CF_3$)$NH_2$, -JC(O)$C_0$-$C_2$alkyl($C_3$-$C_7$cycloalkyl), -$JNR^9$($C_2$-$C_6$alkanoyl), -$JNR^9$C(O)$NR^9R^{10}$, -$JSO_2$($C_1$-$C_6$alkyl), -$JSO_2$($C_1$-$C_6$haloalkyl), -$JSO_2NR^7R^7$, -JSO═NH($C_1$-$C_6$alkyl), -J-nitro, -J-halogen, -J-hydroxyl, -J-phenyl, a 5- to 6-membered heteroaryl, -J-cyano, -J-cyanoimino, -J-amino, -J-imino, —$C_1$-$C_6$alkyl, —$C_0$-$C_4$alkyl($C_3$-$C_7$heterocycloalkyl), —$C_0$-$C_4$alkyl($C_3$-$C_7$cycloalkyl),

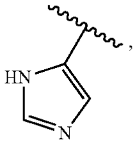,
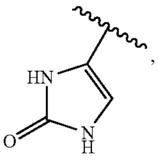,
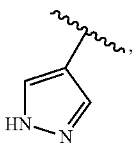,
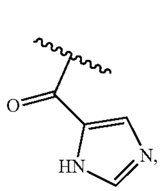
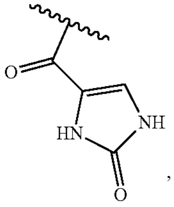,
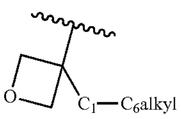
and
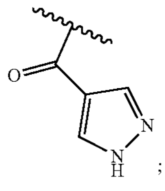;

each of which $R^4$, $R^5$ and $R^6$ other than hydrogen, nitro, halogen, cyano, cyanoimino, or —CHO, is optionally substituted with one or more of amino, imino, halogen, hydroxyl, cyano, cyanoimino, alkyl including $C_1$-$C_6$alkyl, alkoxy including $C_1$-$C_6$alkoxy, —$C_0$-$C_2$alkyl(mono- and di-$C_1$-$C_4$alkylamino), —$C_1$-$C_6$haloalkyl, and haloalkoxy including $C_1$-$C_6$haloalkoxy;

in an alternative embodiment $R^4$, $R^5$, or $R^6$ is a heterocycle substituted with an oxo group, for example

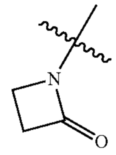;

$R^{4'}$ is selected from -JCHO, -$JCONH_2$, -$JCONR^9R^{10}$, $JC_2$-$C_6$alkanoyl, -$JSO_2NH_2$, -$JSO_2NR^{21}R^{22}$, -JC($CH_2$)$_2$F, -JCH($CF_3$)$NH_2$, -J-haloalkyl-$NH_2$, -J-haloalkyl-$NR^9R^{10}$, alkyl including $C_1$-$C_6$alkyl, —$C_0$-$C_4$alkyl($C_3$-$C_7$cycloalkyl), -JC(O)$C_0$-$C_2$alkyl($C_3$-$C_7$cycloalkyl), -$JNR^9$($C_2$-$C_6$alkanoyl), -$JNR^9$C(O)$NR^9R^{10}$,

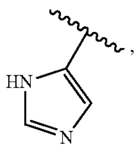,
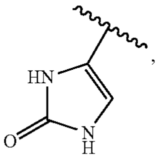,
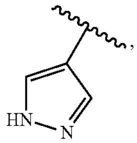,
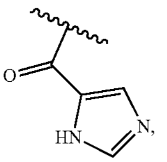
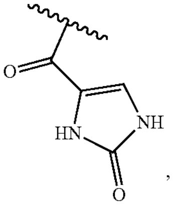,
and
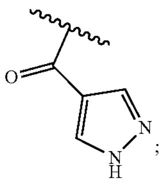;

each of which $R^{4'}$ other than —CHO, is optionally substituted with one or more of amino, imino, halogen, hydroxyl, cyano, cyanoimino, alkyl including $C_1$-$C_6$alkyl, alkoxy including $C_1$-$C_6$alkoxy, —$C_0$-$C_2$alkyl(mono- and di-$C_1$-$C_4$alkylamino), haloalkyl including $C_1$-$C_6$haloalkyl, and haloalkoxy including $C_1$-$C_6$haloalkoxy.

$R^{6'}$ is hydrogen, halogen, hydroxyl, $C_1$-$C_4$alkyl, —$C_0$-$C_4$alkyl($C_3$-$C_7$cycloalkyl), or $C_1$-$C_4$alkoxy;

or $R^6$ and $R^{6'}$ may be taken together to form an oxo, vinyl, or imino group;

$R^7$ is hydrogen, alkyl including $C_1$-$C_6$alkyl, or —$C_0$-$C_4$alkyl($C_3$-$C_7$cycloalkyl);

$R^8$ and $R^{8'}$ are selected from hydrogen, halogen, hydroxyl, alkyl including $C_1$-$C_6$alkyl, —$C_0$-$C_4$alkyl($C_3$-$C_7$cycloalkyl), alkoxy including $C_1$-$C_6$alkoxy, and ($C_1$-$C_4$alkylamino)$C_0$-$C_2$alkyl;

or $R^8$ and $R^{8'}$ are taken together to form an oxo group;

or $R^8$ and $R^{8'}$ are taken together with the carbon that they are bonded to form a 3-membered carbocyclic ring;

$R^{16}$ is independently selected from hydrogen, halogen, hydroxyl, nitro, cyano, —$C_1$-$C_6$alkyl, alkenyl including $C_2$-$C_6$alkenyl, alkanoyl including $C_2$-$C_6$alkanoyl, alkoxy including $C_1$-$C_6$alkoxy, —$C_0$-$C_4$alkyl(mono- and di-$C_1$-$C_6$alkylamino), —$C_0$-$C_4$alkyl($C_3$-$C_7$cycloalkyl), haloalkyl including $C_1$-$C_6$haloalkyl, and haloalkoxy including $C_1$-$C_6$haloalkoxy;

$R^{19}$ is hydrogen, alkyl including $C_1$-$C_6$alkyl, alkenyl including $C_2$-$C_6$alkenyl, alkanoyl including $C_2$-$C_6$alkanoyl, —$SO_2C_1$-$C_6$alkyl, (mono- and di-$C_1$-$C_6$alkylamino)$C_1$-$C_4$alkyl, —$C_0$-$C_4$alkyl($C_3$-$C_7$cycloalkyl), —$C_0$-$C_4$alkyl($C_3$-$C_7$heterocycloalkyl), —$C_0$-$C_4$alkyl(aryl), or $C_0$-$C_4$alkyl(heteroaryl), wherein each $R^{19}$ other than hydrogen is optionally substituted with one or more substituents independently selected from halogen, hydroxyl, amino, —COOH, and —C(O)O$C_1$-$C_4$alkyl;

$X^{11}$ is N or $CR^{11}$;

$X^{12}$ is N or $CR^{12}$;

$X^{13}$ is N or $CR^{13}$;

$X^{14}$ is N or $CR^{14}$;

wherein no more than 2 of $X^{11}$, $X^{12}$, $X^{13}$, and $X^{14}$ are N;

wherein at least one of $R^{11}$, $R^{12}$, $R^{13}$, and $R^{14}$ is $R^{32}$ and the others are $R^{31}$ or $R^{32}$;

in one embodiment $R^{12}$ and $R^{13}$ are both $R^{32}$;

$R^{31}$ is independently selected from hydrogen, $R^{48}$, halogen, hydroxyl, nitro, cyano, amino, —COOH, haloalkyl including $C_1$-$C_6$haloalkyl, haloalkoxy including $C_1$-$C_6$haloalkoxy, alkyl including $C_1$-$C_6$alkyl, —$C_0$-$C_4$alkyl ($C_3$-$C_7$cycloalkyl), alkenyl including $C_2$-$C_6$alkenyl, alkanoyl including $C_2$-$C_6$alkanoyl, alkoxy including $C_1$-$C_6$alkoxy, alkenyloxy including $C_2$-$C_6$alkenyloxy, —C(O)$OR^9$, thioalkyl including $C_1$-$C_6$thioalkyl, —$C_0$-$C_4$alkyl$NR^9R^{10}$, —C(O)$NR^9R^{10}$, —$SO_2R^9$, —$SO_2NR^9R^{10}$, —OC(O)$R^9$, and —C($NR^9$)$NR^9R^{10}$, each of which $R^{31}$ other than hydrogen, halogen, hydroxyl, nitro, cyano, haloalkyl including $C_1$-$C_6$haloalkyl, and $C_1$-$C_6$haloalkoxy is optionally substituted with one or more substituents independently selected from halogen, hydroxyl, nitro, cyano, amino, —COOH, —$CONR^9R^{10}$, haloalkyl including $C_1$-$C_6$haloalkyl, haloalkoxy including $C_1$-$C_6$haloalkoxy, phenyl, and 4- to 7-membered heterocycle containing 1, 2, or 3 heteroatoms independently selected from N, O, and S; each of which phenyl or 4- to 7-membered heterocycle is optionally substituted with one or more substituents independently selected from halogen, hydroxyl, nitro, cyano, alkyl including $C_1$-$C_6$alkyl, alkenyl including $C_2$-$C_6$alkenyl, alkanoyl including $C_2$-$C_6$alkanoyl, alkoxy including $C_1$-$C_6$alkoxy, (mono- and di-$C_1$-$C_6$alkylamino)$C_0$-$C_4$alkyl, alkyl including $C_1$-$C_6$alkyl ester, —$C_0$-$C_4$alkyl)($C_3$-$C_7$cycloalkyl), $C_1$-$C_6$haloalkyl, and haloalkoxy including $C_1$-$C_6$haloalkoxy;

$R^{32}$ is selected from aryl, heteroaryl; and heterocycle. wherein the aryl, heteroaryl, or heterocycle ring can be optionally substituted;

or $R^{32}$ is —$C_2$-$C_6$alkynyl$R^{30}$, and each $R^{32}$ can be optionally substituted with any appropriate group including $R^{201}$ examples of $R^{32}$ include, but are not limited to,

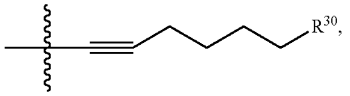

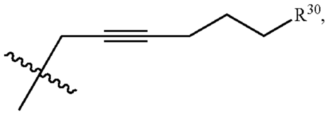

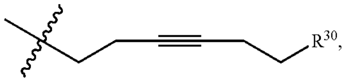

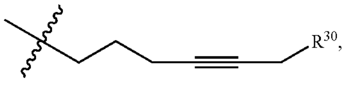

-continued

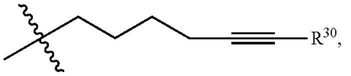

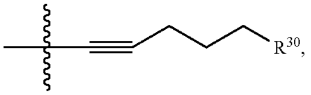

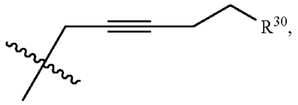

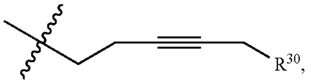

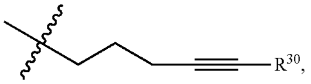

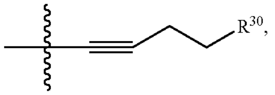

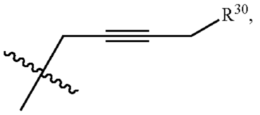

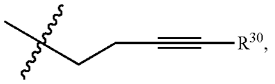

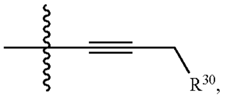

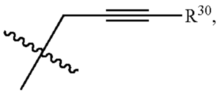

and

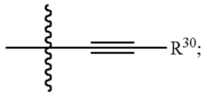

or $R^{32}$ is selected from C(O)$NR^{21}R^{71}$, —C(O)$NR^{24}R^{25}$, —C(O)$NR^9R^{71}$, —C(O)$NR^{21}SO_2R^{22}$, —$NR^9$C(O)$OR^{10}$, —$NR^9$C(O)$OR^{23}$, —$NR^9$C(O)$R^{21}$, —$NR^9$C(O)$NR^9R^{10}$, —$NR^9$C(O)$NR^{10}R^{23}$, and —$NR^9$C(O)$NR^{24}R^{25}$, each of which can be optionally can be optionally substituted with any appropriate group including $R^{201}$;

or $R^{32}$ is selected from $NR^{72}R^{73}$, $NR^9SO_2R^{73}$, and N($SO_2R^9$)$CH_2$C(O)$R^{74}$ each of which can be optionally can be optionally substituted with any appropriate group including $R^{201}$;

or $R^{32}$ is selected from —OC(O)$(CH_2)_{1-4}R^{21}$, —OC(O)$NR^{21}R^{22}$, —OC(O)$NR^{24}R^{25}$, —OC(O)($C_{1-6}$alkyl or $C_{3-6}$cycloalkyl)(aryl), —OC(O)($C_{1-6}$alkyl or $C_{3-6}$cycloalkyl)(heteroaryl), —OC(O)($C_{1-6}$alkyl or $C_{3-6}$cycloalkyl)(heterocycle), —OC(O)(heteroaryl), —OC(O)(aryl), —OC(O)($C_{1-6}$alkyl or $C_{3-6}$cycloalkyl), —OC(O)$NR^9(CH_2)_{1-4}$P(O)($OR^{21}$)($OR^{22}$), —C(O)($C_{1-6}$alkyl or $C_{3-6}$cycloalkyl)(aryl), —C(O)($C_{1-6}$alkyl or $C_{3-6}$cycloalkyl)(heteroaryl), —C(O)($C_{1-6}$alkyl or $C_{3-6}$cycloalkyl)(heterocycle), —C(O)(heteroaryl), —C(O)(heterocycle), —C(O)(aryl), —C(O)($C_{1-6}$alkyl or $C_{3-6}$cycloalkyl) and —C(O)($CH_2$)S(O)$R^{21}$, O-heteroalkyl, and O-heteroaliphatic each of which can be optionally can be optionally substituted with any appropriate group including $R^{201}$;

or $R^{32}$ is selected from —$O(CH_2)_{1-4}R^{23a}$, —$OC_2$-$C_4$alkenyl$R^{23a}$, —$OC_2$-$C_4$alkynyl$R^{23}$, —$O(CH_2)_{1-4}$paracyclophane, —$O(CH_2)_{1-4}$P(O)$R^{23b}R^{23b}$, —$O(CH_2)_{1-4}$S(O)

$NR^{21}R^{22}$, —$O(CH_2)_{1-4}S(O)NR^{24}R^{25}$, —$O(CH_2)_{1-4}SO_2NR^{21}R^{22}$, —$O(CH_2)_{1-4}SO_2NR^{24}R^{25}$, —O($C_3$-$C_7$ cycloalkyl), —O(aryl), —O(heteroaryl), —O residue of a carbohydrate, and —O(heterocycle) each of which can be optionally can be optionally substituted with any appropriate group including $R^{201}$;

or $R^{32}$ is $P(O)R^{75}R^{75}$, each of which can be optionally can be optionally substituted with any appropriate group including $R^{201}$;

or $R^{32}$ is selected from $R^{48}$, S(O)=$NHR^{21}$, S(O)=N($R^{21}$)$R^{21}$, $SF_5$, S=$NHR^{21}$, S=N($R^{21}$)$R^{21}$, JC($R^9$)=$NR^{21}$ and $SO_2OR^{21}$;

or in an alternative embodiment, $R^{32}$ is selected from —$O(CH_2)_{1-4}S(O)NR^{24}R^{30}$ and —$O(CH_2)_{1-4}SO_2NR^{24}R^{30}$;

or in an alternative embodiment, $R^{32}$ is hydrogen $R^{23a}$ is independently selected at each occurrence from ($C_3$-$C_7$cycloalkyl), and each $R^{23a}$ can be optionally substituted;

$R^{23b}$ is independently selected at each occurrence from hydroxyl, $C_1$-$C_6$alkoxy, $C_1$-$C_6$alkyl, ($C_3$-$C_7$cycloalkyl)$C_0$-$C_4$alkyl, (phenyl)$C_0$-$C_4$alkyl, —$O(CH_2)_{2-4}O(CH_2)_{8-18}$, —$OC(R^{23c})_2OC(O)OR^{23d}$, —$OC(R^{23c})_2OC(O)R^{23d}$, an N-linked amino acid or an N-linked amino acid ester, and each $R^{23b}$ can be optionally substituted;

$R^{23c}$ is independently selected at each occurrence from hydrogen, $C_1$-$C_8$alkyl, $C_2$-$C_8$alkenyl, $C_2$-$C_8$alkynyl, (aryl)$C_0$-$C_4$alkyl, (aryl)$C_2$-$C_8$alkenyl- or (aryl)$C_2$-$C_8$alkynyl; or two $R^{23c}$ groups can be taken together with the carbon that they are bonded to form a 3-6 membered heterocycloalkyl having 1, 2, or 3 heteroatoms independently selected from N, O, and S, or a 3-6 membered carbocyclic ring, and each $R^{23c}$ can be optionally substituted;

$R^{23d}$ is independently selected at each occurrence from $C_1$-$C_8$alkyl, $C_2$-$C_8$alkenyl, $C_2$-$C_8$alkynyl, (aryl)$C_0$-$C_4$alkyl, (aryl)$C_2$-$C_8$alkenyl or (aryl)$C_2$-$C_8$alkynyl, and each $R^{23d}$ can be optionally substituted;

$R^{71}$ is independently selected at each occurrence from hydroxyl, $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O)O$C_1$-$C_6$alkyl, —$C_1$-$C_4$alkylOC(O)$C_1$-$C_6$alkyl, —$C_1$-$C_4$alkylC(O)O$C_1$-$C_6$alkyl, (4- to 7-membered heterocycloalkyl)$C_0$-$C_4$alkyl having 1, 2, or 3 heteroatoms independently selected from N, O, and S, and (5- or 6-membered unsaturated or aromatic heterocycle) $C_0$-$C_4$alkyl having 1, 2, or 3 heteroatoms independently selected from N, O, and S, and each can be optionally substituted;

$R^{72}$ is independently selected at each occurrence from aryl, heteroaryl, heterocycle, alkynyl, hydroxyl, $C_1$-$C_6$alkoxy, ($C_3$-$C_7$cycloalkyl)$C_0$-$C_4$alkyl, (aryl)$C_0$-$C_4$alkyl, (heterocycle)$C_0$-$C_4$alkyl, (heteroaryl)$C_0$-$C_4$alkyl, —$C_1$-$C_4$alkylOC(O)O$C_1$-$C_6$alkyl, —$C_1$-$C_4$alkylOC(O)$C_1$-$C_6$alkyl, —$C_1$-$C_4$alkylC(O)O$C_1$-$C_6$alkyl, —S(O)(O)(alkyl), —S(O)(alkyl), —S(O)(O)(heteroalkyl), —S(O)(heteroalkyl), —S(O)(O)(aryl), —S(O)(aryl), —S(O)(O)(heteroaryl), —S(O)(heteroaryl), (and in some embodiments is a (4- to 7-membered heterocycloalkyl)$C_0$-$C_4$alkyl having 1, 2, or 3 heteroatoms independently selected from N, O, and S, and (5- or 6-membered saturated or partially unsaturated heterocycle)$C_0$-$C_4$alkyl having 1, 2, or 3 heteroatoms independently selected from N, O, and S), each of which groups can be optionally substituted;

$R^{73}$ is independently selected at each occurrence from hydrogen, hydroxyl, cyano, amino, $C_1$-$C_6$alkyl, $C_1$-$C_6$haloalkyl, $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O)O$C_1$-$C_6$alkyl, —$C_1$-$C_4$alkylOC(O)$C_1$-$C_6$alkyl, —$C_1$-$C_4$alkylC(O)O$C_1$-$C_6$alkyl, (4- to 7-membered heterocycloalkyl)$C_0$-$C_4$alkyl having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S, each of which groups can be optionally substituted;

$R^{74}$ is an optionally substituted proline, and in one embodiment the proline is substituted with a —C(O)$NR^9R^{10}$;

$R^{75}$ is independently selected at each occurrence from hydroxyl, $C_1$-$C_6$alkoxy, $C_1$-$C_6$haloalkoxy, $C_1$-$C_6$alkyl, ($C_3$-$C_7$cycloalkyl)$C_0$-$C_4$alkyl-, (aryl)$C_0$-$C_4$alkyl-, —O—$C_0$-$C_4$alkyl(aryl), —O—$C_0$-$C_4$alkyl($C_3$-$C_7$cycloalkyl), (4- to 7-membered heterocycloalkyl)$C_0$-$C_4$alkyl-O— having 1, 2, or 3 heteroatoms independently selected from N, O, and S; (5- or 6-membered unsaturated or aromatic heterocycle)$C_0$-$C_4$alkyl-O— having 1, 2, or 3 heteroatoms independently selected from N, O, and S; —$O(CH_2)_{2-4}O(CH_2)_{8-18}$, —$OC(R^{75a})_2OC(O)OR^{75b}$, —$OC(R^{75a})_2OC(O)R^{75b}$, —$NR^9R^{10}$, an N-linked amino acid or an N-linked amino acid ester and each $R^{75}$ can be optionally substituted;

$R^{75a}$ is independently selected at each occurrence from hydrogen, $C_1$-$C_8$alkyl, $C_2$-$C_8$alkenyl, $C_2$-$C_8$alkynyl, (aryl)$C_0$-$C_4$alkyl-, (aryl)$C_2$-$C_8$alkenyl- or (aryl)$C_2$-$C_8$alkynyl-;

or two $R^{75a}$ groups can be taken together with the carbon that they are bonded to form a 3-6 membered heterocycloalkyl having 1, 2, or 3 heteroatoms independently selected from N, O, and S, or a 3-6 membered carbocyclic ring;

$R^{75b}$ is independently selected at each occurrence from $C_1$-$C_8$alkyl, $C_2$-$C_8$alkenyl, $C_2$-$C_8$alkynyl, (aryl)$C_0$-$C_4$alkyl, (aryl)$C_2$-$C_8$alkenyl or (aryl)$C_2$-$C_8$alkynyl;

$R^{30a}$ is $C_1$-$C_6$alkyl, $C_2$-$C_6$alkenyl, $C_2$-$C_6$alkynyl, ($C_3$-$C_7$cycloalkyl)$C_0$-$C_4$alkyl-, (aryl)$C_0$-$C_4$alkyl-, (3- to 7-membered heterocycloalkyl)$C_0$-$C_4$alkyl- having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S, each of which $R^{30a}$ can be optionally substituted;

$R^{15}$, and in an alternative embodiment $R^{11}$ and $R^{14}$, are independently selected from hydrogen, $R^{48}$, halogen, hydroxyl, nitro, cyano, —$O(PO)(OR^9)_2$, —$(PO)(OR^9)_2$, alkyl including $C_1$-$C_6$alkyl, alkenyl including $C_2$-$C_6$alkenyl, alkynyl including $C_2$-$C_6$alkynyl, $C_2$-$C_6$alkenyl(aryl), $C_2$-$C_6$alkenyl(cycloalkyl), $C_2$-$C_6$alkenyl(heterocycle), $C_2$-$C_6$alkenyl(heteroaryl), $C_2$-$C_6$alkynyl(aryl), $C_2$-$C_6$alkynyl(cycloalkyl), $C_2$-$C_6$alkynyl(heterocycle), $C_2$-$C_6$alkynyl(heteroaryl), alkanoyl including $C_2$-$C_6$alkanoyl, alkoxy including $C_1$-$C_6$alkoxy, thioalkyl including $C_1$-$C_6$thioalkyl, —$C_0$-$C_4$alkyl(mono- and di-$C_1$-$C_6$alkylamino), —$C_0$-$C_4$alkyl($C_3$-$C_7$cycloalkyl), —$C_0$-$C_4$alkoxy($C_3$-$C_7$cycloalkyl), haloalkyl including $C_1$-$C_6$haloalkyl, and haloalkoxy including $C_1$-$C_6$haloalkoxy;

$X^{15}$ is NH, O, or S;

$X^{16}$ is $CR^{12}$;

$X^{17}$ is N or $CR^{13}$;

$X^{18}$ is $CR^{12}$;

$X^{19}$ is N or $CR^{13}$;

$X^{20}$ is NH or O;

$X^{21}$ is N or $CR^{14}$;

$X^{22}$ is N or $CR^{13}$;

$X^{23}$ is $CR^{12}$;

$X^{24}$ and $X^{25}$ are each independently O or S;

$X^{26}$ is N or $CR^{41}$;

$X^{27}$ is $CR^{12}$, NH, or O;

$X^{28}$ is N or CH;

$X^{30}$ is N or $CR^5$;

$X^{31}$ is N, $C(R^{54})_2$, or $CR^{54}$;

$X^{32}$ is NH, $C(R^{54})_2$, or $CR^{54}$;

$X^{33}$ is —CO—, —SO—, or —$SO_2$—;

$X^{34}$ is $CHR^{13}$, NH, O, or S;

wherein no more than 2 of $X^{28}$ are N;

$R^{41}$ is hydrogen, alkyl including $C_1$-$C_6$alkyl, or —($C_0$-$C_2$alkyl)($C_3$-$C_5$cycloalkyl);

$R^{48}$ and $R^{48a}$ are selected from hydrogen, halogen, hydroxyl, nitro, cyano, amino, alkyl including $C_1$-$C_6$alkyl, haloalkyl including $C_1$-$C_6$haloalkyl, alkenyl including $C_2$-$C_6$alkenyl, alkynyl including $C_2$-$C_6$alkynyl, thioalkyl including $C_1$-$C_6$thioalkyl, alkoxy including $C_1$-$C_6$alkoxy, -J$C_3$-$C_7$cycloalkyl, —$B(OH)_2$, -JC(O)$NR^9R^{23}$, -$JOSO_2OR^{21}$, —$C(O)(CH_2)_{1-4}S(O)R^{21}$, —$O(CH_2)_{1-4}S(O)NR^{21}R^{22}$, -JOP(O)($OR^{21}$)($OR^{22}$), -JP(O)($OR^{21}$)($OR^{22}$), -JOP(O)($OR^{21}$)$R^{22}$, -JP(O)($OR^{21}$)$R^{22}$, -JOP(O)$R^{21}R^{22}$, -JP(O)$R^{21}R^{22}$, -JSP(O)($OR^{21}$)($OR^{22}$), -JSP(O)($OR^{21}$)($R^{22}$), -JSP(O)($R^{21}$)($R^{22}$), -$JNR^9$P(O)($NHR^{21}$)($NHR^{22}$), -$JNR^9$P(O)($OR^{21}$)($NHR^{22}$), -$JNR^9$P(O)($OR^{21}$)($OR^{22}$), -JC(S)$R^{21}$, -$JNR^{21}SO_2R^{22}$, -$JNR^9S(O)NR^{10}R^{22}$, -$JNR^9SO_2NR^{10}R^{22}$, -$JSO_2NR^9COR^{22}$, -$JSO_2NR^9CONR^{21}R^{22}$, -$JNR^{21}SO_2R^{22}$, -JC(O)$NR^{21}SO_2R^{22}$, -JC($NH_2$)═$NR^{22}$, -JCH($NH_2$)$NR^9S(O)_2R^{22}$, -JOC(O)$NR^{21}R^{22}$, -$JNR^{21}$C(O)$OR^{22}$, -$JNR^{21}$OC(O)$R^{22}$, —$(CH_2)_{1-4}$C(O)$NR^{21}R^{22}$, -JC(O)$NR^{24}R^{30}$, -$JNR^9$C(O)$R^{21}$, -JC(O)$R^{21}$, -$JNR^9$C(O)$NR^{10}R^{22}$, —$CCR^{21}$, —$(CH_2)_{1-4}$OC(O)$R^{21}$, -JC(O)$OR^{23}$, and $R^{103}$; each of which $R^{48}$ may be optionally substituted with one or more substituents selected from halogen, hydroxyl, nitro, cyano, amino, oxo, —$B(OH)_2$, —$Si(CH_3)_3$, —COOH, —$CONR^9R^{10}$, —$P(O)(OH)_2$, alkyl including $C_1$-$C_6$alkyl, —$C_0$-$C_4$alkyl($C_3$-$C_7$cycloalkyl), $C_1$-$C_6$alkoxy, —$C_0$-$C_4$alkyl(mono- and di-$C_1$-$C_4$alkyl$NR^9R^{10}$), alkyl including $C_1$-$C_6$alkyl ester, $C_1$-$C_4$alkylamino, $C_1$-$C_4$hydroxylalkyl, haloalkyl including $C_1$-$C_6$haloalkyl, —OC(O)$R^9$, —$NR^9$C(O)$R^{10}$, —C(O)$NR^9R^{10}$, —OC(O)$NR^9R^{10}$, —$NR^9$C(O)$OR^{10}$, haloalkyl including $C_1$-$C_6$haloalkyl, S(O)═$NHR^{21}$, $SF_5$, JC($R^9$)═$NR^{21}$, $SO_2OR^{21}$, and haloalkoxy including $C_1$-$C_6$haloalkoxy;

$R^{54}$ is hydrogen, alkyl including $C_1$-$C_6$alkyl, alkenyl including $C_2$-$C_6$alkenyl, alkynyl including $C_2$-$C_6$alkynyl, alkoxy including $C_1$-$C_6$alkoxy, $C_2$-$C_6$alkynyl, alkanoyl including $C_2$-$C_6$alkanoyl, thioalkyl including $C_1$-$C_6$thioalkyl, hydroxy$C_1$-$C_6$alkyl, amino$C_1$-$C_6$alkyl, —$C_0$-$C_4$alkyl($C_3$-$C_7$cycloalkyl), (phenyl)$C_0$-$C_4$alkyl-, (heterocycloalkyl)$C_0$-$C_4$alkyl or (heteroaryl)$C_0$-$C_4$alkyl- wherein each $R^{54}$ is optionally substituted;

s is 1 or 2;

L1 is a bond,

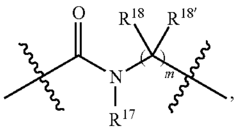,
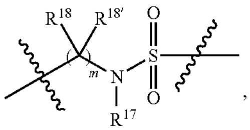,
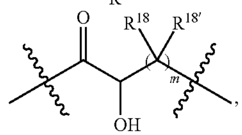,
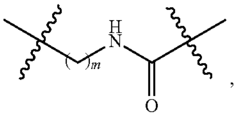,
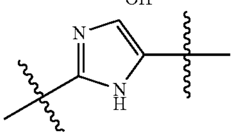,
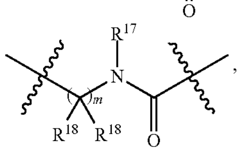, or -continued

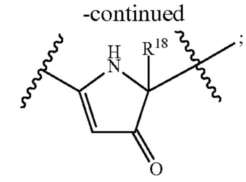;

$R^{17}$ is hydrogen, alkyl including $C_1$-$C_6$alkyl, or —$C_0$-$C_4$alkyl($C_3$-$C_7$cycloalkyl);

$R^{18}$ and $R^{18'}$ are independently selected from hydrogen, halogen, hydroxymethyl, and methyl;

m is 0, 1, 2, or 3;

L2 is selected from:

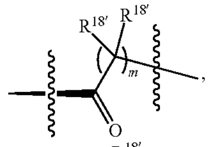,
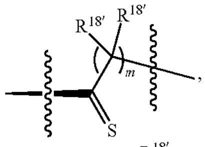,
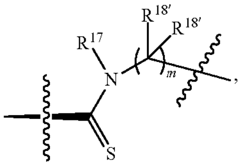,
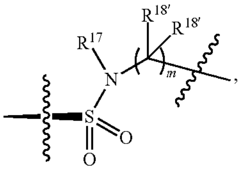,
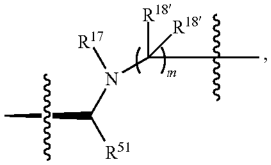,
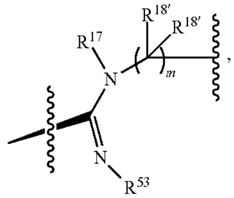,
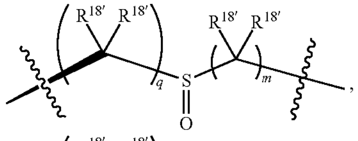,
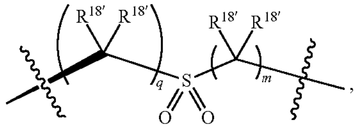,
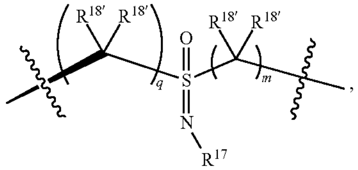,
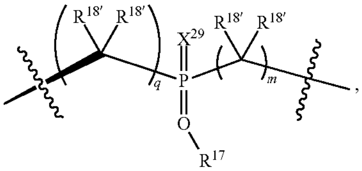,
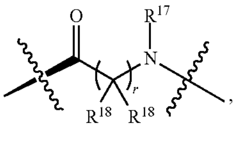,
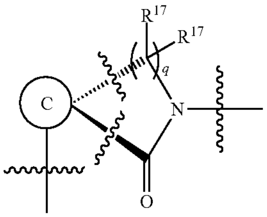, and -continued

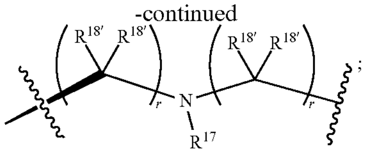

or L2 is selected from an optionally substituted monocyclic or bicyclic carbocyclic; an optionally substituted monocyclic or bicyclic carbocyclic-oxy group; an optionally substituted monocyclic or bicyclic heterocycle group having 1, 2, 3, or 4 heteroatoms independently selected from N, O, and S and from 4 to 7 ring atoms per ring, an optionally substituted —($C_0$-$C_4$alkyl)(aryl); an optionally substituted —($C_0$-$C_4$alkyl)(5-membered heteroaryl); an optionally substituted —($C_0$-$C_4$alkyl)(6-membered heteroaryl); an optionally substituted —($C_0$-$C_4$alkyl)(8-membered heteroaryl); an optionally substituted —($C_0$-$C_4$alkyl)(9-membered heteroaryl); and —($C_0$-$C_4$alkyl)(10-membered heteroaryl);

q is 1, 2 or 3;

$R^{51}$ is $CH_3$, $CH_2F$, $CHF_2$ or $CF_3$;

$R^{53}$ is cyano, nitro, hydroxyl, or alkoxy including $C_1$-$C_6$alkoxy;

$X^{29}$ can be O or S;

each $R^{52}$ is independently selected from halo, hydrogen, or optionally substituted alkyl including $C_1$-$C_6$alkyl;

or two $R^{52}$ groups are taken together to form a 3- to 6-membered carbocyclic spiro ring or a 3- to 6-membered heterocyclic spiro ring containing 1 or 2 heteroatoms independently selected from N, O, or S;

B1 is heteroaryl; aryl; biphenyl, a monocyclic or bicyclic carbocycle; a monocyclic or bicyclic carbocyclic-oxy group; a monocyclic, bicyclic, or tricyclic heterocycle group having 1, 2, 3, or 4 heteroatoms independently selected from Boron, Si, N, O, and S and from 4 to 8 ring atoms per ring; alkenyl including $C_2$-$C_6$alkenyl; or alkynyl including $C_2$-$C_6$alkynyl; each of which B1 is optionally substituted with one or more substituents independently selected from $R^{33}$, $R^{34}$, $R^{35}$, and $R^{36}$;

$R^{33}$ is independently selected from halogen, hydroxyl, —COOH, cyano, alkyl including $C_1$-$C_6$alkyl, alkanoyl including $C_2$-$C_6$alkanoyl, alkoxy including $C_1$-$C_6$alkoxy, —$C_0$-$C_4$alkyl$NR^9R^{10}$, —$SO_2R^9$, haloalkyl including $C_1$-$C_6$haloalkyl, S(O)═$NHR^{21}$, $SF_5$, and $JC(R^9)$═$NR^{21}$, and haloalkoxy including $C_1$-$C_6$haloalkoxy;

$R^{34}$ is independently selected from nitro, alkenyl including $C_2$-$C_6$alkenyl, alkynyl including $C_2$-$C_6$alkynyl, thioalkyl including $C_1$-$C_6$thioalkyl, -$JC_3$-$C_7$cycloalkyl, -$JB(OH)_2$, -$JC(O)NR^9R^{23}$, -$JOSO_2OR^{21}$, -$JC(O)(CH_2)_{1-4}S(O)R^{21}$, —$O(CH_2)_{1-4}S(O)NR^{21}R^{22}$, -$JOP(O)(OR^{21})(OR^{22})$, -$JP(O)(OR^{21})(OR^{22})$, -$JOP(O)(OR^{21})R^{22}$, -$JP(O)(OR^{21})R^{22}$, -$JOP(O)R^{21}R^{22}$, -$JP(O)R^{21}R^{22}$, -$JSP(O)(OR^{21})(OR^{22})$, -$JSP(O)(OR^{21})(R^{22})$, -$JSP(O)(R^{21})(R^{22})$, -$JNR^9P(O)(NHR^{21})(NHR^{22})$, -$JNR^9P(O)(OR^{21})(NHR^{22})$, -$JNR^9P(O)(OR^{21})(OR^{22})$, -$JC(S)R^{21}$, -$JNR^{21}SO_2R^{22}$, -$JNR^9S(O)NR^{10}R^{22}$, -$JNR^9SO_2NR^{10}R^{22}$, -$JSO_2NR^9COR^{22}$, -$JSO_2NR^9CONR^{21}R^{22}$, -$JNR^{21}SO_2R^{22}$, -$JC(O)NR^{21}SO_2R^{22}$, -$JC(NH_2)$═$NR^{22}$, -$JCH(NH_2)NR^9S(O)_2R^{22}$, -$JOC(O)NR^{21}R^{22}$, -$JNR^{21}C(O)OR^{22}$, -$JNR^{21}OC(O)R^{22}$, —$(CH_2)_{1-4}C(O)NR^{21}R^{22}$, -$JC(O)R^{24}R^{30}$, -$JNR^9C(O)R^{21}$, -$JC(O)R^{21}$, -$JNR^9C(O)NR^{10}R^{22}$, —$CCR^{21}$, —$(CH_2)_{1-4}OC(O)R^{21}$, —$S(O)_2OR^{21}$, and -$JC(O)OR^{23}$; each of which $R^{34}$ may be unsubstituted or substituted with one or more substituents independently selected from halogen, hydroxyl, nitro, cyano, amino, oxo, —$B(OH)_2$, —$Si(CH_3)_3$, —COOH, —$CONR^9R^{10}$, —$P(O)(OH)_2$, $C_1$-$C_6$alkyl, —$C_0$-$C_4$alkyl($C_3$-$C_7$cycloalkyl), alkoxy including $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, haloalkyl including $C_1$-$C_6$haloalkyl, and $C_1$-$C_6$haloalkoxy;

$R^{35}$ is independently selected from naphthyl, naphthyloxy, indanyl, (4- to 7-membered heterocycloalkyl)$C_0$-$C_4$alkyl containing 1 or 2 heteroatoms selected from N, O, and S, and bicyclic heterocycle containing 1, 2, or 3 heteroatoms independently selected from N, O, and S, and containing 4- to 8-ring atoms in each ring; each of which $R^{35}$ is optionally substituted with one or more substituents independently selected from halogen, hydroxyl, nitro, cyano, $C_1$-$C_6$alkyl, alkenyl including $C_2$-$C_6$alkenyl, alkanoyl including $C_2$-$C_6$alkanoyl, alkoxy including $C_1$-$C_6$alkoxy, $C_1$-$C_6$alkylester, —$C_0$-$C_4$alkyl($C_3$-$C_7$ cycloalkyl), —$SO_2R^9$, haloalkyl including $C_1$-$C_6$haloalkyl, and haloalkoxy including $C_1$-$C_6$haloalkoxy;

$R^{36}$ is independently selected from tetrazolyl, (phenyl)$C_0$-$C_2$alkyl, (phenyl)$C_1$-$C_6$alkoxy, phenoxy, and 5- or 6-membered heteroaryl containing 1, 2, or 3 heteroatoms independently selected from N, O, Boron, Si, and S, each of which $R^{36}$ is optionally substituted with one or more substituents independently selected from halogen, hydroxyl, nitro, cyano, alkyl including $C_1$-$C_6$alkyl, alkenyl including $C_2$-$C_6$alkenyl, alkanoyl including $C_2$-$C_6$alkanoyl, alkoxy including $C_1$-$C_6$alkoxy, $C_1$-$C_6$alkylester, —$C_0$-$C_4$alkyl($C_3$-$C_7$cycloalkyl), —$SO_2R^9$, —$OSi(CH_3)_2C(CH_3)_3$, —$Si(CH_3)_2C(CH_3)_3$, haloalkyl including $C_1$-$C_6$haloalkyl, and haloalkoxy including $C_1$-$C_6$haloalkoxy;

$R^{21}$ and $R^{22}$ are independently selected from hydrogen, cyano, hydroxyl, cyano, amino, $C_1$-$C_6$alkyl, haloalkyl including $C_1$-$C_6$haloalkyl, alkoxy including $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O)O$C_1$-$C_6$alkyl, —$C_1$-$C_4$alkylOC(O)$C_1$-$C_6$alkyl, —C(O)haloalkyl, —$C_1$-$C_4$alkylC(O)O$C_1$-$C_6$alkyl, (4- to 8-membered heterocycloalkyl)$C_0$-$C_4$alkyl having 1, 2, or 3 heteroatoms independently selected from N, O, and S, and (5- or 6-membered unsaturated or aromatic heterocycle) $C_0$-$C_4$alkyl having 1, 2, or 3 heteroatoms independently selected from N, O, and S, and each $R^{21}$ and $R^{22}$ can be optionally substituted;

or $R^{21}$ and $R^{22}$ can be taken together to form a carbocyclic or heterocyclic ring;

$R^{23}$ is independently selected at each occurrence from alkyl including $C_1$-$C_6$alkyl, haloalkyl including $C_1$-$C_6$haloalkyl, (aryl)$C_0$-$C_4$alkyl, ($C_3$-$C_7$cycloalkyl)$C_0$-$C_4$alkyl, (phenyl)$C_0$-$C_4$alkyl, (4- to 8-membered heterocycle)$C_0$-$C_4$alkyl having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S, wherein each $R^{23}$ can be optionally substituted;

$R^{30}$ is independently selected at each occurrence from hydrogen, $C_1$-$C_6$alkyl, $C_1$-$C_6$haloalkyl, (aryl)$C_0$-$C_4$alkyl, ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently selected from N, O, and S; (5- or 6-membered unsaturated or aromatic heterocycle)$C_0$-$C_4$alkyl having 1, 2, or 3 heteroatoms independently selected from N, O, and S; COOH, $Si(CH_3)_3$, $COOR^{30a}$, $C_2$-$C_6$alkanoyl, —$B(OH)_2$, —$C(O)(CH_2)_{1-4}S(O)R^{21}$, —$P(O)(OR^{21})(OR^{22})$, —$P(O)(OR^{21})R^{22}$, —$P(O)R^{21}R^{22}$, —$NR^9P(O)(NHR^{21})(NHR^{22})$, —$NR^9P(O)(OR^{21})(NHR^{22})$, —$NR^9P(O)(OR^{21})(OR^{22})$, —$C(S)R^{21}$, —$NR^{21}SO_2R^{22}$, —$NR^9S(O)NR^{10}R^{22}$, —$NR^9SO_2NR^{10}R^{22}$, —$SO_2NR^9COR^{22}$, —$SO_2NR^9CONR^{21}R^{22}$, —$NR^{21}SO_2R^{22}$, —$C(O)NR^{21}SO_2R^{22}$, —$C(NH_2)NR^9R^{22}$, —$C(NH_2)NR^9S(O)_2R^{22}$, —$NR^9C(O)OR^{10}$, —$NR^{21}OC(O)R^{22}$, —$(CH_2)_{1-4}C(O)NR^{21}R^{22}$, —$C(O)R^{24}R^{25}$, —$NR^9C(O)R^{21}$, —$C(O)R^{21}$, —$NR^9C(O)NR^9R^{10}$, —$NR^9C(O)NR^{24}R^{25}$, —$(CH_2)_{1-4}OC(O)R^{21}$, each of which $R^{30}$ can be optionally substituted; or if $R^{24}$ and $R^{30}$ are both substituents on a nitrogen they are taken together with the nitrogen to which they are attached to form a 4- to 7-membered monocyclic heterocycle, or a 6- to 10-membered bicyclic heterocycle group having fused, spiro, or bridged rings, wherein each ring can be optionally substituted;

J is independently selected from a covalent bond, alkylene including $C_1$-$C_4$alkylene, O-alkylene including —$OC_1$-$C_4$alkylene, alkenylene including $C_2$-$C_4$alkenylene, and alkynylene $C_2$-$C_4$alkynylene;

B2 is selected from:

a 4-membered carbocycle fused to a 5- or 6-membered heteroaryl having 1, 2, or 3 heteroatoms independently selected from N, O, and S; wherein the 4-5 or 4-6 ring system can be optionally substituted;

(optionally substituted alkyl)-(optionally substituted cycloalkyl), (optionally substituted alkenyl)-(optionally substituted cycloalkyl), or (optionally substituted alkynyl)-(optionally substituted cycloalkyl);

a 4-membered carbocycle fused to a 6-membered aryl ring wherein the 4-6 ring system can be optionally substituted;

(cycloalkyl)-(optionally substituted aryl), (cycloalkyl)-(optionally substituted heteroaryl), (cycloalkyl)-(optionally substituted heterocycle), (alkyl)-alkenyl), cycloalkyl-alkenyl;

alkyl, (alkyl)-(alkenyl), alkyl(alkynyl), cycloalkyl-alkenyl each of which can be optionally substituted;

wherein B2 can be further substituted 1, 2, 3, or 4 times or more with the substituents independently selected from $R^{33}$, $R^{34}$, $R^{35}$, $R^{36}$, and $R^{48}$;

B3 is a monocyclic or bicyclic carbocycle; a monocyclic or bicyclic carbocyclic-oxy group; a monocyclic, bicyclic, or tricyclic heterocycle group having 1, 2, 3, or 4 heteroatoms independently selected from Boron, Si, N, O, and S and from 4 to 8 ring atoms per ring; alkenyl including $C_2$-$C_6$alkenyl; alkynyl including $C_2$-$C_6$alkynyl; —($C_0$-$C_4$alkyl)(aryl); —($C_0$-$C_4$alkyl)(heteroaryl); or —($C_0$-$C_4$alkyl)(biphenyl), each of which B3 is substituted with at least one $R^{201}$ and optionally substituted with one or more substituents independently selected from $R^{33}$, $R^{34}$, $R^{35}$, and $R^{36}$;

or B3

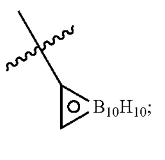

B4 is a six membered heteroaryl ring with at least two substituents selected from $R^{25}$, $R^{26}$, $R^{27}$ and $R^{28}$;

or B4 is a six membered heteroaryl ring with at least three substituents selected from $R^{25}$, $R^{26}$, $R^{27}$ and $R^{28}$;

or B4 is a pyridine with at least two substituents selected from $R^{25}$, $R^{26}$, $R^{27}$ and $R^{28}$;

or B4 is selected from:

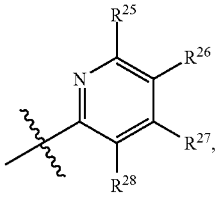

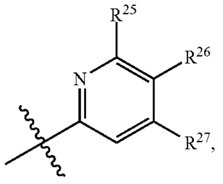

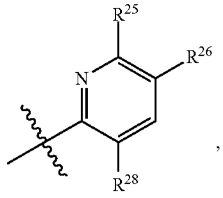

,

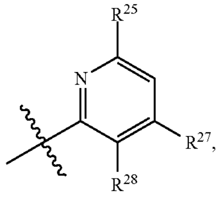

and

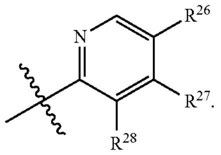

$R^{25}$, $R^{26}$, $R^{27}$, and $R^{28}$ are selected from halogen, hydroxyl, nitro, cyano, alkyl including $C_1$-$C_6$alkyl, alkenyl including $C_2$-$C_6$alkenyl, alkanoyl including $C_2$-$C_6$alkanoyl, alkoxy including $C_1$-$C_6$alkoxy, thioalkyl including $C_1$-$C_6$thioalkyl, (mono- and di-$C_1$-$C_6$alkylamino)$C_0$-$C_4$alkyl, ($C_3$-$C_7$cycloalkyl)$C_0$-$C_4$alkyl, (aryl)$C_0$-$C_4$alkyl-, (heteroaryl)$C_0$-$C_4$alkyl-, and —$C_0$-$C_4$alkoxy($C_3$-$C_7$cycloalkyl); each of which $R^{25}$, $R^{26}$, $R^{27}$, and $R^{28}$ other than hydrogen, halogen, hydroxyl, nitro, cyano, is unsubstituted or substituted with one or more substituents independently selected from halogen, hydroxyl, amino, alkoxy including $C_1$-$C_6$alkoxy, haloalkyl including $C_1$-$C_6$haloalkyl, ($C_3$-$C_7$cycloalkyl)$C_0$-$C_4$alkyl-, and haloalkoxy including $C_1$-$C_6$haloalkoxy;

and wherein it should be understood and is intended by the inventors that each specific combination of each specific variable of $R^{25}$, $R^{26}$, $R^{27}$, and $R^{28}$ is considered specifically and independently disclosed, notwithstanding that the variable definitions are provided as a group; such that no combination of variables is considered a multiple selection because each is hereby specifically disclosed and only grouped for convenience of space;

and wherein any of these groups may be further optionally substituted as that term is defined in the Terminology Section below, if desired to achieve the target effect, results in a stable compound that makes chemical sense to the skilled artisan, and the group is not redundant (i.e., as known in the art, alkyl substituted with alkyl is redundant; however for examples, alkoxy substituted with alkoxy is not redundant); and wherein any of the structures illustrated herein, e.g., A1, A2, A3, B1, B2, B3, B4, C1, C2, C3, C4, C5, L, L3, or any of the R moieties, can be optionally independently substituted with 0, 1, 2, 3, or 4, as appropriate, $R^{48}$ substituents.

In one embodiment C is C5. In one embodiment B is B4.

In another aspect the invention provides a compound of Formula IV:

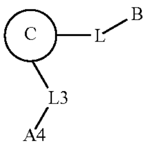

(IV)

or a pharmaceutically acceptable salt, isotopic analog, prodrug, N-oxide, or isolated isomer thereof optionally in pharmaceutically acceptable carrier;

wherein:

B is as defined above.

C is as defined above.

L is as defined above.

L3 is as defined above.

A4 is selected from:

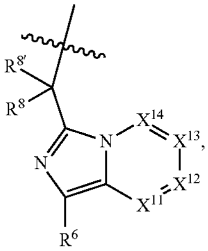

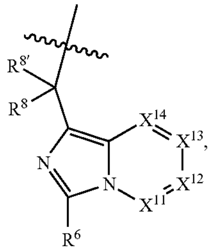

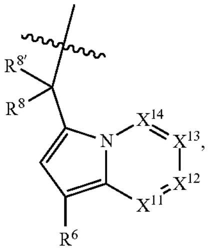

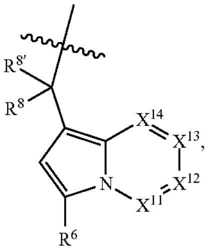

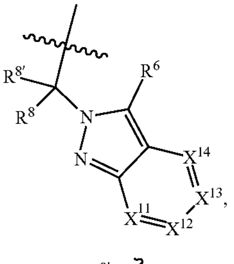

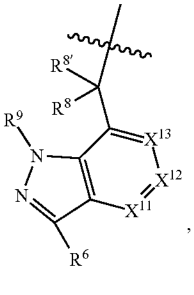

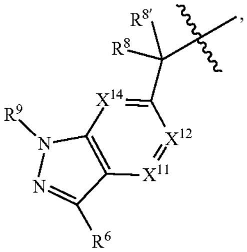

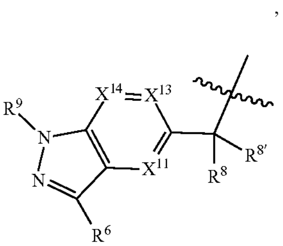

-continued

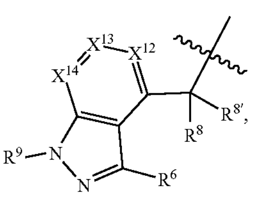

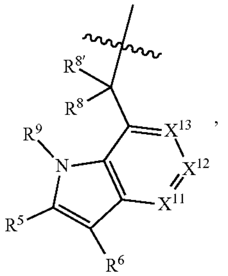

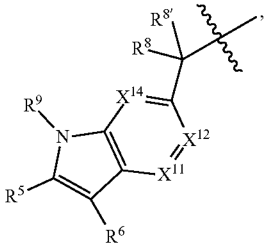

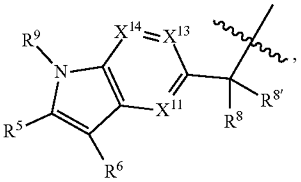

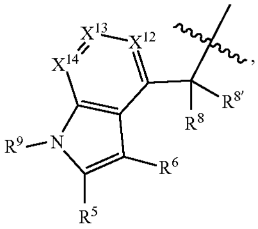

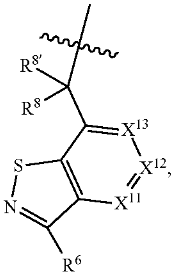

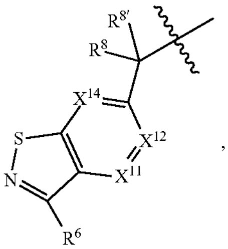

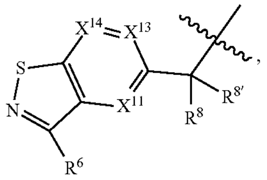

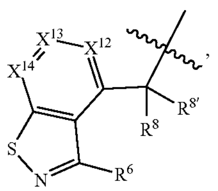

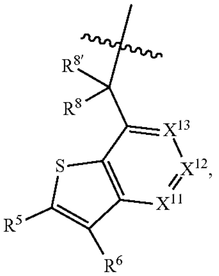

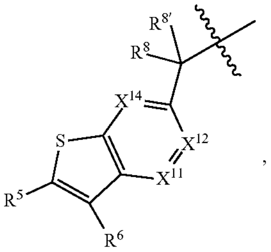

-continued

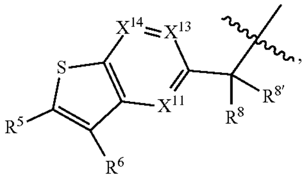
,
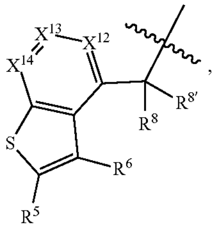
,
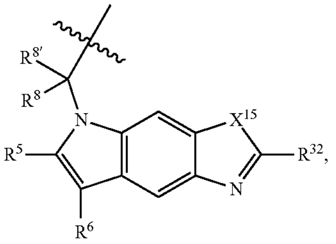
,
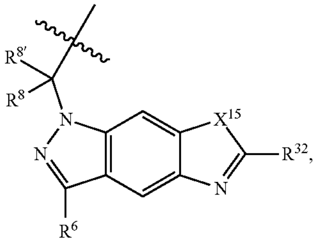
and
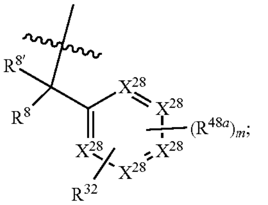
;

wherein m, $R^5$, $R^6$, $R^8$, $R^{8'}$, $R^9$, $R^{32}$, $R^{48}$, $X^{11}$, $X^{12}$, $X^{13}$, and $X^{14}$ are all defined above.

Pharmaceutical compositions comprising a compound or salt of Formula I, Formula II, Formula III, or Formula IV together with a pharmaceutically acceptable carrier are also disclosed.

The present invention thus includes at least the following features: a compound Formula I, Formula II, Formula III, or Formula IV or a pharmaceutically acceptable salt, prodrug, isotopic analog, or isolated isomer thereof, optionally in a pharmaceutically acceptable composition, for use in treating or preventing a disorder, including but not limited to the development of fatty liver and conditions stemming from fatty liver, such as nonalcoholic steatohepatitis (NASH), liver inflammation, cirrhosis, or liver failure; dermatomyocitis; amyotrophic lateral sclerosis; cytokine or inflammatory reactions in response to biotherapeutics (e.g. CAR T-cell therapy); paroxysmal nocturnal hemoglobinuria (PNH), rheumatoid arthritis, multiple sclerosis, age-related macular degeneration (AMD), retinal degeneration, other ophthalmic diseases (e.g., geographic atrophy), a respiratory disease or a cardiovascular disease;

a. a pharmaceutically acceptable composition of a compound of Formula I, Formula II, Formula III, or Formula IV or its pharmaceutically acceptable salt, prodrug, isotopic analog, or isolated isomer thereof;

b. a compound selected from Formula I, Formula II, Formula III, or Formula IV or a pharmaceutically acceptable salt, prodrug, isotopic analog, or isolated isomer thereof, optionally in a pharmaceutically acceptable composition, for use in treating or preventing a disorder mediated by the complement pathway, and for example, cascade Factor D;

c. use of a compound of Formula I, Formula II, Formula III, or Formula IV as described herein, or a pharmaceutically acceptable salt, prodrug, isotopic analog, or isolated isomer thereof, optionally in a pharmaceutically acceptable composition, in the manufacture of a medicament for treating or preventing a disorder including but not limited to the development of fatty liver and conditions stemming from fatty liver, such as nonalcoholic steatohepatitis (NASH), liver inflammation, cirrhosis, liver failure; dermatomyocitis; amyotrophic lateral sclerosis; cytokine or inflammatory reactions in response to biotherapeutics (e.g. CAR T-cell therapy); paroxysmal nocturnal hemoglobinuria (PNH), rheumatoid arthritis, multiple sclerosis, age-related macular degeneration (AMD), retinal degeneration, other ophthalmic diseases (e.g., geographic atrophy), a respiratory disease or a cardiovascular disease;

d. a process for manufacturing a medicament intended for the therapeutic use for treating or preventing a disorder or generally for treating or preventing disorders mediated by complement cascade Factor D, characterized in that a compound selected from Formula I, Formula II, Formula III, or Formula IV or an embodiment of the active compound is used in the manufacture;

e. a compound selected from Formula I, Formula II, Formula III, or Formula IV or a salt thereof as described herein in substantially pure form (e.g., at least 90 or 95%):

f. a compound of Formula I, Formula II, Formula III, or Formula IV as described herein, or a pharmaceutically acceptable salt, prodrug, isotopic analog, or isolated isomer thereof, optionally in a carrier to form a pharmaceutically acceptable composition, for use in treating a medical disorder which is an inflammatory or immune condition, a disorder mediated by the complement cascade (including a dysfunctional cascade), a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration.

g. For each of (a) through (f) above, and otherwise herein, each assembly of moieties in the Figures and each active compound made therefrom or its use is considered and deemed specifically and individually disclosed, as such depiction is for convenience of space only and not intended to describe a only a genus or even a subgenus for such indication.

DETAILED DESCRIPTION

Terminology

Figure 1:
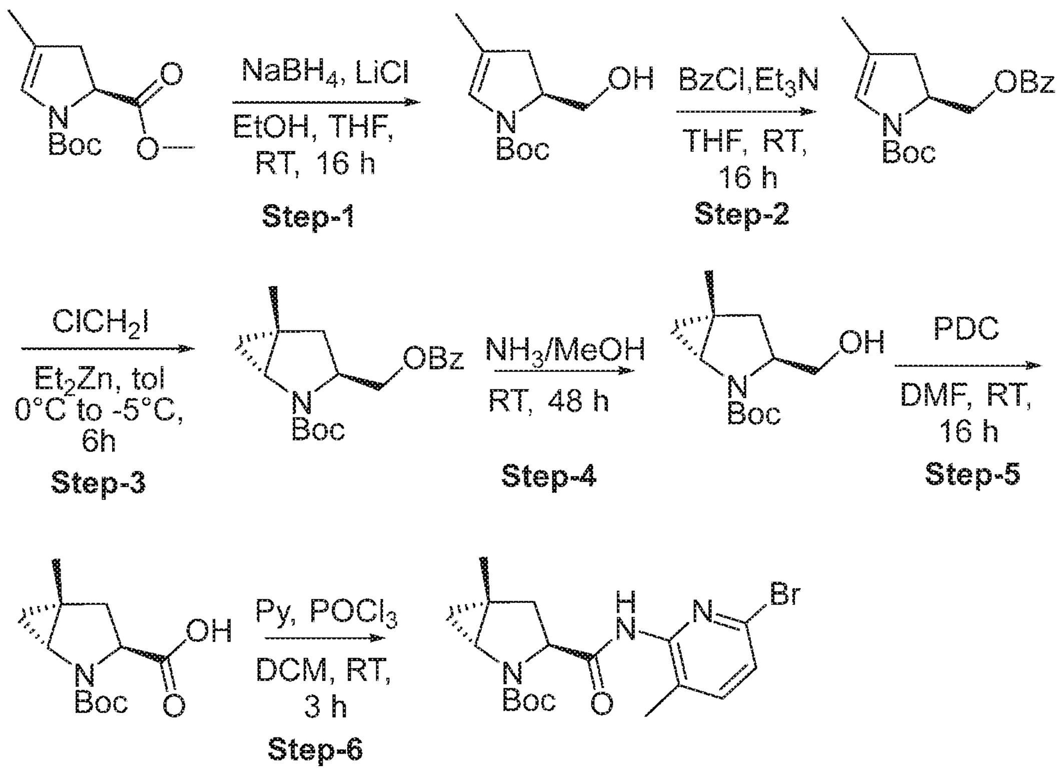
FIG. 1 is a six-step procedure to synthesize intermediate tert-butyl (1R,3S,5R)-3-((6-bromo-3-methylpyridin-2-yl)carbamoyl)-5-methyl-2-azabicyclo[3.1.0]hexane-2-carboxylate.
Figure 2:
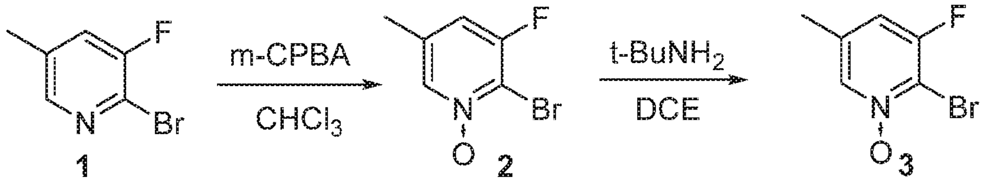
FIG. 2 is a two-step synthesis of intermediate 2-bromo-3-fluoro-5-methylpyridine 1-oxide (Compound 3 in FIG. 2).
Figure 3:
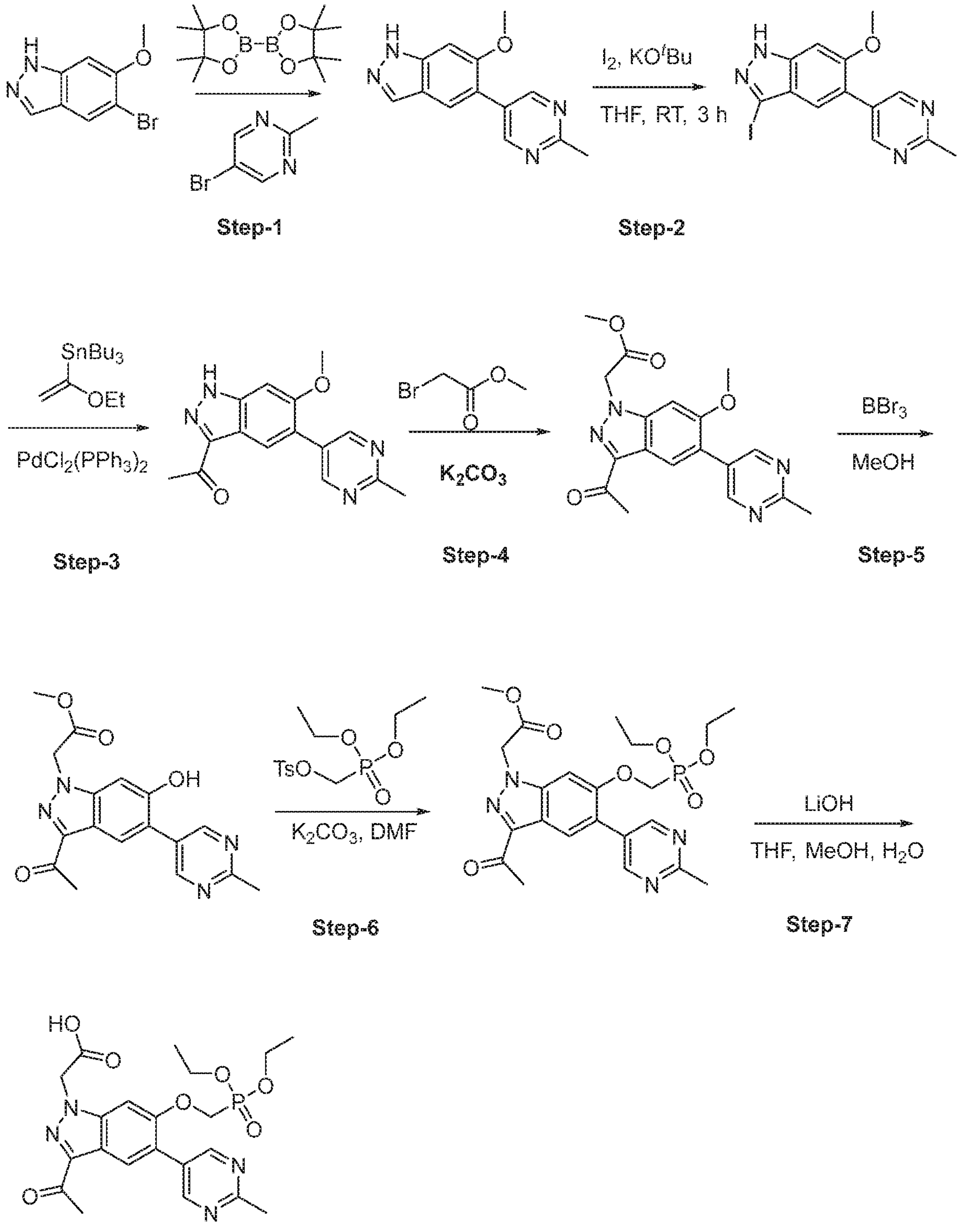
FIG. 3 is a seven-step procedure to synthesize 2-(3-acetyl-6-((diethoxyphosphoryl)methoxy)-5-(2-methylpyrimidin-5-yl)-1H-indazol-1-yl)acetic acid.
Figure 4:
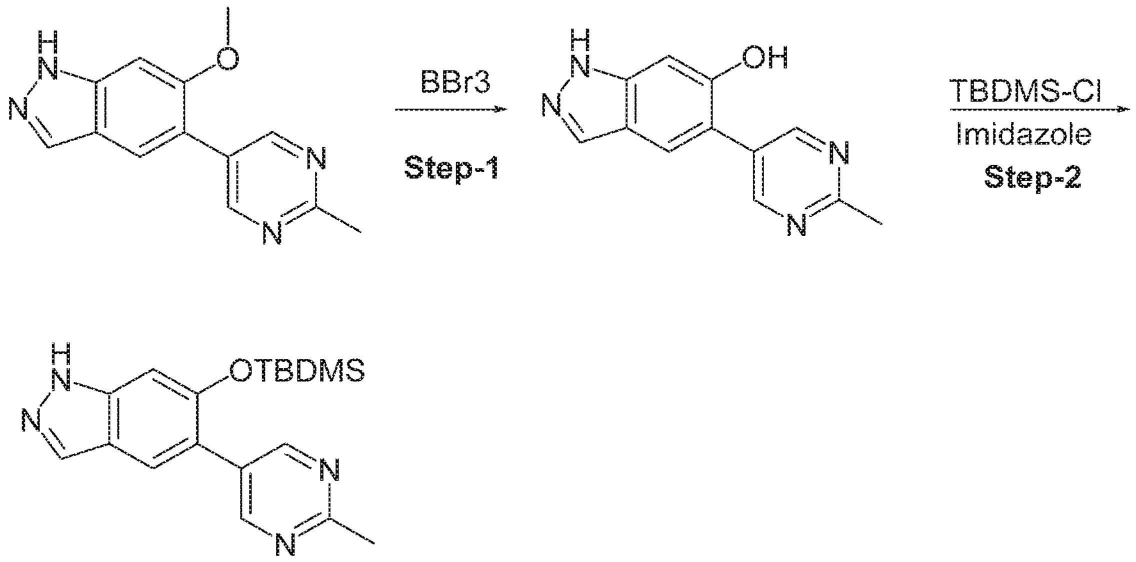
FIG. 4 is a two-step synthesis to synthesize the intermediate 6-((tert-butyldimethylsilyl)oxy)-5-(2-methylpyrimidin-5-yl)-1H-indazole.
Figure 5:
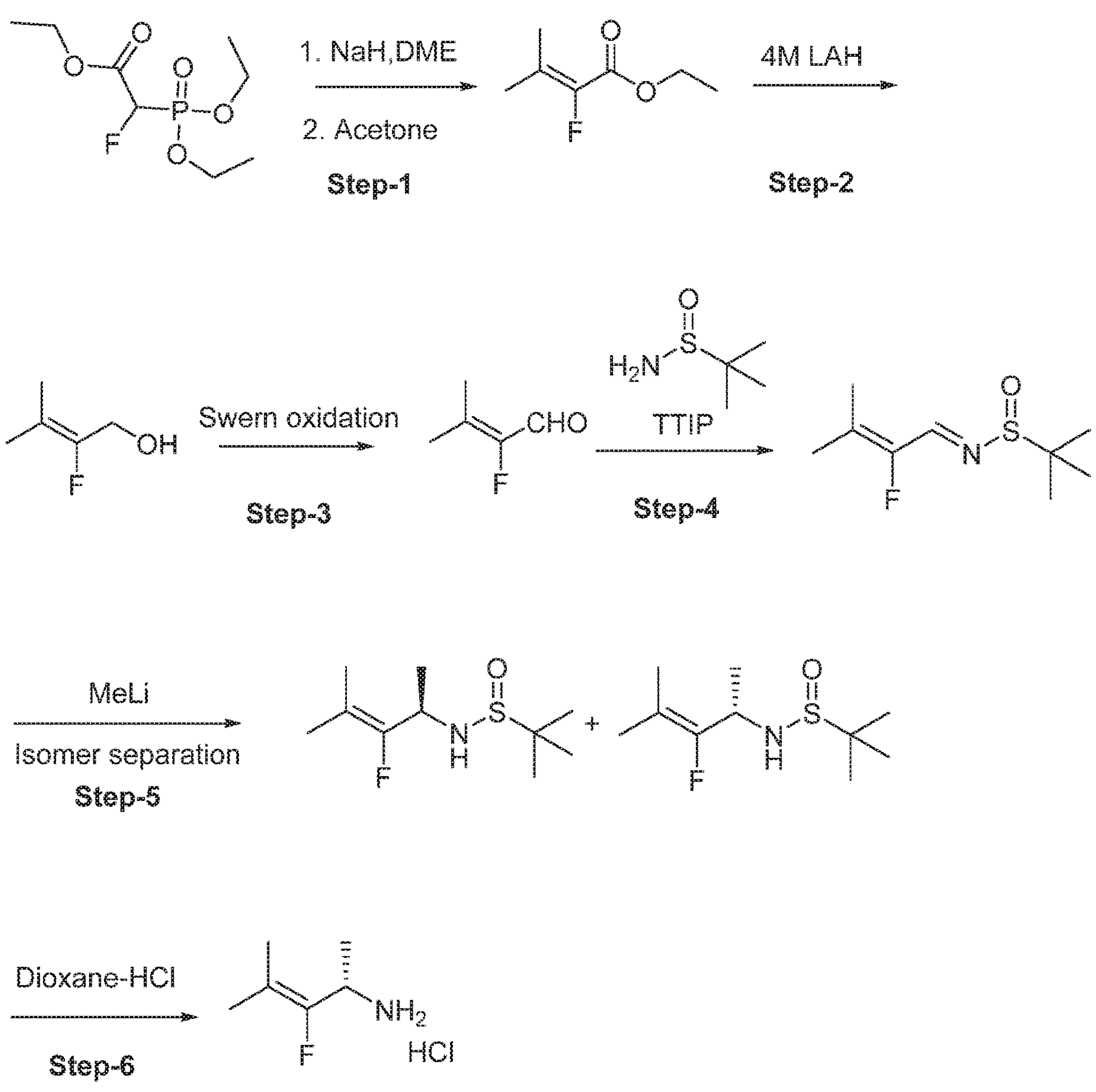
FIG. 5 is a six-step procedure to synthesize intermediate (S)-3-fluoro-4-methylpent-3-en-2-amine hydrochloric acid salt.
Figure 6:
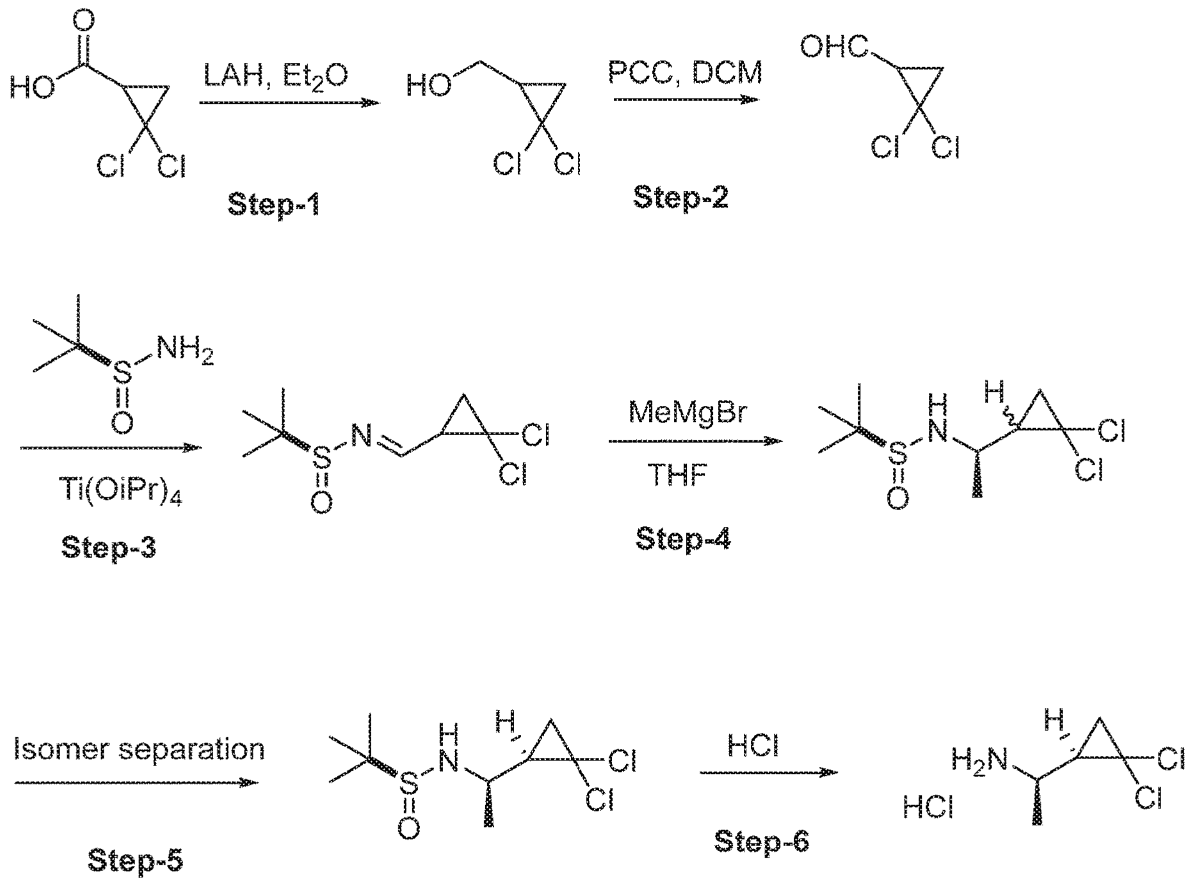
FIG. 6 is a six-step procedure to synthesize intermediate (R)-1-((R)-2,2-dichlorocyclopropyl)ethan-1-amine hydrochloric acid salt.
Figure 7:
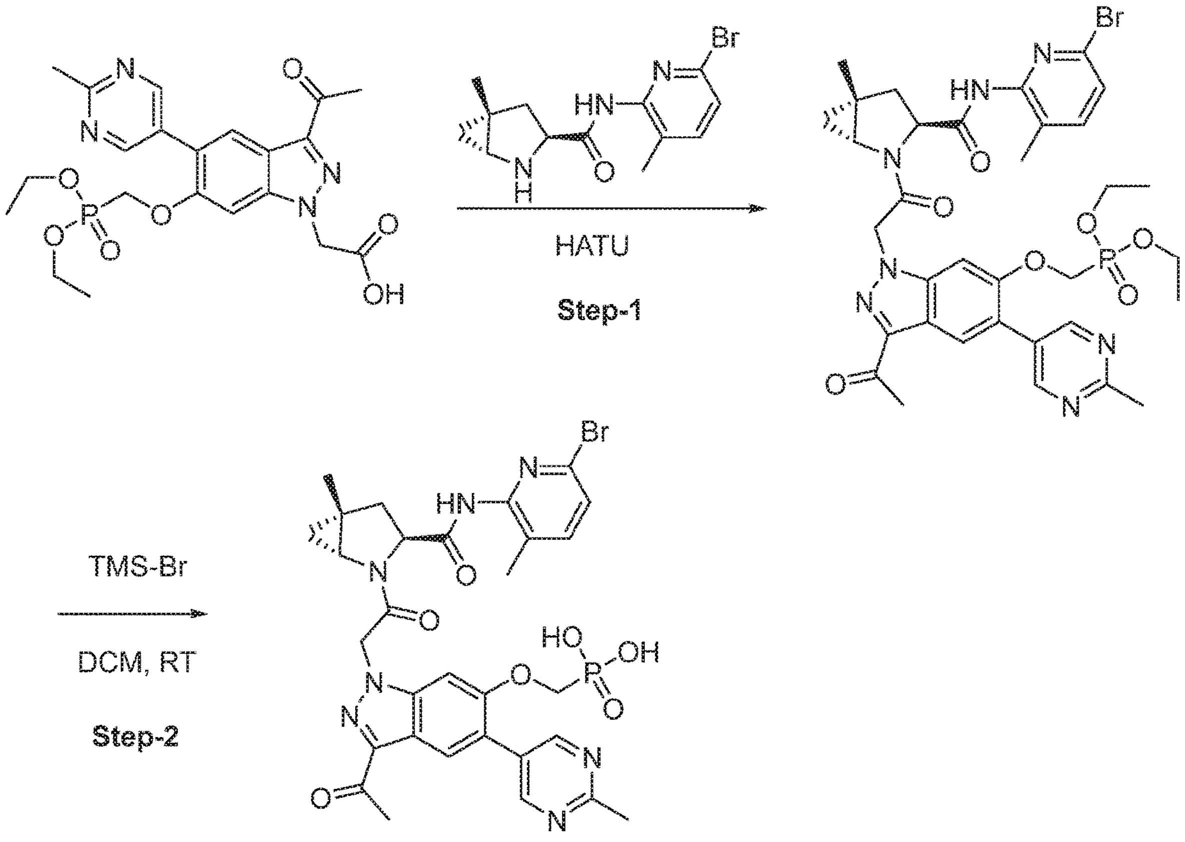
FIG. 7 is a two-step synthesis to synthesize (((3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-5-(2-methylpyrimidin-5-yl)-1H-indazol-6-yl)oxy) methyl)phosphonic acid.
Figure 8:
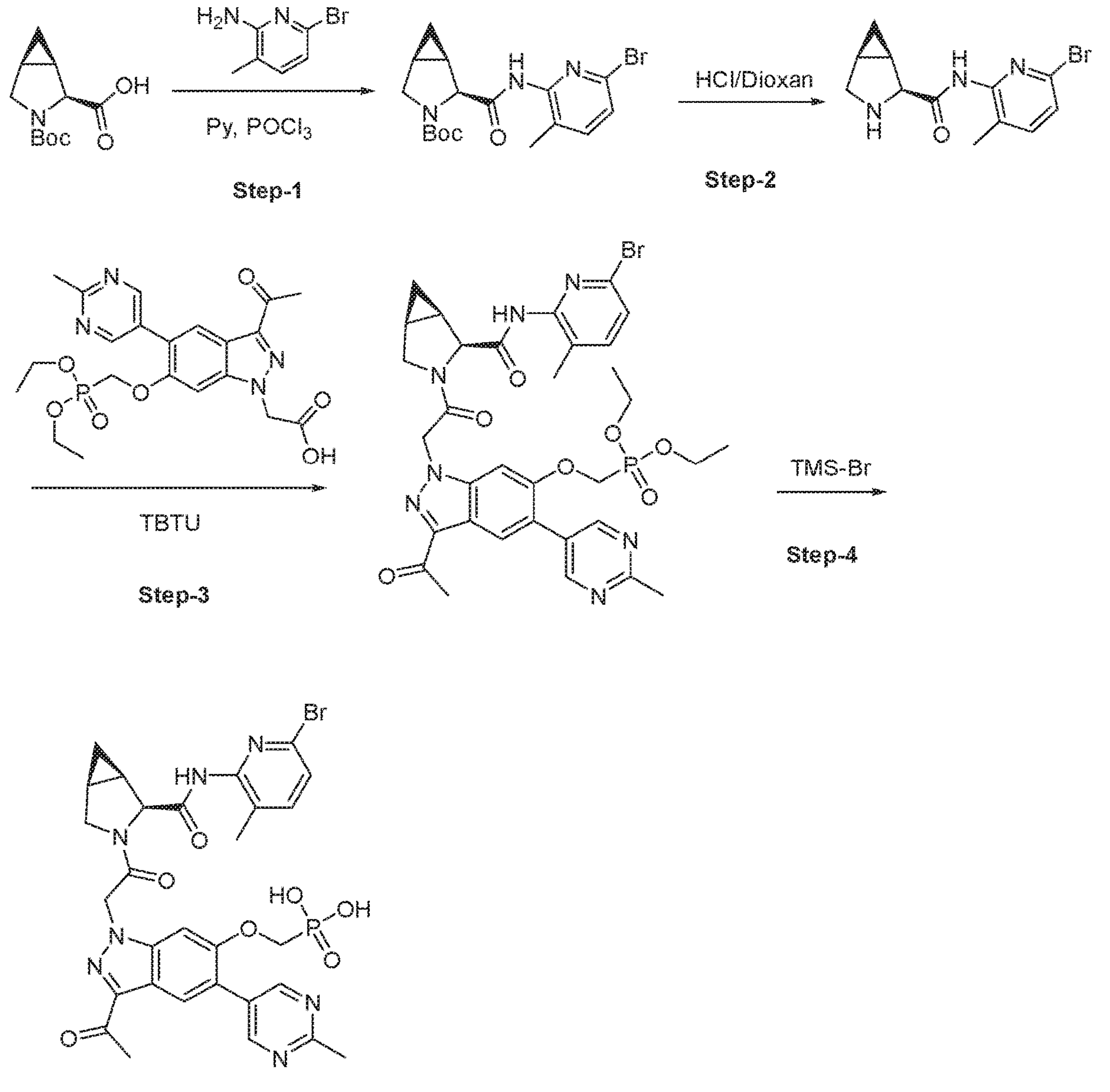
FIG. 8 is a four-step synthesis to synthesize (((3-acetyl-1-(2-((1R,2S,5S)-2-((6-bromo-3-methylpyridin-2-yl)carbamoyl)-3-azabicyclo[3.1.0]hexan-3-yl)-2-oxoethyl)-5-(2-methylpyrimidin-5-yl)-1H-indazol-6-yl)oxy)methyl) phosphonic acid.
Figure 9:
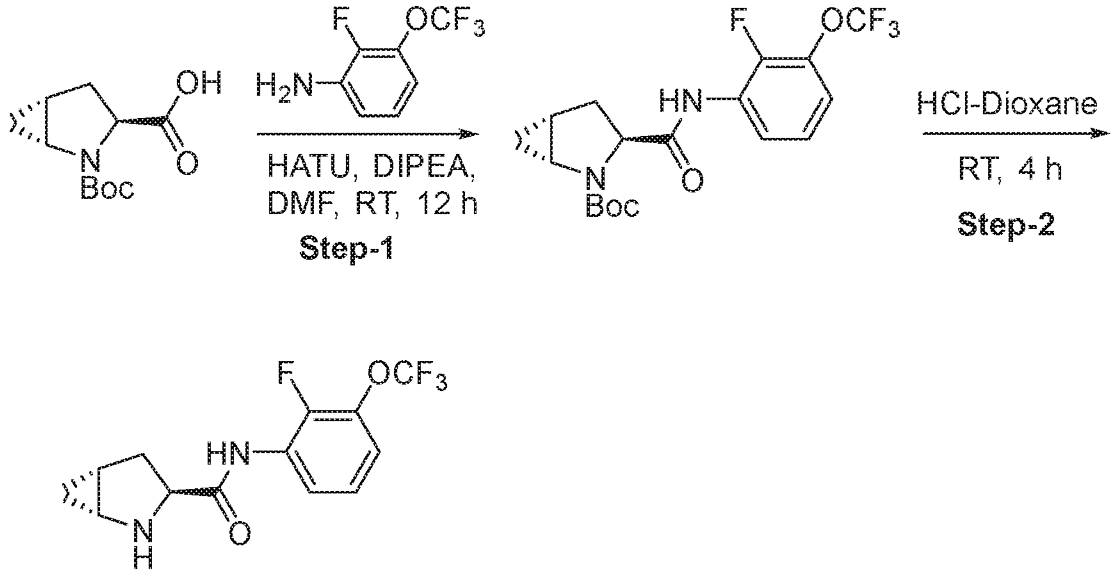
FIG. 9 is a two-step procedure to synthesize intermediate (1R,3S,5R)—N-(2-fluoro-3-(trifluoromethoxy)phenyl)-2-azabicyclo[3.1.0]hexane-3-carboxamide.
Figure 10:
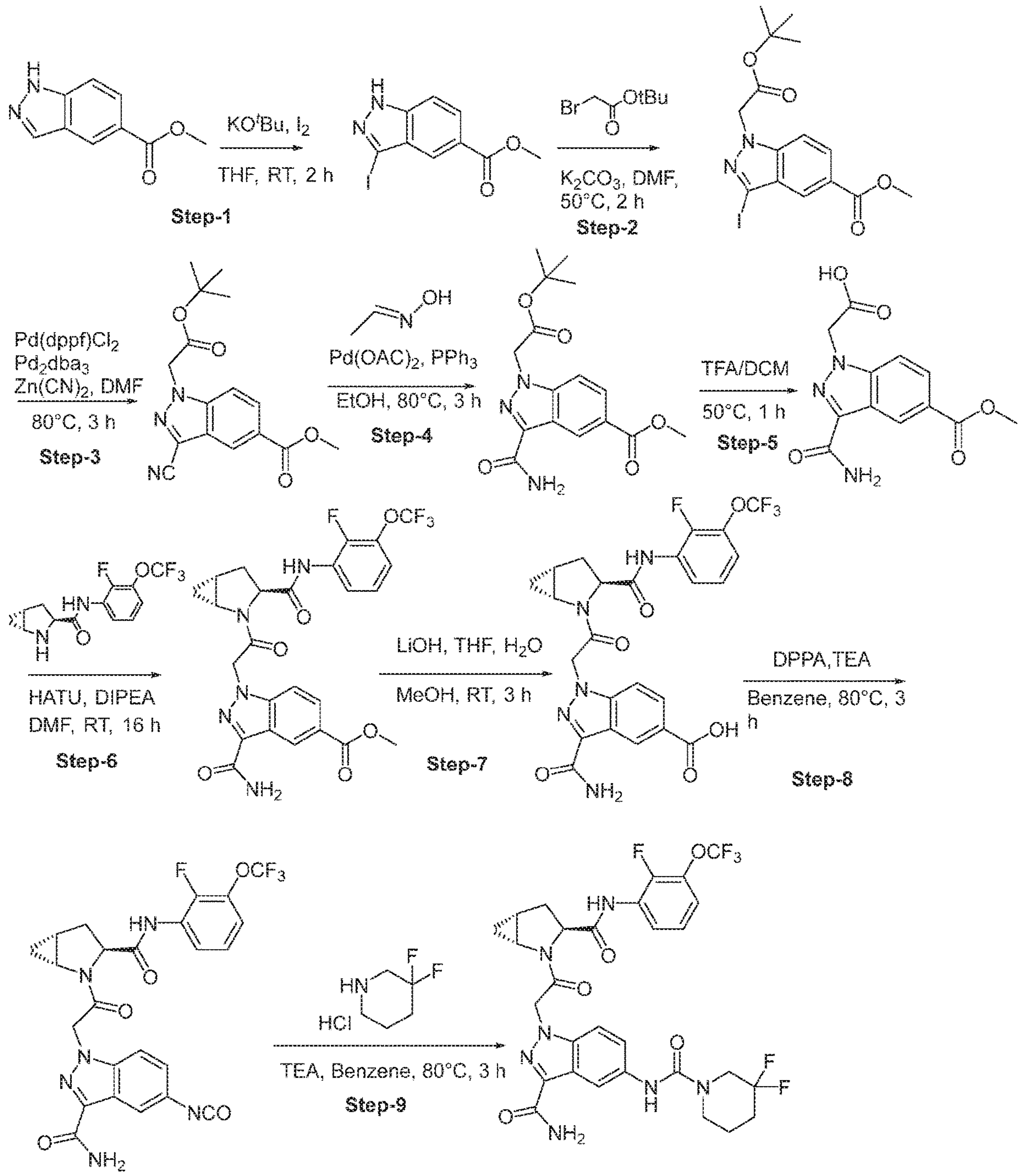
FIG. 10 is a nine-step synthesis to synthesize 5-(3,3-difluoropiperidine-1-carboxamido)-1-(2-((1R,3S,5R)-3-((2-fluoro-3-(trifluoromethoxy)phenyl)carbamoyl)-2-azabicyclo[3.1.0]hexan-2-yl)-2-oxoethyl)-1H-indazole-3-carboxamide.
Figure 11:
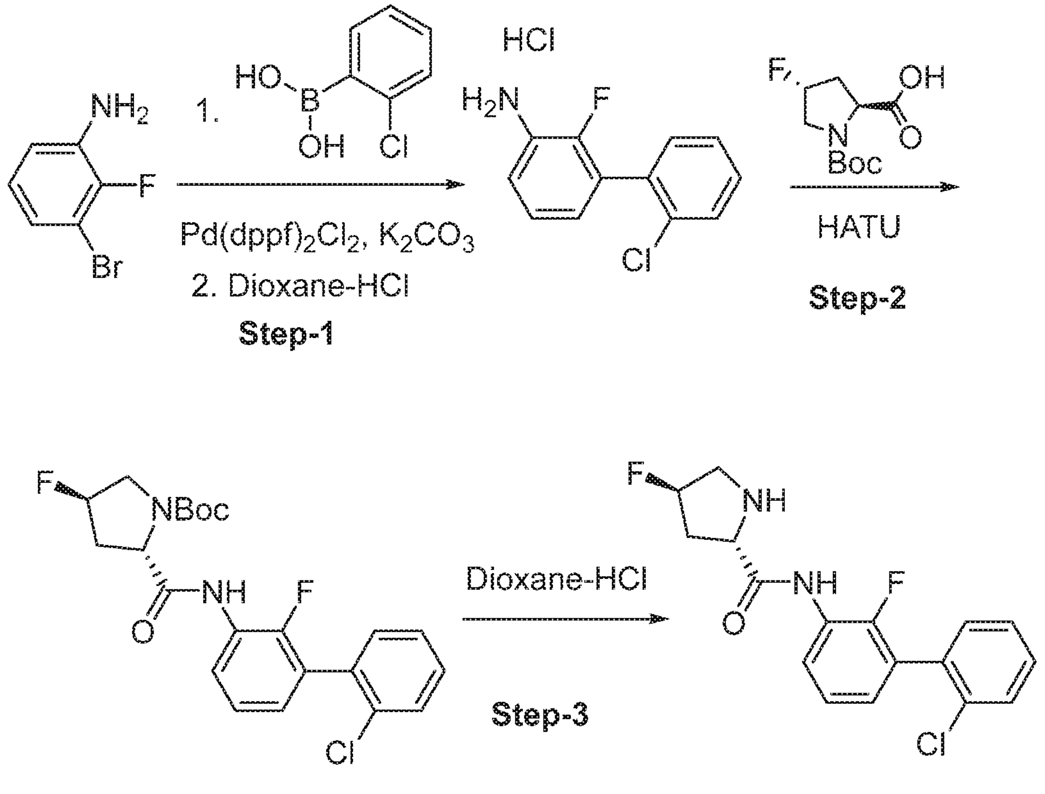
FIG. 11 is a three-step procedure to synthesize intermediate (2S,4R)—N-(2'-chloro-2-fluoro-[1,1'-biphenyl]-3-yl)-4-fluoropyrrolidine-2-carboxamide.
Figure 12:
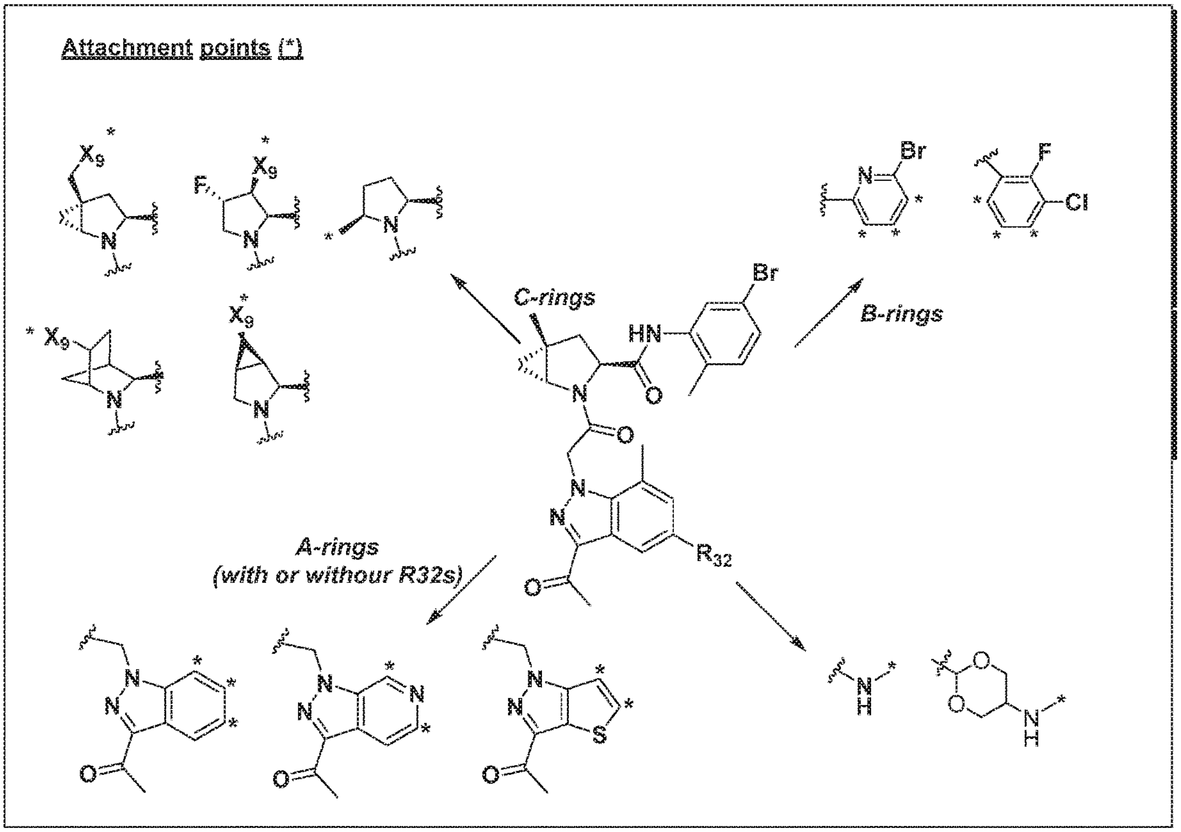
FIG. 12 is a schematic showing the various potential attachment points for $R^{301}$ functionality on the A-ring, B-ring, C-ring, or $R_{32}$ group.
Figure 13A:
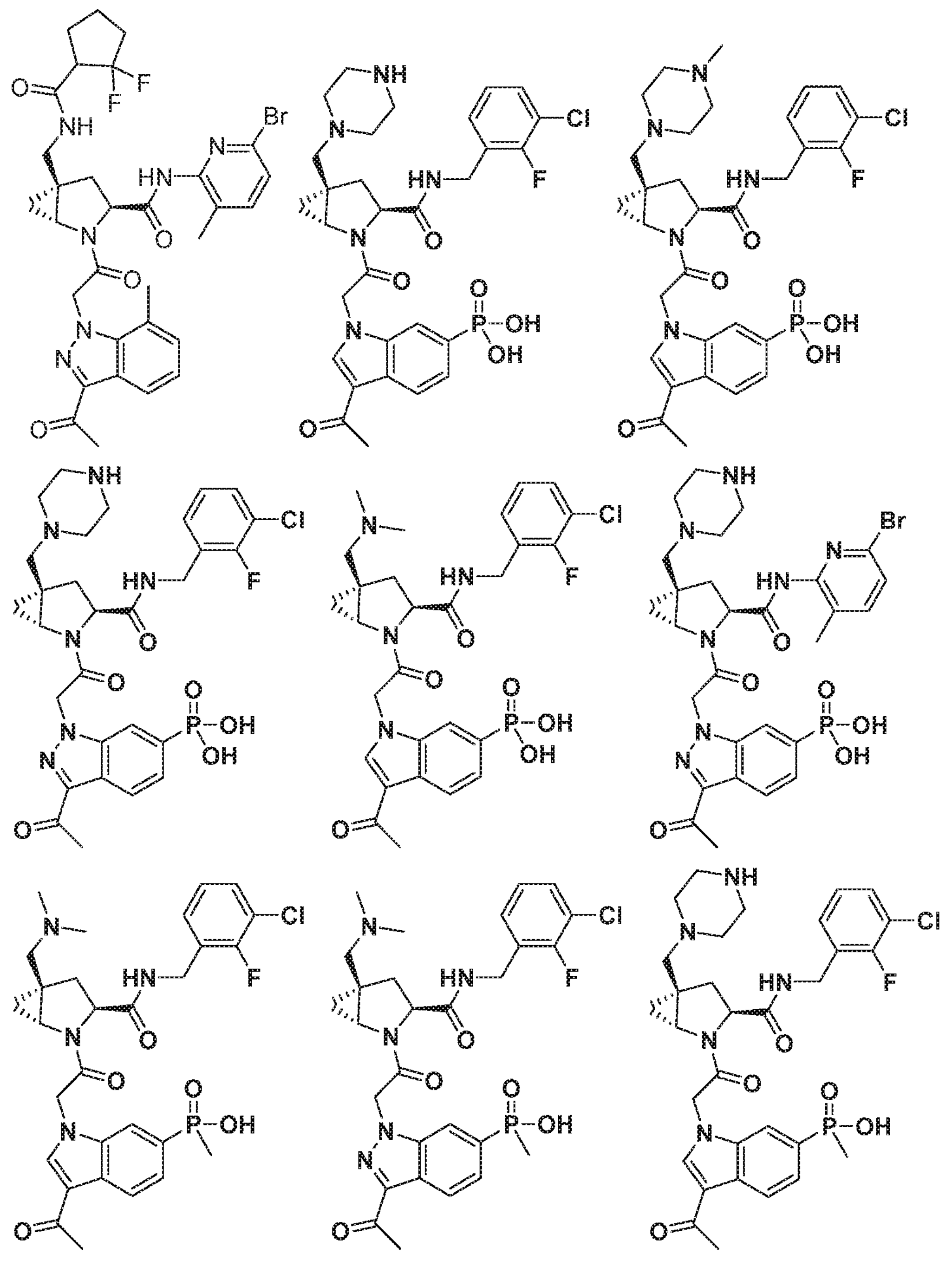
FIGS. 13A, 13B, and 13C are examples of compounds that exemplify Formula I, Formula II, and Formula III.
Figure 13B:
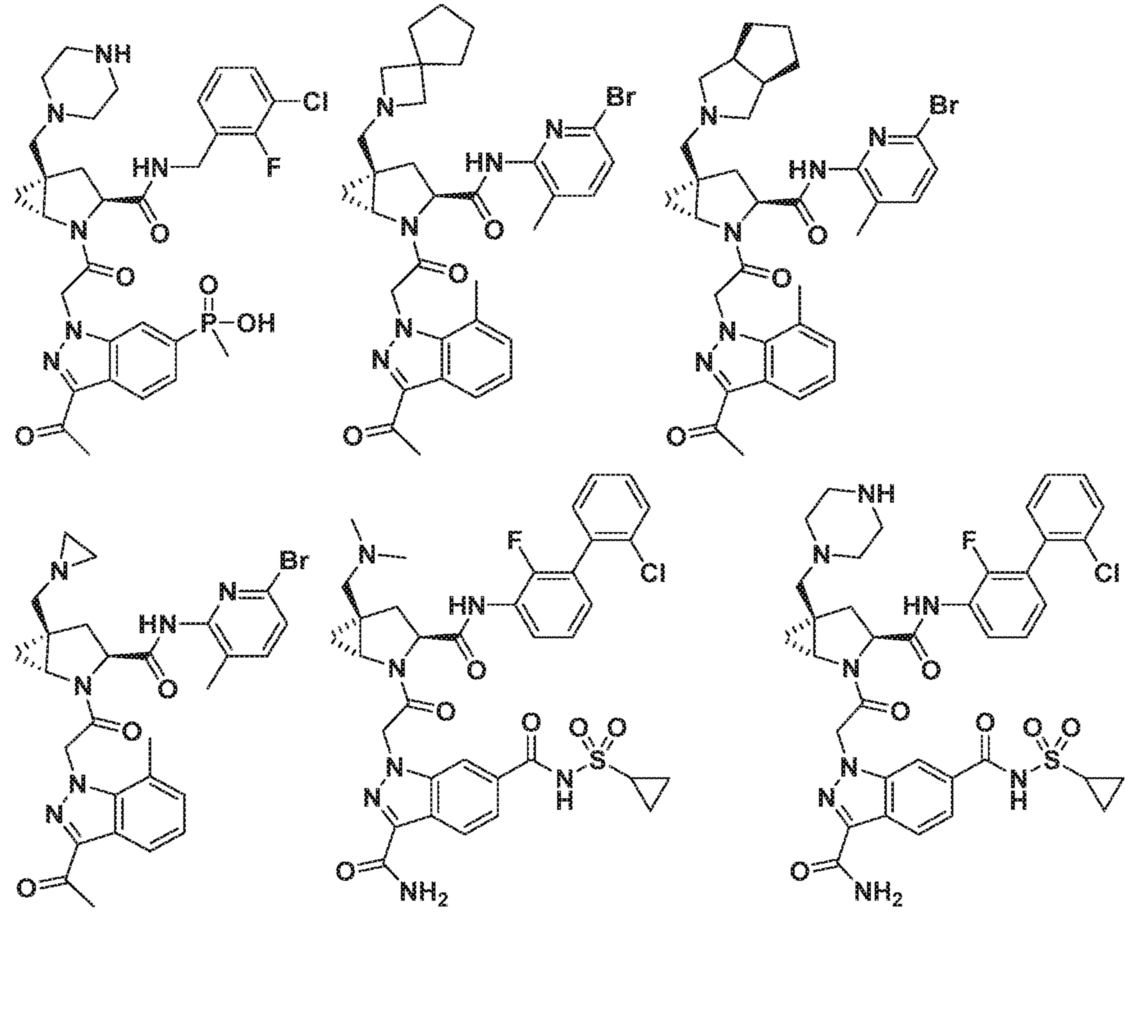
Figure 13C:
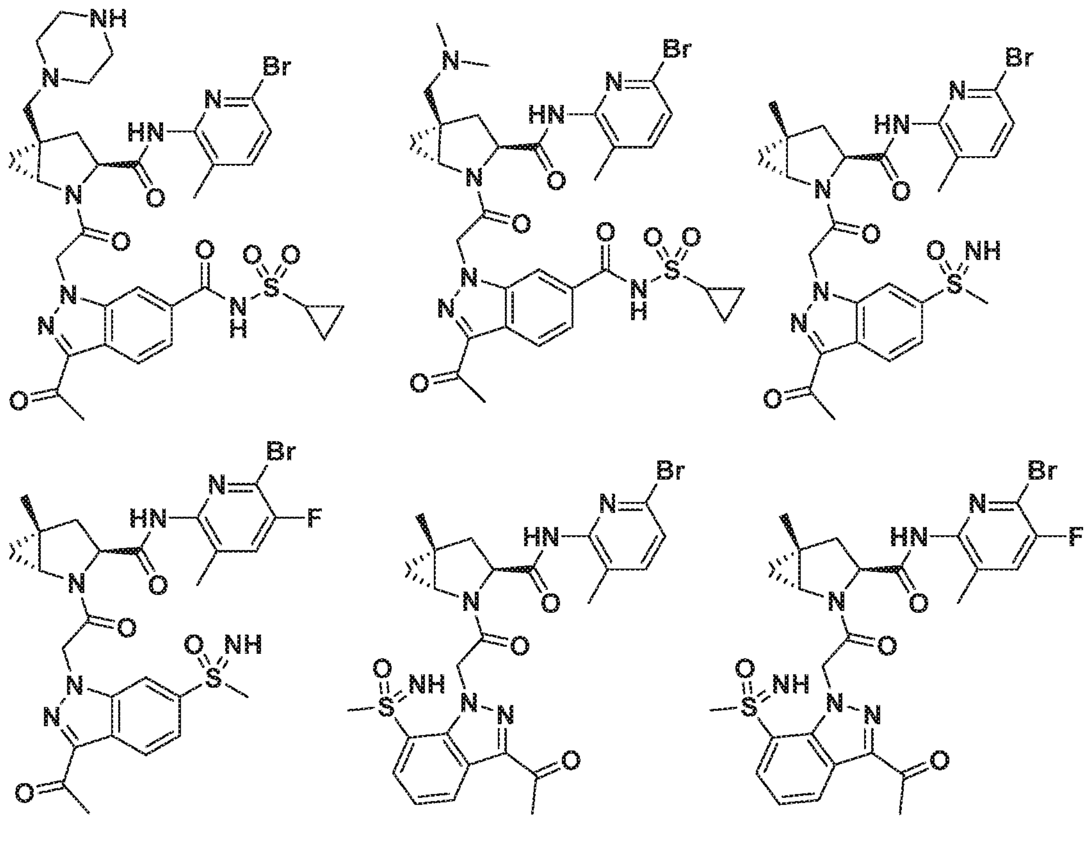
Figure 14:
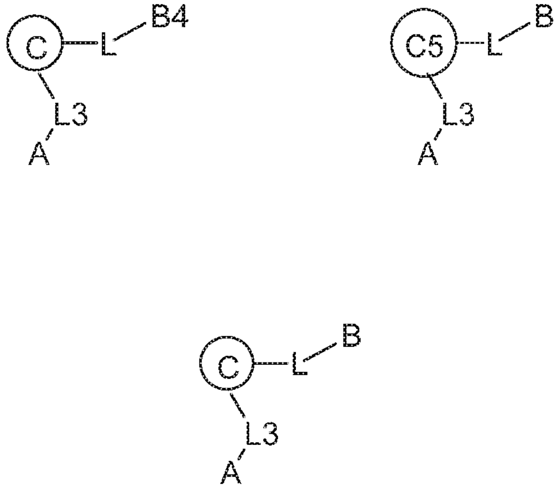
FIG. 14 depicts Formula I, Formula II, and Formula III.

Compounds are described using standard nomenclature. Unless defined otherwise, all technical and scientific terms used herein have the same meaning as is commonly understood by one of skill in the art to which this invention belongs.

The compounds in any of the Formulas described herein include enantiomers, mixtures of enantiomers, diastereomers, tautomers, racemates and other isomers, such as rotamers, as if each is specifically described, unless otherwise indicated or otherwise excluded by context.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

The present invention includes compounds of Formula I, Formula II, Formula III, or Formula IV with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. In one embodiment, isotopically labelled compounds can be used in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2H$) and tritium ($^3H$) may optionally be used anywhere in described structures that achieves the desired result. Alternatively or in addition, isotopes of carbon, e.g., $^{13}C$ and $^{14}C$, may be used. In one embodiment, the isotopic substitution is replacing hydrogen with a deuterium at one or more locations on the molecule to improve the performance of the drug, for example, the pharmacodynamics, pharmacokinetics, biodistribution, half-life, stability, AUC, Tmax, Cmax, etc. For example, the deuterium can be bound to carbon in a location of bond breakage during metabolism (an $\alpha$-deuterium kinetic isotope effect) or next to or near the site of bond breakage (a $\beta$-deuterium kinetic isotope effect).

Isotopic substitutions, for example deuterium substitutions, can be partial or complete. Partial deuterium substitution means that at least one hydrogen is substituted with deuterium. In certain embodiments, the isotope is 80, 85, 90, 95 or 99% or more enriched in an isotope at any location of interest. In one embodiments deuterium is 80, 85, 90, 95 or 99% enriched at a desired location. Unless otherwise stated, the enrichment at any point is above natural abundance. And in an embodiment is enough to alter a detectable property of the drug in a human.

In one embodiment, the substitution of a hydrogen atom for a deuterium atom can be provided in any of A1, A1', A2, B1, B1', B2, B3, B4, C1, C1', C2, C3, C4, L1, L1', L2, L2', L4 or L5. In one embodiment, the substitution of a hydrogen atom for a deuterium atom occurs within any R group. In one embodiment the R group is selected from any of R, R', $R^1$, $R^{1'}$, $R^2$, $R^{2'}$, $R^3$, $R^{3'}$, $R^4$, $R^5$, $R^6$, $R^{6'}$, $R^7$, $R^8$, $R^{8'}$, $R^{11}$, $R^{12}$, $R^{13}$, $R^{14}$, $R^{15}$, $R^{16}$, $R^{19}$, $R^{21}$, $R^{22}$, $R^{23}$, $R^{30}$, $R^{31}$, $R^{32}$, $R^{33}$, $R^{34}$, $R^{35}$, $R^{36}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{71}$, $R^{72}$, $R^{73}$, $R^{74}$, $R^{75}$, $R^{101}$, $R^{102}$, $R^{103}$, $R^{104}$, $R^{201}$, $R^{202}$, and $R^{301}$. For example, when any of R groups are, or contain for example through substitution, methyl, ethyl, or methoxy, the alkyl residue may be deuterated (in nonlimiting embodiments, $CD_3$, $CH_2CD_3$, $CD_2CD_3$, $CDH_2$, $CD_2H$, $CD_3$, $CHDCH_2D$, $CH_2CD_3$, CHD- $CHD_2$, $OCDH_2$, $OCD_2H$, or $OCD_3$ etc.). In certain other embodiments, an R group has a "'" or an "a" designation, which in one embodiment can be deuterated. In certain other embodiments, when two substituents of the central core ring are combined to form a cyclopropyl ring, the unsubstituted methylene carbon may be deuterated.

The compound of the present invention may form a solvate with solvents (including water). Therefore, in one embodiment, the invention includes a solvated form of the active compound. The term "solvate" refers to a molecular complex of a compound of the present invention (including a salt thereof) with one or more solvent molecules. Nonlimiting examples of solvents are water, ethanol, dimethyl sulfoxide, acetone and other common organic solvents. The term "hydrate" refers to a molecular complex comprising a compound of the invention and water. Pharmaceutically acceptable solvates in accordance with the invention include those wherein the solvent of crystallization may be isotopically substituted, e.g. $D_2O$, $d_6$-acetone, $d_6$-DMSO. A solvate can be in a liquid or solid form.

A dash ("-") that is not between two letters or symbols is used to indicate a point of attachment for a substituent. For example, —(C═O)$NH_2$ is attached through carbon of the keto (C═O) group.

The term "substituted", as used herein, means that any one or more hydrogens on the designated atom or group is replaced with a moiety selected from the indicated group, provided that the designated atom's normal valence is not exceeded and the resulting compound is stable. For example, when the substituent is oxo (i.e., ═O) then two hydrogens on the atom are replaced. For example a pyridyl group substituted by oxo is a pyridone. Combinations of substituents and/or variables are permissible only if such combinations result in stable compounds or useful synthetic intermediates.

A stable active compound refers to a compound that can be isolated and can be formulated into a dosage form with a shelf life of at least one month. A stable manufacturing intermediate or precursor to an active compound is stable if it does not degrade within the period needed for reaction or other use. A stable moiety or substituent group is one that does not degrade, react or fall apart within the period necessary for use. Nonlimiting examples of unstable moieties are those that combine heteroatoms in an unstable arrangement, as typically known and identifiable to those of skill in the art.

Any suitable group may be present on a "substituted" or "optionally substituted" position that forms a stable molecule and meets the desired purpose of the invention and includes, but is not limited to, e.g., halogen (which can independently be F, Cl, Br or I); cyano; hydroxyl; nitro; azido; alkanoyl (such as a $C_2$-$C_6$ alkanoyl group); carboxamide; alkyl, cycloalkyl, alkenyl, alkynyl, alkoxy, aryloxy such as phenoxy; thioalkyl including those having one or more thioether linkages; alkylsulfinyl; alkylsulfonyl groups including those having one or more sulfonyl linkages; aminoalkyl groups including groups having more than one N atoms; aryl (e.g., phenyl, biphenyl, naphthyl, or the like, each ring either substituted or unsubstituted); arylalkyl having for example, 1 to 3 separate or fused rings and from 6 to about 14 or 18 ring carbon atoms, with benzyl being an exemplary arylalkyl group; arylalkoxy, for example, having 1 to 3 separate or fused rings with benzyloxy being an exemplary arylalkoxy group; or a saturated or partially unsaturated heterocycle having 1 to 3 separate or fused rings with one or more N, O or S atoms, or a heteroaryl having 1 to 3 separate or fused rings with one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such groups may be further substituted, e.g. with hydroxy, alkyl, alkoxy, halogen and amino. In certain embodiments "optionally substituted" includes one or more substituents independently selected from halogen, hydroxyl, amino, cyano, —CHO, —COOH, —$CONH_2$, alkyl including $C_1$-$C_6$alkyl, alkenyl including $C_2$-$C_6$alkenyl, alkynyl including $C_2$-$C_6$alkynyl, —$C_1$-$C_6$alkoxy, alkanoyl including $C_2$-$C_6$alkanoyl, $C_1$-$C_6$alkylester, (mono- and di-$C_1$-$C_6$alkylamino)$C_0$-$C_2$alkyl, haloalkyl including $C_1$-$C_6$haloalkyl, hydoxy$C_1$-$C_6$alkyl, ester, carbamate, urea, sulfonamide, —$C_1$-$C_6$alkyl(heterocyclo), $C_1$-$C_6$alkyl(heteroaryl), —$C_1$-$C_6$alkyl($C_3$-$C_7$cycloalkyl), O—$C_1$-$C_6$alkyl ($C_3$-$C_7$cycloalkyl), $B(OH)_2$, phosphate, phosphonate and haloalkoxy including $C_1$-$C_6$haloalkoxy.

"Alkyl" is a branched or straight chain saturated aliphatic hydrocarbon group. In one embodiment, the alkyl contains from 1 to about 12 carbon atoms, more generally from 1 to about 6 carbon atoms or from 1 to about 4 carbon atoms. In one embodiment, the alkyl contains from 1 to about 8 carbon atoms. In certain embodiments, the alkyl is $C_1$-$C_2$, $C_1$-$C_3$, $C_1$-$C_4$, $C_1$-$C_5$ or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species. For example, the term $C_1$-$C_4$alkyl as used herein indicates a straight or branched alkyl group having from 1, 2, 3, or 4 carbon atoms and is intended to mean that each of these is described as an independent species. When $C_0$-$C_n$ alkyl is used herein in conjunction with another group, for example, ($C_3$-$C_7$cycloalkyl)$C_0$-$C_4$ alkyl, or —$C_0$-$C_4$alkyl($C_3$-$C_7$cycloalkyl), the indicated group, in this case cycloalkyl, is either directly bound by a single covalent bond ($C_0$alkyl), or attached by an alkyl chain in this case 1, 2, 3, or 4 carbon atoms. Alkyls can also be attached via other groups such as heteroatoms as in —O—$C_0$-$C_4$alkyl ($C_3$-$C_7$cycloalkyl). Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, 2,3-dimethylbutane, and hexyl. In one embodiment, the alkyl group is optionally substituted as described above. In one embodiment, trimethylsilyl can be used instead of t-butyl.

"Aliphatic" refers to a saturated or unsaturated, straight, branched, or cyclic hydrocarbon. "Aliphatic" is intended herein to include, but is not limited to, alkyl, alkenyl, alkynyl, cycloalkyl, cycloalkenyl, and cycloalkynyl moieties, and thus incorporates each of these definitions. In one embodiment, "aliphatic" is used to indicate those aliphatic groups having 1-20 carbon atoms. The aliphatic chain can be, for example, mono-unsaturated, di-unsaturated, tri-unsaturated, or polyunsaturated, or alkynyl. Unsaturated aliphatic groups can be in a cis or trans configuration. In one embodiment, the aliphatic group contains from 1 to about 12 carbon atoms, more generally from 1 to about 6 carbon atoms or from 1 to about 4 carbon atoms. In one embodiment, the aliphatic group contains from 1 to about 8 carbon atoms. In certain embodiments, the aliphatic group is $C_1$-$C_2$, $C_1$-$C_3$, $C_1$-$C_4$, $C_1$-$C_5$ or $C_1$-$C_6$. The specified ranges as used herein indicate an aliphatic group having each member of the range described as an independent species. For example, the term $C_1$-$C_6$ aliphatic as used herein indicates a straight or branched alkyl, alkenyl, or alkynyl group having from 1, 2, 3, 4, 5, or 6 carbon atoms and is intended to mean that each of these is described as an independent species. For example, the term $C_1$-$C_4$ aliphatic as used herein indicates a straight or branched alkyl, alkenyl, or alkynyl group having from 1, 2, 3, or 4 carbon atoms and is intended to mean that each of these is described as an independent species. In one embodiment, the aliphatic group is substituted with one or more functional groups that results in the formation of a stable moiety.

The term "heteroaliphatic" refers to an aliphatic moiety that contains at least one heteroatom in the chain, for example, an amine, carbonyl, carboxy, oxo, thio, phosphate, phosphonate, nitrogen, phosphorus, silicon, or boron atoms in place of a carbon atom. In one embodiment, the only heteroatom is nitrogen. In one embodiment, the only heteroatom is oxygen. In one embodiment, the only heteroatom is sulfur. "Heteroaliphatic" is intended herein to include, but is not limited to, heteroalkyl, heteroalkenyl, heteroalkynyl, heterocycloalkyl, heterocycloalkenyl, and heterocycloalkynyl moieties. In one embodiment, "heteroaliphatic" is used to indicate a heteroaliphatic group (cyclic, acyclic, substituted, unsubstituted, branched or unbranched) having 1-20 carbon atoms. In one embodiment, the heteroaliphatic group is optionally substituted in a manner that results in the formation of a stable moiety. Nonlimiting examples of heteroaliphatic moieties are polyethylene glycol, polyalkylene glycol, amide, polyamide, polylactide, polyglycolide, thioether, ether, alkyl-heterocycle-alkyl, —O-alkyl-O-alkyl, alkyl-O-haloalkyl, etc.

In one embodiment, when a term is used that includes "alk" it should be understood that "cycloalkyl" or "carbocyclic" can be considered part of the definition, unless unambiguously excluded by the context. For example and without limitation, the terms alkyl, alkenyl, alkynyl, alkoxy, alkanoyl, alkenloxy, haloalkyl, aminoalkyl, alkylene, alkenylene, alkynylene, etc. can all be considered to include the cyclic forms of alkyl, unless unambiguously excluded by context.

"Alkenyl" is a branched or straight chain aliphatic hydrocarbon group having one or more carbon-carbon double bonds that may occur at a stable point along the chain. Nonlimiting examples are $C_2$-$C_8$alkenyl, $C_2$-$C_7$alkenyl, $C_2$-$C_6$alkenyl, $C_2$-$C_5$alkenyl and $C_2$-$C_4$alkenyl. The specified ranges as used herein indicate an alkenyl group having each member of the range described as an independent species, as described above for the alkyl moiety. Examples of alkenyl include, but are not limited to, ethenyl and propenyl. In one embodiment, the alkenyl group is optionally substituted as described above.

"Alkynyl" is a branched or straight chain aliphatic hydrocarbon group having one or more carbon-carbon triple bonds that may occur at any stable point along the chain, for example, $C_2$-$C_8$alkynyl or $C_2$-$C_6$alkynyl. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In one embodiment, the alkynyl group is optionally substituted as described above.

"Alkylene" is a bivalent saturated hydrocarbon. Alkylenes, for example, can be a 1, 2, 3, 4, 5, 6, 7 to 8 carbon moiety, 1 to 6 carbon moiety, or an indicated number of carbon atoms, for example $C_1$-$C_2$alkylene, $C_1$-$C_3$alkylene, $C_1$-$C_4$alkylene, $C_1$-$C_5$alkylene, or $C_1$-$C_6$alkylene.

"Alkenylene" is a bivalent hydrocarbon having at least one carbon-carbon double bond. Alkenylenes, for example, can be a 2 to 8 carbon moiety, 2 to 6 carbon moiety, or an indicated number of carbon atoms, for example $C_2$-$C_4$alkenylene.

"Alkynylene" is a bivalent hydrocarbon having at least one carbon-carbon triple bond. Alkynylenes, for example, can be a 2 to 8 carbon moiety, 2 to 6 carbon moiety, or an indicated number of carbon atoms, for example $C_2$-$C_4$alkynylene.

"Alkoxy" is an alkyl group as defined above covalently bound through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly an "alkylthio" or a "thioalkyl" group is an alkyl group as defined above with the indicated number of carbon atoms covalently bound through a sulfur bridge (—S—). In one embodiment, the alkoxy group is optionally substituted as described above.

"Alkenyloxy" is an alkenyl group as defined covalently bound to the group it substitutes by an oxygen bridge (—O—).

"Alkanoyl" is an alkyl group as defined above covalently bound through a carbonyl (C═O) bridge. The carbonyl carbon is included in the number of carbons, that is $C_2$alkanoyl is a $CH_3$(C═O)— group. In one embodiment, the alkanoyl group is optionally substituted as described above.

"Alkylester" is an alkyl group as defined herein covalently bound through an ester linkage. The ester linkage may be in either orientation, e.g., a group of the formula —O(C═O)alkyl or a group of the formula —(C═O)Oalkyl.

"Amide" or "carboxamide" is —C(O)N$R^a$$R^b$ wherein $R^a$ and $R^b$ are each independently selected from hydrogen, alkyl, for example, alkyl including $C_1$-$C_6$alkyl, alkenyl, for example, $C_2$-$C_6$alkenyl, alkynyl, for example, $C_2$-$C_6$alkynyl, —$C_0$-$C_4$alkyl($C_3$-$C_7$cycloalkyl), —$C_0$-$C_4$alkyl($C_3$-$C_7$heterocycloalkyl), —$C_0$-$C_4$alkyl(aryl), and —$C_0$-$C_4$alkyl(heteroaryl); or together with the nitrogen to which they are bonded, $R^a$ and $R^b$ can form a $C_3$-$C_7$heterocyclic ring. In one embodiment, the $R^a$ and $R^b$ groups are each independently be optionally substituted as described herein.

"Carbocyclic group", "carbocyclic ring", or "cycloalkyl" is a saturated or partially unsaturated (i.e., not aromatic) group containing all carbon ring atoms. A carbocyclic group typically contains 1 ring of 3 to 7 carbon atoms or 2 fused rings each containing 3 to 7 carbon atoms. Cycloalkyl substituents may be pendant from a substituted nitrogen or carbon atom, or a substituted carbon atom that may have two substituents can have a cycloalkyl group, which is attached as a spiro group. Examples of carbocyclic rings include cyclohexenyl, cyclohexyl, cyclopentenyl, cyclopentyl, cyclobutenyl, cyclobutyl and cyclopropyl rings. In one embodiment, the carbocyclic ring is optionally substituted as described above. In one embodiment, the cycloalkyl is a partially unsaturated (i.e., not aromatic) group containing all carbon ring atoms. In another embodiment, the cycloalkyl is a saturated group containing all carbon ring atoms.

"Carbocyclic-oxy group" is a monocyclic carbocyclic ring or a mono- or bi-cyclic carbocyclic group as defined above attached to the group it substitutes via an oxygen, —O—, linker.

"Haloalkyl" indicates both branched and straight-chain alkyl groups substituted with 1 or more halogen atoms, up to the maximum allowable number of halogen atoms. Examples of haloalkyl include, but are not limited to, trifluoromethyl, monofluoromethyl, difluoromethyl, 2-fluoroethyl, and penta-fluoroethyl.

"Haloalkoxy" indicates a haloalkyl group as defined herein attached through an oxygen bridge (oxygen of an alcohol radical).

"Hydroxyalkyl" is an alkyl group as previously described, substituted with at least one hydroxyl substituent.

"Aminoalkyl" is an alkyl group as previously described, substituted with at least one amino substituent.

"Halo" or "halogen" indicates independently, any of fluoro, chloro, bromo or iodo.

"Aryl" indicates an aromatic group containing only carbon in the aromatic ring or rings. In one embodiment, the aryl group contains 1 to 3 separate or fused rings and is 6 to about 14 or 18 ring atoms, without heteroatoms as ring members. When indicated, such aryl groups may be further substituted with carbon or non-carbon atoms or groups. Such substitution may include fusion to a 4 to 7 or a 5 to 7-membered saturated or partially unsaturated cyclic group that optionally contains 1, 2 or 3 heteroatoms independently selected from N, O, B, P, Si and/or S, to form, for example, a 3,4-methylenedioxyphenyl group. Aryl groups include, for example, phenyl and naphthyl, including 1-naphthyl and 2-naphthyl. In one embodiment, aryl groups are pendant. An example of a pendant ring is a phenyl group substituted with a phenyl group. In one embodiment, the aryl group is optionally substituted as described above.

The term "heterocycle," or "heterocyclic ring" as used herein refers to a saturated or a partially unsaturated (i.e., having one or more double and/or triple bonds within the ring without aromaticity) cyclic moiety of 3 to about 12, and more typically 3, 4, 5, 6, 7, 8 to 10 ring atoms in which at least one ring atom is a heteroatom selected from nitrogen, oxygen, phosphorus, sulfur, silicon, and boron, the remaining ring atoms being C, where one or more ring atoms is optionally substituted independently with one or more substituents described above. A heterocycle may be a monocycle having 3 to 7 ring members (2 to 6 carbon atoms and 1 to 4 heteroatoms selected from N, O, P, S, Si and B) or a bicycle having 6 to 10 ring members (4 to 9 carbon atoms and 1 to 6 heteroatoms selected from N, O, P, S, Si and B), for example: a bicyclo [4,5], [5,5], [5,6], or [6,6] system. In one embodiment, the only heteroatom is nitrogen. In one embodiment, the only heteroatom is oxygen. In one embodiment, the only heteroatom is sulfur, boron, or silicon. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. Examples of heterocyclic rings include, but are not limited to, pyrrolidinyl, dihydrofuranyl, tetrahydrothienyl, tetrahydropyranyl, dihydropyranyl, tetrahydrothiopyranyl, piperidino, piperidonyl, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, dihydroisoquinolinyl, tetrahydroisoquinolinyl, pyrazolidinylimidazolinyl, imidazolidinyl, 2-oxa-5-azabicyclo[2.2.2]octane, 3-oxa-8-azabicyclo[3.2.1]octane, 8-oxa-3-azabicyclo[3.2.1]octane, 6-oxa-3-azabicyclo[3.1.1]heptane, 2-oxa-5-azabicyclo[2.2.1]heptane, 3-azabicyco[3.1.0]hexanyl, 3-azabicyclo[4.1.0]heptanyl, azabicyclo[2.2.2]hexanyl, 3H-indolyl, quinolizinyl, N-pyridyl ureas, and pyrrolopyrimidine. Spiro moieties are also included within the scope of this definition. Examples of a heterocyclic group wherein 1 or 2 ring carbon atoms are substituted with oxo (═O) moieties are pyrimidinonyl and 1,1-dioxo-thiomorpholinyl. The heterocycle groups herein are optionally substituted independently with one or more substituents described herein, for example, 1, 2, or 3 substituents.

"Heterocyclicoxy group" is a monocyclic heterocyclic ring or a bicyclic heterocyclic group as described previously linked to the group it substitutes via an oxygen, —O—, linker.

"Heteroaryl" refers to a stable monocyclic, bicyclic, or multicyclic aromatic ring which contains from 1 to 3, or in some embodiments from 1, 2, or 3 heteroatoms selected from N, O, S, B or P with remaining ring atoms being carbon, or a stable bicyclic or tricyclic system containing at least one 5, 6, or 7 membered aromatic ring which contains from 1 to 3, or in some embodiments from 1 to 2, heteroatoms selected from N, O, S, B or P with remaining ring atoms being carbon. In one embodiment, the only heteroatom is nitrogen. In one embodiment, the only heteroatom is oxygen. In one embodiment, the only heteroatom is sulfur. Monocyclic heteroaryl groups typically have from 5, 6, or 7 ring atoms. In some embodiments bicyclic heteroaryl groups are 8- to 10-membered heteroaryl groups, that is, groups containing 8 or 10 ring atoms in which one 5, 6, or 7 member aromatic ring is fused to a second aromatic or non-aromatic ring. When the total number of S and O atoms in the heteroaryl group exceeds 1, these heteroatoms are not adjacent to one another. In one embodiment, the total number of S and O atoms in the heteroaryl group is not more than 2. In another embodiment, the total number of S and O atoms in the aromatic heterocycle is not more than 1. Examples of heteroaryl groups include, but are not limited to, pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, tetrahydrofuranyl, and furopyridinyl. In another embodiment "heteroaryl" is tetrazole. Heteroaryl groups are optionally substituted independently with one or more substituents described herein. "Heteroaryloxy" is a heteroaryl group as described bound to the group it substituted via an oxygen, —O—, linker.

"Heterocycloalkyl" is a fully saturated heterocycle as defined herein. It may have, for example, include 1, 2, 3, or 4 heteroatoms independently selected from N, S, O, Si and B with the remaining ring atoms being carbon. In a typical embodiment, nitrogen is the heteroatom. Monocyclic heterocycloalkyl groups typically have from 3 to about 8 ring atoms or from 4 to 6 ring atoms.

The term "mono- and/or di-alkylamino" indicate a secondary or tertiary alkylamino group, wherein the alkyl groups are independently selected as defined herein. The point of attachment of the alkylamino group is on the nitrogen. Examples of mono- and di-alkylamino groups include ethylamino, dimethylamino, and methyl-propyl-amino.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

"Pharmaceutical compositions" are compositions comprising at least one active agent, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

A "pharmaceutically acceptable salt" is a derivative of the disclosed compound in which the parent compound is modified by making inorganic and organic, pharmaceutically acceptable, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include salts which are acceptable for human consumption and the quaternary ammonium salts of the parent compound formed, for example, from inorganic or organic acids. Examples, of such salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC—(CH_2)_n—COOH$ where n is 0-4, and the like, or using a different acid that produces the same counterion. Lists of additional suitable salts may be found, e.g., in *Remington's Pharmaceutical Sciences,* 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, acceptable for human consumption, and neither biologically nor otherwise inappropriate for administration to a host, typically a human. In one embodiment, an excipient is used that is acceptable for veterinary use.

A "patient" or "host" or "subject" is a human or non-human animal in need of treatment or prevention of any of the disorders as specifically described herein, including but not limited to by modulation of the Complement Factor D pathway or with a condition that is treatable with one of the compounds described herein. Typically the host is a human. A "patient" or "host" or "subject" also refers to for example, a mammal, primate (e.g., human), cows, sheep, goat, horse, dog, cat, rabbit, rat, mice, bird and the like.

A "prodrug" as used herein, means a compound which when administered to a host in vivo is converted into a parent drug. As used herein, the term "parent drug" means any of the presently described chemical compounds herein. Prodrugs can be used to achieve any desired effect, including to enhance properties of the parent drug or to improve the pharmaceutic or pharmacokinetic properties of the parent, including to increase the half-life of the drug in vivo. Prodrug strategies provide choices in modulating the conditions for in vivo generation of the parent drug. Nonlimiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others. In certain embodiments, the prodrug renders the parent compound more lipophilic. In certain embodiments, a prodrug can be provided that has several prodrug moieties in linear, branched or cyclic manner. For example, nonlimiting embodiments include the use of a divalent linker moiety such as a dicarboxylic acid, amino acid, diamine, hydroxycarboxylic acid, hydroxyamine, di-hydroxy compound, or other compound that has at least two functional groups that can link the parent molecule with another prodrug moiety, and is typically biodegradable in vivo. In some embodiments, 2, 3, 4 or 5 prodrug biodegradable moieties are covalently bound in sequence, branched or cyclic fashion to the parent compound. Nonlimiting examples of prodrugs according to the present invention are formed with:

a. a carboxylic acid on the parent drug and a hydroxylated prodrug moiety to form an ester;
b. a carboxylic acid on the parent drug and an amine prodrug to form an amide;
c. an amino on the parent drug and a carboxylic acid prodrug moiety to form an amide,
d. an amino on the parent drug and a sulfonic acid to form a sulfonamide;
e. a sulfonic acid on the parent drug and an amino on the prodrug moiety to form a sulfonamide;
f. a hydroxyl group on the parent drug and a carboxylic acid on the prodrug moiety to form an ester;
g. a hydroxyl on the parent drug and a hydroxylated prodrug moiety to form an ether;
h. a phosphonate on the parent drug and a hydroxylated prodrug moiety to form a phosphonate ester;
i. a phosphoric acid on the parent drug and a hydroxylated prodrug moiety to form a phosphate ester;
j. a hydroxyl on the parent drug and a phosphonate on the prodrug to form a phosphonate ester;
k. a hydroxyl on the parent drug and a phosphoric acid prodrug moiety to form a phosphate ester;

l. a carboxylic acid on the parent drug and a prodrug of the structure HO—$(CH_2)_2$—O—($C_{2-24}$ aliphatic group), for example, HO—$(CH_2)_2$—O—($C_{2-24}$ alkyl group) to form an ester;

m. a carboxylic acid on the parent drug and a prodrug of the structure HO—$(CH_2)_2$—S—($C_{2-24}$ aliphatic group), for example, HO—$(CH_2)_2$—S—($C_{2-24}$ alkyl group) to form a thioester;

n. a hydroxyl on the parent drug and a prodrug of the structure HO—$(CH_2)_2$—O—($C_{2-24}$ aliphatic group), for example, HO—$(CH_2)_2$—O—($C_{2-24}$ alkyl group) to form an ether;

o. a carboxylic acid on the parent drug and a prodrug of the structure HO—$(CH_2)_2$—S—($C_{2-24}$ aliphatic group), for example, HO—$(CH_2)_2$—S—($C_{2-24}$ alkyl group), to form a thioether; and p. a carboxylic acid, oxime, hydrazide, hydrazone, amine or hydroxyl on the parent compound and a prodrug moiety that is a biodegradable polymer or oligomer including but not limited to polylactic acid, polylactide-co-glycolide, polyglycolide, polyethylene glycol, polyanhydride, polyester, polyamide or a peptide.

An exemplary synthesis of Oxime linkages is provided in the paper published by Jin et. al. titled "Oxime Linkage: A Robust Tool for the Design of PH-Sensitive Polymeric Drug Carriers" in BioMacromolecules, 2011, 12(10), 3460-3468.

In one embodiment, a prodrug is provided by attaching a natural or non-natural amino acid to an appropriate functional moiety on the parent compound, for example, oxygen, nitrogen or sulfur, and typically oxygen or nitrogen, usually in a manner such that the amino acid can be cleaved in vivo to provide the parent drug. The amino acid can be used alone or covalently linked (straight, branched or cyclic) to one or more other prodrug moieties to modify the parent drug to achieve the desired performance, such as increased half-life, lipophilicity, or other drug delivery or pharmacokinetic properties. The amino acid can be any compound with an amino group and a carboxylic acid, which includes an aliphatic amino acid, alkyl amino acid, aromatic amino acid, heteroaliphatic amino acid, heteroalkyl amino acid, or heterocyclic amino acid or heteroaryl amino acid.

"Providing a compound with at least one additional active agent," for example, in one embodiment can mean that the compound and the additional active agent(s) are provided simultaneously in a single dosage form, provided concomitantly in separate dosage forms, or provided in separate dosage forms for administration. In one embodiment, the compound administrations are separated by some amount of time that is within the time in which both the compound and the at least one additional active agent are within the blood stream of a patient. In certain embodiments the compound and the additional active agent need not be prescribed for a patient by the same medical care worker. In certain embodiments the additional active agent or agents need not require a prescription. Administration of the compound or the at least one additional active agent can occur via any appropriate route, for example, oral tablets, oral capsules, oral liquids, inhalation, injection, suppositories, parenteral, sublingual, buccal, intravenous, intraaortal, transdermal, polymeric controlled delivery, non-polymeric controlled delivery, nano or microparticles, liposomes, and/or topical contact. In one embodiment, the instructions for administration in a form of combination therapy is provided in the drug labeling.

A "therapeutically effective amount" of a pharmaceutical composition/combination of this invention means an amount effective, when administered to a host, to provide a therapeutic benefit such as an amelioration of symptoms or reduction or dimunition of the disease itself. In one embodiment, a therapeutically effective amount is an amount sufficient to prevent a significant increase or will significantly reduce the detectable level of Complement Factor D in the patient's blood, serum, or tissues.

Detailed Description of the Active Compounds

N-Oxides

In certain embodiments, any of the active compounds can be provided in its N-oxide form to a patient in need thereof. In one embodiment, an N-oxide of an active compound or a precursor of the active compound is used in a manufacturing scheme. In yet another embodiment, the N-oxide is a metabolite of administration of one of the active compounds herein, and may have independent activity. The N-oxide can be formed by treating the compound of interest with an oxidizing agent, for example a suitable peroxyacid or peroxide, to generate an N-oxide compound. For example, a heteroaryl group, for example a pyridyl group, can be treated with an oxidizing agent such as sodium percarbonate in the presence of a rhenium-based catalyst under mild reaction conditions to generate an N-oxide compound. A person skilled in the art will understand that appropriate protecting groups may be necessary to carry out the chemistry. See, Jain, S. L. et al., "Rhenium-Catalyzed Highly Efficient Oxidations of Tertiary Nitrogen Compounds to N-Oxides Using Sodium Percarbonate as Oxygen Source, Synlett, 2261-2663, 2006.

In one embodiment the N-oxide is in the A-Ring. In one embodiment the N-oxide is in the B-Ring. In one embodiment the N-oxide is on the $R^{32}$ group.

In other embodiments, any of the active compounds with a sulfur can be provided in its sulfoxide or sulfone form to a patient in need thereof. In a different embodiment, a sulfoxide or sulfone of one of the active compounds or a precursor of the active compound is used in a manufacturing scheme. A sulfur atom in a selected compound as described herein can be oxidized to form a sulfoxide

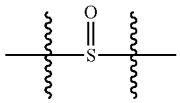 [SMILES: *S(*)=O]

or a sulfone

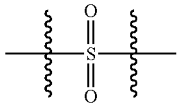 [SMILES: *S(*)(=O)=O]

using known methods. For example, the compound 1,3,5-triazo-2,4,6-triphosphorine-2,2,4,4,6,6-tetrachloride (TAPC) is an efficient promoter for the oxidation of sulfides to sulfoxides. See, Bahrami, M. et al., "TAPC-Promoted Oxidation of sulfides and Deoxygenation of Sulfoxides", J. Org. Chem., 75, 6208-6213 (2010). Oxidation of sulfides with 30% hydrogen peroxide catalyzed by tantalum carbide provides sulfoxides in high yields, see, Kirihara, A., et al., "Tantalum Carbide or Niobium Carbide Catalyzed Oxidation of Sulfides with Hydrogen Peroxide: Highly Efficient and Chemoselective Syntheses of Sulfoxides and Sulfones", Synlett, 1557-1561 (2010). Sulfides can be oxidized to sulfones using, for example, niobium carbide as the catalyst, see, Kirihara, A., et al., "Tantalum Cardide or Niobium Carbide Catalyzed Oxidation of Sulfides with Hydrogen Peroxide: Highly Efficient and Chemoselective Syntheses of Sulfoxides and Sulfones", Synlett, 1557-1561 (2010). Urea-hydrogen peroxide adduct is a stable inexpensive and easily handled reagent for the oxidation of sulfides to sulfones, see Varma, R. S. and Naicker, K. P., "The Urea-Hydrogen Peroxide Complex: Solid-State Oxidative Protocols for Hydroxylated Aldehydes and Ketones (Dakin Reaction), Nitriles, Sulfides, and Nitrogen Heterocycles", Org. Lett., 1, 189-191 (1999). One skilled in the art will appreciate that other heteroatoms, such as nitrogen, may need to be protected and then deprotected while carrying out the oxidation of a sulfur atom to produce the desired compound.

Embodiments of "Alkyl"

In one embodiment "alkyl" is a $C_1$-$C_{10}$alkyl, $C_1$-$C_9$alkyl, $C_1$-$C_8$alkyl, $C_1$-$C_7$alkyl, $C_1$-$C_6$alkyl, $C_1$-$C_5$alkyl, $C_1$-$C_4$alkyl, $C_1$-$C_3$alkyl, or $C_1$-$C_2$alkyl.

In one embodiment "alkyl" has one carbon.

In one embodiment "alkyl" has two carbons.

In one embodiment "alkyl" has three carbons.

In one embodiment "alkyl" has four carbons.

In one embodiment "alkyl" has five carbons.

In one embodiment "alkyl" has six carbons.

Non-limiting examples of"alkyl" include: methyl, ethyl, propyl, butyl, pentyl, and hexyl.

Additional non-limiting examples of "alkyl" include: isopropyl, isobutyl, isopentyl, and isohexyl.

Additional non-limiting examples of "alkyl" include: sec-butyl, sec-pentyl, and sec-hexyl.

Additional non-limiting examples of "alkyl" include: tert-butyl, tert-pentyl, and tert-hexyl.

Additional non-limiting examples of "alkyl" include: neopentyl, 3-pentyl, and active pentyl.

In one embodiment "alkyl" is "substituted alkyl"

In one embodiment "alkenyl" is "substituted alkenyl"

In one embodiment "alkynyl" is "substituted alkynyl"

Embodiments of "Haloalkyl"

In one embodiment "haloalkyl" is a $C_1$-$C_{10}$haloalkyl, $C_1$-$C_9$haloalkyl, $C_1$-$C_8$haloalkyl, $C_1$-$C_7$haloalkyl, $C_1$-$C_6$haloalkyl, $C_1$-$C_5$haloalkyl, $C_1$-$C_4$haloalkyl, $C_1$-$C_3$haloalkyl, and $C_1$-$C_2$haloalkyl.

In one embodiment "haloalkyl" has one carbon.

In one embodiment "haloalkyl" has one carbon and one halogen.

In one embodiment "haloalkyl" has one carbon and two halogens.

In one embodiment "haloalkyl" has one carbon and three halogens.

In one embodiment "haloalkyl" has two carbons.

In one embodiment "haloalkyl" has three carbons.

In one embodiment "haloalkyl" has four carbons.

In one embodiment "haloalkyl" has five carbons.

In one embodiment "haloalkyl" has six carbons.

Non-limiting examples of "haloalkyl" include:

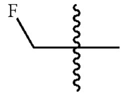,
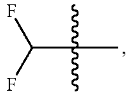, and
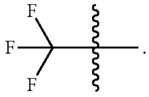.

Additional non-limiting examples of "haloalkyl" include:

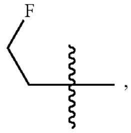,
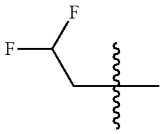,
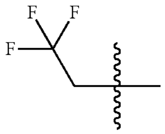,
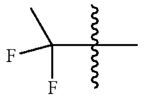,
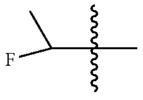,
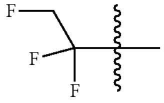,
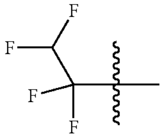,
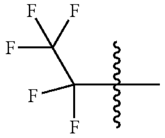,
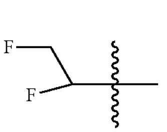,
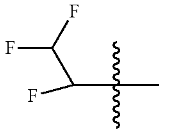, and
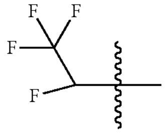.

Additional non-limiting examples of"haloalkyl" include:

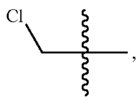,
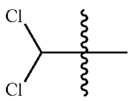, and
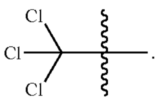.

Additional non-limiting examples of "haloalkyl" include:

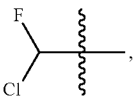,
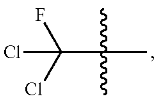, and
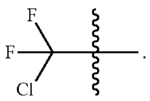.

Embodiments of "Aryl"

In one embodiment "aryl" is a 6 carbon aromatic group (phenyl)

In one embodiment "aryl" is a 10 carbon aromatic group (napthyl)

In one embodiment "aryl" is "substituted aryl".

Embodiments of "Heteroaryl"

In one embodiment "heteroaryl" is a 5 membered aromatic group containing 1, 2, or 3, nitrogen atoms.

Non-limiting examples of 5 membered "heteroaryl" groups include pyrrole, furan, thiophene, pyrazole, imidazole, triazole, isoxazole, oxazole, oxadiazole, oxatriazole, isothiazole, thiazole, thiadiazole, and thiatriazole.

Additional non-limiting examples of 5 membered "heteroaryl" groups include:

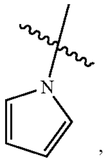,
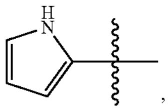,
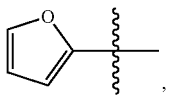,

-continued

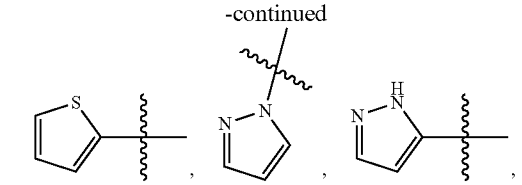

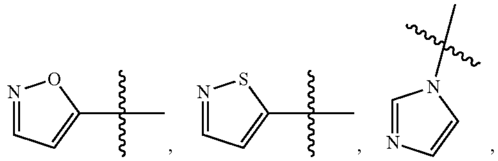

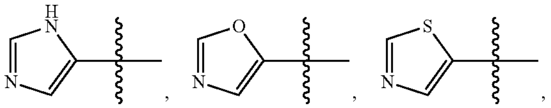

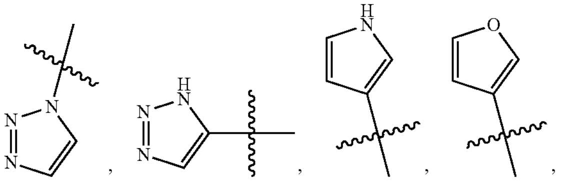

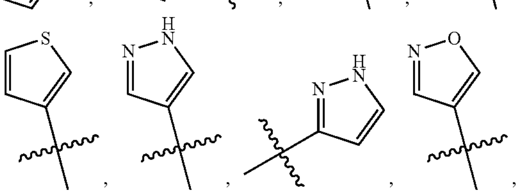

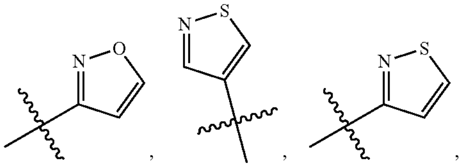

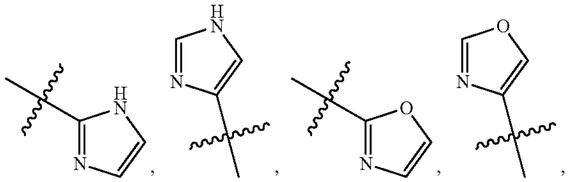

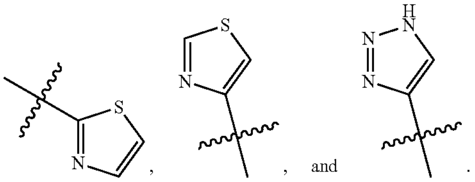

and

In one embodiment “heteroaryl” is a 6 membered aromatic group containing 1, 2, or 3 nitrogen atoms (i.e. pyridinyl, pyridazinyl, triazinyl, pyrimidinyl, and pyrazinyl).

Non-limiting examples of 6 membered “heteroaryl” groups with 1 or 2 nitrogen atoms include:

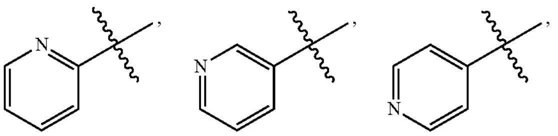

-continued

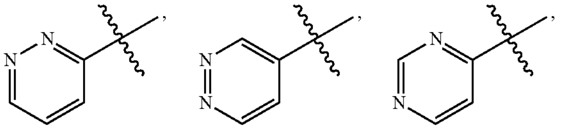

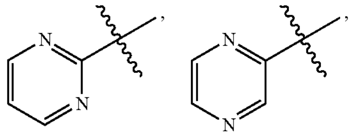

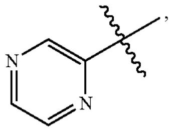

and

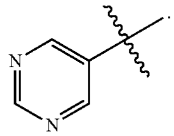

In one embodiment “heteroaryl” is a 9 membered bicyclic aromatic group containing 1 or 2 atoms selected from nitrogen, oxygen, and sulfur.

Non-limiting examples of“heteroaryl” groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

Additional non-limiting examples of “heteroaryl” groups that are bicyclic include:

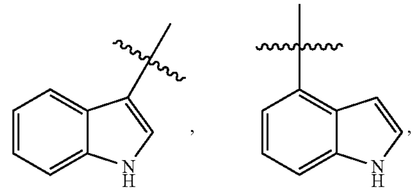

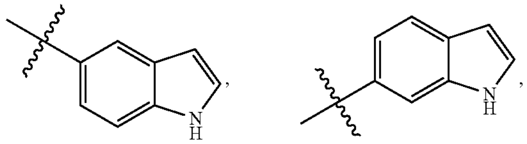

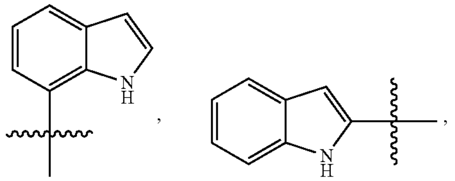

and

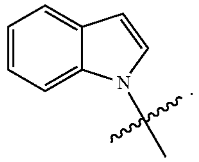

Additional non-limiting examples of "heteroaryl" groups that are bicyclic include:

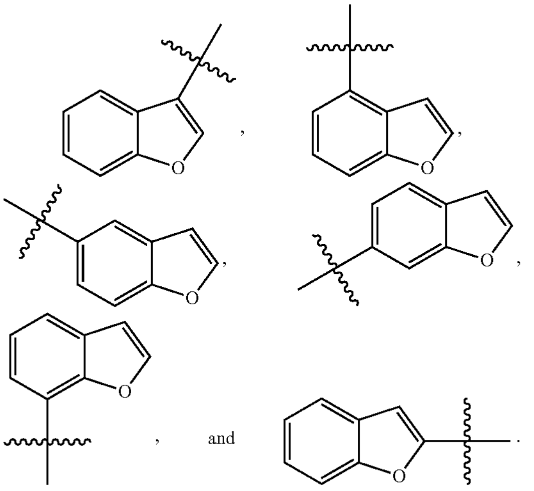

, and .

Additional non-limiting examples of "heteroaryl" groups that are bicyclic include:

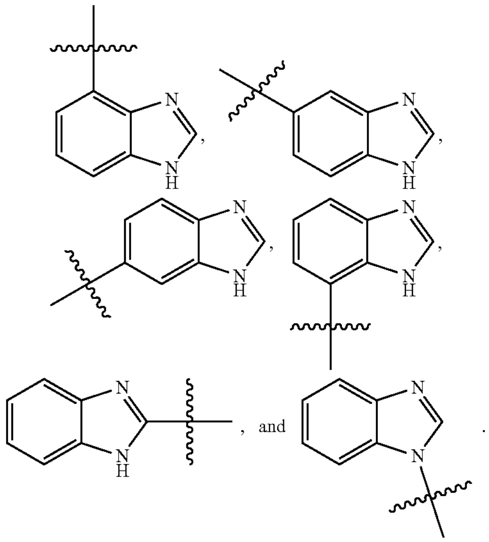

, and .

In one embodiment "heteroaryl" is a 10 membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

Additional non-limiting examples of "heteroaryl" groups that are bicyclic include:

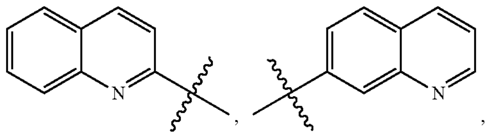

-continued

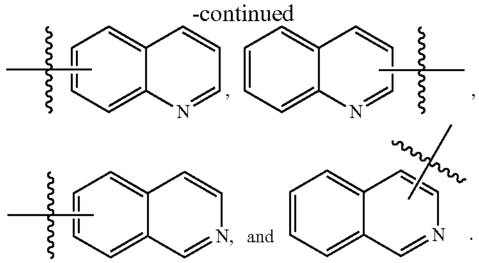

, and .

In one embodiment "heteroaryl" is "substituted heteroaryl"

Embodiments of "Cycloalkyl"

In one embodiment "cycloalkyl" is a $C_3$-$C_8$cycloalkyl, $C_3$-$C_7$cycloalkyl, $C_3$-$C_6$cycloalkyl, $C_3$-$C_5$cycloalkyl, $C_3$-$C_4$cycloalkyl, $C_4$-$C_8$cycloalkyl, $C_5$-$C_8$cycloalkyl, or $C_6$-$C_8$cycloalkyl.

In one embodiment "cycloalkyl" has three carbons.

In one embodiment "cycloalkyl" has four carbons.

In one embodiment "cycloalkyl" has five carbons.

In one embodiment "cycloalkyl" has six carbons.

In one embodiment "cycloalkyl" has seven carbons.

In one embodiment "cycloalkyl" has eight carbons.

In one embodiment "cycloalkyl" has nine carbons.

In one embodiment "cycloalkyl" has ten carbons.

Non-limiting examples of "cycloalkyl" include: cyclopropyl, cyclobutyl, cyclopentyl, cyclohexyl, cycloheptyl, cyclooctyl, and cyclodecyl.

In one embodiment "cycloalkyl" is a "substituted cycloalkyl"

Embodiments of "Heterocycle"

In one embodiment "heterocycle" refers to a cyclic ring with one nitrogen and 3, 4, 5, 6, 7, or 8 carbon atoms.

In one embodiment "heterocycle" refers to a cyclic ring with one nitrogen and one oxygen and 3, 4, 5, 6, 7, or 8 carbon atoms.

In one embodiment "heterocycle" refers to a cyclic ring with two nitrogens and 3, 4, 5, 6, 7, or 8 carbon atoms.

In one embodiment "heterocycle" refers to a cyclic ring with one oxygen and 3, 4, 5, 6, 7, or 8 carbon atoms.

In one embodiment "heterocycle" refers to a cyclic ring with one sulfur and 3, 4, 5, 6, 7, or 8 carbon atoms.

Non-limiting examples of "heterocycle" include aziridine, oxirane, thiirane, azetidine, 1,3-diazetidine, oxetane, and thietane.

Additional non-limiting examples of "heterocycle" include pyrrolidine, 3-pyrroline, 2-pyrroline, pyrazolidine, and imidazolidine.

Additional non-limiting examples of "heterocycle" include tetrahydrofuran, 1,3-dioxolane, tetrahydrothiophene, 1,2-oxathiolane, and 1,3-oxathiolane.

Additional non-limiting examples of "heterocycle" include piperidine, piperazine, tetrahydropyran, 1,4-dioxane, thiane, 1,3-dithiane, 1,4-dithiane, morpholine, and thiomorpholine.

Non-limiting examples of "heterocycle" also include:

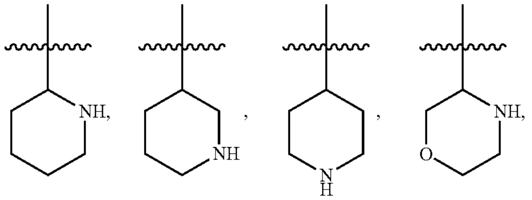

-continued

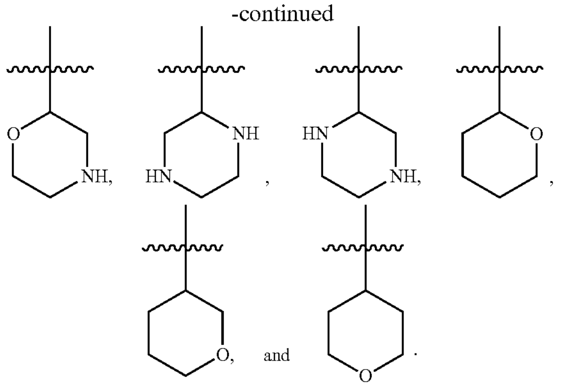

Additional non-limiting examples of "heterocycle" include:

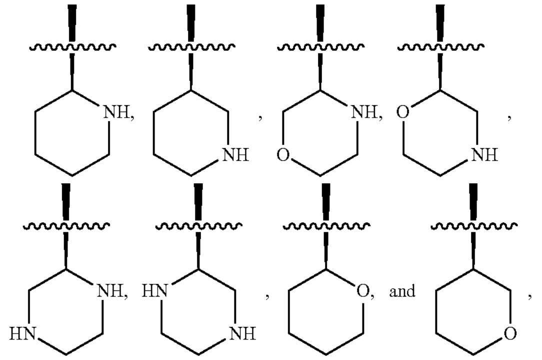

Additional non-limiting examples of "heterocycle" include:

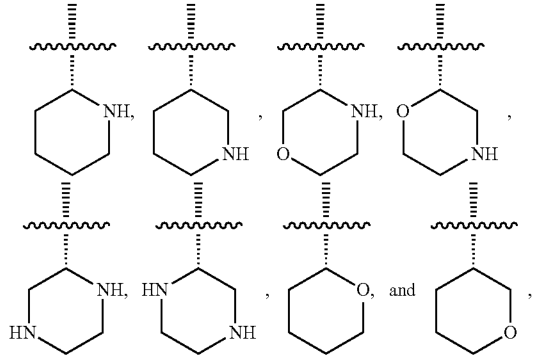

Non-limiting examples of "heterocycle" also include:

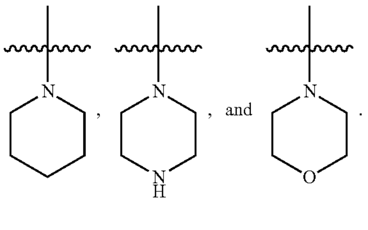

Non-limiting examples of "heterocycle" also include:

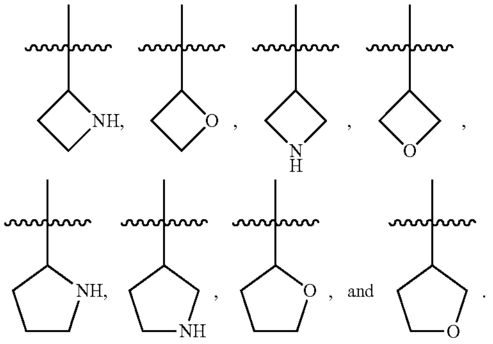

Additional non-limiting examples of "heterocycle" include:

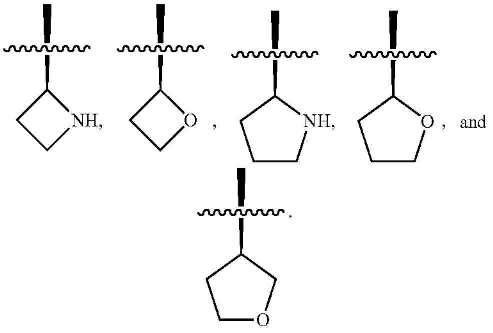

Additional non-limiting examples of "heterocycle" include:

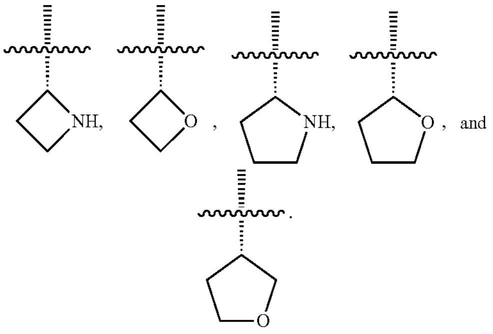

In one embodiment "heterocycle" is "substituted heterocycle".

Embodiments of $R^{201}$

In one embodiment $R^{201}$ is selected from $—(CH_2)_m—O$-heterocycle, $—(CH_2)_m—NH$-heterocycle, or $—(CH_2)_m—NR^9$-heterocycle;

In one embodiment $R^{201}$ is selected from $—(CH_2)_m—NR^9R^{10}$, $—(CH_2)_m—OR^9$, or $—(CH_2)_m$-heterocycle;

In one embodiment $R^{201}$ is selected from $—CH_2—O$-heterocycle, $—CH_2—NH$-heterocycle, or $—CH_2—NR^9$-heterocycle;

In one embodiment $R^{201}$ is selected from $—CH_2—NR^9R^{10}$, $—CH_2—OR^9$, or $—CH_2$-heterocycle;

In one embodiment $R^{201}$ is selected from $—(CH_2)_m—NH_2$, $—(CH_2)_m—OH$, or $—(CH_2)_m—OC_1$-$C_6$alkyl;

In one embodiment $R^{201}$ is selected from:
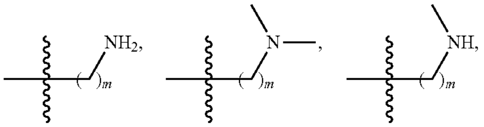
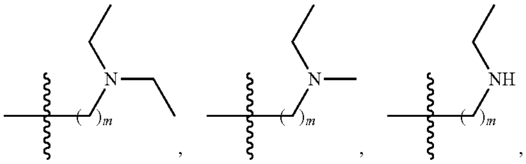
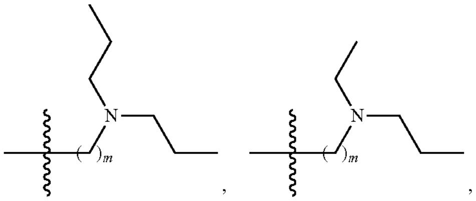
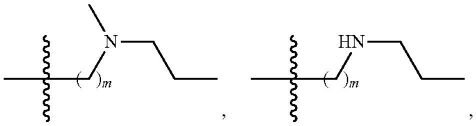
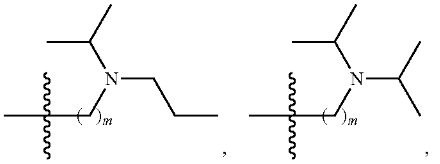
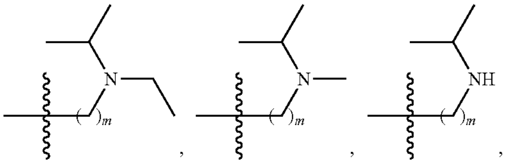
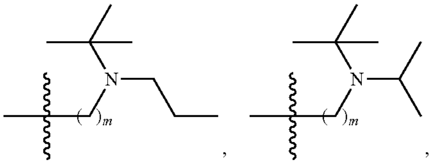
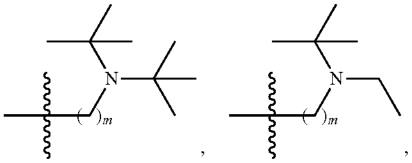
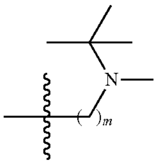
, and
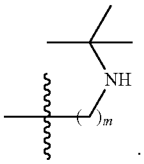
.
In one embodiment $R^{201}$ is selected from:
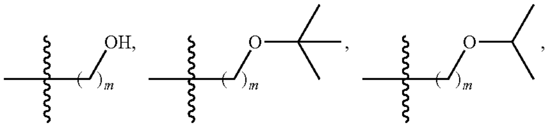
-continued
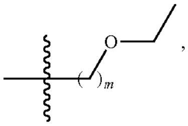
, and
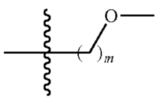
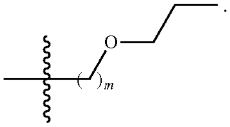
.
In one embodiment $R^{201}$ is selected from:
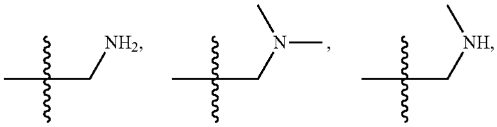
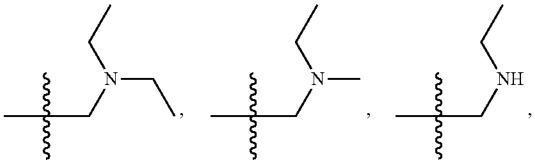
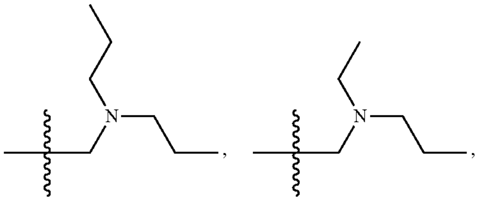
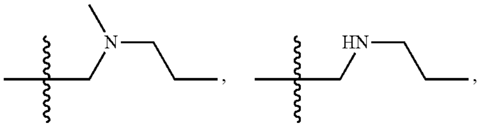
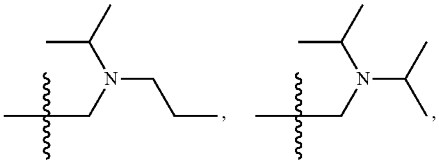
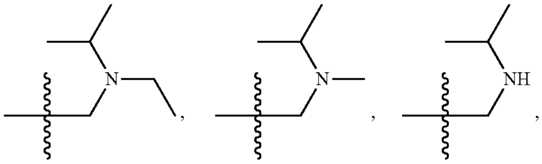
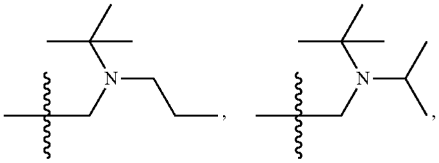
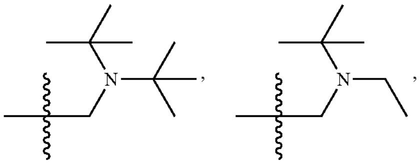

-continued
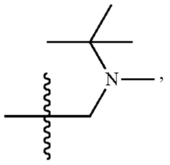 and 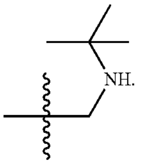
In one embodiment $R^{201}$ is selected from:
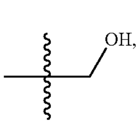 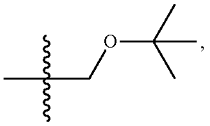 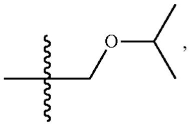
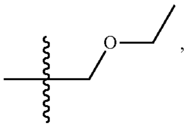 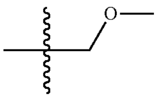 and
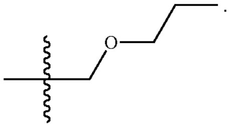
In one embodiment $R^{201}$ is selected from:
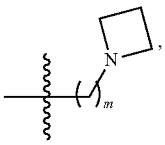 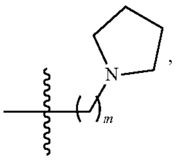
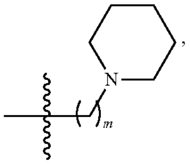 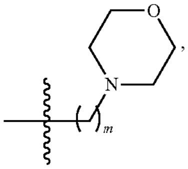
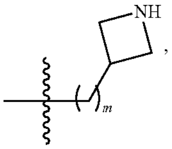 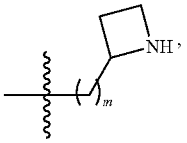
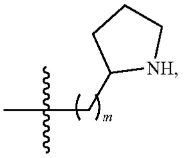 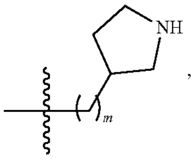
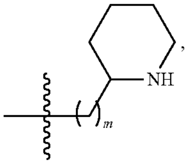 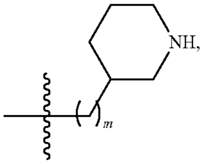
-continued
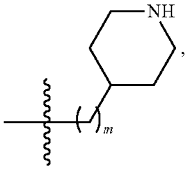 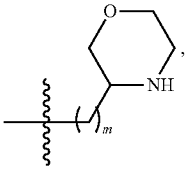 and
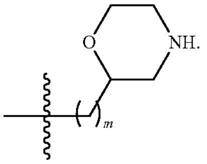
In one embodiment $R^{201}$ is selected from:
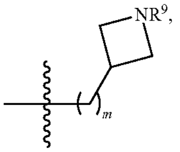 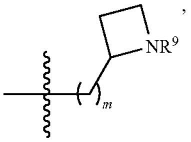
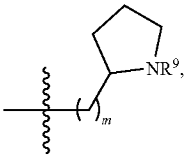 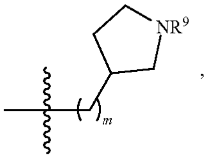
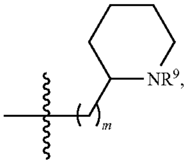 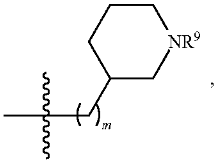
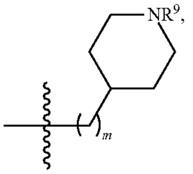 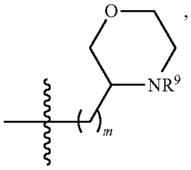 and
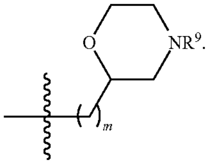
In one embodiment $R^{201}$ is selected from:
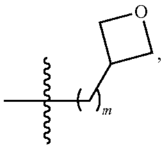 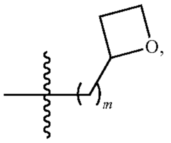
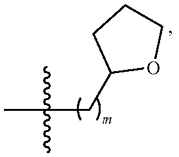 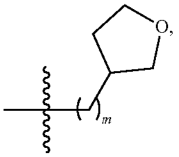

-continued
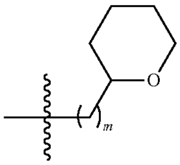,
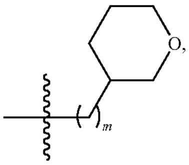
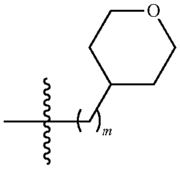,
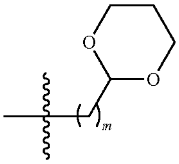, and
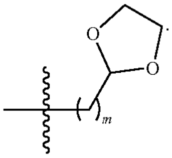.
In one embodiment $R^{201}$ is selected from:
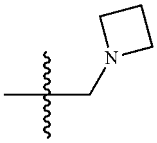,
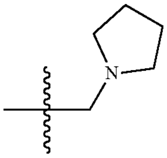,
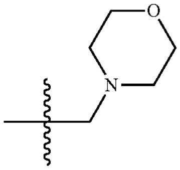,
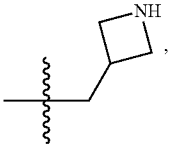,
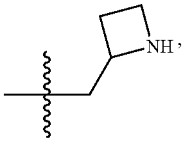
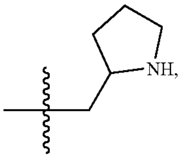
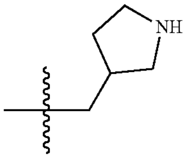,
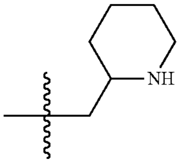,
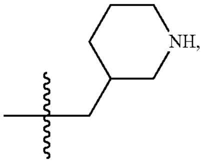
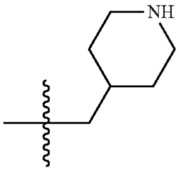,
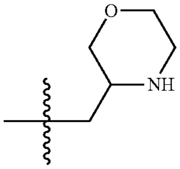, and
-continued
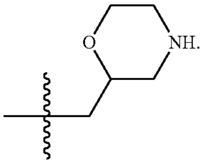
In one embodiment $R^{201}$ is selected from:
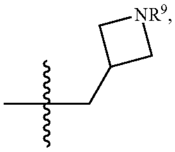
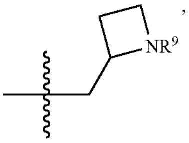,
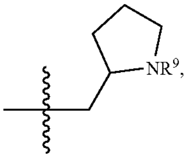
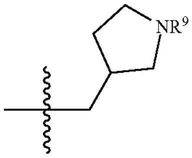,
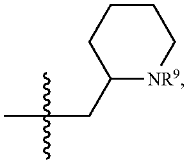
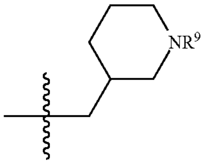,
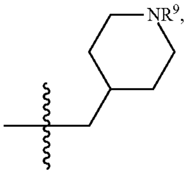
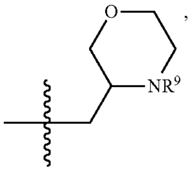, and
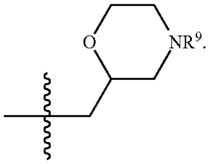
In one embodiment $R^{201}$ is selected from:
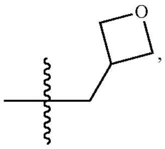
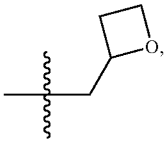
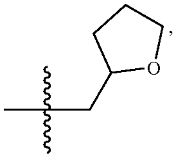
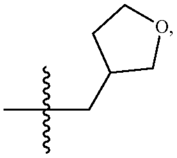
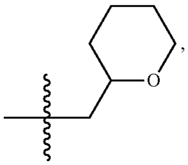
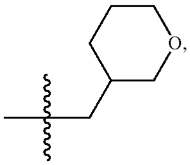

-continued
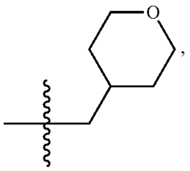
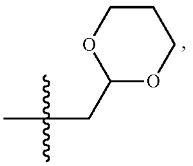
and
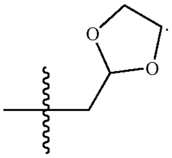
In one embodiment $R^{201}$ is selected from:
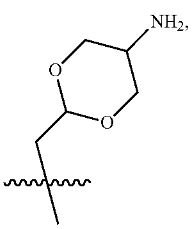
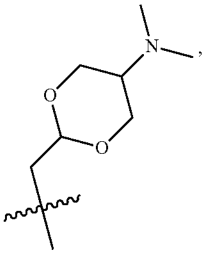
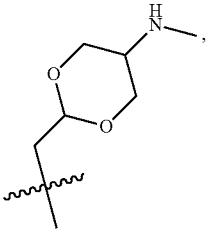
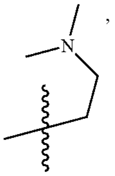
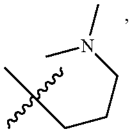
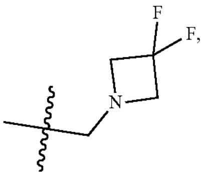
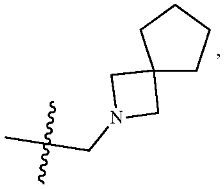
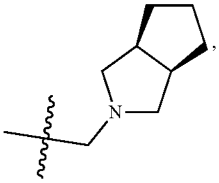
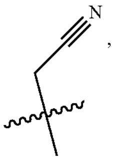
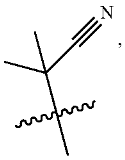
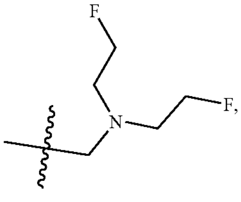
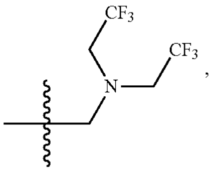
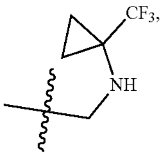
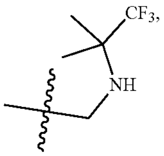
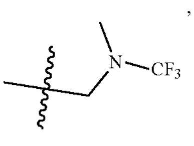
-continued
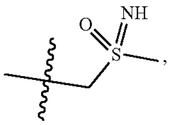
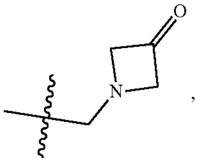
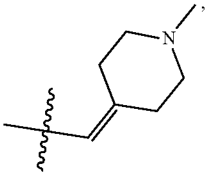
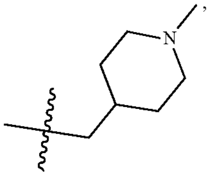
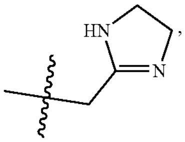
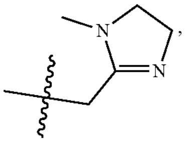
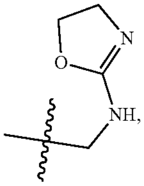
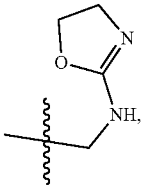
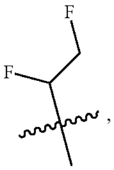
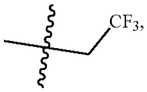
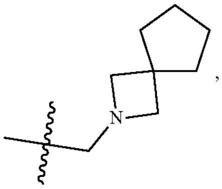
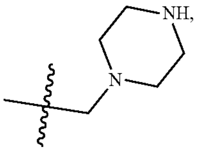
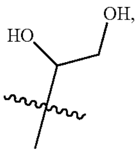
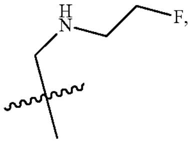
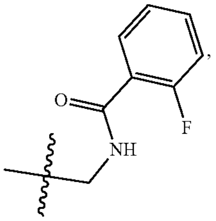
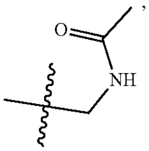
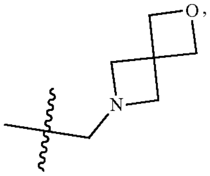
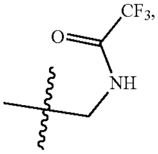
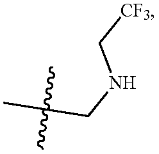
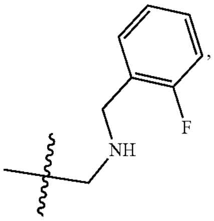
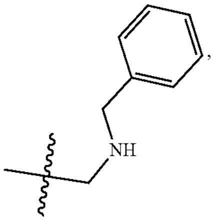

-continued
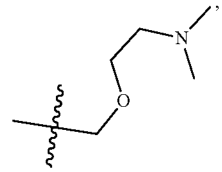,
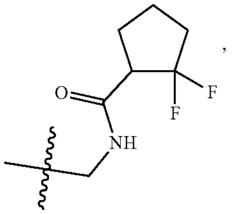,
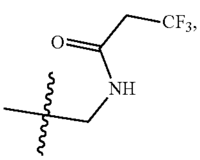,
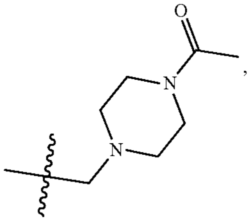,
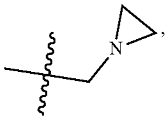, and
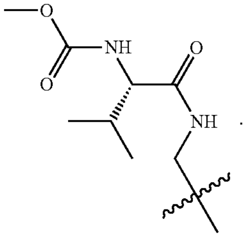.
Embodiments of C
In one embodiment C1 is selected from:
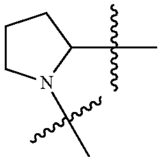
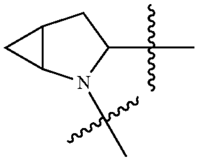
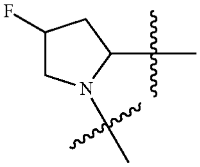
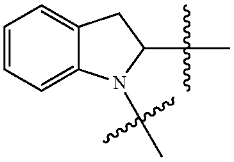
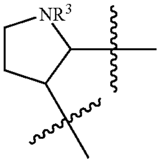
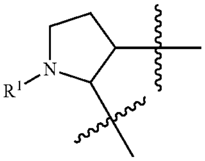
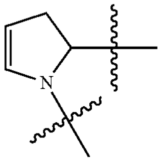
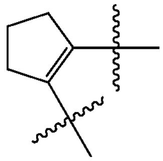
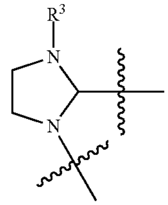
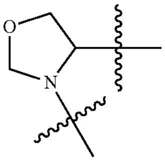
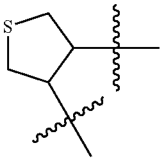
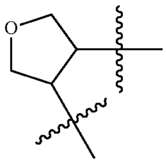
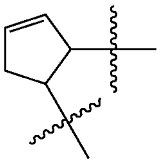
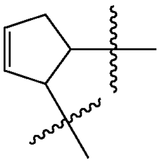
-continued
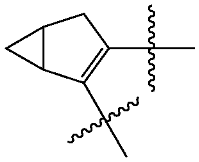
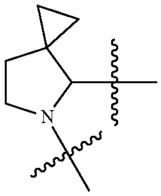
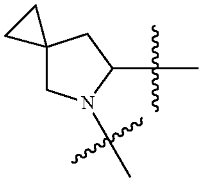
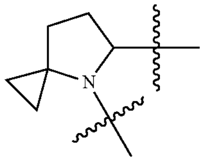
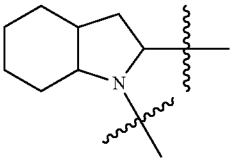
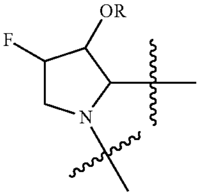
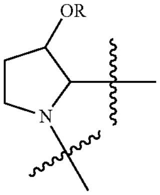
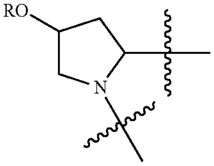
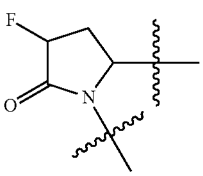
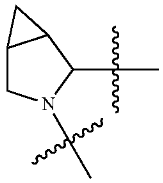
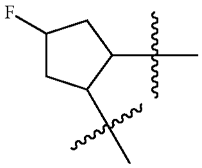
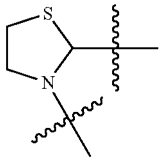
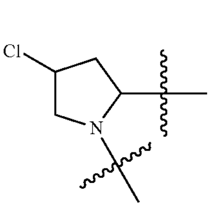
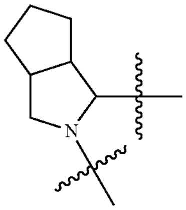
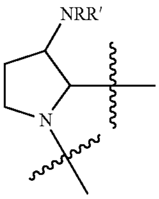
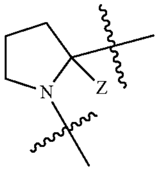

-continued
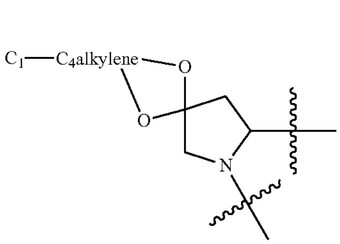
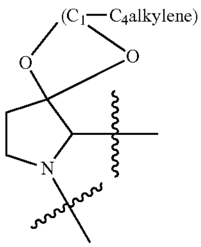
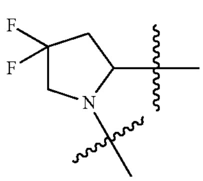
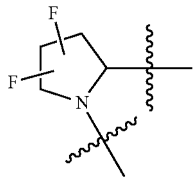
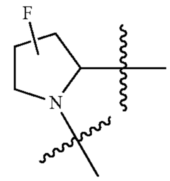
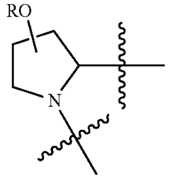
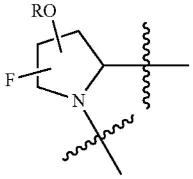
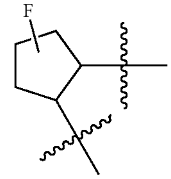
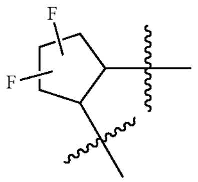
and
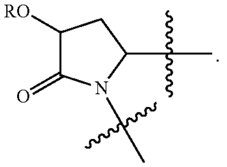
.
In one embodiment C1 is selected from:
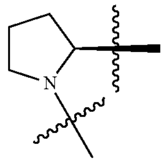
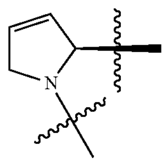
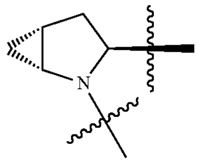
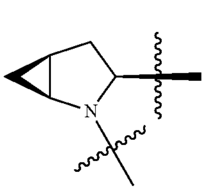
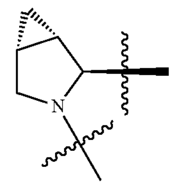
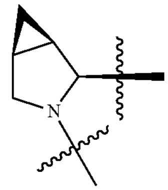
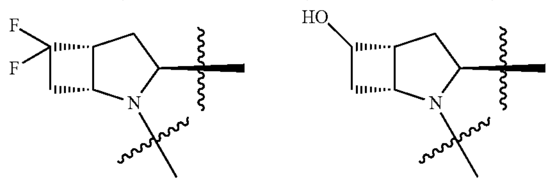
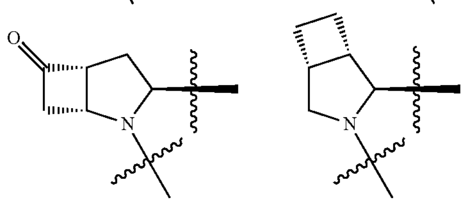
-continued
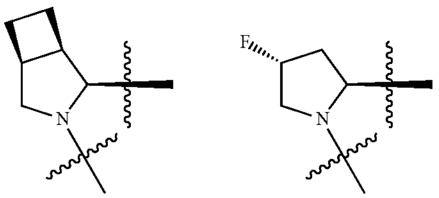
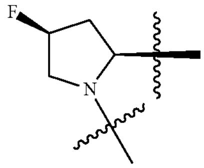
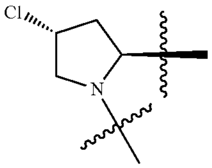
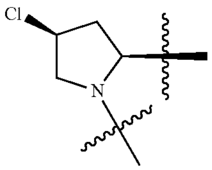
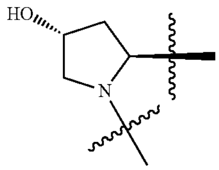
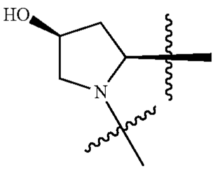
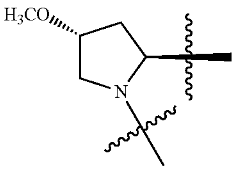
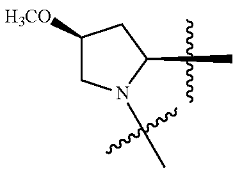
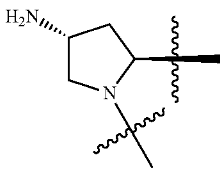
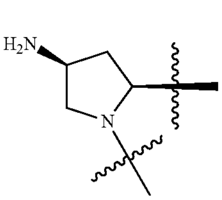
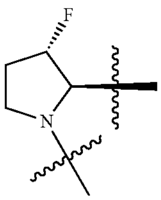
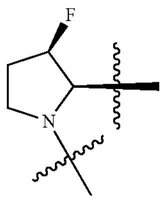
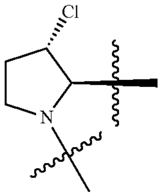
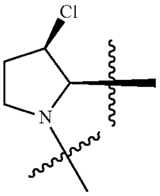
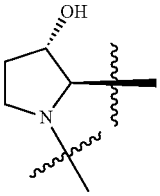
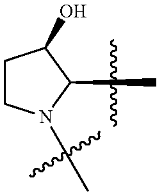
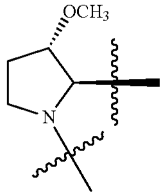
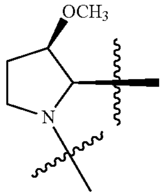
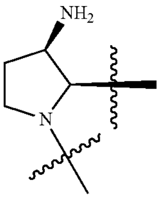
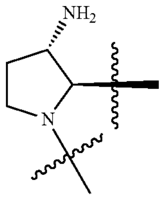
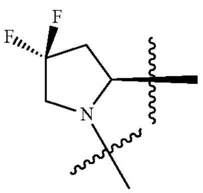

-continued

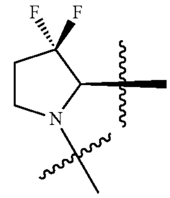 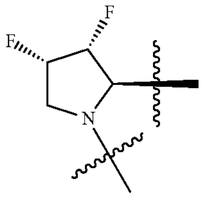

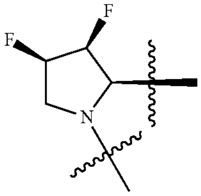 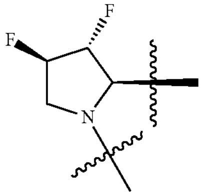

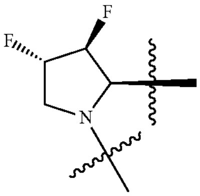 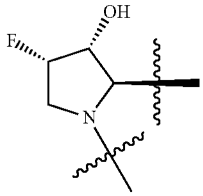

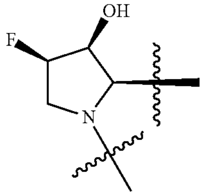 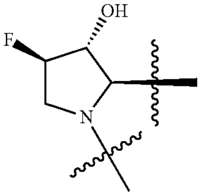

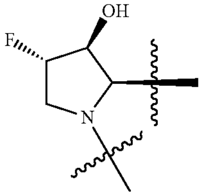 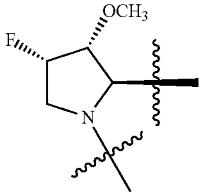

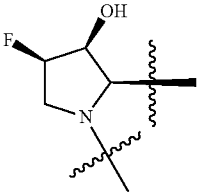 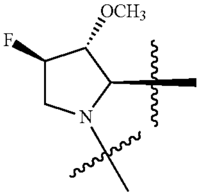

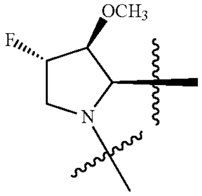 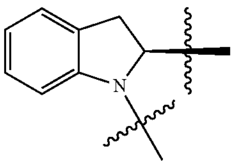

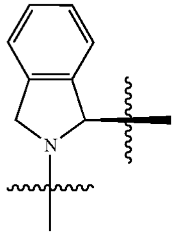 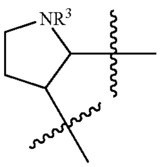 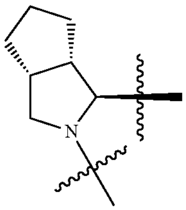

-continued

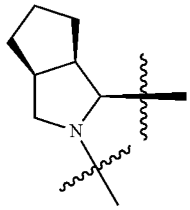 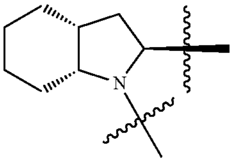

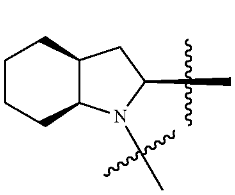 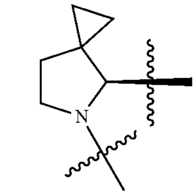

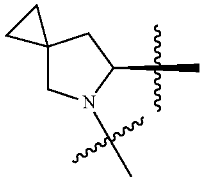 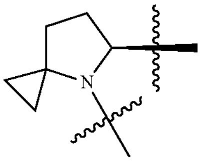

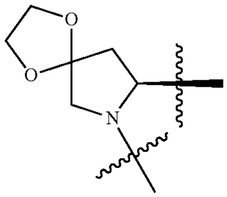 and 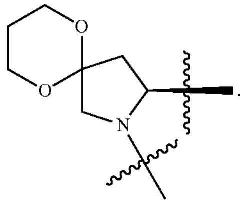.

In one embodiment, a methyl group in a structure illustrated in above can be replaced with a different alkyl group, as defined herein. In another embodiment, the fluoro atoms in the structures illustrated in above can be replaced with any other halogen. Any of the structures illustrated in above or otherwise can be optionally substituted with 0, 1, 2, 3, or 4, as appropriate, and independently, with an $R^{48}$ substituent.

Examples of central core small mimetics of a beta-turn, beta turn inducers, reverse turn mimetics and foldamer monomers include:

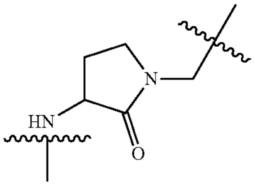 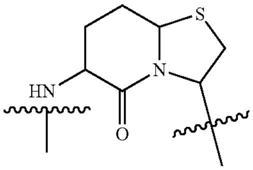

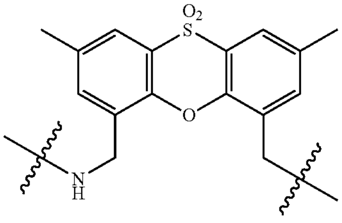

-continued
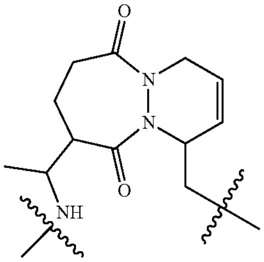
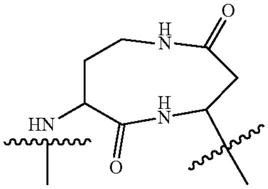
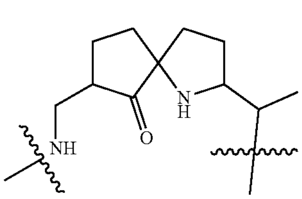
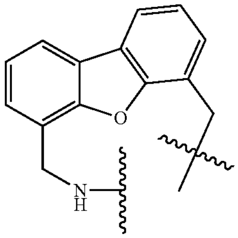
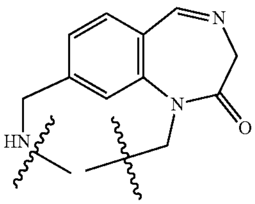
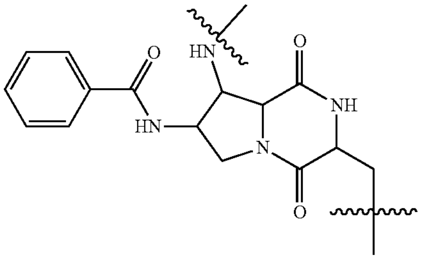
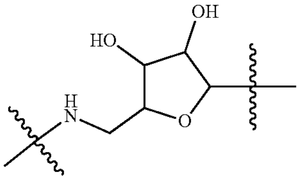
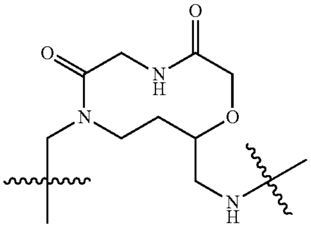
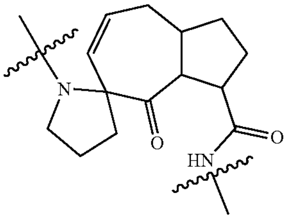
-continued
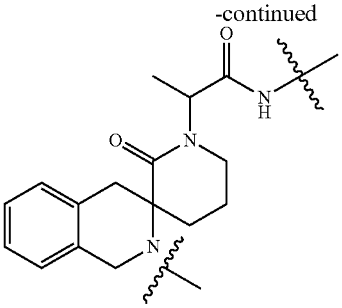
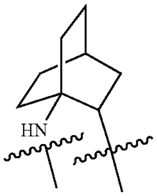
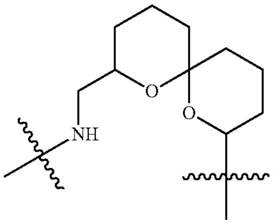
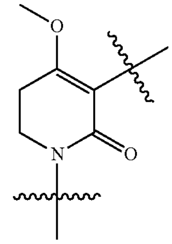
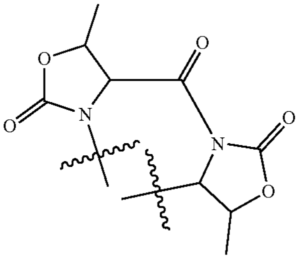
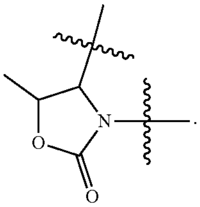
In one embodiment C is selected from:
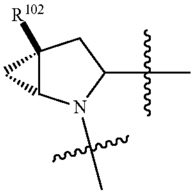
,
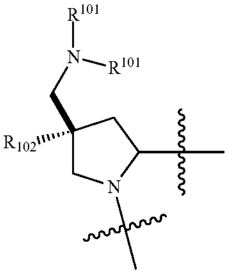
,
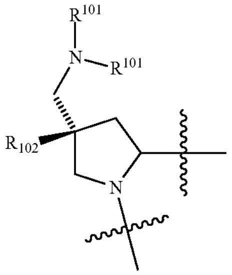
,
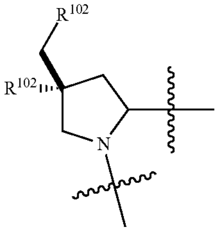
,
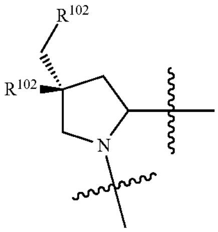
,
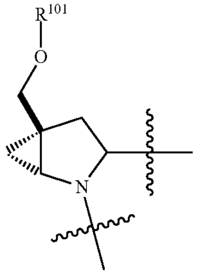
, -continued
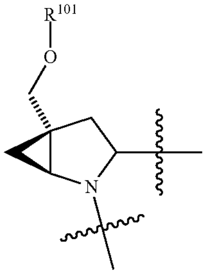,
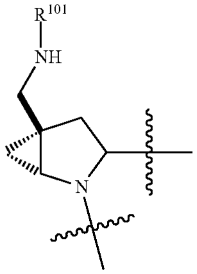,
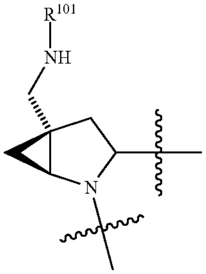,
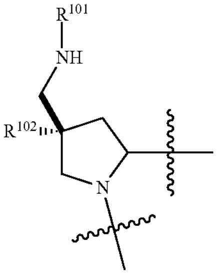,
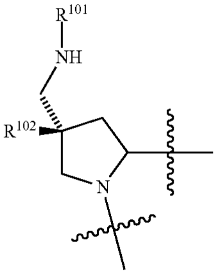,
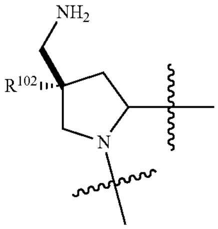,
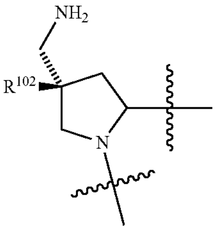,
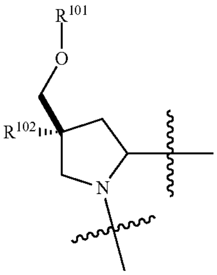,
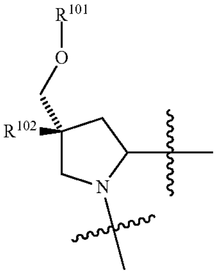,
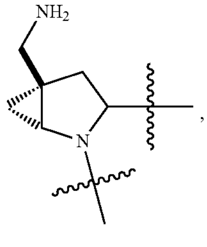,
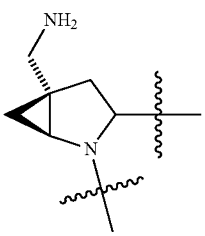,
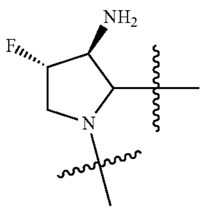,
-continued
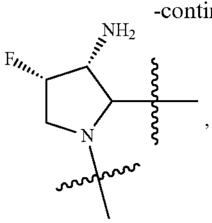,
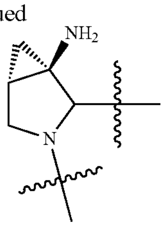,
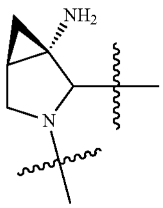,
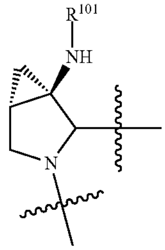,
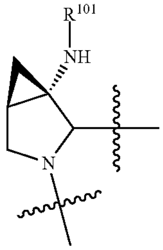,
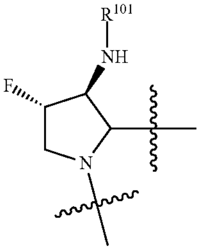,
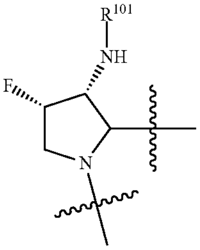,
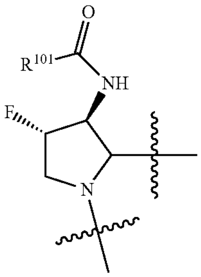,
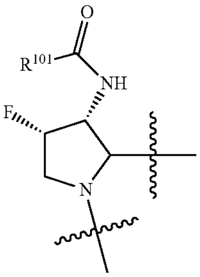,
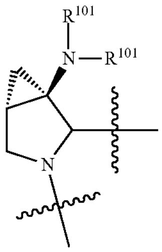,
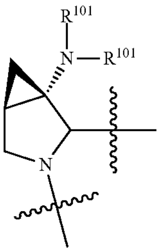,
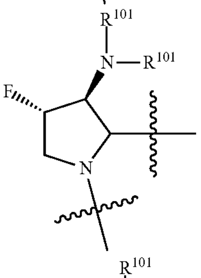,
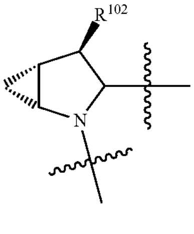,
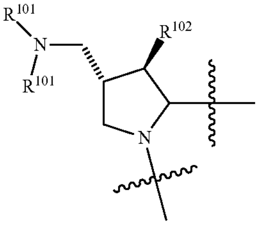, -continued
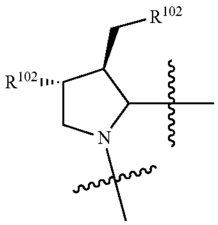,
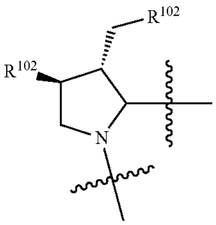,
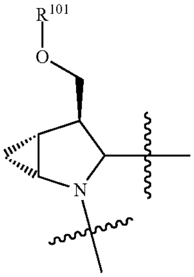,
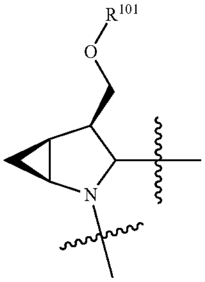,
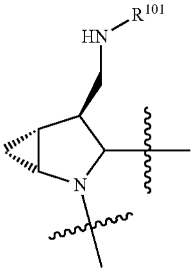,
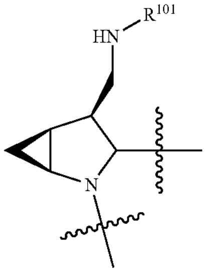,
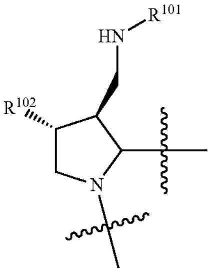,
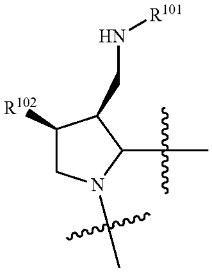,
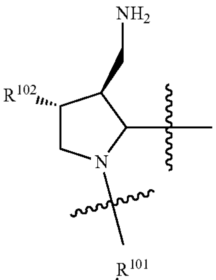,
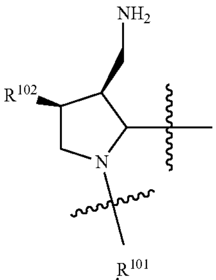,
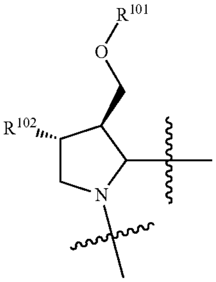,
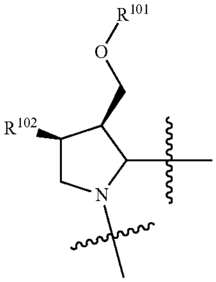,
-continued
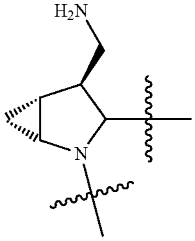,
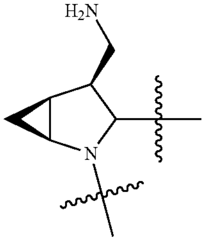,
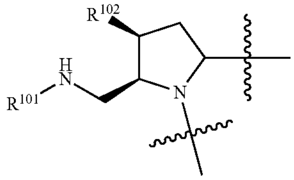,
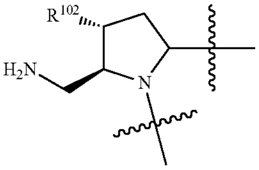,
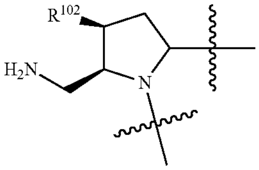,
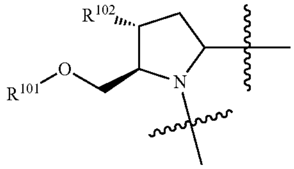,
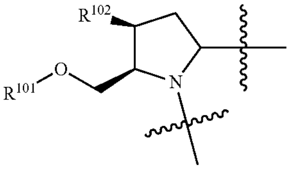,
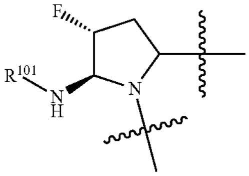,
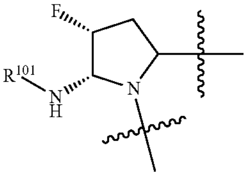,
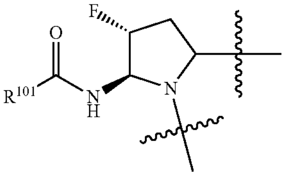,
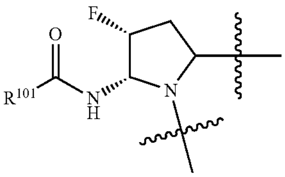,
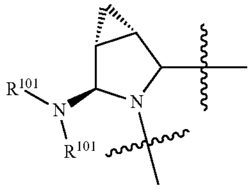,
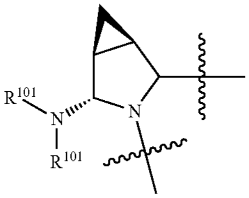,
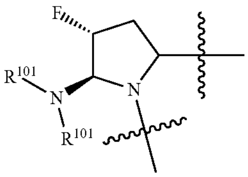,
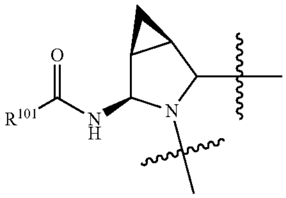, -continued
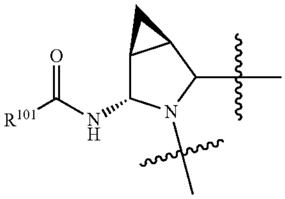,
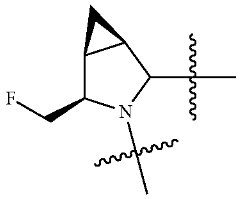,
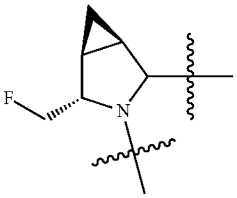
and
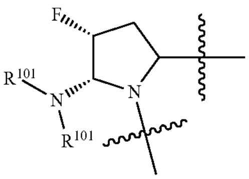;
wherein:
$R^{101}$ is $C_1$-$C_4$ alkyl or $C_3$-$C_7$ cycloalkyl; and
$R^{102}$ is $C_1$-$C_4$ alkyl, fluorine, chlorine, or bromine.
In one embodiment C4 is selected from:
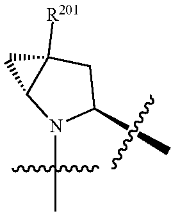
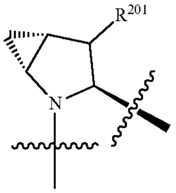
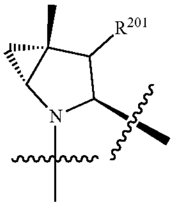
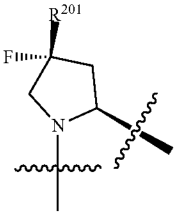
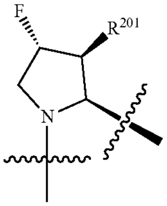
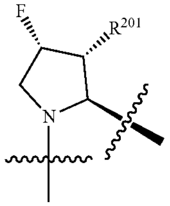
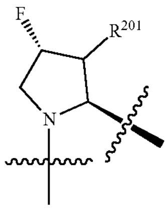
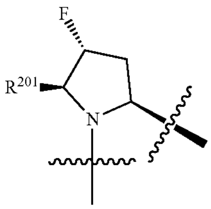
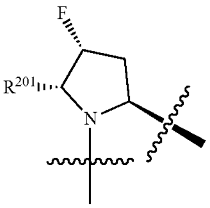
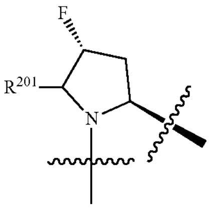
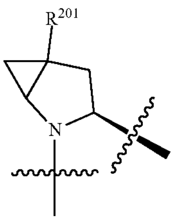
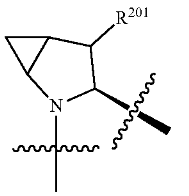
-continued
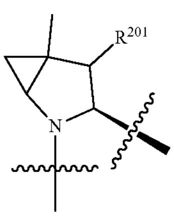
and
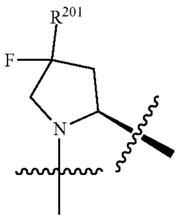.
In one embodiment C4 is selected from:
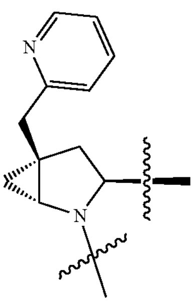,
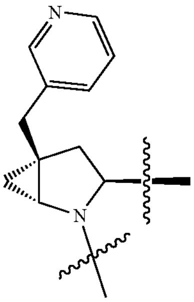,
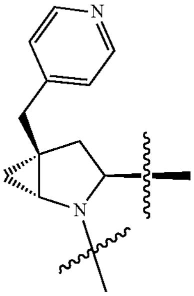,
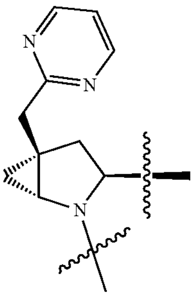,
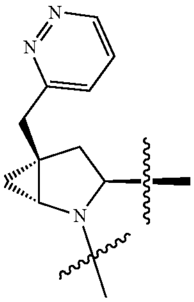,
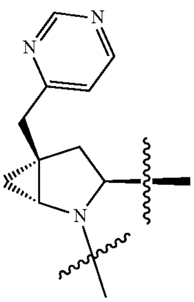, and
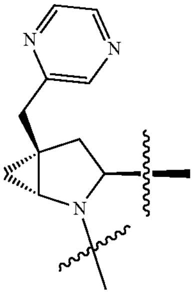.

In one embodiment C4 is selected from:
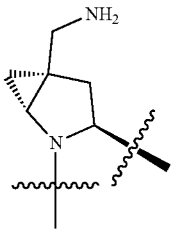
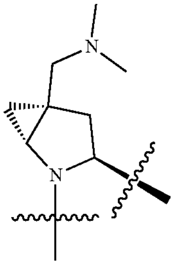
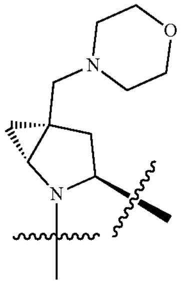
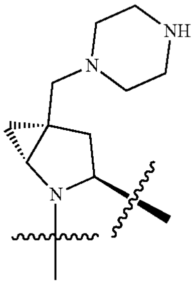
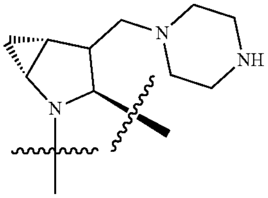
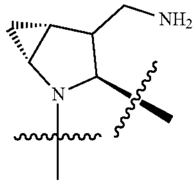
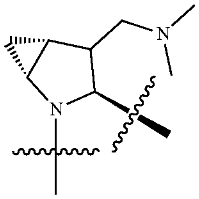
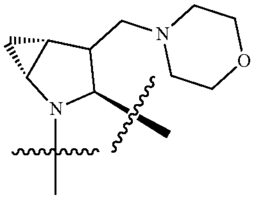
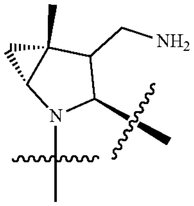
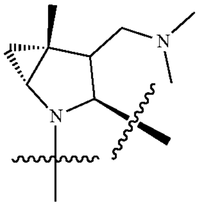
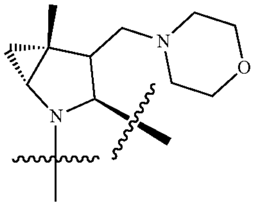
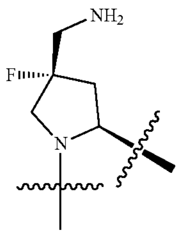
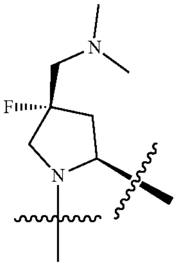
-continued
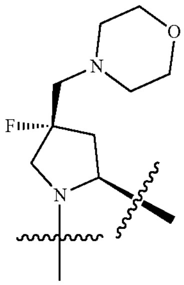
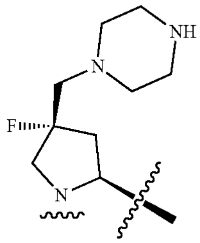
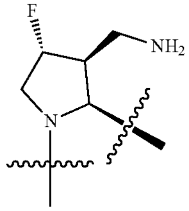
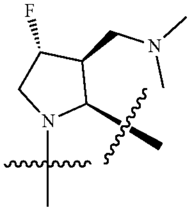
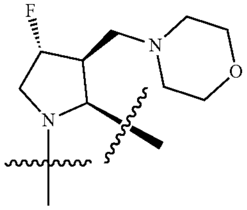
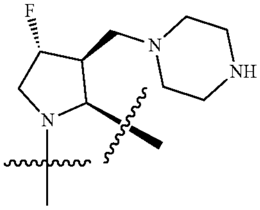
In one embodiment C4 is selected from:
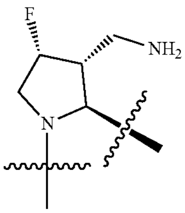
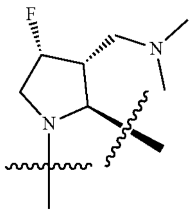
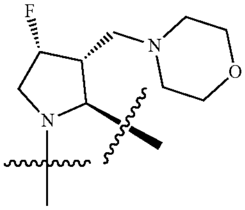
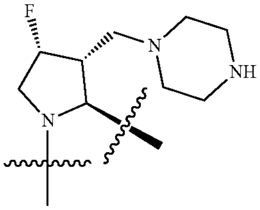
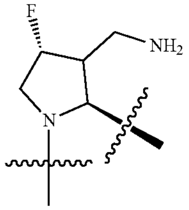
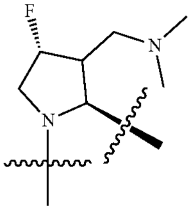
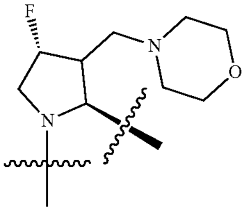
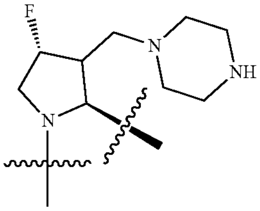

-continued
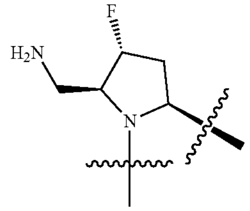
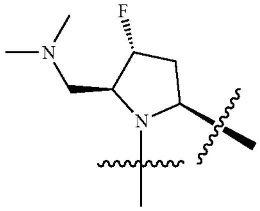
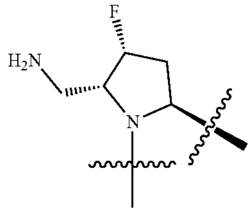
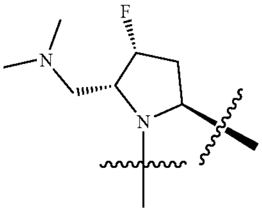
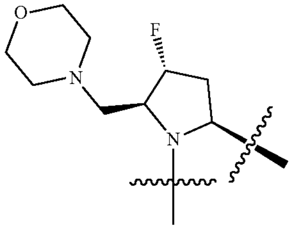
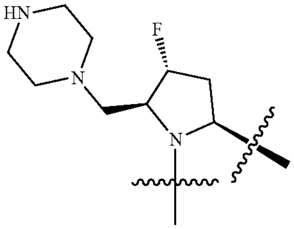
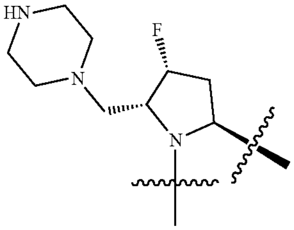
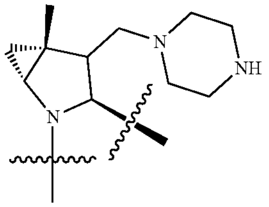
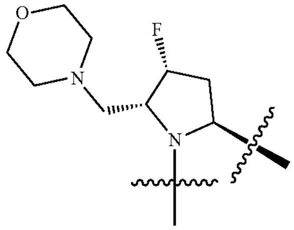
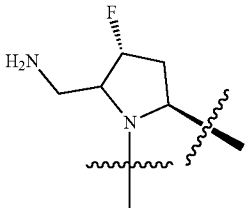
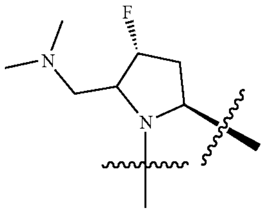
-continued
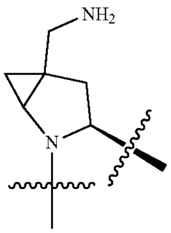
In one embodiment C4 is selected from:
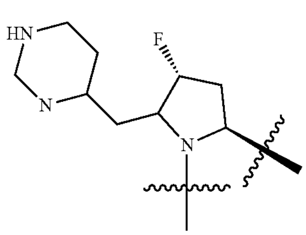
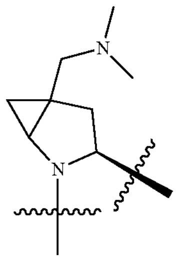
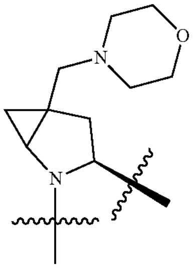
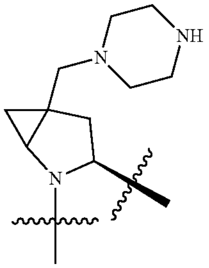
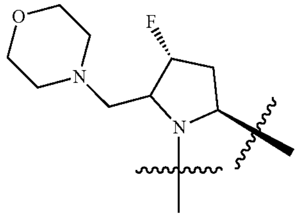
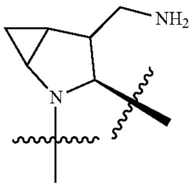
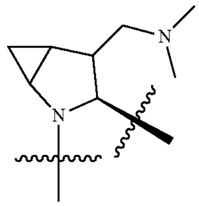
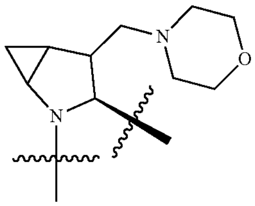
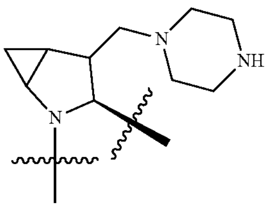
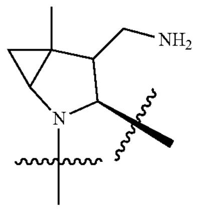
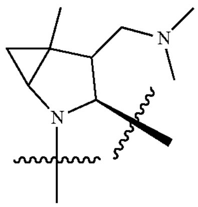
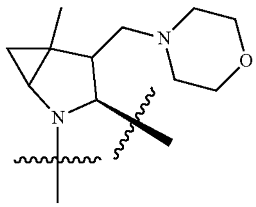

-continued
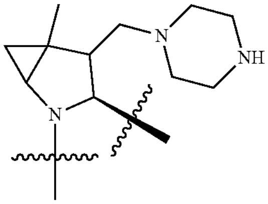
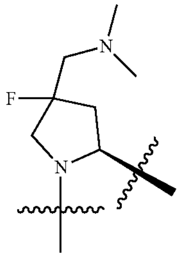
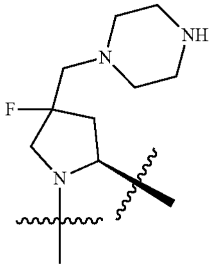
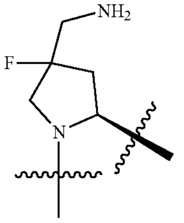
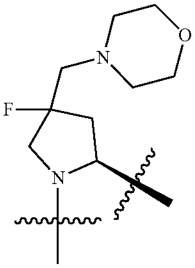
In one embodiment C is selected from:
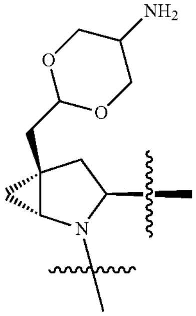
,
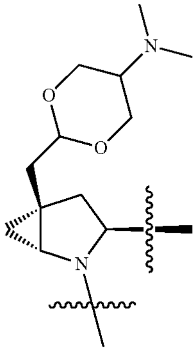
,
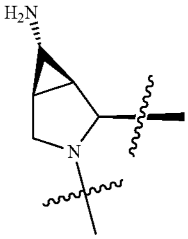
,
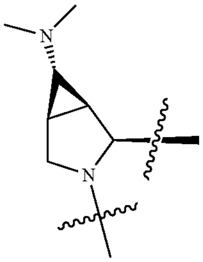
,
-continued
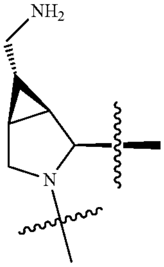
,
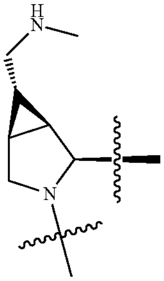
,
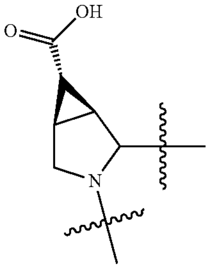
,
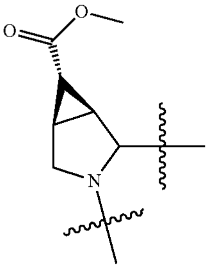
,
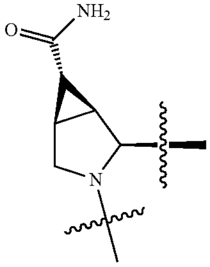
,
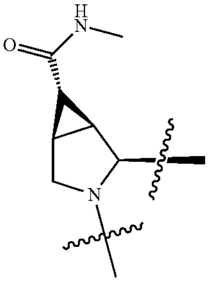
,
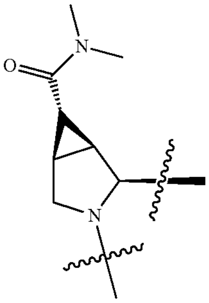
,
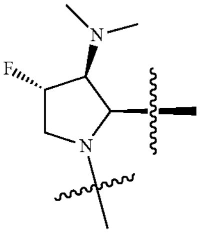
,
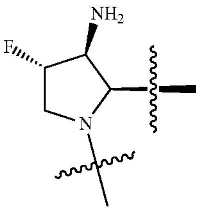
,
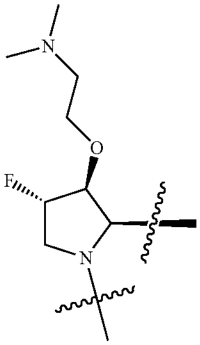
,
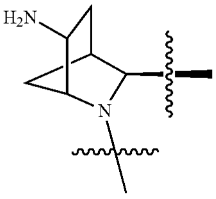
,
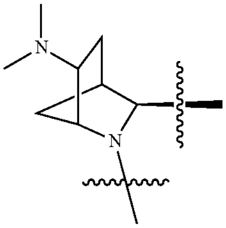
, -continued
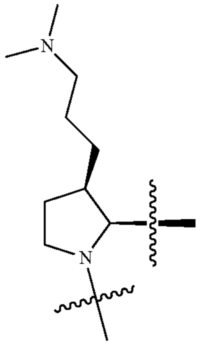,
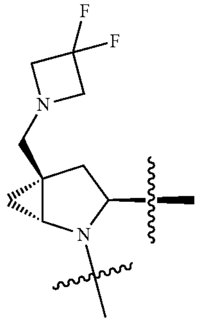,
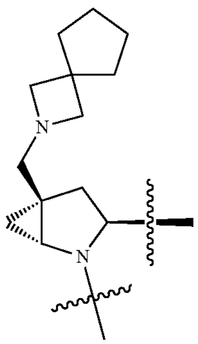,
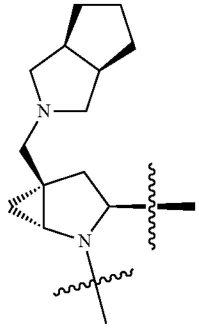,
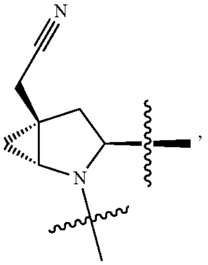,
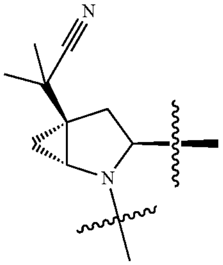,
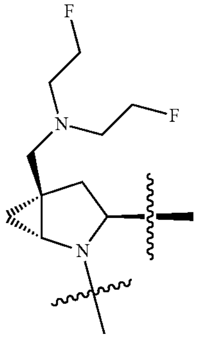,
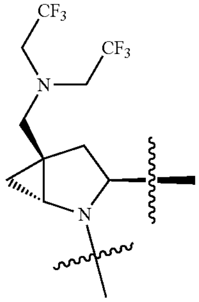,
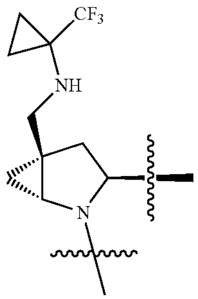,
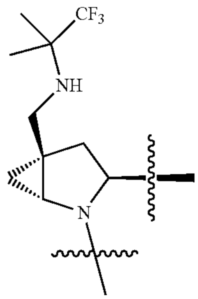,
-continued
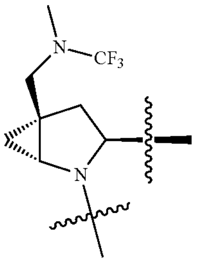,
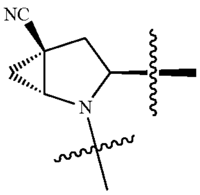,
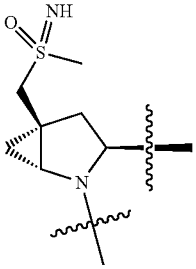,
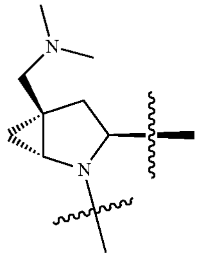,
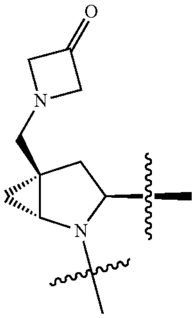,
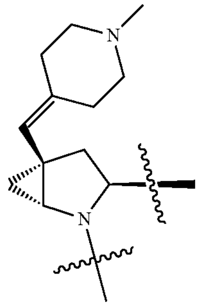,
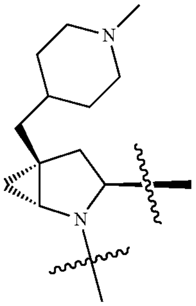,
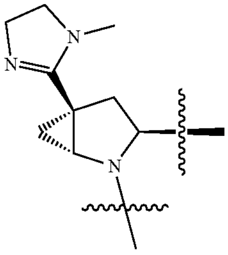,
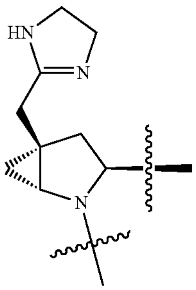,
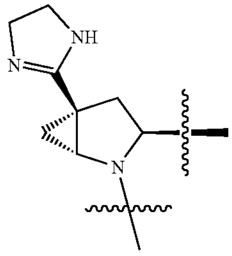, -continued
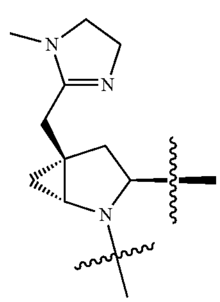,
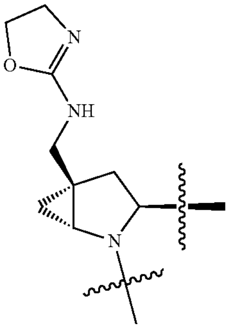,
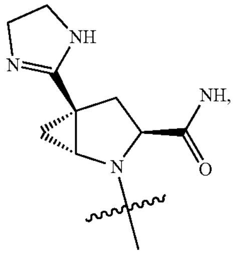
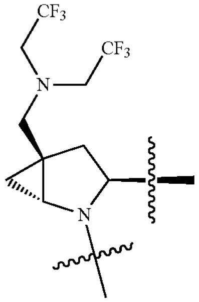,
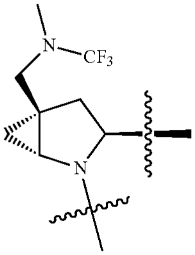,
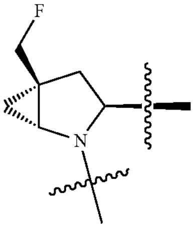,
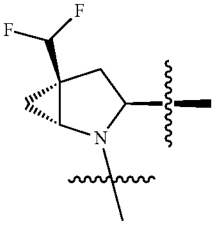,
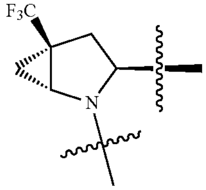,
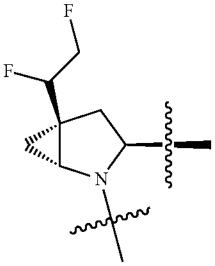,
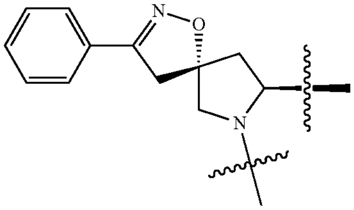,
-continued
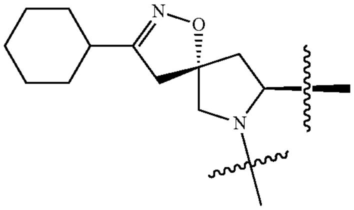,
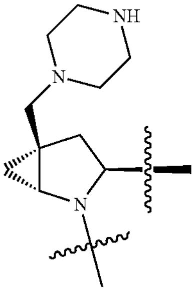,
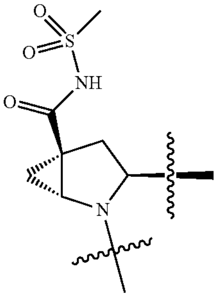,
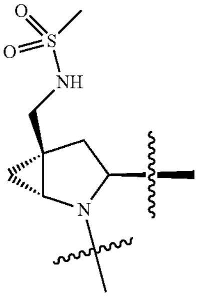,
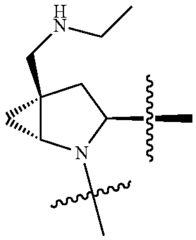,
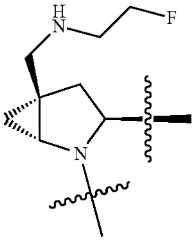,
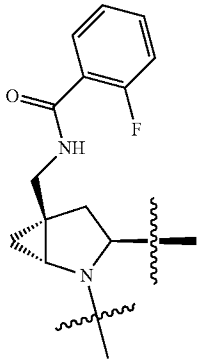,
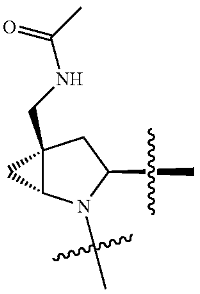,
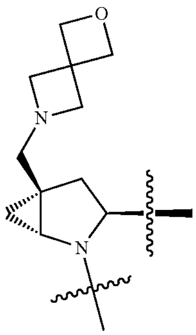, -continued
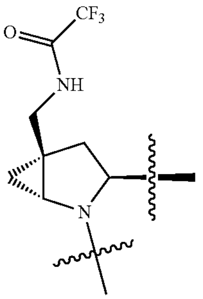
,
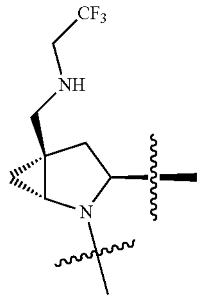
,
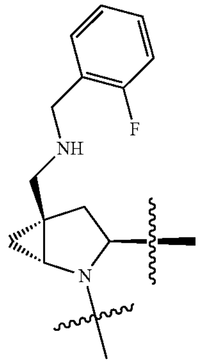
,
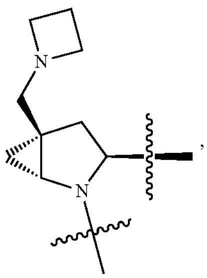
,
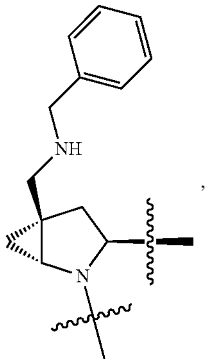
,
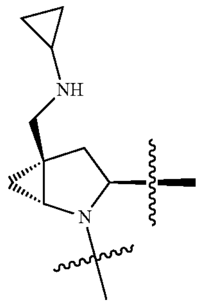
,
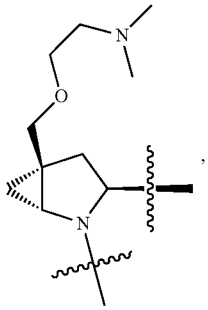
,
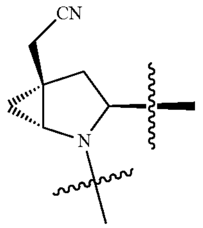
,
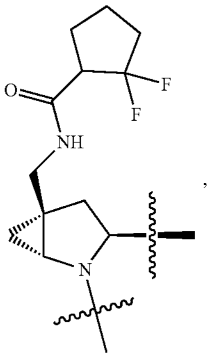
,
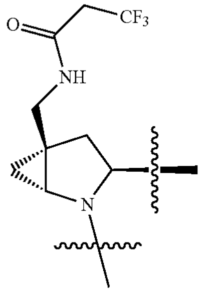
,
-continued
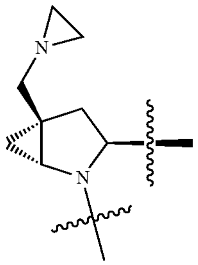
,
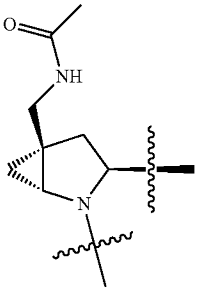
,
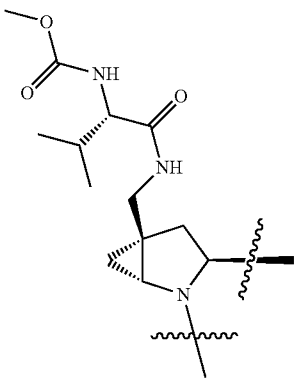
,
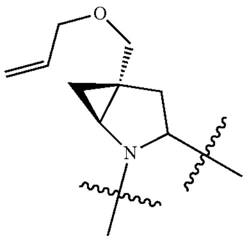
,
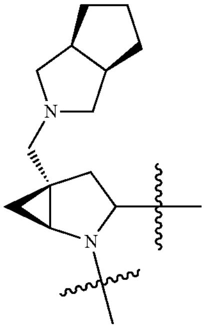
,
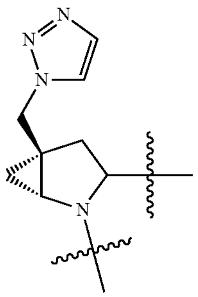
,
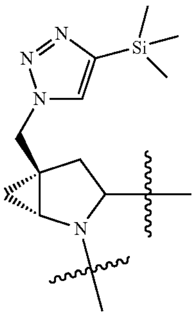
,
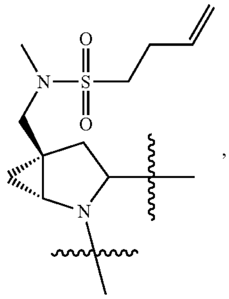
,
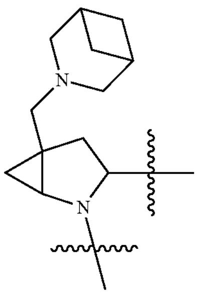
, -continued

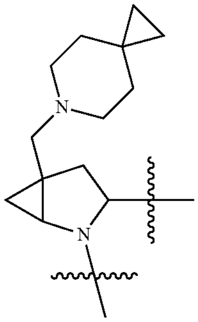,
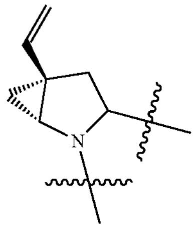,
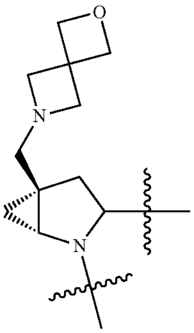,
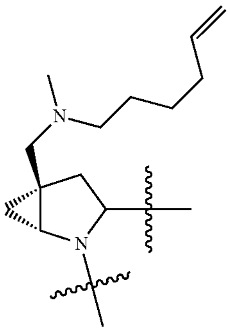,
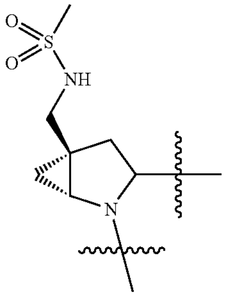,
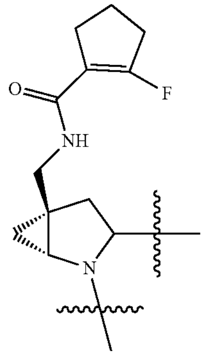,
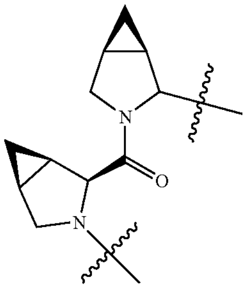,
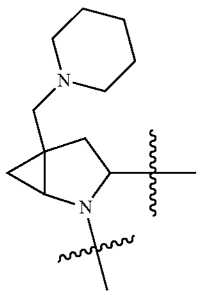,
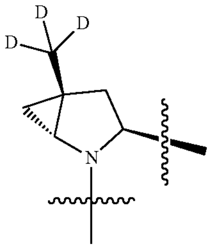,
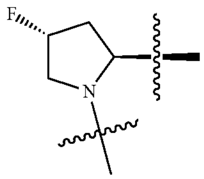, -continued

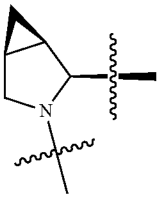,
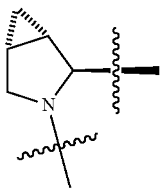

In one embodiment $R^1$ is selected from F, Cl, Br, and $C_1$-$C_6$alkyl.

In one embodiment $R^1$ is selected from hydroxyl and $C_1$-$C_6$alkoxy.

In one embodiment $R^1$ is selected from $C_2$-$C_6$alkynyl, $C_2$-$C_6$alkanoyl, and $C_1$-$C_6$thioalkyl.

In one embodiment $R^1$ is selected from amino$C_1$-$C_6$alkyl and —$C_0$-$C_4$alkylNR$^9$R$^{10}$.

Embodiments of A

Non-limiting examples of A1 include:

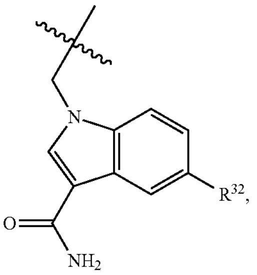
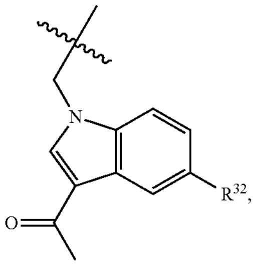
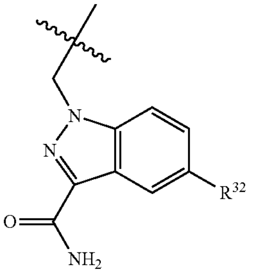
and
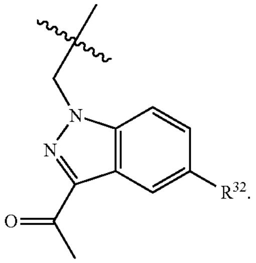

Additional non-limiting examples of A1 include:

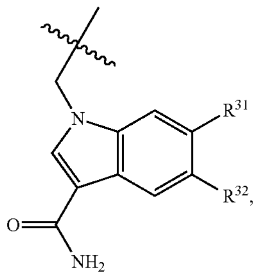
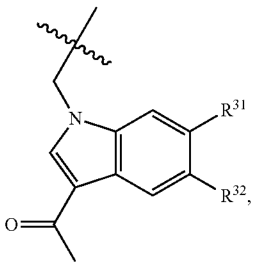

-continued
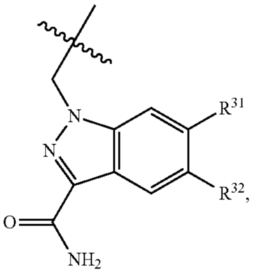
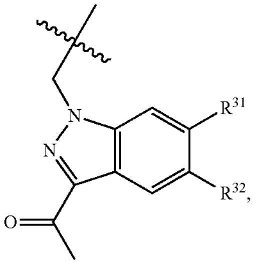
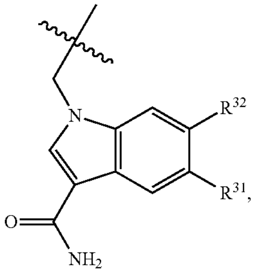
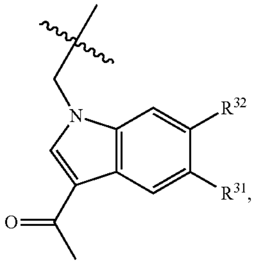
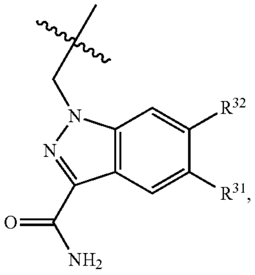
and
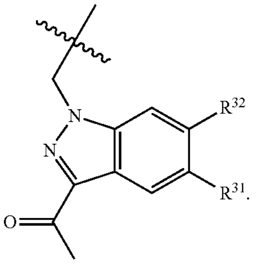
Additional non-limiting examples of A1 include:
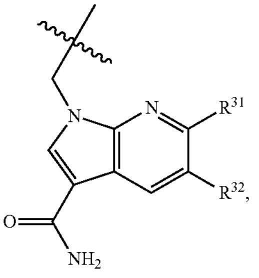
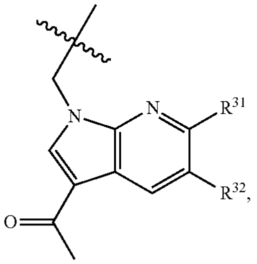
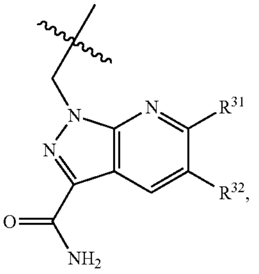
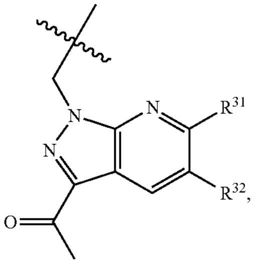
-continued
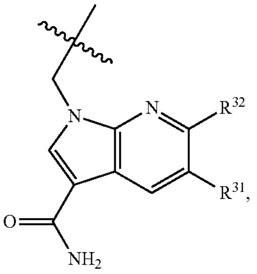
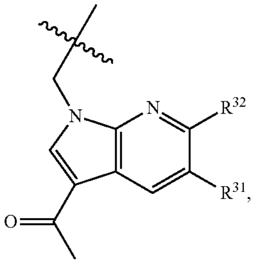
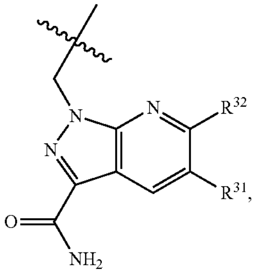
and
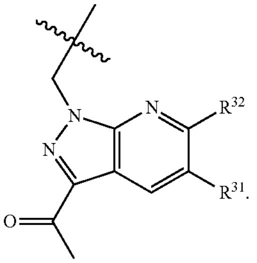
In one embodiment A1 is selected from:
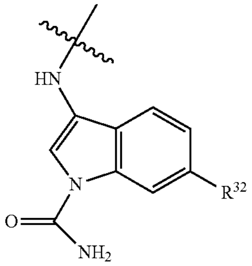
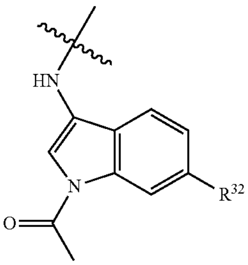
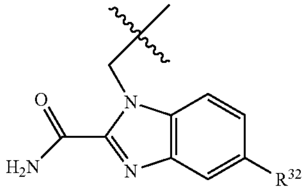
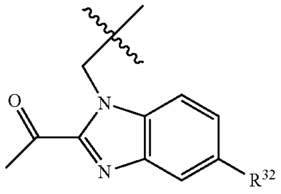
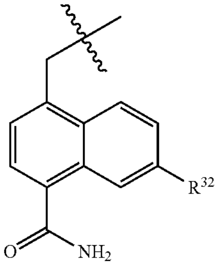
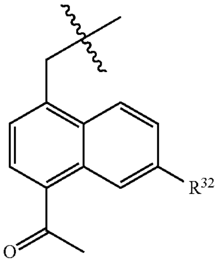
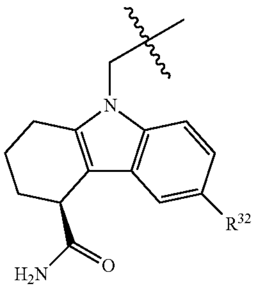

-continued
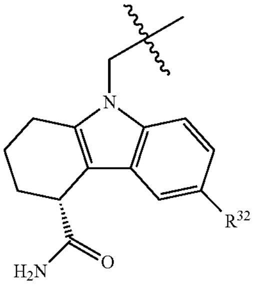
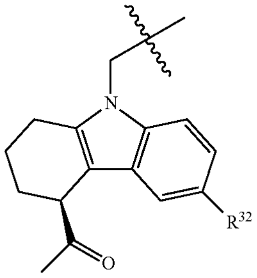
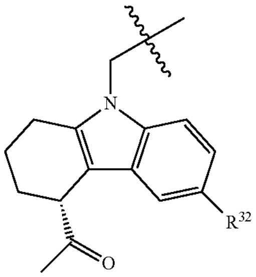
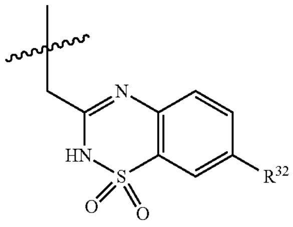
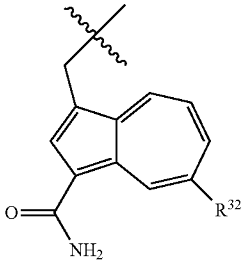
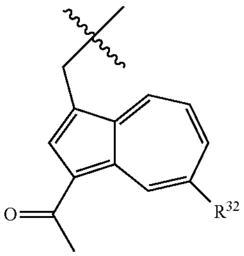
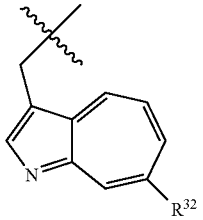
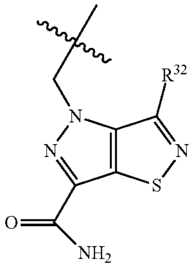
and
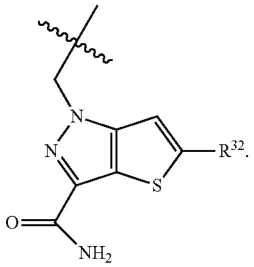
In one embodiment A3 is selected from:
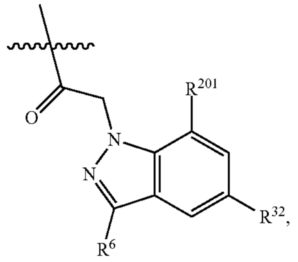
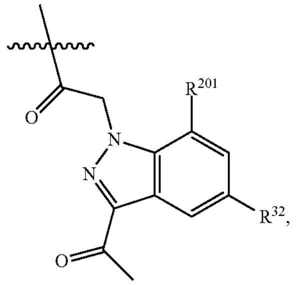
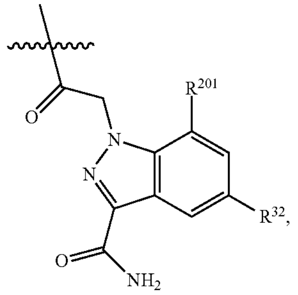
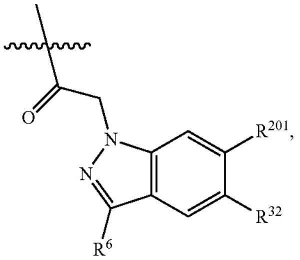
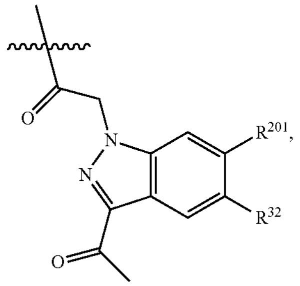
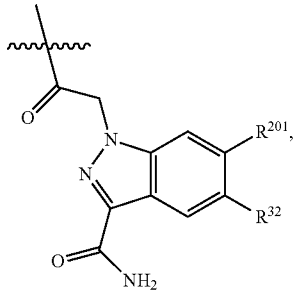

-continued
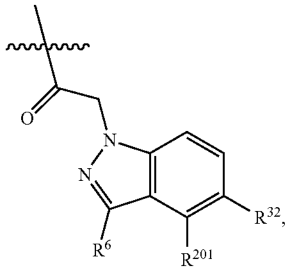
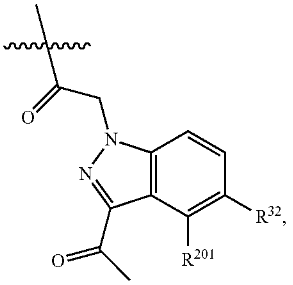
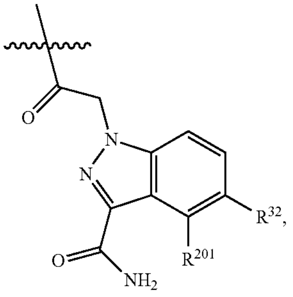
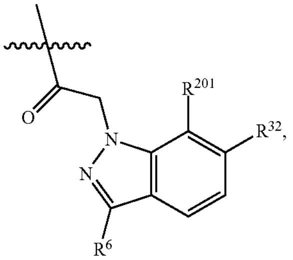
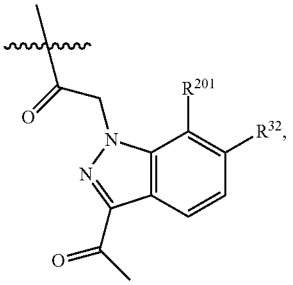
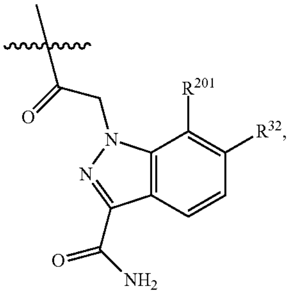
-continued
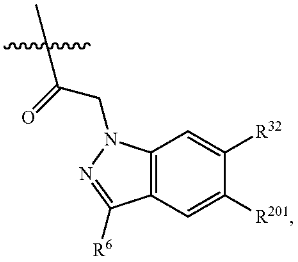
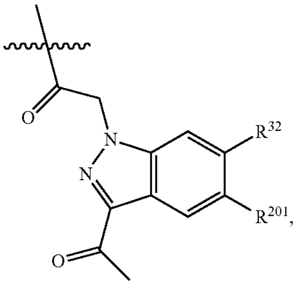
and
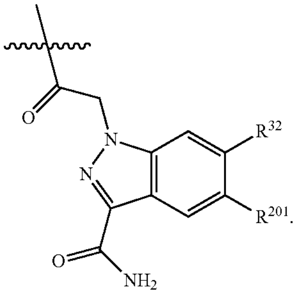
In one embodiment A3 is selected from:
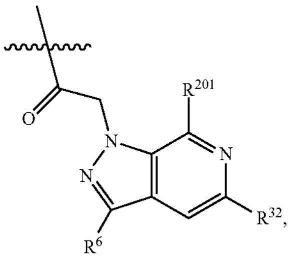
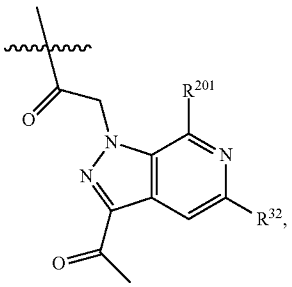

-continued
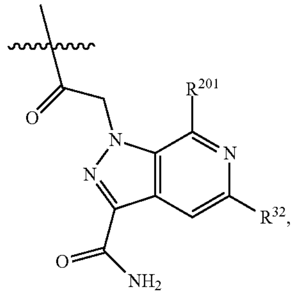
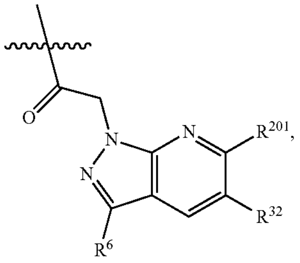
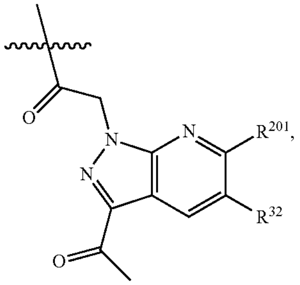
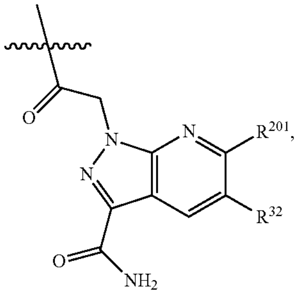
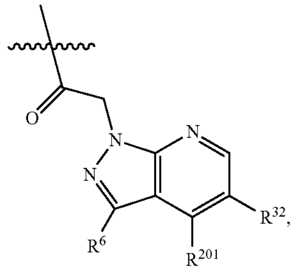
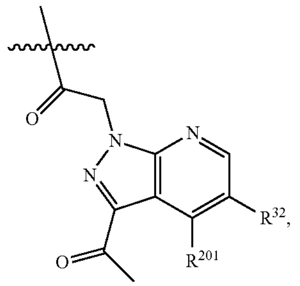
-continued
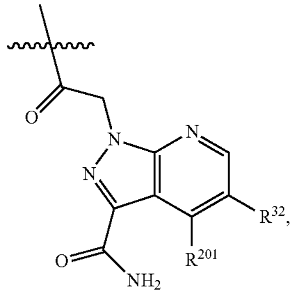
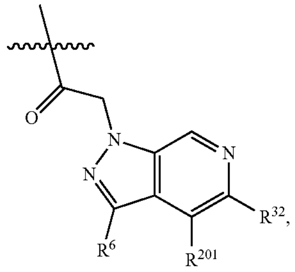
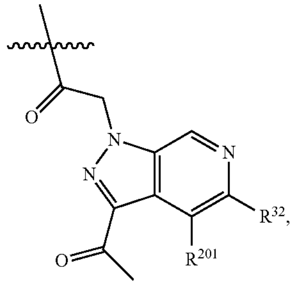
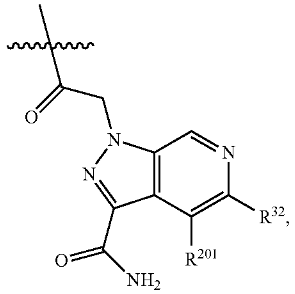
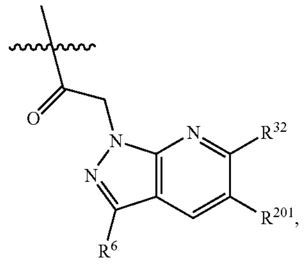
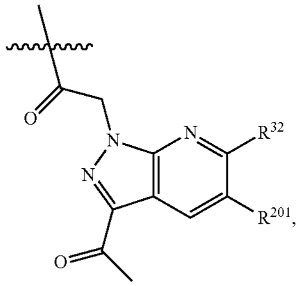
and -continued
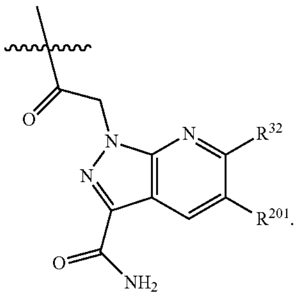
In one embodiment A3 is selected from:
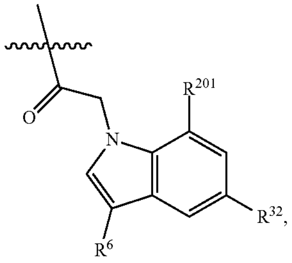
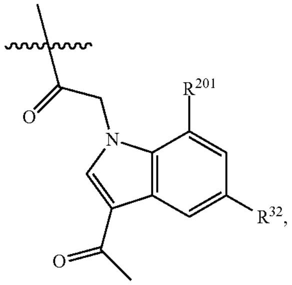
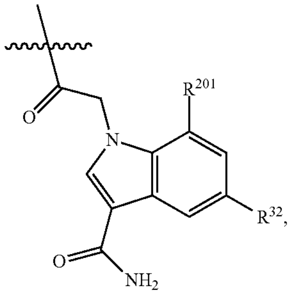
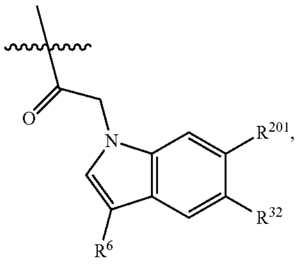
-continued
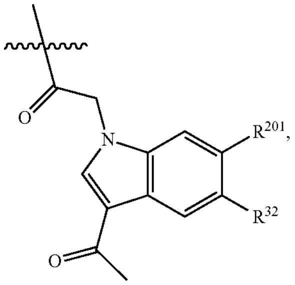
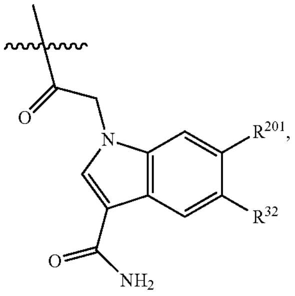
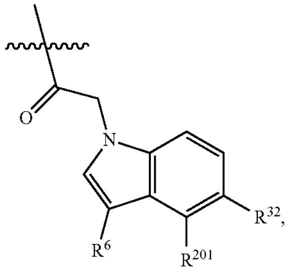
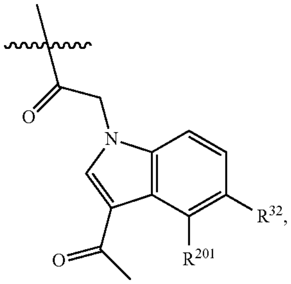
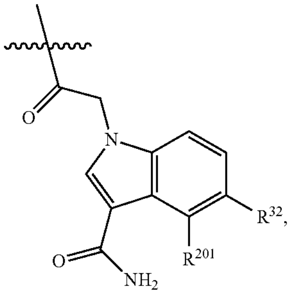
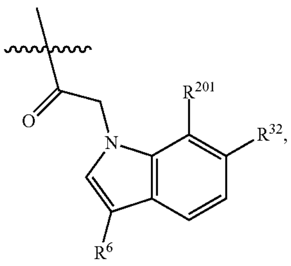

-continued
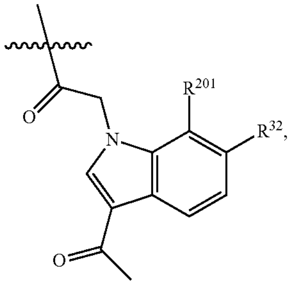
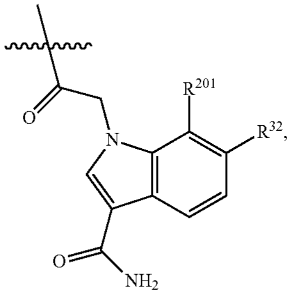
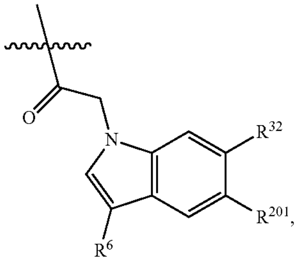
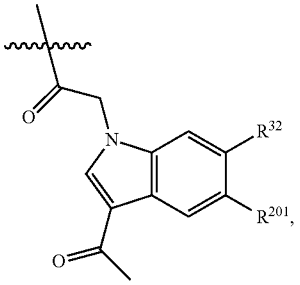
and
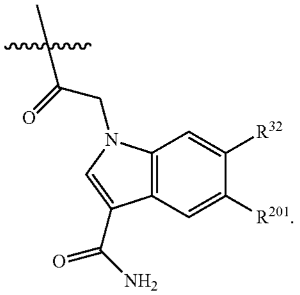
In one embodiment A3 is selected from:
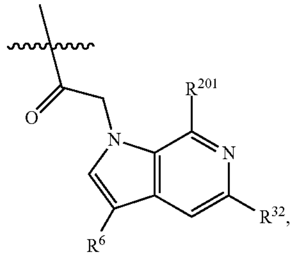
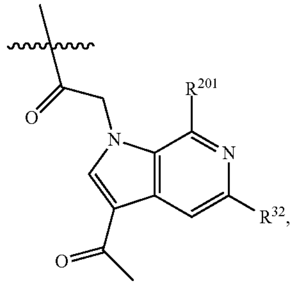
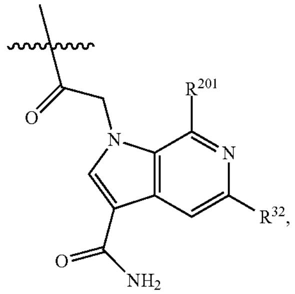
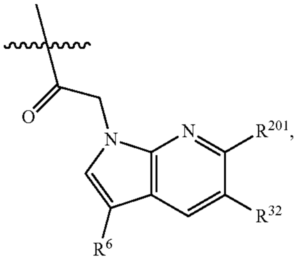
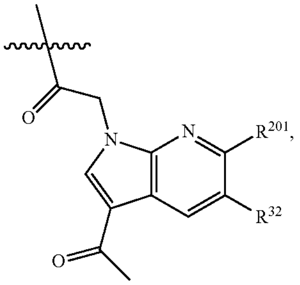
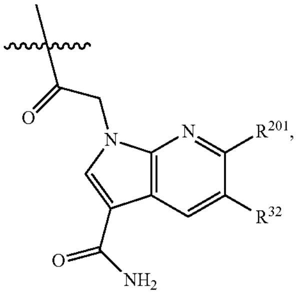

-continued
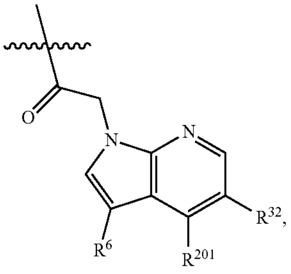
,
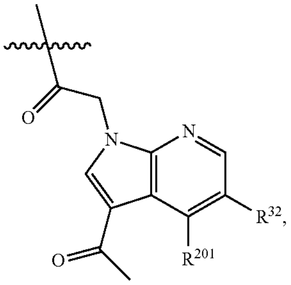
,
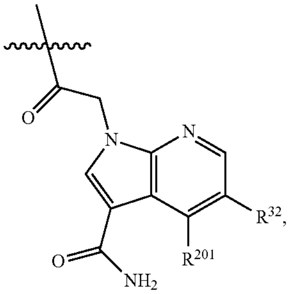
,
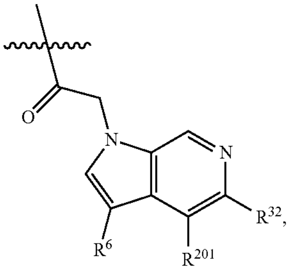
,
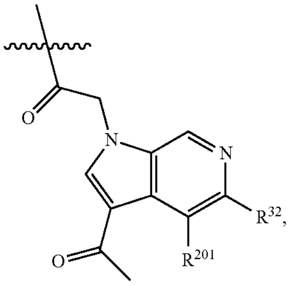
,
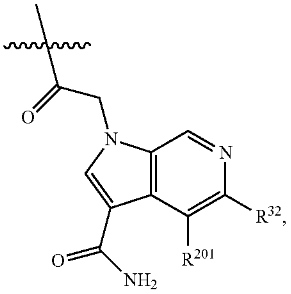
,
-continued
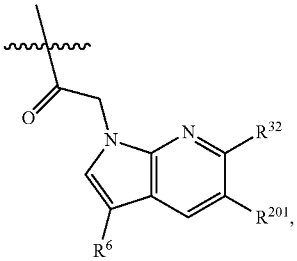
,
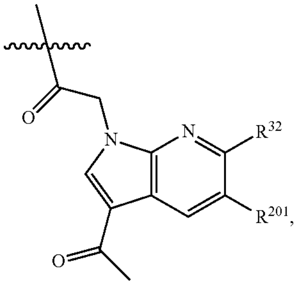
,
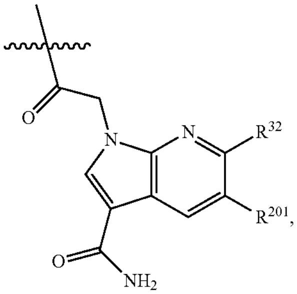
,
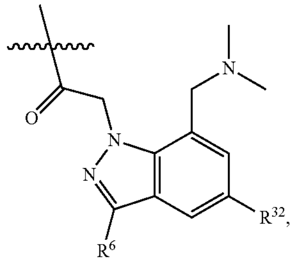
,
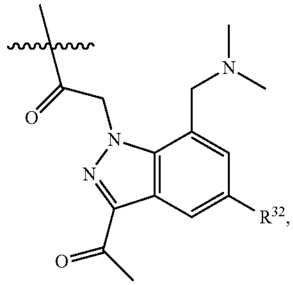
,
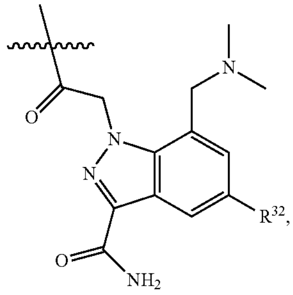
, -continued
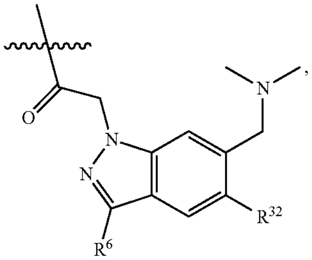
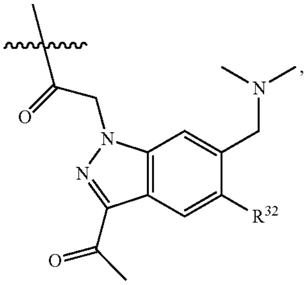
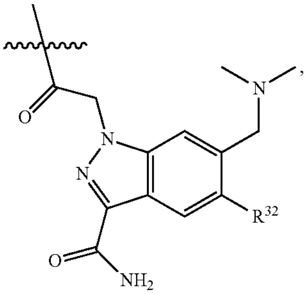
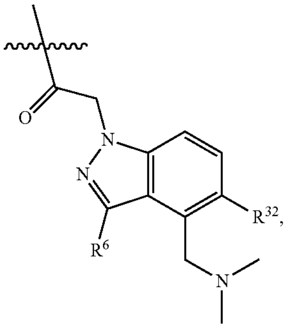
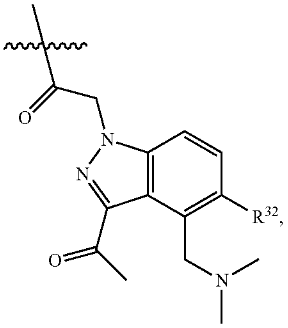
-continued
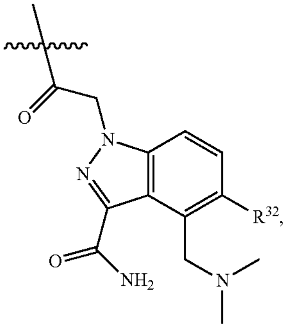
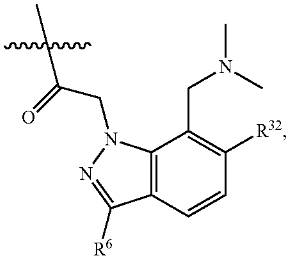
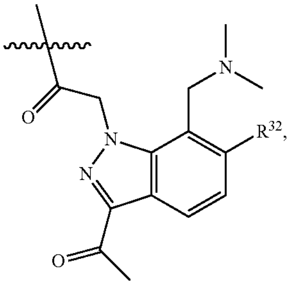
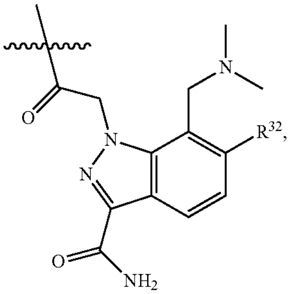
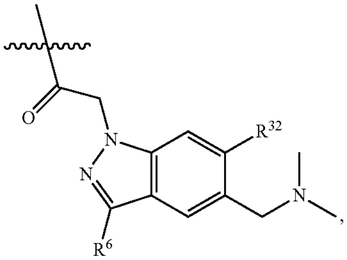
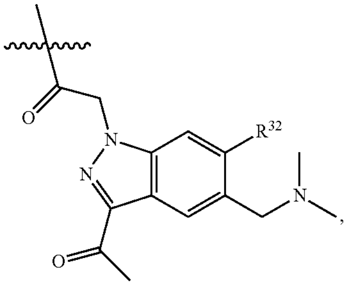
and -continued
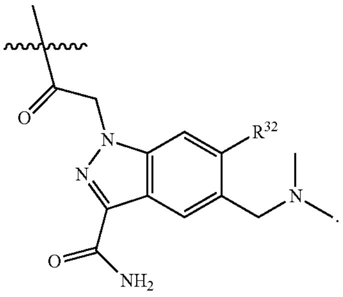
In one embodiment A3 is selected from:
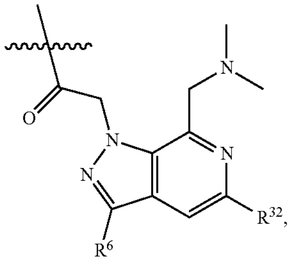
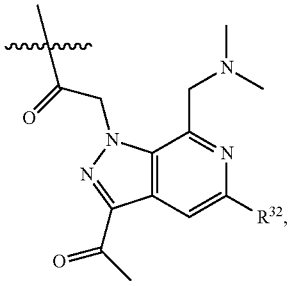
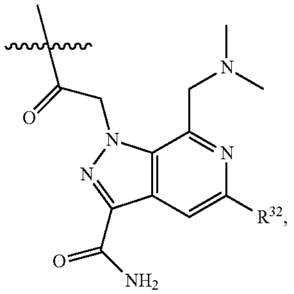
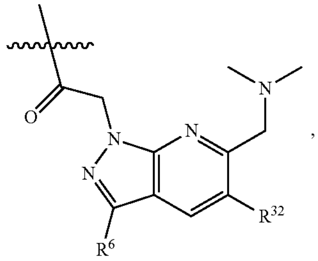
-continued
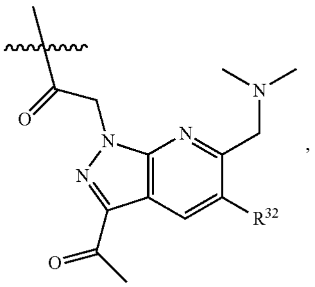
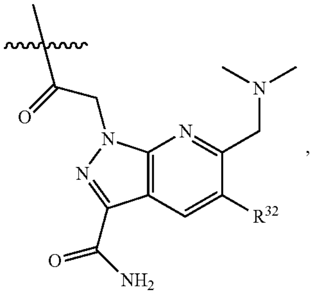
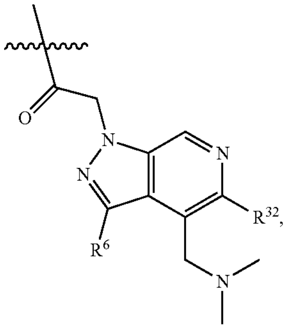
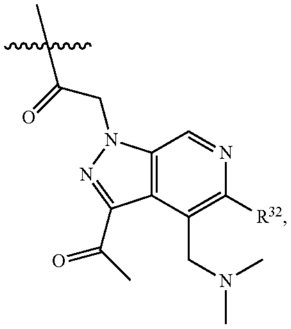
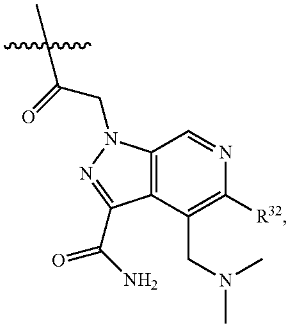

-continued
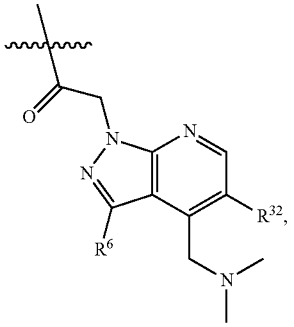
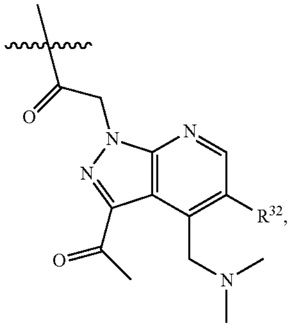
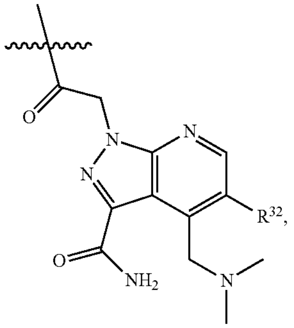
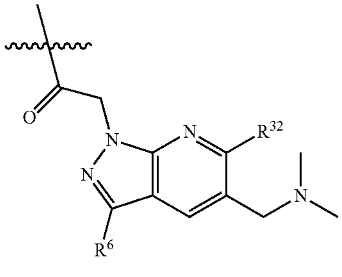
,
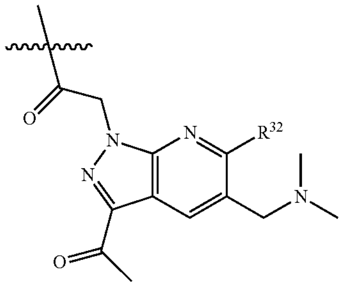
, and
-continued
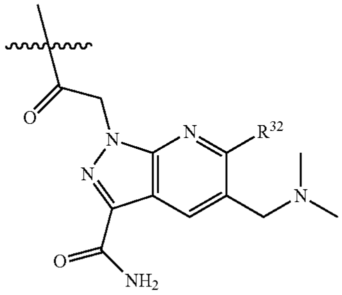
.
In one embodiment A3 is selected from:
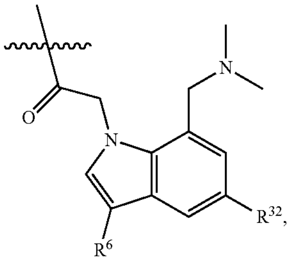
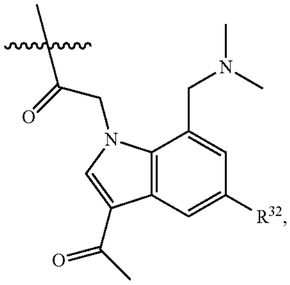
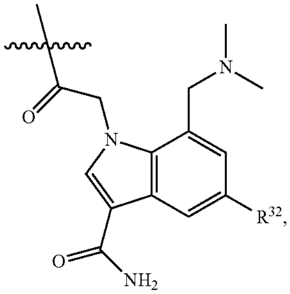
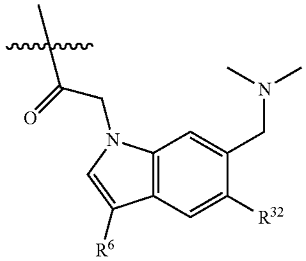
, -continued
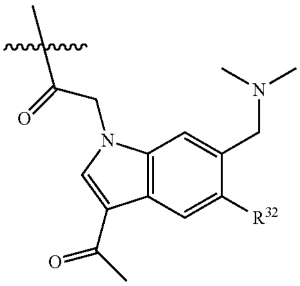
,
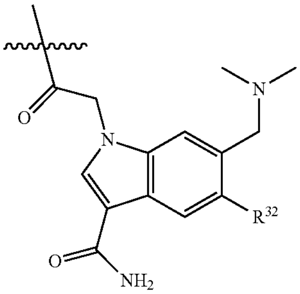
,
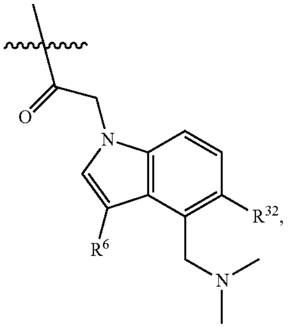
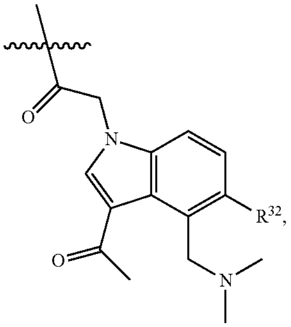
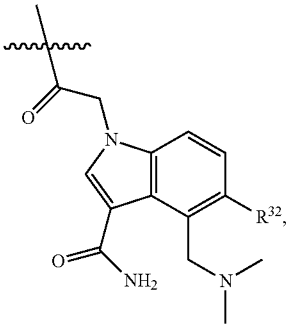
-continued
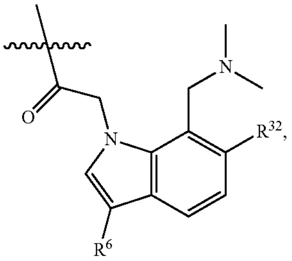
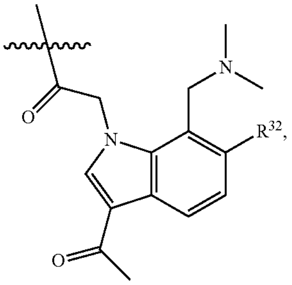
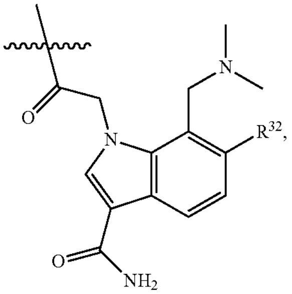
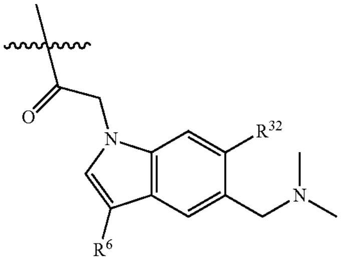
,
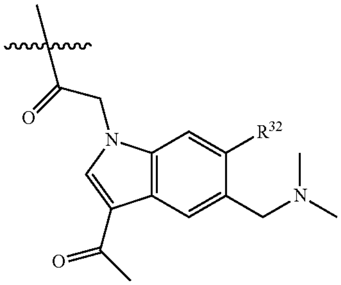
, and
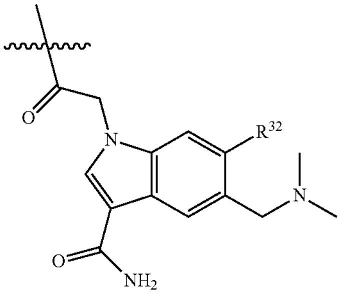
.

In one embodiment A3 is selected from:
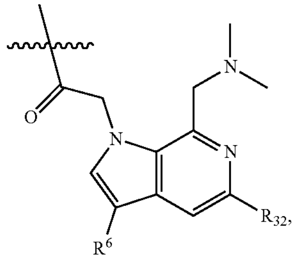
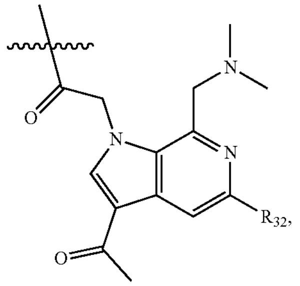
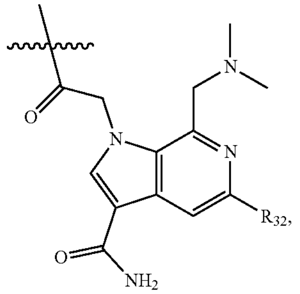
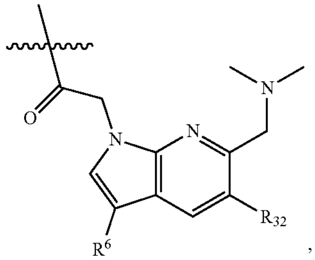
,
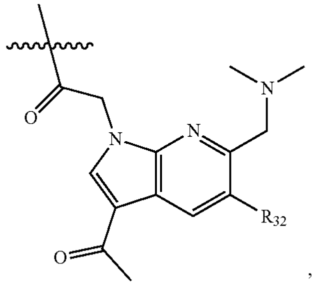
,
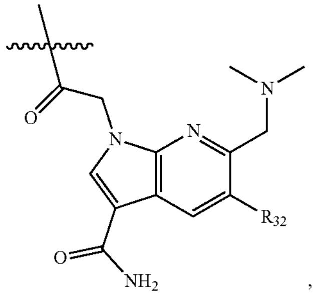
,
-continued
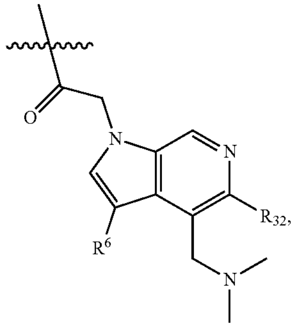
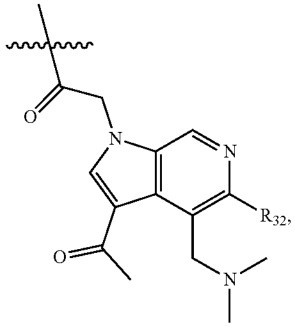
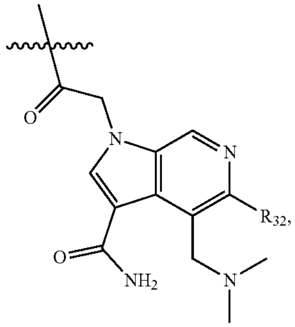
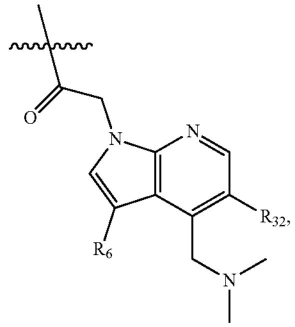
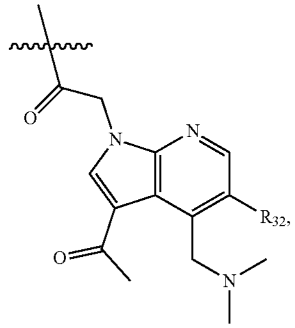

-continued
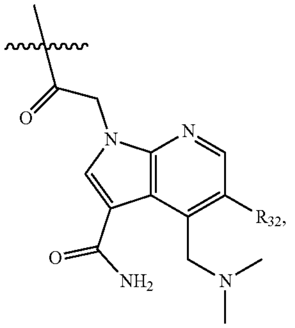
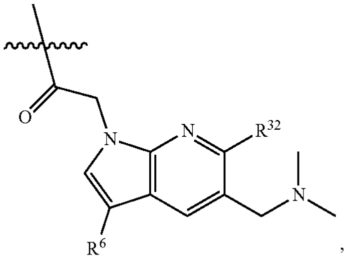
,
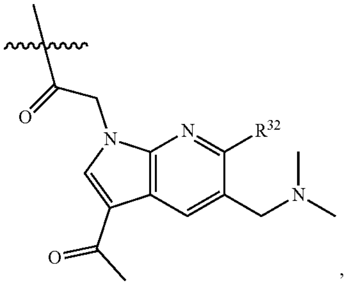
, and
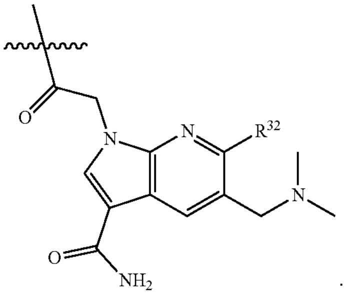
.
In one embodiment A1 is selected from:
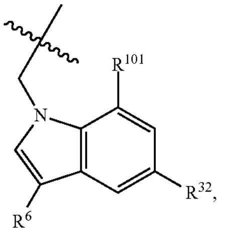
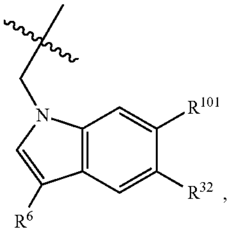
and
-continued
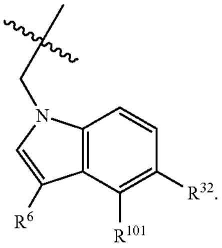
In one embodiment A1 is selected from:
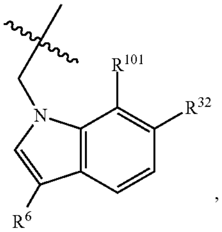
,
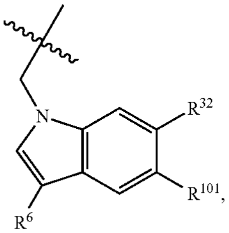
and
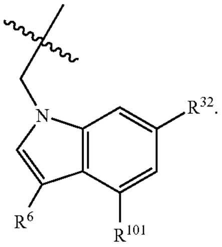
In one embodiment A1 is selected from:
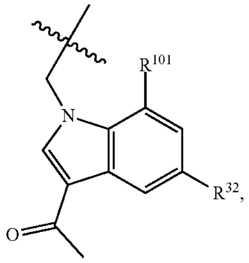
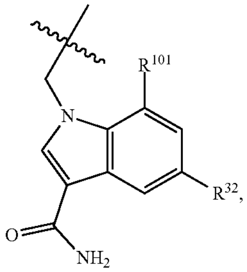
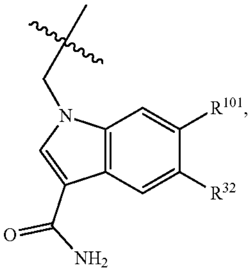
and
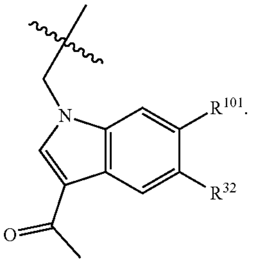

In one embodiment A1 is selected from:
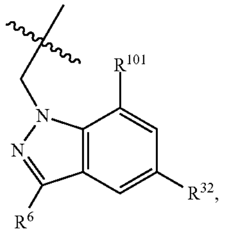
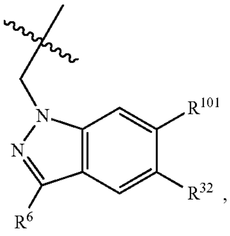
and
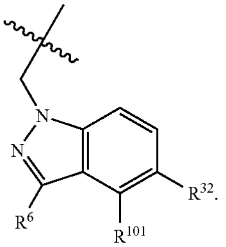
In one embodiment A1 is selected from:
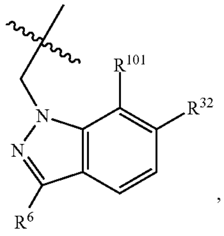
,
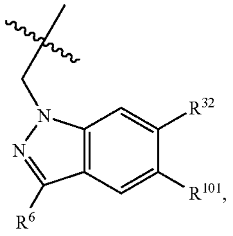
and
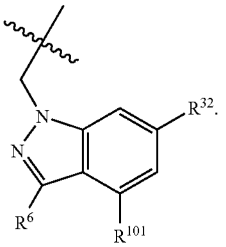
In one embodiment A1 is selected from:
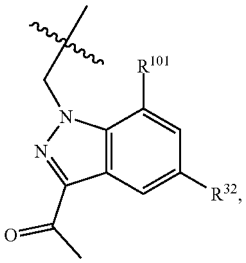
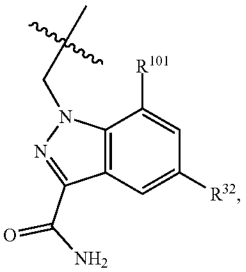
-continued
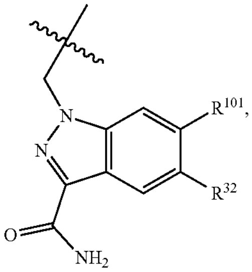
and
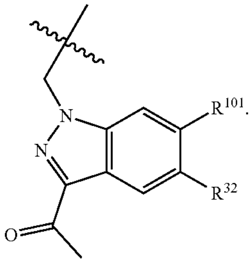
In the above embodiments and throughout this specification $R^{101}$ is $C_1$-$C_4$ alkyl or $C_3$-$C_7$ cycloalkyl.
In another embodiment A1 is selected from:
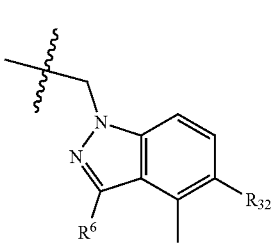
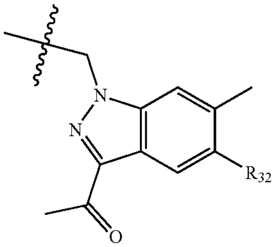
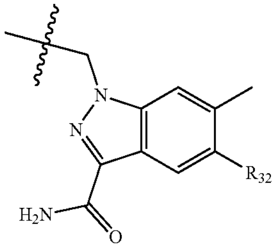
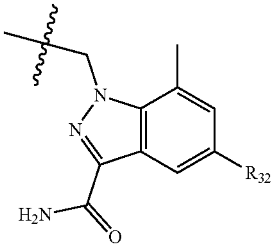
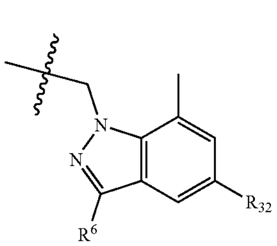
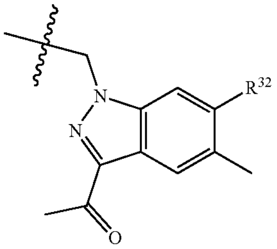
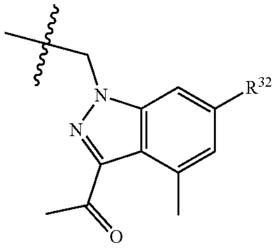
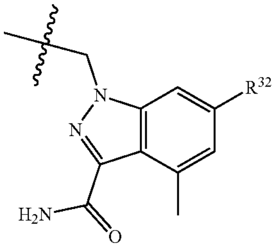
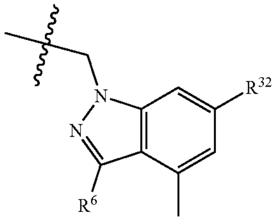
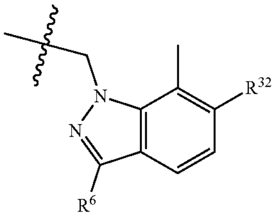

-continued
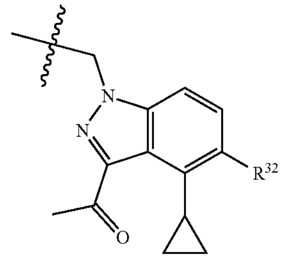
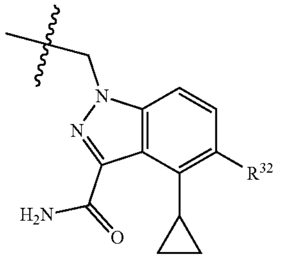
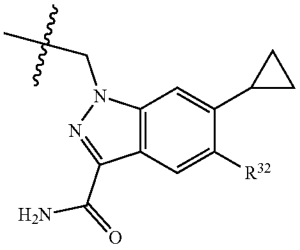
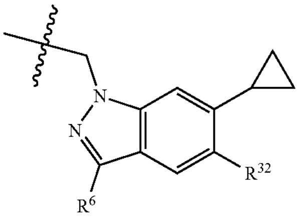
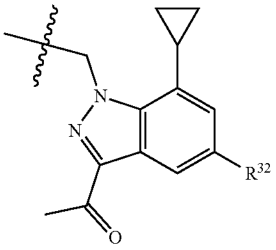
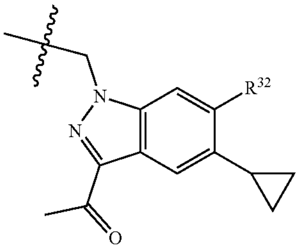
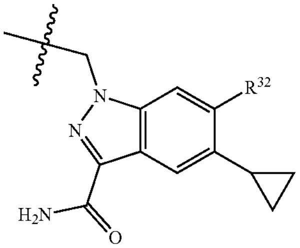
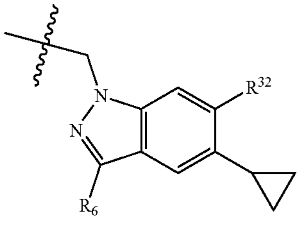
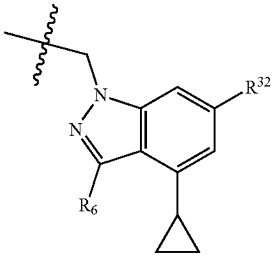
-continued
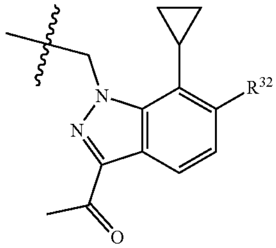
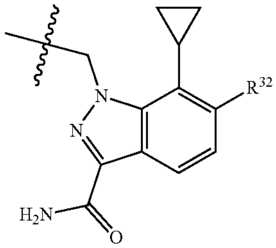
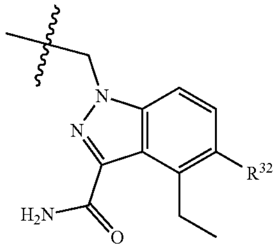
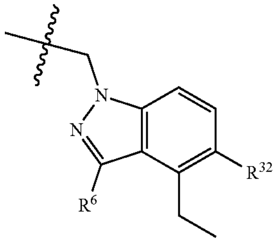
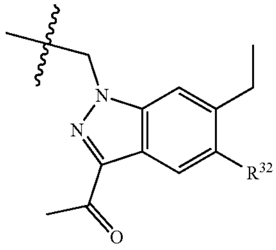
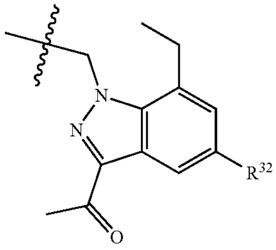
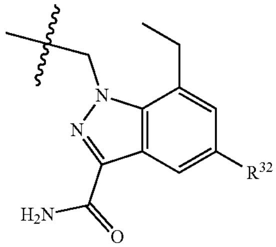
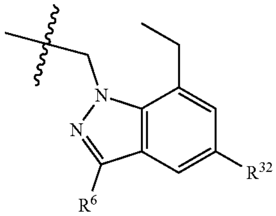
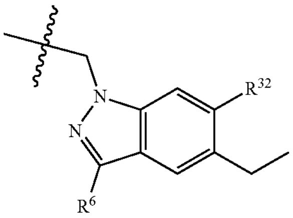
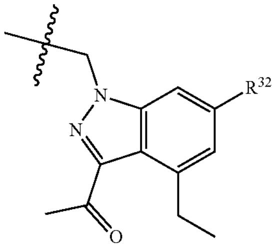
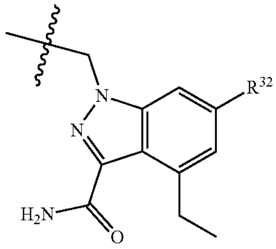
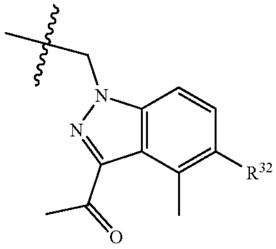

-continued
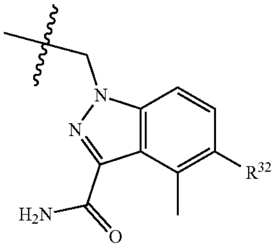
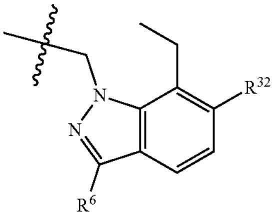
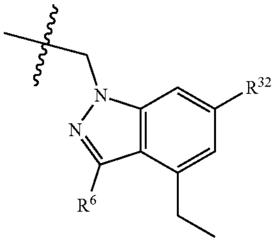
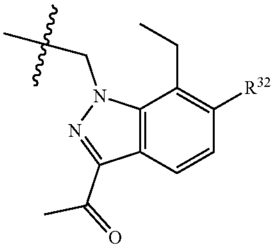
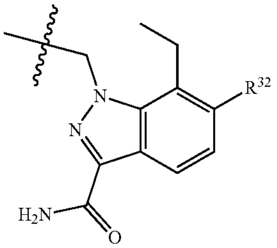
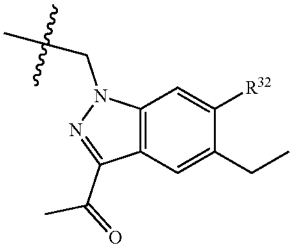
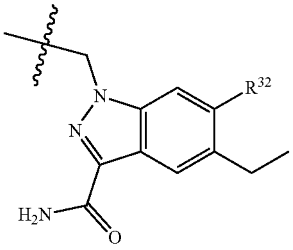
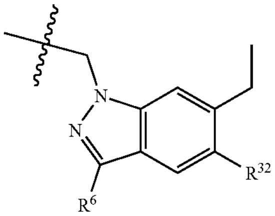
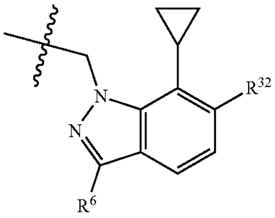
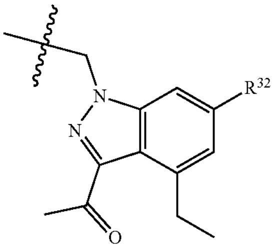
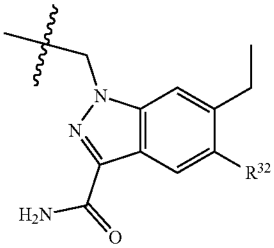
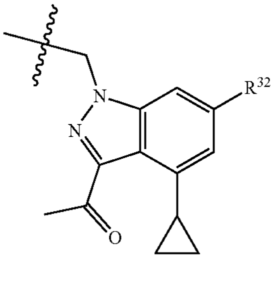
-continued
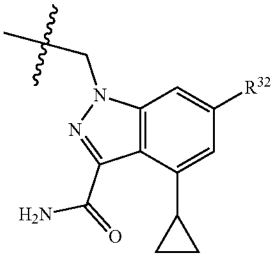
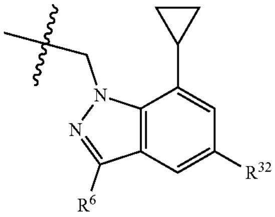
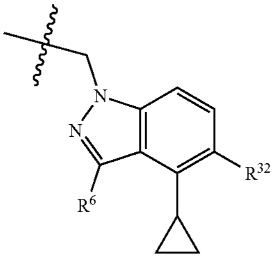
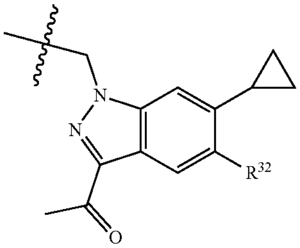
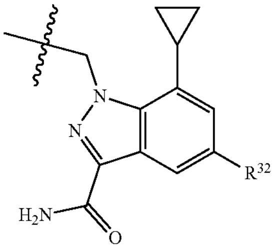
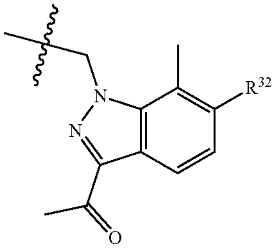
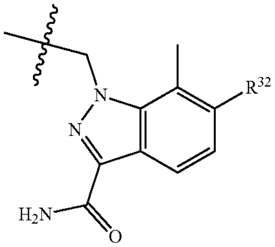
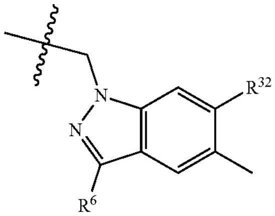
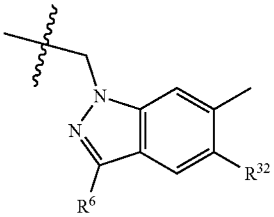
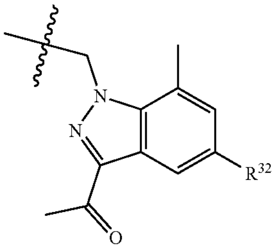
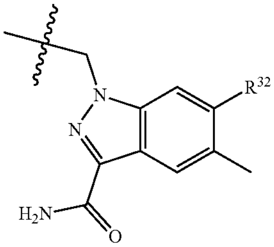
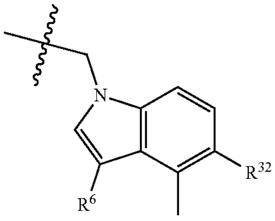

-continued
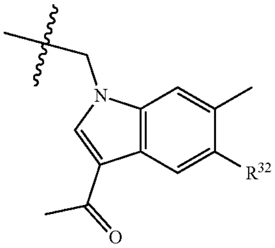
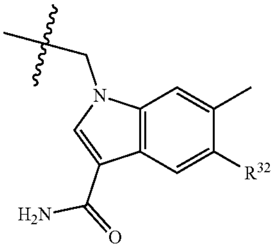
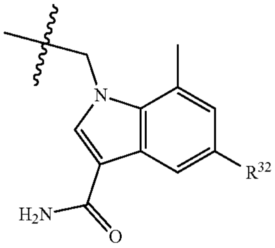
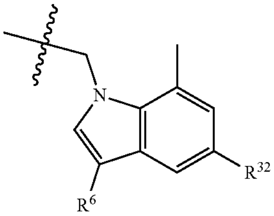
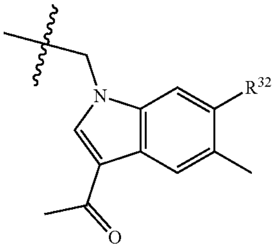
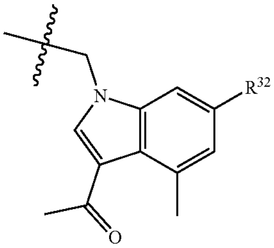
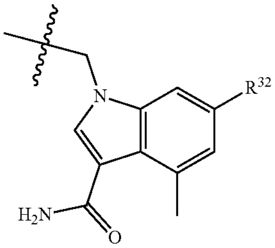
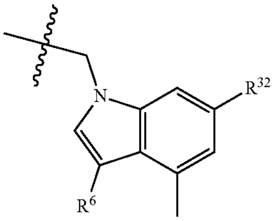
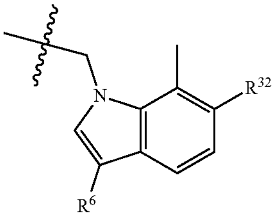
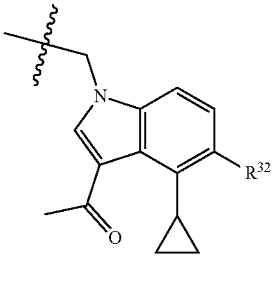
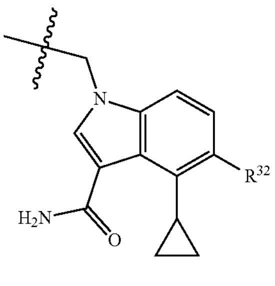
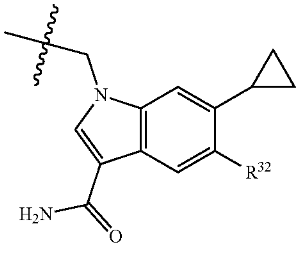
-continued
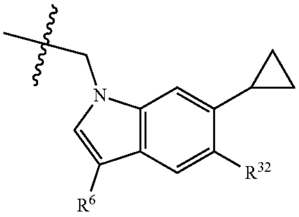
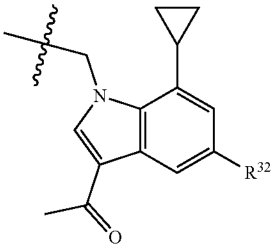
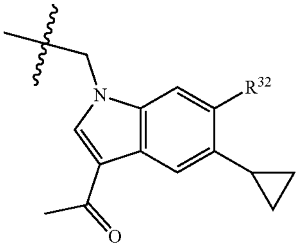
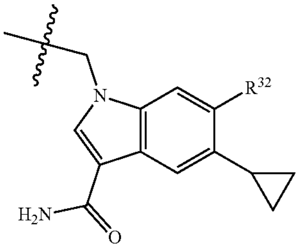
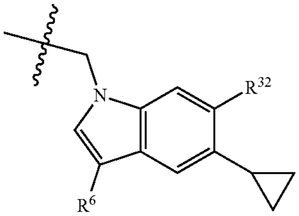
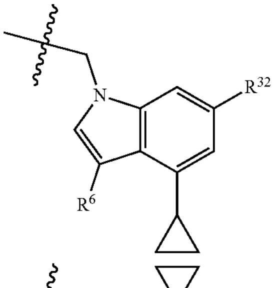
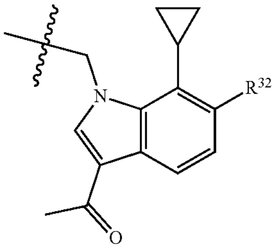
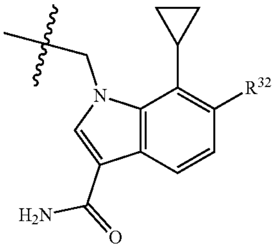
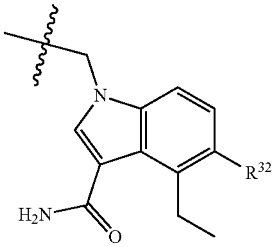
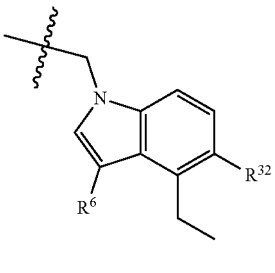
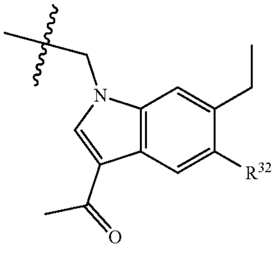

-continued
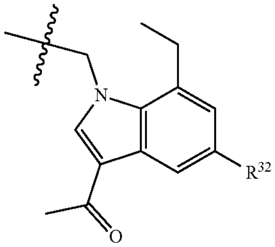
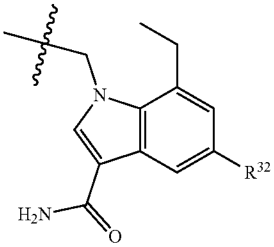
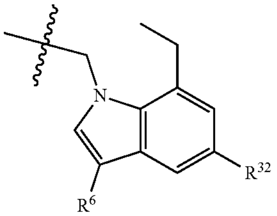
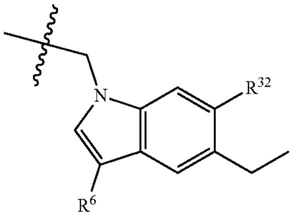
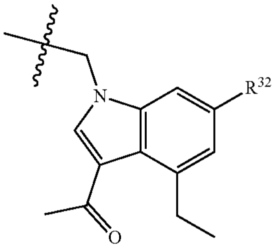
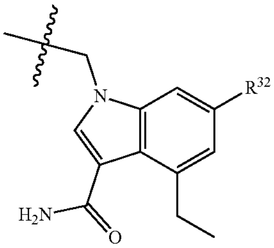
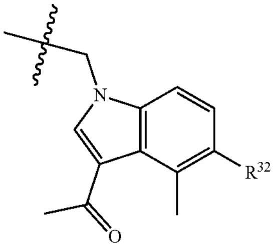
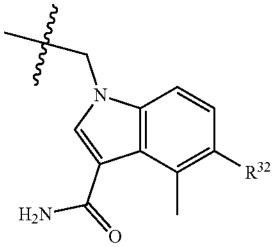
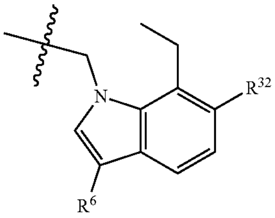
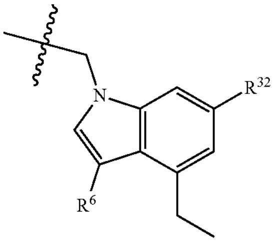
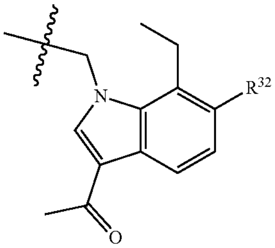
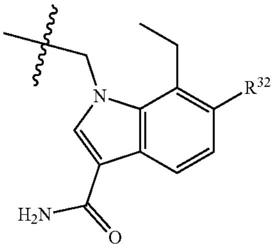
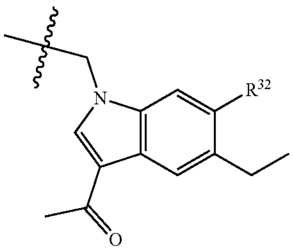
-continued
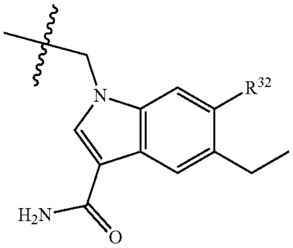
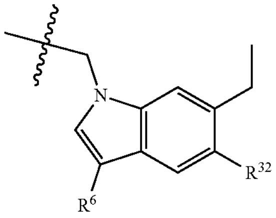
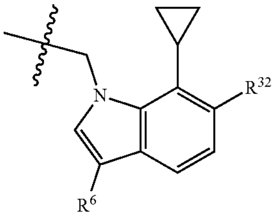
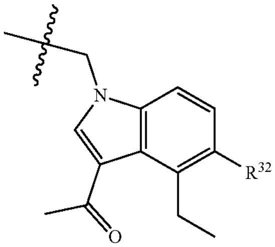
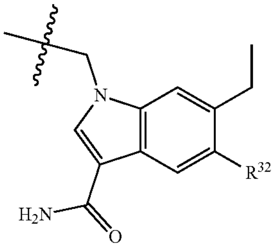
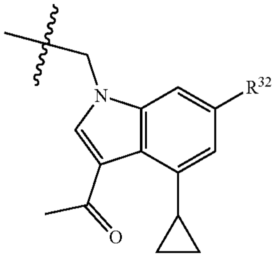
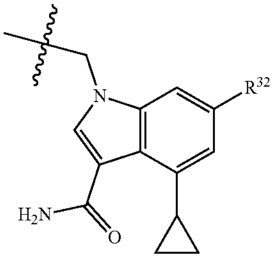
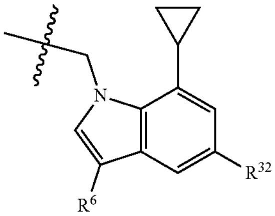
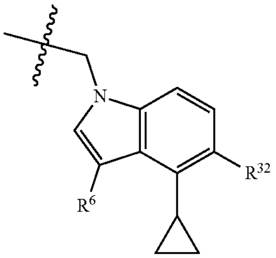
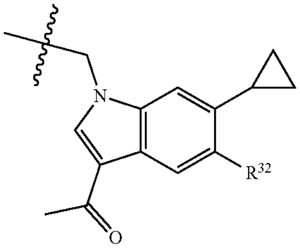
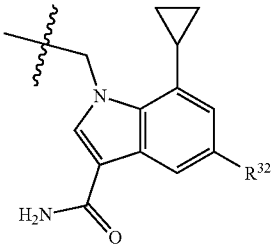
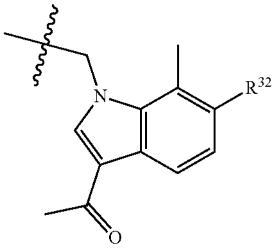

-continued
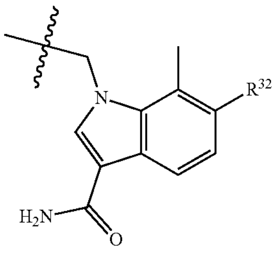
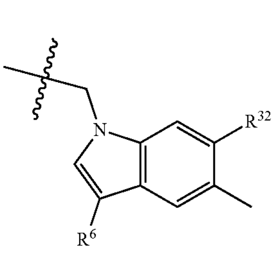
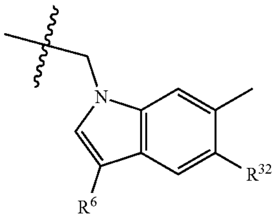
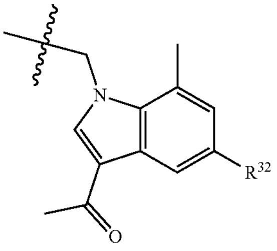
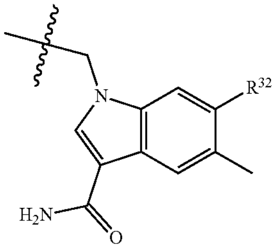
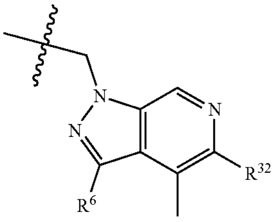
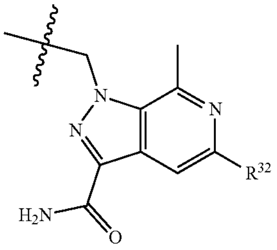
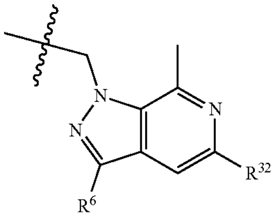
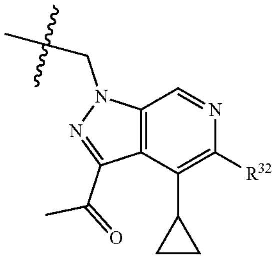
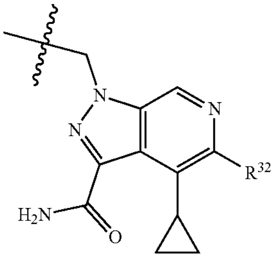
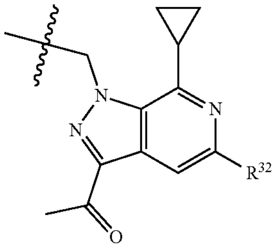
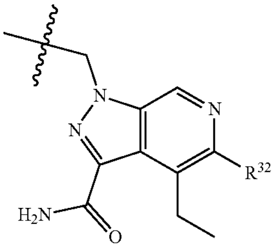
-continued
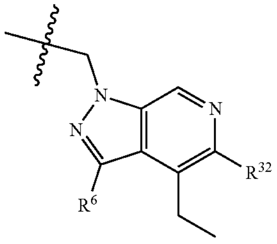
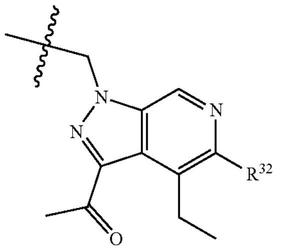
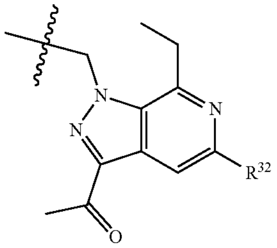
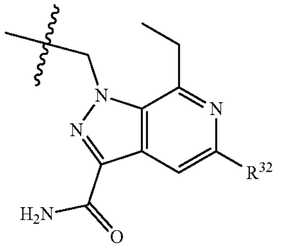
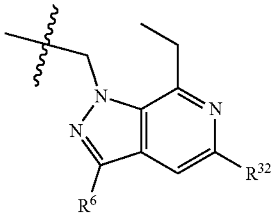
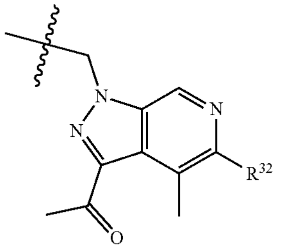
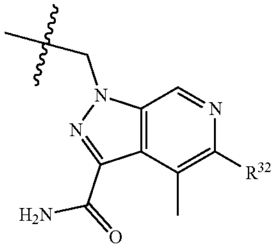
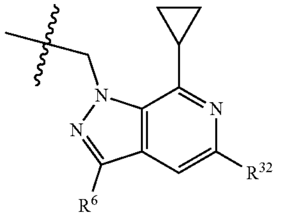
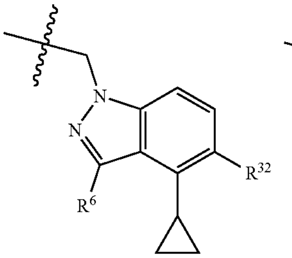
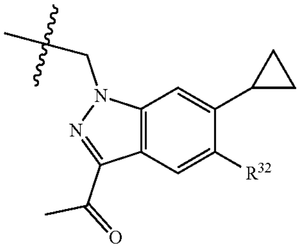
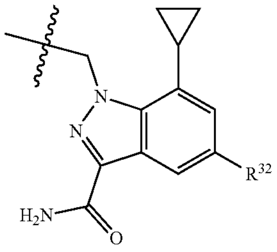
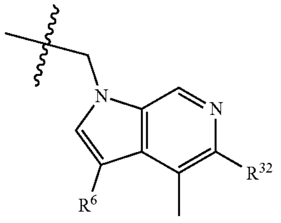

-continued
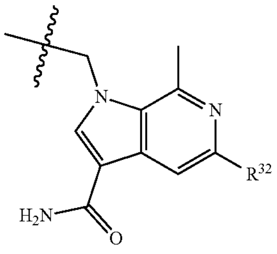
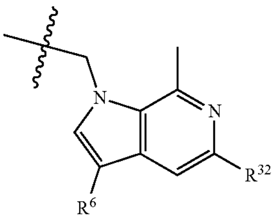
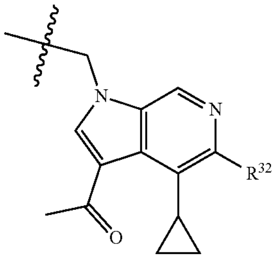
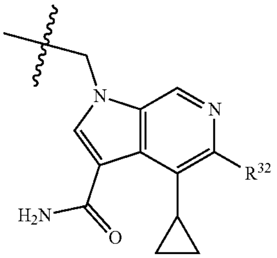
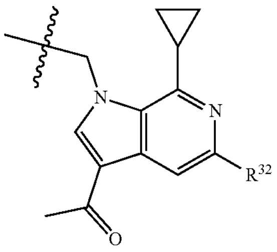
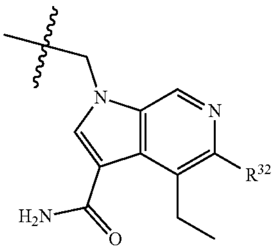
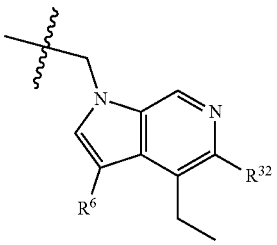
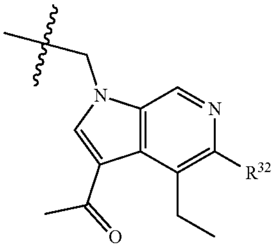
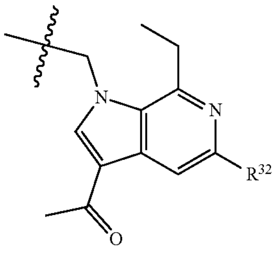
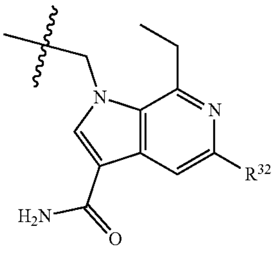
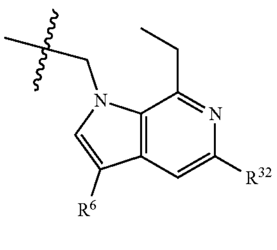
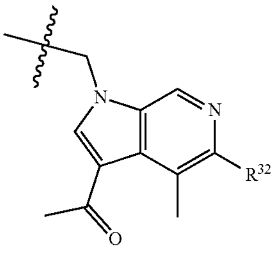
-continued
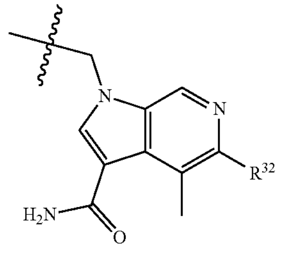
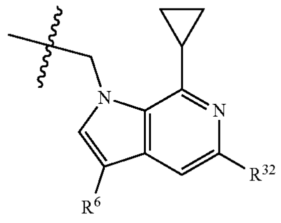
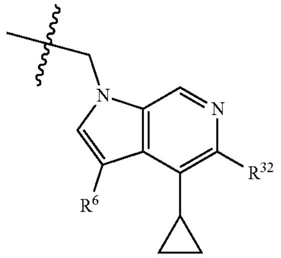
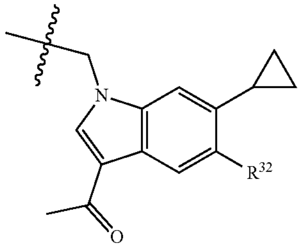
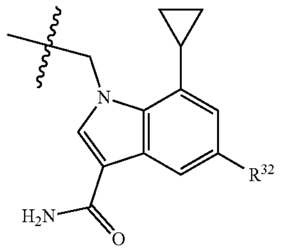
In another embodiment, A3 is selected from:
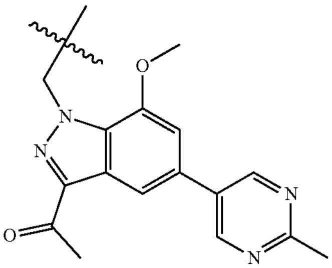
,
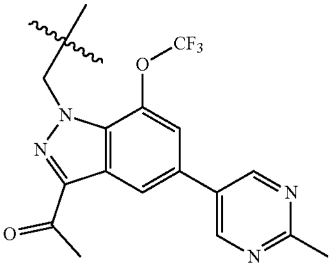
,
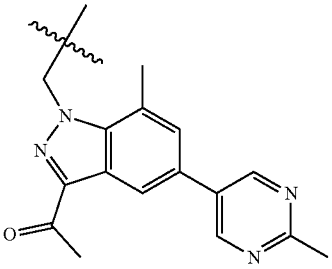

In another embodiment A is selected from:
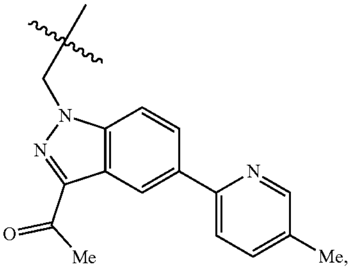
,
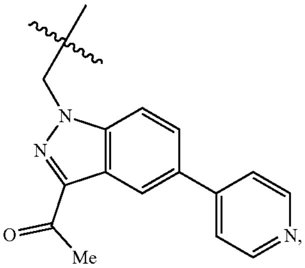
,
In an alternative embodiment A3 is selected from:
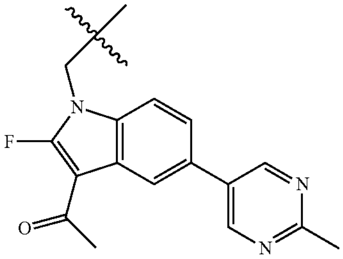
,
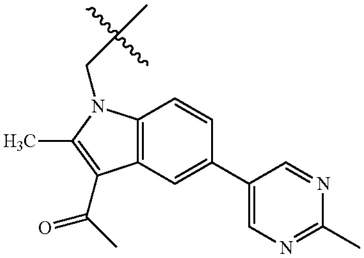
,
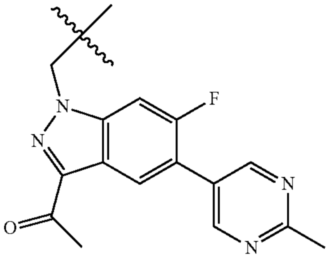
,
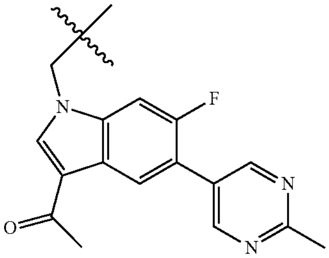
,
-continued
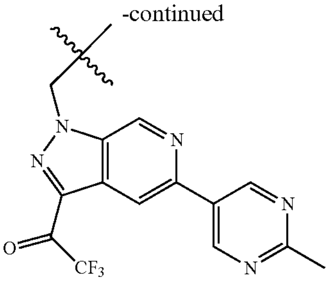
,
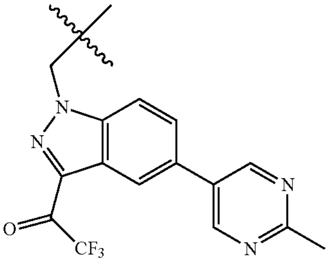
,
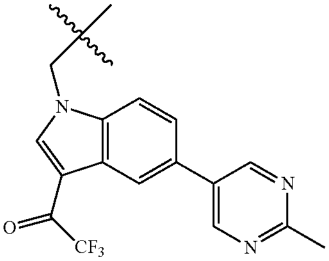
,
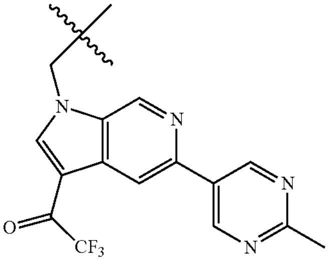
,
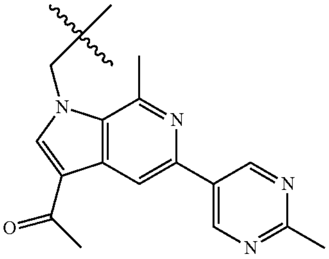
,
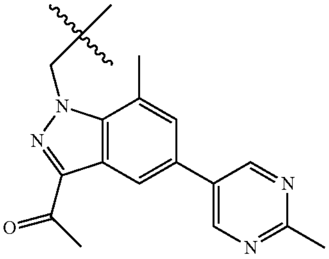
, -continued
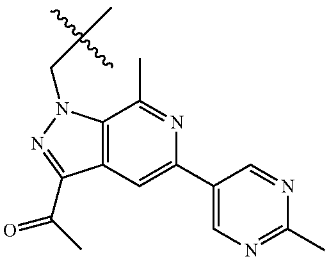
,
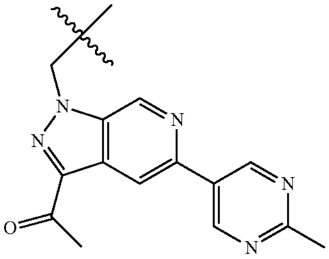
,
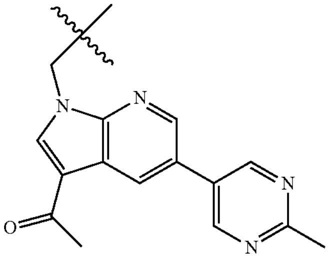
,
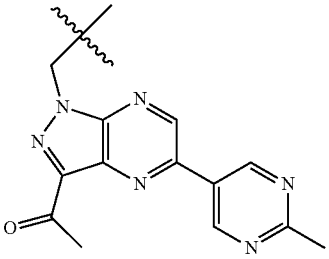
,
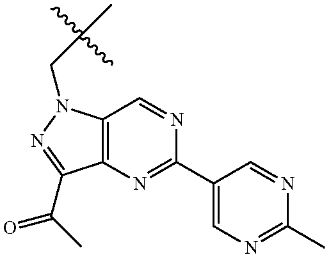
,
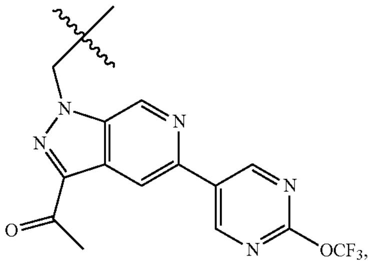
and
-continued
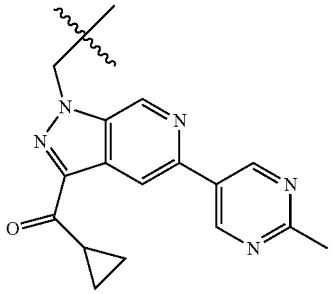
.
In another embodiment A1 is selected from:
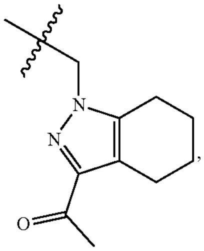
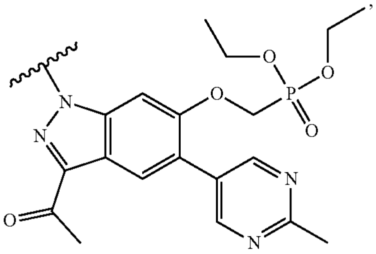
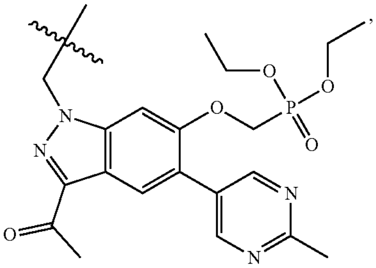
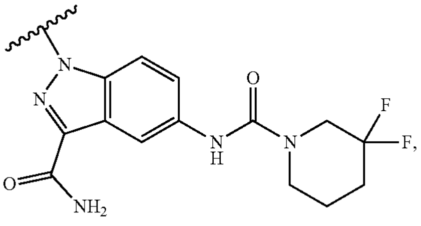
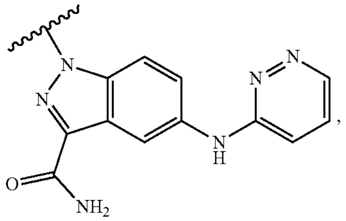

-continued
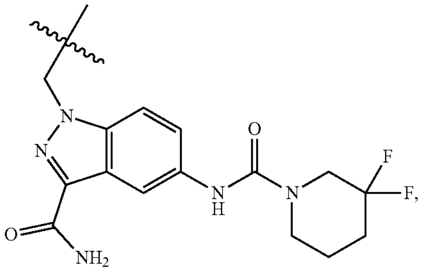
and
-continued
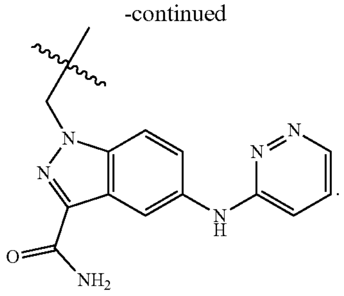
In an alternative embodiment A1 is selected from:
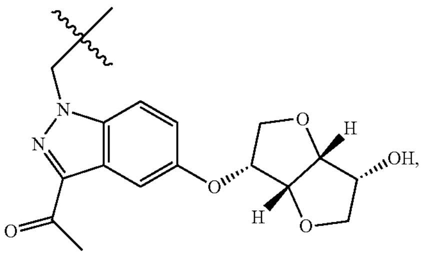
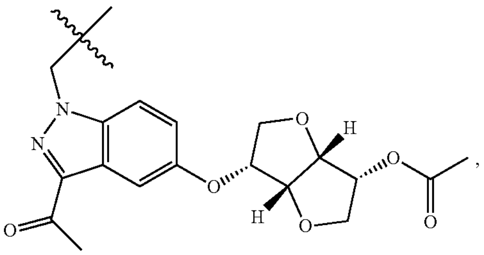
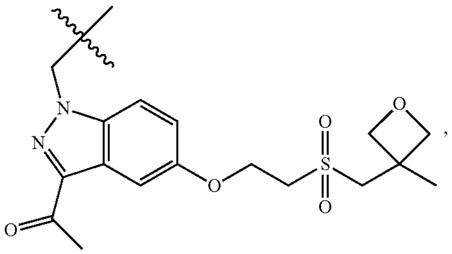
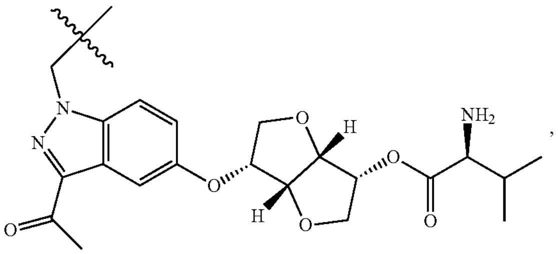
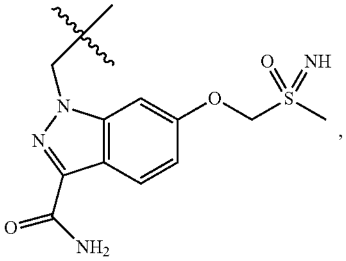
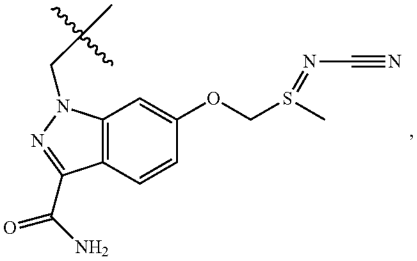
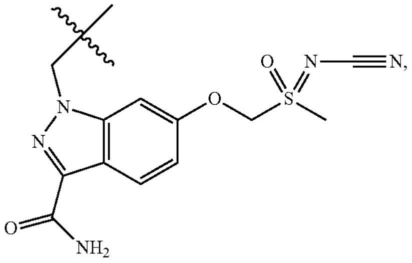
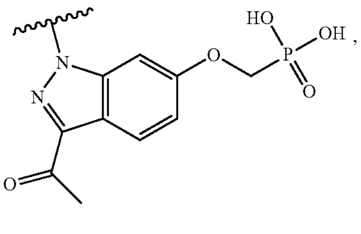
and
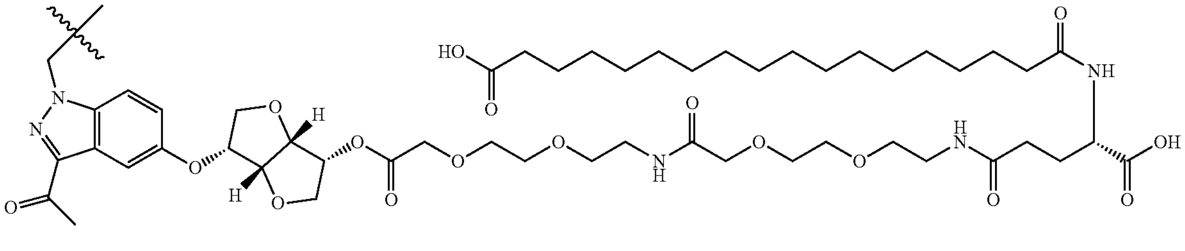

A4 is selected from:
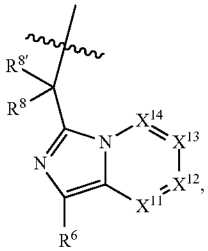
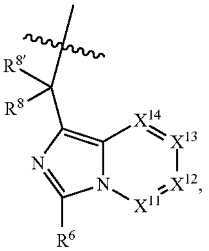
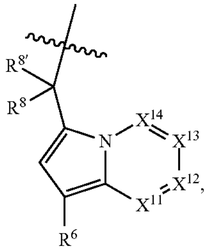
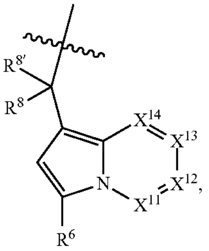
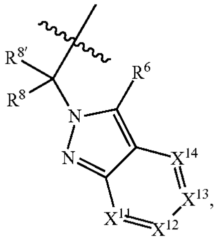
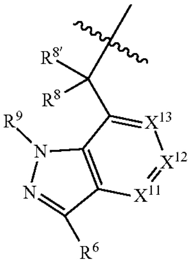
,
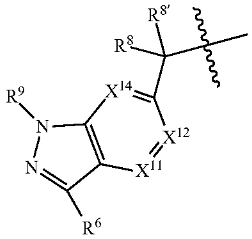
,
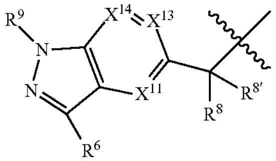
,
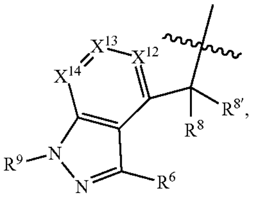
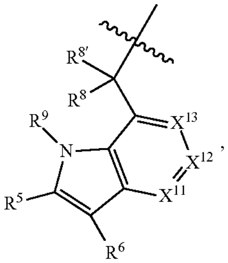
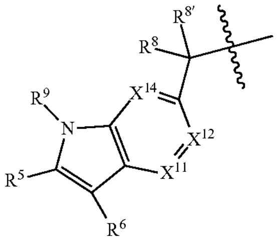
,
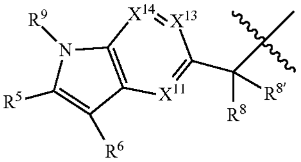
,
-continued
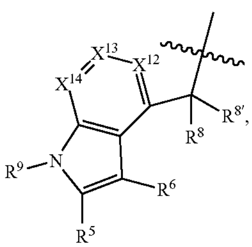
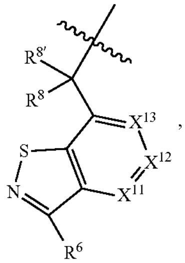
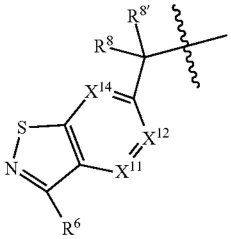
,
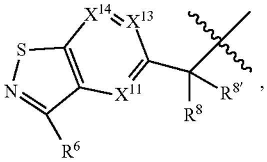
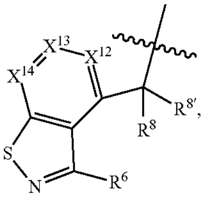
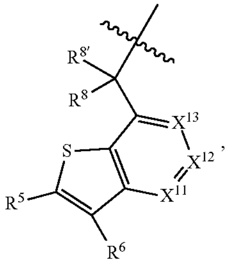
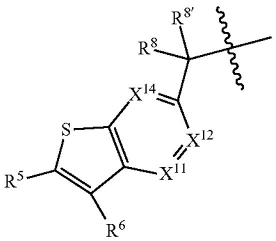
,
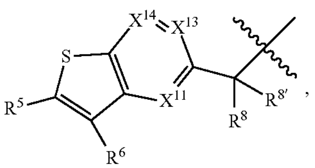
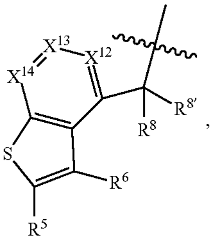
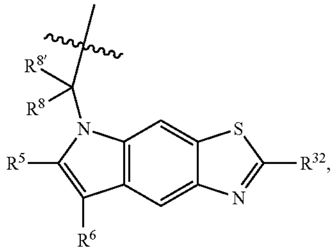

-continued
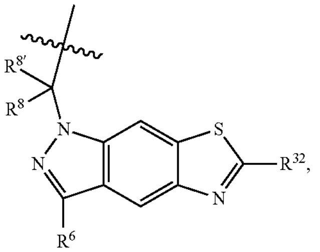
and
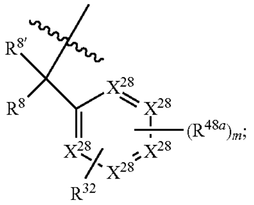
wherein m, $R^5$, $R^6$, $R^8$, $R^{8'}$, $R^9$, $R^{32}$, $R^{48}$, $X^{11}$, $X^{12}$, $X^{13}$, and $X^{14}$ are all defined above.
In one embodiment A4 is selected from:
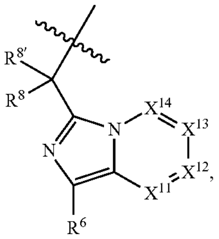
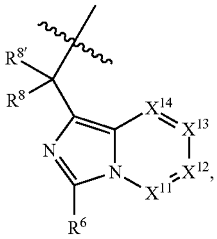
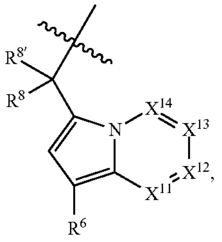
and
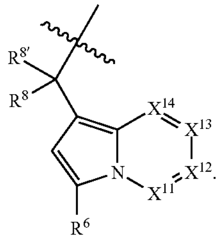
In one embodiment A4 is
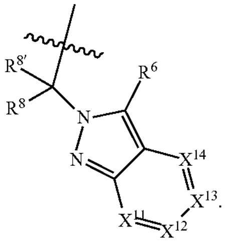
In one embodiment A4 is selected from:
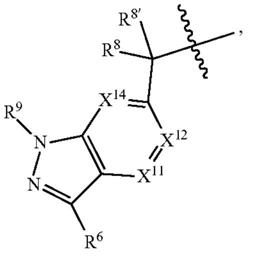
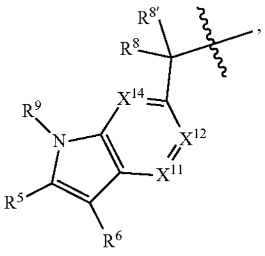
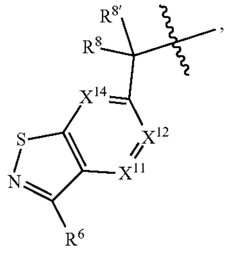
and
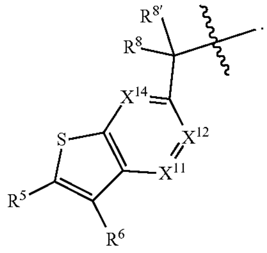
In one embodiment A4 is selected from:
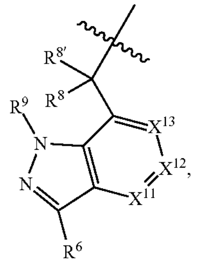
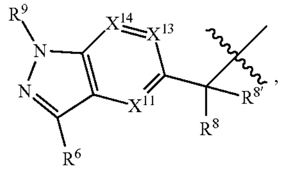
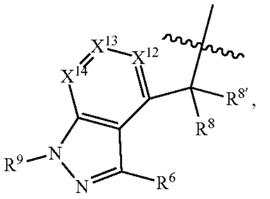
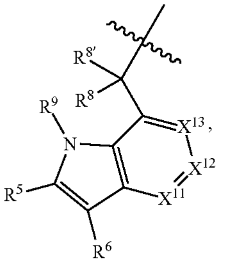
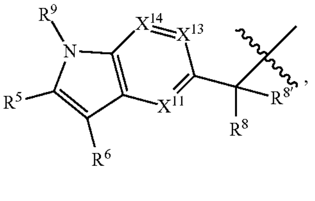
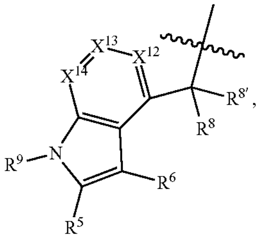
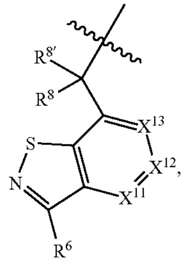
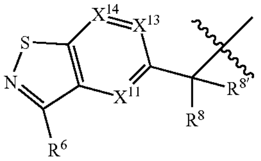

-continued
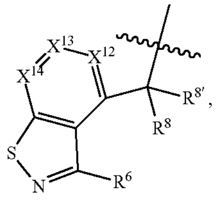
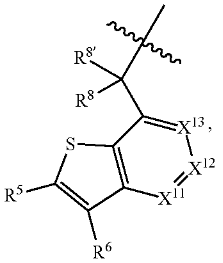
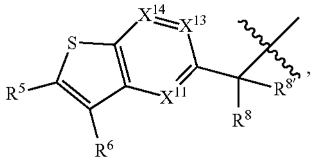
and
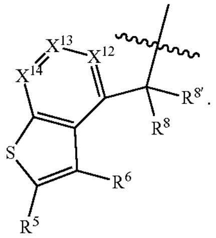
In one embodiment A4 is selected from:
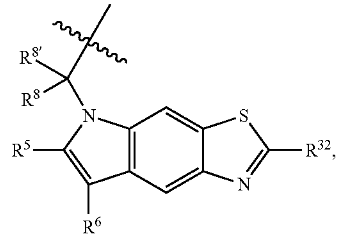
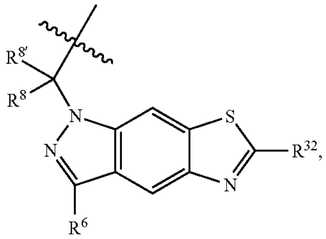
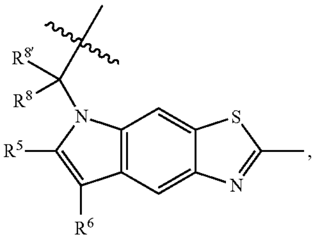
and
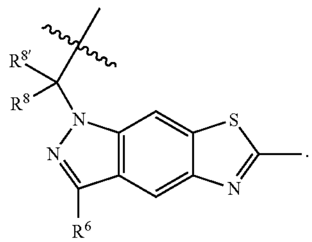
In one embodiment A4 is
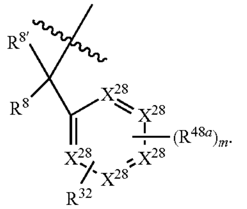
Embodiments of L
In one embodiment L1 is selected from:
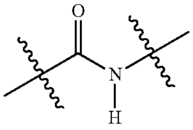
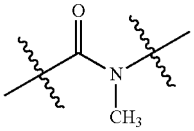
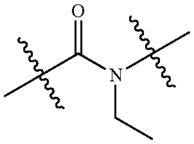
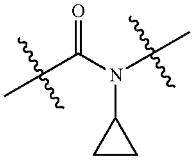
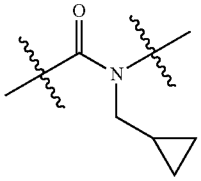
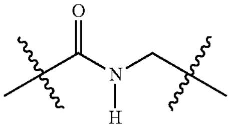
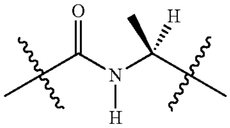
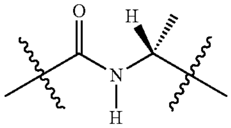
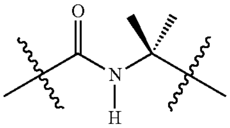
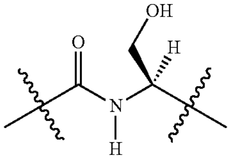
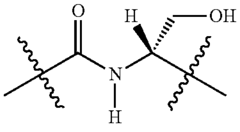
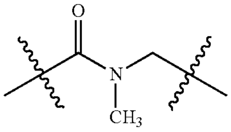
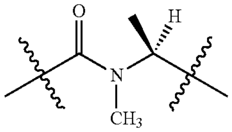
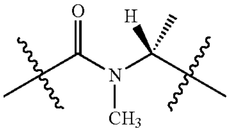
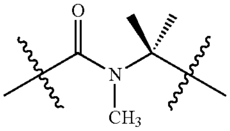
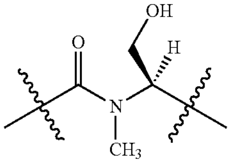
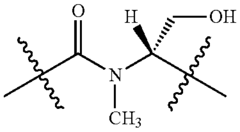
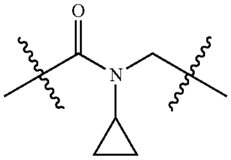

-continued
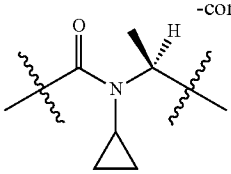
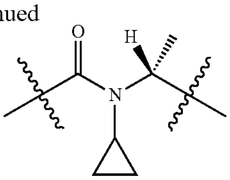
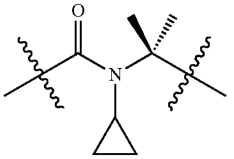
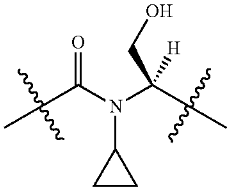
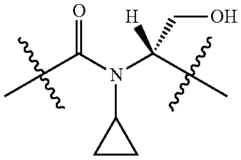
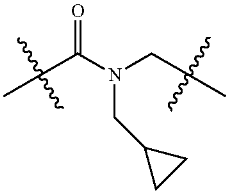
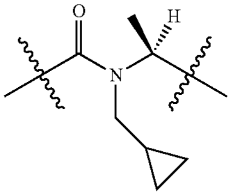
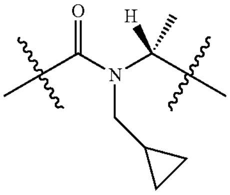
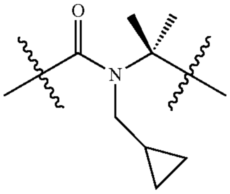
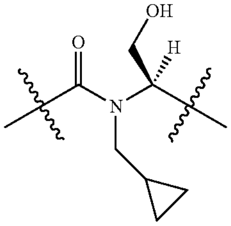
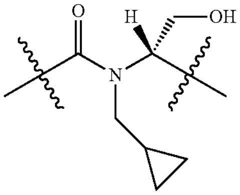
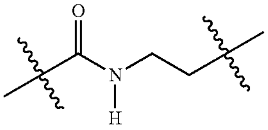
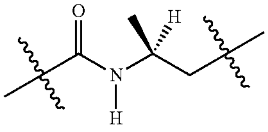
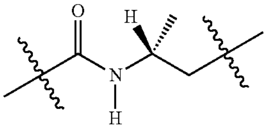
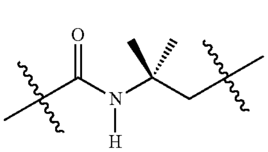
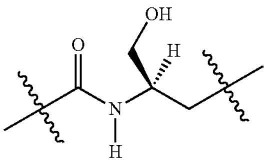
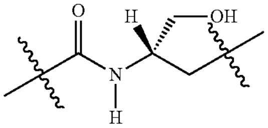
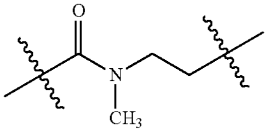
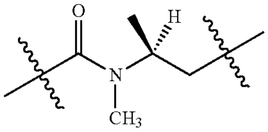
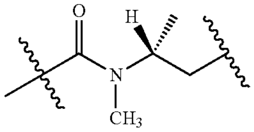
-continued
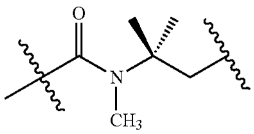
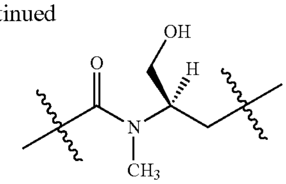
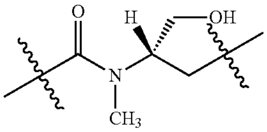
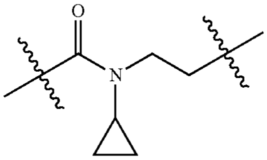
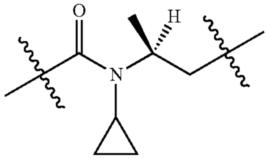
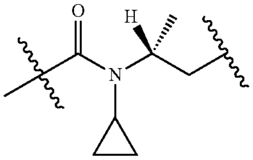
and
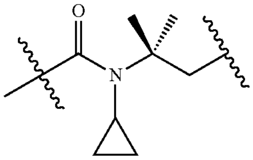
.
In one embodiment L1 is selected from:
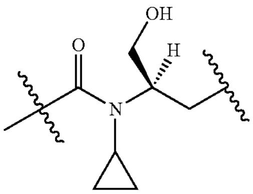
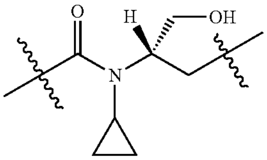
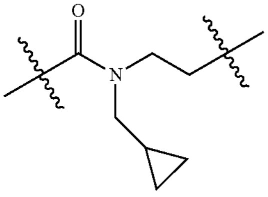
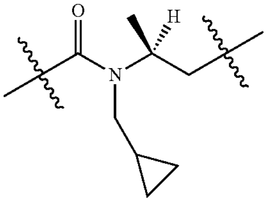
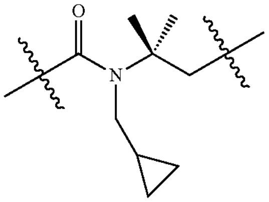
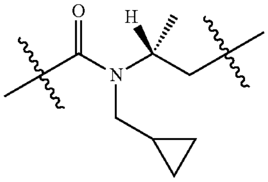
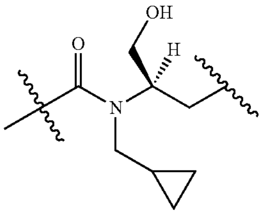
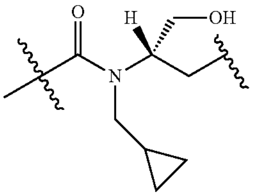

-continued
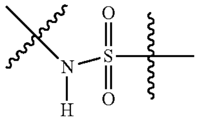
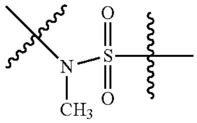
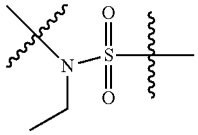
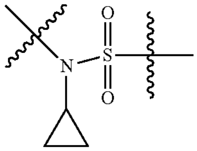
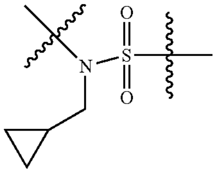
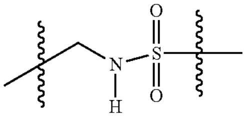
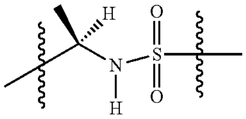
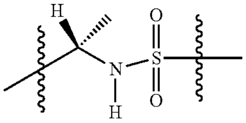
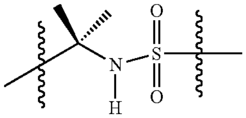
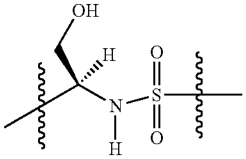
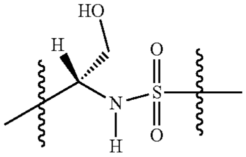
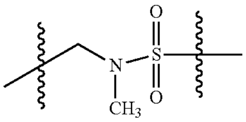
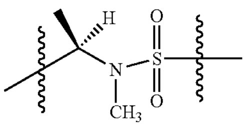
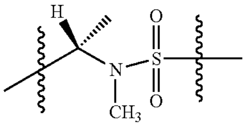
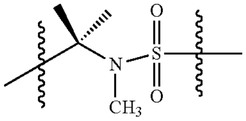
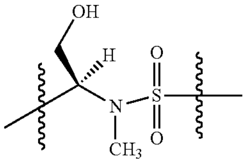
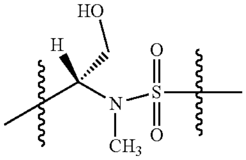
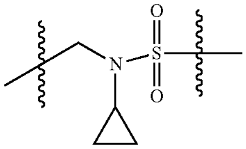
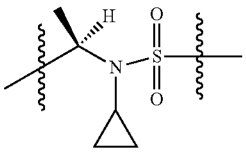
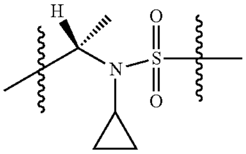
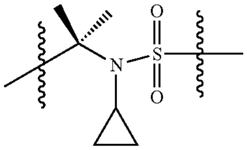
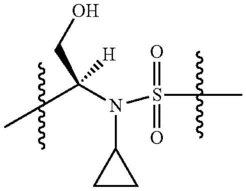
-continued
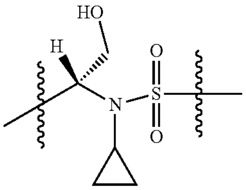
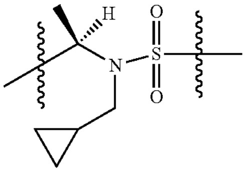
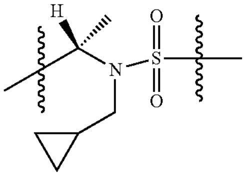
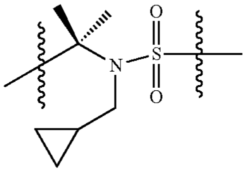
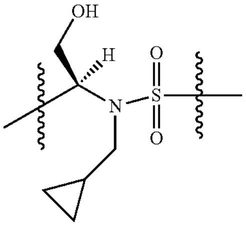
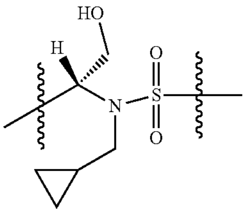
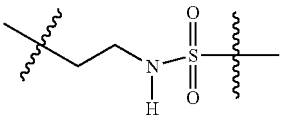
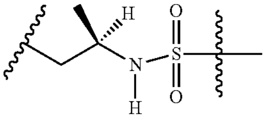
and
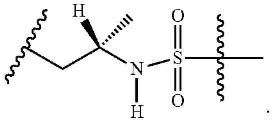
.
In one embodiment L1 is selected from:
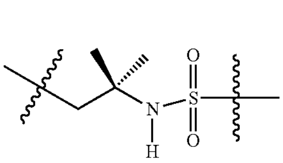
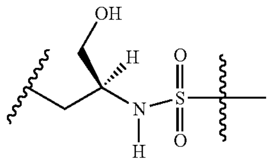
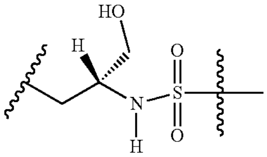
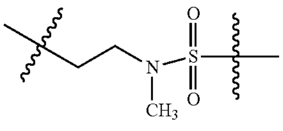
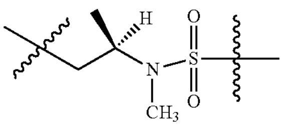
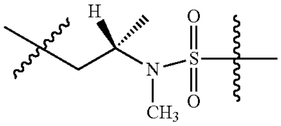
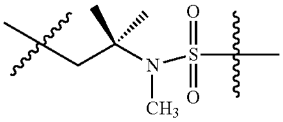
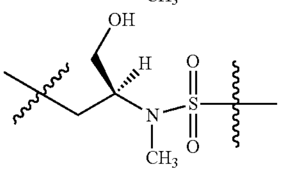

-continued
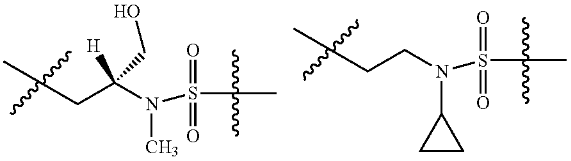
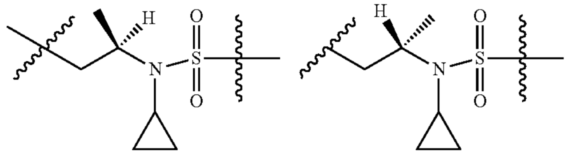
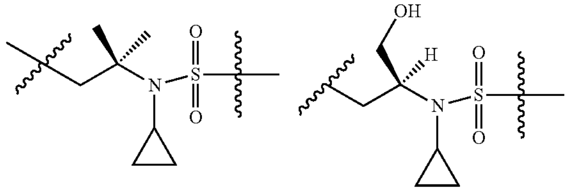
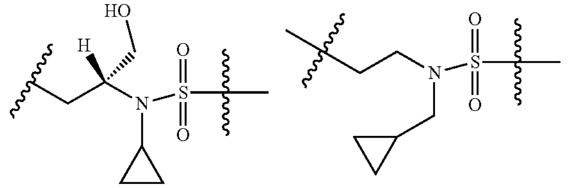
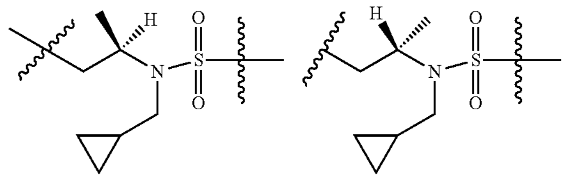
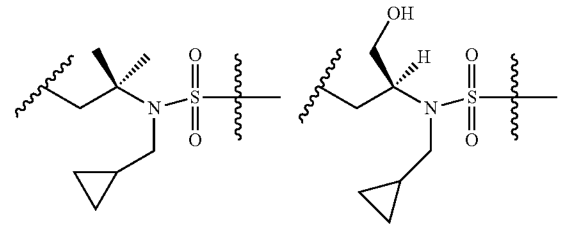
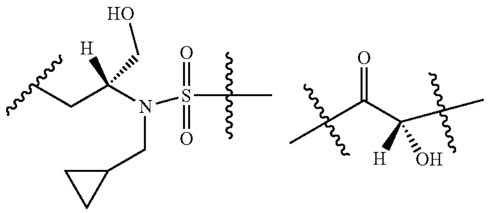
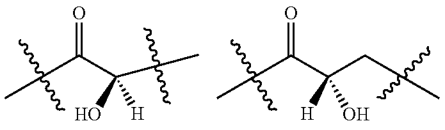
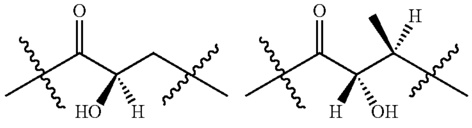
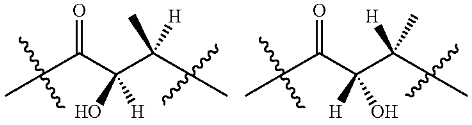
-continued
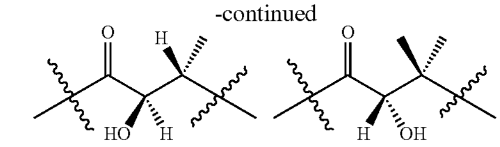
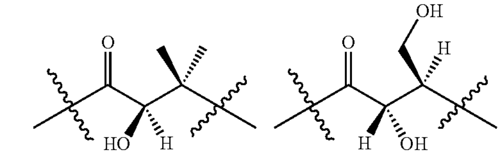
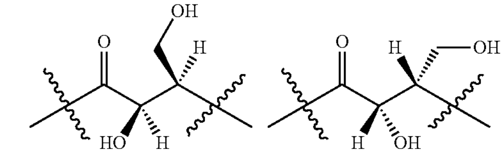
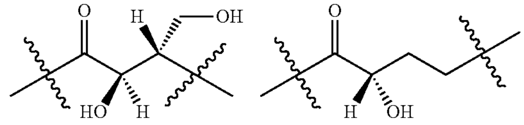
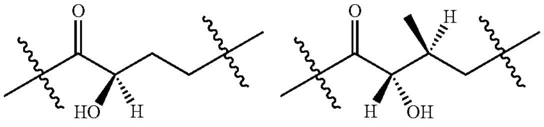
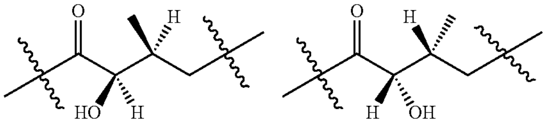
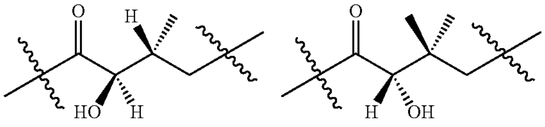
In one embodiment L1 is selected from:
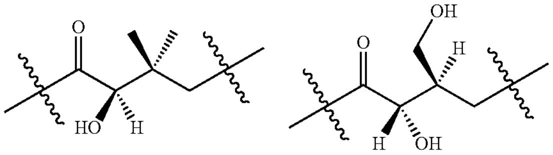
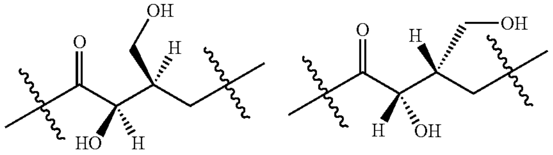
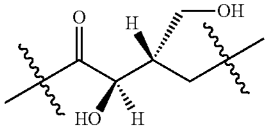
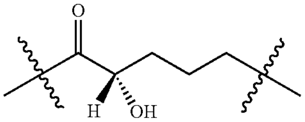
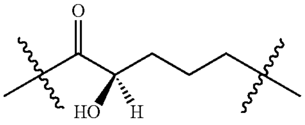

-continued
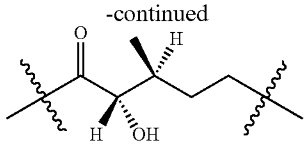
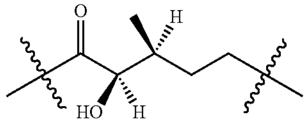
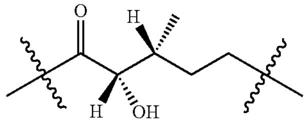
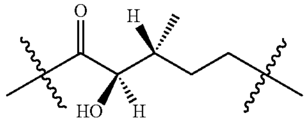
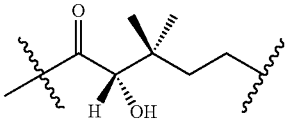
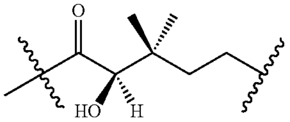
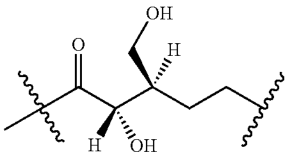
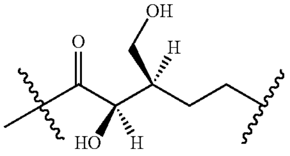
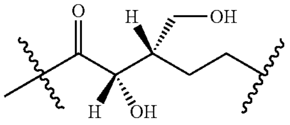
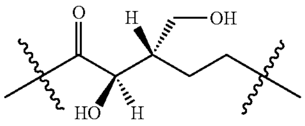
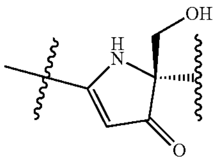
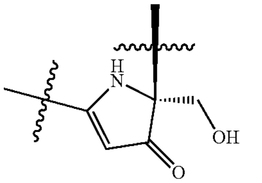
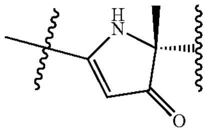
and
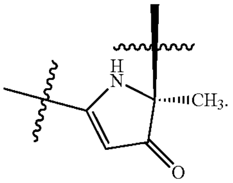
In one embodiment, L1 is selected from:
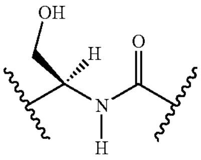
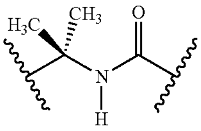
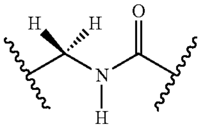
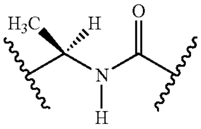
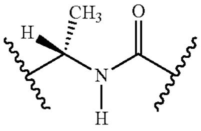
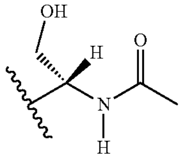
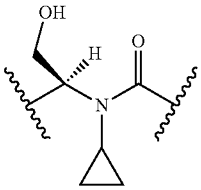
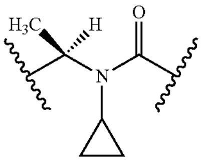
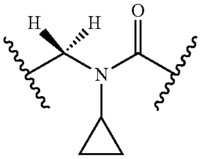
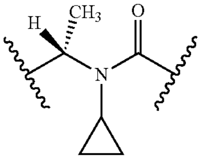
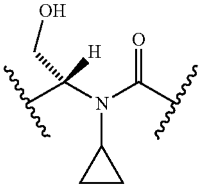
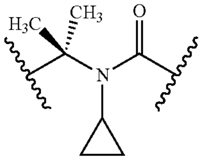
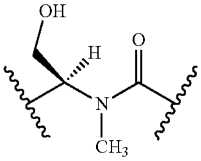
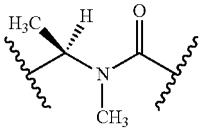
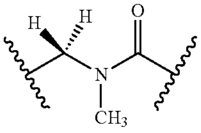
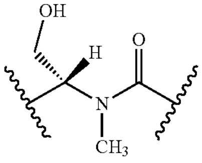
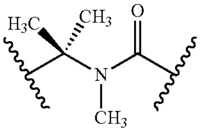
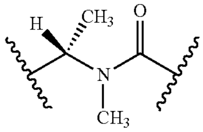
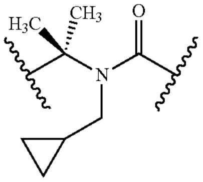
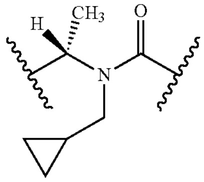

-continued
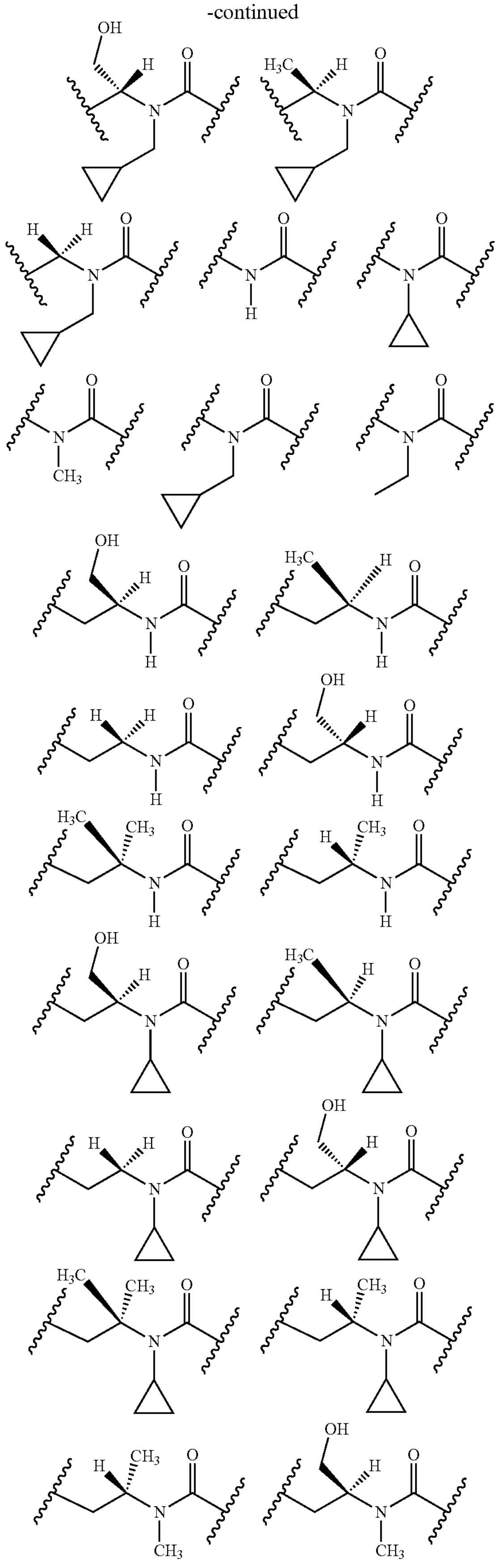
-continued
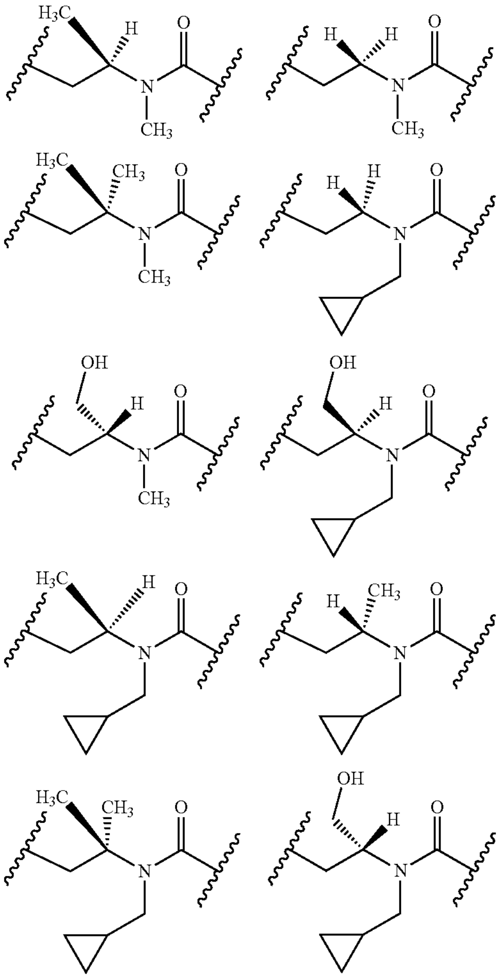
In one embodiment, the methyl groups in the structures illustrated above can be replaced with another alkyl group, as defined herein.
In one embodiment L2 is selected from:
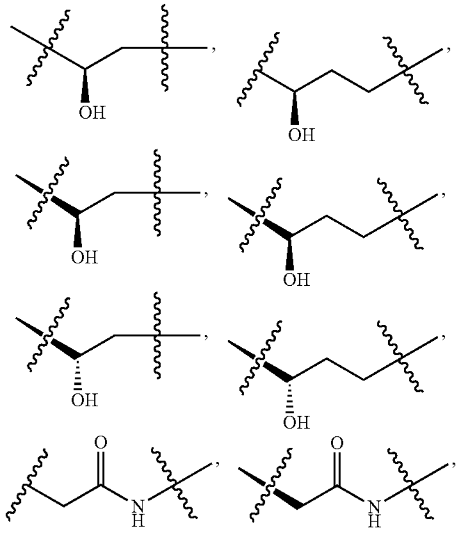

-continued
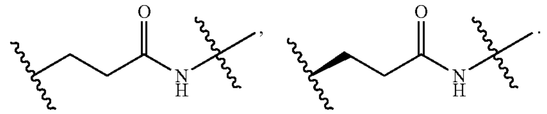
,
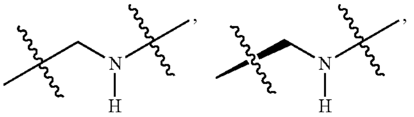
,
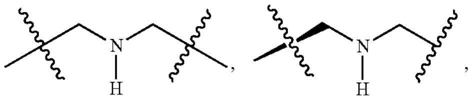
,
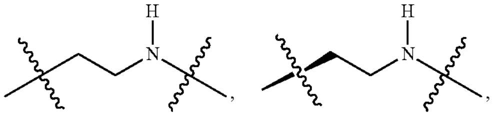
,
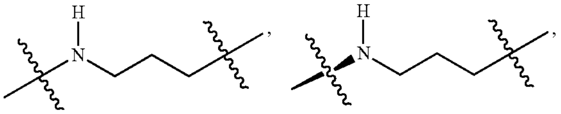
,
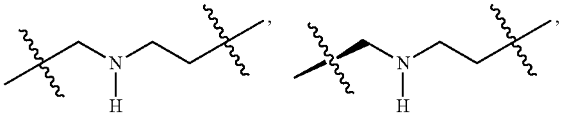
,
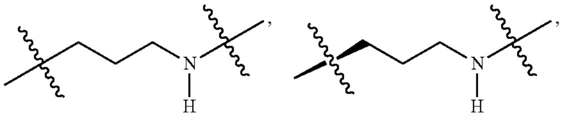
,
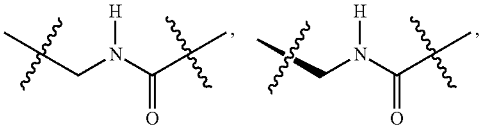
,
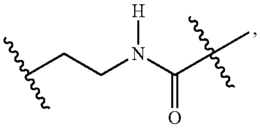
, and
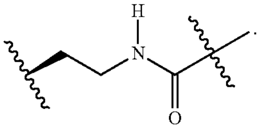
.
Non-limiting examples of L2 include:
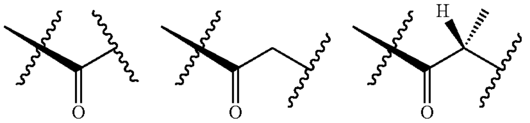
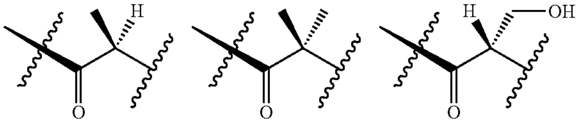
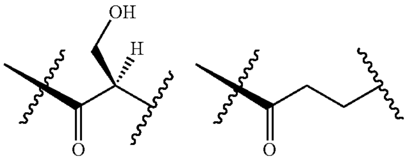
-continued
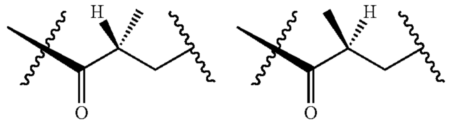
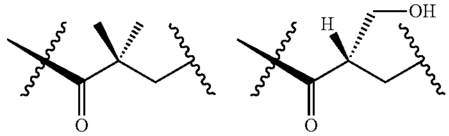
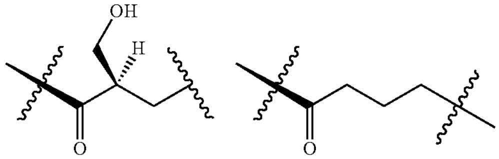
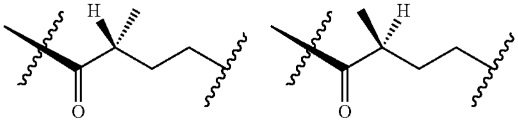
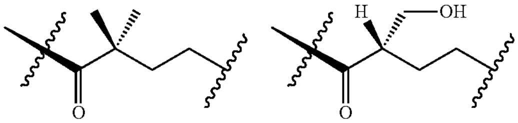
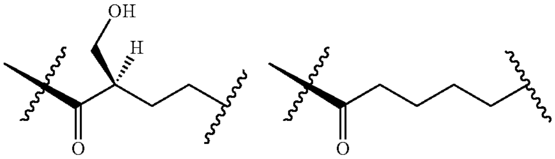
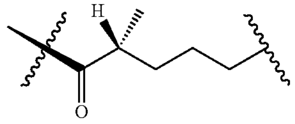
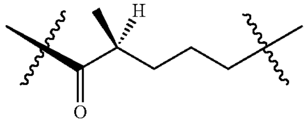
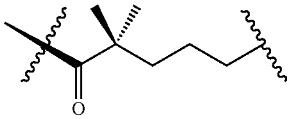
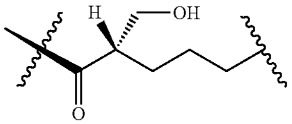
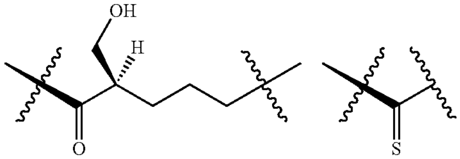
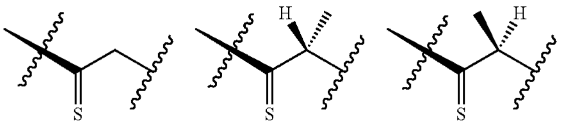

-continued
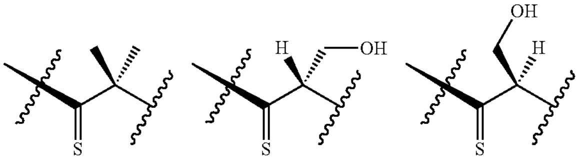
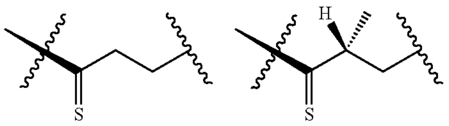
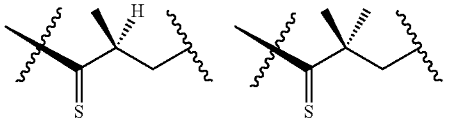
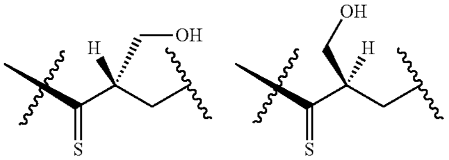
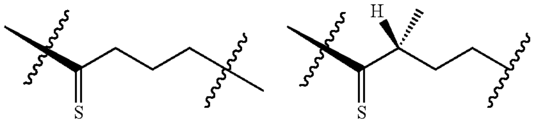
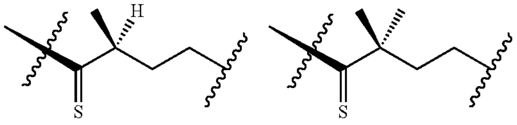
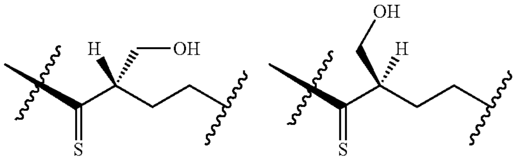
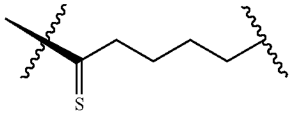
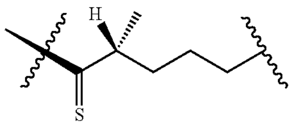
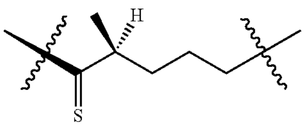
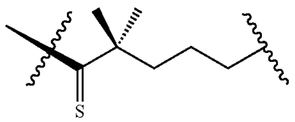 and
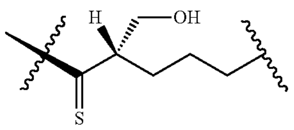 .
Non-limiting examples of L2 include:
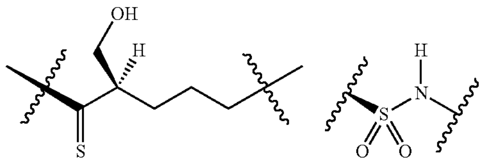
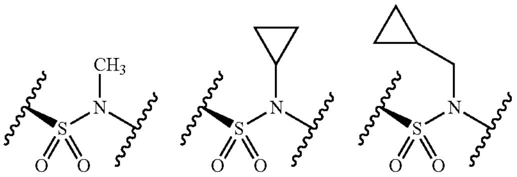
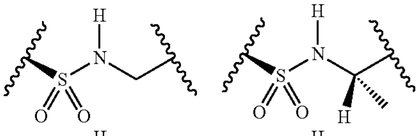
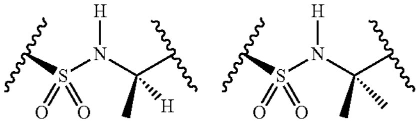
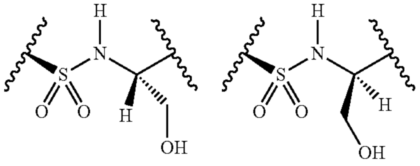
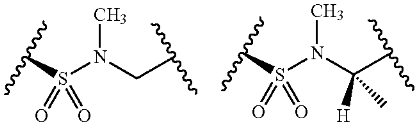
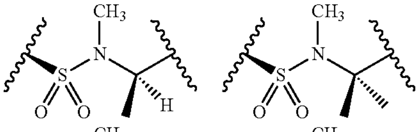
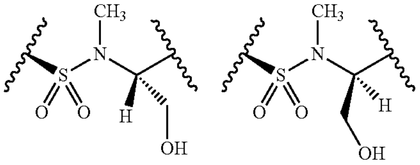
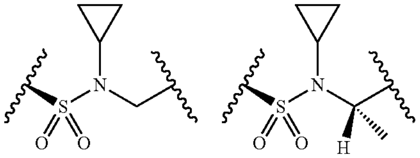
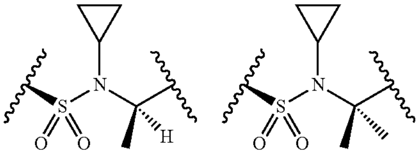
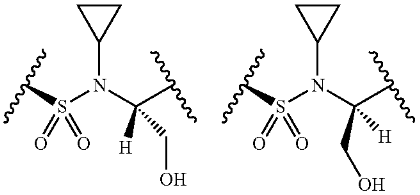

-continued
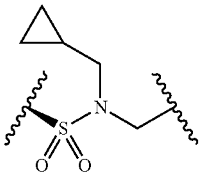 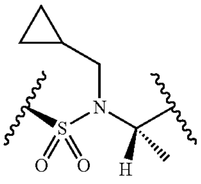
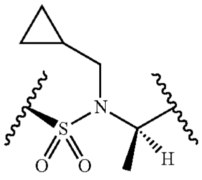 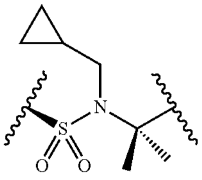
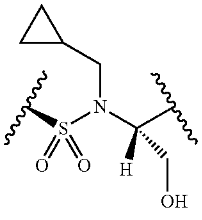 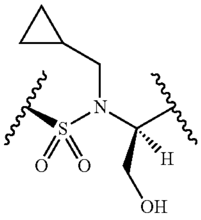
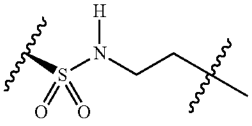 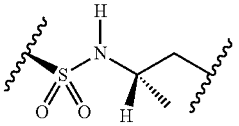
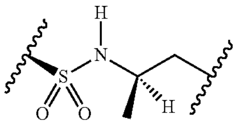 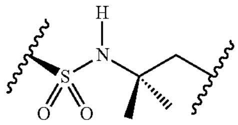
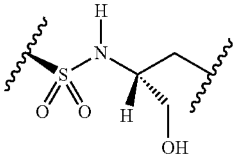 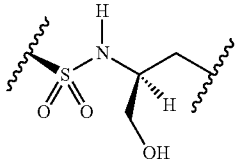
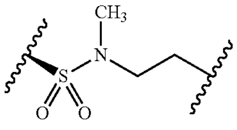 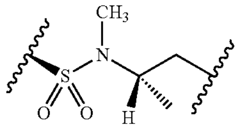
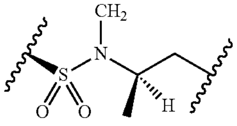 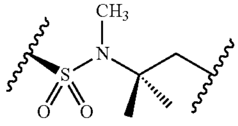
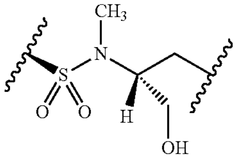 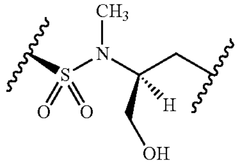
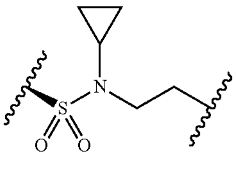 and 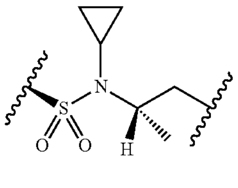 .
Non-limiting examples of L2 include:
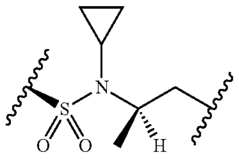 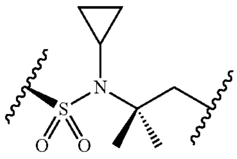
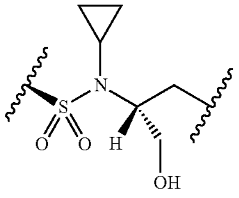 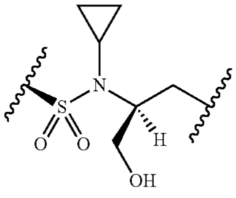
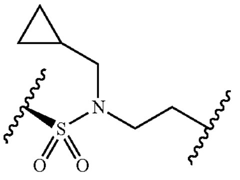 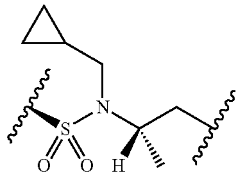
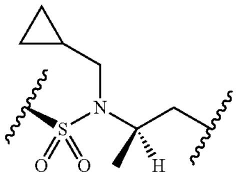 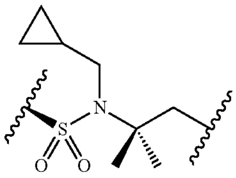
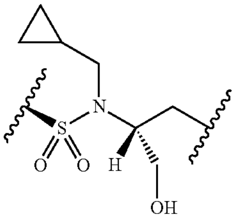 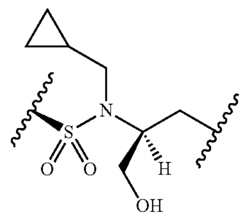
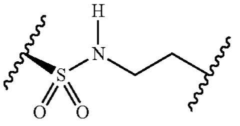 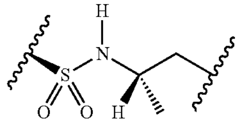
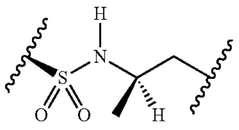 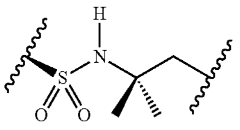
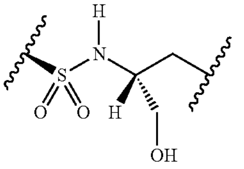 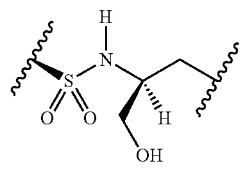
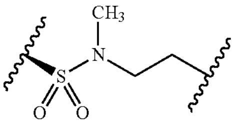 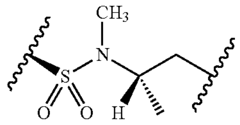
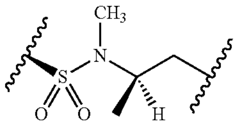 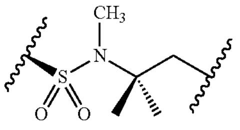

-continued
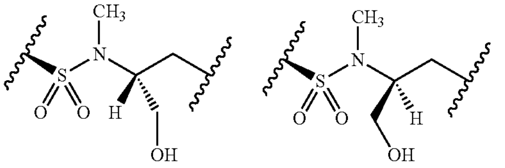
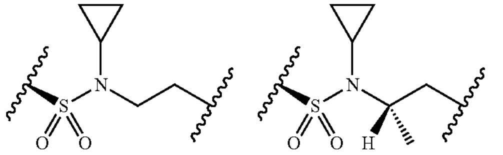
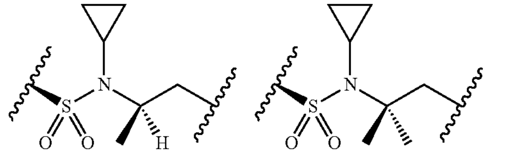
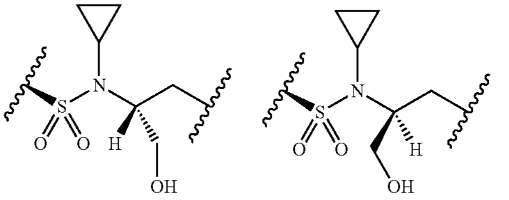
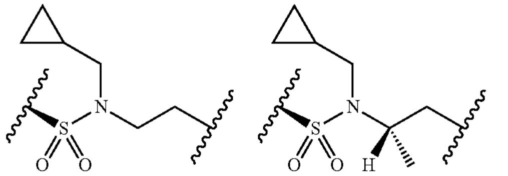
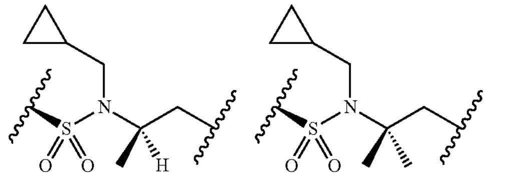
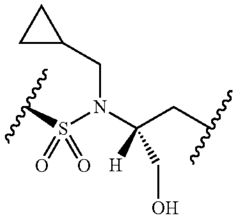
and
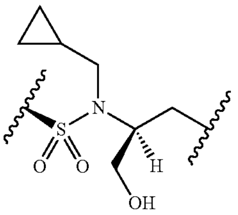
Non-limiting examples of L2 include:
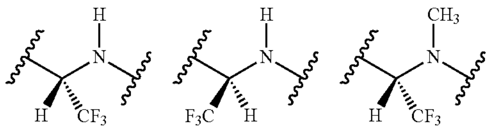
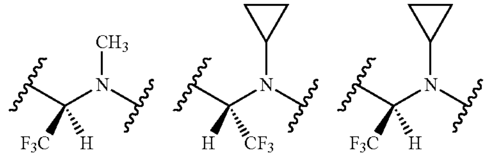
-continued
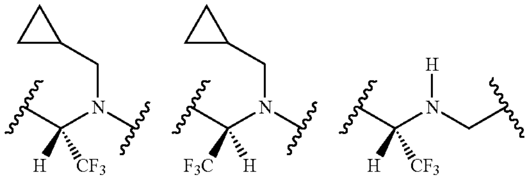
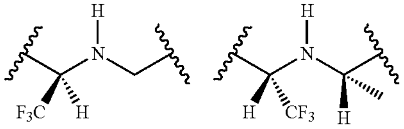
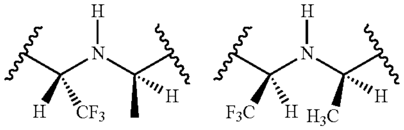
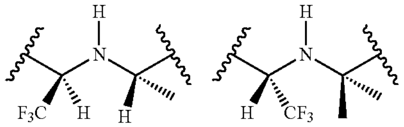
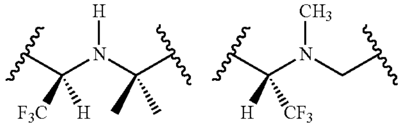
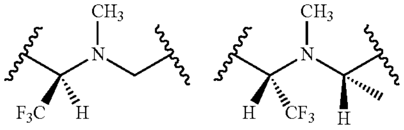
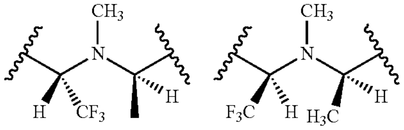
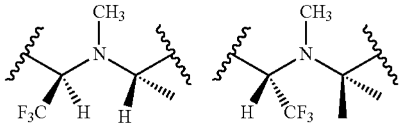
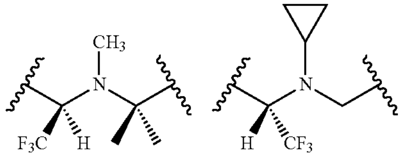
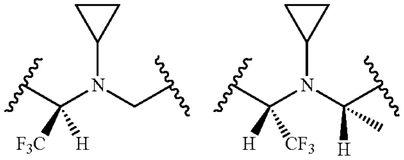
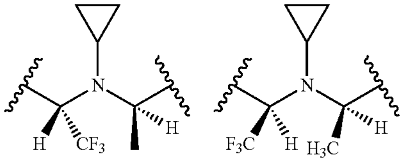
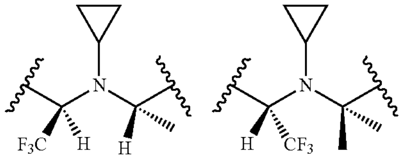

-continued
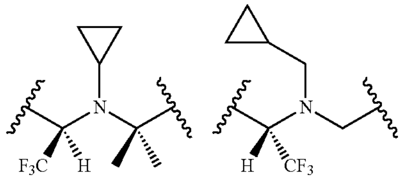
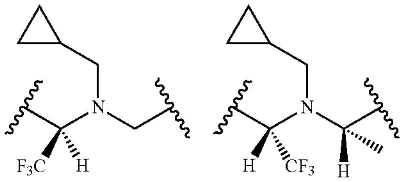
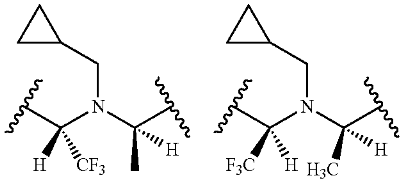
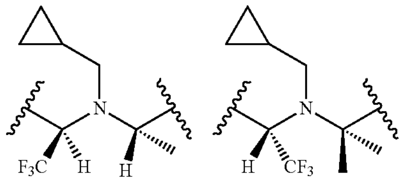
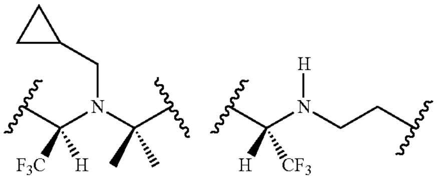
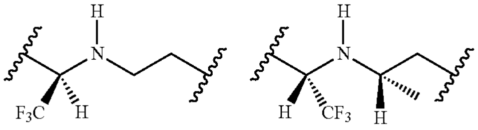
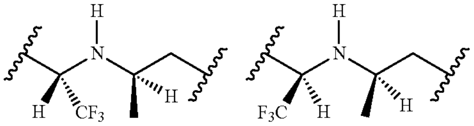
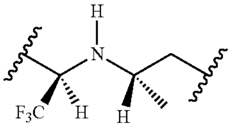
and
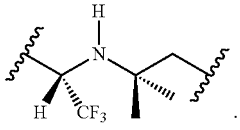
.
Non-limiting examples of L2 include:
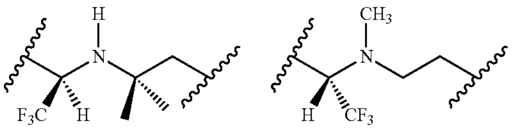
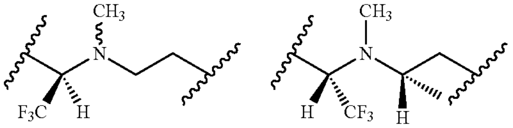
-continued
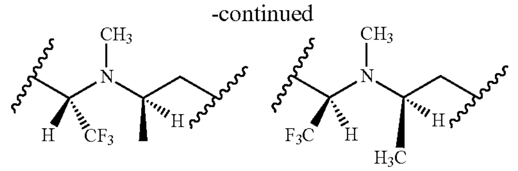
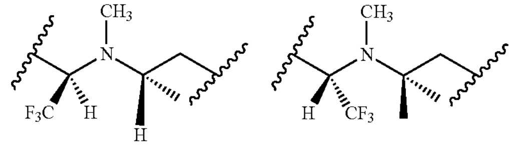
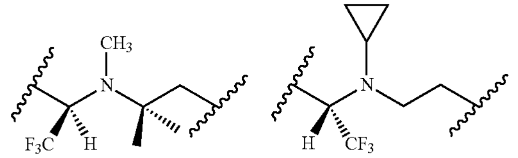
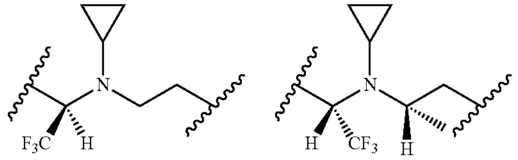
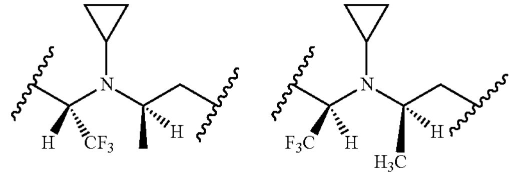
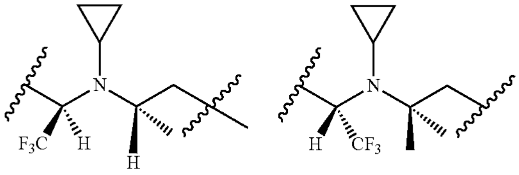
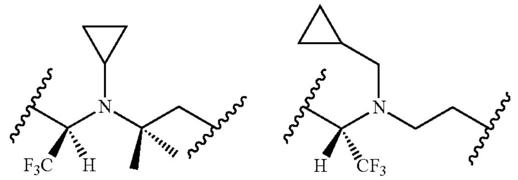
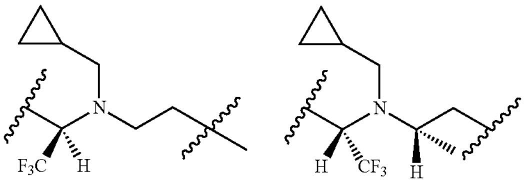
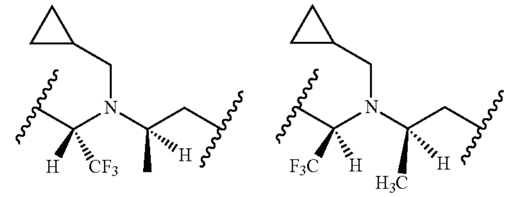
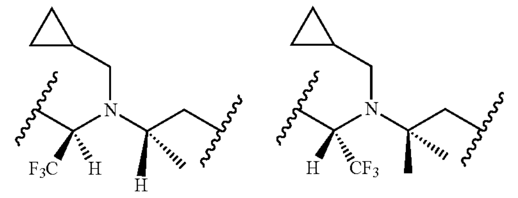

-continued

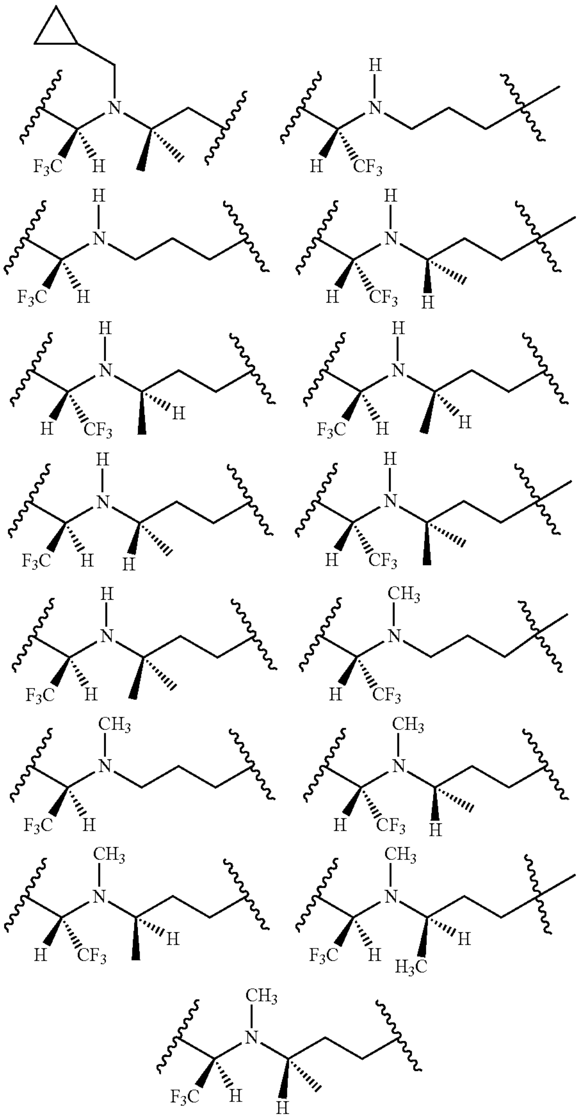

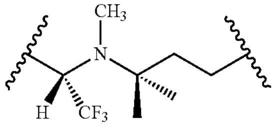

and

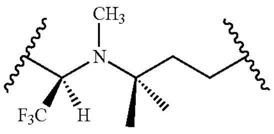.

In one embodiment, the methyl groups in the structures illustrated in above can be replaced with another alkyl or acyl, as defined herein. In another embodiment, the carbocyclic, heterocyclic, aryl or heteroaryl rings can be optionally substituted. As indicated above, any of the structures illustrated above or below can be optionally substituted with 0, 1, 2, 3, or 4, as appropriate, and independently, of an $R^{48}$ substituent.

In certain embodiment, L2 is a bond. In certain embodiments, if L2 is heterocyclic or heteroaryl, then B can be hydrogen.

Embodiments of B

In one additional alternative embodiment B is selected from:

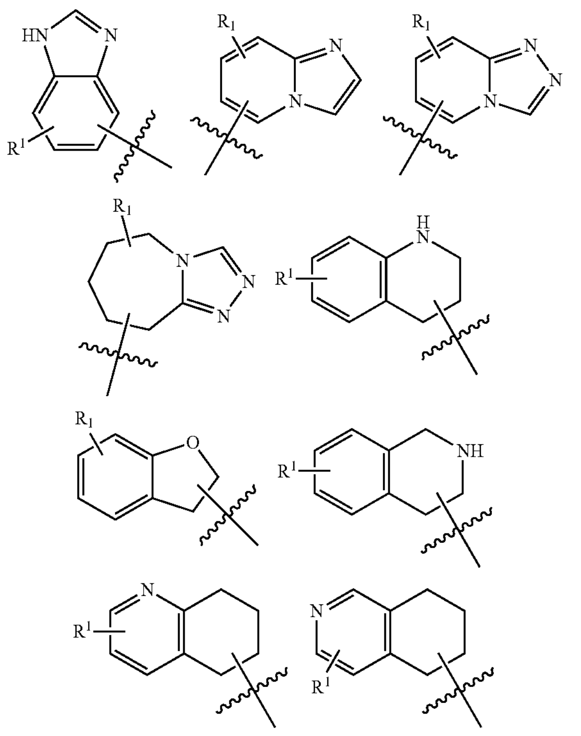

In one additional alternative embodiment $R^{36}$ is selected from:

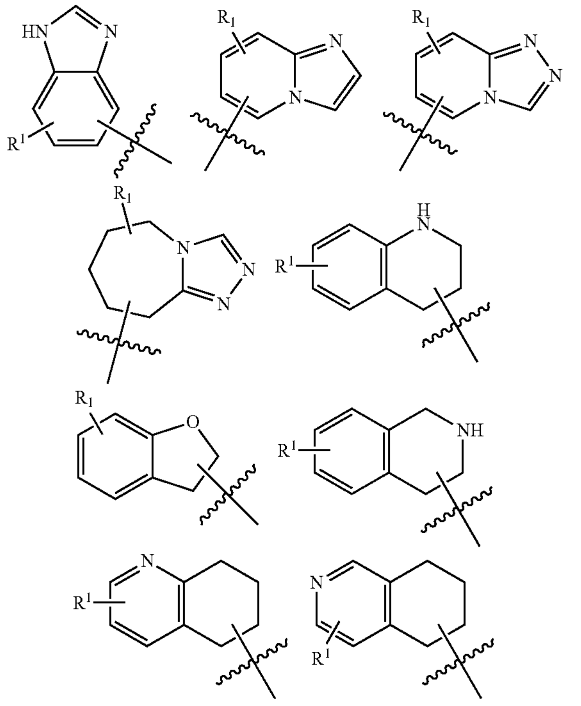

In one embodiment, B is selected from:
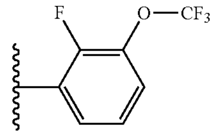
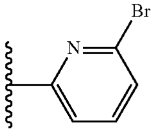
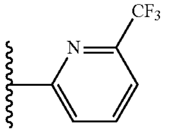
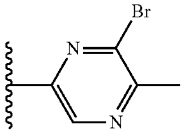
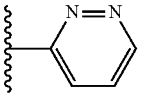
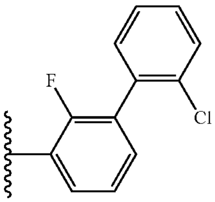
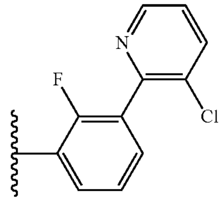
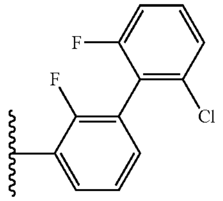
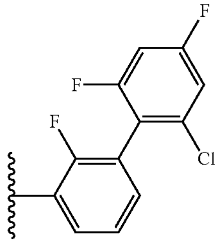
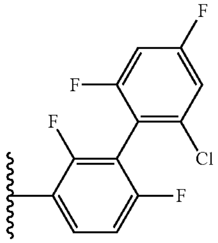
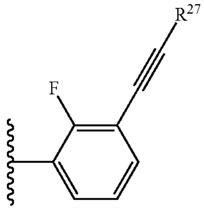
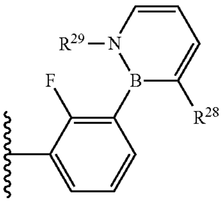
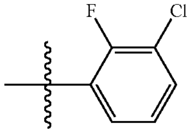
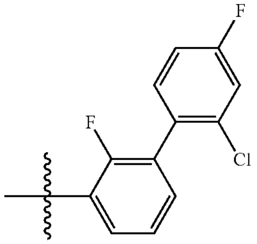
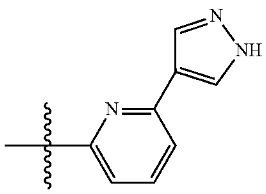
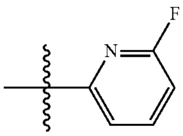
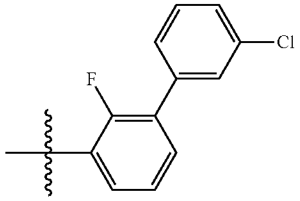
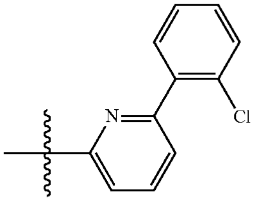
-continued
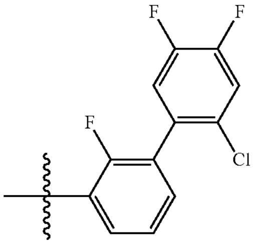
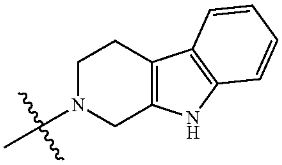
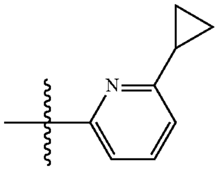
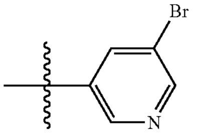
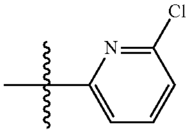
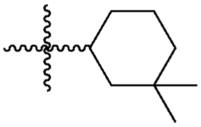
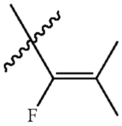
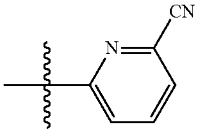
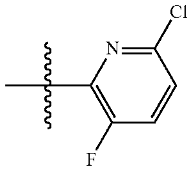
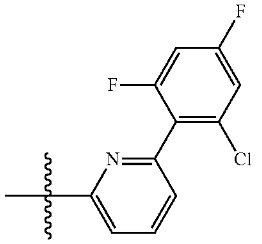
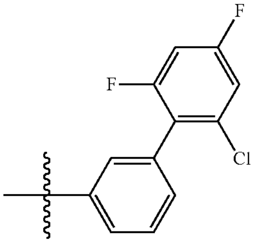
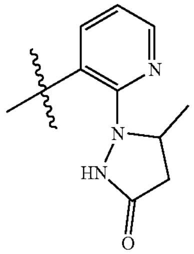
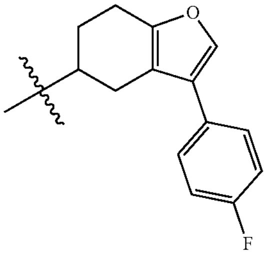
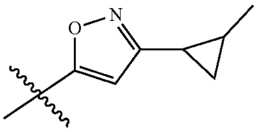
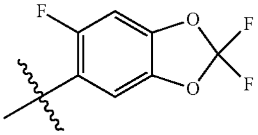
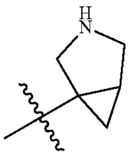
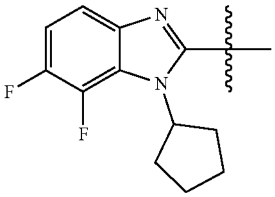

-continued
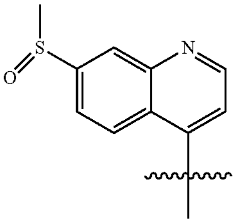
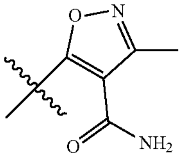
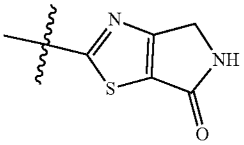
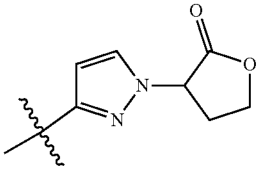
and
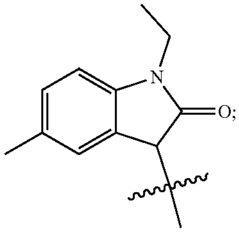
wherein $R^{27}$ is hydrogen, methyl, or trifluoromethyl; $R^{28}$ is hydrogen or halogen; and $R^{29}$ is hydrogen, methyl, trifluoromethyl, or $—Si(CH_3)_2C(CH_3)_3$.
In one embodiment, B is selected from:
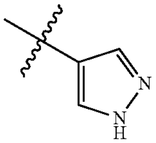
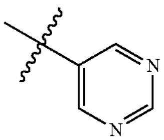
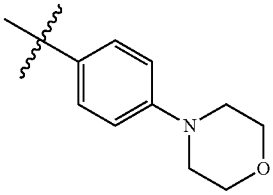
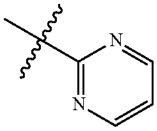
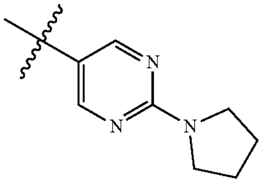
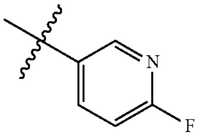
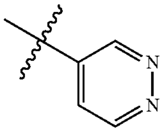
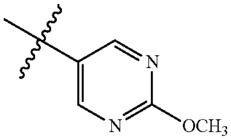
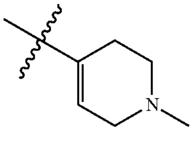
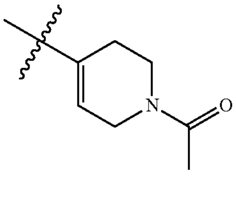
-continued
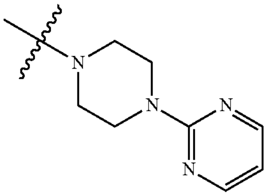
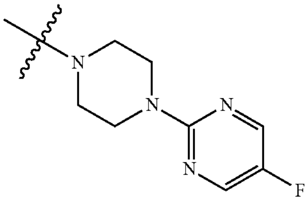
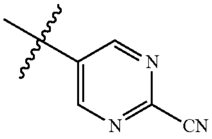
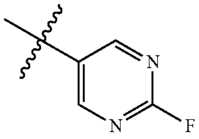
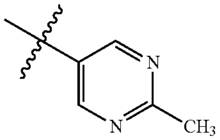
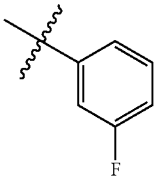
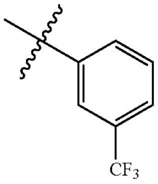
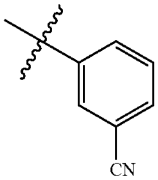
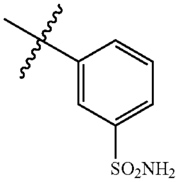
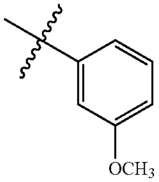
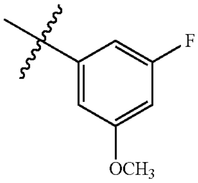
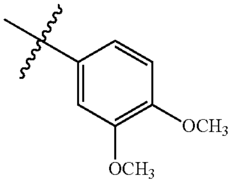
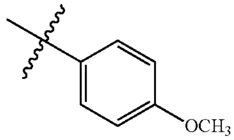
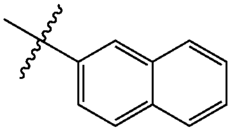
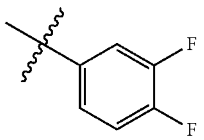
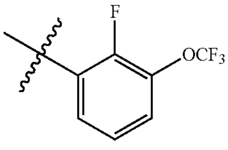
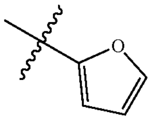
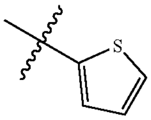
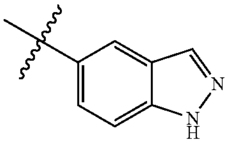
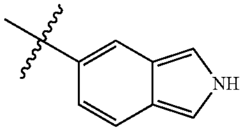
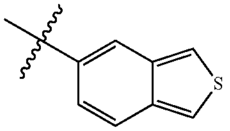
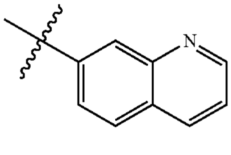
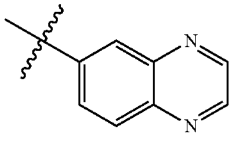

-continued
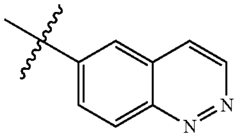 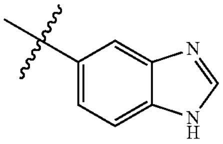
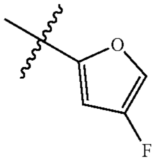
Examples of B moieties include, but are not limited to
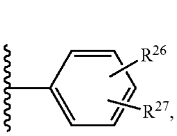 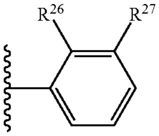 , 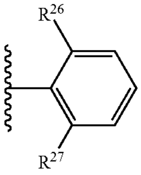 ,
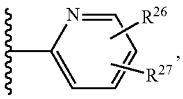 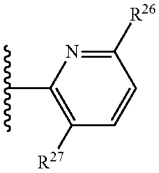 , 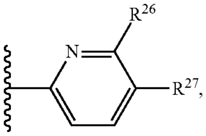
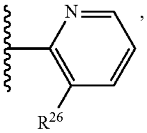 , 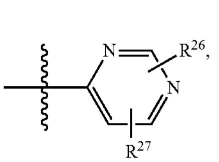 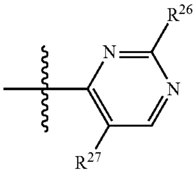 ,
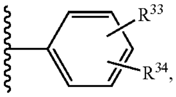 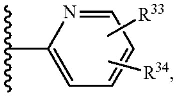 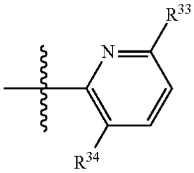 ,
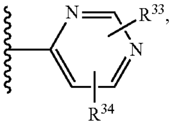 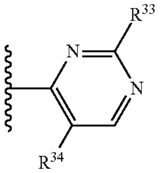 , 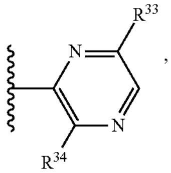 ,
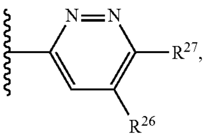 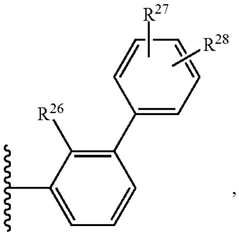 ,
-continued
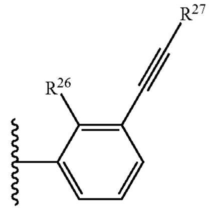 , 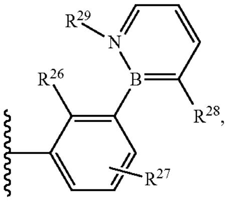
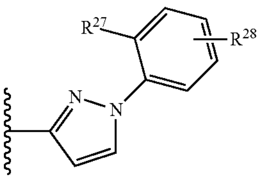 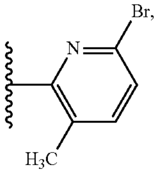
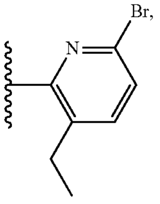 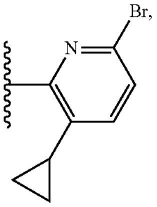 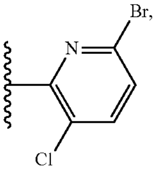
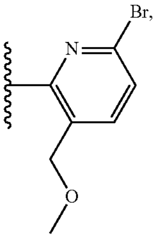 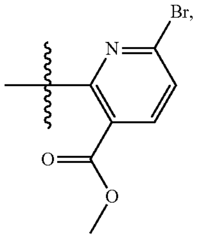
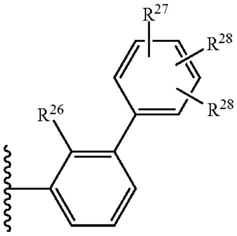 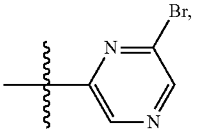 and
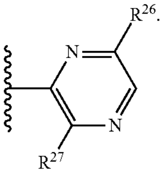
In one embodiment, B4 is selected from:
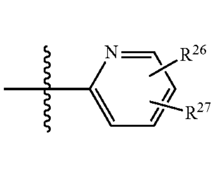 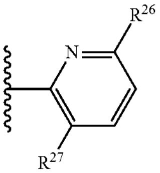 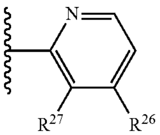

-continued
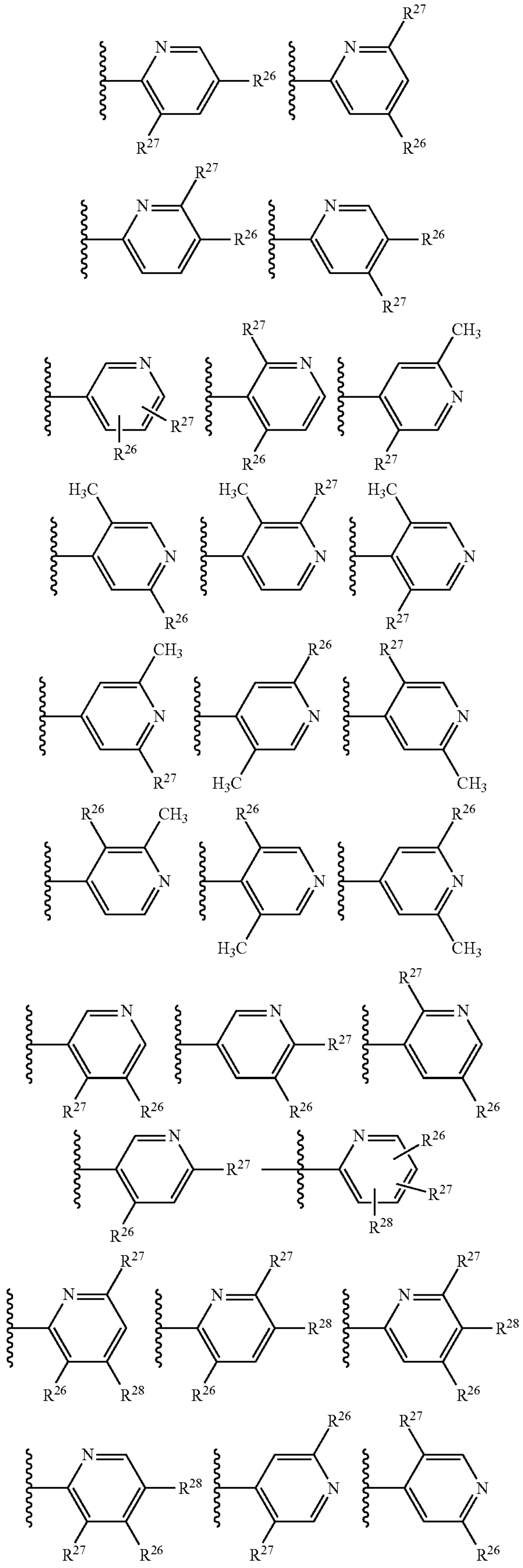
-continued
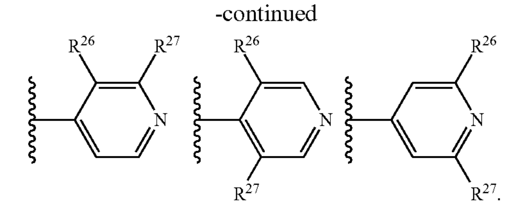
In one embodiment, B4 is selected from:
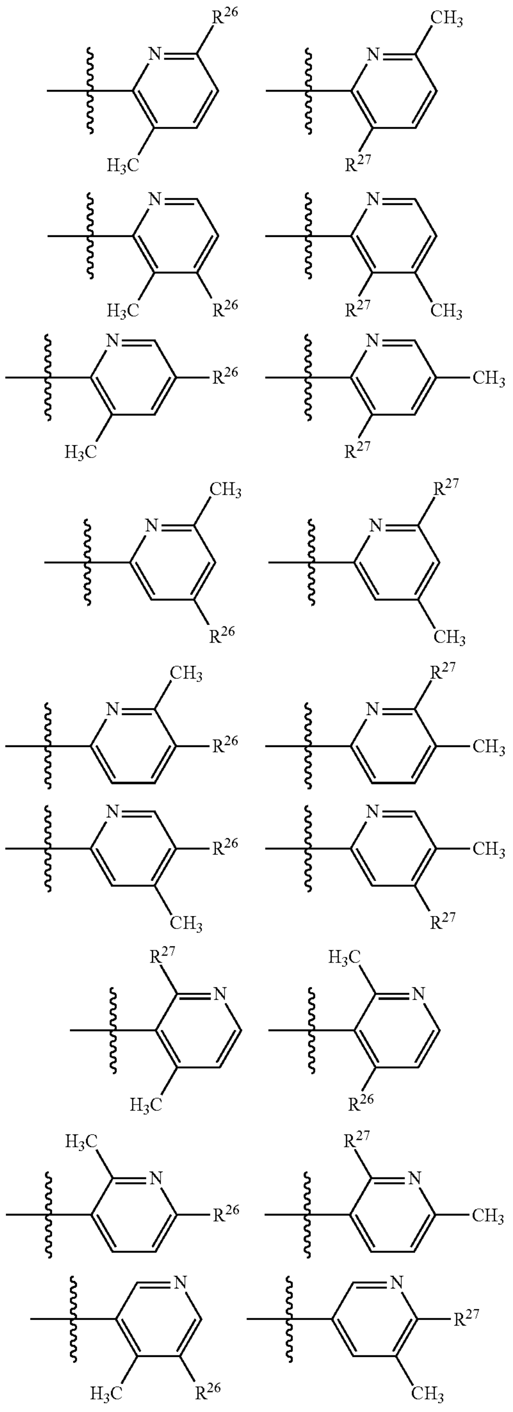

-continued
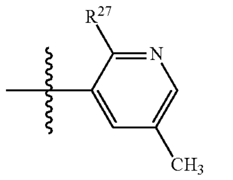
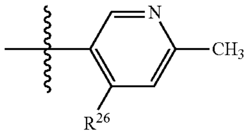
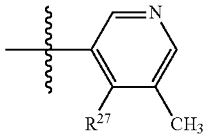
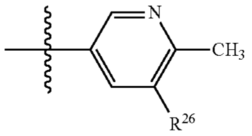
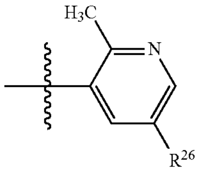
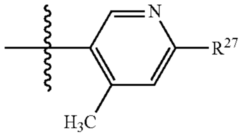
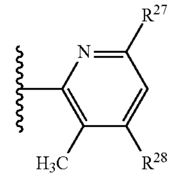
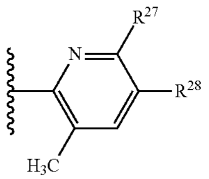
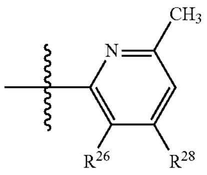
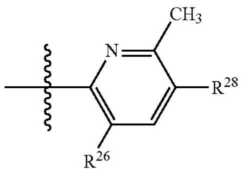
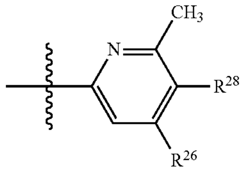
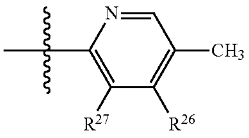
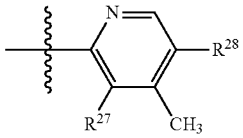
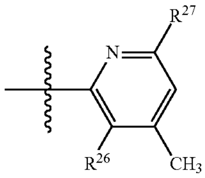
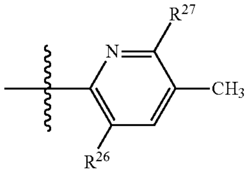
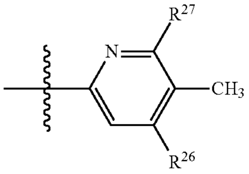
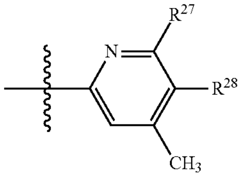
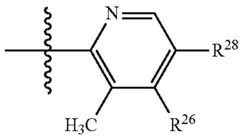
In one embodiment, B4 is selected from:
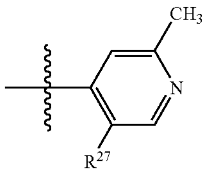
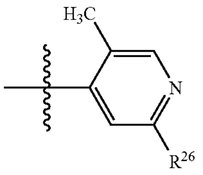
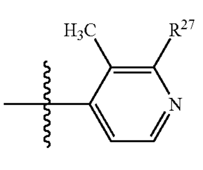
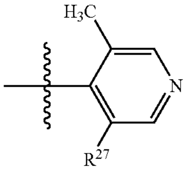
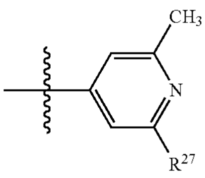
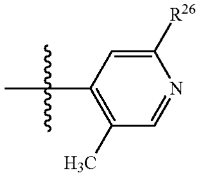
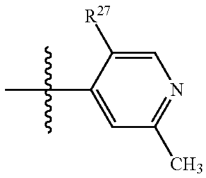
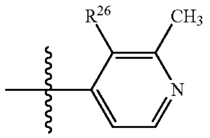
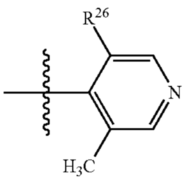
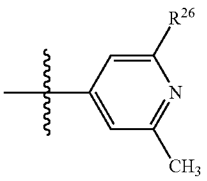
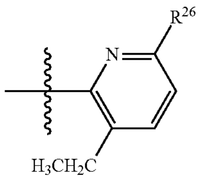
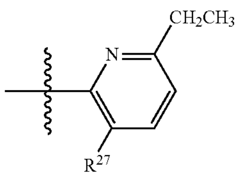
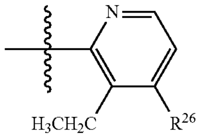
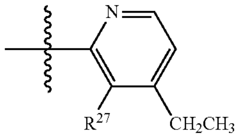
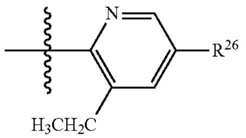
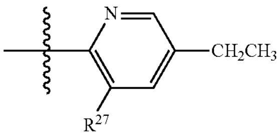
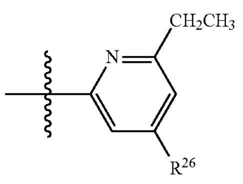
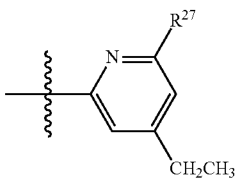
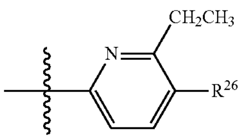
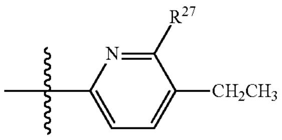

-continued
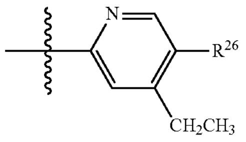
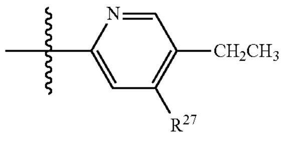
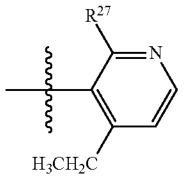
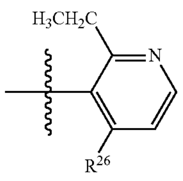
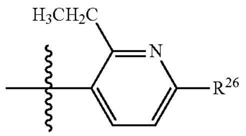
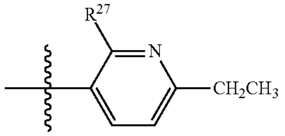
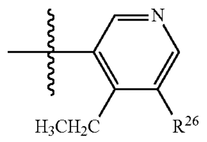
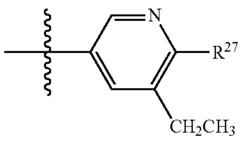
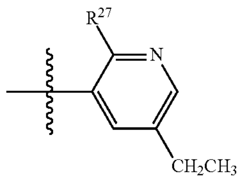
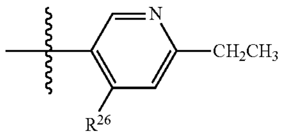
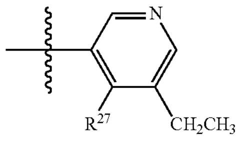
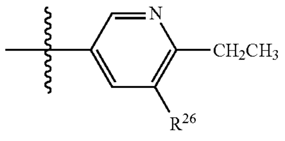
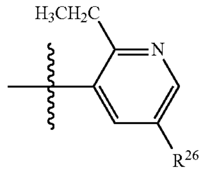
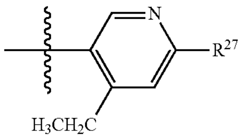
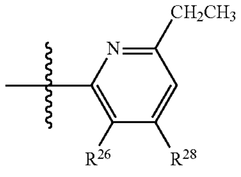
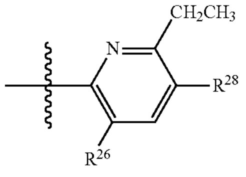
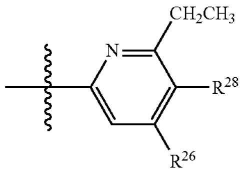
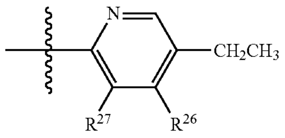
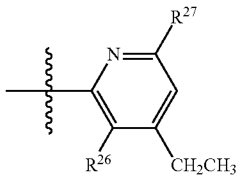
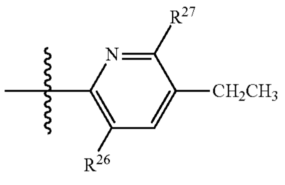
-continued
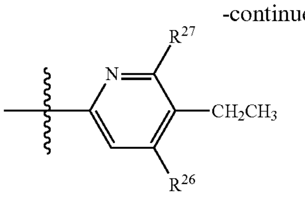
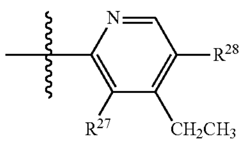
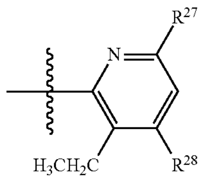
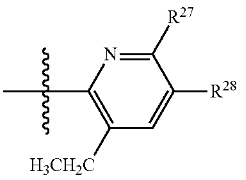
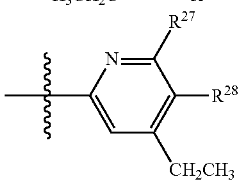
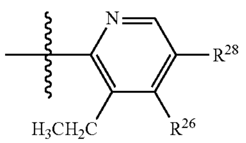
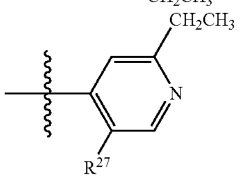
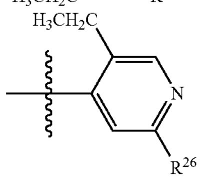
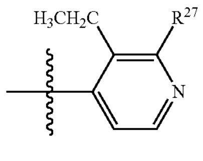
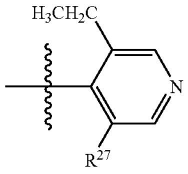
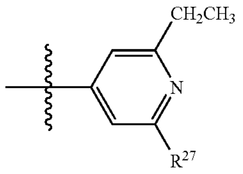
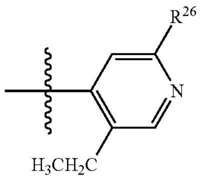
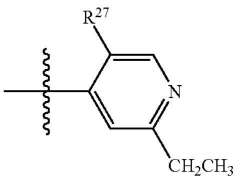
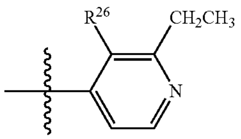
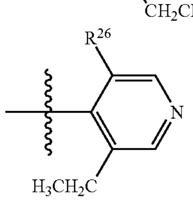
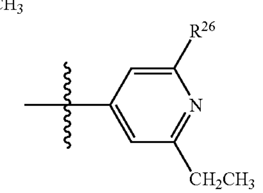
In one embodiment, B4 is selected from:
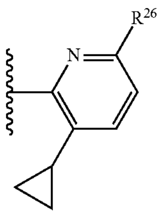
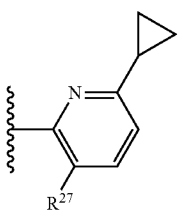
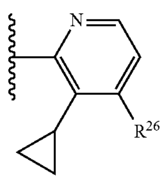

-continued
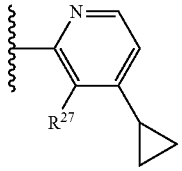
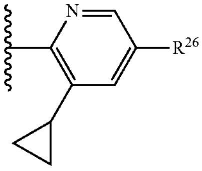
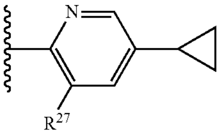
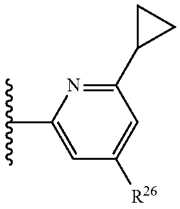
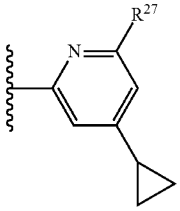
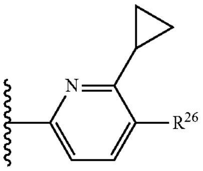
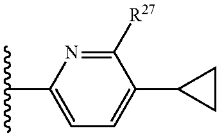
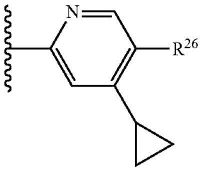
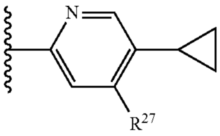
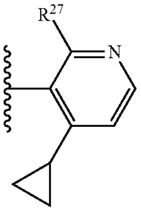
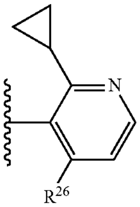
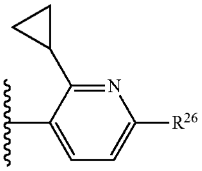
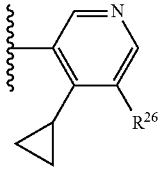
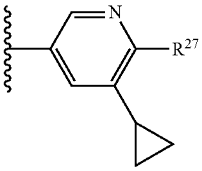
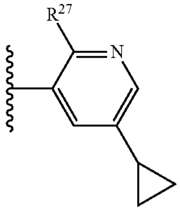
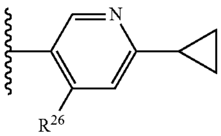
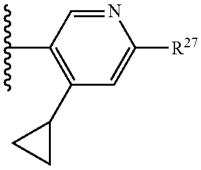
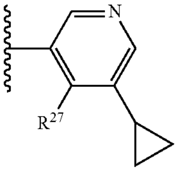
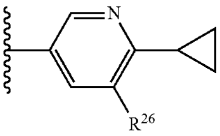
-continued
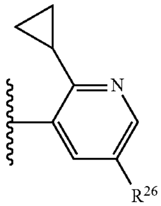
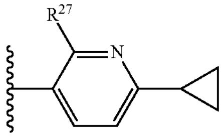
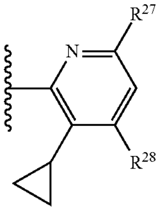
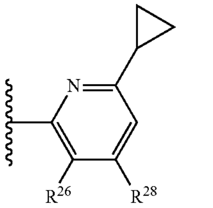
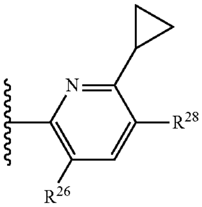
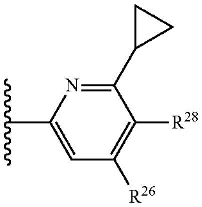
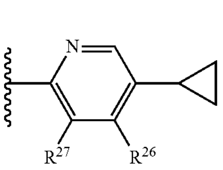
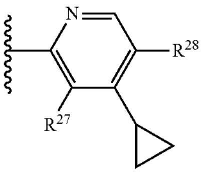
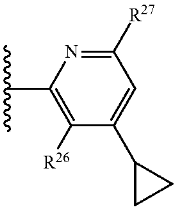
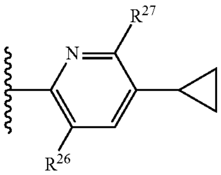
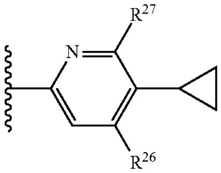
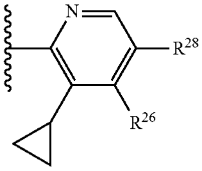
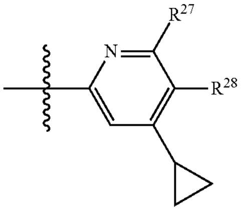
In one embodiment, B4 is selected from:
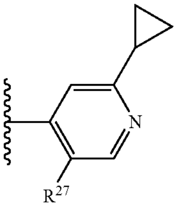
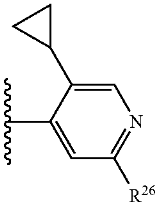
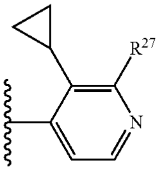

-continued
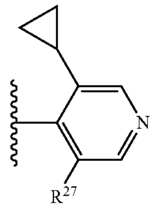
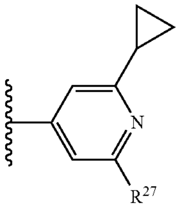
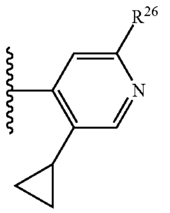
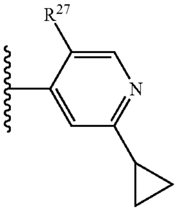
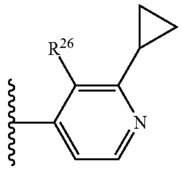
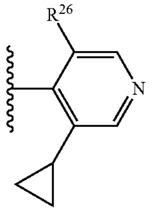
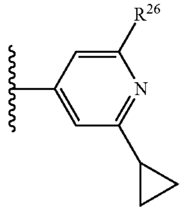
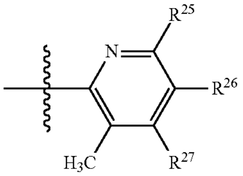
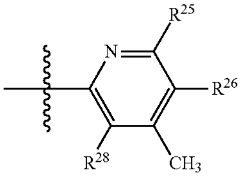
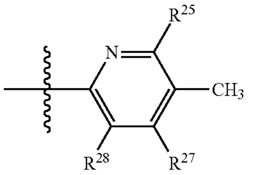
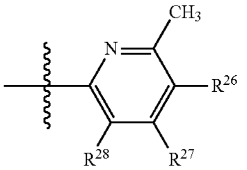
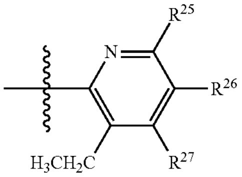
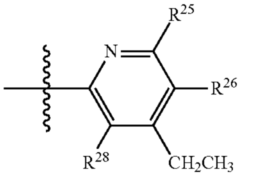
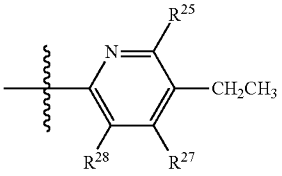
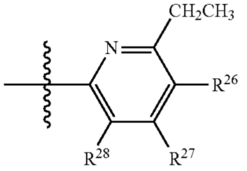
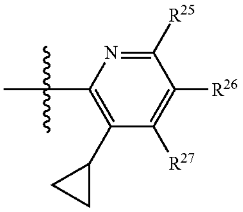
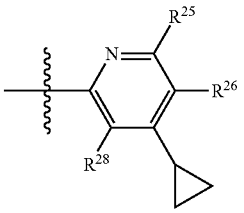
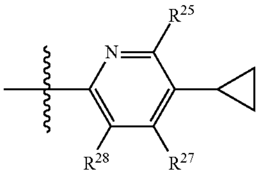
-continued
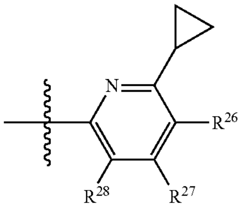
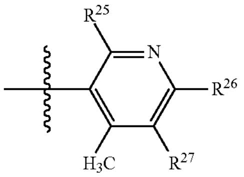
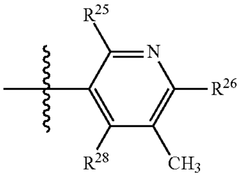
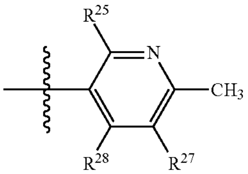
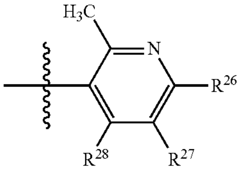
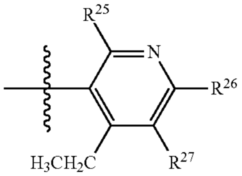
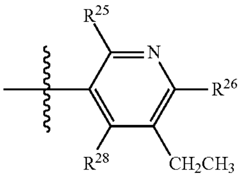
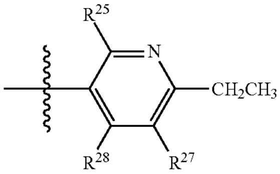
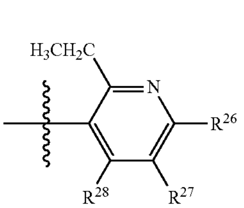
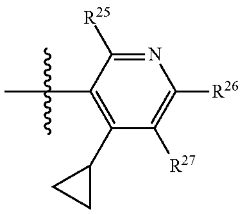
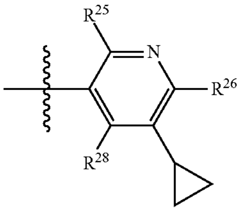
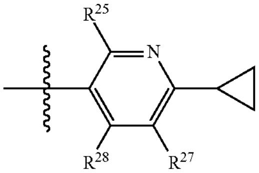
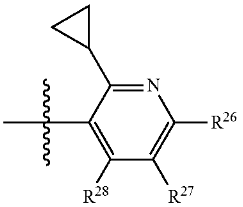
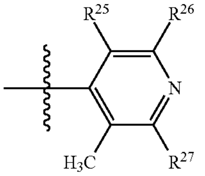
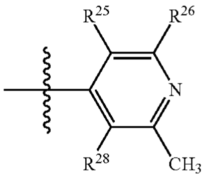
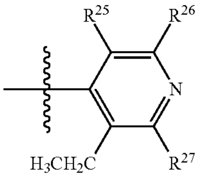

-continued
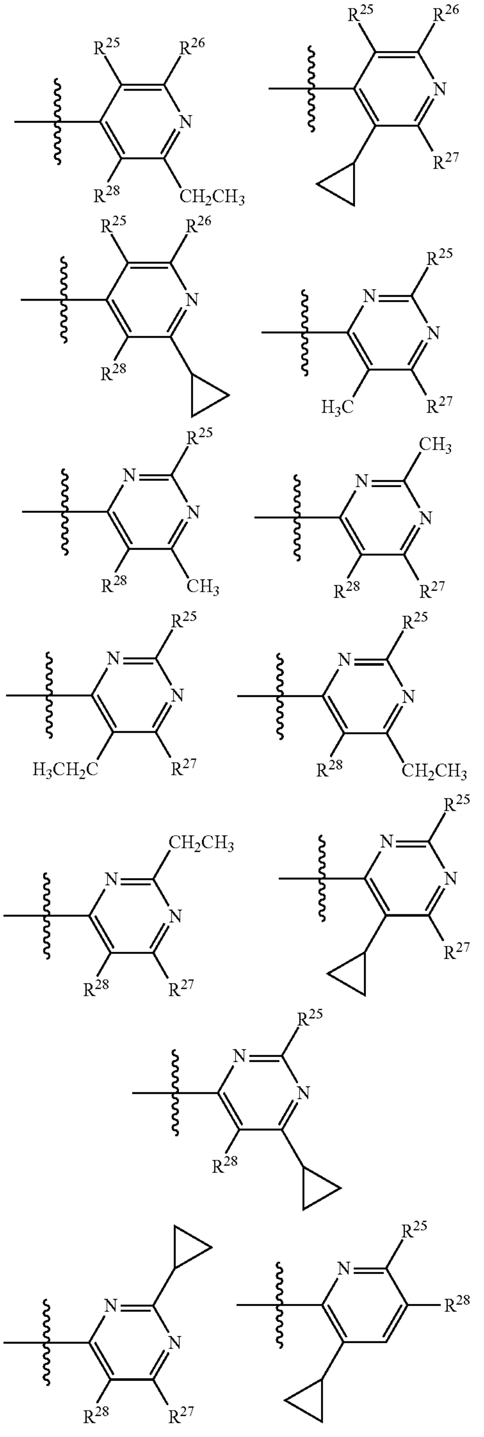
In one embodiment, B4 is selected from:
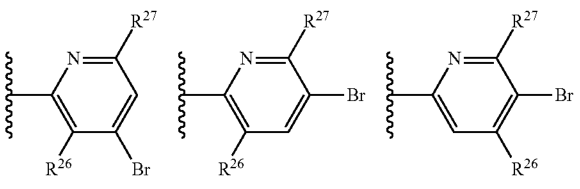
-continued
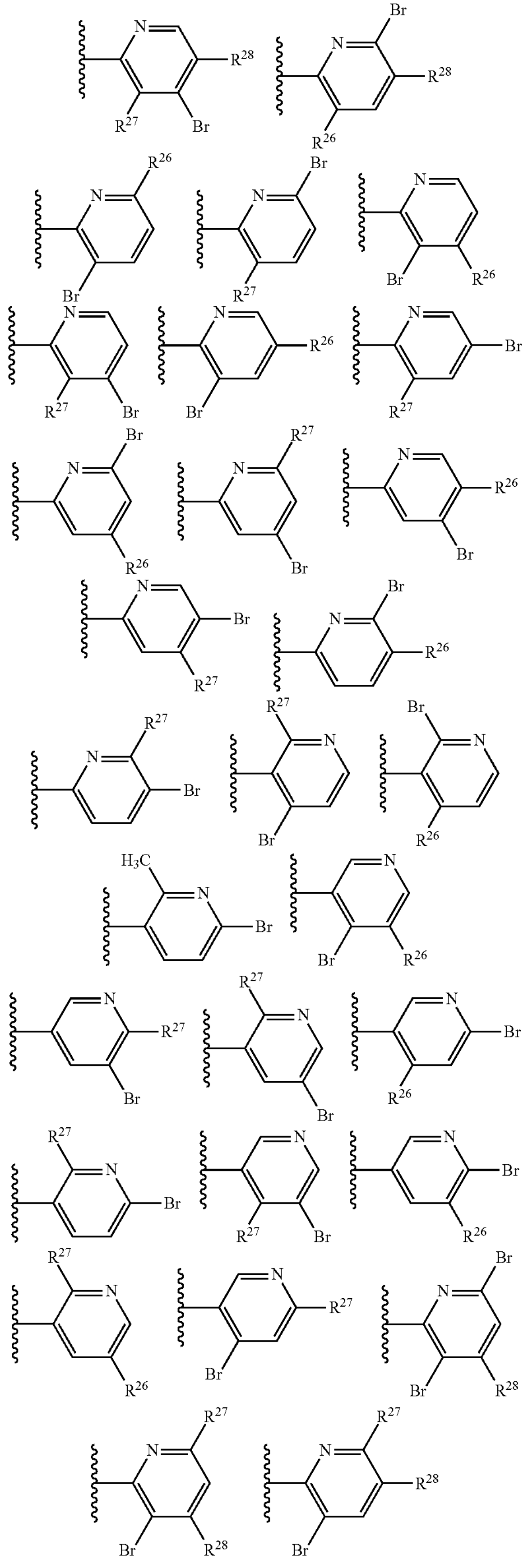

-continued
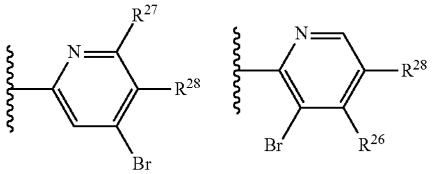
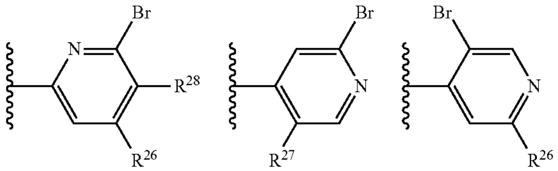
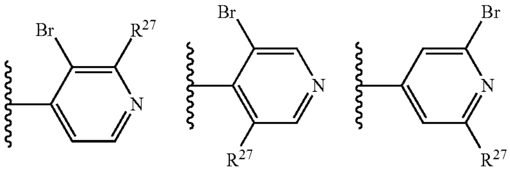
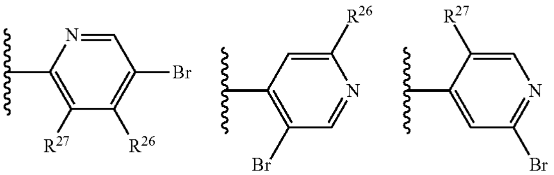
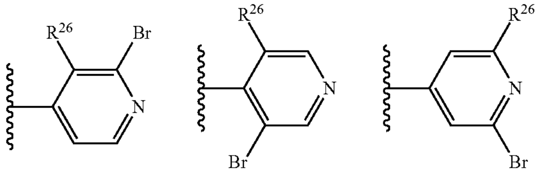
In one embodiment, B4 is selected from:
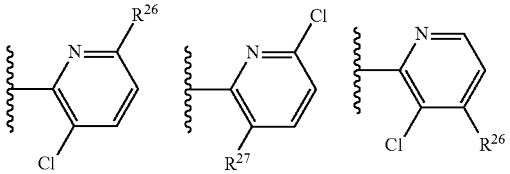
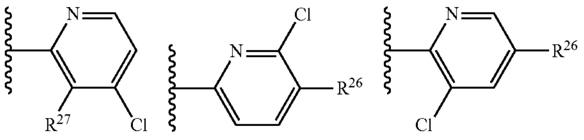
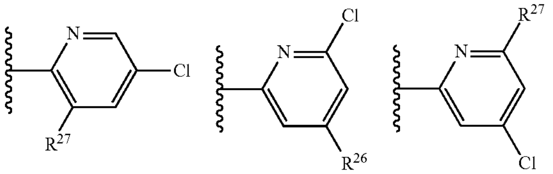
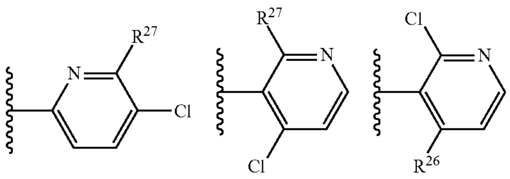
-continued
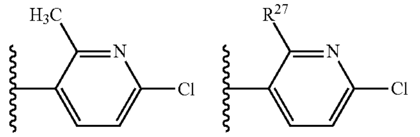
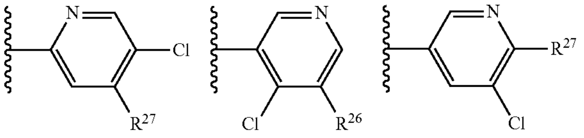
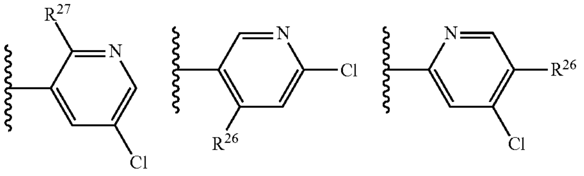
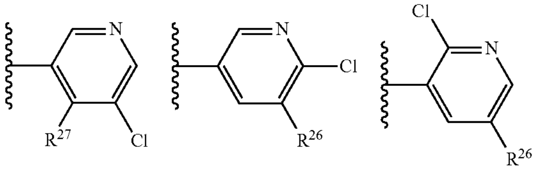
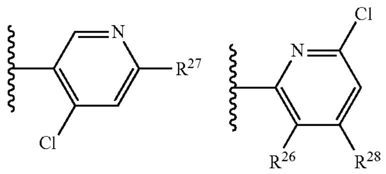
In one embodiment, B4 is selected from:
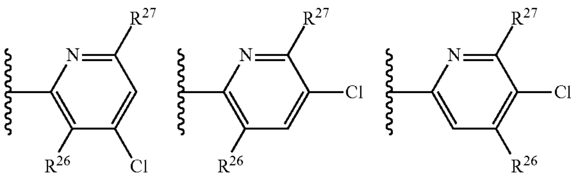
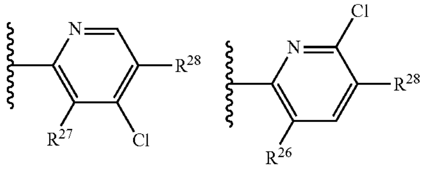
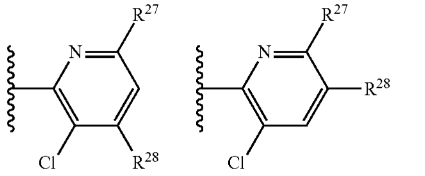
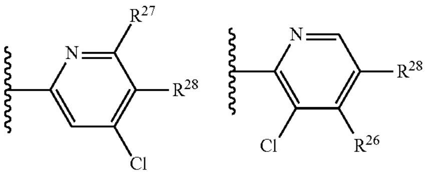

-continued
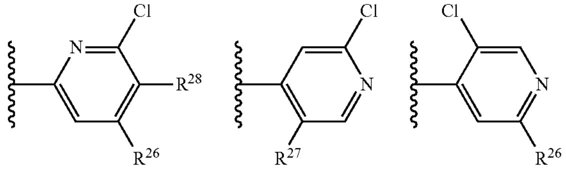
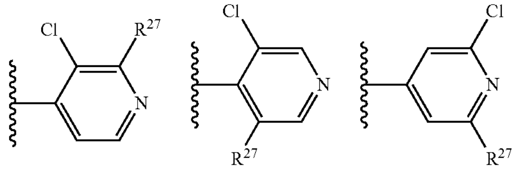
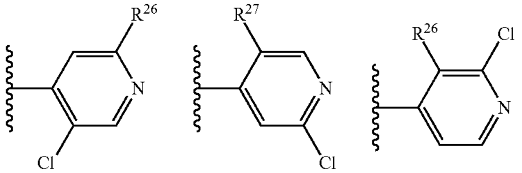
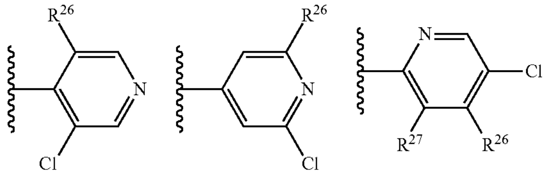
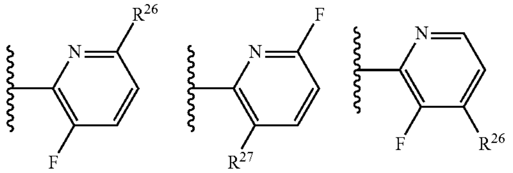
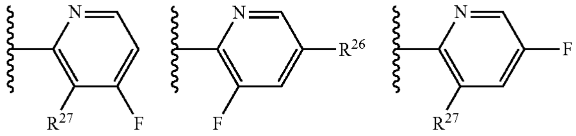
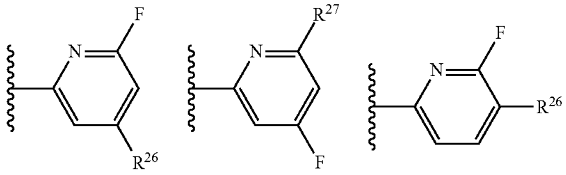
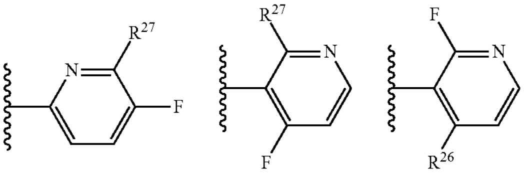
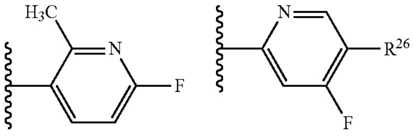
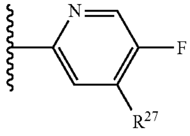
In one embodiment, B4 is selected from:
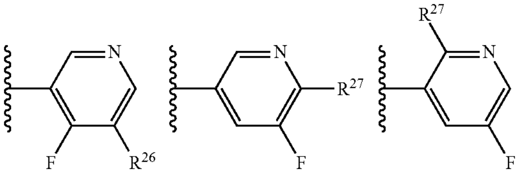
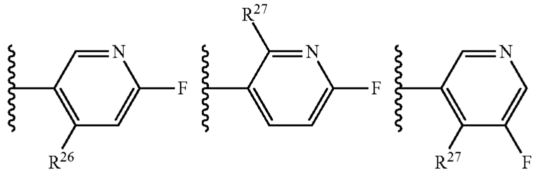
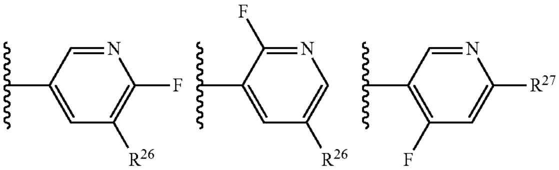
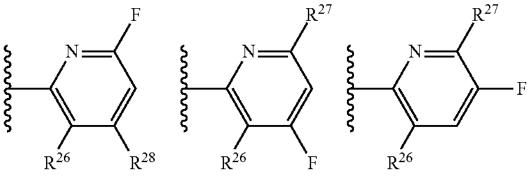
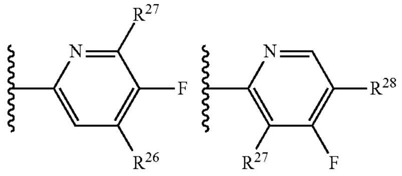
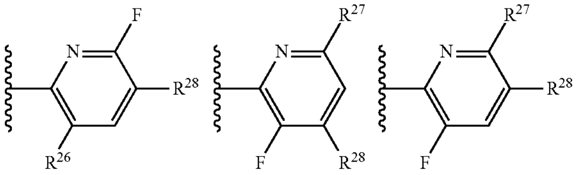
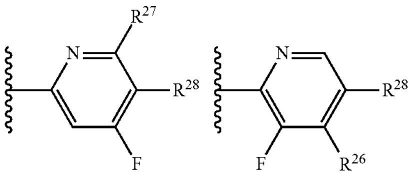
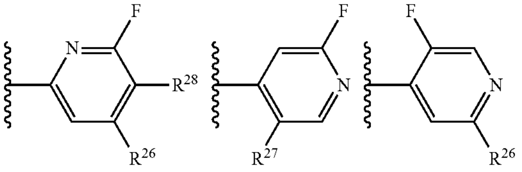
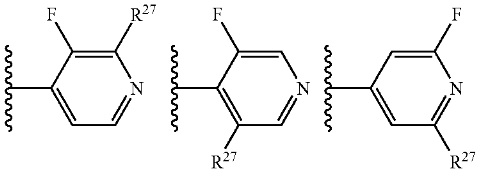

-continued
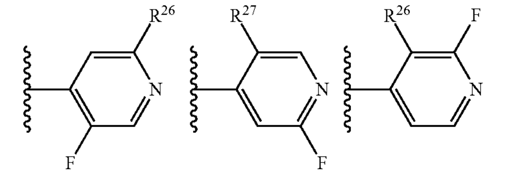
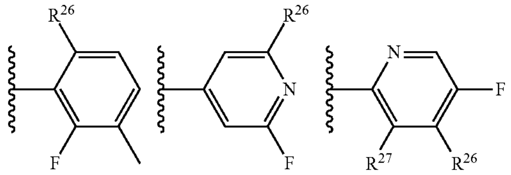
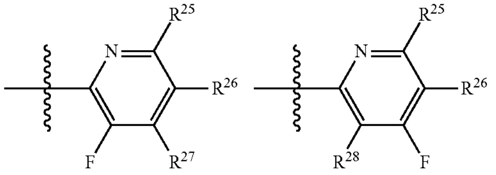
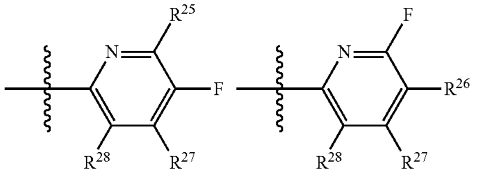
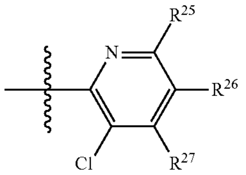
In one embodiment, B4 is selected from:
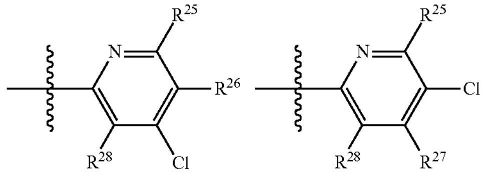
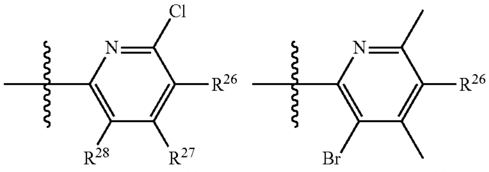
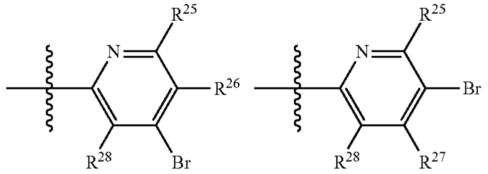
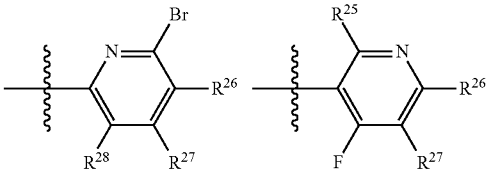
-continued
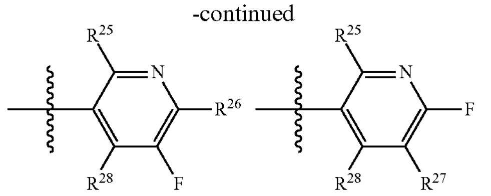
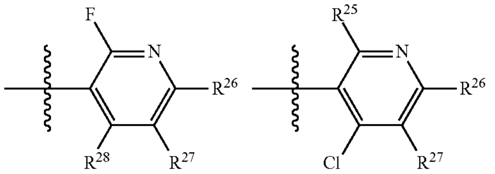
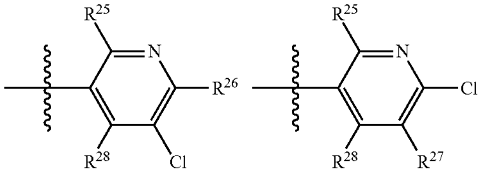
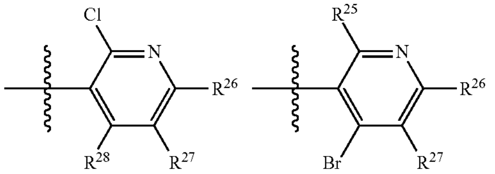
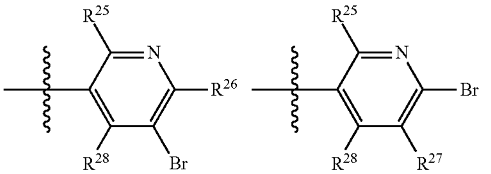
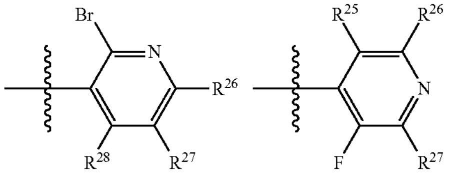
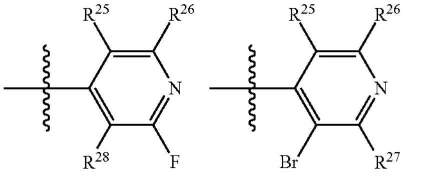
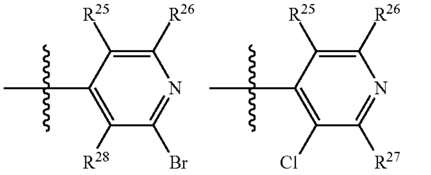
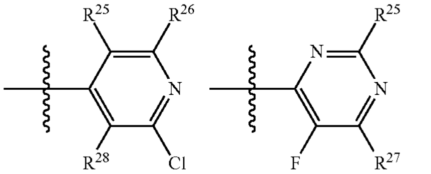
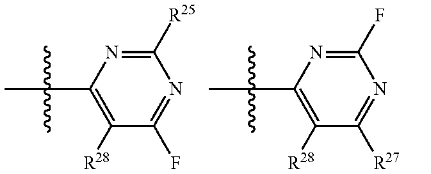

-continued
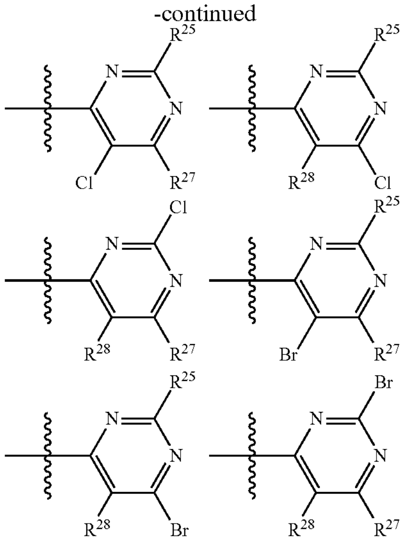
In one embodiment, B4 is selected from:
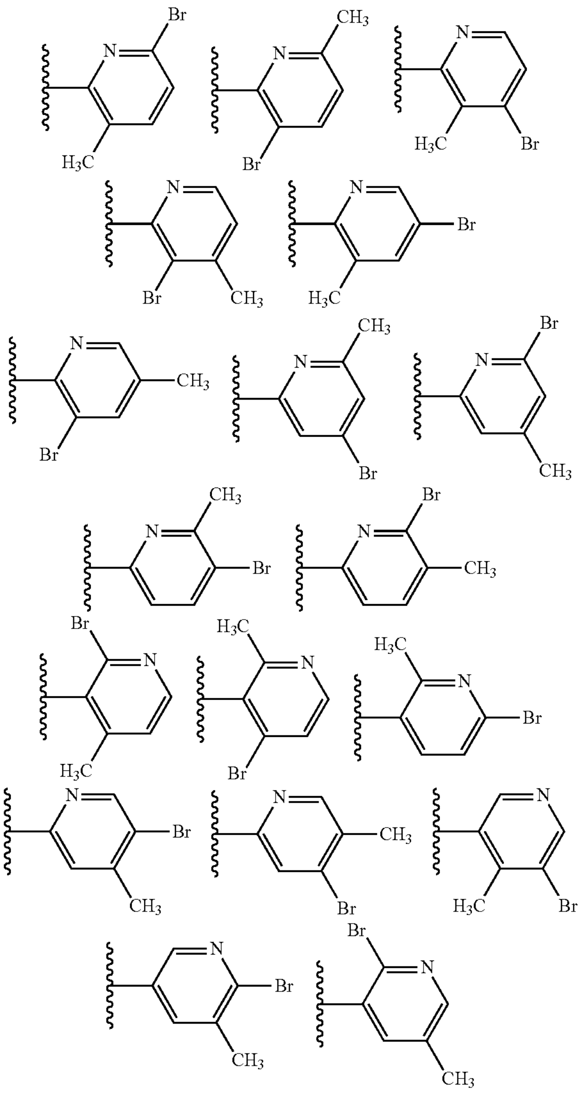
-continued
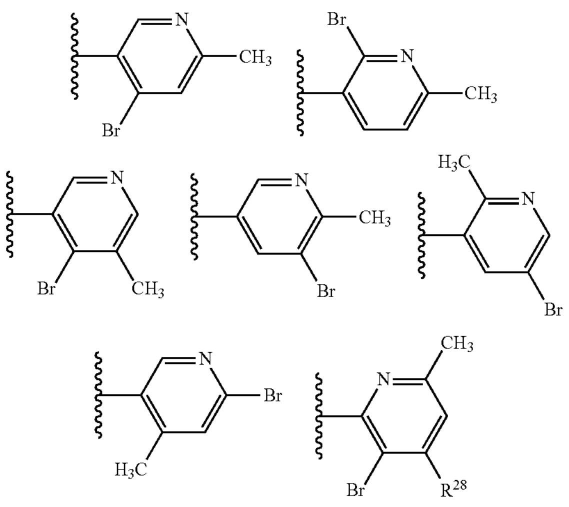
In one embodiment, B4 is selected from:
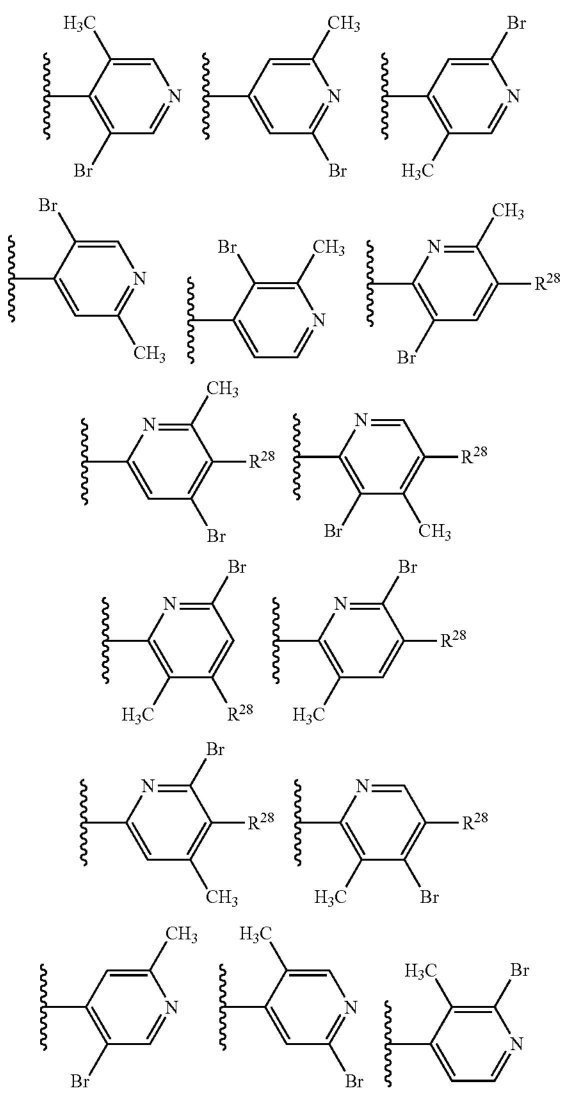

-continued
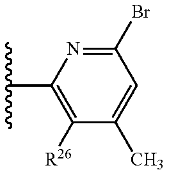
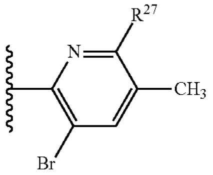
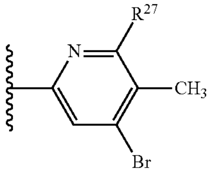
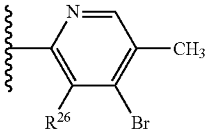
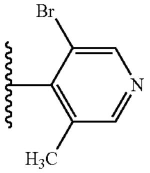
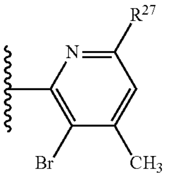
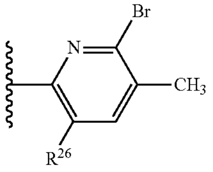
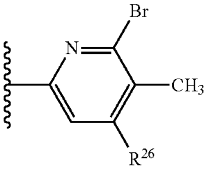
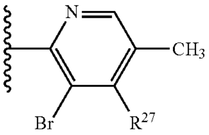
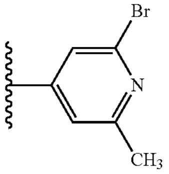
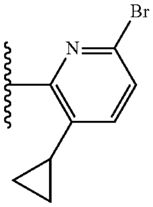
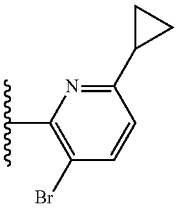
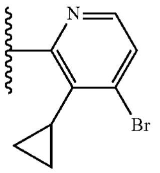
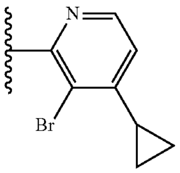
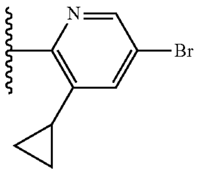
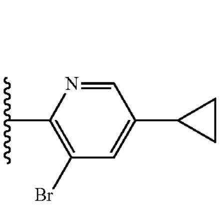
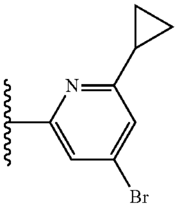
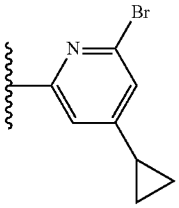
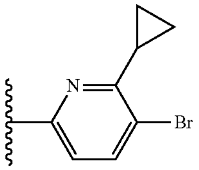
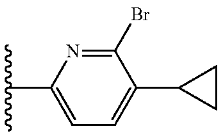
In one embodiment, B4 is selected from:
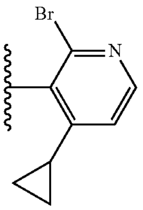
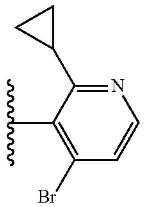
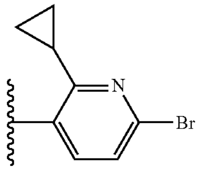
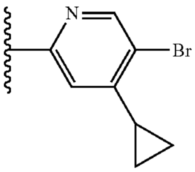
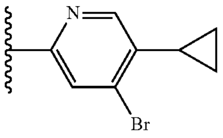
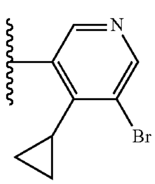
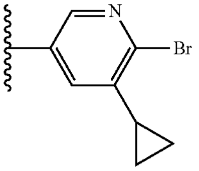
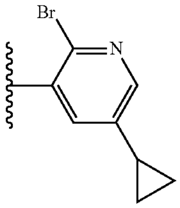
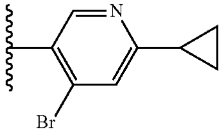
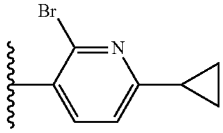
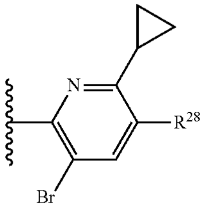
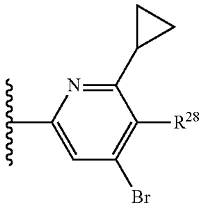
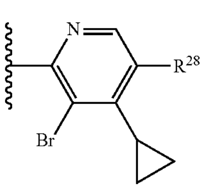
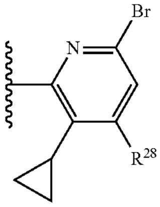
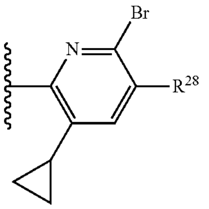
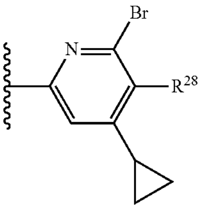
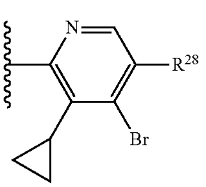
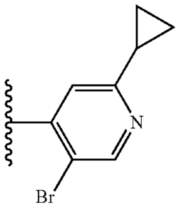

-continued
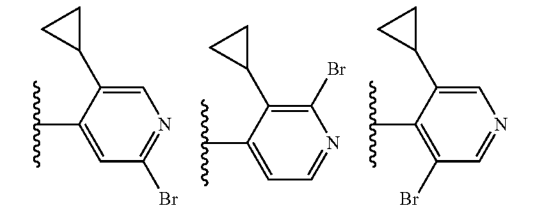
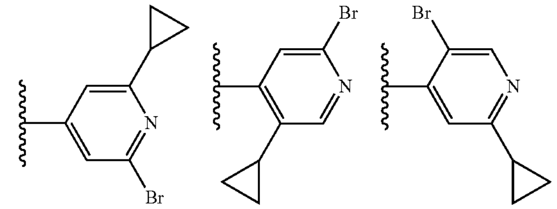
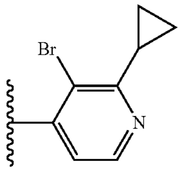
In one embodiment, B4 is selected from:
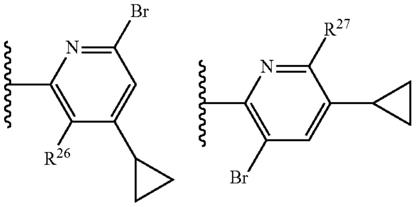
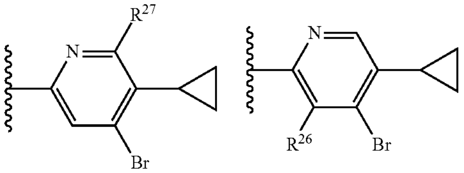
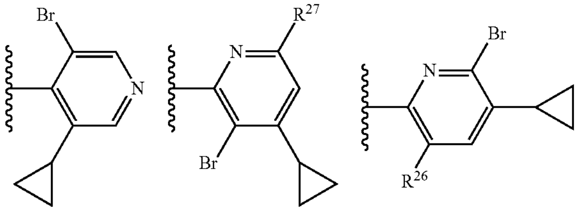
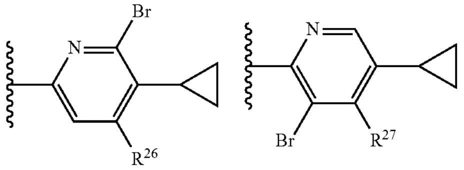
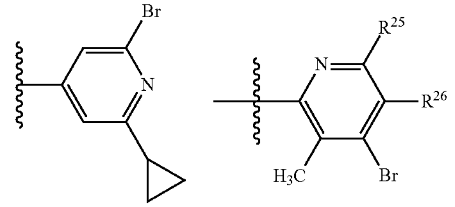
-continued
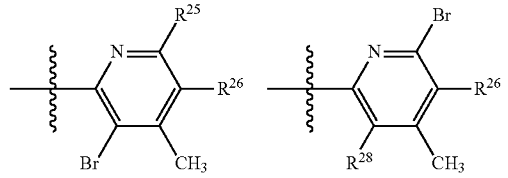
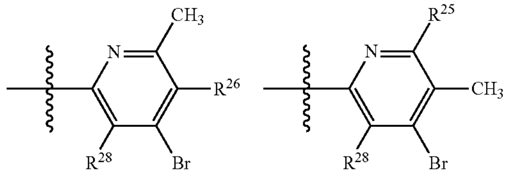
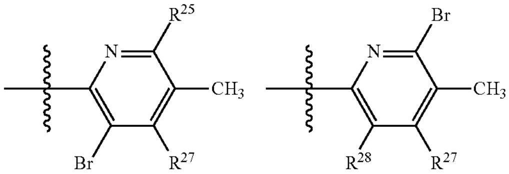
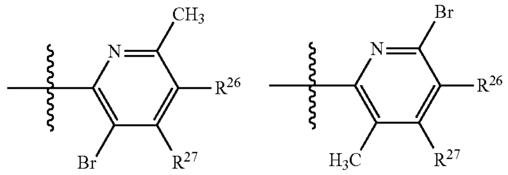
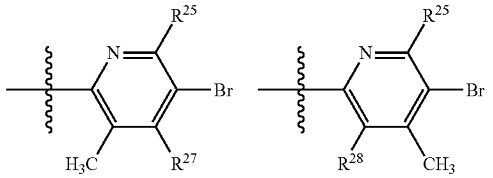
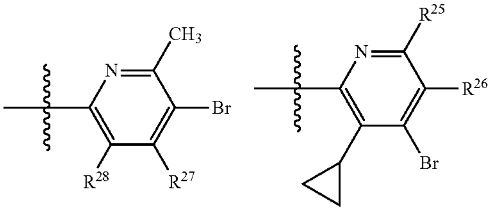
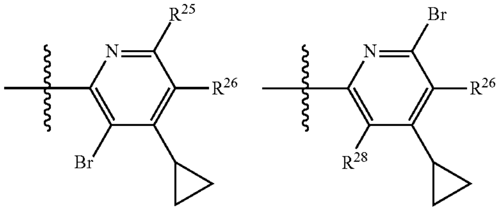
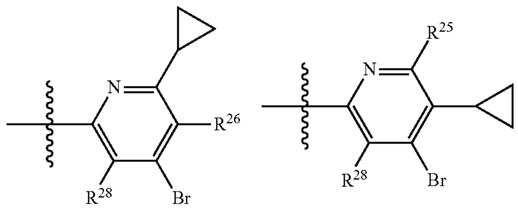
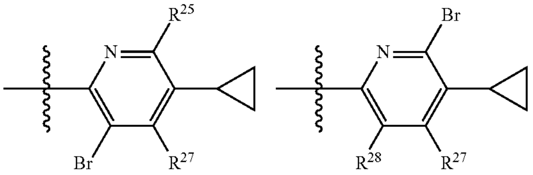 and -continued
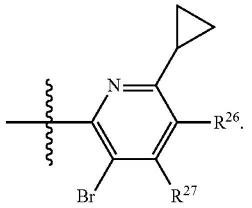
In one embodiment, B4 is selected from:
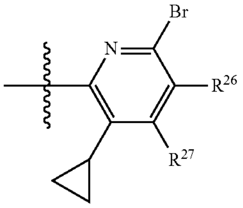
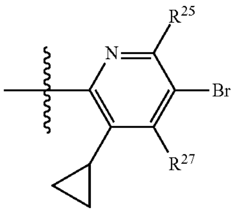
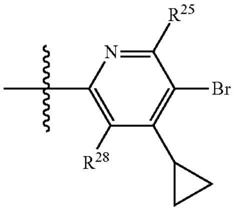
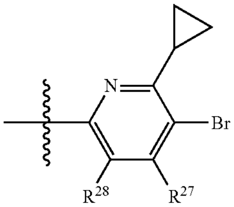
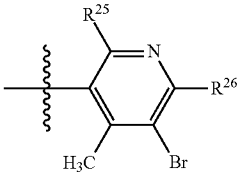
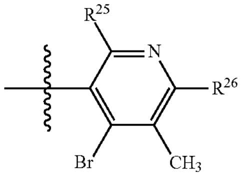
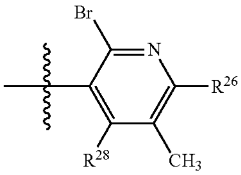
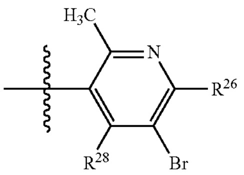
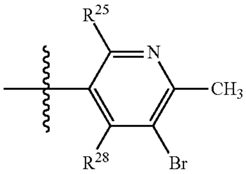
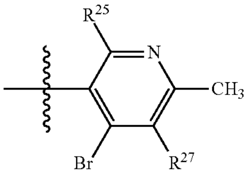
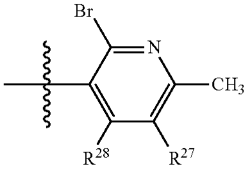
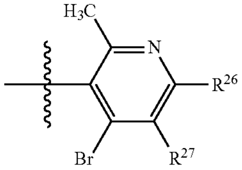
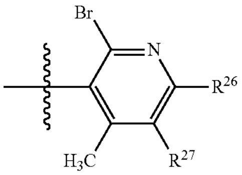
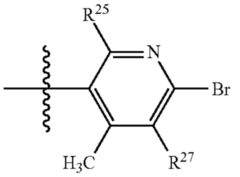
-continued
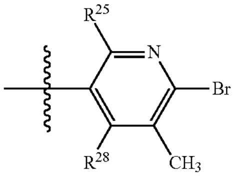
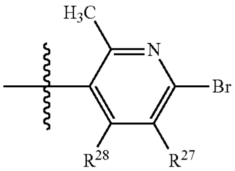
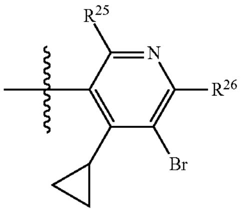
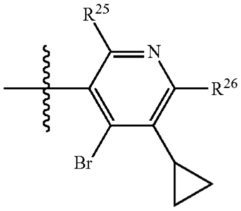
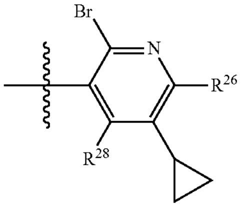
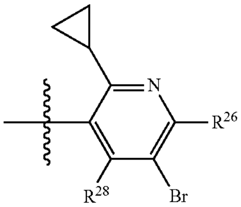
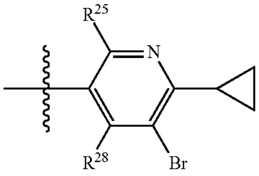
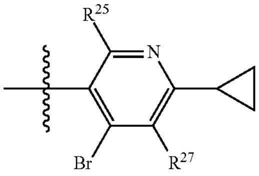
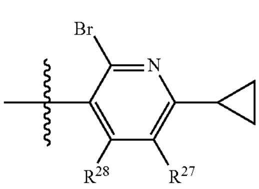
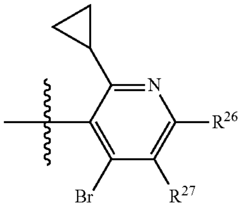
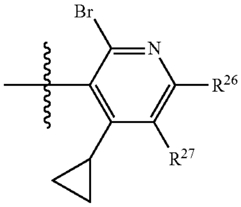
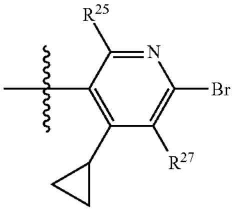
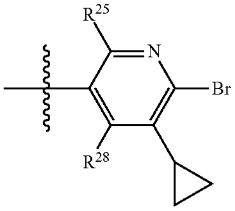
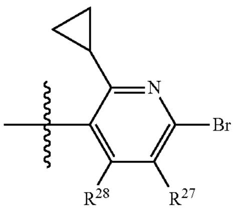
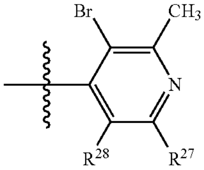
and
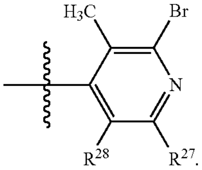

In one embodiment, B4 is selected from:
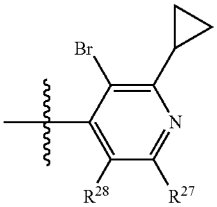
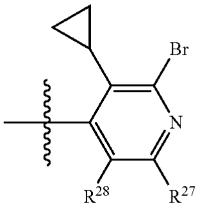
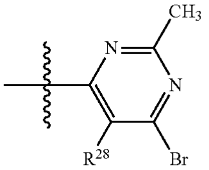
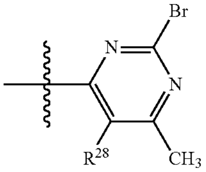
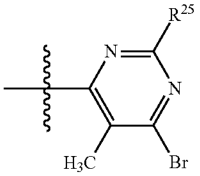
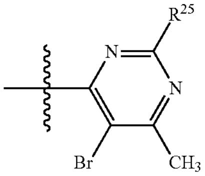
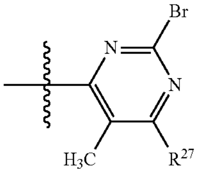
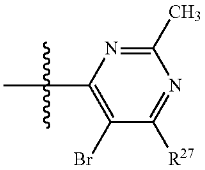
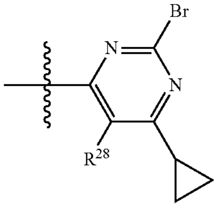
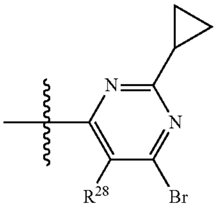
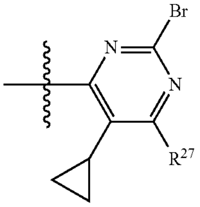
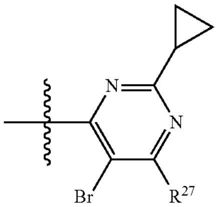
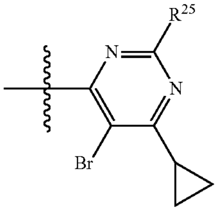
and
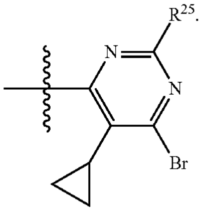
In one embodiment, B4 is selected from:
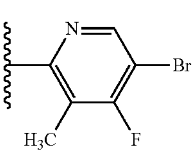
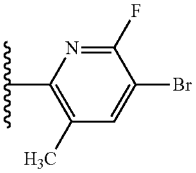
-continued
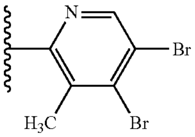
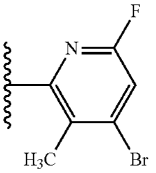
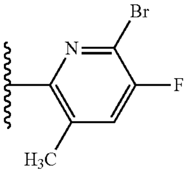
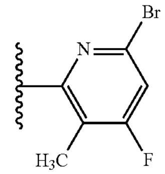
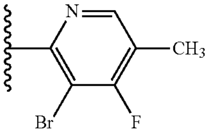
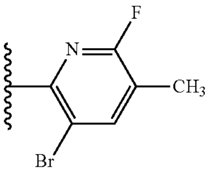
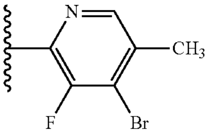
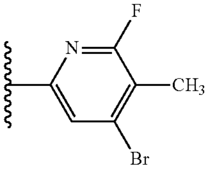
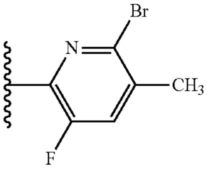
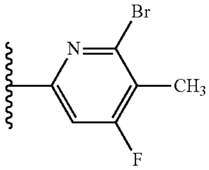
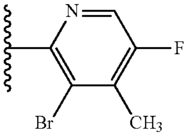
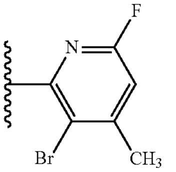
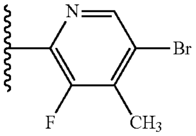
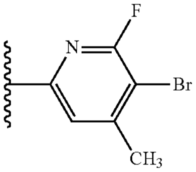
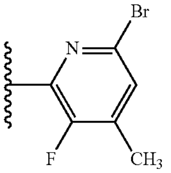
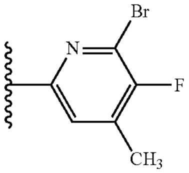
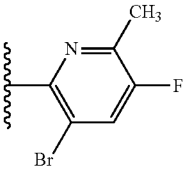
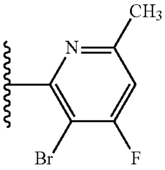
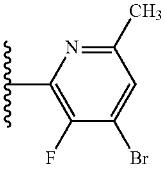
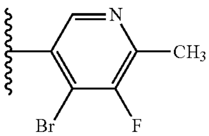 [SMILES: *c1cnc(C)c(F)c1Br]

In one embodiment, B4 is selected from:
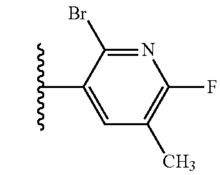
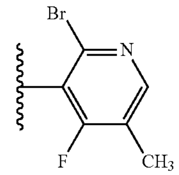
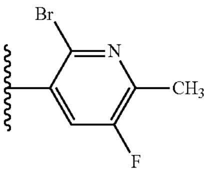
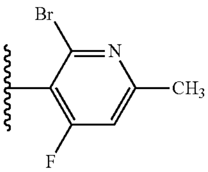
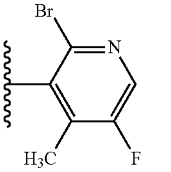
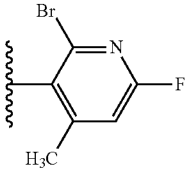
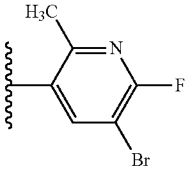
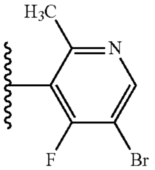
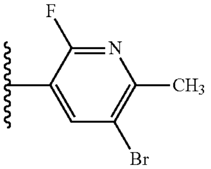
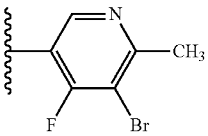
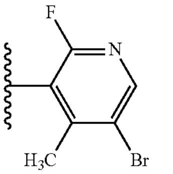
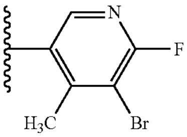
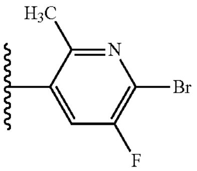
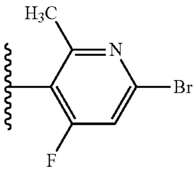
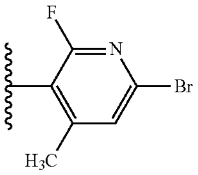
In one embodiment, B4 is selected from:
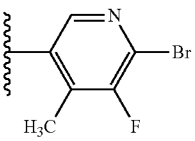
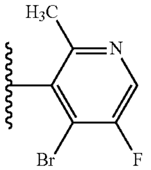
-continued
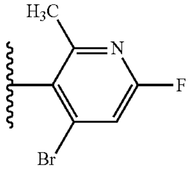
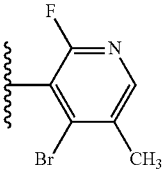
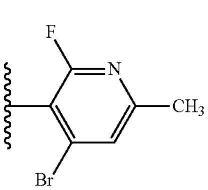
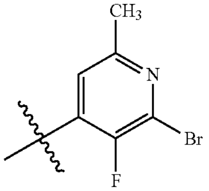
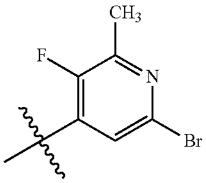
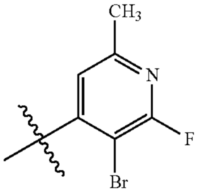
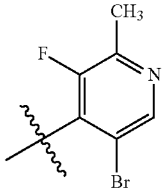
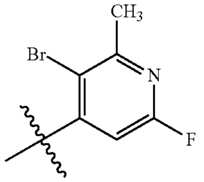
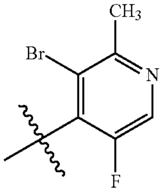
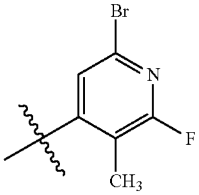
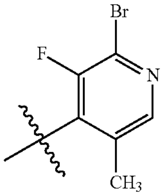
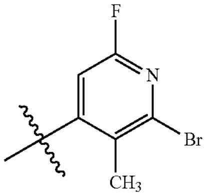
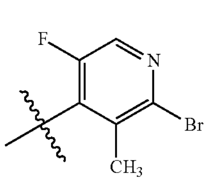
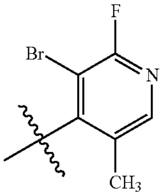
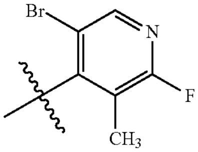

In one embodiment, B4 is selected from:
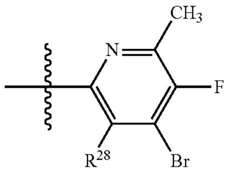
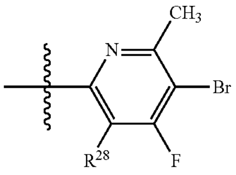
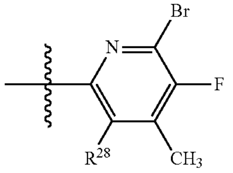
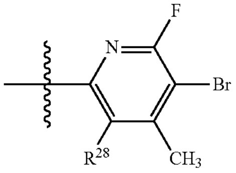
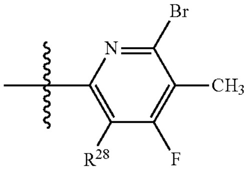
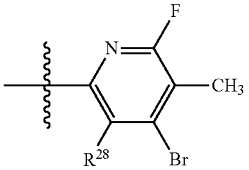
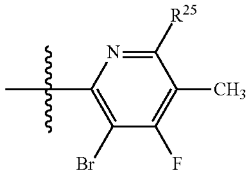
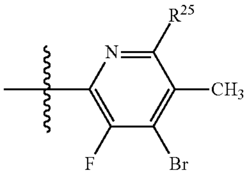
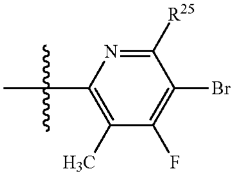
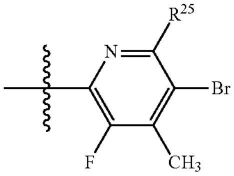
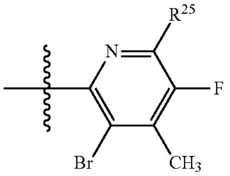
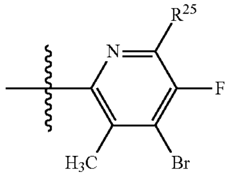
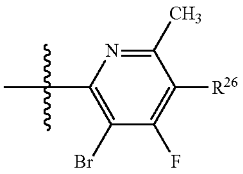
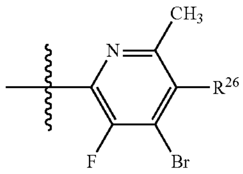
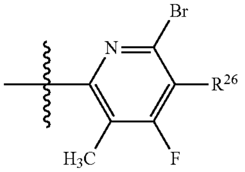
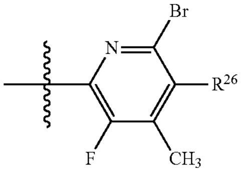
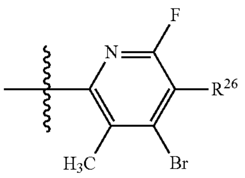
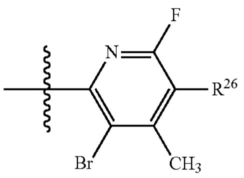
-continued
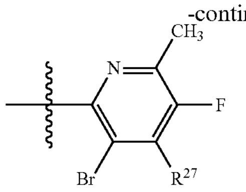
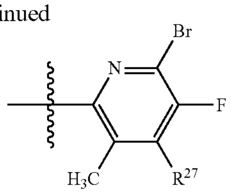
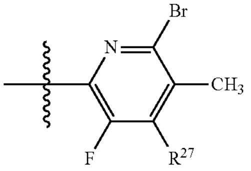
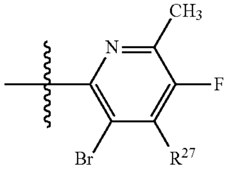
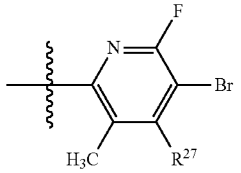
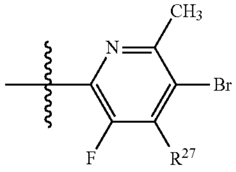
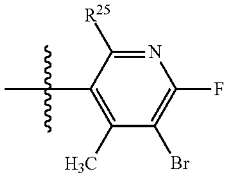
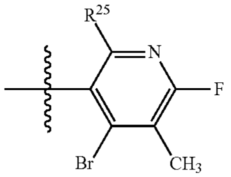
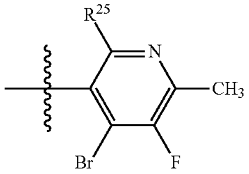
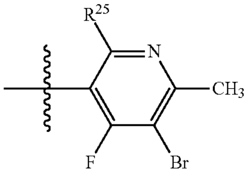
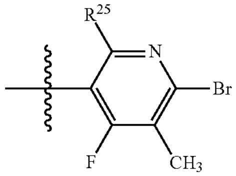
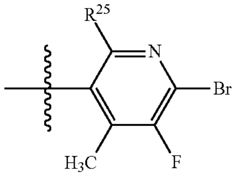
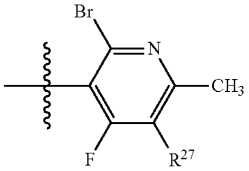
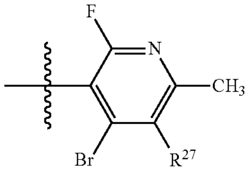
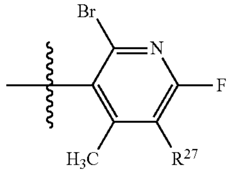
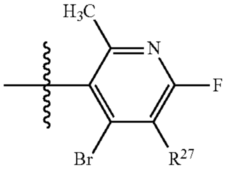
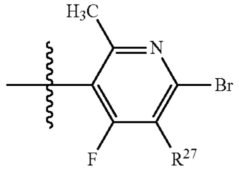
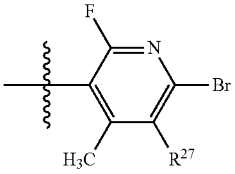
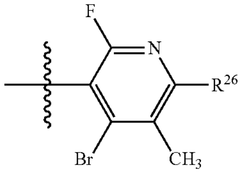
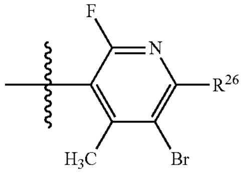

-continued
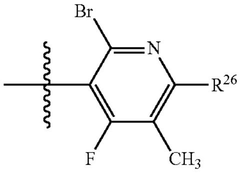 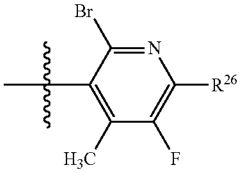
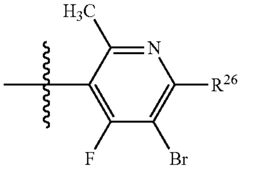 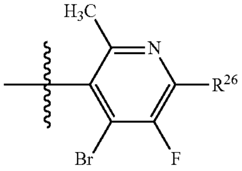
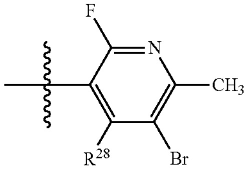 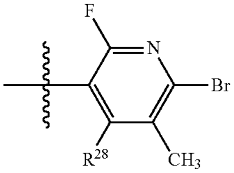
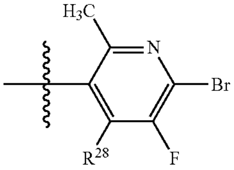 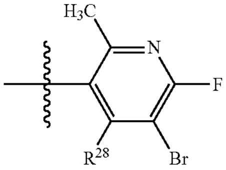
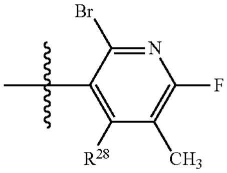 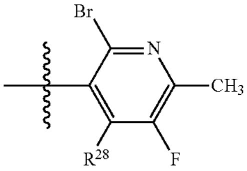
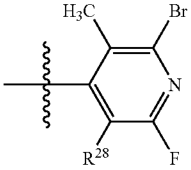 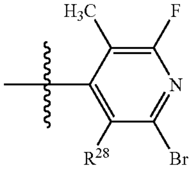
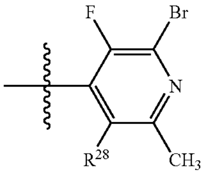 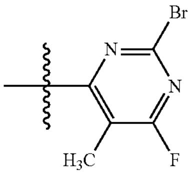
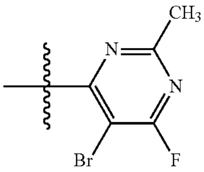 and 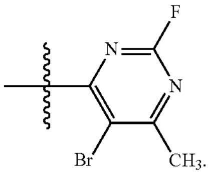
In one embodiment, B4 is selected from:
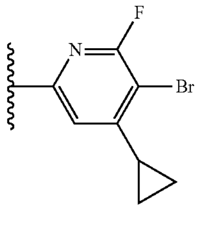 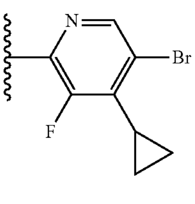
-continued
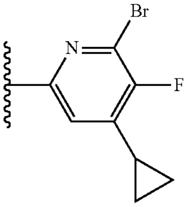 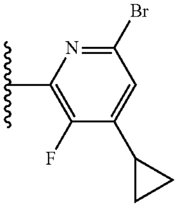
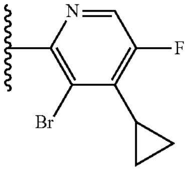 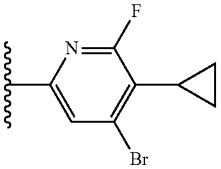
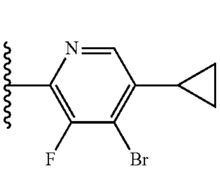 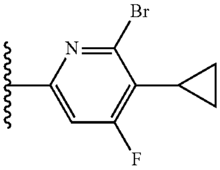
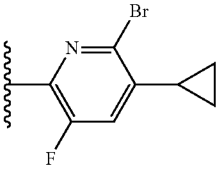 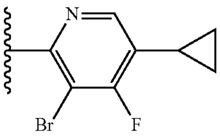
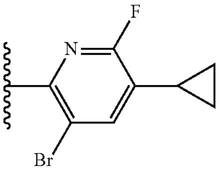 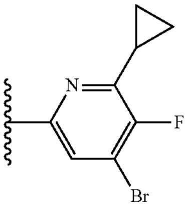
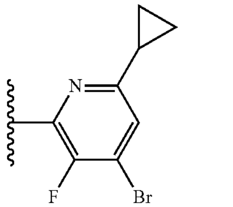 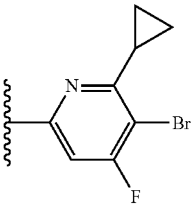
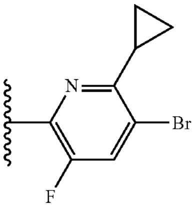 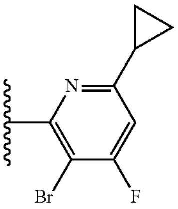
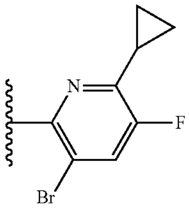 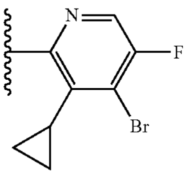 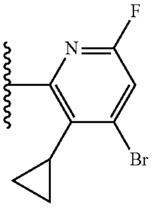
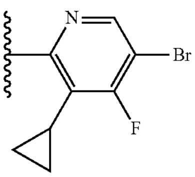 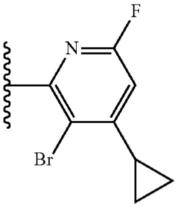 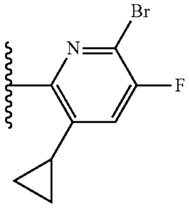

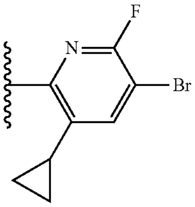
In one embodiment, B4 is selected from:
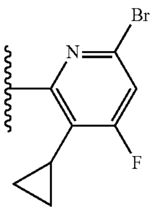
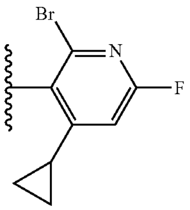
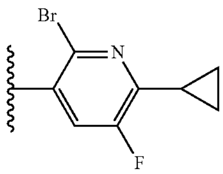
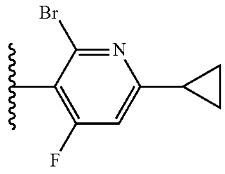
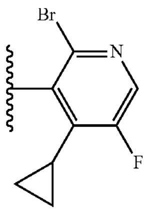
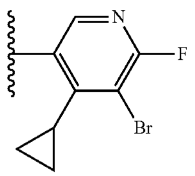
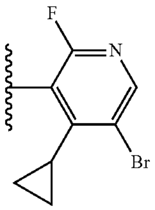
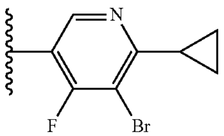
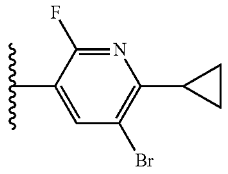
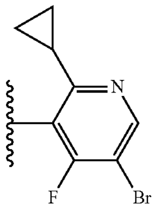
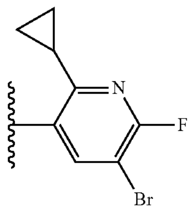
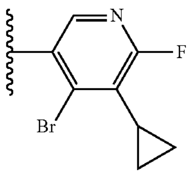
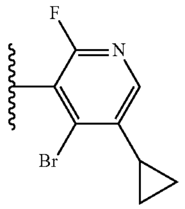
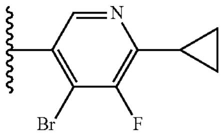
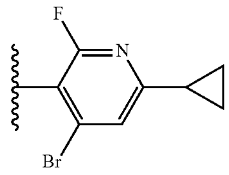
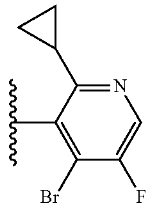
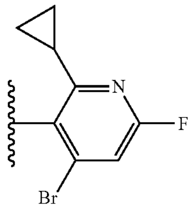
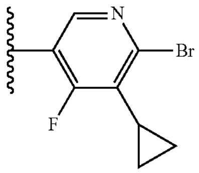
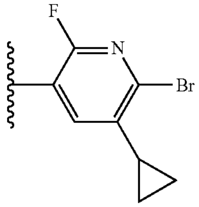
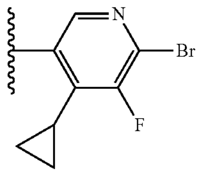
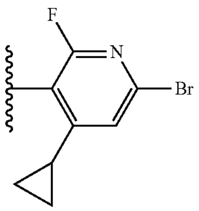
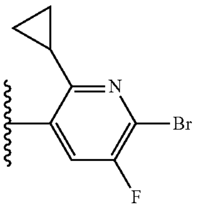
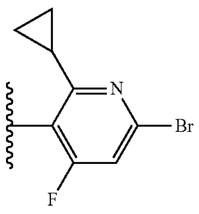
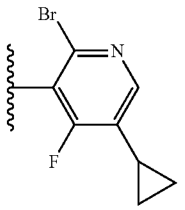
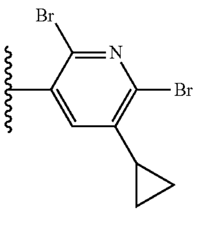

In one embodiment, B4 is selected from:
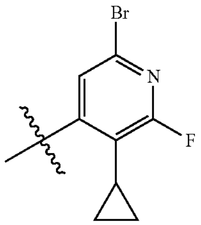
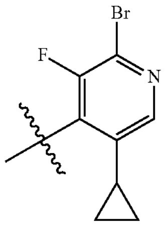
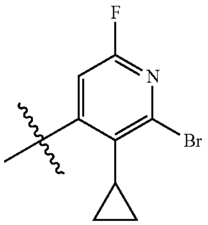
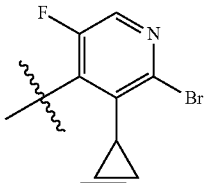
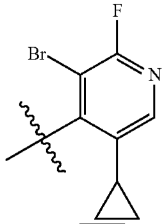
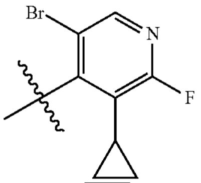
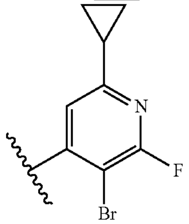
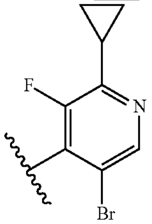
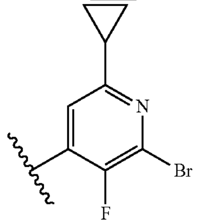
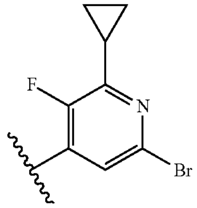
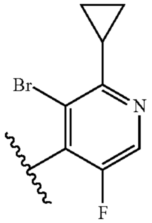
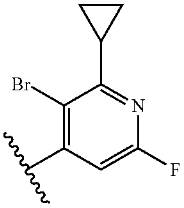
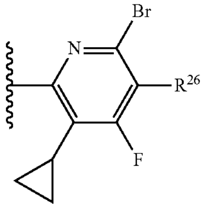
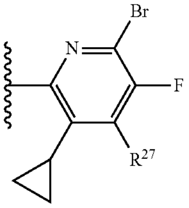
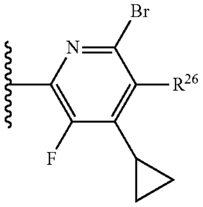
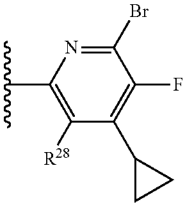
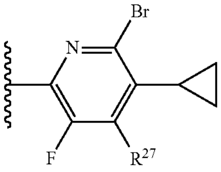
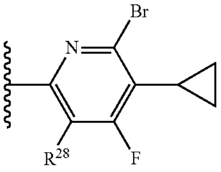
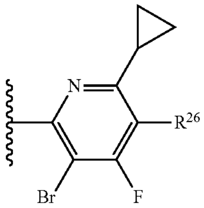
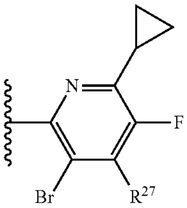
-continued
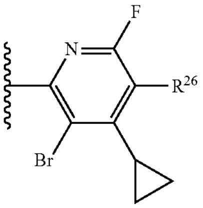
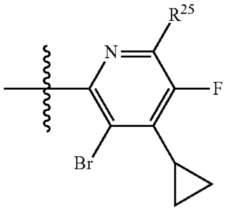
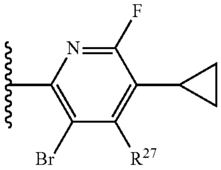
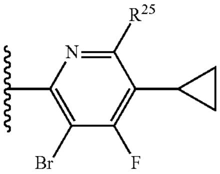
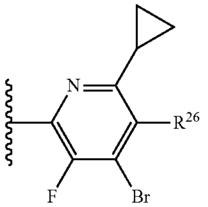
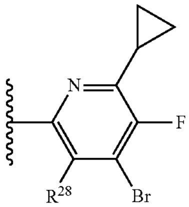
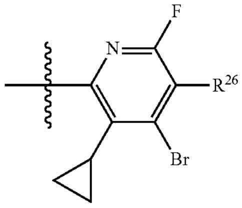
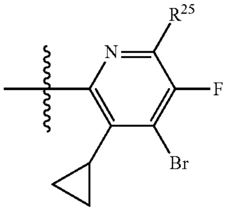
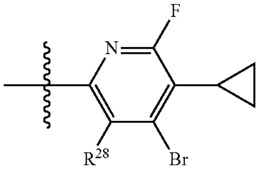
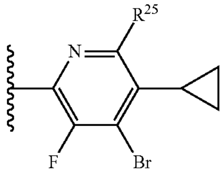
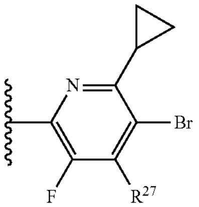
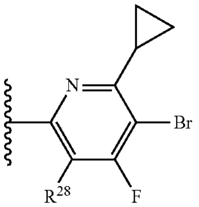
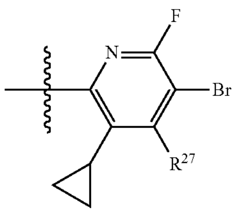
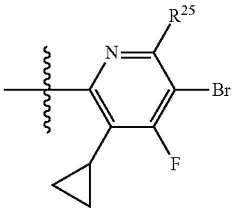
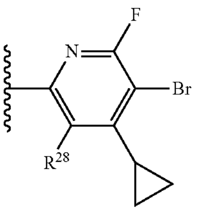
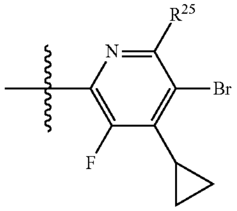

In one embodiment, B4 is selected from:
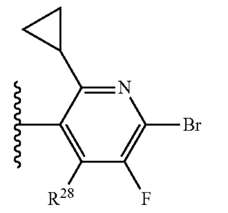
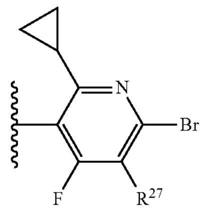
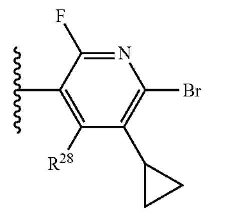
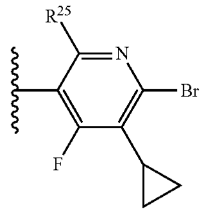
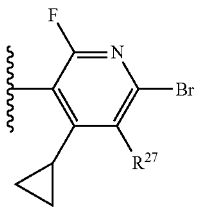
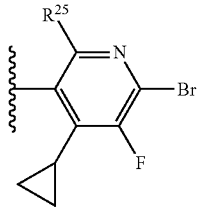
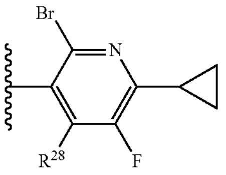
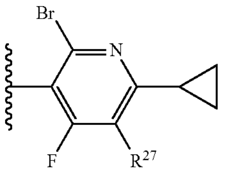
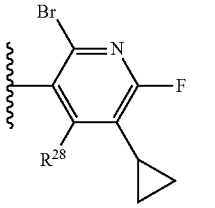
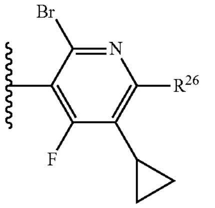
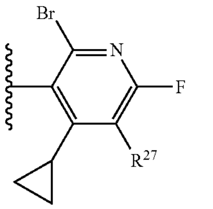
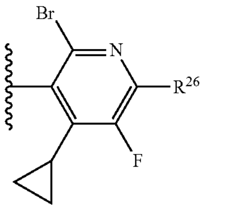
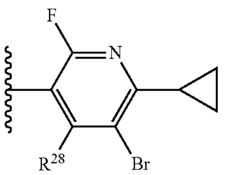
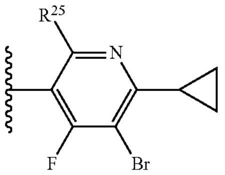
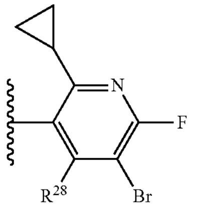
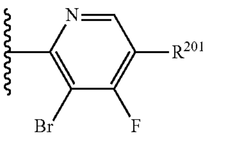
-continued
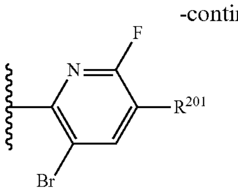
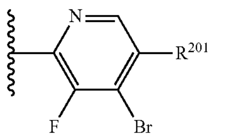
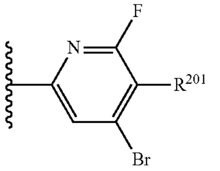
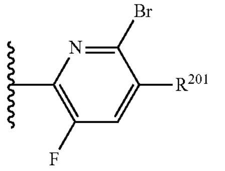
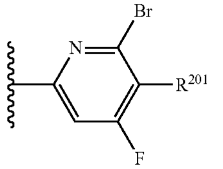
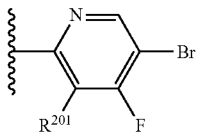
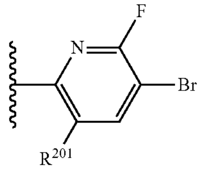
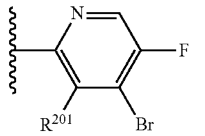
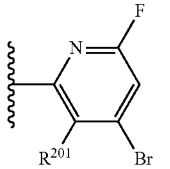
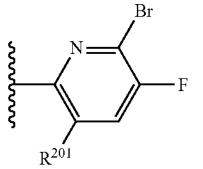
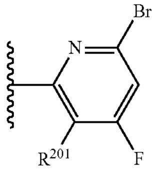
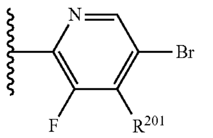
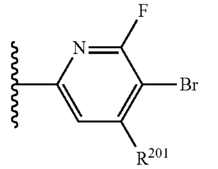
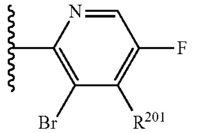
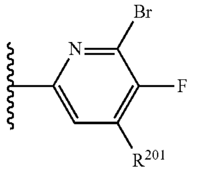
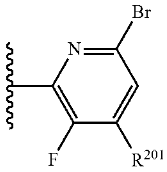
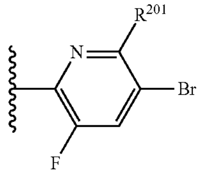
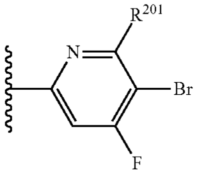
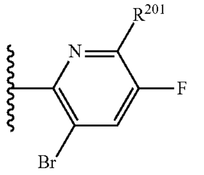
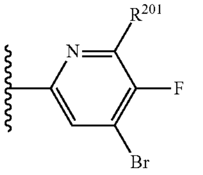

-continued
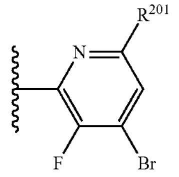
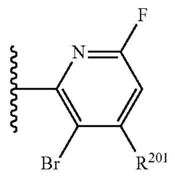
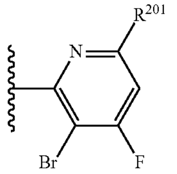
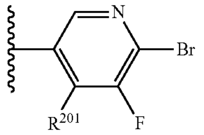
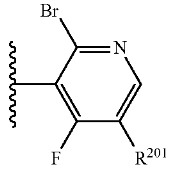
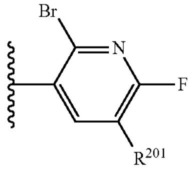
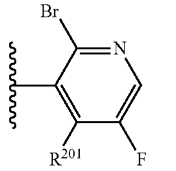
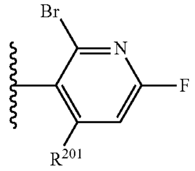
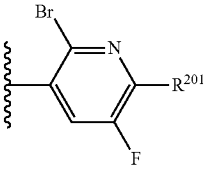
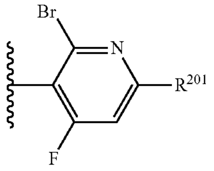
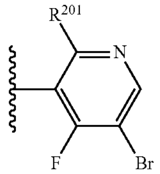
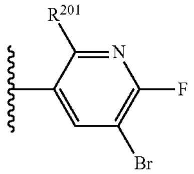
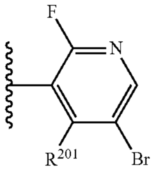
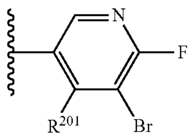
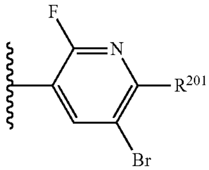
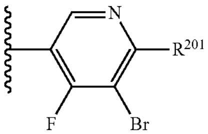
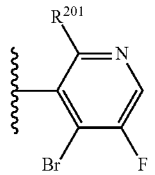
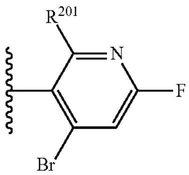
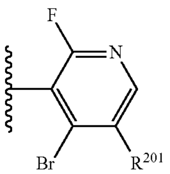
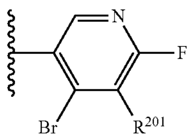
-continued
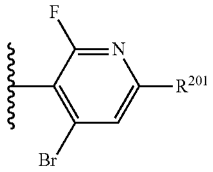
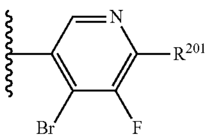
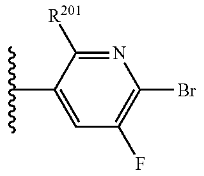
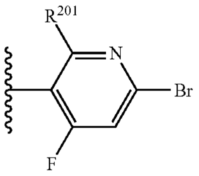
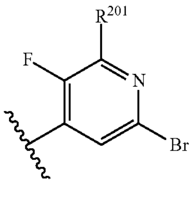
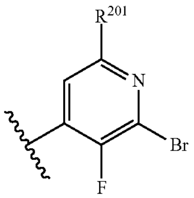
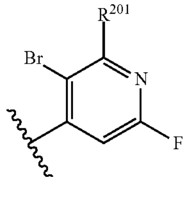
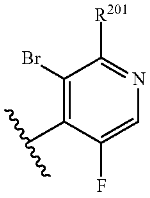
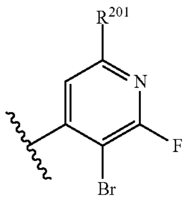
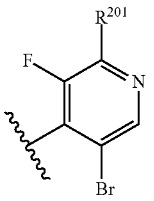
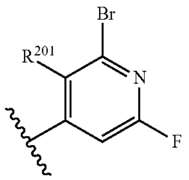
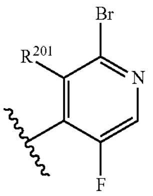
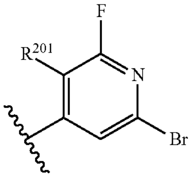
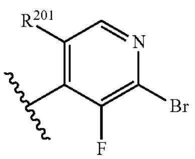
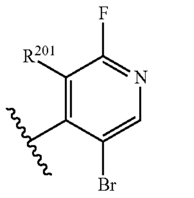
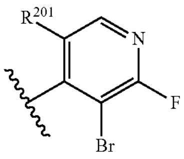

In one embodiment, B4 is selected from:
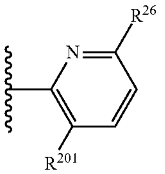
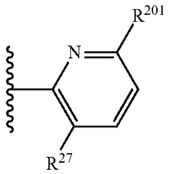
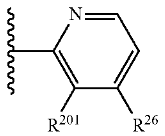
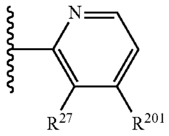
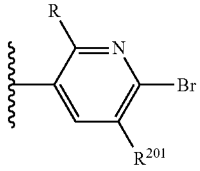
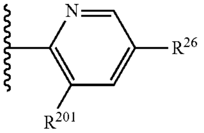
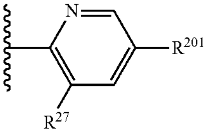
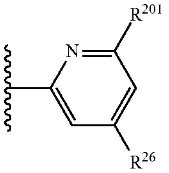
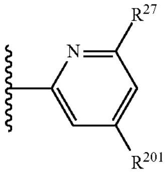
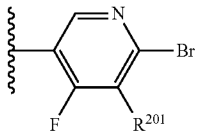
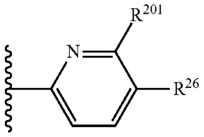
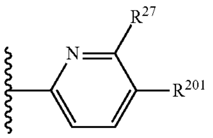
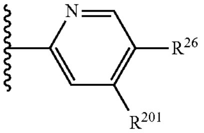
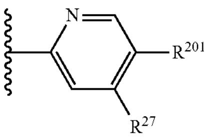
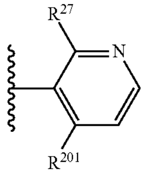
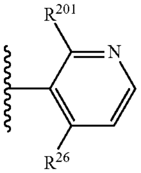
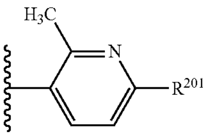
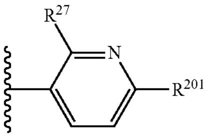
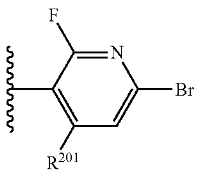
-continued
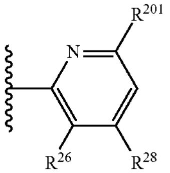
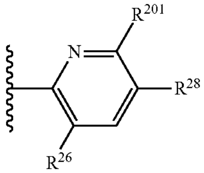
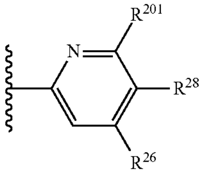
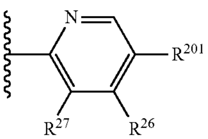
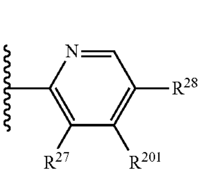
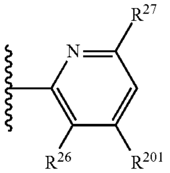
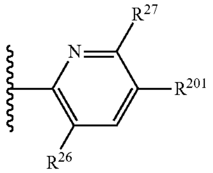
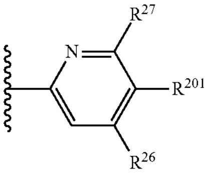
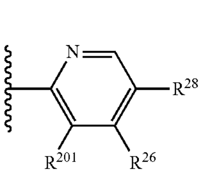
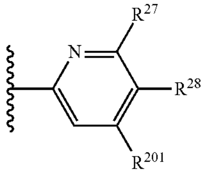
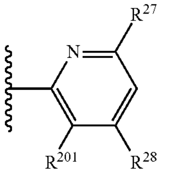
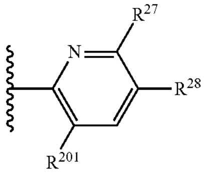
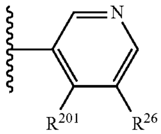
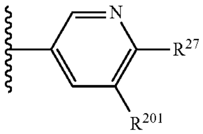
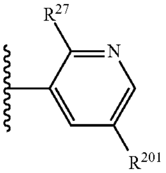
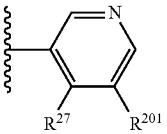
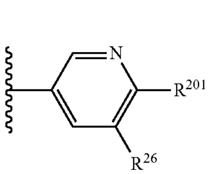
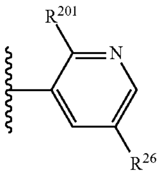
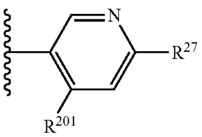
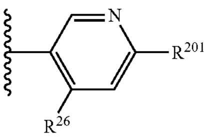

-continued
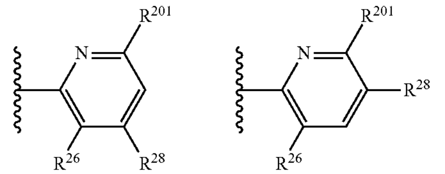
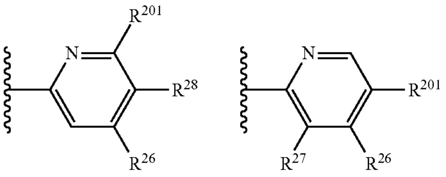
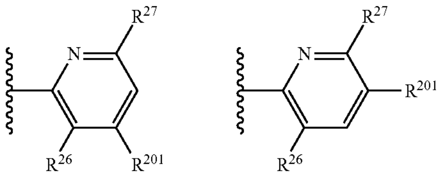
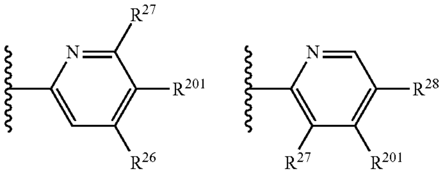
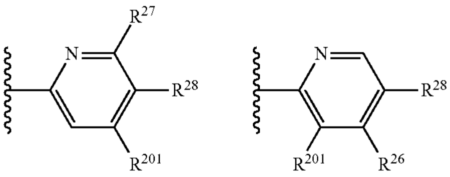
In one embodiment, B4 is selected from:
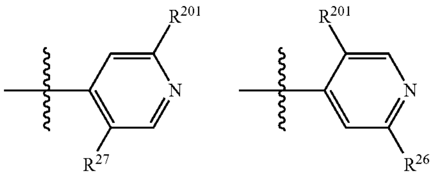
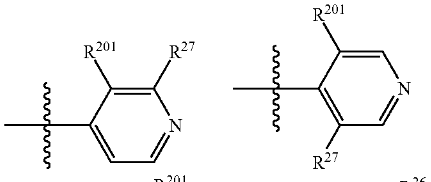
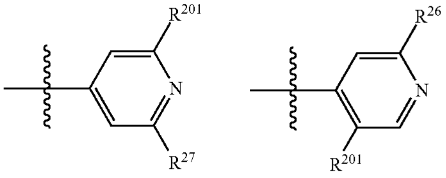
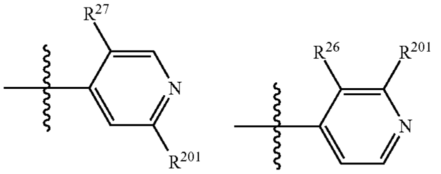
-continued
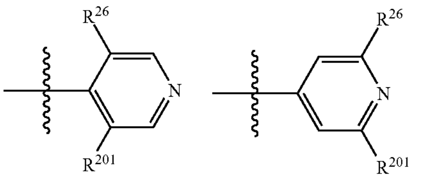
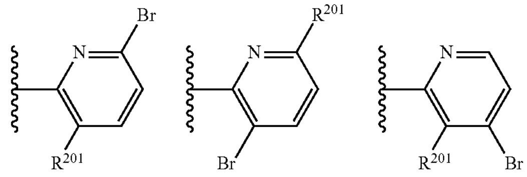
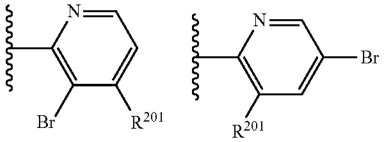
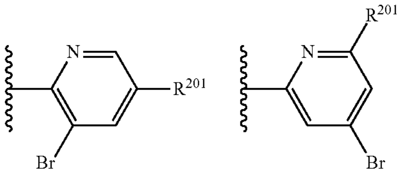
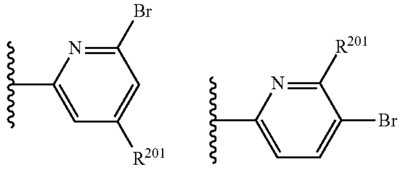
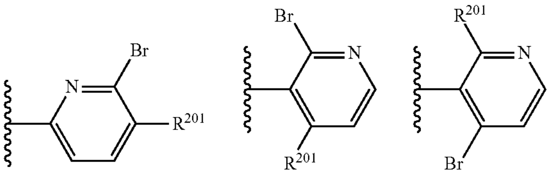
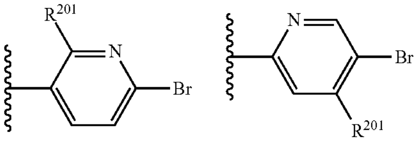
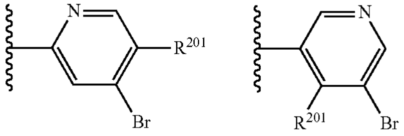
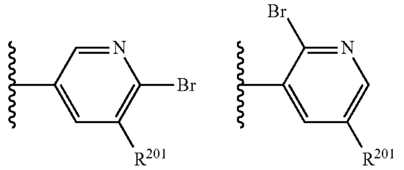
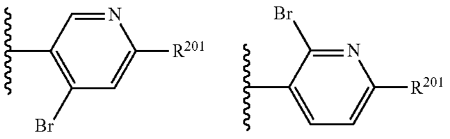

-continued
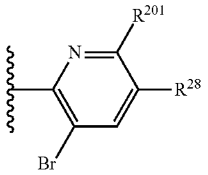
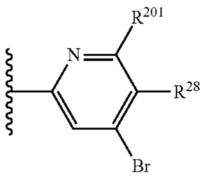
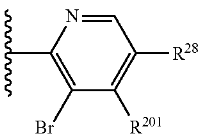
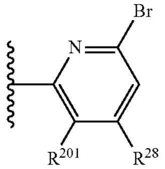
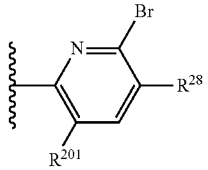
In one embodiment, B4 is selected from:
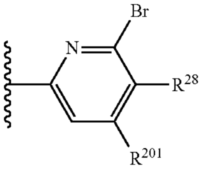
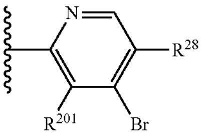
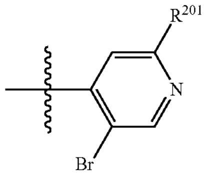
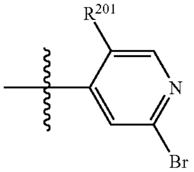
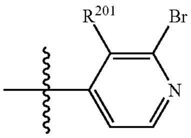
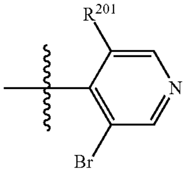
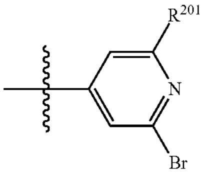
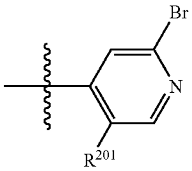
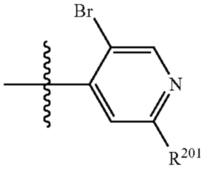
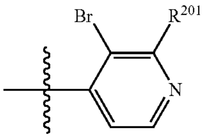
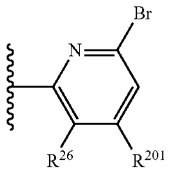
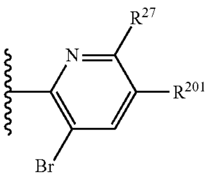
-continued
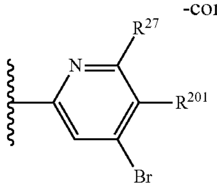
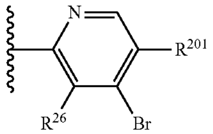
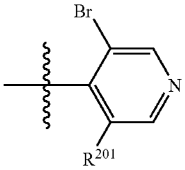
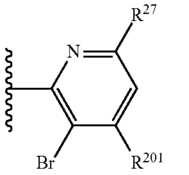
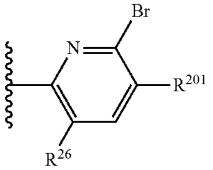
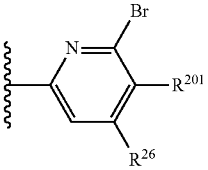
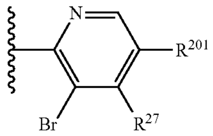
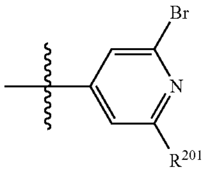
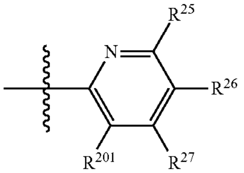
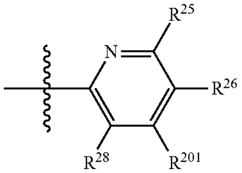
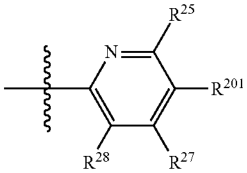
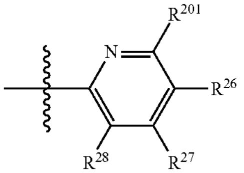
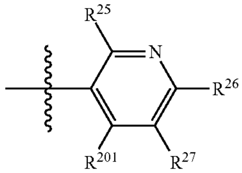
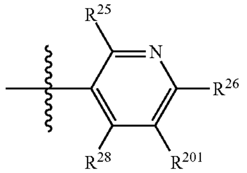
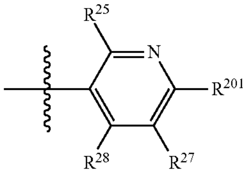
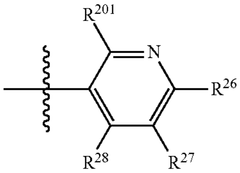
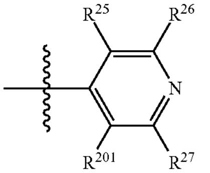
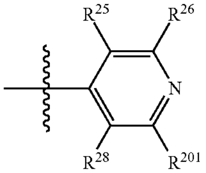
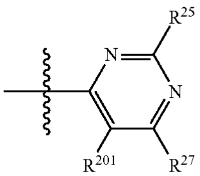
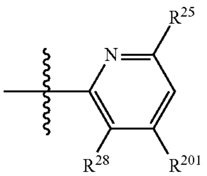

-continued
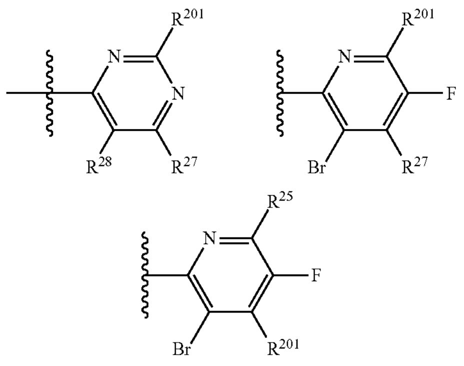
In one embodiment, B4 is selected from:
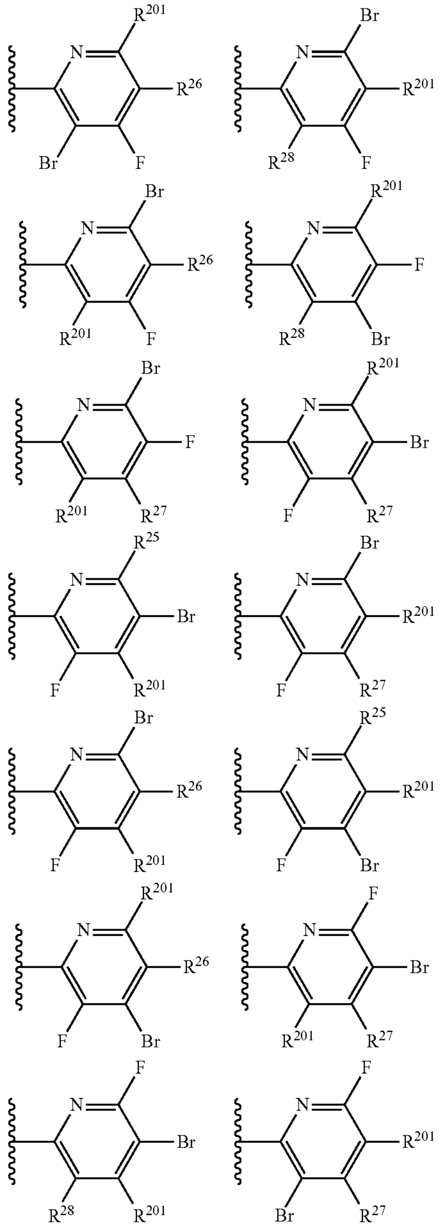
-continued
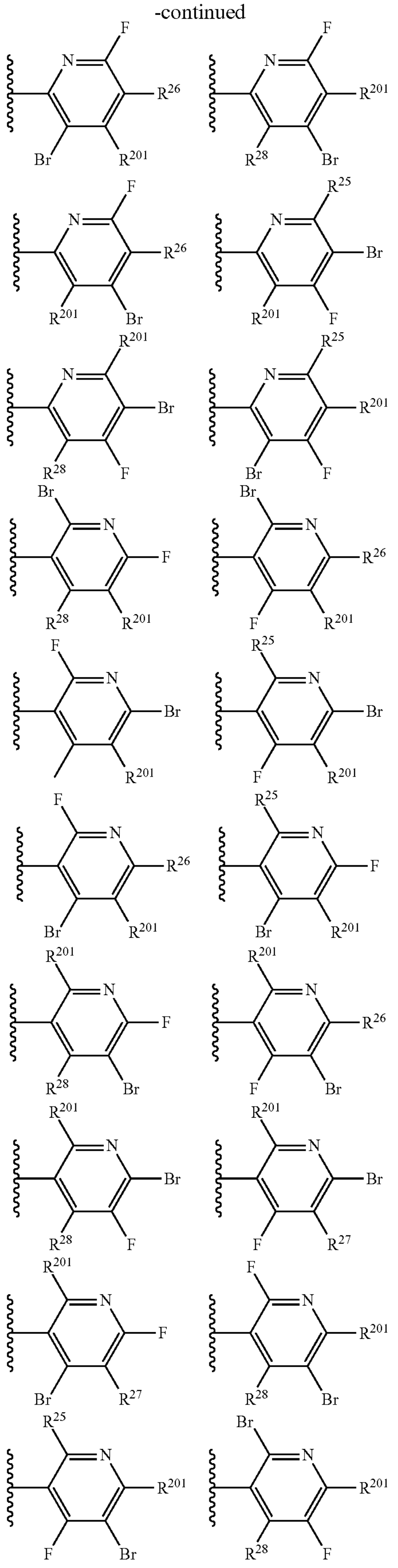

-continued
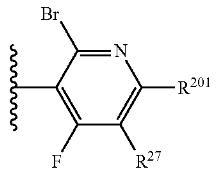
In one embodiment, B4 is selected from:
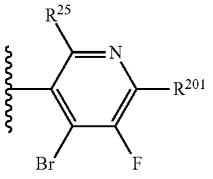
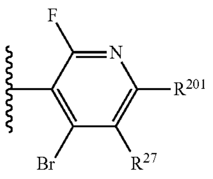
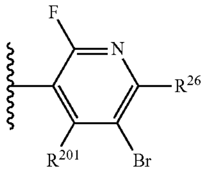
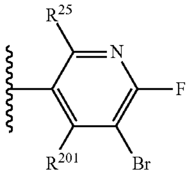
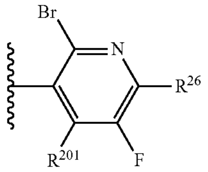
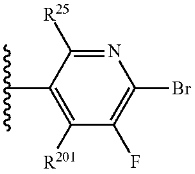
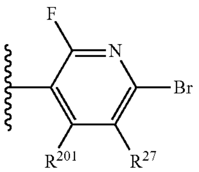
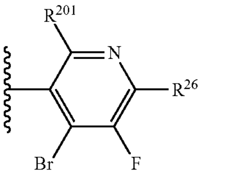
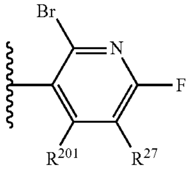
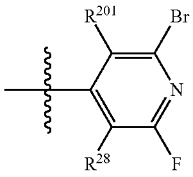
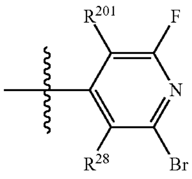
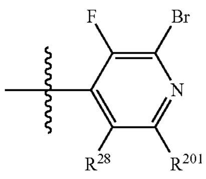
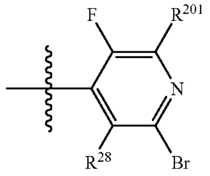
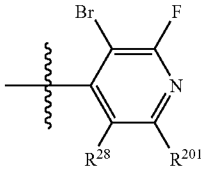
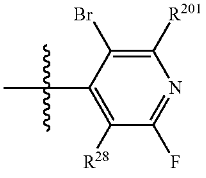
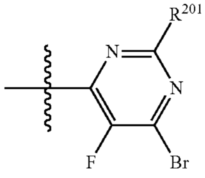
-continued
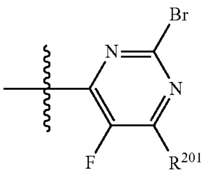
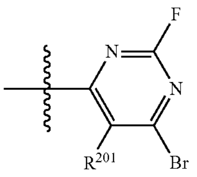
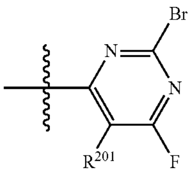
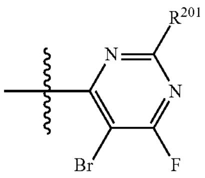
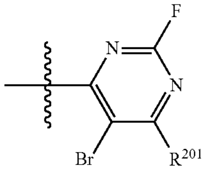
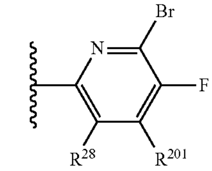
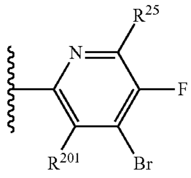
In one embodiment, B4 is selected from:
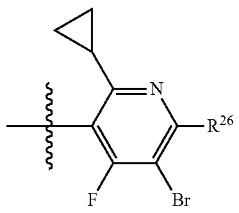
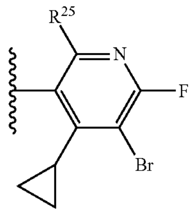
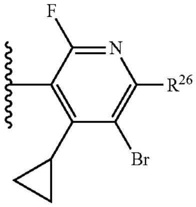
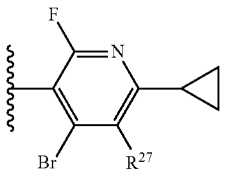
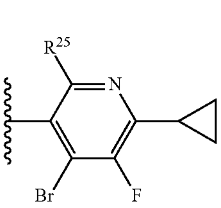
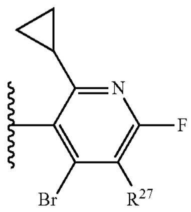
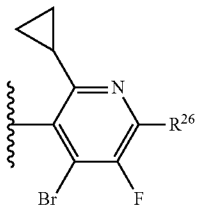
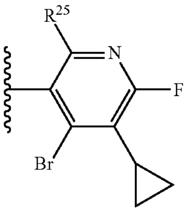

-continued
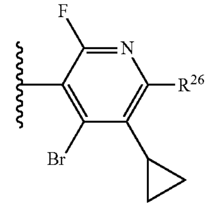
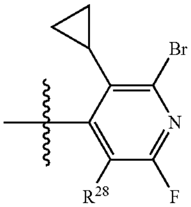
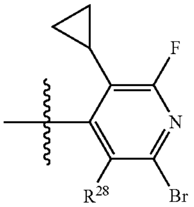
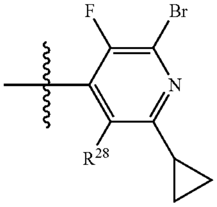
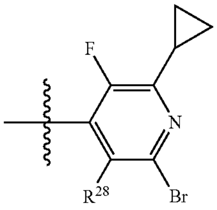
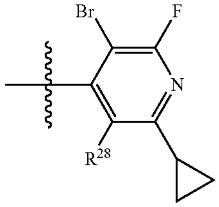
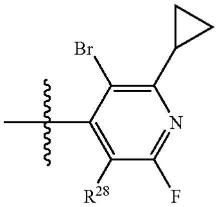
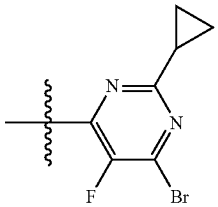
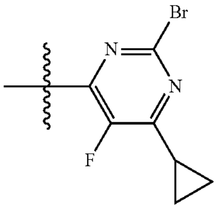
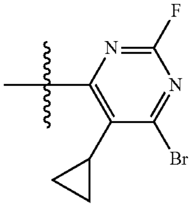
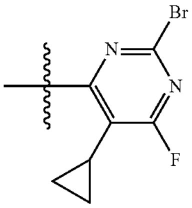
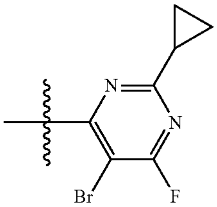
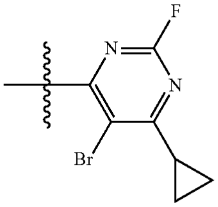
In one embodiment, B4 is selected from:
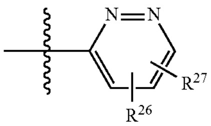
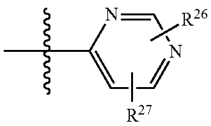
-continued
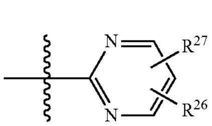
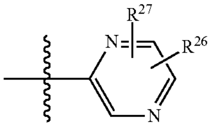
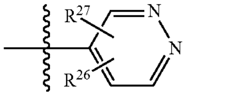
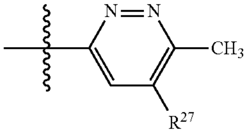
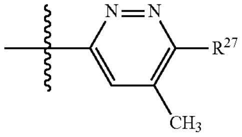
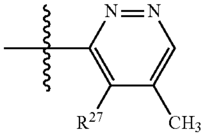
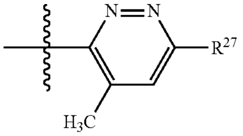
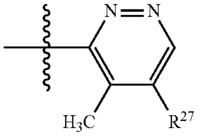
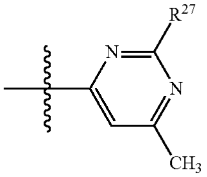
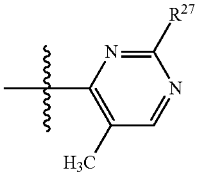
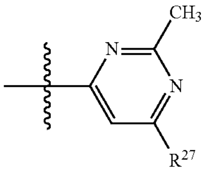
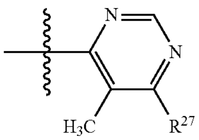
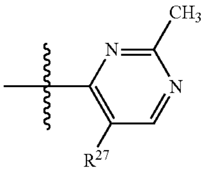
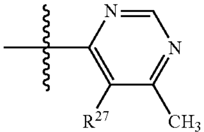
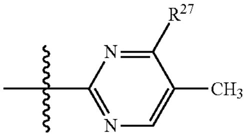
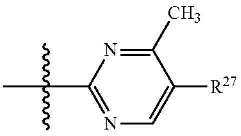
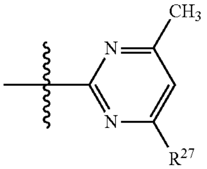
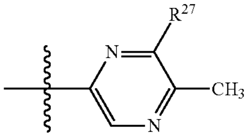
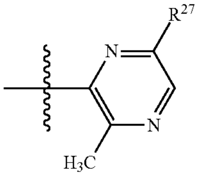
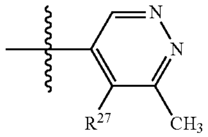
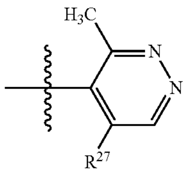
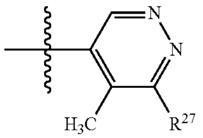

-continued
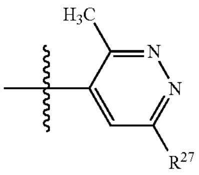
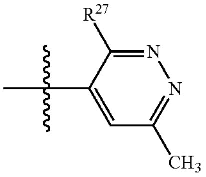
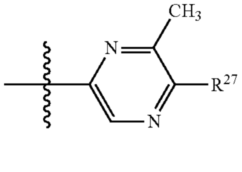
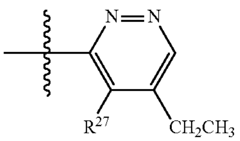
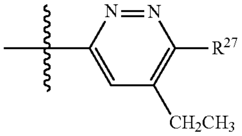
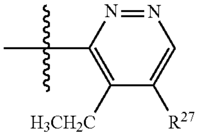
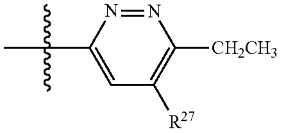
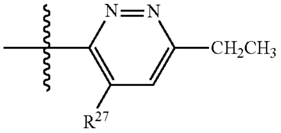
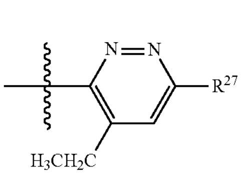
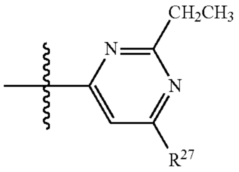
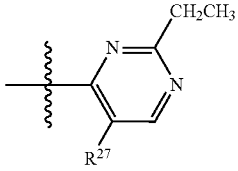
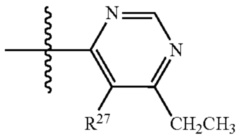
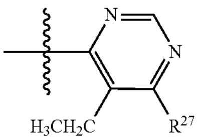
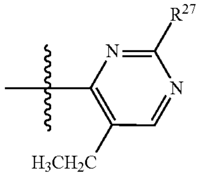
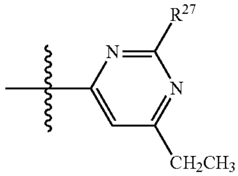
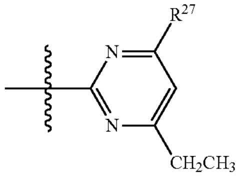
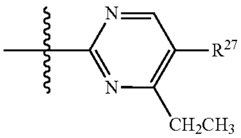
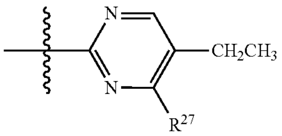
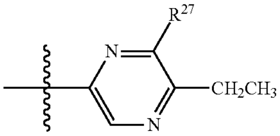
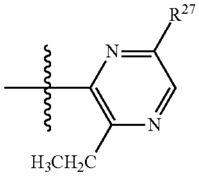
-continued
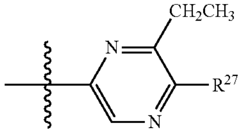
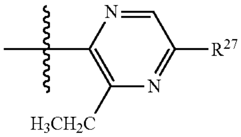
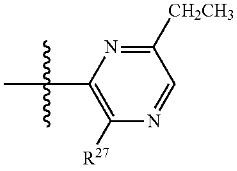
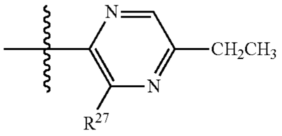
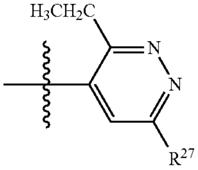
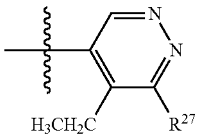
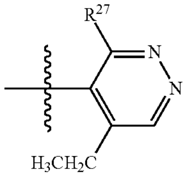
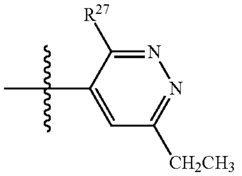
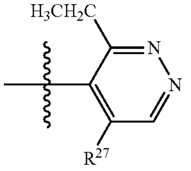
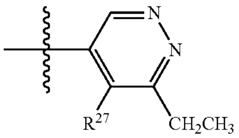
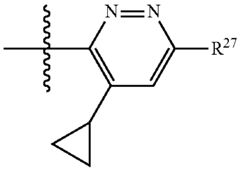
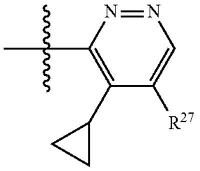
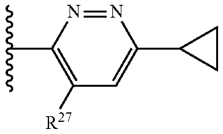
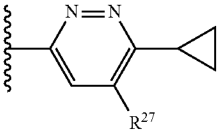
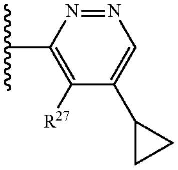
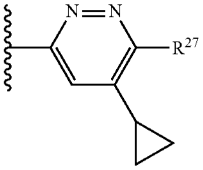
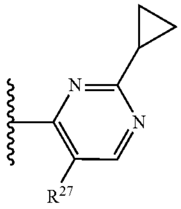
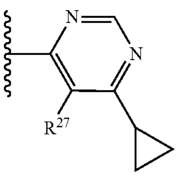

-continued
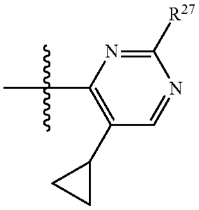
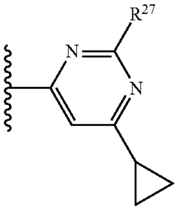
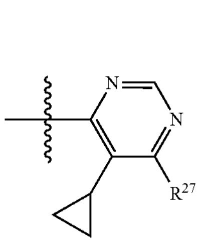
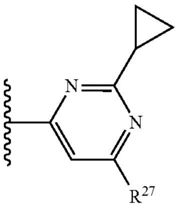
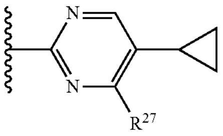
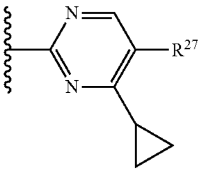
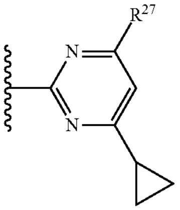
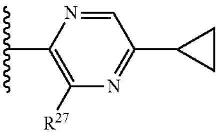
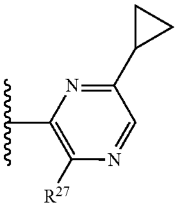
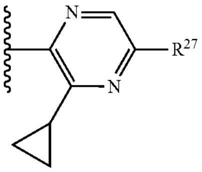
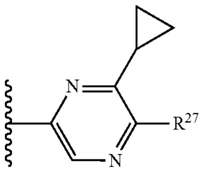
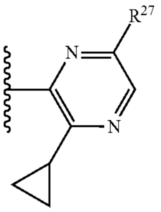
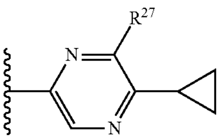
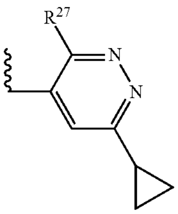
-continued
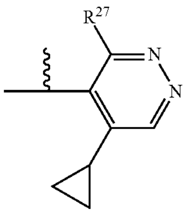
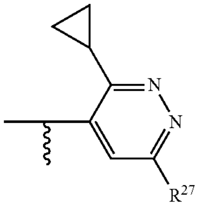
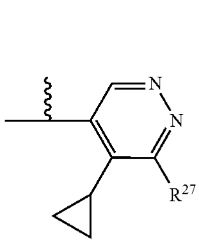
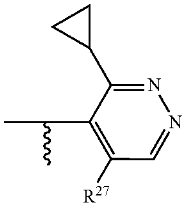
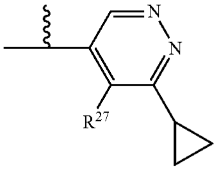
In one embodiment, B4 is selected from:
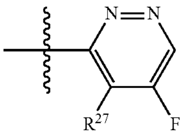
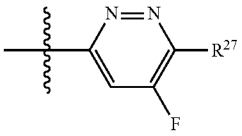
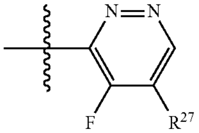
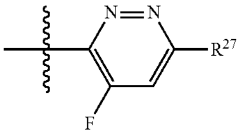
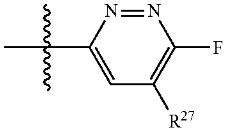
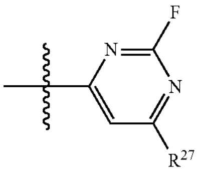
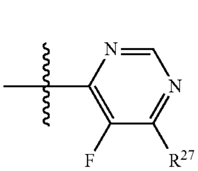
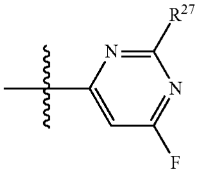
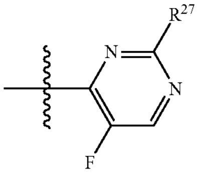
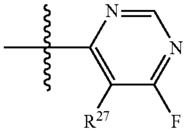
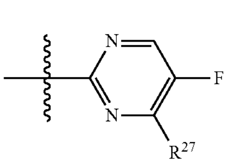
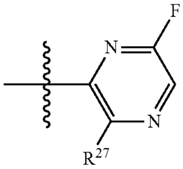

-continued
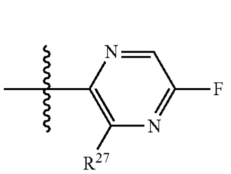
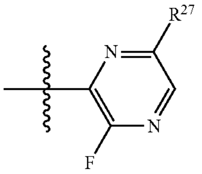
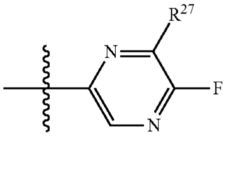
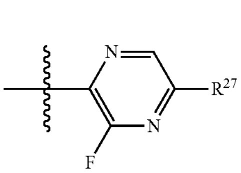
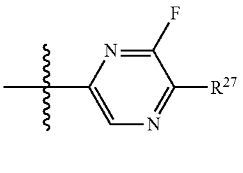
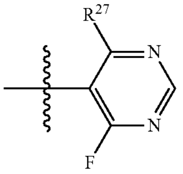
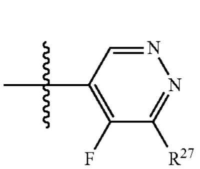
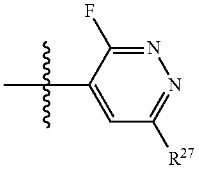
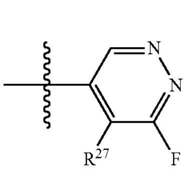
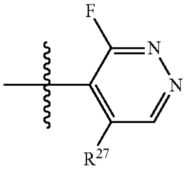
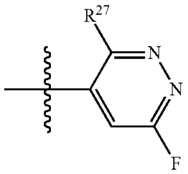
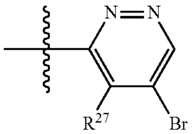
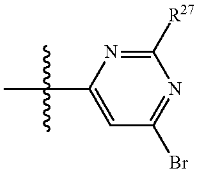
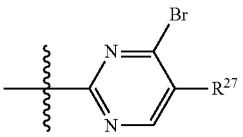
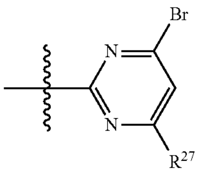
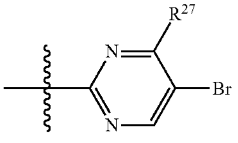
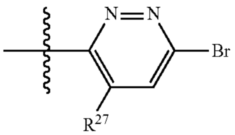
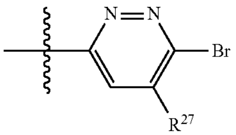
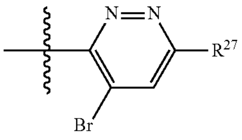
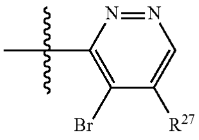
-continued
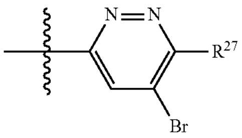
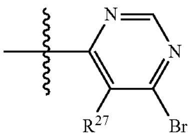
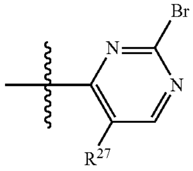
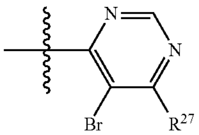
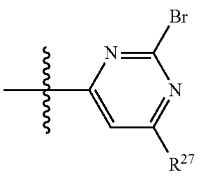
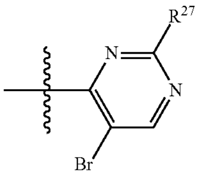
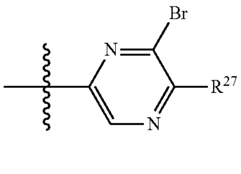
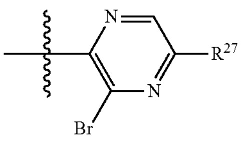
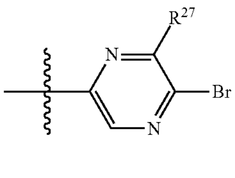
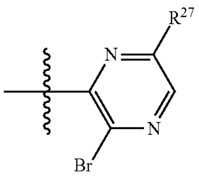
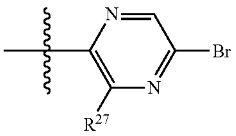
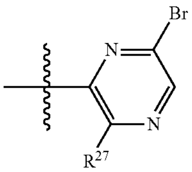
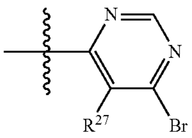
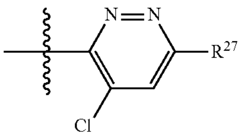
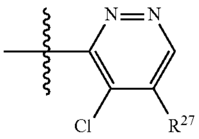
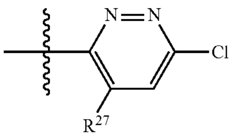
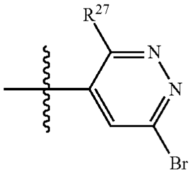
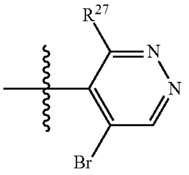
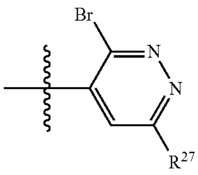
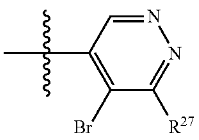

-continued
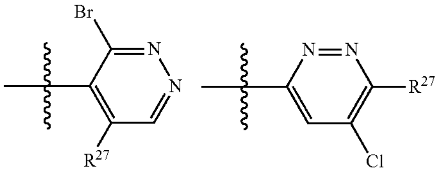
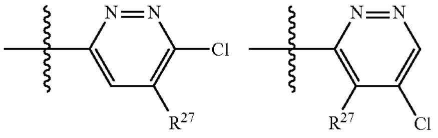
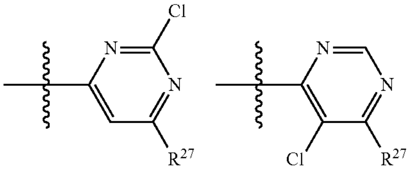
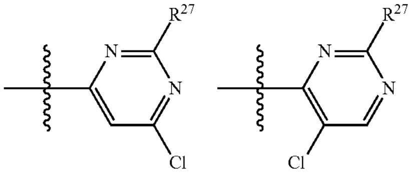
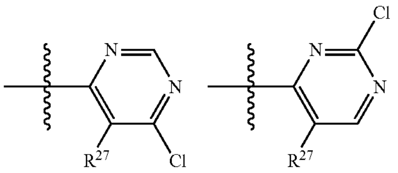
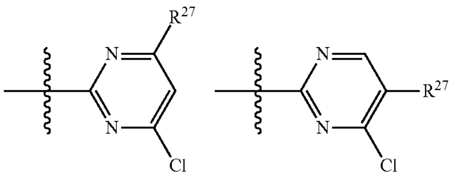
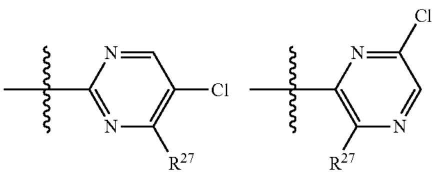
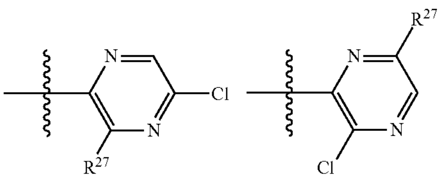
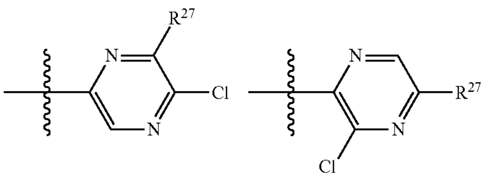
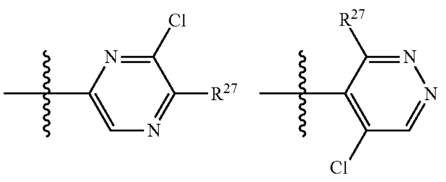
-continued
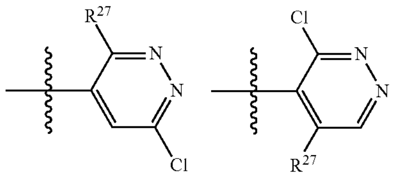
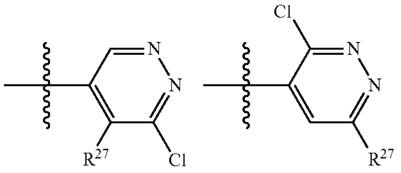
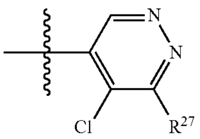
In one embodiment, B4 is selected from:
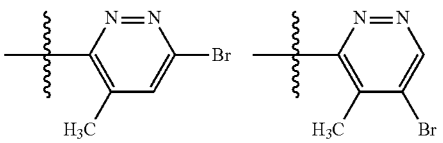
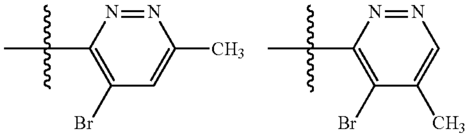
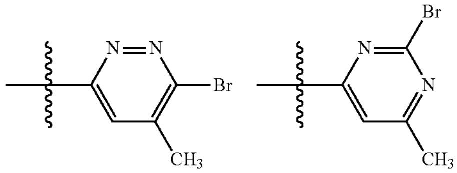
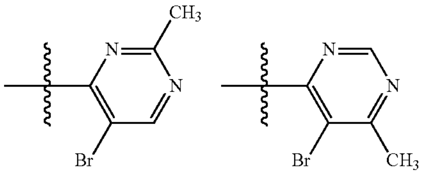
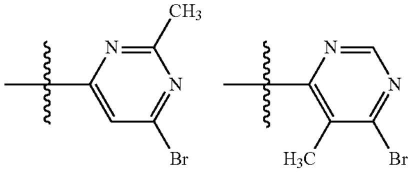
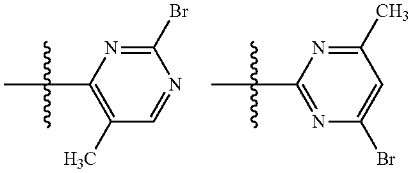
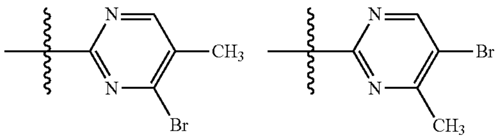

-continued
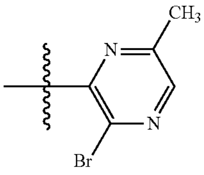
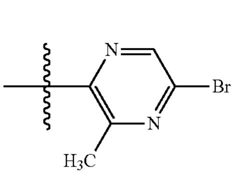
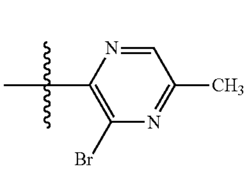
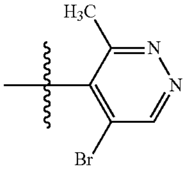
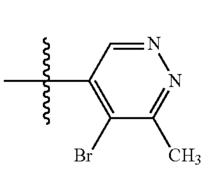
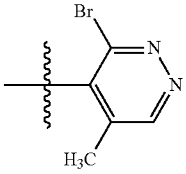
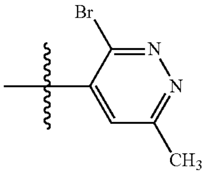
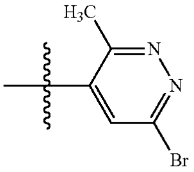
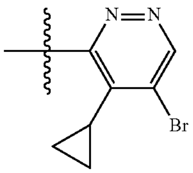
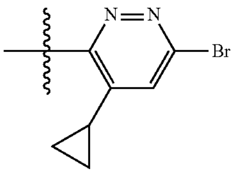
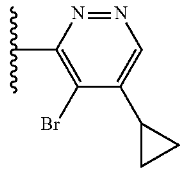
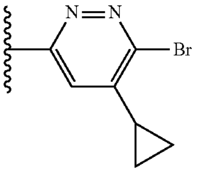
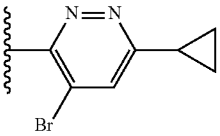
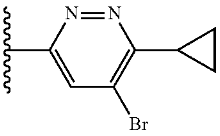
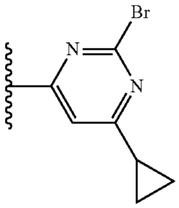
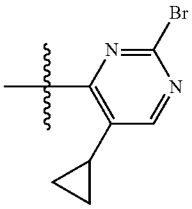
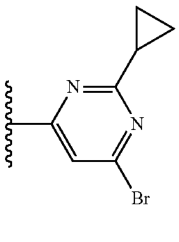
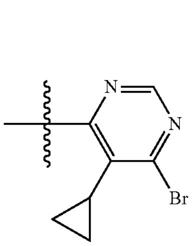
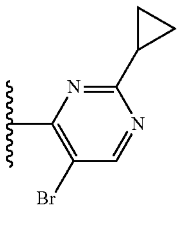
-continued
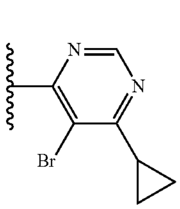
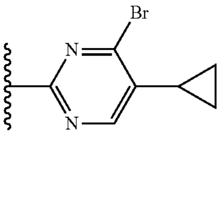
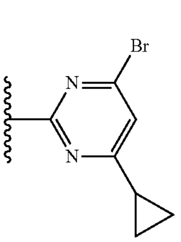
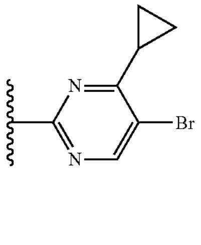
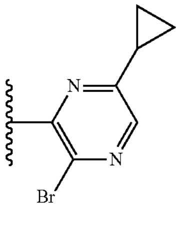
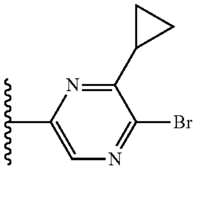
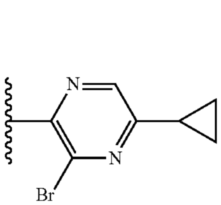
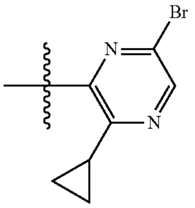
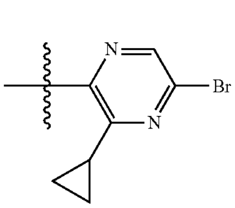
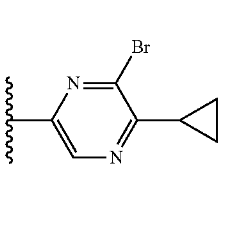
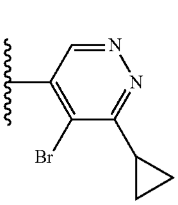
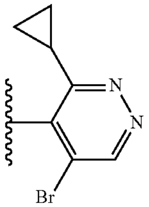
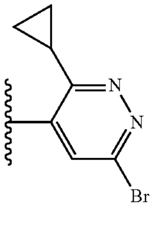
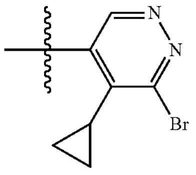
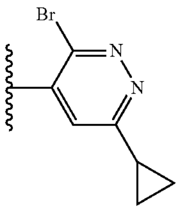
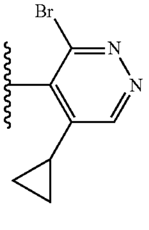

In one embodiment, B4 is selected from:
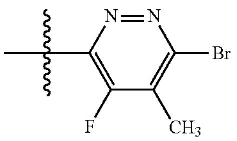
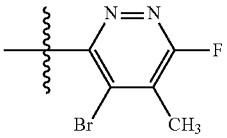
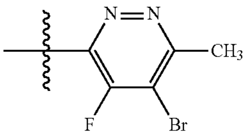
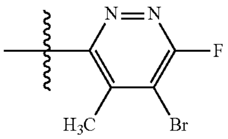
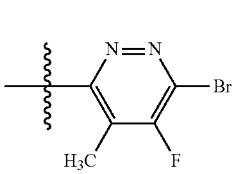
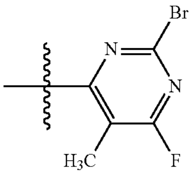
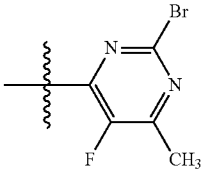
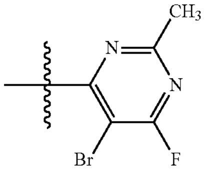
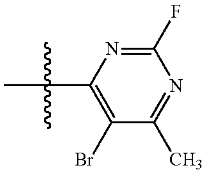
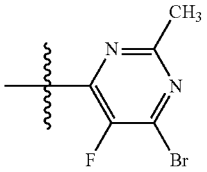
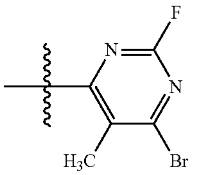
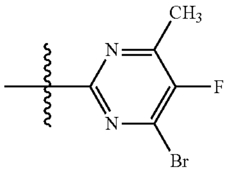
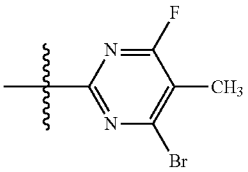
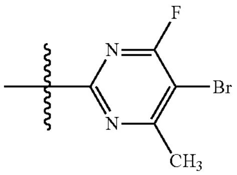
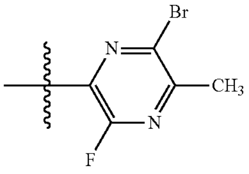
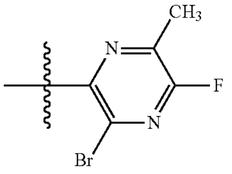
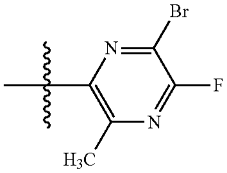
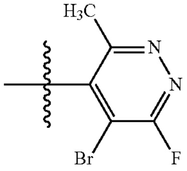
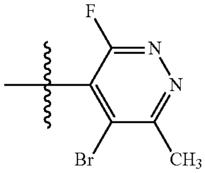
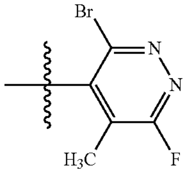
-continued
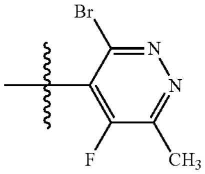
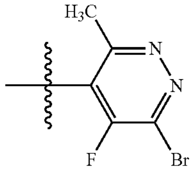
In one embodiment, B4 is selected from:
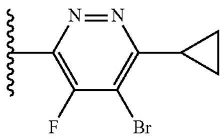
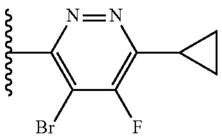
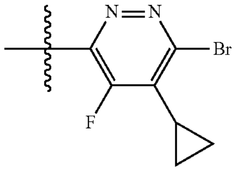
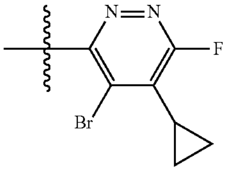
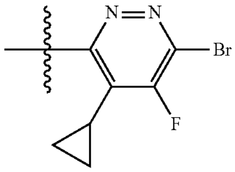
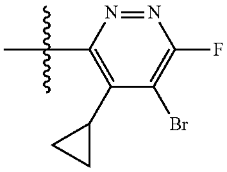
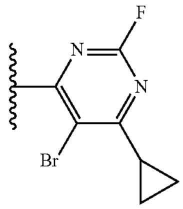
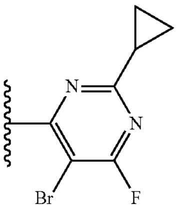
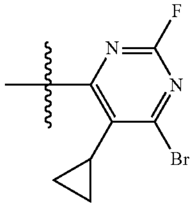
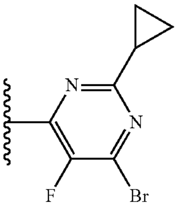
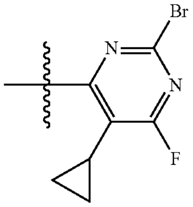
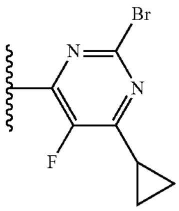
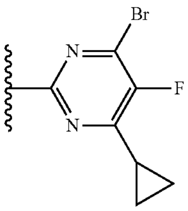
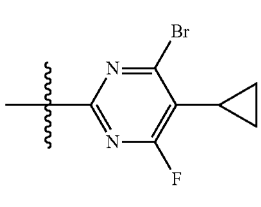
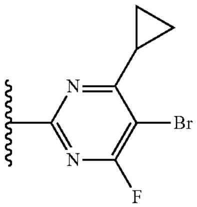

-continued
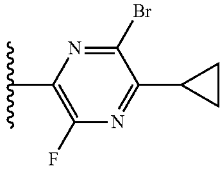
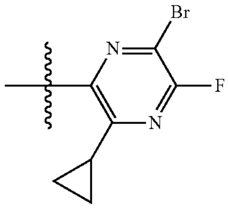
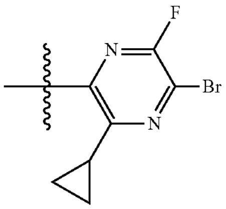
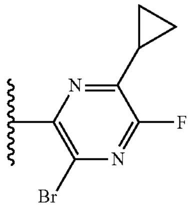
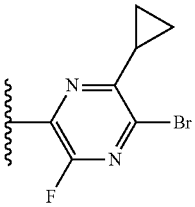
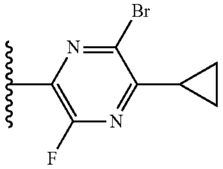
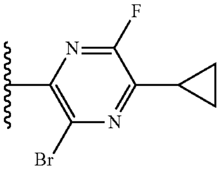
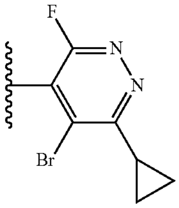
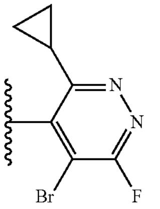
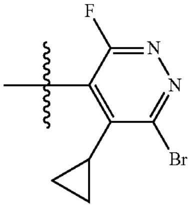
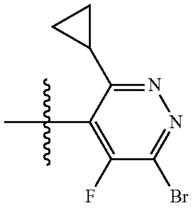
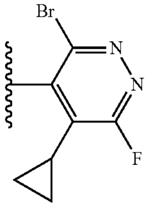
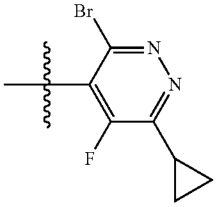
In one embodiment, B4 is selected from:
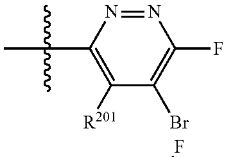
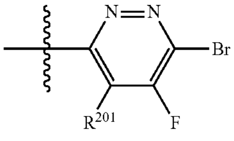
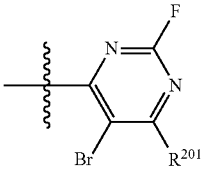
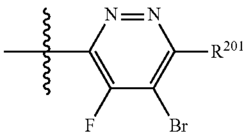
-continued
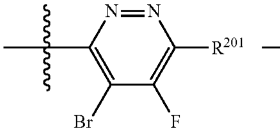
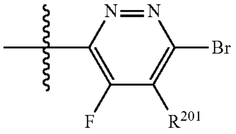
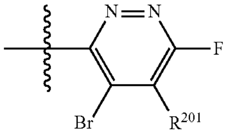
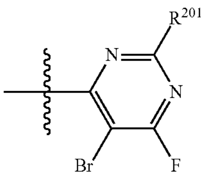
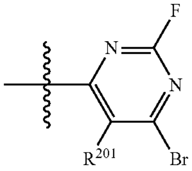
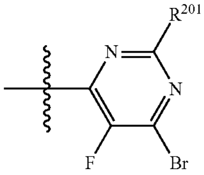
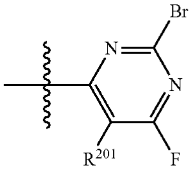
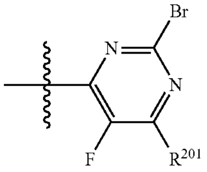
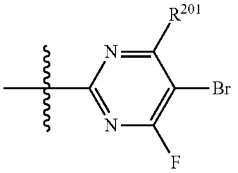
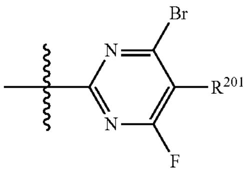
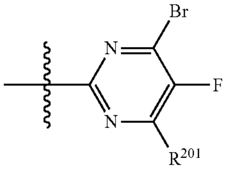
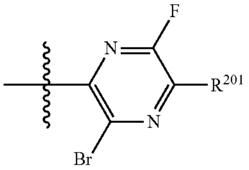
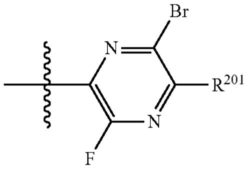
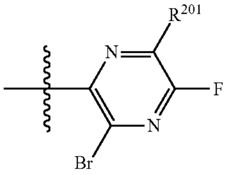
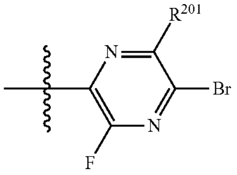
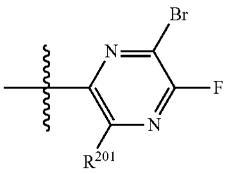
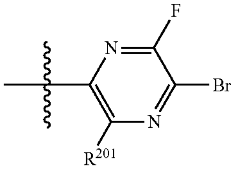
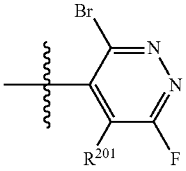
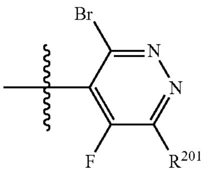
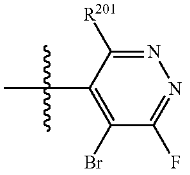

-continued
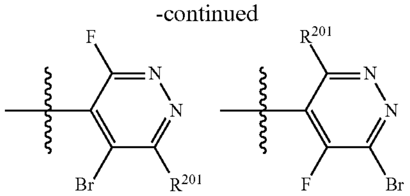
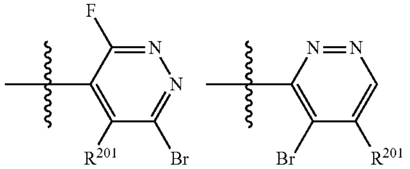
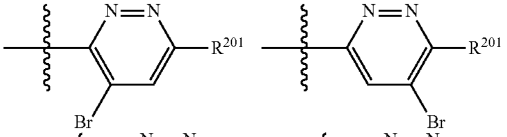
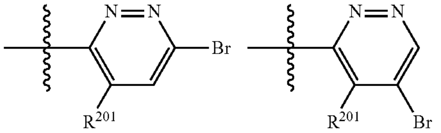
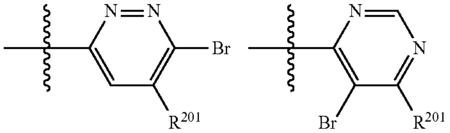
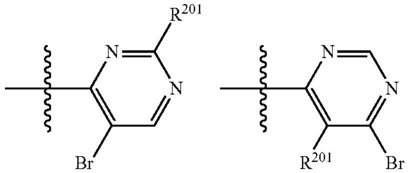
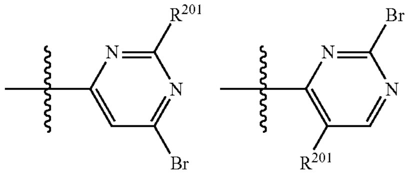
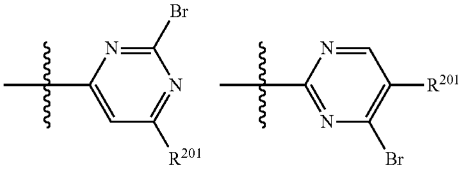
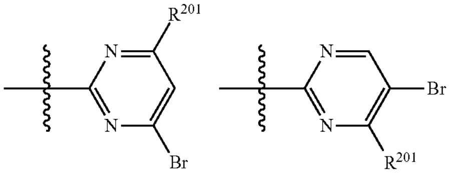
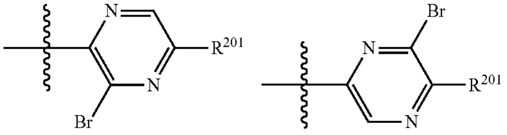
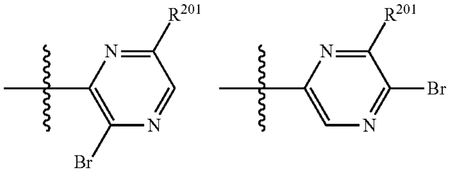
-continued
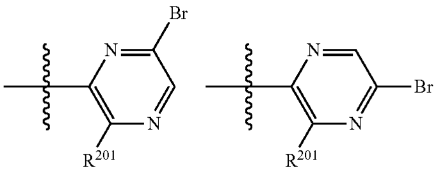
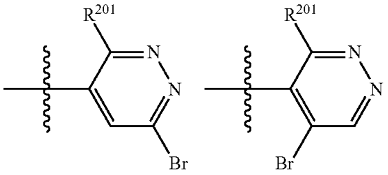
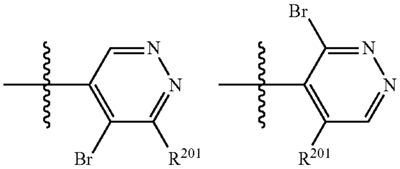
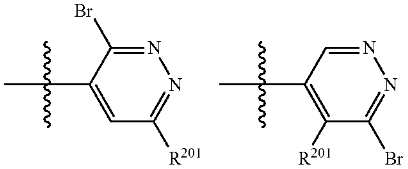
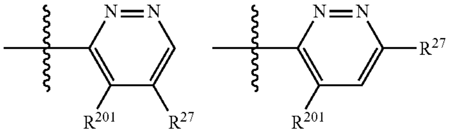
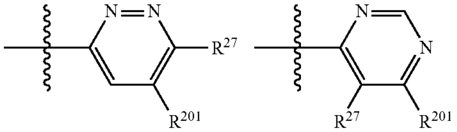
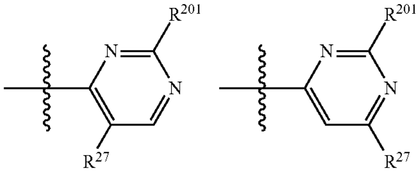
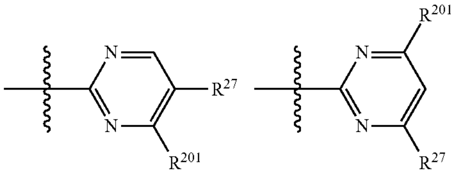
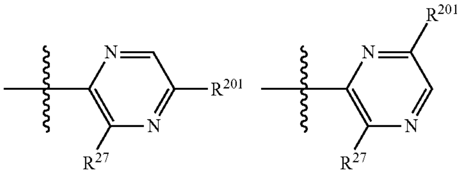
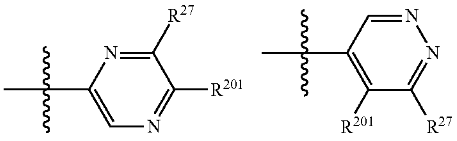

-continued
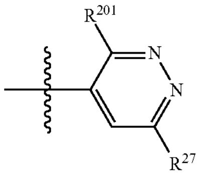
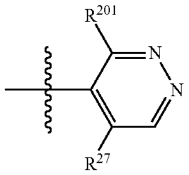
In one embodiment $R^{25}$, $R^{26}$, $R^{27}$, and $R^{28}$ are independently selected from hydrogen, halogen, and $C_1$-$C_6$alkyl.
In another embodiment, B4 is selected from:
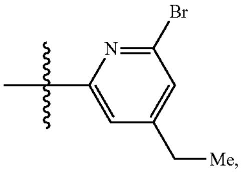
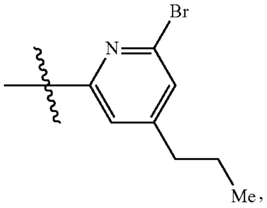
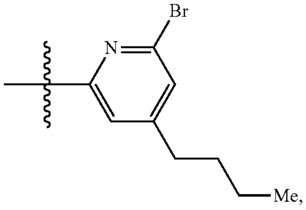
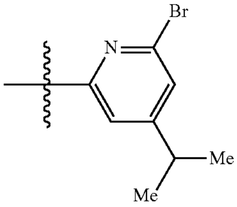
,
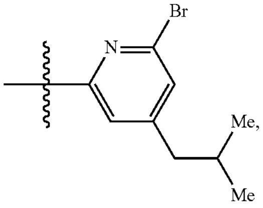
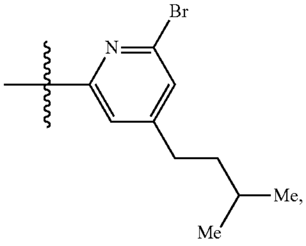
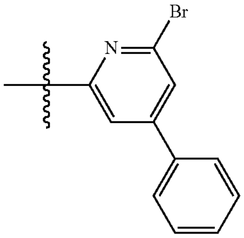
,
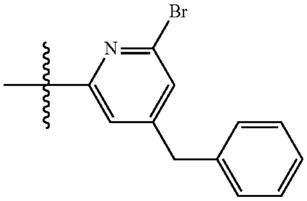
,
-continued
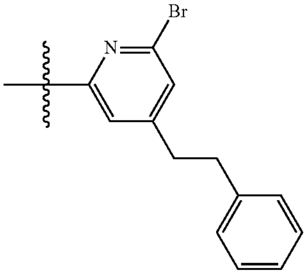
,
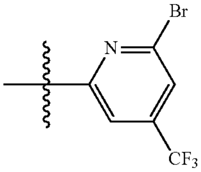
,
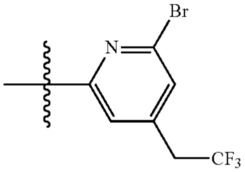
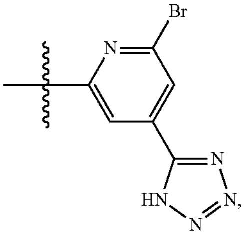
and
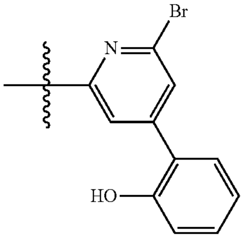
.
In another embodiment, B4 is selected from:
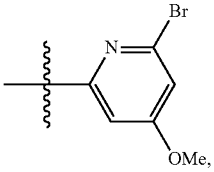
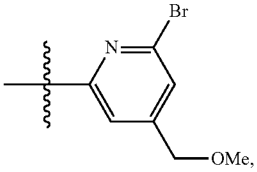
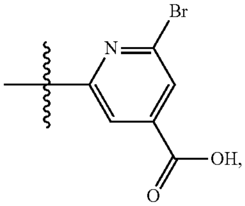
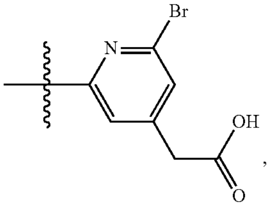
,
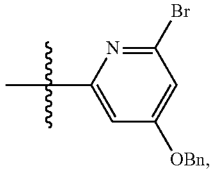
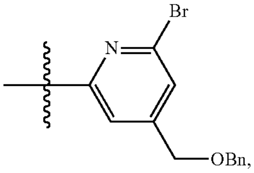

-continued
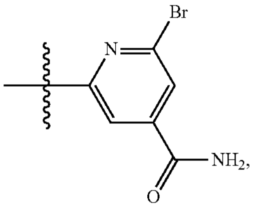
and
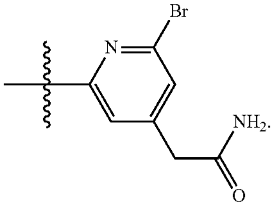
In another embodiment, B4 is selected from:
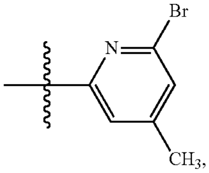
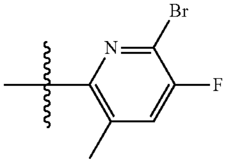
,
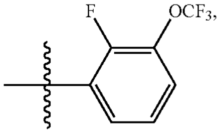
and
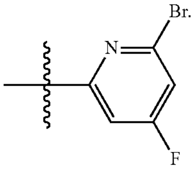
In another embodiment, B4 is selected from:
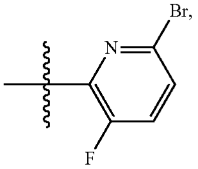
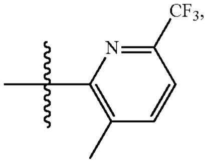
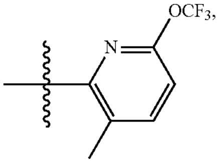
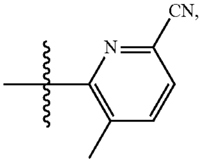
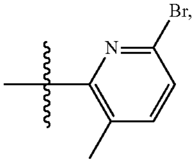
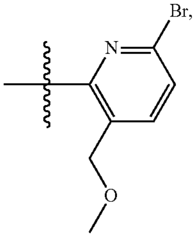
-continued
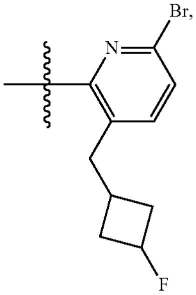
and
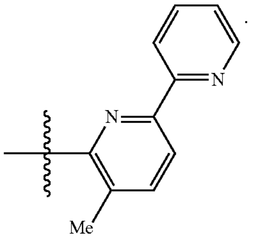
In another embodiment, B4 is selected from:
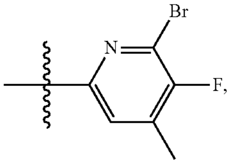
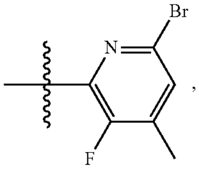
,
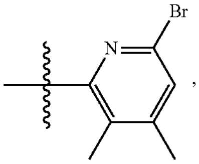
,
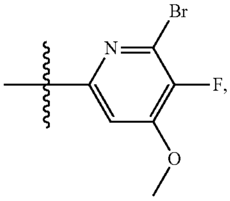
and
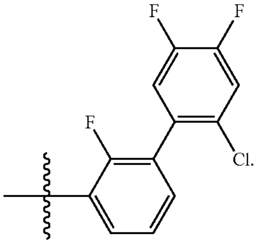
In another embodiment, B4 is selected from:
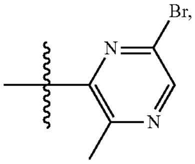
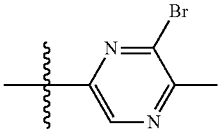
,
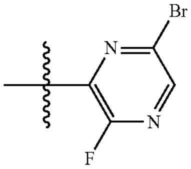
,
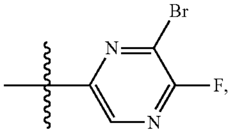
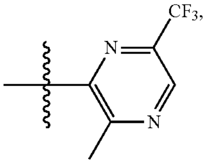
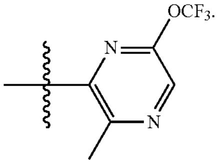

In an alternative embodiment, B4 is selected from:

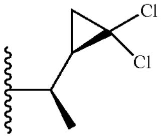, 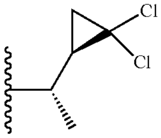, 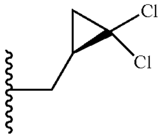, 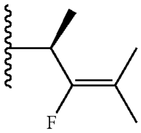, 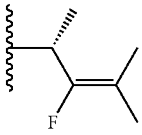, 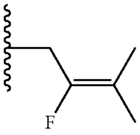, 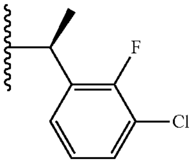, 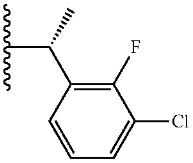, 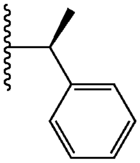, 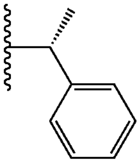, 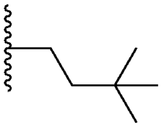, 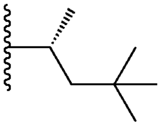, 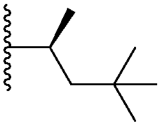, 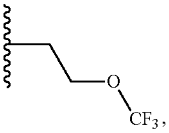 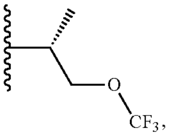 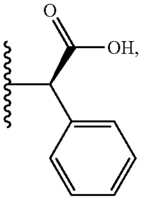 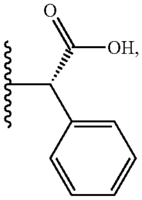 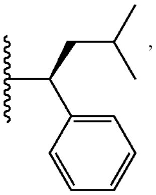, 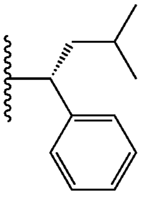, and 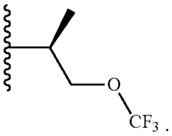.

In another alternative embodiment, B4 is selected from:

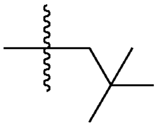, 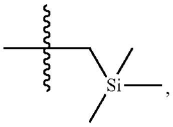, 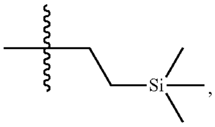,

-continued

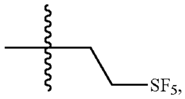 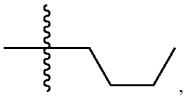, and

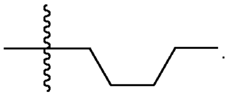.

In another alternative embodiment, B4 is -alkyl-Si(alkyl)$_3$ or -alkyl-$SF_5$.

In another alternative embodiment, B4 is a B ring substituted with oxo. In this embodiment if the B ring is a nitrogen containing heteroaryl group then the nitrogen may also be substituted as defined herein. For example:

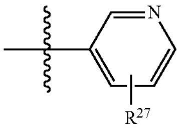

substituted with an oxo can be selected from the following compounds:

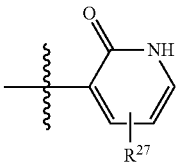 and 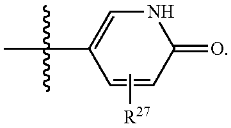.

And examples of

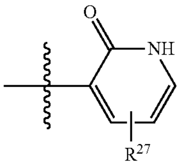

include:

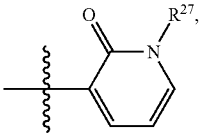 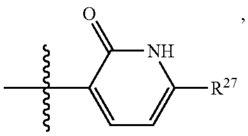, 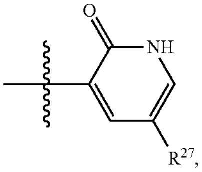 and 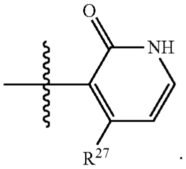.

In another alternative embodiment, B4 is selected from:

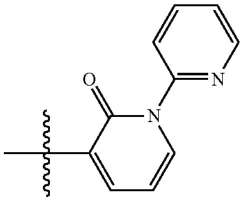

and

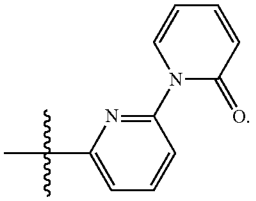

In another alternative embodiment, B4 is an alkyl group.

In another alternative embodiment, B4 is an alkenyl group.

In one embodiment B is selected from:

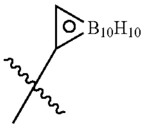

,

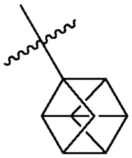

,

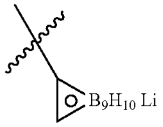

,

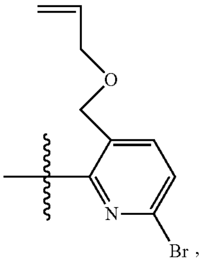

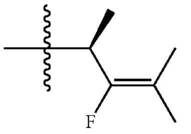

,

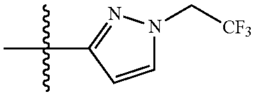

.

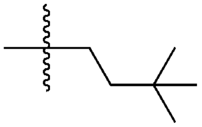

,

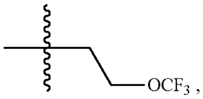

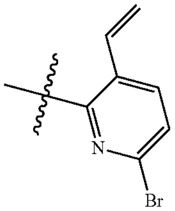

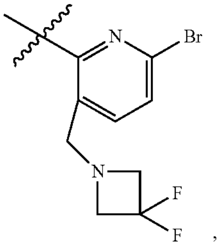

,

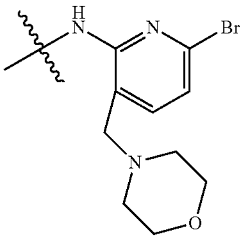

,

-continued

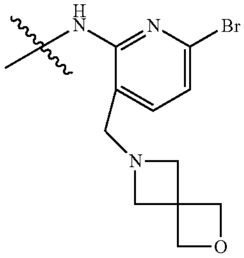

,

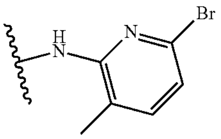

,

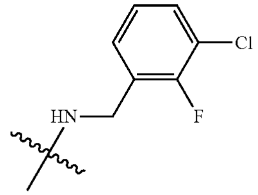

,

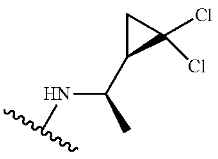

,

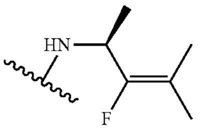

,

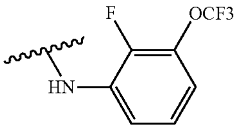

, and

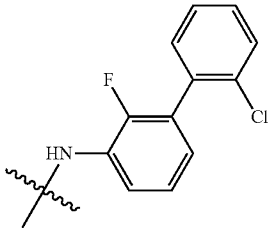

.

Additional Embodiments of $R^{32}$

To further illustrate the invention, various embodiments of Formula IA, IB, IC and ID are provided. These are presented by way of example to show some of the variations among presented compounds within the invention can be applied to any of the Formulas herein, and are not intended to limit the invention.

In one aspect, this disclosure includes compounds and salts of Formula IA:

(IA)

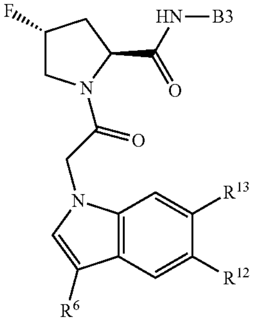

where $R^6$, $R^{13}$, and B3 may carry any of the definitions set forth herein for this variable.

In another aspect, this disclosure includes compounds and salts of Formula IB, IC, and ID.

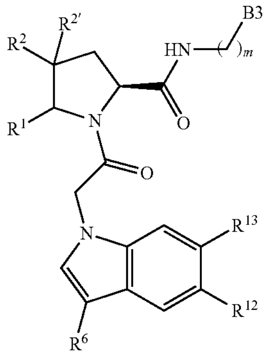

IB

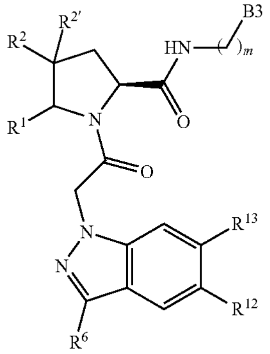

IC

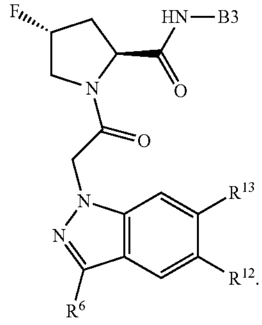

ID

In Formulas IA, IB, IC, and ID, the variables may include any of the definitions set forth herein that results in a stable compound. In certain embodiments, the following conditions apply for Formula IB and IC.

In some embodiments, structures are provided including Formulas IB and IC, wherein m=0, $R^1$ is H, $R^2$ is F, $R^6$ is alkanoyl, $R^{12}$ is $R^{32}$, $R^{32}$ is —$O(CH_2)_{1-4}P(O)R^{23b}R^{23b}$, $R^{13}$ is H.

In some embodiments, structures are provided including Formulas IB and IC, wherein m=0, $R^1$ and $R^2$ are joined to form a 3 membered ring, $R^6$ is alkanoyl, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=0, $R^1$ is H, $R^2$ is F, $R^6$ is amide, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=0, $R^1$ and $R^2$ are joined to form a 3 membered ring, $R^6$ is amide, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=0, $R^1$ is H, $R^2$ is F, $R^6$ is alkanoyl, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=0, $R^1$ and $R^2$ are joined to form a 3 membered ring, $R^6$ is alkanoyl, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=0, $R^1$ is H, $R^2$ is F, $R^6$ is amide, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=0, $R^1$ and $R^2$ are joined to form a 3 membered ring, $R^6$ is amide, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=0, $R^1$ is H, $R^2$ is F, $R^6$ is alkanoyl, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=0, $R^1$ and $R^2$ are joined to form a 3 membered ring, $R^6$ is alkanoyl, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=0, $R^1$ is H, $R^2$ is F, $R^6$ is amide, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=0, $R^1$ and $R^2$ are joined to form a 3 membered ring, $R^6$ is amide, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=0, $R^1$ is H, $R^2$ is F, $R^6$ is alkanoyl, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=0, $R^1$ and $R^2$ are joined to form a 3 membered ring, $R^6$ is alkanoyl, $R^{12}$ is H, $R^{13}$ is $R^{32}$, $R^{32}$ is $(CH_2)_{1-4}P(O)R^{23b}R^{23b}$.

In some embodiments, structures are provided including Formulas IB and IC, wherein m=0, $R^1$ is H, $R^2$ is F, $R^6$ is amide, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=0, $R^1$ and $R^2$ are joined to form a 3 membered ring, $R^6$ is amide, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=1, $R^1$ is H, $R^2$ is F, $R^6$ is alkanoyl, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=1, $R^1$ and $R^2$ are joined to form a 3 membered ring, $R^6$ is alkanoyl, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=1, $R^1$ is H, $R^2$ is F, $R^6$ is amide, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=1, $R^1$ and $R^2$ are joined to form a 3 membered ring, $R^6$ is amide, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=1, $R^1$ is H, $R^2$ is F, $R^6$ is alkanoyl, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=1, $R^1$ and $R^2$ are joined to form a 3 membered ring, $R^6$ is alkanoyl, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=1, $R^1$ is H, $R^2$ is F, $R^6$ is amide, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=1, $R^1$ and $R^2$ are joined to form a 3 membered ring, $R^6$ is amide, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=1, $R^1$ is H, $R^2$ is F, $R^6$ is alkanoyl, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=1, $R^1$ and $R^2$ are joined to form a 3 membered ring, $R^6$ is alkanoyl, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=1, $R^1$ is H, $R^2$ is F, $R^6$ is amide, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=1, $R^1$ and $R^2$ are joined to form a 3 membered ring, $R^6$ is amide, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=1, $R^1$ is H, $R^2$ is F, $R^6$ is alkanoyl, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=1, $R^1$ and $R^2$ are joined to form a 3 membered ring, $R^6$ is alkanoyl, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=1, $R^1$ is H, $R^2$ is F, $R^6$ is amide, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=1, $R^1$ and $R^2$ are joined to form a 3 membered ring, $R^6$ is amide, $R^{12}$ is H, $R^{13}$ is $R^{32}$, $R^{32}$ is $O(CH_2)_{1-4}P(O)R^{23b}R^{23b}$.

In the above embodiments, structures are provided including Formulas IB and IC, wherein;

$R^{23b}$ is independently selected at each occurrence from hydroxyl, $C_1$-$C_6$alkoxy, $C_1$-$C_6$alkyl, ($C_3$-$C_7$cycloalkyl)$C_0$-$C_4$alkyl, (phenyl)$C_0$-$C_4$alkyl, —$O(CH_2)_{2-4}O(CH_2)_{8-18}$, —$OC(R^{23c})_2OC(O)OR^{23d}$, —$OC(R^{23c})_2OC(O)R^{23d}$, an N-linked amino acid or an N-linked amino ester, and each R23b can be optionally substituted;

$R^{23c}$ is independently selected at each occurrence from hydrogen, $C_1$-$C_8$alkyl, $C_2$-$C_8$alkenyl, $C_2$-$C_8$alkynyl, (aryl)$C_0$-$C_4$alkyl, (aryl)$C_2$-$C_8$alkenyl- or (aryl)$C_2$-$C_8$alkynyl; or two $R^{23c}$ groups can be taken together with the carbon that they are bonded to form a 3-6 membered heterocycloalkyl having 1, 2, or 3 heteroatoms independently selected from N, O, and S, or a 3-6 membered carbocyclic ring, and each $R^{23c}$ can be optionally substituted;

$R^{23d}$ is independently selected at each occurrence from $C_1$-$C_8$alkyl, $C_2$-$C_8$alkenyl, $C_2$-$C_8$alkynyl, (aryl)$C_0$-$C_4$alkyl, (aryl)$C_2$-$C_8$alkenyl or (aryl)$C_2$-$C_8$alkynyl, and each $R^{23d}$ can be optionally substituted.

In an alternative embodiment, $R^{32}$ is selected from

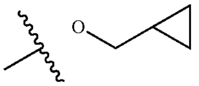
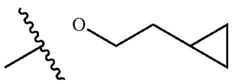
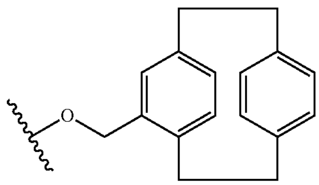

-continued

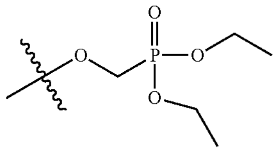
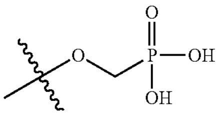
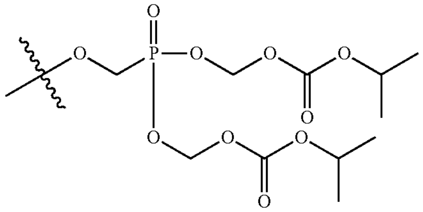
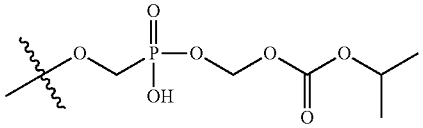
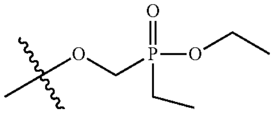
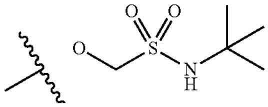
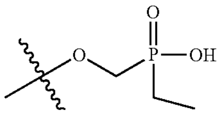
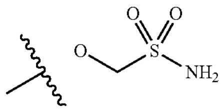
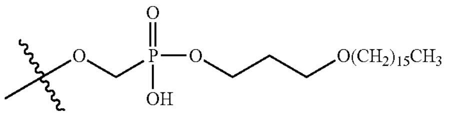
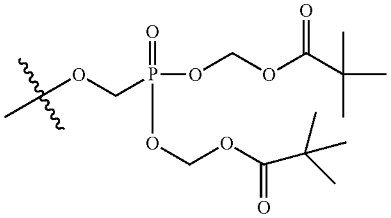
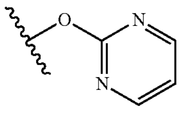
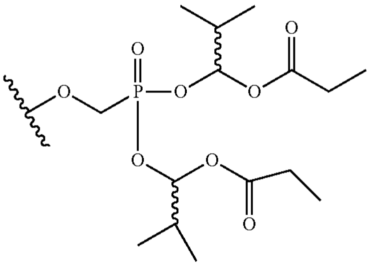
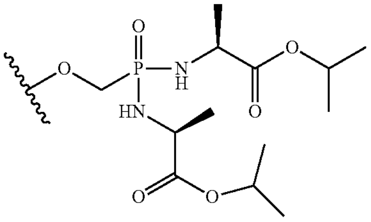
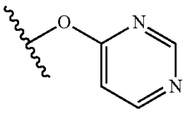
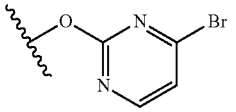
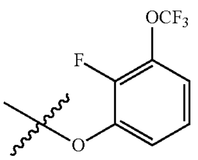

-continued
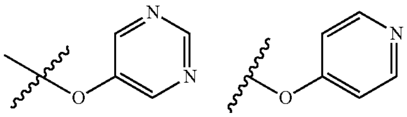
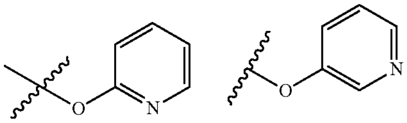
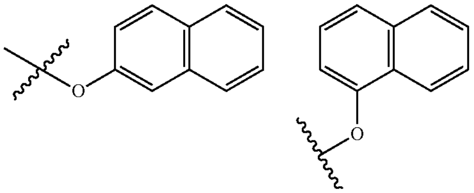
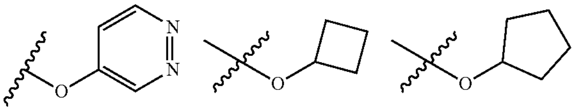
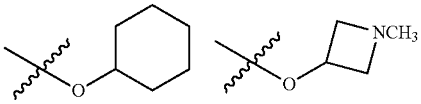
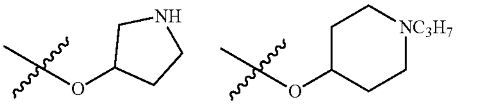
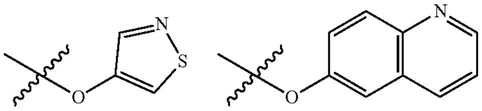
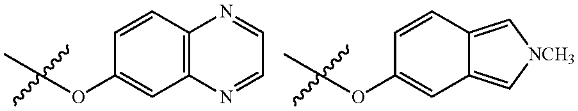
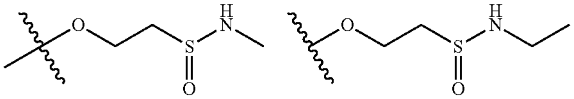
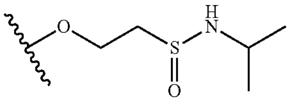
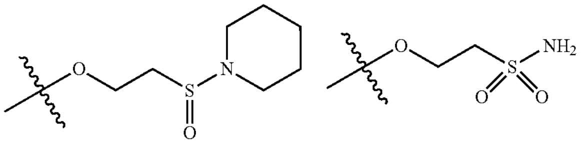
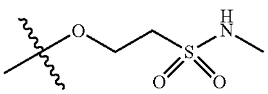
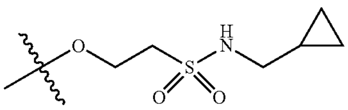
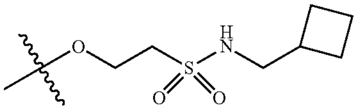
-continued
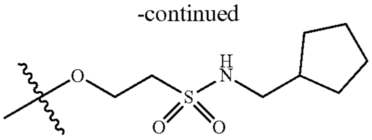
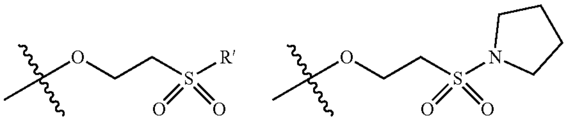
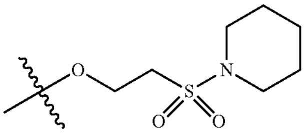
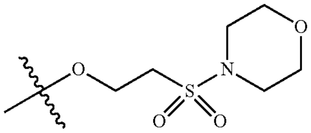
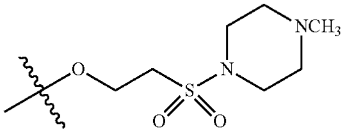
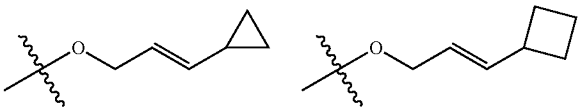
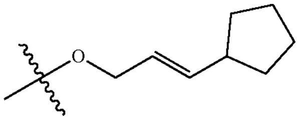
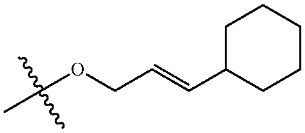
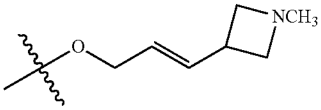
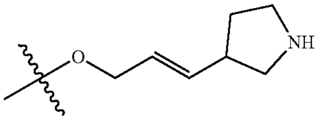
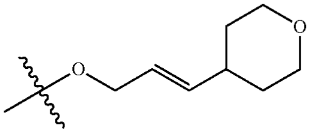
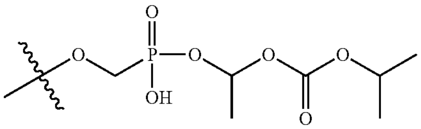
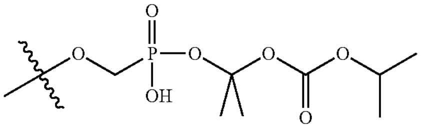
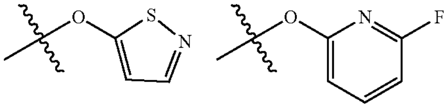

-continued

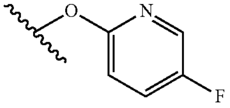
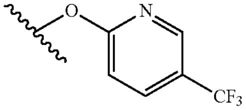
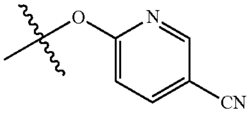
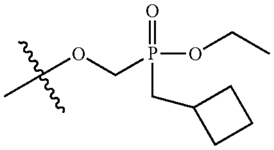
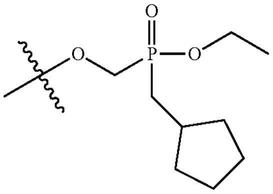
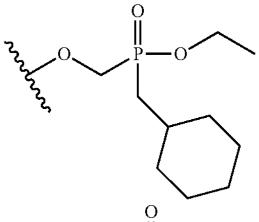
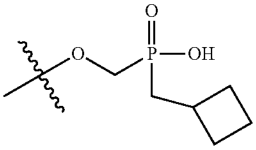
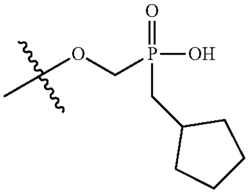
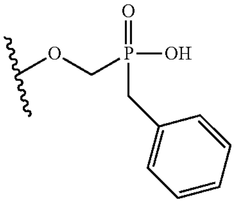
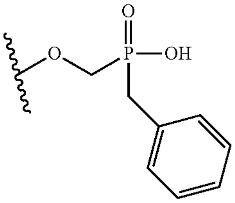
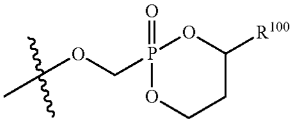
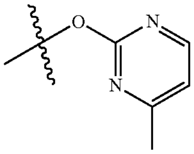
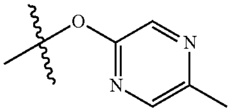
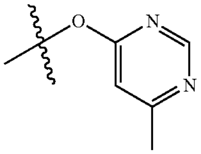
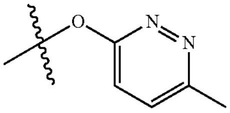
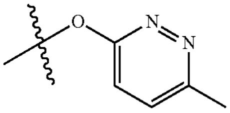

-continued

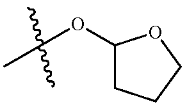
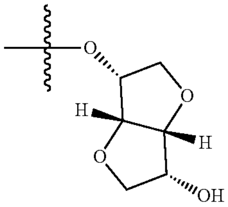
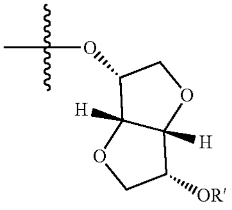
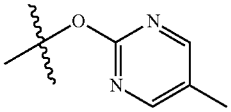
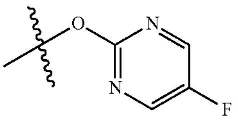
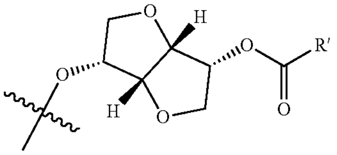
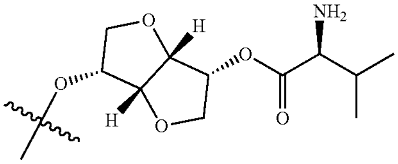
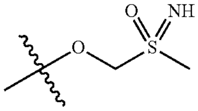
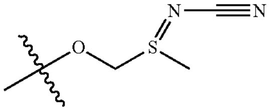
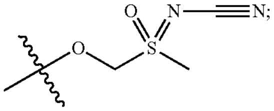

and $R^{100}$ is aryl, heteroaryl, alkyl, cycloalkyl, hetercyclic, alkenyl, or alkynyl.

Embodiments of $R^{30}$

Examples of $R^{301}$ are provided below. In the compounds of the present invention, $R^{301}$ is monovalently attached to the molecule. The divalent species below are presented to illustrate that the $R^{301}$ can be linked at either point and the other is capped for example with H, alkyl, halogen, haloalkyl, aryl, heteroaryl, and heterocycle, each of which may be optionally substituted as described herein. In one embodiment $R^{301}$ is selected from:

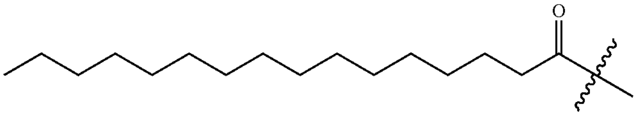
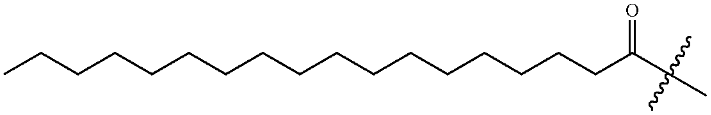
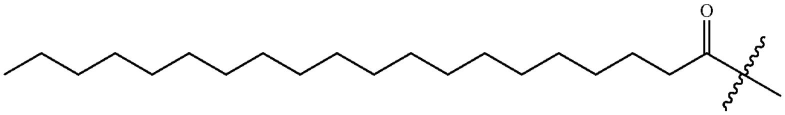

-continued
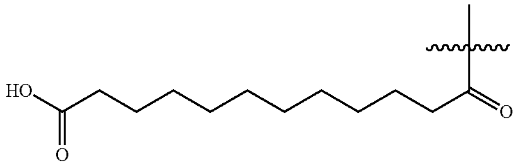
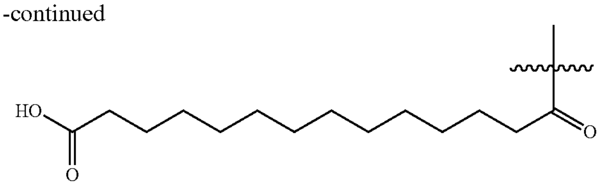
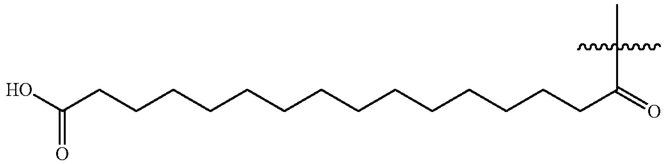
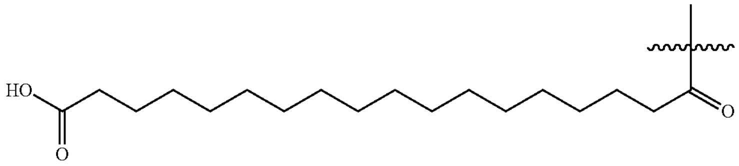
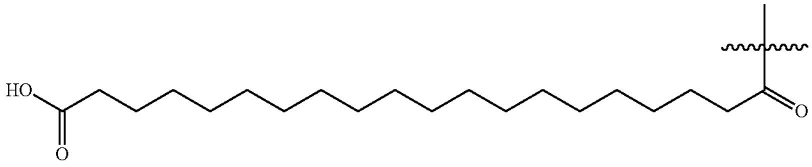
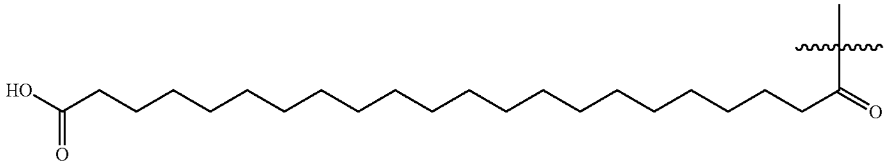
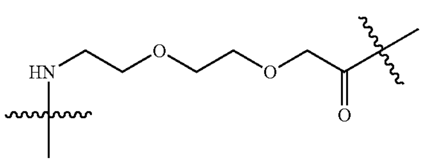
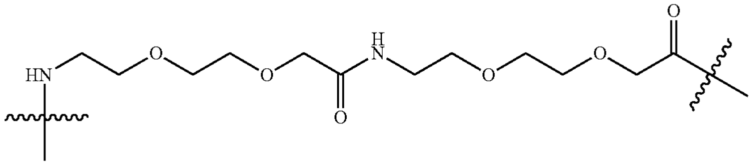
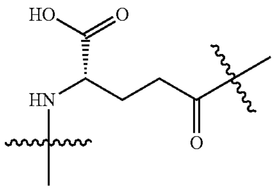
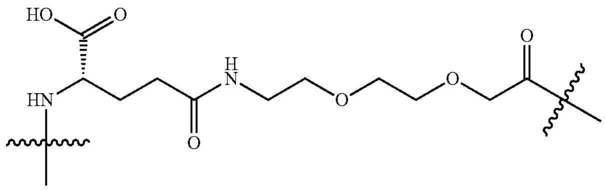
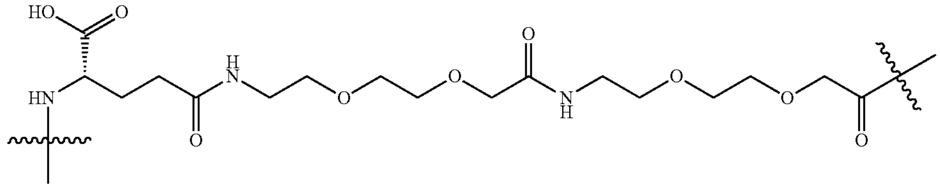
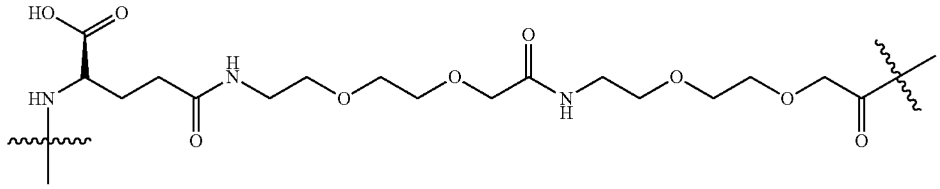
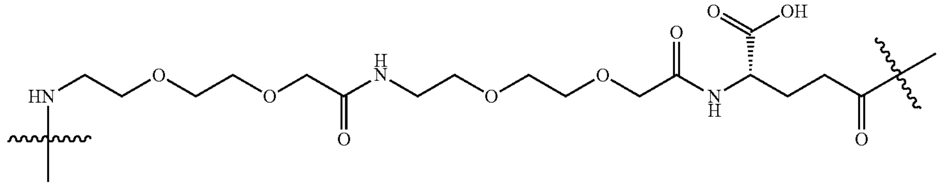

-continued
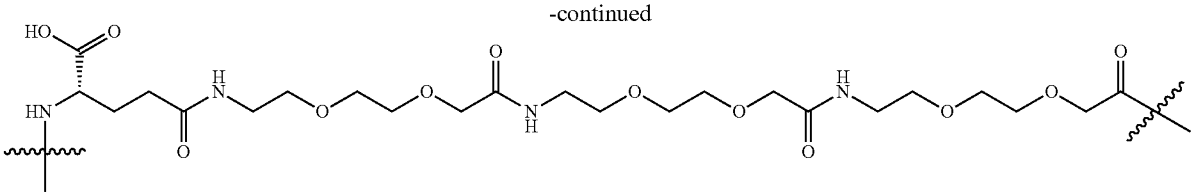
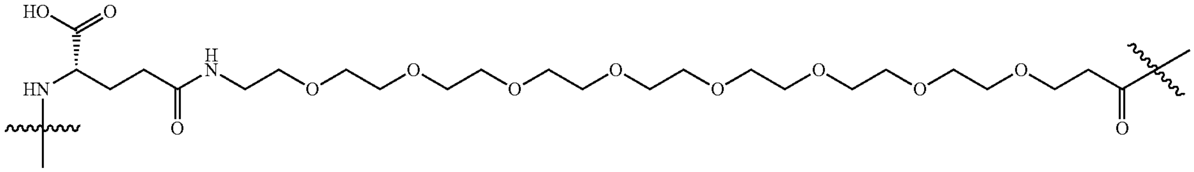
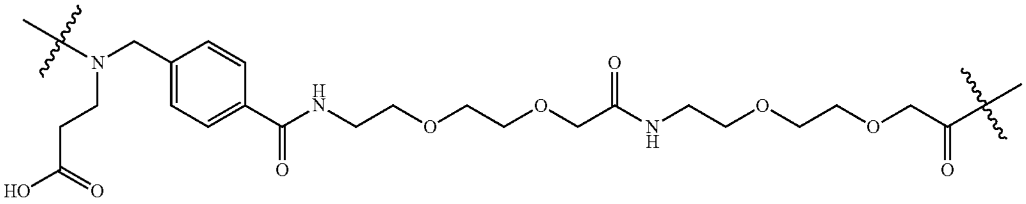
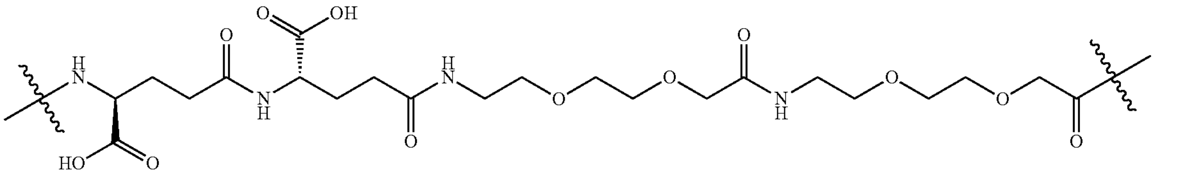
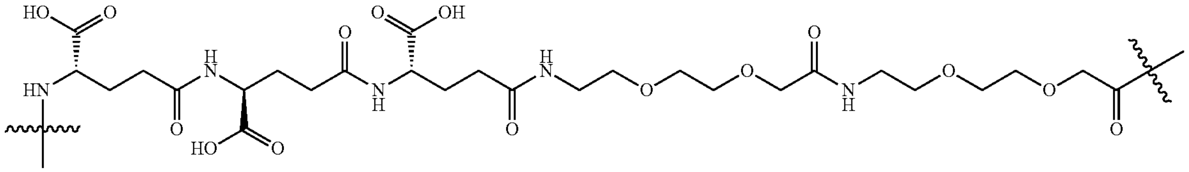
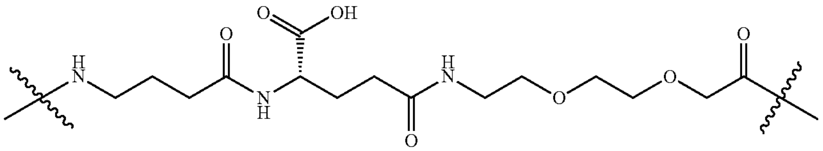
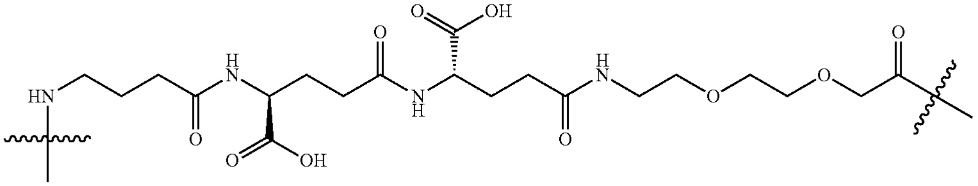
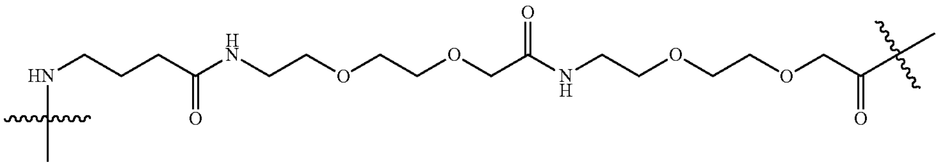
wherein if the moiety is shown as a divalent species, it can also be capped with a bioactive moiety or prodrug moiety.

In one embodiment $R^{301}$ is selected from:
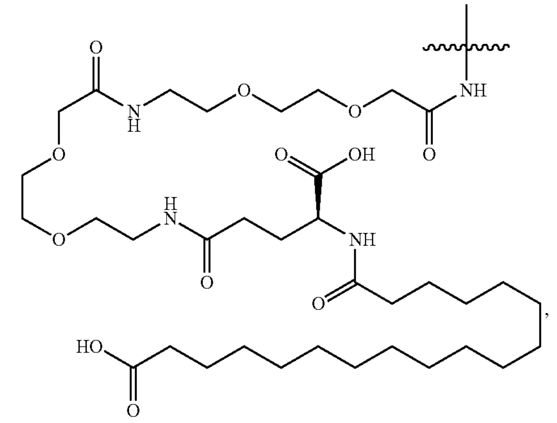
,
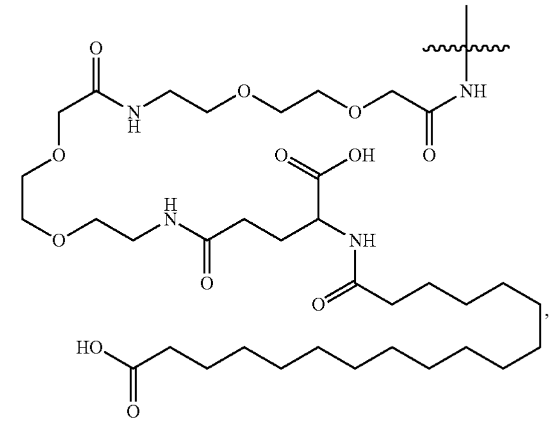
,
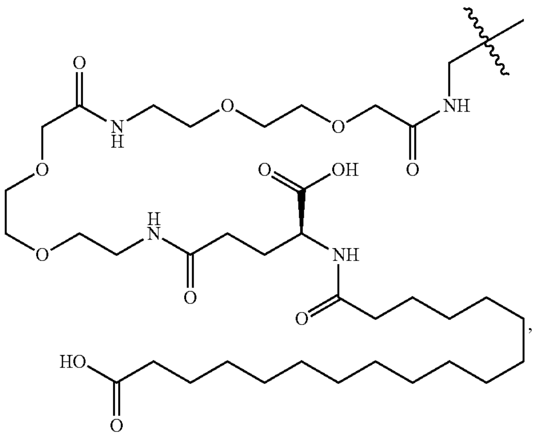
, and
-continued
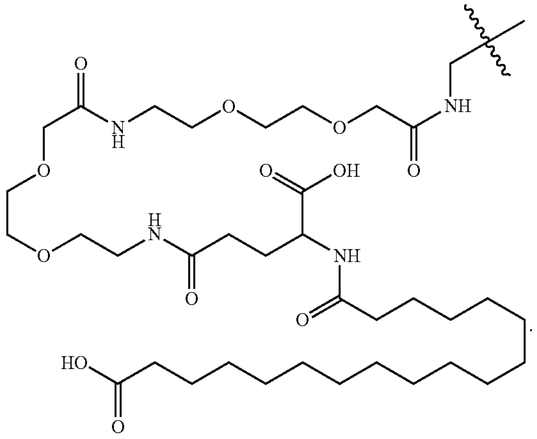
.
In one embodiment $R^{301}$ is
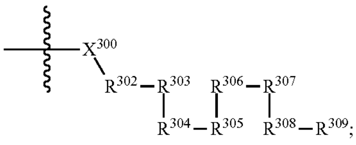
;
wherein $R^{302}$, $R^{303}$, $R^{304}$, $R^{305}$, $R^{306}$, $R^{307}$, and $R^{308}$ are selected from: bond, polyethylene glycol, a natural amino acid, an unnatural amino acid,
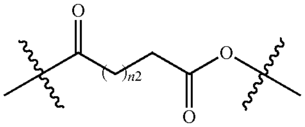
,
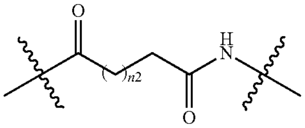
,
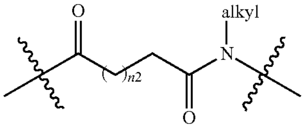
,
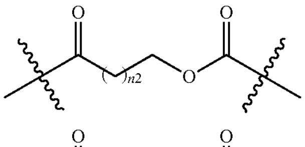
,
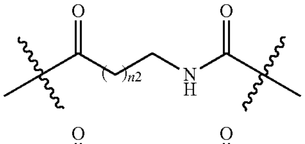
,
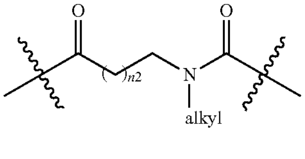
, -continued
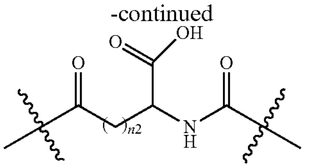,
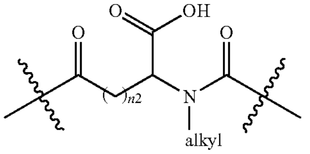,
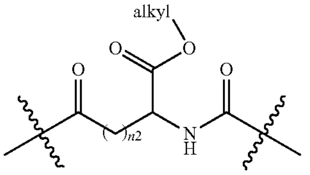,
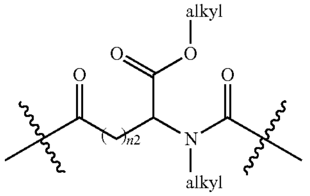,
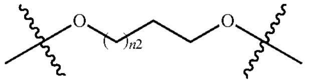,
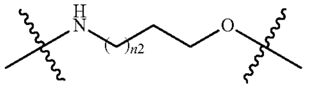,
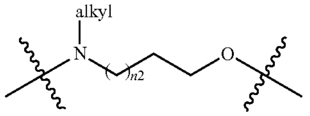,
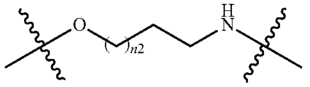,
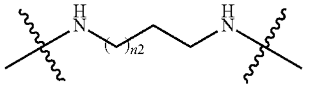,
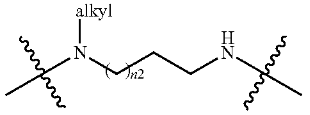,
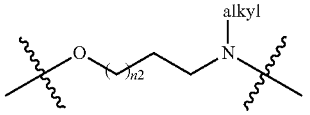,
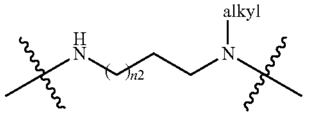,
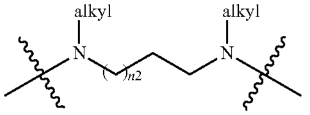,
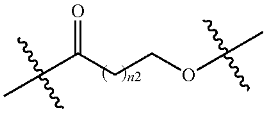, 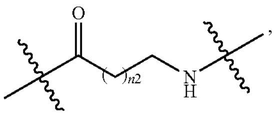,
-continued
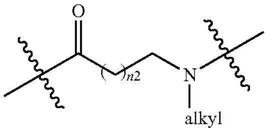, 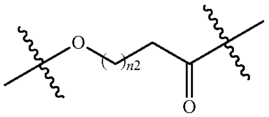,
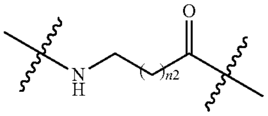, 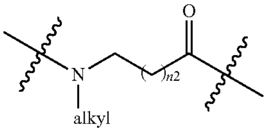,
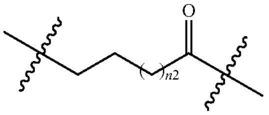, 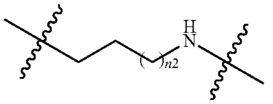,
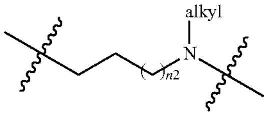, 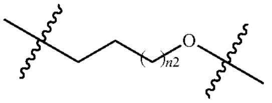,
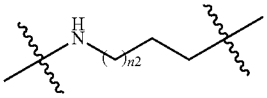, 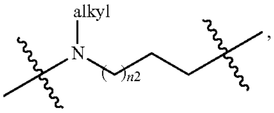,
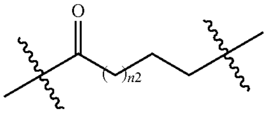, and
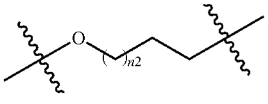.
$R^{309}$ is selected from: alkyl, hydrogen,
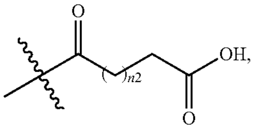 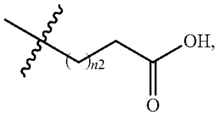
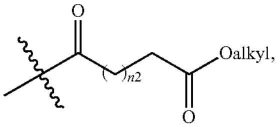 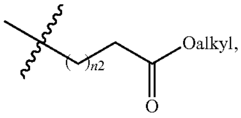
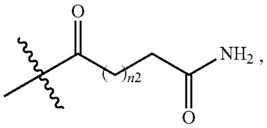 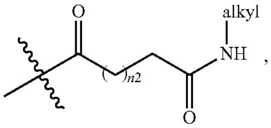
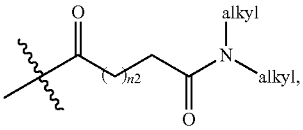
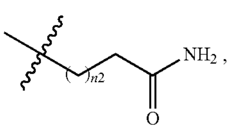 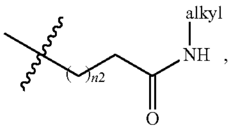

-continued

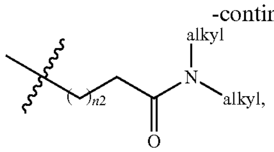

and

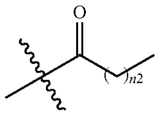

;

n2 is independently selected at each instance from 0, 1, 2, 3, 4, 5, 6, 7, 8, 9, 10, 11, 12, 13, 14, 15, 16, 17, 18, 19, and 20; and $X^{300}$ is selected from bond, —NH—, —N(alkyl)-, O, —$CH_2$—O—, —$CH_2$—NH—, and —$CH_2$—N(alkyl).

In one embodiment only 1, 2, 3, 4, or 5 of $R^{302}$, $R^{303}$, $R^{304}$, $R^{305}$, $R^{306}$, $R^{307}$, and $R^{308}$ are selected to be bond.

In one embodiment none of $R^{302}$, $R^{303}$, $R^{304}$, $R^{305}$, $R^{306}$, $R^{307}$, and $R^{308}$ are selected to be bond.

In one embodiment only 1 of $R^{302}$, $R^{303}$, $R^{304}$, $R^{305}$, $R^{306}$, $R^{307}$, and $R^{308}$ are selected to be bond.

In one embodiment only 2 of $R^{302}$, $R^{303}$, $R^{304}$, $R^{305}$, $R^{306}$, $R^{307}$, and $R^{308}$ are selected to be bond.

In one embodiment only 3 of $R^{302}$, $R^{303}$, $R^{304}$, $R^{305}$, $R^{306}$, $R^{307}$, and $R^{308}$ are selected to be bond.

In one embodiment only 4 of $R^{302}$, $R^{303}$, $R^{304}$, $R^{305}$, $R^{306}$, $R^{307}$, and $R^{308}$ are selected to be bond.

In one embodiment only 5 of $R^{302}$, $R^{303}$, $R^{304}$, $R^{305}$, $R^{306}$, $R^{307}$, and $R^{308}$ are selected to be bond.

Non-limiting examples of compounds with an $R^{301}$ substituent of the present invention include the following, wherein this alternative includes the use of $R^{32}$ as a divalent species, wherein the linkage can be located at any site that produces a stable molecule and achieves the desired result:

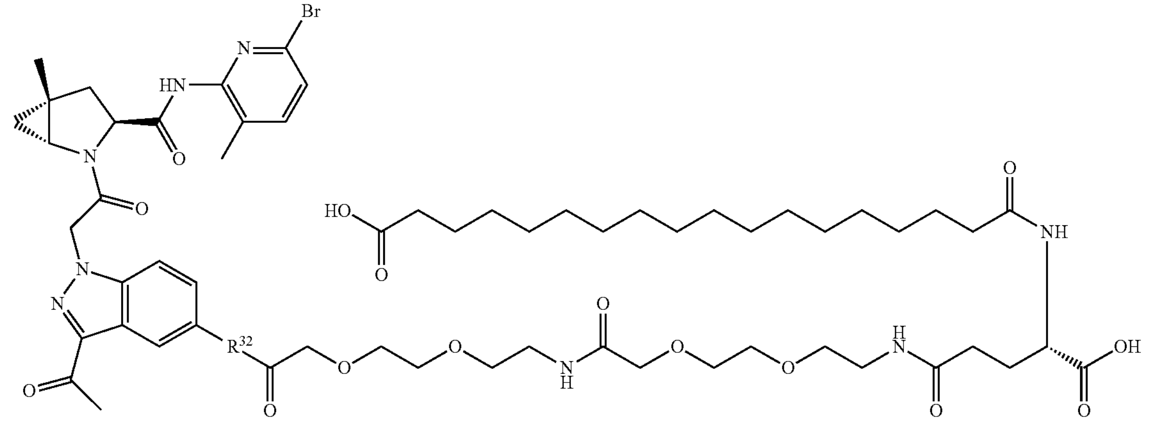

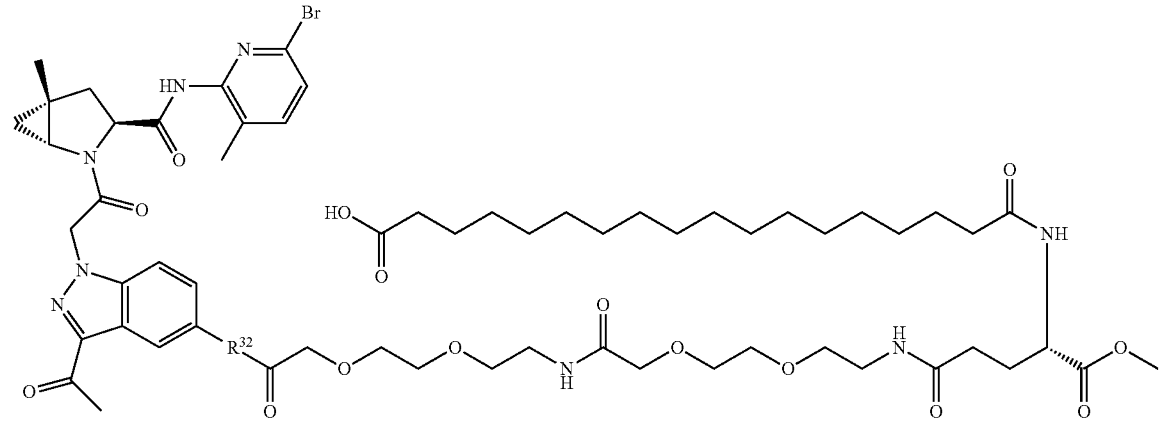

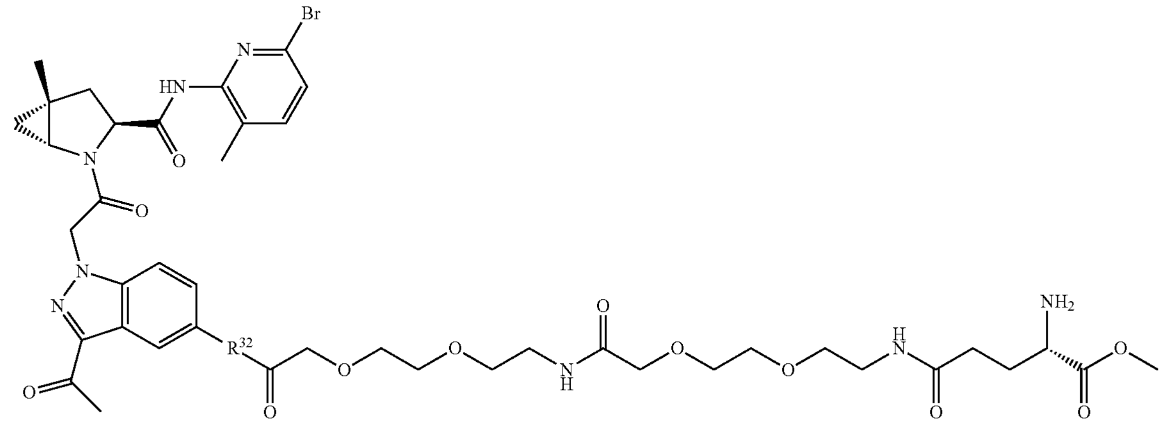

-continued
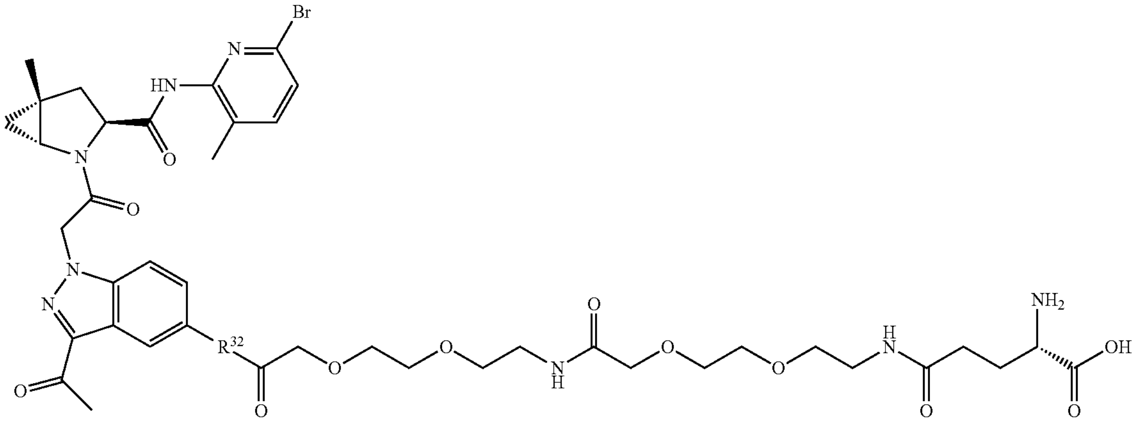
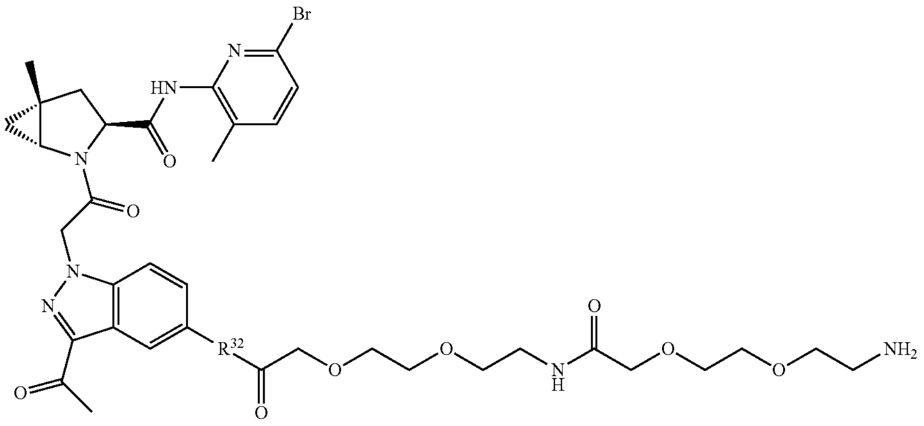
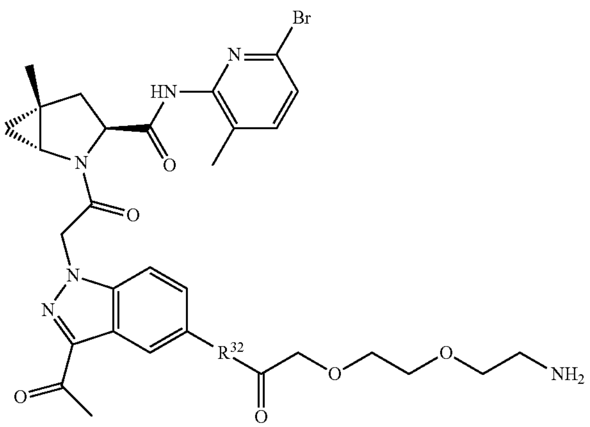

-continued
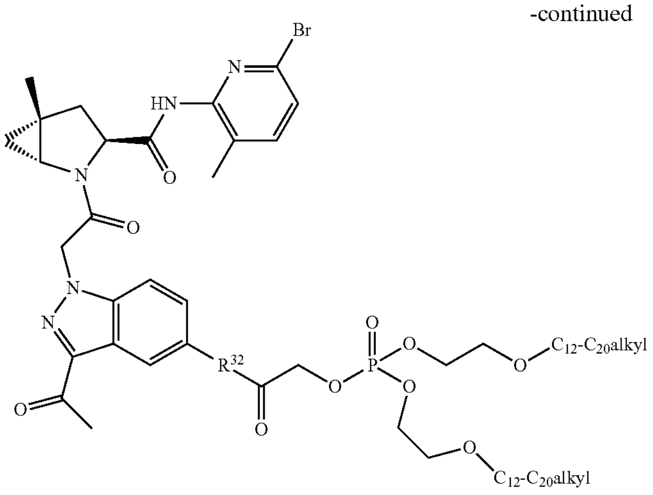
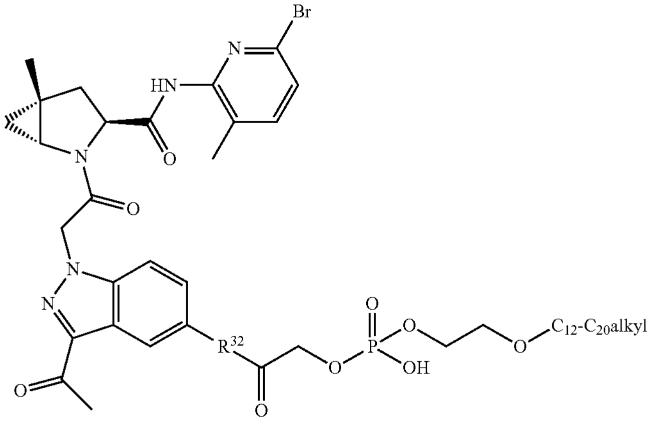
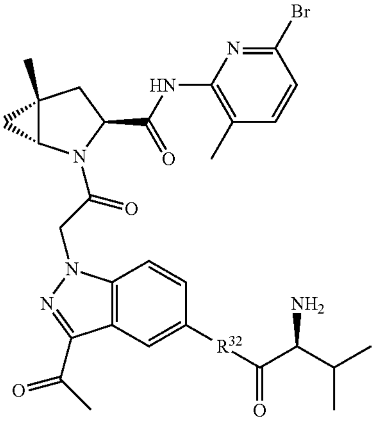
Additional non-limiting examples of compounds with an $R^{301}$ substituent include:
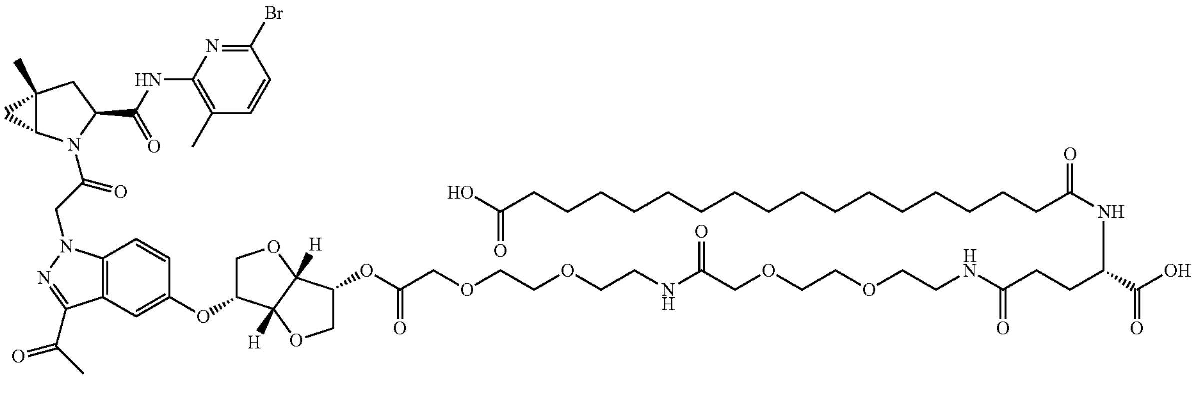

-continued
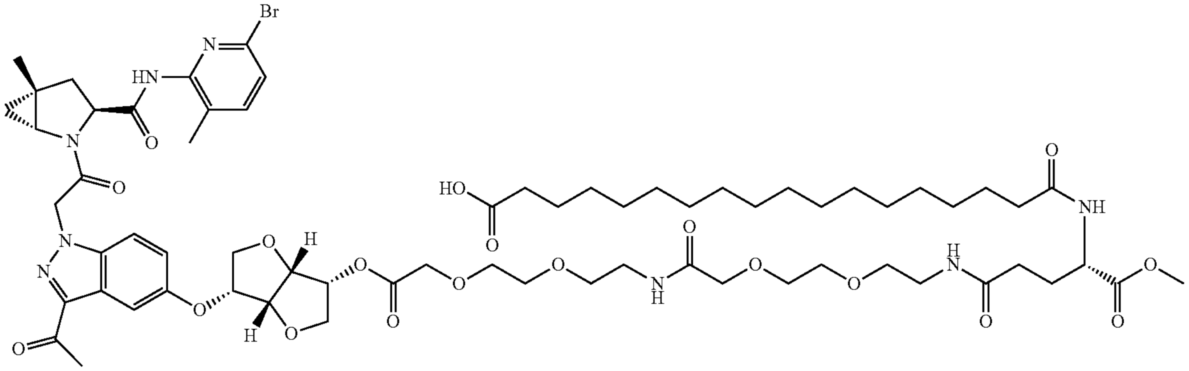
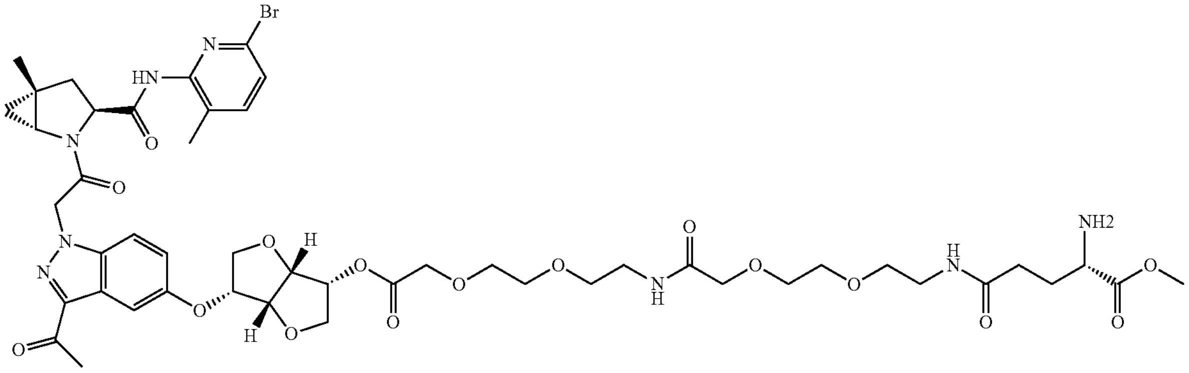
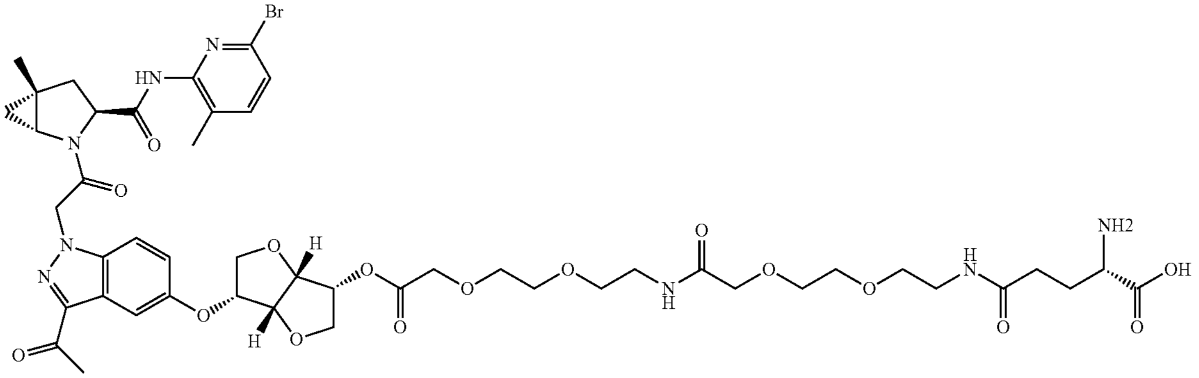
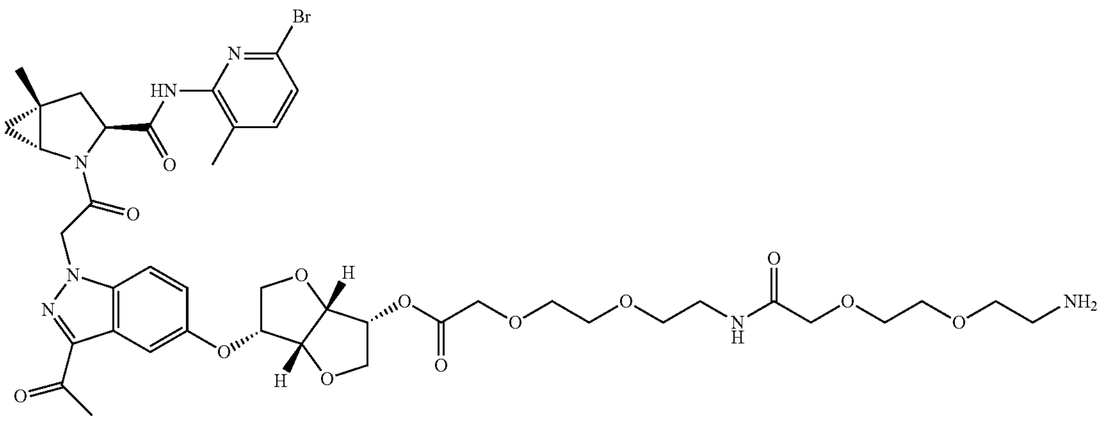

-continued
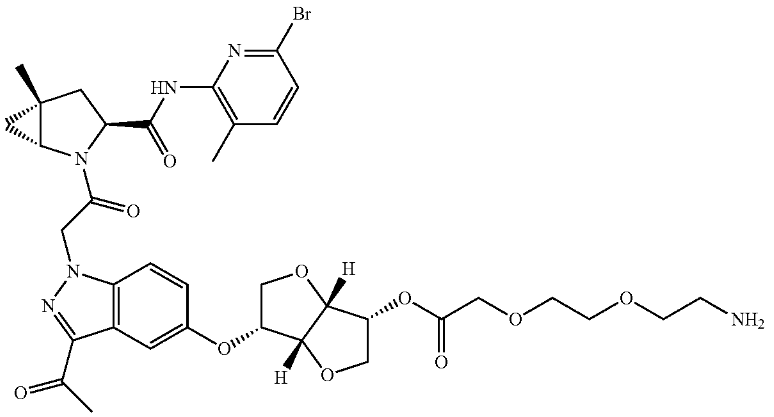
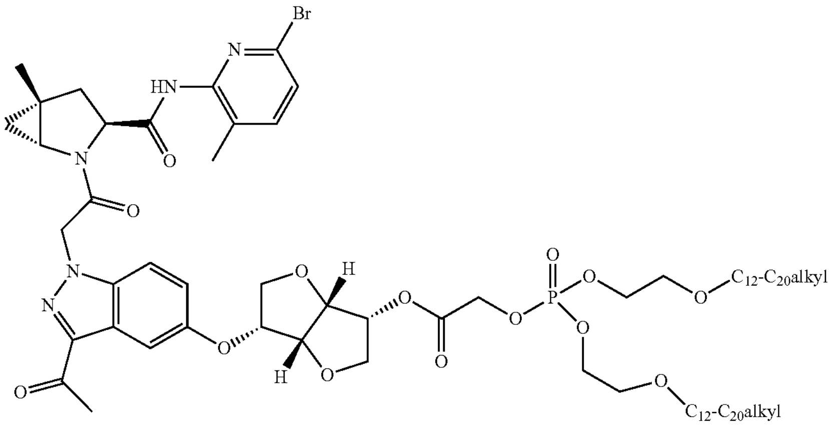
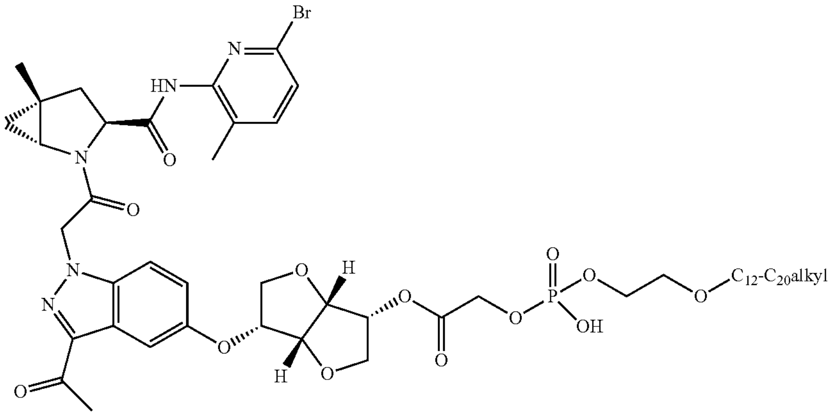
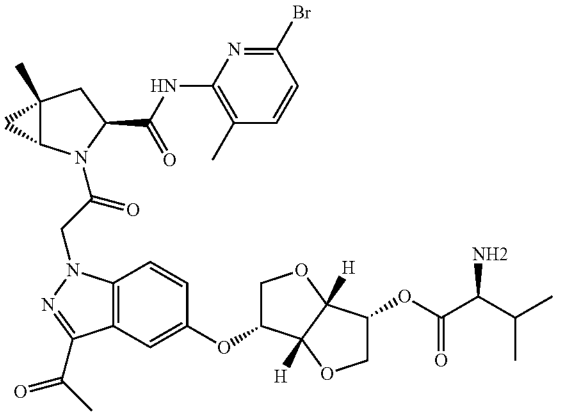 [SMILES: CC(=O)c1nn(CC(=O)N2[C@H](C(=O)Nc3nc(Br)ccc3C)C[C@@]3(C)C[C@@H]23)c2ccc(O[C@@H]3CO[C@H]4[C@@H]3OC[C@H]4OC(=O)[C@@H](N)C(C)C)cc12]

Non-limiting examples of compounds of the present invention with a $R^{301}$ group include:
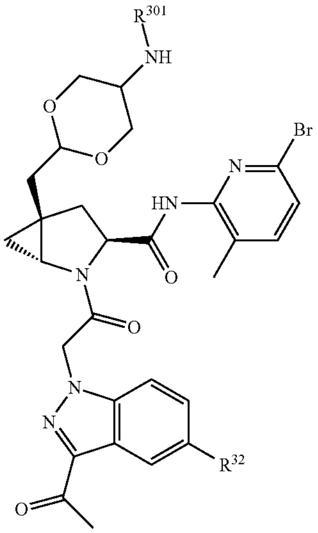
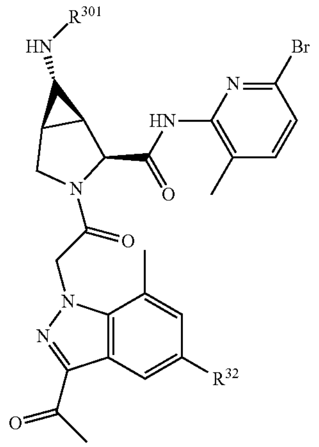
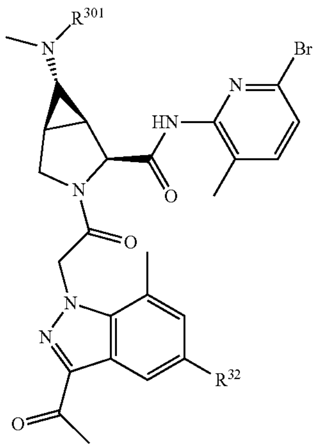
-continued
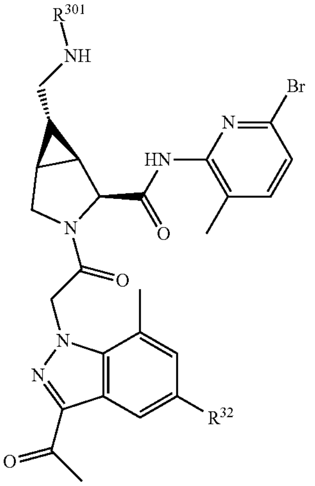
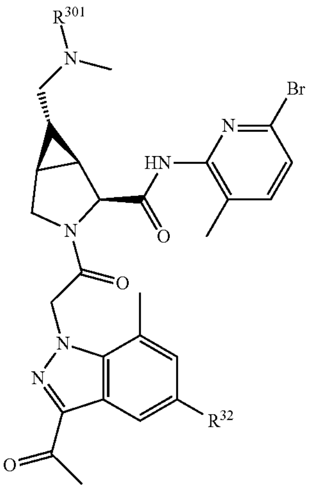
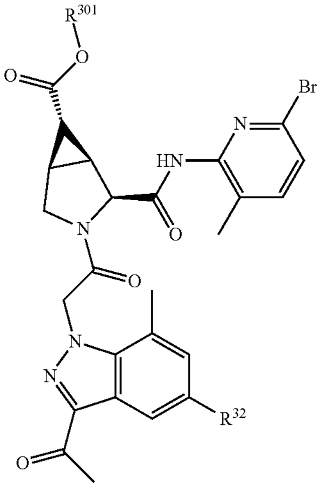

-continued
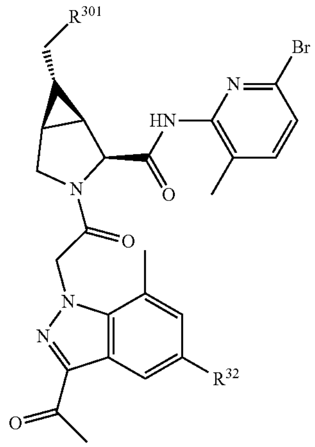
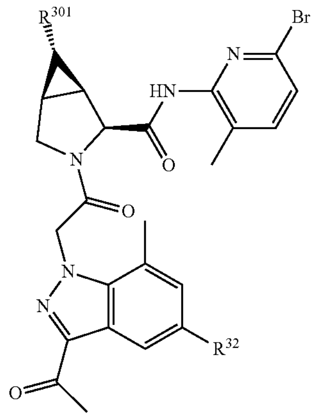
Non-limiting examples of compounds of the present invention with a $R^{301}$ group include:
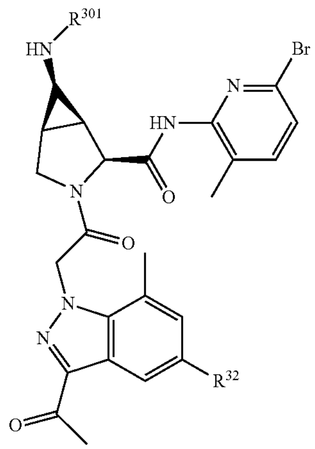
-continued
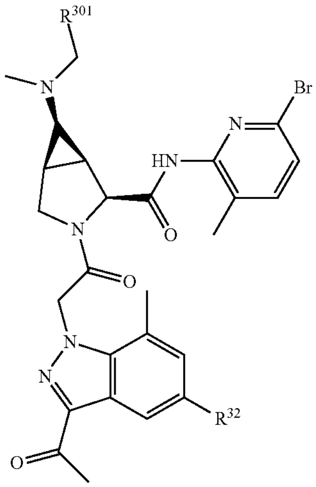
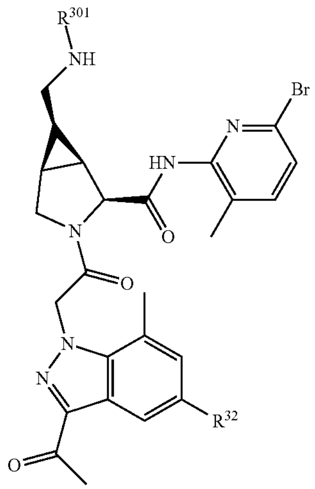
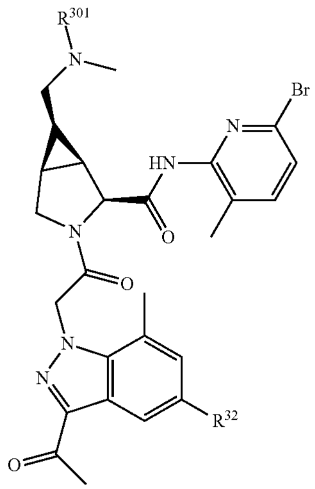

-continued
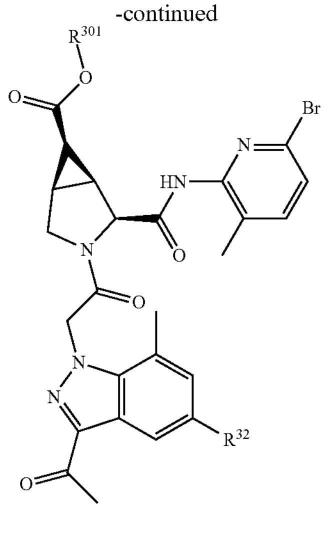
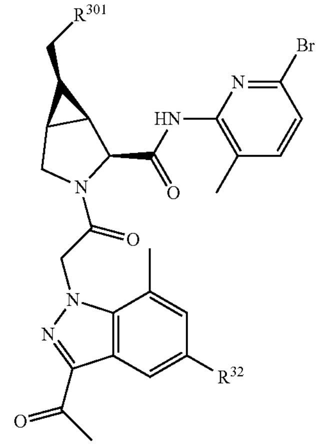
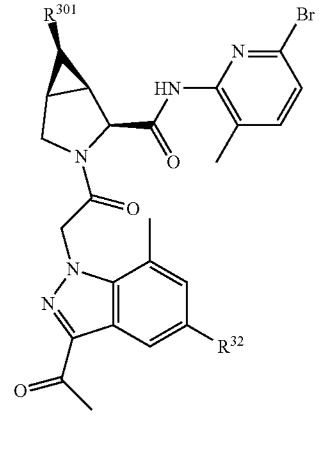
Non-limiting examples of compounds of the present invention with a $R^{301}$ group include:
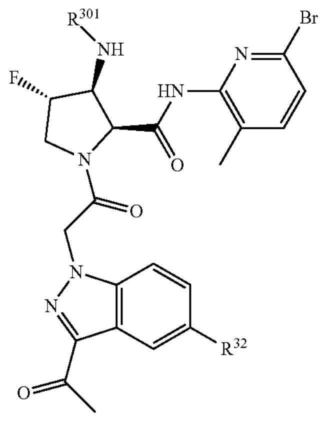
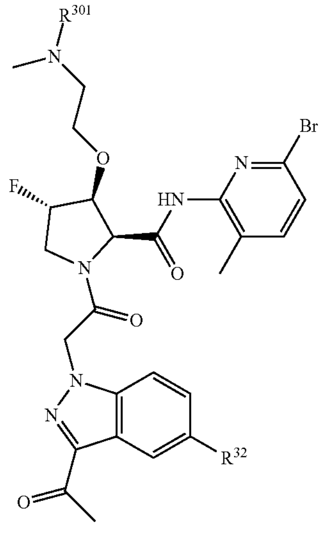
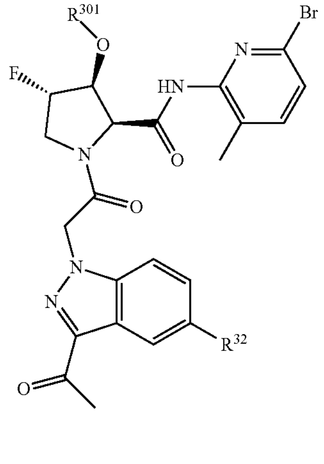

-continued
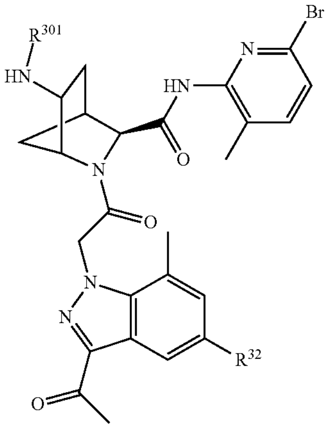
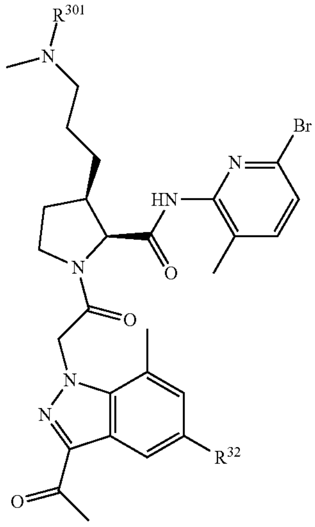
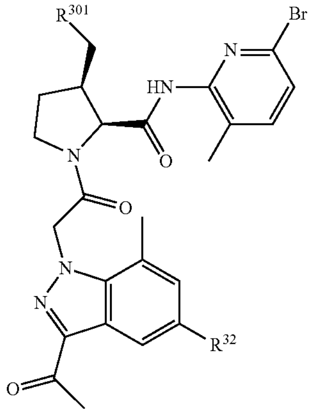
Non-limiting examples of compounds of the present invention with a $R^{301}$ group include:
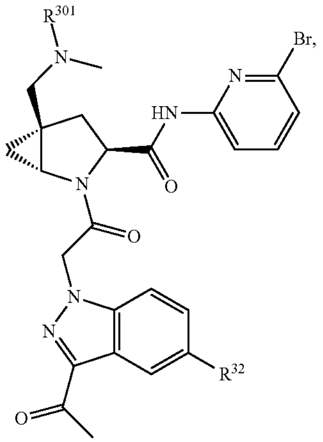
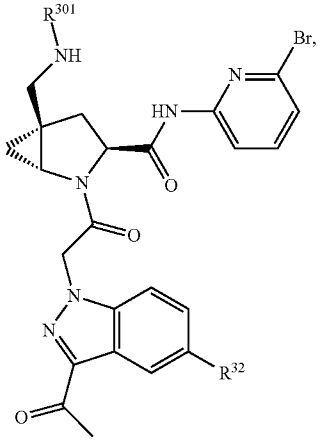
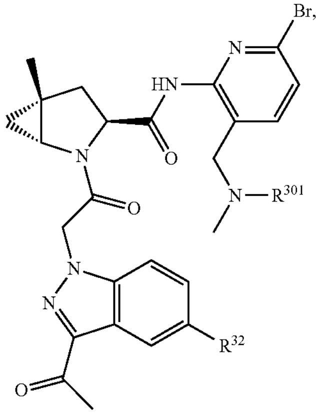
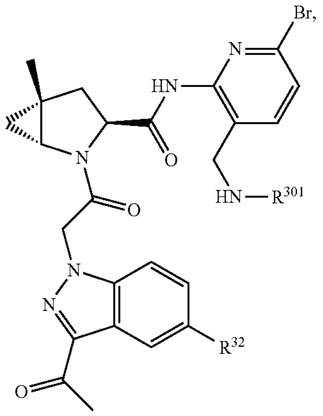

-continued
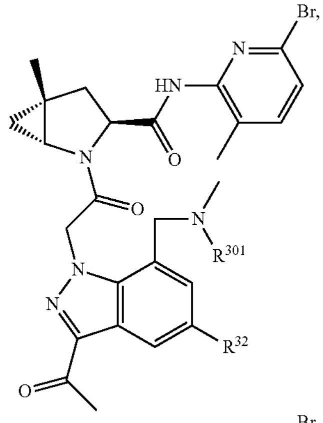
,
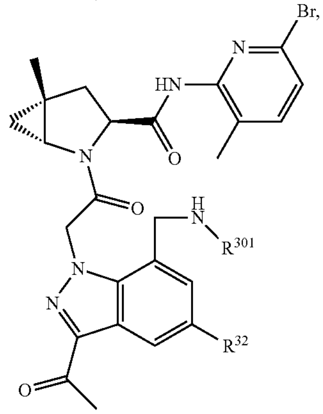
,
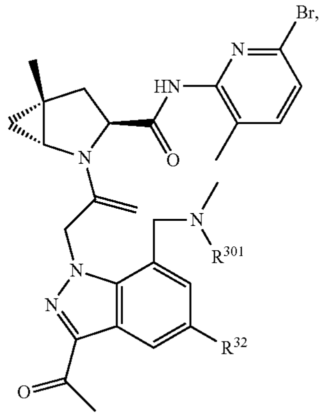
, and
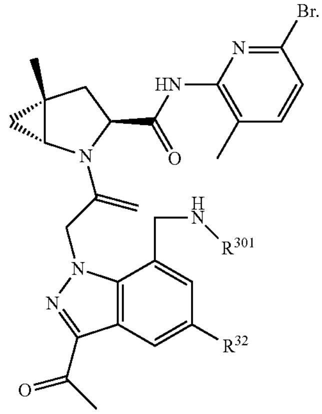
.
Non-limiting examples of compounds of the present invention with a $R^{301}$ group also include (and wherein the $-O(CH_2)_{1-4}P(O)R^{23b}R^{23b}$ is illustrated as the ether for convenience and space only and wherein each ether group described herein is considered independently exemplified):
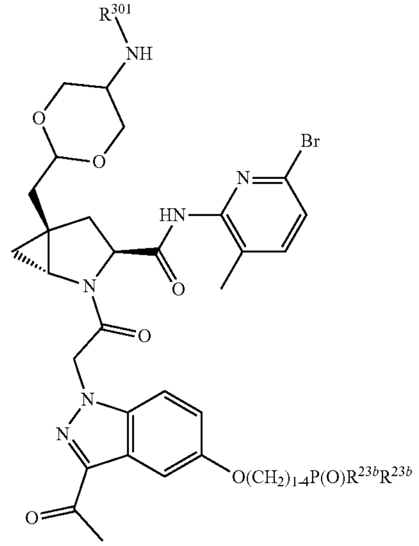
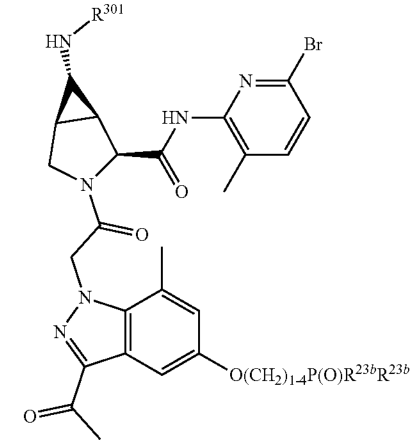
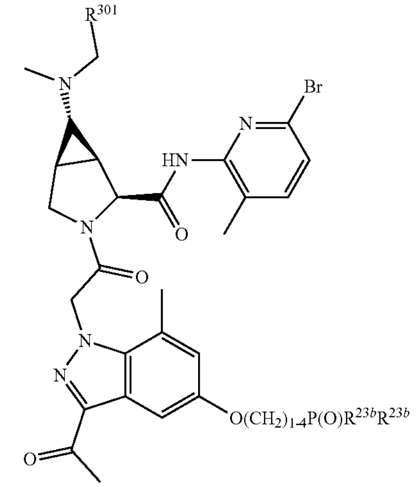

-continued
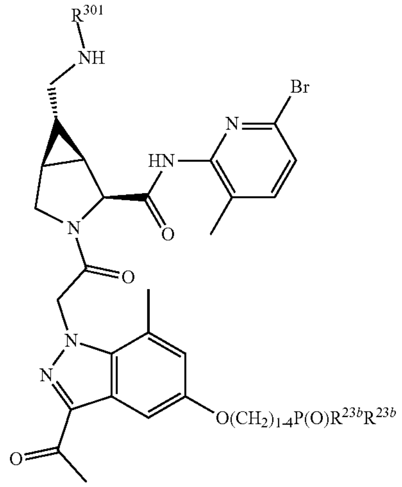
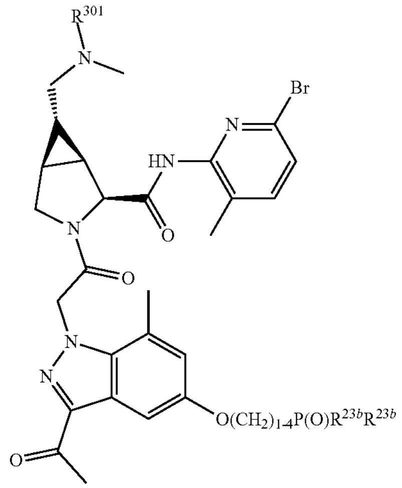
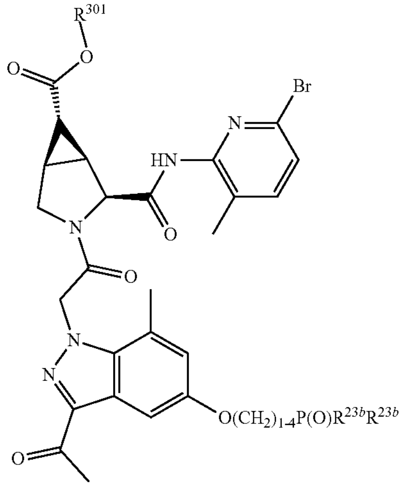
-continued
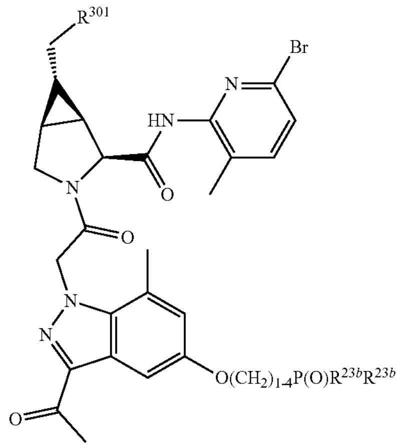
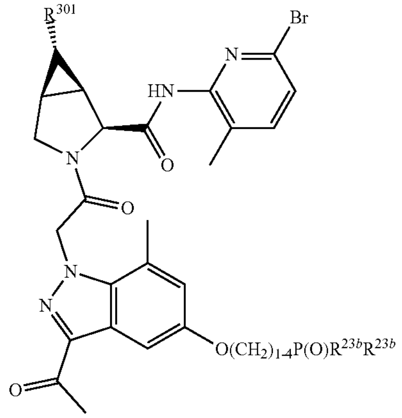
Additional non-limiting examples of compounds of the present invention with a $R^{301}$ group include:
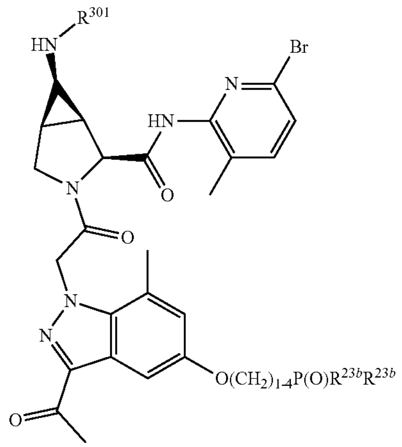

-continued
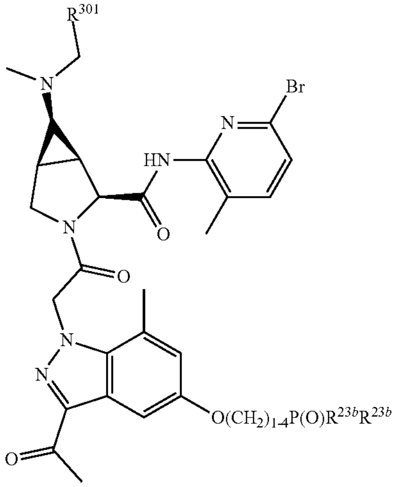
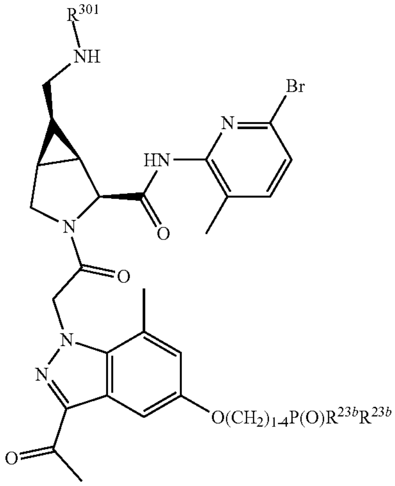
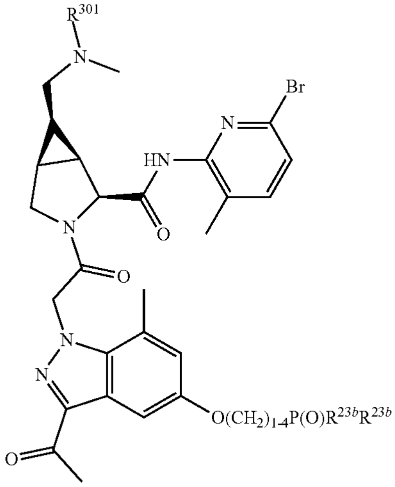
-continued
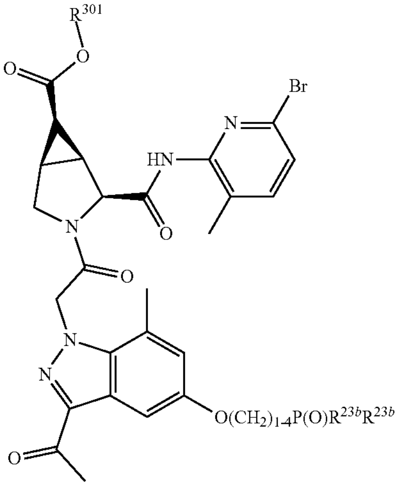
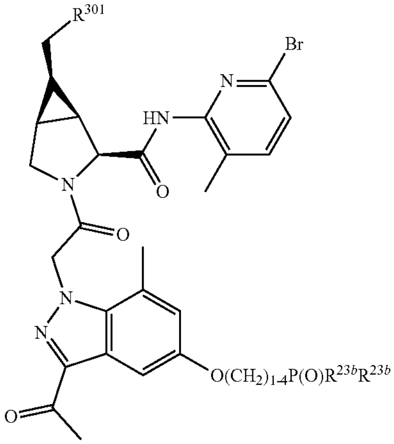
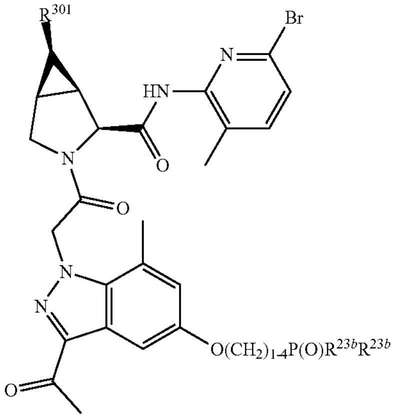

Additional non-limiting examples of compounds of the present invention with a $R^{301}$ group include:
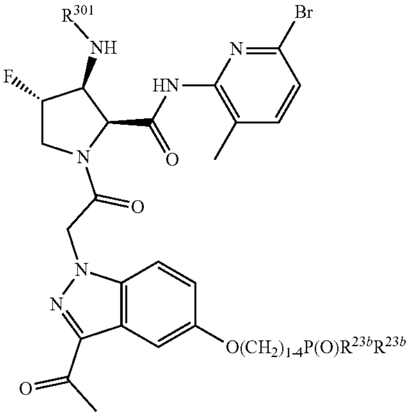
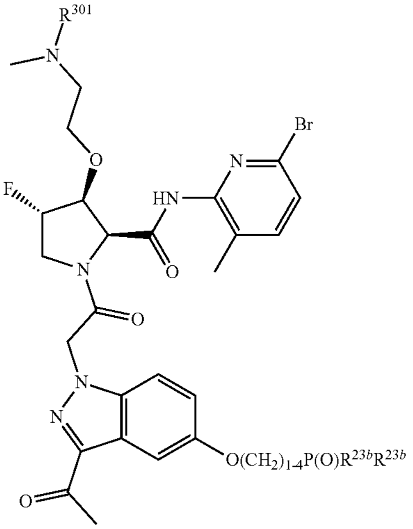
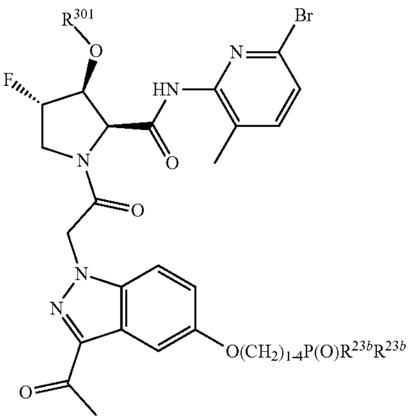
-continued
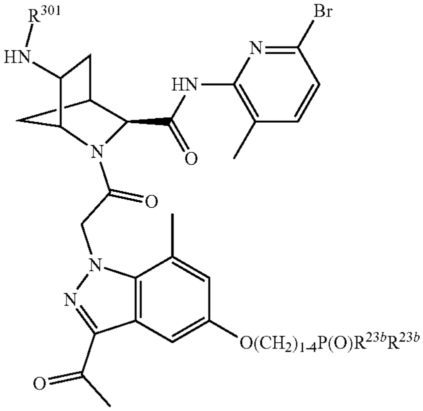
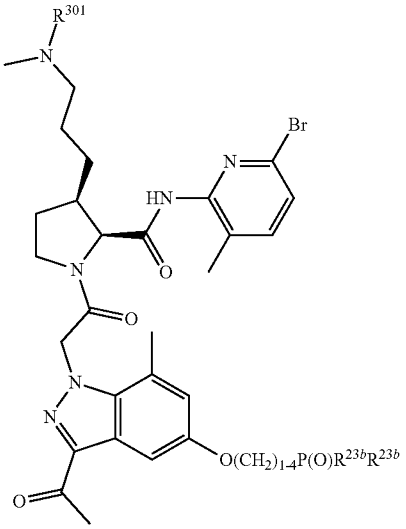
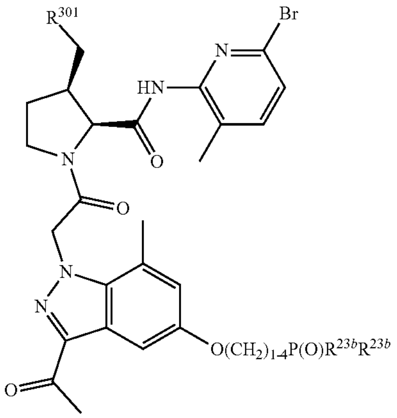
Additional non-limiting examples of compounds of the present invention with a $R^{301}$ group include:

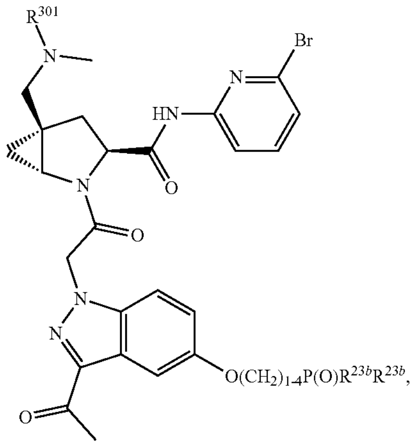
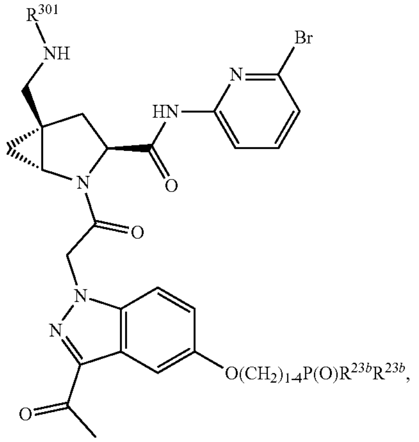
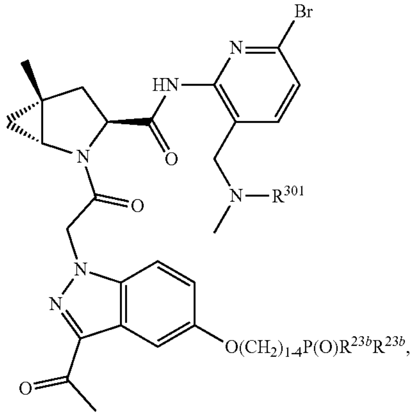
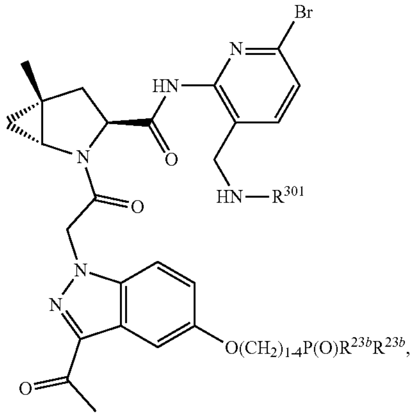
-continued
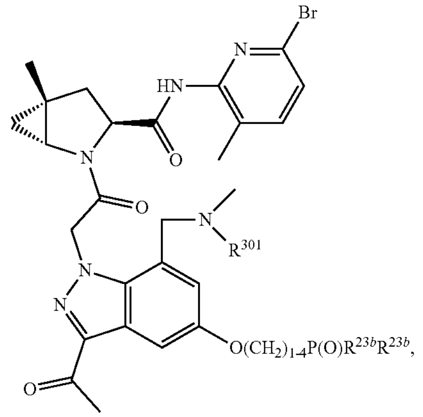
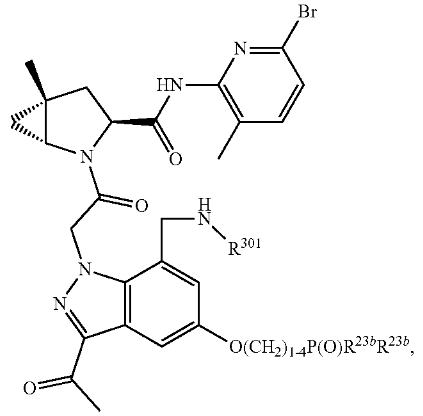
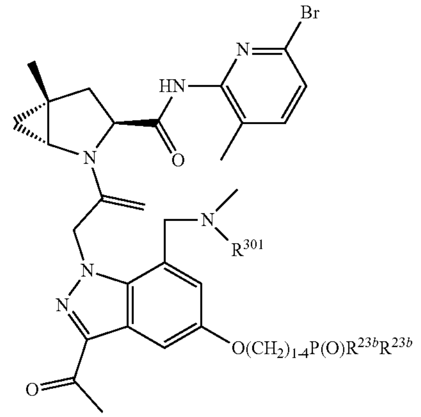
and
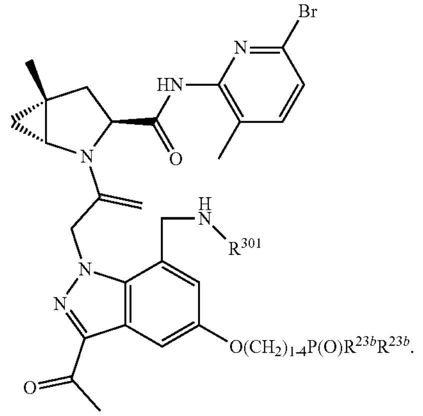

In one embodiment C is selected from:
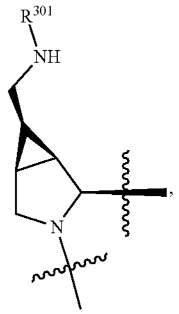
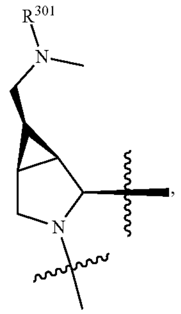
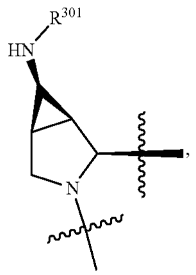
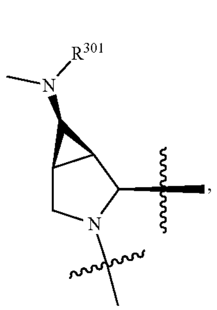
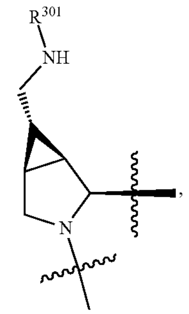
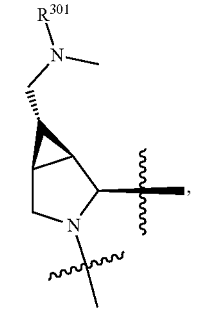
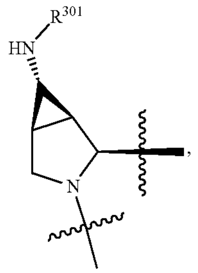
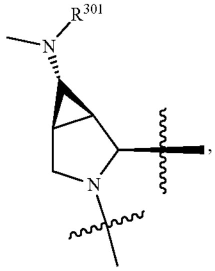
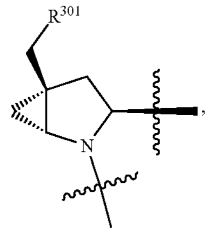
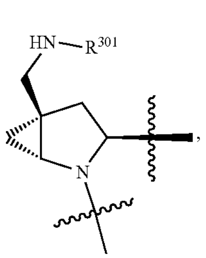
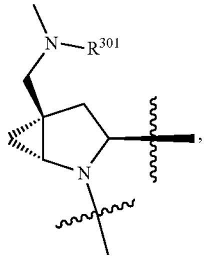
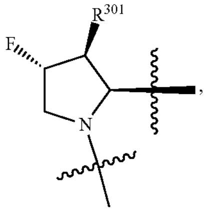
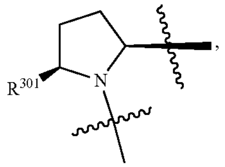
-continued
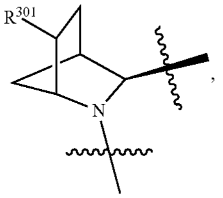
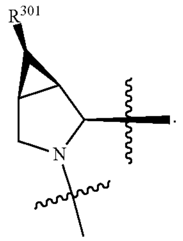
In one embodiment A is selected from:
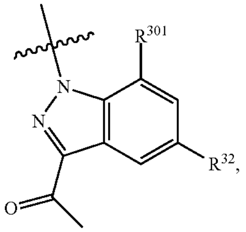
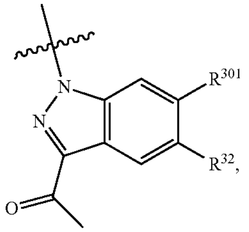
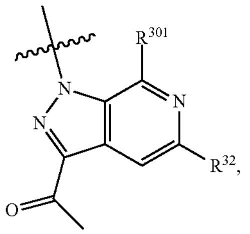
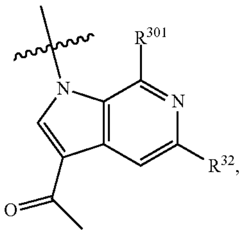
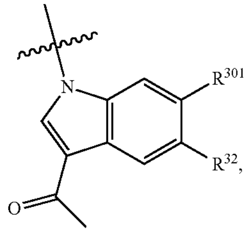
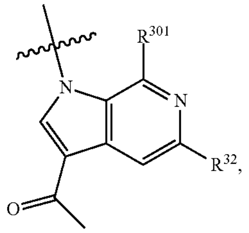
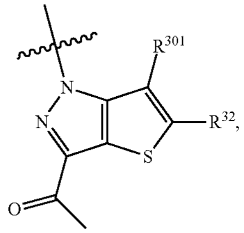
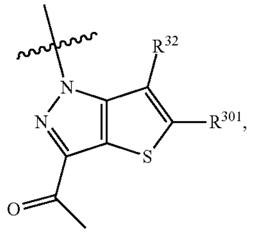
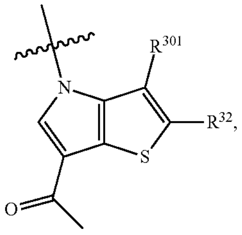
and
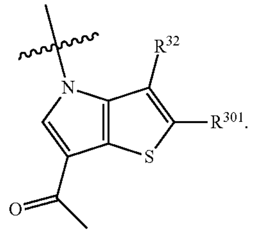

In one embodiment B is selected from:

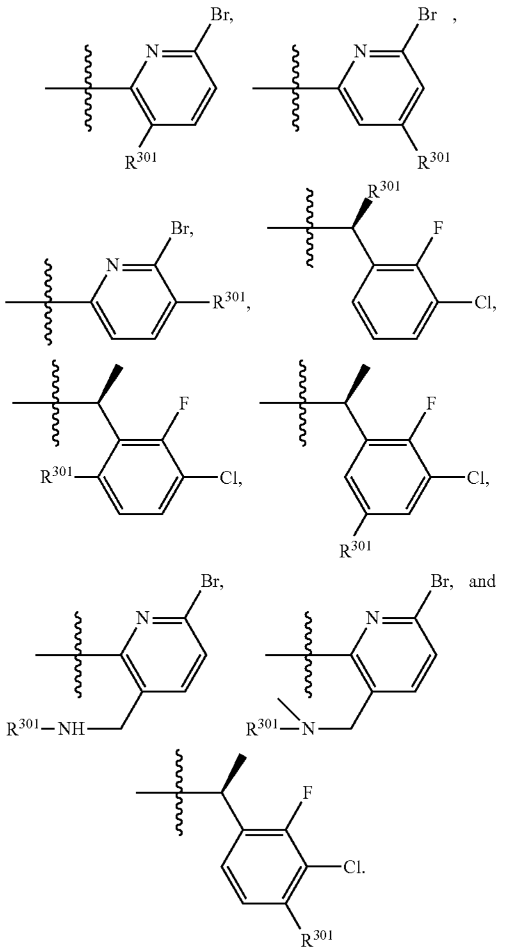

In an alternative embodiment $R^{32}$ is:

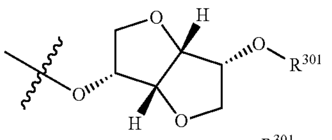

or

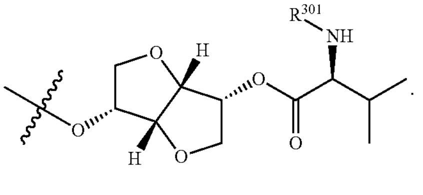

In one embodiment $X^{31}$ is selected from N and $CR^{54}$;

In another embodiment $X^{31}$ is $C(R^{54})_2$;

In one embodiment $X^{25}$ is O or S;

In one embodiment $R^{4'}$ is selected from -JCHO, -$JCONH_2$, -$JCONR^9R^{10}$, $JC_2$-$C_6$alkanoyl, -$JSO_2NH_2$, -$JSO_2NR^{21}R^{22}$, -$JC(CH_2)_2F$, -$JCH(CF_3)NH_2$, -J-haloalkyl-$NH_2$, -J-haloalkyl-$NR^9R^{10}$, alkyl including $C_1$-$C_6$alkyl, —$C_0$-$C_4$alkyl($C_3$-$C_7$cycloalkyl), -JC(O)$C_0$-$C_2$alkyl($C_3$-$C_7$cycloalkyl), -$JNR^9$($C_2$-$C_6$alkanoyl), -$JNR^9C(O)NR^9R^{10}$,

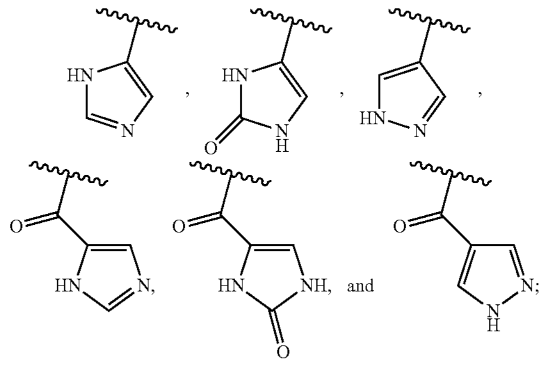

each of which $R^{4'}$ other than —CHO, is optionally substituted with one or more of amino, imino, halogen, hydroxyl, cyano, cyanoimino, alkyl including $C_1$-$C_6$alkyl, alkoxy including $C_1$-$C_6$alkoxy, —$C_0$-$C_2$alkyl(mono- and di-$C_1$-$C_4$alkylamino), haloalkyl including $C_1$-$C_6$haloalkyl, and haloalkoxy including $C_1$-$C_6$haloalkoxy.

In one embodiment L2 is a spirocyclic linker attached to the C ring so that the resultant compound of Formula I is:

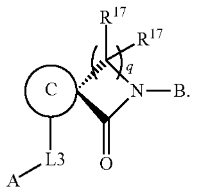

In one embodiment L2 is a spirocyclic linker attached to the C ring so that the resultant compound of Formula II is:

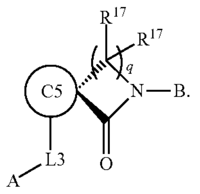

In one embodiment L2 is a spirocyclic linker attached to the C ring so that the resultant compound of Formula III is:

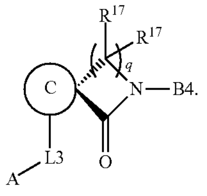

Additional Formulas

In one aspect, the disclosure includes compounds and salts of Formulas in Table 1 for any use and in any composition described in this application.

In some of the below Formulas for convenience and space purposes only, $R^{32}$ is illustrated as the group $NR^9C(O)$ $NR^{24}R^{25}$, however each described or illustrated $R^{32}$ in this application is considered to be independently shown in each of these Formulas.

TABLE 1A

Additional Exemplary Formulas within the Present Invention.

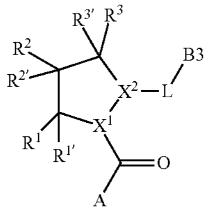

Formula I-1

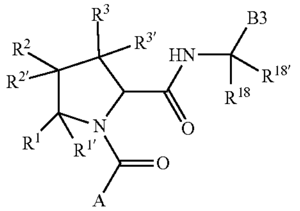

Formula I-2

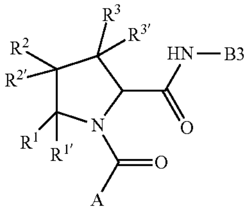

Formula I-3

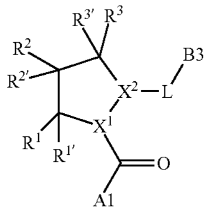

Formula I-4

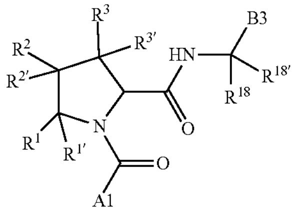

Formula I-5

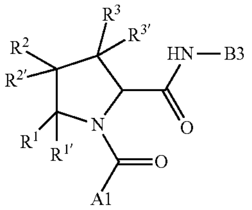

Formula I-6

TABLE 1A-continued

Additional Exemplary Formulas within the Present Invention.

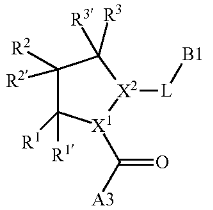

Formula I-7

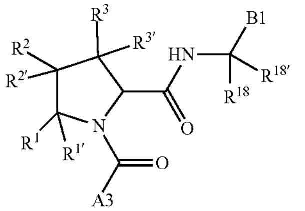

Formula I-8

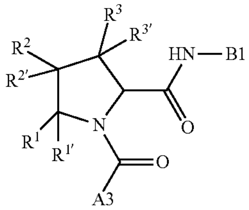

Formula I-9

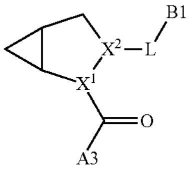

Formula I-10

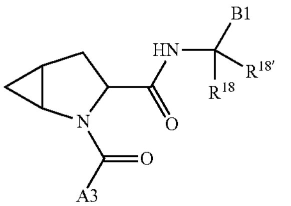

Formula I-11

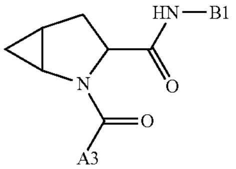

Formula I-12

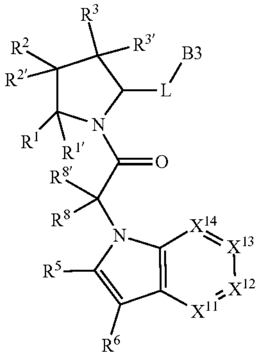

Formula I-13

TABLE 1A-continued
| Additional Exemplary Formulas within the Present Invention. |
| --- |
Formula I-14
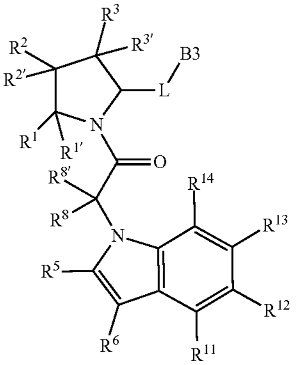
Formula I-15
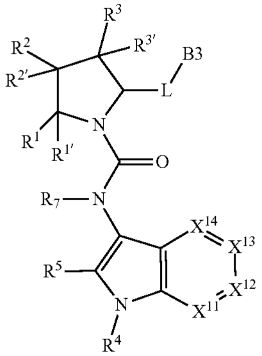
Formula I-16
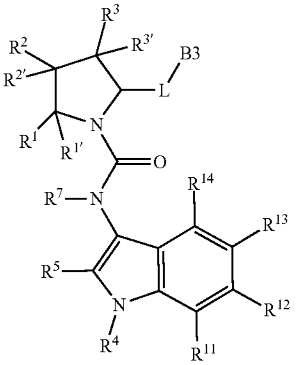
Formula I-17
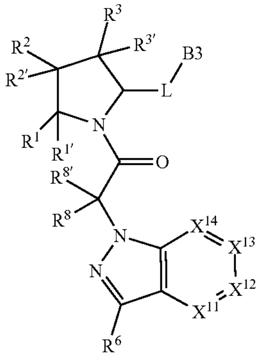
Formula I-18
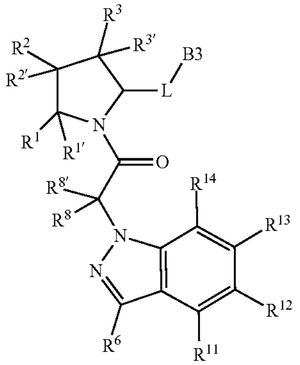
Formula I-19
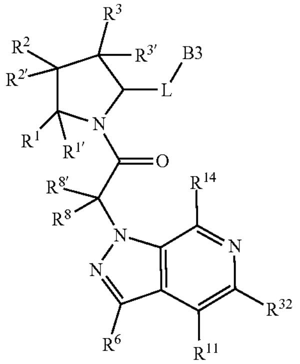
Formula I-20
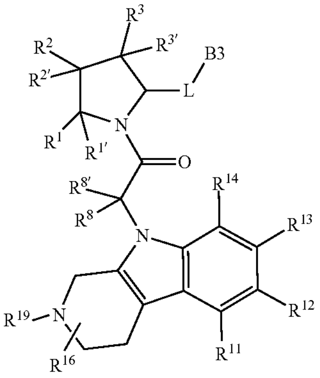
Formula I-21
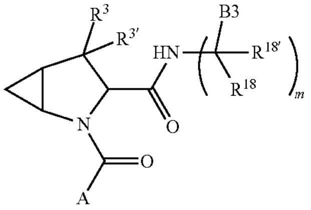
Formula I-22
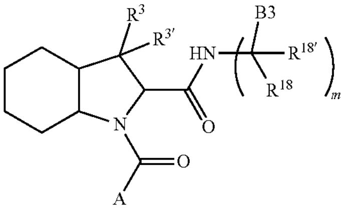

TABLE 1A-continued
Additional Exemplary Formulas within the Present Invention.
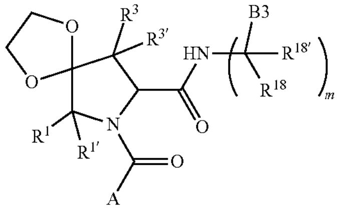
Formula I-23
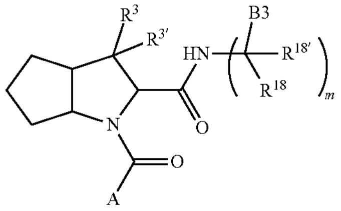
Formula I-24
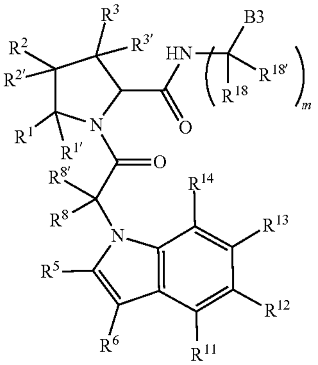
Formula I-25
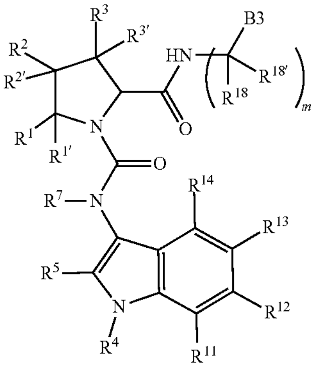
Formula I-26
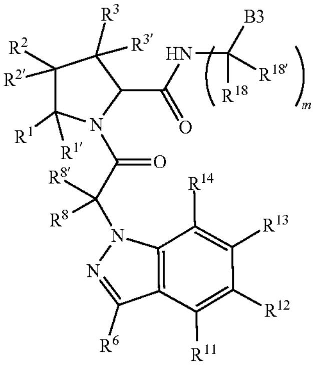
Formula I-27
TABLE 1A-continued
Additional Exemplary Formulas within the Present Invention.
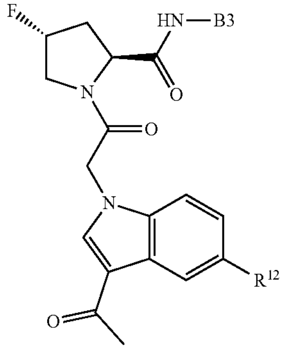
Formula I-28
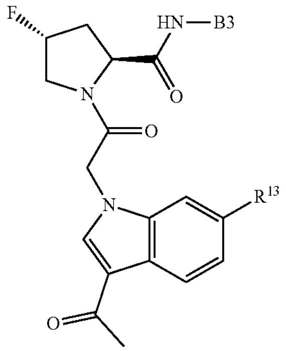
Formula I-29
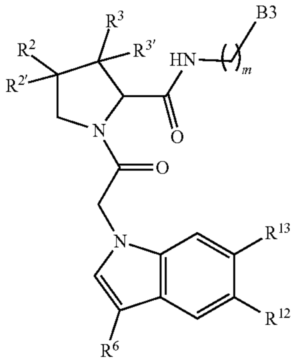
Formula I-30
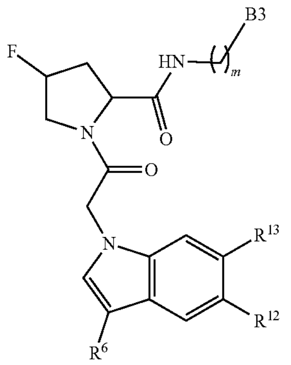
Formula I-31

TABLE 1A-continued
| Additional Exemplary Formulas within the Present Invention. |
|---|
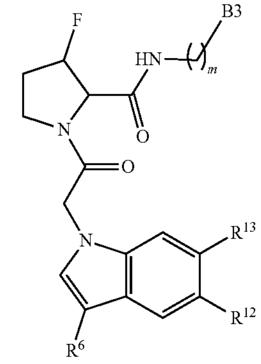
Formula I-32
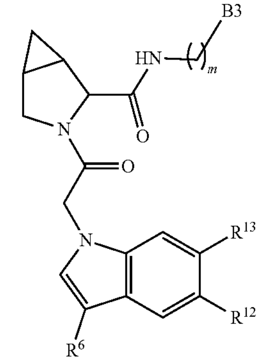
Formula I-33
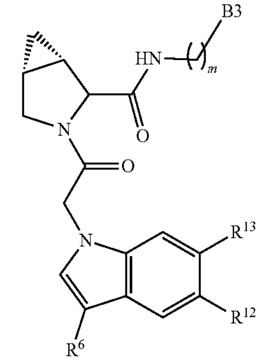
Formula I-34
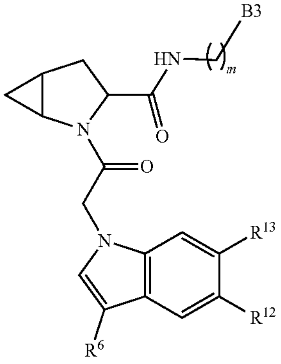
Formula I-35
TABLE 1A-continued
| Additional Exemplary Formulas within the Present Invention. |
|---|
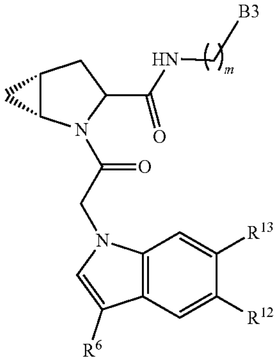
Formula I-36
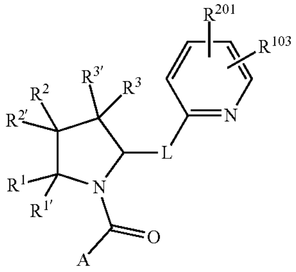
Formula I-37
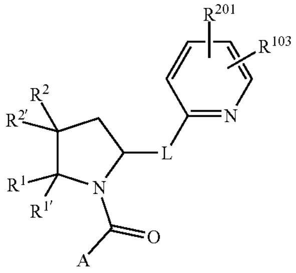
Formula I-38
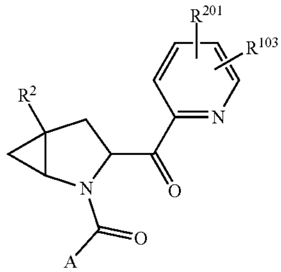
Formula I-39
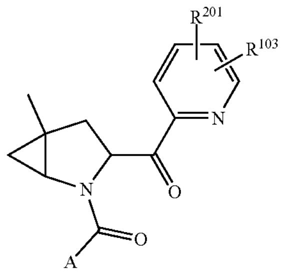
Formula I-40

TABLE 1A-continued
Additional Exemplary Formulas within the Present Invention.
Formula I-41
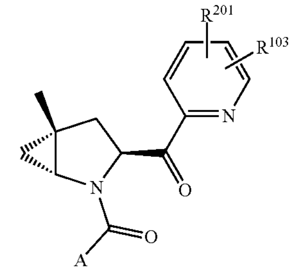
Formula I-42
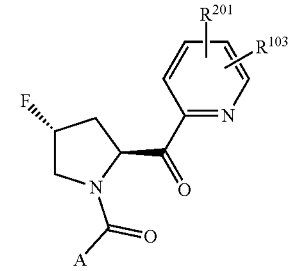
Formula I-43
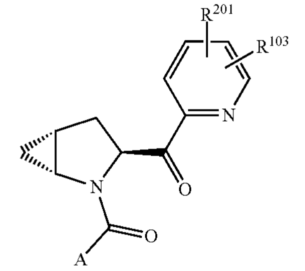
Formula I-44
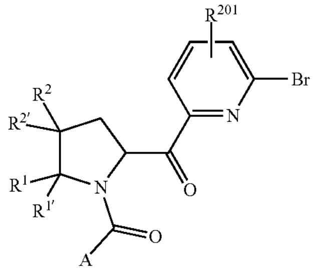
Formula I-45
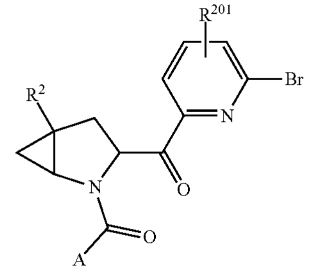
TABLE 1A-continued
Additional Exemplary Formulas within the Present Invention.
Formula I-46
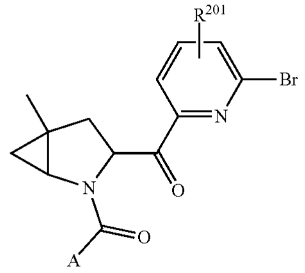
Formula I-47
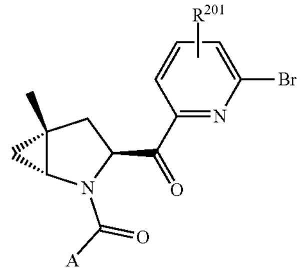
Formula I-48
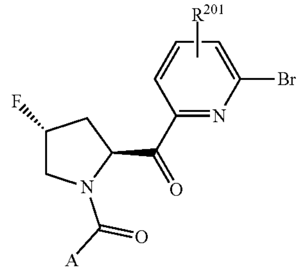
Formula I-49
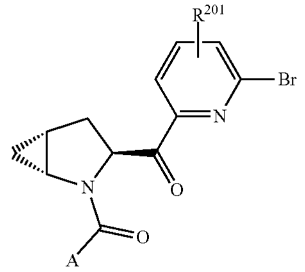
Formula I-50
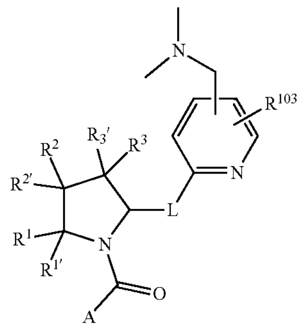

TABLE 1A-continued
| Additional Exemplary Formulas within the Present Invention. |
| --- |
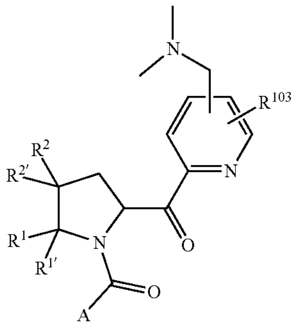
Formula I-51
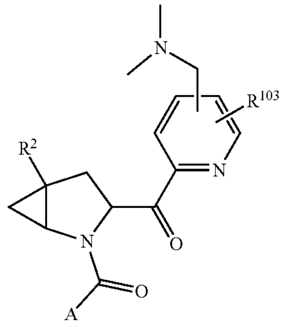
Formula I-52
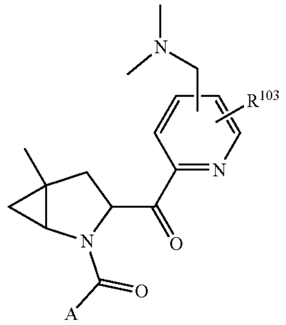
Formula I-53
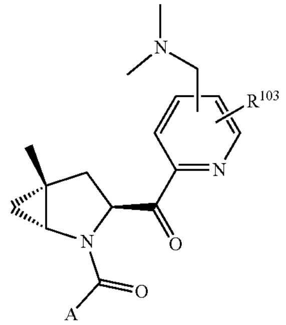
Formula I-54
TABLE 1A-continued
| Additional Exemplary Formulas within the Present Invention. |
| --- |
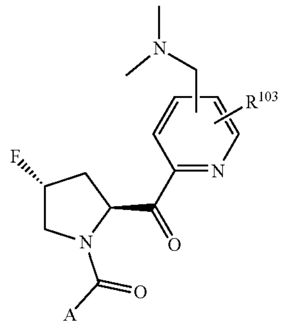
Formula I-55
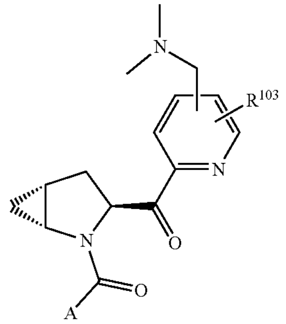
Formula I-56
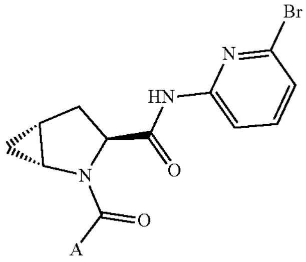
Formula I-57
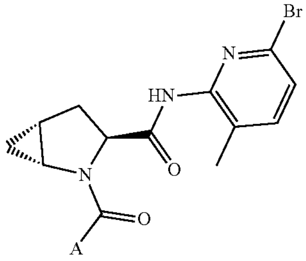
Formula I-58
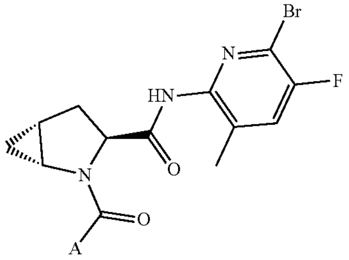
Formula I-59

TABLE 1A-continued
Additional Exemplary Formulas within the Present Invention.
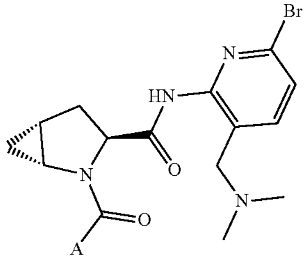
Formula I-60
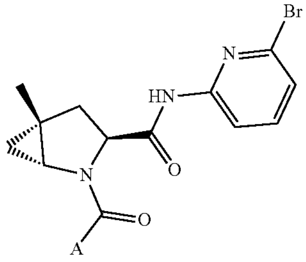
Formula I-61
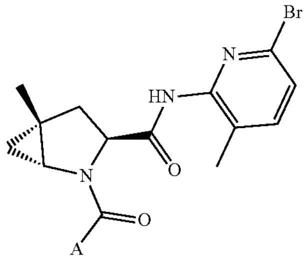
Formula I-62
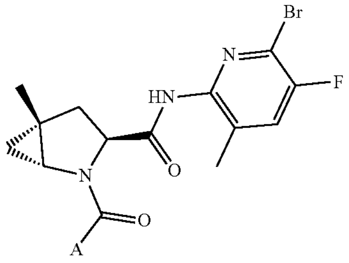
Formula I-63
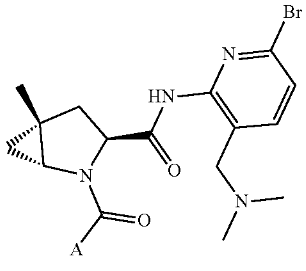
Formula I-64
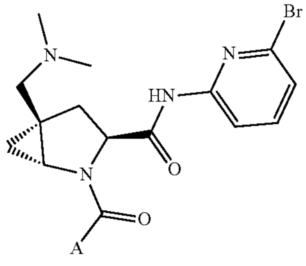
Formula I-65
TABLE 1A-continued
Additional Exemplary Formulas within the Present Invention.
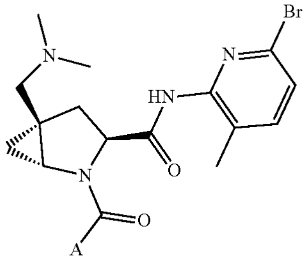
Formula I-66
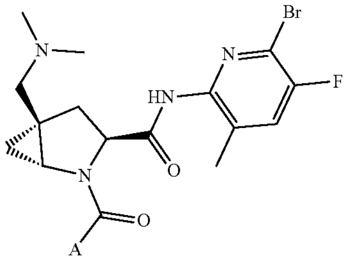
Formula I-67
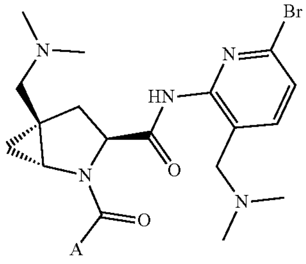
Formula I-68
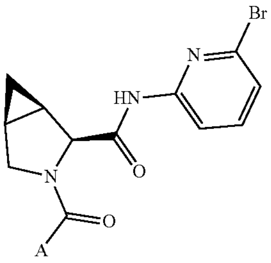
Formula I-69
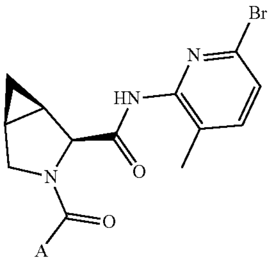
Formula I-70

TABLE 1A-continued
| Additional Exemplary Formulas within the Present Invention. |
| --- |
Formula I-71
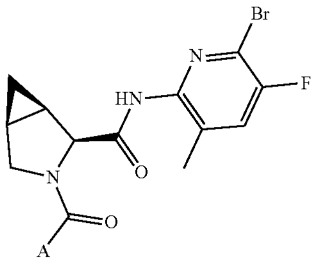
Formula I-72
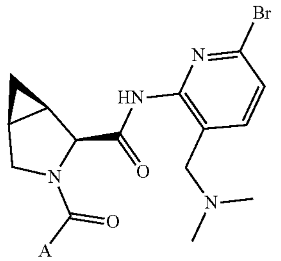
Formula I-73
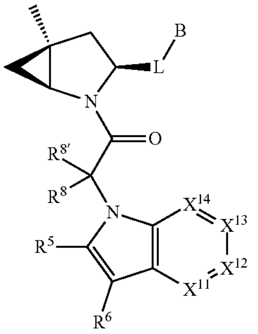
Formula I-74
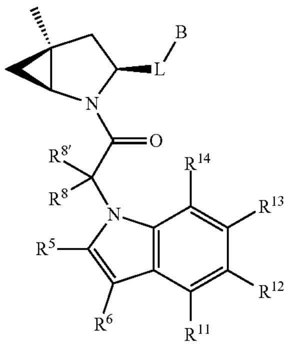
Formula I-75
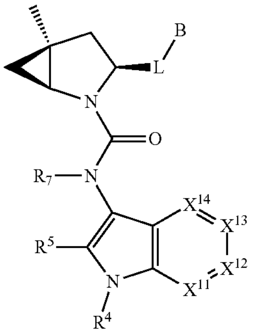
TABLE 1A-continued
| Additional Exemplary Formulas within the Present Invention. |
| --- |
Formula I-76
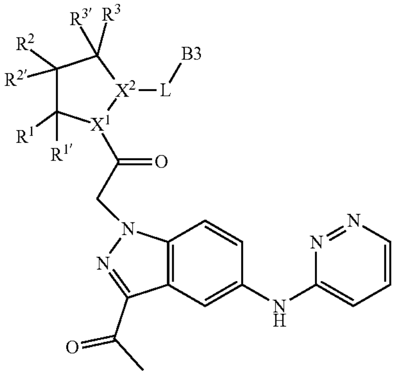
Formula I-77
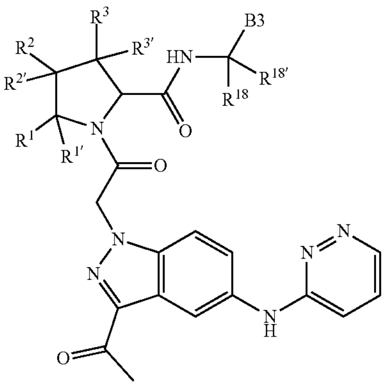
Formula I-78
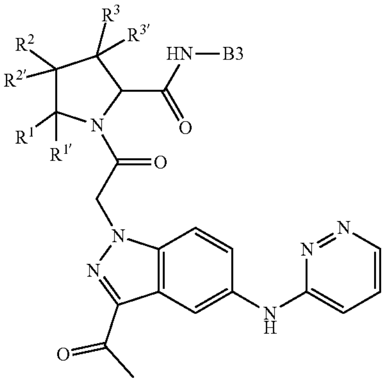
Formula I-79
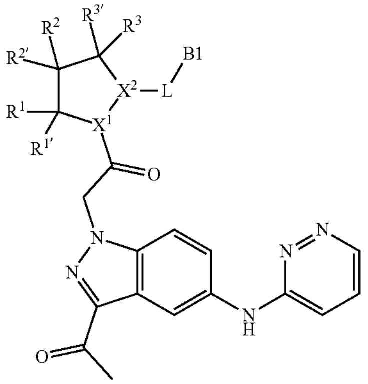

TABLE 1A-continued
| Additional Exemplary Formulas within the Present Invention. |
| --- |
Formula I-80
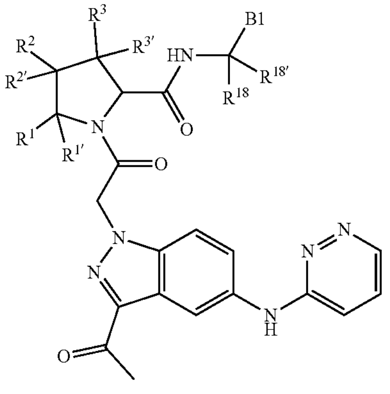
Formula I-81
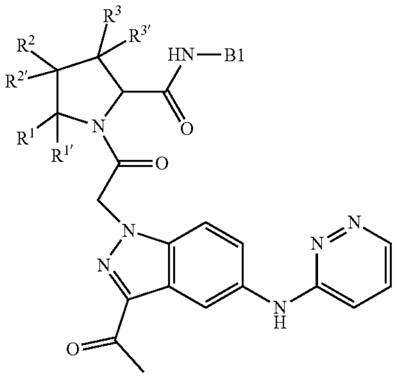
Formula I-83
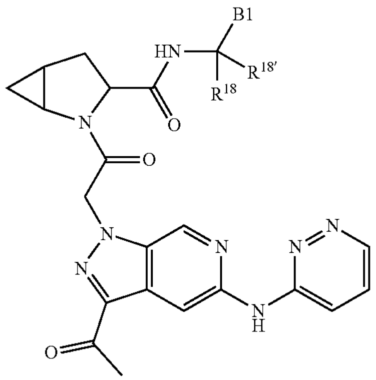
Formula I-84
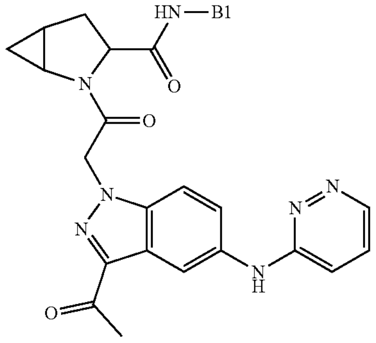
TABLE 1A-continued
| Additional Exemplary Formulas within the Present Invention. |
| --- |
Formula I-85
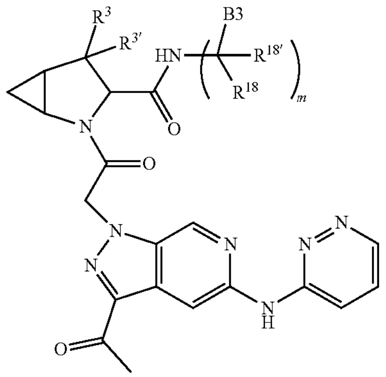
Formula I-86
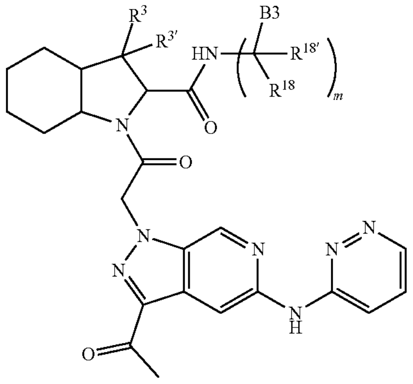
Formula I-87
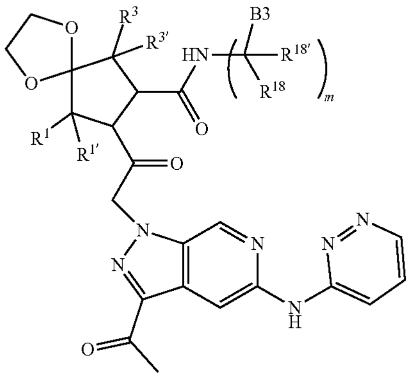
Formula I-88
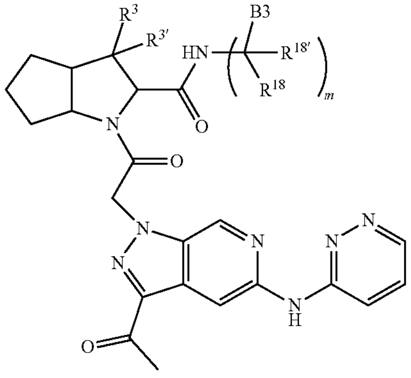

TABLE 1A-continued
| Additional Exemplary Formulas within the Present Invention. |
|---|
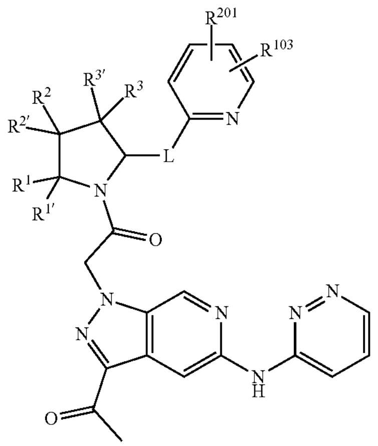
Formula I-89
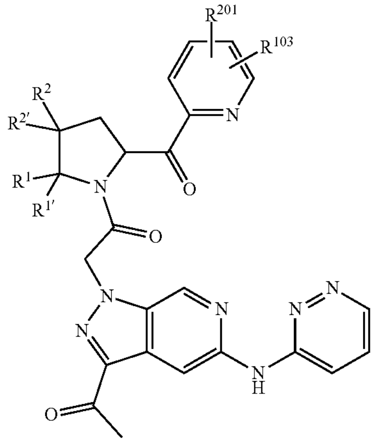
Formula I-90
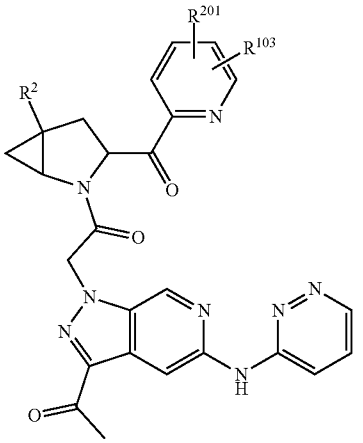
Formula I-91
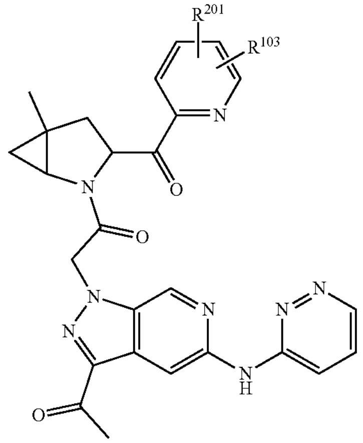
Formula I-92
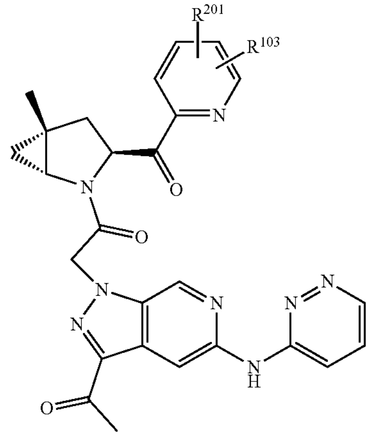
Formula I-93
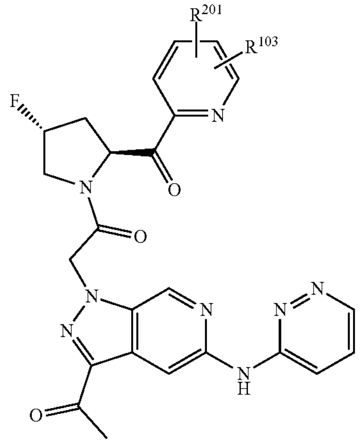
Formula I-94

TABLE 1A-continued
Additional Exemplary Formulas within the Present Invention.
Formula I-95
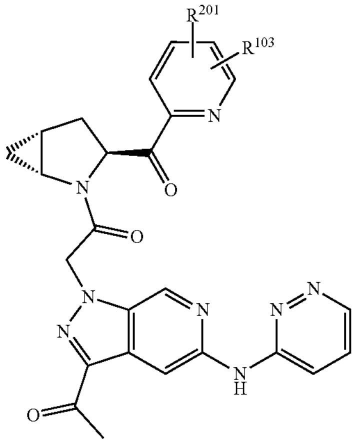
Formula I-96
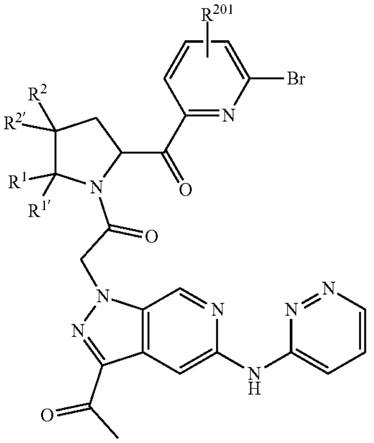
Formula I-97
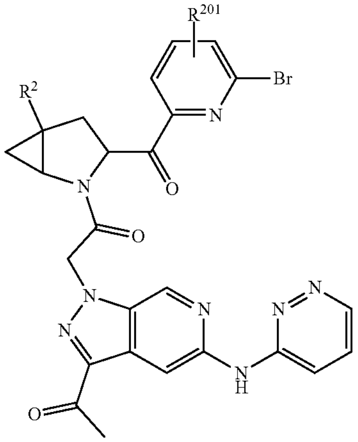
TABLE 1A-continued
Additional Exemplary Formulas within the Present Invention.
Formula I-98
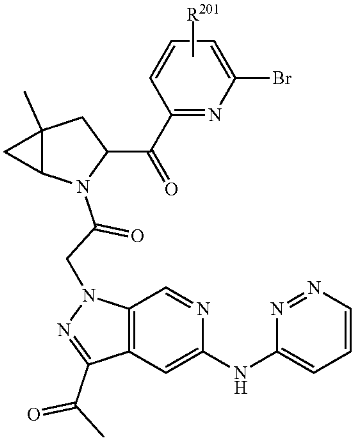
Formula I-99
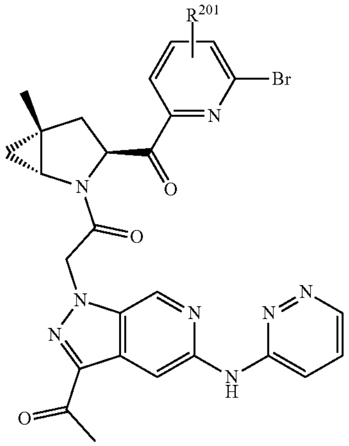
Formula I-100
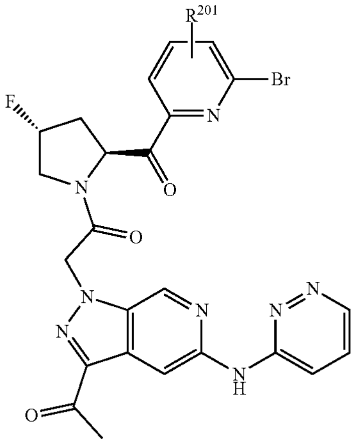

TABLE 1A-continued
Additional Exemplary Formulas within the Present Invention.
Formula I-101
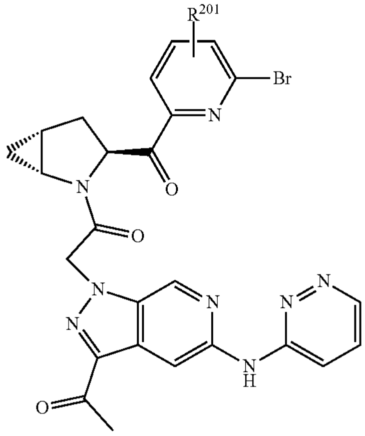
Formula I-102
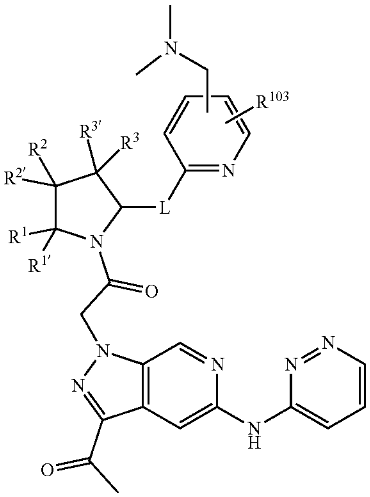
Formula I-103
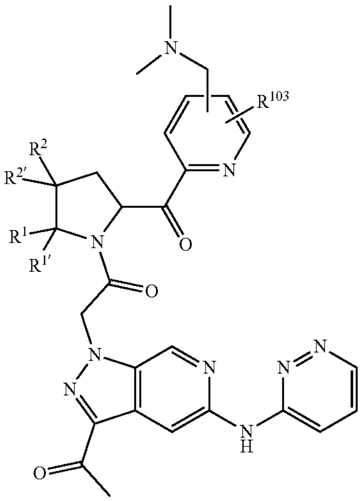
TABLE 1A-continued
Additional Exemplary Formulas within the Present Invention.
Formula I-104
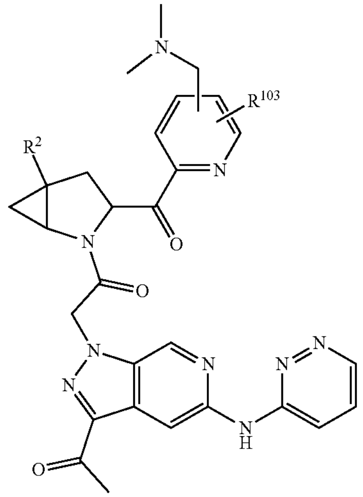
Formula I-105
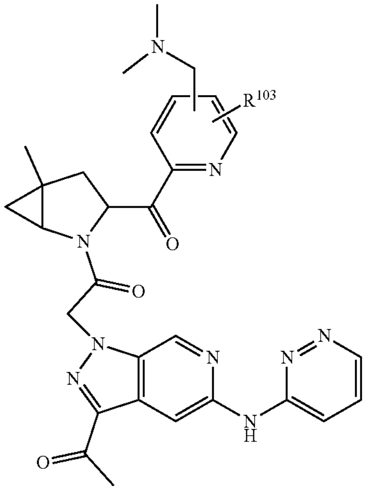
Formula I-106
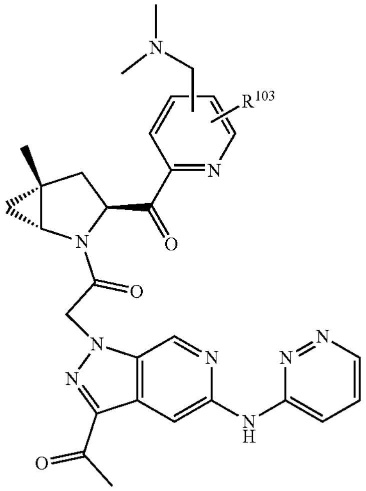

TABLE 1A-continued
| Additional Exemplary Formulas within the Present Invention. |
| --- |
Formula I-107
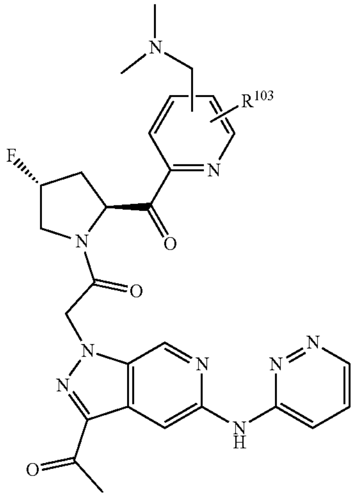
Formula I-108
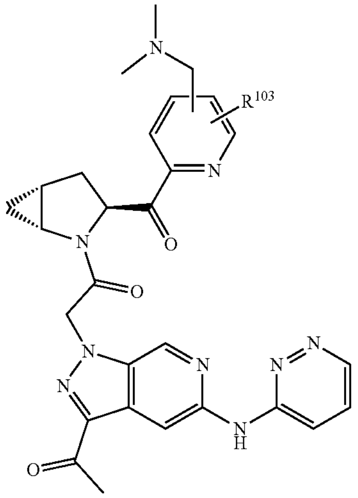
Formula I-109
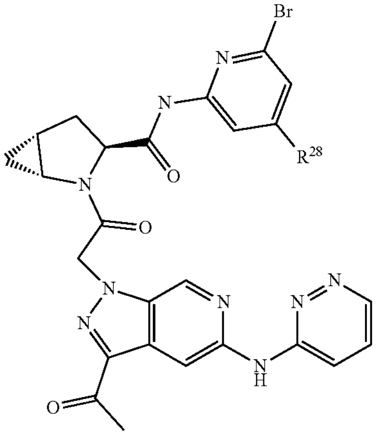
TABLE 1A-continued
| Additional Exemplary Formulas within the Present Invention. |
| --- |
Formula I-110
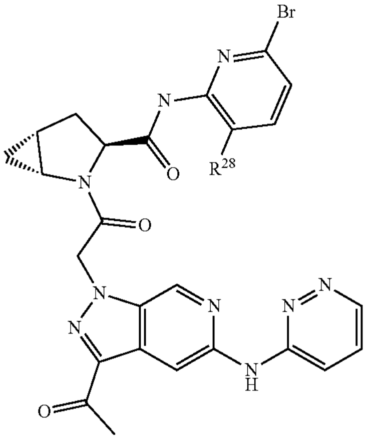
Formula I-111
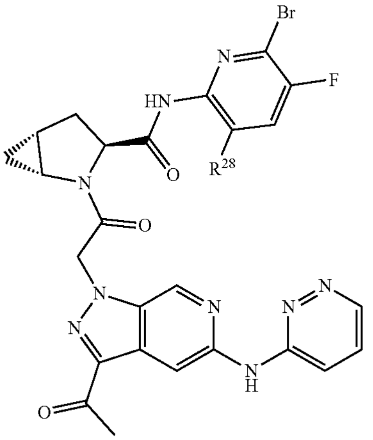
Formula I-112
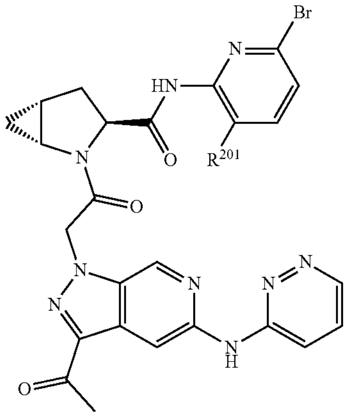

TABLE 1A-continued
Additional Exemplary Formulas within the Present Invention.
Formula I-113
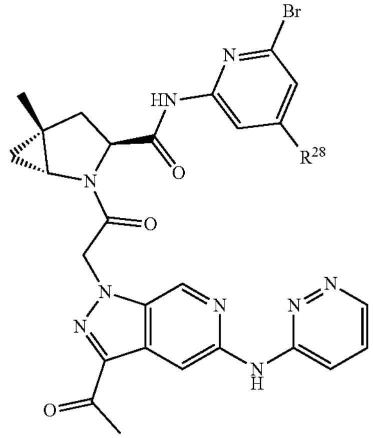
Formula I-114
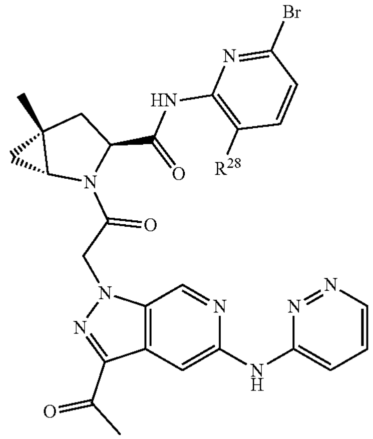
Formula I-115
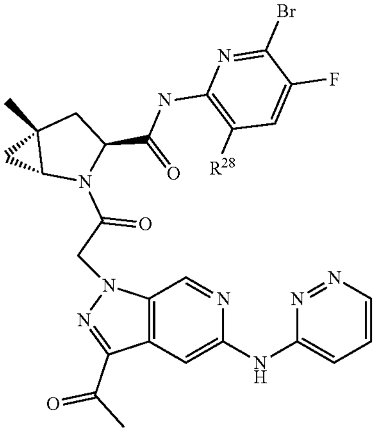
TABLE 1A-continued
Additional Exemplary Formulas within the Present Invention.
Formula I-116
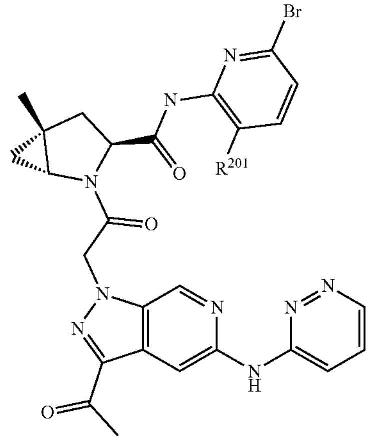
Formula I-117
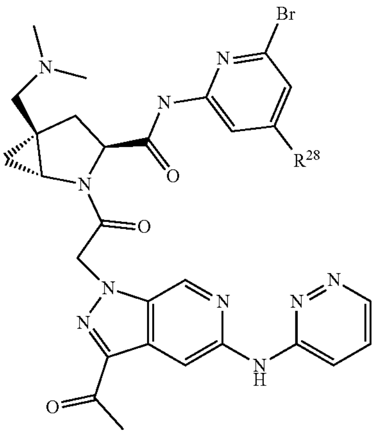
Formula I-118
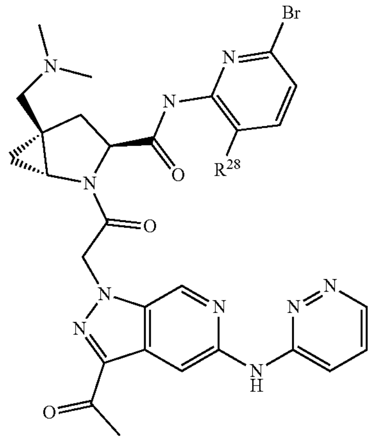

TABLE 1A-continued
Additional Exemplary Formulas within the Present Invention.
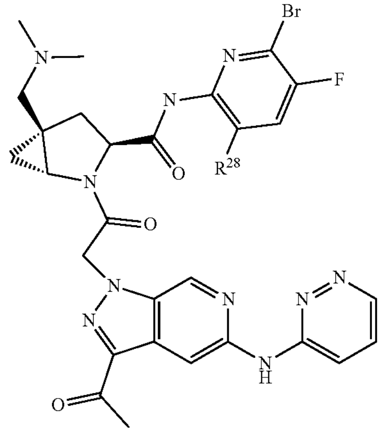
Formula I-119
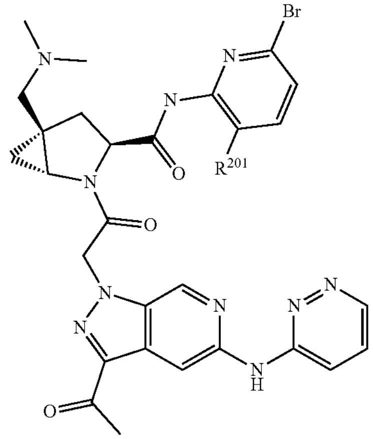
Formula I-120
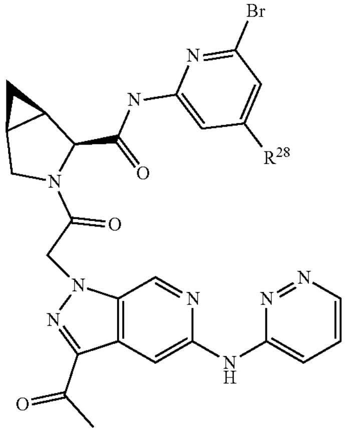
Formula I-121
TABLE 1A-continued
Additional Exemplary Formulas within the Present Invention.
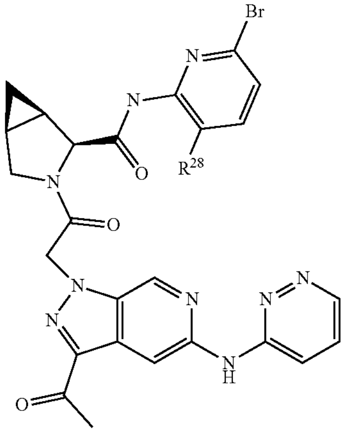
Formula I-122
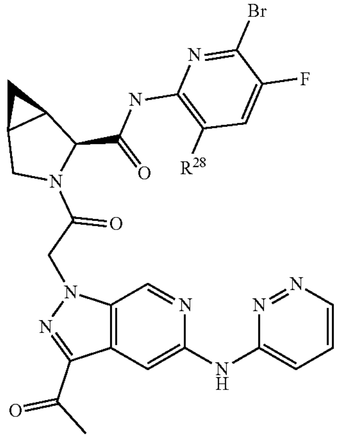
Formula I-123
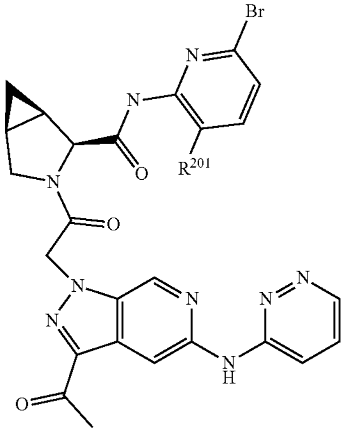
Formula I-124

TABLE 1A-continued
Additional Exemplary Formulas within the Present Invention.
Formula I-125
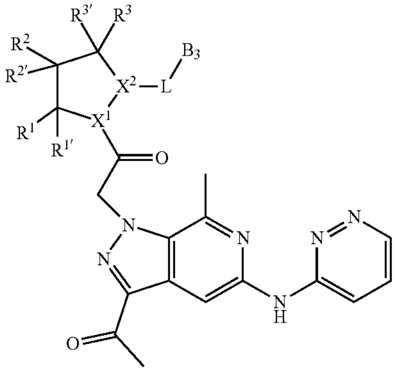
Formula I-126
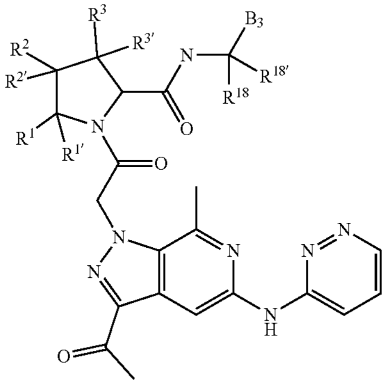
Formula I-127
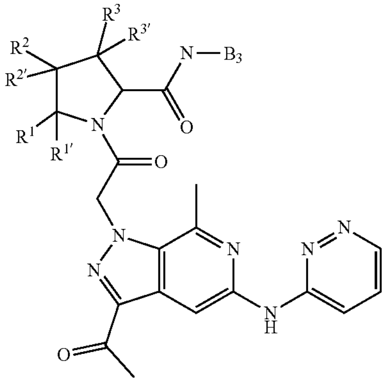
Formula I-128
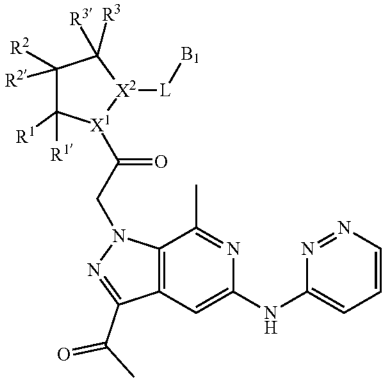
TABLE 1A-continued
Additional Exemplary Formulas within the Present Invention.
Formula I-129
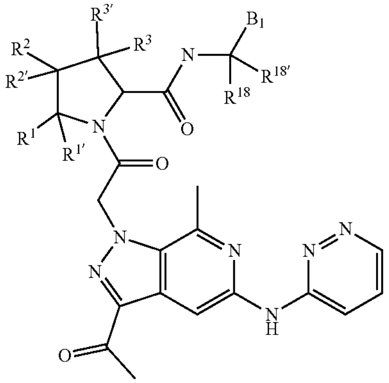
Formula I-130
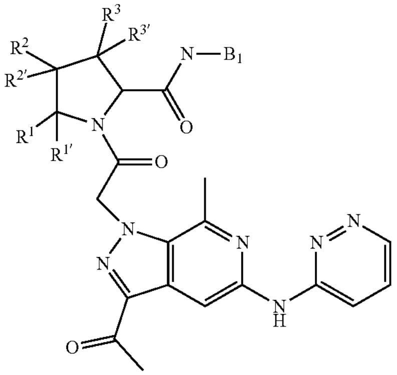
Formula I-131
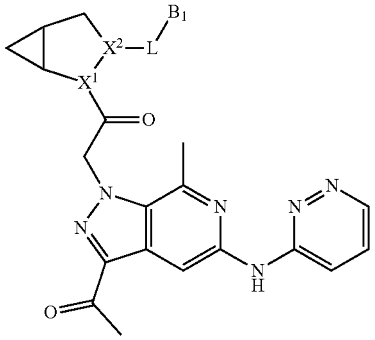
Formula I-132
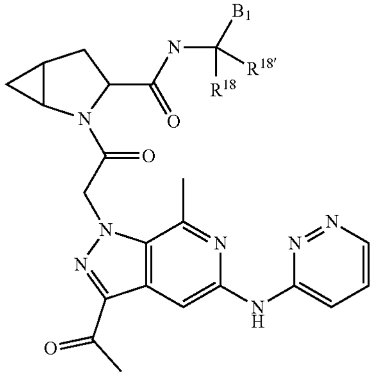

TABLE 1A-continued
Additional Exemplary Formulas within the Present Invention.
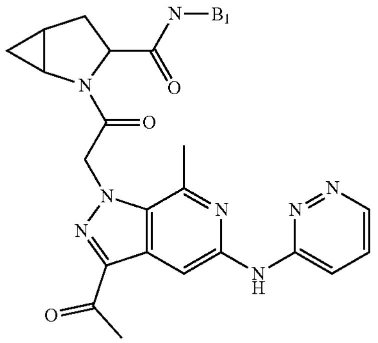
Formula I-133
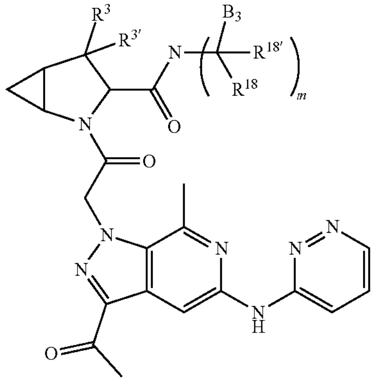
Formula I-134
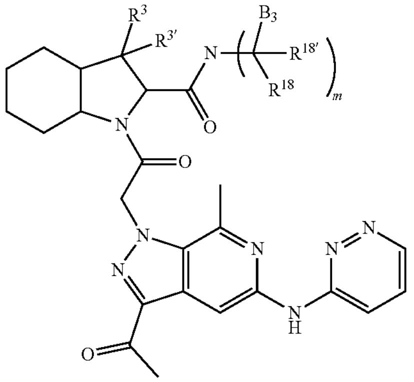
Formula I-135
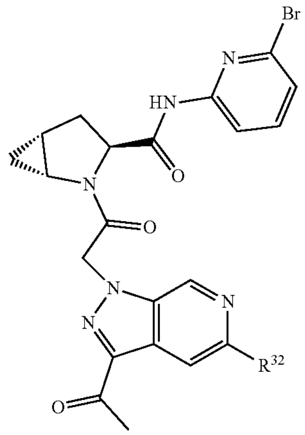
Formula I-223
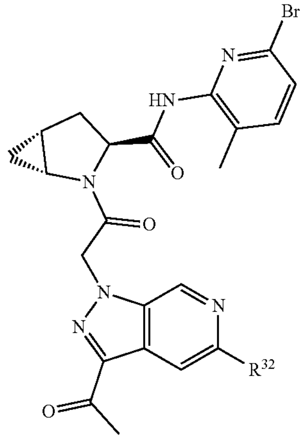
Formula I-224
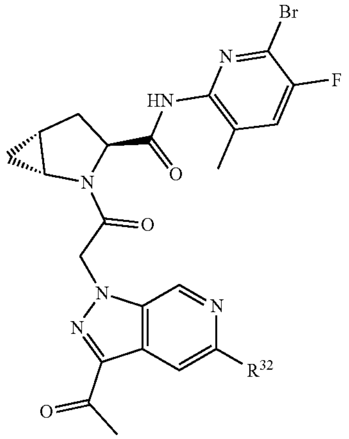
Formula I-225
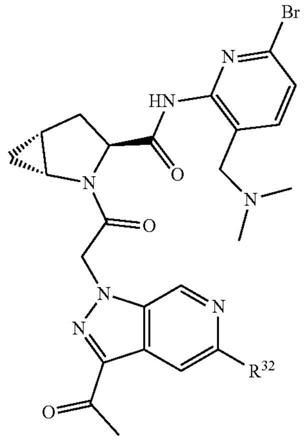
Formula I-226

TABLE 1A-continued
Additional Exemplary Formulas within the Present Invention.
Formula I-227
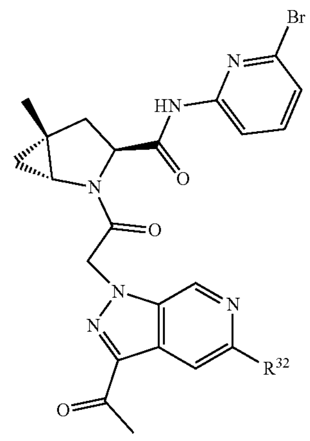
Formula I-228
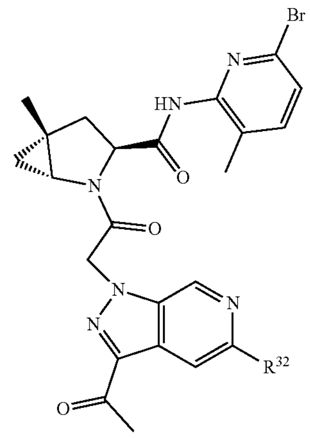
Formula I-229
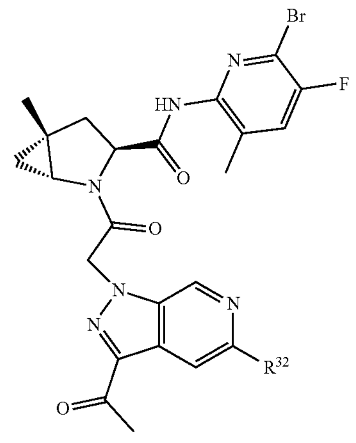
TABLE 1A-continued
Additional Exemplary Formulas within the Present Invention.
Formula I-230
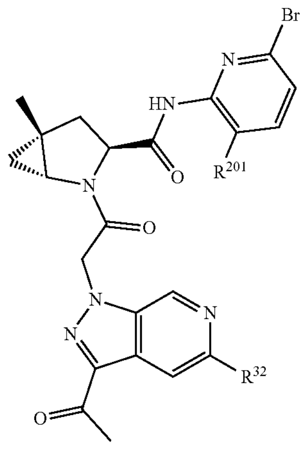
Formula I-232
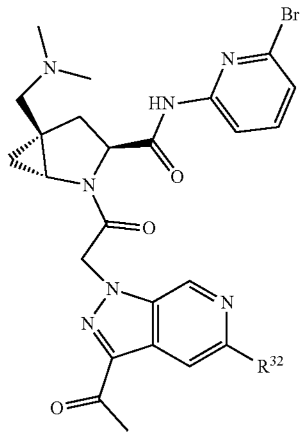
Formula I-233
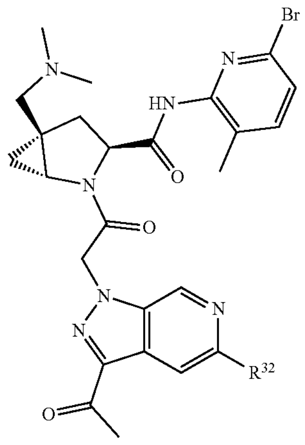

TABLE 1A-continued
Additional Exemplary Formulas within the Present Invention.
Formula I-234
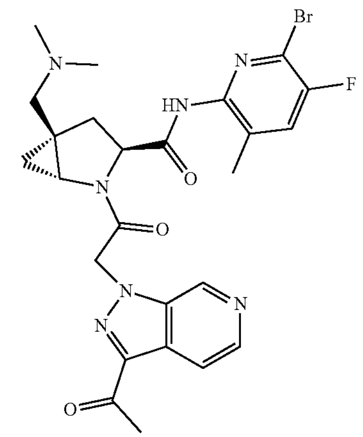 [SMILES: CC(=O)c1nn(CC(=O)N2[C@H](C(=O)Nc3nc(Br)c(F)cc3C)C[C@@]3(CN(C)C)C[C@@H]23)c2cnccc12]
Formula I-235
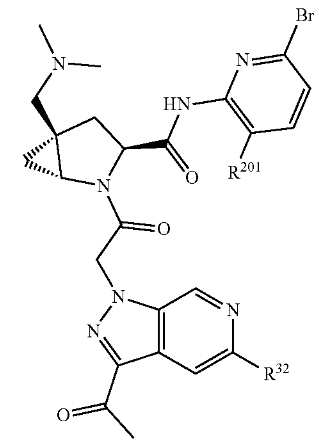
Formula I-236
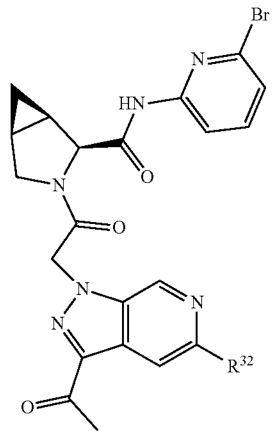
TABLE 1A-continued
Additional Exemplary Formulas within the Present Invention.
Formula I-237
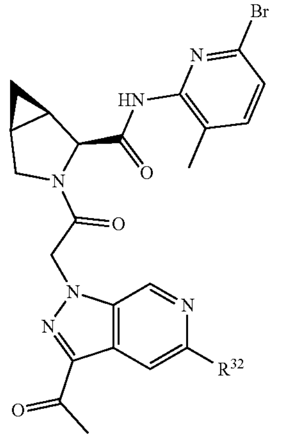
Formula I-238
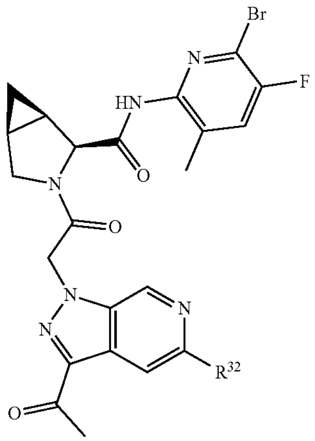
Formula I-239
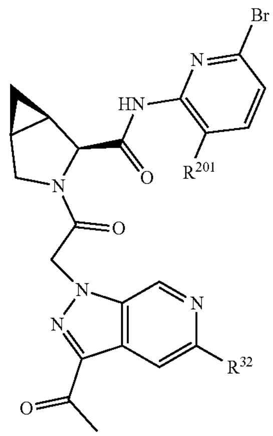

TABLE 1A-continued
Additional Exemplary Formulas within the Present Invention.
Formula I-91
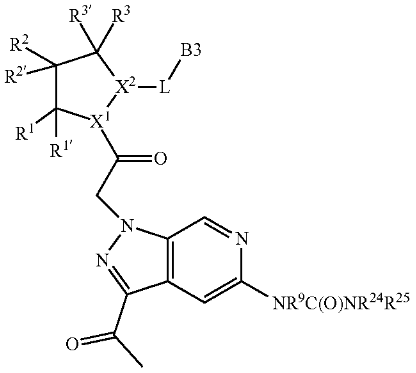
Formula I-92
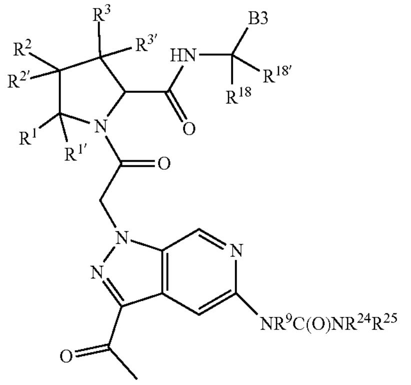
Formula I-93
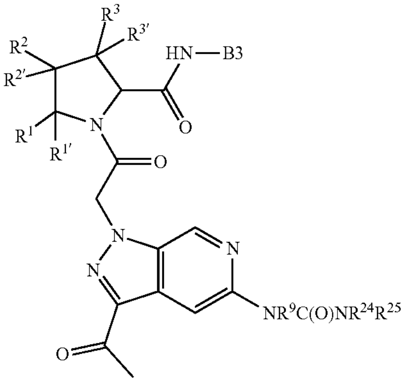
Formula I-94
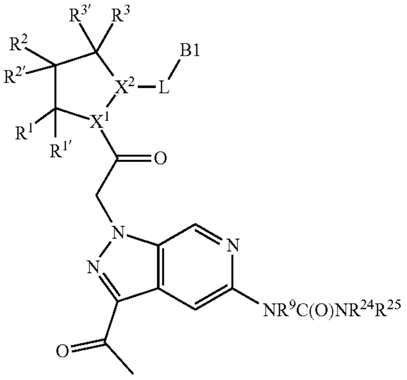
TABLE 1A-continued
Additional Exemplary Formulas within the Present Invention.
Formula I-95
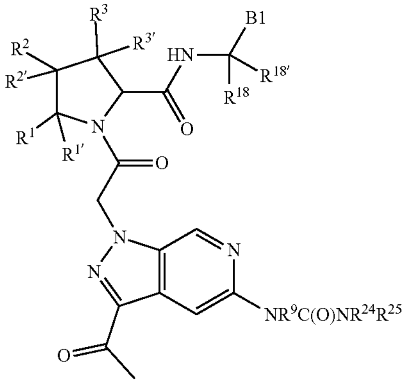
Formula I-96
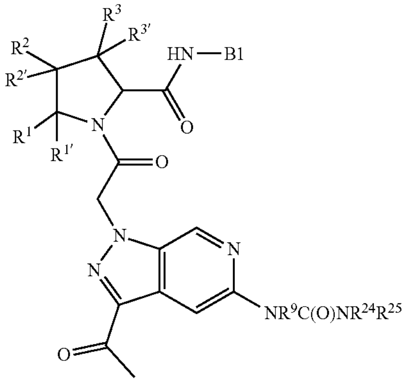
Formula I-97
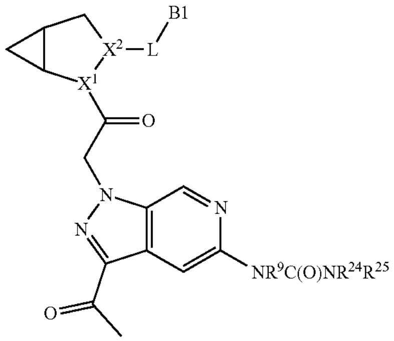
Formula I-98
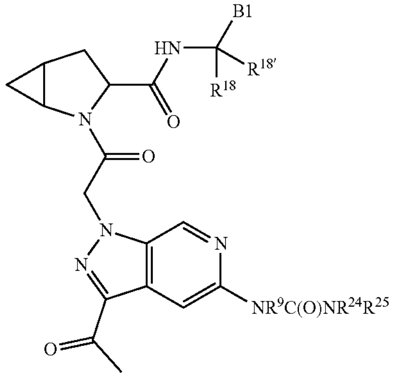

TABLE 1A-continued
Additional Exemplary Formulas within the Present Invention.
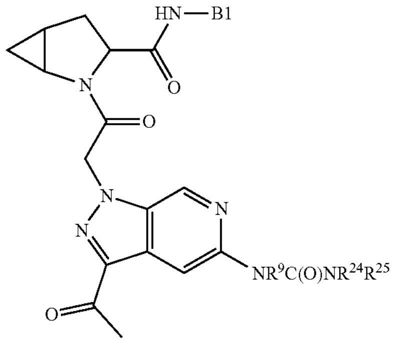
Formula I-99
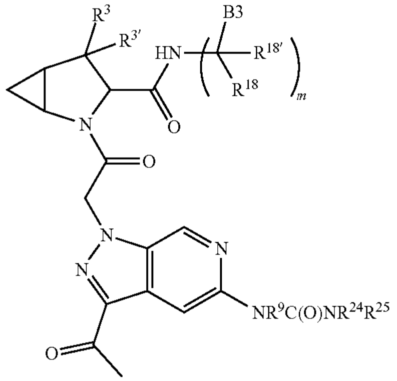
Formula I-100
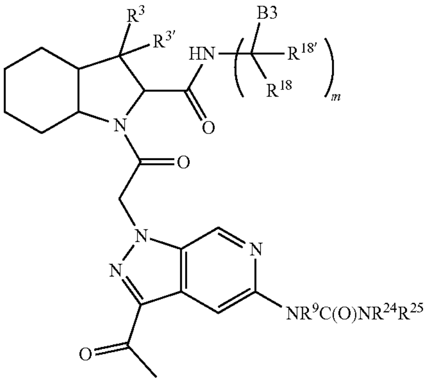
Formula I-101
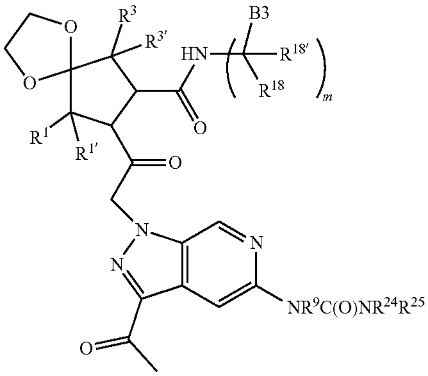
Formula I-102
TABLE 1A-continued
Additional Exemplary Formulas within the Present Invention.
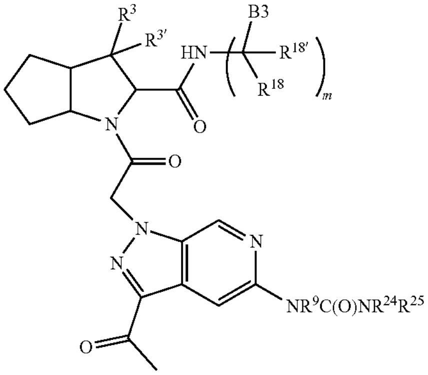
Formula I-103
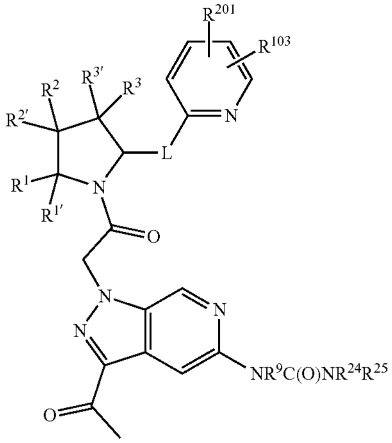
Formula I-104
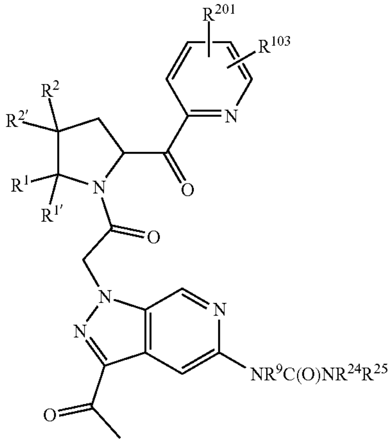
Formula I-105

TABLE 1A-continued
Additional Exemplary Formulas within the Present Invention.
Formula I-106
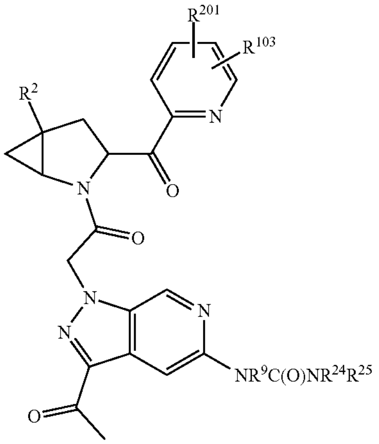
Formula I-107
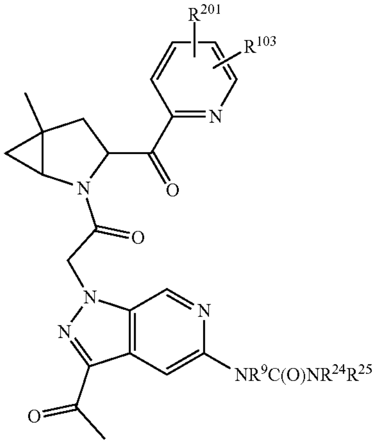
Formula I-108
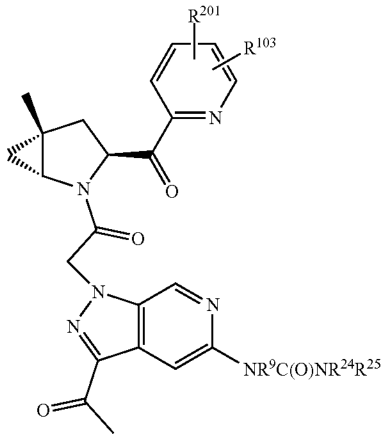
TABLE 1A-continued
Additional Exemplary Formulas within the Present Invention.
Formula I-109
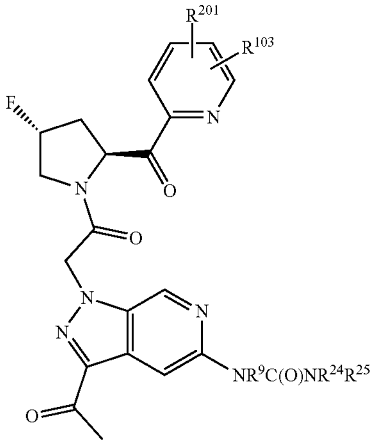
Formula I-110
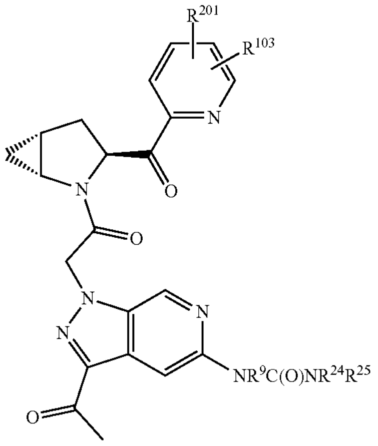
Formula I-111
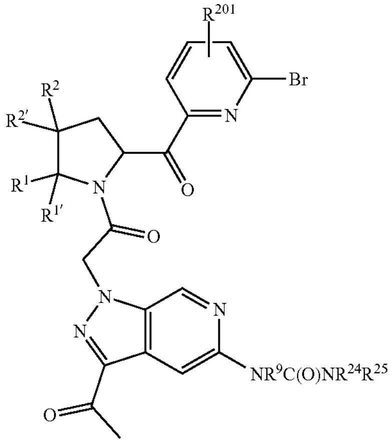

TABLE 1A-continued
Additional Exemplary Formulas within the Present Invention.
Formula I-112
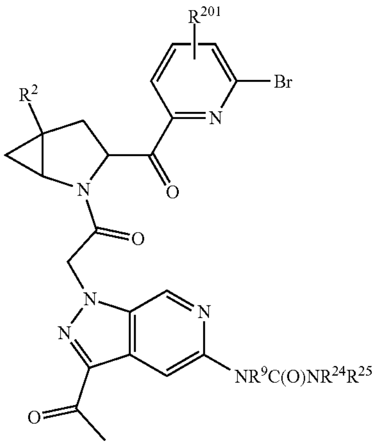
Formula I-113
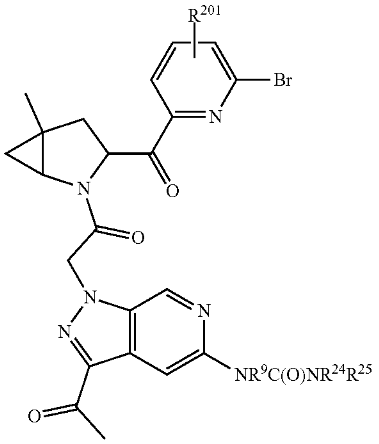
Formula I-114
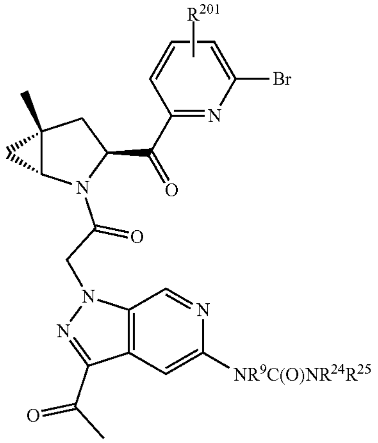
Formula I-115
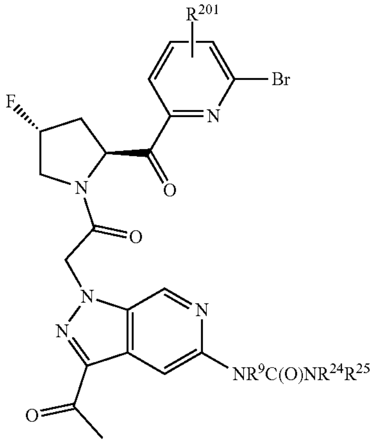
Formula I-116
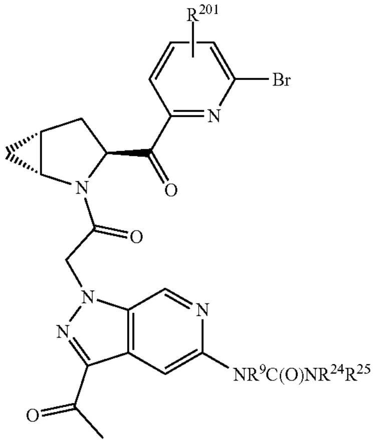
Formula I-117
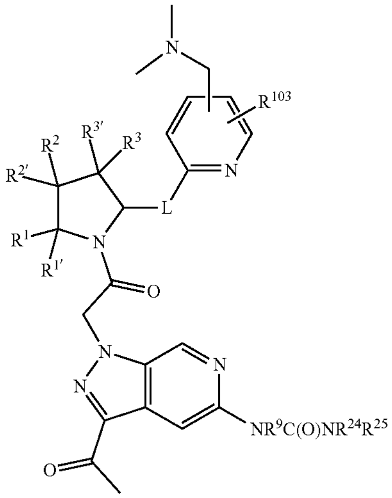

TABLE 1A-continued
Additional Exemplary Formulas within the Present Invention.
Formula I-118
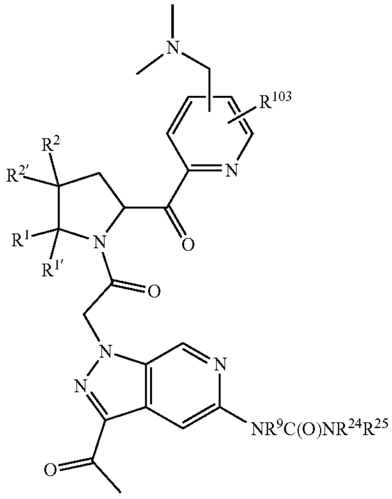
Formula I-119
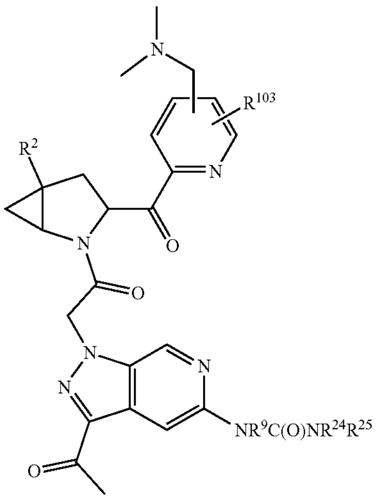
Formula I-120
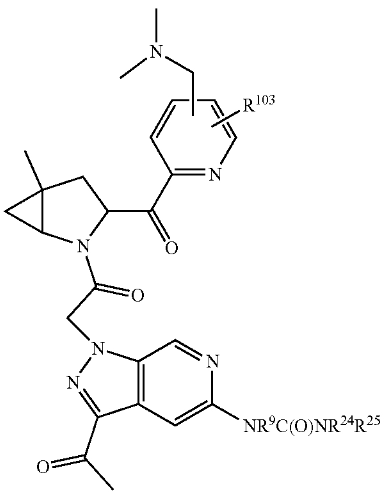
TABLE 1A-continued
Additional Exemplary Formulas within the Present Invention.
Formula I-121
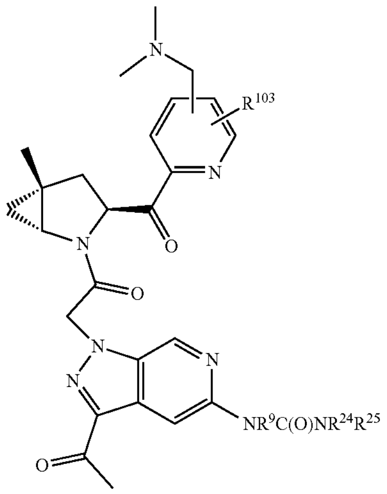
Formula I-122
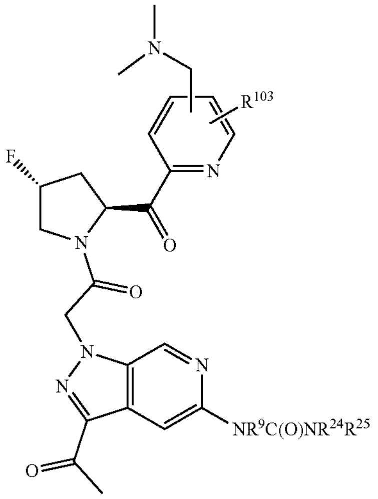
Formula I-123
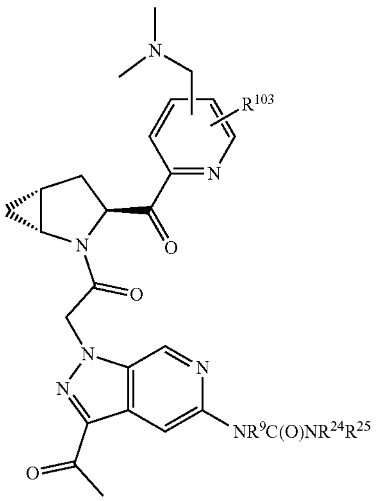

TABLE 1A-continued
Additional Exemplary Formulas within the Present Invention.
Formula I-124
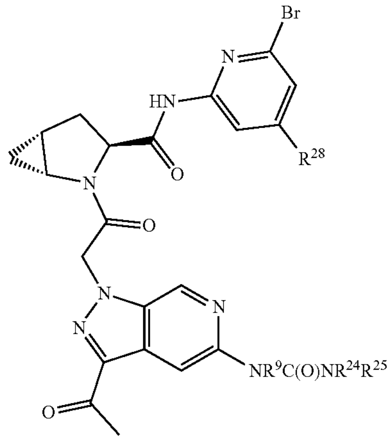
Formula I-125
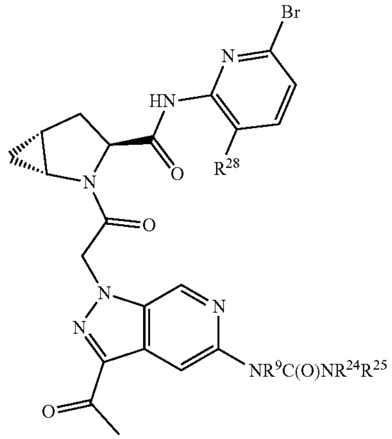
Formula I-126
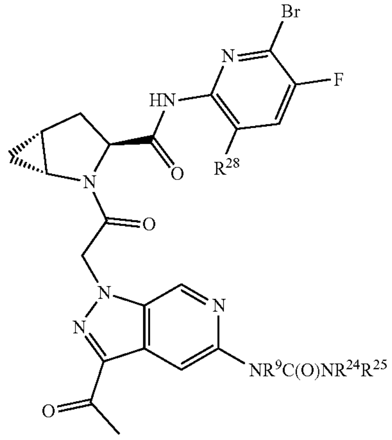
TABLE 1A-continued
Additional Exemplary Formulas within the Present Invention.
Formula I-127
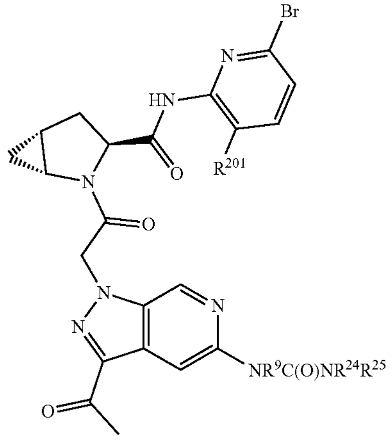
Formula I-128
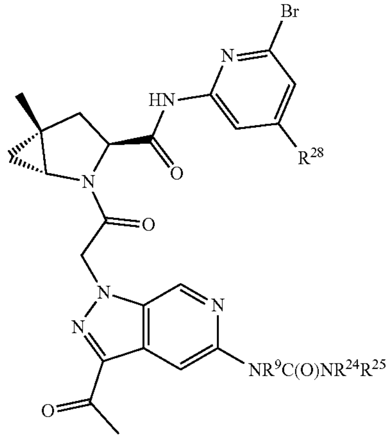
Formula I-129
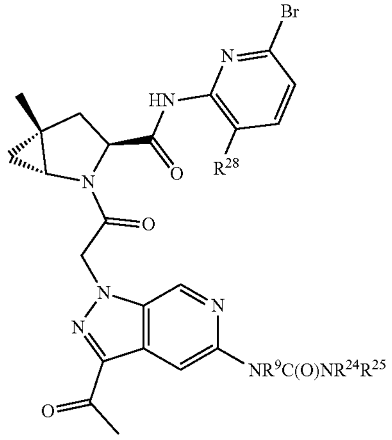

TABLE 1A-continued
| Additional Exemplary Formulas within the Present Invention. |
| --- |
Formula I-130
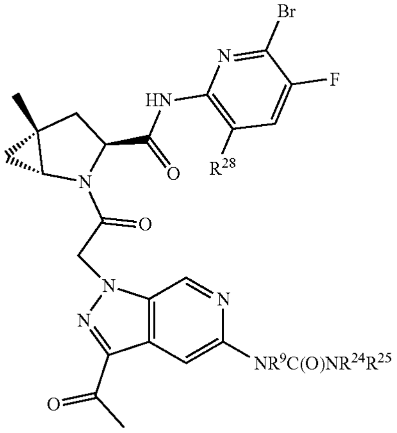
Formula I-131
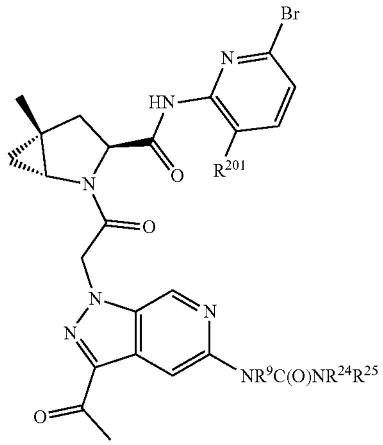
Formula I-132
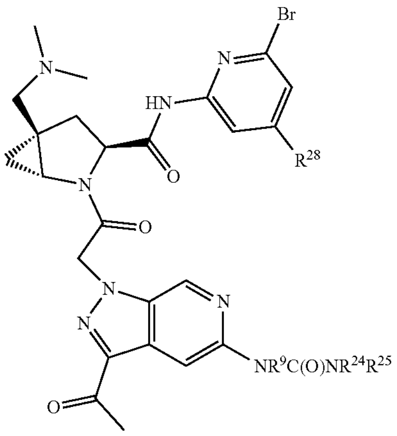
TABLE 1A-continued
| Additional Exemplary Formulas within the Present Invention. |
| --- |
Formula I-133
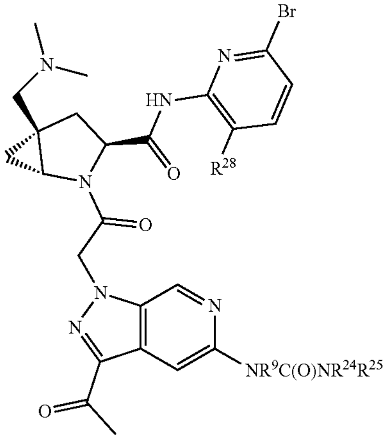
Formula I-134
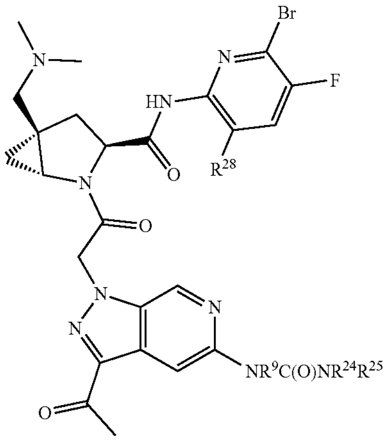
Formula I-135
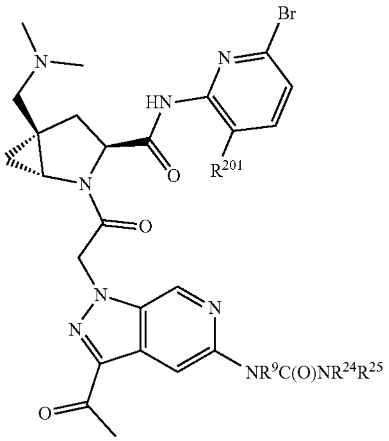

TABLE 1A-continued
Additional Exemplary Formulas within the Present Invention.
Formula I-136
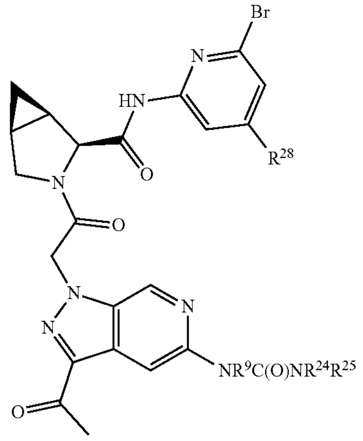
Formula I-137
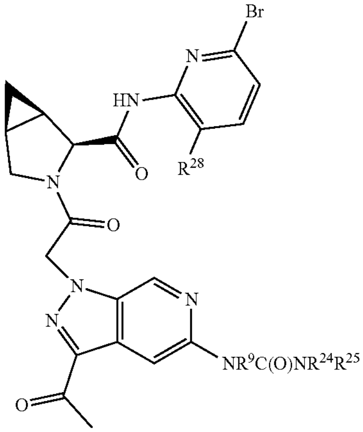
Formula I-138
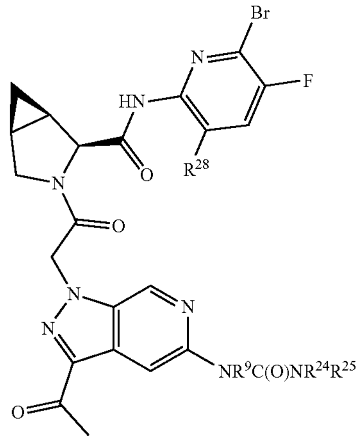
Formula I-139
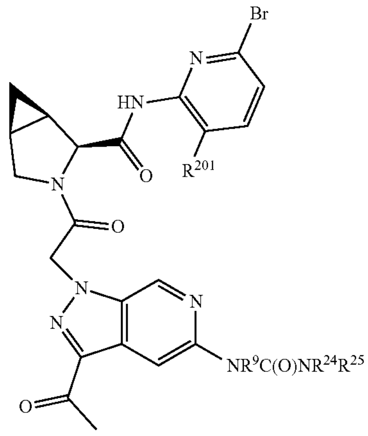
Formula I-140
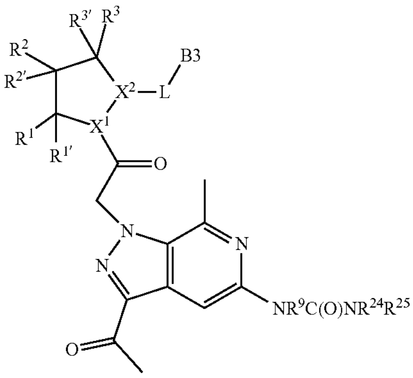
Formula I-141
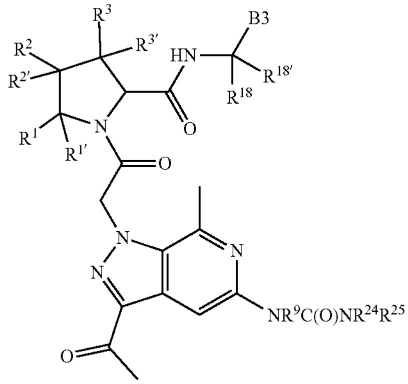
Formula I-142
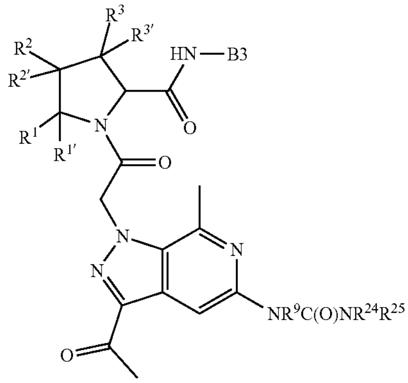

TABLE 1A-continued
| Additional Exemplary Formulas within the Present Invention. |
| --- |
Formula I-143
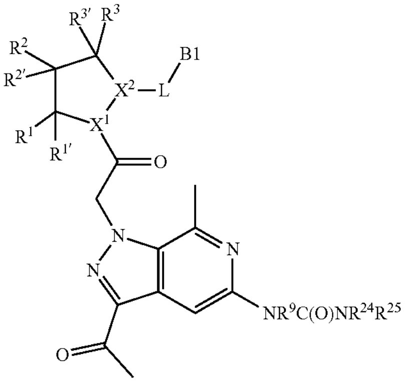
Formula I-144
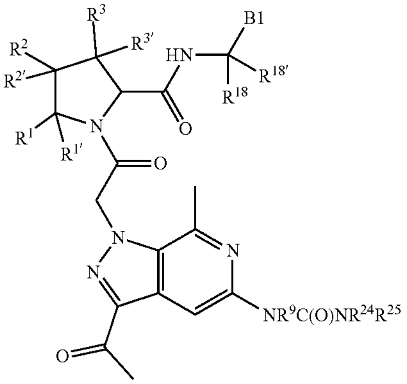
Formula I-145
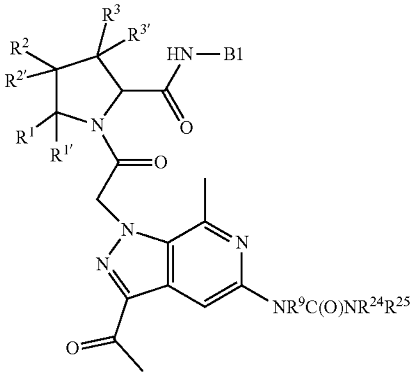
Formula I-146
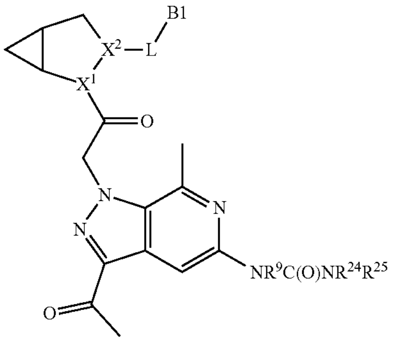
TABLE 1A-continued
| Additional Exemplary Formulas within the Present Invention. |
| --- |
Formula I-147
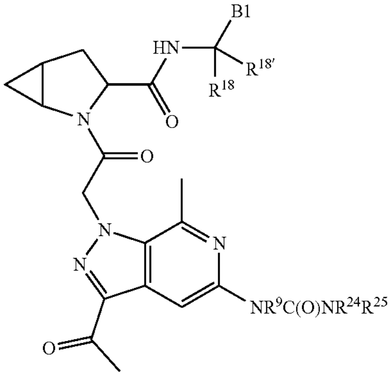
Formula I-148
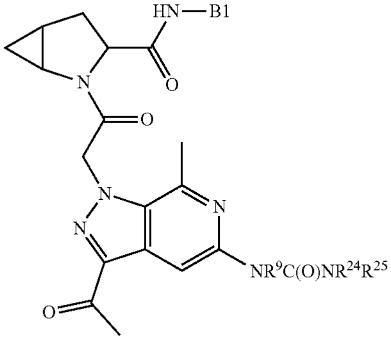
Formula I-149
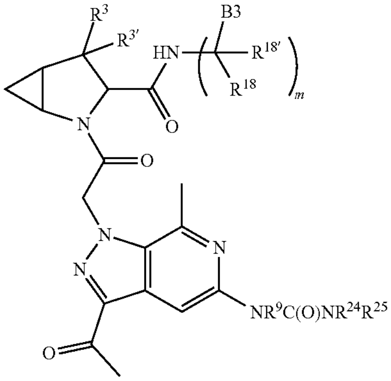
Formula I-150
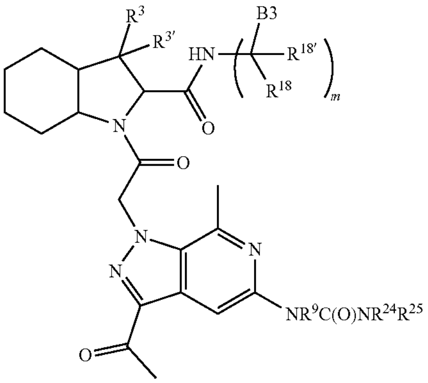

TABLE 1A-continued
| Additional Exemplary Formulas within the Present Invention. |
|---|
| 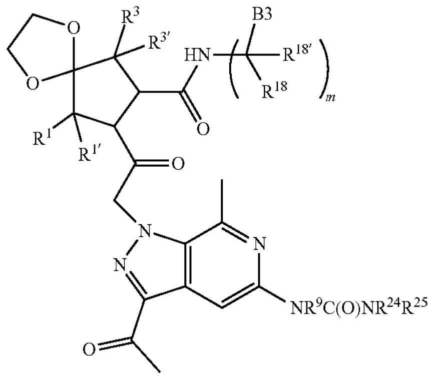 Formula I-151 |
| 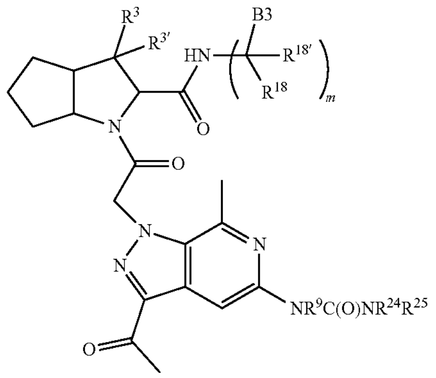 Formula I-152 |
| 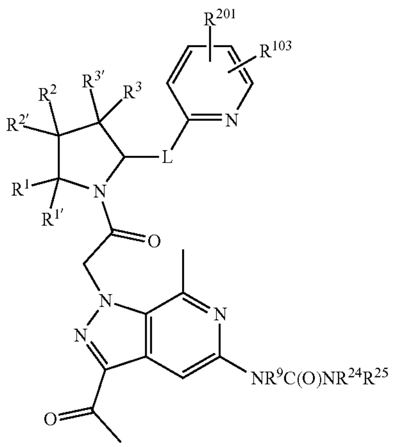 Formula I-153 |
TABLE 1A-continued
| Additional Exemplary Formulas within the Present Invention. |
|---|
| 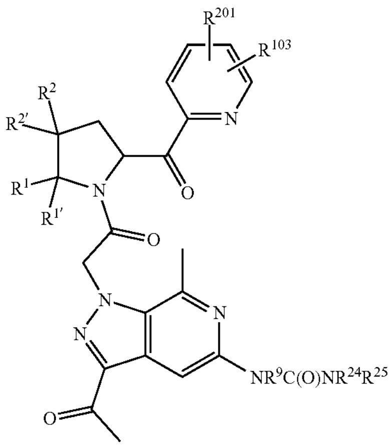 Formula I-154 |
| 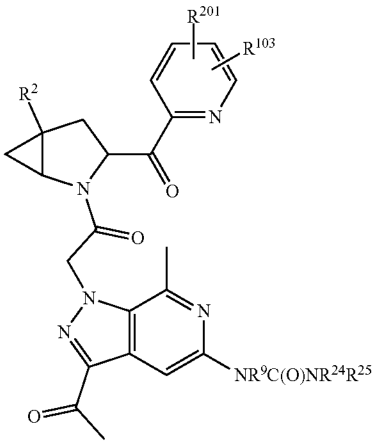 Formula I-155 |
| 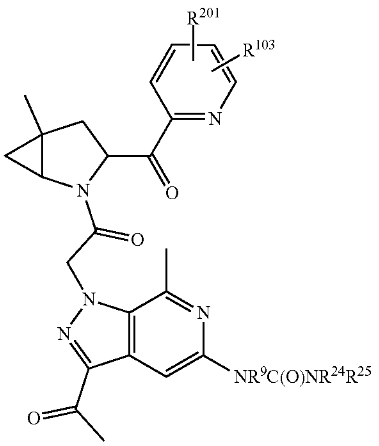 Formula I-156 |

TABLE 1A-continued
Additional Exemplary Formulas within the Present Invention.
Formula I-157
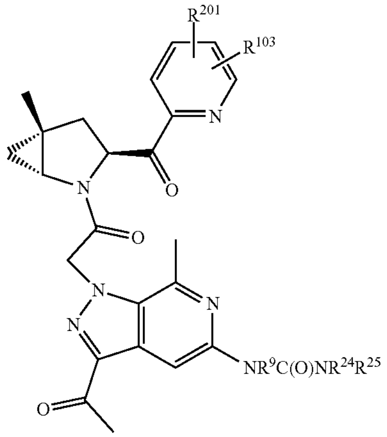
Formula I-158
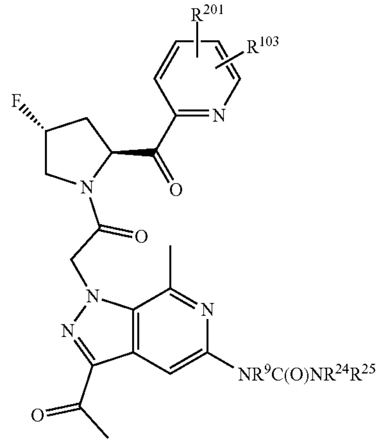
Formula I-159
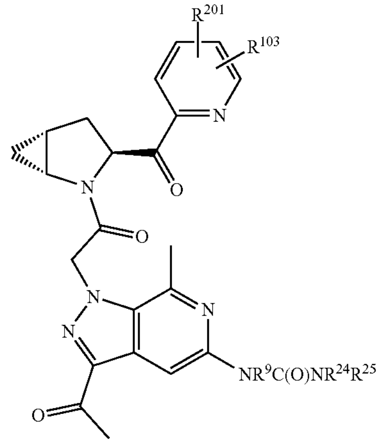
TABLE 1A-continued
Additional Exemplary Formulas within the Present Invention.
Formula I-160
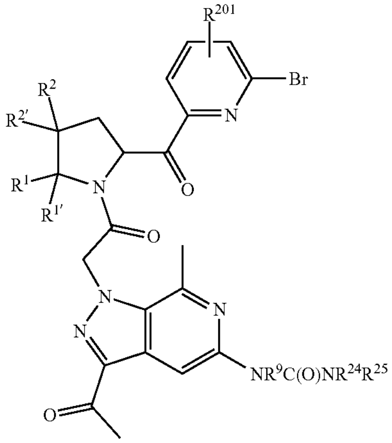
Formula I-161
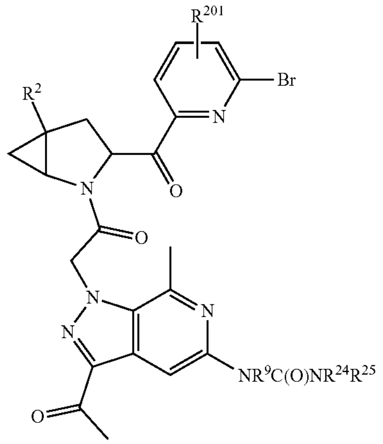
Formula I-162
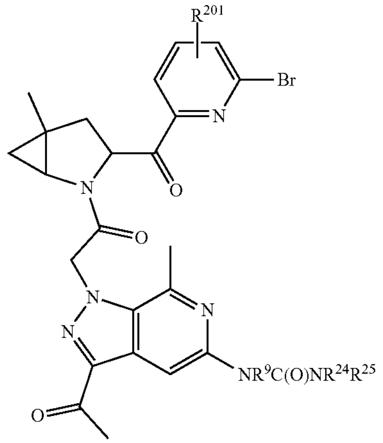

TABLE 1A-continued
| Additional Exemplary Formulas within the Present Invention. |
| --- |
Formula I-163
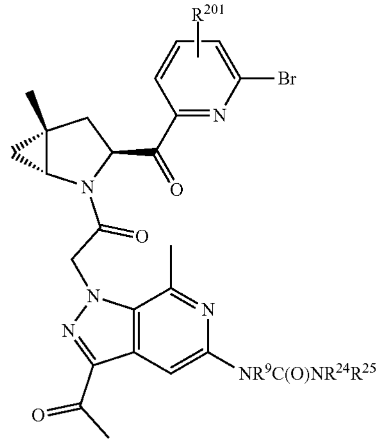
Formula I-164
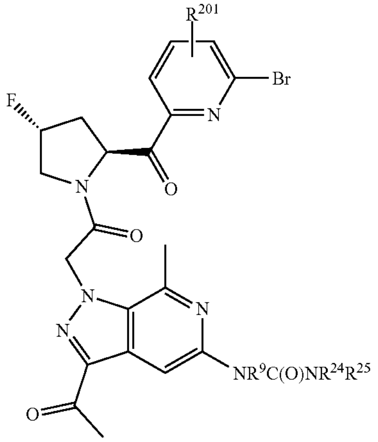
Formula I-165
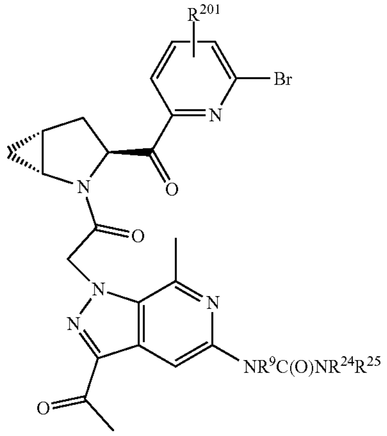
TABLE 1A-continued
| Additional Exemplary Formulas within the Present Invention. |
| --- |
Formula I-166
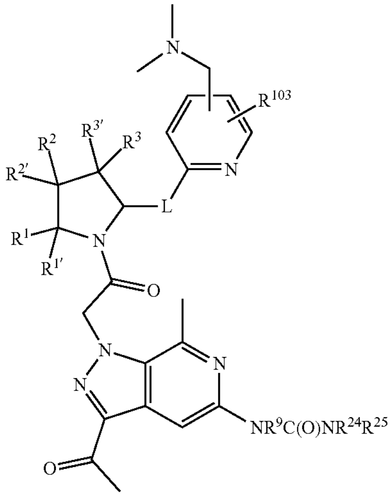
Formula I-167
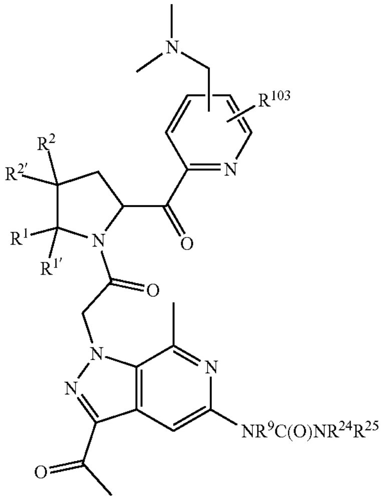
Formula I-168
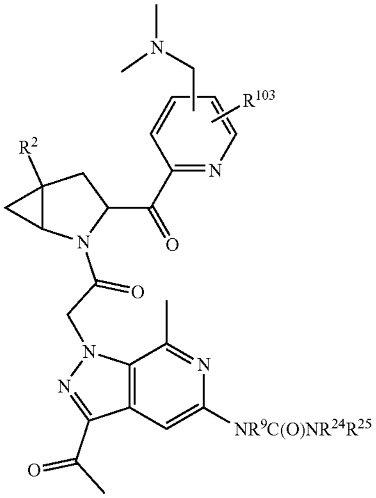

TABLE 1A-continued
Additional Exemplary Formulas within the Present Invention.
Formula I-169
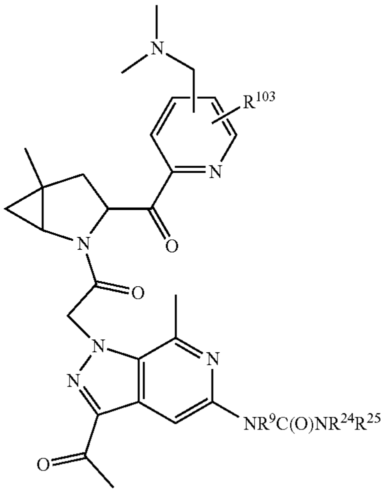
Formula I-170
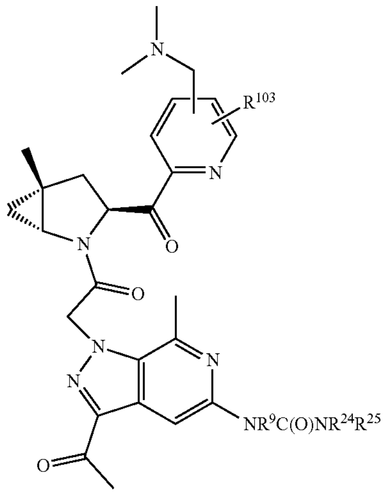
Formula I-171
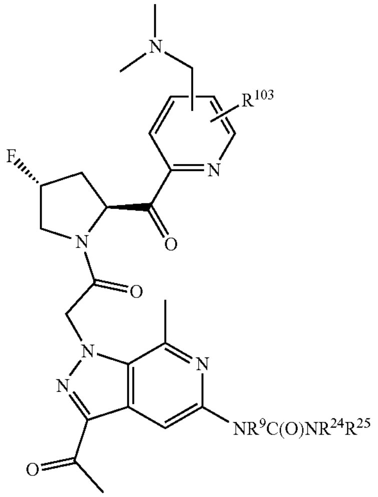
TABLE 1A-continued
Additional Exemplary Formulas within the Present Invention.
Formula I-172
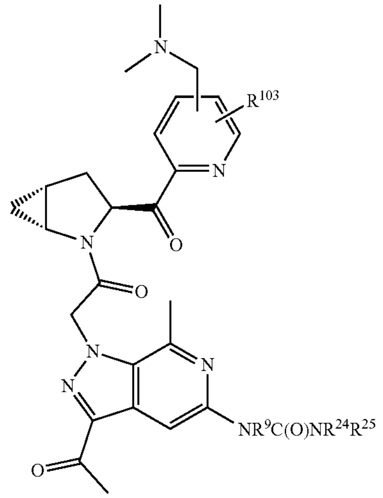
Formula I-173
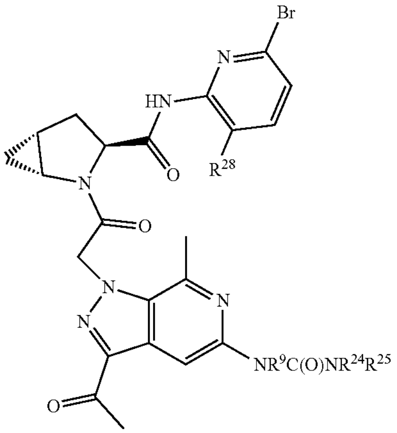
Formula I-174
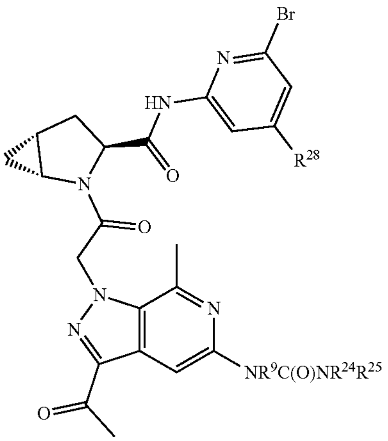

TABLE 1A-continued
Additional Exemplary Formulas within the Present Invention.
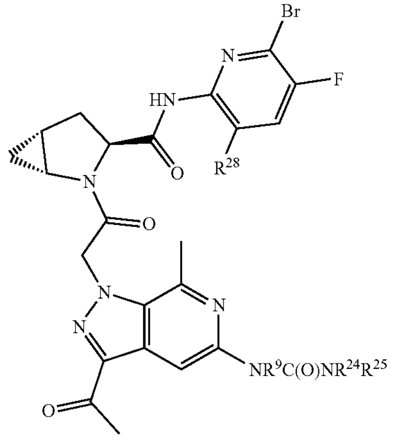
Formula I-175
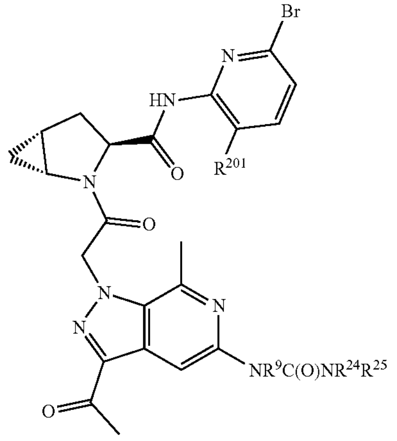
Formula I-176
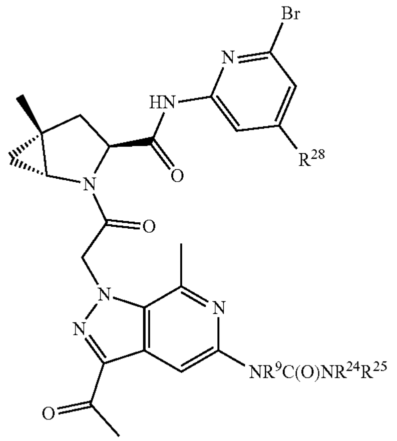
Formula I-177
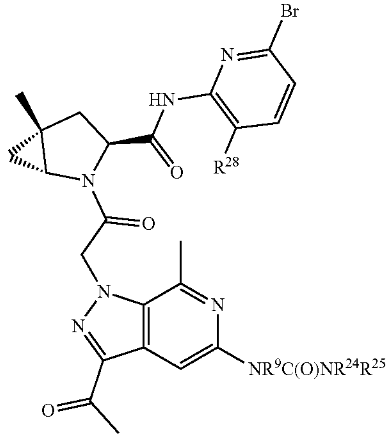
Formula I-178
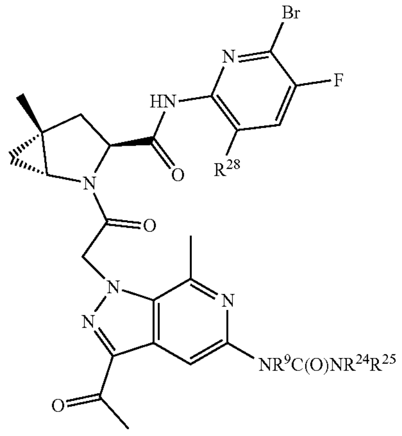
Formula I-179
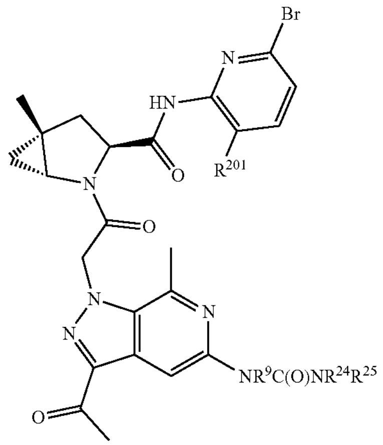
Formula I-180

TABLE 1A-continued
Additional Exemplary Formulas within the Present Invention.
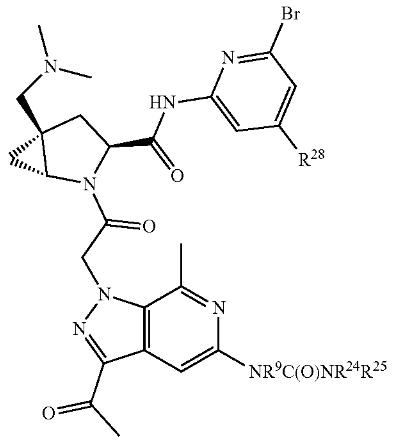
Formula I-181
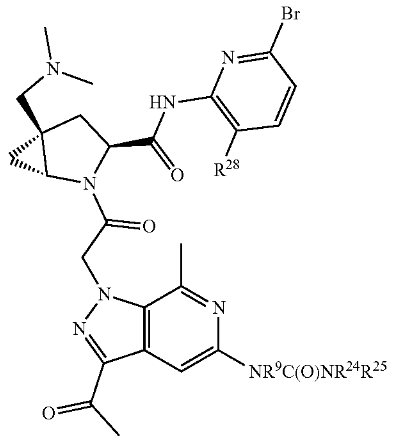
Formula I-182
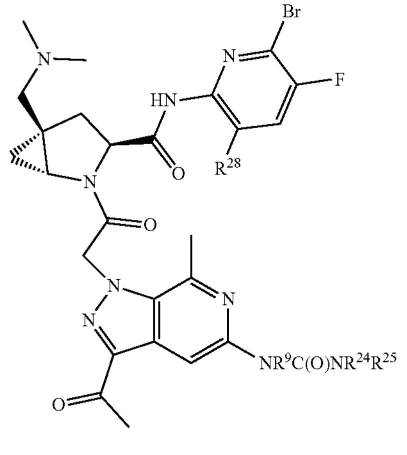
Formula I-183
TABLE 1A-continued
Additional Exemplary Formulas within the Present Invention.
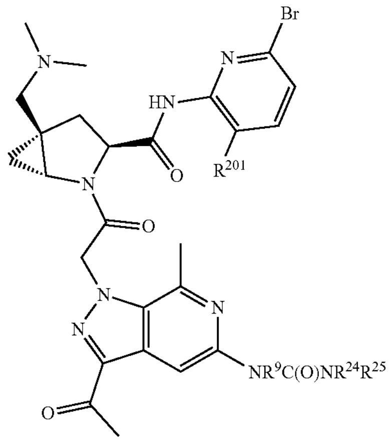
Formula I-184
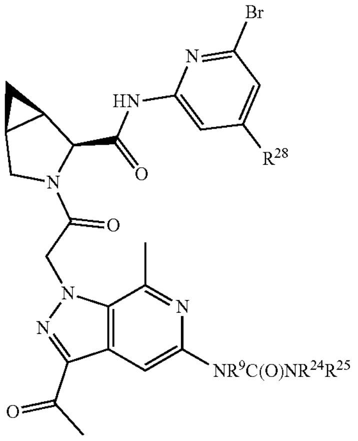
Formula I-185
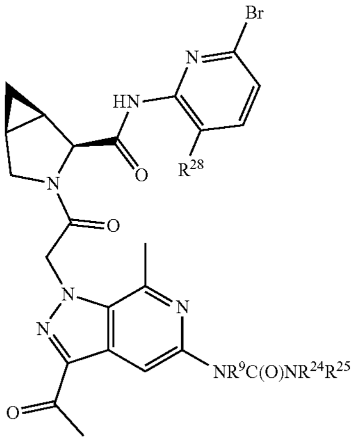
Formula I-186

TABLE 1A-continued

| Additional Exemplary Formulas within the Present Invention. |
|---|
| Formula I-187 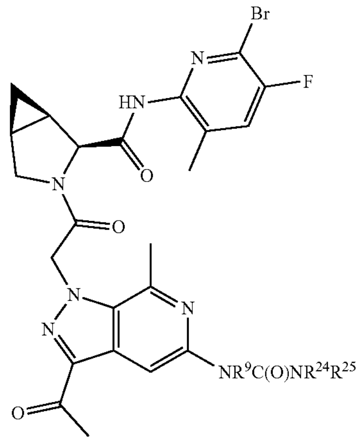 |
| Formula I-188 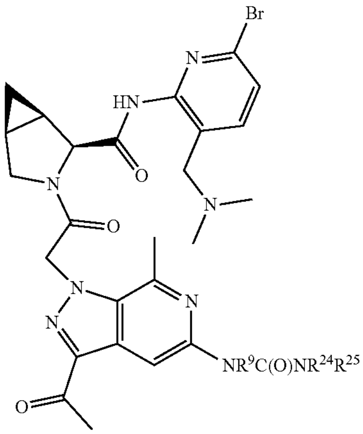 |

wherein $R^{103}$ is $C_1$-$C_4$ alkyl, $C_3$-$C_6$ cycloalkyl, fluorine, chlorine, or bromine.

TABLE 1B

| Additional Exemplary Formulas within the Present Invention. |
|---|
| Formula I-376 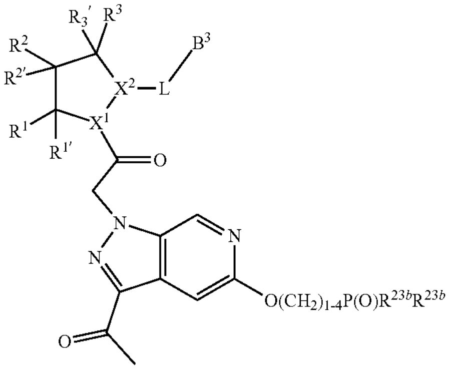 |

TABLE 1B-continued

| Additional Exemplary Formulas within the Present Invention. |
|---|
| Formula I-377 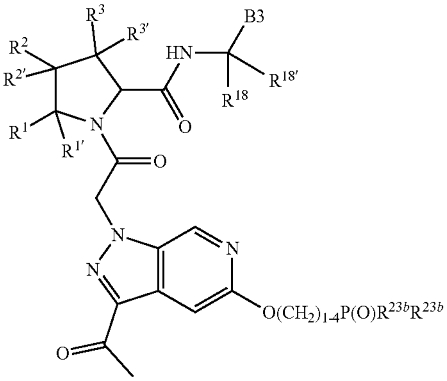 |
| Formula I-378 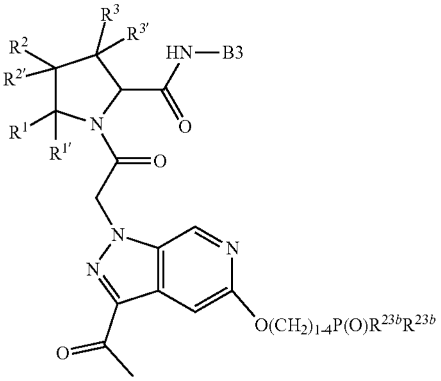 |
| Formula I-379 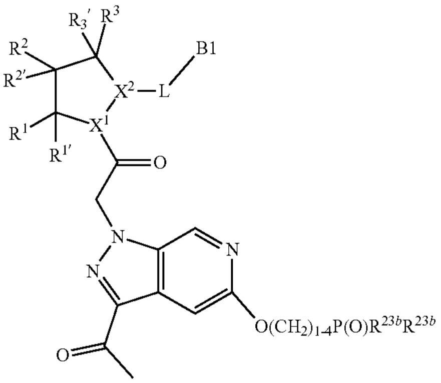 |
| Formula I-380 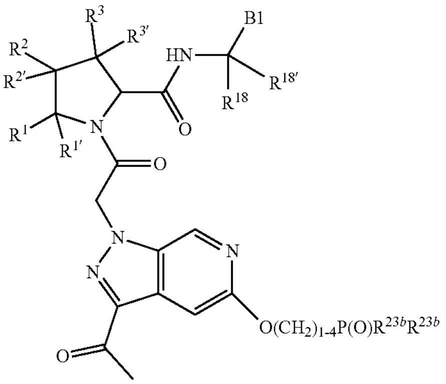 |

TABLE 1B-continued
| Additional Exemplary Formulas within the Present Invention. |
| --- |
Formula I-381
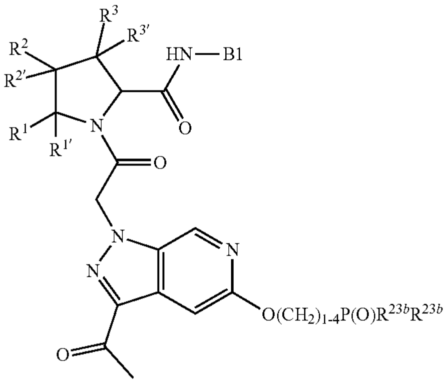
Formula I-382
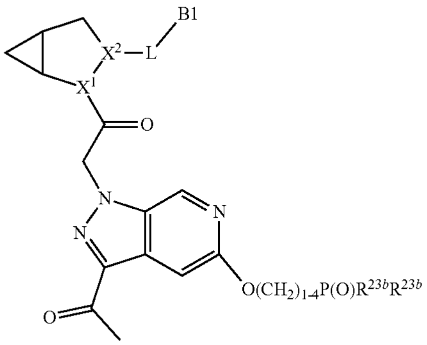
Formula I-383
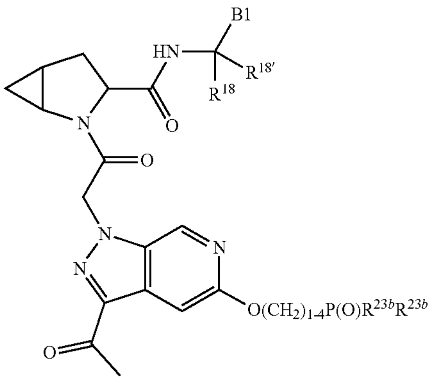
Formula I-384
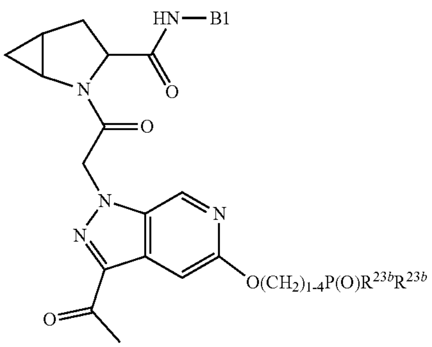
TABLE 1B-continued
| Additional Exemplary Formulas within the Present Invention. |
| --- |
Formula I-385
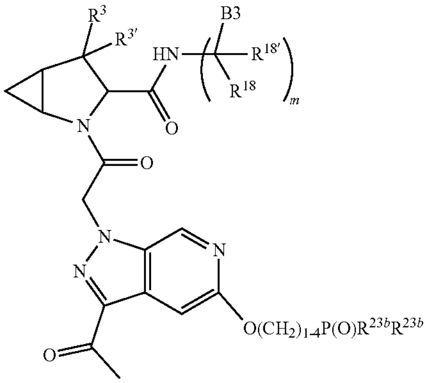
Formula I-386
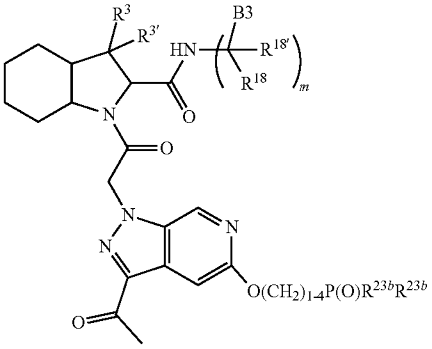
Formula I-387
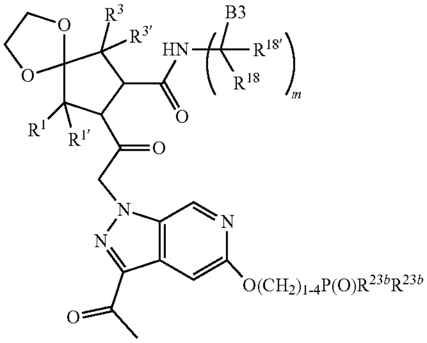
Formula I-388
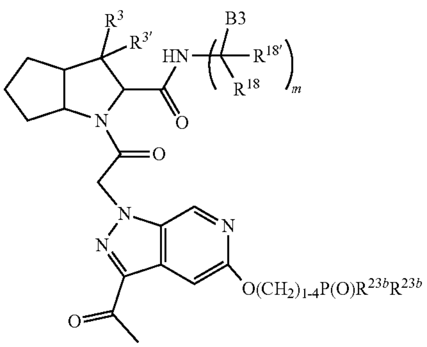

TABLE 1B-continued
| Additional Exemplary Formulas within the Present Invention. |
| --- |
Formula I-389
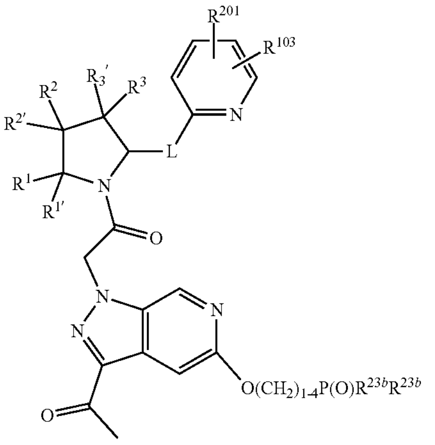
Formula I-390
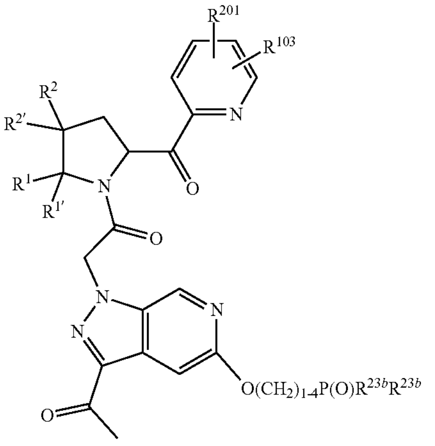
Formula I-391
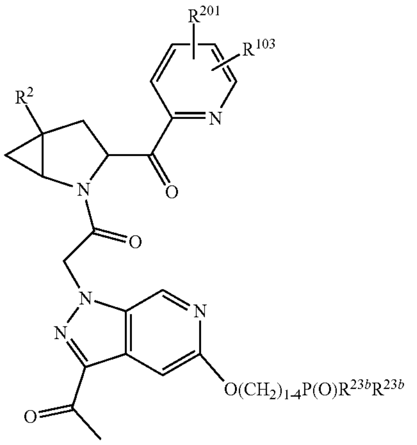
TABLE 1B-continued
| Additional Exemplary Formulas within the Present Invention. |
| --- |
Formula I-392
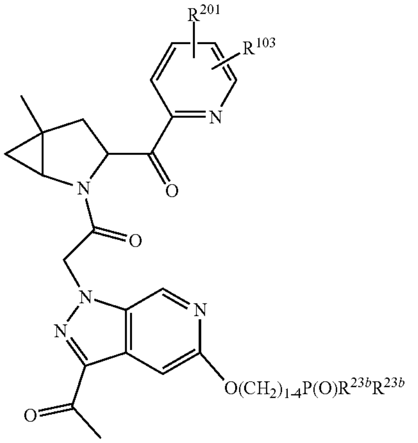
Formula I-393
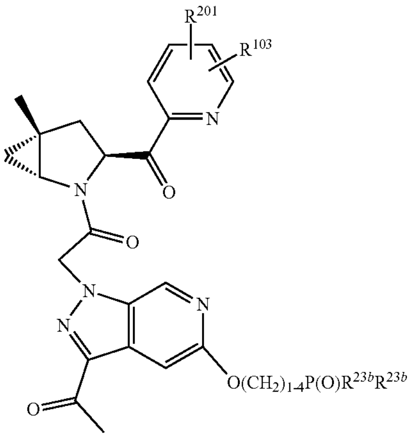
Formula I-394
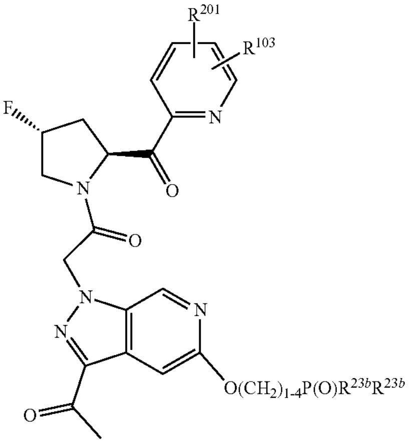

TABLE 1B-continued
Additional Exemplary Formulas within the Present Invention.
Formula I-395
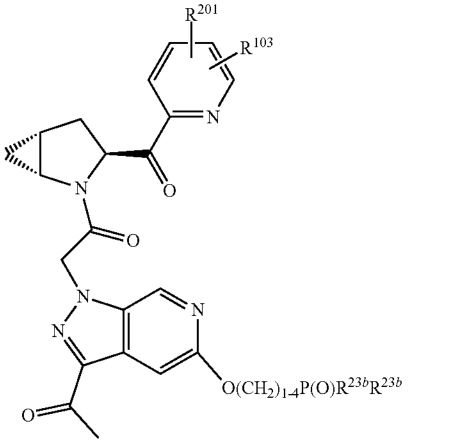
Formula I-396
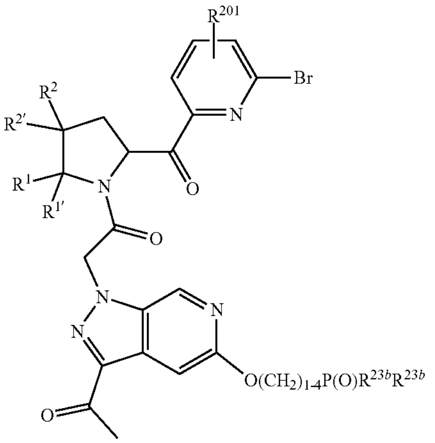
Formula I-397
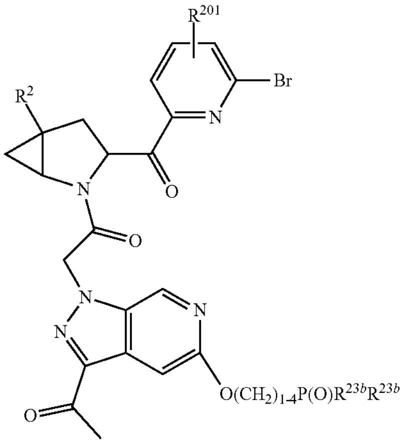
TABLE 1B-continued
Additional Exemplary Formulas within the Present Invention.
Formula I-398
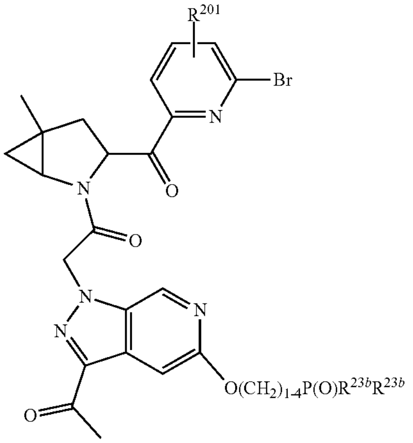
Formula I-399
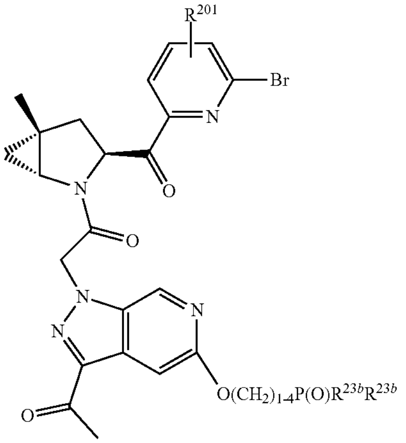
Formula I-400
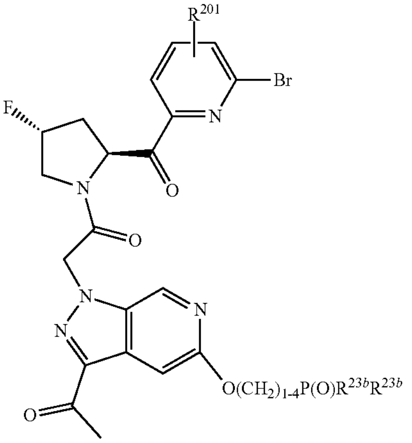

TABLE 1B-continued
| Additional Exemplary Formulas within the Present Invention. |
| --- |
Formula I-401
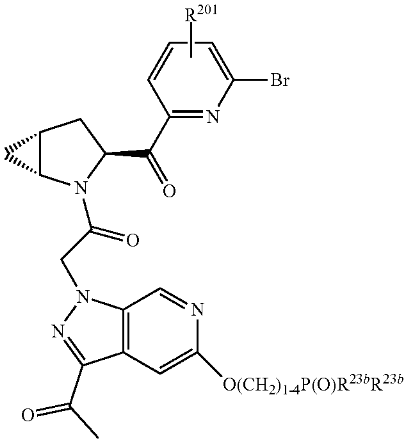
Formula I-402
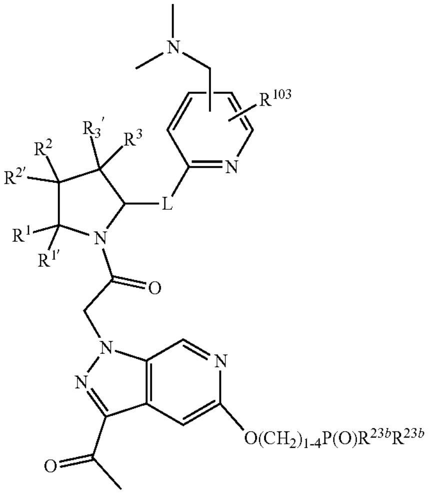
Formula I-403
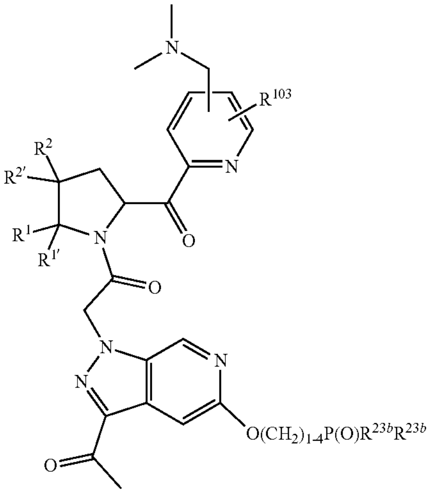
TABLE 1B-continued
| Additional Exemplary Formulas within the Present Invention. |
| --- |
Formula I-404
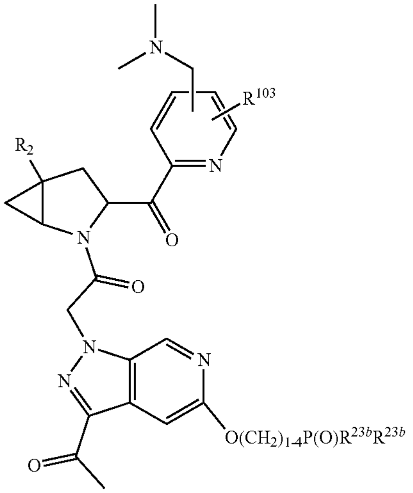
Formula I-405
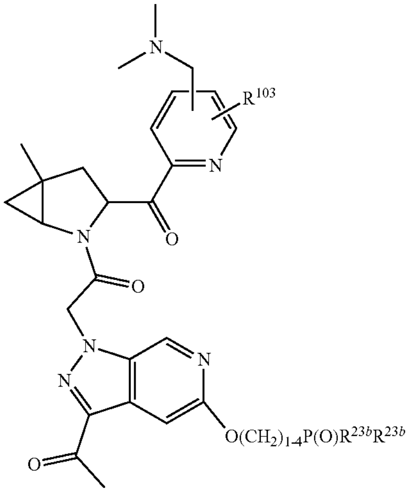
Formula I-406
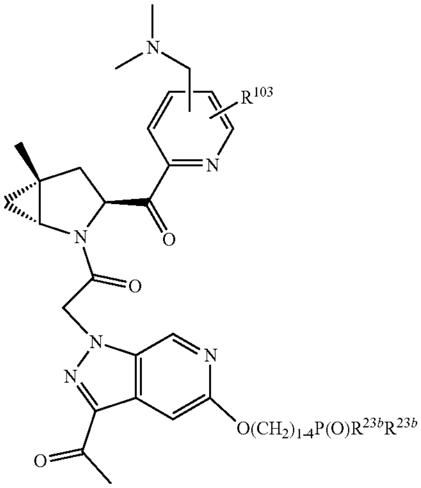

TABLE 1B-continued
| Additional Exemplary Formulas within the Present Invention. |
| --- |
Formula I-407
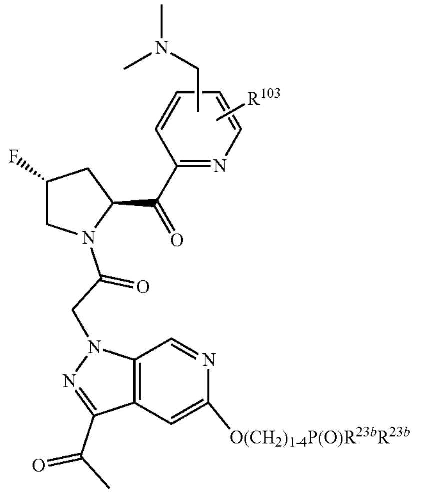
Formula I-408
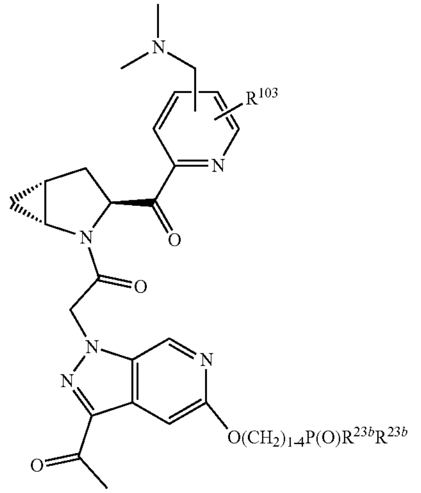
Formula I-409
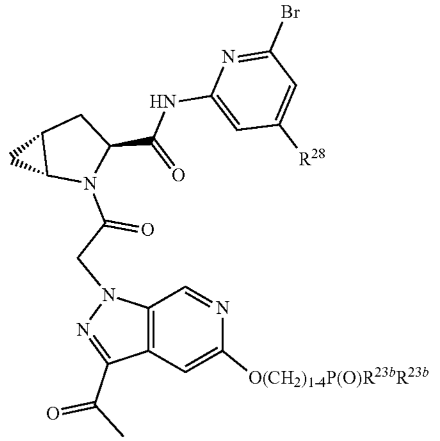
Formula I-410
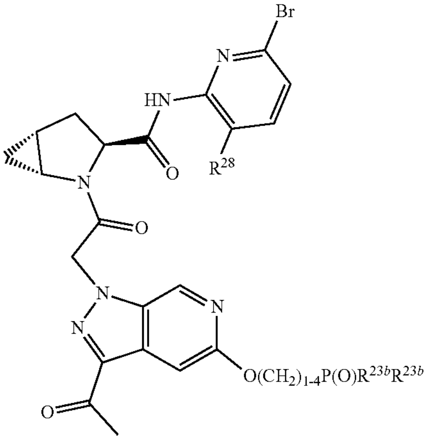
Formula I-411
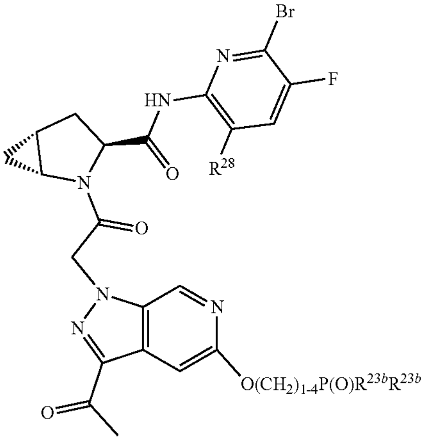
Formula I-412
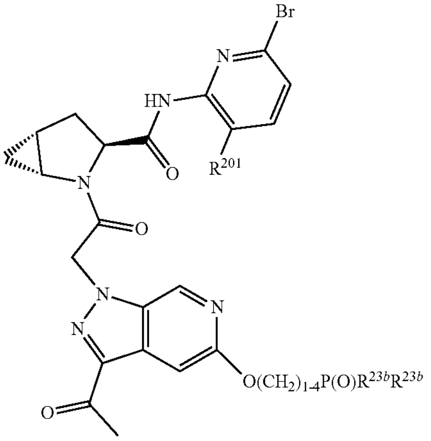

TABLE 1B-continued
| Additional Exemplary Formulas within the Present Invention. |
| --- |
Formula I-413
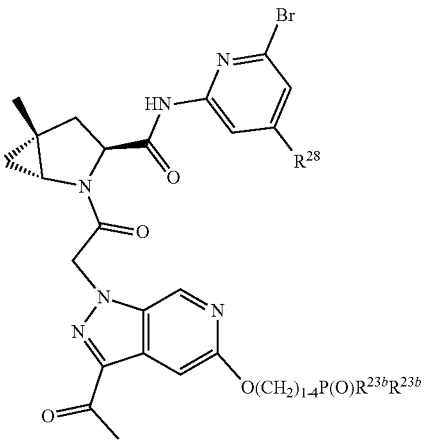
Formula I-414
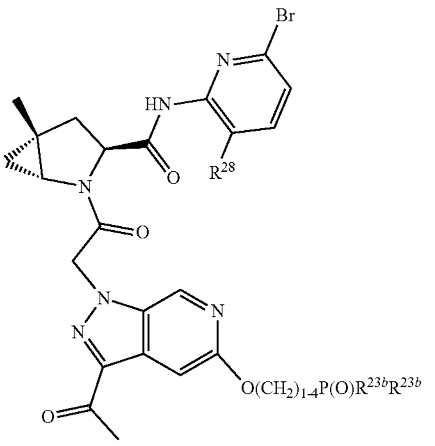
Formula I-415
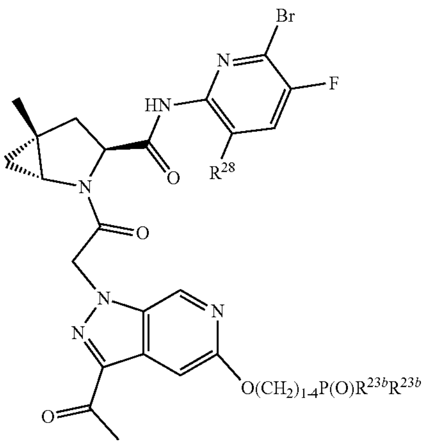
TABLE 1B-continued
| Additional Exemplary Formulas within the Present Invention. |
| --- |
Formula I-416
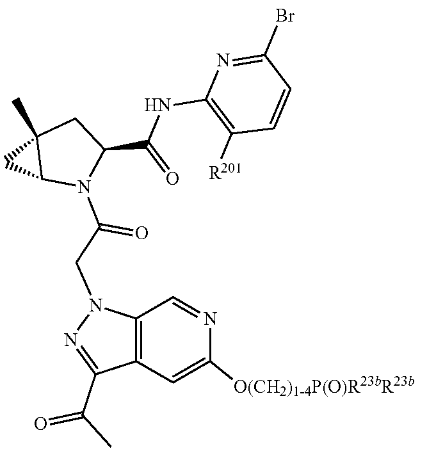
Formula I-417
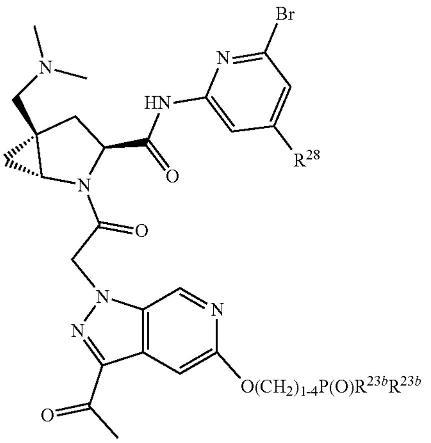
Formula I-418
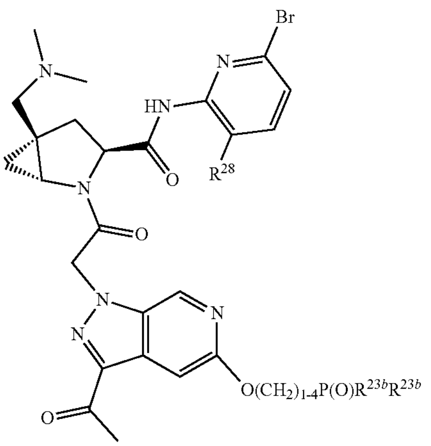

TABLE 1B-continued
Additional Exemplary Formulas within the Present Invention.
Formula I-419
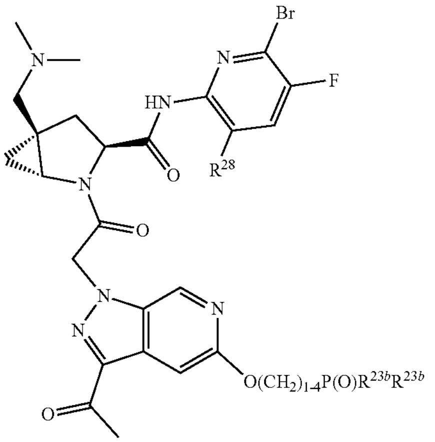
Formula I-420
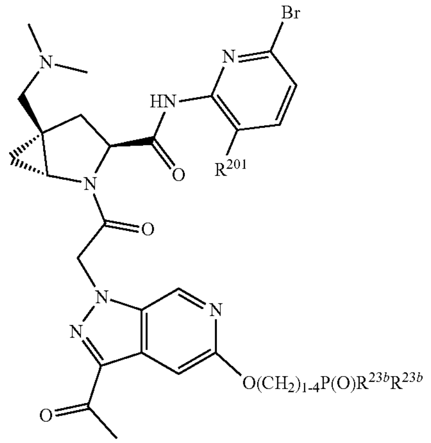
Formula I-421
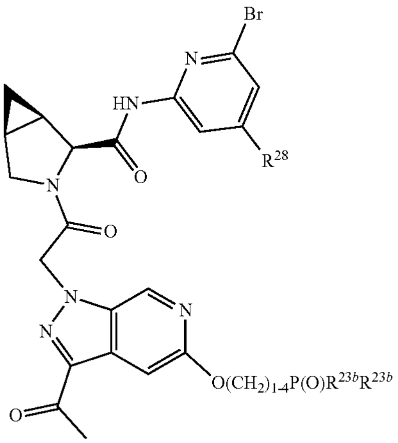
TABLE 1B-continued
Additional Exemplary Formulas within the Present Invention.
Formula I-422
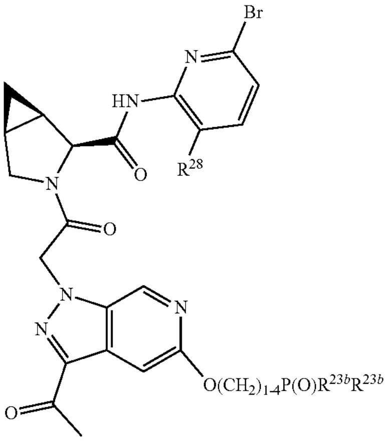
Formula I-423
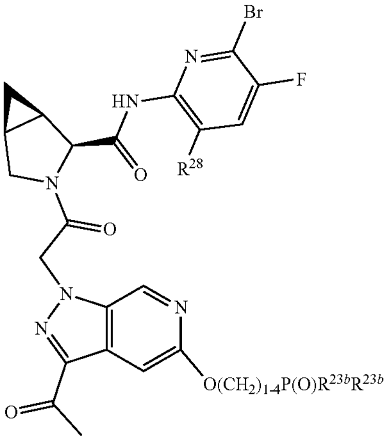
Formula I-424
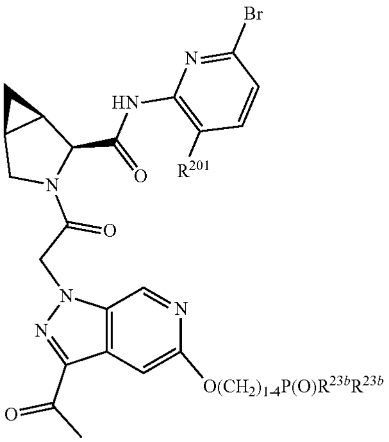

TABLE 1B-continued
Additional Exemplary Formulas within the Present Invention.
Formula I-425
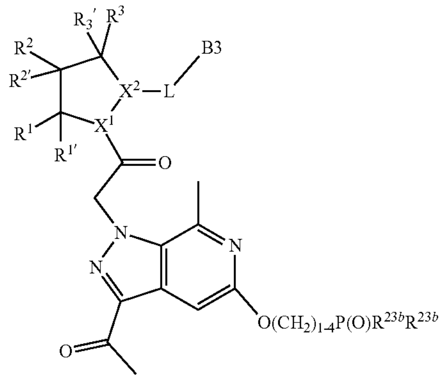
Formula I-426
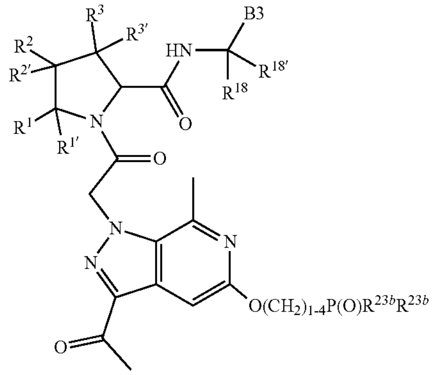
Formula I-427
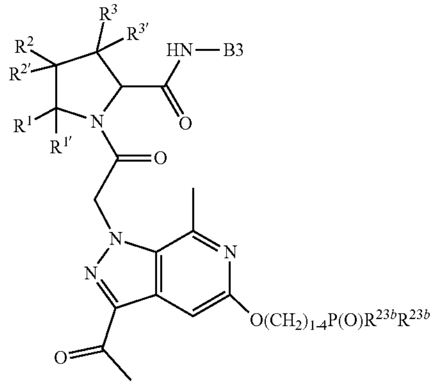
Formula I-428
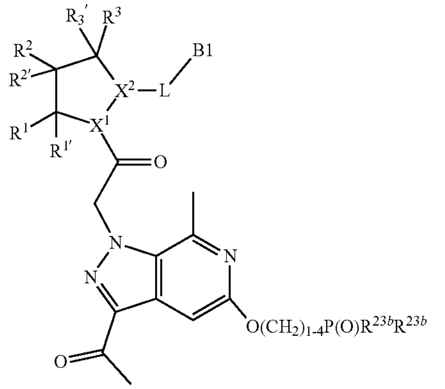
TABLE 1B-continued
Additional Exemplary Formulas within the Present Invention.
Formula I-429
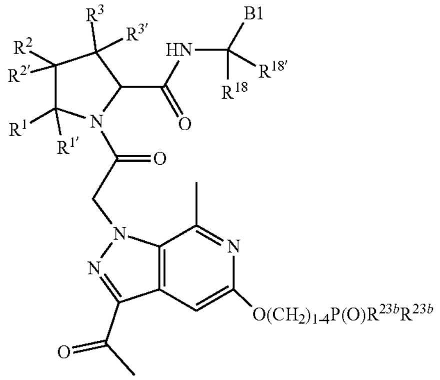
Formula I-430
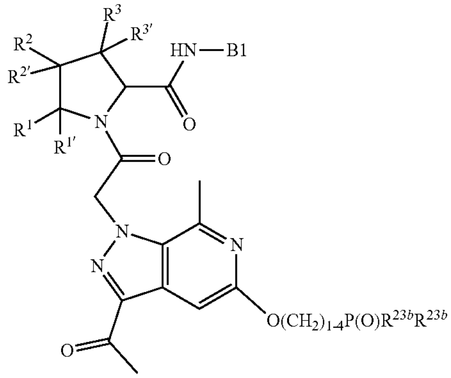
Formula I-431
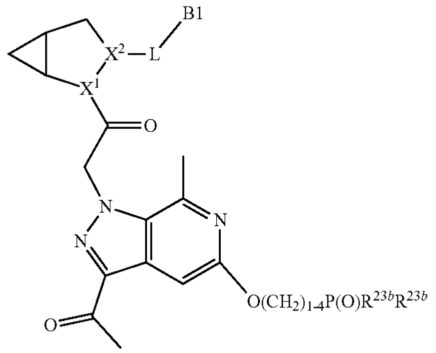
Formula I-432
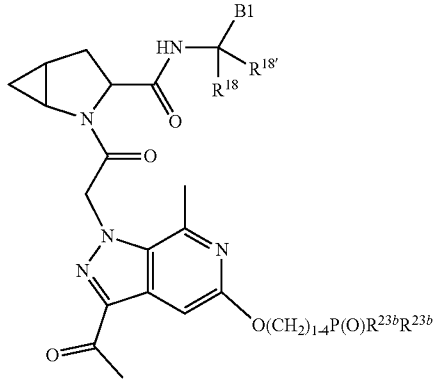

TABLE 1B-continued
| Additional Exemplary Formulas within the Present Invention. |
|---|
Formula I-433
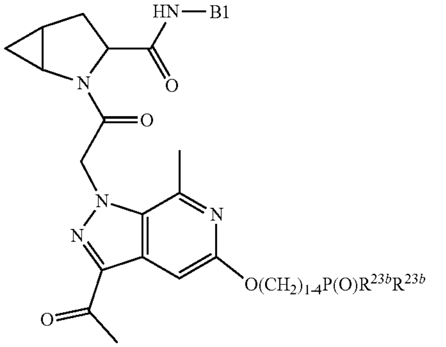
Formula I-434
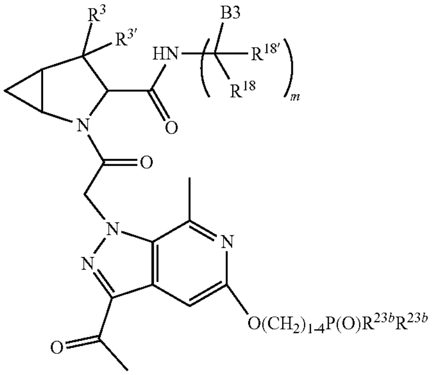
Formula I-435
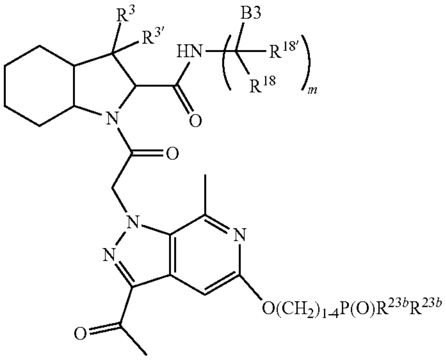
Formula I-436
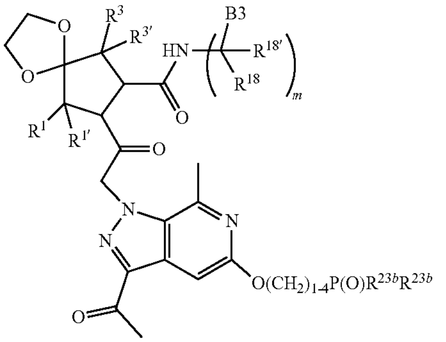
TABLE 1B-continued
| Additional Exemplary Formulas within the Present Invention. |
|---|
Formula I-437
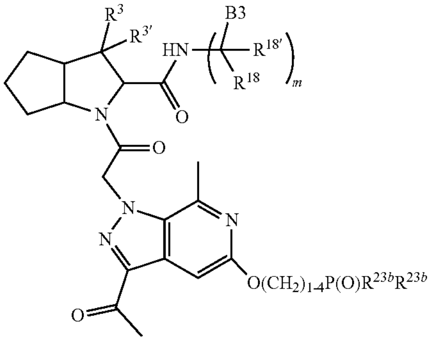
Formula I-438
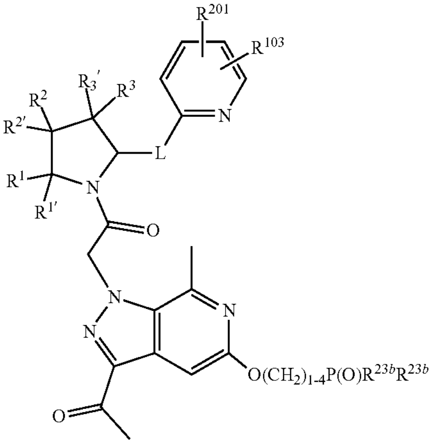
Formula I-439
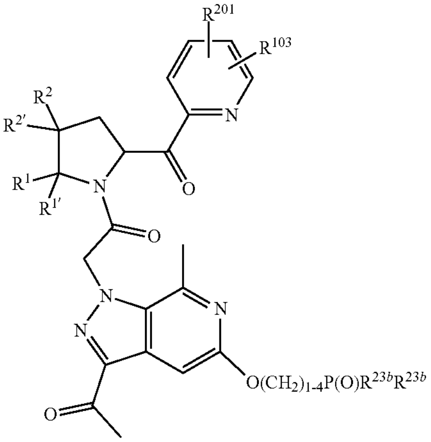

Additional Exemplary Formulas within the Present Invention.
Formula I-440
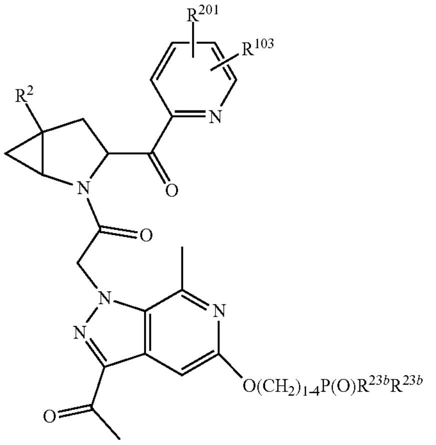
Formula I-441
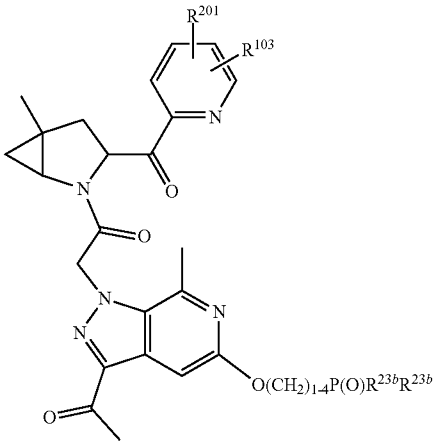
Formula I-442
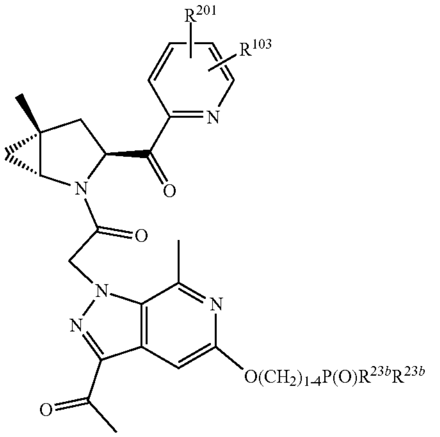
Additional Exemplary Formulas within the Present Invention.
Formula I-443
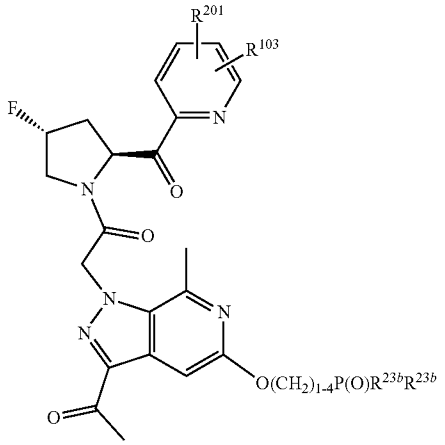
Formula I-444
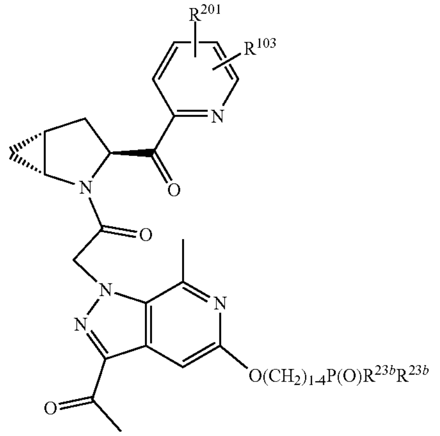
Formula I-445
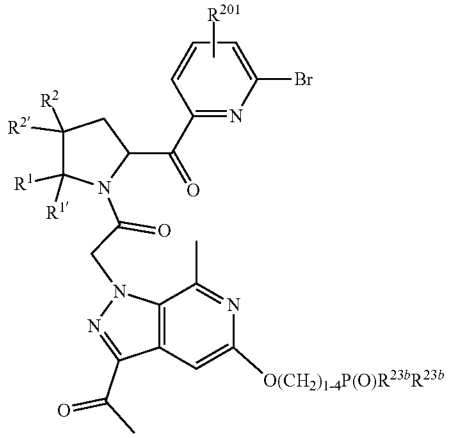

TABLE 1B-continued
Additional Exemplary Formulas within the Present Invention.
Formula I-446
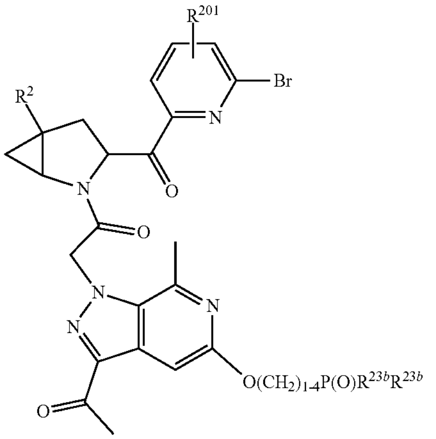
Formula I-447
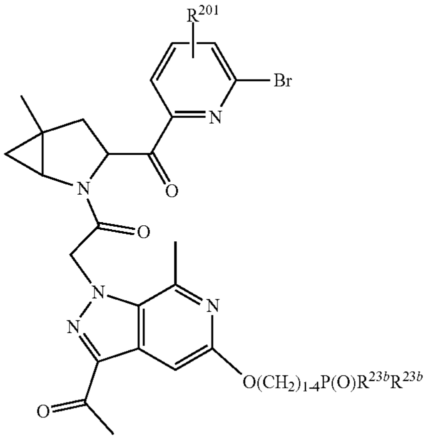
Formula I-448
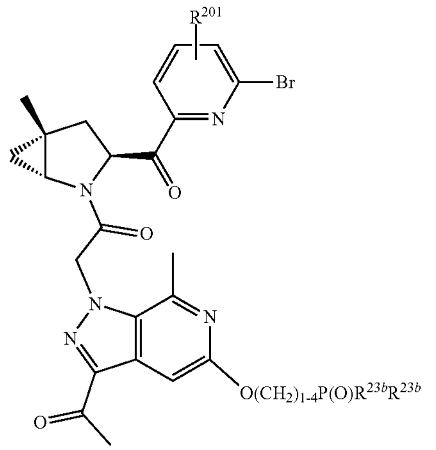
TABLE 1B-continued
Additional Exemplary Formulas within the Present Invention.
Formula I-449
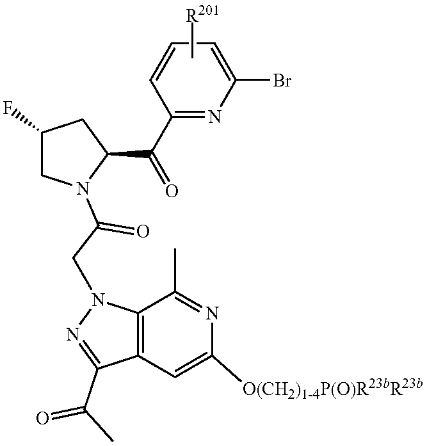
Formula I-450
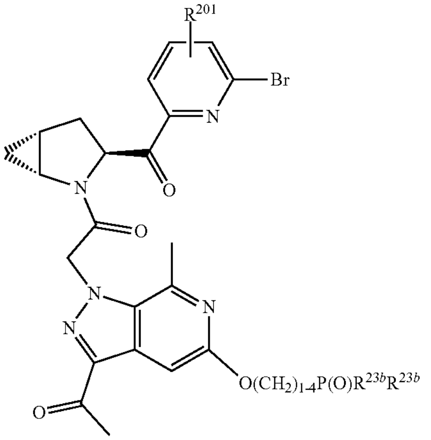
Formula I-451
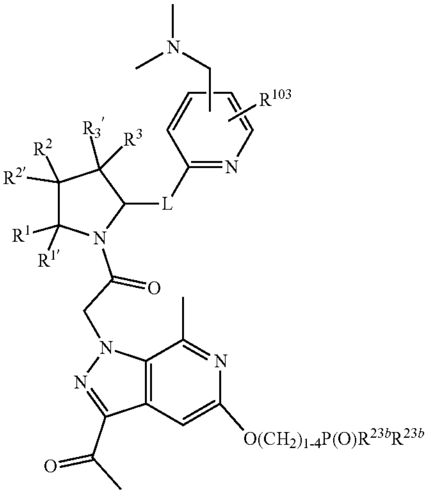

Additional Exemplary Formulas within the Present Invention.
Formula I-452
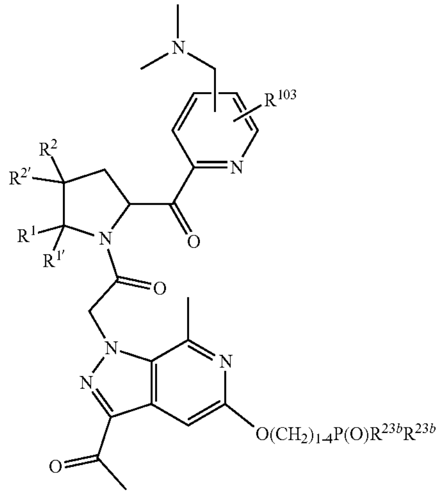
Formula I-453
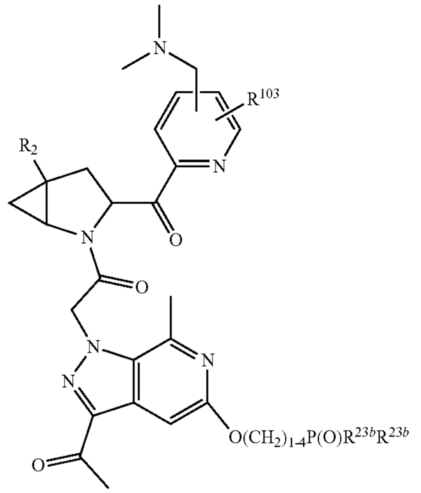
Formula I-454
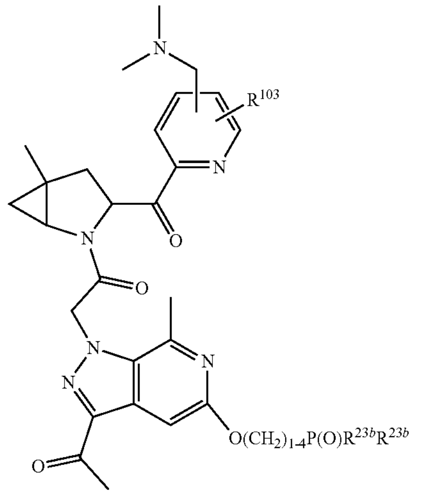
Additional Exemplary Formulas within the Present Invention.
Formula I-455
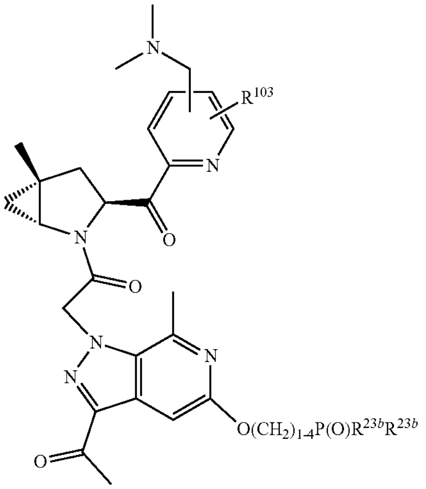
Formula I-456
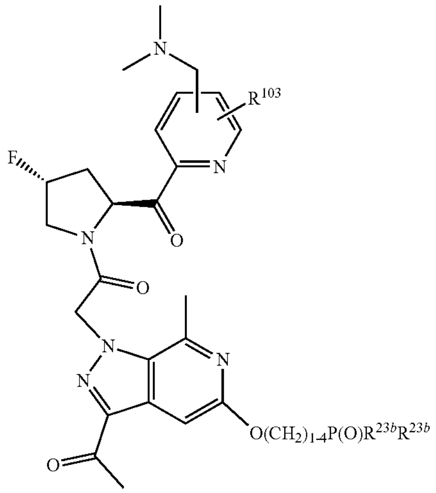
Formula I-457
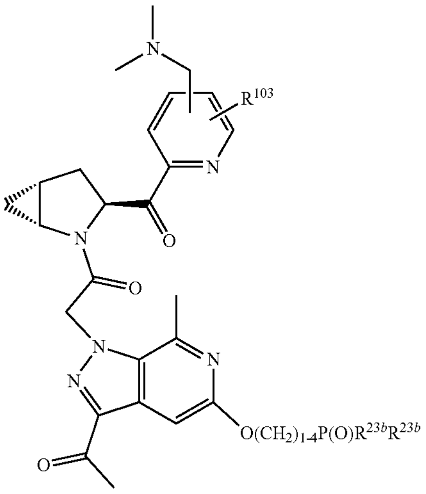

TABLE 1B-continued
Additional Exemplary Formulas within the Present Invention.
Formula I-458
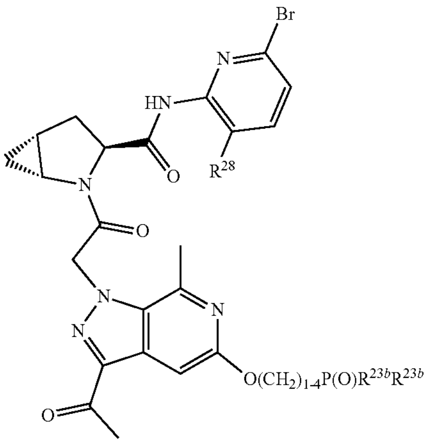
Formula I-459
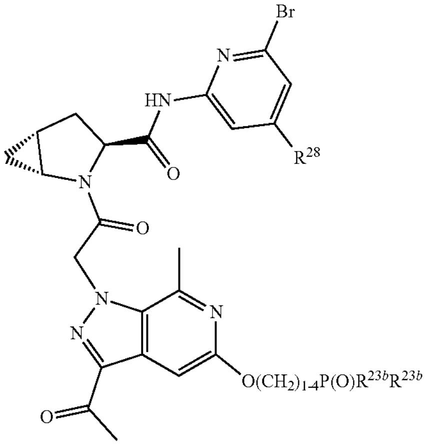
Formula I-460
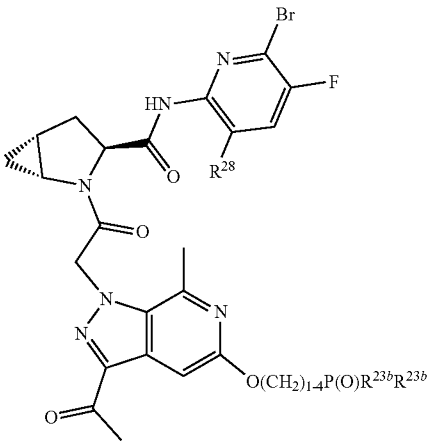
TABLE 1B-continued
Additional Exemplary Formulas within the Present Invention.
Formula I-461
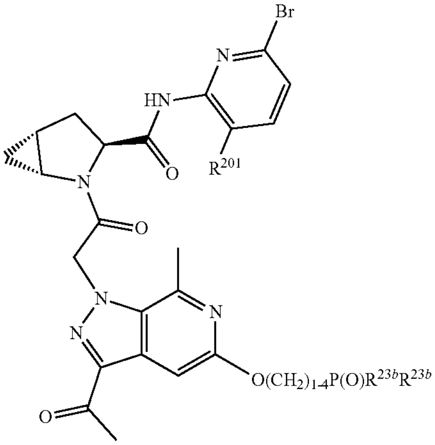
Formula I-462
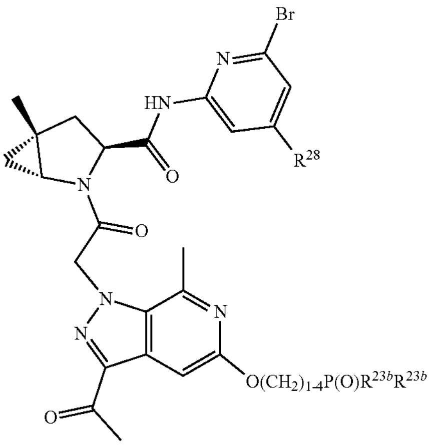
Formula I-463
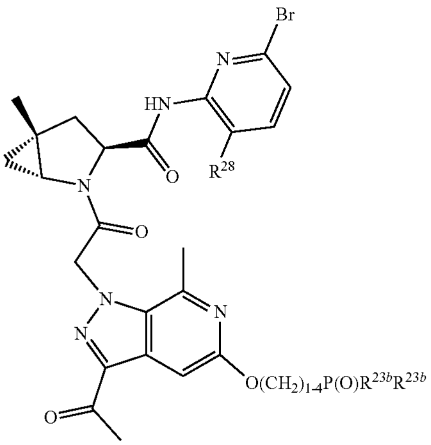

TABLE 1B-continued
Additional Exemplary Formulas within the Present Invention.
Formula I-464
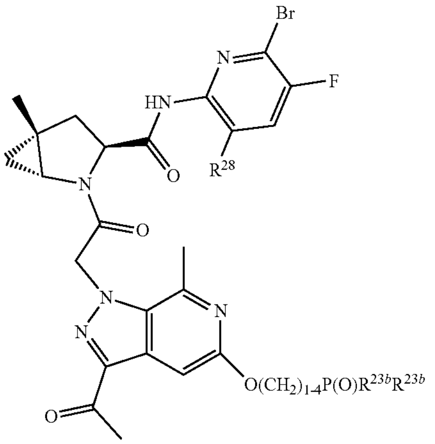
Formula I-465
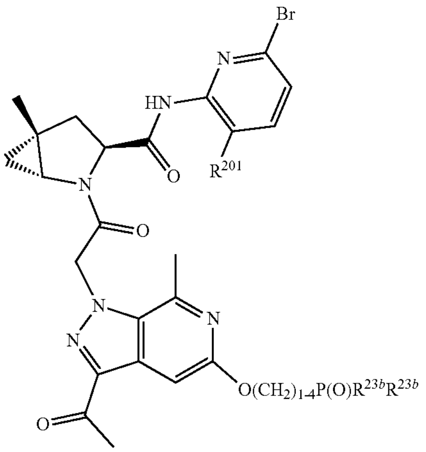
Formula I-466
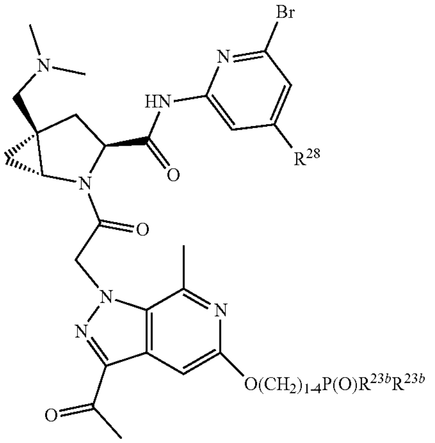
TABLE 1B-continued
Additional Exemplary Formulas within the Present Invention.
Formula I-467
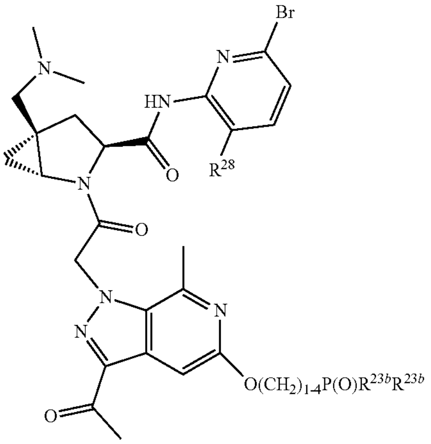
Formula I-468
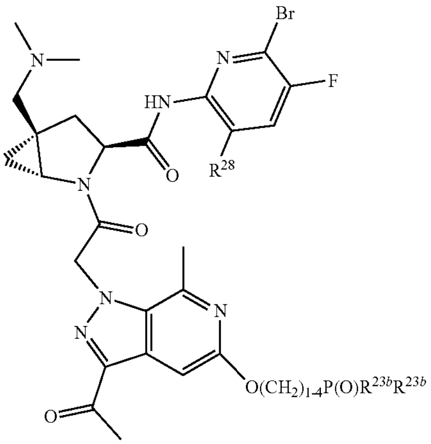
Formula I-469
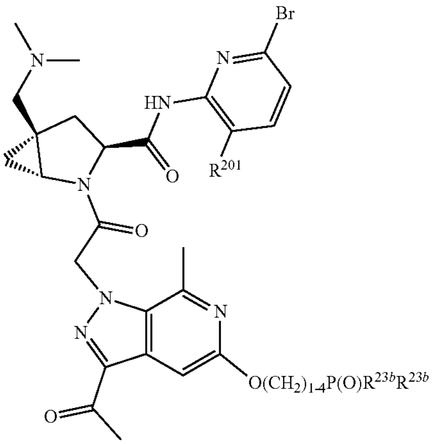

TABLE 1B-continued

| Additional Exemplary Formulas within the Present Invention. |
| --- |

Formula I-470

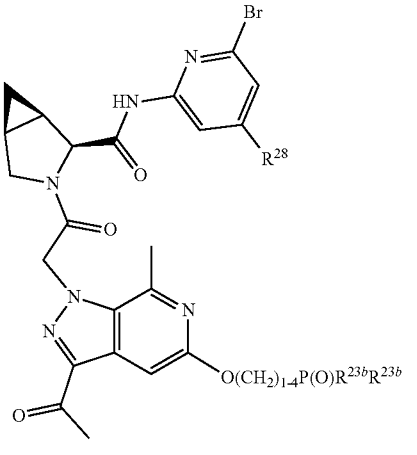

Formula I-471

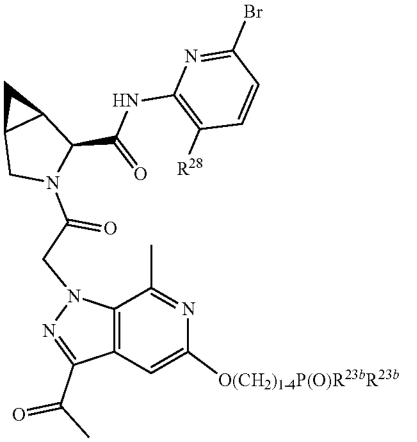

Formula I-472

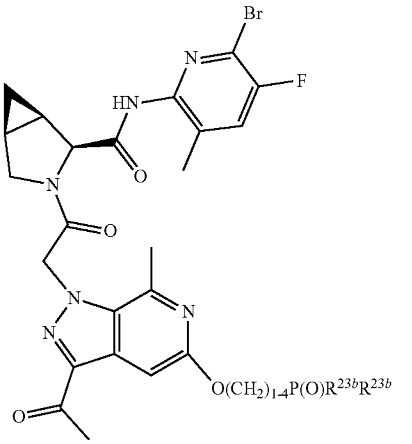

TABLE 1B-continued

| Additional Exemplary Formulas within the Present Invention. |
| --- |

Formula I-473

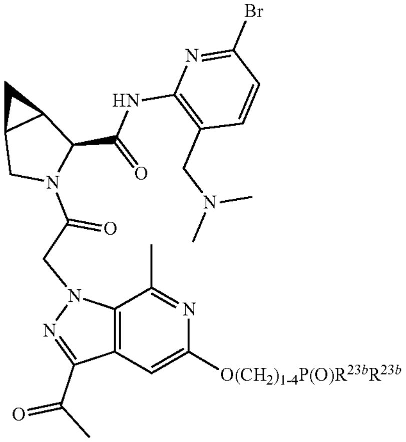

wherein $R^{103}$ is $C_1$-$C_4$ alkyl, $C_3$-$C_6$ cycloalkyl, fluorine, chlorine, or bromine. In Formulas I-376 to I-473 for convenience and space purposes only, $R^{32}$ is illustrated as the group $O(CH_2)_{1\text{-}4}P(O)R^{23b}R^{23b}$, however each described or illustrated $R^{32}$ in this application is considered to be independently shown in each of these Formulas.

TABLE 2A

| Additional Exemplary Formulas within the Present Invention. |
| --- |

Formula II-1

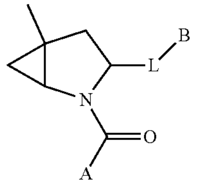

Formula II-2

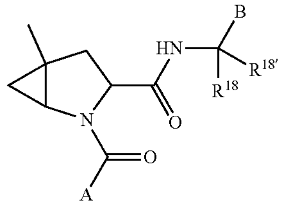

Formula II-3

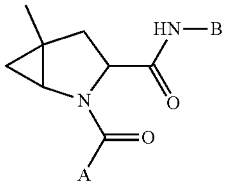

Formula II-4

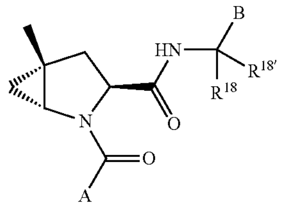

TABLE 2A-continued
Additional Exemplary Formulas within the Present Invention.
Formula II-5
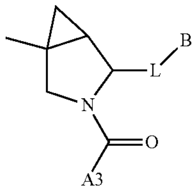
Formula II-6
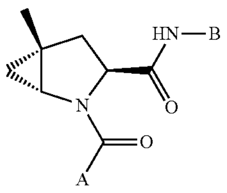
Formula II-7
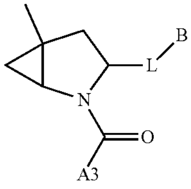
Formula II-8
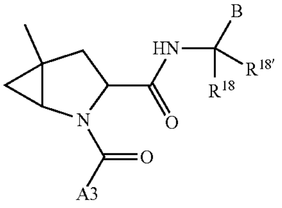
Formula II-9
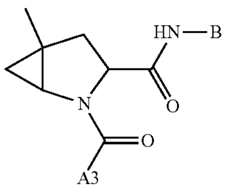
Formula II-10
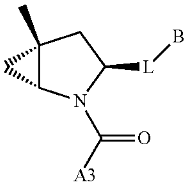
Formula II-11
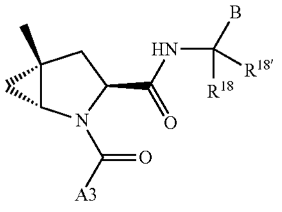
TABLE 2A-continued
Additional Exemplary Formulas within the Present Invention.
Formula II-12
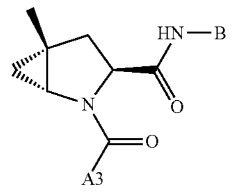
Formula II-13
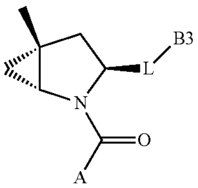
Formula II-14
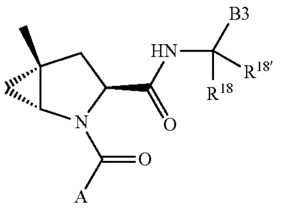
Formula II-15
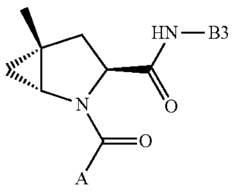
Formula II-16
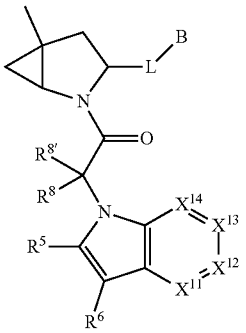
Formula II-17
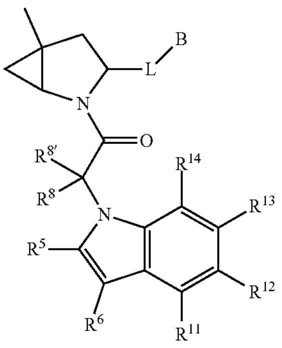

TABLE 2A-continued
| Additional Exemplary Formulas within the Present Invention. |
| --- |
Formula II-18
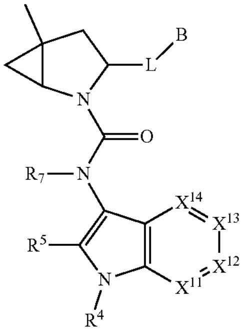
Formula II-19
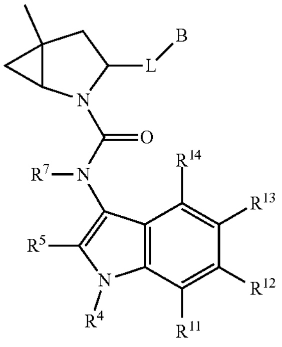
Formula II-20
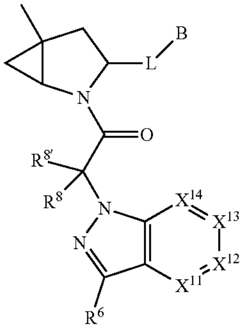
Formula II-21
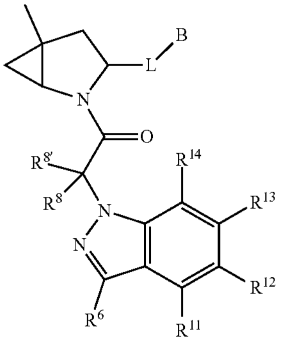
Formula II-22
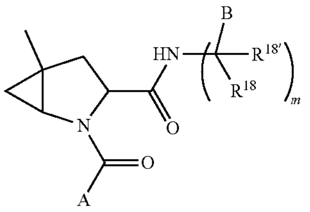
TABLE 2A-continued
| Additional Exemplary Formulas within the Present Invention. |
| --- |
Formula II-23
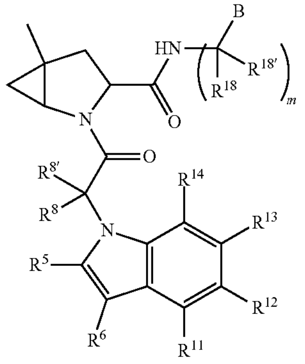
Formula II-24
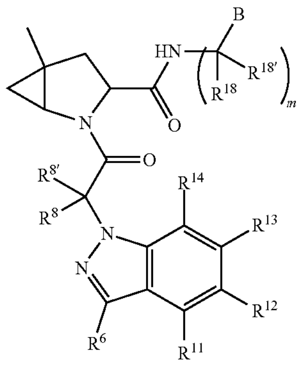
Formula II-25
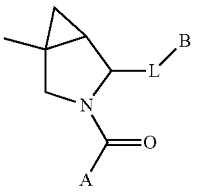
Formula II-26
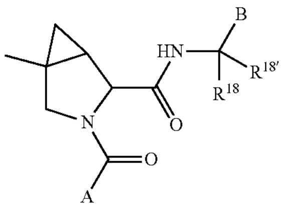
Formula II-27
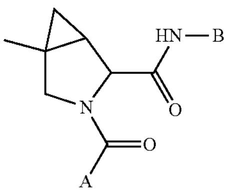

TABLE 2A-continued
Additional Exemplary Formulas within the Present Invention.
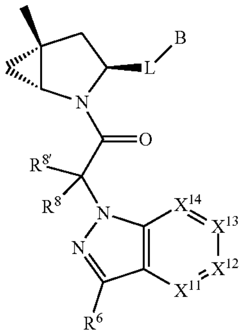
Formula II-28
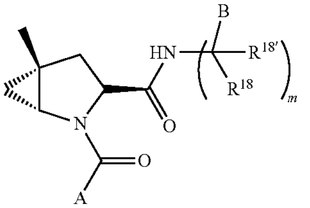
Formula II-29
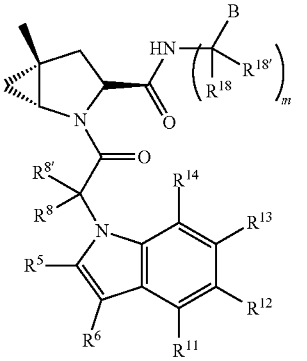
Formula II-30
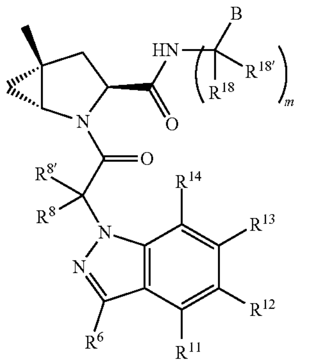
Formula II-31
TABLE 2A-continued
Additional Exemplary Formulas within the Present Invention.
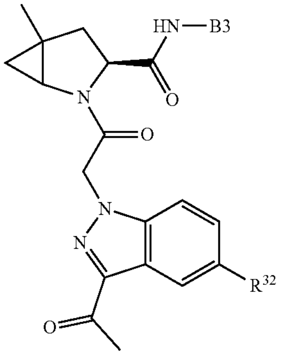
Formula II-34
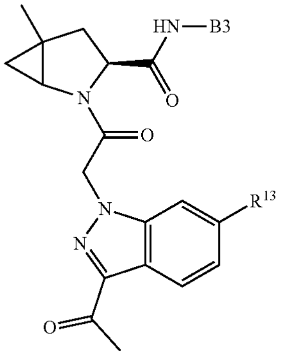
Formula II-35
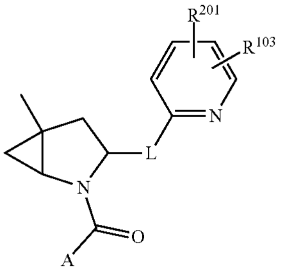
Formula II-36
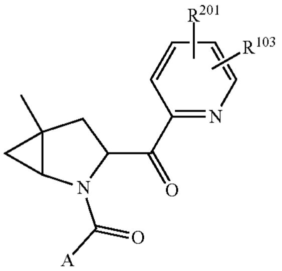
Formula II-37
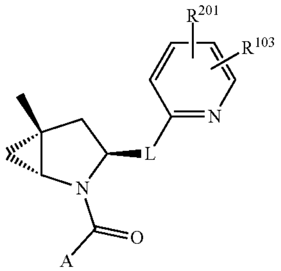
Formula II-38

TABLE 2A-continued
Additional Exemplary Formulas within the Present Invention.
Formula II-39
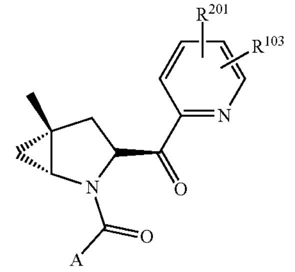
Formula II-40
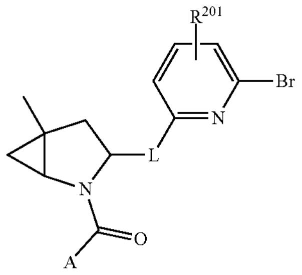
Formula II-41
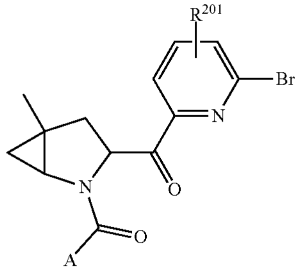
Formula II-42
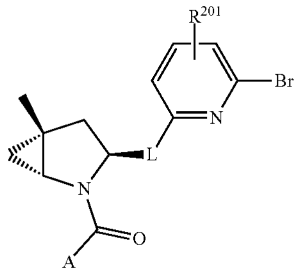
Formula II-43
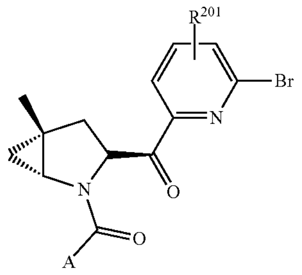
TABLE 2A-continued
Additional Exemplary Formulas within the Present Invention.
Formula II-44
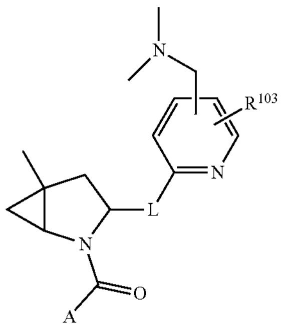
Formula II-45
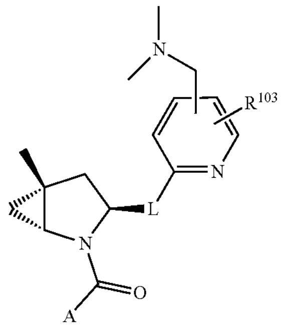
Formula II-46
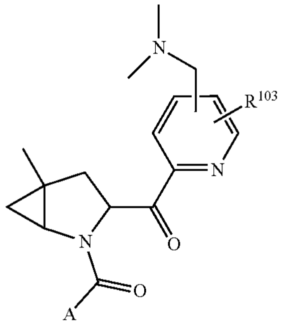
Formula II-47
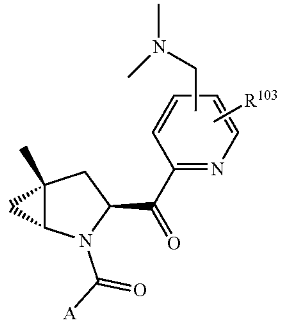
Formula II-48
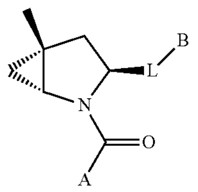

TABLE 2A-continued
Additional Exemplary Formulas within the Present Invention.
Formula II-130
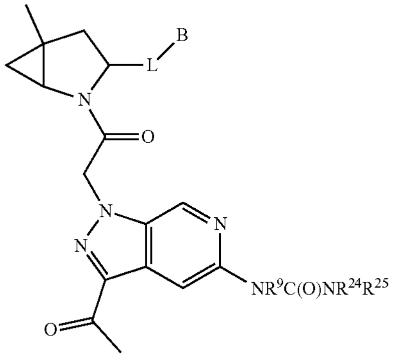
Formula II-131
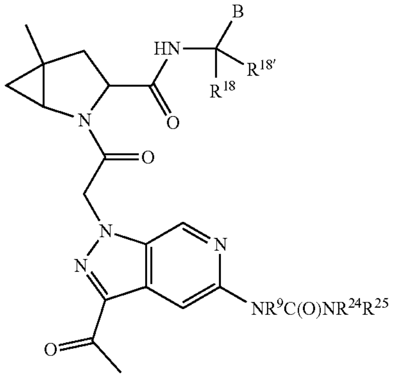
Formula II-132
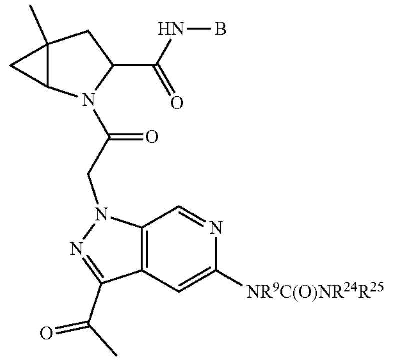
Formula II-133
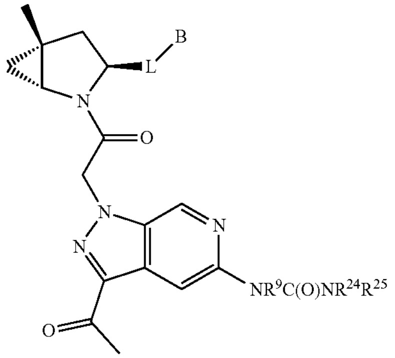
TABLE 2A-continued
Additional Exemplary Formulas within the Present Invention.
Formula II-134
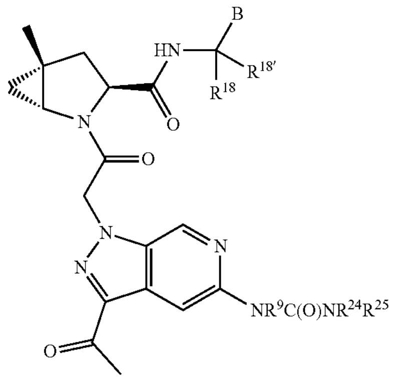
Formula II-135
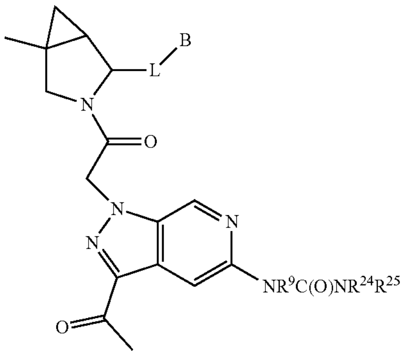
Formula II-136
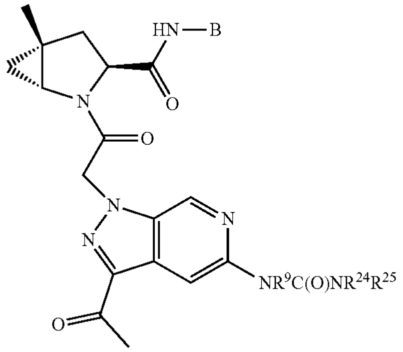
Formula II-137
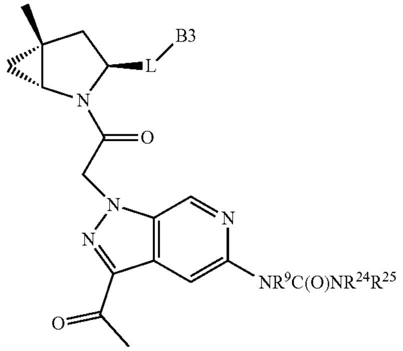

TABLE 2A-continued
| Additional Exemplary Formulas within the Present Invention. |
| --- |
Formula II-138
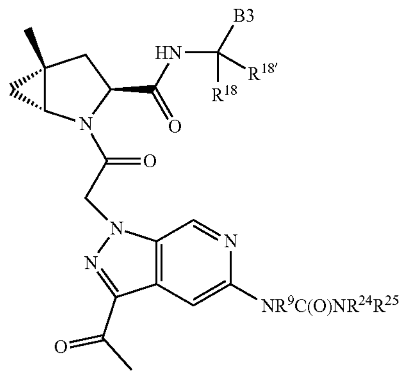
Formula II-139
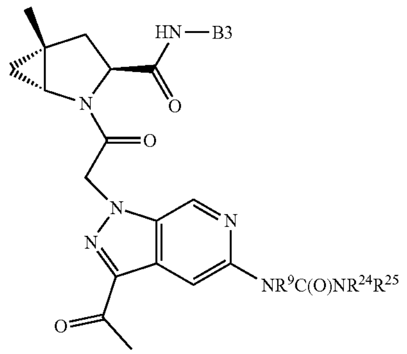
Formula II-140
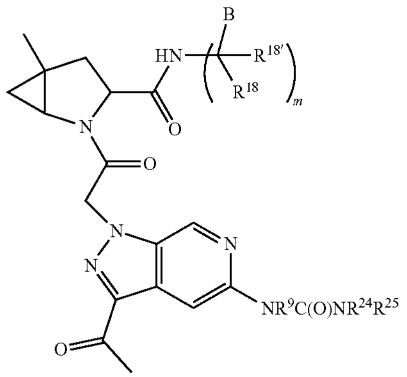
Formula II-141
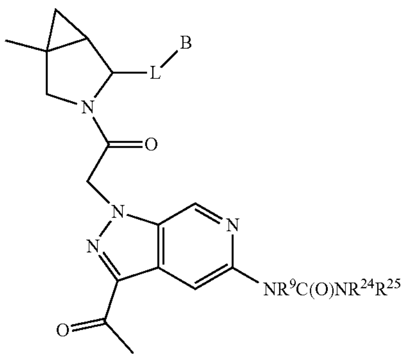
TABLE 2A-continued
| Additional Exemplary Formulas within the Present Invention. |
| --- |
Formula II-142
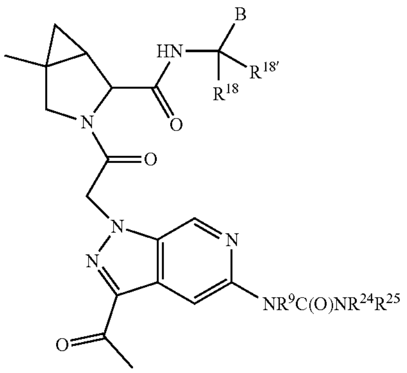
Formula II-143
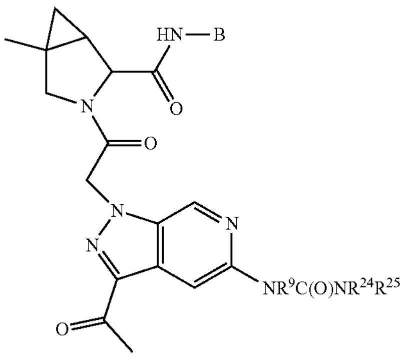
Formula II-144
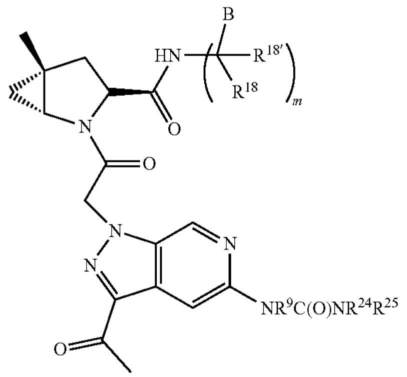
Formula II-145
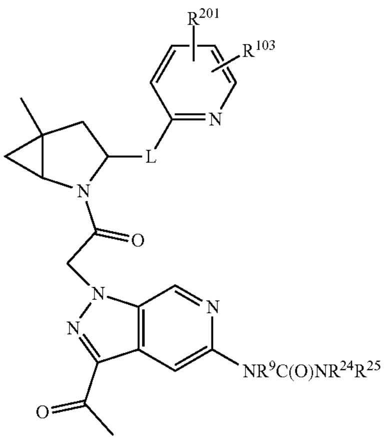

TABLE 2A-continued
| Additional Exemplary Formulas within the Present Invention. |
|---|
Formula II-146
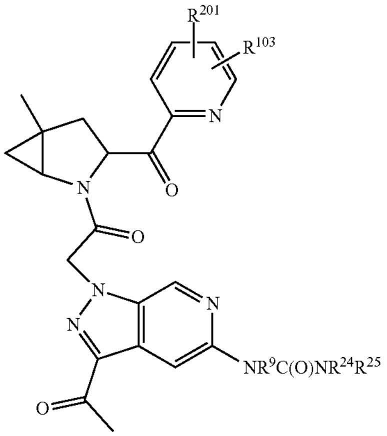
Formula II-147
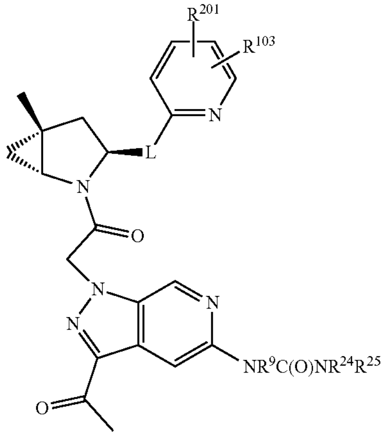
Formula II-148
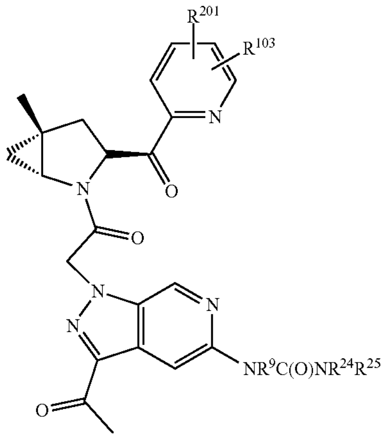
TABLE 2A-continued
| Additional Exemplary Formulas within the Present Invention. |
|---|
Formula II-149
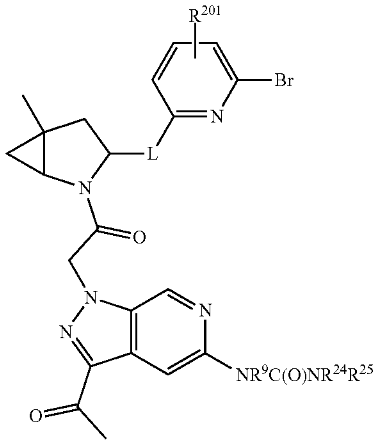
Formula II-150
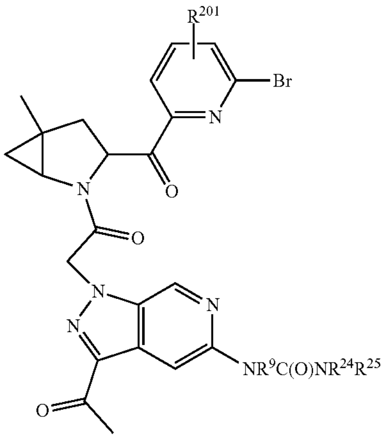
Formula II-151
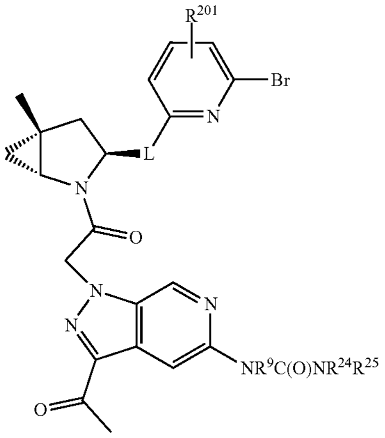

TABLE 2A-continued
Additional Exemplary Formulas within the Present Invention.
Formula II-152
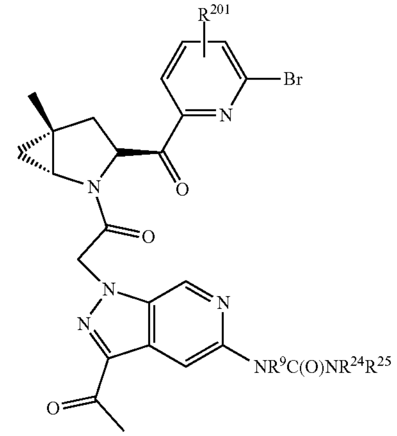
Formula II-153
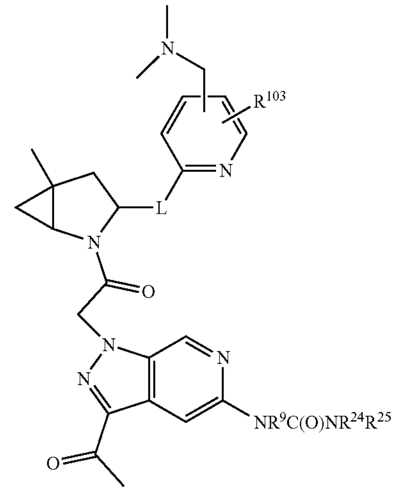
Formula II-154
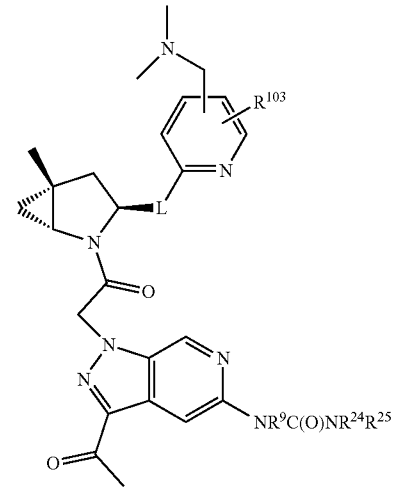
Formula II-155
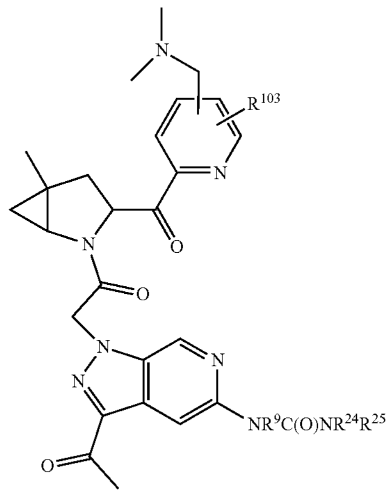
Formula II-156
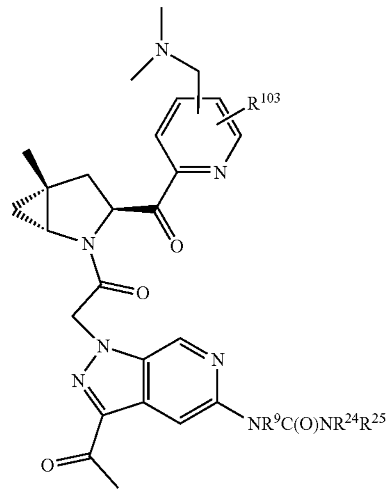
Formula II-157
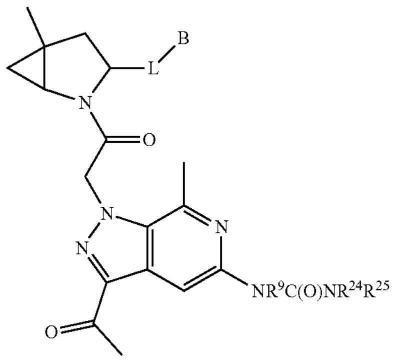

TABLE 2A-continued
| Additional Exemplary Formulas within the Present Invention. |
| --- |
Formula II-158
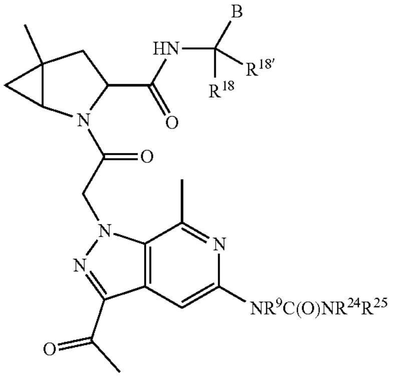
Formula II-159
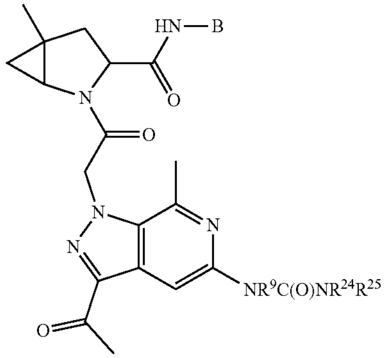
Formula II-160
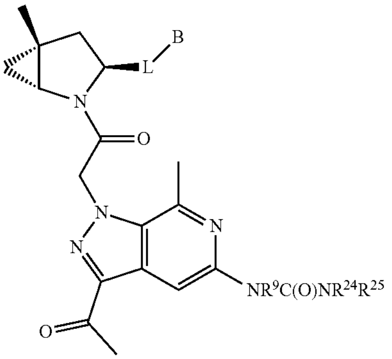
Formula II-161
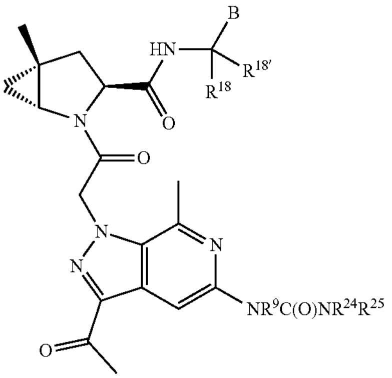
TABLE 2A-continued
| Additional Exemplary Formulas within the Present Invention. |
| --- |
Formula II-162
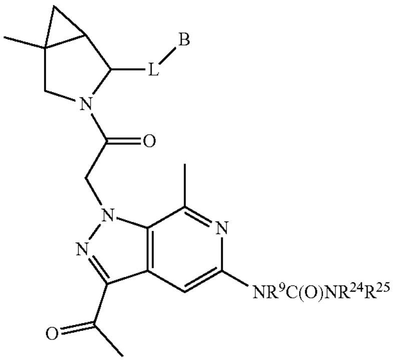
Formula II-163
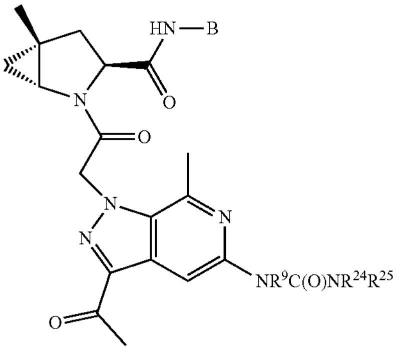
Formula II-164
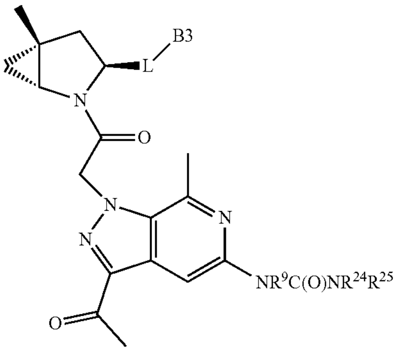
Formula II-165
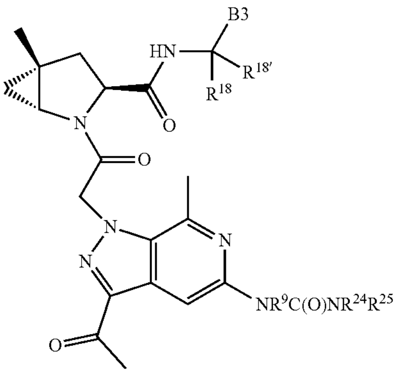

Additional Exemplary Formulas within the Present Invention.
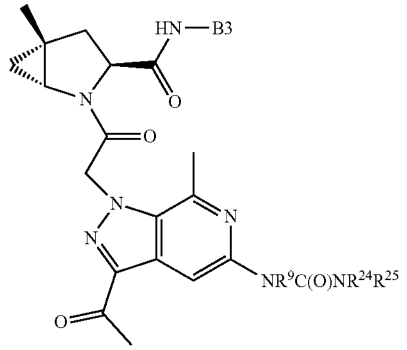
Formula II-166
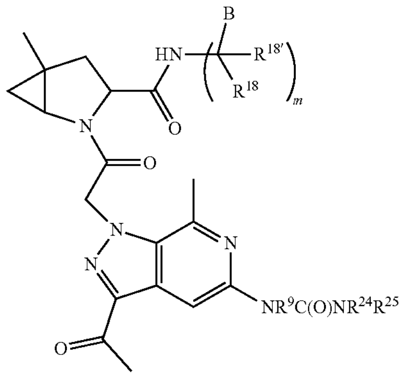
Formula II-167
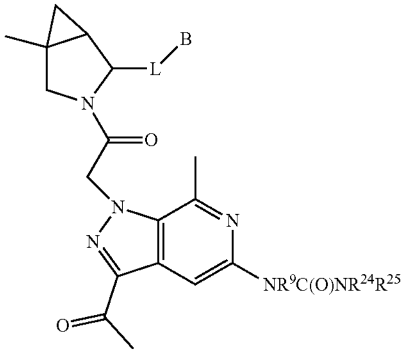
Formula II-168
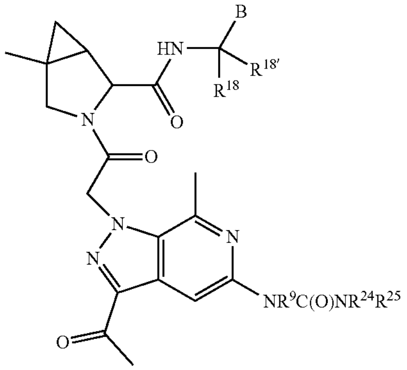
Formula II-169
Additional Exemplary Formulas within the Present Invention.
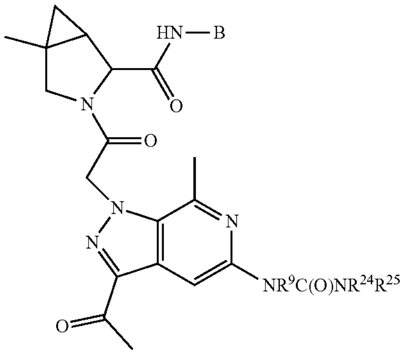
Formula II-170
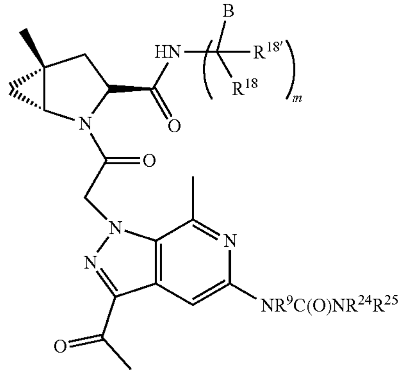
Formula II-171
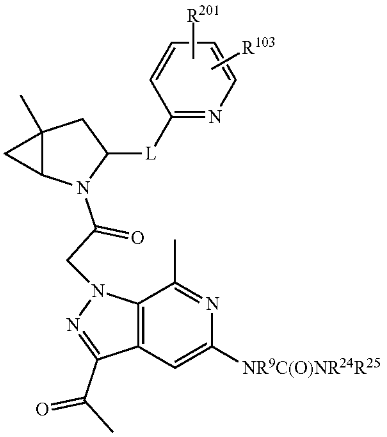
Formula II-172
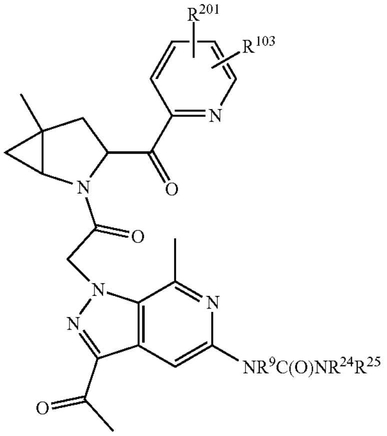
Formula II-173

TABLE 2A-continued
Additional Exemplary Formulas within the Present Invention.
Formula II-174
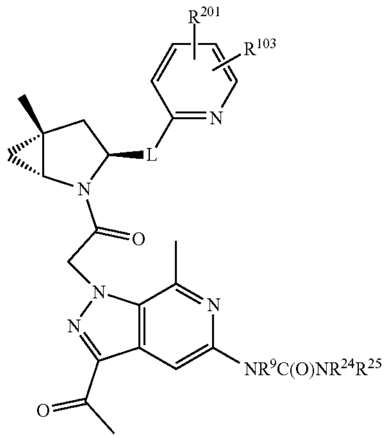
Formula II-175
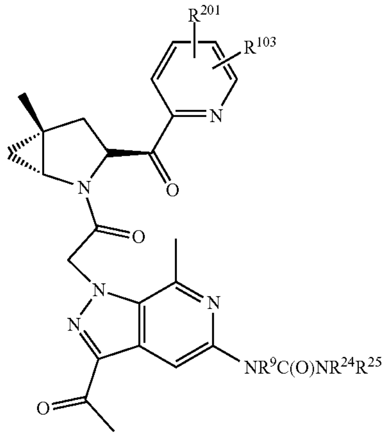
Formula II-176
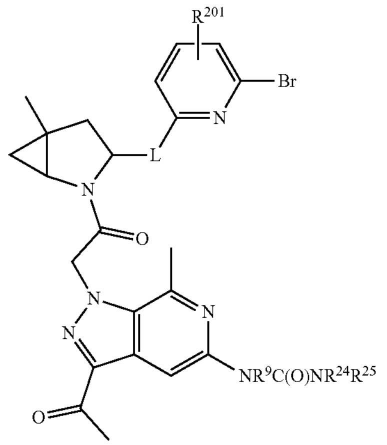
TABLE 2A-continued
Additional Exemplary Formulas within the Present Invention.
Formula II-177
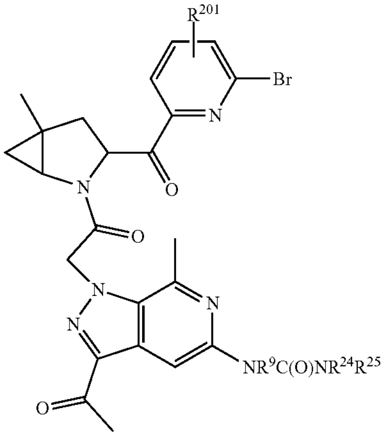
Formula II-178
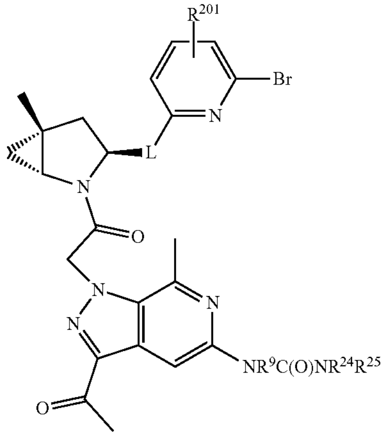
Formula II-179
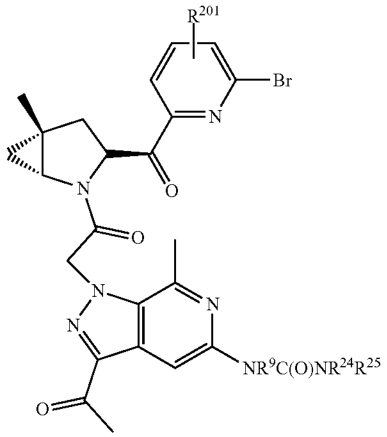

TABLE 2A-continued
Additional Exemplary Formulas within the Present Invention.
Formula II-180
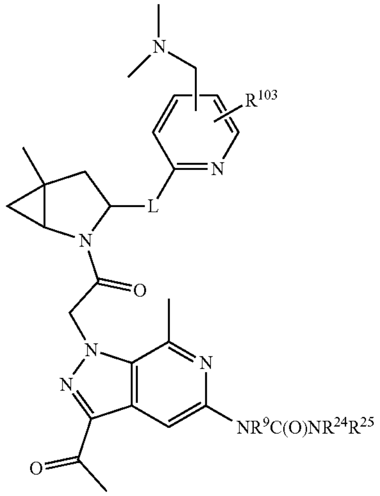
Formula II-181
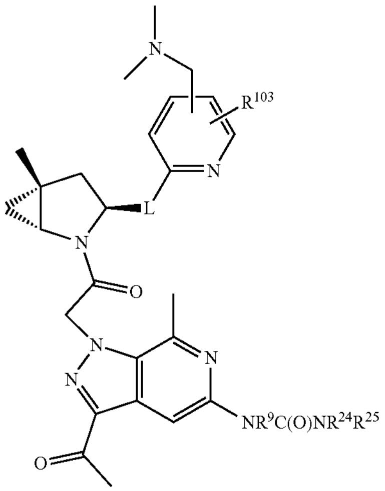
Formula II-182
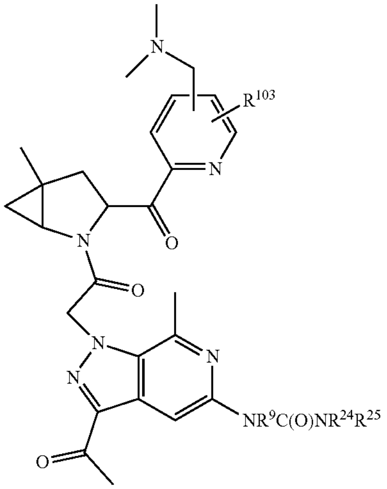
Formula II-183
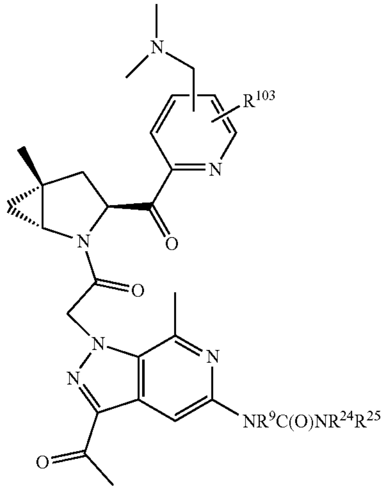
wherein $R^{103}$ is $C_1$-$C_4$ alkyl, $C_3$-$C_6$ cycloalkyl, fluorine, chlorine, or bromine.
TABLE 2B
Additional Exemplary Formulas within the Present Invention.
Formula II-249
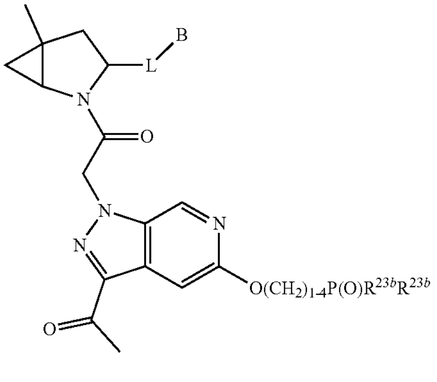

TABLE 2B-continued
Additional Exemplary Formulas within the Present Invention.
Formula II-250
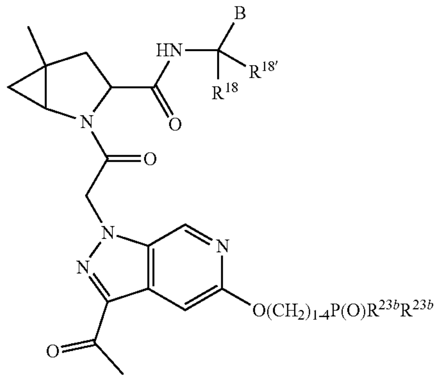
Formula II-251
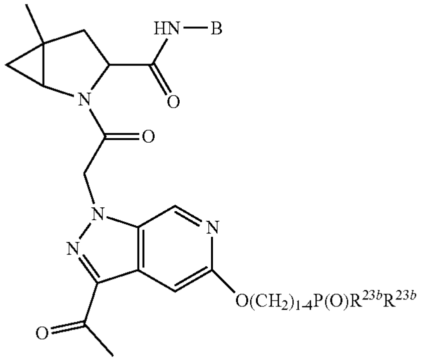
Formula II-252
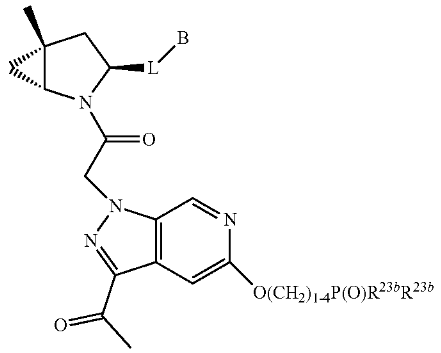
Formula II-253
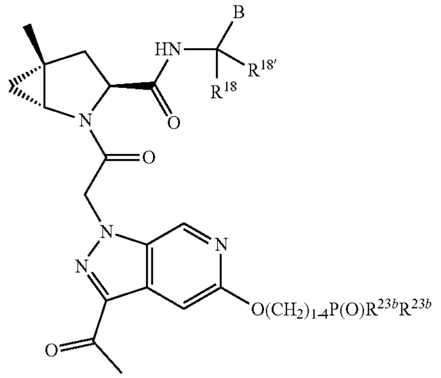

TABLE 2B-continued
| Additional Exemplary Formulas within the Present Invention. |
| --- |
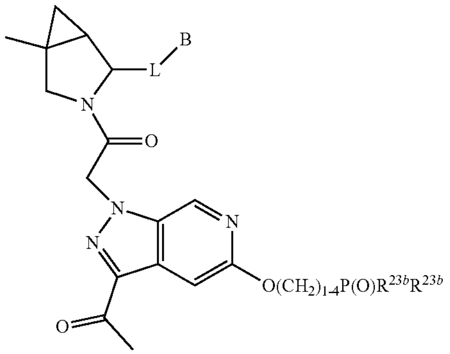
Formula II-254
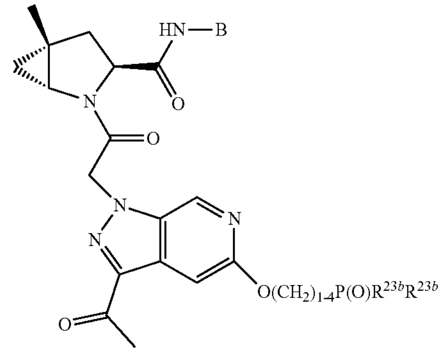
Formula II-255
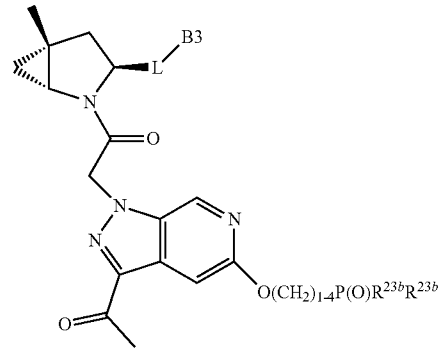
Formula II-256
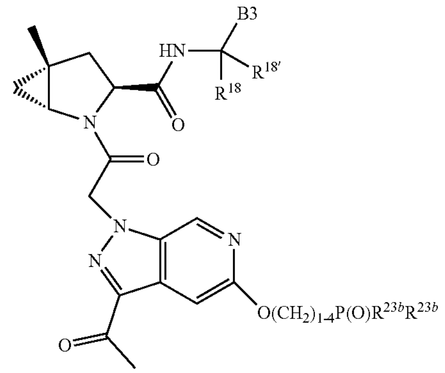
Formula II-257

TABLE 2B-continued
| Additional Exemplary Formulas within the Present Invention. |
| --- |
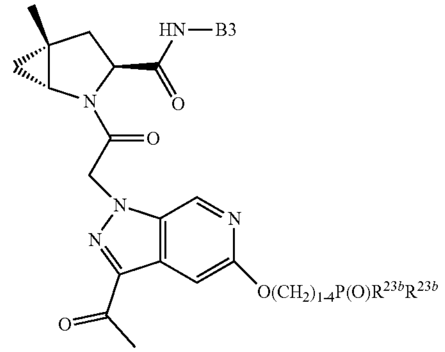
Formula II-258
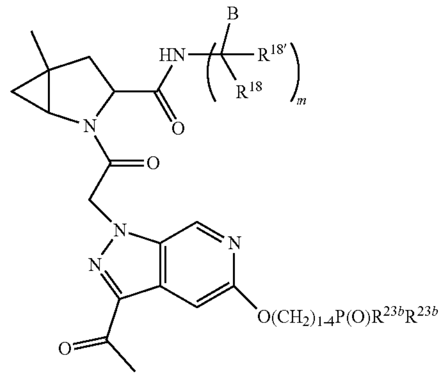
Formula II-259
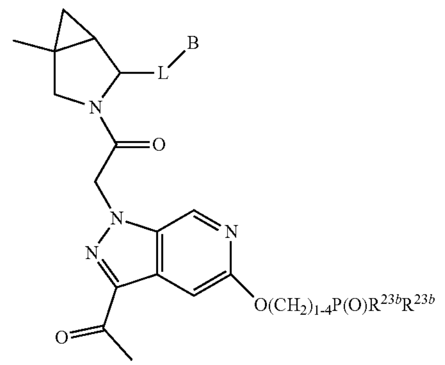
Formula II-260
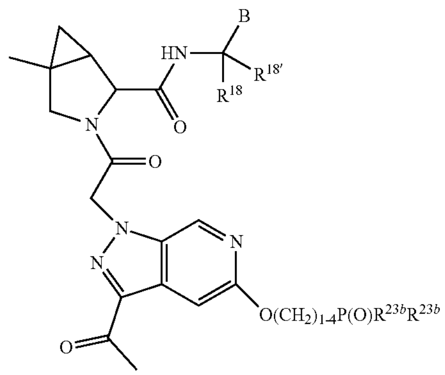
Formula II-261

TABLE 2B-continued
Additional Exemplary Formulas within the Present Invention.
Formula II-262
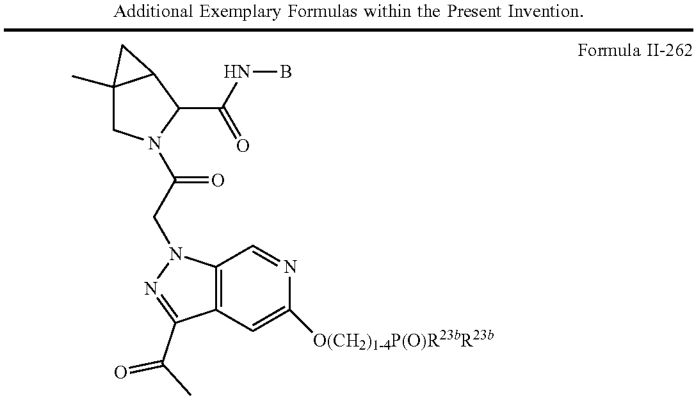
Formula II-263
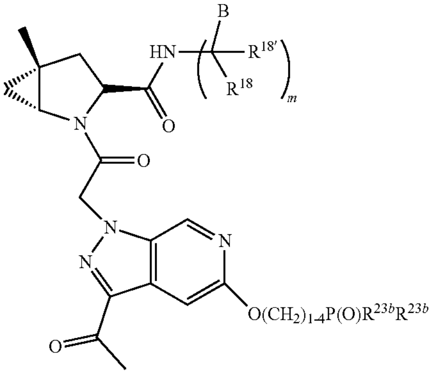
Formula II-264
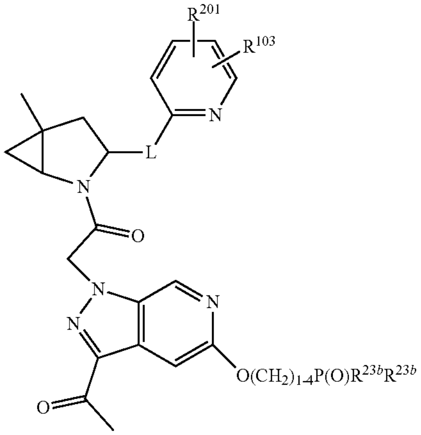
Formula II-265
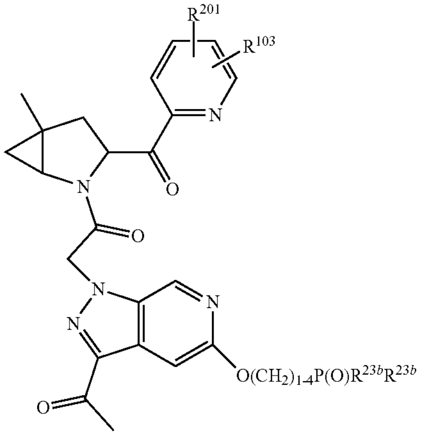

TABLE 2B-continued
Additional Exemplary Formulas within the Present Invention.
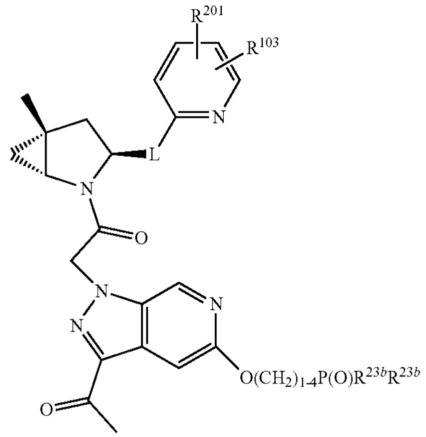
Formula II-266
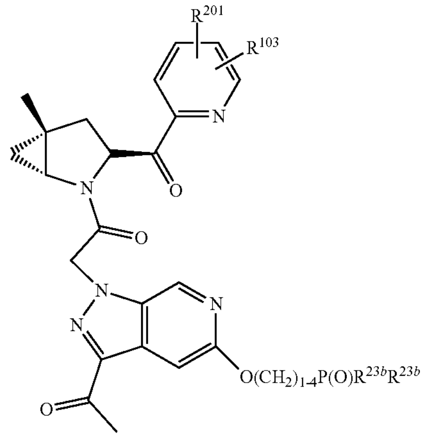
Formula II-267
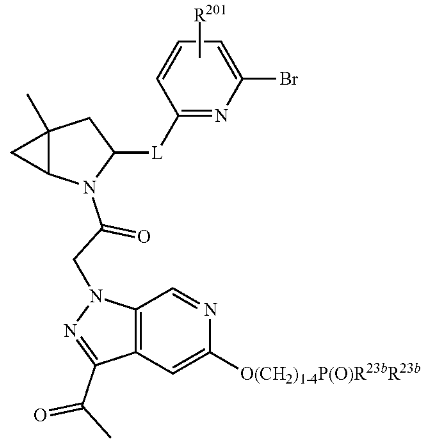
Formula II-268

TABLE 2B-continued
| Additional Exemplary Formulas within the Present Invention. |
| --- |
Formula II-269
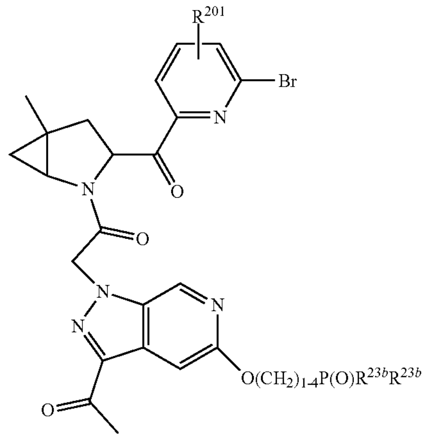
Formula II-270
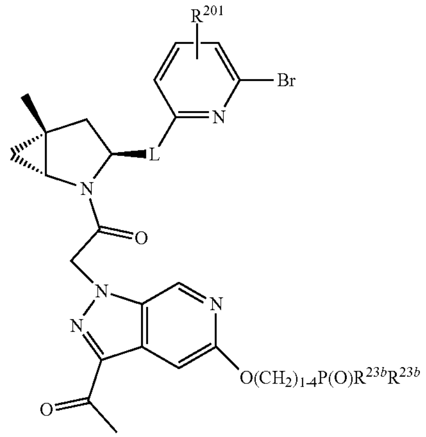
Formula II-271
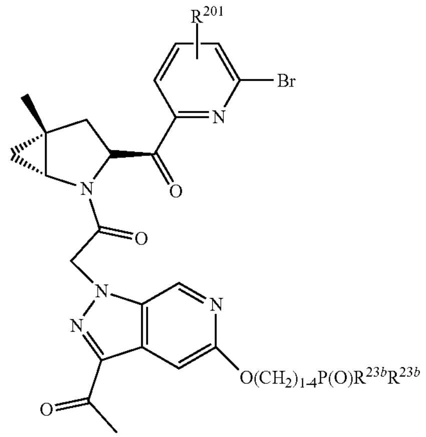

TABLE 2B-continued
| Additional Exemplary Formulas within the Present Invention. |
| --- |
Formula II-272
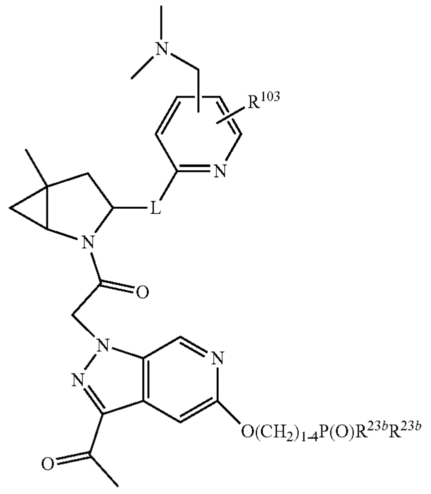
Formula II-273
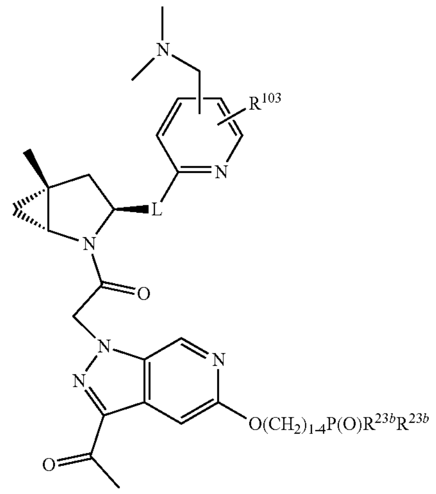
Formula II-274
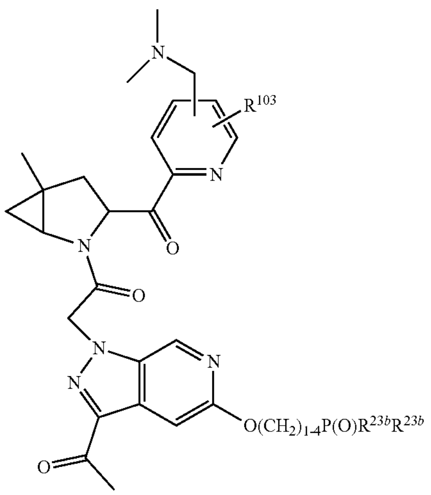

TABLE 2B-continued
Additional Exemplary Formulas within the Present Invention.
Formula II-275
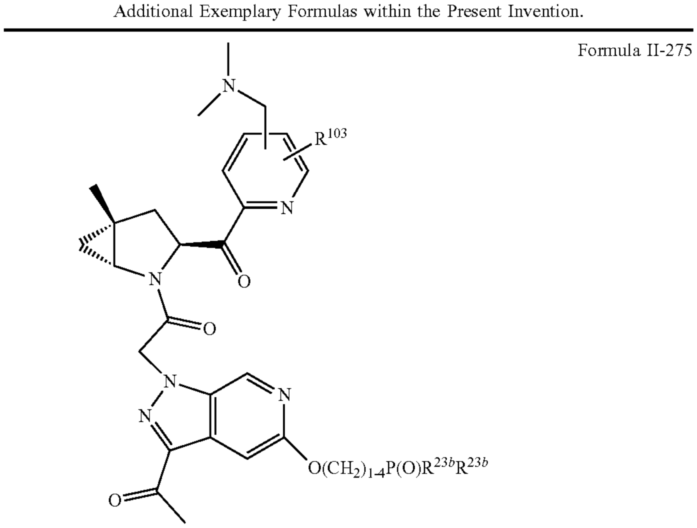
Formula II-276
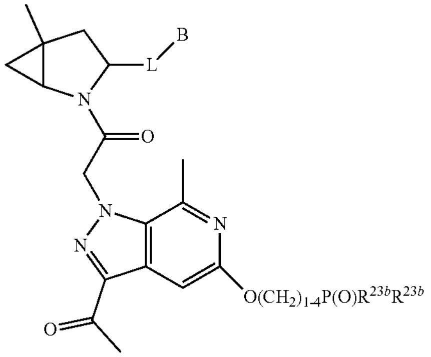
Formula II-277
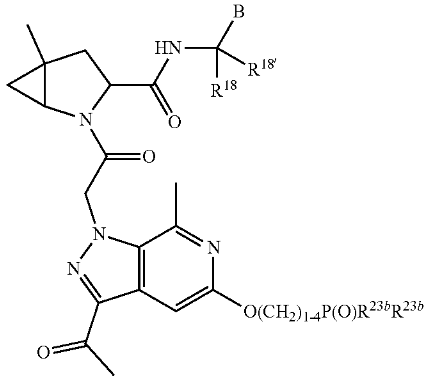
Formula II-278
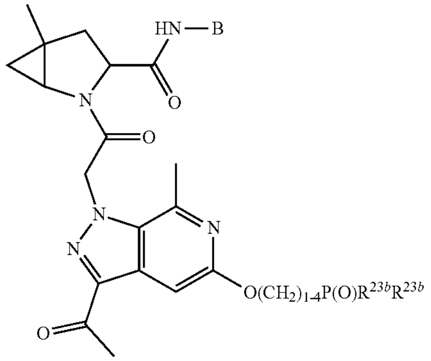

TABLE 2B-continued
Additional Exemplary Formulas within the Present Invention.
Formula II-279
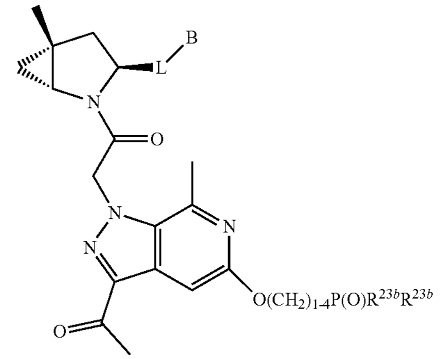
Formula II-280
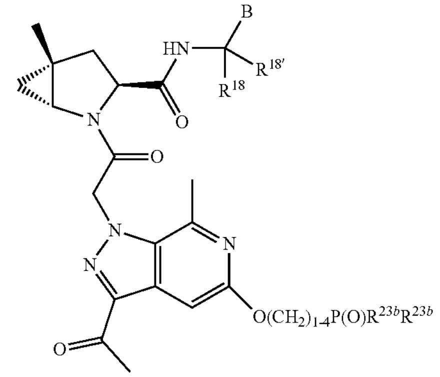
Formula II-281
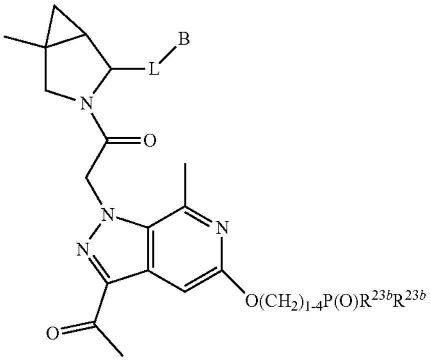
Formula II-282
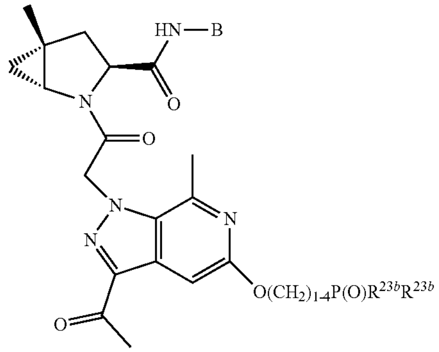

TABLE 2B-continued
Additional Exemplary Formulas within the Present Invention.
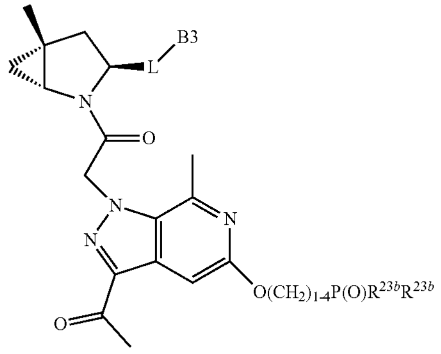
Formula II-283
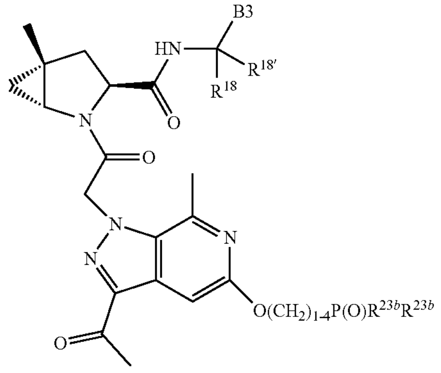
Formula II-284
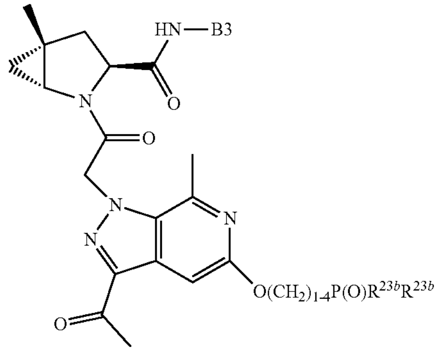
Formula II-285
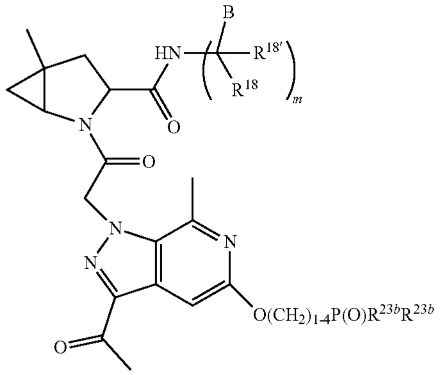
Formula II-286

TABLE 2B-continued
Additional Exemplary Formulas within the Present Invention.
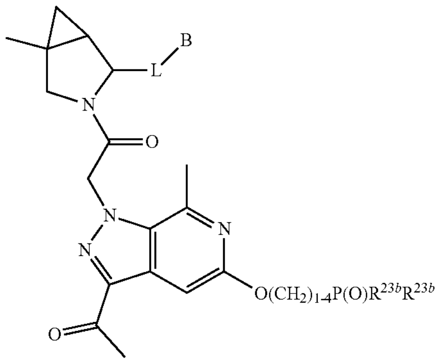
Formula II-287
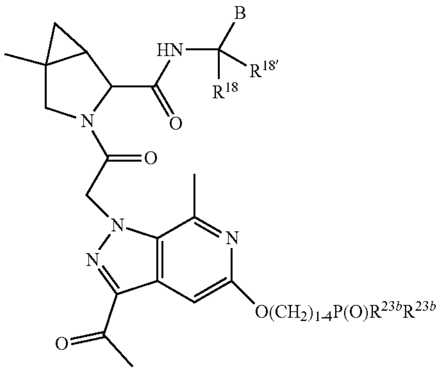
Formula II-288
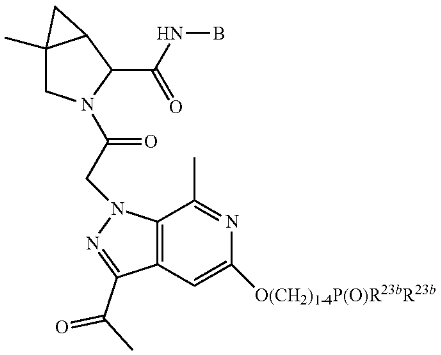
Formula II-289
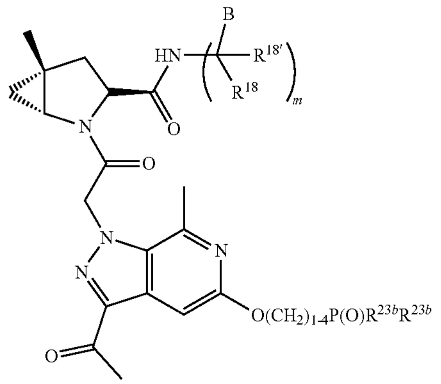
Formula II-290

TABLE 2B-continued
Additional Exemplary Formulas within the Present Invention.
Formula II-291
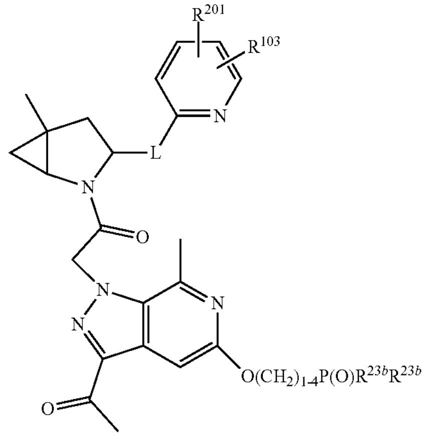
Formula II-292
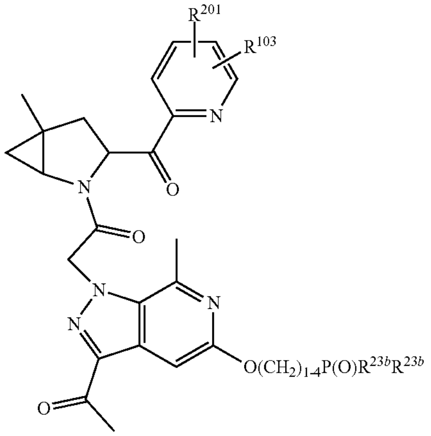
Formula II-293
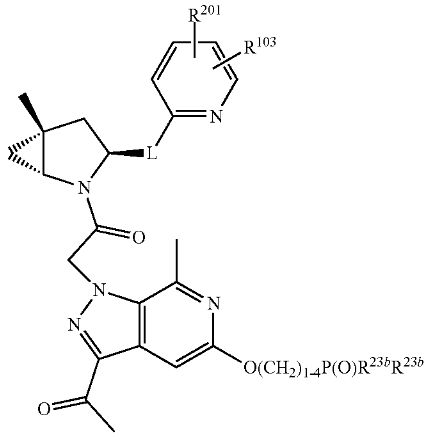

TABLE 2B-continued
Additional Exemplary Formulas within the Present Invention.
Formula II-294
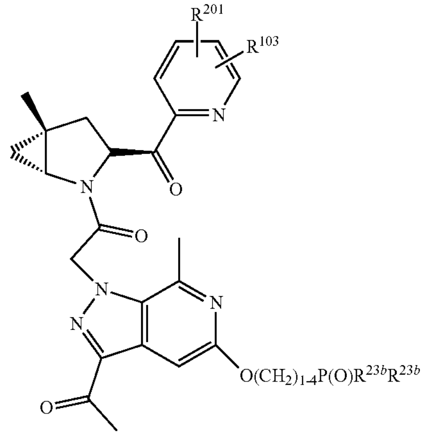
Formula II-295
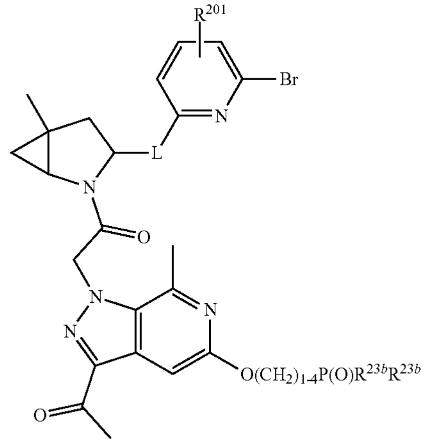
Formula II-296
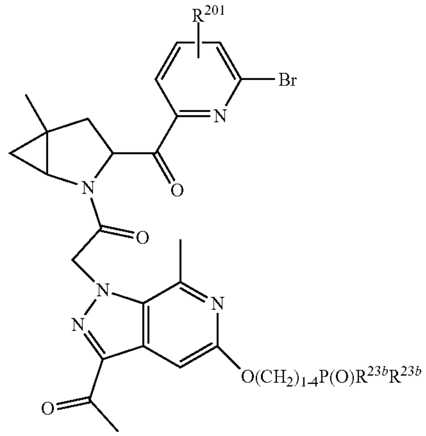

TABLE 2B-continued
| Additional Exemplary Formulas within the Present Invention. |
| --- |
Formula II-297
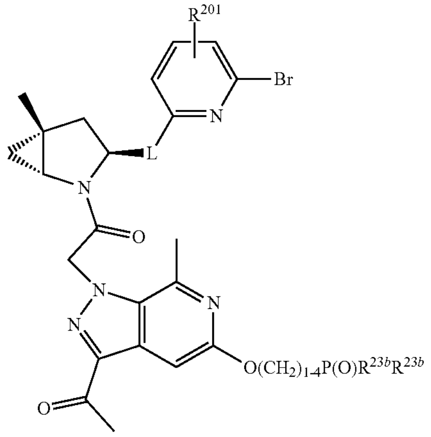
Formula II-298
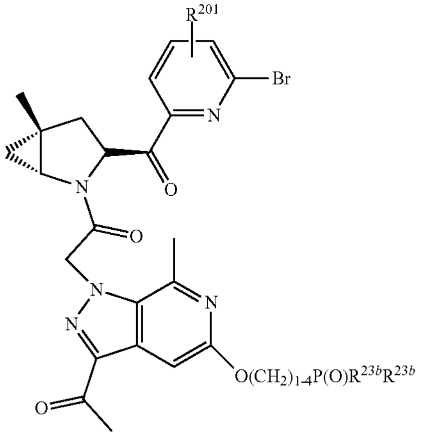
Formula II-299
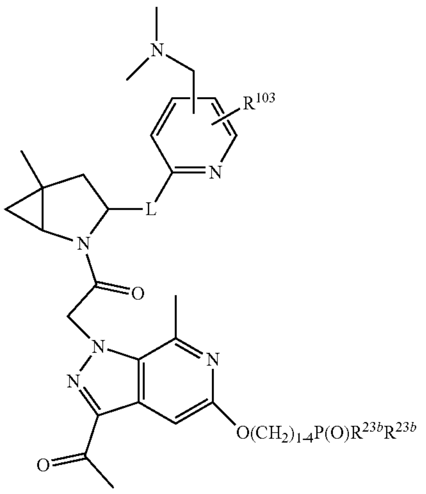

TABLE 2B-continued
Additional Exemplary Formulas within the Present Invention.
Formula II-300
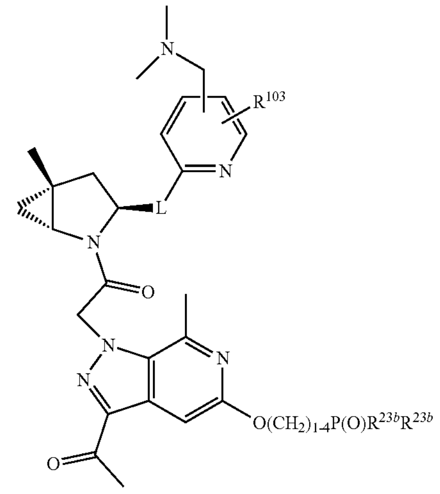
Formula II-301
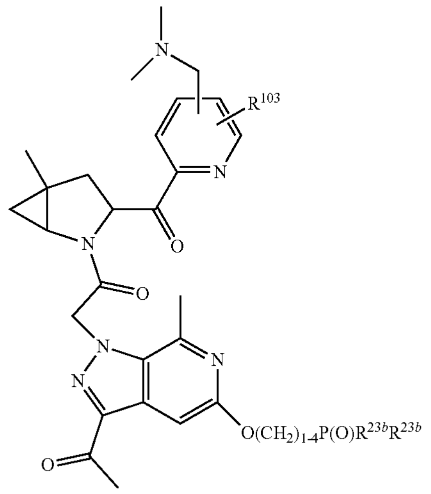
Formula II-302
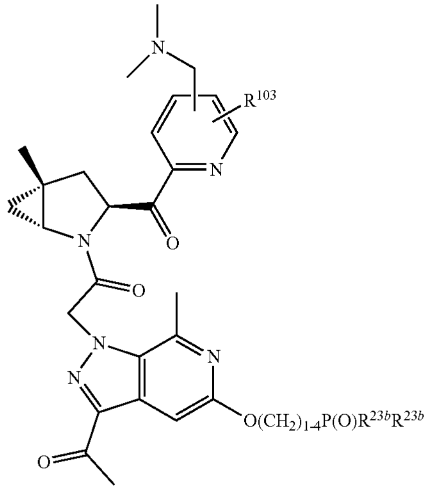

TABLE 2B-continued
| Additional Exemplary Formulas within the Present Invention. |
| --- |
Formula II-303
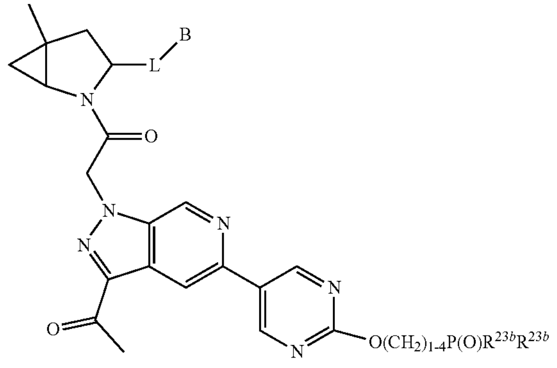
Formula II-304
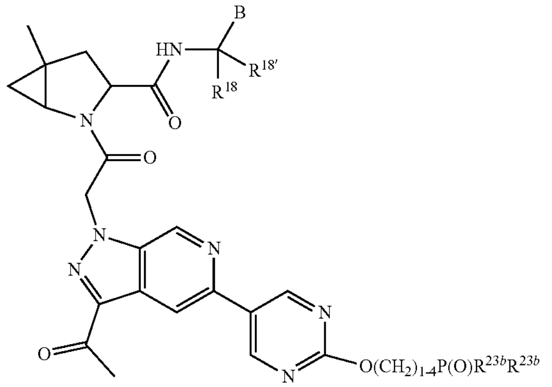
Formula II-305
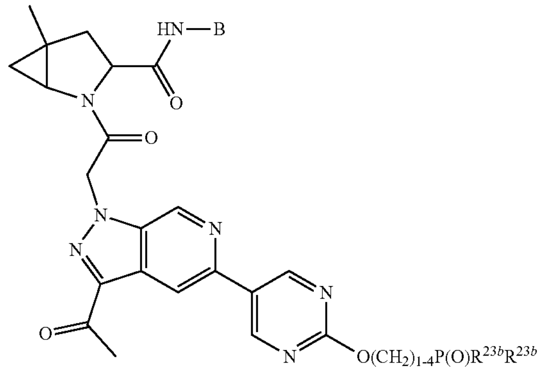
Formula II-306
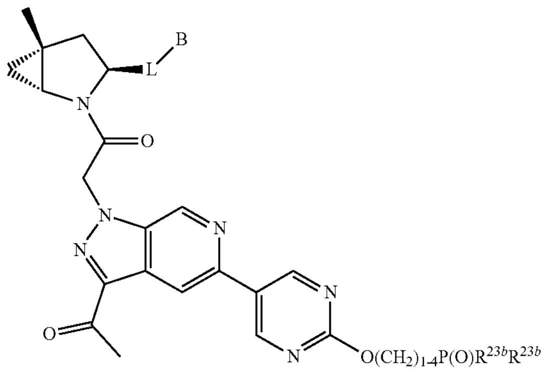

TABLE 2B-continued
Additional Exemplary Formulas within the Present Invention.
Formula II-307
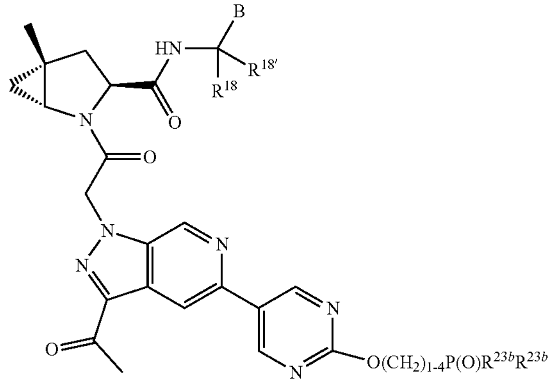
Formula II-308
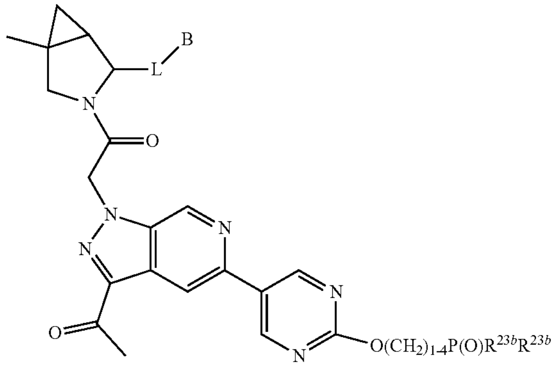
Formula II-309
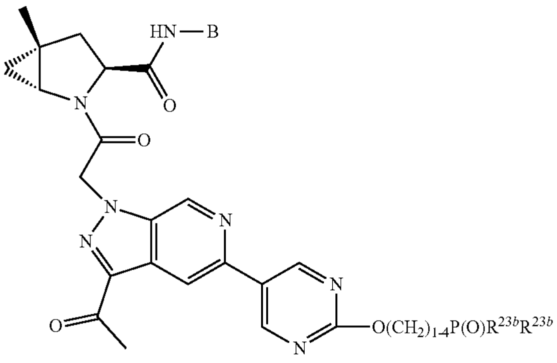
Formula II-310
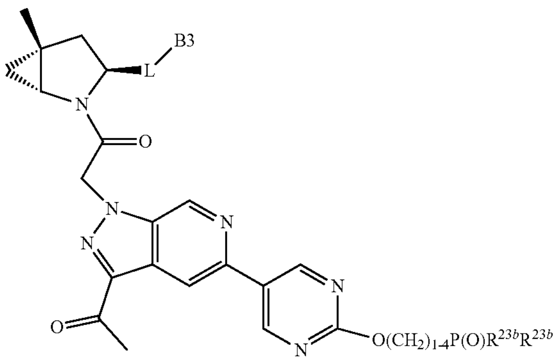

TABLE 2B-continued
Additional Exemplary Formulas within the Present Invention.
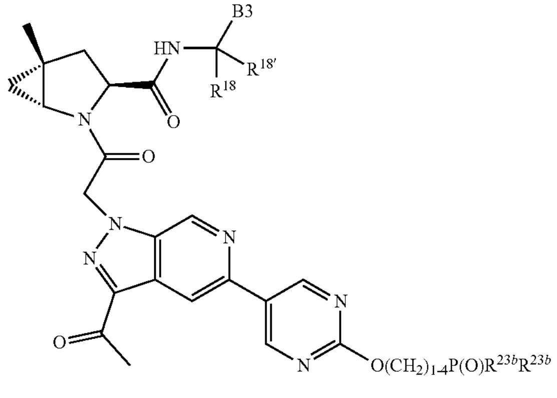
Formula II-311
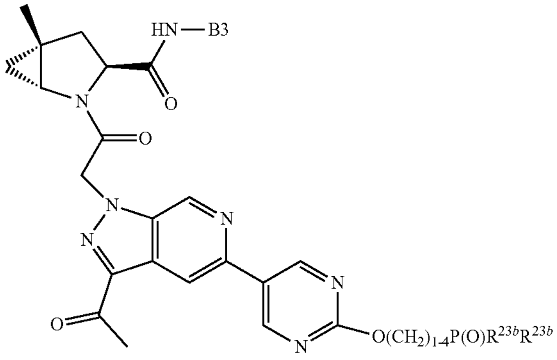
Formula II-312
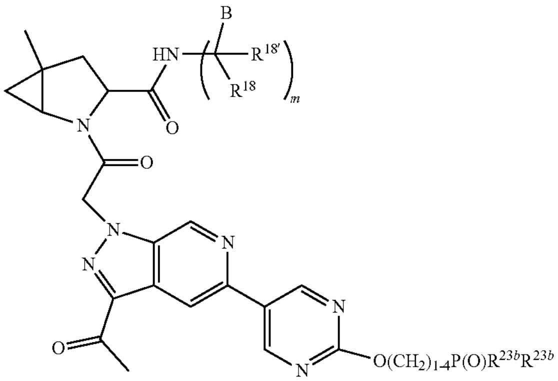
Formula II-313
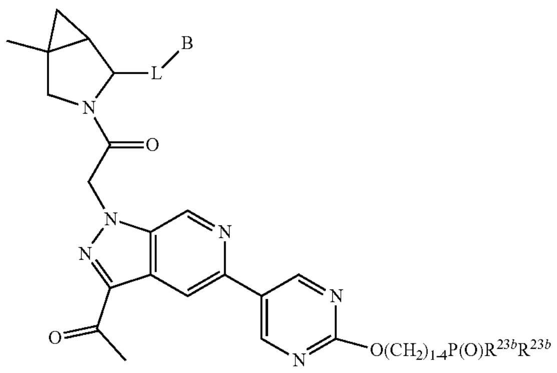
Formula II-314

TABLE 2B-continued
Additional Exemplary Formulas within the Present Invention.
Formula II-315
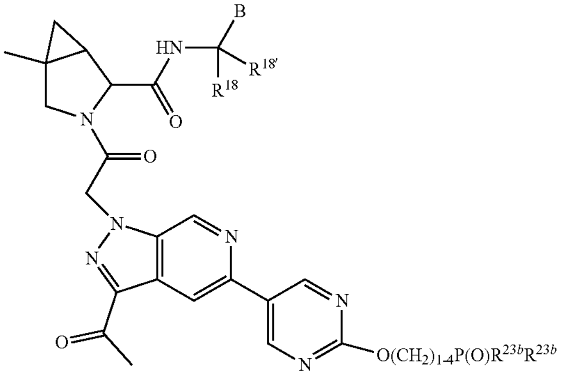
Formula II-316
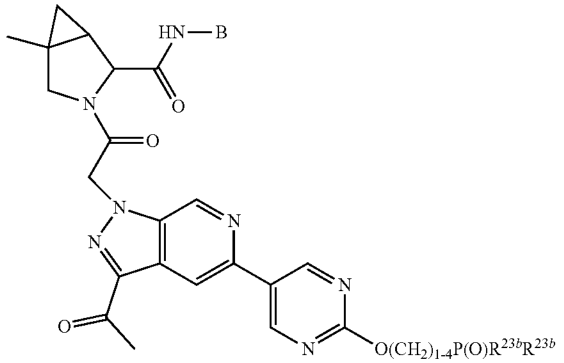
Formula II-317
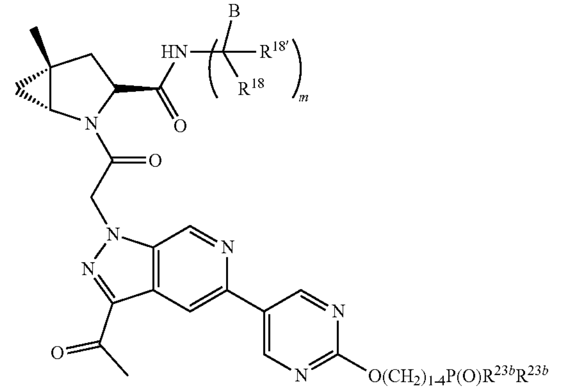
Formula II-318
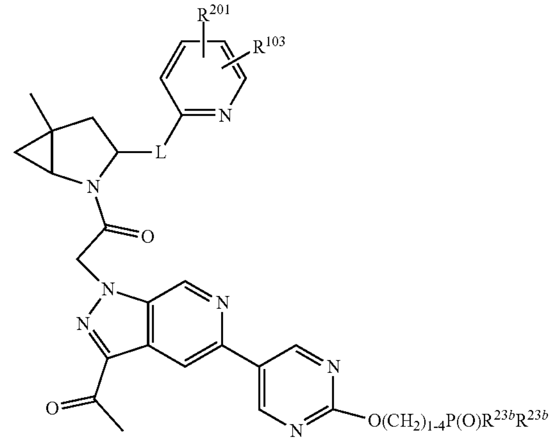

TABLE 2B-continued
| Additional Exemplary Formulas within the Present Invention. |
| --- |
Formula II-319
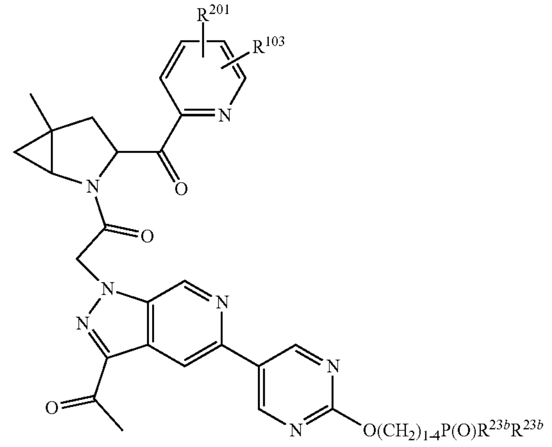
Formula II-320
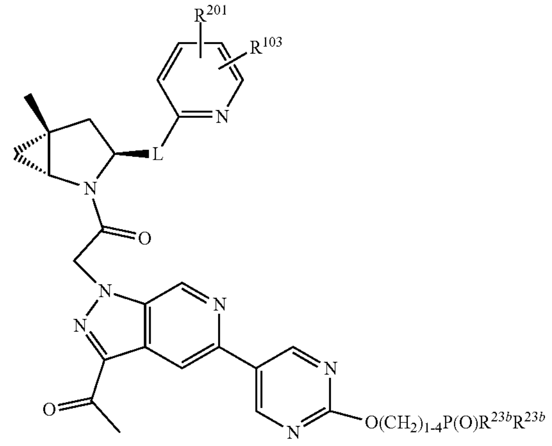
Formula II-321
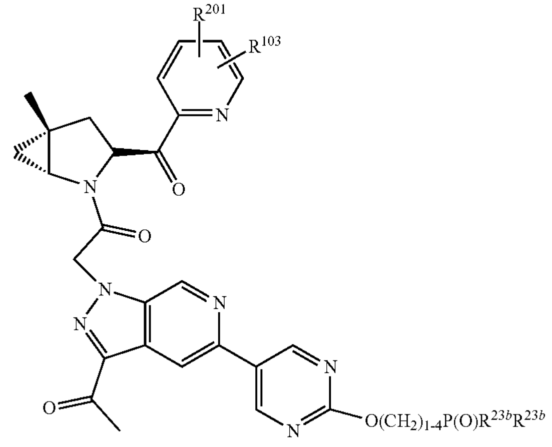

TABLE 2B-continued
| Additional Exemplary Formulas within the Present Invention. |
| --- |
Formula II-322
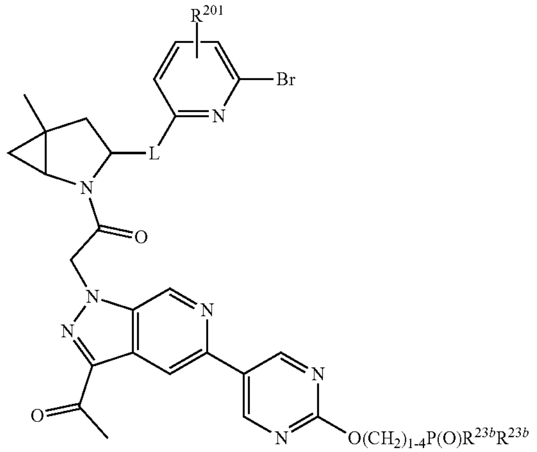
Formula II-323
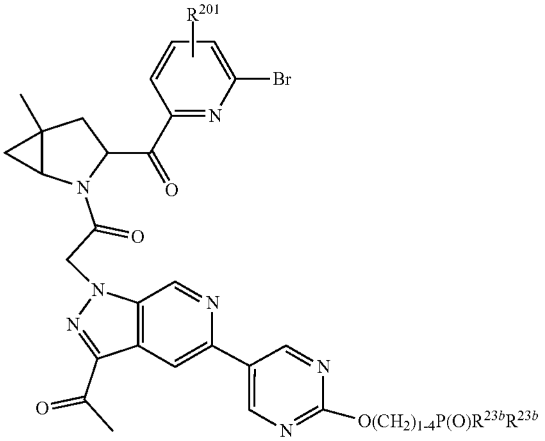
Formula II-324
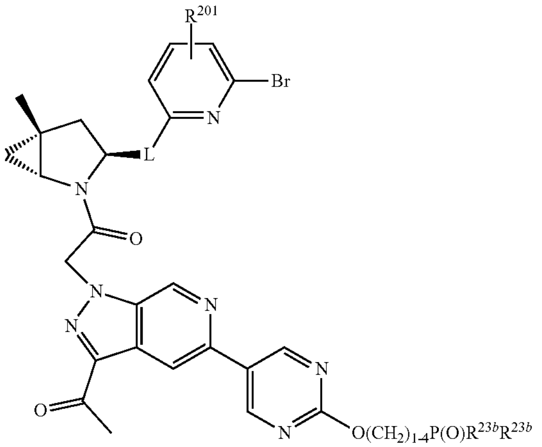

TABLE 2B-continued
| Additional Exemplary Formulas within the Present Invention. |
| --- |
Formula II-325
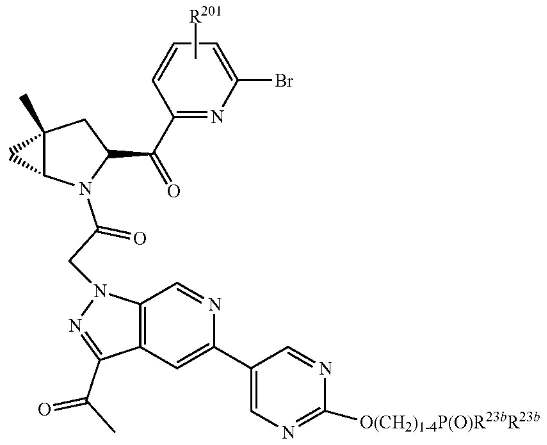
Formula II-326
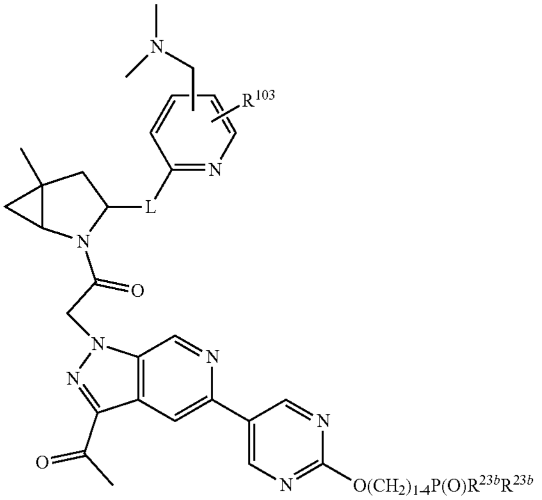
Formula II-327
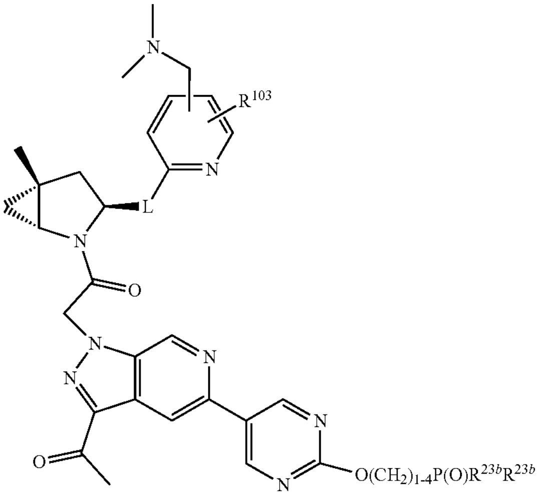

TABLE 2B-continued

Additional Exemplary Formulas within the Present Invention.

Formula II-328

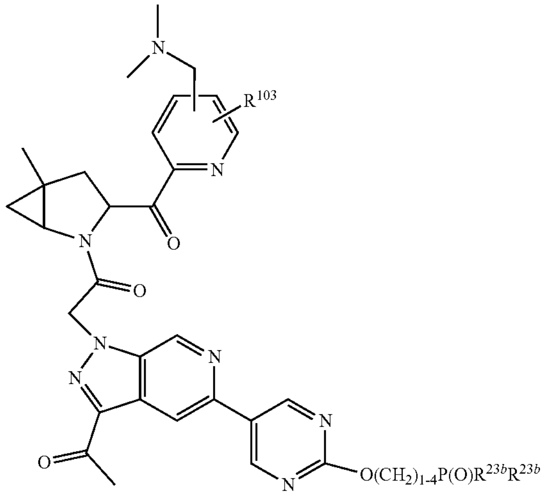

Formula II-329

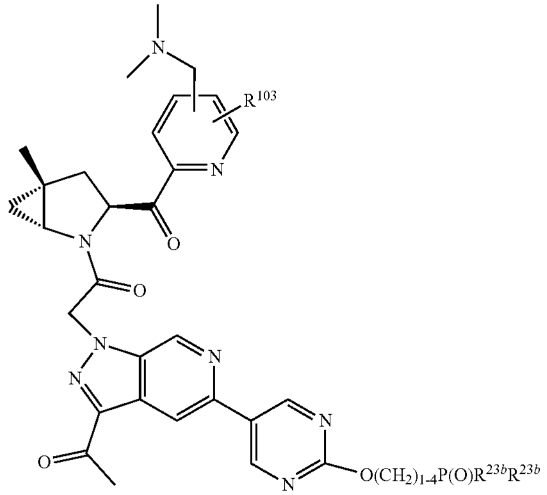

wherein $R^{103}$ is $C_1$-$C_4$ alkyl, $C_3$-$C_6$ cycloalkyl, fluorine, chlorine, or bromine. In Formulas II-249 to II-329 for convenience and space purposes only, $R^{32}$ is illustrated as the group $O(CH_2)_{1-4}P(O)R^{23b}R^{23b}$, however each described or illustrated $R^{32}$ in this application is considered to be independently shown in each of these Formulas.

TABLE 3

Additional Exemplary Formulas within the Present Invention.

Formula III-1

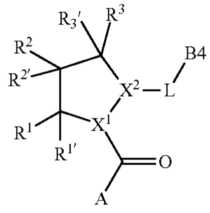

TABLE 3-continued

Additional Exemplary Formulas within the Present Invention.

Formula III-2

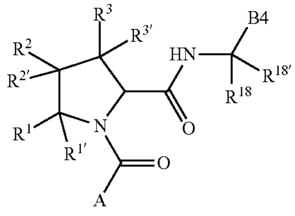

Formula III-3

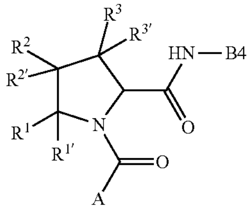

TABLE 3-continued
| Additional Exemplary Formulas within the Present Invention. |
|---|
| 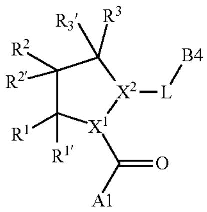 Formula III-4 |
| 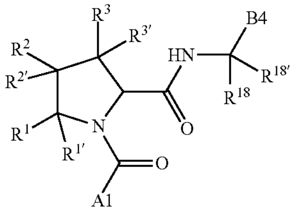 Formula III-5 |
| 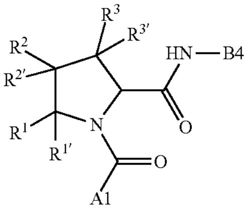 Formula III-6 |
| 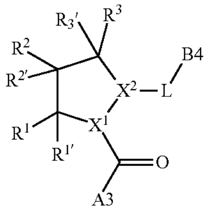 Formula III-7 |
| 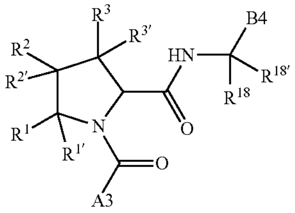 Formula III-8 |
| 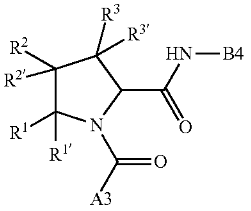 Formula III-9 |
| 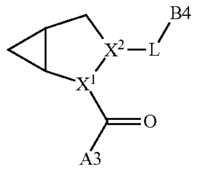 Formula III-10 |
TABLE 3-continued
| Additional Exemplary Formulas within the Present Invention. |
|---|
| 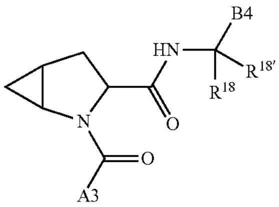 Formula III-11 |
| 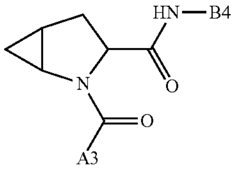 Formula III-12 |
| 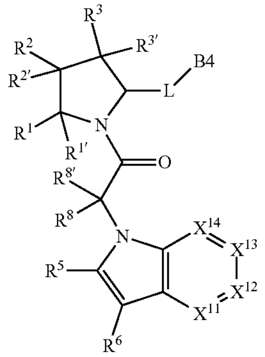 Formula III-13 |
| 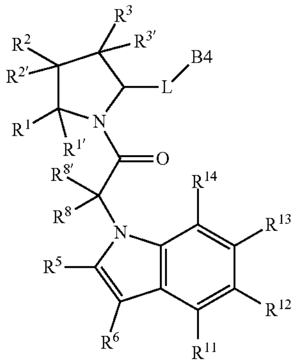 Formula III-14 |
| 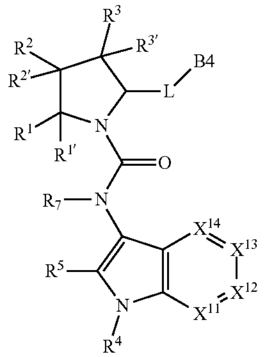 Formula III-15 |

TABLE 3-continued
| Additional Exemplary Formulas within the Present Invention. |
|---|
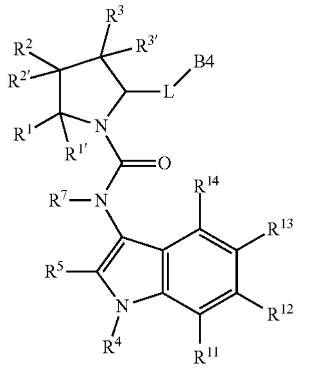
Formula III-16
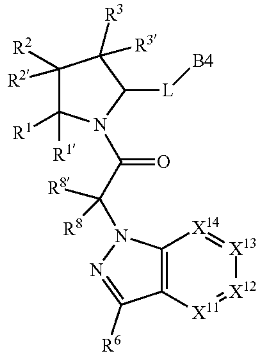
Formula III-17
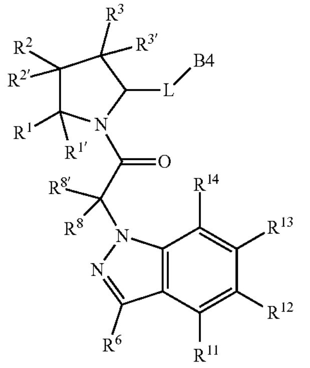
Formula III-18
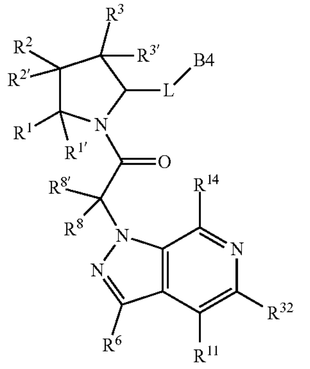
Formula III-19
TABLE 3-continued
| Additional Exemplary Formulas within the Present Invention. |
|---|
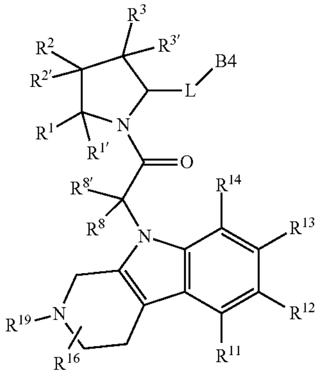
Formula III-20
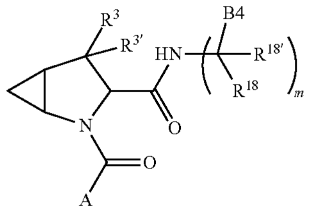
Formula III-21
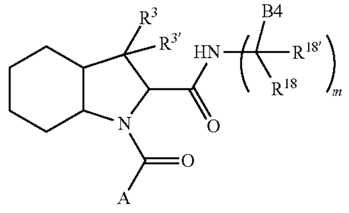
Formula III-22
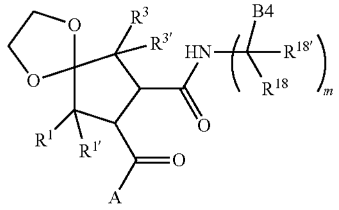
Formula III-23
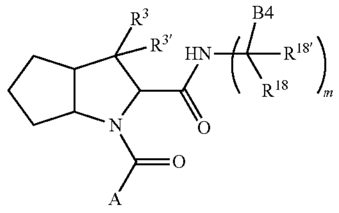
Formula III-24

TABLE 3-continued
Additional Exemplary Formulas within the Present Invention.
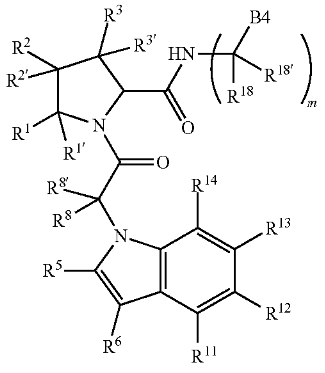
Formula III-25
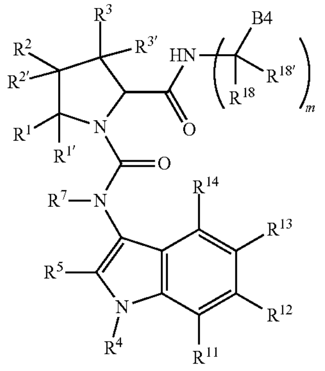
Formula III-26
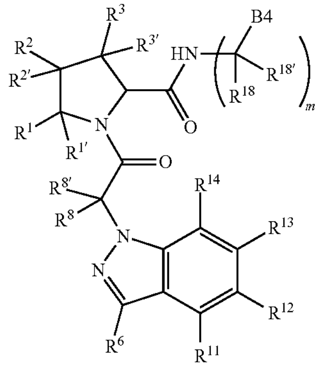
Formula III-27
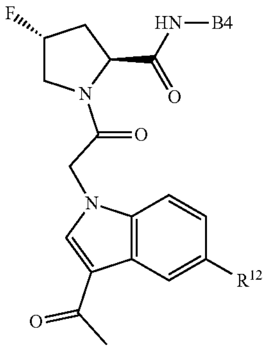
Formula III-28
TABLE 3-continued
Additional Exemplary Formulas within the Present Invention.
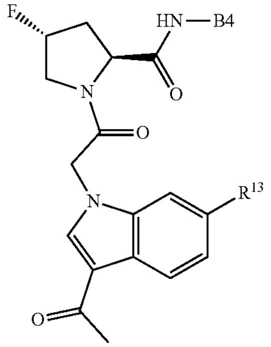
Formula III-29
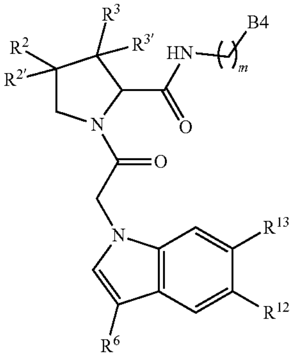
Formula III-30
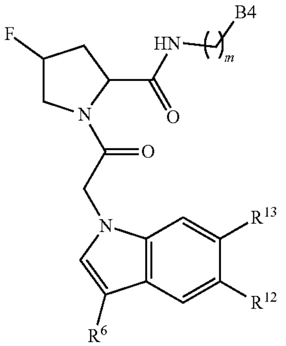
Formula III-31
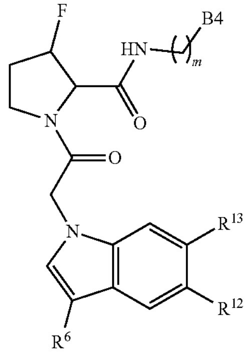
Formula III-32

TABLE 3-continued
Additional Exemplary Formulas within the Present Invention.
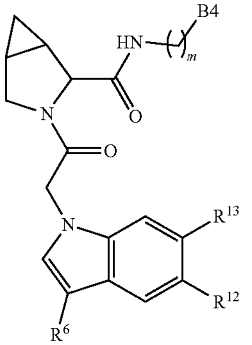
Formula III-33
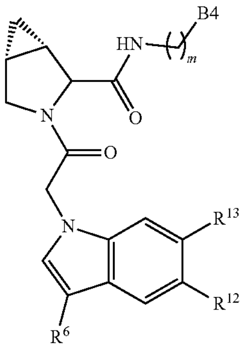
Formula III-34
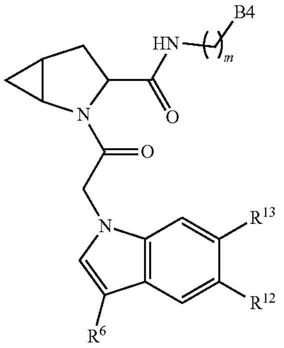
Formula III-35
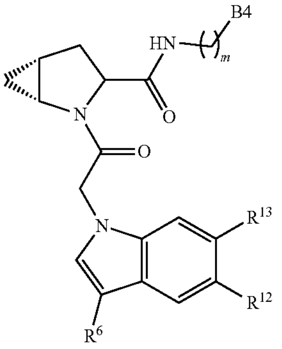
Formula III-36
TABLE 3-continued
Additional Exemplary Formulas within the Present Invention.
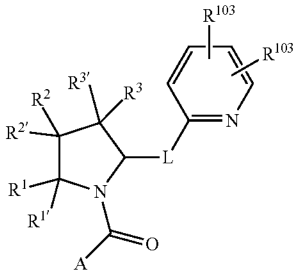
Formula III-37
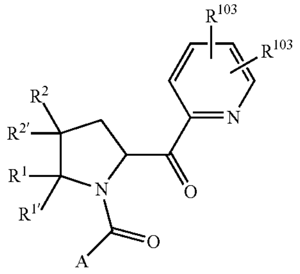
Formula III-38
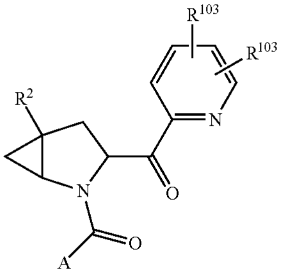
Formula III-39
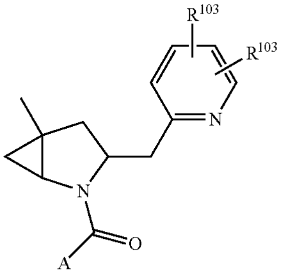
Formula III-40
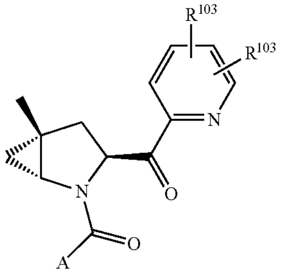
Formula III-41

TABLE 3-continued

| Additional Exemplary Formulas within the Present Invention. |
|---|
| Formula III-42 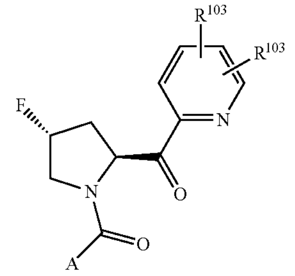 |
| Formula III-43 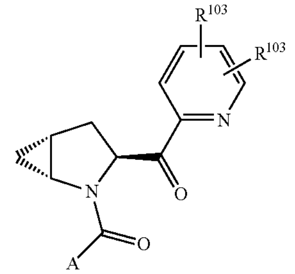 |
| Formula III-44 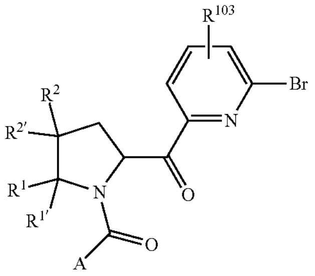 |
| Formula III-45 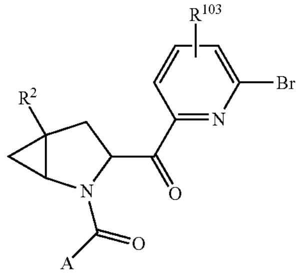 |
| Formula III-46 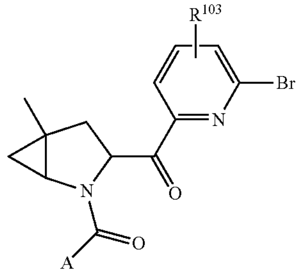 |

TABLE 3-continued

| Additional Exemplary Formulas within the Present Invention. |
|---|
| Formula III-47 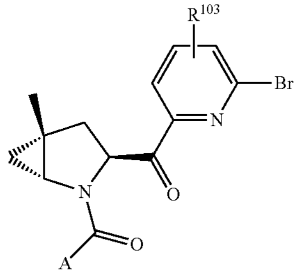 |
| Formula III-48 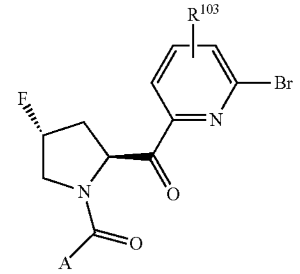 |
| Formula III-49 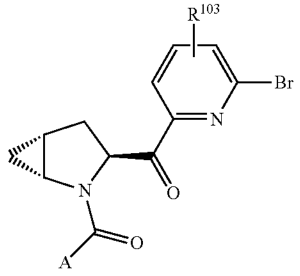 |

wherein $R^{103}$ is independently $C_1$-$C_4$ alkyl, $C_3$-$C_6$ cycloalkyl, fluorine, chlorine, or bromine.

Any of the compounds in Table 4 can also, if desired, include an additional $R^{13}$ substituent on the A ring, if appropriate, and considered individually drawn and illustrated

TABLE 4

| Additional Exemplary Formulas within the Present Invention. |
|---|
| 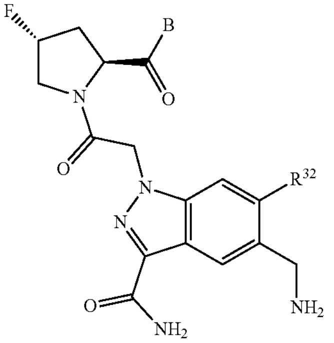 |

TABLE 4-continued
| Additional Exemplary Formulas within the Present Invention. |
| --- |
| 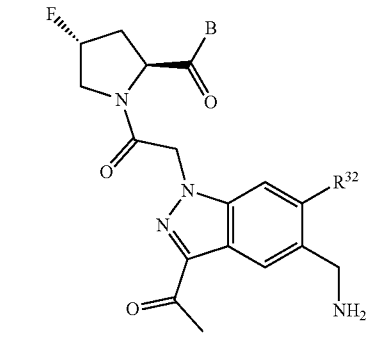 |
| 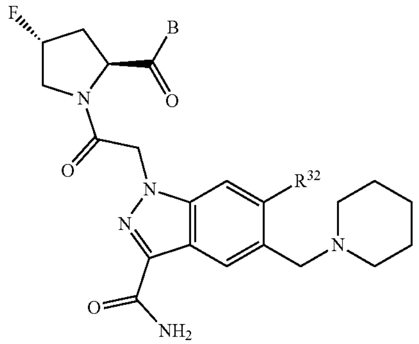 |
| 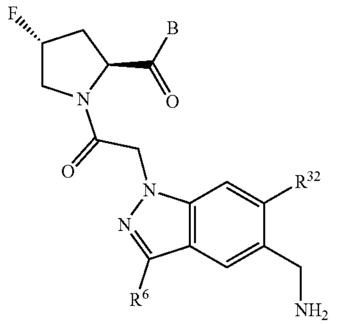 |
| 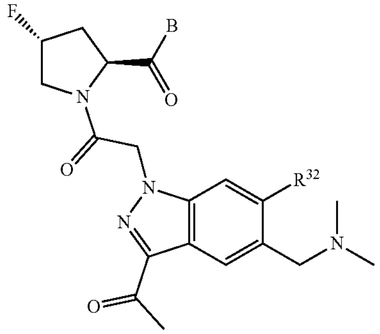 |
TABLE 4-continued
| Additional Exemplary Formulas within the Present Invention. |
| --- |
| 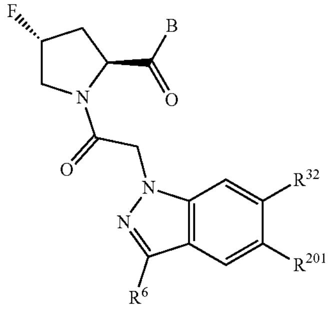 |
| 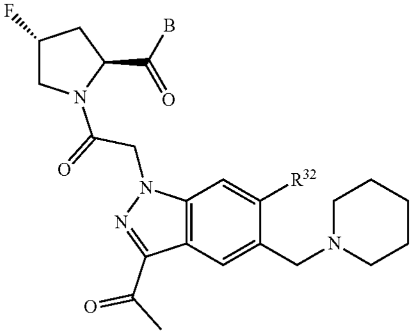 |
| 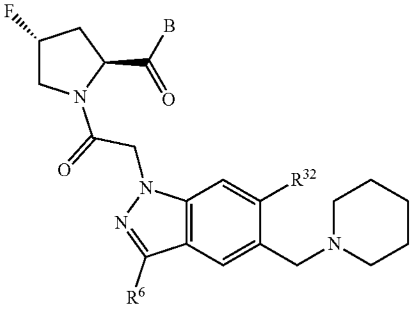 |
| 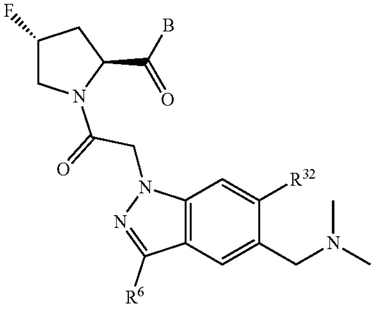 |

TABLE 4-continued
| Additional Exemplary Formulas within the Present Invention. |
|---|
| 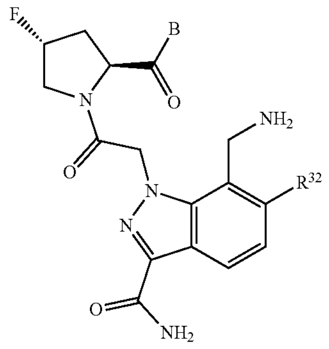 |
| 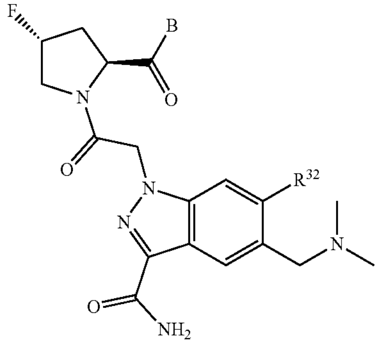 |
| 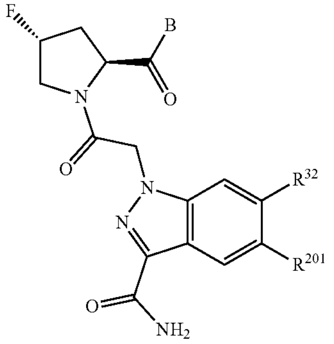 |
| 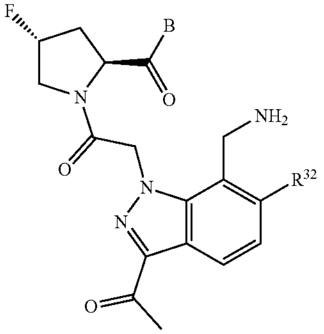 |
TABLE 4-continued
| Additional Exemplary Formulas within the Present Invention. |
|---|
| 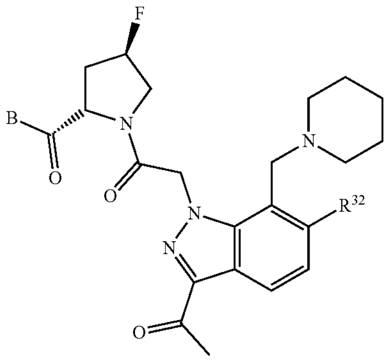 |
| 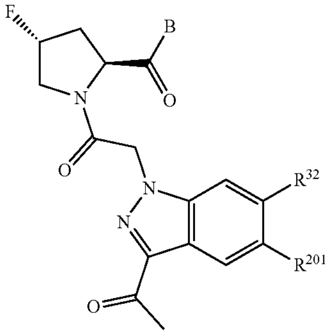 |
| 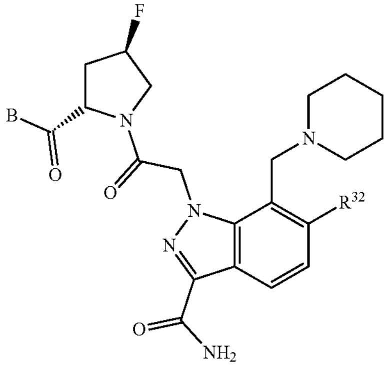 |
| 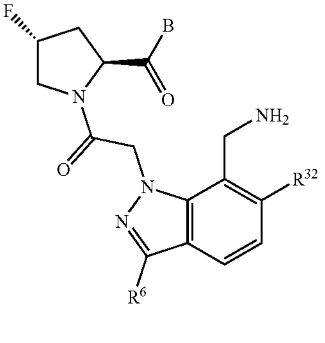 |

TABLE 4-continued
| Additional Exemplary Formulas within the Present Invention. |
|---|
| 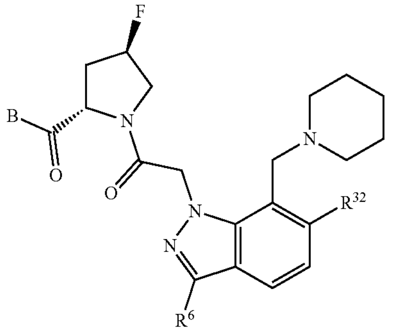 |
| 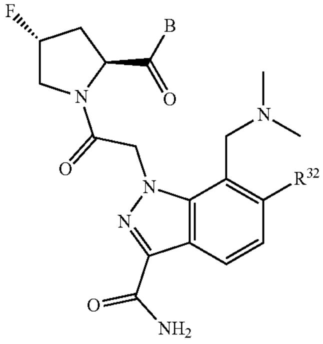 |
| 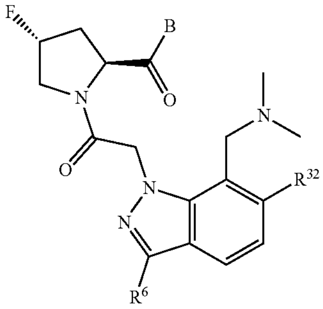 |
| 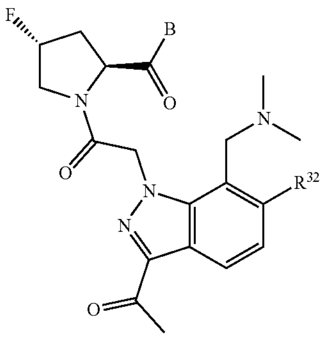 |
TABLE 4-continued
| Additional Exemplary Formulas within the Present Invention. |
|---|
| 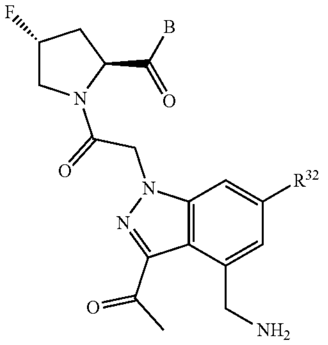 |
| 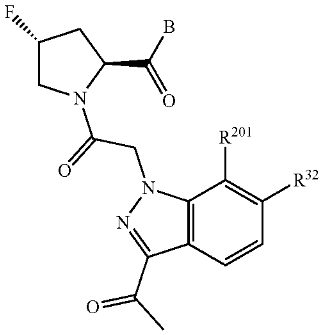 |
| 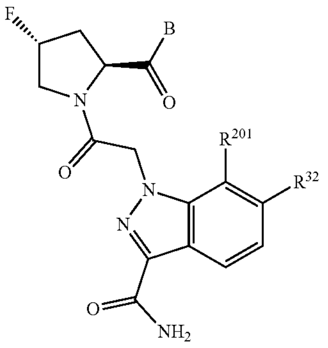 |
| 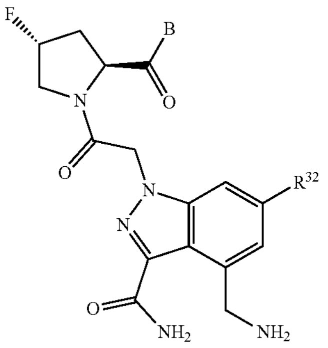 |

TABLE 4-continued
| Additional Exemplary Formulas within the Present Invention. |
| --- |
| 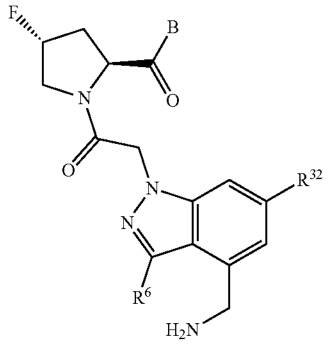 |
| 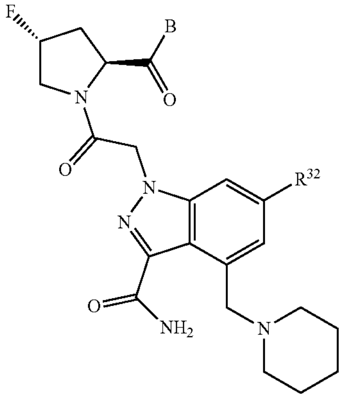 |
| 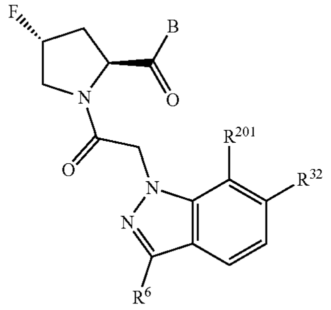 |
| 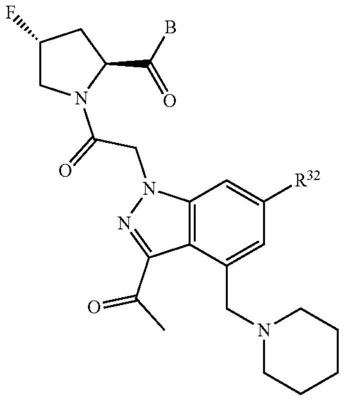 |
| 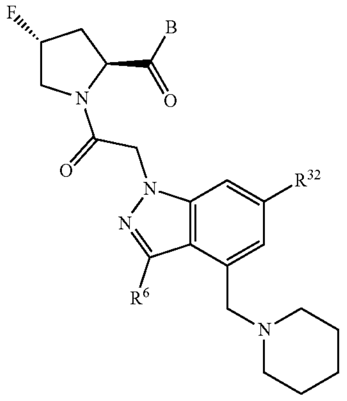 |
| 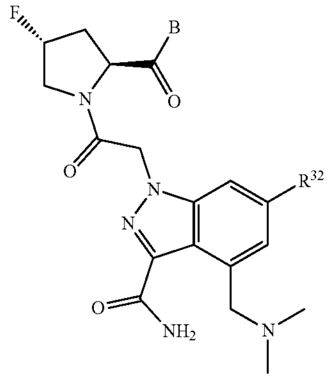 |
| 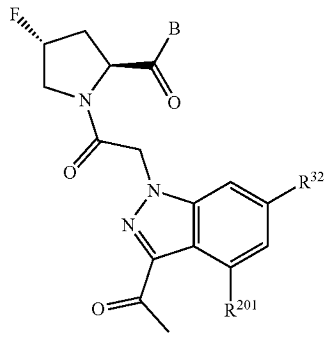 |
| 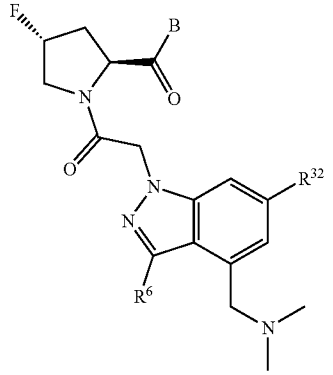 |

TABLE 4-continued
| Additional Exemplary Formulas within the Present Invention. |
|---|
| 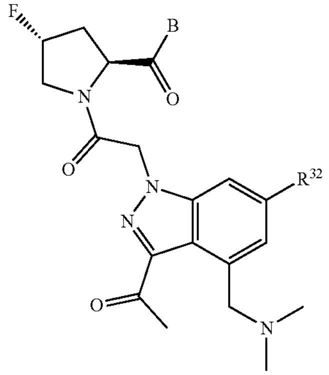 |
| 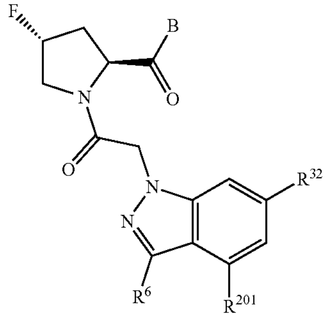 |
| 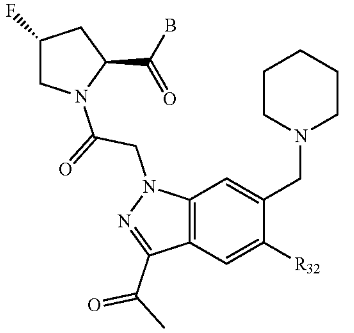 |
| 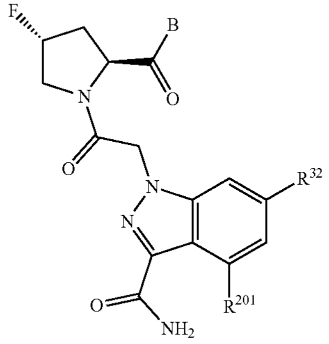 |
TABLE 4-continued
| Additional Exemplary Formulas within the Present Invention. |
|---|
| 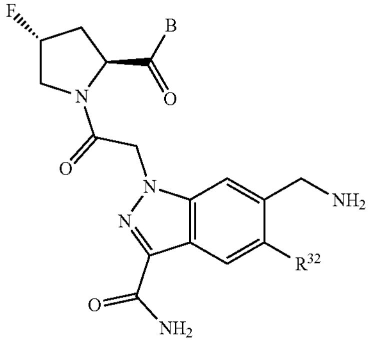 |
| 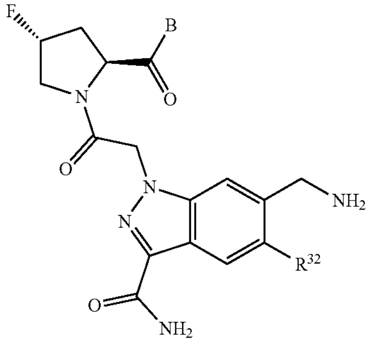 |
| 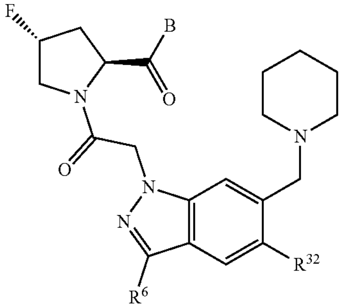 |
| 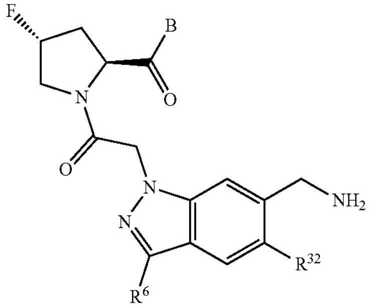 |

TABLE 4-continued
| Additional Exemplary Formulas within the Present Invention. |
|---|
| 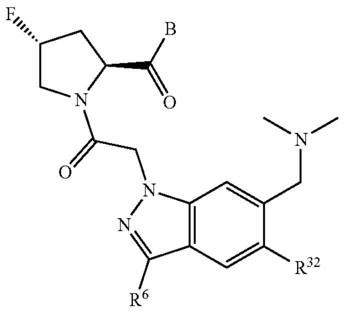 |
| 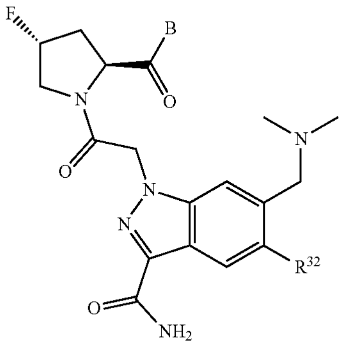 |
| 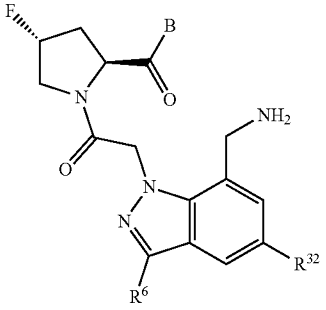 |
| 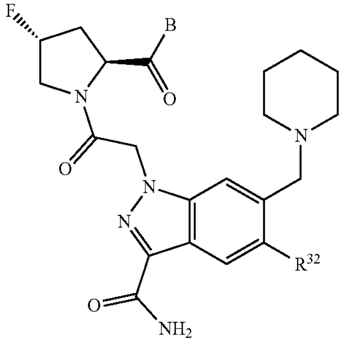 |
TABLE 4-continued
| Additional Exemplary Formulas within the Present Invention. |
|---|
| 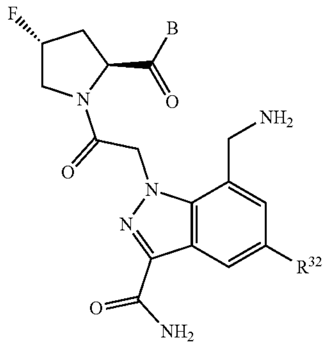 |
| 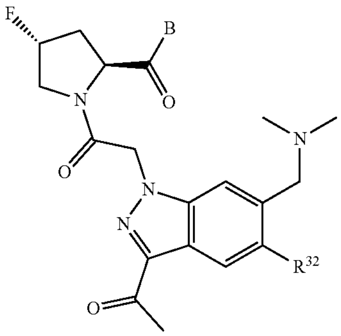 |
| 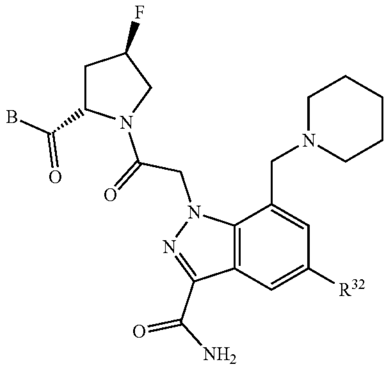 |
| 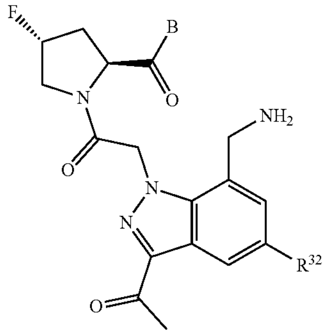 |

TABLE 4-continued
| Additional Exemplary Formulas within the Present Invention. |
| --- |
| 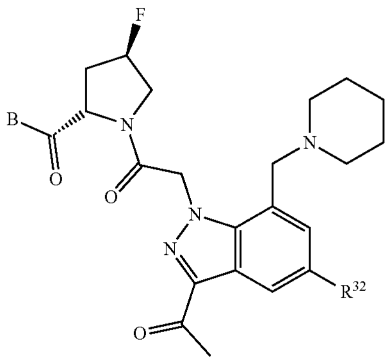 |
| 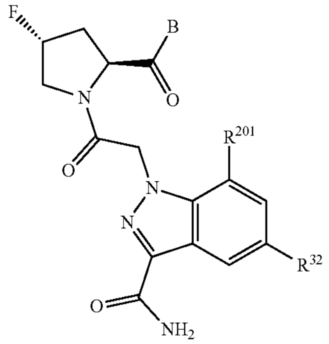 |
| 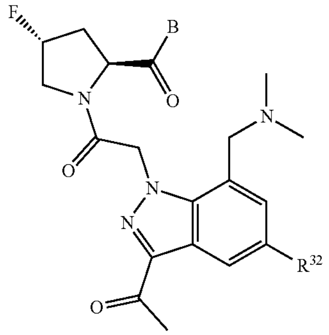 |
| 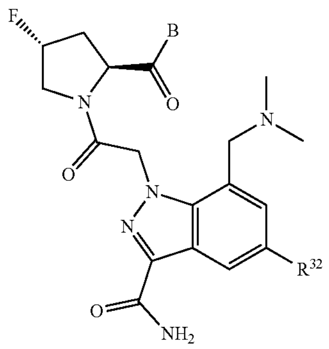 |
TABLE 4-continued
| Additional Exemplary Formulas within the Present Invention. |
| --- |
| 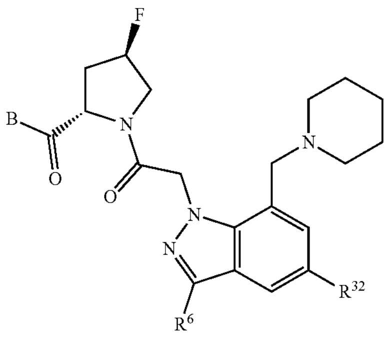 |
| 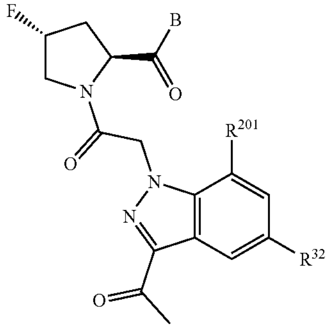 |
| 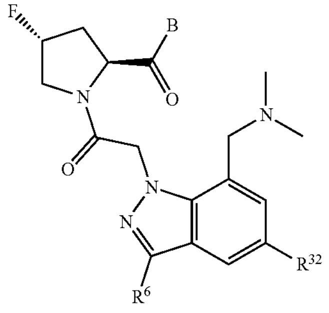 |
| 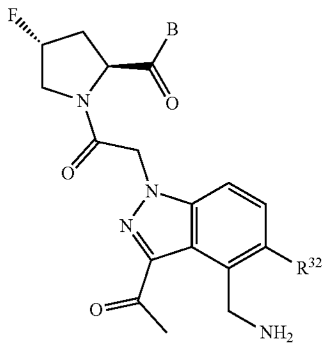 |

TABLE 4-continued
| Additional Exemplary Formulas within the Present Invention. |
|---|
| 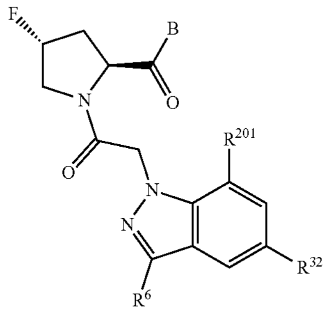 |
| 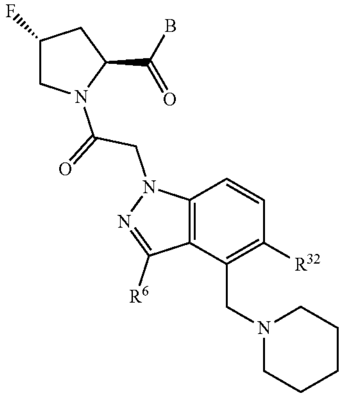 |
| 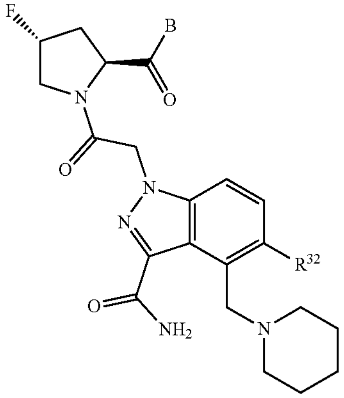 |
| 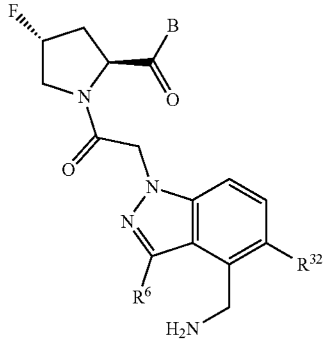 |
TABLE 4-continued
| Additional Exemplary Formulas within the Present Invention. |
|---|
| 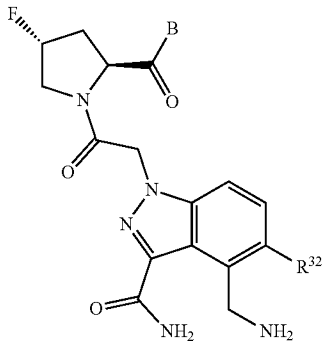 |
| 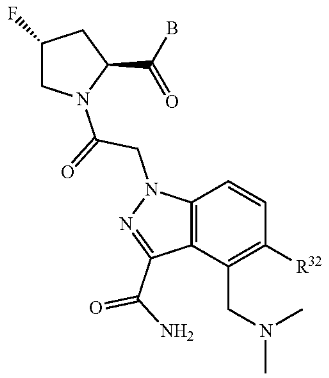 |
| 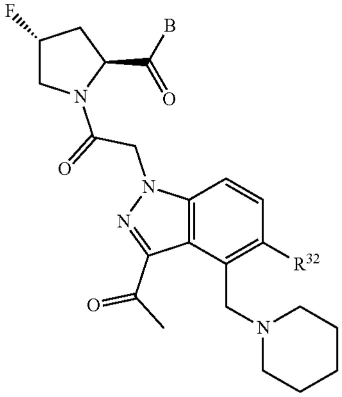 |
| 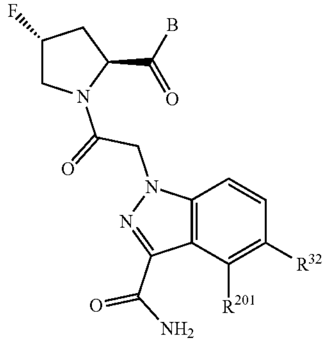 |

TABLE 4-continued
| Additional Exemplary Formulas within the Present Invention. |
|---|
| 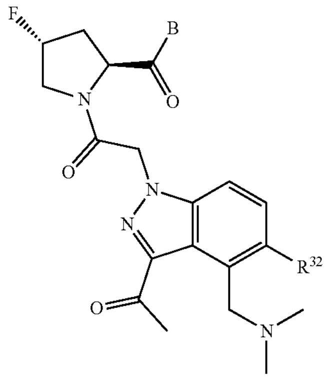 |
| 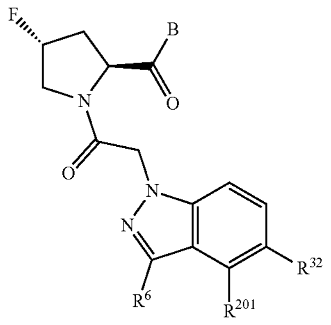 |
| 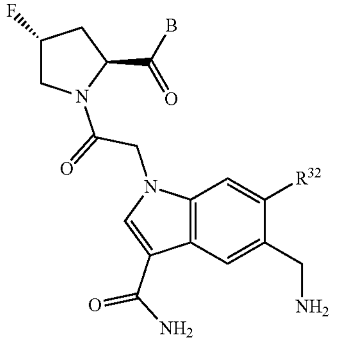 |
| 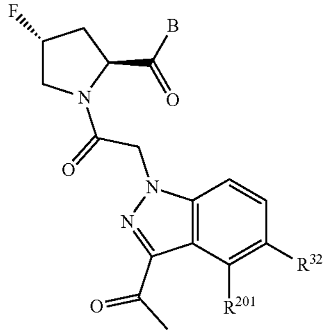 |
TABLE 4-continued
| Additional Exemplary Formulas within the Present Invention. |
|---|
| 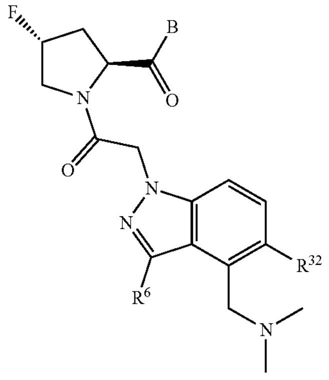 |
| 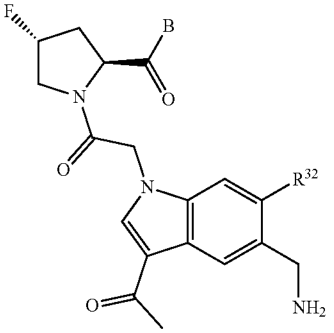 |
| 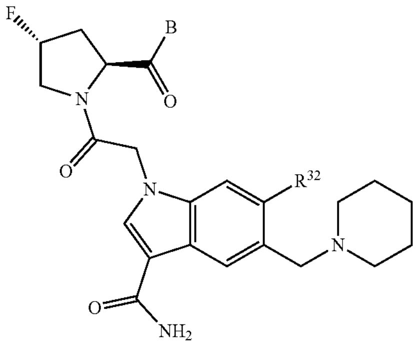 |
| 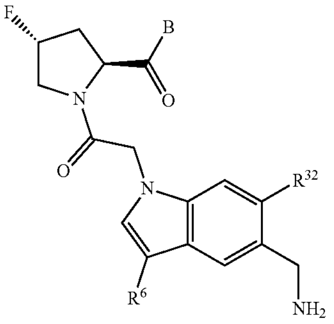 |

TABLE 4-continued
| Additional Exemplary Formulas within the Present Invention. |
| --- |
| 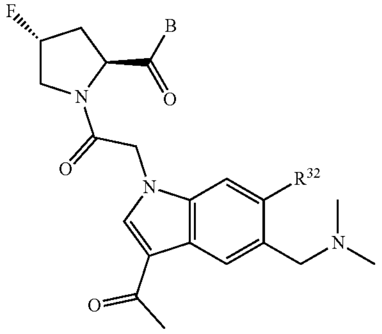 |
| 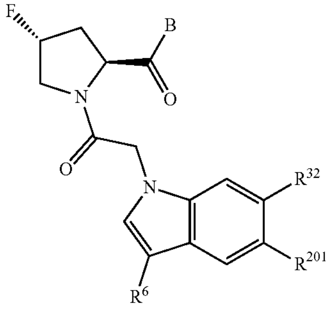 |
| 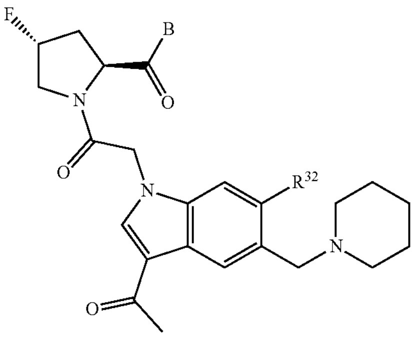 |
| 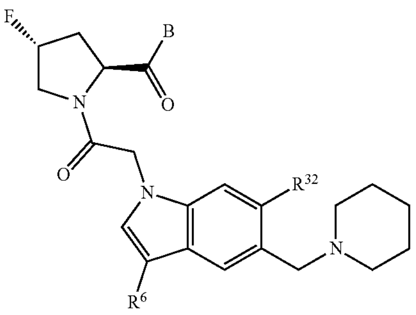 |
TABLE 4-continued
| Additional Exemplary Formulas within the Present Invention. |
| --- |
| 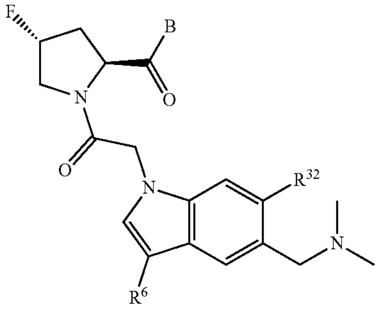 |
| 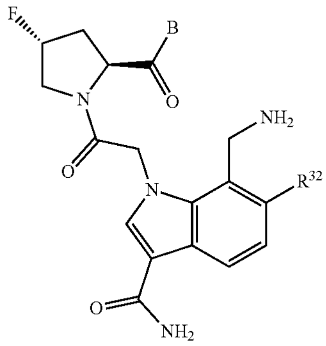 |
| 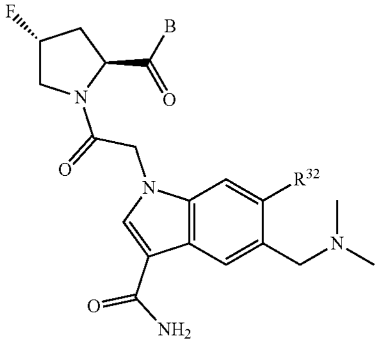 |
| 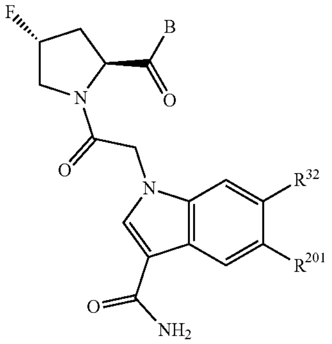 |

TABLE 4-continued
| Additional Exemplary Formulas within the Present Invention. |
|---|
| 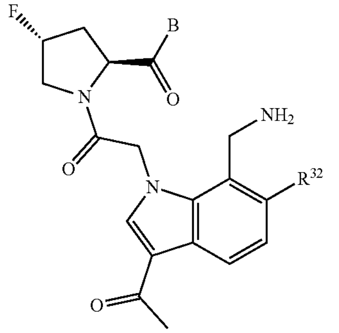 |
| 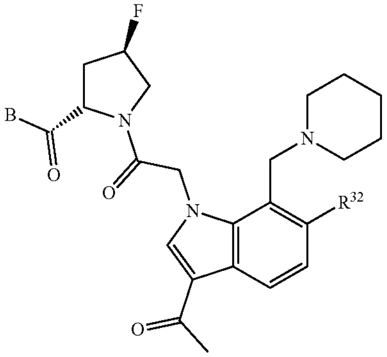 |
| 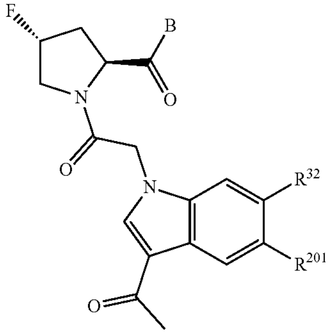 |
| 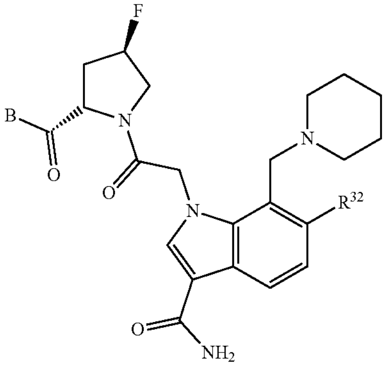 |
TABLE 4-continued
| Additional Exemplary Formulas within the Present Invention. |
|---|
| 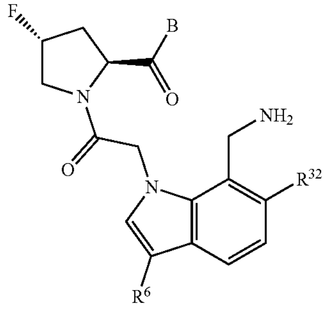 |
| 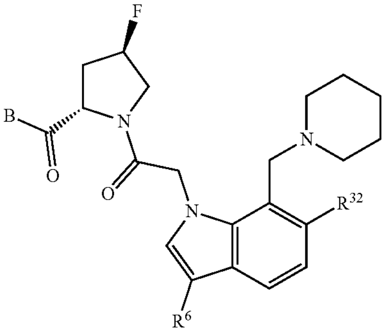 |
| 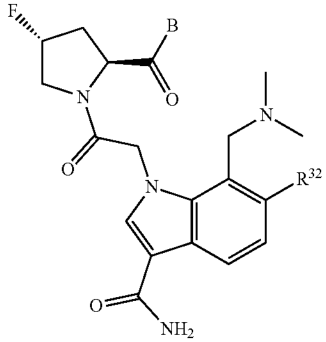 |
| 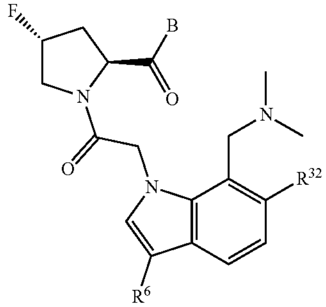 |

TABLE 4-continued
Additional Exemplary Formulas within the Present Invention.
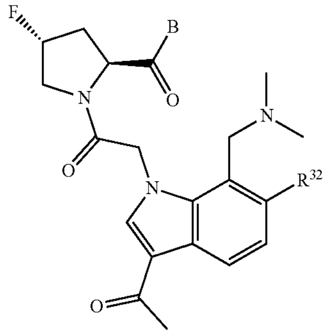
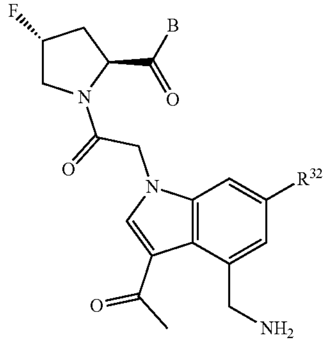
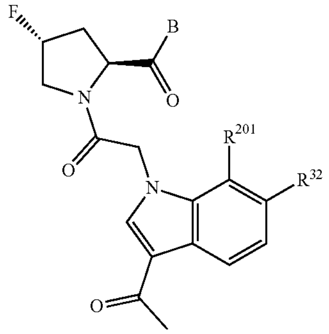
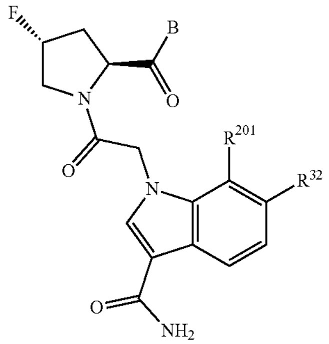
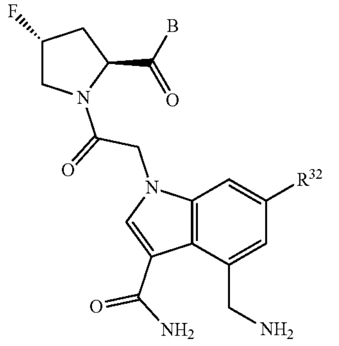
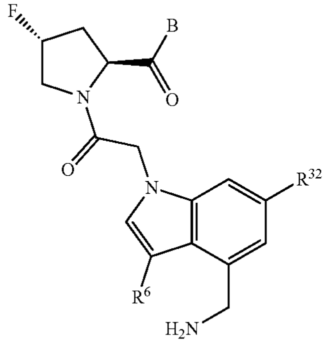
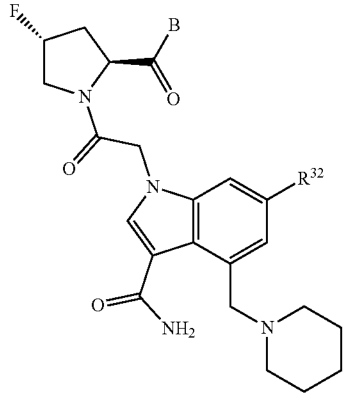
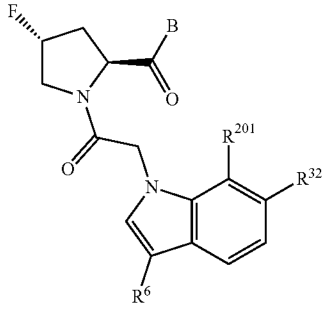

TABLE 4-continued
| Additional Exemplary Formulas within the Present Invention. |
| --- |
| 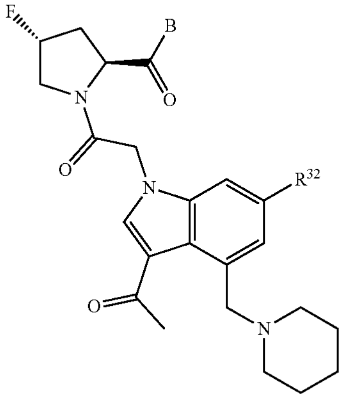 |
| 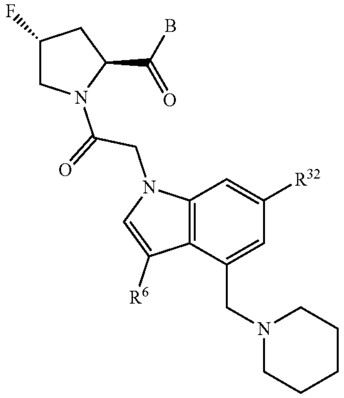 |
| 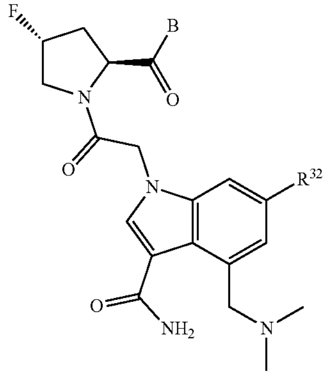 |
| 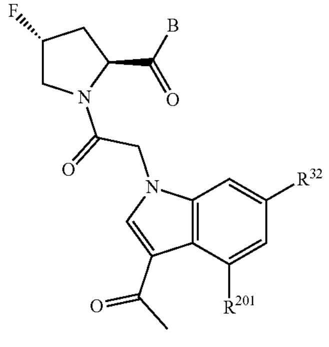 |
TABLE 4-continued
| Additional Exemplary Formulas within the Present Invention. |
| --- |
| 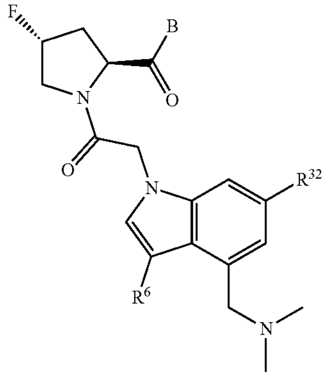 |
| 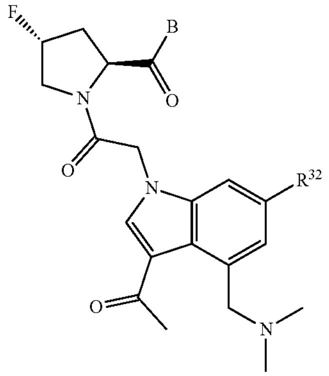 |
| 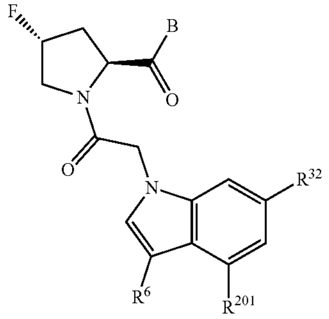 |
| 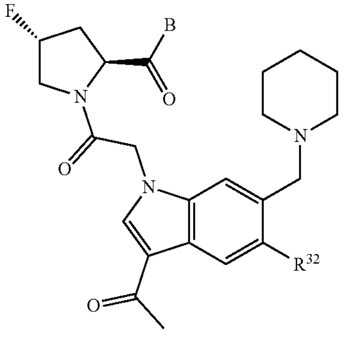 |

TABLE 4-continued
Additional Exemplary Formulas within the Present Invention.
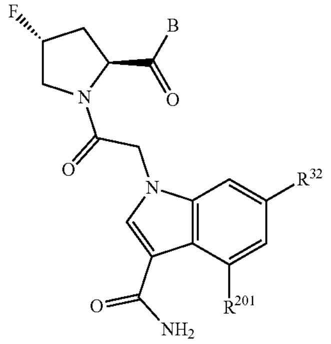
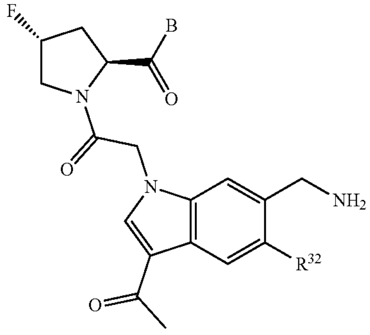
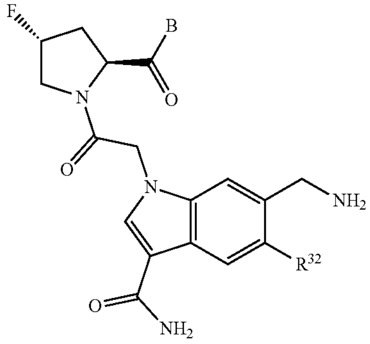
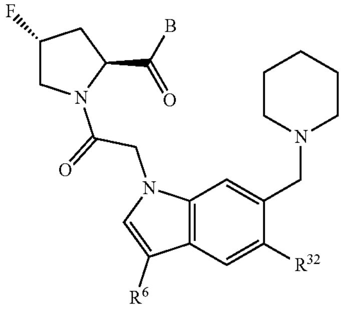
TABLE 4-continued
Additional Exemplary Formulas within the Present Invention.
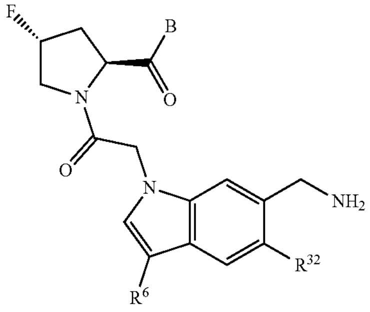
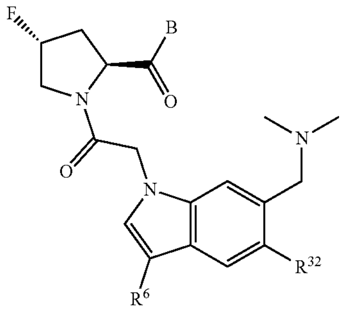
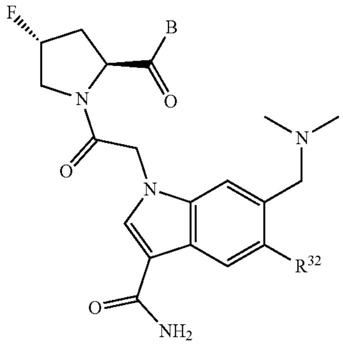
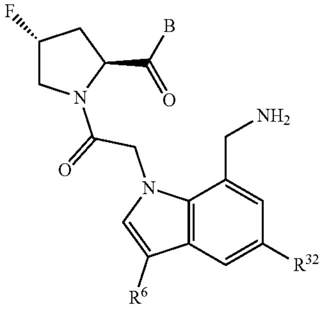

TABLE 4-continued
Additional Exemplary Formulas within the Present Invention.
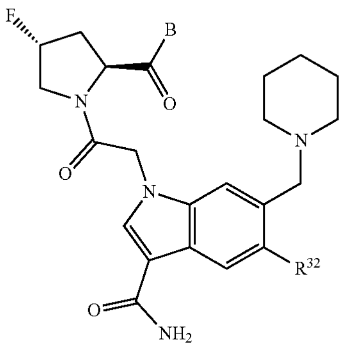
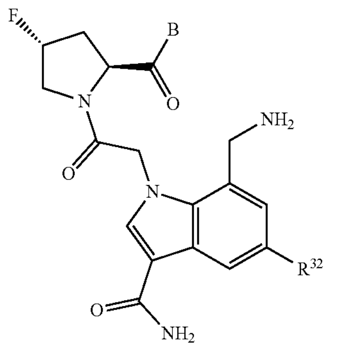
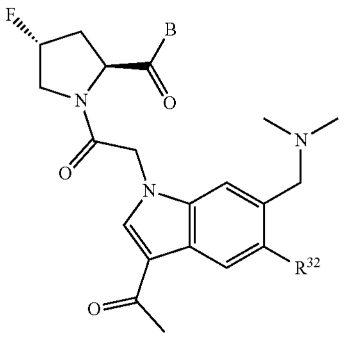
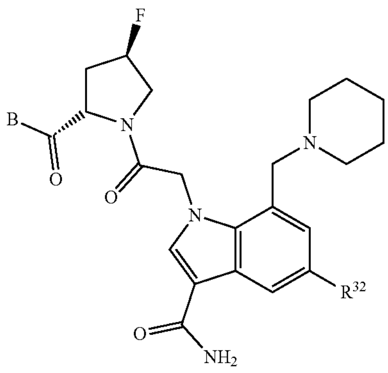
TABLE 4-continued
Additional Exemplary Formulas within the Present Invention.
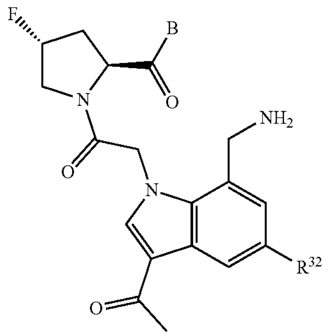
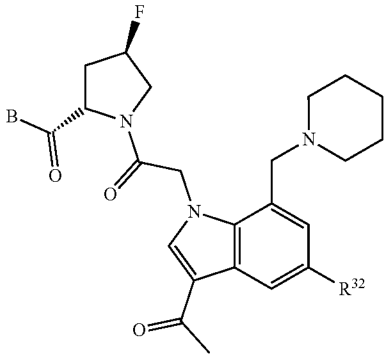
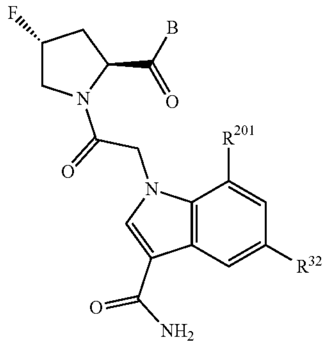
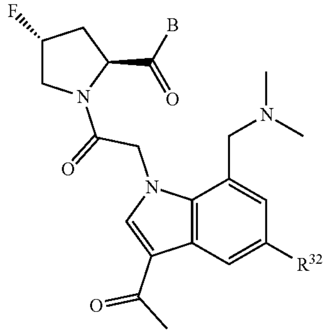

TABLE 4-continued
| Additional Exemplary Formulas within the Present Invention. |
|---|
| 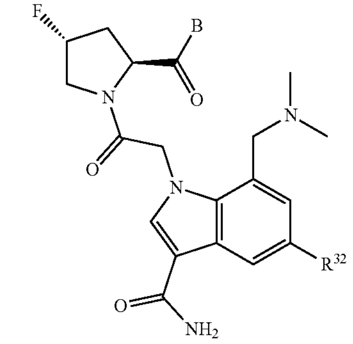 |
| 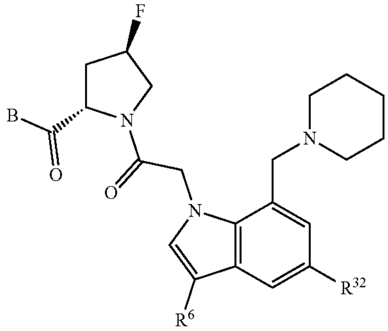 |
| 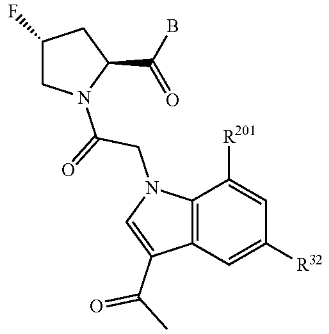 |
| 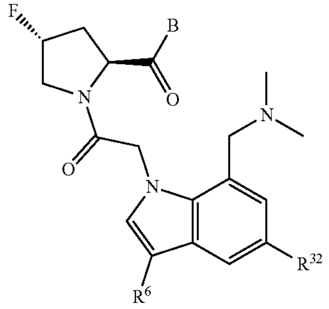 |
TABLE 4-continued
| Additional Exemplary Formulas within the Present Invention. |
|---|
| 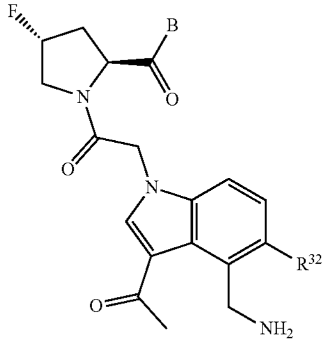 |
| 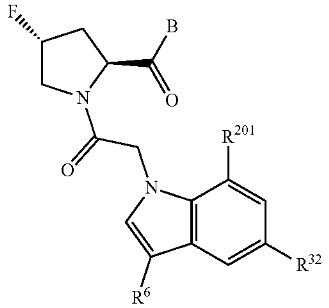 |
| 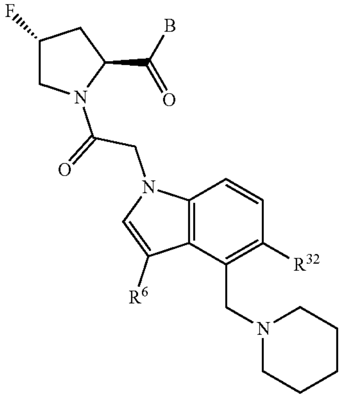 |
| 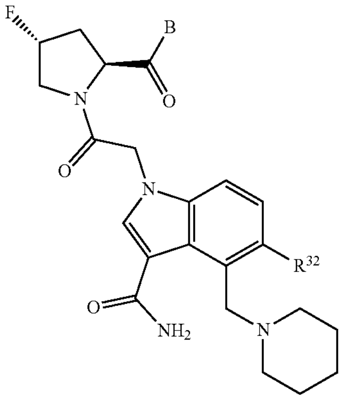 |

TABLE 4-continued
| Additional Exemplary Formulas within the Present Invention. |
|---|
| 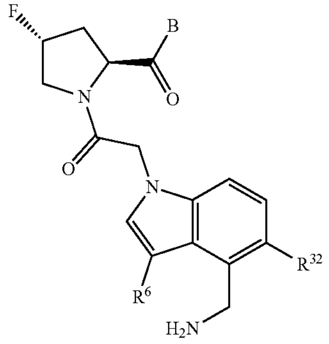 |
| 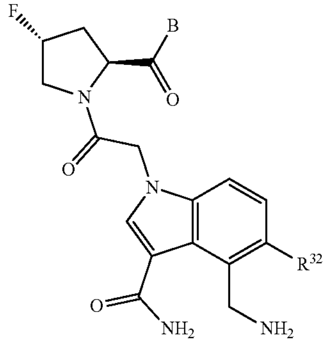 |
| 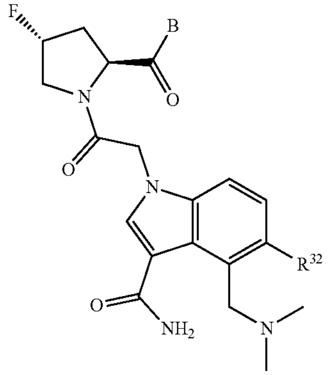 |
| 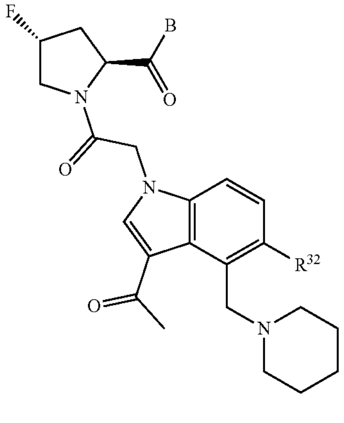 |
TABLE 4-continued
| Additional Exemplary Formulas within the Present Invention. |
|---|
| 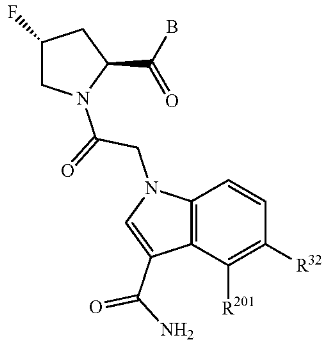 |
| 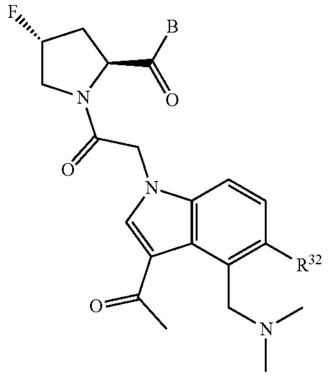 |
| 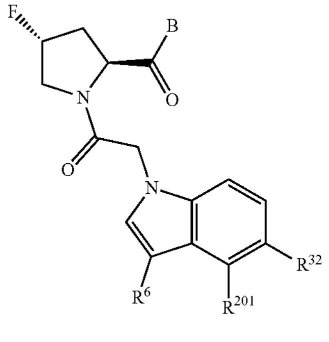 |
| 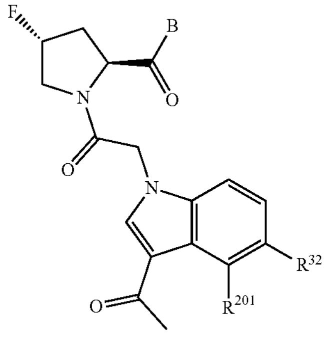 |

TABLE 4-continued
| Additional Exemplary Formulas within the Present Invention. |
| --- |
| 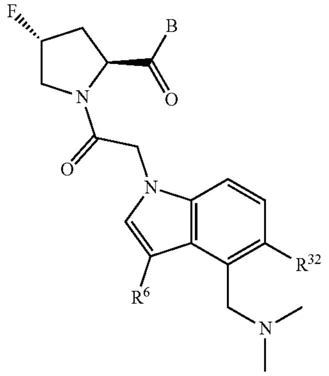 |
TABLE 5
| Additional Exemplary Formulas within the Present Invention. |
| --- |
| 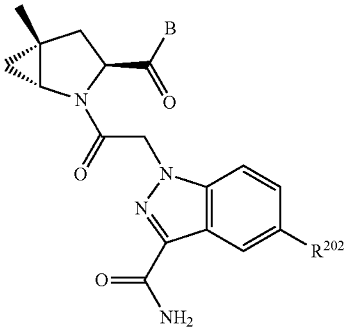 |
| 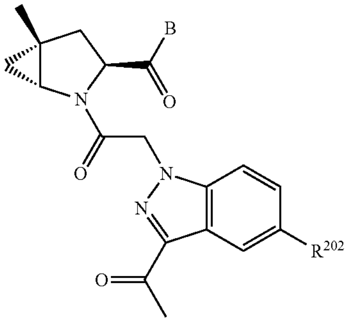 |
| 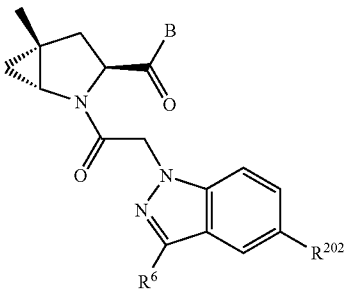 |
TABLE 5-continued
| Additional Exemplary Formulas within the Present Invention. |
| --- |
| 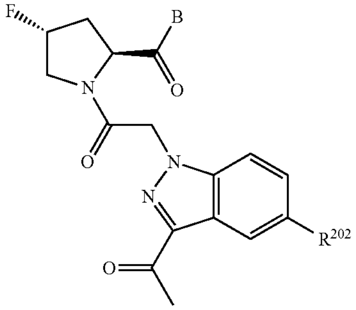 |
| 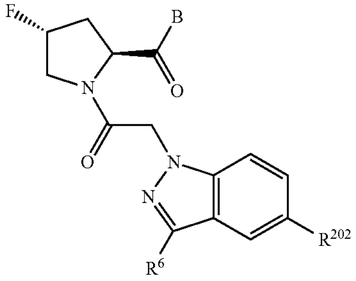 |
| 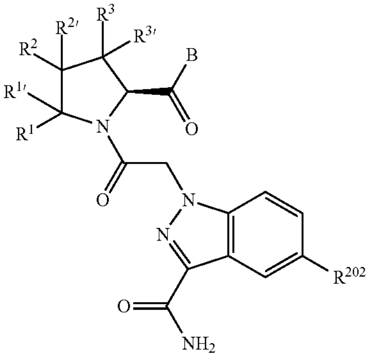 |
| 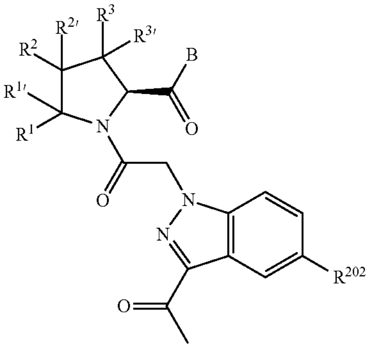 |

TABLE 5-continued
| Additional Exemplary Formulas within the Present Invention. |
|---|
| 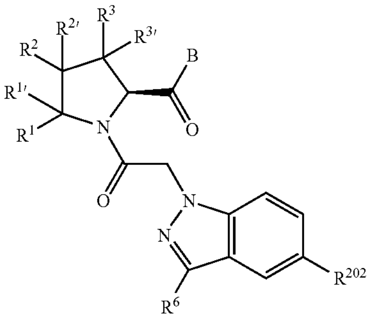 |
| 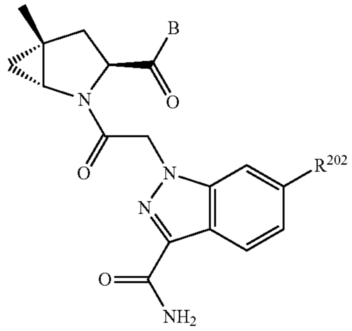 |
| 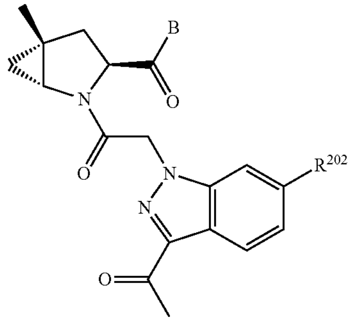 |
| 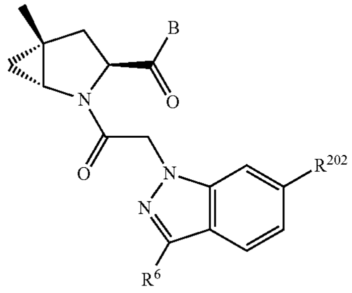 |
| 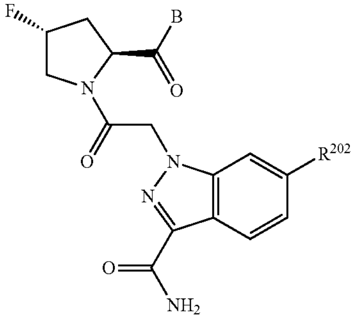 |
TABLE 5-continued
| Additional Exemplary Formulas within the Present Invention. |
|---|
| 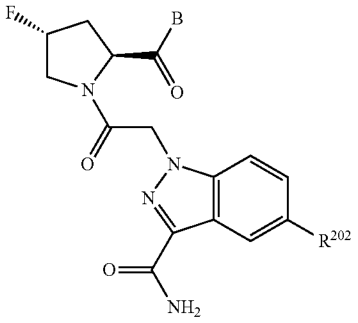 |
| 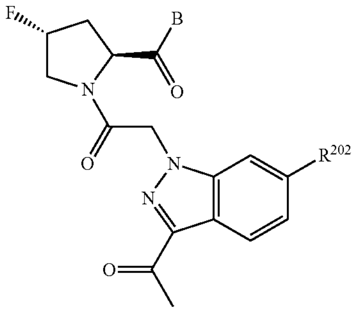 |
| 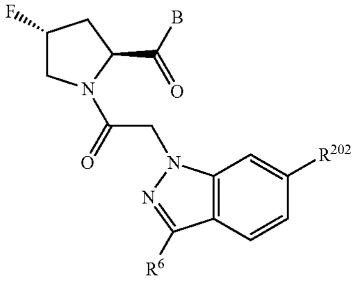 |
| 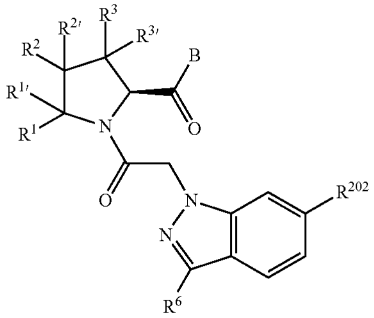 |

TABLE 5-continued
| Additional Exemplary Formulas within the Present Invention. |
| --- |
| 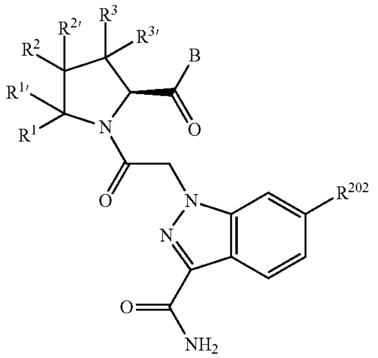 |
| 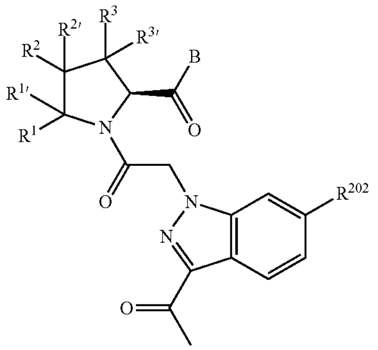 |
| 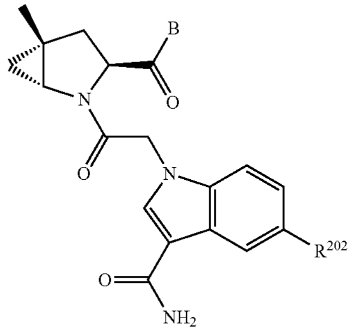 |
| 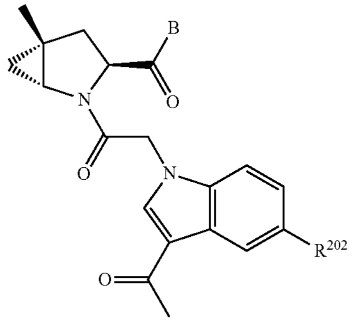 |
TABLE 5-continued
| Additional Exemplary Formulas within the Present Invention. |
| --- |
| 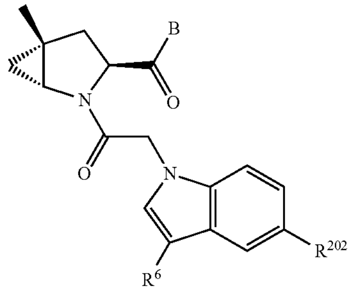 |
| 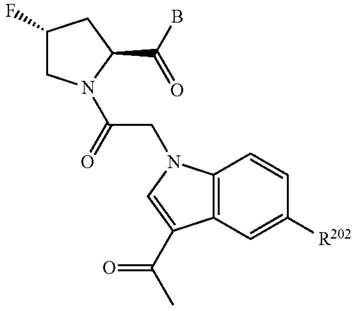 |
| 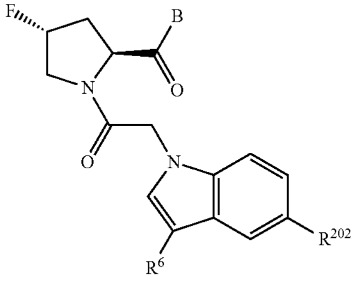 |
| 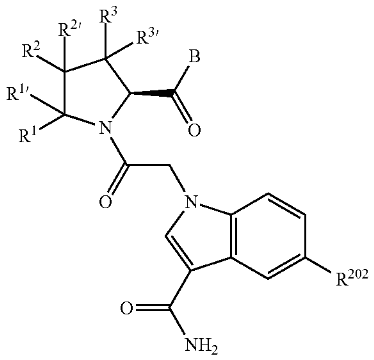 |
| 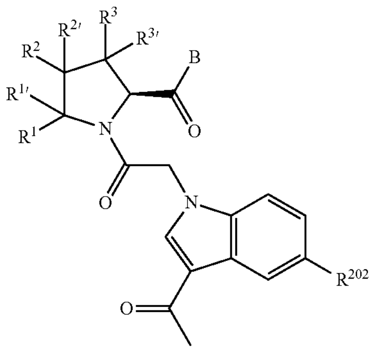 |

TABLE 5-continued
Additional Exemplary Formulas within the Present Invention.
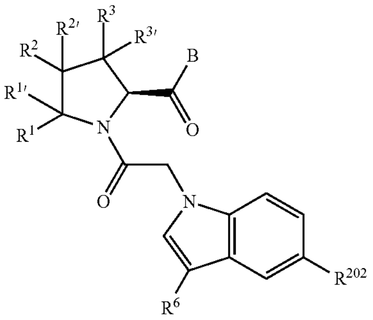
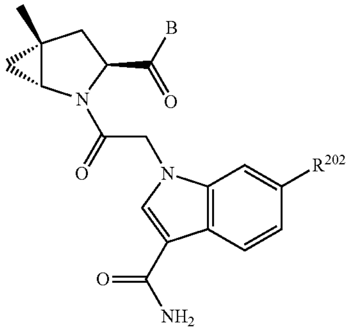
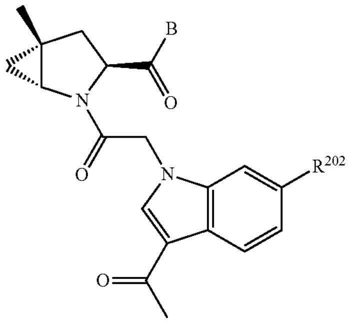
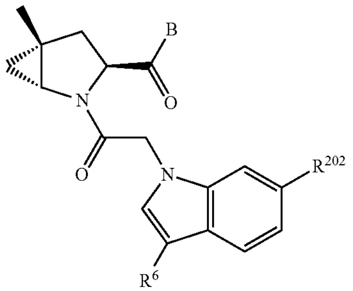
TABLE 5-continued
Additional Exemplary Formulas within the Present Invention.
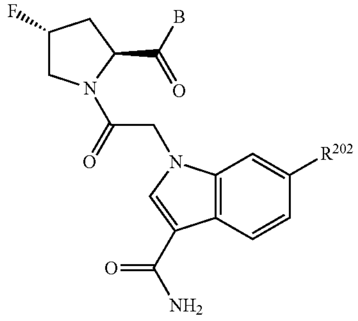
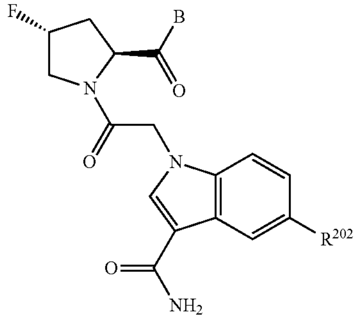
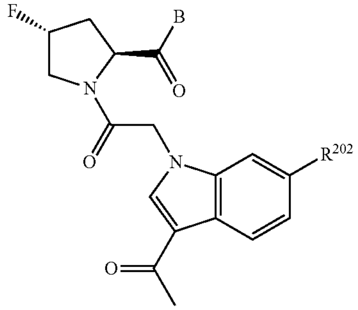
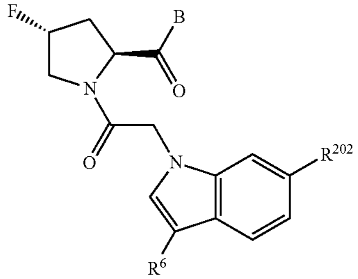
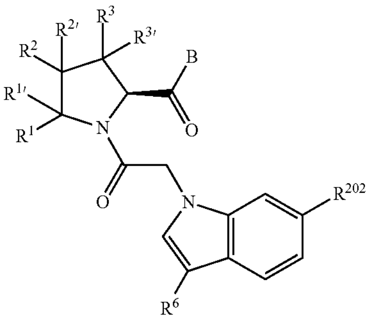

TABLE 5-continued

Additional Exemplary Formulas within the Present Invention.

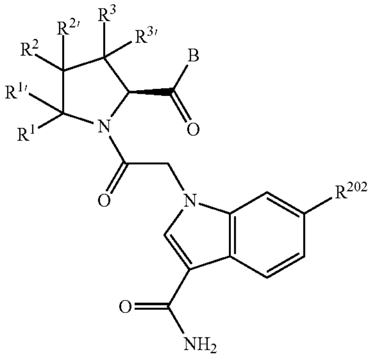

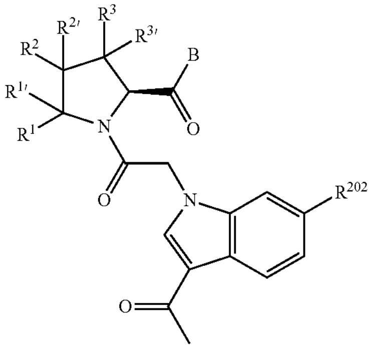

In one aspect, this disclosure includes compounds and salts of Formula IA:

(IA)

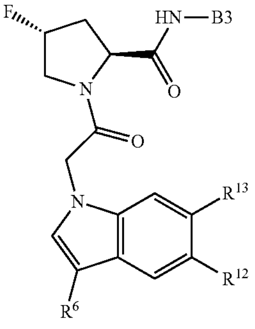

where $R^6$, $R^{13}$, and B3 may carry any of the definitions set forth herein for this variable.

In another aspect, this disclosure includes compounds and salts of Formula IB, IC, and ID.

IB

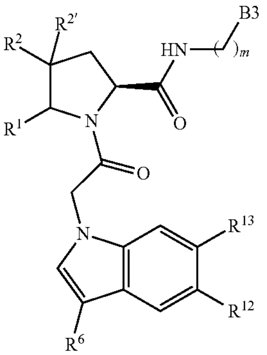

IC

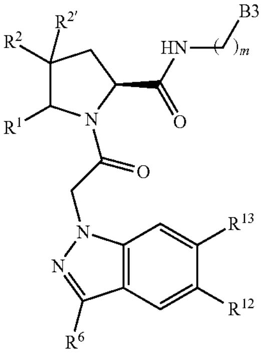

ID

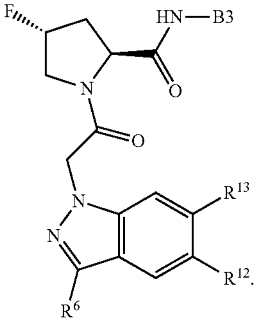

The $R^{12}$ and $R^{13}$ Heteroaryl, and Heterocycle Substituents

The invention includes a compound of Formula I, Formula II, Formula III, or Formula IV a pharmaceutically acceptable salt, prodrug, isotopic analog, or isolated isomer thereof, optionally in a pharmaceutically acceptable composition, wherein at least one of $R^{12}$ or $R^{13}$ on the A group is an $R^{32}$ group.

One of $R^{12}$ and $R^{13}$ is selected from $R^{31}$ and the other of $R^{12}$ and $R^{13}$ is selected from $R^{32}$. In another embodiment, each of $R^{12}$ and $R^{13}$ can be independently selected from $R^{32}$.

$R^{31}$ is selected from hydrogen, halogen, hydroxyl, nitro, cyano, amino, —COOH, haloalkyl including $C_1$-$C_6$haloalkyl, haloalkoxy including $C_1$-$C_6$haloalkoxy, alkyl including $C_1$-$C_6$alkyl, —$C_0$-$C_4$alkyl($C_3$-$C_7$cycloalkyl), alkenyl including $C_2$-$C_6$alkenyl, alkanoyl including $C_2$-$C_6$alkanoyl, alkoxy including $C_1$-$C_6$alkoxy, alkenyloxy including $C_2$-$C_6$alkenyloxy, —C(O)OR$^9$, thioalkyl including $C_1$-$C_6$thioalkyl, —$C_0$-$C_4$alkylNR$^9$R$^{10}$, —C(O)NR$^9$R$^{10}$, —SO$_2$R$^9$, —SO$_2$NR$^9$R$^{10}$, —OC(O)R$^9$, and —C(NR$^9$)NR$^9$R$^{10}$, each of which $R^{31}$ other than hydrogen, halogen, hydroxyl, nitro, cyano, haloalkyl including $C_1$-$C_6$haloalkyl, and haloalkoxy including $C_1$-$C_6$haloalkoxy is unsubstituted or substituted with one or more substituents independently selected from halogen, hydroxyl, nitro, cyano, amino, —COOH, —$CONH_2$, haloalkyl including $C_1$-$C_6$haloalkyl, and haloalkoxy including $C_1$-$C_6$haloalkoxy, and each of which $R^{31}$ is also optionally substituted with one substituent selected from phenyl and 4- to 7-membered heterocycle containing 1, 2, or 3 heteroatoms independently selected from N, O, and S; which phenyl or 4- to 7-membered heterocycle is unsubstituted or substituted with one or more substituents independently selected from halogen, hydroxyl, nitro, cyano, alkyl including $C_1$-$C_6$alkyl, alkenyl including $C_2$-$C_6$alkenyl, alkanoyl including $C_2$-$C_6$alkanoyl, alkoxy including $C_1$-$C_6$alkoxy, (mono- and di-$C_1$-$C_6$alkylamino)$C_0$-$C_4$alkyl, $C_1$-$C_6$alkylester, —$C_0$-$C_4$alkyl)($C_3$-$C_7$cycloalkyl), haloalkyl including $C_1$-$C_6$haloalkyl, and haloalkoxy including $C_1$-$C_6$haloalkoxy;

$R^{32}$ is selected from heteroaryl; saturated heterocycle or partially unsaturated heterocycle; wherein the heteroaryl, saturated heterocycle or partially unsaturated heterocycle ring can be optionally substituted, or $R^{32}$ is —$C_2$-$C_6$alkynyl$R^{30}$, and each $R^{32}$ can be optionally substituted with any appropriate group including $R^{201}$ examples of $R^{32}$ include, but are not limited to,

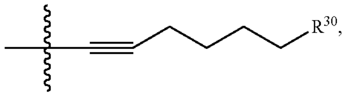,

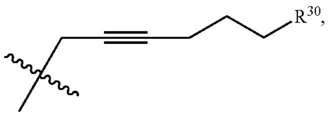,

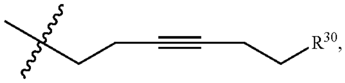,

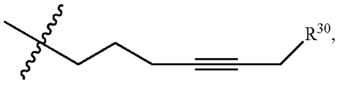,

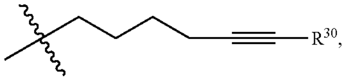,

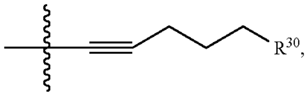,

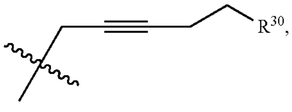,

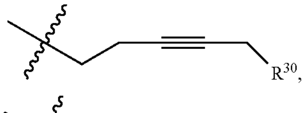,

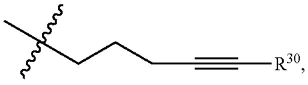,

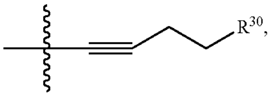, 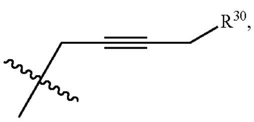,

-continued

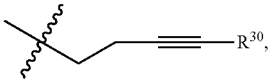, 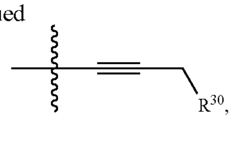,

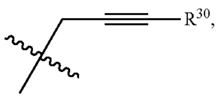, and 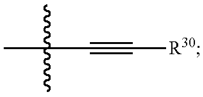;

or $R^{32}$ is selected from $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, and —$NR^9C(O)NR^{24}R^{25}$, each of which can be optionally can be optionally substituted with any appropriate group including $R^{201}$;

or $R^{32}$ is selected from $NR^{72}R^{73}$, $NR^9SO_2R^{73}$, and $N(SO_2R^9)CH_2C(O)R^{74}$ each of which can be optionally can be optionally substituted with any appropriate group including $R^{201}$;

or $R^{32}$ is selected from —$OC(O)(CH_2)_{1-4}R^{21}$, —$OC(O)NR^{21}R^{22}$, —$OC(O)NR^{24}R^{25}$, —$OC(O)(C_{1-6}$alkyl or $C_{3-6}$cycloalkyl)(aryl), —$OC(O)(C_{1-6}$alkyl or $C_{3-6}$cycloalkyl)(heteroaryl), —$OC(O)(C_{1-6}$alkyl or $C_{3-6}$cycloalkyl)(heterocycle), —OC(O)(heteroaryl), —OC(O)(aryl), —$OC(O)(C_{1-6}$alkyl or $C_{3-6}$cycloalkyl), —$OC(O)NR^9(CH_2)_{1-4}P(O)(OR^{21})(OR^{22})$, —$C(O)(C_{1-6}$alkyl or $C_{3-6}$cycloalkyl)(aryl), —$C(O)(C_{1-6}$alkyl or $C_{3-6}$cycloalkyl)(heteroaryl), —$C(O)(C_{1-6}$alkyl or $C_{3-6}$cycloalkyl)(heterocycle), —C(O)(heteroaryl), —C(O)(heterocycle), —C(O)(aryl), —$C(O)(C_{1-6}$alkyl or $C_{3-6}$cycloalkyl) and —$C(O)(CH_2)S(O)R^{21}$, O-heteroalkyl, and O-heteroaliphatic each of which can be optionally can be optionally substituted with any appropriate group including $R^{201}$;

or $R^{32}$ is selected from —$O(CH_2)_{1-4}R^{23a}$, —$OC_2$-$C_4$alkenyl$R^{23a}$, —$OC_2$-$C_4$alkynyl$R^{23}$, —$O(CH_2)_{1-4}$paracyclophane, —$O(CH_2)_{1-4}P(O)R^{23b}R^{23b}$, —$O(CH_2)_{1-4}S(O)NR^{21}R^{22}$, —$O(CH_2)_{1-4}S(O)NR^{24}R^{25}$, —$O(CH_2)_{1-4}SO_2NR^{21}R^{22}$, —$O(CH_2)_{1-4}SO_2NR^{24}R^{25}$, —$O(C_3$-$C_7$cycloalkyl), —O(aryl), —O(heteroaryl), —O residue of a carbohydrate, and —O(heterocycle) each of which can be optionally can be optionally substituted with any appropriate group including $R^{201}$;

or $R^{32}$ is $P(O)R^{75}R^{75}$, each of which can be optionally can be optionally substituted with any appropriate group including $R^{201}$;

or $R^{32}$ is selected from $R^{48}$, $S(O)=NHR^{21}$, $S(O)=N(R^{21})R^{21}$, $SF_5$, $S=NHR^{21}$, $S=N(R^{21})R^{21}$, $JC(R^9)=NR^{21}$ and $SO_2OR^{21}$;

or in an alternative embodiment, $R^{32}$ is selected from —$O(CH_2)_{1-4}S(O)NR^{24}R^{30}$ and —$O(CH_2)_{1-4}SO_2NR^{24}R^{30}$;

or in an alternative embodiment $R^{32}$ is tetrazole.

Non-Limiting $R^{12}/R^{13}$ Embodiments

In one embodiment, $R^{12}$ is $R^{32}$.

In one embodiment, $R^{13}$ is $R^{32}$.

In one embodiment, $R^{12}$ is an optionally substituted heteroaryl.

In one embodiment, $R^{13}$ is an optionally substituted heteroaryl.

In one embodiment, $R^{12}$ is $R^{32}$.

In one embodiment, $R^{12}$ is $R^{32}$, which is (4- to 7-membered heterocycloalkyl) having 1, 2, or 3 heteroatoms independently selected from N, O, and S.

In one embodiment, the disclosure provides compounds of Formula I, wherein;

one of $R^{12}$ and $R^{13}$ is H and the other of $R^{12}$ and $R^{13}$ is $R^{32}$, where In another embodiment, the disclosure provides compounds of Formula I, Formula II, Formula III, or Formula IV wherein;

$R^1$, $R^{1'}$, $R^2$, and $R^{3'}$ are all hydrogen;

$R^2$ is fluoro and $R^3$ is hydrogen, —$C_0$-$C_4$alkyl($C_3$-$C_7$cycloalkyl), or —O—$C_0$-$C_4$alkyl($C_3$-$C_7$cycloalkyl);

$R^5$ is hydrogen, halogen, or $C_1$-$C_6$alkyl;

$R^{11}$, $R^{13}$, $R^{14}$, and $R^{15}$ if present, are independently selected at each occurrence from hydrogen, halogen, hydroxyl, amino, $C_1$-$C_4$alkyl, $C_1$-$C_4$alkoxy, —$C_0$-$C_2$alkyl (mono- and di-$C_1$-$C_6$alkylamino), trifluoromethyl, and trifluoromethoxy;

$X^{12}$ is $CR^{12}$; and $R^{12}$ is selected from heteroaryl; saturated heterocycle or partially unsaturated heterocycle; wherein the heteroaryl; saturated heterocycle or partially unsaturated heterocycle ring can be optionally substituted.

In one embodiment, the disclosure provides compounds of Formula I, wherein;

m is 0 or 1;

$R^2$ is halogen, $R^{2'}$ is hydrogen or halogen, and $R^3$ is hydrogen, halogen, —$C_0$-$C_4$alkyl($C_3$-$C_7$cycloalkyl), or —O—$C_0$-$C_4$alkyl($C_3$-$C_7$cycloalkyl);

$R^6$ is —C(O)$C_1$-$C_4$alkyl, —C(O)$NH_2$, —C(O)$CF_3$, —C(O)($C_3$-$C_7$cycloalkyl), or -ethyl(cyanoimino);

one of $R^{12}$ and $R^{13}$ is selected from hydrogen, halogen, $C_1$-$C_4$alkyl, $C_1$-$C_4$alkoxy, trifluoromethyl, and trifluoromethoxy; the other of $R^{12}$ and $R^{13}$ is $R^{32}$, where $R^{32}$ is selected from aryl, heteroaryl; saturated or unsaturated heterocycle; wherein the aryl, heteroaryl, saturated or unsaturated heterocycle ring can be optionally substituted.

In one embodiment, the disclosure provides compounds of Formula I, Formula II, Formula III, or Formula IV, wherein one of $R^{12}$ and $R^{13}$ is hydrogen, hydroxyl, halogen, methyl, or methoxy; and the other of $R^{12}$ and $R^{13}$ is $R^{32}$, where In one embodiment, $R^{32}$ may be unsubstituted or substituted with one or more substituents independently selected from halogen, hydroxyl, nitro, cyano, amino, oxo, —B$(OH)_2$, —Si$(CH_3)_3$, —COOH, —CON$H_2$, —P(O)$(OH)_2$, $C_1$-$C_6$alkyl, alkoxy including $C_1$-$C_6$alkoxy, —$C_0$-$C_2$alkyl (mono- and di-$C_1$-$C_4$alkylamino), $C_1$-$C_6$alkylester, $C_1$-$C_4$alkylamino, $C_1$-$C_4$hydroxylalkyl, haloalkyl including $C_1$-$C_6$haloalkyl, and haloalkoxy including $C_1$-$C_6$haloalkoxy.

In one embodiment, $R^{31}$ is hydrogen and $R^{32}$ is pyrimidinyl.

In another embodiment, $R^{31}$ is hydrogen and $R^{32}$ is pyrimidine substituted with a methyl group.

In one embodiment $R^{32}$ is selected from:

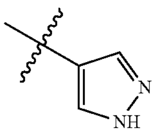
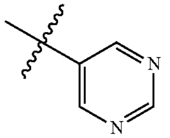
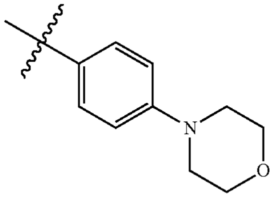
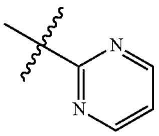

-continued

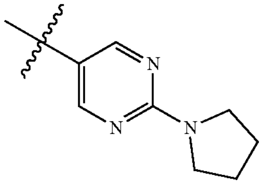
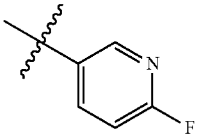
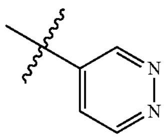
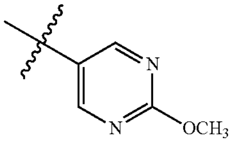
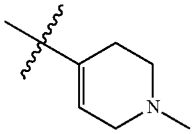
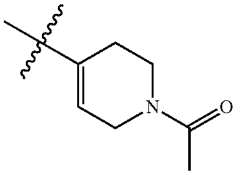
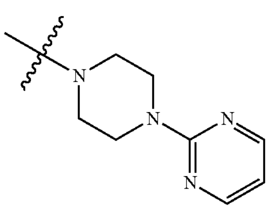
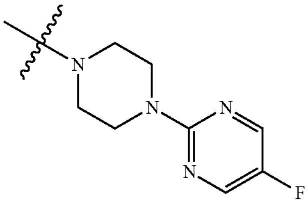
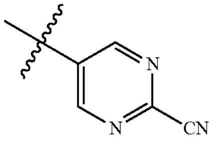
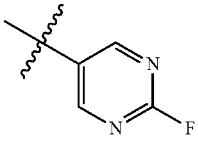
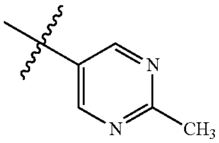
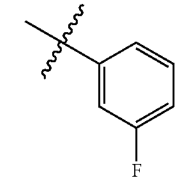
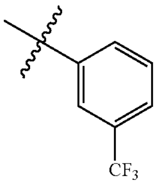
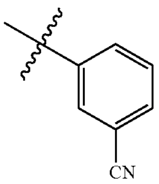
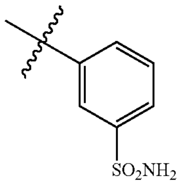
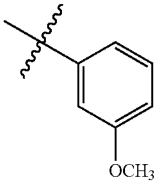
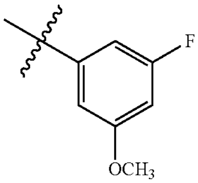

-continued
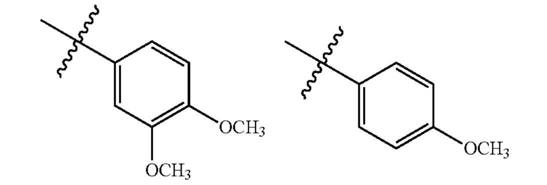
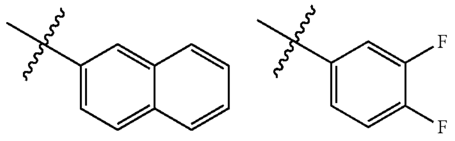
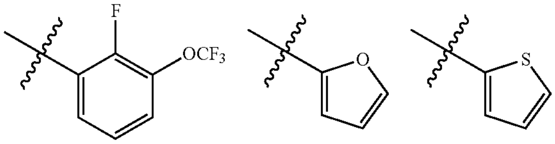
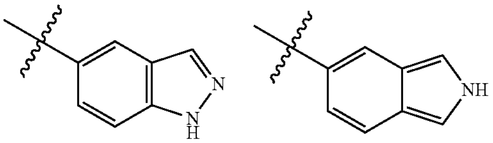
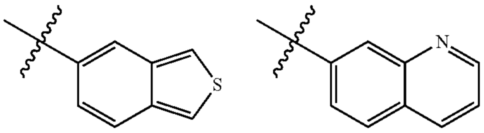
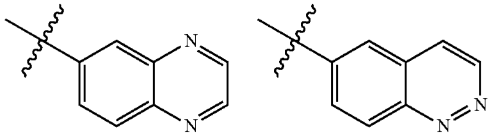
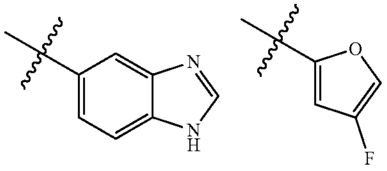
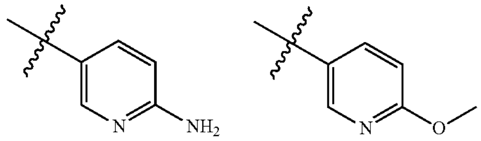
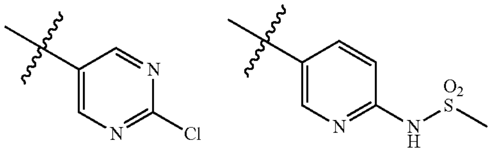
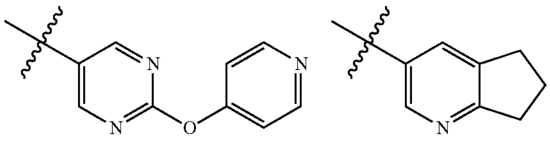
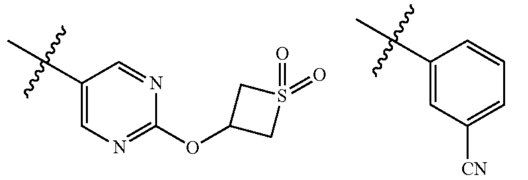
-continued
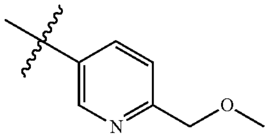
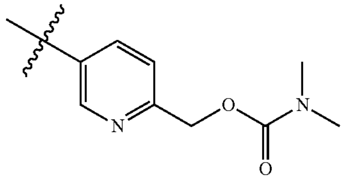
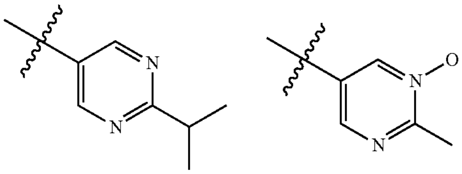
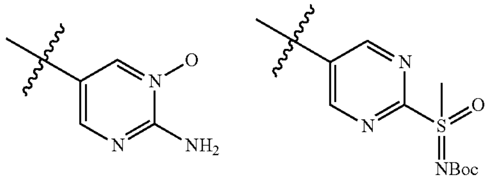
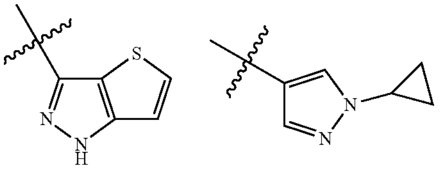
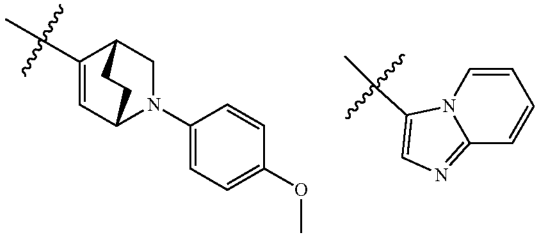
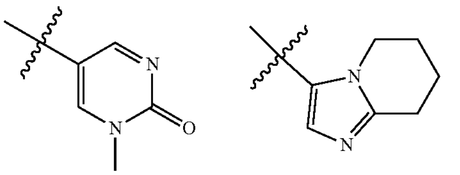
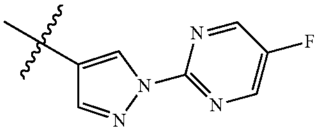
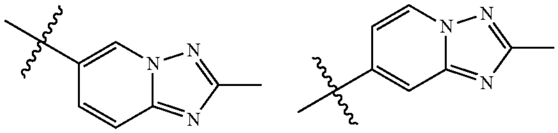
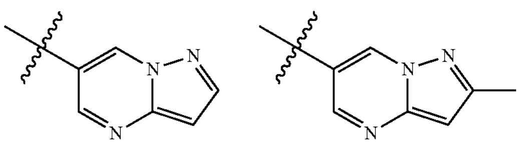

-continued
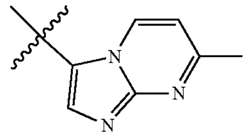
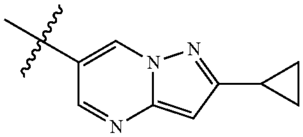
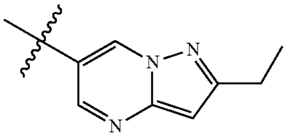
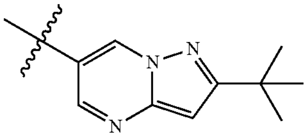
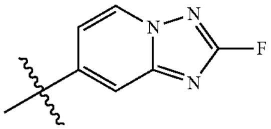
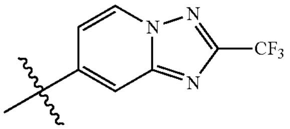
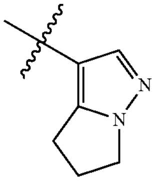
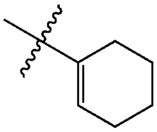
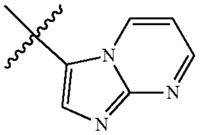
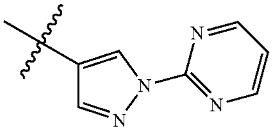
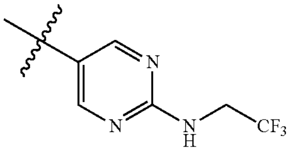
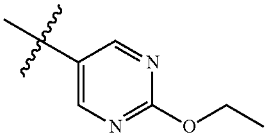
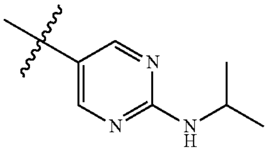
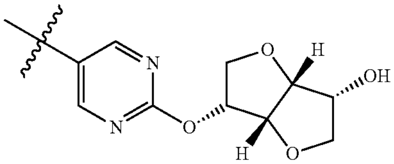
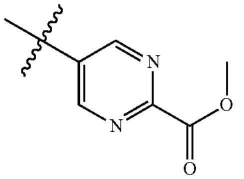
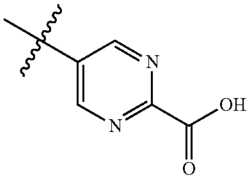
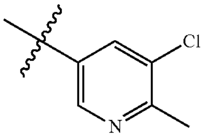
-continued
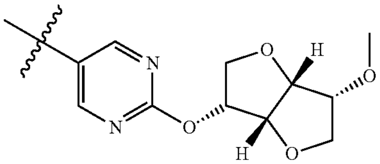
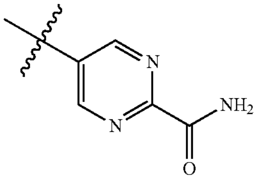
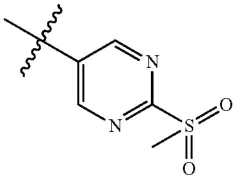
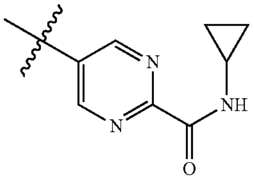
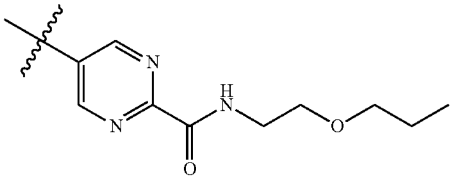
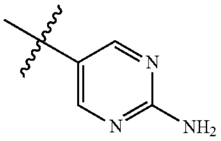
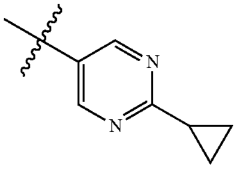
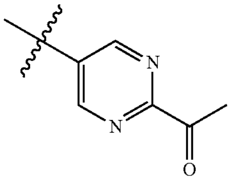
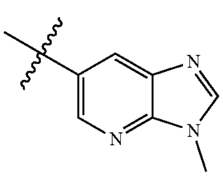
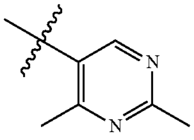
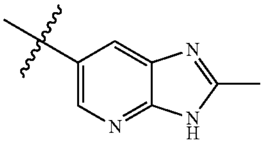
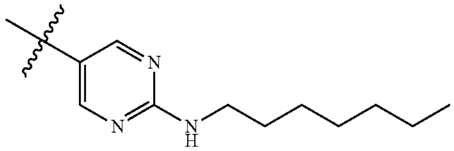
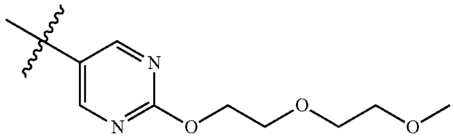
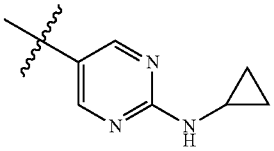
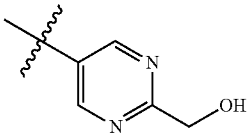

-continued
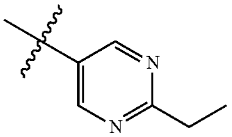
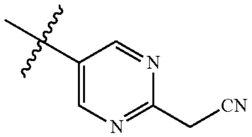
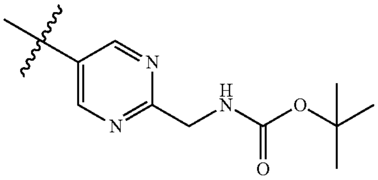
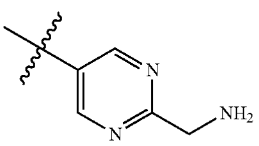
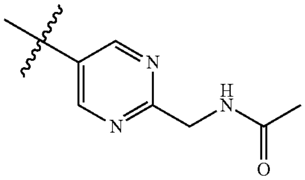
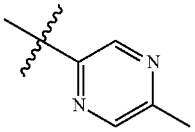
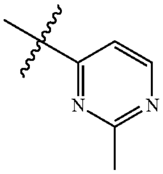
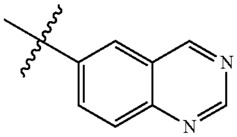
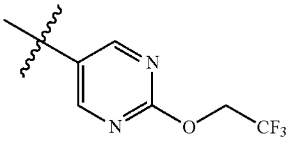
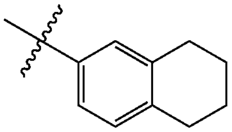
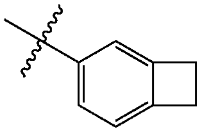
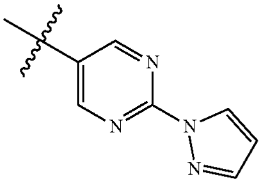
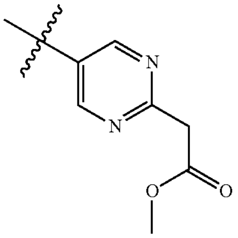
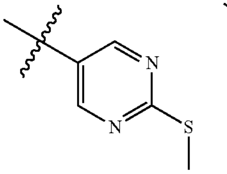
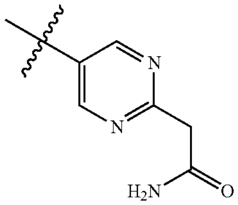
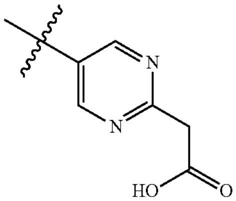
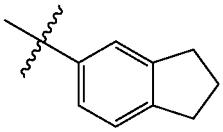
-continued
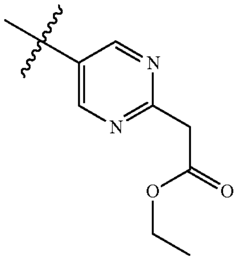
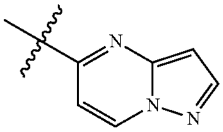
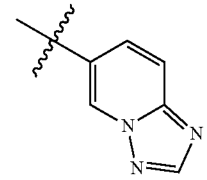
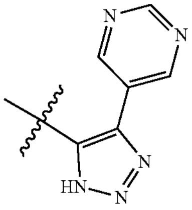
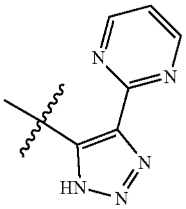
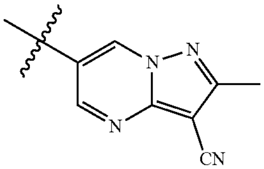
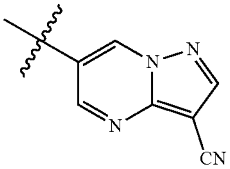
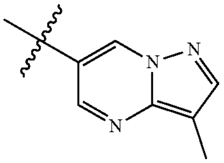
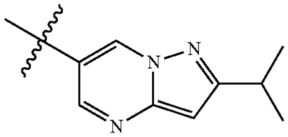
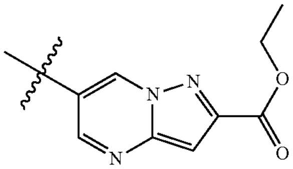
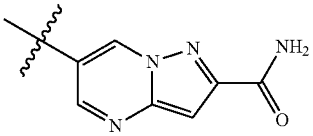
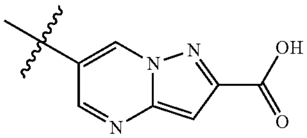
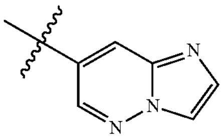
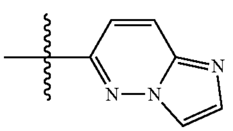
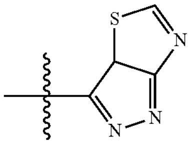

-continued

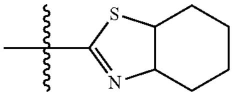 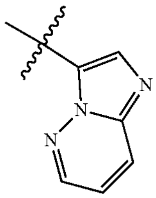

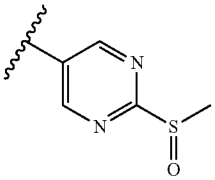 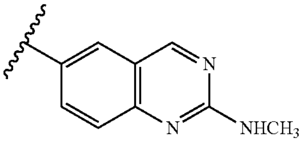

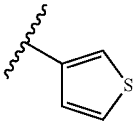 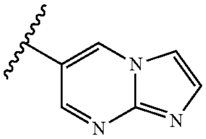

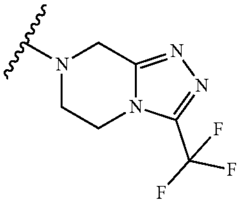 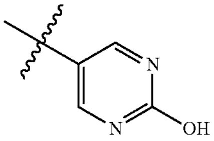

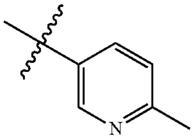 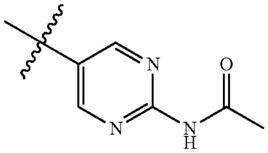

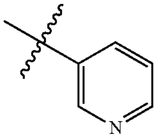 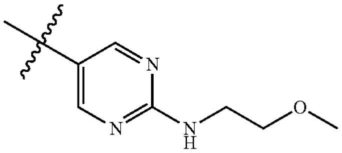

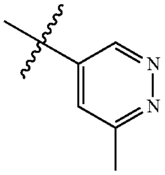 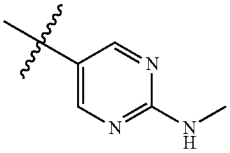

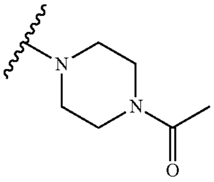 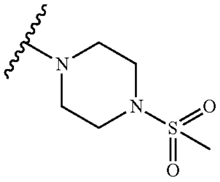

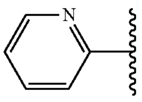 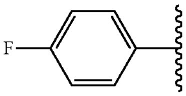 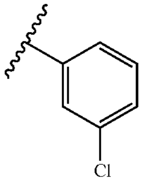

-continued

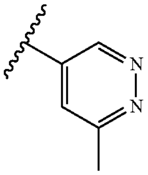 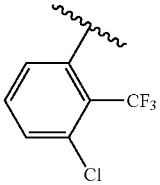 and

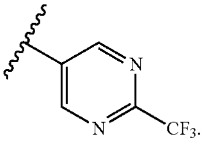

$R^{32}$ Alkynes

In one embodiment, $R^{12}$ is $R^{32}$, which is $C_2$-$C_4$alkynyl$R^{30}$.

In one embodiment, $R^{13}$ is $R^{32}$, which is $C_2$-$C_4$alkynyl$R^{30}$.

In one embodiment, the disclosure provides compounds of Formula I, Formula II, Formula III, or Formula IV wherein;

one of $R^{12}$ and $R^{13}$ is H and the other of $R^{12}$ and $R^{13}$ is $R^{32}$, where $R^{32}$ is $C_2$-$C_6$alkynyl$R^{30}$ (which can be, for example, $C_2$-$C_3$alkynyl$R^{30}$, $C_2$-$C_4$alkynyl$R^{30}$, $C_2$-$C_5$alkynyl$R^{30}$, or $C_2$-$C_6$alkynyl$R^{30}$), wherein $R^{30}$ is independently selected at each occurrence from hydrogen, $C_1$-$C_6$alkyl, $C_1$-$C_6$haloalkyl, (aryl)$C_0$-$C_4$alkyl, ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently selected from N, O, and S; (5- or 6-membered unsaturated or aromatic heterocycle)$C_0$-$C_4$alkyl having 1, 2, or 3 heteroatoms independently selected from N, O, and S; COOH, $Si(CH_3)_3$, $COOR^{30a}$, $C_2$-$C_6$alkanoyl, —C(O)$(CH_2)_{1-4}S(O)R^{21}$, —P(O)($OR^{21}$)($OR^{22}$), —P(O)$R^{21}R^{22}$, —$NR^{21}SO_2R^{22}$, —$NR^9SO_2NR^{10}R^{22}$, —$SO_2NR^9COR^{22}$, —$SO_2NR^9CONR^{21}R^{22}$, —C(O)$NR^{21}SO_2R^{22}$, —$NR^9$C(O)$OR^{10}$, —$NR^{21}$OC(O)$R^{22}$, —$(CH_2)_{1-4}$C(O)$NR^{21}R^{22}$, —C(O)$R^{24}R^{30}$, —C(O)$R^{21}$, —$NR^9$C(O)$NR^9R^{10}$, —$NR^9$C(O)$NR^{24}R^{30}$, —$(CH_2)_{1-4}$OC(O)$R^{21}$, each of which $R^{30}$ can be optionally substituted;

wherein $R^9$, $R^{10}$, $R^{21}$, $R^{22}$, $R^{24}$, $R^{30}$, and $R^{30a}$ are as defined in the summary section above.

In another embodiment, the disclosure provides compounds of Formula I, Formula II, Formula III, or Formula IV, wherein;

$R^1$, $R^{1'}$, $R^2$, and $R^{3'}$ are all hydrogen;

$R^2$ is fluoro and $R^3$ is hydrogen, —$C_0$-$C_4$alkyl($C_3$-$C_7$cycloalkyl), or —O—$C_0$-$C_4$alkyl($C_3$-$C_7$cycloalkyl);

$R^5$ is hydrogen, halogen, or $C_1$-$C_2$alkyl;

$R^{11}$, $R^{13}$, $R^{14}$, and $R^{15}$ if present, are independently selected at each occurrence from hydrogen, halogen, hydroxyl, amino, $C_1$-$C_4$alkyl, $C_1$-$C_4$alkoxy, —$C_0$-$C_2$alkyl (mono- and di-$C_1$-$C_2$alkylamino), trifluoromethyl, and trifluoromethoxy;

$X^{12}$ is $CR^{12}$; and $R^{12}$ is $C_2$-$C_6$alkynyl$R^{30}$.

In one embodiment, the disclosure provides compounds of Formula I, Formula II, Formula III, or Formula IV, wherein;

m is 0 or 1;

$R^2$ is halogen, $R^{2'}$ is hydrogen or halogen, and $R^3$ is hydrogen, halogen, —$C_0$-$C_4$alkyl($C_3$-$C_7$cycloalkyl), or —O—$C_0$-$C_4$alkyl($C_3$-$C_7$cycloalkyl);

$R^6$ is —$C(O)C_1$-$C_4$alkyl, —$C(O)NH_2$, —$C(O)CF_3$, —$C(O)(C_3$-$C_7$cycloalkyl), or -ethyl(cyanoimino);

one of $R^{12}$ and $R^{13}$ is selected from hydrogen, halogen, $C_1$-$C_4$alkyl, $C_1$-$C_4$alkoxy, trifluoromethyl, and trifluoromethoxy; the other of $R^{12}$ and $R^{13}$ is $R^{32}$, where $R^{32}$ is $C_2$-$C_6$alkynyl$R^{30}$, wherein $R^{30}$ is independently selected at each occurrence from hydrogen, $C_1$-$C_6$alkyl, $C_1$-$C_6$haloalkyl, (aryl)$C_0$-$C_4$alkyl, ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently selected from N, O, and S; (5- or 6-membered unsaturated or aromatic heterocycle)$C_0$-$C_4$alkyl having 1, 2, or 3 heteroatoms independently selected from N, O, and S; COOH, $Si(CH_3)_3$, $COOR^{30a}$, $C_2$-$C_6$alkanoyl, —$B(OH)_2$, —$C(O)(CH_2)_{1-4}S(O)R^{21}$, —$P(O)(OR^{21})(OR^{22})$, —$P(O)(OR^{21})R^{22}$, —$P(O)R^{21}R^{22}$, —$NR^9P(O)(NHR^{21})(NHR^{22})$, —$NR^9P(O)(OR^{21})(NHR^{22})$, —$NR^9P(O)(OR^{21})(OR^{22})$, —$C(S)R^{21}$, —$NR^{21}SO_2R^{22}$, —$NR^9S(O)NR^{10}R^{22}$, —$NR^9SO_2NR^{10}R^{22}$, —$SO_2NR^9COR^{22}$, —$SO_2NR^9CONR^{21}R^{22}$, —$NR^{21}SO_2R^{22}$, —$C(O)NR^{21}SO_2R^{22}$, —$C(NH_2)NR^9R^{22}$, —$C(NH_2)NR^9S(O)_2R^{22}$, —$NR^9C(O)OR^1$, —$NR^{21}OC(O)R^{22}$, —$(CH_2)_{1-4}C(O)NR^{21}R^{22}$, —$C(O)R^{24}R^{30}$, —$NR^9C(O)R^{21}$, —$C(O)R^{21}$, —$NR^9C(O)NR^9R^{10}$, and —$NR^9C(O)NR^{24}R^{30}$, —$(CH_2)_{1-4}OC(O)R^{21}$, each of which $R^{30}$ can be optionally substituted;

wherein $R^9$, $R^{10}$, $R^{21}$, $R^{22}$, $R^{24}$, $R^{30}$, and $R^{30a}$ are as defined in the summary section above.

In one embodiment, the disclosure provides compounds of Formula I, Formula II, Formula III, or Formula IV, wherein;

one of $R^{12}$ and $R^{13}$ is hydrogen, hydroxyl, halogen, methyl, or methoxy; and the other of $R^{12}$ and $R^{13}$ is $R^{32}$, where $R^{32}$ is $C_2$-$C_6$alkynyl$R^{30}$, wherein $R^{30}$ is independently selected at each occurrence from hydrogen, $C_1$-$C_6$alkyl, $C_1$-$C_6$haloalkyl, (aryl)$C_0$-$C_4$alkyl, ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently selected from N, O, and S; (5- or 6-membered unsaturated or aromatic heterocycle)$C_0$-$C_4$alkyl having 1, 2, or 3 heteroatoms independently selected from N, O, and S; COOH, $Si(CH_3)_3$, $COOR^{30a}$, $C_2$-$C_6$alkanoyl, —$B(OH)_2$, —$C(O)(CH_2)_{1-4}S(O)R^{21}$, —$P(O)(OR^{21})(OR^{22})$, —$P(O)(OR^{21})R^{22}$, —$P(O)R^{21}R^{22}$, —$NR^9P(O)(NHR^{21})(NHR^{22})$, —$NR^9P(O)(OR^{21})(NHR^{22})$, —$NR^9P(O)(OR^{21})(OR^{22})$, —$C(S)R^{21}$, —$NR^{21}SO_2R^{22}$, —$NR^9S(O)NR^1R^{22}$, —$NR^9SO_2NR^{10}R^{22}$, —$SO_2NR^9COR^{22}$, —$SO_2NR^9CONR^{21}R^{22}$, —$NR^{21}SO_2R^{22}$, —$C(O)NR^{21}SO_2R^{22}$, —$C(NH_2)NR^9R^{22}$, —$C(NH_2)NR^9S(O)_2R^{22}$, —$NR^9C(O)OR^1$, —$NR^{21}OC(O)R^{22}$, —$(CH_2)_{1-4}C(O)NR^{21}R^{22}$, —$C(O)R^{24}R^{30}$, —$NR^9C(O)R^{21}$, —$C(O)R^{21}$, —$NR^9C(O)NR^9R^{10}$, and —$NR^9C(O)NR^{24}R^{30}$, —$(CH_2)_{1-4}OC(O)R^{21}$, each of which $R^{30}$ can be optionally substituted;

wherein $R^9$, $R^{10}$, $R^{21}$, $R^{22}$, $R^{24}$, $R^{30}$, and $R^{30a}$ are as defined in the summary section above.

In one embodiment, $R^{32}$ may be unsubstituted or substituted with one or more substituents independently selected from halogen, hydroxyl, nitro, cyano, amino, oxo, —$B(OH)_2$, —$Si(CH_3)_3$, —COOH, —$CONH_2$, —$P(O)(OH)_2$, $C_1$-$C_6$alkyl, $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy.

In one embodiment $R^{32}$ is selected from:

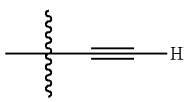

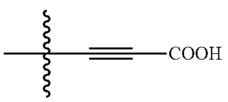

-continued

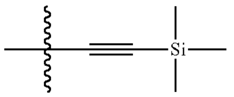

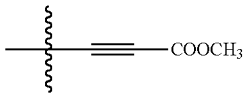

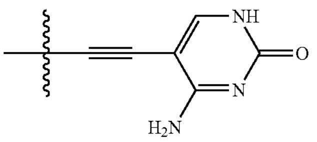

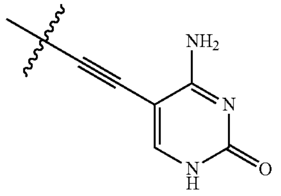

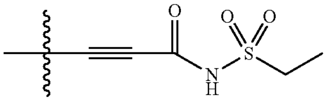

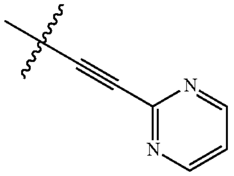

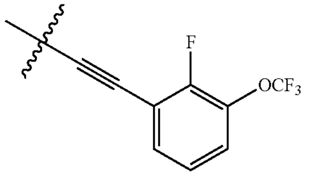

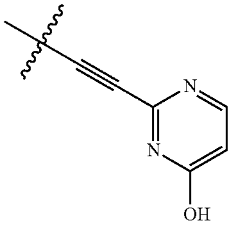

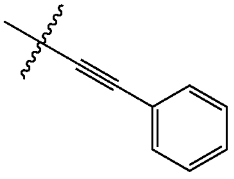

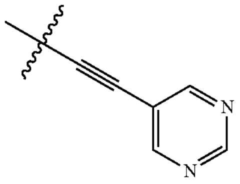

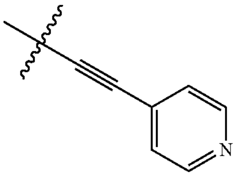

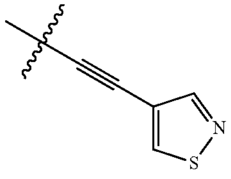

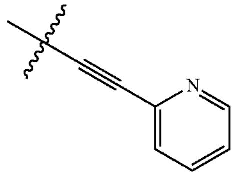

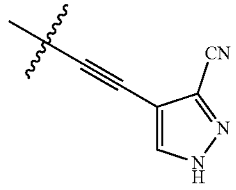

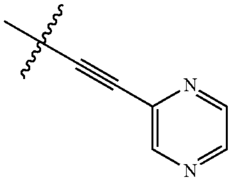

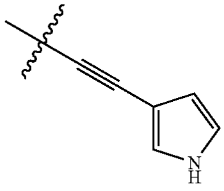

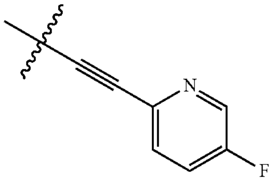

-continued
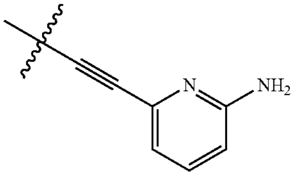
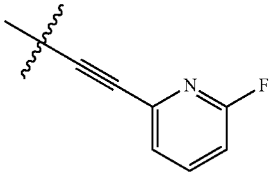
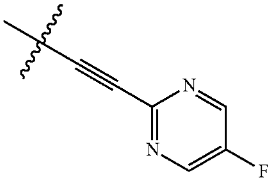
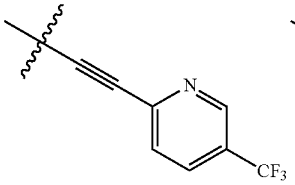
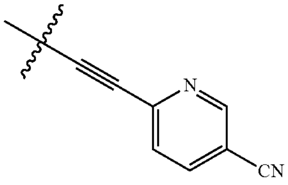
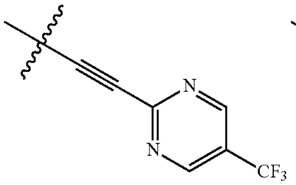
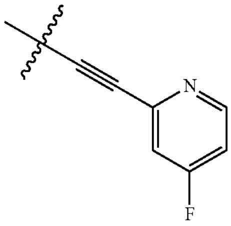
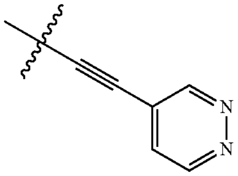
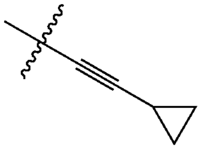
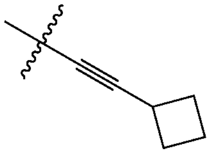
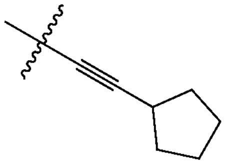
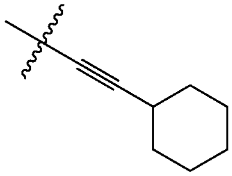
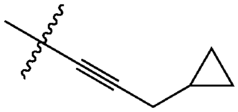
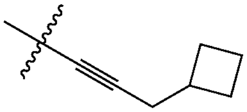
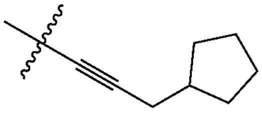
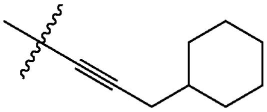
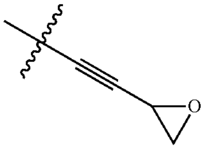
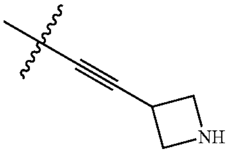
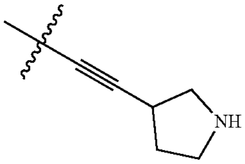
-continued
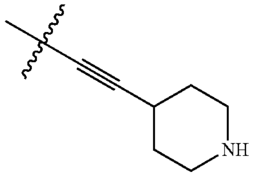
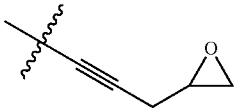
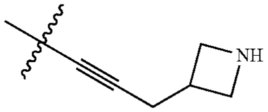
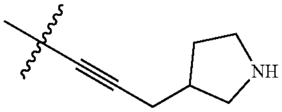
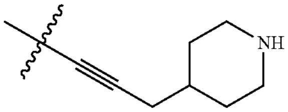
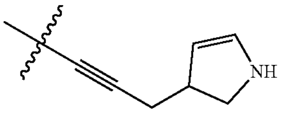
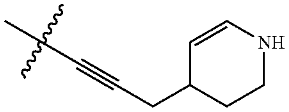
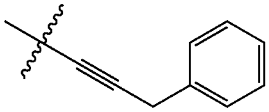
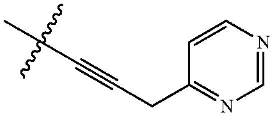
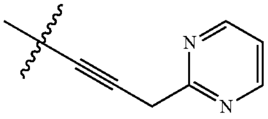
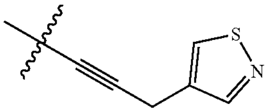
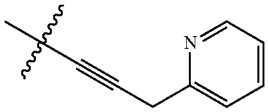
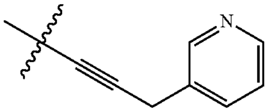
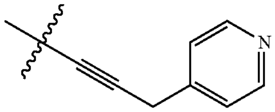
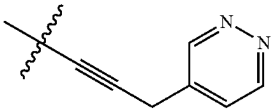
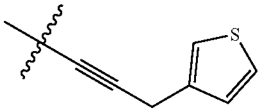
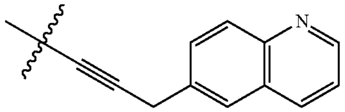
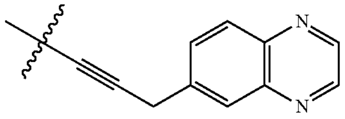
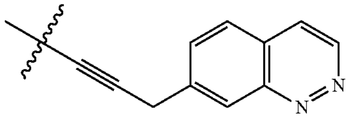
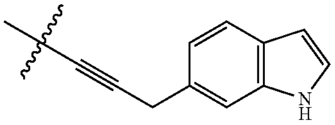
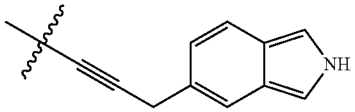

-continued
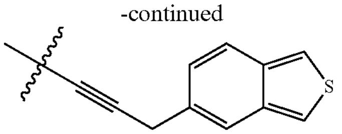
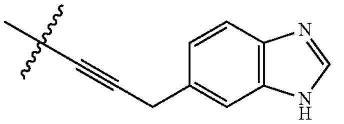
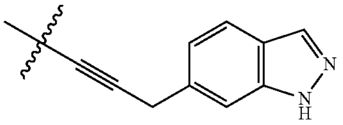
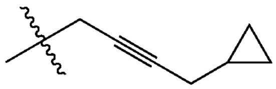
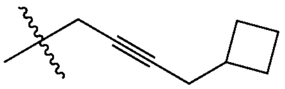
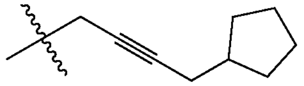
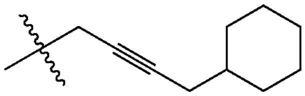
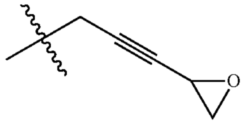
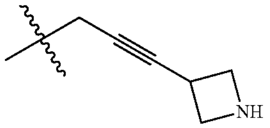
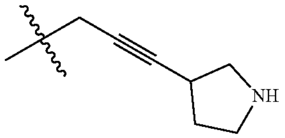
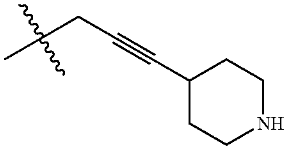
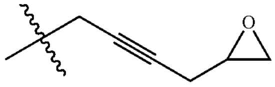
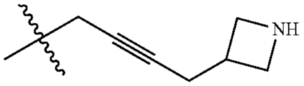
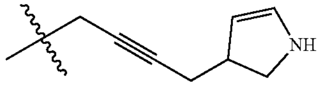
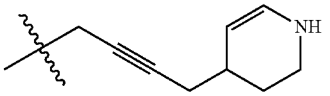
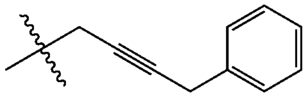
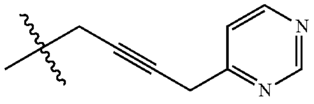
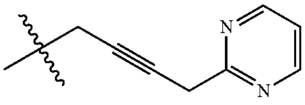
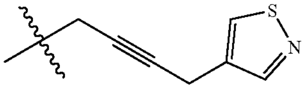
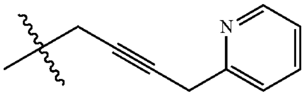
-continued
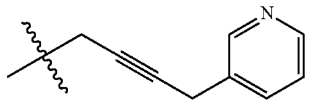
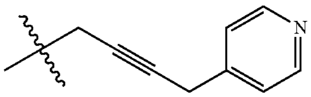
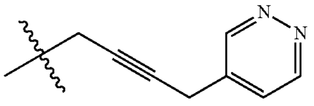
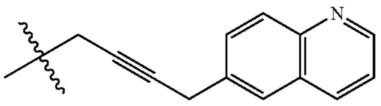
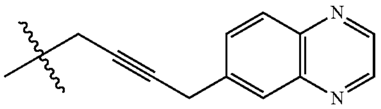
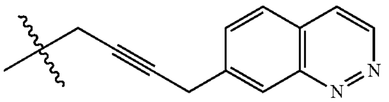
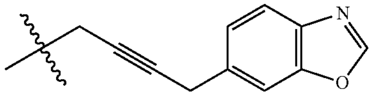
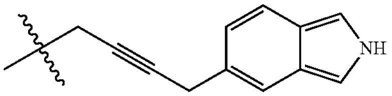
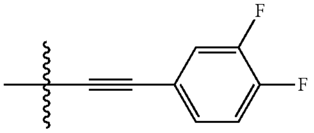
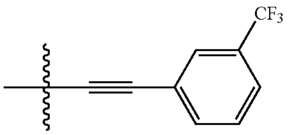
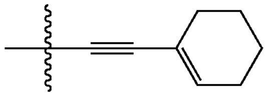
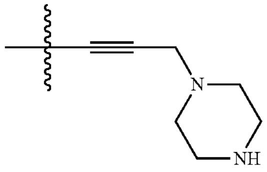
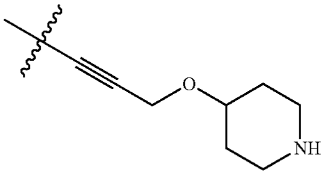
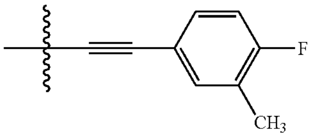
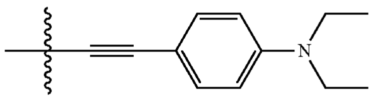

-continued

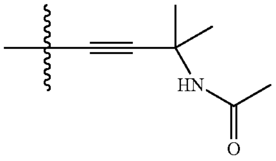

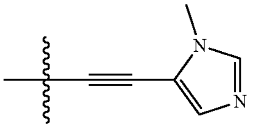

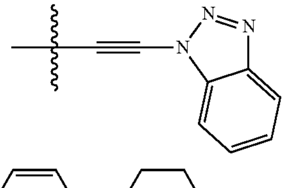

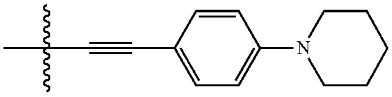

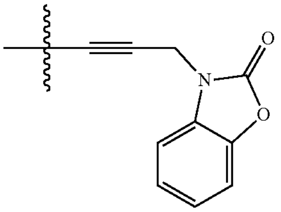

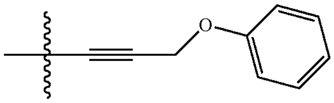

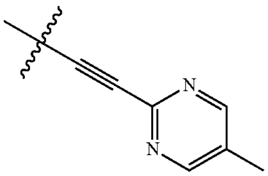

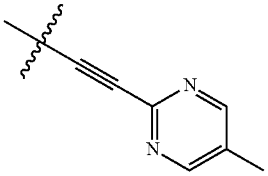

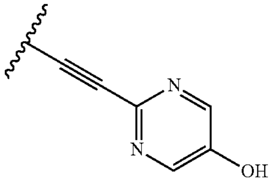

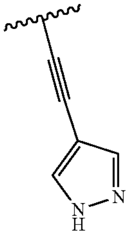

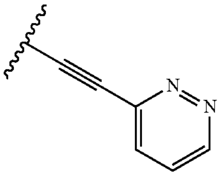

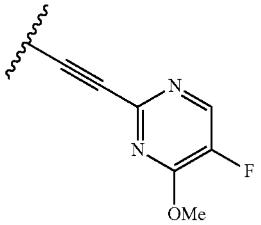

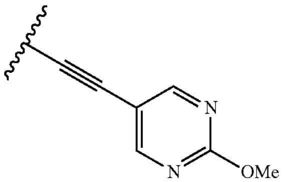

and

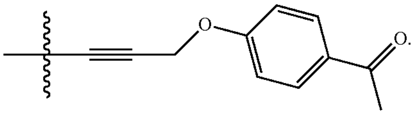

$R^{32}$ Amides

In some embodiments, structures are provided including Formulas IB and IC, wherein m=0, $R^1$ is H, $R^2$ is F, $R^6$ is alkanoyl, $R^{12}$ is $R^{32}$, $R^{32}$ is $C(O)NR^{21}R^{71}$, —$C(O)NR^{24}R^{30}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, —$NR^9C(O)NR^{24}R^{30}$, and $R^{13}$ is H.

In some embodiments, structures are provided including Formulas IB and IC, wherein m=0, $R^1$ and $R^2$ are joined to form a 3 membered ring, $R^6$ is alkanoyl, $R^{12}$ is $R^{32}$, $R^{32}$ is $C(O)NR^{21}R^{71}$, —$C(O)NR^{24}R^{30}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, —$NR^9C(O)NR^{24}R^{30}$, and $R^{13}$ is H.

In some embodiments, structures are provided including Formulas IB and IC, wherein m=0, $R^1$ is H, $R^2$ is F, $R^6$ is amide, $R^{12}$ is $R^{32}$, $R^{32}$ is $C(O)NR^{21}R^{71}$, —$C(O)NR^{24}R^{30}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, —$NR^9C(O)NR^{24}R^{30}$, and $R^{13}$ is H.

In some embodiments, structures are provided including Formulas IB and IC, wherein m=0, $R^1$ and $R^2$ are joined to form a 3 membered ring, $R^6$ is amide, $R^{12}$ is $R^{32}$, $R^{32}$ is $C(O)NR^{21}R^{71}$, —$C(O)NR^{24}R^{30}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, —$NR^9C(O)NR^{24}R^{30}$, and $R^{13}$ is H.

In some embodiments, structures are provided including Formulas IB and IC, wherein m=0, $R^1$ is H, $R^2$ is F, $R^6$ is alkanoyl, $R^{12}$ is H, $R^{13}$ is $R^{32}$, $R^{32}$ is $C(O)NR^{21}R^{71}$, —$C(O)NR^{24}R^{30}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, or —$NR^9C(O)NR^{24}R^{25}$.

In some embodiments, structures are provided including Formulas IB and IC, wherein m=0, $R^1$ and $R^2$ are joined to form a 3 membered ring, $R^6$ is alkanoyl, $R^{12}$ is H, $R^{13}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, or —$NR^9C(O)NR^{24}R^{25}$.

In some embodiments, structures are provided including Formulas IB and IC, wherein m=0, $R^1$ is H, $R^2$ is F, $R^6$ is amide, $R^{12}$ is H, $R^{13}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, or —$NR^9C(O)NR^{24}R^{25}$.

In some embodiments, structures are provided including Formulas IB and IC, wherein m=0, $R^1$ and $R^2$ are joined to form a 3 membered ring, $R^6$ is amide, $R^{12}$ is H, $R^{13}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, or —$NR^9C(O)NR^{24}R^{25}$.

In some embodiments, structures are provided including Formulas IB and IC, wherein m=0, $R^1$ is H, $R^2$ is F, $R^6$ is alkanoyl, $R^{12}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, —$NR^9C(O)NR^{24}R^{25}$, or $R^{13}$ is H.

In some embodiments, structures are provided including Formulas IB and IC, wherein m=0, $R^1$ and $R^2$ are joined to form a 3 membered ring, $R^6$ is alkanoyl, $R^{12}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^0R^{23}$, —$NR^9C(O)NR^{24}R^{25}$, or $R^{13}$ is H, and B3.

In some embodiments, structures are provided including Formulas IB and IC, wherein m=0, $R^1$ is H, $R^2$ is F, $R^6$ is amide, $R^{12}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, —$NR^9C(O)NR^{24}R^{25}$, or $R^{13}$ is H.

In some embodiments, structures are provided including Formulas IB and IC, wherein m=0, $R^1$ and $R^2$ are joined to form a 3 membered ring, $R^6$ is amide, $R^{12}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, —$NR^9C(O)NR^{24}R^{25}$, and $R^{13}$ is H.

In some embodiments, structures are provided including Formulas IB and IC, wherein m=0, $R^1$ is H, $R^2$ is F, $R^6$ is alkanoyl, $R^{12}$ is H, $R^{13}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, or —$NR^9C(O)NR^{24}R^{25}$.

In some embodiments, structures are provided including Formulas IB and IC, wherein m=0, $R^1$ and $R^2$ are joined to form a 3 membered ring, $R^6$ is alkanoyl, $R^{12}$ is H, $R^{13}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, or —$NR^9C(O)NR^{24}R^{25}$.

In some embodiments, structures are provided including Formulas IB and IC, wherein m=0, $R^1$ is H, $R^2$ is F, $R^6$ is amide, $R^{12}$ is H, $R^{13}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, or —$NR^9C(O)NR^{24}R^{25}$.

In some embodiments, structures are provided including Formulas IB and IC, wherein m=0, $R^1$ and $R^2$ are joined to form a 3 membered ring, $R^6$ is amide, $R^{12}$ is H, $R^{13}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, or —$NR^9C(O)NR^{24}R^{25}$.

In some embodiments, structures are provided including Formulas IB and IC, wherein m=1, $R^1$ is H, $R^2$ is F, $R^6$ is alkanoyl, $R^{12}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, —$NR^9C(O)NR^{24}R^{25}$, and $R^{13}$ is H.

In some embodiments, structures are provided including Formulas IB and IC, wherein m=1, $R^1$ and $R^2$ are joined to form a 3 membered ring, $R^6$ is alkanoyl, $R^{12}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, —$NR^9C(O)NR^{24}R^{25}$, and $R^{13}$ is H.

In some embodiments, structures are provided including Formulas IB and IC, wherein m=1, $R^1$ is H, $R^2$ is F, $R^6$ is amide, $R^{12}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, —$NR^9C(O)NR^{24}R^{25}$, and $R^{13}$ is H.

In some embodiments, structures are provided including Formulas IB and IC, wherein m=1, $R^1$ and $R^2$ are joined to form a 3 membered ring, $R^6$ is amide, $R^{12}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, —$NR^9C(O)NR^{24}R^{25}$, and $R^{13}$ is H.

In some embodiments, structures are provided including Formulas IB and IC, wherein m=1, $R^1$ is H, $R^2$ is F, $R^6$ is alkanoyl, $R^{12}$ is H, $R^{13}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, or —$NR^9C(O)NR^{24}R^{25}$.

In some embodiments, structures are provided including Formulas IB and IC, wherein m=1, $R^1$ and $R^2$ are joined to form a 3 membered ring, $R^6$ is alkanoyl, $R^{12}$ is H, $R^{13}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, or —$NR^9C(O)NR^{24}R^{25}$.

In some embodiments, structures are provided including Formulas IB and IC, wherein m=1, $R^1$ is H, $R^2$ is F, $R^6$ is amide, $R^{12}$ is H, $R^{13}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, or —$NR^9C(O)NR^{24}R^{25}$.

In some embodiments, structures are provided including Formulas IB and IC, wherein m=1, $R^1$ and $R^2$ are joined to form a 3 membered ring, $R^6$ is amide, $R^{12}$ is H, $R^{13}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, or —$NR^9C(O)NR^{24}R^{25}$.

In some embodiments, structures are provided including Formulas IB and IC, wherein m=1, $R^1$ is H, $R^2$ is F, $R^6$ is alkanoyl, $R^{12}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, —$NR^9C(O)NR^{24}R^{25}$, and $R^{13}$ is H.

In some embodiments, structures are provided including Formulas IB and IC, wherein m=1, $R^1$ and $R^2$ are joined to form a 3 membered ring, $R^6$ is alkanoyl, $R^{12}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, —$NR^9C(O)NR^{24}R^{25}$, and $R^{13}$ is H.

In some embodiments, structures are provided including Formulas IB and IC, wherein m=1, $R^1$ is H, $R^2$ is F, $R^6$ is amide, $R^{12}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, —$NR^9C(O)NR^{24}R^{25}$, and $R^{13}$ is H.

In some embodiments, structures are provided including Formulas IB and IC, wherein m=1, $R^1$ and $R^2$ are joined to form a 3 membered ring, $R^6$ is amide, $R^{12}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, —$NR^9C(O)NR^{24}R^{25}$, and $R^{13}$ is H.

In some embodiments, structures are provided including Formulas IB and IC, wherein m=1, $R^1$ is H, $R^2$ is F, $R^6$ is alkanoyl, $R^{12}$ is H, $R^{13}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, or —$NR^9C(O)NR^{24}R^{25}$.

In some embodiments, structures are provided including Formulas IB and IC, wherein m=1, $R^1$ and $R^2$ are joined to form a 3 membered ring, $R^6$ is alkanoyl, $R^{12}$ is H, $R^{13}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, or —$NR^9C(O)NR^{24}R^{25}$.

In some embodiments, structures are provided including Formulas IB and IC, wherein m=1, $R^1$ is H, $R^2$ is F, $R^6$ is amide, $R^{12}$ is H, $R^{13}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C$ (O)$OR^{10}$, —$NR^9C(O)OR^{23}$, —$NR^9C(O)R^{21}$, $NR^9C(O)NR^9R^{10}$, —$NR^9C(O)NR^{10}R^{23}$, or —$NR^9C(O)NR^{24}R^{25}$.

In some embodiments, structures are provided including Formulas IB and IC, wherein m=1, $R^1$ and $R^2$ are joined to form a 3 membered ring, $R^6$ is amide, $R^{12}$ is H, $R^{13}$ is $R^{32}$, $R^{32}$ is $C(O)NR^{21}R^{71}$, —$C(O)NR^{24}R^{25}$, —$C(O)NR^9R^{71}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, or —$NR^9C(O)NR^{24}R^{25}$.

In one embodiment $R^{32}$ is selected from:

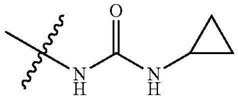
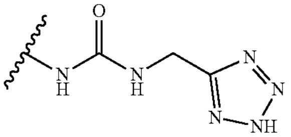
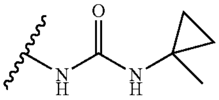
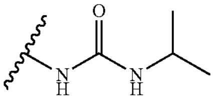
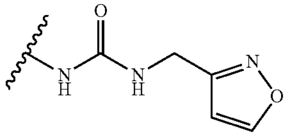
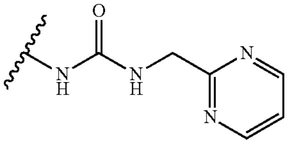
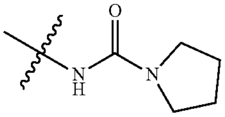
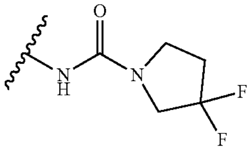
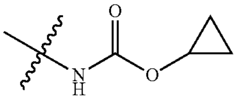
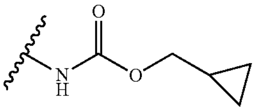
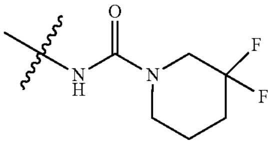
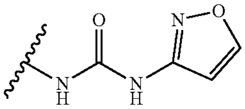
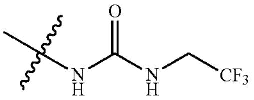
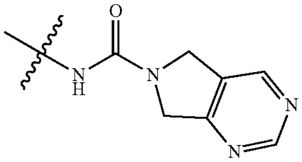
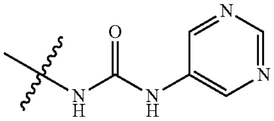
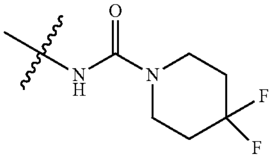
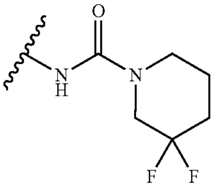
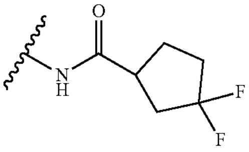

-continued

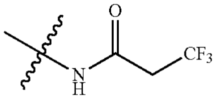
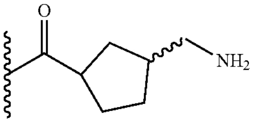
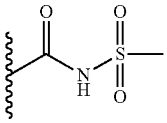
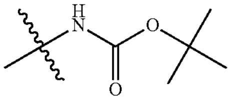
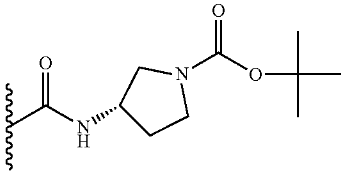
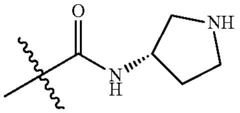
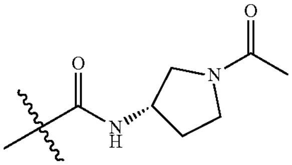
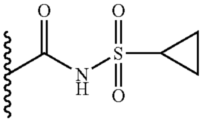
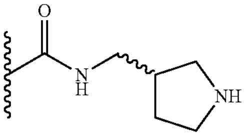
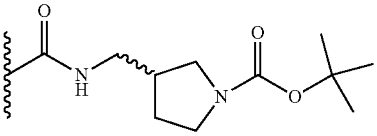
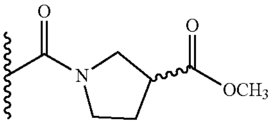
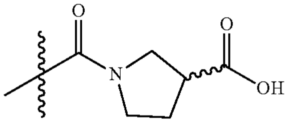
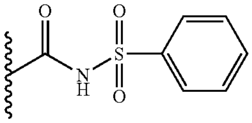
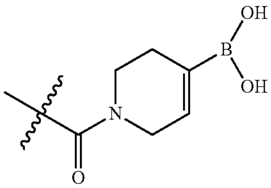
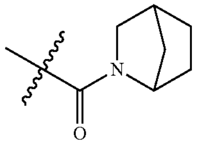
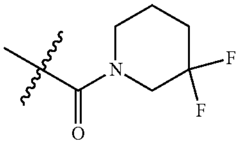
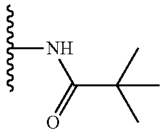
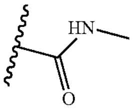
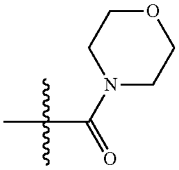
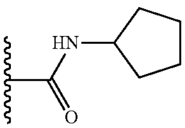
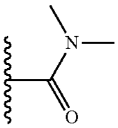
and -continued

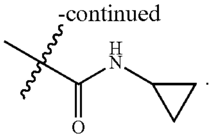

$R^{32}$ Amines

In one embodiment, $R^{12}$ is $NR^{72}R^{73}$.

In one embodiment, $R^{12}$ is $NR^9SO_2R^{73}$.

In one embodiment, $R^{12}$ is $N(SO_2R^9)CH_2C(O)R^{74}$.

In one embodiment, $R^{13}$ is hydrogen

In one embodiment, $R^{13}$ is $NR^{72}R^{73}$.

In one embodiment, $R^{13}$ is $NR^9SO_2R^{73}$.

In one embodiment, $R^{13}$ is $N(SO_2R^9)CH_2C(O)R^{74}$.

In one embodiment, $R^{72}$ is aryl.

In one embodiment, $R^{72}$ is heteroaryl.

In one embodiment, $R^{72}$ is hetercycle.

In one embodiment, $R^{72}$ is selected from alkynyl, hydroxyl and $C_1$-$C_6$alkoxy.

In one embodiment, $R^{72}$ is ($C_3$-$C_7$cycloalkyl)$C_0$-$C_4$alkyl or (aryl)$C_0$-$C_4$alkyl.

In one embodiment, $R^{72}$ is (heterocycle)$C_0$-$C_4$alkyl or (heteroaryl)$C_0$-$C_4$alkyl.

In one embodiment, $R^{72}$ is —$C_1$-$C_4$alkylOC(O)O$C_1$-$C_6$alkyl or —$C_1$-$C_4$alkylOC(O)$C_1$-$C_6$alkyl In one embodiment, $R^{72}$ is —$C_1$-$C_4$alkylC(O)O$C_1$-$C_6$alkyl.

In one embodiment, $R^{72}$ is selected from —S(O)(O)(alkyl), —S(O)(alkyl), —S(O)(O)(heteroalkyl), —S(O)(heteroalkyl), —S(O)(O)(aryl), —S(O)(aryl), —S(O)(O)(heteroaryl) and —S(O)(heteroaryl).

In one embodiment, $R^{73}$ is hydroxyl.

In one embodiment, $R^{73}$ is selected from cyano and amino.

In one embodiment, $R^{73}$ is selected from $C_1$-$C_6$alkyl, $C_1$-$C_6$haloalkyl and $C_1$-$C_6$alkoxy.

In one embodiment, $R^{73}$ is ($C_3$-$C_7$cycloalkyl)$C_0$-$C_4$alkyl, (phenyl)$C_0$-$C_4$alkyl, or —$C_1$-$C_4$alkylOC(O)O$C_1$-$C_6$alkyl.

In one embodiment, $R^{73}$ is —$C_1$-$C_4$alkylOC(O)$C_1$-$C_6$alkyl, —$C_1$-$C_4$alkylC(O)O$C_1$-$C_6$alkyl, In one embodiment, the disclosure provides compounds of Formula I, Formula II, Formula III, or Formula IV, wherein;

one of $R^{12}$ and $R^{13}$ is H and the other of $R^{12}$ and $R^{13}$ is $R^{32}$, where $R^{32}$ is selected from $NR^{72}R^{73}$, $NR^9SO_2R^{73}$, or $N(SO_2R^9)CH_2C(O)R^{74}$, each of which is optionally substituted;

wherein $R^9$, $R^{72}$, $R^{73}$, and $R^{74}$ are as defined in the summary section above.

In another embodiment, the disclosure provides compounds of Formula I, Formula II, Formula III, or Formula IV, wherein;

$R^1$, $R^{1'}$, $R^2$, and $R^{3'}$ are all hydrogen;

$R^2$ is fluoro and $R^3$ is hydrogen, —$C_0$-$C_4$alkyl($C_3$-$C_7$cycloalkyl), or —O—$C_0$-$C_4$alkyl($C_3$-$C_7$cycloalkyl);

$R^5$ is hydrogen, halogen, or $C_1$-$C_2$alkyl;

$R^{11}$, $R^{13}$, $R^{14}$, and $R^{15}$ if present, are independently selected at each occurrence from hydrogen, halogen, hydroxyl, amino, $C_1$-$C_4$alkyl, $C_1$-$C_4$alkoxy, —$C_0$-$C_2$alkyl (mono- and di-$C_1$-$C_2$alkylamino), trifluoromethyl, and trifluoromethoxy;

$X^{12}$ is $CR^{12}$; and $R^{12}$ is selected from $NR^{72}R^{73}$, $NR^9SO_2R^{73}$, or $N(SO_2R^9)CH_2C(O)R^{74}$, each of which is optionally substituted;

wherein $R^9$, $R^{72}$, $R^{73}$, and $R^{74}$ are as defined in the summary section above.

In one embodiment, the disclosure provides compounds of Formula I, Formula II, Formula III, or Formula IV, wherein;

m is 0 or 1;

$R^2$ is halogen, $R^{2'}$ is hydrogen or halogen, and $R^3$ is hydrogen, halogen, —$C_0$-$C_4$alkyl($C_3$-$C_7$cycloalkyl), or —O—$C_0$-$C_4$alkyl($C_3$-$C_7$cycloalkyl);

$R^6$ is —C(O)$C_1$-$C_4$alkyl, —C(O)$NH_2$, —C(O)$CF_3$, —C(O)($C_3$-$C_7$cycloalkyl), or -ethyl(cyanoimino);

one of $R^{12}$ and $R^{13}$ is selected from hydrogen, halogen, $C_1$-$C_4$alkyl, $C_1$-$C_4$alkoxy, trifluoromethyl, and trifluoromethoxy; the other of $R^{12}$ and $R^{13}$ is $R^{32}$, where $R^{32}$ is selected from $NR^{72}R^{73}$, $NR^9SO_2R^{73}$, or $N(SO_2R^9)CH_2C(O)R^{74}$, which can be optionally substituted;

wherein $R^9$, $R^{72}$, $R^{73}$, and $R^{74}$ are as defined in the summary section above.

In one embodiment, the disclosure provides compounds of Formula I, Formula II, Formula III, or Formula IV, wherein;

one of $R^{12}$ and $R^{13}$ is hydrogen, hydroxyl, halogen, methyl, or methoxy; and the other of $R^{12}$ and $R^{13}$ is $R^{32}$, where $R^{32}$ is selected from $NR^{72}R^{73}$, $NR^9SO_2R^{73}$, or $N(SO_2R^9)CH_2C(O)R^{74}$, each of which is optionally substituted;

wherein $R^9$, $R^{72}$, $R^{73}$, and $R^{74}$ are as defined in the summary section above.

In one embodiment, $R^{32}$ may be unsubstituted or substituted with one or more substituents independently selected from halogen, hydroxyl, nitro, cyano, amino, oxo, —B$(OH)_2$, —Si$(CH_3)_3$, —COOH, —$CONH_2$, —P(O)$(OH)_2$, $C_1$-$C_6$alkyl, $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy.

In one embodiment $R^{32}$ is selected from:

FIG. 6B

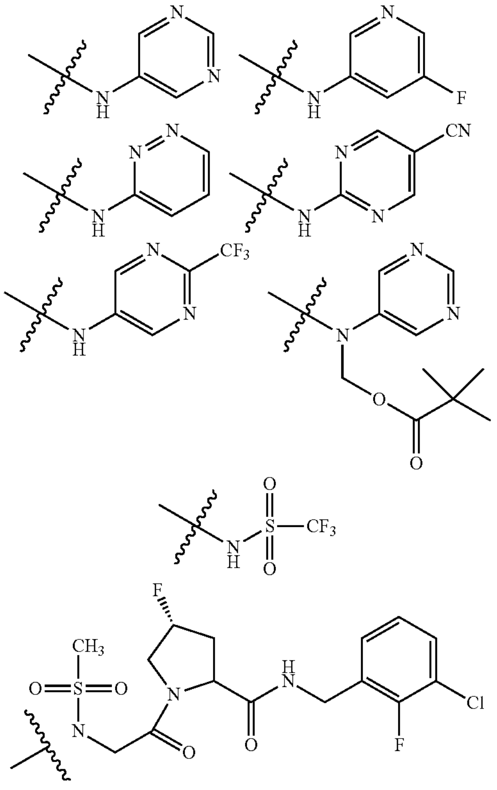

-continued
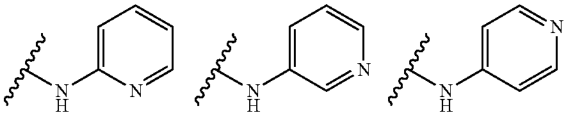
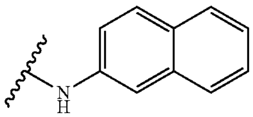
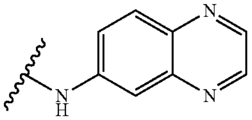
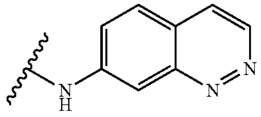
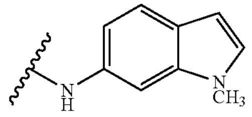
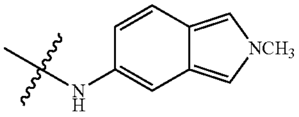
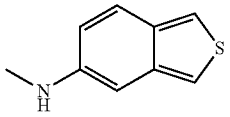
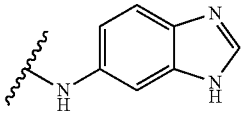
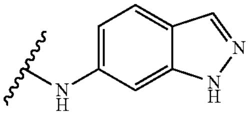
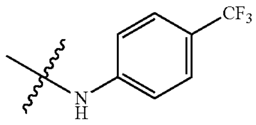
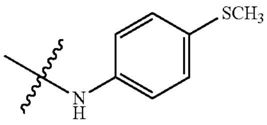
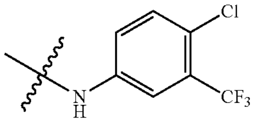 [SMILES: *Nc1ccc(Cl)c(C(F)(F)F)c1]
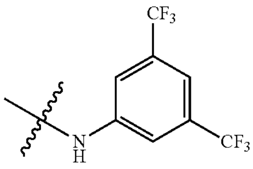
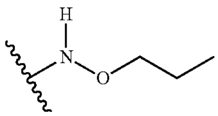
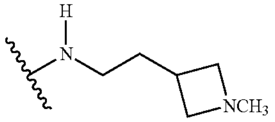
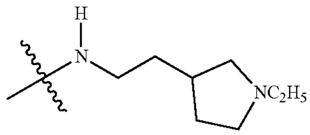
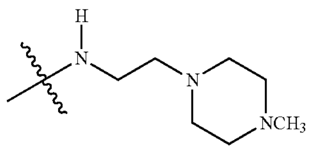
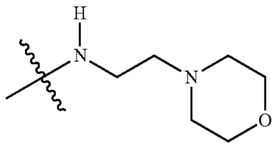
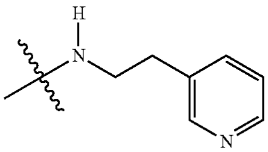
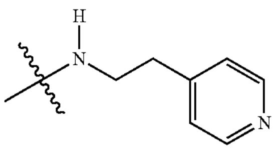
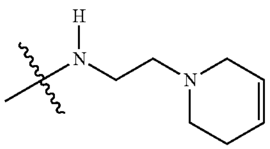
-continued
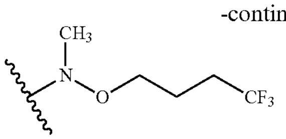
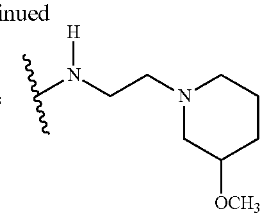
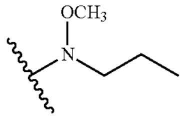
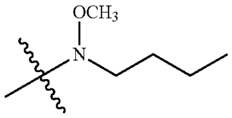
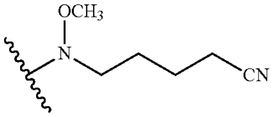
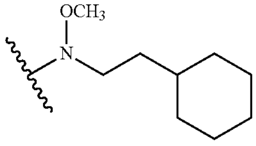
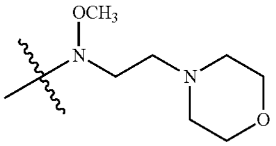
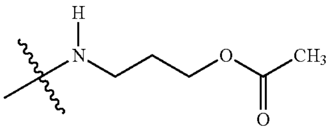
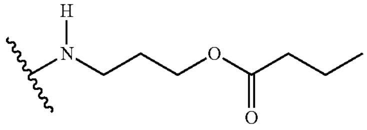
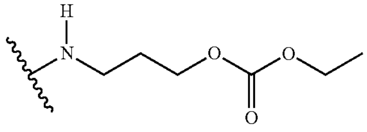
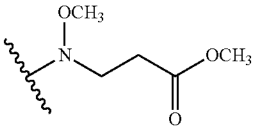
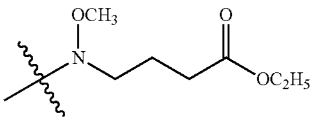
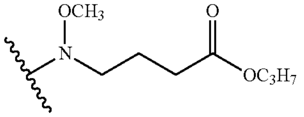
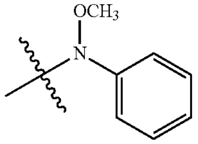
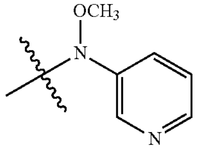
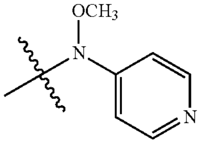
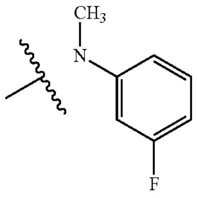
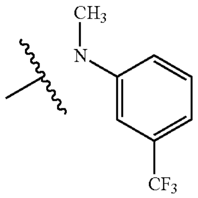

-continued

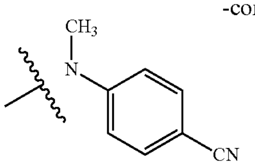

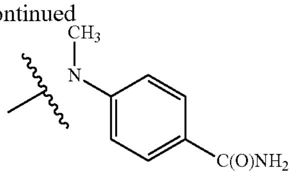

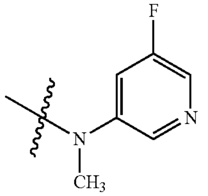

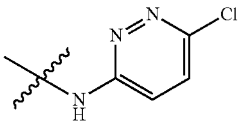

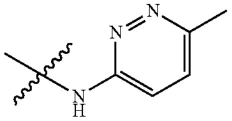

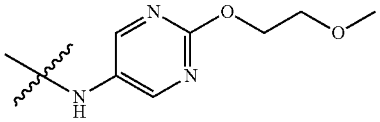

and

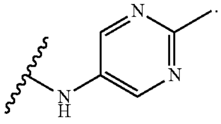

.

$R^{32}$ Carbamates

In some embodiments, structures are provided including Formulas IB and IC, wherein m=0, $R^1$ is H, $R^2$ is F, $R^6$ is alkanoyl, $R^{12}$ is $R^{32}$, $R^{32}$ is —OC(O)$NR^{21}R^{22}$, and $R^{13}$ is H.

In some embodiments, structures are provided including Formulas IB and IC, wherein m=0, $R^1$ and $R^2$ are joined to form a 3 membered ring, $R^6$ is alkanoyl, $R^{12}$ is $R^{32}$, $R^{32}$ is —OC(O)$NR^{21}R^{22}$, and $R^{13}$ is H.

In some embodiments, structures are provided including Formulas IB and IC, wherein m=0, $R^1$ is H, $R^2$ is F, $R^6$ is amide, $R^{12}$ is $R^{32}$, $R^{32}$ is —OC(O)$NR^{21}R^{22}$, and $R^{13}$ is H.

In some embodiments, structures are provided including Formulas IB and IC, wherein m=0, $R^1$ and $R^2$ are joined to form a 3 membered ring, $R^6$ is amide, $R^{12}$ is $R^{32}$, $R^{32}$ is —OC(O)$NR^{21}R^{22}$, and $R^{13}$ is H.

In some embodiments, structures are provided including Formulas IB and IC, wherein m=0, $R^1$ is H, $R^2$ is F, $R^6$ is alkanoyl, $R^{12}$ is H, $R^{13}$ is $R^{32}$, and $R^{32}$ is —OC(O)$NR^{21}R^{22}$.

In some embodiments, structures are provided including Formulas IB and IC, wherein m=0, $R^1$ and $R^2$ are joined to form a 3 membered ring, $R^6$ is alkanoyl, $R^{12}$ is H, $R^{13}$ is $R^{32}$, and $R^{32}$ is —OC(O)$NR^{21}R^{22}$.

In some embodiments, structures are provided including Formulas IB and IC, wherein m=0, $R^1$ is H, $R^2$ is F, $R^6$ is amide, $R^{12}$ is H, $R^{13}$ is $R^{32}$, and $R^{32}$ is —OC(O)$NR^{21}R^{22}$.

In some embodiments, structures are provided including Formulas IB and IC, wherein m=0, $R^1$ and $R^2$ are joined to form a 3 membered ring, $R^6$ is amide, $R^{12}$ is H, $R^{13}$ is $R^{32}$, and $R^{32}$ is —OC(O)$NR^{21}R^{22}$.

In some embodiments, structures are provided including Formulas IB and IC, wherein m=0, $R^1$ is H, $R^2$ is F, $R^6$ is alkanoyl, $R^{12}$ is $R^{32}$, $R^{32}$ is —OC(O)$NR^{21}R^{22}$, and $R^{13}$ is H.

In some embodiments, structures are provided including Formulas IB and IC, wherein m=0, $R^1$ and $R^2$ are joined to form a 3 membered ring, $R^6$ is alkanoyl, $R^{12}$ is $R^{32}$, $R^{32}$ is —OC(O)$NR^{21}R^{22}$, and $R^{13}$ is H.

In some embodiments, structures are provided including Formulas IB and IC, wherein m=0, $R^1$ is H, $R^2$ is F, $R^6$ is amide, $R^{12}$ is $R^{32}$, $R^{32}$ is —OC(O)$NR^{21}R^{22}$, and $R^{13}$ is H.

In some embodiments, structures are provided including Formulas IB and IC, wherein m=0, $R^1$ and $R^2$ are joined to form a 3 membered ring, $R^6$ is amide, $R^{12}$ is $R^{32}$, $R^{32}$ is —OC(O)$NR^{21}R^{22}$, and $R^{13}$ is H.

In some embodiments, structures are provided including Formulas IB and IC, wherein m=0, $R^1$ is H, $R^2$ is F, $R^6$ is alkanoyl, $R^{12}$ is H, $R^{13}$ is $R^{32}$, and $R^{32}$ is —OC(O)$NR^{21}R^{22}$.

In some embodiments, structures are provided including Formulas IB and IC, wherein m=0, $R^1$ and $R^2$ are joined to form a 3 membered ring, $R^6$ is alkanoyl, $R^{12}$ is H, $R^{13}$ is $R^{32}$, and $R^{32}$ is —OC(O)$NR^{21}R^{22}$.

In some embodiments, structures are provided including Formulas IB and IC, wherein m=0, $R^1$ is H, $R^2$ is F, $R^6$ is amide, $R^{12}$ is H, $R^{13}$ is $R^{32}$, and $R^{32}$ is —OC(O)$NR^{21}R^{22}$.

In some embodiments, structures are provided including Formulas IB and IC, wherein m=0, $R^1$ and $R^2$ are joined to form a 3 membered ring, $R^6$ is amide, $R^{12}$ is H, $R^{13}$ is $R^{32}$, and $R^{32}$ is —OC(O)$NR^{21}R^{22}$.

In some embodiments, structures are provided including Formulas IB and IC, wherein m=1, $R^1$ is H, $R^2$ is F, $R^6$ is alkanoyl, $R^{12}$ is $R^{32}$, $R^{32}$ is —OC(O)$NR^{21}R^{22}$, and $R^{13}$ is H.

In some embodiments, structures are provided including Formulas IB and IC, wherein m=1, $R^1$ and $R^2$ are joined to form a 3 membered ring, $R^6$ is alkanoyl, $R^{12}$ is $R^{32}$, $R^{32}$ is —OC(O)$NR^{21}R^{22}$, and $R^{13}$ is H.

In some embodiments, structures are provided including Formulas IB and IC, wherein m=1, $R^1$ is H, $R^2$ is F, $R^6$ is amide, $R^{12}$ is $R^{32}$, $R^{32}$ is —OC(O)$NR^{21}R^{22}$, and $R^{13}$ is H.

In some embodiments, structures are provided including Formulas IB and IC, wherein m=1, $R^1$ and $R^2$ are joined to form a 3 membered ring, $R^6$ is amide, $R^{12}$ is $R^{32}$, $R^{32}$ is —OC(O)$NR^{21}R^{22}$, and $R^{13}$ is H.

In some embodiments, structures are provided including Formulas IB and IC, wherein m=1, $R^1$ is H, $R^2$ is F, $R^6$ is alkanoyl, $R^{12}$ is H, $R^{13}$ is $R^{32}$, and $R^{32}$ is —OC(O)$NR^{21}R^{22}$.

In some embodiments, structures are provided including Formulas IB and IC, wherein m=1, $R^1$ and $R^2$ are joined to form a 3 membered ring, $R^6$ is alkanoyl, $R^{12}$ is H, $R^{13}$ is $R^{32}$, and $R^{32}$ is —OC(O)$NR^{21}R^{22}$.

In some embodiments, structures are provided including Formulas IB and IC, wherein m=1, $R^1$ is H, $R^2$ is F, $R^6$ is amide, $R^{12}$ is H, $R^{13}$ is $R^{32}$, and $R^{32}$ is —OC(O)$NR^{21}R^{22}$.

In some embodiments, structures are provided including Formulas IB and IC, wherein m=1, $R^1$ and $R^2$ are joined to form a 3 membered ring, $R^6$ is amide, $R^{12}$ is H, $R^{13}$ is $R^{32}$, and $R^{32}$ is —OC(O)$NR^{21}R^{22}$.

In some embodiments, structures are provided including Formulas IB and IC, wherein m=1, $R^1$ is H, $R^2$ is F, $R^6$ is alkanoyl, $R^{12}$ is $R^{32}$, $R^{32}$ is —OC(O)$NR^{21}R^{22}$, and $R^{13}$ is H.

In some embodiments, structures are provided including Formulas IB and IC, wherein m=1, $R^1$ and $R^2$ are joined to form a 3 membered ring, $R^6$ is alkanoyl, $R^{12}$ is $R^{32}$, $R^{32}$ is —OC(O)$NR^{21}R^{22}$, and $R^{13}$ is H.

In some embodiments, structures are provided including Formulas IB and IC, wherein m=1, $R^1$ is H, $R^2$ is F, $R^6$ is amide, $R^{12}$ is $R^{32}$, $R^{32}$ is —OC(O)$NR^{21}R^{22}$, and $R^{13}$ is H.

In some embodiments, structures are provided including Formulas IB and IC, wherein m=1, $R^1$ and $R^2$ are joined to form a 3 membered ring, $R^6$ is amide, $R^{12}$ is $R^{32}$, $R^{32}$ is —OC(O)$NR^{21}R^{22}$, and $R^{13}$ is H.

In some embodiments, structures are provided including Formulas IB and IC, wherein m=1, $R^1$ is H, $R^2$ is F, $R^6$ is alkanoyl, $R^{12}$ is H, $R^{13}$ is $R^{32}$, and $R^{32}$ is —OC(O)$NR^{21}R^{22}$.

In some embodiments, structures are provided including Formulas IB and IC, wherein m=1, $R^1$ and $R^2$ are joined to form a 3 membered ring, $R^6$ is alkanoyl, $R^{12}$ is H, $R^{13}$ is $R^{32}$, and $R^{32}$ is —OC(O)$NR^{21}R^{22}$.

In some embodiments, structures are provided including Formulas IB and IC, wherein m=1, $R^1$ is H, $R^2$ is F, $R^6$ is amide, $R^{12}$ is H, $R^{13}$ is $R^{32}$, and $R^{32}$ is —OC(O)$NR^{21}R^{22}$.

In some embodiments, structures are provided including Formulas IB and IC, wherein m=1, $R^1$ and $R^2$ are joined to form a 3 membered ring, $R^6$ is amide, $R^{12}$ is H, $R^{13}$ is $R^{32}$, and $R^{32}$ is —OC(O)$NR^{21}R^{22}$.

In one embodiment $R^{32}$ is selected from:

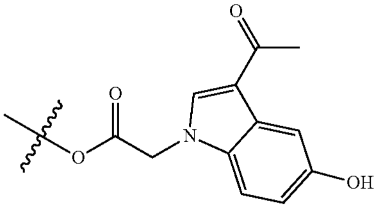

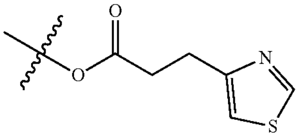
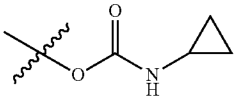

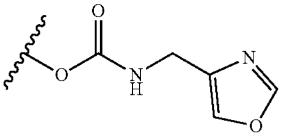
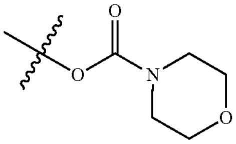

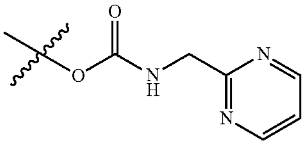

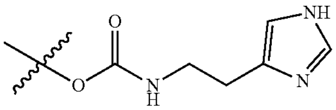

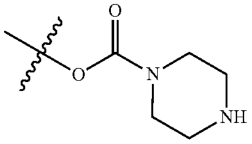

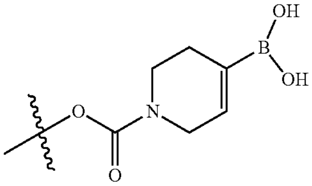

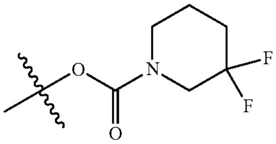
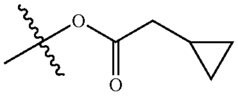

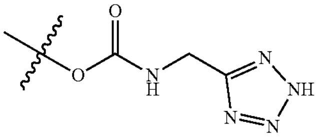

-continued

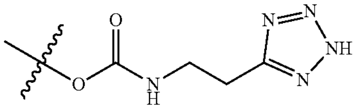

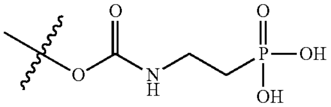

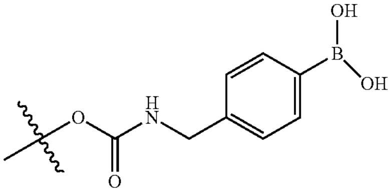

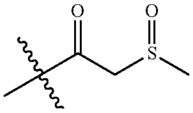
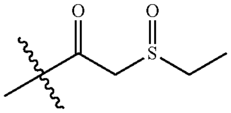

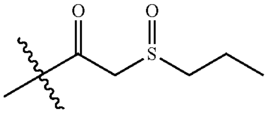

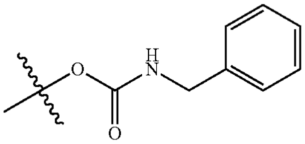

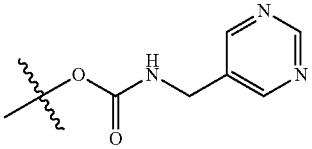
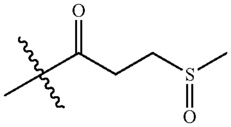

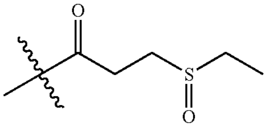
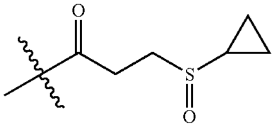

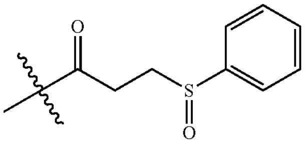

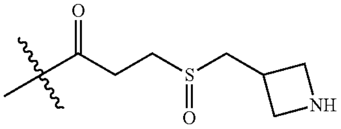

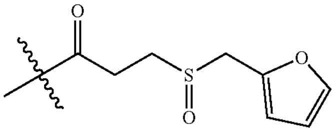

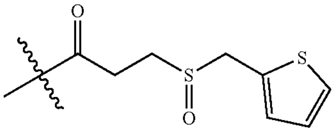

-continued

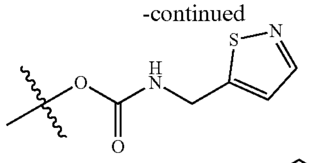

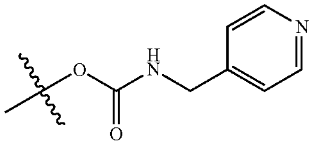

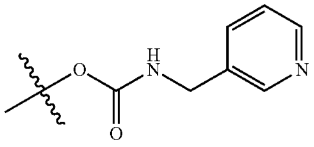 [SMILES: *OC(=O)NCc1cccnc1]

$R^{32}$ Ether

In Formulas IA, IB, IC, and ID, the variables may include any of the definitions set forth herein that results in a stable compound. In certain embodiments, the following conditions apply for Formula IB and IC.

In some embodiments, structures are provided including Formulas IB and IC, wherein m=0, $R^1$ is H, $R^2$ is F, $R^6$ is alkanoyl, $R^{12}$ is $R^{32}$, $R^{32}$ is —$O(CH_2)_{1-4}P(O)R^{23b}R^{23b}$, $R^{13}$ is H.

In some embodiments, structures are provided including Formulas IB and IC, wherein m=0, $R^1$ and $R^2$ are joined to form a 3 membered ring, $R^6$ is alkanoyl, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=0, $R^1$ is H, $R^2$ is F, $R^6$ is amide, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=0, $R^1$ and $R^2$ are joined to form a 3 membered ring, $R^6$ is amide, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=0, $R^1$ is H, $R^2$ is F, $R^6$ is alkanoyl, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=0, $R^1$ and $R^2$ are joined to form a 3 membered ring, $R^6$ is alkanoyl, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=0, $R^1$ is H, $R^2$ is F, $R^6$ is amide, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=0, $R^1$ and $R^2$ are joined to form a 3 membered ring, $R^6$ is amide, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=0, $R^1$ is H, $R^2$ is F, $R^6$ is alkanoyl, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=0, $R^1$ and $R^2$ are joined to form a 3 membered ring, $R^6$ is alkanoyl, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=0, $R^1$ is H, $R^2$ is F, $R^6$ is amide, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=0, $R^1$ and $R^2$ are joined to form a 3 membered ring, $R^6$ is amide, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=0, $R^1$ is H, $R^2$ is F, $R^6$ is alkanoyl, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=0, $R^1$ and $R^2$ are joined to form a 3 membered ring, $R^6$ is alkanoyl, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=0, $R^1$ is H, $R^2$ is F, $R^6$ is amide, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=0, $R^1$ and $R^2$ are joined to form a 3 membered ring, $R^6$ is amide, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=1, $R^1$ is H, $R^2$ is F, $R^6$ is alkanoyl, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=1, $R^1$ and $R^2$ are joined to form a 3 membered ring, $R^6$ is alkanoyl, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=1, $R^1$ is H, $R^2$ is F, $R^6$ is amide, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=1, $R^1$ and $R^2$ are joined to form a 3 membered ring, $R^6$ is amide, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=1, $R^1$ is H, $R^2$ is F, $R^6$ is alkanoyl, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=1, $R^1$ and $R^2$ are joined to form a 3 membered ring, $R^6$ is alkanoyl, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=1, $R^1$ is H, $R^2$ is F, $R^6$ is amide, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=1, $R^1$ and $R^2$ are joined to form a 3 membered ring, $R^6$ is amide, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=1, $R^1$ is H, $R^2$ is F, $R^6$ is alkanoyl, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=1, $R^1$ and $R^2$ are joined to form a 3 membered ring, $R^6$ is alkanoyl, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=1, $R^1$ is H, $R^2$ is F, $R^6$ is amide, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=1, $R^1$ and $R^2$ are joined to form a 3 membered ring, $R^6$ is amide, $R^{12}$ is $R^{32}$, $R^{32}$ is $O(CH_2)_{1-4}P(O)R^{23b}R^{23b}$, $R^{13}$ is H.

In some embodiments, structures are provided including Formulas IB and IC, wherein m=1, $R^1$ is H, $R^2$ is F, $R^6$ is alkanoyl, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=1, $R^1$ and $R^2$ are joined to form a 3 membered ring, $R^6$ is alkanoyl, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=1, $R^1$ is H, $R^2$ is F, $R^6$ is amide, $R^{12}$ is H, $R^{13}$ is $R^{32}$, $R^{32}$ is $O(CH_2)_{1-4}P(O)R^{23b}R^{23b}$.

In some embodiments, structures are provided including Formulas IB and IC, wherein m=1, $R^1$ and $R^2$ are joined to form a 3 membered ring, $R^6$ is amide, $R^{12}$ is H, $R^{13}$ is $R^{32}$, $R^{32}$ is $O(CH_2)_{1-4}P(O)R^{23b}R^{23b}$.

In the above embodiments, structures are provided including Formulas IB and IC, wherein;

$R^{23b}$ is independently selected at each occurrence from hydroxyl, $C_1$-$C_6$alkoxy, $C_1$-$C_6$alkyl, ($C_3$-$C_7$cycloalkyl)$C_0$-$C_4$alkyl, (phenyl)$C_0$-$C_4$alkyl, $—O(CH_2)_{2-4}O(CH_2)_{8-18}$, $—OC(R^{23c})_2OC(O)OR^{23d}$, $—OC(R^{23c})_2OC(O)R^{23d}$, an N-linked amino acid or an N-linked amino acid ester, and each $R^{23b}$ can be optionally substituted;

$R^{23c}$ is independently selected at each occurrence from hydrogen, $C_1$-$C_8$alkyl, $C_2$-$C_8$alkenyl, $C_2$-$C_8$alkynyl, (aryl)$C_0$-$C_4$alkyl, (aryl)$C_2$-$C_8$alkenyl- or (aryl)$C_2$-$C_8$alkynyl; or two $R^{23c}$ groups can be taken together with the carbon that they are bonded to form a 3-6 membered heterocycloalkyl having 1, 2, or 3 heteroatoms independently selected from N, O, and S, or a 3-6 membered carbocyclic ring, and each $R^{23c}$ can be optionally substituted;

$R^{23d}$ is independently selected at each occurrence from $C_1$-$C_8$alkyl, $C_2$-$C_8$alkenyl, $C_2$-$C_8$alkynyl, (aryl)$C_0$-$C_4$alkyl, (aryl)$C_2$-$C_8$alkenyl or (aryl)$C_2$-$C_8$alkynyl, and each $R^{23d}$ can be optionally substituted.

In one embodiment $R^{32}$ is selected from:

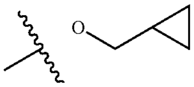 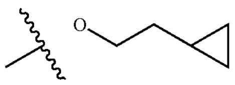

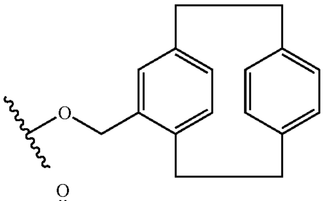

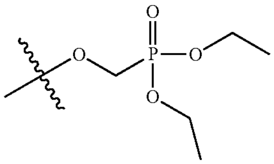 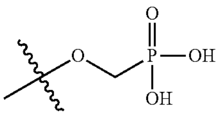

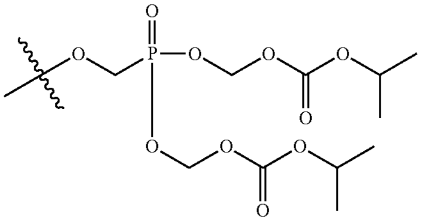

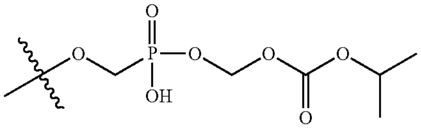

-continued

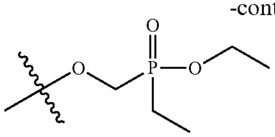 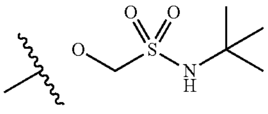

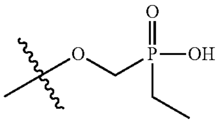 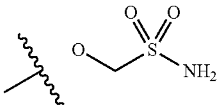

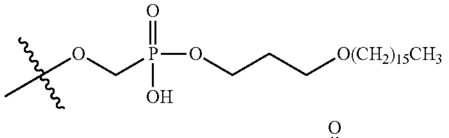

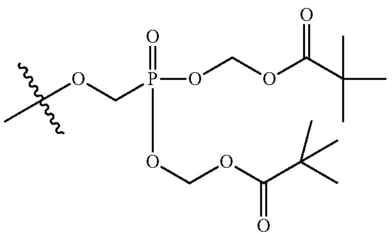

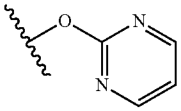 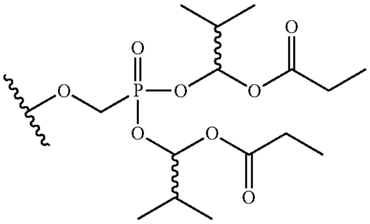

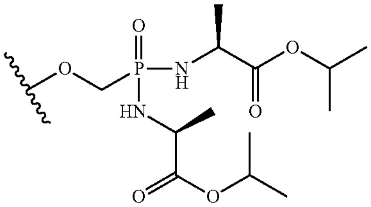 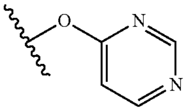

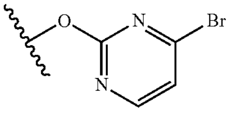 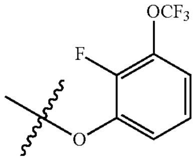

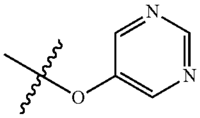 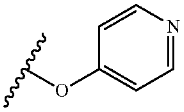

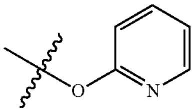 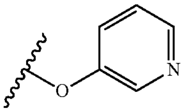

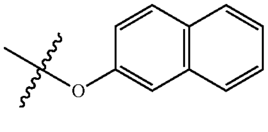 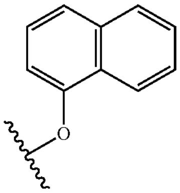

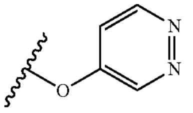 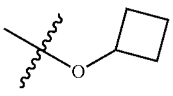 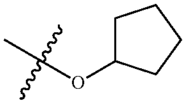

-continued
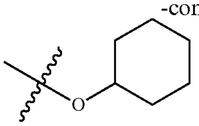 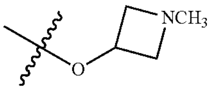
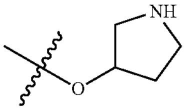 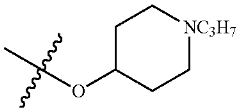
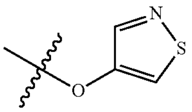 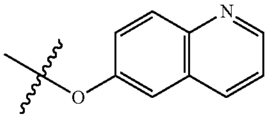
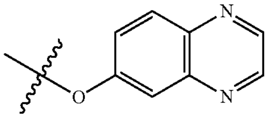
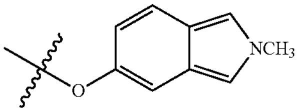
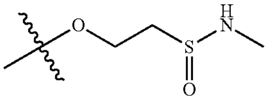
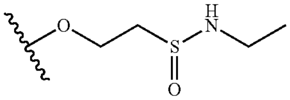
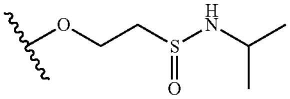
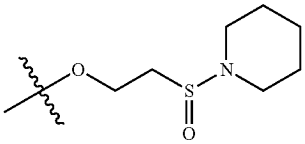 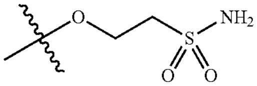
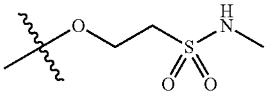
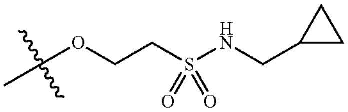
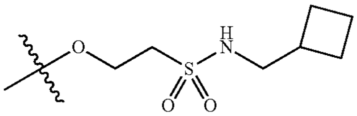
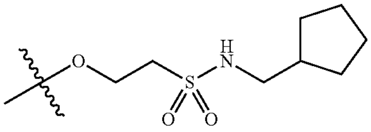
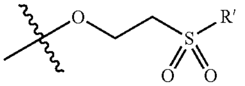 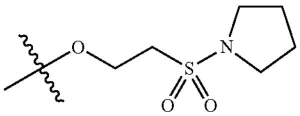
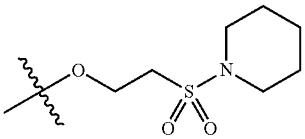
-continued
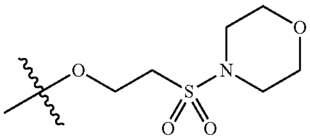
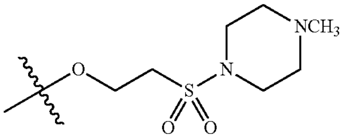
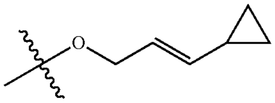 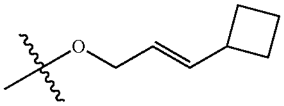
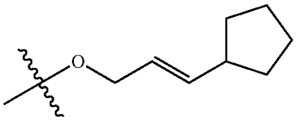
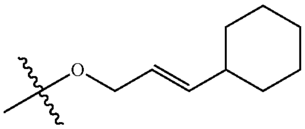
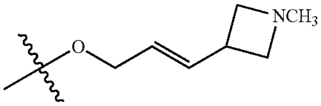
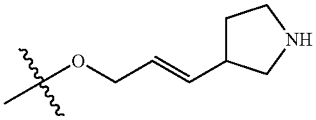
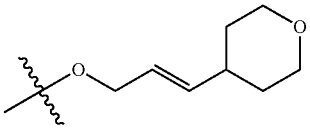
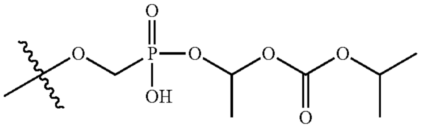
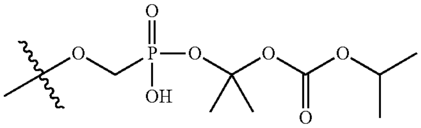
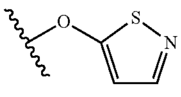 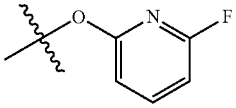
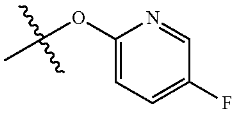 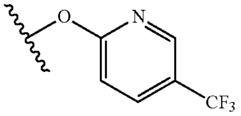
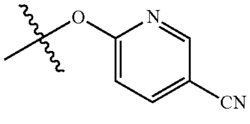 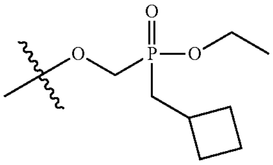

-continued

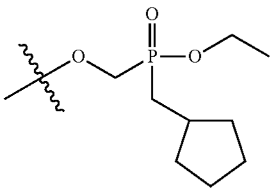

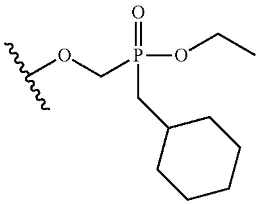

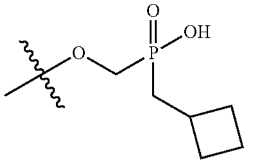

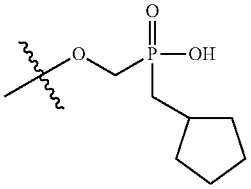

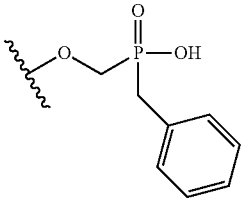

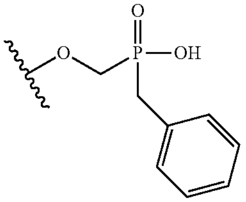

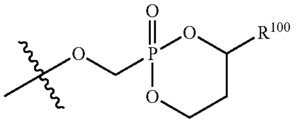

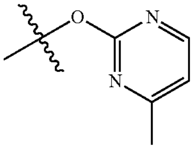

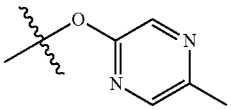

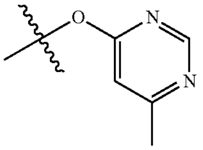

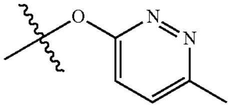

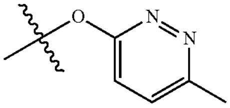

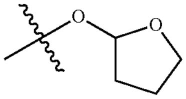

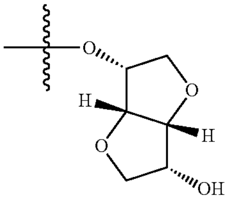

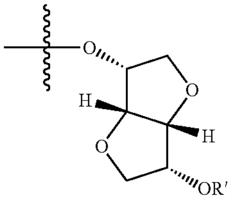

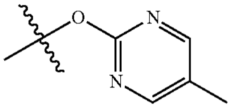

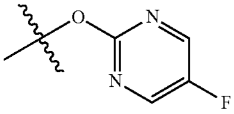

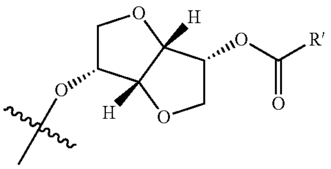

-continued

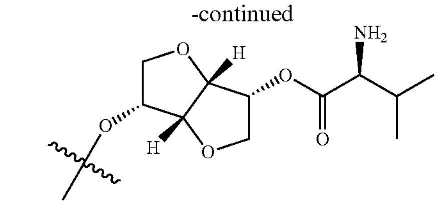

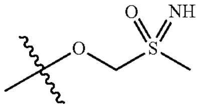

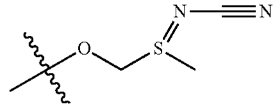

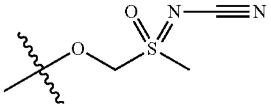

$R^{32}$ Phosphonate

In some embodiments, structures are provided including Formulas IB and IC, wherein m=0, $R^1$ is H, $R^2$ is F, $R^6$ is alkanoyl, $R^{12}$ is $R^{32}$, $R^{32}$ is —P(O)$R^{75}R^{75}$, $R^{13}$ is H.

In some embodiments, structures are provided including Formulas IB and IC, wherein m=0, $R^1$ and $R^2$ are joined to form a 3 membered ring, $R^6$ is alkanoyl, $R^{12}$ is $R^{32}$, $R^{32}$ is —P(O)$R^{75}R^{75}$, $R^{13}$ is H.

In some embodiments, structures are provided including Formulas IB and IC, wherein m=0, $R^1$ is H, $R^2$ is F, $R^6$ is amide, $R^{12}$ is $R^{32}$, $R^{32}$ is —P(O)$R^{75}R^{75}$, $R^{13}$ is H.

In some embodiments, structures are provided including Formulas IB and IC, wherein m=0, $R^1$ and $R^2$ are joined to form a 3 membered ring, $R^6$ is amide, $R^{12}$ is $R^{32}$, $R^{32}$ is —P(O)$R^{75}R^{75}$, $R^{13}$ is H.

In some embodiments, structures are provided including Formulas IB and IC, wherein m=0, $R^1$ is H, $R^2$ is F, $R^6$ is alkanoyl, $R^{12}$ is H, $R^{13}$ is $R^{32}$, $R^{32}$ is —P(O)$R^{75}R^{75}$.

In some embodiments, structures are provided including Formulas IB and IC, wherein m=0, $R^1$ and $R^2$ are joined to form a 3 membered ring, $R^6$ is alkanoyl, $R^{12}$ is H, $R^{13}$ is $R^{32}$, $R^{32}$ is —P(O)$R^{75}R^{75}$.

In some embodiments, structures are provided including Formulas IB and IC, wherein m=0, $R^1$ is H, $R^2$ is F, $R^6$ is amide, $R^{12}$ is H, $R^{13}$ is $R^{32}$, $R^{32}$ is —P(O)$R^{75}R^{75}$.

In some embodiments, structures are provided including Formulas IB and IC, wherein m=0, $R^1$ and $R^2$ are joined to form a 3 membered ring, $R^6$ is amide, $R^{12}$ is H, $R^{13}$ is $R^{32}$, $R^{32}$ is —P(O)$R^{75}R^{75}$.

In some embodiments, structures are provided including Formulas IB and IC, wherein m=0, $R^1$ is H, $R^2$ is F, $R^6$ is alkanoyl, $R^{12}$ is $R^{32}$, $R^{32}$ is —P(O)$R^{75}R^{75}$, $R^{13}$ is H.

In some embodiments, structures are provided including Formulas IB and IC, wherein m=0, $R^1$ and $R^2$ are joined to form a 3 membered ring, $R^6$ is alkanoyl, $R^{12}$ is $R^{32}$, $R^{32}$ is —P(O)$R^{75}R^{75}$, $R^{13}$ is H.

In some embodiments, structures are provided including Formulas IB and IC, wherein m=0, $R^1$ is H, $R^2$ is F, $R^6$ is amide, $R^{12}$ is $R^{32}$, $R^{32}$ is —P(O)$R^{75}R^{75}$, $R^{13}$ is H.

In some embodiments, structures are provided including Formulas IB and IC, wherein m=0, $R^1$ and $R^2$ are joined to form a 3 membered ring, $R^6$ is amide, $R^{12}$ is $R^{32}$, $R^{32}$ is —P(O)$R^{75}R^{75}$, $R^{13}$ is H.

In some embodiments, structures are provided including Formulas IB and IC, wherein m=0, $R^1$ is H, $R^2$ is F, $R^6$ is alkanoyl, $R^{12}$ is H, $R^{13}$ is $R^{32}$, $R^{32}$ is —P(O)$R^{75}R^{75}$.

In some embodiments, structures are provided including Formulas IB and IC, wherein m=0, $R^1$ and $R^2$ are joined to form a 3 membered ring, $R^6$ is alkanoyl, $R^{12}$ is H, $R^{13}$ is $R^{32}$, $R^{32}$ is —P(O)$R^{75}R^{75}$.

In some embodiments, structures are provided including Formulas IB and IC, wherein m=0, $R^1$ is H, $R^2$ is F, $R^6$ is amide, $R^{12}$ is H, $R^{13}$ is $R^{32}$, $R^{32}$ is —$P(O)R^{75}R^{75}$.

In some embodiments, structures are provided including Formulas IB and IC, wherein m=0, $R^1$ and $R^2$ are joined to form a 3 membered ring, $R^6$ is amide, $R^{12}$ is H, $R^{13}$ is $R^{32}$, $R^{32}$ is —$P(O)R^{75}R^{75}$.

In some embodiments, structures are provided including Formulas IB and IC, wherein m=1, $R^1$ is H, $R^2$ is F, $R^6$ is alkanoyl, $R^{12}$ is $R^{32}$, $R^{32}$ is —$P(O)R^{75}R^{75}$, $R^{13}$ is H.

In some embodiments, structures are provided including Formulas IB and IC, wherein m=1, $R^1$ and $R^2$ are joined to form a 3 membered ring, $R^6$ is alkanoyl, $R^{12}$ is $R^{32}$, $R^{32}$ is —$P(O)R^{75}R^{75}$, $R^{13}$ is H.

In some embodiments, structures are provided including Formulas IB and IC, wherein m=1, $R^1$ is H, $R^2$ is F, $R^6$ is amide, $R^{12}$ is $R^{32}$, $R^{32}$ is —$P(O)R^{75}R^{75}$, $R^{13}$ is H.

In some embodiments, structures are provided including Formulas IB and IC, wherein m=1, $R^1$ and $R^2$ are joined to form a 3 membered ring, $R^6$ is amide, $R^{12}$ is $R^{32}$, $R^{32}$ is —$P(O)R^{75}R^{75}$, $R^{13}$ is H.

In some embodiments, structures are provided including Formulas IB and IC, wherein m=1, $R^1$ is H, $R^2$ is F, $R^6$ is alkanoyl, $R^{12}$ is H, $R^{13}$ is $R^{32}$, $R^{32}$ is —$P(O)R^{75}R^{75}$.

In some embodiments, structures are provided including Formulas IB and IC, wherein m=1, $R^1$ and $R^2$ are joined to form a 3 membered ring, $R^6$ is alkanoyl, $R^{12}$ is H, $R^{13}$ is $R^{32}$, $R^{32}$ is —$P(O)R^{75}R^{75}$.

In some embodiments, structures are provided including Formulas IB and IC, wherein m=1, $R^1$ is H, $R^2$ is F, $R^6$ is amide, $R^{12}$ is H, $R^{13}$ is $R^{32}$, $R^{32}$ is —$P(O)R^{75}R^{75}$.

In some embodiments, structures are provided including Formulas IB and IC, wherein m=1, $R^1$ and $R^2$ are joined to form a 3 membered ring, $R^6$ is amide, $R^{12}$ is H, $R^{13}$ is $R^{32}$, $R^{32}$ is —$P(O)R^{75}R^{75}$.

In some embodiments, structures are provided including Formulas IB and IC, wherein m=1, $R^1$ is H, $R^2$ is F, $R^6$ is alkanoyl, $R^{12}$ is $R^{32}$, $R^{32}$ is —$P(O)R^{75}R^{75}$, $R^{13}$ is H.

In some embodiments, structures are provided including Formulas IB and IC, wherein m=1, $R^1$ and $R^2$ are joined to form a 3 membered ring, $R^6$ is alkanoyl, $R^{12}$ is $R^{32}$, $R^{32}$ is —$P(O)R^{75}R^{75}$, $R^{13}$ is H.

In some embodiments, structures are provided including Formulas IB and IC, wherein m=1, $R^1$ is H, $R^2$ is F, $R^6$ is amide, $R^{12}$ is $R^{32}$, $R^{32}$ is —$P(O)R^{75}R^{75}$, $R^{13}$ is H.

In some embodiments, structures are provided including Formulas IB and IC, wherein m=1, $R^1$ and $R^2$ are joined to form a 3 membered ring, $R^6$ is amide, $R^{12}$ is $R^{32}$, $R^{32}$ is —$P(O)R^{75}R^{75}$.

In some embodiments, structures are provided including Formulas IB and IC, wherein m=1, $R^1$ is H, $R^2$ is F, $R^6$ is alkanoyl, $R^{12}$ is H, $R^{13}$ is $R^{32}$, $R^{32}$ is —$P(O)R^{75}R^{75}$.

In some embodiments, structures are provided including Formulas IB and IC, wherein m=1, $R^1$ and $R^2$ are joined to form a 3 membered ring, $R^6$ is alkanoyl, $R^{12}$ is H, $R^{13}$ is $R^{32}$, $R^{32}$ is —$P(O)R^{75}R^{75}$.

In some embodiments, structures are provided including Formulas IB and IC, wherein m=1, $R^1$ is H, $R^2$ is F, $R^6$ is amide, $R^{12}$ is H, $R^{13}$ is $R^{32}$, $R^{32}$ is —$P(O)R^{75}R^{75}$.

In some embodiments, structures are provided including Formulas IB and IC, wherein m=1, $R^1$ and $R^2$ are joined to form a 3 membered ring, $R^6$ is amide, $R^{12}$ is H, $R^{13}$ is $R^{32}$, $R^{32}$ is —$P(O)R^{75}R^{75}$.

In one embodiment $R^{32}$ is selected from:

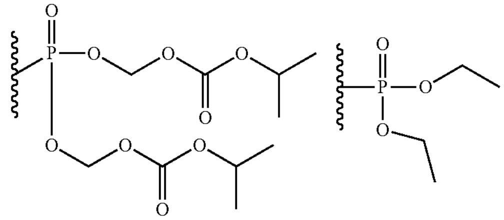

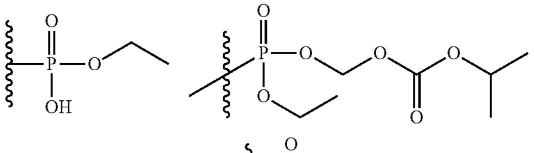

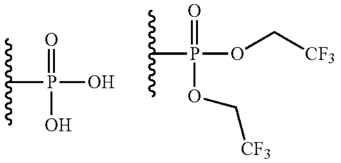

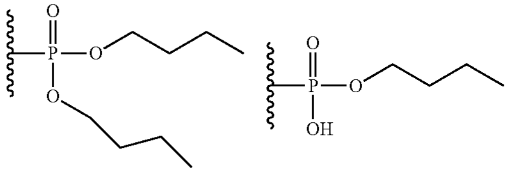

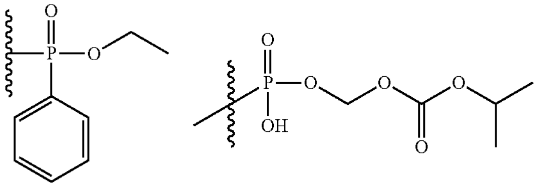

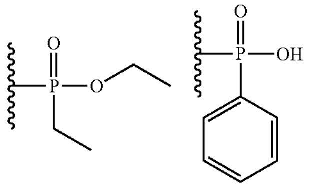

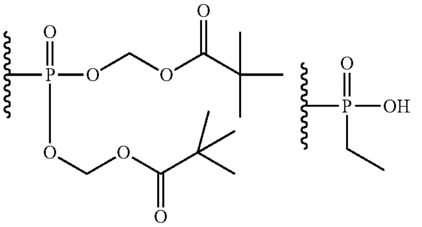

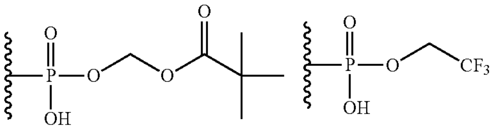

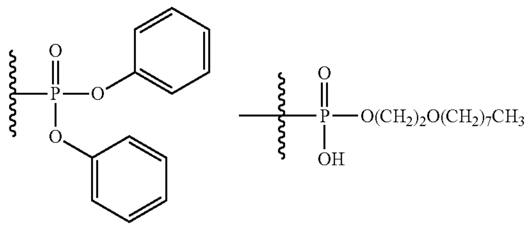

-continued
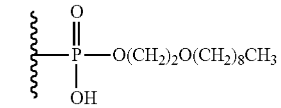 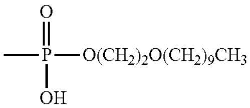
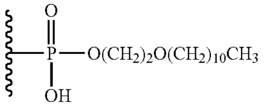 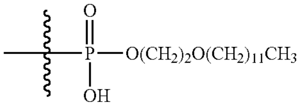
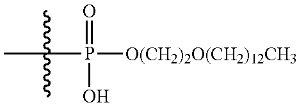
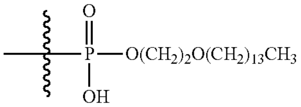
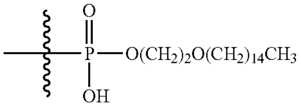
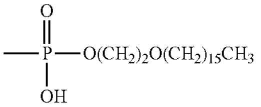 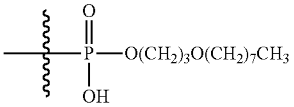
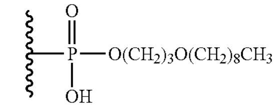 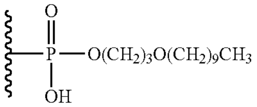
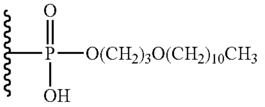 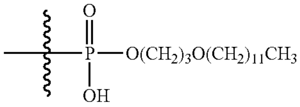
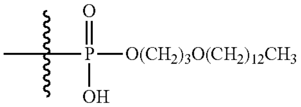
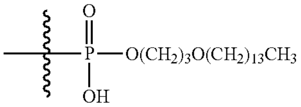
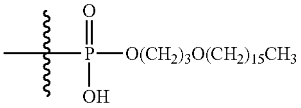
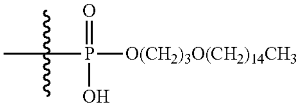
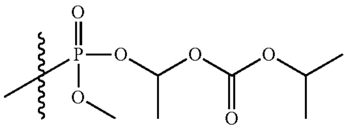
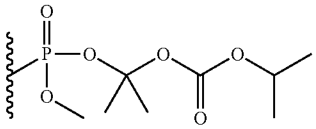
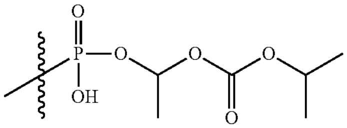
-continued
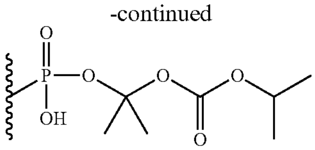
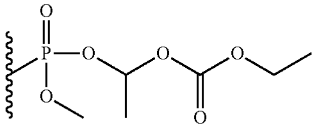
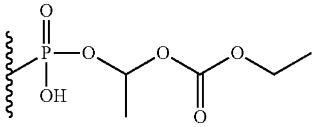
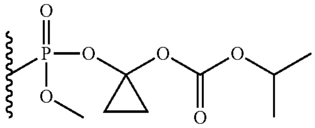
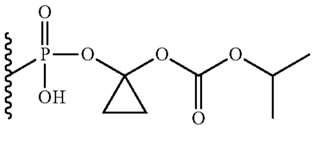 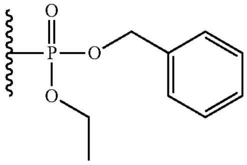
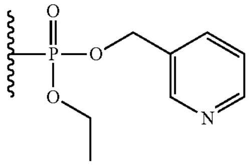 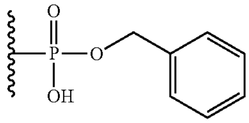
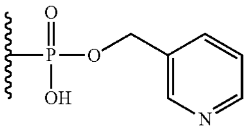 and 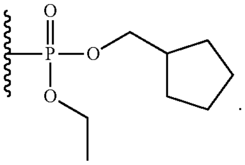 .
Additional $R^{32s}$:
In one embodiment $R^{32}$ is selected from:
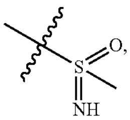, 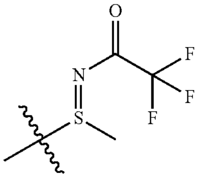, 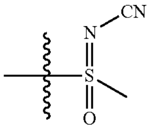,
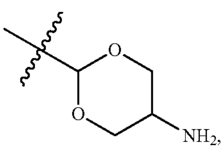, 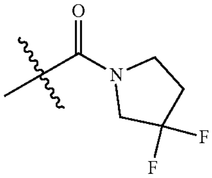,
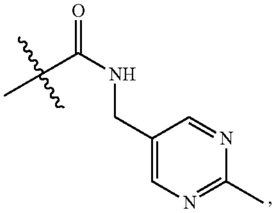, 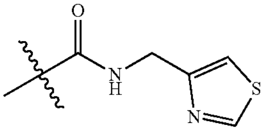, -continued

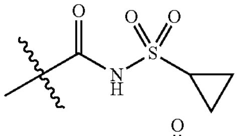, 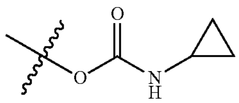, 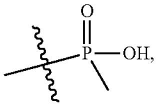, 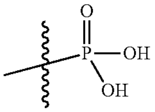

Non-Limiting Central Core Embodiments

In certain embodiments, $R^1$ and $R^{1'}$ or $R^3$ and $R^{3'}$ may be taken together to form a 3- to 6-membered carbocyclic spiro ring or a 3- to 6-membered heterocyclic spiro ring containing 1 or 2 heteroatoms independently selected from N, O, or S; $R^2$ and $R^{2'}$ may be taken together to form a 3- to 6-membered carbocyclic spiro ring; or $R^2$ and $R^{2'}$ may be taken together to form a 3- to 6-membered heterocyclic spiro ring; each of which ring may be unsubstituted or substituted with 1 or more substituents independently selected from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), haloalkyl including $C_1$-$C_6$haloalkyl, and haloalkoxy including $C_1$-$C_6$haloalkoxy.

In other embodiments, $R^1$ and $R^2$ may be taken together to form a 3-membered carbocyclic ring; $R^1$ and $R^2$ may be taken together to form a 4, 5 or 6-membered carbocyclic or an aryl ring or a 4, 5 to 6-membered heterocyclic or heteroaryl ring containing 1 or 2 heteroatoms independently selected from N, O, and S; or $R^2$ and $R^3$, if bound to adjacent carbon atoms, may be taken together to form a 3- to 6-membered carbocyclic or aryl ring or a 3- to 6-membered heterocyclic or heteroaryl ring;

each of which ring may be unsubstituted or substituted with 1 or more substituents independently selected from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), haloalkyl including $C_1$-$C_6$haloalkyl, and haloalkoxy including $C_1$-$C_6$haloalkoxy.

In one embodiment, the central core moiety is proline.

In one embodiment, the central core moiety is 4-fluoroproline.

In one embodiment, $R^1$, $R^{1'}$, $R^{2'}$, $R^3$, and $R^{3'}$, if present, are all hydrogen; and $R^2$ is fluoro.

In one embodiment, $R^1$, $R^{1'}$, $R^{2'}$, and $R^{3'}$, if present, are all hydrogen; and $R^2$ is fluoro and $R^3$ is —$C_0$-$C_4$alkyl($C_3$-$C_7$cycloalkyl) or —O—$C_0$-$C_4$alkyl($C_3$-$C_7$cycloalkyl).

In one embodiment, $R^1$ and $R^2$ are taken together to form a 3- to 6-membered cycloalkyl group, and $R^{1'}$, $R^{2'}$, $R^3$, and $R^{3'}$, where present, are all hydrogen. In one embodiment, the bicycle is fused in a cis fashion. In one embodiment, the bicyclic ring is fused in a trans fashion.

In one embodiment, $R^1$ and $R^2$ are taken together to form a 3- to 6-membered cycloalkyl group that is cis with respect to the carboxyl group of L-proline as shown below:

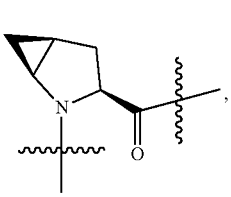 [SMILES: *C(=O)[C@@H]1C[C@@H]2C[C@@H]2N1*], 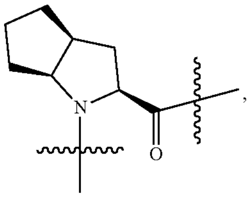, and

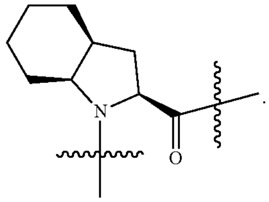.

In one embodiment, $R^1$ and $R^2$ are taken together to form a 3- to 6-membered cycloalkyl group that is trans with respect to the carboxyl group of L-proline as shown below:

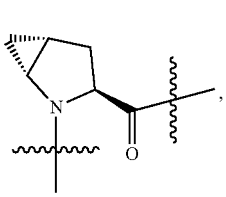 [SMILES: *C(=O)[C@@H]1C[C@H]2C[C@H]2N1*], 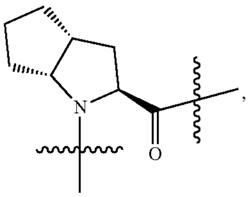, and

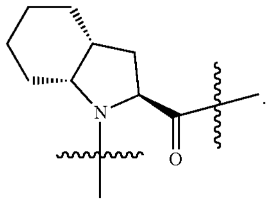.

In one embodiment, $R^1$, $R^{1'}$, $R^3$, and $R^{3'}$, if present, are all hydrogen, and $R^2$ and $R^{2'}$ are taken together to form a 5- or 6-membered heterocycloalkyl group having 1 or 2 oxygen atoms.

In one embodiment, $R^1$ is hydrogen and $R^2$ is fluoro.

In one embodiment, $R^1$ and $R^2$ are joined to form a 3 membered ring.

In one embodiment, $R^1$ and $R^2$ are taken together to form a 3-membered cycloalkyl group that is cis with respect to the carboxyl group of L-proline as shown below:

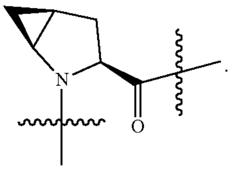.

In one embodiment, $R^1$ and $R^2$ are taken together to form a 3-membered cycloalkyl group that is trans with respect to the carboxyl group of L-proline as shown below:

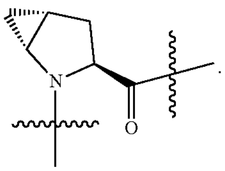

In one embodiment, $R^2$ and $R^3$ are taken together to form a 3- to 6-membered cycloalkyl group, and $R^1$, $R^{1'}$, $R^{2'}$ and $R^{3'}$, where present, are selected from hydrogen, $C_1$-$C_3$ alkyl or $C_1$-$C_3$ alkoxy.

In one embodiment, $R^2$ and $R^3$ are taken together to form a 3- to 6-membered cycloalkyl group that is cis with respect to the carboxyl group of L-proline as shown below:

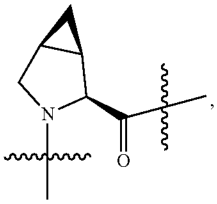 [SMILES: *C(=O)[C@@H]1[C@@H]2C[C@@H]2CN1*]
,
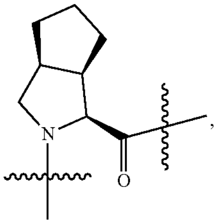
, and

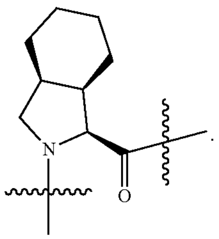

In one embodiment, $R^2$ and $R^3$ are taken together to form a 3- to 6-membered cycloalkyl group that is trans with respect to the carboxyl group of L-proline as shown below:

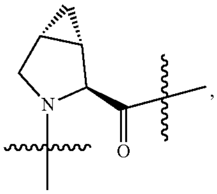
,
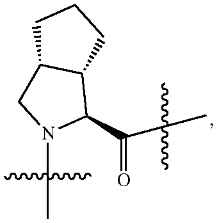
, and

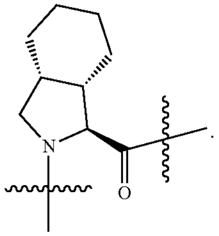

In one embodiment, $R^2$ and $R^3$ are taken together to form a 3-membered cycloalkyl group that is cis with respect to the carboxyl group of L-proline as shown below:

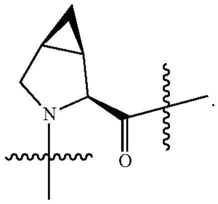

In one embodiment, $R^2$ and $R^3$ are taken together to form a 3-membered cycloalkyl group that is trans with respect to the carboxyl group of L-proline as shown below:

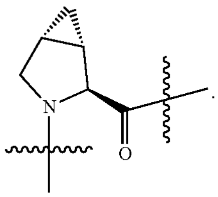 [SMILES: *C(=O)[C@@H]1[C@H]2C[C@H]2CN1*]

In one embodiment, $R^1$, $R^{1'}$, $R^3$, and $R^{3'}$, if present, are all hydrogen, and $R^2$ and $R^{2'}$ are taken together to form a 5- or 6-membered heterocycloalkyl group having 1 or 2 oxygen atoms.

In one embodiment, $R^1$ is hydrogen and $R^2$ is fluoro.

In one embodiment, $R^1$ and $R^2$ are joined to form a 3 membered ring.

Central Core L-B Substituents

Illustrative core L substituents and B substituents in Formula I, Formula II, Formula III, or Formula IV are described below:

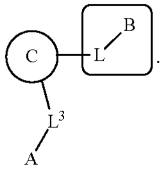

L is a bond or is selected from the formulas:

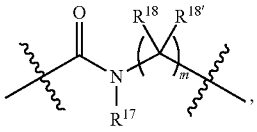
,

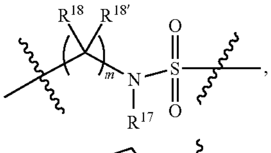
,
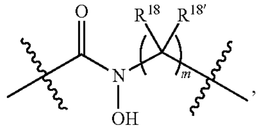
,

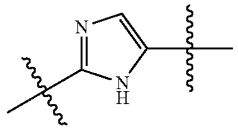
and
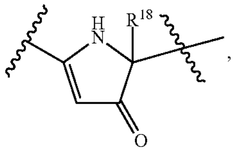
, where $R^{17}$ is hydrogen, $C_1$-$C_6$alkyl, or —$C_0$-$C_4$alkyl($C_3$-$C_7$cycloalkyl) and $R^{18}$ and $R^{18'}$ are independently selected from hydrogen, halogen, hydroxymethyl, and methyl; and m is 0, 1, 2, or 3.

Non-Limiting L-B Embodiments

In one embodiment, -L1-B1- is:

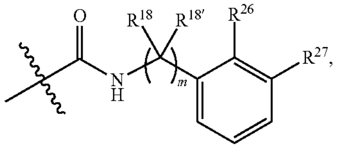

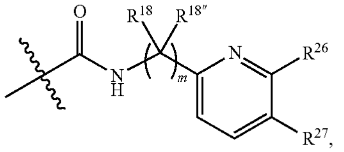

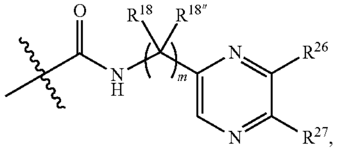

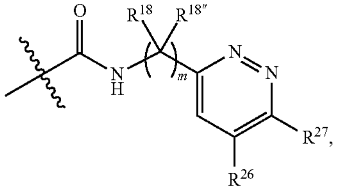

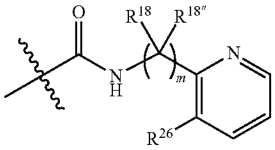
,
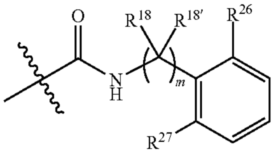
,

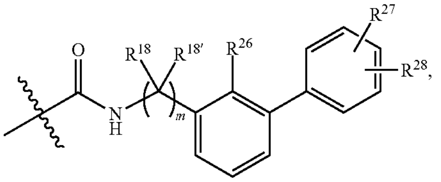

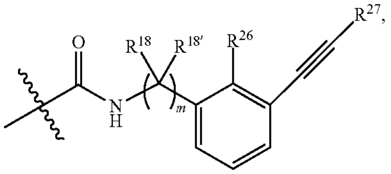

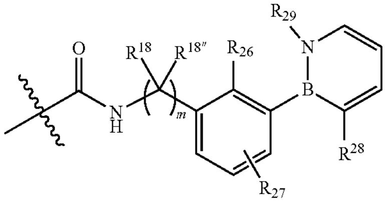
,

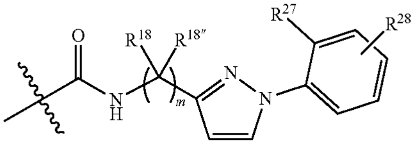
or

-continued

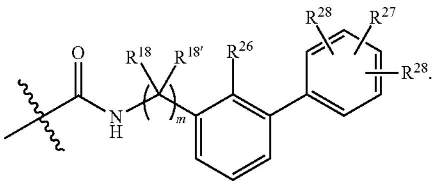

wherein $R^{18}$ and $R^{18'}$ are independently selected from hydrogen, halogen, hydroxymethyl, and methyl; and m is 0 or 1; and $R^{26}$, $R^{27}$, and $R^{28}$ are independently selected from hydrogen, halogen, hydroxyl, nitro, cyano, alkyl including $C_1$-$C_6$alkyl, alkenyl including $C_2$-$C_6$alkenyl, alkanoyl including $C_2$-$C_6$alkanoyl, alkoxy including $C_1$-$C_6$alkoxy, thioalkyl including $C_1$-$C_6$thioalkyl, (mono- and di-$C_1$-$C_6$alkylamino)$C_0$-$C_4$alkyl, ($C_3$-$C_7$cycloalkyl)$C_0$-$C_4$alkyl, (aryl)$C_0$-$C_4$alkyl-, (heteroaryl)$C_0$-$C_4$alkyl-, and —$C_0$-$C_4$alkoxy($C_3$-$C_7$cycloalkyl); each of which $R^{26}$, $R^{27}$, and $R^{28}$ other than hydrogen, halogen, hydroxyl, nitro, cyano, is unsubstituted or substituted with one or more substituents independently selected from halogen, hydroxyl, amino, alkoxy including $C_1$-$C_6$alkoxy, haloalkyl including $C_1$-$C_6$haloalkyl, ($C_3$-$C_7$cycloalkyl)$C_0$-$C_4$alkyl-, and haloalkoxy including $C_1$-$C_6$haloalkoxy; and $R^{29}$ is hydrogen, alkyl including $C_1$-$C_6$alkyl, $C_1C_2$haloalkyl or —$Si(CH_3)_2C(CH_3)_3$.

In one embodiment, -L-B1-moiety is selected:

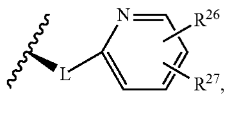
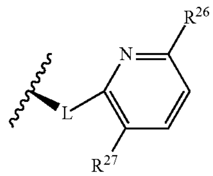
,

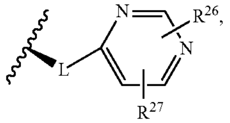
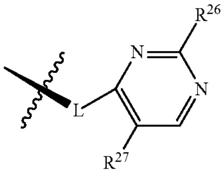
,

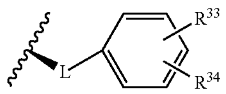
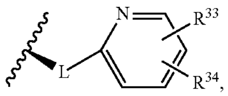

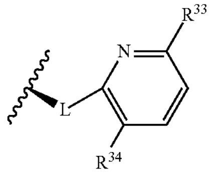
,
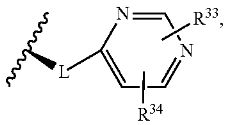

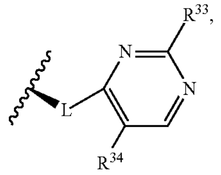
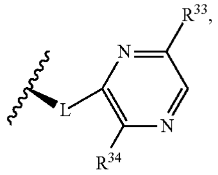

-continued
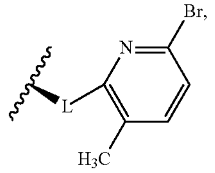
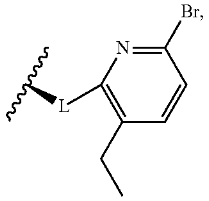
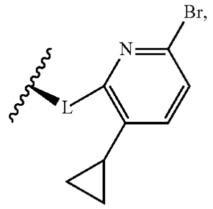
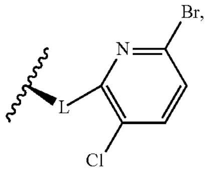
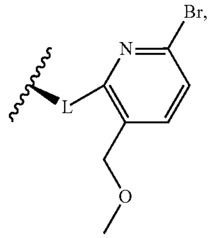
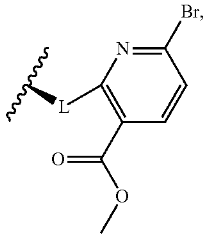
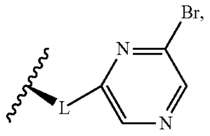
and
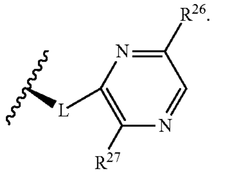
In one embodiment, -L1-B1-moiety is selected:
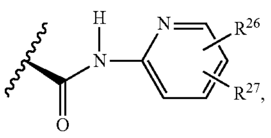
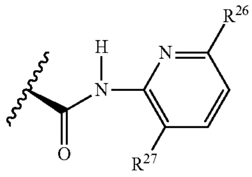
,
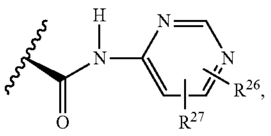
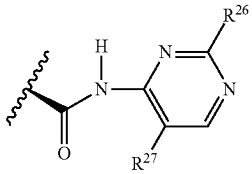
,
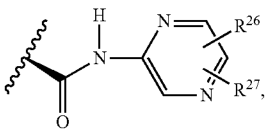
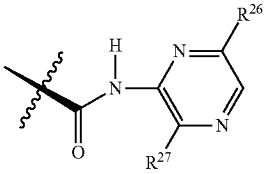
,
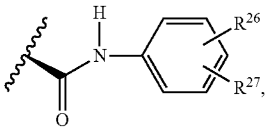
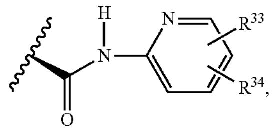
-continued
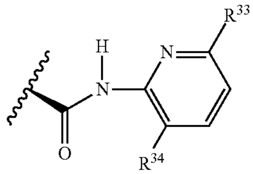
,
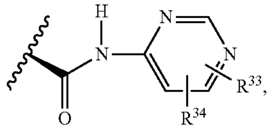
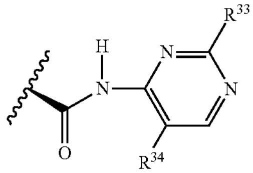
,
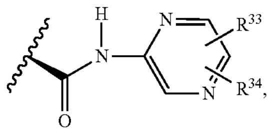
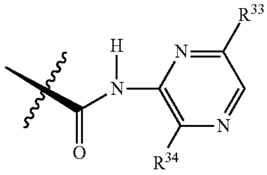
,
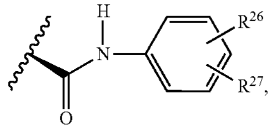
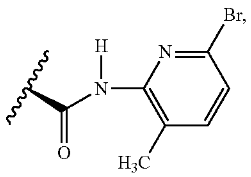
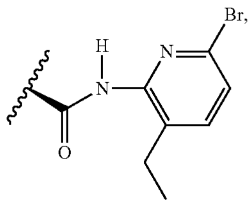
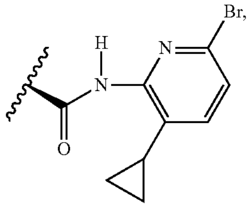
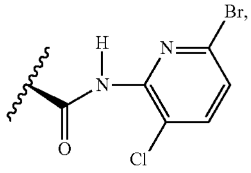
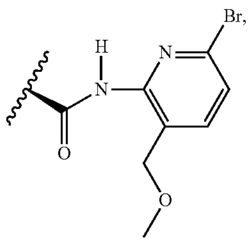
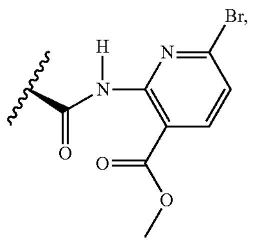
and
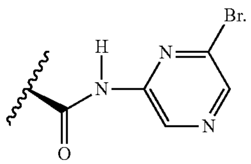
In one embodiment, -L2-B1-moiety is selected:
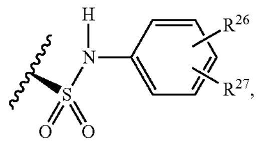
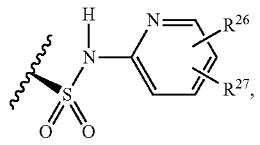

-continued

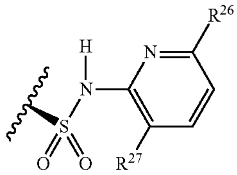
,
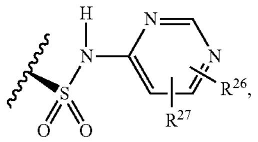

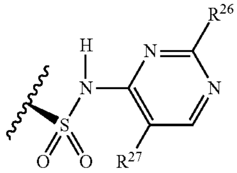
,
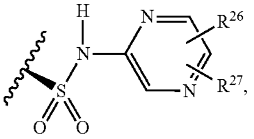

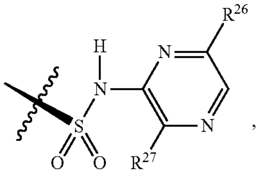
,
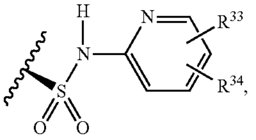

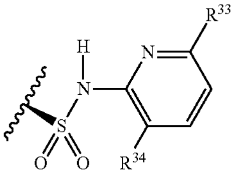
,
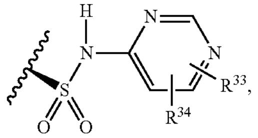

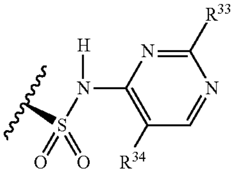
,
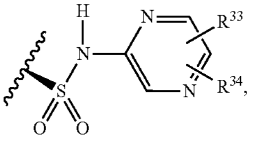

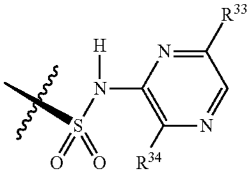
,
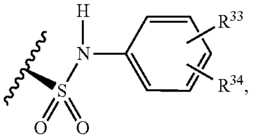

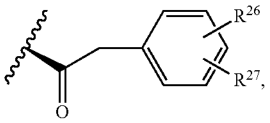
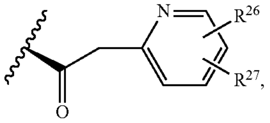

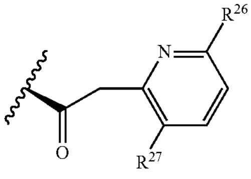
,
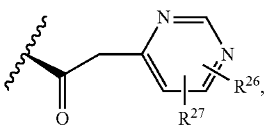

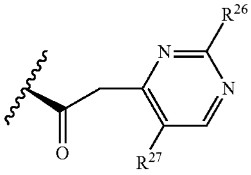
,
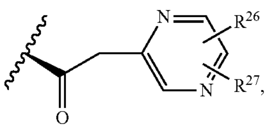

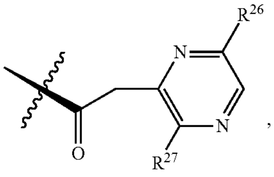
,
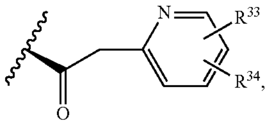

-continued

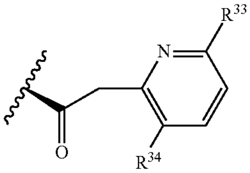
,
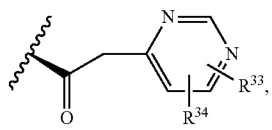

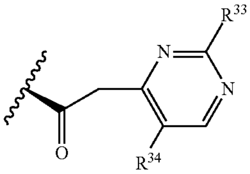
,
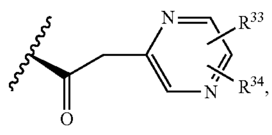

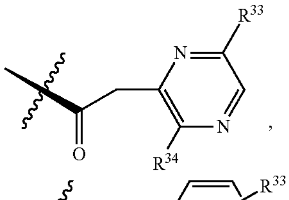
, and

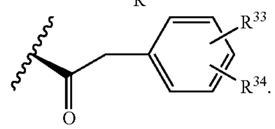

In one embodiment, -L2-B1-moiety is selected:

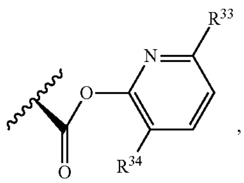
,
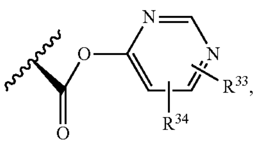

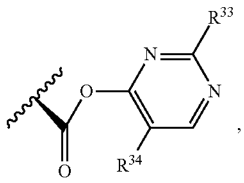
,
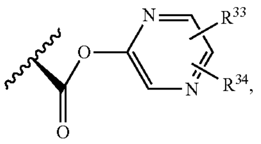

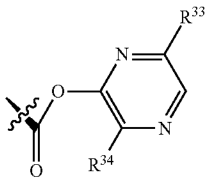
, and
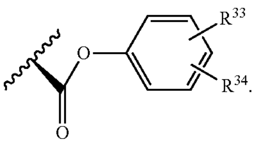

In one embodiment, m is 0.

In one embodiment, the disclosure further includes compounds and salts of Formula I, Formula II, Formula III, or Formula IV in which B1 is 2-fluoro-3-chlorophenyl. In another embodiment, another carbocyclic, aryl, heterocyclic, or heteroaryl group such as 2-bromo-pyridin-6-yl, 1-(2,2,2-trifluoroethyl)-1H-pyrazol-3-yl, 2,2-dichlorocyclopropylmethyl, or 2-fluoro-3-trimethylsilylphenyl is used.

In another embodiment, B1 is phenyl, pyridyl, or indanyl each of which is unsubstituted or substituted with one or more substituents independently selected from hydrogen, halogen, hydroxyl, nitro, cyano, alkyl including $C_1$-$C_6$alkyl, alkenyl including $C_2$-$C_6$alkenyl, alkanoyl including $C_2$-$C_6$alkanoyl, alkoxy including $C_1$-$C_6$alkoxy, thioalkyl including $C_1$-$C_6$thioalkyl, (mono- and di-$C_1$-$C_6$alkylamino)$C_0$-$C_4$alkyl, ($C_3$-$C_7$cycloalkyl)$C_0$-$C_4$alkyl, —$C_0$-$C_4$alkoxy ($C_3$-$C_7$cycloalkyl), (phenyl)$C_0$-$C_2$alkyl, (pyridyl)$C_0$-$C_2$alkyl; each of which substituents other than hydrogen, halogen, hydroxyl, nitro, cyano, is unsubstituted or substituted with one or more substituents independently selected from halogen, hydroxyl, amino, alkyl including $C_1$-$C_6$alkyl, alkoxy including $C_1$-$C_6$alkoxy, —OSi$(CH_3)_2C(CH_3)_3$, —Si$(CH_3)_2C(CH_3)_3$, haloalkyl including $C_1$-$C_6$haloalkyl, and haloalkoxy including $C_1$-$C_6$haloalkoxy.

In another embodiment, B1 is phenyl or pyridyl substituted with 1, 2, or 3 substituents selected from chloro, bromo, hydroxyl, —$SCF_3$, $C_1$-$C_6$alkyl, $C_1$-$C_6$alkoxy, trifluoromethyl, phenyl and trifluoromethoxy each of which substituents other than chloro, bromo, hydroxyl, —$SCF_3$, can be optionally substituted.

In certain embodiments, B1 is a 2-fluoro-3-chlorophenyl or a 2-fluoro-3-trifluoromethoxyphenyl group.

In one embodiment, B1 is pyridyl, optionally substituted with halogen, $C_1$-$C_6$alkoxy, and trifluoromethyl.

In one embodiment, B1 is phenyl, substituted with 1, 2, or 3 substituents independently selected from halogen, $C_1$-$C_6$alkyl, $C_1$-$C_6$alkoxy, trifluoromethyl, and optionally substituted phenyl.

In one embodiment, $R^{23}$ is independently selected at each occurrence from ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S.

In an alternative embodiment, L1-B3 is:

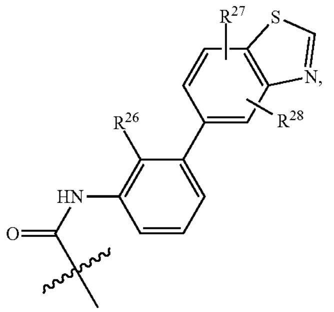

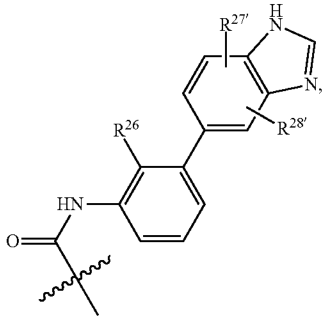

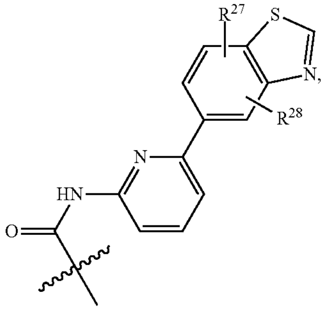

or

-continued

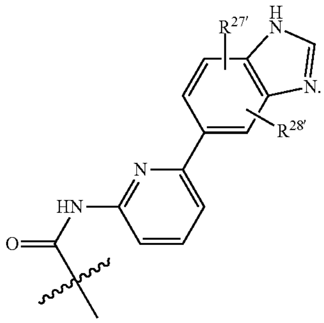

$R^{27'}$, and $R^{28'}$ are independently selected from hydrogen, fluoro, bromo, iodo, hydroxyl, nitro, cyano, alkyl including $C_1$-$C_6$alkyl, alkenyl including $C_2$-$C_6$alkenyl, alkanoyl including $C_2$-$C_6$alkanoyl, $C_2$-$C_6$alkoxy, $C_2$-$C_6$thioalkyl, (mono- and di-$C_1$-$C_6$alkylamino)$C_0$-$C_4$alkyl, ($C_3$-$C_7$cycloalkyl)$C_0$-$C_4$alkyl, (aryl)$C_0$-$C_4$alkyl-, (heteroaryl)$C_0$-$C_4$alkyl-, and —$C_0$-$C_4$alkoxy($C_3$-$C_7$cycloalkyl); each of which $R^{27'}$, and $R^{28'}$ other than hydrogen, fluoro, bromo, iodo, hydroxyl, nitro, and cyano, is unsubstituted or substituted with one or more substituents independently selected from halogen, hydroxyl, amino, alkoxy including $C_1$-$C_6$alkoxy, haloalkyl including $C_1$-$C_6$haloalkyl, ($C_3$-$C_7$cycloalkyl)$C_0$-$C_4$alkyl-, and haloalkoxy including $C_1$-$C_6$haloalkoxy.

Central Core (L3)-A Substituent

The central core (L3)-A substituent in Formula I, Formula II, Formula III, or Formula IV is illustrated below:

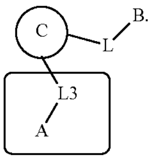

In one embodiment, $R^5$ and $R^6$ of the A ring are independently selected from —CHO, —C(O)$NH_2$, —C(O)NH$(CH_3)$, $C_2$-$C_6$alkanoyl, and hydrogen.

In one embodiment, each $R^5$ and $R^6$ other than hydrogen, hydroxyl, cyano, and —COOH is unsubstituted or substituted with one or more substituents independently selected from halogen, hydroxyl, amino, imino, cyano, cyanoimino, alkyl including $C_1$-$C_6$alkyl, $C_1$-$C_4$alkoxy, —$C_0$-$C_2$alkyl(mono- and di-$C_1$-$C_4$alkylamino), haloalkyl including $C_1$-$C_6$haloalkyl, and haloalkoxy including $C_1$-$C_6$haloalkoxy.

In one embodiment, $R^8$ and $R^{8'}$ are independently hydrogen or methyl.

In one embodiment, $R^8$ and $R^{8'}$ are hydrogen.

In one embodiment, $R^7$ is hydrogen or methyl.

In one embodiment, $R^7$ is hydrogen.

Compounds of Formula IV

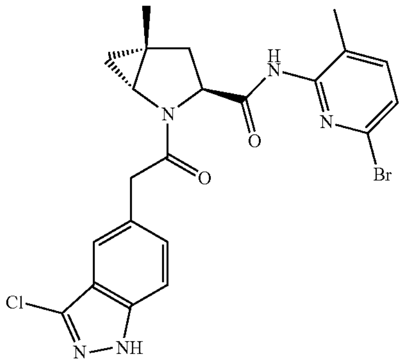
,

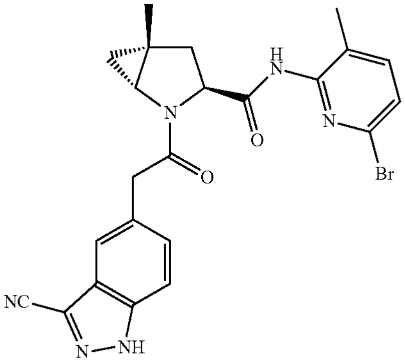
,

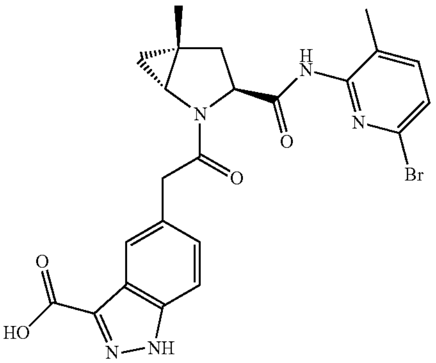
,

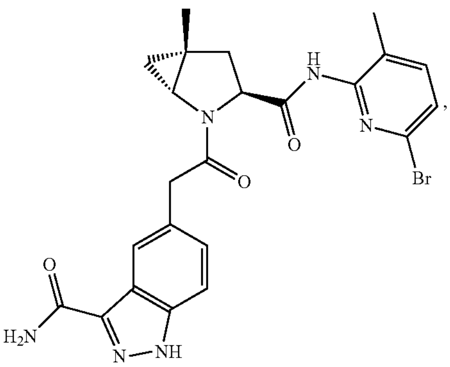
,

-continued

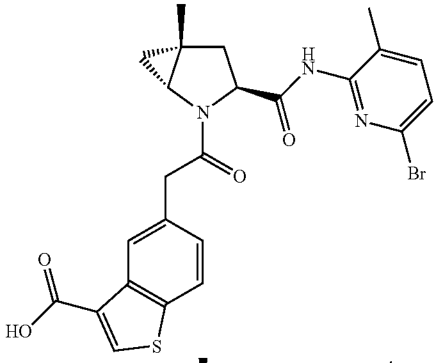
, and

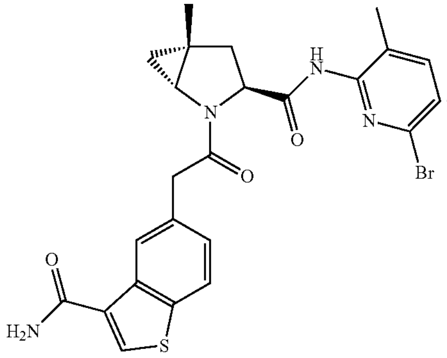
.

Pharmaceutical Preparations

Active compounds described herein can be administered to a host in need thereof as the neat chemical, but are more typically administered as a pharmaceutical composition that includes an effective amount for a host, typically a human, in need of such treatment of an active compound as described herein or its pharmaceutically acceptable salt, prodrug, isotopic analog, or isolated isomer thereof. Thus, in one embodiment, the disclosure provides pharmaceutical compositions comprising an effective amount of compound or pharmaceutically acceptable salt, prodrug, isotopic analog, or isolated isomer thereof together with at least one pharmaceutically acceptable carrier for any of the uses described herein. The pharmaceutical composition may contain a compound or salt as the only active agent, or, in an alternative embodiment, the compound and at least one additional active agent.

An effective amount of an active compound as described herein, or the active compound described herein in combination or alternation with, or preceded by, concomitant with or followed by another active agent, can be used in an amount sufficient to (a) inhibit the progression of a disorder mediated by the complement pathway, including an inflammatory, immune, including an autoimmune, disorder or Complement Factor D related disorder; (b) cause a regression of an inflammatory, immune, including an autoimmune, disorder or Complement Factor D related disorder; (c) cause a cure of an inflammatory, immune, including an autoimmune, disorder or Complement Factor D related disorder; or inhibit or prevent the development of an inflammatory, immune, including an autoimmune, disorder or Complement Factor D related disorder.

Accordingly, an effective amount of an active compound or its salt or composition described herein will provide a sufficient amount of the active agent when administered to a patient to provide a clinical benefit.

The exact amount of the active compound or pharmaceutical composition described herein to be delivered to the host, typically a human, in need thereof, will be determined by the health care provider to achieve the desired clinical benefit.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least about 0.5, 1, 1.5, 2, 2.5, 3, 3.5, 4, 4.5, 5, 10, 15, 20, 25, 50, 75, 100, 150, 200, 250, 300, 350, 400, 450, 500, 550, 600, 650, 700, 750, 800, 900, 1000, 1100, 1200, 1250, 1300, 1400, 1500, or 1600 mg of active compound, or its salt or prodrug. In one embodiment, the dosage form has at least about 1 mg, 5 mg, 10 mg, 25 mg, 50 mg, 75 mg, 100 mg, 200 mg, 400 mg, 500 mg, 600 mg, 1000 mg, 1200 mg, or 1600 mg of active compound, or its salt. The amount of active compound in the dosage form is calculated without reference to the salt. The dosage form can be administered, for example, once a day (q.d.), twice a day (b.i.d.), three times a day (t.i.d.), four times a day (q.i.d.), once every other day (Q2d), once every third day (Q3d), as needed, or any dosage schedule that provides treatment of a disorder described herein.

The pharmaceutical composition may for example include a molar ratio of the active compound and an additional active agent that achieves the desired result. For example, the pharmaceutical composition may contain a molar ratio of about 0.5:1, about 1:1, about 2:1, about 3:1 or from about 1.5:1 to about 4:1 of an additional active agent in combination with the active compound (additional active agent: active compound), or its salt, described herein. In one embodiment, the additional active agent is an anti-inflammatory or immunosuppressing agent.

Compounds disclosed herein or used as described herein may be administered orally, topically, parenterally, by inhalation or spray, sublingually, via implant, including ocular implant, transdermally, via buccal administration, rectally, as an ophthalmic solution, injection, including ocular injection, intravenous, intra-aortal, intracranial, subdermal, intraperitoneal, subcutaneous, transnasal, sublingual, intrathecal, or rectal or by other means, in dosage unit formulations containing conventional pharmaceutically acceptable carriers. For ocular delivery, the compound can be administered, as desired, for example, as a solution, suspension, or other formulation via intravitreal, intrastromal, intracameral, sub-tenon, sub-retinal, retro-bulbar, peribulbar, suprachorodial, subchorodial, chorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device, injection, or topically administered formulation, for example a solution or suspension provided as an eye drop.

The pharmaceutical composition may be formulated as any pharmaceutically useful form, e.g., as an aerosol, a cream, a gel, a gel cap, a pill, a microparticle, a nanoparticle, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution or suspension. Some dosage forms, such as tablets and capsules, are subdivided into suitably sized unit doses containing appropriate quantities of the active components, e.g., an effective amount to achieve the desired purpose.

Pharmaceutical compositions, and methods of manufacturing such compositions, suitable for administration as contemplated herein are known in the art. Examples of known techniques include, for example, U.S. Pat. Nos. 4,983,593, 5,013,557, 5,456,923, 5,576,025, 5,723,269, 5,858,411, 6,254,889, 6,303,148, 6,395,302, 6,497,903, 7,060,296, 7,078,057, 7,404,828, 8,202,912, 8,257,741, 8,263,128, 8,337,899, 8,431,159, 9,028,870, 9,060,938, 9,211,261, 9,265,731, 9,358,478, and 9,387,252, incorporated by reference herein.

The pharmaceutical compositions contemplated here can optionally include a carrier. Carriers must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound. Classes of carriers include, but are not limited to binders, buffering agents, coloring agents, diluents, disintegrants, emulsifiers, fillers, flavorants, glidents, lubricants, pH modifiers, preservatives, stabilizers, surfactants, solubilizers, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Examples of other matrix materials, fillers, or diluents include lactose, mannitol, xylitol, microcrystalline cellulose, calcium diphosphate, and starch. Examples of surface active agents include sodium lauryl sulfate and polysorbate 80. Examples of drug complexing agents or solubilizers include the polyethylene glycols, caffeine, xanthene, gentisic acid and cylodextrins. Examples of disintegrants include sodium starch gycolate, sodium alginate, carboxymethyl cellulose sodium, methyl cellulose, colloidal silicon dioxide, and croscarmellose sodium. Examples of binders include methyl cellulose, microcrystalline cellulose, starch, and gums such as guar gum, and tragacanth. Examples of lubricants include magnesium stearate and calcium stearate. Examples of pH modifiers include acids such as citric acid, acetic acid, ascorbic acid, lactic acid, aspartic acid, succinic acid, phosphoric acid, and the like; bases such as sodium acetate, potassium acetate, calcium oxide, magnesium oxide, trisodium phosphate, sodium hydroxide, calcium hydroxide, aluminum hydroxide, and the like, and buffers generally comprising mixtures of acids and the salts of said acids. Optional other active agents may be included in a pharmaceutical composition, which do not substantially interfere with the activity of the compound of the present invention.

In certain embodiments, the pharmaceutical composition for administration further includes a compound or salt of Formula I, Formula II, Formula III, or Formula IV and optionally comprises one or more of a phosphoglyceride; phosphatidylcholine; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohol such as polyethylene glycol (PEG); polyoxyethylene-9-lauryl ether; a surface active fatty acid, such as palmitic acid or oleic acid; fatty acid; fatty acid monoglyceride; fatty acid diglyceride; fatty acid amide; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebroside; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipid; synthetic and/or natural detergent having high surfactant properties; deoxycholate; cyclodextrin; chaotropic salt; ion pairing agent; glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid; pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan, mannitol, sorbitol, xylitol, erythritol, maltitol, and lactitol, a pluronic polymer, polyethylene, polycarbonate (e.g. poly(1,3-dioxan-2one)), polyanhydride (e.g. poly(sebacic anhydride)), polypropylfumerate, polyamide (e.g. polycaprolactam), polyacetal, polyether, polyester (e.g., polylactide, polyglycolide, polylactide-co-glycolide, polycaprolactone, polyhydroxyacid (e.g. poly((β-hydroxyalkanoate))), poly(orthoester), polycyanoacrylate, polyvinyl alcohol, polyurethane, polyphosphazene, polyacrylate, polymethacrylate, polyurea, polystyrene, and polyamine, polylysine, polylysine-PEG copolymer, and poly (ethyleneimine), poly(ethylene imine)-PEG copolymer, glycerol monocaprylocaprate, propylene glycol, Vitamin E TPGS (also known as d-α-Tocopheryl polyethylene glycol 1000 succinate), gelatin, titanium dioxide, polyvinylpyrrolidone (PVP), hydroxypropyl methyl cellulose (HPMC), hydroxypropyl cellulose (HPC), methyl cellulose (MC), block copolymers of ethylene oxide and propylene oxide (PEO/PPO), polyethyleneglycol (PEG), sodium carboxymethylcellulose (NaCMC), hydroxypropylmethyl cellulose acetate succinate (HPMCAS).

In some embodiments, the pharmaceutical preparation may include polymers for controlled delivery of the described compounds, including, but not limited to pluronic polymers, polyesters (e.g., polylactic acid, poly(lactic-co-glycolic acid), polycaprolactone, polyvalerolactone, poly(1, 3-dioxan-2one)); polyanhydrides (e.g., poly(sebacic anhydride)); polyethers (e.g., polyethylene glycol); polyurethanes; polymethacrylates; polyacrylates; and polycyanoacrylates. In some embodiments, polymers may be modified with polyethylene glycol (PEG), with a carbohydrate, and/or with acyclic polyacetals derived from polysaccharides. See, e.g., Papisov, 2001, ACS Symposium Series, 786:301, incorporated by reference herein.

The compounds of the present invention can be formulated as particles. In one embodiment the particles are or include microparticles. In an alternative embodiment the particles are or include nanoparticles.

In an additional alternative embodiment, common techniques for preparing particles include, but are not limited to, solvent evaporation, solvent removal, spray drying, phase inversion, coacervation, and low temperature casting. Suitable methods of particle formulation are briefly described below. Pharmaceutically acceptable excipients, including pH modifying agents, disintegrants, preservatives, and antioxidants, can optionally be incorporated into the particles during particle formation.

In one embodiment, the particles are derived through a solvent evaporation method. In this method, a compound described herein (or polymer matrix and one or more compounds described herein) is dissolved in a volatile organic solvent, such as methylene chloride. The organic solution containing a compound described herein is then suspended in an aqueous solution that contains a surface active agent such as poly(vinyl alcohol). The resulting emulsion is stirred until most of the organic solvent evaporated, leaving solid nanoparticles or microparticles. The resulting nanoparticles or microparticles are washed with water and dried overnight in a lyophilizer. Nanoparticles with different sizes and morphologies can be obtained by this method.

Pharmaceutical compositions which contain labile polymers, such as certain polyanhydrides, may degrade during the fabrication process due to the presence of water. For these polymers, methods which are performed in completely or substantially anhydrous organic solvents can be used to make the particles.

Solvent removal can also be used to prepare particles from a compound that is hydrolytically unstable. In this method, the compound (or polymer matrix and one or more compounds) is dispersed or dissolved in a volatile organic solvent such as methylene chloride. This mixture is then suspended by stirring in an organic oil (such as silicon oil) to form an emulsion. Solid particles form from the emulsion, which can subsequently be isolated from the supernatant. The external morphology of spheres produced with this technique is highly dependent on the identity of the drug.

In one embodiment an active compound as described herein is administered to a patient in need thereof as particles formed by solvent removal. In another embodiment the present invention provides particles formed by solvent removal comprising a compound of the present invention and one or more pharmaceutically acceptable excipients as defined herein. In another embodiment the particles formed by solvent removal comprise a compound of the present invention and an additional therapeutic agent. In a further embodiment the particles formed by solvent removal comprise a compound of the present invention, an additional therapeutic agent, and one or more pharmaceutically acceptable excipients. In another embodiment any of the described particles formed by solvent removal can be formulated into a tablet and then coated to form a coated tablet. In an alternative embodiment the particles formed by solvent removal are formulated into a tablet but the tablet is uncoated.

In one embodiment, the particles are derived by spray drying. In this method, a compound (or polymer matrix and one or more compounds) is dissolved in an organic solvent such as methylene chloride. The solution is pumped through a micronizing nozzle driven by a flow of compressed gas, and the resulting aerosol is suspended in a heated cyclone of air, allowing the solvent to evaporate from the micro droplets, forming particles. Microparticles and nanoparticles can be obtained using this method.

In one embodiment an active compound as described herein is administered to a patient in need thereof as a spray dried dispersion (SDD). In another embodiment the present invention provides a spray dried dispersion (SDD) comprising a compound of the present invention and one or more pharmaceutically acceptable excipients as defined herein. In another embodiment the SDD comprises a compound of the present invention and an additional therapeutic agent. In a further embodiment the SDD comprises a compound of the present invention, an additional therapeutic agent, and one or more pharmaceutically acceptable excipients. In another embodiment any of the described spray dried dispersions can be coated to form a coated tablet. In an alternative embodiment the spray dried dispersion is formulated into a tablet but is uncoated. Particles can be formed from the active compound as described herein using a phase inversion method. In this method, the compound (or polymer matrix and one or more active compounds) is dissolved in a suitable solvent, and the solution is poured into a strong non-solvent for the compound to spontaneously produce, under favorable conditions, microparticles or nanoparticles. The method can be used to produce nanoparticles in a wide range of sizes, including, for example, from nanoparticles to microparticles, typically possessing a narrow particle size distribution.

In one embodiment, an active compound as described herein is administered to a patient in need thereof as particles formed by phase inversion. In another embodiment the present invention provides particles formed by phase inversion comprising a compound of the present invention and one or more pharmaceutically acceptable excipients as defined herein. In another embodiment the particles formed by phase inversion comprise a compound of the present invention and an additional therapeutic agent. In a further embodiment the particles formed by phase inversion comprise a compound of the present invention, an additional therapeutic agent, and one or more pharmaceutically acceptable excipients. In another embodiment any of the described particles formed by phase inversion can be formulated into a tablet and then coated to form a coated tablet. In an alternative embodiment the particles formed by phase inversion are formulated into a tablet but the tablet is uncoated.

Techniques for particle formation using coacervation are known in the art, for example, as described in GB-B-929 406; GB-B-929 40 1; and U.S. Pat. Nos. 3,266,987, 4,794, 000, and 4,460,563. Coacervation involves the separation of a compound (or polymer matrix and one or more compounds) solution into two immiscible liquid phases. One phase is a dense coacervate phase, which contains a high concentration of the compound, while the second phase contains a low concentration of the compound. Within the dense coacervate phase, the compound forms nanoscale or microscale droplets, which harden into particles. Coacervation may be induced by a temperature change, addition of a non-solvent or addition of a micro-salt (simple coacervation), or by the addition of another polymer thereby forming an interpolymer complex (complex coacervation).

In one embodiment an active compound as described herein is administered to a patient in need thereof as particles formed by coacervation. In another embodiment the present invention provides particles formed by coacervation comprising a compound of the present invention and one or more pharmaceutically acceptable excipients as defined herein. In another embodiment the particles formed by coacervation comprise a compound of the present invention and an additional therapeutic agent. In a further embodiment the particles formed by coacervation comprise a compound of the present invention, an additional therapeutic agent, and one or more pharmaceutically acceptable excipients. In another embodiment any of the described particles formed by coacervation can be formulated into a tablet and then coated to form a coated tablet. In an alternative embodiment the particles formed by coacervation are formulated into a tablet but the tablet is uncoated.

Methods for very low temperature casting of controlled release microspheres are described in U.S. Pat. No. 5,019, 400 to Gombotz et al. In this method, the compound is dissolved in a solvent. The mixture is then atomized into a vessel containing a liquid non-solvent at a temperature below the freezing point of the drug solution which freezes the compound droplets. As the droplets and non-solvent for the compound are warmed, the solvent in the droplets thaws and is extracted into the non-solvent, hardening the microspheres.

In one embodiment, a compound of the present invention is administered to a patient in need thereof as particles formed by low temperature casting. In another embodiment the present invention provides particles formed by low temperature casting comprising a compound of the present invention and one or more pharmaceutically acceptable excipients as defined herein. In another embodiment the particles formed by low temperature casting comprise a compound of the present invention and an additional therapeutic agent. In a further embodiment the particles formed by low temperature casting comprise a compound of the present invention, an additional therapeutic agent, and one or more pharmaceutically acceptable excipients. In another embodiment any of the described particles formed by low temperature casting can be formulated into a tablet and then coated to form a coated tablet. In an alternative embodiment the particles formed by low temperature casting are formulated into a tablet but the tablet is uncoated.

In one aspect of the present invention, an effective amount of an active compound as described herein is incorporated into a nanoparticle, e.g. for convenience of delivery and/or extended release delivery. The use of materials in nanoscale provides one the ability to modify fundamental physical properties such as solubility, diffusivity, blood circulation half-life, drug release characteristics, and/or immunogenicity. A number of nanoparticle-based therapeutic and diagnostic agents have been developed for the treatment of cancer, diabetes, pain, asthma, allergy, and infections. These nanoscale agents may provide more effective and/or more convenient routes of administration, lower therapeutic toxicity, extend the product life cycle, and ultimately reduce health-care costs. As therapeutic delivery systems, nanoparticles can allow targeted delivery and controlled release.

In addition, nanoparticle-based compound delivery can be used to release compounds at a sustained rate and thus lower the frequency of administration, deliver drugs in a targeted manner to minimize systemic side effects, or deliver two or more drugs simultaneously for combination therapy to generate a synergistic effect and suppress drug resistance. A number of nanotechnology-based therapeutic products have been approved for clinical use. Among these products, liposomal drugs and polymer-based conjugates account for a large proportion of the products. See, Zhang, L., et al., Nanoparticles in Medicine: Therapeutic Applications and Developments, Clin. Pharm. and Ther., 83(5):761-769, 2008.

Methods for producing nanoparticles are known in the art. For example, see Muller, R. H., et al., Solid lipid nanoparticles (SLN) for controlled drug delivery—a review of the state of the art, *Eur. H. Pharm. Biopharm.,* 50:161-177, 2000; U.S. Pat. No. 8,691,750 to Consien et al.; WO 2012/145801 to Kanwar. U.S. Pat. No. 8,580,311 to Armes, S. et al.; Petros, R. A. and DeSimone, J. M., Strategies in the design of nanoparticles for therapeutic applications, Nature Reviews/Drug Discovery, vol. 9:615-627, 2010; U.S. Pat. Nos. 8,465,775; 8,444,899; 8,420,124; 8,263,129; 8,158,728; 8,268,446; Pellegrino et al., 2005, Small, 1:48; Murray et al., 2000, Ann. Rev. Mat. Sci., 30:545; and Trindade et al., 2001, Chem. Mat., 13:3843; all incorporated herein by reference. Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755; U.S. Pat. Nos. 5,578,325 and 6,007,845; P. Paolicelli et al., "Surface-modified PLGA-based Nanoparticles that can Efficiently Associate and Deliver Virus-like Particles" Nanomedicine. 5(6):843-853 (2010)), U.S. Pat. No. 5,543,158 to Gref et al., or WO publication WO2009/051837 by Von Andrian et al. Zauner et al., 1998, Adv. Drug Del. Rev., 30:97; and Kabanov et al., 1995, Bioconjugate Chem., 6:7; (PEI; Boussif et al., 1995, Proc. Natl. Acad. Sci., USA, 1995, 92:7297), and poly(amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372; Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633; U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181; Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732; C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006); P. Paolicelli et al., "Surface-modified PLGA-based Nanoparticles that can Efficiently Associate and Deliver Virus-like Particles" Nanomedicine. 5(6):843-853 (2010); U.S. Pat. No. 6,632,671 to Unger Oct. 14, 2003, all incorporated herein by reference.

In one embodiment, the polymeric particle is between about 0.1 nm to about 10000 nm, between about 1 nm to about 1000 nm, between about 10 nm and 1000 nm, between about 1 and 100 nm, between about 1 and 10 nm, between about 1 and 50 nm, between about 100 nm and 800 nm, between about 400 nm and 600 nm, or about 500 nm. In one embodiment, the micro-particles are no more than about 0.1 nm, 0.5 nm, 1.0 nm, 5.0 nm, 10 nm, 25 nm, 50 nm, 75 nm, 100 nm, 150 nm, 200 nm, 250 nm, 300 nm, 400 nm, 450 nm, 500 nm, 550 nm, 600 nm, 650 nm, 700 nm, 750 nm, 800 nm, 850 nm, 900 nm, 950 nm, 1000 nm, 1250 nm, 1500 nm, 1750 nm, or 2000 nm. In some embodiments, a compound described herein may be covalently coupled to a polymer used in the nanoparticle, for example a polystyrene particle, PLGA particle, PLA particle, or other nanoparticle.

The pharmaceutical compositions can be formulated for oral administration. These compositions can contain any amount of active compound that achieves the desired result, for example between 0.1 and 99 weight % (wt. %) of the compound and usually at least about 5 wt. % of the compound. Some embodiments contain at least about 10%, 15%, 20%, 25 wt. % to about 50 wt. % or from about 5 wt. % to about 75 wt. % of the compound.

Pharmaceutical compositions suitable for rectal administration are typically presented as unit dose suppositories. These may be prepared by admixing the active compound with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Pharmaceutical compositions suitable for transdermal administration may be presented as discrete patches adapted to remain in intimate contact with the epidermis of the recipient for a prolonged period of time. Pharmaceutical compositions suitable for transdermal administration may also be delivered by iontophoresis (see, for example, *Pharmaceutical Research* 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Pharmaceutical compositions suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Additional non-limiting examples of inhalation drug delivery devices and methods include, for example, U.S. Pat. No. 7,383,837 titled "Inhalation device" (SmithKline Beecham Corporation); WO/2006/033584 titled "Powder inhaler" (Glaxo SmithKline Pharmaceuticals SA); WO/2005/044186 titled "Inhalable pharmaceutical formulations employing desiccating agents and methods of administering the same" (Glaxo Group Ltd and SmithKline Beecham Corporation); U.S. Pat. No. 9,095,670 titled "Inhalation device and method of dispensing medicament", U.S. Pat. No. 8,205,611 titled "Dry powder inhaler" (Astrazeneca AB); WO/2013/038170 titled "Inhaler" (Astrazeneca AB and Astrazeneca UK Ltd.); US/2014/0352690 titled "Inhalation Device with Feedback System", U.S. Pat. No. 8,910,625 and US/2015/0165137 titled "Inhalation Device for Use in Aerosol Therapy" (Vectura GmbH); U.S. Pat. No. 6,948,496 titled "Inhalers", US/2005/0152849 titled "Powders comprising anti-adherent materials for use in dry powder inhalers", U.S. Pat. Nos. 6,582,678, 8,137,657, US/2003/0202944, and US/2010/0330188 titled "Carrier particles for use in dry powder inhalers", U.S. Pat. No. 6,221,338 titled "Method of producing particles for use in dry powder inhalers", U.S. Pat. No. 6,989,155 titled "Powders", US/2007/0043030 titled "Pharmaceutical compositions for treating premature ejaculation by pulmonary inhalation", U.S. Pat. No. 7,845,349 titled "Inhaler", US/2012/0114709 and U.S. Pat. No. 8,101,160 titled "Formulations for Use in Inhaler Devices", US/2013/0287854 titled "Compositions and Uses", US/2014/0037737 and U.S. Pat. No. 8,580,306 titled "Particles for Use in a Pharmaceutical Composition", US/2015/0174343 titled "Mixing Channel for an Inhalation Device", U.S. Pat. No. 7,744,855 and US/2010/0285142 titled "Method of making particles for use in a pharmaceutical composition", U.S. Pat. No. 7,541,022, US/2009/0269412, and US/2015/0050350 titled "Pharmaceutical formulations for dry powder inhalers" (Vectura Limited).

Many methods and devices for drug delivery to the eye are known in the art. Non-limiting examples are described in the following patents and patent applications (fully incorporated herein by reference). Examples are U.S. Pat. No. 8,192,408 titled "Ocular trocar assembly" (Psivida Us, Inc.); U.S. Pat. No. 7,585,517 titled "Transcleral delivery" (Macusight, Inc.); U.S. Pat. Nos. 5,710,182 and 5,795,913 titled "Ophthalmic composition" (Santen OY); U.S. Pat. No. 8,663,639 titled "Formulations for treating ocular diseases and conditions", U.S. Pat. No. 8,486,960 titled "Formulations and methods for vascular permeability-related diseases or conditions", U.S. Pat. Nos. 8,367,097 and 8,927,005 titled "Liquid formulations for treatment of diseases or conditions", U.S. Pat. No. 7,455,855 titled "Delivering substance and drug delivery system using the same" (Santen Pharmaceutical Co., Ltd.); WO/2011/050365 titled "Conformable Therapeutic Shield For Vision and Pain" and WO/2009/145842 titled "Therapeutic Device for Pain Management and Vision" (Forsight Labs, LLC); U.S. Pat. Nos. 9,066,779 and 8,623,395 titled "Implantable therapeutic device", WO/2014/160884 titled "Ophthalmic Implant for Delivering Therapeutic Substances", U.S. Pat. Nos. 8,399,006, 8,277,830, 8,795,712, 8,808,727, 8,298,578, and WO/2010/088548 titled "Posterior segment drug delivery", WO/2014/152959 and US20140276482 titled "Systems for Sustained Intraocular Delivery of Low Solubility Compounds from a Port Delivery System Implant", U.S. Pat. Nos. 8,905,963 and 9,033,911 titled "Injector apparatus and method for drug delivery", WO/2015/057554 titled "Formulations and Methods for Increasing or Reducing Mucus", U.S. Pat. Nos. 8,715,712 and 8,939,948 titled "Ocular insert apparatus and methods", WO/2013/116061 titled "Insertion and Removal Methods and Apparatus for Therapeutic Devices", WO/2014/066775 titled "Ophthalmic System for Sustained Release of Drug to the Eye", WO/2015/085234 and WO/2012/019176 titled "Implantable Therapeutic Device", WO/2012/065006 titled "Methods and Apparatus to determine Porous Structures for Drug Delivery", WO/2010/141729 titled "Anterior Segment Drug Delivery", WO/2011/050327 titled "Corneal Denervation for Treatment of Ocular Pain", WO/2013/022801 titled "Small Molecule Delivery with Implantable Therapeutic Device", WO/2012/019047 titled "Subconjunctival Implant for Posterior Segment Drug Delivery", WO/2012/068549 titled "Therapeutic Agent Formulations for Implanted Devices", WO/2012/019139 titled "Combined Delivery Methods and Apparatus", WO/2013/040426 titled "Ocular Insert Apparatus and Methods", WO/2012/019136 titled "Injector Apparatus and Method for Drug Delivery", WO/2013/040247 titled "Fluid Exchange Apparatus and Methods" (ForSight Vision4, Inc.).

Additional non-limiting examples of how to deliver the active compounds are provided in WO/2015/085251 titled "Intracameral Implant for Treatment of an Ocular Condition" (Envisia Therapeutics, Inc.); WO/2011/008737 titled "Engineered Aerosol Particles, and Associated Methods", WO/2013/082111 titled "Geometrically Engineered Particles and Methods for Modulating Macrophage or Immune Responses", WO/2009/132265 titled "Degradable compounds and methods of use thereof, particularly with particle replication in non-wetting templates", WO/2010/099321 titled "Interventional drug delivery system and associated methods", WO/2008/100304 titled "Polymer particle composite having high fidelity order, size, and shape particles", WO/2007/024323 titled "Nanoparticle fabrication methods, systems, and materials" (Liquidia Technologies, Inc. and the University of North Carolina at Chapel Hill); WO/2010/009087 titled "Iontophoretic Delivery of a Controlled-Release Formulation in the Eye", (Liquidia Technologies, Inc. and Eyegate Pharmaceuticals, Inc.) and WO/2009/132206 titled "Compositions and Methods for Intracellular Delivery and Release of Cargo", WO/2007/133808 titled "Nanoparticles for cosmetic applications", WO/2007/056561 titled "Medical device, materials, and methods", WO/2010/065748 titled "Method for producing patterned materials", WO/2007/081876 titled "Nanostructured surfaces for biomedical/biomaterial applications and processes thereof" (Liquidia Technologies, Inc.).

Additional non-limiting examples of methods and devices for drug delivery to the eye include, for example, WO2011/106702 and U.S. Pat. No. 8,889,193 titled "Sustained delivery of therapeutic agents to an eye compartment", WO2013/138343 and U.S. Pat. No. 8,962,577 titled "Controlled release formulations for the delivery of HIF-1 inhibitors", WO/2013/138346 and US2013/0272994 titled "Non-Linear Multiblock Copolymer-Drug Conjugates for the Delivery of Active Agents", WO2005/072710 and U.S. Pat. No. 8,957,034 titled "Drug and Gene Carrier Particles that Rapidly Move Through Mucus Barriers", WO2008/030557, US2010/0215580, US2013/0164343 titled "Compositions and Methods for Enhancing Transport Through Mucous", WO2012/061703, US2012/0121718, and US2013/0236556 titled "Compositions and Methods Relating to Reduced Mucoadhesion", WO2012/039979 and US2013/0183244 titled "Rapid Diffusion of Large Polymeric Nanoparticles in the Mammalian Brain", WO2012/109363 and US2013/0323313 titled "Mucus Penetrating Gene Carriers", WO 2013/090804 and US2014/0329913 titled "Nanoparticles with enhanced mucosal penetration or decreased inflammation", WO2013/110028 titled "Nanoparticle formulations with enhanced mucosal penetration", WO2013/166498 and US2015/0086484 titled "Lipid-based drug carriers for rapid penetration through mucus linings" (The Johns Hopkins University); WO2013/166385 titled "Pharmaceutical Nanoparticles Showing Improved Mucosal Transport", US2013/0323179 titled "Nanocrystals, Compositions, And Methods that Aid Particle Transport in Mucus" (The Johns Hopkins University and Kala Pharmaceuticals, Inc.); WO/2015/066444 titled "Compositions and methods for ophthalmic and/or other applications", WO/2014/020210 and WO/2013/166408 titled "Pharmaceutical nanoparticles showing improved mucosal transport" (Kala Pharmaceuticals, Inc.); U.S. Pat. No. 9,022,970 titled "Ophthalmic injection device including dosage control device", WO/2011/153349 titled "Ophthalmic compositions comprising pbo-peo-pbo block copolymers", WO/2011/140203 titled "Stabilized ophthalmic galactomannan formulations", WO/2011/068955 titled "Ophthalmic emulsion" WO/2011/037908 titled "Injectable aqueous ophthalmic composition and method of use therefor", US2007/0149593 titled "Pharmaceutical Formulation for Delivery of Receptor Tyrosine Kinase Inhibiting (RTKi) Compounds to the Eye", U.S. Pat. No. 8,632,809 titled "Water insoluble polymer matrix for drug delivery" (Alcon, Inc.).

Additional non-limiting examples of drug delivery devices and methods include, for example, US20090203709 titled "Pharmaceutical Dosage Form For Oral Administration Of Tyrosine Kinase Inhibitor" (Abbott Laboratories); US20050009910 titled "Delivery of an active drug to the posterior part of the eye via subconjunctival or periocular delivery of a prodrug", US 20130071349 titled "Biodegradable polymers for lowering intraocular pressure". U.S. Pat. No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved injectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drugloading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc.); U.S. Pat. Nos. 6,007,845 and 5,578,325 titled "Nanoparticles and microparticles of non-linear hydrophilichydrophobic multiblock copolymers" (Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US 20070071756 titled "Delivery of an agent to ameliorate inflammation" (Peyman); US 20080166411 titled "Injectable Depot Formulations And Methods For Providing Sustained Release Of Poorly Soluble Drugs Comprising Nanoparticles" (Pfizer, Inc.); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

Uses of Active Compounds for Treatment of Selected Disorders

In one aspect, an effective amount of an active compound or its salt or composition as described herein is used to treat a medical disorder which is an inflammatory or immune condition, a disorder mediated by the complement cascade (including a dysfunctional cascade) including a Complement Factor D-related disorder or alternative complement pathway-related disorder, a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration.

In one embodiment, the disorder is selected from fatty liver and conditions stemming from fatty liver, such as nonalcoholic steatohepatitis (NASH), liver inflammation, cirrhosis and liver failure. In one embodiment of the present invention, a method is provided for treating fatty liver disease in a host by administering an effective amount of an active compound or its salt or composition as described herein.

In another embodiment, an active compound or its salt or composition as described herein is used to modulate an immune response prior to or during surgery or other medical procedure. One non-limiting example is use in connection with acute or chronic graft versus host disease, which is a common complication as a result of allogeneic tissue transplant, and can also occur as a result of a blood transfusion.

In one embodiment, the present invention provides a method of treating or preventing dermatomyositis by administering to a subject in need thereof an effective amount of an active compound or its salt or composition as described herein.

In one embodiment, the present invention provides a method of treating or preventing amyotrophic lateral sclerosis by administering to a subject in need thereof an effective amount of an active compound or its salt or composition as described herein.

In one embodiment, the present invention provides a method of treating or preventing abdominal aortic aneurysm, hemodialysis complications, hemolytic anemia, or hemodialysis by administering to a subject in need thereof an effective amount of an active compound or its salt or composition as described herein.

In another embodiment, a method is provided for the treatment or prevention of cytokine or inflammatory reactions in response to the administration of pharmaceutical or biotherapeutic (e.g. CAR T-cell therapy or monoclonal antibody therapy) in a host by administering an effective amount of an active compound or its salt or composition as described herein. Various types of cytokine or inflammatory reactions may occur in response to a number of factors, such as the administrations of biotherapeutics. In one embodiment, the cytokine or inflammatory reaction is cytokine release syndrome. In one embodiment, the cytokine or inflammatory reaction is tumor lysis syndrome (which also leads to cytokine release). Symptoms of cytokine release syndrome range from fever, headache, and skin rashes to bronchospasm, hypotension and even cardiac arrest. Severe cytokine release syndrome is described as cytokine storm, and can be fatal.

Fatal cytokine storms have been observed in response to infusion with several monoclonal antibody therapeutics. See, Abramowicz D, et al. "Release of tumor necrosis factor, interleukin-2, and gamma-interferon in serum after injection of OKT3 monoclonal antibody in kidney transplant recipients" *Transplantation* (1989) 47(4):606-8; Chatenoud L, et al. "In vivo cell activation following OKT3 administration. Systemic cytokine release and modulation by corticosteroids" *Transplantation* (1990) 49(4):697-702; and Lim L C, Koh L P, and Tan P. "Fatal cytokine release syndrome with chimeric anti-CD20 monoclonal antibody rituximab in a 71-year-old patient with chronic lymphocytic leukemia" *J. Clin Oncol.* (1999) 17(6):1962-3.

Also contemplated herein, is the use of an active compound or its salt or composition as described herein to mediate an adverse immune response in patients receiving bi-specific T-cell engagers (BiTE). A bi-specific T-cell engager directs T-cells to target and bind with a specific antigen on the surface of a cancer cell. For example, Blinatumomab (Amgen), a BiTE has recently been approved as a second line therapy in Philadelphia chromosome-negative relapsed or refractory acute lymphoblastic leukemia. Blinatumomab is given by continuous intravenous infusion in 4-week cycles. The use of BiTE agents has been associated with adverse immune responses, including cytokine release syndrome. The most significantly elevated cytokines in the CRS associated with ACT include IL-10, IL-6, and IFN-γ (Klinger et al., Immunopharmacologic response of patients with B-lineage acute lymphoblastic leukemia to continuous infusion of T cell-engaging CD19/CD3-bispecific BiTE antibody blinatumomab. Blood (2012) 119:6226-6233).

In another embodiment, the disorder is episcleritis, idiopathic episcleritis, anterior episcleritis, or posterior episcleritis. In one embodiment, the disorder is idiopathic anterior uveitis, HLA-B27 related uveitis, herpetic keratouveitis, Posner Schlossman syndrome, Fuch's heterochromic iridocyclitis, or cytomegalovirus anterior uveitis.

In one embodiment, the present invention provides a method of treating or preventing a C3 glomurenopathy by administering to a subject in need thereof an effective amount of an active compound or its salt or composition as described herein. In one embodiment, the disorder is selected from dense deposit disease (DDD) and C3 glomerulonephritis (C3GN).

In one embodiment, the present invention provides a method of treating or preventing a IC-MPGN by administering to a subject in need thereof an effective amount of an active compound or its salt or composition as described herein.

In one embodiment, the present invention provides a method of treating or preventing a paroxysmal nocturnal hemoglobinuria (PNH) by administering to a subject in need thereof an effective amount of an active compound or its salt or composition as described herein.

In one embodiment, the present invention provides a method of treating or preventing age-related macular degeneration (AMD) by administering to a subject in need thereof an effective amount of an active compound or its salt or composition as described herein.

In one embodiment, the present invention provides a method of treating or preventing rheumatoid arthritis by administering to a subject in need thereof an effective amount of an active compound or its salt or composition as described herein.

In one embodiment, the present invention provides a method of treating or preventing multiple sclerosis by administering to a subject in need thereof an effective amount of an active compound or its salt or composition as described herein.

In one embodiment, the present invention provides a method of treating or preventing myasthenia gravis by administering to a subject in need thereof an effective amount of an active compound or its salt or composition as described herein.

In one embodiment, the present invention provides a method of treating or preventing atypical hemolytic uremic syndrome (aHUS) by administering to a subject in need thereof an effective amount of an active compound or its salt or composition as described herein.

In one embodiment, the present invention provides a method of treating or preventing neuromyelitis optica (NMO) by administering to a subject in need thereof an effective amount of an active compound or its salt or composition as described herein.

In yet another embodiment, the present invention provides a method of treating or preventing a disorder as described below by administering to a subject in need thereof an effective amount of an active compound or its salt or composition as described herein, including:

vitritis, sarcoidosis, syphilis, tuberculosis, or Lyme disease; retinal vasculitis, Eales disease, tuberculosis, syphilis, or toxoplasmosis; neuroretinitis, viral retinitis, or acute retinal necrosis; varicella zoster virus, herpes simplex virus, cytomegalovirus, Epstein-Barr virus, lichen planus, or Dengue-associated disease (e.g., hemorraghic Dengue Fever); Masquerade syndrome, contact dermatitis, trauma induced inflammation, UVB induced inflammation, eczema, granuloma annulare, or acne.

In an additional embodiment, the disorder is selected from: acute myocardial infarction, aneurysm, cardiopulmonary bypass, dilated cardiomyopathy, complement activation during cardiopulmonary bypass operations, coronary artery disease, restenosis following stent placement, or percutaneous transluminal coronary angioplasty (PTCA); antibody-mediated transplant rejection, anaphylactic shock, anaphylaxis, allogenic transplant, humoral and vascular transplant rejection, graft dysfunction, graft-versus-host disease, Graves' disease, adverse drug reactions, or chronic graft vasculopathy; allergic bronchopulmonary aspergillosis, allergic neuritis, drug allergy, radiation-induced lung injury, eosinophilic pneumonia, radiographic contrast media allergy, bronchiolitis obliterans, or interstitial pneumonia; parkinsonism-dementia complex, sporadic frontotemporal dementia, frontotemporal dementia with Parkinsonism linked to chromosome 17, frontotemporal lobar degeneration, tangle only dementia, cerebral amyloid angiopathy, cerebrovascular disorder, certain forms of frontotemporal dementia, chronic traumatic encephalopathy (CTE), PD with dementia (PDD), argyrophilic grain dementia, dementia pugilistica, dementia with Lewy Bodies (DLB), or multi-infarct dementia; Creutzfeldt-Jakob disease, Huntington's disease, multifocal motor neuropathy (MMN), prion protein cerebral amyloid angiopathy, polymyositis, postencephalitic parkinsonism, subacute sclerosing panencephalitis, non-Guamanian motor neuron disease with neurofibrillary tangles, neural regeneration, or diffuse neurofibrillary tangles with calcification.

In one embodiment, the disorder is selected from: atopic dermatitis, dermatitis, dermatomyositis bullous pemphigoid, scleroderma, sclerodermatomyositis, psoriatic arthritis, pemphigus vulgaris, Discoid lupus erythematosus, cutaneous lupus, chilblain lupus erythematosus, or lupus erythematosus-lichen planus overlap syndrome; cryoglobulinemic vasculitis, mesenteric/enteric vascular disorder, peripheral vascular disorder, antineutrophil cytoplasm antibody (ANCA)-associated vasculitis (AAV), IL-2 induced vascular leakage syndrome, or immune complex vasculitis; angioedema, low platelets (HELLP) syndrome, sickle cell disease, platelet refractoriness, red cell casts, or typical or infectious hemolytic uremic syndrome (tHUS); hematuria, hemorrhagic shock, drug-induced thrombocytopenia, autoimmune hemolytic anemia (AIHA), azotemia, blood vessel and/or lymph vessel inflammation, rotational atherectomy, or delayed hemolytic transfusion reaction; British type amyloid angiopathy, Buerger's disease, bullous pemphigoid, C1q nephropathy, cancer, or catastrophic antiphospholipid syndrome.

In another embodiment, the disorder is selected from: wet (exudative) AMD, dry (non-exudative) AMD, chorioretinal degeneration, choroidal neovascularization (CNV), choroiditis, loss of RPE function, loss of vision (including loss of visual acuity or visual field), loss of vision from AMD, retinal damage in response to light exposure, retinal degeneration, retinal detachment, retinal dysfunction, retinal neovascularization (RNV), retinopathy of prematurity, pathological myopia, or RPE degeneration; pseudophakic bullous keratopathy, symptomatic macular degeneration related disorder, optic nerve degeneration, photoreceptor degeneration, cone degeneration, loss of photoreceptor cells, pars planitis, scleritis, proliferative vitreoretinopathy, or formation of ocular drusen; chronic urticaria, Churg-Strauss syndrome, cold agglutinin disease (CAD), corticobasal degeneration (CBD), cryoglobulinemia, cyclitis, damage of the Bruch's membrane, Degos disease, diabetic angiopathy, elevated liver enzymes, endotoxemia, epidermolysis bullosa, or epidermolysis bullosa acquisita; essential mixed cryoglobulinemia, excessive blood urea nitrogen-BUN, focal segmental glomerulosclerosis, Gerstmann-Straussler-Scheinker disease, giant cell arteritis, gout, Hallervorden-Spatz disease, Hashimoto's thyroiditis, Henoch-Schonlein purpura nephritis, or abnormal urinary sediments; hepatitis, hepatitis A, hepatitis B, hepatitis C or human immunodeficiency virus (HIV), a viral infection more generally, for example selected from Flaviviridae, Retroviruses, Coronaviridae, Poxviridae, Adenoviridae, Herpesviridae, Caliciviridae, Reoviridae, Picornaviridae, Togaviridae, Orthomyxoviridae, Rhabdoviridae, or Hepadnaviridae; *Neisseria meningitidis*, shiga toxin *E. coli*-related hemolytic uremic syndrome (STEC-HUS), hemolytic uremic syndrome (HUS); *Streptococcus*, or poststreptococcal glomerulonephritis.

In a further embodiment, the disorder is selected from: hyperlipidemia, hypertension, hypoalbuminemia, hypobolemic shock, hypocomplementemic urticarial vasculitis syndrome, hypophosphastasis, hypovolemic shock, idiopathic pneumonia syndrome, or idiopathic pulmonary fibrosis; inclusion body myositis, intestinal ischemia, iridocyclitis, iritis, juvenile chronic arthritis, Kawasaki's disease (arteritis), or lipiduria; membranoproliferative glomerulonephritis (MPGN) I, microscopic polyangiitis, mixed cryoglobulinemia, molybdenum cofactor deficiency (MoCD) type A, pancreatitis, panniculitis, Pick's disease, polyarteritis nodosa (PAN), progressive subcortical gliosis, proteinuria, reduced glomerular filtration rate (GFR), or renovascular disorder; multiple organ failure, multiple system atrophy (MSA), myotonic dystrophy, Niemann-Pick disease type C, chronic demyelinating diseases, or progressive supranuclear palsy; spinal cord injury, spinal muscular atrophy, spondyloarthropathies, Reiter's syndrome, spontaneous fetal loss, recurrent fetal loss, pre-eclampsia, synucleinopathy, Takayasu's arteritis, post-partum thryoiditis, thyroiditis, Type I cryoglobulinemia, Type II mixed cryoglobulinemia, Type III mixed cryoglobulinemia, ulcerative colitis, uremia, urticaria, venous gas embolus (VGE), or Wegener's granulomatosis; von Hippel-Lindau disease, histoplasmosis of the eye, hard drusen, soft drusen, pigment clumping, or photoreceptor and/or retinal pigmented epithelia (RPE) loss.

In one embodiment, an active compound or its salt or composition as described herein is useful for treating or preventing a disorder selected from autoimmune oophoritis, endometriosis, autoimmune orchitis, Ord's thyroiditis, autoimmune enteropathy, coeliac disease, Hashimoto's encephalopathy, antiphospholipid syndrome (APLS) (Hughes syndrome), aplastic anemia, autoimmune lymphoproliferative syndrome (Canale-Smith syndrome), autoimmune neutropenia, Evans syndrome, pernicious anemia, pure red cell aplasia, thrombocytopenia, adipose dolorosa (Dercum's disease), adult onset Still's disease, ankylosing spondylitis, CREST syndrome, drug-induced lupus, eosinophilic fasciitis (Shulman's syndrome), Felty syndrome, IgG4-related disease, mixed connective tissue disease (MCTD), palindromic rheumatism (Hench-Rosenberg syndrome), Parry-Romberg syndrome, Parsonage-Turner syndrome, relapsing polychondritis (Meyenburg-Altherr-Uehlinger syndrome), retroperitonial fibrosis, rheumatic fever, Schnitzler syndrome, fibromyalgia, neuromyotonia (Isaac's disease), paraneoplastic degeneration, autoimmune inner ear disease, Meniere's disease, interstitial cystitis, autoimmune pancreatitis, zika virus-related disorders, chikungunya virus-related disorders, subacute bacterial endocarditis (SBE), IgA nephropathy, IgA vasculitis, polymyalgia rheumatic, rheumatoid vasculitis, alopecia areata, autoimmune progesterone dermatitis, dermatitis herpetiformis, erythema nodosum, gestational pemphigoid, hidradenitis suppurativa, lichen sclerosus, linear IgA disease (LAD), morphea, myositis, pityriasis lichenoides et varioliformis acuta, vitiligo post-myocardial infarction syndrome (Dressler's syndrome), post-pericardiotomy syndrome, autoimmune retinopathy, Cogan syndrome, Graves opthalmopathy, ligneous conjunctivitis, Mooren's ulcer, opsoclonus myoclonus syndrome, optic neuritis, retinocochleocerebral vasculopathy (Susac's syndrome), sympathetic opthalmia, Tolosa-Hunt syndrome, interstitial lung disease, antisynthetase syndrome, Addison's disease, autoimmune polyendocrine syndrome (APS) type I, autoimmune polyendocrine syndrome (APS) type II, autoimmune polyendocrine syndrome (APS) type III, disseminated sclerosis (multiple sclerosis, pattern II), rapidly progressing glomerulonephritis (RPGN), juvenile rheumatoid arthritis, enthesitis-related arthritis, reactive arthritis (Reiter's syndrome), autoimmune hepatitis or lupoid hepatitis, primary biliary cirrhosis (PBS), primary sclerosing cholangitis, microscopic colitis, latent lupus (undifferentiated connective tissue disease (UCTD)), acute disseminated encephalomyelitis (ADEM), acute motor axonal neuropathy, anti-n-methyl-D-aspartate receptor encephalitis, Balo concentric sclerosis (Schilders disease), Bickerstaff's encephalitis, chronic inflammatory demyelinating polyneuropathy, idiopathic inflammatory demyelinating disease, Lambert-Eaton mysathenic syndrome, Oshtoran syndrome, pediatric autoimmune neuropsychiatric disorder associated with *streptococcus* (PANDAS), progressive inflammatory neuropathy, restless leg syndrome, stiff person syndrome, Sydenhem syndrome, transverse myelitis, lupus vasculitis, leukocytoclastic vasculitis, Microscopic Polyangiitis, polymyositis or ischemic-reperfusion injury of the eye.

Examples of eye disorders that may be treated according to the compositions and methods disclosed herein include amoebic keratitis, fungal keratitis, bacterial keratitis, viral keratitis, onchorcercal keratitis, bacterial keratoconjunctivitis, viral keratoconjunctivitis, corneal dystrophic diseases, Fuchs' endothelial dystrophy, Sjogren's syndrome, Stevens-Johnson syndrome, autoimmune dry eye diseases, environmental dry eye diseases, corneal neovascularization diseases, post-corneal transplant rejection prophylaxis and treatment, autoimmune uveitis, infectious uveitis, posterior uveitis (including toxoplasmosis), pan-uveitis, an inflammatory disease of the vitreous or retina, endophthalmitis prophylaxis and treatment, macular edema, macular degeneration, age related macular degeneration, proliferative and non-proliferative diabetic retinopathy, hypertensive retinopathy, an autoimmune disease of the retina, primary and metastatic intraocular melanoma, other intraocular metastatic tumors, open angle glaucoma, closed angle glaucoma, pigmentary glaucoma and combinations thereof.

In a further embodiment, the disorder is selected from glaucoma, diabetic retinopathy, blistering cutaneous diseases (including bullous pemphigoid, pemphigus, and epidermolysis bullosa), ocular cicatrical pemphigoid, uveitis, adult macular degeneration, diabetic retinopa retinitis pigmentosa, macular edema, diabetic macular edema, Behcet's uveitis, multifocal choroiditis, Vogt-Koyangi-Harada syndrome, imtermediate uveitis, birdshot retino-chorioditis, sympathetic ophthalmia, ocular dicatricial pemphigoid, ocular pemphigus, nonartertic ischemic optic neuropathy, postoperative inflammation, and retinal vein occlusion, or central retinal vein occulusion (CVRO).

In some embodiments, complement mediated diseases include ophthalmic diseases (including early or neovascular age-related macular degeneration and geographic atrophy), autoimmune diseases (including arthritis, rheumatoid arthritis), respiratory diseases, cardiovascular diseases. In other embodiments, the compounds of the invention are suitable for use in the treatment of diseases and disorders associated with fatty acid metabolism, including obesity and other metabolic disorders.

Disorders that may be treated or prevented by an active compound or its salt or composition as described herein also include, but are not limited to: hereditary angioedema, capillary leak syndrome, hemolytic uremic syndrome (HUS), neurological disorders, Guillain Barre Syndrome, diseases of the central nervous system and other neurodegenerative conditions, glomerulonephritis (including membrane proliferative glomerulonephritis), SLE nephritis, proliferative nephritis, liver fibrosis, tissue regeneration and neural regeneration, or Barraquer-Simons Syndrome; inflammatory effects of sepsis, systemic inflammatory response syndrome (SIRS), disorders of inappropriate or undesirable complement activation, interleukin-2 induced toxicity during IL-2 therapy, inflammatory disorders, inflammation of autoimmune diseases, system lupus erythematosus (SLE), lupus nephritides, arthritis, immune complex disorders and autoimmune diseases, systemic lupus, or lupus erythematosus; ischemia/reperfusion injury (I/R injury), myocardial infarction, myocarditis, post-ischemic reperfusion conditions, balloon angioplasty, atherosclerosis, post-pump syndrome in cardiopulmonary bypass or renal bypass, renal ischemia, mesenteric artery reperfusion after aortic reconstruction, antiphospholipid syndrome, autoimmune heart disease, ischemia-reperfusion injuries, obesity, or diabetes; Alzheimer's dementia, stroke, schizophrenia, traumatic brain injury, trauma, Parkinson's disease, epilepsy, transplant rejection, prevention of fetal loss, biomaterial reactions (e.g. in hemodialysis, inplants), hyperacute allograft rejection, xenograft rejection, transplantation, psoriasis, burn injury, thermal injury including burns or frostbite, or crush injury; asthma, allergy, acute respiratory distress syndrome (ARDS), cystic fibrosis, adult respiratory distress syndrome, dyspnea, hemoptysis, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), bronchoconstriction, hypersensitivity pneumonitis, parasitic diseases, Goodpasture's Syndrome (anti-glomerular basement membrane nephritis), pulmonary vasculitis, Pauci-immune vasculitis, or immune complex-associated inflammation.

In one embodiment, a method for the treatment of sickle cell in a host is provided that includes the administration of an effective amount of an active compound or its salt or composition as described herein. In one embodiment, a method for the treatment of immunothrombocytopenic purpura (ITP), thrombotic thrombocytopenic purpura (TTP), or idiopathic thrombocytopenic purpura (ITP) in a host is provided that includes the administration of an effective amount of an active compound or its salt or composition as described herein. In one embodiment, a method for the treatment of ANCA-vasculitis in a host is provided that includes the administration of an effective amount of an active compound or its salt or composition as described herein. In one embodiment, a method for the treatment of IgA nephropathy in a host is provided that includes the administration of an effective amount of an active compound or its salt or composition as described herein. In one embodiment, a method for the treatment of rapidly progressing glomerulonephritis (RPGN), in a host is provided that includes the administration of an effective amount of an active compound or its salt or composition as described herein. In one embodiment, a method for the treatment of lupus nephritis, in a host is provided that includes the administration of an effective amount of an active compound or its salt or composition as described herein. In one embodiment, a method for the treatment of hemorraghic dengue fever, in a host is provided that includes the administration of an effective amount of an active compound or its salt or composition as described herein.

In an additional alternative embodiment, an active compound or its salt or composition as described herein is used in the treatment of an autoimmune disorder.

The complement pathway enhances the ability of antibodies and phagocytic cells to clear microbes and damaged cells from the body. It is part of the innate immune system and in healthy individuals is an essential process. Inhibiting the complement pathway will decrease the body's immune system response. Therefore, it is an object of the present invention to treat autoimmune disorders by administering an effective does of an active compound or its salt or composition as described herein to a subject in need thereof.

In one embodiment the autoimmune disorder is caused by activity of the complement system. In one embodiment the autoimmune disorder is caused by activity of the alternative complement pathway. In one embodiment the autoimmune disorder is caused by activity of the classical complement pathway. In another embodiment the autoimmune disorder is caused by a mechanism of action that is not directly related to the complement system, such as the over-proliferation of T-lymphocytes or the over-production of cytokines.

Non-limiting examples of autoimmune disorders include: lupus, allograft rejection, autoimmune thyroid diseases (such as Graves' disease and Hashimoto's thyroiditis), autoimmune uveoretinitis, giant cell arteritis, inflammatory bowel diseases (including Crohn's disease, ulcerative colitis, regional enteritis, granulomatous enteritis, distal ileitis, regional ileitis, and terminal ileitis), diabetes, multiple sclerosis, pernicious anemia, psoriasis, rheumatoid arthritis, sarcoidosis, and scleroderma.

In one embodiment, an active compound or its salt or composition as described herein is used in the treatment of lupus. Non-limiting examples of lupus include lupus erythematosus, cutaneous lupus, discoid lupus erythematosus, chilblain lupus erythematosus, or lupus erythematosus-lichen planus overlap syndrome.

Lupus erythematosus is a general category of disease that includes both systemic and cutaneous disorders. The systemic form of the disease can have cutaneous as well as systemic manifestations. However, there are also forms of the disease that are only cutaneous without systemic involvement. For example, SLE is an inflammatory disorder of unknown etiology that occurs predominantly in women, and is characterized by articular symptoms, butterfly erythema, recurrent pleurisy, pericarditis, generalized adenopathy, splenomegaly, as well as CNS involvement and progressive renal failure. The sera of most patients (over 98%) contain antinuclear antibodies, including anti-DNA antibodies. High titers of anti-DNA antibodies are essentially specific for SLE. Conventional treatment for this disease has been the administration of corticosteroids or immunosuppressants.

There are three forms of cutaneous lupus: chronic cutaneous lupus (also known as discoid lupus erythematosus or DLE), subacute cutaneous lupus, and acute cutaneous lupus. DLE is a disfiguring chronic disorder primarily affecting the skin with sharply circumscribed macules and plaques that display erythema, follicular plugging, scales, telangiectasia and atrophy. The condition is often precipitated by sun exposure, and the early lesions are erythematous, round scaling papules that are 5 to 10 mm in diameter and display follicular plugging. DLE lesions appear most commonly on the cheeks, nose, scalp, and ears, but they may also be generalized over the upper portion of the trunk, extensor surfaces of the extremities, and on the mucous membranes of the mouth. If left untreated, the central lesion atrophies and leaves a scar. Unlike SLE, antibodies against double-stranded DNA (e.g., DNA-binding test) are almost invariably absent in DLE.

Multiple Sclerosis is an autoimmune demyelinating disorder that is believed to be T lymphocyte dependent. MS generally exhibits a relapsing-remitting course or a chronic progressive course. The etiology of MS is unknown, however, viral infections, genetic predisposition, environment, and autoimmunity all appear to contribute to the disorder. Lesions in MS patients contain infiltrates of predominantly T lymphocyte mediated microglial cells and infiltrating macrophages. CD4+T lymphocytes are the predominant cell type present at these lesions. The hallmark of the MS lesion is plaque, an area of demyelination sharply demarcated from the usual white matter seen in MRI scans. Histological appearance of MS plaques varies with different stages of the disease. In active lesions, the blood-brain barrier is damaged, thereby permitting extravasation of serum proteins into extracellular spaces. Inflammatory cells can be seen in perivascular cuffs and throughout white matter. CD4+ T-cells, especially Th1, accumulate around postcapillary venules at the edge of the plaque and are also scattered in the white matter. In active lesions, up-regulation of adhesion molecules and markers of lymphocyte and monocyte activation, such as IL2-R and CD26 have also been observed. Demyelination in active lesions is not accompanied by destruction of oligodendrocytes. In contrast, during chronic phases of the disease, lesions are characterized by a loss of oligodendrocytes and hence, the presence of myelin oligodendrocyte glycoprotein (MOG) antibodies in the blood.

Diabetes can refer to either type 1 or type 2 diabetes. In one embodiment an active compound or its salt or composition as described herein is provided at an effective dose to treat a patient with type 1 diabetes. In one embodiment an active compound or its salt or composition as described herein is provided at an effective dose to treat a patient with type 2 diabetes. Type 1 diabetes is an autoimmune disease. An autoimmune disease results when the body's system for fighting infection (the immune system) turns attacks a part of the body. In the case of diabetes type 1, the pancreas then produces little or no insulin.

Combination Therapy

In one embodiment an active compound or its salt or composition as described herein may be provided in combination or alternation with or preceded by, concomitant with or followed by, an effective amount of at least one additional therapeutic agent, for example, for treatment of a disorder listed herein. Non-limiting examples of second active agents for such combination therapy are provided below.

In one embodiment, an active compound or its salt or composition as described herein may be provided in combination or alternation with at least one additional inhibitor of the complement system or a second active compound with a different biological mechanism of action. In the description below and herein generally, whenever any of the terms referring to an active compound or its salt or composition as described herein are used, it should be understood that pharmaceutically acceptable salts, prodrugs or compositions are considered included, unless otherwise stated or inconsistent with the text.

In non-limiting embodiments, an active compound or its salt or composition as described herein may be provided together with a protease inhibitor, a soluble complement regulator, a therapeutic antibody (monoclonal or polyclonal), complement component inhibitor, receptor agonist, or siRNA.

In other embodiments, an active compound described herein is administered in combination or alternation with an antibody against tumor necrosis factor (TNF), including but not limited to infliximab (Remicade), adalimumab, certolizumab, golimumab, or a receptor fusion protein such as etanercept (Embrel).

In another embodiment, an active compound as described herein can be administered in combination or alternation with an anti-CD20 antibody, including but not limited to rituximab (Rituxan), adalimumab (Humira), ofatumumab (Arzerra), tositumomab (Bexxar), obinutuzumab (Gazyva), or ibritumomab (Zevalin).

In an alternative embodiment, an active compound as described herein can be administered in combination or alternation with an anti-IL6 antibody, including but not limited to tocilizumab (Actemra) and siltuximab (Sylvant).

In an alternative embodiment, an active compound as described herein can be administered in combination or alternation with an IL17 inhibitor, including but not limited to secukibumab (Cosentyx).

In an alternative embodiment, an active compound as described herein can be administered in combination or alternation with a p40 (IL12/IL23) inhibitor, including but not limited to ustekinumab (Stelara).

In an alternative embodiment, an active compound as described herein can be administered in combination or alteration with an IL23 inhibitor, including but not limited to risankizumab.

In an alternative embodiment, an active compound as described herein can be administered in combination or alteration with an anti-interferon α antibody, for example but not limited to sifalimumab.

In an alternative embodiment, an active compound as described herein can be administered in combination or alteration with a kinase inhibitor, for example but not limited to a JAK1/JAK3 inhibitor, for example but not limited to tofacitinib (Xelianz). In an alternative embodiment, an active compound as described herein can be administered in combination or alteration with a JAK1/JAK2 inhibitor, for example but not limited to baracitibib.

In an alternative embodiment, an active compound as described herein can be administered in combination or alteration with an anti-VEGF agent, for example but not limited to: aflibercept (Eylea®; Regeneron Pharmaceuticals); ranibizumab (Lucentis®: Genentech and Novartis); pegaptanib (Macugen®; OSI Pharmaceuticals and Pfizer); bevacizumab (Avastin; Genentech/Roche); lapatinib (Tykerb); sunitinib (Sutent); axitinib (Inlyta); pazopanib; sorafenib (Nexavar); ponatinib (Inclusig); regorafenib (Stivarga); cabozantinib (Abometyx; Cometriq); vendetanib (Caprelsa); ramucirumab (Cyramza); lenvatinib (Lenvima); ziv-aflibercept (Zaltrap); cediranib (Recentin); anecortane acetate, squalamine lactate, and corticosteroids.

In another embodiment, an active compound as described herein can be administered in combination or alternation with an immune checkpoint inhibitor. Non-limiting examples of checkpoint inhibitors include anti-PD-1 or anti-PDL1 antibodies, for example, nivolumab (Opdivo), pembrolizumab (Keytruda), pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-L1/VISTA inhibitor CA-170 (Curis Inc.), atezolizumab, durvalumab, and KN035, or anti-CTLA4 antibodies, for example Ipilimumab, Tremelimumab, AGEN1884 and AGEN2041 (Agenus).

Non-limiting examples of active agents that can be used in combination with active compounds described herein are:

Protease inhibitors: plasma-derived C1-INH concentrates, for example Cetor® (Sanquin), Berinert-P® (CSL Behring, Lev Pharma), and Cinryze®; recombinant human C1-inhibitors, for example Rhucin®; ritonavir (Norvir®, Abbvie, Inc.);

Soluble complement regulators: Soluble complement receptor 1 (TP10) (Avant Immunotherapeutics); sCR1-sLe$^x$/TP-20 (Avant Immunotherapeutics); MLN-2222/CAB-2 (Millenium Pharmaceuticals); Mirococept (Inflazyme Pharmaceuticals);

Therapeutic antibodies: Eculizumab/Soliris (Alexion Pharmaceuticals); Pexelizumab (Alexion Pharmaceuticals); Ofatumumab (Genmab A/S); TNX-234 (Tanox); TNX-558 (Tanox); TA106 (Taligen Therapeutics); Neutrazumab (G2 Therapies); Anti-properdin (Novelmed Therapeutics); HuMax-CD38 (Genmab A/S);

Complement component inhibitors: Compstatin/POT-4 (Potentia Pharmaceuticals); ARC1905 (Archemix); 4(1MEW)APL-1,APL-2 (Appelis); CP40/AMY-101,PEG-Cp40 (Amyndas);

PDGF inhibitors: Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TKI258) Lactate; Sennoside B; Sunitinib; AZD2932; and Trapidil;

Anti-factor H or anti-factor B agents: Anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas);

Complement C3 or CAP C3 Convertase targeting molecules: TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); CRIg/CFH; Anti-CR3, anti-MASP2, anti C1s, and anti-C1n molecules: Cynryze (ViroPharma/Baxter); TNT003 (True North); OMS721 (Omeros); OMS906 (Omeros); and Imprime PGG (Biothera);

Receptor agonists: PMX-53 (Peptech Ltd.); JPE-137 (Jerini); JSM-7717 (Jerini);

Others: Recombinant human MBL (rhMBL; Enzon Pharmaceuticals); Imides and glutarimide derivatives such as thalidomide, lenalidomide, pomalidomide; Additional non-limiting examples that can be used in combination or alternation with an active compound or its salt or composition as described herein include the following.

| Non-limiting examples of potential therapeutics for combination therapy | | | |
|---|---|---|---|
| Name | Target | Company | Class of Molecule |
| LFG316 | C5 | Novartis/Morphosys | Monoclonal antibody |
| 4(1MEW)APL-1, APL-2 | C3/C3b | Apellis | Compstatin Family |
| 4(1MeW)POT-4 | C3/C3b | Potentia | Compstatin Family |
| Anti-C5 siRNA | C5 | Alnylam | Si-RNA |
| Anti-FB siRNA | CFB | Alnylam | SiRNA |
| ARC1005 | C5 | Novo Nordisk | Aptamers |
| ATA | C5 | N.A. | Chemical |
| Coversin | C5 | Volution Immuno-Pharmaceuticals | Small animal protein |
| CP40/AMY-101, PEG-Cp40 | C3/C3b | Amyndas | Compstatin Family |
| CRIg/CFH | CAP C3 convertase | NA | CFH-based protein |
| Cynryze | C1n/C1s | ViroPharma/Baxter | Human purified protein |
| FCFD4514S | CFD | Genentech/Roche | Monoclonal antibody |
| H17 | C3 (C3b/iC3b) | EluSys Therapeutics | Monoclonal antibody |

-continued

| Non-limiting examples of potential therapeutics for combination therapy | | | |
|---|---|---|---|
| Name | Target | Company | Class of Molecule |
| Mini-CFH | CAP C3 convertase | Amyndas | CFH-based protein |
| Mirococept (APT070) | CAP and CCP C3 | NA | CR1-based protein |
| Mubodine | C5 | Adienne | Monoclonal antibody |
| RA101348 | C5 | Rapharma | Small molecule |
| sCR1 (CDX-1135) | CAP and CP C3 | Celldex | CR1-based protein |
| SOBI002 | C5 | Swedish Orphan Biovitrum | Affibody |
| SOMAmers | C5 | SomaLogic | Aptamers |
| SOMAmers | CFB and CFD | SomaLogic | Aptamers (SELEX) |
| TA106 | CFB | Alexion Pharmaceuticals | Monoclonal antibody |
| TNT003 | C1s | True North | Monoclonal antibody |
| TT30 (CR2/CFH) | CAP C3 convertase | Alexion | CFH-based protein |
| TT32 (CR2/CR1) | CAP and CCP C3 | Alexion Pharmaceuticals | CR1-based protein |
| Nafamostat (FUT-175, Futhan) | C1s, CFD, other proteases | Torri Pharmaceuticals | Small molecule |
| OMS721 | MASP-2 | Omeros | Monoclonal antibody |
| OMS906 | MASP-2 | Omeros | Monoclonal antibody |
| Bikaciomab, NM9308 | CFB | Novelmed | Monoclonal antibody |
| NM9401 | Properdin | Novelmed | Monoclonal antibody |
| CVF, HC-1496 | C3 | InCode | Recombinant peptide |
| ALXN1102/ALXN1103 (TT30) | C3-conv, C3b | Alexion Pharmaceuticals | Regulator |
| rFH | C3-conv, C3b | Optherion | Regulator |
| 5C6, AMY-301 | CFH | Amyndas | Regulator |
| Erdigna | C5 | Adienne Pharma | Antibody |
| ARC1905 | C5 | Opthotech | Monoclonal Antibody |
| MEDI7814 | C5/C5a | MedImmune | Monoclonal Antibody |
| NOX-D19 | C5a | Noxxon | Aptamer (Spiegelmer) |
| IFX-1, CaCP29 | C5a | InflaRx | Monoclonal Antibody |
| PMX53, PMX205 | C5aR | Cephalon, Teva | Peptidomimetic |
| CCX168 | C5aR | ChemoCentryx | Small molecule |
| ADC-1004 | C5aR | Alligator Bioscience | Small molecule |
| Anti-C5aR-151, NN8209; Anti-C5aR-215, NN8210 | C5aR | Novo Nordisk | Monoclonal Antibody |
| Imprime PGG | CR3 | Biothera | Soluble beta-glucan |
| ANX005; ANX007 | C1q | Annexon | Monoclonal Antibody |
| Lampalizumab | fD | Roche | Monoclonal Antibody |
| avacincaptad pegol | C5 | Opthotech | Aptamer |
| regenemab | C6 | Regenesance | Monoclonal Antibody |
| BIVV020 | C1s | Bioverativ | Monoclonal Antibody |
| PRO-02 | C2 | Broteio/Argen-x | Monoclonal Antibody |
| 5C6, compsorbin | fH | Amyndas | Peptide |
| SOBI005 | C5 | Sobi | Protein |
| ISU305 | C5 | ISU ABXIS | Monoclonal Antibody |
| Mubodina | C5 | Adienne | Monoclonal Antibody |
| IFX-2, IFX-3 | C5a | InflaRx | Monoclonal Antibody |
| ALS-205 | C5aR1 | Alsonex | Peptide |
| DF2593A | C5aR1 | Dompe | Small Molecule |
| IPH5401 | C5aR1 | Innate Pharma | Monoclonal Antibody |
| C6-LNA | C6 | Regenesance | Oligonucleotide |
| SKY59 | C5 | Roche | Monoclonal Antibody |
| REGN3918 | C5 | Regeneron | Monoclonal Antibody |
| Aptamers to Factor D | fD | Vitrisa Therapeutics | Aptamer |
| CLG561 | Properdin | Novartis | Monoclonal Antibody |
| Tesidolumab; LFG316 | C5 | Novartis and MorphoSys | Monoclonal Antibody |

In one embodiment, an active compound or its salt or composition as described herein may be provided together with a compound that inhibits an enzyme that metabolizes an administered protease inhibitor. In one embodiment, a compound or salt may be provided together with ritonavir.

In one embodiment, an active compound or its salt or composition as described herein may be provided in combination with a complement C5 inhibitor or C5 convertase inhibitor. In another embodiment, an active compound or its salt or composition as described herein may be provided in combination with eculizumab, a monoclonal antibody directed to the complement factor C5 and manufactured and marketed by Alexion Pharmaceuticals under the tradename Soliris. Eculizumab has been approved by the U.S. FDA for the treatment of PNH and aHUS.

In one embodiment, an active compound or its salt or composition as described herein may be provided together with a compound that inhibits Complement Factor D. In one embodiment of the invention, an active compound or its salt or composition as described herein as described herein can be used in combination or alternation with a compound described in Biocryst Pharmaceuticals U.S. Pat. No. 6,653,340 titled "Compounds useful in the complement, coagulate and kallikrein pathways and method for their preparation" describes fused bicyclic ring compounds that are potent inhibitors of Factor D; Novartis PCT patent publication WO2012/093101 titled "Indole compounds or analogues thereof useful for the treatment of age-related macular degeneration" describes certain Factor D inhibitors; Novartis PCT patent publications WO2013/164802, WO2013/192345, WO2014/002051, WO2014/002052, WO2014/002053, WO2014/002054, WO2014/002057, WO2014/002058, WO2014/002059, WO2014/005150, WO2014/009833, WO2014/143638, WO2015/009616, WO2015/009977, WO2015/066241, Bristol-Myers Squibb PCT patent publication WO2004/045518 titled "Open chain prolyl urea-related modulators of androgen receptor function"; Japan Tobacco Inc. PCT patent publication WO1999/048492 titled "Amide derivatives and nociceptin antagonists"; Ferring B. V. and Yamanouchi Pharmaceutical Co. LTD. PCT patent publication WO1993/020099 titled "CCK and/or gastrin receptor ligands"; Alexion Pharmaceuticals PCT patent publication WO1995/029697 titled "Methods and compositions for the treatment of glomerulonephritis and other inflammatory diseases"; or Achillion Pharmaceuticals filed PCT Patent Application No. PCT/US2015/017523 and U.S. patent application Ser. No. 14/631,090 titled "Alkyne Compounds for Treatment of Complement Mediated Disorders"; PCT Patent Application No. PCT/US2015/017538 and U.S. patent application Ser. No. 14/631,233 titled "Amide Compounds for Treatment of Complement Mediated Disorders"; PCT Patent Application No. PCT/US2015/017554 and U.S. patent application Ser. No. 14/631,312 titled "Amino Compounds for Treatment of Complement Mediated Disorders"; PCT Patent Application No. PCT/US2015/017583 and U.S. patent application Ser. No. 14/631,440 titled "Carbamate, Ester, and Ketone Compounds for Treatment of Complement Mediated Disorders"; PCT Patent Application No. PCT/US2015/017593 and U.S. patent application Ser. No. 14/631,625 titled "Aryl, Heteroaryl, and Heterocyclic Compounds for Treatment of Complement Mediated Disorders"; PCT Patent Application No. PCT/US2015/017597 and U.S. patent application Ser. No. 14/631,683 titled "Ether Compounds for Treatment of Complement Mediated Disorders"; PCT Patent Application No. PCT/US2015/017600 and U.S. patent application Ser. No. 14/631,785 titled "Phosphonate Compounds for Treatment of Complement Mediated Disorders"; and PCT Patent Application No. PCT/US2015/017609 and U.S. patent application Ser. No. 14/631,828 titled "Compounds for Treatment of Complement Mediated Disorders."

In one embodiment, an active compound or its salt or composition as described herein is administered in combination with an anti-inflammatory drug, antimicrobial agent, anti-angiogenesis agent, immunosuppressant, antibody, steroid, ocular antihypertensive drug or combinations thereof. Examples of such agents include amikacin, anecortane acetate, anthracenedione, anthracycline, an azole, amphotericin B, bevacizumab, camptothecin, cefuroxime, chloramphenicol, chlorhexidine, chlorhexidine digluconate, clortrimazole, a clotrimazole cephalosporin, corticosteroids, dexamethasone, desamethazone, econazole, eftazidime, epipodophyllotoxin, fluconazole, flucytosine, fluoropyrimidines, fluoroquinolines, gatifloxacin, glycopeptides, imidazoles, itraconazole, ivermectin, ketoconazole, levofloxacin, macrolides, miconazole, miconazole nitrate, moxifloxacin, natamycin, neomycin, nystatin, ofloxacin, polyhexamethylene biguanide, prednisolone, prednisolone acetate, pegaptanib, platinum analogues, polymicin B, propamidine isethionate, pyrimidine nucleoside, ranibizumab, squalamine lactate, sulfonamides, triamcinolone, triamcinolone acetonide, triazoles, vancomycin, anti-vascular endothelial growth factor (VEGF) agents, VEGF antibodies, VEGF antibody fragments, vinca alkaloid, timolol, betaxolol, travoprost, latanoprost, bimatoprost, brimonidine, dorzolamide, acetazolamide, pilocarpine, ciprofloxacin, azithromycin, gentamycin, tobramycin, cefazolin, voriconazole, gancyclovir, cidofovir, foscarnet, diclofenac, nepafenac, ketorolac, ibuprofen, indomethacin, fluoromethalone, rimexolone, anecortave, cyclosporine, methotrexate, tacrolimus, anti-PDGFR molecule, and combinations thereof.

In one embodiment of the present invention, an active compound or its salt or composition as described herein can be administered in combination or alternation with at least one immunosuppressive agent. The immunosuppressive agent as non-limiting examples, may be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, tocilizumab (Actemra), siltuximab (Sylvant), secukibumab (Cosentyx), ustekinumab (Stelara), risankizumab, sifalimumab, aspirin and ibuprofen.

Examples of anti-inflammatory agents include methotrexate, dexamethasone, dexamethasone alcohol, dexamethasone sodium phosphate, fluromethalone acetate, fluromethalone alcohol, lotoprendol etabonate, medrysone, prednisolone acetate, prednisolone sodium phosphate, difluprednate, rimexolone, hydrocortisone, hydrocortisone acetate, lodoxamide tromethamine, aspirin, ibuprofen, suprofen, piroxicam, meloxicam, flubiprofen, naproxan, ketoprofen, tenoxicam, diclofenac sodium, ketotifen fumarate, diclofenac sodium, nepafenac, bromfenac, flurbiprofen sodium, suprofen, celecoxib, naproxen, rofecoxib, glucocorticoids, diclofenac, and any combination thereof. In one embodiment, an active compound or its salt or composition as described herein is combined with one or more non-steroidal anti-inflammatory drugs (NSAIDs) selected from naproxen sodium (Anaprox), celecoxib (Celebrex), sulindac (Clinoril), oxaprozin (Daypro), salsalate (Disalcid), diflunisal (Dolobid), piroxicam (Feldene), indomethacin (Indocin), etodolac (Lodine), meloxicam (Mobic), naproxen (Naprosyn), nabumetone (Relafen), ketorolac tromethamine (Toradol), naproxen/esomeprazole (Vimovo), and diclofenac (Voltaren), and combinations thereof.

In one embodiment, an active compound or its salt or composition as described herein is administered in combination or alteration with an omega-3 fatty acid or a peroxisome proliferator-activated receptor (PPARs) agonist. Omega-3 fatty acids are known to reduce serum triglycerides by inhibiting DGAT and by stimulating peroxisomal and mitochondrial beta oxidation. Two omega-3 fatty acids, eicosapentaenoic acid (EPA) and docosahexaenoic acid (DHA), have been found to have high affinity for both PPAR-alpha and PPAR-gamma. Marine oils, e.g., fish oils, are a good source of EPA and DHA, which have been found to regulate lipid metabolism. Omega-3 fatty acids have been found to have beneficial effects on the risk factors for cardiovascular diseases, especially mild hypertension, hypertriglyceridemia and on the coagulation factor VII phospholipid complex activity. Omega-3 fatty acids lower serum triglycerides, increase serum HDL-cholesterol, lower systolic and diastolic blood pressure and the pulse rate, and lower the activity of the blood coagulation factor VII-phospholipid complex. Further, omega-3 fatty acids seem to be well tolerated, without giving rise to any severe side effects. One such form of omega-3 fatty acid is a concentrate of omega-3, long chain, polyunsaturated fatty acids from fish oil containing DHA and EPA and is sold under the trademark Omacor®. Such a form of omega-3 fatty acid is described, for example, in U.S. Pat. Nos. 5,502,077, 5,656,667 and 5,698,594, the disclosures of which are incorporated herein by reference.

Peroxisome proliferator-activated receptors (PPARs) are members of the nuclear hormone receptor superfamily ligand-activated transcription factors that are related to retinoid, steroid and thyroid hormone receptors. There are three distinct PPAR subtypes that are the products of different genes and are commonly designated PPAR-alpha, PPAR-beta/delta (or merely, delta) and PPAR-gamma. General classes of pharmacological agents that stimulate peroxisomal activity are known as PPAR agonists, e.g., PPAR-alpha agonists, PPAR-gamma agonists and PPAR-delta agonists. Some pharmacological agents are combinations of PPAR agonists, such as alpha/gamma agonists, etc., and some other pharmacological agents have dual agonist/antagonist activity. Fibrates such as fenofibrate, bezafibrate, clofibrate and gemfibrozil, are PPAR-alpha agonists and are used in patients to decrease lipoproteins rich in triglycerides, to increase HDL and to decrease atherogenic-dense LDL. Fibrates are typically orally administered to such patients. Fenofibrate or 2-[4-(4-chlorobenzoyl)phenoxy]-2-methyl-propanoic acid, 1-methylethyl ester, has been known for many years as a medicinally active principle because of its efficacy in lowering blood triglyceride and cholesterol levels.

In one embodiment, the present invention provides a method of treating or preventing age-related macular degeneration (AMD) by administering to a subject in need thereof an effective amount of an active compound or its salt or composition as described herein in combination with an anti-VEGF agent. Non-limiting examples of anti-VEGF agents include, but are not limited to, aflibercept (Eylea®; Regeneron Pharmaceuticals); ranibizumab (Lucentis®: Genentech and Novartis); pegaptanib (Macugen®; OSI Pharmaceuticals and Pfizer); bevacizumab (Avastin; Genentech/Roche); lapatinib (Tykerb); sunitinib (Sutent); axitinib (Inlyta); pazopanib; sorafenib (Nexavar); ponatinib (Inclusig); regorafenib (Stivarga); Cabozantinib (Abometyx; Cometriq); vendetanib (Caprelsa); ramucirumab (Cyramza); lenvatinib (Lenvima); ziv-aflibercept (Zaltrap); cediranib (Recentin); anecortane acetate, squalamine lactate, and corticosteroids, including, but not limited to, triamcinolone acetonide.

In one embodiment, the present invention provides a method of treating or preventing age-related macular degeneration (AMD) by administering to a subject in need thereof an effective amount of an active compound or its salt or composition as described herein in combination with a complement C5 inhibitor, for example, a complement C5 inhibitor described herein and in the table above titled Non-limiting examples of potential therapeutics for combination therapy, including, but not limited to, eculizumab; LFG316 (Novartis/Morphosys); Anti-C5 siRNA (Alnylam); ARC1005 (Novo Nordisk); Coversin (Volution Immuno-Pharmaceuticals); Mubodine (Adienne Pharma); RA101348 (Ra Pharma); SOBI002 (Swedish Orphan Biovitrum); SOMAmers (SomaLogic); Erdigna (Adienne Pharma); ARC1905 (Opthotech); MEDI7814 (MedImmune); NOX-D19 (Noxxon); IFX-1, CaCP29 (InflaRx); PMX53, PMX205 (Cephalon, Teva); CCX168 (ChemoCentryx); ADC-1004 (Alligator Bioscience); and Anti-C5aR-151, NN8209; Anti-C5aR-215, NN8210 (Novo Nordisk).

In one embodiment, the present invention provides a method of treating or preventing age-related macular degeneration (AMD) by administering to a subject in need thereof an effective amount of an active compound or its salt or composition as described herein in combination with anti-properidin agent, for example, an anti-properidin agent as described above, including but not limited to NM9401 (Novelmed).

In one embodiment, the present invention provides a method of treating or preventing age-related macular degeneration (AMD) by administering to a subject in need thereof an effective amount of an active compound or its salt or composition as described herein in combination with a complement C3 inhibitor for example, a complement C3 inhibitor described above, including, but not limited to, a compstatin or compstatin analogue, for example Compstatin/POT-4 (Potentia Pharmaceuticals); ARC1905 (Archemix); 4(1MEW)APL-1,APL-2 (Appelis); CP40/AMY-101, PEG-Cp40 (Amyndas) Complement C3 or CAP C3 Convertase targeting molecules: TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); and CRIg/CFH.

In one embodiment, the present invention provides a method of treating or preventing age-related macular degeneration (AMD) by administering to a subject in need thereof an effective amount of an active compound or its salt or composition as described herein in combination with an anti-factor H or anti-factor B agent selected from Anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas).

In one embodiment, the present invention provides a method of treating or preventing age-related macular degeneration (AMD) by administering to a subject in need thereof an effective amount of an active compound or its salt or composition as described herein in combination with an anti-MASP2, anti-C1s or anti-CR3 molecules, for example, but not limited to: Cynryze (ViroPharma/Baxter); TNT003 (True North); OMS721 (Omeros); OMS906 (Omeros); and Imprime PGG (Biothera).

In one embodiment, the present invention provides a method of treating or preventing age-related macular degeneration (AMD) by administering to a subject in need thereof an effective amount of an active compound or its salt or composition as described herein in combination with an PDGF inhibitor, for example as described herein including but not limited to Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TKI258) Lactate; Sennoside B; Sunitinib; AZD2932; and Trapidil.

In one embodiment, the present invention provides a method of treating or preventing paroxysmal nocturnal hemoglobinuria (PNH) by administering to a subject in need thereof an effective amount of an active compound or its salt or composition as described herein with an additional inhibitor of the complement system or another active compound with a different biological mechanism of action. In another embodiment, the present invention provides a method of treating or preventing paroxysmal nocturnal hemoglobinuria (PNH) by administering to a subject in need thereof an effective amount of an active compound or its salt or composition as described herein in combination or alternation with eculizumab. In another embodiment, the present invention provides a method of treating or preventing paroxysmal nocturnal hemoglobinuria (PNH) by administering to a subject in need thereof an effective amount of an active compound or its salt or composition as described herein in combination or alternation with CP40. In one embodiment, the additional agent is PEGylated-CP40. CP40 is a peptide inhibitor that shows a strong binding affinity for C3b and inhibits hemolysis of paroxysmal nocturnal hemoglobinuria (PNH) erythrocytes. In one embodiment, the additional agent is a complement component inhibitor, for example but not limited to Compstatin/POT-4 (Potentia Pharmaceuticals); ARC1905 (Archemix); 4(1MEW)APL-1,APL-2 (Appelis); CP40/AMY-101,PEG-Cp40 (Amyndas); a PDGF inhibitor, for example, but not limited to Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TKI258) Lactate; Sennoside B; Sunitinib; AZD2932; and Trapidil; an anti-factor H or anti-factor B agent, for example anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas); a complement C3 or CAP C3 convertase targeting molecule, for example but not limited to TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); CRIg/CFH, an anti-CR3, anti-MASP2, anti C1s, or anti-C1n molecule, for example but not limited to Cynryze (ViroPharma/Baxter); TNT003 (True North); OMS721 (Omeros); OMS906 (Omeros); and Imprime PGG (Biothera)

In one embodiment, the present invention provides a method of treating or preventing rheumatoid arthritis by administering to a subject in need thereof an effective amount of a composition comprising an active compound or its salt or composition as described herein in combination or alternation with an additional inhibitor of the complement system, or an active agent that functions through a different mechanism of action. In another embodiment, the present invention provides a method of treating or preventing rheumatoid arthritis by administering to a subject in need thereof an effective amount of an active compound or its salt or composition as described herein in combination or alternation with methotrexate. In certain embodiments, an active compound or its salt or composition as described herein is administered in combination or alternation with at least one additional therapeutic agent selected from: salicylates including aspirin (Anacin, Ascriptin, Bayer Aspirin, Ecotrin) and salsalate (Mono-Gesic, Salgesic); nonsteroidal anti-inflammatory drugs (NSAIDs); nonselective inhibitors of the cyclo-oxygenase (COX-1 and COX-2) enzymes, including diclofenac (Cataflam, Voltaren), ibuprofen (Advil, Motrin), ketoprofen (Orudis), naproxen (Aleve, Naprosyn), piroxicam (Feldene), etodolac (Lodine), indomethacin, oxaprozin (Daypro), nabumetone (Relafen), and meloxicam (Mobic); selective cyclo-oxygenase-2 (COX-2) inhibitors including Celecoxib (Celebrex); disease-modifying anti-rheumatic drugs (DMARDs), including azathioprine (Imuran), cyclosporine (Sandimmune, Neoral), gold salts (Ridaura, Solganal, Aurolate, Myochrysine), hydroxychloroquine (Plaquenil), leflunomide (Arava), methotrexate (Rheumatrex), penicillamine (Cuprimine), and sulfasalazine (Azulfidine); biologic drugs including abatacept (Orencia), etanercept (Enbrel), infliximab (Remicade), adalimumab (Humira), and anakinra (Kineret); corticosteroids including betamethasone (Celestone Soluspan), cortisone (Cortone), dexamethasone (Decadron), methylprednisolone (SoluMedrol, DepoMedrol), prednisolone (Delta-Cortef), prednisone (Deltasone, Orasone), and triamcinolone (Aristocort); gold salts, including Auranofin (Ridaura); Aurothioglucose (Solganal); Aurolate; Myochrysine; or any combination thereof.

In one embodiment, the present invention provides a method of treating or preventing multiple sclerosis by administering to a subject in need thereof an effective amount of an active compound or its salt or composition as described herein in combination or alternation with an additional inhibitor of the complement system, or an active agent that functions through a different mechanism of action. In another embodiment, the present invention provides a method of treating or preventing multiple sclerosis by administering to a subject in need thereof an effective amount of an active compound or its salt or composition as described herein in combination or alternation with a corticosteroid. Examples of corticosteroids include, but are not limited to, prednisone, dexamethasone, solumedrol, and methylprednisolone. In one embodiment, an active compound or its salt or composition as described herein is combined with at least one anti-multiple sclerosis drug, for example, selected from: Aubagio (teriflunomide), Avonex (interferon beta-1a), Betaseron (interferon beta-1b), Copaxone (glatiramer acetate), Extavia (interferon beta-1b), Gilenya (fingolimod), Lemtrada (alemtuzumab), Novantrone (mitoxantrone), Plegridy (peginterferon beta-1a), Rebif (interferon beta-1a), Tecfidera (dimethyl fumarate), Tysabri (natalizumab), SoluMedrol (methylprednisolone), High-dose oral Deltasone (prednisone), H.P. Acthar Gel (ACTH), or a combination thereof.

In one embodiment, an active compound or its salt or composition as described herein is useful in a combination with another pharmaceutical agent to ameliorate or reduce a side effect of the agent. For example, in one embodiment, an active compound or its salt or composition as described herein may be used in combination with adoptive cell transfer therapies to reduce an associated inflammatory response associated with such therapies, for example, a cytokine mediated response such as cytokine release syndrome. In one embodiment, the adoptive cell transfer therapy includes the use of a chimeric antigen receptor T-Cell (CAR T). In one embodiment, the adoptive cell transfer therapy includes the use of a chimeric antigen receptor T-Cell (CAR T) or a dendritic cell to treat a hematologic or solid tumor, for example, a B-cell related hematologic cancer. In one embodiment, the hematologic or solid tumor is acute lymphoblastic leukemia (ALL), acute myeloid leukemia (AML), non-Hodgkin's lymphoma, chronic lymphocytic leukemia (CLL), pancreatic cancer, glioblastoma, or a cancer that expresses CD19.

In an additional alternative embodiment, an active compound or its salt or composition as described herein may be provided in combination with eculizumab for the treatment of PNH, aHUSs, STEC-HUS, ANCA-vasculitis, AMD, CAD, C3 glomerulopathy, for example DDD or C3GN, chronic hemolysis, neuromyelitis optica, or transplantation rejection. In one embodiment, an active compound or its salt or composition as described herein may be provided in combination with compstatin or a compstatin derivative for the treatment of PNH, aHUSs, STEC-HUS, ANCA-vasculitis, AMD, CAD, C3 glomerulopathy, for example DDD or C3GN, chronic hemolysis, neuromyelitis optica, or transplantation rejection. In one embodiment, the additional agent is a complement component inhibitor, for example but not limited to Compstatin/POT-4 (Potentia Pharmaceuticals); ARC1905 (Archemix); 4(1MEW)APL-1,APL-2 (Appelis); CP40/AMY-101,PEG-Cp40 (Amyndas); a PDGF inhibitor, for example, but not limited to Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TKI258) Lactate; Sennoside B; Sunitinib; AZD2932; and Trapidil; an anti-factor H or anti-factor B agent, for example anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas); a complement C3 or CAP C3 convertase targeting molecule, for example but not limited to TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); CRIg/CFH, an anti-CR3, anti-MASP2, anti C1s, or anti-C1n molecule, for example but not limited to Cynryze (ViroPharma/Baxter); TNT003 (True North); OMS721 (Omeros); OMS906 (Omeros); and Imprime PGG (Biothera).

In one embodiment, an active compound or its salt or composition as described herein may be provided in combination with rituxan for the treatment of a complement mediated disorder. In one embodiment, the complement mediated disorder is, for example, rheumatoid arthritis, Granulomatosis with Polyangiitis (GPA) (Wegener's Granulomatosis), and Microscopic Polyangiitis (MPA). In one embodiment, the disorder is Lupus.

In one embodiment, an active compound or its salt or composition as described herein may be provided in combination with cyclophosphamide for the treatment of a complement mediated disorder. In one embodiment, the disorder is an autoimmune disease. In one embodiment, the complement mediated disorder is, for example, rheumatoid arthritis, Granulomatosis with Polyangiitis (GPA) (Wegener's Granulomatosis), and Microscopic Polyangiitis (MPA). In one embodiment, the disorder is Lupus.

In one embodiment, an active compound or its salt or composition as described herein is dosed in combination with a conventional DLE treatment for the treatment of lupus to a subject in need thereof.

Examples of conventional DLE treatments include topical corticosteroid ointments or creams, such as triamcinolone acetonide, fluocinolone, flurandrenolide, betamethasone valerate, or betamethasone dipropionate. Resistant plaques can be injected with an intradermal corticosteroid. Other potential DLE treatments include calcineurin inhibitors such as pimecrolimus cream or tacrolimus ointment. Particularly resistant cases can be treated with systemic antimalarial drugs, such as hydroxychloroquine (PLAQUENIL).

In one embodiment, an active compound or its salt or composition as described herein may be provided in combination with methotrexate for the treatment of Lupus.

In one embodiment, an active compound or its salt or composition as described herein may be provided in combination with azathioprine for the treatment of Lupus.

In one embodiment, an active compound or its salt or composition as described herein may be provided in combination with a non-steroidal anti-inflammatory drug for the treatment of Lupus.

In one embodiment, an active compound or its salt or composition as described herein may be provided in combination with a corticosteroid for the treatment of Lupus.

In one embodiment, an active compound or its salt or composition as described herein may be provided in combination with a belimumab (Benlysta) for the treatment of Lupus.

In one embodiment, an active compound or its salt or composition as described herein may be provided in combination with hydroxychloroquine (Plaquenil) for the treatment of Lupus.

In one embodiment, an active compound or its salt or composition as described herein may be provided in combination with sifalimumab for the treatment of Lupus.

In one embodiment, an active compound or its salt or composition as described herein may be provided in combination with OMS721 (Omeros) for the treatment of a complement mediated disorder. In one embodiment, an active compound or its salt or composition as described herein may be provided in combination with OMS906 (Omeros) for the treatment of a complement mediated disorder. In one embodiment, the complement mediated disorder is, for example, thrombotic thrombocytopenic purpura (TTP) or aHUS.

In one embodiment, an active compound or its salt or composition as described herein may be provided in combination with an anti-inflammatory agent, immunosuppressive agent, or anti-cytokine agent for the treatment or prevention of cytokine or inflammatory reactions in response to the administration of pharmaceuticals or biotherapeutics (e.g. adoptive T-cell therapy (ACT) such as CAR T-cell therapy, or monoclonal antibody therapy). In one embodiment, an active compound or its salt or composition as described herein may be provided in combination with a corticosteroid, for example prednisone, dexamethasone, solumedrol, and methylprednisolone, and/or anti-cytokine compounds targeting, e.g., IL-4, IL-10, IL-11, IL-13 and TGFβ. In one embodiment, an active compound or its salt or composition as described herein may be provided in combination with an anti-cytokine inhibitor including, but are not limited to, adalimumab, infliximab, etanercept, protopic, efalizumab, alefacept, anakinra, siltuximab, secukibumab, ustekinumab, golimumab, and tocilizumab, or a combination thereof. Additional anti-inflammatory agents that can be used in combination with an active compound or its salt or composition as described herein include, but are not limited to, non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kdTNFR-IgG/etanercept (75 kD TNF receptor-IgG fusion protein; Immunex); 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline); DAB 486-IL-2 and/or DAB 389-IL-2 (IL-2 fusion proteins; Seragen); Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1RA (IL-1 receptor antagonist; Synergen/Amgen); anakinra (Kineret®/Amgen); TNF-bp/s-TNF (soluble TNF binding protein); R973401 (phosphodiesterase Type IV inhibitor); MK-966 (COX-2 Inhibitor); Iloprost, leflunomide (anti-inflammatory and cytokine inhibition); tranexamic acid (inhibitor of plasminogen activation); T-614 (cytokine inhibitor); prostaglandin E1; Tenidap (non-steroidal anti-inflammatory drug); Naproxen (non-steroidal anti-inflammatory drug); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine; Azathioprine; ICE inhibitor (inhibitor of the enzyme interleukin-1β converting enzyme); zap-70 and/or lck inhibitor (inhibitor of the tyrosine kinase zap-70 or lck); TNF-convertase inhibitors; anti-IL-12 antibodies; anti-IL-18 antibodies; interleukin-11; interleukin-13; interleukin-17 inhibitors; gold; penicillamine; chloroquine; chlorambucil; hydroxychloroquine; cyclosporine; cyclophosphamide; anti-thymocyte globulin; anti-CD4 antibodies; CD5-toxins; orally-administered peptides and collagen; lobenzarit disodium; Cytokine Regulating Agents (CRAB) HP228 and HP466 (Houghten Pharmaceuticals, Inc.); ICAM-1 antisense phosphorothioate oligo-deoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine).

In a specific embodiment, an active compound or its salt or composition as described herein may be provided in combination with a corticosteroid for the treatment or prevention of cytokine or inflammatory reactions in response to the administration of pharmaceuticals or biotherapeutics. In another embodiment, an active compound or its salt or composition as described herein may be provided in combination with etarnercept for the treatment or prevention of cytokine or inflammatory reactions in response to the administration of pharmaceuticals or biotherapeutics. In another embodiment, an active compound or its salt or composition as described herein may be provided in combination with tocilizumab for the treatment or prevention of cytokine or inflammatory reactions in response to the administration of pharmaceuticals or biotherapeutics. In another embodiment, an active compound or its salt or composition as described herein may be provided in combination with etarnercept and tocilizumab for the treatment or prevention of cytokine or inflammatory reactions in response to the administration of pharmaceuticals or biotherapeutics. In another embodiment, an active compound or its salt or composition as described herein may be provided in combination with infliximab for the treatment or prevention of cytokine or inflammatory reactions in response to the administration of pharmaceuticals or biotherapeutics. In another embodiment, an active compound or its salt or composition as described herein may be provided in combination with golimumab for the treatment or prevention of cytokine or inflammatory reactions in response to the administration of pharmaceuticals or biotherapeutics.

Combinations for Prophylactic or Concommitant Anti-Bacterial Therapy

In one aspect of the present invention, a method is provided for treating a host in need thereof that comprises administering an effective amount of a prophylactic anti-bacterial vaccine prior to administration of an active compound or its salt or composition for any of the disorders described herein. In another aspect of the present invention, a method is provided for treating a host in need thereof that comprises administering an effective amount of a prophylactic anti-bacterial drug, such as a pharmaceutical drug, prior to administration of an active compound or its salt or composition for any of the disorders described herein. In one aspect of the present invention, a method is provided for treating a host in need thereof that comprises administering an effective amount of an anti-bacterial vaccine after administration of an active compound or its salt or composition for any of the disorders described herein. In another aspect of the present invention, a method is provided for treating a host in need thereof that comprises administering an effective amount of an anti-bacterial drug, such as a pharmaceutical drug, after administration of an active compound or its salt or composition for any of the disorders described herein. In one embodiment, the disorder is PNH, C3G, or aHUS. In one embodiment, the host has received an organ or other tissue or biological fluid transplant. In one embodiment, the host is also administered eculizumab.

In one aspect of the present invention, an active compound or its salt or composition as described herein is administered to a host concomitantly to a subject following the prophylactic administration of a vaccine against a bacterial infection. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present invention, an active compound or its salt or composition as described herein is administered to a subject concomitantly with the prophylactic administration of a vaccine against a bacterial infection. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present invention, an active compound or its salt or composition as described herein is administered to a subject and, during the administration period of the compound or salt, a vaccine against a bacterial infection is administered to the subject. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present invention, the subject is administered an active compound or its salt or composition as described herein in combination with an antibiotic compound for the duration of Factor D inhibitor administration. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present invention, an active compound or its salt or composition as described herein is administered to a subject following the prophylactic administration of a vaccine against a bacterial infection, and in combination with an antibiotic compound for the duration of Factor D inhibitor administration. In one embodiment, the complement mediated disorder is PNH or aHUS. In one embodiment, the subject has received an organ or other tissue or biological fluid transplant. In one embodiment, the subject is also administered eculizumab. In one embodiment, the subject, prior to receiving an active compound or its salt or composition as described herein, is vaccinated against a bacterial infection caused by the bacterium *Neisseria meningitidis*. In one embodiment, the subject is vaccinated against a bacterial infection caused by the bacterium *Haemophilus influenzae*. In one embodiment, the *Haemophilus influenzae* is *Haemophilus influenzae* serotype B (Hib). In one embodiment, the subject is vaccinated against a bacterial infection caused by *Streptococcus pneumoniae*. In one embodiment, the subject is vaccinated against a bacterial infection caused by the bacterium *Nisseria meningitidis, Haemophilus influenzae*, or *Streptococcus pneumoniae*, or a combination of one or more of *Nisseria meningitidis, Haemophilus influenzae*, or *Streptococcus pneumoniae*. In one embodiment, the subject is vaccinated against a bacterial infection caused by the bacterium *Nisseria meningitidis, Haemophilus influenzae*, and *Streptococcus pneumoniae*.

In other embodiments, the subject is vaccinated against a bacterial infection caused by a bacterium selected from a Gram-negative bacterium. In one embodiment, the subject is vaccinated against a bacterial infection caused by a bacterium selected from a Gram-positive bacterium. In one embodiment, the subject is vaccinated against a bacterial infection caused by the bacterium *Nisseria meningitidis, Haemophilus influenzae*, or *Streptococcus pneunemoniae*, or a combination of one or more of *Nisseria meningitidis, Haemophilus influenzae*, or *Streptococcus pneumoniae*, and one or more of, but not limited to, *Bacillus anthracis, Bordetella pertussis, Clostridium tetani, Corynebacterium diphtheria, Coxiella burnetii, Mycobacterium tuberculosis, Salmonella typhi, Vibrio cholerae, Anaplasma phagocytophilum, Ehrlichia ewingii, Ehrlichia chaffeensis, Ehrlichia canis, Neorickettsia sennetsu, Mycobacterium leprae, Borrelia burgdorferi, Borrelia mayonii, Borrelia afzelii, Borrelia garinii, Mycobacterium bovis, Staphylococcus aureus, Streptococcus pyogenes, Treponema pallidum, Francisella tularensis, Yersinia pestis,*

In one embodiment, the subject is vaccinated with one or more vaccines selected from, but not limited to, typhoid vaccine, live (Vivotif Berna Vaccine, PaxVax), typhoid Vi polysaccharide vaccine (Typhim Vi, Sanofi), pneumococcal 23-polyvalent vaccine, PCV13 (Pneumovax 23, Merck), pneumococcal 7-valent vaccine, PCV7 (Prevnar, Pfizer), pneumococcal 13-valent vaccine, PCV13 (Prevnar 13, Pfizer), *Haemophilus* b conjugate (prp-t) vaccine (ActHIB, Sanofi; Hibrix, GSK), *Haemophilus* b conjugate (hboc) vaccine (HibTITER, Neuron Biotech), *Haemophilus* b conjugate (prp-omp) vaccine (PedvaxHIB, Merck), *Haemophilus* b conjugate (prp-t) vaccine/meningococcal conjugate vaccine (MenHibrix, GSK), *Haemophilus* b conjugate (prp-t) vaccine/meningococcal conjugate vaccine/Hepatitis B vaccine (Comvax, Merck), meningococcal polysaccharide vaccine (Menomune A/C/Y/W-135, Sanofi), meningococcal conjugate vaccine/diphtheria CRM197 conjugate (Menveo, GSK; Menactra, Sanofi), meningococcal group B vaccine (Bexsero, GSK; Trumenba, Pfizer), anthrax vaccine adsorbed (Biothrax, Emergent Biosolutions), tetanus toxoid (Te Anatoxal Berna, Hendricks Regional Health), *Bacillus* Calmette and Guérin, live, intravesical (TheraCys, Sanofi; Tice BCG, Organon), cholera vaccine, live, oral (Vachora, Sanofi; Dukoral, SBL Vaccines; ShanChol, Shantha Biotec; Micromedex, Truven Health), tetanus toxoids and diphtheria absorbed (Tdap; Decavac, Sanofi; Tenivac, Sanofi; td, Massachusetts Biological Labs), diphtheria and tetanus toxois and pertussis (DTap; Daptacel, Sanofi; Infanrix, GSK; Tripedia, Sanofi), diphtheria and tetanus toxois and pertussis/polio (Kinrix, GSK; Quadracel, Sanofi), diphtheria and tetanus toxois and pertussis tetanus/hepatitis B/polio (Pediarix, GSK), diphtheria and tetanus toxois and pertussis/polio, *Haemophilus* influenza type b (Pentacel, Sanofi), and/or diphtheria, and pertussis (Tdap; Boostrix, GSK; Adacel, Sanofi), or a combination thereof.

As described above, a subject receiving a compound of the present invention to treat a disorder is prophylactically administered an antibiotic compound in addition to a Factor D inhibitor described herein. In one embodiment, the subject is administered an antibiotic compound for the duration of administration of the active compound to reduce the development of a bacterial infection. Antibiotic compounds for concomitant administration with a Factor D inhibitor described herein can be any antibiotic useful in preventing or reducing the effect of a bacterial infection. Antibiotics are well known in the art and include, but are not limited to, amikacin (Amikin), gentamicin (Garamycin), kanamycin (Kantrex), neomycin (Neo-Fradin), netilmicin (Netromycin), tobramycin (Nebcin), paromomycin (Humatin), streptomycin, spectinomycin (Trobicin), geldanamycin, herbimycin, rifaximin (Xifaxan), loracarbef (Lorabid), ertapenem (Invanz), doripenem (Doribax), imipenem/cilastatin (Primaxin), meropenem (Merrem), cefadroxil (Duricef), cefazolin (Ancef), cefalotin/cefalothin (Keflin), cephalexin (Keflex), cefaclor (Distaclor), cefamandole (Mandol), cefoxitin (Mefoxin), cefprozil (Cefzil), cefuroxime (Ceftin, Zinnat), cefixime (Cefspan), cefdinir (Omnicef, Cefdiel), cefditoren (Spectracef, Meiact), cefoperazone (Cefobid), cefotaxime (Claforan), cefpodoxime (Vantin) ceftazidime (Fortaz), ceftibuten (Cedax), ceftizoxime (Cefizox), ceftriaxone (Rocephin), cefepime (Maxipime), ceftaroline fosamil (Teflaro), ceftobiprole (Zeftera), teicoplanin (Targocid), vancomycin (Vancocin), telavancin (Vibativ), dalbavancin (Dalvance), oritavancin (Orbactiv), clindamycin (Cleocin), lincomycin (Lincocin), daptomycin (Cubicin), azithromycin (Zithromax, Sumamed, Xithrone), clarithromycin (Biaxin), dirithromycin (Dynabac), erythromycin (Erythocin, Erythroped), roxithromycin, troleandomycin (Tao), telithromycin (Ketek), spiramycin (Rovamycine), aztreonam (Azactam), furazolidone (Furoxone), nitrofurantoin (Macrodantin, Macrobid), linezolid (Zyvox), posizolid, radezolid, torezolid, amoxicillin (Novamox, Amoxil), ampicillin (Principen), azlocillin, carbenicillin (Geocillin), cloxacillin (Tegopen), dicloxacillin (Dynapen), flucloxacillin (Floxapen), mezlocillin (Mezlin), methicillin (Staphcillin), nafcillin (Unipen), oxacillin (Prostaphlin), penicillin G (Pentids), penicillin V (Veetids (Pen-Vee-K), piperacillin (Pipracil), penicillin G (Pfizerpen), temocillin (Negaban), ticarcillin (Ticar), amoxicillin/clavulanate (Augmentin), ampicillin/sulbactam (Unasyn), piperacillin/tazobactam (Zosyn), ticarcillin/clavulanate (Timentin), bacitracin, colistin (Coly-Mycin-S), polymyxin B, ciprofloxacin (Cipro, Ciproxin, Ciprobay), enoxacin (Penetrex), gatifloxacin (Tequin), gemifloxacin (Factive), levofloxacin (Levaquin), lomefloxacin (Maxaquin), moxifloxacin (Avelox), nalidixic acid (NegGram), norfloxacin (Noroxin), ofloxacin (Floxin, Ocuflox), trovafloxacin (Trovan), grepafloxacin (Raxar), sparfloxacin (Zagam), temafloxacin (Omniflox), mafenide (Sulfamylon), sulfacetamide (Sulamyd, Bleph-10), sulfadiazine (Micro-Sulfon), silver sulfadiazine (Silvadene), sulfadimethoxine (Di-Methox, Albon), sulfamethizole (Thiosulfil Forte), sulfamethoxazole (Gantanol), sulfanilamide, sulfasalazine (Azulfidine), sulfisoxazole (Gantrisin), trimethoprim-sulfamethoxazole (Co-trimoxazole) (TMP-SMX) (Bactrim, Septra), sulfonamidochrysoidine (Prontosil), demeclocycline (Declomycin), doxycycline (Vibramycin), minocycline (Minocin), oxytetracycline (Terramycin), tetracycline (Sumycin, Achromycin V, Steclin), clofazimine (Lamprene), dapsone (Avlosulfon), capreomycin (Capastat), cycloserine (Seromycin), ethambutol (Myambutol), ethionamide (Trecator), isoniazid (I.N.H.), pyrazinamide (Aldinamide), rifampicin (Rifadin, Rimactane), rifabutin (Mycobutin), rifapentine (Priftin), streptomycin, arsphenamine (Salvarsan), chloramphenicol (Chloromycetin), fosfomycin (Monurol, Monuril), fusidic acid (Fucidin), metronidazole (Flagyl), mupirocin (Bactroban), platensimycin, quinupristin/dalfopristin (Synercid), thiamphenicol, tigecycline (Tigacyl), tinidazole (Tindamax Fasigyn), trimethoprim (Proloprim, Trimpex), and/or teixobactin, or a combination thereof.

In one embodiment, the subject is administered a prophylactic antibiotic selected from cephalosporin, for example, ceftriaxone or cefotaxime, ampicillin-sulbactam, Penicillin G, ampicillin, chloramphenicol, fluoroquinolone, aztreonam, levofloxacin, moxifloxacin, gemifloxacin, vancomycin, clindamycin, cefazolin, azithromycin, meropenem, ceftaroline, tigecycline, clarithromycin, moxifloxacin, trimethoprim/sulfamethoxazole, cefuroxime, axetil, ciprofloxacin, rifampin, minocycline, spiramycin, and cefixime, or a combination of two or more thereof.

Process of Preparation of Compounds of the Present Invention

Abbreviations

ACN Acetonitrile
Ac Acetyl
$Ac_2O$ Acetic anhydride
AcOEt, EtOAc ethyl acetate
AcOH Acetic acid
$Boc_2O$ di-tert-butyl dicarbonate
Bu Butyl
CAN Ceric ammonium nitrate
CBz Carboxybenzyl
CDI Carbonyldiimidazole
$CH_3OH$, MeOH Methanol
CsF Cesium fluoride
CuI Cuprous iodide
DCM, $CH_2Cl_2$ Dichloromethane
DIEA, DIPEA N,N-diisopropylethylamine
DMA N,N-dimethylacetamide
DMAP 4-Dimethylaminopyridine
DMF N,N-dimethylformamide
DMS Dimethyl sulfide
DMSO Dimethylsulfoxide
DPPA Diphenyl phosphoryl azide
EDCI 1-Ethyl-3-(3-dimethylaminopropyl)carbodiimide
Et Ethyl
$Et_3N$, TEA Triethylamine
EtOAc Ethylacetate
EtOH Ethanol
HATU 1-[Bis(dimethylamino)methylene]-1H-1,2,3-triazolo[4,5-b]pyridinium3-oxide hexafluorophosphate
HCl Hydrochloric acid
HOBT Hydroxybenzotriazole
iBu, i-Bu, isoBu Isobutyl
iPr, i-Pr, isoPr Isopropyl
$^iPr_2NEt$ N,N-diisopropylethylamine
$K_2CO_3$ Potassium carbonate
$K_2CO_3$ Potassium carbonate
LiOH Lithium hydroxide
Me Methyl
MeI Methyl iodide
Ms Mesyl
MsCl Mesylchloride
MTBE Methyl $^t$butylether
$Na_2SO_4$ Sodium sulfate
NaCl Sodium chloride
NaH Sodium hydride
$NaHCO_3$Sodium bicarbonate
NBS N-bromo succinimide
NCS N-chloro succinimide
$NEt_3$ Trimethylamine
NMP N-Methyl-2-pyrrolidone
PCC Pyridinium chlorochromate
Pd $(OAc)_2$ Palladium acetate
$Pd(dppf)Cl_2$ [1,1'-Bis(diphenylphosphino) ferrocene]dichloropalladium(II)
$Pd(PPh_3)_2Cl_2$ Bis(triphenylphosphine)palladium(II) dichloride
$Pd(PPh_3)_4$ Tetrakis(triphenylphosphine)palladium(0)
Pd/C Palladium on carbon
$Pd_2$ $(dba)_3$ Tris(dibenzylideneacetone)dipalladium(0)
PMB 4-Methoxybenzyl ether
$PPh_3$ Triphenylphosphine
Pr Propyl
Py, py Pyridine RT Room temperature
TBAF Tetra-n-butylammonium fluoride
TBAT Tetrabutylammonium difluorotriphenyl silicate
tBu, t-Bu tertbutyl
tBuOK Potassium tert-butoxide
TEA Trimethylamine
$Tf_2O$ Trifluoromethanesulfonic anhydride
TFA Trifluoroacetic acid
THF Tetrahydrofuran
TMS Trimethylsilane
TMSBr Bromotrimethylsilane
$t_R$ Retention time
Troc 2,2,2-Trichlorethoxycarbonyl chloride
$Zn(CN)_2$ Zinc cyanide General Methods All nonaqueous reactions were performed under an atmosphere of dry argon or nitrogen gas using anhydrous solvents. The progress of reactions and the purity of target compounds were determined using one of the two liquid chromatography (LC) methods listed below. The structure of starting materials, intermediates, and final products was confirmed by standard analytical techniques, including NMR spectroscopy and mass spectrometry.

LC Method A

Instrument: Waters Acquity Ultra Performance LC

Column: ACQUITY UPLC BEH C18 2.1×50 mm, 1.7 μm

Column Temperature: 40° C.

Mobile Phase: Solvent A: $H_2O$+0.05% FA; Solvent B: $CH_3CN$+0.05% FA

Flow Rate: 0.8 mL/min

Gradient: 0.24 min @ 15% B, 3.26 min gradient (15-85% B), then 0.5 min @ 85% B.

Detection: UV (PDA), ELS, and MS (SQ in EI mode)

LC Method B

Instrument: Shimadzu LC-2010A HT

Column: Athena, C18-WP, 50×4.6 mm, 5 μm

Column Temperature: 40° C.

Mobile Phase: Solvent A: $H_2O/CH_3OH$/FA=90/10/0.1; Solvent B: $H_2O/CH_3OH$/FA=10/90/0.1

Flow Rate: 3 mL/min

Gradient: 0.4 min @ 30% B, 3.4 min gradient (30-100% B), then 0.8 min @ 100% B

Detection: UV (220/254 nm)

LC Method C

Instrument: Agilent 1100/1200 series LC system with DAD detector

Column: Atlantis dC18 (250×4.6) mm, 5 μm

Column Temperature: Ambient

Mobile Phase A: 0.1% TFA in water, Mobile Phase B: Acetonitrile

Flow Rate: 1.0 mL/min

Gradient:

| | Time | | | | |
|---|---|---|---|---|---|
| | 0.0 | 15 | 20 | 23 | 30 |
| % B | 10 | 100 | 100 | 10 | 10 |

Detection: (210-400 nm)

LC Method D

Instrument: Shimadzu LC 20AD system with PDA detector

Column: Phenomenex Gemini NX C18 (150×4.6) mm, 5 μm

Column Temperature: Ambient

Mobile Phase A: 10 mM $NH_4OAC$ in water, Mobile Phase B: Acetonitrile

Flow Rate: 1.0 mL/min

Gradient:

| | Time | | | | |
|---|---|---|---|---|---|
| | 0.0 | 15 | 20 | 23 | 30 |
| % B | 10 | 100 | 100 | 10 | 10 |

Detection: (210-400 nm)

Example 1. General Route of Synthesis

A compound of the present invention can be prepared, for example, from a central core. In one embodiment, for example, the central core Structure 1 is an N-protected aminoacid where $X^1$ is nitrogen and PG=protecting group. In one embodiment, the central core is coupled to an amine to generate an amide of Structure 2 (wherein L-B includes a C(O)N moiety). Structure 2 can then be deprotected to generate Structure 3. Structure 3 is coupled to Structure 4 (A-COOH) to generate a second amide bond, forming a compound within Formula I. The chemistry is illustrated in Route 1.

Route 1

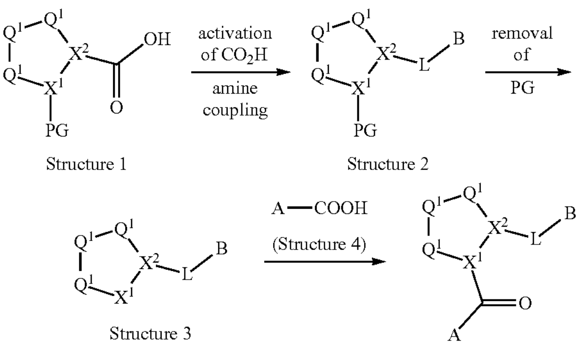

Structure 1

Structure 2

Structure 3

Formula I

In an alternative embodiment, central core Structure 5 is reacted with a heterocyclic or heteroaryl compound to generate a compound of Structure 6. In one embodiment, Structure 6 is deprotected to generate a carboxylic acid, Structure 7. In one embodiment, Structure 7 is coupled to an amine to generate a compound of Formula I. This chemistry is illustrated in Route 2.

Route 2

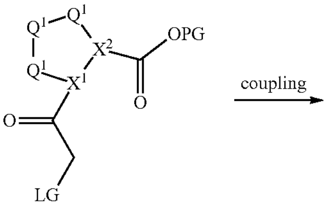

Structure 5

-continued

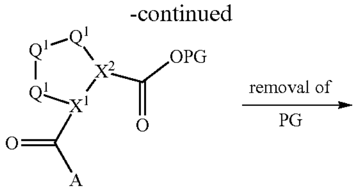

Structure 6

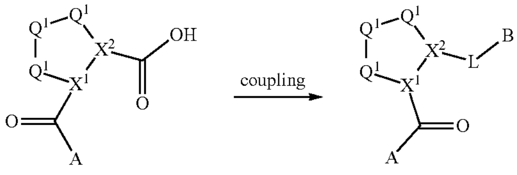

Structure 7

Formula I

In an alternative embodiment, Structure 8 is deprotected to generate an amine which is Structure 9. Structure 9 is then coupled to generate an amide which is Structure 6. Structure 6 is then deprotected to generate a carboxylic acid which is Structure 7. Structure 7 is then coupled to form the amide which falls within Formula I. The chemistry is illustrated in Route 3.

Route 3

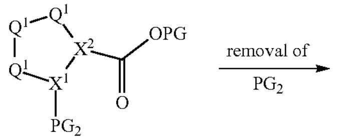

Structure 8

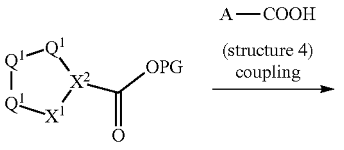

Structure 9

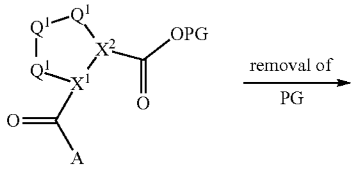

Structure 6

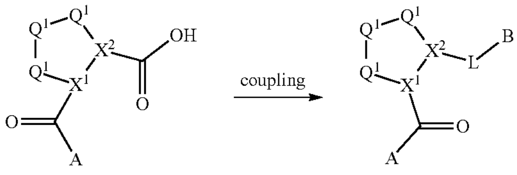

Structure 7

Formula I

In an alternate embodiment, a heteroaryl or aryl moiety, 4-1, is coupled to a central core to generate 4-2. The protected acid, 4-2 is deblocked to form the carboxylic acid, 4-3. The carboxylic acid is then coupled to form an amide (L-B) which is 4-4. The heteroaryl or aryl moiety, A', can then be further derivitized to add substituents at the $X^{11}$, $X^{12}$, $X^{13}$ and $X^{14}$ positions to generate compounds of Formula I. This chemistry is illustrated in Route 4.

Route 4

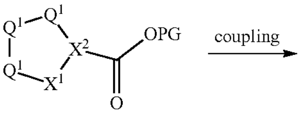

4-1

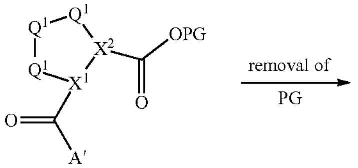

4-2

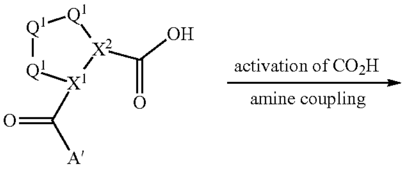

4-3

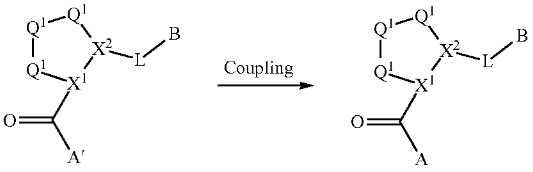

4-4

Formula I

In an alternate embodiment, Structure 5-1 is coupled to an acid, Structure 5-2, to generate Structure 5-3. The carboxylic acid, Structure 5-3, is deblocked to generate a carboxylic acid which is Structure 5-4. Carboxylic acid Structure 5-4 is coupled to an amine to form the product amide (L-B) which is a compound within Formula I. This chemistry is illustrated in Route 5.

Route 5

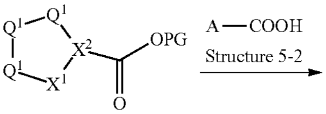

Structure 5-1

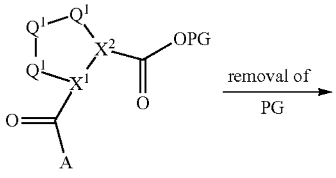

Structure 5-3

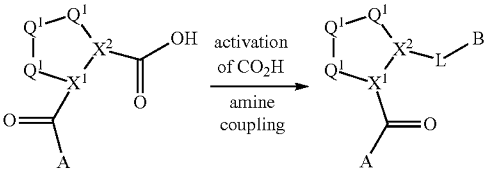

Structure 5-4

Formula I

In an alternate embodiment, a heteroaryl compound of Structure 10 is acylated to generate a compound of Structure 11, wherein LG is a leaving group. As an example, the leaving group can be a halide, for example bromide. Structure 11 is coupled to Structure 12 to generate Structure 13. In some embodiments, $LG_1$ is a leaving group. In some embodiments, the $LG_1$ is a halide. Structure 13 is coupled to an aryl, heteroaryl or heterocylic compound to generate Structure 14. In some embodiments, Structure 13 is treated with an aryl, heteroaryl or heterocylic boronic acid, an organometallic catalyst, a base and an organic solvent. In some embodiments, the organometallic catalyst is tetrakis (triphenylphosphine)palladium (0). In some embodiments, the base is cesium carbonate. In some embodiments, the organic solvent is DMF. Structure 14 is treated with an organic acid such as, but not limited to, trifluoroacetic acid to generate Structure 15. Structure 15 is coupled to Structure 3 from Route 1 to generate a compound within Formula I. This chemistry is illustrated in Route 6.

Route 6

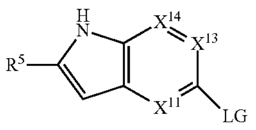

Structure 10

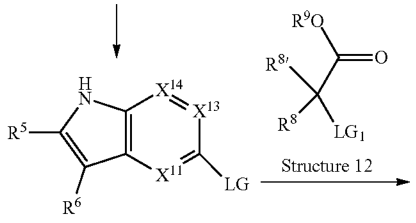

Structure 12

Structure 11

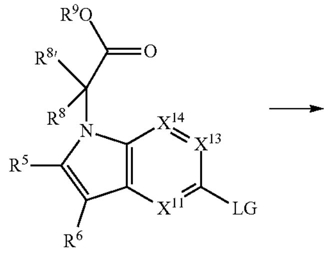

Structure 13

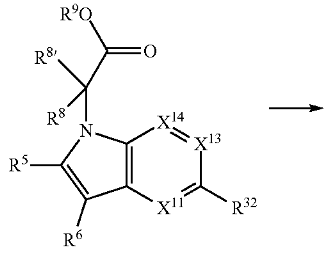

Structure 14

-continued

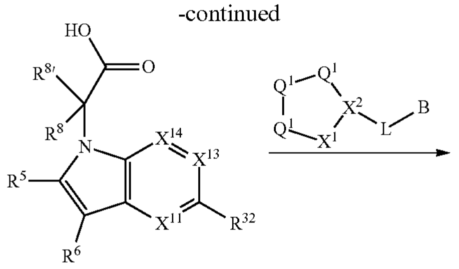

Structure 15

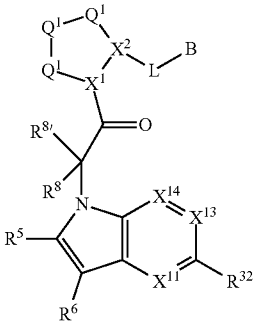

Formula I

In an alternate embodiment, a heteroaryl compound of Structure 17 is acylated to generate a compound of Structure 18, wherein LG is a leaving group. As an example, the leaving group can be a halide, for example bromide. Structure 18 is coupled to an activated ester, Structure 12 from Route 6, wherein $LG_1$ can be a halogen to generate Structure 19.

Structure 19 is coupled to a compound to generate Structure 20. In some embodiments, Structure 19 is treated with an aryl, heteroaryl or heterocylic boronic acid, an organometallic catalyst, a base and an organic solvent. In some embodiments, the organometallic catalyst is tetrakis(triphenylphosphine)palladium (0). In some embodiments, the base is cesium carbonate. In some embodiments, the organic solvent is DMF. Structure 20 is treated with an organic acid such as, but not limited to, trifluoroacetic acid to generate Structure 21. Structure 21 is coupled to Structure 3 from Route 1 to generate a compound within Formula I. This chemistry is illustrated Route 7

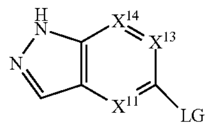

Structure 17

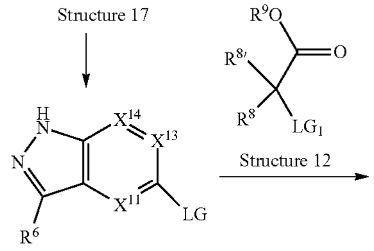

Structure 12

Structure 18

-continued

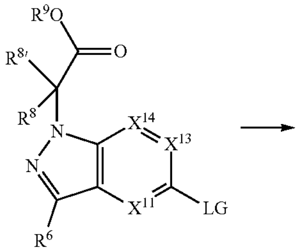

Structure 19

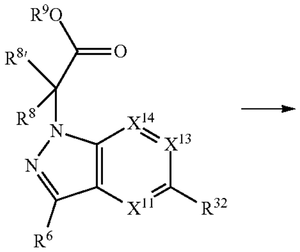

Structure 20

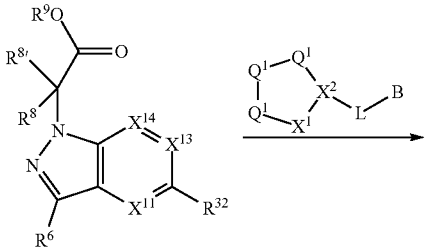

Structure 21

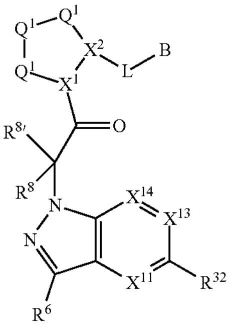

Formula I

In an alternate embodiment, a heteroaryl compound of Structure 8-1 is acylated to generate a compound of Structure 8-2, wherein LG is a leaving group. As an example, the leaving group can be a halide, for example bromide. Structure 8-2 is coupled to Structure 8-3 to generate Structure 8-4. In some embodiments, $LG_1$ is a leaving group. In some embodiments, the $LG_1$ is a halide.

Structure 8-4 is coupled to an aryl, heteroaryl or heterocylic compound to generate Structure 8-5. In some embodiments, Structure 8-4 is treated with an aryl, heteroaryl or heterocylic boronic acid, an organometallic catalyst, a base and an organic solvent. In some embodiments, the organometallic catalyst is tetrakis(triphenylphosphine)palladium (0). In some embodiments, the base is cesium carbonate. In some embodiments, the organic solvent is DMF. Structure 8-5 is treated with an organic acid such as, but not limited to, trifluoroacetic acid to generate Structure 8-6. Structure 8-6 is coupled to Structure 3 from Route 1 to generate a compound within Formula I. This chemistry is illustrated in Route 8.

Route 8

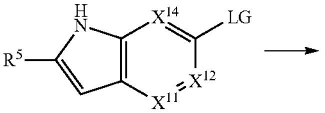

Structure 8-1

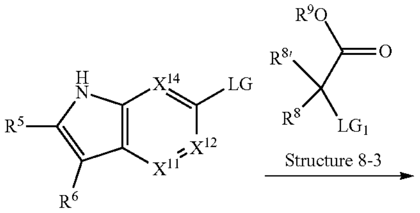

Structure 8-3

Structure 8-2

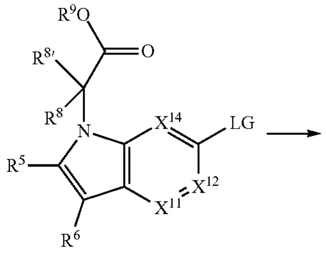

Structure 8-4

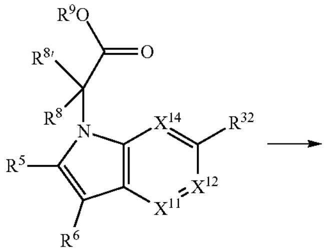

Structure 8-5

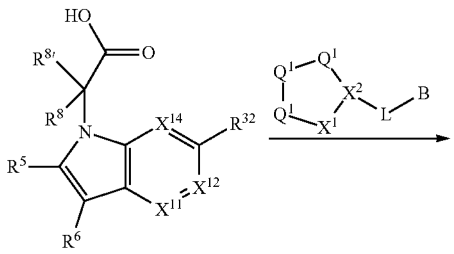

Structure 8-6

-continued

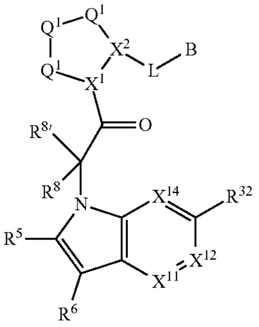

Formula I

In an alternate embodiment, a compound of Structure 9-1 is acylated to generate a compound of Structure 9-2, wherein LG is a leaving group. As an example, the leaving group can be a halide, for example bromide. Structure 9-2 is coupled to an activated ester, Structure 9-3, wherein $LG_1$ can be a halide to generate Structure 9-4. Structure 9-4 is coupled to an aryl, heteroaryl or heterocylic compound to generate Structure 9-5. In some embodiments, Structure 9-4 is treated with c boronic acid, an organometallic catalyst, a base and an organic solvent. In some embodiments, the organometallic catalyst is tetrakis(triphenylphosphine)palladium (0). In some embodiments, the base is cesium carbonate. In some embodiments, the organic solvent is DMF. Structure 9-5 is treated with an organic acid such as, but not limited to, trifluoroacetic acid to generate Structure 9-6. Structure 9-6 is coupled to Structure 3 from Route 1 to generate a compound within Formula I. This chemistry is illustrated in Route 9.

Route 9

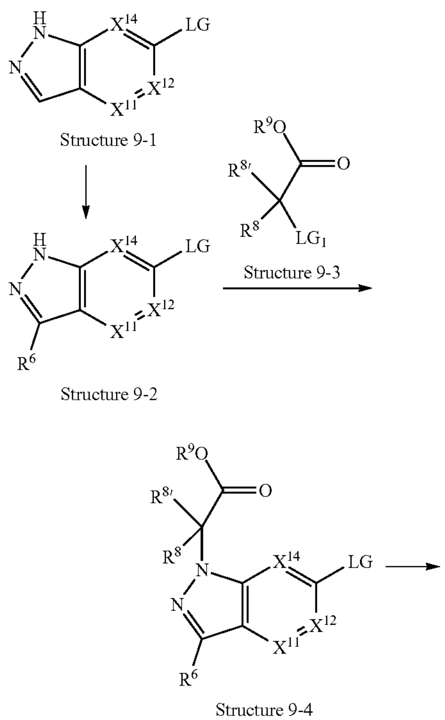

Structure 9-1

Structure 9-3

Structure 9-2

Structure 9-4

-continued

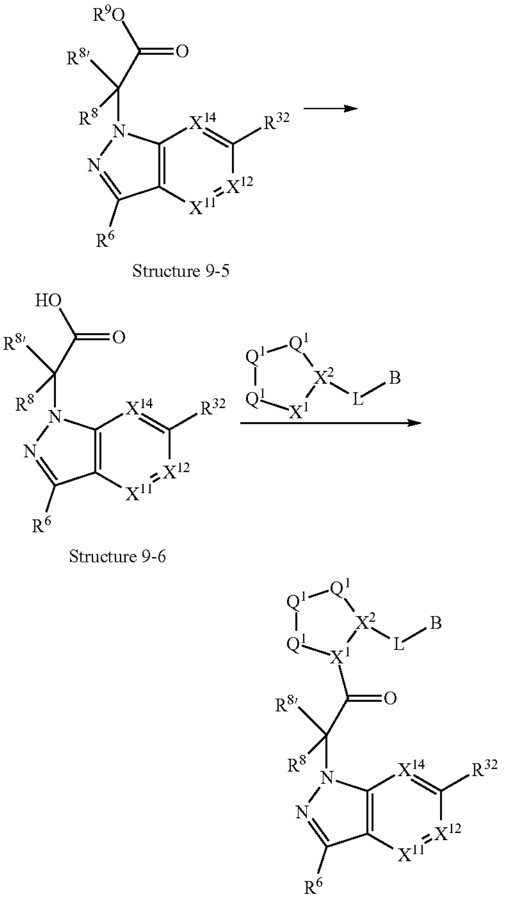

Structure 9-5

Structure 9-6

Formula I

In an alternate embodiment, Structure 10-1 is coupled to an amine to generate an amide (L-B), and Structure 10-2. Structure 10-2, is coupled to an amine to generate compounds within Formula I. This chemistry is illustrated in Route 10.

Route 10

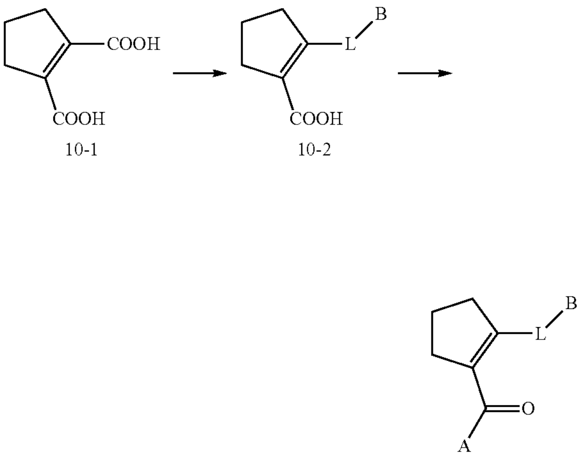

10-1

10-2

Formula I

Example 2. Examples of Central Synthons
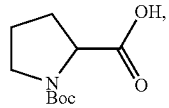
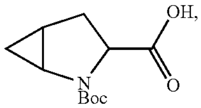
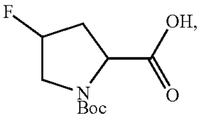
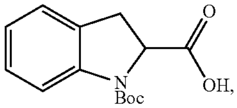
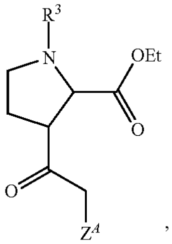
,
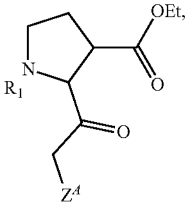
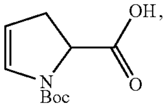
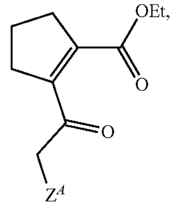
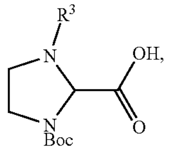
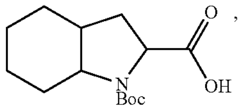
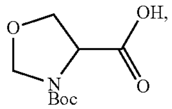
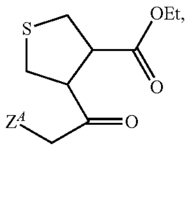
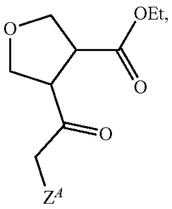
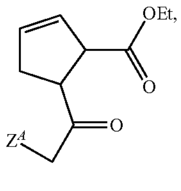
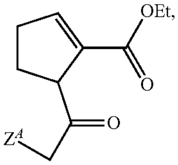
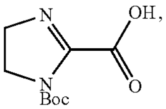
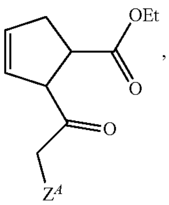
,
-continued
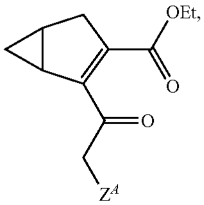
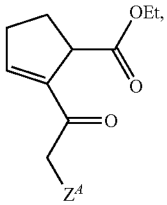
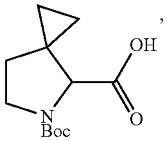
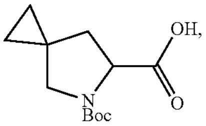
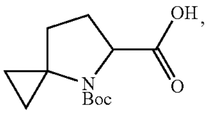
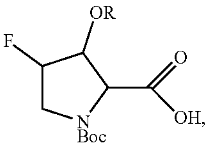
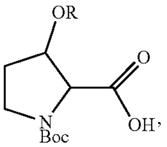
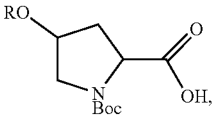
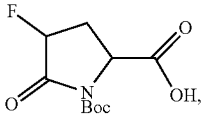
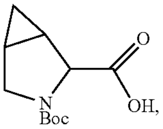
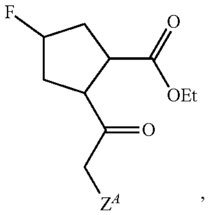
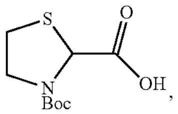
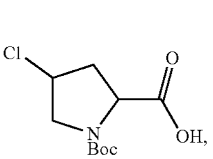
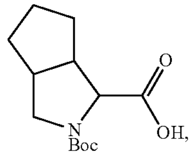
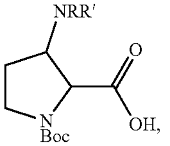
and
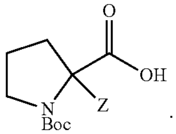
.
$Z^A$ is halogen.
In one embodiment, deuterated L-proline synthons are disclosed. Deuterated synthons include, but are not limited to, for example, the following compounds:

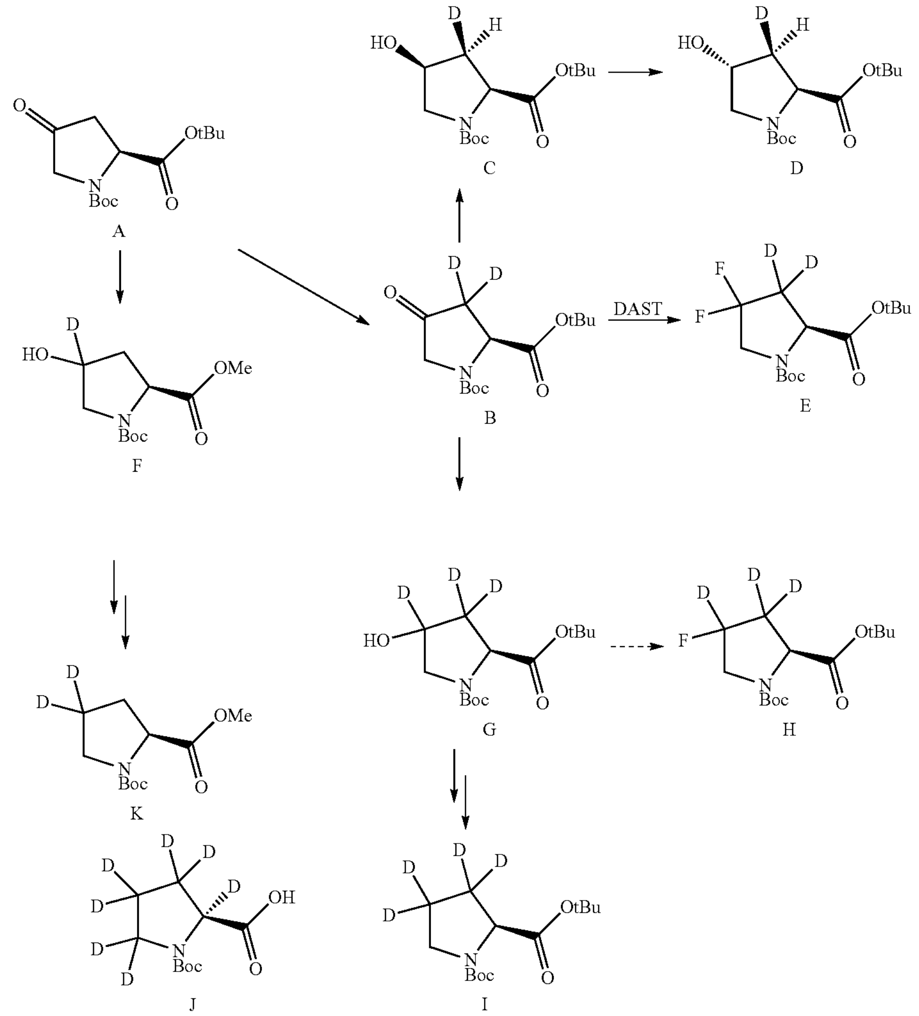

Structure A can be treated with deuterium oxide to generate Structure B. See, Barraclough, P. et al. Tetrahedron Lett. 2005, 46, 4653-4655; Barraclough, P. et al. Org. Biomol. Chem. 2006, 4, 1483-1491 and WO 2014/037480 (p. 103). Structure B can be reduced to generate Structure C. See, Barraclough, P. et al. Tetrahedron Lett. 2005, 46, 4653-4655; Barraclough, P. et al. Org. Biomol. Chem. 2006, 4, 1483-1491. Structure C can be treated with Mitsunobu reaction conditions to generate Structure D. Structure B can be treated with DAST to generate Structure E. See, WO 2014/037480. Structure A can be treated with sodium borodeuteride to generate Structure F. See, Dormoy, J.-R.; Castro, B. *Synthesis* 1986, 81-82. Compound F can be used to generate Structure K. See, Dormoy, J.-R.; Castro, B. *Synthesis* 1986, 81-82. Structure B can be treated with a deuterated reducing agent, for example sodium borodeuteride to generate Structure G. Structure G can be treated with DAST to generate Structure H. Structure F can be used to generate Structure K. See, Dormoy, J.-R.; Castro, B. *Synthesis* 1986, 81-82. Structure G can be used to generate Structure I. Structure J can be prepared according to Hruby, V. J. et al. *J. Am. Chem. Soc.* 1979, 101, 202-212. Structures A-J can be used to prepare compounds of Formula I.

Example 3. Preparation of Central-L-B Synthons (1a)

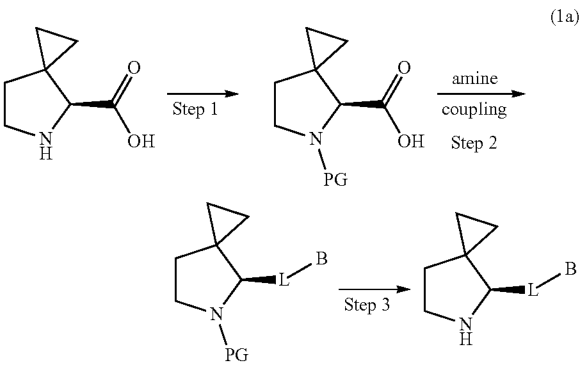

(1b)

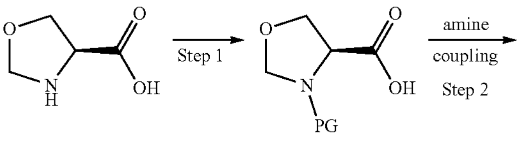

-continued

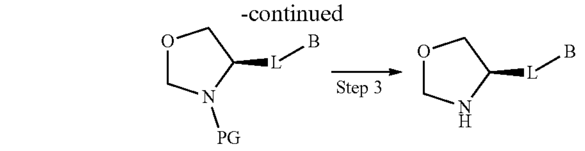

(1c)

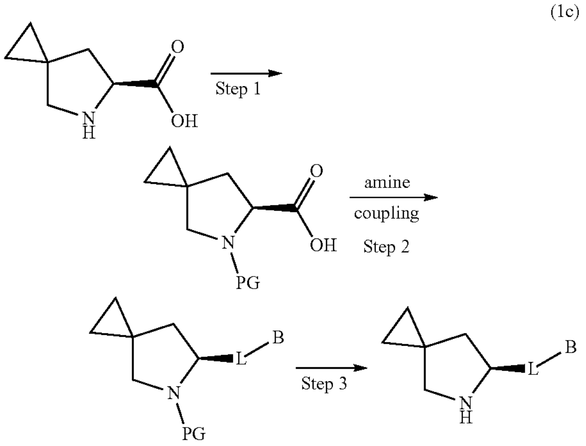

Routes 1a, 1b and 1c.

In Route 1a, 5-azaspiro[2.4]heptane-4,5-dicarboxylic acid, 5-(1,1-dimethylethyl) ester, (4S)—, CAS 209269-08-9, can be prepared as described in Tandon, M. et al. Bioorg. Med. Chem. Lett. 1998, 8, 1139-1144. In Step 2, the protected azaspiro[2.4]heptane is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

In Route 1b, (4S) 4-oxazolidinecarboxylic acid, hydrochloride is treated with an amine protecting reagent. In one embodiment, the amine protecting reagent is di-tert-butyl dicarbonate. In another embodiment, 3,4-oxazolidinedicarboxylic acid, 3-(1,1-dimethylethyl) ester, (4S)—, is commercially available from JPM2 Pharmaceuticals. In one embodiment the reaction is carried out in an organic solvent in the presence of a base. In one embodiment, the organic solvent is acetonitrile. In one embodiment, the base is 4-dimentylaminopyridine (DMAP). In Step 2, the protected 4-oxazolidinecarboxylic acid is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

In Route 1c, (S)-5-(tert-Butoxycarbonyl)-5-azaspiro[2.4]heptane-6-caboxylic acid, CAS 1129634-44-1, is commercially available from Ark Pharm. In Step 2, the carboxylic acid is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

2a

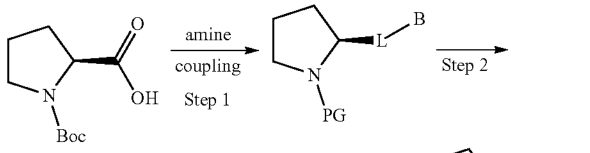

2b

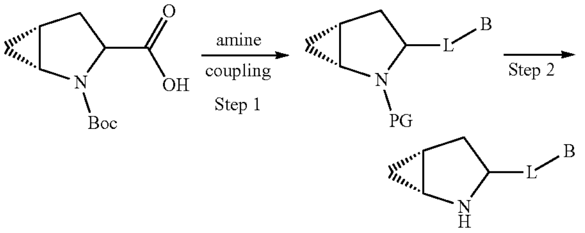

2c

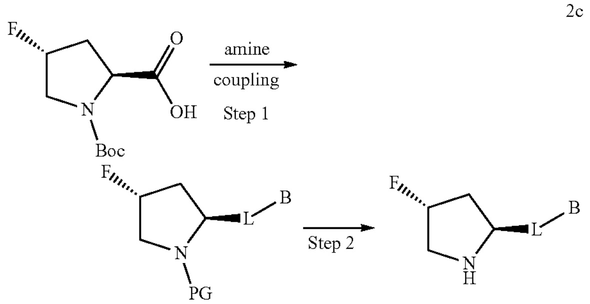

2d

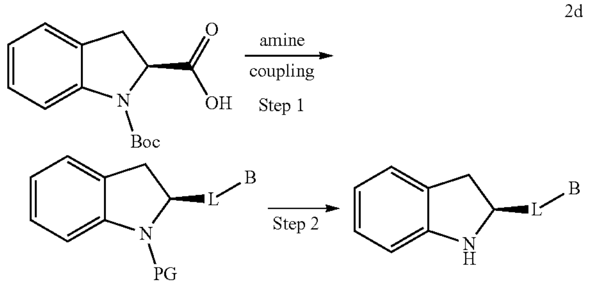

Routes 2a, 2b, 2c, and 2d.

In Route 2a, commercially available Boc-L-proline is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2b, commercially available (1R, 3S, 5R)-2-[(tert-butoxy)carbonyl]-2-azabicyclo[3.1.0]hexane-3-carboxylic acid, from Enamine, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2c, commercially available (2S,4R)-1-(tert-butoxycarbonyl)-4-fluoropyrrolidine-2-carboxylic acid, from Manchester Organics, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2d, commercially available (S)-1-(tert-butoxycarbonyl)indoline-2-carboxylic acid, from Chem-Impex, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane. This chemistry is illustrated in Scheme 2.

Additional starting materials that can readily be converted to Central-L-B-Synthons include, but are not limited to: (S)-1-(tert-butoxycarbonyl)-2,3-dihydro-1H-pyrrole-2-carboxylic acid, CAS 90104-21-5, available from Ark Pharm; cyclopent-1-ene-1,2-dicarboxylic acid, CAS 3128-15-2, purchased from Ark Pharm; imidazole, 1H-imidazole-1,2-dicarboxylic acid, 1-(1,1-dimethylethyl) 2-ethyl ester, CAS 553650-00-3, commercially available from FCH Group; Boc-L-octahydroindole-2-carboxylic acid can be purchased from Chem Impex. The compound,

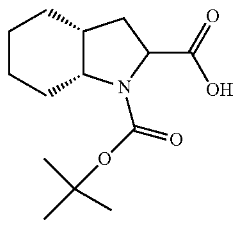 [SMILES: CC(C)(C)OC(=O)N1C(C(=O)O)C[C@H]2CCCC[C@H]21]

can be prepared according to the procedures disclosed in WO 2004/111041; (S)-Boc-5-oxopyrrolidine-2-carboxylic acid is available from the Aldrich Chemical Co.; (1S,2S,5R)-3-(tert-butoxycarbonyl)-3-azabicyclo[3.3.0]hexane-2-carboxylic acid is available from Ark Pharm; (S)-3-Boc-thiazolidine-2-carboxylic acid is available from Alfa Aesar; (2S,4R)-1-(tert-butoxycarbonyl)-4-chloropyrrolidine-2-carboxylic acid is available from Arch Bioscience; (1S,3aR,6aS)-2-(tert-butoxycarbonyl)octahydrocyclopenta[c]pyrrole-1-carboxylic acid is available from Ark Pharm; 1,2-pyrrolidinedicarboxylic acid, 3-[[(phenylmethoxy)carbonyl]amino]-, 1-(1,1-dimethylethyl) ester, (2S,3R) can be prepared as disclosed in WO 2004/007501. The Cbz group can be removed and the amino group can be alkylated to generate central core compounds of the present invention.

The compound

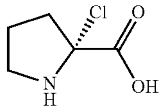

can be prepared as disclosed by Braun, J. V.; Heymons, Albrecht Berichte der Deutschen Chemischen Gesellschaft [Abteilung] B: Abhandlungen (1930) 63B, 502-7.

The compounds (2S,3S,4S)-4-fluoro-3-methoxy-pyrrolidine-1,2-dicarboxylic acid 1-tert-butyl ester and (2R,3R,4R)-3-fluoro-4-methoxy-pyrrolidine-1,2-dicarboxylic acid 1-tert-butyl ester can be prepared as a mixture according to WO 2012/093101 to Novartis and the regioisomers can be ultimately separated once coupled to generate the central core-L-B synthons. The compound (S)-Boc-5-oxopyrrolidine-2-carboxylic acid is available from the Aldrich Chemical Co.

Example 4. Synthesis of L-B Moieties

Scheme 4-1

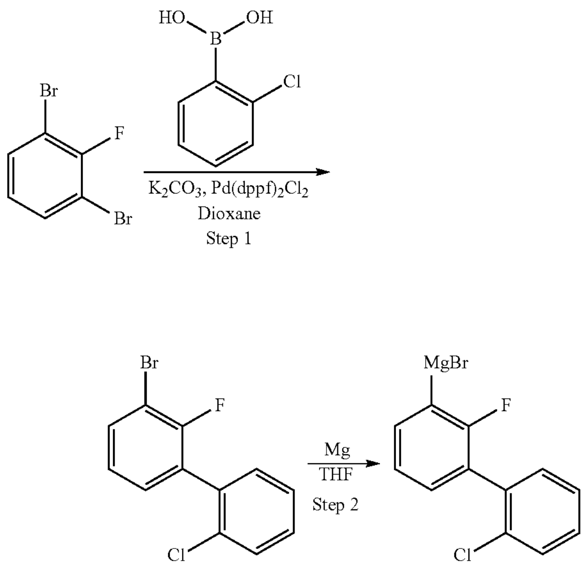

-continued

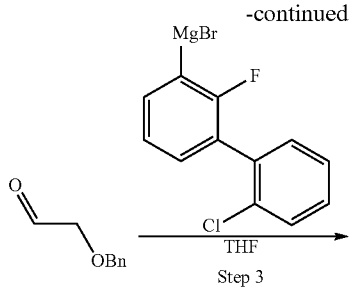

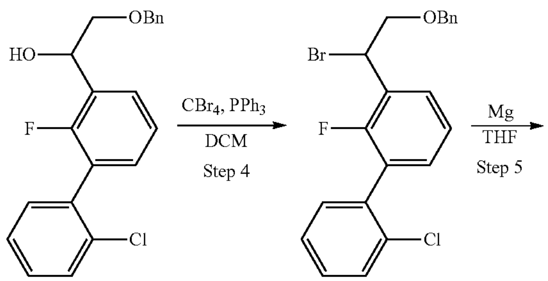

-continued

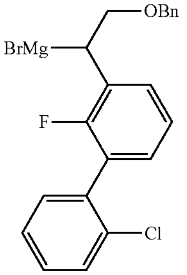

Scheme 4-1: In Step 1 the appropriately substituted dibromo species is coupled with an appropriate boronic acid as known in the art to form a mixture of biaryl and triaryl products from which the desired biaryl compound is isolated. In Step 2 the appropriately substituted biaryl species is converted to the Grignard reagent with activated magnesium. In Step 3 the appropriately substituted aldehyde is treated with the previously prepared Grignard reagent to form an alcohol. In Step 4 the appropriately substituted alcohol is converted to a bromide as known in the art with carbon tetrabromide and triphenyl phosphine. In Step 5 the appropriately substituted bromide is converted to the Grignard reagent with activated magnesium.

Example 5. Synthesis of C-L-B Moieties

Scheme 5-1

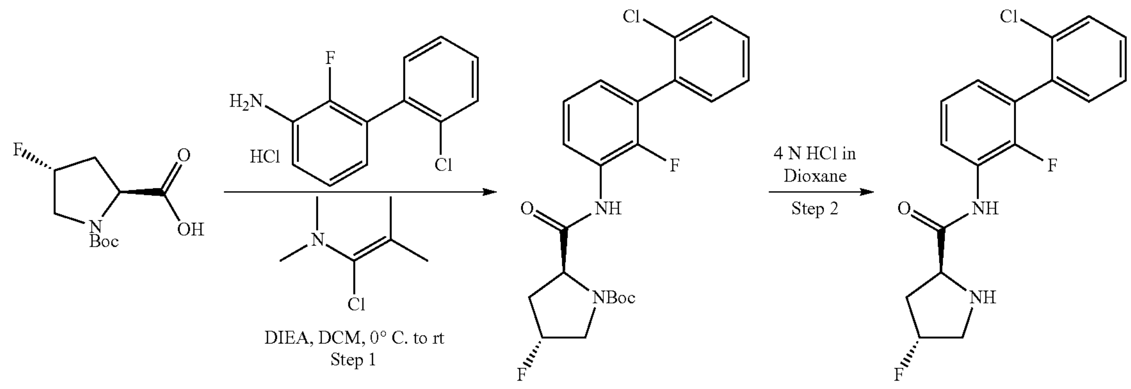

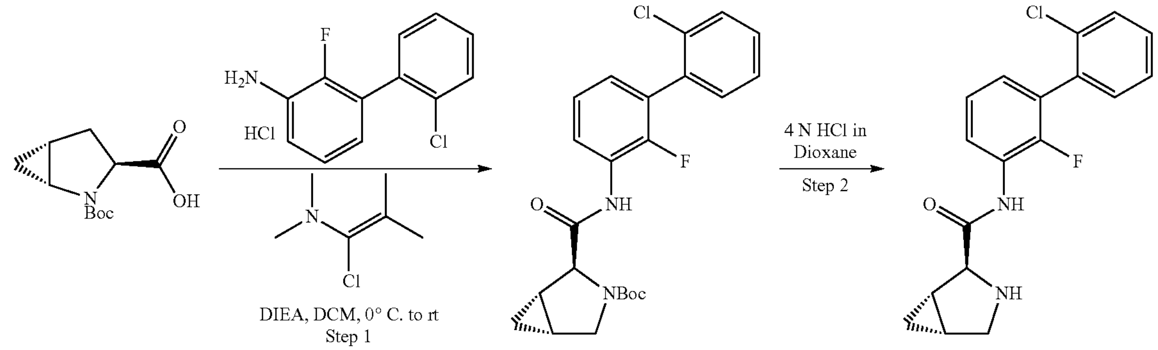

-continued
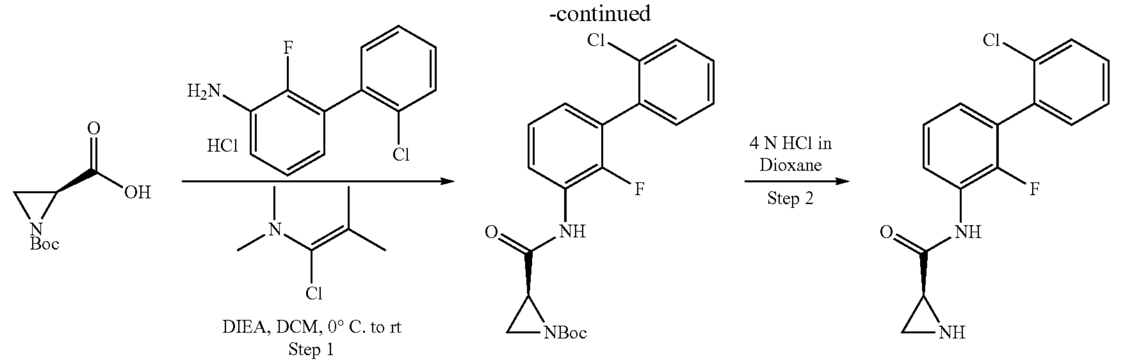
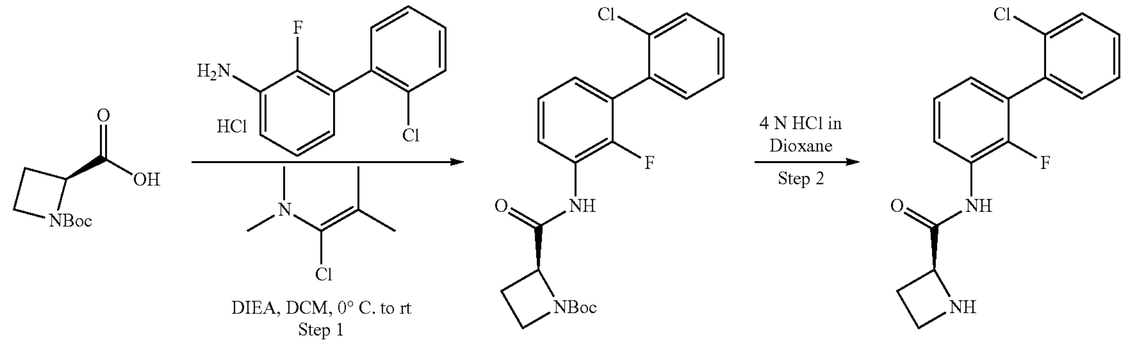
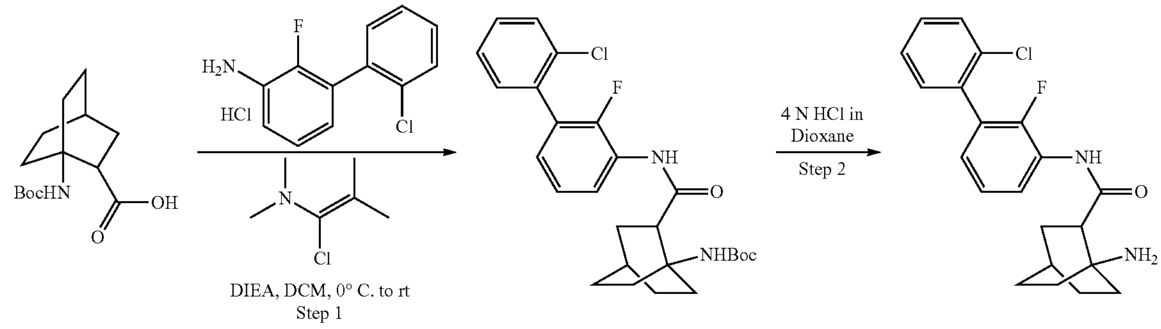
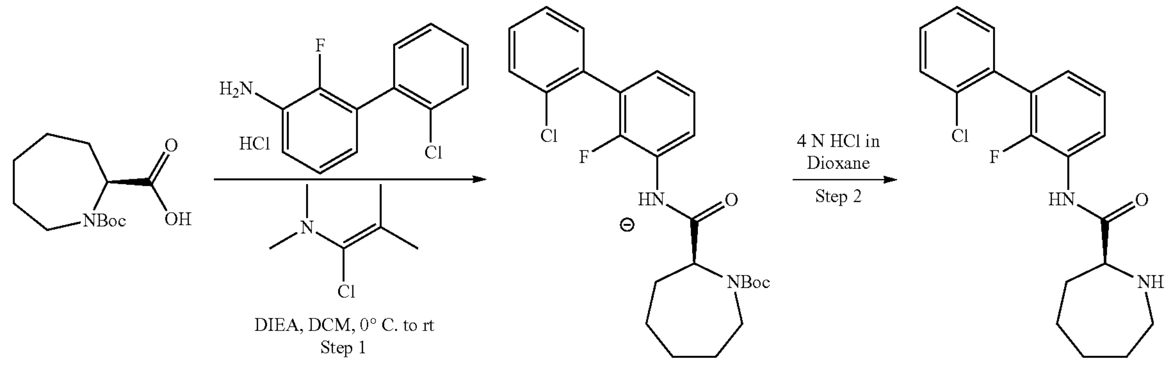

-continued

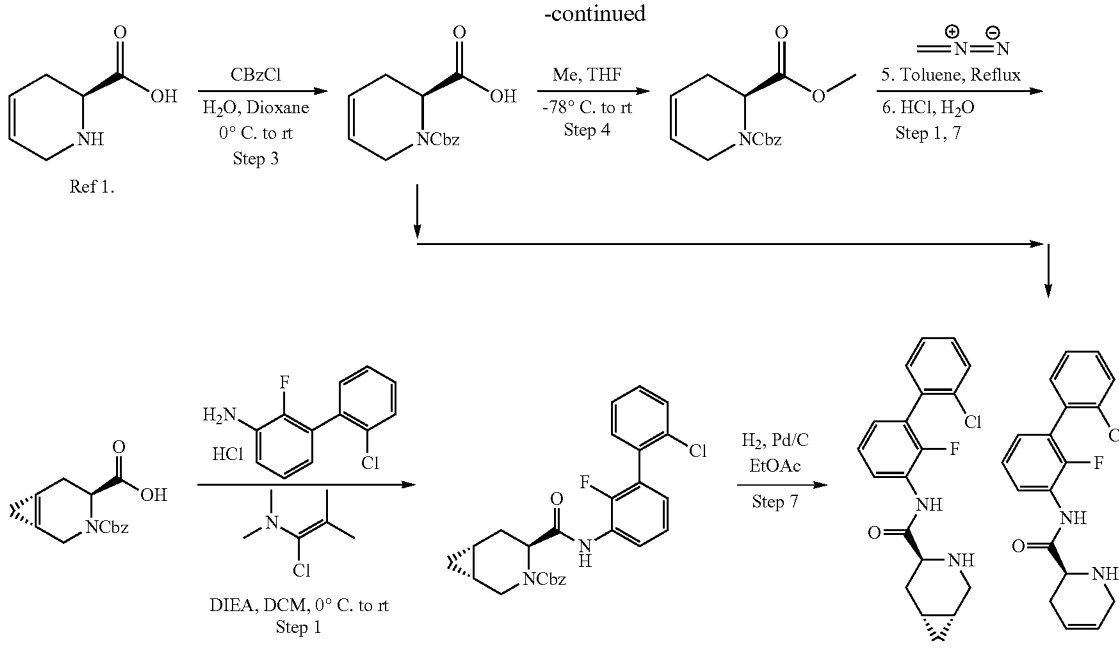

1. Herdeis, C., et al. (1994). Liebigs Ann. Chem.(11): 1117-1120.

Scheme 5-1: In Step 1 the appropriately substituted carboxylic acid is coupled to the appropriately substituted amine as known in the art to form an amide. In Step 2 the appropriately substituted Boc-protected species is deprotected with acid to liberate the free amine. In Step 3 the appropriately substituted amine is Cbz-protected as known in the art to form a protected carboxylic acid. In Step 4 the appropriately substituted carboxylic acid can be orthogonally protected as known in the art to form an ester. In Step 5 the appropriately substituted and protected alkene is subjected to a carbene to form a bicyclic ring. In Step 6 the appropriately substituted ester is saponified with acid to liberate the carboxylic acid. In Step 7 the appropriately substituted Cbz-protected species is deprotected with hydrogen to liberate the free amine.

Scheme 5-2

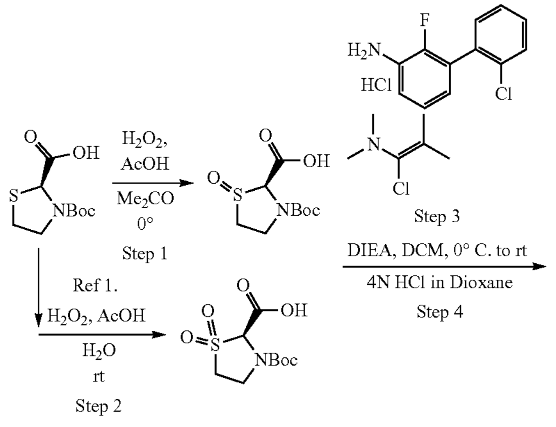

-continued

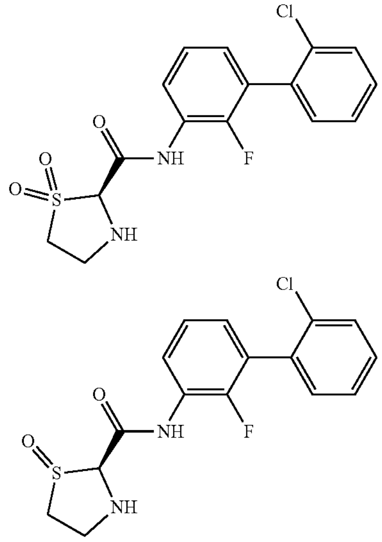

1. Vasil'eva. T. P. (2003). Russ. Chem. Bull. 52(4): 958-960.

Scheme 5-2: In Step 1 the appropriately substituted sulfide is oxidized to a sulfoxide as known in the art. Alternatively, in Step 2 the appropriately substituted sulfide is oxidized to a sulfone as known in the art. In Step 3 the appropriately substituted carboxylic acid is coupled to the appropriately substituted amine as known in the art to form an amide. In Step 4 the appropriately substituted Boc-protected species is deprotected with acid to liberate the free amine.

Scheme 5-3

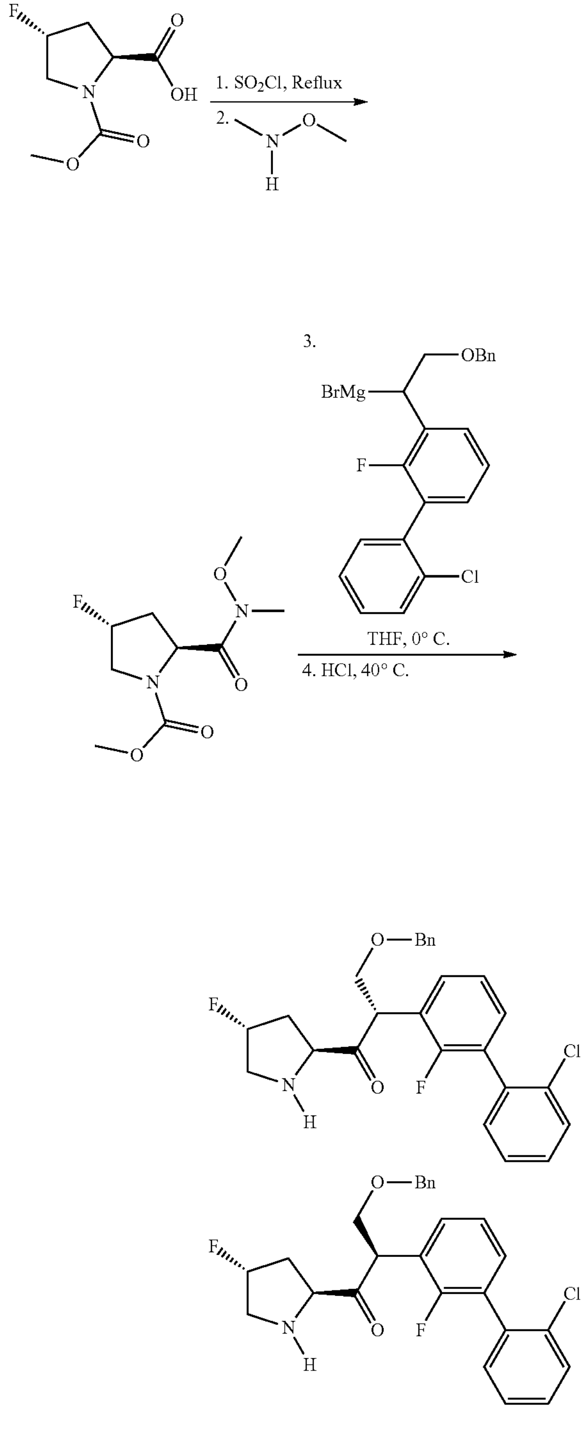

Scheme 5-3: In Step 1 the appropriately substituted carboxylic acid is converted to the acyl chloride as known in the art. In Step 2 the appropriately substituted acyl chloride is converted to the Weinreb amide as known in the art. In Step 3 the appropriately substituted Weinreb amide is reacted with a Grignard reagent to afford a ketone. The synthesis of complex Grignard reagents is described in Example 4. In Step 4 the appropriately substituted carbamate protected amine is deprotected to liberate the free amine.

Scheme 5-4

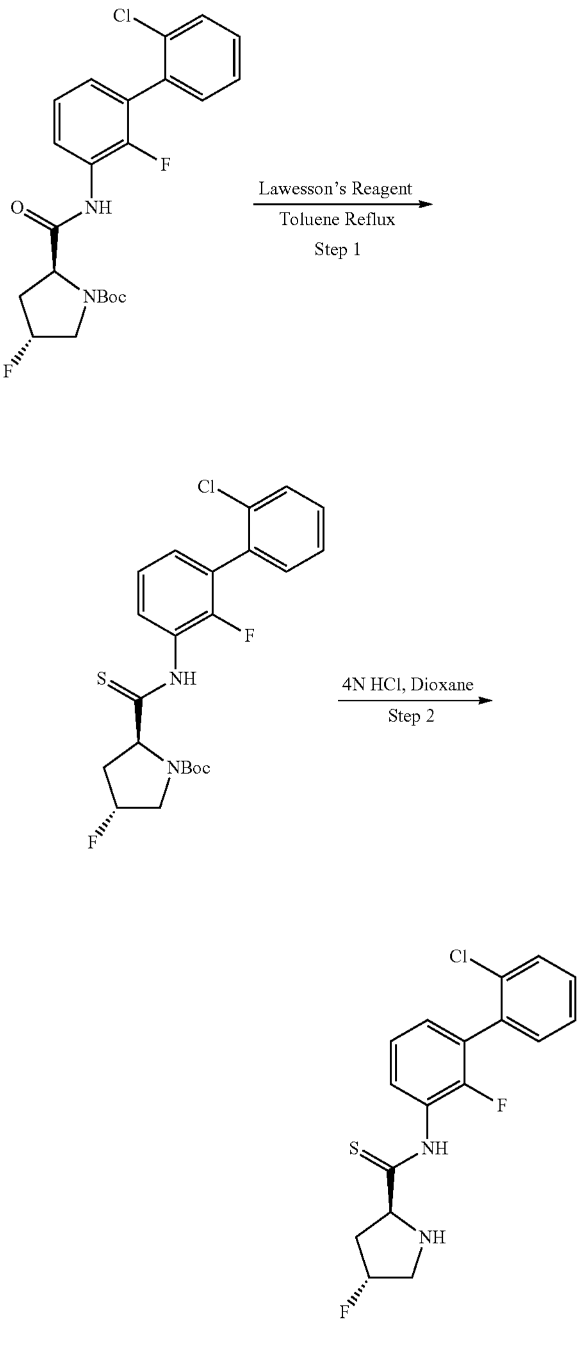

Scheme 5-4: In Step 1 the appropriately substituted amide is converted to a thioamide with Lawesson's reagent. In Step 2 the appropriately substituted Boc-protected amine is deprotected with acid to liberate the free amine.

Scheme 5-5

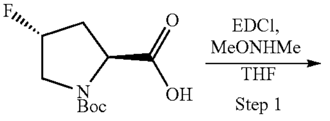

-continued

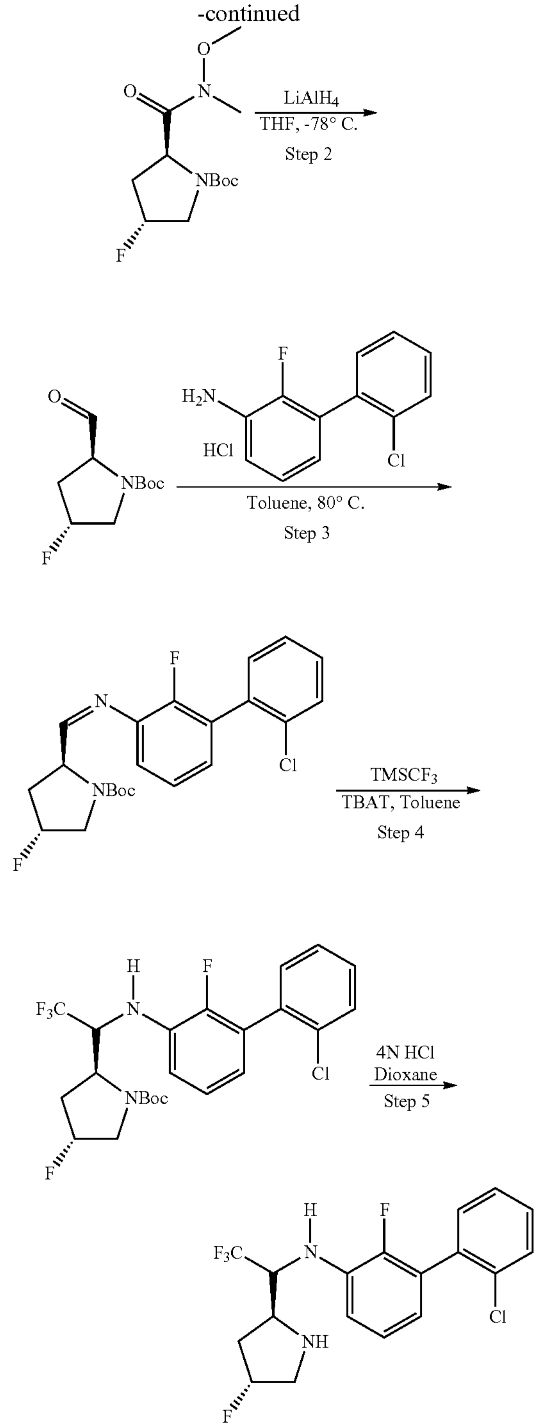

Scheme 5-5: In Step 1 the appropriately substituted carboxylic acid is converted to a Weinreb amide as known in the art. In Step 2 the appropriately substituted Weinreb amide is reduced as known in the art to afford an aldehyde. In Step 3 the appropriately substituted aldehyde is subjected to an amine to form a Schiff base which is subsequently quenched in Step 4. In Step 4 the appropriately substituted Schiff base is subjected to an appropriate nucleophile to form a complex amine. In Step 5 the appropriately substituted Boc-protected species is deprotected with acid to liberate the free amine.

Scheme 5-6

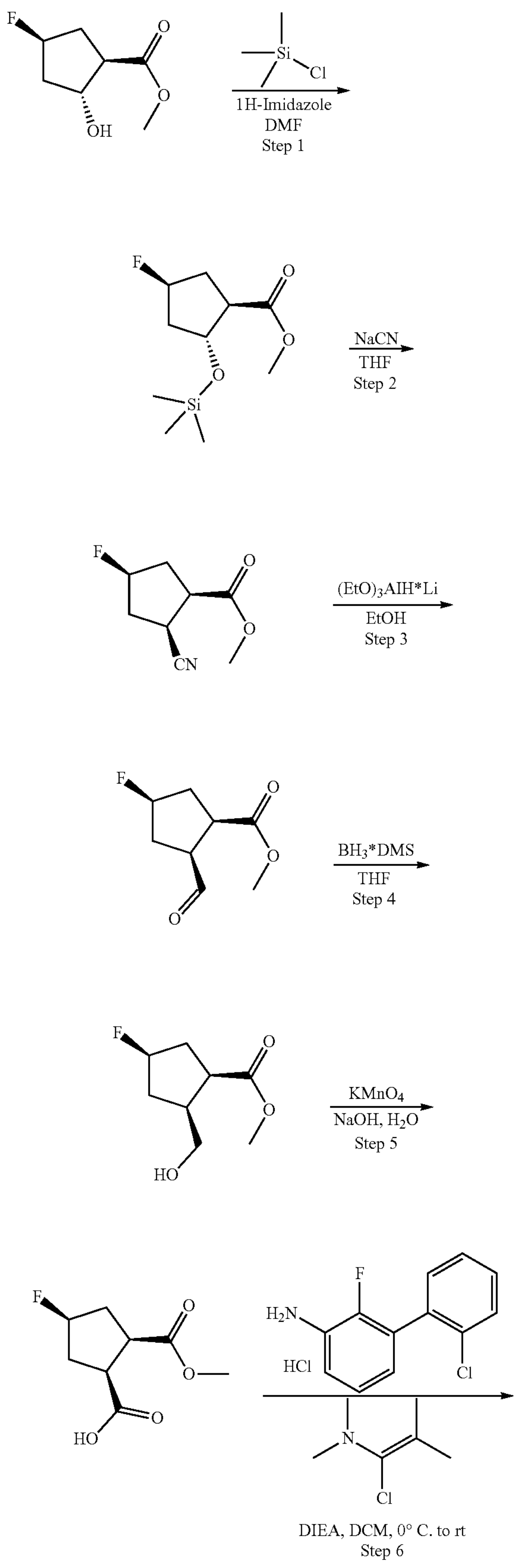

-continued

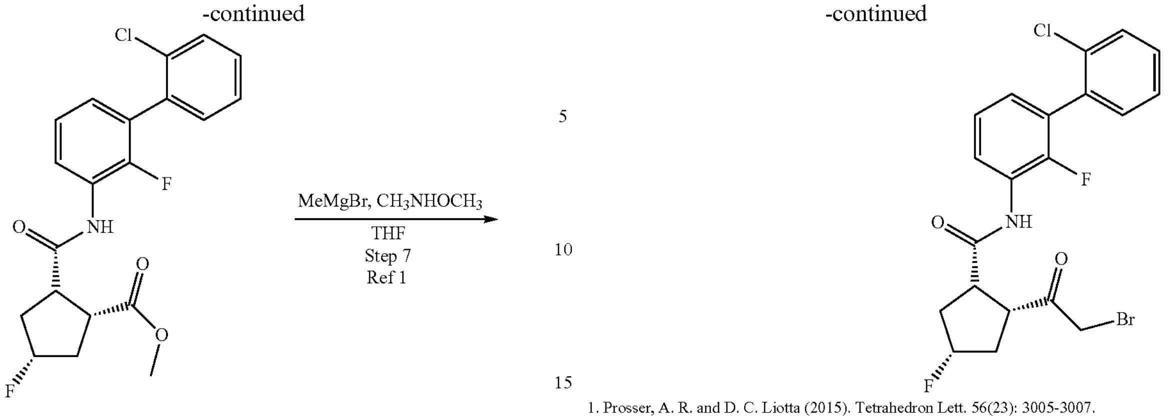

1. Prosser, A. R. and D. C. Liotta (2015). Tetrahedron Lett. 56(23): 3005-3007.

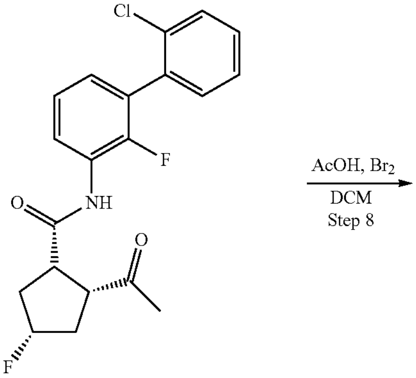

Scheme 5-6: In Step 1 the appropriately substituted alcohol is subjected to TMS-Cl as known in the art to afford a silyl ether. In Step 2 the appropriately substituted silyl ether is subjected with sodium cyanide to afford a cyano species. In Step 3 the appropriately substituted cyano species is reduced as known in the art to afford an aldehyde. In Step 4 the appropriately substituted aldehyde is further reduced with borane to afford an alcohol. In Step 5 the appropriately substituted alcohol is oxidized as known in the art to afford a carboxylic acid. In Step 6 the appropriately substituted carboxylic acid is coupled to the appropriately substituted amine as known in the art to form an amide. In Step 7 the appropriately substituted ester is converted to a methyl ketone by insitu formation of the Weinreb amide with subsequent attack by the methyl Grignard reagent. In Step 8 the appropriately substituted methyl ketone is subjected to bromine to afford a bromide. By choice of the appropriate starting material all mixtures of chiral centers may be prepared as described.

Example 6. Synthesis of A Moieties

Scheme 6-1

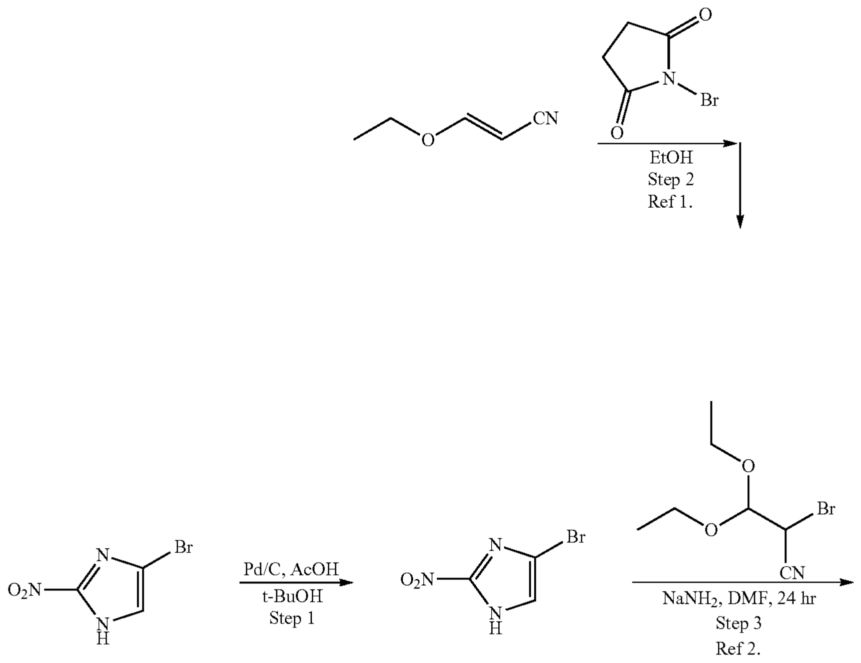

-continued
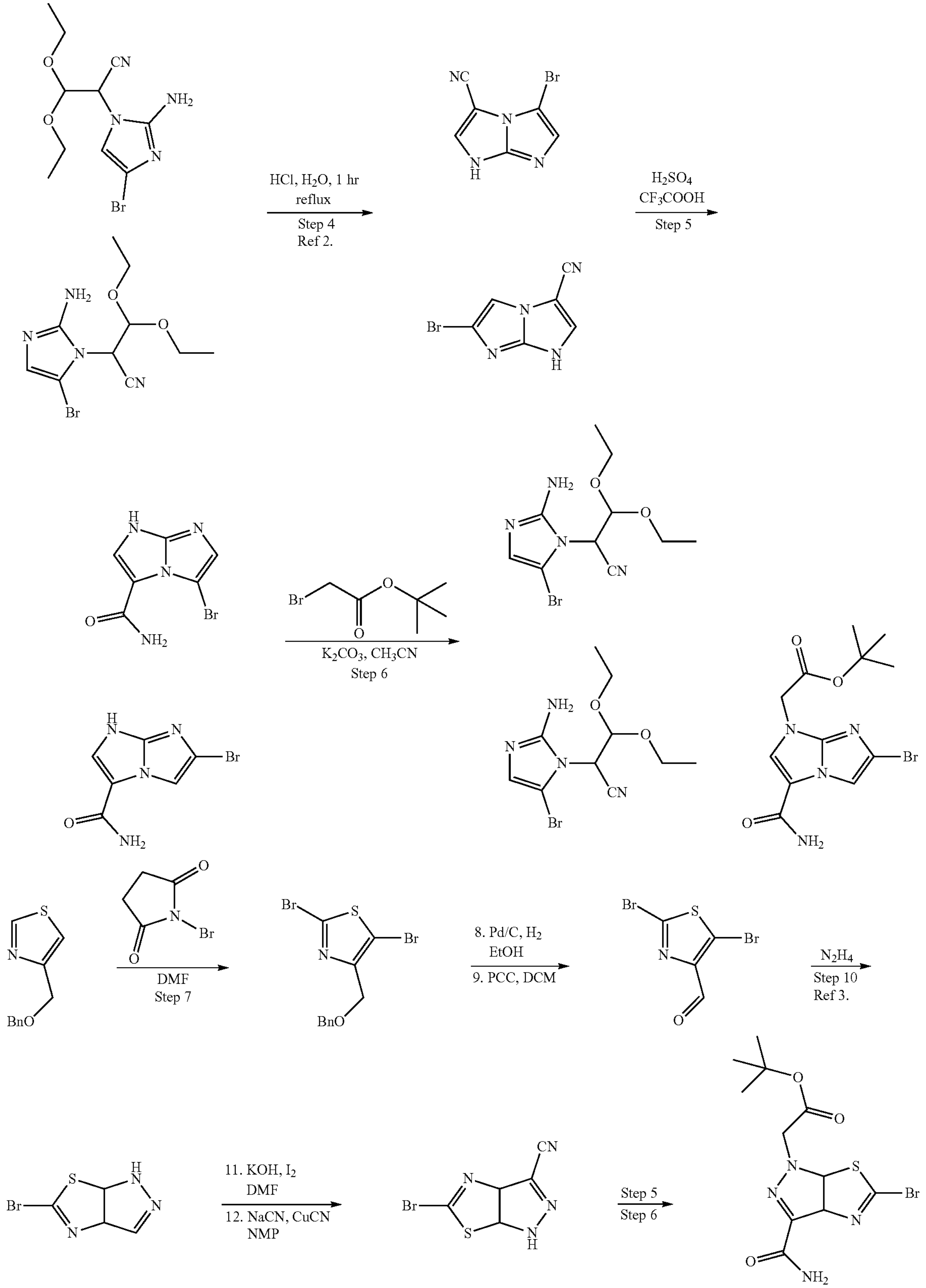
1. Babler, J. H. (1987). Synth. Commun. 17(1): 77-84.
2. Mass, T., et al. (2002). ARKIVOC (Gainesville, FL, U. S.) (5): 48-61.
3. Lebedev, A. Y., et al. (2005). J. Org. Chem. 70(2): 596-602.

Scheme 6-1: In Step 1 the appropriately substituted nitro species is reduced with palladium as known in the art to afford an amine. In Step 2 the appropriately substituted alkene species is brominated with concurrent addition of ethanol as known in the art to afford the bromide species. In Step 3 the appropriately substituted mixture of tautomers is subjected to the previously prepared bromide species as known in the art to afford the two isomers. The appropriately substituted isomers corresponding to each tautomer may either be separated or used as a mixture in the subsequent reactions with separation at a later step. In Step 4 the appropriately substituted ketal species is deprotected and subsequently cyclized in the presence of acid as known in the art. In Step 5 the appropriately substituted cyano species is subjected to strong acid to afford a primary amide. In Step 6 the appropriately substituted heterocycle is subjected to a bromide species of the appropriate linker to afford the appropriately protected species. Various 5-5 fused bicyclic systems can be appropriately prepared by slight modifications of this synthetic protocol, another non-limiting example is presented in Steps 5 through 12 with the same conditions for formation of a primary amide and installation of linker. In Step 7 the appropriately substituted aryl species is brominated as known in the art. In Step 8 the appropriately substituted ether species is deprotected with palladium as known in the art to afford an alcohol. In Step 9 the appropriately substituted alcohol is oxidized as known in the art to afford an aldehyde. In Step 10 the appropriately substituted aldehyde is subjected to hydrazine to first form a Schiff base and subsequently cyclize to afford a bicyclic system. In Step 11 the appropriately substituted bicyclic system is iodinated as known in the art. In Step 12 the appropriately substituted iodide is subjected to sodium cyanide to afford the cyano species.

Scheme 6-2

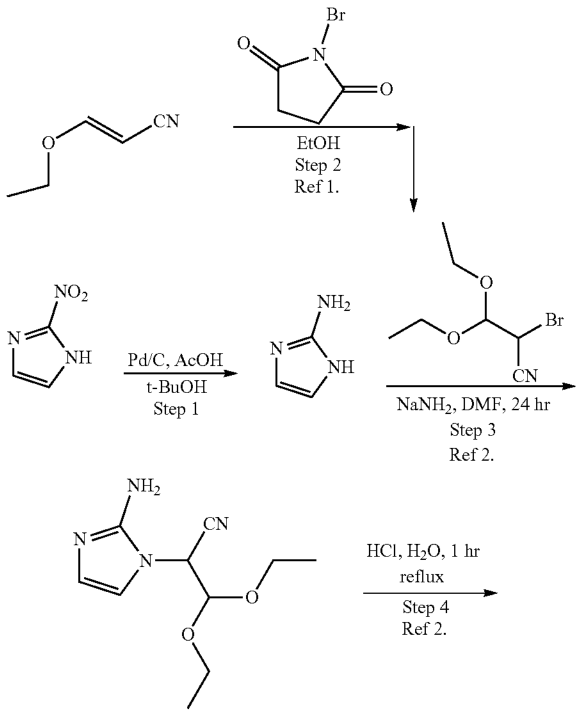

-continued

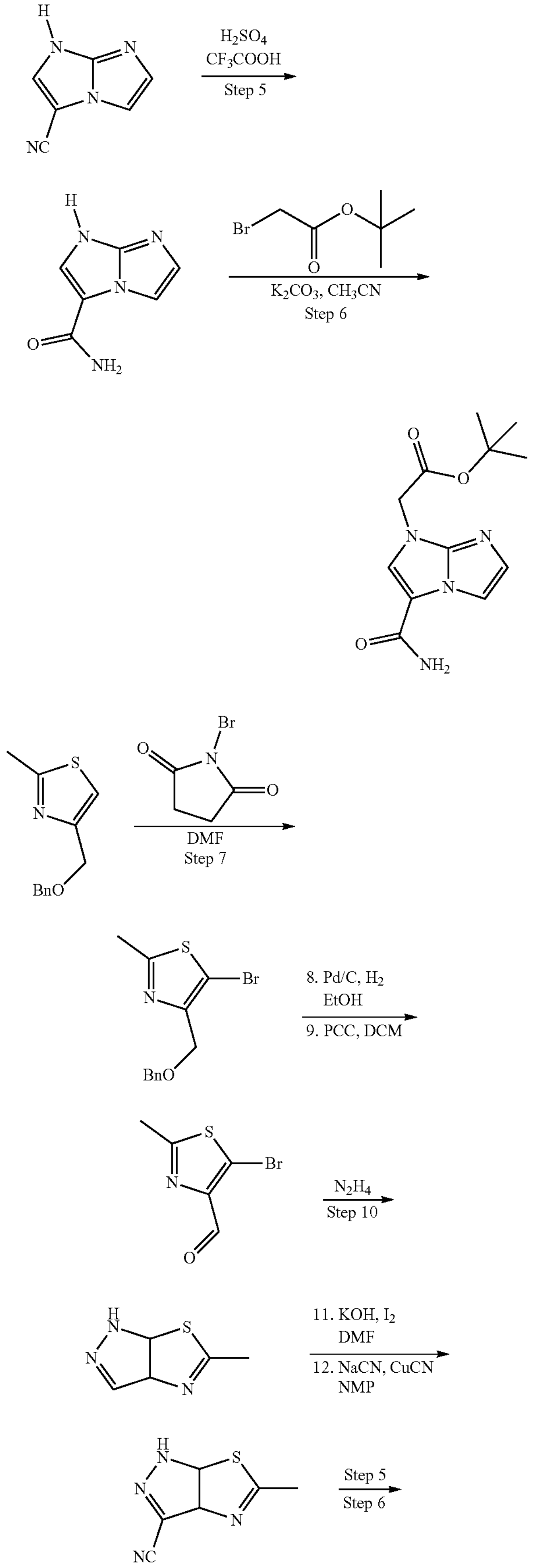

-continued

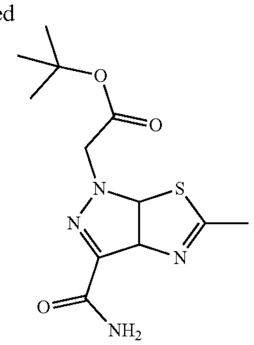

1. Babler, J. H. (1987). Synth. Commun. 17(1): 77-84
2. Mass. T., et al. (2002). ARKIVOC (Gainesville, FL, U. S.) (5): 48-61.

Scheme 6-2: In Step 1 the appropriately substituted nitro species is reduced with palladium as known in the art to afford an amine. In Step 2 the appropriately substituted alkene species is brominated with concurrent oxidation with ethanol as known in the art to afford the bromide species. In Step 3 the appropriately substituted aryl species is subjected to the previously prepared bromide species as known in the art to afford a bicycle precursor. In Step 4 the appropriately substituted ketal species is deprotected and subsequently cyclized in the presence of acid as known in the art. In Step 5 the appropriately substituted cyano species is subjected to strong acid to afford a primary amide. In Step 6 the appropriately substituted heterocycle is subjected to a bromide species of the appropriate linker to afford the appropriately protected species. Various 5-5 fused bicyclic systems can be appropriately prepared by slight modifications of this synthetic protocol, another non-limiting example is presented in Steps 5 through 12 with the same conditions for formation of a primary amide and installation of linker. In Step 7 the appropriately substituted aryl species is brominated as known in the art. In Step 8 the appropriately substituted ether species is deprotected with palladium as known in the art to afford an alcohol. In Step 9 the appropriately substituted alcohol is oxidized as known in the art to afford an aldehyde. In Step 10 the appropriately substituted aldehyde is subjected to hydrazine to first form a Schiff base and subsequently cyclize to afford a bicyclic system. In Step 11 the appropriately substituted bicyclic system is iodinated as known in the art. In Step 12 the appropriately substituted iodide is subjected to sodium cyanide to afford a cyano species.

Example 7. Synthesis of L3-A Moieties

Scheme 7-1

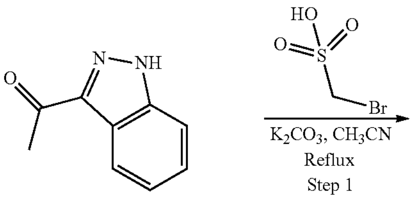

-continued

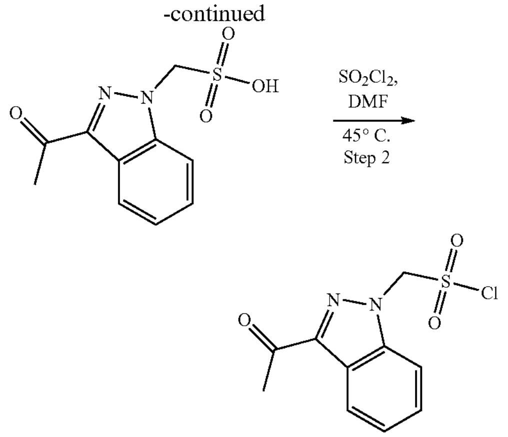

Scheme 7-1: In Step 1 the appropriately substituted aryl compound is subjected to a bromide to afford a sulfonic acid substituted species. In Step 2 the appropriately substituted sulfonic acid

Example 8. Coupling of L3-A to C-L-B

Scheme 8-1

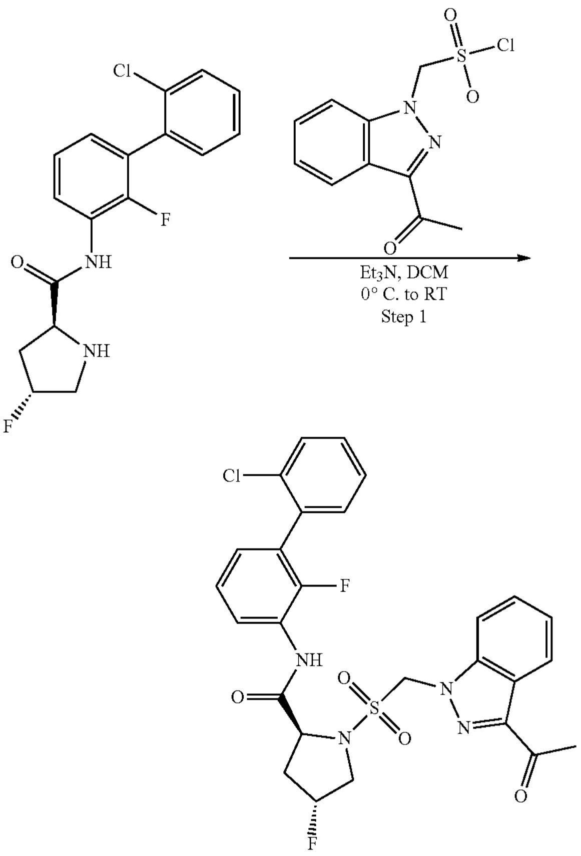

Scheme 8-1: In Step 1 the appropriately substituted amine is subjected to a sulfonyl chloride which can be prepared as described in Scheme 7-1 to afford a compound of Formula I.

Scheme 8-2

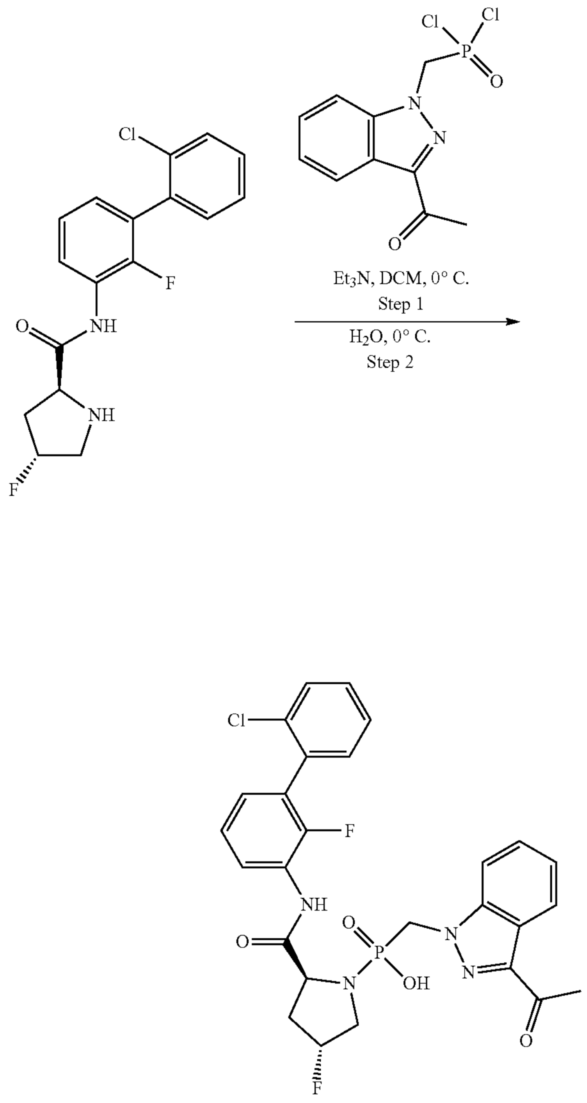

Scheme 8-2: In Step 1 the appropriately substituted amine is subjected to a phosphonic dichloride which can be prepared as described in Scheme 7-2 followed by a subsequent quench with water to afford a compound of Formula I.

Scheme 8-3

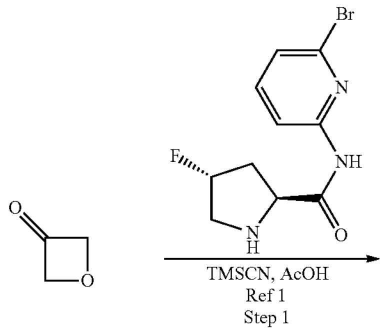

-continued

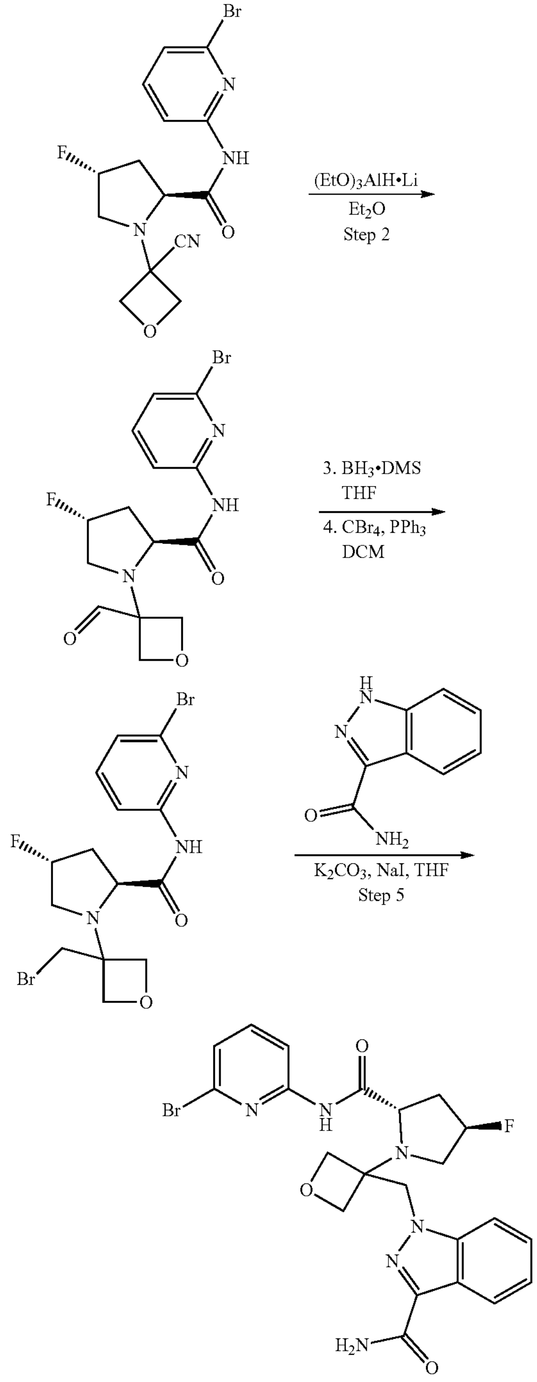

1.Wuitschik, Georg. Thesis, http://dx.doi.org/10.3929/ethz-a-005697432, ETH (2008)

Scheme 8-3: In Step 1 the appropriately substituted oxetane is subjected to conditions known in the art to form an amino/cyano substituted species. In Step 2 the appropriately substituted cyano species is reduced as known in the art to afford an aldehyde. In Step 3 the appropriately substituted aldehyde is reduced with borane to afford an alcohol. In Step 4 the appropriately substituted alcohol is converted to a bromide as known in the art. In Step 5 the appropriately substituted bromide is subjected to a heteroaryl species as known in the art to afford a compound of Formula I.

Scheme 8-4
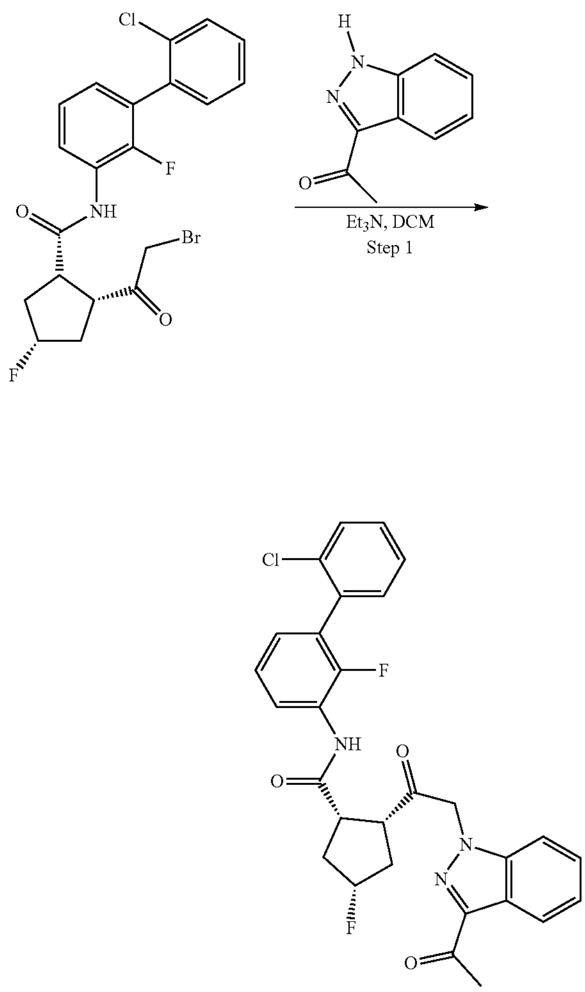
Scheme 8-4: In Step 1 the appropriately substituted bromide is subjected to a heteroaryl species to afford a compound of Formula I.
Scheme 8-5
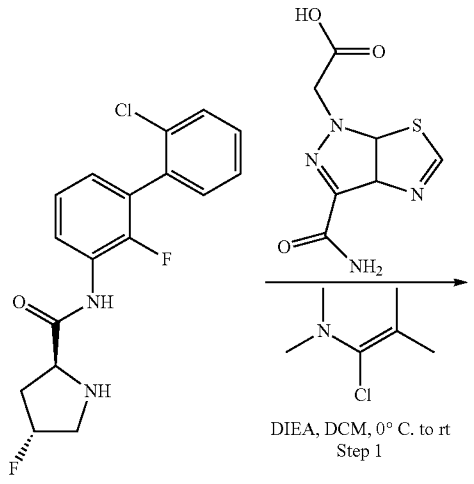
-continued
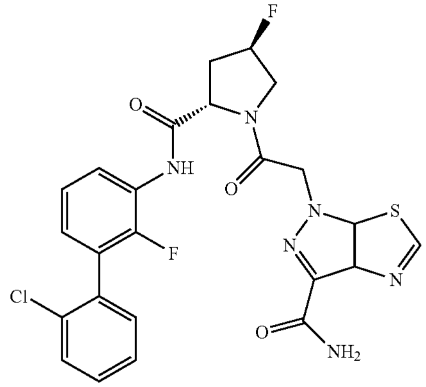
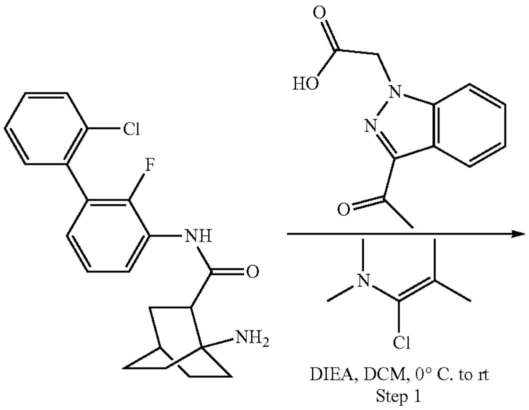
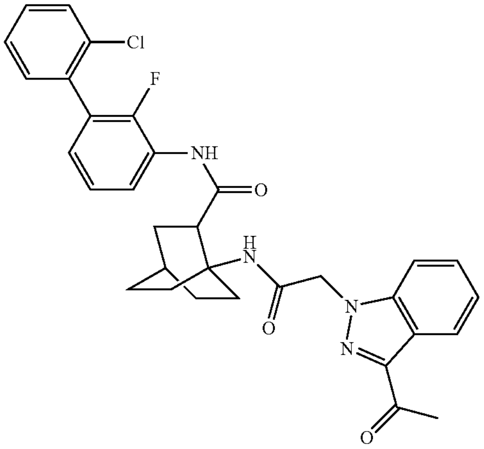
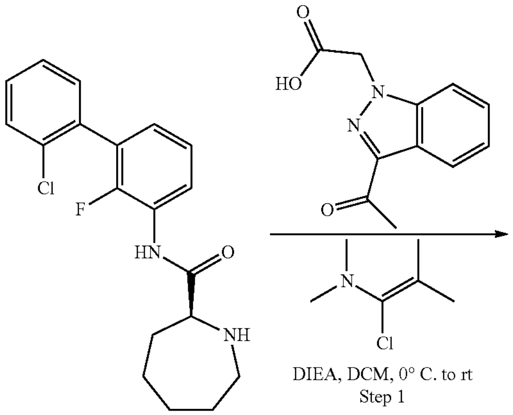

-continued
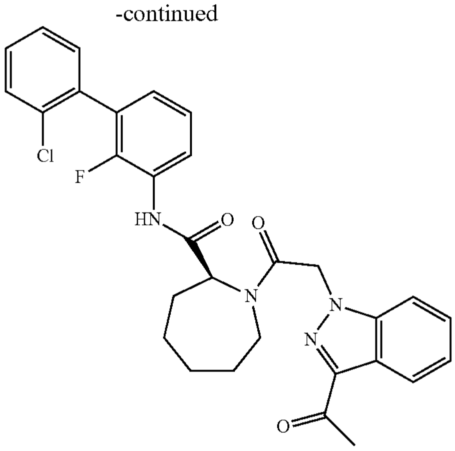
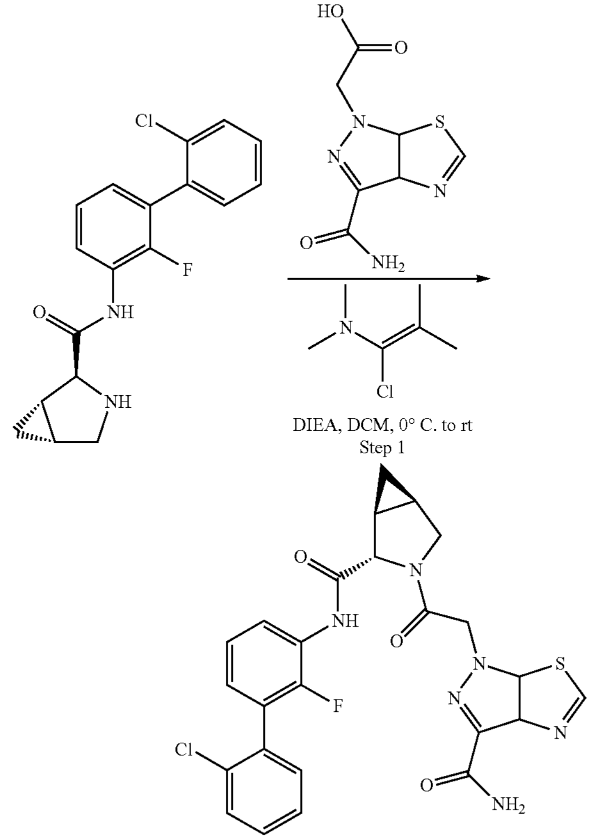
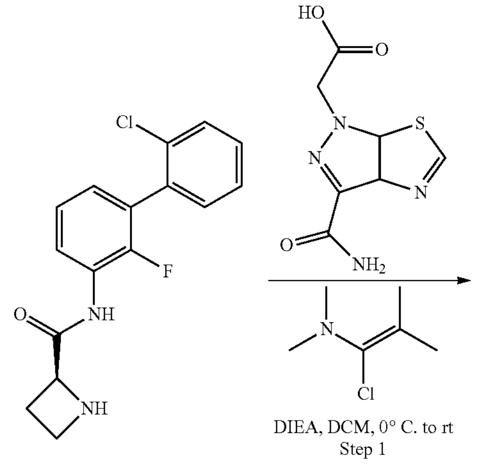
-continued
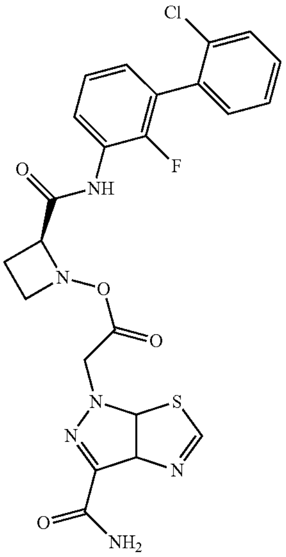
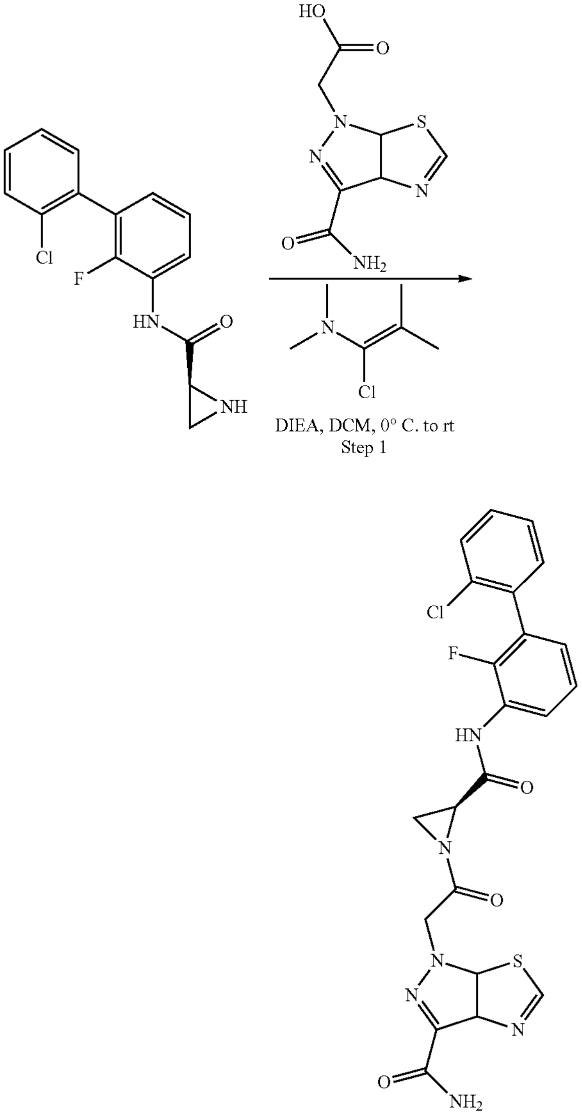

Scheme 8-5: In Step 1 the appropriately substituted carboxylic acid is coupled to the appropriately substituted amine as known in the art to form a compound of Formula I.

Synthetic Procedures to Synthesize Compounds of the Present Invention

Scheme 1. Synthesis of (((2S,4R)-1-(2-(3-Acetyl-1H-indazol-1-yl)-4-fluoropyrrolidine-2-carbonyl)amino)mentyl)-o-carborane (1)

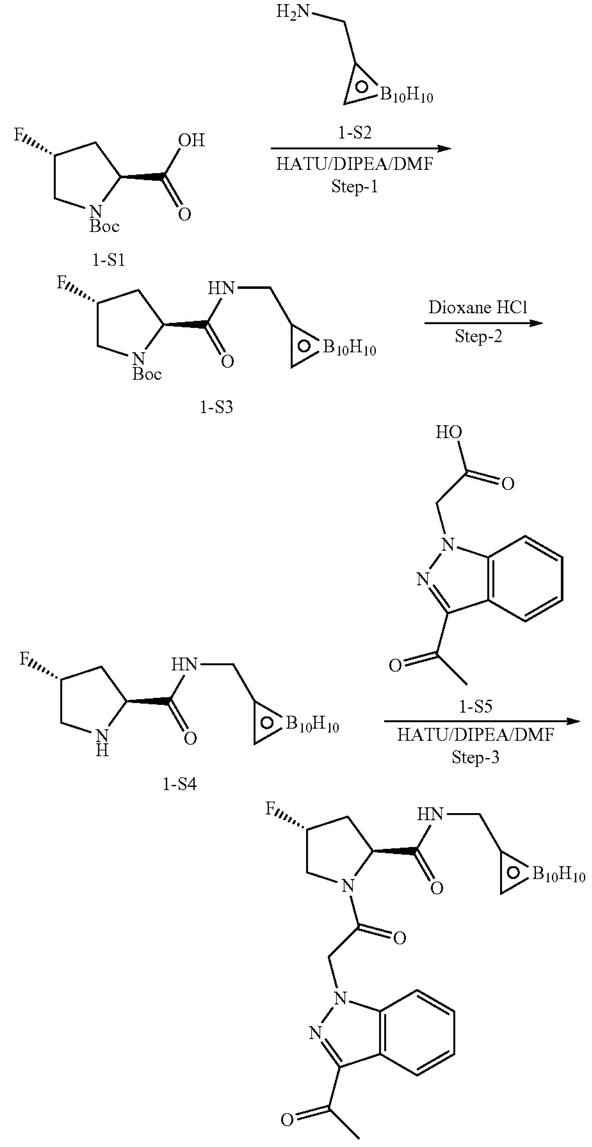

Step 1: (((2S,4R)-1-(tert-Butoxycarbonyl)-4-fluoropyrrolidine-2-carbonyl)amino)methyl)-o-carborane (1-S3)

To a solution of (2S,4R)-1-(tert-butoxycarbonyl)-4-fluoropyrrolidine-2-carboxylic acid (1-S1, 1 equiv) in DMF (10 vol) at 0° C. under nitrogen atmosphere was added (aminomethyl)-o-carborane hydrochloride (1-S2, 1.2 equiv), HATU (1.5 equiv) and DIPEA (3 equiv). The reaction mixture was stirred at room temperature for 3 hours. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using EtOAc/hexane to afford compound 1-S3.

Step 2: (((2S,4R)-4-Fluoropyrrolidine-2-carbonyl)amino)methyl)-o-carborane hydrochloride (1-S4)

To a solution of compound 1-S3 (1 equiv) in 1,4-dioxane (3 vol) at 0° C. under nitrogen atmosphere was added 4 N HCl in 1,4-dioxane (10 vol) and stirred at room temperature for 3 hours. The reaction mixture was concentrated to afford compound 1-S4.

Step 3: (((2S,4R)-1-(2-(3-Acetyl-1H-indazol-1-yl)acetyl)-4-fluoropyrrolidine-2-carbonyl)amino)methyl)-o-carborane (1)

To a solution of compound 1-S4 (1 equiv) in DMF (10 vol) at 0° C. under nitrogen atmosphere was added 2-(3-acetyl-1H-indazol-1-yl)acetic acid (1-S5, 1.2 equiv), HATU (1.5 equiv) and DIPEA (3 equiv). The reaction mixture was stirred at room temperature for 3 hours. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to afford compound 1. $^1H$ NMR (400 MHz, DMSO-$d_6$) δ: 8.52 (t, J=6.4 Hz, 1H), 8.18 (d, J=8.1 Hz, 1H), 7.65 (d, J=8.4 Hz, 1H), 7.48-7.46 (m, 1H), 7.37-7.33 (m, 1H), 5.80-5.76 (m, 1H), 5.58-5.45 (m, 2H), 4.71-4.70 (m, 1H), 4.38-4.34 (m, 1H), 4.28-4.16 (m, 2H), 3.97-3.75 (m, 3H), 2.68 (s, 3H), 2.13-1.96 (b, 10H).

Scheme 2: Synthesis of (1R, 2S, 5S)-3(2-(3-Acetyl-5-methyl-1H-thieno [3, 2-c] pyrazol-1-yl) acetyl)-N-(6-bromo-3-methylpyridin-2-yl)-3-azabicyclo [3.1.0] hexane-2-carboxamide (2)

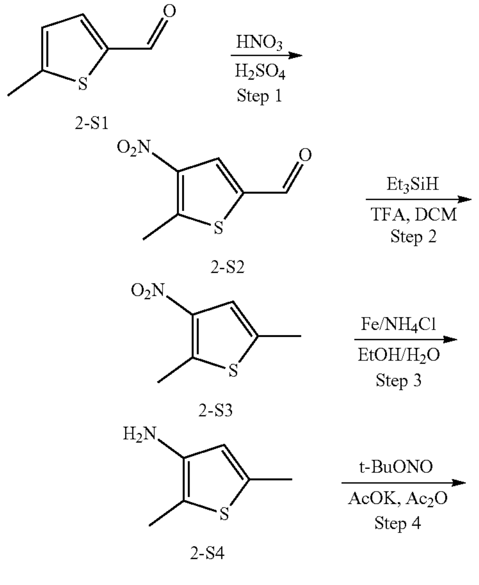

-continued

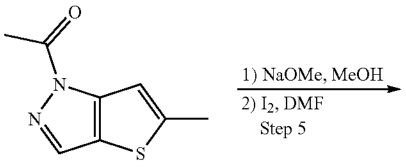

2-S5

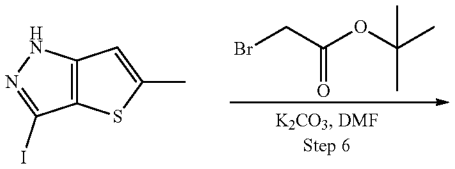

2-S6

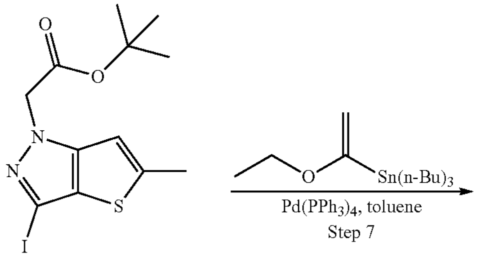

2-S7

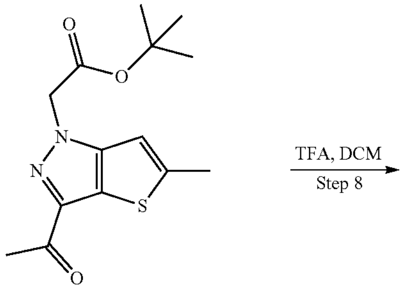

2-S8

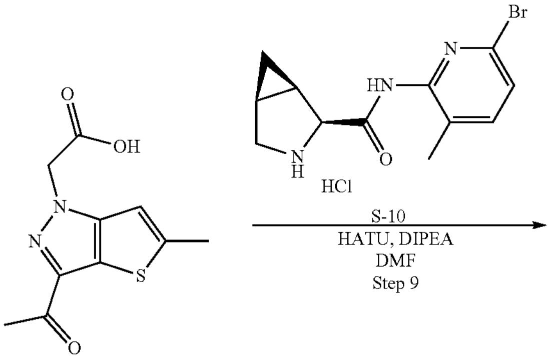

2-S9

-continued

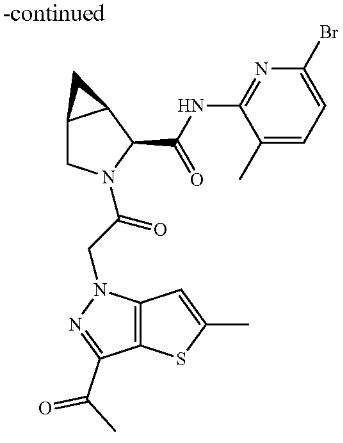

2

Step 1: 5-Methyl-4-nitrothiophene-2-carbaldehyde (2-S2)

To a solution of 2-S1 (5.0 g, 39.68 mmol) in concentrated $H_2SO_4$ (50 mL) was added $HNO_3$ (3.0 mL, 43.65 mmol) dropwise at 0° C. The resulting mixture was stirred at 0° C. for 1 hour and was poured into ice water and filtered. The filter cake was washed with water and dried under vacuum to afford the crude product, which was purified by column chromatography on silica gel (eluted with PE/EtOAc=80:1 to 50:1) to afford 2-S2 (3.1 g, 45.7% yield) as a white solid. LC/MS (ESI) m/z: 172 $(M+H)^+$.

Step 2: 2,5-Dimethyl-3-nitrothiophene (2-S3)

To a solution of TFA (25 mL, 336.6 mmol) in DCM (50 mL) was added $Et_3SiH$ (10.1 mL, 63.45 mmol) at 0° C. followed by 2-S2 (3.1 g, 18.11 mmol) in portions at 0° C. The resulting mixture was stirred at room temperature overnight. Ice-cold water was added at 0° C. and the mixture was extracted with DCM twice. The combined organic layers were washed with brine, dried over $Na_2SO_4$, filtered, and concentrated to dryness. The remaining residue was purified by column chromatography on silica gel (eluted with PE/EtOAc=80:1 to 50:1) to afford 2-S3 (1.2 g, 42.1% yield) as colorless oil.

Step 3: 3, 5-Dimethylthiophen-3-amine (2-S4)

To a solution of 2-S3 (1.05 g, 6.7 mmol) in ethanol (10 mL) and $H_2O$ (2 mL) was added $NH_4Cl$ (1.07 g, 20 mmol) and Fe (1.87 g, 33.4 mmol). The resulting mixture was stirred at 90° C. for 1 hour. The mixture was filtered and the filtrate was concentrated to dryness under reduced pressure. The mixture was diluted with EtOAc, washed with brine, dried over $Na_2SO_4$, and concentrated under reduced pressure. The remaining residue was purified by column chromatography on silica gel (eluted with PE/EtOAc=30:1) to afford 2-S4 (365 mg, 42.99% yield) as light a yellow oil. LC/MS (ESI) m/z: 128 $(M+H)^+$.

Step 4:1-(5-Methyl-1H-thieno [3, 2-c] pyrazol-1-yl) ethanone (2-S5)

To a solution of 2-S4 (365 mg, 2.874 mmol) in toluene (5 mL) were added acetic anhydride (1.079 mL, 11.496 mmol)

and potassium acetate (140.83 mg, 1.437 mmol). The resulting mixture was stirred at 100° C. for 3 hours. The mixture was cooled to room temperature and tert-butyl nitrite (1.024 mL, 8.622 mmol) was added. The resulting mixture was stirred at 100° C. overnight. The mixture was diluted with EtOAc and water. The separated organic layer was washed with brine, dried over $Na_2SO_4$, and concentrated under reduced pressure. The remaining residue was purified by column chromatography on silica gel (eluted with PE/EtOAc=20:1) to afford 2-S5 (140 mg, 27% yield) as a yellow oil. LC/MS (ESI) m/z: 181 $(M+H)^+$.

Step 5: 3-Iodo-5-methyl-1H-thieno [3, 2-c] pyrazole (2-S6)

To a solution of 2-S5 (140 mg, 0.778 mmol) in MeOH (4 mL) was added MeONa/MeOH solution (3 mL, 30% wt). The mixture was stirred at 60° C. for 1 hour. The reaction mixture was cooled to room temperature, 12 (3.85 g, 15.157 mmol) was added in portions, and the resulting mixture was stirred at 60° C. for 1 hour. The mixture was diluted with EtOAc and water. The separated organic layer was washed with brine, dried over $Na_2SO_4$, and concentrated under reduced pressure. The remaining residue was purified by column chromatography on silica gel (eluted with PE/EtOAc=20:1 to 10:1) to afford 2-S6 (201 mg, 98% yield) as a white solid. LC/MS (ESI) m/z: 265 $(M+H)^+$.

Step 6: tert-Butyl 2-(3-iodo-5-methyl-1H-thieno [3, 2-c] pyrazol-1-yl) acetate (2-S7)

To a solution of 2-S6 (201 mg, 0.76 mmol) in DMF (4 mL) was added $K_2CO_3$ (315.2 mg, 2.284 mmol) and tert-butyl bromoacetate (0.166 mL, 1.142 mmol). The reaction mixture was stirred at room temperature for 16 hours. The mixture was partitioned with EtOAc and water. The organic layer was washed with brine, dried over $Na_2SO_4$, and concentrated under reduced pressure. The remaining residue was purified by column chromatography on silica gel (eluted with PE/EtOAc=50:1) to afford 2-S7 (268 mg, 93% yield) as a white solid. LC/MS (ESI) m/z: 379 $(M+H)^+$.

Step 7: tert-Butyl 2-(3-acetyl-5-methyl-1H-thieno [3, 2-c] pyrazol-1-yl) acetate (2-S8)

To a solution of 2-S7 (268 mg, 0.71 mmol) in toluene (5 mL) was added $Pd(PPh_3)_4$ (81.96 mg, 0.071 mmol) and 1-ethoxyvinyltri-n-butyltin (0.359 mL, 1.06 mmol). The resulting mixture was stirred at 100° C. for 16 hours under an atmosphere of nitrogen. The mixture was diluted with EtOAc, washed with brine, dried over $Na_2SO_4$, and concentrated under reduced pressure. The remaining residue was purified by column chromatography on silica gel (PE/EtOAc=30:1 to 10:1) to afford 2-S8 (89 mg, 43% yield) as a white solid. LC/MS (ESI) m/z: 295 $(M+H)^+$.

Step 8: 2-(3-Acetyl-5-methyl-1H-thieno [3, 2-c] pyrazol-1-yl) acetic acid (2-S9)

To a solution of 2-S8 (89 mg, 0.30 mmol) in DCM (2 mL) was added TFA (1 mL) at 0° C., and the mixture was stirred at room temperature for 2 hours. The mixture was concentrated to dryness to afford 2-S9 (72 mg, 100% yield) as a white solid, which was carried forward in the next synthetic step without further purification. LC/MS (ESI) m/z: 239 $(M+H)^+$.

Step 9: (1R, 2S, 5S)-3(2-(3-Acetyl-5-methyl-1H-thieno [3, 2-c] pyrazol-1-yl) acetyl)-N-(6-bromo-3-methylpyridin-2-yl)-3-azabicyclo[3.1.0]hexane-2-carboxamide (2)

To a mixture of 2-S9 (36 mg, 0.15 mmol) and (1R,2S, 5S)—N-(6-bromo-3-methylpyridin-2-yl)-3-azabicyclo [3.1.0] hexane-2-carboxamide (2-S10, 46.89 mg, 0.15 mmol) in DMF (1 mL) were added DIPEA (0.075 mL, 0.45 mmol) and HATU (86.22 mg, 0.23 mmol). The mixture was stirred at room temperature for 16 hours, diluted with EtOAc, washed with 10% aqueous LiCl solution and brine, dried over $Na_2SO_4$, and concentrated under reduced pressure. The remaining residue was purified by preparative HPLC to afford 2 (4.1 mg, 5.3% yield) as a white solid. $^1H$ NMR (400 MHz, $CD_3OD$) δ 7.54 (d, J=8.0 Hz, 1H), 7.37 (d, J=7.9 Hz, 1H), 6.81 (d, J=1.2 Hz, 1H), 5.35-5.20 (m, 2H), 4.71 (s, 1H), 3.99 (dd, J=9.7, 5.2 Hz, 1H), 3.85 (d, J=9.7 Hz, 1H), 2.55 (s, 3H), 2.52 (d, J=1.1 Hz, 3H), 2.16 (s, 4H), 2.00-1.85 (m, 1H), 0.98-0.77 (m, 2H). LC/MS (ESI) m/z: 516 $(M+H)^+$.

Scheme 3: Synthesis of (2S,4R,)-1-(2-(3-Acetyl-5-(S-methylsulfonimidoyl-1H-indazol-1-yl)acetyl)-N-(6-bromopyridin-2-yl)-4-fluoropyrrolidine-2-carboxamide (3)

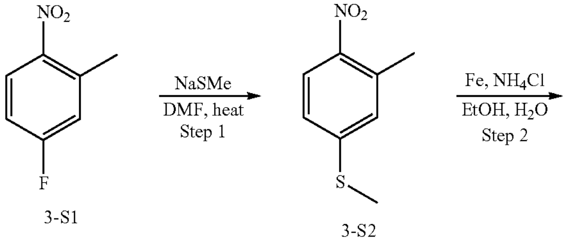

3-S1 3-S2

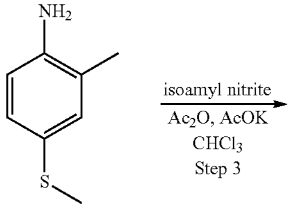

3-S3

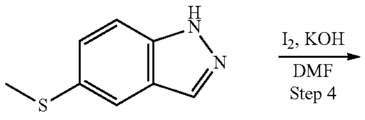

3-S4

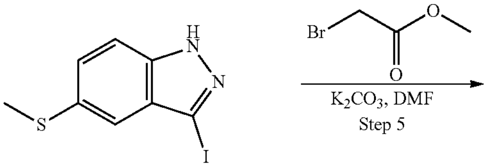

3-S5

-continued

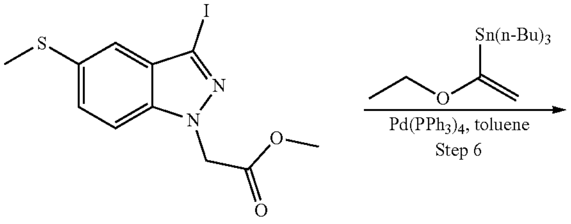

3-S6

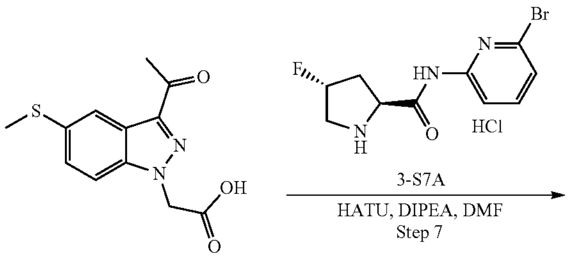

3-S7

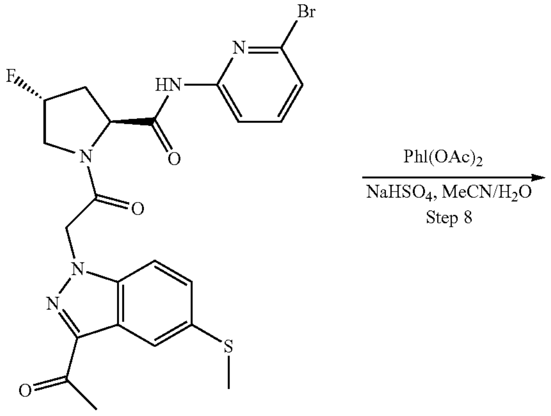

3-S8

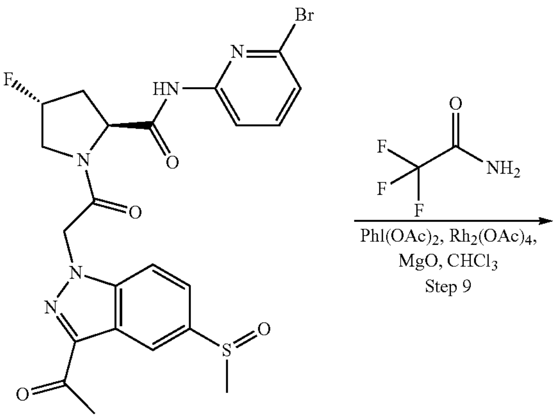

3-S9

-continued

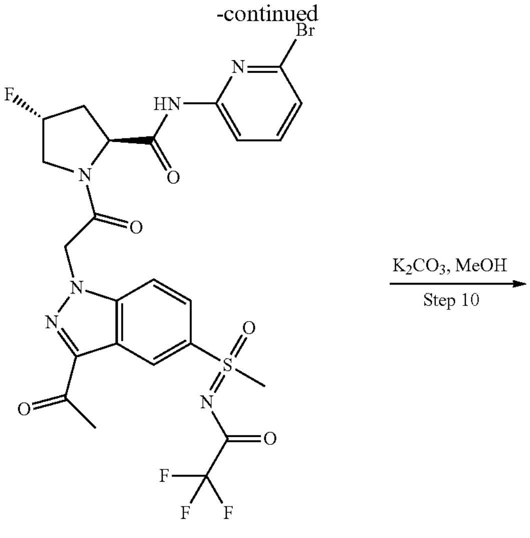

3-S10

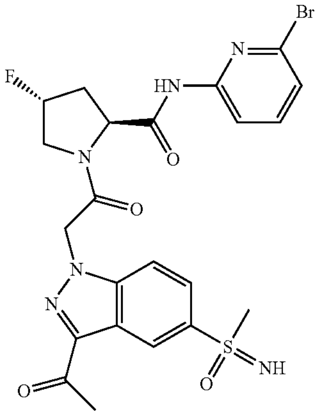

3

Step 1: Methyl(3-methyl-4-nitrophenyl)sulfane (3-S2)

To a solution of 3-S1 (4 g, 25.78 mmol) in DMF (40 mL) was added sodium thiomethoxide (3.6 g, 38.68 mmol) at 0° C. The reaction mixture was stirred at room temperature overnight. The mixture was diluted with EtOAc, washed with 10% aqueous LiCl solution and brine, dried over anhydrous $Na_2SO_4$, and concentrated to afford the crude product, which was purified by column chromatography on silica gel (eluted with PE/EtOAc=50:1 to 15:1) to afford 3-S2 (1.4 g, 29.6% yield) as a yellow solid.

Step 2: 2-Methyl-4-(methylthio)aniline (3-S3)

A mixture of 3-S2 (972 mg, 5.30 mmol), iron powder (1.49 g, 26.61 mmol), and ammonium chloride (845 mg, 15.80 mmol) in EtOH (10 mL) in water (2 mL) was stirred at 85° C. for 2 hours under an atmosphere of nitrogen. The mixture was filtered and the filtrate was diluted with EtOAc, washed with brine, dried over anhydrous $Na_2SO_4$, and concentrated to afford the crude product, which was purified by column chromatography on silica gel (eluted with PE/EtOAc=20:1 to 3:1) to afford 3-S3 (657 mg, 80.9% yield) as a yellow solid. LC/MS (ESI) m/z: 154 $(M+H)^+$.

Step 3: 5-(Methylthio)-1H-indazole (3-S4)

To a solution of 3-S3 (657 mg, 4.29 mmol) in $CHCl_3$ (5 mL) was added acetic anhydride (994 mg, 9.74 mmol) dropwise over 2 minutes at 0° C. The reaction mixture was warmed to 25° C. and stirred for 3 hours. The mixture was heated to 60° C. and KOAc (122 mg, 1.24 mmol) and isoamyl nitrite (951 mg, 9.22 mmol) was added. The reaction mixture was stirred at 60° C. overnight before the volatiles were removed under reduced pressure and hydrochloric acid (6M, 5 mL) was added to the remaining residue. The resulting mixture was stirred at 60° C. for 2 hours, cooled to room temperature, and adjusted to pH 10 by the addition of 1 M aqueous sodium hydroxide solution. The mixture was diluted with EtOAc, washed with water and brine, dried, and concentrated to dryness. The crude product was purified by column chromatography on silica gel (eluted with PE/EtOAc=20:1 to 3:1) to afford 3-S4 (500 mg, 71.0% yield) as a white solid. LC/MS (ESI) m/z: 165 $(M+H)^+$.

Step 4: 3-Iodo-5-(methylthio)-1H-indazole (3-S5)

To a mixture of 3-S4 (500 mg, 3.07 mmol) in DMF (2 mL) were added potassium hydroxide (384 mg, 6.84 mmol) and iodine (1.169 g, 4.60 mmol) at 0° C. The reaction mixture was stirred at room temperature overnight. The mixture was diluted with EtOAc, washed with 10% aqueous LiCl solution and brine, dried over anhydrous $Na_2SO_4$, and concentrated to afford the crude product, which was purified by column chromatography on silica gel (eluted with PE/EtOAc=50:1 to 10:1) to afford 3-S5 (521 mg, 58.5% yield) as a white solid. LC/MS (ESI) m/z: 290 $(M+H)^+$.

Step 5: Methyl 2-(3-iodo-5-(methylthio)-1H-indazol-1-yl) acetate (3-S6)

To a solution of 3-iodo-5-(methylthio)-1H-indazole (3-S5, 600 mg, 2.07 mmol) in DMF (6 mL) was added $K_2CO_3$ (856 mg, 6.21 mmol) and methyl 2-bromoacetate (314 mg, 2.07 mmol). The resulting mixture was stirred at room temperature overnight, diluted with EtOAc, washed with brine, dried over anhydrous $Na_2SO_4$, and concentrated. The remaining crude product was purified by column chromatography on silica gel (eluted with PE/acetone=100:1 to 30:1) to afford 3-S6 (560 mg, 74.8% yield) as a yellow solid. LC/MS (ESI) m/z: 363 $(M+H)^+$.

Step 6: 2-(3-Acetyl-5-(methylthio)-1H-indazol-1-yl) acetic acid (3-S7)

To a solution of methyl 2-(3-iodo-5-(methylthio)-1H-indazol-1-yl) acetate (3-S6, 0.30 g, 0.83 mmol) in dry toluene (6 mL) was added tributyl (1-ethoxyvinyl)stannane (0.45 g, 1.24 mmol) and $Pd(PPh_3)_4$ (96 mg, 0.08 mmol). The resulting mixture was stirred at 100° C. under an atmosphere of nitrogen overnight. The mixture was filtered and the filtrate was concentrated. The remaining residue was diluted with EtOAc, washed with brine, dried over anhydrous $Na_2SO_4$, and concentrated. The remaining residue was dissolved in 0.5 M aqueous HCl (5 mL) and the mixture was stirred at room temperature for 1 hour, extracted with isopropanol/chloroform (3:1), dried over anhydrous $Na_2SO_4$, and concentrated. The remaining crude product was purified by column chromatography on silica gel eluted with DCM/MeOH (100:1 to 30:1) to afford 3-S7 (0.18 g, 81.8% yield) as a yellow solid. LC/MS (ESI) m/z: 265 $(M+H)^+$.

Step 7: (2S, 4R)-1-(2-(3-Acetyl-6-(methylthio)-1H-indazol-1-yl) acetyl)-N-(6-bromopyridin-2-yl)-4-fluoropyrrolidine-2-carboxamide (3-S8)

To a solution of 2-(3-acetyl-5-(methylthio)-1H-indazol-1-yl) acetic acid (3-S7, 90 mg, 0.35 mmol), (2S, 4R)—N-(6-bromopyridin-2-yl)-4-fluoropyrrolidine-2-carboxamide hydrochloride (3S-7A, 113.6 mg, 0.35 mmol) and DIPEA (225 mg, 1.74 mmol) in DMF (2 mL) was added HATU (291 mg, 0.77 mmol). The resulting mixture was stirred at room temperature for 1 hour, diluted with water, extracted with EtOAc, washed with brine, dried over anhydrous $Na_2SO_4$, and concentrated. The remaining residue was purified by column chromatography on silica gel (eluted with PE/EtOAc=30:1 to 3:1) to afford 3-S8 (0.13 g, 72.0% yield) as a white solid. LC/MS (ESI) m/z: 533 $(M+H)^+$.

Step 8: (2S, 4R)-1-(2-(3-Acetyl-6-(methylsulfinyl)-1H-indazol-1-yl) acetyl)-N-(6-bromopyridin-2-yl)-4-fluoropyrrolidine-2-carboxamide (3-S9)

To a solution of (2S, 4R)-1-(2-(3-acetyl-6-(methylthio)-1H-indazol-1-yl)acetyl)-N-(6-bromopyridin-2-yl)-4-fluoropyrrolidine-2-carboxamide (3-S8, 0.1 g, 0.19 mmol) in $MeCN/H_2O$ (6 mL, 5:1 v/v) was added $NaHSO_4$ (25 mg, 0.20 mmol) followed by $PhI(OAc)_2$ (64 mg, 0.20 mmol) in portions at 0° C. The reaction mixture was stirred at room temperature for 10 minutes, quenched with aqueous $NaS_2SO_3$ solution, and extracted with EtOAc. The organic layer was washed with aqueous $NaHCO_3$ solution and brine, dried over anhydrous $Na_2SO_4$, and concentrated. The remaining residue was purified by column chromatography on silica gel (eluted with DCM/MeOH=100:1 to 30:1) to afford 3-S9 (100 mg, 97.1% yield) as a white solid. LC/MS (ESI) m/z: 550 $(M+H)^+$.

Step 9: (2S, 4R)-1-(2-(3-Acetyl-6-(S-methyl-N-(2, 2, 2-trifluoroacetyl) sulfonimidoyl)-1H-indazol-1-yl) acetyl)-N-(6-bromopyridin-2-yl)-4-fluoropyrrolidine-2-carboxamide (3-S10)

To a solution of (2S, 4R)-1-(2-(3-acetyl-6-(methylsulfinyl)-1H-indazol-1-yl) acetyl)-N-(6-bromopyridin-2-yl)-4-fluoropyrrolidine-2-carboxamide (3-S9, 0.1 g, 0.18 mmol) in $CHCl_3$ (5 mL) was added 2,2,2-trifluoroacetamide (20 mg, 0.18 mmol), $PhI(OAc)_2$ (91 mg, 0.27 mmol), $Rh_2(OAc)_4$ (2 mg, 0.004 mmol), and MgO (15 mg, 0.36 mmol). The reaction mixture was stirred at room temperature under an atmosphere of nitrogen overnight, quenched with aqueous $NaS_2SO_3$ solution, and extracted with DCM. The organic layer was washed with aqueous $NaHCO_3$ solution and brine, dried over anhydrous $Na_2SO_4$, and concentrated. The remaining residue was purified by column chromatography on silica gel (eluted with DCM/MeOH=100:1 to 30:1) to afford 3-S10 (40 mg, 33.3% yield) as a white solid. LC/MS (ESI) m/z: 661 $(M+H)^+$.

Step 10: (2S, 4R)-1-(2-(3-Acetyl-6-(S-methylsulfonimidoyl)-1H-indazol-1-yl) acetyl)-N-(6-bromopyridin-2-yl)-4-fluoropyrrolidine-2-carboxamide (3)

To a solution of (2S, 4R)-1-(2-(3-acetyl-6-(S-methyl-N-(2, 2, 2-trifluoroacetyl) sulfonimidoyl)-1H-indazol-1-yl) acetyl)-N-(6-bromopyridin-2-yl)-4-fluoropyrrolidine-2-carboxamide (3-S10, 40 mg, 0.061 mmol) in MeOH (3 mL) was added $K_2CO_3$ (42 mg, 0.30 mmol). The reaction mixture was stirred at room temperature for 1 hour, diluted with $H_2O$, and extracted with EtOAc. The organic layer was washed with brine, dried over anhydrous $Na_2SO_4$, and concentrated. The remaining crude product was purified by preparative HPLC to afford 3 (5 mg, 14.7% yield) as a white solid. $^1H$ NMR (400 MHz, DMSO-$d_6$) δ 11.00 (s, 1H), 8.74 (s, 1H), 8.07-7.97 (m, 2H), 7.94-7.81 (m, 1H), 7.71 (t, J=8.4 Hz, 1H), 7.32 (d, J=8.0 Hz, 1H), 5.94-5.10 (m, 3H), 4.65 (t, J=8.4 Hz, 1H), 4.29 (s, 1H), 4.22 (dd, J=22.8, 13.2 Hz, 1H), 4.11-3.93 (m, 1H), 3.09 (s, 3H), 2.69-2.54 (m, 4H), 2.27-2.03 (m, 1H). LC/MS (ESI) m/z: 565 $(M+H)^+$.

Scheme 4: Synthesis of (2S,4R)-1-(2-(3-Acetyl-6-((E)-S- methyl-N-(2,2,2-trifluoroacetyl)sulfinimidoyl)-1H-indazol-1-yl)acetyl)-N-(6-bromopyridin-2-yl)-4-fluoropyrrolidine-2-carboxamide (4) and (2S,4R)-1-(2-(3-Acetyl-6-(S-methylsulfonimidoyl)-1H-indazol-1-yl)acetyl)-N-(6-bromopyridin-2-yl)-4-fluoropyrrolidine-2-carboxamide (5)

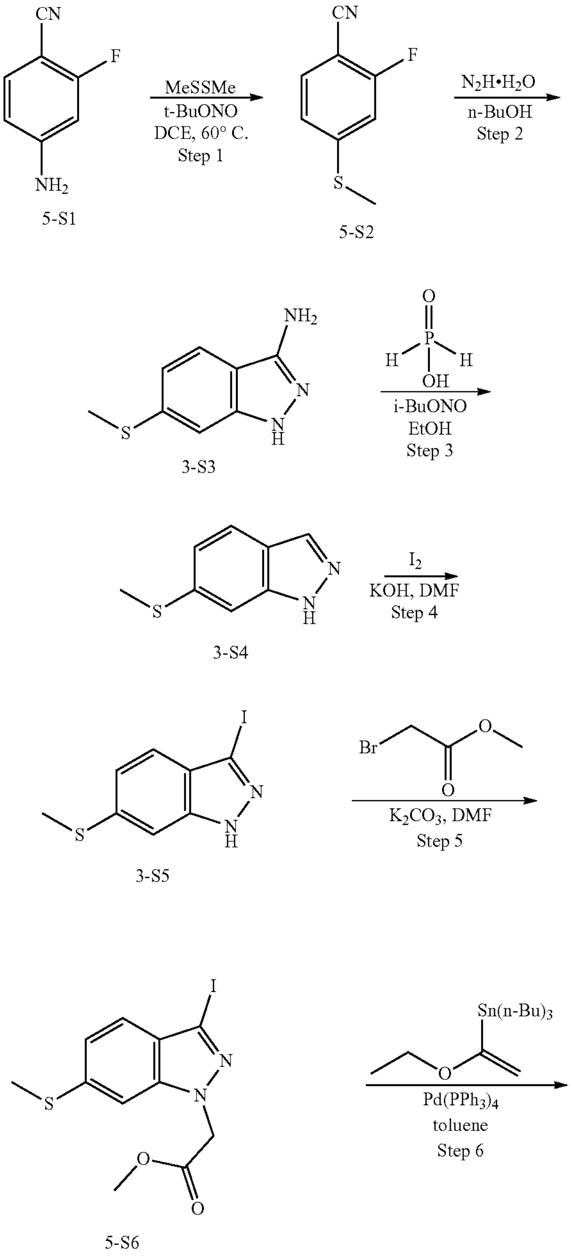

5-S1
5-S2
3-S3
3-S4
3-S5
5-S6

-continued

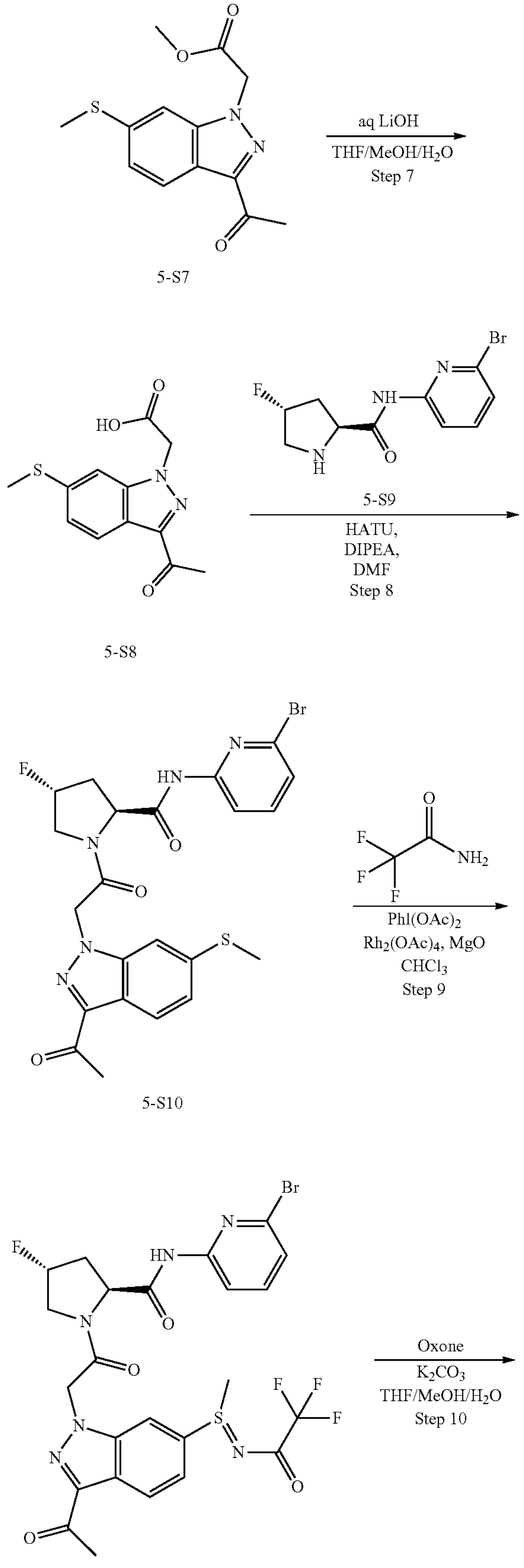

5-S7
5-S8
5-S9
5-S10
4

-continued

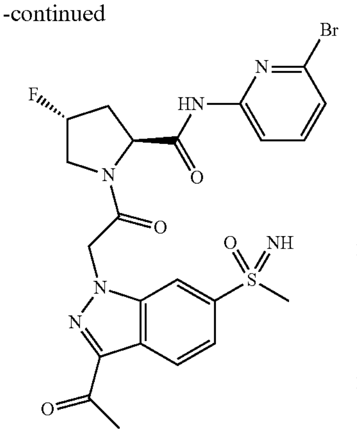

5

Step 1: 2-Fluoro-4-(methylthio)benzonitrile (5-S2)

To a mixture of 5-S1 (4 g, 29.38 mmol) and dimethyl disulfide (3.6 g, 38.19 mol) in DCE (100 mL) was added tert-butyl nitrite (4.1 g, 39.66 mol) dropwise at 60° C. under an atmosphere of nitrogen. The reaction mixture was stirred at 60° C. for 3 hours, diluted with DCM, and washed successively with 2 N aqueous HCl and brine. The organic layer was dried over anhydrous $Na_2SO_4$, filtered, and concentrated to dryness to afford the crude product, which was purified by column chromatography on silica gel (eluted with PE/EtOAc=5:1 to 2:1) to afford 5-S2 (3.3 g, 67.2% yield) as red oil.

Step 2: 6-(Methylthio)-1H-indazol-3-amine (5-S3)

To a solution of 5-S2 (3.3 g, 19.73 mmol) in n-butanol (50 mL) was added hydrazine hydrate (5.8 mL, 98.6 mmol) and the reaction mixture was stirred at 110° C. for 16 hours. The mixture was concentrated to dryness and the remaining residue was dissolved in DCM. The mixture was washed with water and brine, dried, and concentrated to dryness to afford the crude product, which was purified by column chromatography on silica gel (eluted with DCM/MeOH=100:1 to 30:1) to afford 5-S3 (2.9 g, 87.8% yield) as a yellow solid. LC/MS (ESI) m/z: 180 $(M+H)^+$.

Step 3: 6-(Methylthio)-1H-indazol-3-amine (5-S4)

To a solution of 5-S3 (2.9 g, 16.18 mol) in ethanol (50 mL) was added hypophosphorous acid (8.5 g, 64.71 mol, 50% aqueous solution) and the mixture was cooled to 0° C. To the reaction mixture was added isobutyl nitrite (2.6 mL, 22 mmol). The mixture was warmed to room temperature and the yellow suspension was stirred for 2 hours. The mixture was diluted with EtOAc, washed with water and brine, dried over anhydrous $Na_2SO_4$, and concentrated to dryness to afford the crude product, which was purified by column chromatography on silica gel (eluted with DCM/MeOH=40:1 to 20:1) to afford 5-S4 (1.7 g, 63.9% yield) as a yellow solid. LC/MS (ESI) m/z: 165 $(M+H)^+$.

Step 4: 3-Iodo-6-(methylthio)-1H-indazole (5-S5)

To a solution of 5-S4 (2.2 g, 12.20 mmol) in DMF (20 mL) was added potassium hydroxide (1.5 g, 26.83 mmol) and iodine (4.6 g, 18.29 mmol). The reaction mixture was stirred at room temperature overnight. The mixture was diluted with EtOAc, washed with water and brine, dried over anhydrous $Na_2SO_4$, and concentrated to dryness to afford crude 5-S5 (2.8 g, 80.0% yield) as a yellow solid. LC/MS (ESI) m/z: 291 $(M+H)^+$.

Step 5: Methyl 2-(3-iodo-6-(methylthio)-1H-indazol-1-yl)acetate (5-S6)

To a solution of 5-S5 (2.8 g, 9.66 mmol) in DMF (30 mL) was added $K_2CO_3$ (5.05 g, 36.59 mmol) and methyl 2-bromoacetate (1.73 mL, 18.29 mmol). The reaction mixture was stirred at room temperature for 1 hour. The mixture was diluted with EtOAc, washed with water and brine, dried over anhydrous $Na_2SO_4$, and concentrated to dryness to afford the crude product, which was purified by column chromatography on silica gel (eluted with DCM/MeOH=80:1 to 50:1) to afford 5-S6 (1.7 g, 48.6% yield) as a white solid. LC/MS (ESI) m/z: 363 $(M+H)^+$.

Step 6: Methyl 2-(3-acetyl-6-(methylthio)-1H-indazol-1-yl)acetate (5-S7)

To a solution of 5-S6 (1.7 g, 4.70 mmol) in toluene (20 mL) were added tributyl(1-ethoxyvinyl)stannane (2.54 g, 7.04 mmol) and $Pd(PPh_3)_4$ (543 mg, 0.47 mmol) at 0° C. The mixture was purged with nitrogen and stirred at 100° C. overnight under an atmosphere of nitrogen. The mixture was diluted with EtOAc and washed with 1 N aqueous HCl twice. The organic phase was dried over anhydrous $Na_2SO_4$, filtered, and concentrated to dryness. The remaining residue was purified by column chromatography on silica gel (eluted with DCM/MeOH=80:1 to 50:1) to afford 5-S7 (1.1 g, 84.6% yield) as a white solid. LC/MS (ESI) m/z: 279 $(M+H)^+$.

Step 7: 2-(3-Acetyl-6-(methylthio)-1H-indazol-1-yl) acetic acid (5-S8)

To a mixture containing 5-S7 (1.1 g, 3.96 mmol), THF (10 mL), MeOH (5 mL), and water (5 mL) was added LiOH (285 mg, 11.9 mmol). The mixture was stirred at room temperature overnight, concentrated, diluted with water, and washed with ether twice. The aqueous layer was acidified by adding 1 N aqueous HCl to pH of approximately 3 and extracted with EtOAc twice. The combined organic layers were washed with brine, dried over $Na_2SO_4$, filtered, and concentrated to dryness to afford 5-S8 (900 mg, 85.7% yield) as a white solid. LC/MS (ESI) m/z: 265 $(M+H)^+$.

Step 8: (2S,4R)-1-(2-(3-Acetyl-6-(methylthio)-1H-indazol-1-yl)acetyl)-N-(6-bromopyridin-2-yl)-4-fluoropyrrolidine-2-carboxamide (5-S10)

A round-bottom flask was charged with 2-(3-acetyl-6-(methylthio)-1H-indazol-1-yl) acetic acid (5-S8, 200 mg, 0.76 mmol), (2S, 4R)—N-(6-bromopyridin-2-yl)-4-fluoropyrrolidine-2-carboxamide (5-S9, 218 mg, 0.76 mmol), DMF (5 mL), DIPEA (488 mg, 3.8 mmol), and HATU (635 mg, 1.66 mmol). The resulting mixture was stirred at room temperature for 1 hour, diluted with EtOAc, washed with water and brine, dried over anhydrous $Na_2SO_4$, and concentrated. The remaining crude product was purified by column chromatography on silica gel (eluted with PE/EtOAc=10:1 to 1:1) to afford 5-S10 (260 mg, 64.4% yield) as light a yellow solid. LC/MS (ESI) m/z: 534 $(M+H)^+$.

Step 9: (2S,4R)-1-(2-(3-Acetyl-6-((E)-S-methyl-N-(2,2,2-trifluoroacetyl)sulfinimidoyl)-1H-indazol-1-yl)acetyl)-N-(6-bromopyridin-2-yl)-4-fluoropyrrolidine-2-carboxamide (4)

To a solution of 5-S10 (128 mg, 0.23 mmol) in DCM (3 mL) was added 2,2,2-trifluoroacetamide (53.5 mg, 0.47 mmol), $Rh_2(OAc)_4$ (2.62 mg, catalytic amount), MgO (19.08 mg, 0.47 mmol), and $PhI(OAc)_2$ (114.35 mg, 0.36 mmol) at 0° C. The reaction mixture was stirred at room temperature for 16 hours and quenched by addition of aqueous sodium thiosulfate solution (1 mL). The mixture was diluted with DCM, washed with brine, dried over $Na_2SO_4$, and concentrated under reduced pressure. The remaining residue was purified by column chromatography on silica gel (DCM/MeOH=100:1 to 80:1) to afford 4 (86 mg, 56.2% yield) as a white solid. $^1H$ NMR (400 MHz, DMSO-$d_6$) δ 11.09 (d, J=7.3 Hz, 1H), 8.51 (d, J=3.9 Hz, 1H), 8.47 (d, J=8.6 Hz, 1H), 8.08 (d, J=8.2 Hz, 1H), 7.87 (ddd, J=8.5, 6.1, 1.5 Hz, 1H), 7.76 (td, J=8.0, 3.4 Hz, 1H), 7.38 (d, J=7.7 Hz, 1H), 5.96 (dd, J=37.6, 17.3 Hz, 1H), 5.77 (dd, J=20.0, 17.3 Hz, 1H), 5.62 (d, J=52.8 Hz, 1H), 4.75 (dd, J=17.4, 9.5 Hz, 1H), 4.26 (m, J=20.6, 13.5 Hz, 1H), 4.16-4.00 (m, 1H), 3.22 (d, J=6.4 Hz, 3H), 2.73-2.67 (d, 3H), 2.65 (m, J=13.5 Hz, 1H), 2.31-2.15 (m, 1H). LC/MS (ESI) m/z: 645 $(M+H)^+$.

Step 10: (2S,4R)-1-(2-(3-Acetyl-6-(S-methylsulfonimidoyl)-1H-indazol-1-yl)acetyl)-N-(6-bromopyridin-2-yl)-4-fluoropyrrolidine-2-carboxamide (5)

To a solution of 4 (72 mg, 0.12 mmol) in MeOH (5 mL), THF (0.7 mL), and water (3.5 mL) was added Oxone (117 mg, 0.19 mmol) followed by a 47% aqueous $K_2CO_3$ solution (pH adjusted to approximately 10). The resulting mixture was stirred at room temperature for 1 hour, diluted with EtOAc, washed with brine, dried over anhydrous $Na_2SO_4$, and concentrated to afford the crude product, which was purified by preparative HPLC to afford 5 (20 mg, 29.5% yield) as a white solid. $^1H$ NMR (400 MHz, DMSO-$d_6$) δ 11.09 (s, 1H), 8.44 (d, J=3.0 Hz, 1H), 8.40 (d, J=8.5 Hz, 1H), 8.08 (dd, J=8.1, 4.0 Hz, 1H), 7.94 (dt, J=8.6, 1.4 Hz, 1H), 7.80-7.71 (m, 1H), 7.38 (d, J=7.7 Hz, 1H), 6.01 (dd, J=17.3, 10.2 Hz, 1H), 5.79 (dd, J=17.3, 5.9 Hz, 1H), 5.62 (d, J=52.9 Hz, 1H), 4.75 (t, J=8.0 Hz, 1H), 4.42 (d, J=5.9 Hz, 1H), 4.29 (dd, J=22.5, 13.0 Hz, 1H), 4.07 (ddd, J=12.6, 11.8, 5.2 Hz, 1H), 3.18 (s, 3H), 2.73-2.67 (m, 3H), 2.63 (dd, J=16.1, 10.8 Hz, 1H), 2.30-2.13 (m, 1H). LC/MS (ESI) m/z: 565 $(M+H)^+$.

Scheme 5: Synthesis of (1R,3S,5R)-2-(2-(3-Acetyl-6-(S-methylsulfonimidoyl)-1H-indazol-1-yl)acetyl)-N-(6-bromopyridin-2-yl)-5-methyl-2-azabicyclo[3.1.0]hexane-3-carboxamide (6)

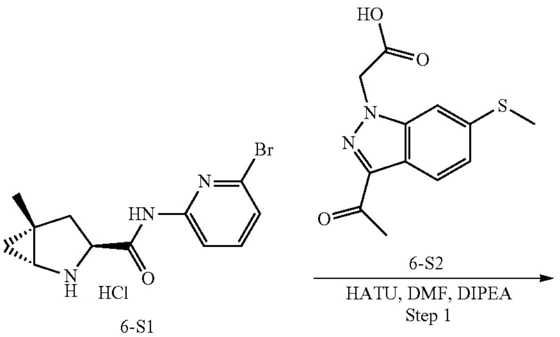

6-S1

6-S2

-continued

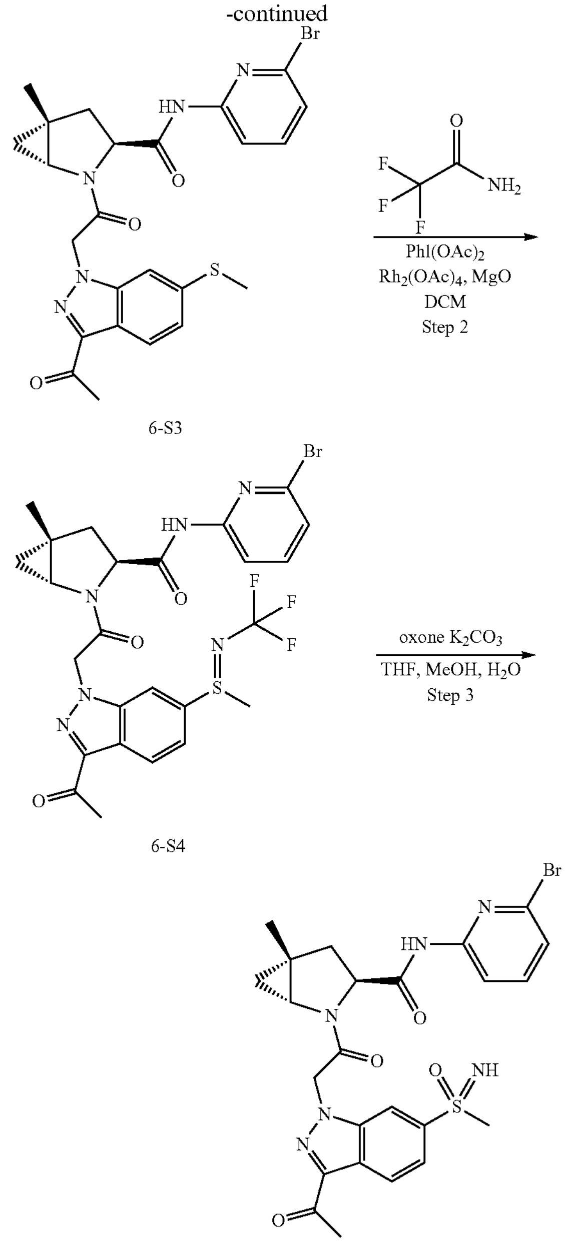

6-S3

6-S4

6

Step 1: (1R,3S,5R)-2-(2-(3-Acetyl-6-(methylthio)-1H-indazol-1-yl)acetyl)-N-(6-bromopyridin-2-yl)-5-methyl-2-azabicyclo[3.1.0]hexane-3-carboxamide (6-S3)

To a mixture of 6-S2 (188 mg, 0.71 mmol) and HATU (491 mg, 1.29 mmol) in DMF (2 mL) was added DIPEA (251 mg, 1.94 mmol) followed by 6-S1 (214 mg, 0.65 mmol). The reaction mixture was stirred at room temperature for 1 hour. The mixture was diluted with EtOAc, washed with 10% aqueous LiCl solution and brine, dried over anhydrous $Na_2SO_4$, and concentrated to afford the crude product, which was purified by column chromatography on silica gel (eluted with DCM/MeOH=50:1 to 15:1) to afford 6-S3 (170 mg, 76.3% yield) as a white solid. LC/MS (ESI) m/z: 543 $(M+H)^+$.

Step 2: (1R,3S,5R)-2-(2-(3-Acetyl-6-((E)-S-methyl-N-(trifluoromethyl)sulfinimidoyl)-1H-indazol-1-yl)acetyl)-N-(6-bromopyridin-2-yl)-5-methyl-2-azabicyclo[3.1.0]hexane-3-carboxamide (6-S4)

Compound 6-S3 (170 mg, 0.31 mmol) was dissolved in DCM (3 mL) and treated with (diacetoxyiodo)benzene (156 mg, 0.45 mmol), 2,2,2-trifluoroacetamide (71 mg, 0.63 mmol), MgO (25 mg, 0.63 mmol), and $Rh_2(OAc)_4$ (4 mg, 0.01 mmol) at room temperature. The reaction mixture was stirred at room temperature for 16 hours and quenched with aqueous $Na_2S_2O_3$ solution. The mixture was diluted with DCM, washed with brine, dried over $Na_2SO_4$, filtered, and concentrated to dryness to afford the crude product, which was purified by column chromatography on silica gel (eluted with PE/EtOAc=2:1 to 1:3) to afford 6-S4 (112 mg, 57.8% yield) as a white solid. LC/MS (ESI) m/z: 625 $(M+H)^+$.

Step 3: (1R,3S,5R)-2-(2-(3-Acetyl-6-(S-methylsulfonimidoyl)-1H-indazol-1-yl)acetyl)-N-(6-bromopyridin-2-yl)-5-methyl-2-azabicyclo[3.1.0]hexane-3-carboxamide (6)

To a solution of 6-S4 (112 mg, 0.18 mmol) in MeOH (7 mL), THF (1 mL), and water (5 mL) was added Oxone (180 mg, 0.29 mmol) followed by a 47% aqueous $K_2CO_3$ solution (pH adjusted to approximately 10). The resulting mixture was stirred at room temperature for 1 hour, diluted with EtOAc, washed with brine, dried over anhydrous $Na_2SO_4$, and concentrated to afford the crude product, which was purified by preparative HPLC to afford 6 (20 mg, 19.4% yield) as a white solid. $^1H$ NMR (400 MHz, DMSO-$d_6$) δ 10.82 (s, 1H), 8.40 (s, 1H), 8.35 (d, J=8.3 Hz, 1H), 8.03 (d, J=8.2 Hz, 1H), 7.88 (d, J=8.5 Hz, 1H), 7.71 (t, J=8.0 Hz, 1H), 7.32 (d, J=7.7 Hz, 1H), 6.08 (dd, J=17.3, 7.2 Hz, 1H), 5.64 (dd, J=17.3, 8.7 Hz, 1H), 4.46-4.37 (m, 2H), 3.66 (d, J=2.7 Hz, 1H), 3.13 (s, 3H), 2.63 (d, J=15.3 Hz, 3H), 2.47 (s, 1H), 1.99 (dd, J=13.0, 6.1 Hz, 1H), 1.30 (s, 3H), 0.98 (d, J=5.1 Hz, 2H). LC/MS (ESI) m/z: 573 $(M+H)^+$.

Scheme 6: Synthesis of (1R, 2S, 5S)-3-(2-(3-Acetyl-6-(S-methylsulfonimidoyl)-1H-indazol-1-yl) acetyl)-N-(6-bromopyridin-2-yl)-3-azabicyclo [3.1.0] hexane-2-carboxamide (7)

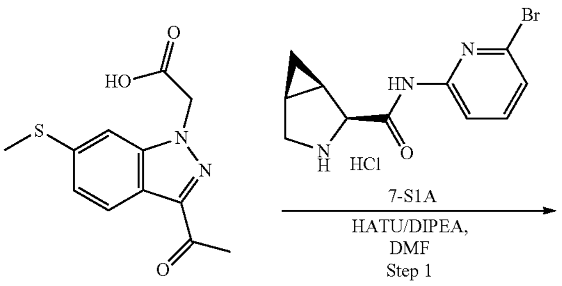

7-S1

-continued

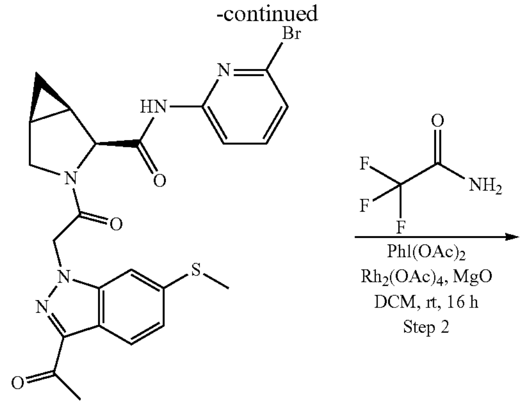

7-S2

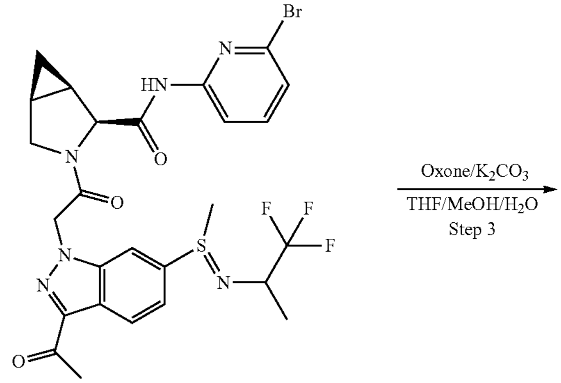

7-S3

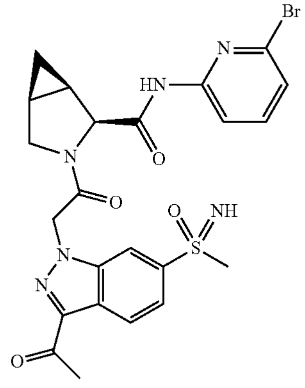

7

Step 1: (1R, 2S, 5S)-3-(2-(3-Acetyl-6-(methylthio)-1H-indazol-1-yl)acetyl)-N-(6-bromopyridin-2-yl)-3-azabicyclo[3.1.0]hexane-2-carboxamide (7-S2)

To a mixture of 7-S1 (109.22 mg, 0.39 mmol) and (1R, 2S, 5S)—N-(6-bromopyridin-2-yl)-3-azabicyclo[3.1.0]hexane-2-carboxamide hydrochloride (7-S1A, 113.1 mg, 0.355 mmol) in DMF (3 mL) were added DIPEA (0.17 mL, 1.06 mmol) and HATU (202.13 mg, 0.532 mmol). The mixture was stirred at room temperature for 16 hours, diluted with EtOAc, washed with 10% aqueous LiCl solution and brine, dried over $Na_2SO_4$, and concentrated under reduced pressure. The remaining residue was purified by column chromatography on silica gel (DCM/MeOH=80:1) to afford 7-S2 (125 mg, 66.8% yield) as a white solid. LC/MS (ESI) m/z: 529 $(M+H)^+$.

Step 2: (1R,2S,5S)-3-(2-(3-Acetyl-6-((E)-S-methyl-N-(2,2,2-trifluoroacetyl)sulfinimidoyl)-1H-indazol-1-yl)acetyl)-N-(6-bromopyridin-2-yl)-3-azabicyclo [3.1.0]hexane-2-carboxamide (7-S3)

To a solution of 7-S2 (125 mg, 0.237 mmol) in DCM (3 mL) was added 2,2,2-trifluoroacetamide (53.5 mg, 0.473 mmol), $Rh_2(OAc)_4$ (2.62 mg, 0.0059 mmol), MgO (19.08 mg, 0.473 mmol), and $PhI(OAc)_2$ (114.35 mg, 0.355 mmol) at 0° C. The reaction mixture was stirred at room temperature for 16 hours, quenched by addition of aqueous sodium thiosulfate solution (1 mL), diluted with DCM, washed with brine, dried over $Na_2SO_4$, and concentrated under reduced pressure. The remaining residue was purified by column chromatography on silica gel (DCM/MeOH=100:1 to 80:1) to afford 7-S3 (62 mg, 41% yield) as a white solid. LC/MS (ESI) m/z: 640 $(M+H)^+$.

Step 3: (1R, 2S, 5S)-3-(2-(3-Acetyl-6-(S-methylsulfonimidoyl)-1H-indazol-1-yl) acetyl)-N-(6-bromopyridin-2-yl)-3-azabicyclo [3.1.0] hexane-2-carboxamide (7)

To a solution of 7-S3 (62 mg, 0.097 mmol), MeOH (1 mL), THF (0.33 mL), and water (0.5 mL) was added Oxone (101.4 mg, 0.165 mmol) in eight portions at 25° C. After each addition, the pH was adjusted to 10 using 47% aqueous potassium carbonate solution. The reaction mixture was stirred at room temperature for 16 hours, diluted with EtOAc, washed with water and brine, dried over $Na_2SO_4$, and concentrated to dryness. The remaining residue was purified by preparative HPLC to afford 7 (3.9 mg, 7.2% yield) as a white solid. $^1H$ NMR (400 MHz, $CD_3OD$) δ 8.44 (dd, J=8.6, 0.7 Hz, 1H), 8.35 (s, 1H), 8.03 (d, J=8.5 Hz, 1H), 7.96-7.85 (m, 1H), 7.63-7.52 (m, 1H), 7.22 (d, J=7.8 Hz, 1H), 5.61 (s, 2H), 4.70 (d, J=5.2 Hz, 1H), 4.09 (dd, J=9.8, 5.4 Hz, 1H), 3.96 (t, J=9.4 Hz, 1H), 3.20 (d, J=4.3 Hz, 3H), 2.72-2.63 (m, 3H), 2.11 (s, 1H), 1.96 (s, 1H), 0.91-0.81 (m, 2H). LC/MS (ESI) m/z: 559 $(M+H)^+$.

Scheme 7. Synthesis of (2S,4R)-1-(2-(3-Acetyl-1H-indazol-1-yl)acetyl)-N-(cuban-1-ylmethyl)-4-fluoropyrrolidine-2-carboxamide (8)

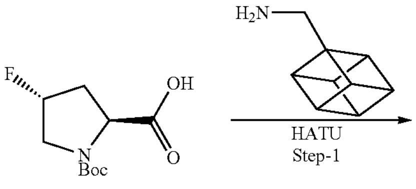

8-S1

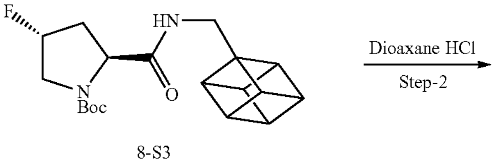

8-S3

-continued

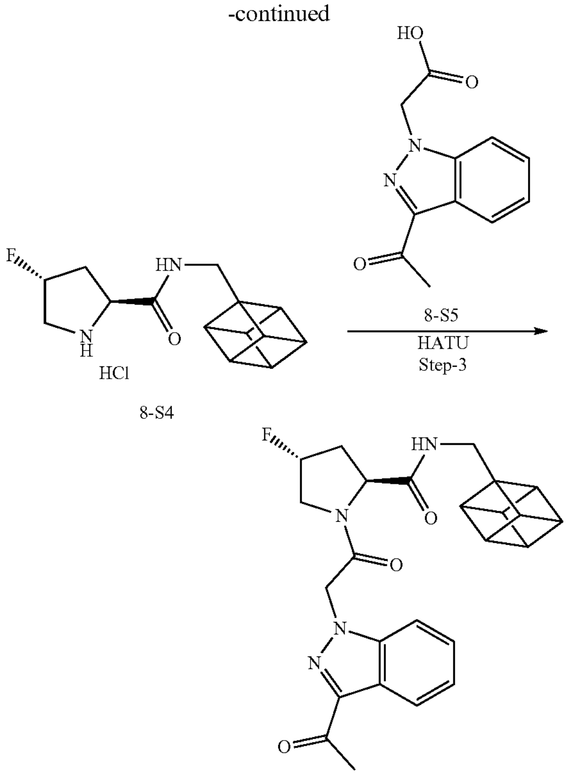

8-S4

8

The above scheme and following detailed description depicts one non-limiting method for synthesizing compounds with amide linked C and B rings. The skilled artisan will recognize that the amine can be replaced with other amines to afford additional compounds of the present invention. The skilled artisan will also recognize that other A rings described herein or in the art can also be coupled to the C-Linker-B ring moiety via coupling with HATU or a related agent.

Step 1: tert-Butyl (2S,4R)-2-(cuban-1-ylmethyl)-4-fluoropyrrolidine-1-carboxylate (8-S3)

To a solution of (2S,4R)-1-(tert-butoxycarbonyl)-4-fluoropyrrolidine-2-carboxylic acid (8-S1, 1 equiv) in DMF (10 vol) at 0° C. under nitrogen atmosphere was added cuban-1-ylmethanamine hydrochloride (8-S2, 1.2 equiv), HATU (1.5 equiv) and DIPEA (3 equiv). The reaction mixture was stirred at room temperature for 3 hours. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using EtOAc/hexane to afford compound 8-S3.

Step 2: (2S,4R)—N-(Cuban-1-ylmethyl)-4-fluoropyrrolidine-2-carboxamide hydrochloride (8-S4)

To a solution of compound 8-S3 (1 equiv) in 1,4-dioxane (3 vol) at 0° C. under nitrogen atmosphere was added 4 N HCl in 1,4-dioxane (10 vol) and stirred at room temperature for 3 hours. The reaction mixture was concentrated to afford compound 8-S4.

Step 3: (2S,4R)-1-(2-(3-Acetyl-1H-indazol-1-yl) acetyl)-N-(cuban-1-ylmethyl)-4-fluoropyrrolidine-2-carboxamide (8)

To a solution of compound 8-S4 (1 equiv) in DMF (10 vol) at 0° C. under nitrogen atmosphere was added 2-(3-acetyl-1H-indazol-1-yl)acetic acid (8-S5, 1.2 equiv), HATU (1.5 equiv) and DIPEA (3 equiv). The reaction mixture was stirred at room temperature for 3 hours. After completion of the reaction, the reaction mixture was quenched with water. The resulting mixture was extracted with DCM. The organic layer was washed with brine, dried over anhydrous $Na_2SO_4$, filtered and then concentrated. The residue was purified by preparative HPLC to afford compound 8. $^1H$ NMR (400 MHz, DMSO-$d_6$) δ: 8.18 (d, J=8.0 Hz, 1H), 8.00-7.99 (m, 1H), 7.67 (d, J=8.4 Hz, 1H), 7.49-7.45 (m, 1H), 7.36-7.33 (m, 1H), 5.77-5.72 (m, 1H), 5.55-5.42 (m, 2H), 4.41-4.37 (m, 1H), 4.21-4.13 (m, 1H), 3.98-3.73 (m, 8H), 3.37-3.32 (m, 2H), 3.14-3.09 (s, 1H), 2.69 (s, 3H), 2.11-1.98 (m, 1H).

Scheme 8: Synthesis of (1R, 2S, 5S)-3-(2-(3-Acetyl-5-methyl-1H-thieno [3,2-c] pyrazol-1-yl)acetyl)-N-(6-bromo-3-cyclopropylpyridin-2-yl)-3-azabicyclo [3.1.0] hexane-2-carboxamide (10)

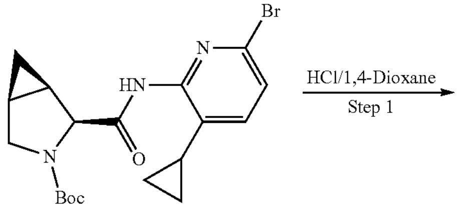

10-S1

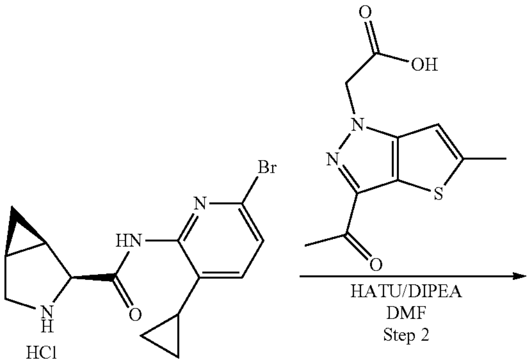

10-S2

-continued

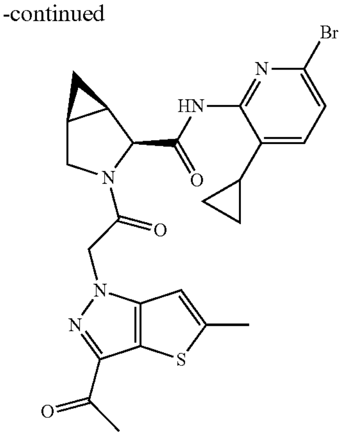

10

Step 1: (1R, 2S, 5S)—N-(6-Bromo-3-cyclopropylpyridin-2-yl)-3-azabicyclo [3.1.0] hexane-2-carboxamide (10-S2)

Compound 10-S1 (100 mg, 0.237 mmol) was treated with HCl/1,4-dioxane solution (2 mL, 2 M) at room temperature for 1 hour. The mixture was concentrated to dryness to afford 10-S2 (71 mg, 100% yield), which was carried forward in the next synthetic step without further purification. LC/MS (ESI) m/z: 323 $(M+H)^+$.

Step 2: (1R, 2S, 5S)-3-(2-(3-Acetyl-5-methyl-1H-thieno [3, 2-c] pyrazol-1-yl) acetyl)-N-(6-bromo-3-cyclopropylpyridin-2-yl)-3-azabicyclo [3.1.0] hexane-2-carboxamide (10)

To a mixture of 10-S2 (53.6 mg, 0.17 mmol) and 2-(3-acetyl-5-methyl-1H-thieno[3,2-c]pyrazol-1-yl)acetic acid (36 mg, 0.15 mmol) in DMF (2 mL) was added DIPEA (0.075 mL, 0.454 mmol) and HATU (86.2 mg, 0.28 mmol). The mixture was stirred at room temperature for 16 hours, diluted with EtOAc, washed with 10% aqueous LiCl solution and brine, dried over $Na_2SO_4$, and concentrated under reduced pressure. The remaining residue was purified by preparative HPLC to afford 10 (7.6 mg, 9.2% yield) as a white solid. $^1H$ NMR (400 MHz, $CD_3OD$) δ 7.36 (d, J=8.1 Hz, 1H), 7.25 (d, J=8.1 Hz, 1H), 5.28 (q, J=17.0 Hz, 2H), 4.79-4.70 (m, 1H), 3.99 (dd, J=9.6, 5.4 Hz, 1H), 3.86 (d, J=9.7 Hz, 1H), 2.56 (d, J=4.1 Hz, 3H), 2.52 (d, J=1.1 Hz, 3H), 2.18 (s, 1H), 2.03-1.87 (m, 2H), 0.97-0.80 (m, 4H), 0.60 (dd, J=9.5, 4.8 Hz, 2H). LC/MS (ESI) m/z: 542 $(M+H)^+$.

Scheme 9: Synthesis of (2S,4R)-1-(2-(3-Acetyl-6-(N-cyano-S-methylsulfonimidoyl)-1H-indazol-1-yl)acetyl)-N-(6-bromopyridin-2-yl)-4-fluoropyrrolidine-2-carboxamide (11)

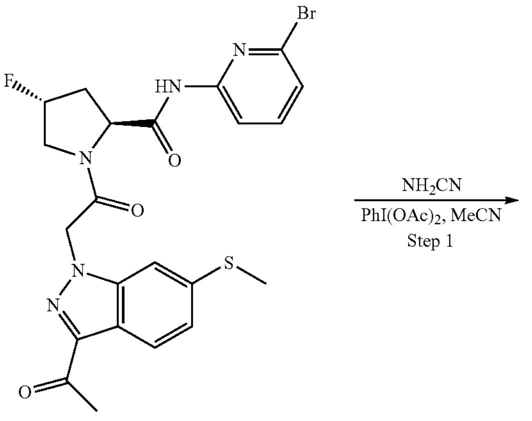

11-S1

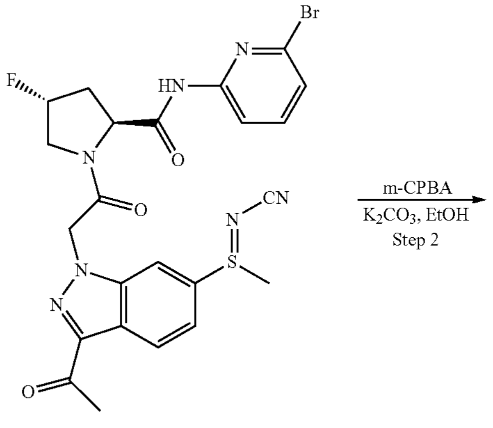

11-S2

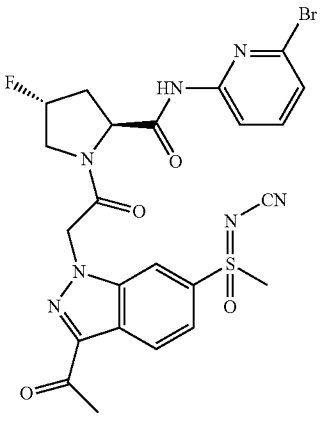

11

Step 1: Synthesis of (2S,4R)-1-(2-(3-Acetyl-6-((E)-N-cyano-S-methylsulfinimidoyl)-1H-indazol-1-yl) acetyl)-N-(6-bromopyridin-2-yl)-4-fluoropyrrolidine-2-carboxamide (11-S2)

To a solution of (2S, 4R)-1-(2-(3-acetyl-6-(methylthio)-1H-indazol-1-yl) acetyl)-N-(6-bromopyridin-2-yl)-4-fluoropyrrolidine-2-carboxamide (11-S1, 100 mg, 0.19 mmol) and cyanamide (12 mg, 0.28 mmol) in MeCN (5 mL) at 0° C. was added $PhI(OAc)_2$ (66 mg, 0.21 mmol). The resulting mixture was stirred at 0° C. for 3 hours, quenched with aqueous $NaS_2SO_3$ solution, and extracted with DCM twice. The combined organic layers were washed with aqueous $NaHCO_3$ solution and brine, dried over anhydrous $Na_2SO_4$, and concentrated. The remaining crude product was purified by column chromatography on silica gel (eluted with DCM/MeOH=100:1 to 30:1) to afford 11-S2 (40 mg, 37.2% yield) as a white solid. LC/MS (ESI) m/z: 574 $(M+H)^+$.

Step 2: Synthesis of (2S,4R)-1-(2-(3-Acetyl-6-(N-cyano-S-methylsulfonimidoyl)-1H-indazol-1-yl) acetyl)-N-(6-bromopyridin-2-yl)-4-fluoropyrrolidine-2-carboxamide (11)

To a solution of 11-S2 (30 mg, 0.052 mmol) in EtOH (3 mL) was added $K_2CO_3$ (22 mg, 0.16 mmol) and m-chloroperoxybenzoic acid (9 mg, 0.052 mmol). The resulting mixture was stirred at 0° C. for 3 hours, diluted with EtOAc, washed with water and brine, dried over anhydrous $Na_2SO_4$, and concentrated. The remaining crude product was purified by preparative HPLC to afford 11 (5 mg, 16.2% yield) as a white solid. $^1H$ NMR (400 MHz, $CD_3OD$) δ 8.57 (d, J=8.8 Hz, 1H), 8.54-8.48 (m, 1H), 8.07 (t, J=8.4 Hz, 1H), 7.95-7.89 (m, 1H), 7.64-7.57 (m, 1H), 7.24 (dd, J=7.6, 0.4 Hz, 1H), 5.86-5.77 (m, 1H), 5.75-5.67 (m, 1H), 5.58-5.41 (m, 1H), 4.76 (t, J=8.4 Hz, 1H), 4.32-4.21 (m, 1H), 4.13-3.96 (m, 1H), 3.59 (d, J=2.4 Hz, 3H), 2.77-2.67 (m, 4H), 2.37-2.16 (m, 1H). LC/MS (ESI) m/z: 590 $(M+H)^+$.

Scheme 10. Synthesis of (2S,4R)-1-(2-(3-Acetyl-5-(5-amino-1,3-dioxan-2-yl)01H-indazol-1-yl)acetyl)-N-(6-bromopyridin-2-yl)-4-fluoropyrrolidine-2-carboxamide (12)

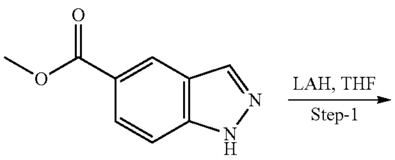

12-S1

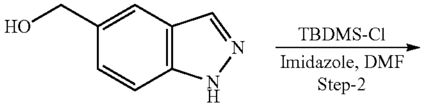

12-S2

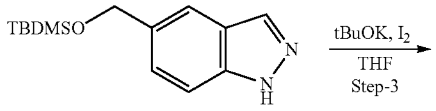

12-S3

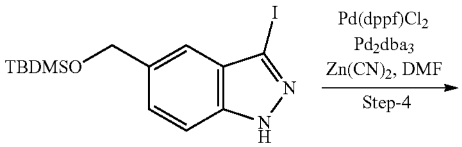

12-S4

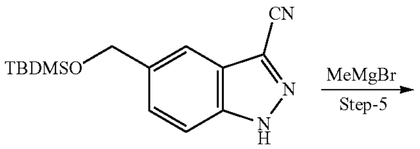

12-S5

-continued

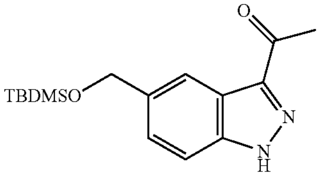

12-S6

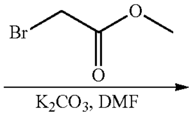

$K_2CO_3$, DMF
Step-6

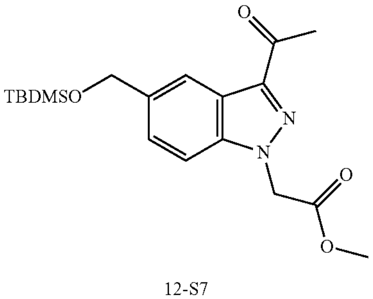

12-S7

LiOH
Step-7

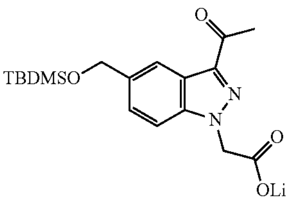

12-S8

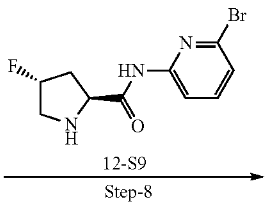

12-S9
Step-8

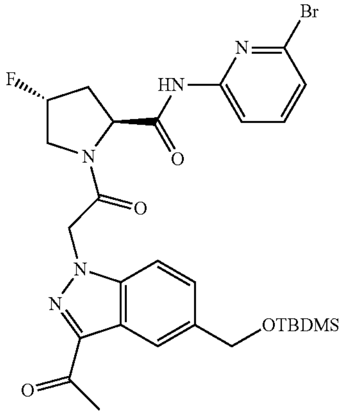

12-S10

TBAF
Step-9

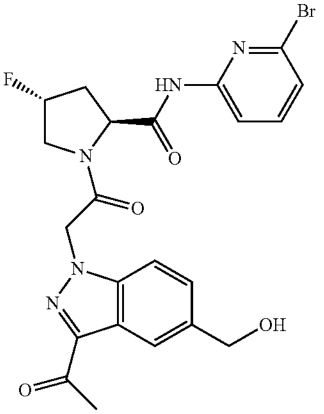

12-S11

IBX
Step-10

-continued

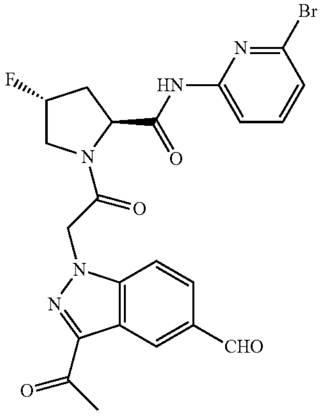

12-S12

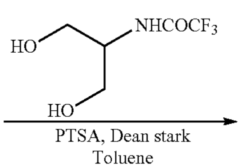

PTSA, Dean stark
Toluene
Step-11

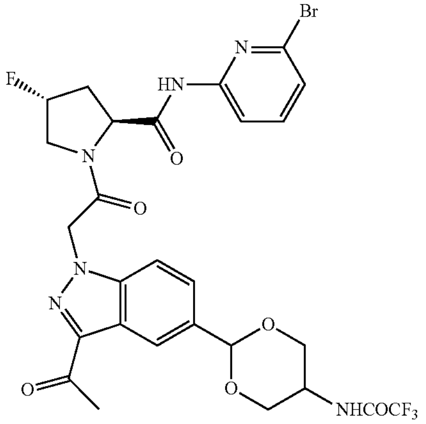

12-S13

NaOH
Step-12

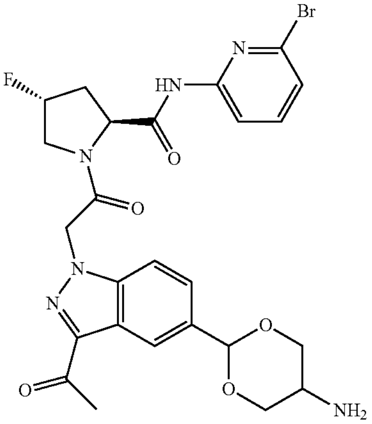

12

Step 1: (1H-Indazol-5-yl)methanol (12-S2)

To a solution of methyl 1H-indazole-5-carboxylate (12-S1, 1 equiv) in THF (10 vol) at 0° C. was added LAH (2 equiv). The reaction mixture was stirred at room temperature for 2 hours and then cooled at 0° C. The resulting mixture was quenched 10% NaOH solution, filtered and then concentrated. The residue was purified by column chromatography on silica gel using DCM/MeOH to afford compound 12-S2.

Step 2: 5-(((tert-Butyldimethylsilyl)oxy)methyl)-1H-indazole (12-S3)

To a solution of compound 12-S2 (1 equiv) in DMF (10 vol) at 0° C. under nitrogen atmosphere was added TBDMS-Cl (1.2 equiv) and imidazole (2.5 equiv). The reaction mixture was stirred at room temperature for 2 hours and then quenched with water. The resulting solid was filtered, taken up in MTBE and stirred for 30 minutes, filtered, and dried to afford compound 12-S3.

Step 3: 5-(((tert-Butyldimethylsilyl)oxy)methyl)-3-iodo-1H-indazole (12-S4)

To a solution of compound 12-S3 (1 equiv) in THF (10 vol) at 0° C. under nitrogen atmosphere was added iodine (1.5 equiv) and KO$^t$Bu (2.5 equiv). The reaction mixture was stirred at room temperature for 16 hours. Water was added to the reaction mixture and the resulting mixture was extracted with ethyl acetate. The organic layer was separated, dried over anhydrous $Na_2SO_4$, filtered and then concentrated. The residue was purified by column chromatography on silica gel using hexane/EtOAc to afford compound 12-S4.

Step 4: 5-(((tert-Butyldimethylsilyl)oxy)methyl)-1H-indazole-3-carbonitrile (12-S5)

To a solution of compound 12-S4 (1 equiv) in DMF (10 vol) at 0° C. under nitrogen atmosphere was added $Zn(CN)_2$ (1.1 eq.), Pd (dppf)$Cl_2$ (0.1 equiv), $Pd_2(dba)_3$ (0.1 equiv) and water (1 vol). The reaction mixture was stirred at 80° C. for 4 hours. Water was added to the reaction mixture and the resulting mixture was extracted with ethyl acetate. The organic layer was separated, dried over anhydrous $Na_2SO_4$, filtered and then concentrated. The residue was purified by column chromatography on silica gel using hexane/EtOAc to afford compound 12-S5.

Step 5: 1-(5-(((tert-Butyldimethylsilyl)oxy)methyl)-1H-indazol-3-yl)ethan-1-one (S6)

To a solution of compound 12-S5 (1 equiv) in THF/DEE (1:1, 30 vol) at 0° C. under nitrogen atmosphere was added methyl magnesium bromide solution (3 M in DEE) (3 equiv). The reaction mixture was stirred at room temperature for 3 hours and then cooled to 0° C. Water was added to the reaction mixture and the resulting mixture was extracted with ethyl acetate. The organic layer was separated, dried over anhydrous $Na_2SO_4$, filtered and then concentrated. The residue was purified by column chromatography on silica gel using hexane/EtOAc to afford compound 12-S6.

Step 6: Methyl 2-(3-acetyl-5-(((tert-butyldimethylsilyl)oxy)methyl)-1H-indazol-1-yl)acetate (12-S7)

To a solution of compound 12-S6 (1 equiv) in DMF (10 vol) was added potassium carbonate (2.5 equiv) and methyl bromoacetate (1.1 equiv). The reaction mixture was stirred at room temperature for 3 hours and then quenched with water. The resulting solid was filtered, taken up in MTBE and stirred for 30 minutes, filtered, and dried to afford compound 12-S7.

Step 7: Lithium 2-(3-acetyl-5-(((tert-butyldimethylsilyl)oxy)methyl)-1H-indazol-1-yl)acetate (12-S8)

To a solution of compound 12-S7 (1 equiv) in THF/water/MeOH (4:1:1) was added LiOH (3 equiv). The reaction mixture was stirred at room temperature for 5 hours and concentrated to afford compound 12-S8.

Step 8: (2S,4R)-1-(2-(3-Acetyl-5-(((tert-butyldimethylsilyl)oxy)methyl)-1H-indazol-1-yl)acetyl)-N-(6-bromopyridin-2-yl)-4-fluoropyrrolidine-2-carboxamide (12-S10)

To a solution of compound 12-S8 (1 equiv) in DMF (10 vol) at 0° C. under nitrogen atmosphere was added 12-S9 (1.2 equiv), HATU (2 equiv) and DIPEA (5 equiv). The reaction mixture was stirred at room temperature for 12 hours. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to afford compound 12-S10.

Step 9: (2S,4R)-1-(2-(3-Acetyl-5-(hydroxymethyl)-1H-indazol-1-yl)acetyl)-N-(6-bromopyridin-2-yl)-4-fluoropyrrolidine-2-carboxamide (12-S11)

To a solution of compound 12-S10 (1 equiv) in THF (10 vol) at 0° C. was added TBAF (0.5 equiv). The reaction mixture was stirred at room temperature for 2 hours and concentrated. The residue was purified by column chromatography on silica gel using DCM/MeOH to afford compound 12-S11.

Step 10: (2S,4R)-1-(2-(3-Acetyl-5-formyl-1H-indazol-1-yl)acetyl)-N-(6-bromopyridin-2-yl)-4-fluoropyrrolidine-2-carboxamide (12-S12)

To a solution of compound 12-S11 (1 equiv) in EtOAc (50 vol) was added IBX (1.1 equiv). The reaction mixture was stirred at 85° C. for 4 hours. After completion of the reaction, the reaction mixture was filtered and concentrated. The residue was purified by column chromatography on silica gel using DCM/MeOH to afford compound 12-S12.

Step 11: (2S,4R)-1-(2-(3-Acetyl-5-(5-(2,2,2-trifluoroacetamido)-1,3-dioxan-2-yl)-1H-indazol-1-yl)acetyl)-N-(6-bromopyridin-2-yl)-4-fluoropyrrolidine-2-carboxamide (12-S13)

To a solution of compound 12-S12 (1 equiv) in toluene (10 vol)) was added N-(1,3-dihydroxypropan-2-yl)-2,2,2-trifluoroacetamide (2.5 equiv) and PTSA (0.1 equiv). The reaction mixture was stirred at 120° C. for 8 hours. After completion of the reaction, the reaction mixture was concentrated and purified by preparative HPLC to afford compound 12-S13.

Step 12: (2S,4R)-1-(2-(3-Acetyl-5-(5-amino-1,3-dioxan-2-yl)-1H-indazol-1-yl)acetyl)-N-(6-bromopyridin-2-yl)-4-fluoropyrrolidine-2-carboxamide (12)

To a solution of compound 12-S13 (1 equiv) in ethanol (10 vol) at 0° C. was added NaOH (1 equiv). The reaction mixture was stirred at room temperature for 3 hours. After completion of the reaction, the reaction mixture was concentrated and purified by column chromatography on silica gel using DCM/MeOH to afford compound 12. $^1$H NMR (400 MHz, $CD_3OD$) δ: 8.40 (s, 1H), 8.07 (d, J=8.0 Hz, 1H), 7.64-7.60 (m, 3H), 7.27 (d, J=8.0 Hz, 1H), 5.76-5.67 (m, 1H), 5.63-5.43 (m, 3H), 4.89-4.88 (m, 1H), 4.33-4.27 (m, 2H), 4.24-4.11 (m, 2H), 2.83-2.03 (m, 1H), 2.77-2.65 (m, 3H), 1.95-1.93 (m, 4H).

Scheme 11. Synthesis of (2S,4R)-1-(2-(3-Acetyl-1H-pyrazol-1-yl)acetyl)-N-(6-bromopyridin-2-yl)-4-fluoropyrrolidine-2-carboxamide (14)

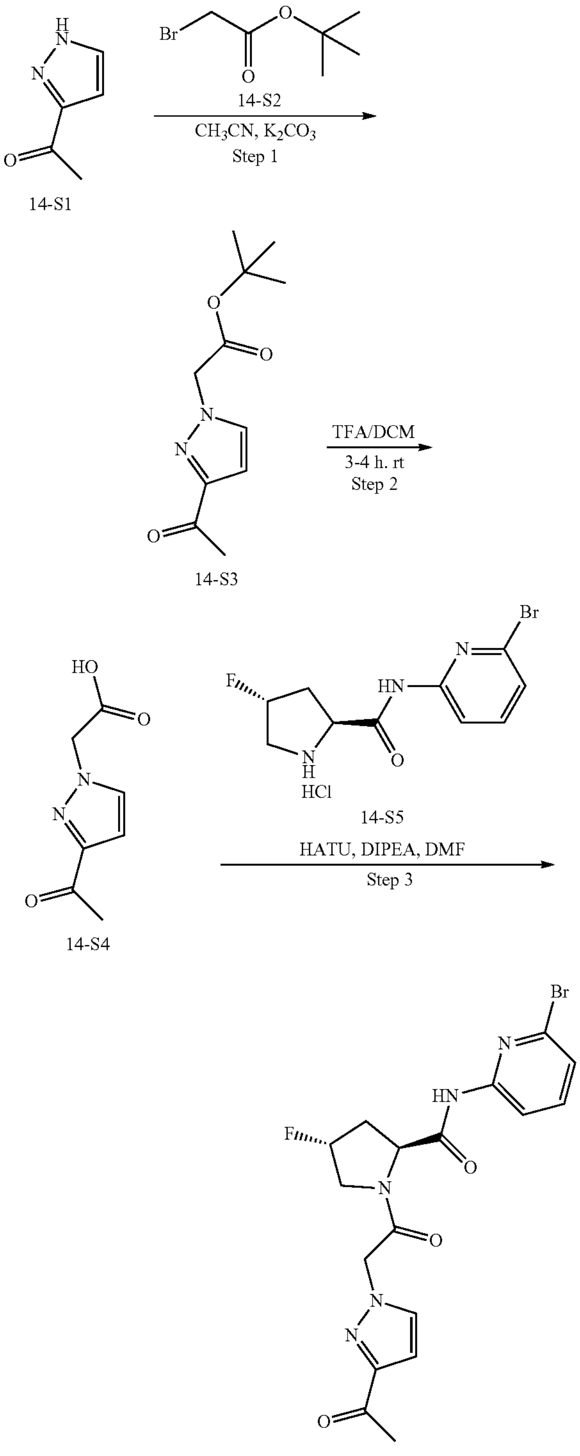

14-S1

14-S2

14-S3

14-S4

14-S5

14

The above scheme and following detailed description depicts one non-limiting method for synthesizing compounds with a pyrazole A-ring. The skilled artisan will recognize that the pyrazole can be replaced with other nucleophilic aryl groups with or without additional substituents.

Step 1: tert-Butyl 2-(3-acetyl-1H-pyrazol-1-yl)acetate (14-S3)

To a solution of 1-(1H-pyrazol-3-yl)ethan-1-one (14-S1, 1 equiv) in $CH_3CN$ (10 vol) was added tert-butyl 2-bromoacetate (14-S2, 1.1 equiv) and potassium carbonate (1.1 equiv). The mixture was refluxed overnight under an atmosphere of argon. After cooling the reaction mixture to room temperature, the mixture was filtered through Celite and washed with $CH_3CN$. The filtrate was concentrated under reduced pressure and the remaining residue was purified by column chromatography on silica gel (eluted with DCM/EtOAc) to afford compound 14-S3.

Step 2: 2-(3-Acetyl-1H-pyrazol-1-yl)acetic acid (14-S4)

To a solution of compound 14-S3 (1 equiv) in DCM (10 vol) at 0° C. under an atmosphere of argon was added TFA (5 vol). The reaction mixture was stirred at room temperature for 3 hours and concentrated to dryness. The remaining material (14-S4) was used directly in the next synthetic step without additional purification.

Step 3: (2S,4R)-1-(2-(3-Acetyl-1H-pyrazol-1-yl)acetyl)-N-(6-bromopyridin-2-yl)-4-fluoropyrrolidine-2-carboxamide (14)

To a solution of compound 14-S4 (1 equiv) in DMF (10 vol) at 0° C. under an atmosphere of argon was added (2S,4R)—N-(6-bromopyridin-2-yl)-4-fluoropyrrolidine-2-carboxamide hydrochloride (14-S5, 1 equiv), HATU (2.1 equiv), and DIPEA (5 equiv). The reaction mixture was stirred at room temperature for 3 hours and quenched with water (30 vol). The resulting mixture was extracted with DCM. The organic layer was washed with brine, dried over anhydrous $Na_2SO_4$, filtered, and concentrated to dryness. The remaining residue was purified by column chromatography on silica gel (eluted with DCM/MeOH) to afford compound 14. $^1H$ NMR (400 MHz, DMSO-$d_6$) δ 2.00-2.24 (m, 1H), 2.46 (s, 3H), 2.53-2.62 (m, 1H), 3.75-3.95 (m, 1H), 4.09 (dd, J=13.0, 21.6 Hz, 1H), 4.69 (t, J=8.5 Hz, 1H), 5.24 (d, J=16.8 Hz, 1H), 5.37-5.61 (m, 2H), 6.70 (d, J=2.4 Hz, 1H), 7.34 (d, J=7.7 Hz, 1H), 7.73 (t, J=8.0 Hz, 1H), 7.78 (d, J=2.5 Hz, 1H), 8.05 (d, J=8.2 Hz, 1H), 11.02 (s, 1H).

Scheme 12. Synthesis of Ethyl (E)-3-(1-(2-((2S,4R)-2-((6-Bromopyridin-2-yl)carbamoyl)-4-fluoropyrrolidin-1-yl)-2-oxoethyl)-3-carbamoyl-1H-pyrazol-4-yl)acrylate (22)

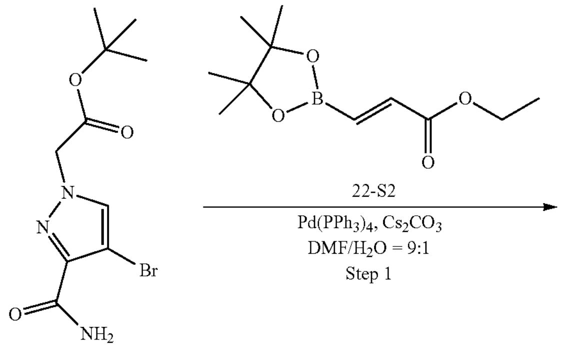

22-S2

22-S1

-continued

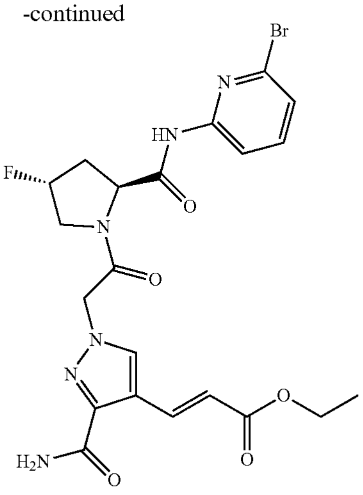

22

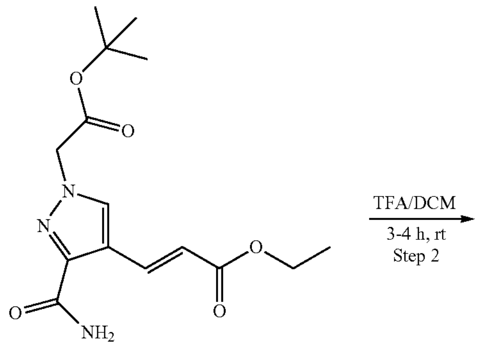

22-S3

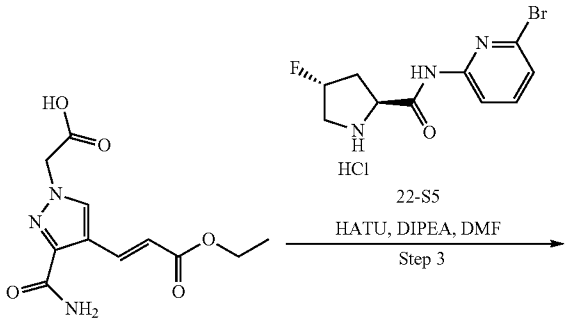

22-S5

22-S4

Step 1: Ethyl (E)-3-(1-(2-(tert-butoxy)-2-oxoethyl)-3-carbamoyl-1H-pyrazol-4-yl)acrylate (22-S3)

To a solution of ethyl (E)-3-(4,4,5,5-tetramethyl-1,3,2-dioxaborolan-2-yl)acrylate (22-S2, 1 equiv) in DMF/$H_2O$ (9:1, 10 vol) was added compound 22-S1 (1 equiv), $Cs_2CO_3$ (3 equiv), and tetrakis(triphenylphosphine)palladium (0.1 equiv). The reaction mixture was stirred at 90° C. for 5 hours and concentrated under reduced pressure. The remaining residue was purified by column chromatography on silica gel (eluted with DCM/MeOH) to afford compound 22-S3.

Step 2: (E)-2-(3-Carbamoyl-4-(3-ethoxy-3-oxoprop-1-en-1-yl)-1H-pyrazol-1-yl)acetic acid (S4)

To a solution of compound 22-S3 (1 equiv) in DCM (10 vol) at 0° C. under an atmosphere of argon was added TFA (5 vol). The reaction mixture was stirred at room temperature for 3 hours and concentrated to dryness. The remaining material (22-S4) was used directly in the next synthetic step without additional purification.

Step 3: Ethyl (E)-3-(1-(2-((2S,4R)-2-((6-bromopyridin-2-yl)carbamoyl)-4-fluoropyrrolidin-1-yl)-2-oxoethyl)-3-carbamoyl-1H-pyrazol-4-yl)acrylate (22)

To a solution of compound 22-S4 (1 equiv) in DMF (10 vol) at 0° C. under an atmosphere of argon was added (2S,4R)—N-(6-bromopyrazin-2-yl)-4-fluoropyrrolidine-2-carboxamide hydrochloride (22-S5, 1 equiv), HATU (2.1 equiv), and DIPEA (5 equiv). The reaction mixture was stirred at room temperature for 3 hours and quenched with water (30 vol). The resulting mixture was extracted with DCM. The organic layer was washed with brine, dried over anhydrous $Na_2SO_4$, filtered, and concentrated to dryness. The remaining residue was purified by column chromatography on silica gel (eluted with DCM/MeOH) to afford compound 22. $^1H$ NMR (400 MHz, DMSO-$d_6$) δ 1.24 (t, J=7.0 Hz, 3H), 1.97-2.25 (m, 1H), 2.54-2.62 (m, 1H), 3.77-3.95 (m, 1H), 4.04-4.20 (m, 3H), 4.69 (t, J=8.5 Hz, 1H), 5.15 (d, J=16.9 Hz, 1H), 5.36 (d, J=17.0 Hz, 1H), 5.50 (dt, J=3.5, 52.8 Hz, 1H), 6.41 (d, J=16.4 Hz, 1H), 7.33-7.39 (m, 2H), 7.51 (s, 1H), 7.73 (t, J=8.0 Hz, 1H), 8.04 (d, J=8.2 Hz, 1H), 8.14 (d, J=16.3 Hz, 1H), 8.35 (s, 1H), 11.05 (s, 1H).

Scheme 13. Synthesis of 3-Acetyl-1-(2-((2S,4R)-2-((6-bromopyridin-2-yl)carbamoyl)-4-fluoropyrrolidin-1-yl)2-oxoethyl)-N-(thiazol-4-ylmethyl)-1H-pyrazole-5-carboxamide (24)

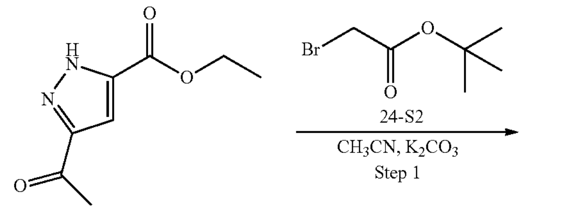

24-S1

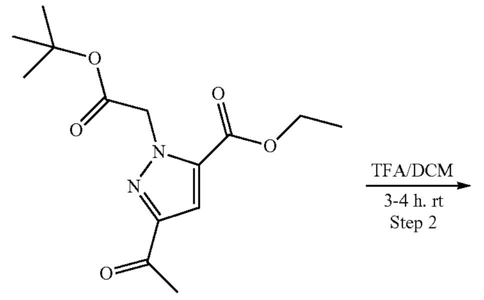

24-S3

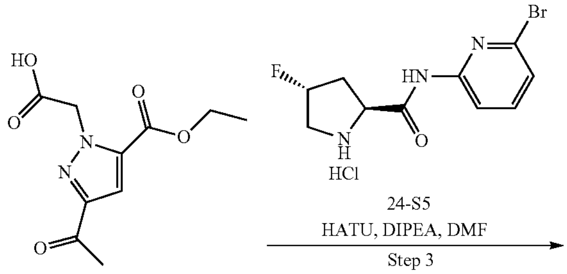

24-S4

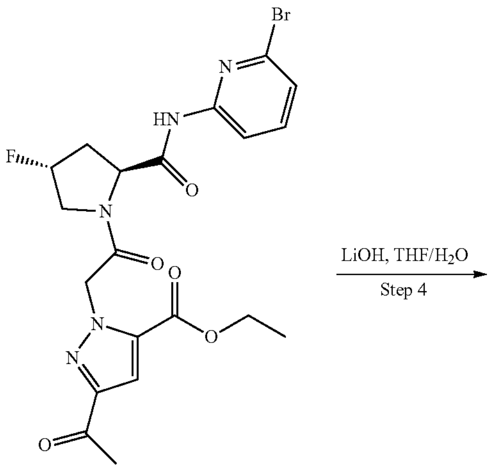

24-S6

-continued

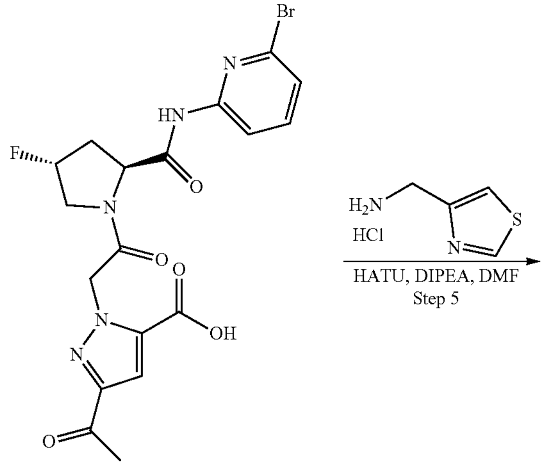

24-S7

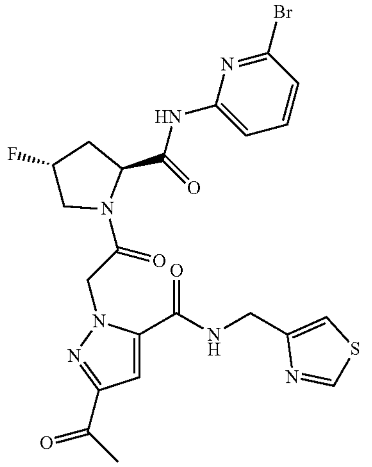

24

Step 1: Ethyl 3-acetyl-1-(2-(tert-butoxy)-2-oxoethyl)-1H-pyrazole-5-carboxylate (24-S3)

To a solution of ethyl 3-acetyl-1H-pyrazole-5-carboxylate (24-S1, 1 equiv) in $CH_3CN$ (10 vol) was added tert-butyl 2-bromoacetate (24-S2, 1.1 equiv) and potassium carbonate (1.1 equiv). The mixture was refluxed overnight under an atmosphere of argon. After cooling the reaction mixture to room temperature, the mixture was filtered through Celite and washed with $CH_3CN$. The filtrate was concentrated under reduced pressure and the remaining residue was purified by column chromatography on silica gel (eluted with DCM/EtOAc) to afford compound 24-S3.

Step 2: 2-(3-Acetyl-5-(ethoxycarbonyl)-1H-pyrazol-1-yl)acetic acid (24-S4)

To a solution of compound 24-S3 (1 equiv) in DCM (10 vol) at 0° C. under an atmosphere of argon was added TFA (5 vol). The reaction mixture was stirred at room temperature for 3 hours and concentrated to dryness. The remaining material (24-S4) was used directly in the next synthetic step without additional purification.

Step 3: Ethyl 3-acetyl-1-(2-((2S,4R)-2-((6-bromopyridin-2-yl)carbamoyl)-4-fluoropyrrolidin-1-yl)-2-oxoethyl)-1H-pyrazole-5-carboxylate (24-S6)

To a solution of compound 24-S4 (1 equiv) in DMF (10 vol) at 0° C. under an atmosphere of argon was added (2S,4R)—N-(6-bromopyridin-2-yl)-4-fluoropyrrolidine-2-carboxamide hydrochloride (24-S5, 1 equiv), HATU (2.1 equiv), and DIPEA (5 equiv). The reaction mixture was stirred at room temperature for 3 hours and quenched with water (30 vol). The resulting mixture was extracted with DCM. The organic layer was washed with brine, dried over anhydrous $Na_2SO_4$, filtered, and concentrated to dryness. The remaining residue was purified by column chromatography on silica gel (eluted with DCM/MeOH) to afford compound 24-S6.

Step 4: 3-Acetyl-1-(2-((2S,4R)-2-((6-bromopyridin-2-yl)carbamoyl)-4-fluoropyrrolidin-1-yl)-2-oxoethyl)-1H-pyrazole-5-carboxylic acid (24-S7)

To a solution of ethyl 3-acetyl-1-(2-((2S,4R)-2-((6-bromopyridin-2-yl)carbamoyl)-4-fluoropyrrolidin-1-yl)-2-oxoethyl)-1H-pyrazole-5-carboxylate (24-S6, 1 equiv) in THF/$H_2O$ (3:1, 10 vol) was added LiOH (2.1 equiv). The reaction mixture was stirred at room temperature for 5 hours and then concentrated under reduced pressure. The remaining residue was neutralized using 2N HCl before the solid was filtered and purified by column chromatography on silica gel (eluted with DCM/MeOH) to afford compound 24-S7.

Step 5: 3-Acetyl-1-(2-((2S,4R)-2-((6-bromopyridin-2-yl)carbamoyl)-4-fluoropyrrolidin-1-yl)-2-oxoethyl)-N-(thiazol-4-ylmethyl)-1H-pyrazole-5-carboxamide (24)

To a solution of compound 24-S7 (1 equiv) in DMF (10 vol) at 0° C. under an atmosphere of argon was added thiazol-4-ylmethanamine hydrochloride (1 equiv), HATU (2.1 equiv), and DIPEA (5 equiv). The reaction mixture was stirred at room temperature for 3 hours and quenched with water (30 vol). The resulting mixture was extracted with DCM. The organic layer was washed with brine, dried over anhydrous $Na_2SO_4$, filtered, and concentrated to dryness. The remaining residue was purified by column chromatography on silica gel (eluted with DCM/MeOH) to afford compound 24. $^1H$ NMR (400 MHz, DMSO-$d_6$) δ 1.95-2.16 (m, 1H), 2.42 (s, 3H), 2.46-2.54 (m, 1H), 3.75-3.91 (m, 1H), 3.94-4.08 (m, 1H), 4.40-4.62 (m, 3H), 5.33-5.50 (m, 2H), 5.69 (d, J=16.5 Hz, 1H), 7.26 (d, J=7.7 Hz, 1H), 7.34-7.39 (m, 2H), 7.64 (t, J=7.9 Hz, 1H), 7.96 (d, J=8.2 Hz, 1H), 8.97 (d, J=2.0 Hz, 1H), 9.14 (t, J=6.0 Hz, 1H), 10.87 (s, 1H).

Scheme 14: Synthesis of 1-(2-((1R,3S,5R)-3-((2′-Chloro-2-fluoro-[1,1′-biphenyl]-3-yl)carbamoyl)-5-((dimethlamino)methyl)-2-azabicyclo[3.1.0]hexan-2-yl)-2-oxoethyl)-N6-(cyclopropylsulfonyl)-1H-indazole-3,6-dicarboxamide (25) and 1-(2-((1S,3S,5S)-3-((2′-Chloro-2-fluoro-[1,1′-biphenyl]-3-yl)carbamoyl)-5-((dimethylamino)methyl)-2-azabicyclo[3.1.0]hexan-2-yl)-2-oxoethyl)-N6-(cyclopropylsulfonyl)-1H-indazole-3,6-dicarboxamide (26)

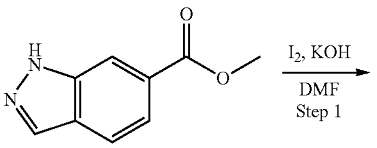

26-S1

-continued

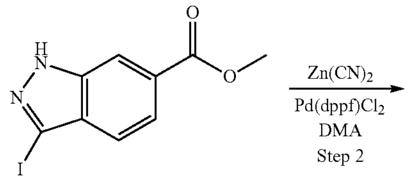

26-S2

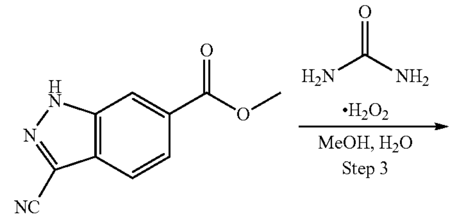

26-S3

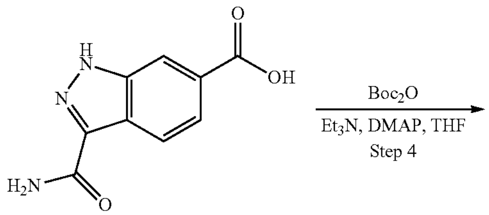

26-S4

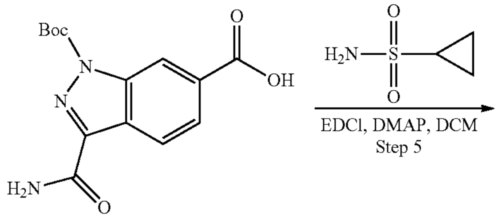

26-S5

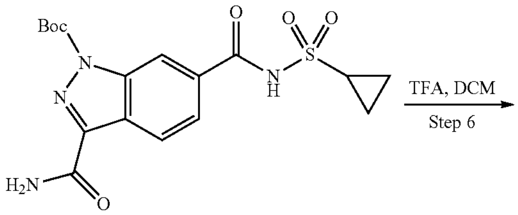

26-S6

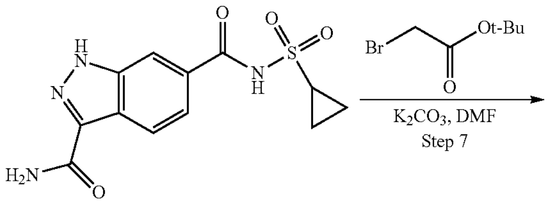

26-S7

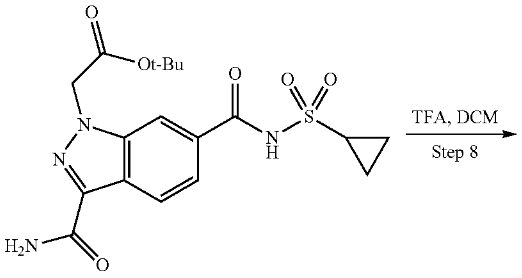
26-S8
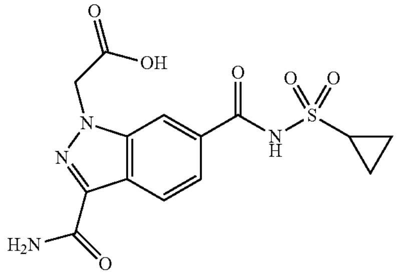
26-S9
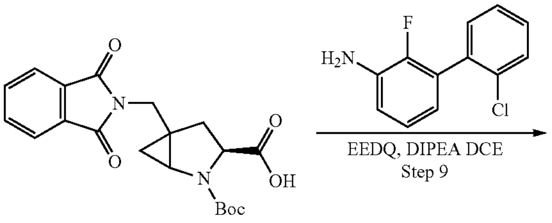
26-S10
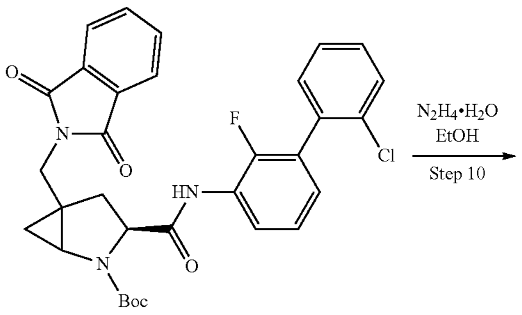
26-S11
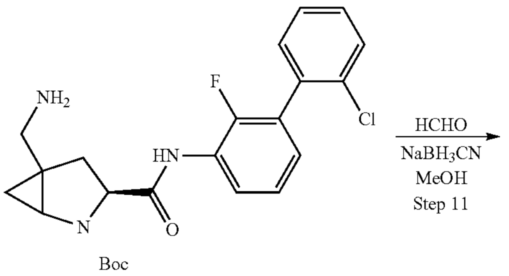
26-S12
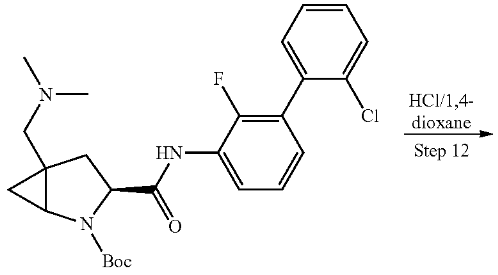
26-S13
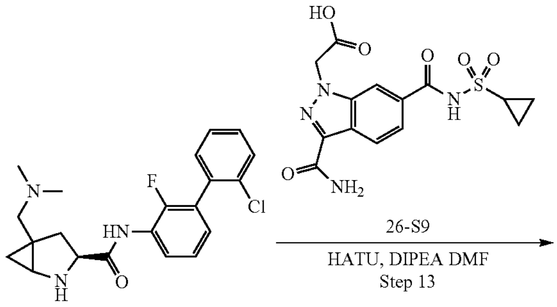
26-S14
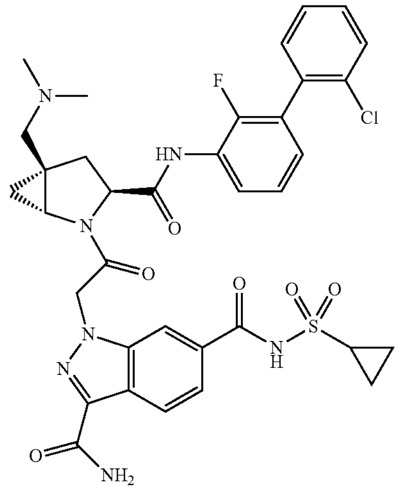
25
+
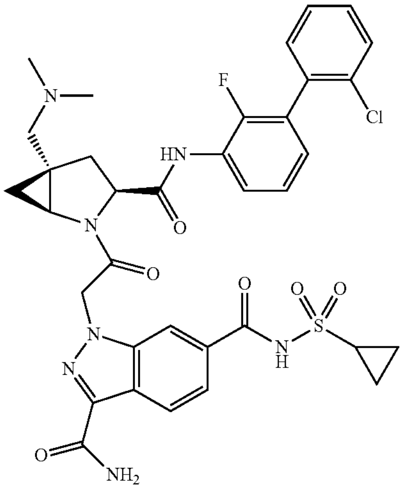
26

Step 1: Methyl 3-iodo-1H-indazole-6-carboxylate (26-S2)

To a solution of 26-S1 (2.5 g, 14.2 mmol) in DMF (30 mL) was added KOH (1.8 g, 31.9 mmol followed by iodine (5.4 g, 21.3 mmol) in portions at 0° C. The reaction mixture was stirred at room temperature for 1 hour. The reaction mixture was poured into ice water and extracted with EtOAc twice. The combined organics were washed with 5% aqueous $Na_2S_2O_4$ solution and brine, dried, and concentrated to dryness to afford 26-S2 (4.0 g, 93.3% yield) as a yellow solid, which was carried forward directly in the next synthetic step without further purification. LC/MS (ESI) m/z: 303 (M+H)+.

Step 2: Methyl 3-cyano-1H-indazole-6-carboxylate (26-S3)

A mixture of 26-S2 (1.0 g, 3.3 mmol), zinc dust (34 mg, 0.50 mmol), zinc cyanide (655 mg, 5.6 mmol), Pd(dppf)$Cl_2$ (220 mg, 0.33 mmol), and copper(I) iodide (627 mg, 3.3 mmol) in dimethylacetamide (10 mL) was purged with nitrogen gas for 5 minutes. The mixture was stirred at 120° C. for 30 minutes in a microwave reactor. The mixture was filtered and the filtrate was partitioned with EtOAc and water. The combined organic layers were washed with brine, dried over $Na_2SO_4$, and concentrated to dryness. The residue was purified by column chromatography on silica gel (eluted with PE/EtOAc=2:1 to 0:1) to afford 26-S3 (390 mg, 58.8% yield) as a yellow solid. LC/MS (ESI) m/z: 202 $(M+H)^+$.

Step 3: 3-Carbamoyl-1H-indazole-6-carboxylic acid (26-S4)

To a solution of 26-S3 (390 mg, 1.94 mmol) in MeOH (10 mL) at 0° C. was added a cold solution of urea hydrogen peroxide (3.5 g, 19.4 mmol) in aqueous NaOH solution (8.0 mL, 2.5 M in water, 20.0 mmol). The resulting yellow solution was stirred at room temperature overnight. The mixture was quenched with 5% aqueous $Na_2S_2O_4$ solution and adjusted with 2 N aqueous HCl to pH~4. The mixture was extracted with DCM twice. The combined organic layers were dried over $Na_2SO_4$ and concentrated to dryness to afford crude 26-S4 (550 mg, 100% yield) as a yellow solid, which was carried forward directly in the next synthetic step without further purification. LC/MS (ESI) m/z: 206 $(M+H)^+$.

Step 4: 1-(tert-Butoxycarbonyl)-3-carbamoyl-1H-indazole-6-carboxylic acid (26-S5)

To a mixture of 26-S4 (550 mg, 1.94 mmol) and TEA (0.43 mL, 0.43 mmol) in THF was added $Boc_2O$ (550 mg, 2.5 mmol) followed by DMAP (23.6 mg, 0.20 mmol). The reaction mixture was stirred at room temperature for 3 hours. The mixture was filtered and the filtrate was evaporated under reduced pressure. The residue was partitioned with $Et_2O$ and saturated $NaHCO_3$ solution. The desired water layer was adjusted with 2 N aqueous HCl to pH~4 and extracted with EtOAc. The combined organic layers were dried over $Na_2SO_4$ and concentrated to dryness to afford crude 26-S5 (244 mg, 41.2% yield) as a yellow solid. LC/MS (ESI) m/z: 306 $(M+H)^+$.

Step 5: tert-Butyl 3-carbamoyl-6-((cyclopropylsulfonyl)carbamoyl)-1H-indazole-1-carboxylate (26-S6)

To a mixture of 26-S5 (210 mg, 0.69 mmol) and DMAP (59 mg, 0.48 mmol) in DCM (5 mL) was added EDCI (185 mg, 0.97 mmol). The mixture was stirred for 5 minutes at room temperature and then cyclopropanesulfonamide (167 mg, 1.38 mmol) was added. The resulting mixture was stirred at room temperature overnight. The mixture was poured into ice water and washed with DCM twice. The aqueous layer was adjusted with 2 N aqueous HCl to pH~4 and extracted with EtOAc. The organic layer was dried over $Na_2SO_4$ and concentrated to afford 26-S6 (200 mg, 70.9% yield) as a yellow solid, which was carried forward directly in the next synthetic step without further purification. LC/MS (ESI) m/z: 409 $(M+H)^+$.

Step 6: N6-(Cyclopropylsulfonyl)-1H-indazole-3,6-dicarboxamide (26-S7)

To a solution of 26-S6 (200 mg, 0.49 mmol) in DCM (3 mL) was added TFA (1 mL) at 0° C. The reaction mixture was stirred at room temperature for 1 hour. The mixture was concentrated under reduced pressure to afford 26-S7 (151 mg, 100% yield) as a yellow solid, which was carried forward directly in the next synthetic step without further purification. LC/MS (ESI) m/z: 309 $(M+H)^+$.

Step 7: N6-(Cyclopropylsulfonyl)-1H-indazole-3,6-dicarboxamide (26-S8)

To a solution of 26-S7 (151 mg, 0.65 mmol) in DMF (5 mL) was added $K_2CO_3$ (224 mg, 1.63 mmol) and tert-butyl 2-bromoacetate (190 mg, 0.97 mmol) at 0° C. After addition, the reaction mixture was stirred at room temperature overnight. The mixture was filtered and the filtrate was partitioned with EtOAc and water. The aqueous layer was adjusted with 2 N aqueous HCl to pH~4 and extracted with EtOAc. The combined organic layers were dried over $Na_2SO_4$ and concentrated under reduced pressure. The remaining residue was purified by column chromatography on silica gel (DCM/MeOH=50:1 to 40:1) to afford 26-S8 (115 mg, 41.8% yield) as a white solid. LC/MS (ESI) m/z: 423 $(M+H)^+$.

Step 8: N6-(Cyclopropylsulfonyl)-1H-indazole-3,6-dicarboxamide (26-S9)

To a solution of 26-S8 (115 mg, 0.27 mmol) in DCM (2 mL) was added TFA (1 mL) at 0° C. The reaction mixture was stirred at room temperature overnight. The mixture was concentrated under reduced pressure to afford 26-S9 (100 mg, 100% yield) as a white solid, which was carried forward directly in the next synthetic step without further purification. LC/MS (ESI) m/z: 367 $(M+H)^+$.

Step 9: (3S)-tert-Butyl 3-(2'-chloro-2-fluorobiphenyl-3-ylcarbamoyl)-5-((1,3-dioxoisoindolin-2-yl)methyl)-2-azabicyclo[3.1.0]hexane-2-carboxylate (26-S11)

To a mixture of 2'-chloro-2-fluorobiphenyl-3-amine (187 mg, 0.84 mmol) and 26-S10 (295 mg, 0.76 mmol) in DCE (2 mL) were added EEDQ (376 mg, 1.52 mmol) and DIPEA (0.5 ml, 3.04 mmol). The reaction mixture was stirred at 85° C. for 16 hours. The mixture was concentrated to dryness and the residue was purified by column chromatography on silica gel (eluted with PE/EtOAc=100:1) to afford compound 26-S11 (321 mg, 65% yield) as a yellow oil. LC/MS (ESI) m/z: 590 $(M+H)^+$.

Step 10: (3S)-tert-Butyl 5-(aminomethyl)-3-(2'-chloro-2-fluorobiphenyl-3-ylcarbamoyl)-2-azabicyclo[3.1.0]hexane-2-carboxylate (26-S12)

To a solution of compound 26-S11 (321 mg, 0.544 mmol) in EtOH (3 mL) was added hydrazine hydrate (0.3 mL, 85% w/w). The reaction mixture was stirred at 75° C. for 2 hours and then cooled to room temperature. The mixture was filtered and the filtrate was concentrated to dryness. The residue was purified by column chromatography on silica gel (eluted with DCM/MeOH=30/1) to afford 26-S12 (98 mg, 39.2% yield) as a colorless oil. LC/MS (ESI) m/z: 460 $(M+H)^+$.

Step 11: (3S)-tert-Butyl 3-(2'-chloro-2-fluorobiphenyl-3-ylcarbamoyl)-5-((dimethylamino)methyl)-2-azabicyclo[3.1.0]hexane-2-carboxylate (26-S13)

To a mixture of 26-S12 (98 mg, 0.213 mmol) and aqueous formaldehyde solution (55 mg, 0.64 mmol, 35% wt) in MeOH (3 mL) was added $NaBH_3CN$ (27 mg, 0.426 mmol) at 0° C. and the reaction mixture was stirred at room temperature for 1 h. The mixture was poured into ice water and extracted with DCM twice. The combined organic phases were dried over anhydrous $Na_2SO_4$, filtered, and concentrated to dryness. The residue was purified by column chromatography on silica gel (eluted with DCM/MeOH=50:1 to 40:1) to afford 26-S13 (65 mg, 62.5% yield) as a colorless oil. LC/MS (ESI) m/z: 488 $(M+H)^+$.

Step 12: (3S)—N-(2'-Chloro-2-fluorobiphenyl-3-yl)-5-((dimethylamino)methyl)-2-azabicyclo[3.1.0]hexane-3-carboxamide hydrochloride (26-S14)

To a solution of 26-S13 (65 mg, 0.133 mmol) in dioxane (1 mL) was added HCl/dioxane (1 mL, 4 M) at 0° C. and the reaction mixture was stirred at room temperature for 1 hour. The mixture was concentrated to dryness to afford 26-S14 (60 mg, 100% yield) as a brown solid, which was carried forward directly in the next synthetic step without further purification. LC/MS (ESI) m/z: 388 $(M+H)^+$.

Step 13: 1-(2-((1R,3S,5R)-3-((2'-Chloro-2-fluoro-[1,1'-biphenyl]-3-yl)carbamoyl)-5-((dimethylamino)methyl)-2-azabicyclo[3.1.0]hexan-2-yl)-2-oxoethyl)-N6-(cyclopropylsulfonyl)-1H-indazole-3,6-dicarboxamide (25) and 1-(2-((1S,3S,5S)-3-((2'-Chloro-2-fluoro-[1,1'-biphenyl]-3-yl)carbamoyl)-5-((dimethylamino)methyl)-2-azabicyclo[3.1.0]hexan-2-yl)-2-oxoethyl)-N6-(cyclopropylsulfonyl)-1H-indazole-3,6-dicarboxamide (26)

To a mixture of compound 26-S14 (30 mg, 0.07 mmol), 26-S9 (26.0 mg, 0.072 mmol), and HATU (47 mg, 0.12 mmol) in DMF (2 ml) was added DIPEA (0.06 mL, 0.36 mmol) and the reaction mixture was stirred at room temperature overnight. The reaction mixture was diluted with EtOAc and washed with 10% aqueous LiCl solution and brine, dried over anhydrous $Na_2SO_4$, and concentrated under reduced pressure. The remaining residue was purified by preparative HPLC to afford 25 (1.5 mg, 2.88% yield) and 26 (1.6 mg, 3.07% yield) as white solids.

Compound 25: $^1H$ NMR (400 MHz, $CD_3OD$) δ 8.17 (s, 2H), 7.78-7.82 (m, 2H), 7.41-7.38 (m, 1H), 7.28-7.21 (m, 3H), 7.14 (t, J=8.8 Hz, 1H), 6.97 (t, J=7.6 Hz, 1H), 5.48 (d, J=10 Hz, 2H), 2.89-2.81 (m, 4H), 2.67 (m, 7H), 2.53-2.39 (m, 2H), 1.19 (m, 2H), 1.09-1.04 (m, 2H), 0.83-0.81 (m, 2H). LC/MS (ESI) m/z: 736 $(M+H)^+$.

Compound 26: $^1H$ NMR (400 MHz, $CD_3OD$) δ 8.19 (s, 1H), 8.07 (d, J=8.4 Hz, 1H), 7.84 (d, J=8.8 Hz, 1H), 7.59 (t, J=14.8 Hz, 1H), 7.39-7.36 (dd, 1H), 7.26-7.21 (m, 3H), 7.03-6.89 (m, 1H), 5.58 (d, J=16.8 Hz, 1H), 5.33 (d, J=16.8 Hz, 1H), 2.96-2.82 (m, 3H), 2.77 (m, 6H), 2.69-2.50 (m, 3H), 2.17 (m, 2H), 1.27-1.06 (m, 4H), 0.84 (d, J=6.4 Hz, 2H). LC/MS (ESI) m/z: 736 $(M+H)^+$.

Scheme 15. Synthesis of 1-(2-((2S,4R)-2-((6-Bromopyridin-2-yl)carbamoyl)-4-fluoropyrrolidin-1-yl)-2-oxoethyl)-4-((E)-3-(cyclopropylamino)-3-oxoprop-1-en-1-yl)-1H-pyrazole-3-carboxamide (28)

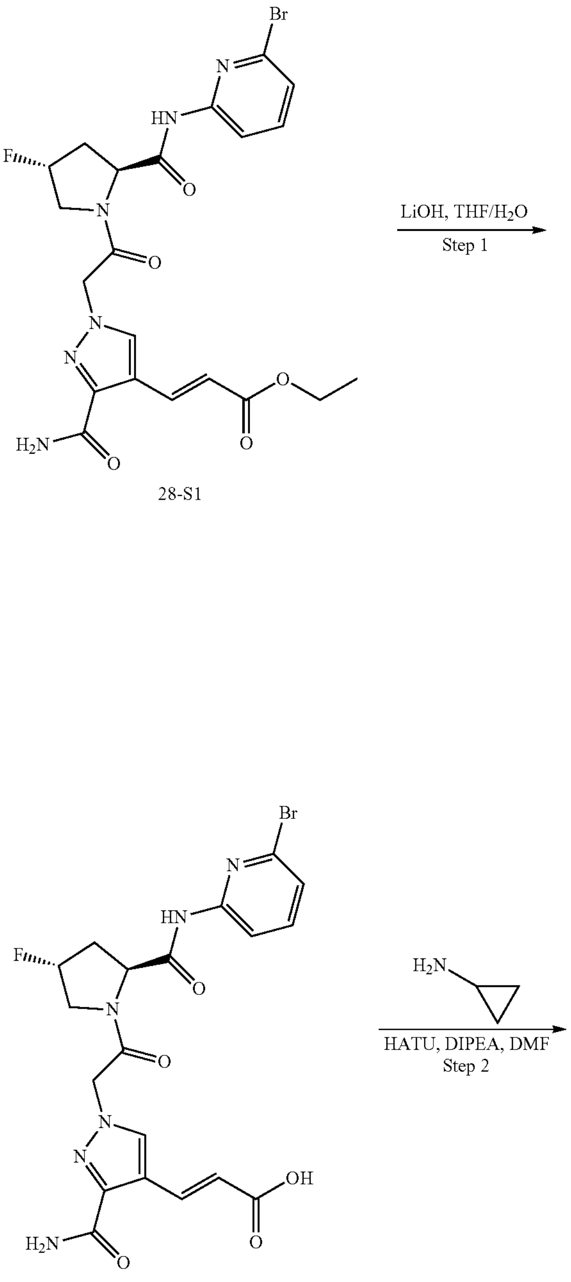

28-S1

28-S2

-continued

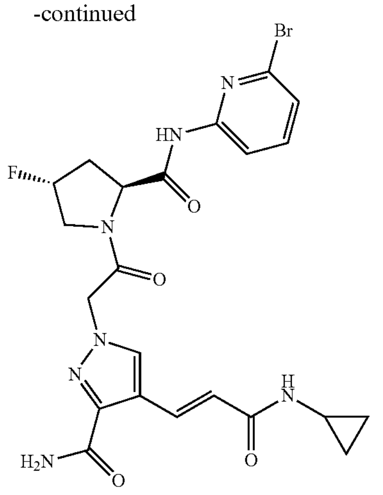

28

Step 1: (E)-3-(1-(2-((2S,4R)-2-((6-Bromopyridin-2-yl)carbamoyl)-4-fluoropyrrolidin-1-yl)-2-oxoethyl)-3-carbamoyl-1H-pyrazol-4-yl)acrylic acid (28-S2)

To a solution of ethyl (E)-3-(1-(2-((2S,4R)-2-((6-bromopyridin-2-yl)carbamoyl)-4-fluoropyrrolidin-1-yl)-2-oxoethyl)-3-carbamoyl-1H-pyrazol-4-yl)acrylate (28-S1, 1 equiv) in THF/$H_2O$ (3:1, 10 vol) was added LiOH (2.1 equiv) and the reaction mixture was stirred at room temperature for 5 hours and concentrated under reduced pressure to remove the volatiles. The remaining water was neutralized using 2N HCl before the solid was filtered and purified by column chromatography on silica gel (eluted with DCM/MeOH) to afford compound 28-S2.

Step 2: 1-(2-((2S,4R)-2-((6-Bromopyridin-2-yl)carbamoyl)-4-fluoropyrrolidin-1-yl)-2-oxoethyl)-4-((E)-3-(cyclopropylamino)-3-oxoprop-1-en-1-yl)-1H-pyrazole-3-carboxamide (28)

To a solution of compound 28-S2 (1 equiv) in DMF (10 vol) at 0° C. under an atmosphere of argon was added cyclopropanamine (1 equiv), HATU (2.1 equiv), and DIPEA (5 equiv). The reaction mixture was stirred at room temperature for 3 hours and quenched with water (30 vol). The resulting mixture was extracted with DCM. The organic layer was washed with brine, dried over anhydrous $Na_2SO_4$, filtered, and concentrated to dryness. The remaining residue was purified by column chromatography on silica gel (eluted with DCM/MeOH) to afford compound 28. $^1H$ NMR (400 MHz, DMSO-$d_6$) δ 0.39-0.46 (m, 2H), 0.59-0.72 (m, 2H), 2.03-2.22 (m, 1H), 2.53-2.61 (m, 1H), 2.67-2.77 (m, 1H), 3.74-3.91 (m, 1H), 4.02-4.15 (m, 1H), 4.69 (t, J=8.5 Hz, 1H), 5.15 (d, J=16.9 Hz, 1H), 5.34 (d, J=16.9 Hz, 1H), 5.50 (d, J=52.1 Hz, 1H), 6.27 (d, J=4.9, 16.0 Hz, 1H), 7.24-7.37 (m, 2H), 7.39-7.48 (m, 1H), 7.73 (t, J=8.0 Hz, 1H), 7.86 (d, J=16.1 Hz, 1H), 7.98-8.09 (m, 3H), 11.04 (s, 1H).

Scheme 16. Synthesis of (2S,4R)-1-(2-(3-Actyl-4,5,6,7-tetrahydro-1H-indazol-1-yl)acetyl)-N-(6-bromopyridin-2-yl)-4-fluoropyrrolidine-2-carboxamide (37)

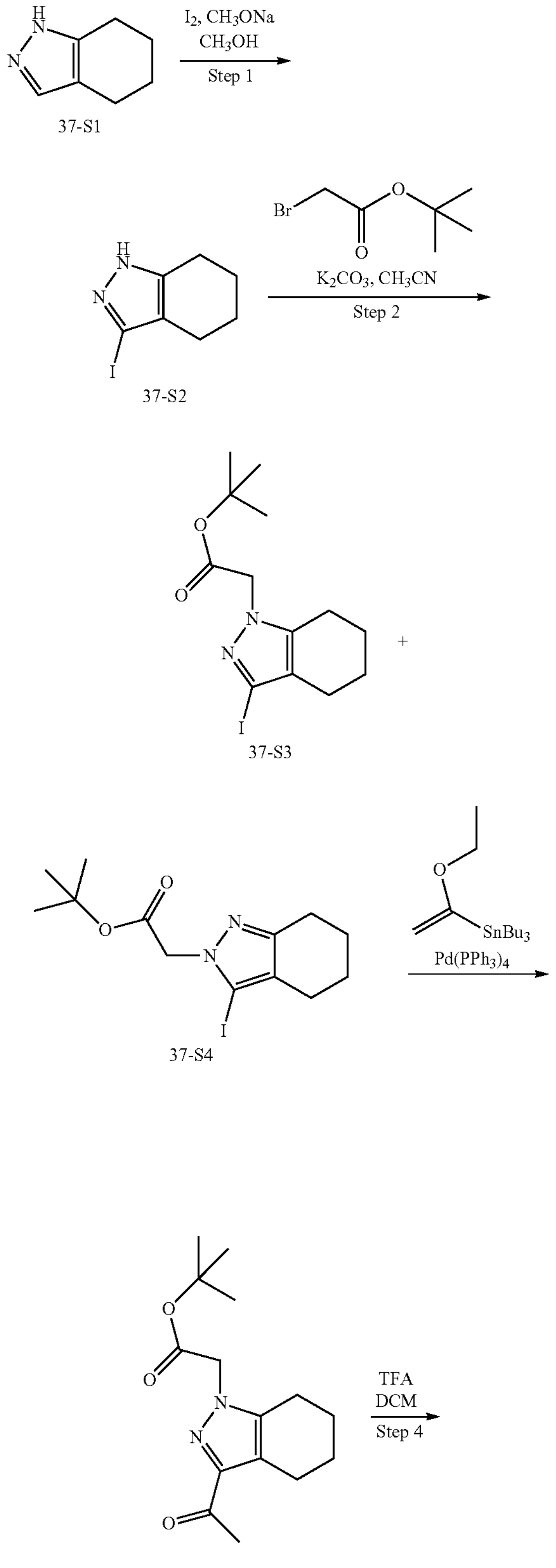

37-S1

37-S2

37-S3

37-S4

37-S5

-continued

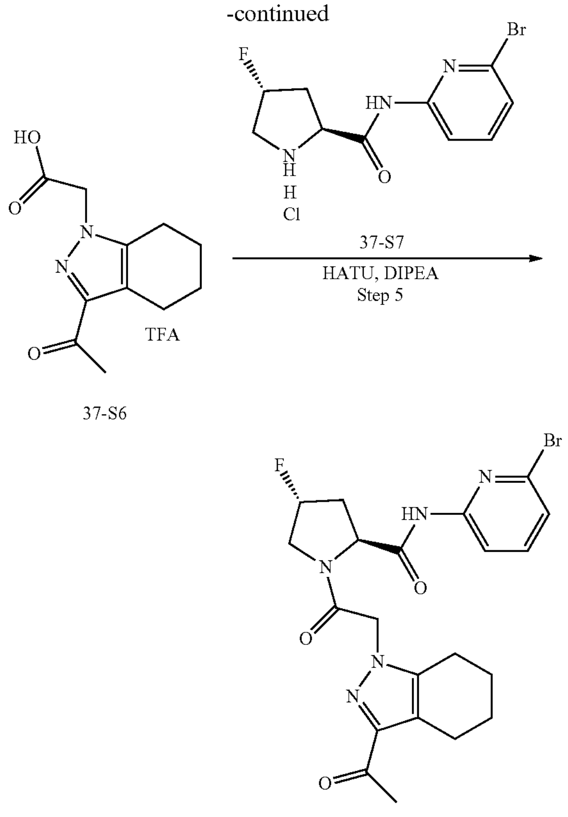

37-S6

37

Step 1: 3-Iodo-4,5,6,7-tetrahydro-1H-indazole (37-S2)

To a solution of 4,5,6,7-tetrahydro-1H-indazole, (37-S1, 1.22 g, 10.0 mmol) in anhydrous methanol (25.0 ml), sodium methoxide (1.1 g) was added followed by iodine (3.57 g) in one portion. The mixture was stirred at room temperature for 2 hours before the volatiles were removed. The residue was mixed with ethyl acetate and filtered through a short pad of silica gel. The filtrate was concentrated and the resulting material (37-S2) was carried forward in the next step without further purification.

Step 2: tert-Butyl 2-(3-iodo-4,5,6,7-tetrahydro-1H-indazol-1-yl)acetate (37-S3)

Crude 37-S2 was dissolved in $CH_3CN$ (30 mL) and to solution, tert-butyl 2-bromoacetate (2.15 g, 1.62 mL, 11.0 mmol) and solid $K_2CO_3$ (2.28 g, 16.5 mmol) were added. The mixture was stirred at room temperature overnight and then filtered. The resulting cake was rinsed with additional $CH_3CN$. The combined filtrate was concentrated and the resulting residue was purified by chromatography on silica gel to afford 37-S3 (1.64 g). $^1$H NMR (400 MHz, DMSO-$d_6$): δ 1.45 (s, 9H), 1.71-1.77 (m, 2H), 1.79-1.84 (m, 2H), 2.32 (t, J=6.0 Hz, 2H), 2.48 (t, J=6.0 Hz, 2H), 4.67 (s, 2H) ppm

Step 3: tert-Butyl 2-(3-acetyl-4,5,6,7-tetrahydro-1H-indazol-1-yl)acetate (37-S5)

To the degassed solution of tert-butyl 2-(3-iodo-4,5,6,7-tetrahydro-1H-indazol-1-yl)acetate (37-S3, 1.64 g, 4.54 mmol) in DMF (10.0 mL), tributyl(1-ethoxyvinyl)stannane (1.81 g, 1.69 mL, 5.0 mmol) and $Pd(PPh_3)_4$ (0.1 eq) were added under argon. The mixture was heated at 100° C. for 5 hours and then cooled to room temperature. Aqueous HCl (1N, 10 mL) was added to the solution and the mixture was stirred for 30 minutes at room temperature. The volatiles were removed and the residue was mixed with ethyl acetate and water. The organic layer was separated from the aqueous phase and washed with brine. The organic phase was dried over $MgSO_4$ and was filtered through a short pad of silica gel. The filtrate was concentrated and the residue was purified by chromatography on silica gel to afford 37-S5 (410 mg). $^1$H NMR (400 MHz, DMSO-$d_6$, 300 K): δ 1.48 (s, 9H), 1.70-1.75 (m, 2H), 1.79-1.85 (m, 2H), 2.51 (t, J=6.0 Hz, 2H), 2.53 (s, 3H), 2.77 (t, J=6.0 Hz, 2H), 4.73 (s, 2H) ppm

Step 4: 2-(3-Acetyl-4,5,6,7-tetrahydro-1H-indazol-1-yl)acetic acid. TFA (37-S6)

tert-Butyl 2-(3-acetyl-4,5,6,7-tetrahydro-1H-indazol-1-yl)acetate (37-S5, 410 mg) was dissolved in DCM (8 mL) and treated with TFA (2 mL). The mixture was stirred overnight at room temperature. The volatiles were evaporated under reduced pressure and the remaining material was co-evaporated with toluene twice. The residue 37-S6 was carried forward in the next step without further purification.

Step 5: (2S,4R)-1-(2-(3-Acetyl-4,5,6,7-tetrahydro-1H-indazol-1-yl)acetyl)-N-(6-bromopyridin-2-yl)-4-fluoropyrrolidine-2-carboxamide (37)

To the solution of (2S,4R)—N-(6-bromopyridin-2-yl)-4-fluoropyrrolidine-2-carboxamide hydrochloride (37-S7, 226 mg, 0.71 mmol), 2-(3-acetyl-4,5,6,7-tetrahydro-1H-indazol-1-yl)acetic acid (37-S6, 223 mg, 0.69 mmol) in DMF (2.0 mL), HATU (293 mg, 0.77 mmol) was added, followed by the dropwise addition of DIEA (4.0 eq) at room temperature. The mixture was stirred for 1 hour at room temperature and the volatiles were evaporated. The residue was diluted with 10% sodium carbonate (50 mL) and extracted with ethyl acetate. The combined organic solution was successively washed with water, brine and dried over $MgSO_4$. The solution was filtered and the solvent was removed. The residue was purified by chromatography on silica gel to afford 37 (194.4 mg). $^1$H NMR (400 MHz, DMSO-$d_6$): (major rotamer) δ 1.57-1.63 (m, 2H), 1.66-1.72 (m, 2H), 2.02-2.21 (m, 1H), 2.40 (s, 3H), 2.43-2.48 (m, 2H), 2.49-2.53 (m, 1H), 2.57-2.63 (m, 2H), 3.83-3.96 (m, 1H), 4.06-4.14 (m, 1H), 4.64 (t, J=8.4 Hz, 1H), 5.07-5.56 (m, 3H), 7.34 (d, J=8.0 Hz, 1H), 7.73 (t, J=7.6 Hz, 1H), 8.03 (d, J=8.0 Hz, 1H), 11.0 (s, 1H) ppm. $^{19}$F NMR (376 MHz, DMSO-$d_6$, 300K): (major rotamer) δ −175.85. LC (method A): $t_R$=1.84 min. LC/MS (EI) m/z: $[M+H]^+$ 492.17, 494.13

Scheme 17. Synthesis of (3-Acetyl-1-(2-((1S,3S,5S)-3-((3-chloro-2-fluorobenzyl)carbamoyl)-5-((dimethylamino)methyl-2-azabicyclo[3.1.0]hexan-2yl)-2-oxoethyl)-1H-indazol-6-yl)(methyl) phosphinic acid (38)

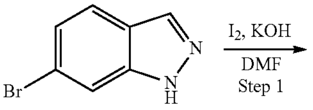

38-S1

-continued

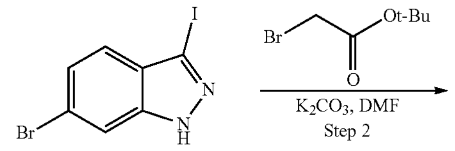

38-S2

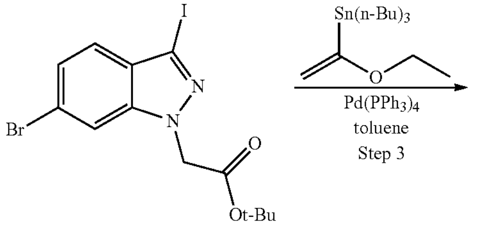

38-S3

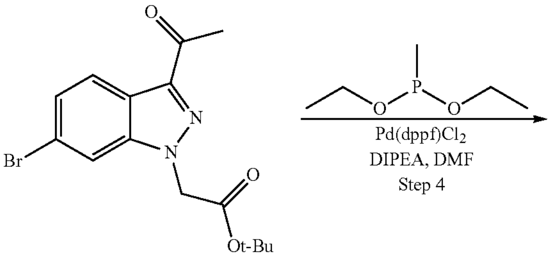

38-S4

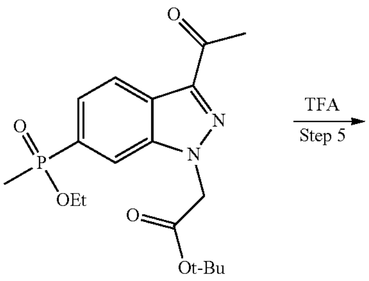

38-S5

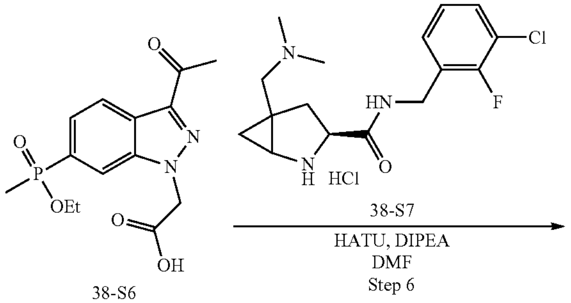

38-S7

38-S6

-continued

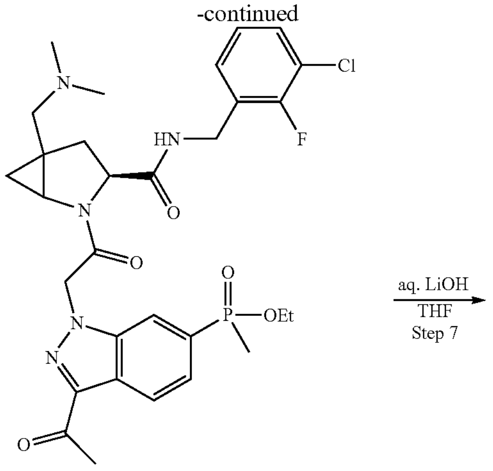

38-S8

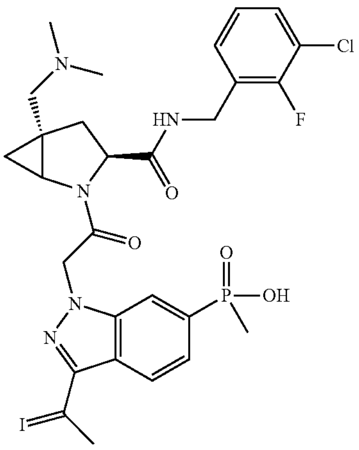

38

Step 1: 6-Bromo-3-iodo-1H-indazole (38-S2)

To a solution of 38-S1 (2.5 g, 12.8 mmol) and DMF (15 mL) was added KOH (1.62 g, 28.8 mmol) and iodine (4.86 g, 19.1 mmol) at 0° C. The reaction mixture was stirred at room temperature overnight, quenched by aqueous $Na_2S_2O_3$ solution (5 mL), diluted with EtOAc, washed with 10% aqueous LiCl solution and brine, dried over $Na_2SO_4$, and concentrated to dryness. The remaining residue was purified by column chromatography on silica gel (eluted with PE/EtOAc=30:1) to afford 38-S2 (3.70 g, 89.8% yield) as a white solid. LC/MS (ESI) m/z: 322 $(M+H)^+$.

Step 2: tert-Butyl 2-(6-bromo-3-iodo-1H-indazol-1-yl)acetate (38-S3)

To a solution of 38-S2 (3.7 g, 11.5 mmol) in DMF (30 mL) was added $K_2CO_3$ (3.98 g, 28.8 mmol) and tert-butyl 2-bromoacetate (2.70 g, 13.8 mmol) at 0° C. The reaction mixture was stirred at room temperature overnight. The mixture was diluted with EtOAc and washed with 10% aqueous LiCl solution and brine, dried over $Na_2SO_4$, and concentrated to dryness. The remaining residue was purified by column chromatography on silica gel (eluted with PE/EtOAc=5:1) to afford 38-S3 (4.5 g, 90.0% yield) as a yellow solid. LC/MS (ESI) m/z: 435 $(M+H)^+$.

Step 3: tert-Butyl 2-(6-bromo-3-iodo-1H-indazol-1-yl)acetate (38-S4)

To a solution of 38-S3 (2 g, 4.6 mmol) in toluene (15 mL) under an atmosphere of nitrogen was added tributyl(1-ethoxyvinyl)stannane (2.49 g, 6.9 mmol) and $Pd(PPh_3)_4$ (265 mg, 0.23 mmol) at 0° C. The mixture was purged with nitrogen and stirred at 100° C. under an atmosphere of nitrogen overnight. The mixture was concentrated to dryness and the remaining residue was purified by column chromatography on silica gel (eluted with PE/EtOAc=5:1) to afford 38-S4 (1.3 g, 79.9% yield) as a yellow solid. LC/MS (ESI) m/z: 354 $(M+H)^+$.

Step 4: tert-Butyl 2-(3-acetyl-6-(ethoxy(methyl)phosphoryl)-1H-indazol-1-yl)acetate (38-S5)

To a solution of 38-S4 (800 mg, 2.27 mmol) in anhydrous DMF (10 mL) was added diethyl methylphosphonite (1.7 mL, 11.36 mmol), DIPEA (1.95 mL, 11.36 mmol), and $Pd(dppf)Cl_2$ (80 mg, 0.11 mmol) under an atmosphere of nitrogen at 0° C. The mixture was purged with nitrogen and stirred at 100° C. under an atmosphere of nitrogen overnight. The mixture was diluted with EtOAc, washed with 10% aqueous LiCl solution and brine, dried over $Na_2SO_4$, and concentrated to dryness. The remaining residue was purified by column chromatography on silica gel (eluted with DCM/MeOH=80:1) to afford 38-S5 (710 mg, 82.1% yield) as a colorless oil. LC/MS (ESI) m/z: 381 $(M+H)^+$.

Step 5: 2-(3-Acetyl-6-(ethoxy(methyl)phosphoryl)-1H-indazol-1-yl)acetic Acid (38-S6)

To a solution of 38-S5 (100 mg, 0.26 mmol) in DCM (3 mL) was added TFA (1 mL) at 0° C. The reaction mixture was stirred at room temperature for 1 hour. The mixture was concentrated and purified by column chromatography on silica gel (eluted with DCM/MeOH=6:1) to afford 38-S6 (50 mg, 59.2% yield) as a brown solid. LC/MS (ESI) m/z: 325 $(M+H)^+$.

Step 6: Ethyl (3-acetyl-1-(2-((3S)-3-((3-chloro-2-fluorobenzyl)carbamoyl)-5-((dimethylamino)methyl)-2-azabicyclo[3.1.0]hexan-2-yl)-2-oxoethyl)-1H-indazol-6-yl)(methyl)phosphinate (38-S8)

To a solution of 38-S6 (50 mg, 0.094 mmol), 38-S7 (35 mg, 0.108 mmol), and HATU (64.22 mg, 0.169 mmol) in DMF (2 mL) was added DIPEA (0.065 mL, 0.376 mmol) at 0° C. The reaction mixture was stirred at room temperature overnight. The mixture was diluted with EtOAc and washed with 10% aqueous LiCl solution and brine, dried over $Na_2SO_4$, and concentrated to dryness. The remaining residue was purified by column chromatography on silica gel (eluted with DCM/MeOH=6:1) to afford 38-S8 (41 mg, 69.0% yield) as a white solid. LC/MS (ESI) m/z: 632 $(M+H)^+$.

Step 6: (3-Acetyl-1-(2-((1S,3S,5S)-3-((3-chloro-2-fluorobenzyl)carbamoyl)-5-((dimethylamino)methyl)-2-azabicyclo[3.1.0]hexan-2-yl)-2-oxoethyl)-1H-indazol-6-yl)(methyl)phosphinic acid (38)

To a solution of 38-S8 (41 mg, 0.065 mmol) in THF (1 mL) and water (1 mL) was added LiOH (8 mg, 195 mmol) at 0° C. The reaction mixture was stirred at room temperature for 1 hour. The mixture was concentrated to dryness and the remaining residue was purified by preparative HPLC to afford 38 (9.5 mg, 24.2% yield) as a white solid. $^1$H NMR (400 MHz, $CD_3OD$) δ 8.27 (d, J=7.8 Hz, 1H), 8.00 (d, J=12.1 Hz, 1H), 7.73 (t, J=9.1 Hz, 1H), 7.13 (t, J=6.9 Hz, 1H), 6.73 (t, J=7.9 Hz, 1H), 6.46 (t, J=6.5 Hz, 1H), 5.91 (d, J=17.3 Hz, 1H), 5.52 (d, J=17.3 Hz, 1H), 4.67 (dd, J=11.5, 3.2 Hz, 1H), 3.98-3.68 (m, 4H), 2.83 (s, 7H), 2.73 (t, J=12.9 Hz, 1H), 2.43 (s, 3H), 1.99-1.86 (m, 1H), 1.67 (d, J=11.4 Hz, 1H), 1.45 (d, J=13.9 Hz, 3H), 1.26 (t, J=6.1 Hz, 1H). LC/MS (ESI) m/z: 604 $(M+H)^+$.

Scheme 18: Synthesis of (1R,3S,5R)-2-(2-(3-Acetyl-7-methyl-1H-indazol-1-yl)acetyl)-N-(6-bromo-3-methylpyridin-2-yl)-5-((3aR,6aS)-hexahydrocyclopenta[c]pyrrol-2(1H)-yl)methyl-2-azabicyclo[3.1.0]hexane-3-carboxamide (39)

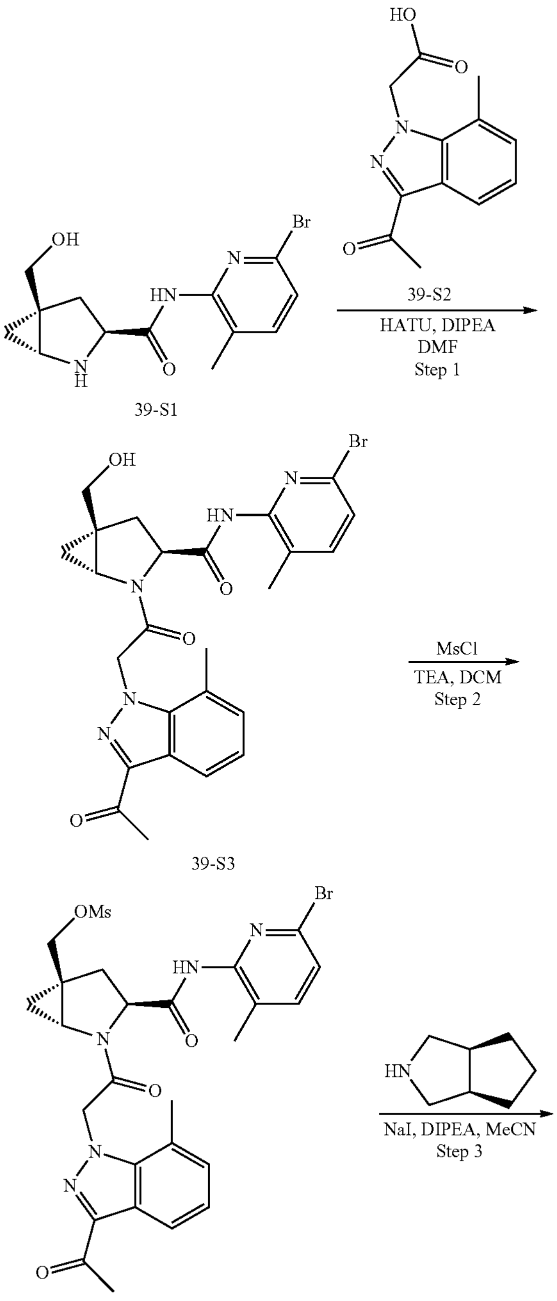

39-S1

39-S3

39-S4

-continued

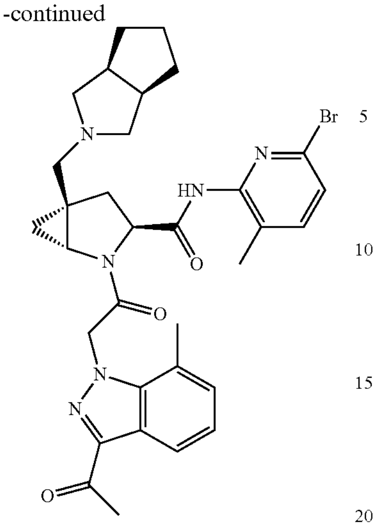

39

The above scheme and following detailed description depicts one non-limiting method for synthesizing compounds with nucleophilic $R^{201}$ groups on the C-Ring. The skilled artisan will recognize that heterocycle can be replaced with other nucleophilic reagents to afford additional compounds of the present invention. Non-limiting examples of groups the skilled artisan can use instead of (3aR,6aS)-octahydrocyclopenta[c]pyrrole include: triazole, pyrazole, imidazole, azetidine, or the like.

Step 1: (1R,3S,5S)-2-(2-(3-Acetyl-7-methyl-1H-indazol-1-yl)acetyl)-N-(6-bromo-3-methylpyridin-2-yl)-5-(hydroxymethyl)-2-azabicyclo[3.1.0]hexane-3-carboxamide (39-S3)

To a mixture of 39-S1 (30 mg, 0.093 mmol), 39-S2 (17.5 mg, 0.075 mmol), and HATU (71 mg, 0.18 mmol) in DMF (2 mL) was added DIPEA (0.06 mL, 0.37 mmol). The reaction mixture was stirred at room temperature for 1 hour and partitioned with DCM and water. The organic layer was washed with brine, dried over anhydrous $Na_2SO_4$, and concentrated under reduced pressure. The remaining residue was purified by column chromatography on silica gel (eluted with DCM/MeOH=70:1) to afford 39-S3 (20 mg, 40.2% yield) as a white solid. LC/MS (ESI) m/z: 540 $(M+H)^+$.

Step 2: ((1R,3S,5S)-2-(2-(3-Acetyl-7-methyl-1H-indazol-1-yl)acetyl)-3-((6-bromo-3-methylpyridin-2-yl)carbamoyl)-2-azabicyclo[3.1.0]hexan-5-yl)methyl methanesulfonate (39-S4)

To a mixture of 39-S3 (20 mg, 0.037 mmol) in dry DCM (3 mL) was added $Et_3N$ (0.012 mL, 0.092 mmol) followed by methanesulfonyl chloride (0.004 mL, 0.055 mmol) at 0° C. The reaction mixture was stirred at 0° C. for 1 hour. The mixture was then diluted with water (3 mL) and extracted with DCM (3 mL×2). The combined organic phases were washed with brine, dried over anhydrous $Na_2SO_4$, filtered, and concentrated to afford 39-S4 (22 mg, 100.1% yield) as a yellow oil, which was carried forward in the next synthetic step without further purification. LC/MS (ESI) m/z: 618 $(M+H)^+$.

Step 3: (1R,3S,5R)-2-(2-(3-Acetyl-7-methyl-1H-indazol-1-yl)acetyl)-N-(6-bromo-3-methylpyridin-2-yl)-5-(((3aR,6aS)-hexahydrocyclopenta[c]pyrrol-2(1H)-yl)methyl)-2-azabicyclo[3.1.0]hexane-3-carboxamide (39)

To a solution of 39-S4 (22 mg, 0.037 mmol) in MeCN (3 mL) were added DIPEA (0.018 mL, 0.11 mmol), NaI (8.4 mg, 0.056 mmol), and (3aR,6aS)-octahydrocyclopenta[c]pyrrole (14.5 mg, 0.11 mmol). The reaction mixture was stirred at 30° C. overnight and was partitioned with EtOAc and water. The organic layer was washed with brine, dried over anhydrous $Na_2SO_4$, and concentrated under reduced pressure. The remaining residue product was purified by preparative HPLC to afford 39 (7.0 mg, 29.8% yield) as a white solid. $^1H$ NMR (400 MHz, $CD_3OD$) δ 8.14 (t, J=4.0 Hz, 1H), 7.58 (d, J=8.0 Hz, 1H), 7.42 (d, J=8.0 Hz, 1H), 7.20-7.22 (m, 2H), 5.93-5.97 (m, 1H), 5.76-5.80 (m, 1H), 4.66-4.70 (m, 1H), 3.68-3.86 (m, 3H), 3.23-3.27 (m, 1H), 2.86-2.89 (m, 2H), 2.61-2.69 (m, 11H), 2.13 (s, 3H), 1.60-1.77 (m, 6H), 1.41-1.44 (m, 1H), 1.27-1.30 (m, 1H). LC/MS (ESI) m/z: 633 $(M+H)^+$.

Scheme 19: Synthesis of (1R,3S,5R)-2-(2-(3-Acetyl-7-(S-methylsulfinimidoyl)-1H-indazol-1-yl)acetyl)-N-(6-bromo-3-methylpyridin-2-yl)-5-methyl-2-azabicyclo[3.1.0]hexane-3-carboxamide (40) and (1R,3S,5R)-2-(2-(3-Acetyl-7-(S-methylsulfonimidoyl)-1H-indazol-1-yl)acetyl)-N-(6-bromo-3-methylpyridin-2-yl)-5-methyl-2-azabicyclo[3.1.0]hexane-3-carboxamide (41)

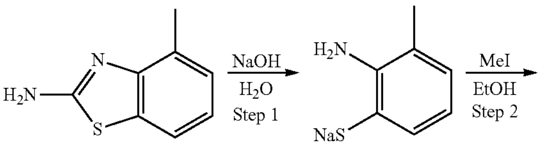

40-S1 40-S2

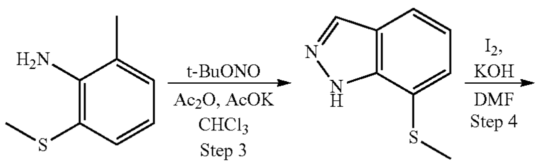

40-S3 40-S4

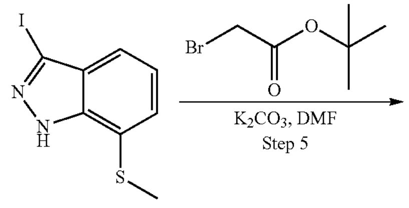

40-S5

-continued

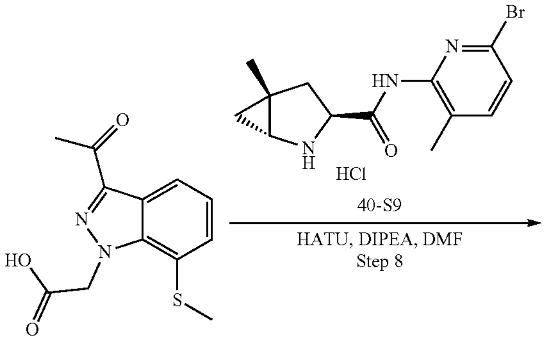

40-S8

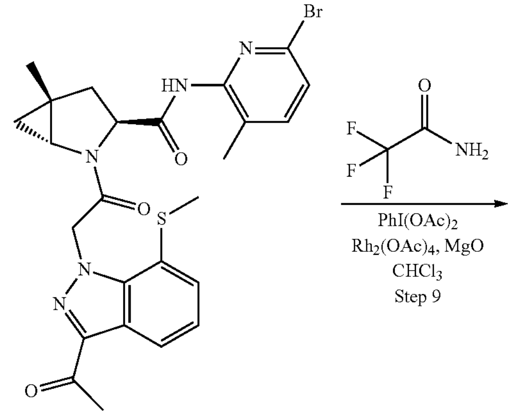

40-S10

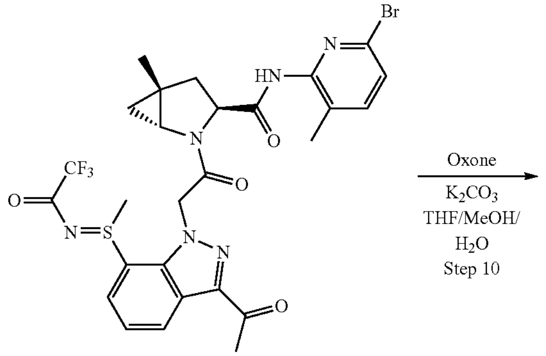

40-S11

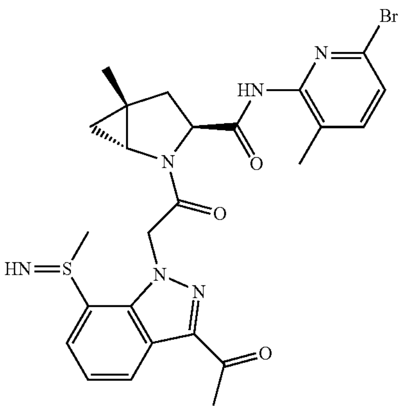

40

-continued

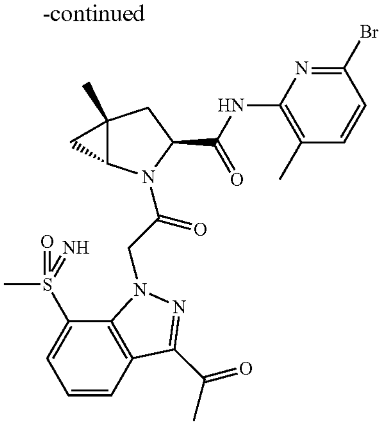

41

Step 1: Sodium 2-amino-3-methylbenzenethiolate (40-S2)

To a solution of 40-S1 (4.5 g, 27.4 mmol) in $H_2O$ (50 mL) was added NaOH (10.96 g, 274 mmol) and the reaction mixture was stirred at 125° C. overnight. The mixture was concentrated under reduced pressure to afford 40-S2 (10 g, 100% yield) as a brown solid, which was carried forward in the next synthetic step without further purification. LC/MS (ESI) m/z: 140 $(M+H)^+$.

Step 2: 2-Methyl-6-(methylthio)aniline (40-S3)

To a solution of 40-S2 (10 g, 27.4 mmol) in EtOH (100 mL) was added MeI (9.7 g, 68.5 mmol) at 0° C. The reaction mixture was stirred at room temperature overnight. The mixture was adjusted to pH 7 with 1 N aqueous HCl and extracted with DCM twice. The combined organic layers were dried over $Na_2SO_4$ and concentrated to dryness. The remaining residue was purified by column chromatography on silica gel (eluted with PE/EtOAc=100:1) to afford 40-S3 (2.8 g, 66.8% yield) as a brown solid. LC/MS (ESI) m/z: 154 $(M+H)^+$.

Step 3: 7-(Methylthio)-1H-indazole (40-S4)

To a solution of 40-S3 (2.5 g, 16.3 mmol) in $CHCl_3$ (100 mL) was added AcOK (1.92 g, 19.6 mmol) and $Ac_2O$ (5 g, 49.0 mmol) at 0° C. The reaction mixture was stirred at room temperature for 1 hour. The mixture was heated to 60° C. and t-BuONO (3.66 g, 32.7 mmol) was added dropwise. The mixture was diluted with DCM, washed with water and brine, dried over $Na_2SO_4$, and concentrated to dryness. The remaining residue was dissolved in THF/MeOH (10 mL/10 mL) and 6 N aqueous HCl solution (10 mL) was added. The mixture was stirred at room temperature for 2 hours, adjusted to pH 8 with aqueous sodium bicarbonate, and extracted with DCM twice. The combined organic layers were dried over $Na_2SO_4$ and concentrated to dryness. The remaining residue was purified by column chromatography on silica gel (eluted with PE/EtOAc=10:1) to afford 40-S4 (1.8 g, 67.4% yield) as a brown solid. LC/MS (ESI) m/z: 165 $(M+H)^+$.

Step 4: 3-Iodo-7-(methylthio)-1H-indazole (40-S5)

To a solution of 40-S4 (1.8 g, 10.98 mmol) in DMF (15 mL) was added KOH (1.39 g, 24.7 mmol) and iodine (4.18 g, 16.47 mmol) at 0° C. The reaction mixture was stirred at room temperature overnight. The reaction mixture was quenched by saturated aqueous $Na_2S_2O_3$ solution (5 mL) and the mixture was extracted with EtOAc twice. The combined organic layers were washed with 10% aqueous LiCl solution and brine, dried over $Na_2SO_4$, and concentrated to dryness. The remaining residue was purified by column chromatography on silica gel (eluted with PE/EtOAc=20:1) to afford 40-S5 (2.6 g, 81.8% yield) as a white solid. LC/MS (ESI) m/z: 291 $(M+H)^+$.

Step 5: tert-Butyl 2-(3-iodo-7-(methylthio)-1H-indazol-1-yl)acetate (40-S6)

To a solution of 40-S5 (1.5 g, 6.2 mmol) in DMF (20 mL) was added $K_2CO_3$ (2.14 g, 15.5 mmol) and tert-butyl 2-bromoacetate (1.27 g, 6.5 mmol) at 0° C. The reaction mixture was stirred at room temperature overnight. The mixture was diluted with EtOAc, washed with 10% aqueous LiCl solution and brine, dried over $Na_2SO_4$, and concentrated to dryness. The remaining residue was purified by column chromatography on silica gel (eluted with PE/EtOAc=60:1) to afford 40-S6 (1.24 g, 50.6% yield) as a yellow solid. LC/MS (ESI) m/z: 404 $(M+H)^+$.

Step 6: tert-Butyl 2-(3-acetyl-7-(methylthio)-1H-indazol-1-yl)acetate (40-S7)

To a solution of 40-S6 (1.24 g, 3.07 mmol) in toluene (15 mL) under an atmosphere of nitrogen was added tributyl(1-ethoxyvinyl)stannane (1.66 g, 4.6 mmol) and $Pd(PPh_3)_4$ (358 mg, 0.31 mmol) at 0° C. The mixture was purged with nitrogen and stirred at 100° C. under an atmosphere of nitrogen overnight. The mixture was diluted with 4 N aqueous HCl (5 mL) and the mixture was stirred at room temperature for 1 hour. The mixture was extracted with EtOAc and the organic layer was washed with water and brine, dried over $Na_2SO_4$, and concentrated to dryness. The remaining residue was purified by column chromatography on silica gel (eluted with PE/EtOAc=40:1) to afford 40-S7 (875 mg, 89.1% yield) as a brown solid. LC/MS (ESI) m/z: 321 $(M+H)^+$.

Step 7: 2-(3-Acetyl-7-(methylthio)-1H-indazol-1-yl) acetic acid (40-S8)

To a solution of 40-S7 (100 mg, 0.313 mmol) in DCM (3 mL) was added TFA (2 mL) at 0° C. The reaction mixture was stirred at room temperature for 1 hour and concentrated to dryness to afford 40-S8 (130 mg, 100% yield) as a brown solid, which was carried forward in the next synthetic step without further purification. LC/MS (ESI) m/z: 325 $(M+H)^+$.

Step 8: (1R,3S,5R)-2-(2-(3-Acetyl-7-(methylthio)-1H-indazol-1-yl)acetyl)-N-(6-bromo-3-methylpyridin-2-yl)-5-methyl-2-azabicyclo[3.1.0]hexane-3-carboxamide (40-S10)

To a solution of 40-S8 (130 mg, 0.313 mmol), 40-S9 (101 mg, 0.313 mmol), and HATU (238 mg, 0.6269 mmol) in DMF (3 mL) was added DIPEA (0.22 mL, 1.25 mmol) at 0° C. The reaction mixture was stirred at room temperature overnight. The mixture was diluted with EtOAc, washed with 10% aqueous LiCl solution and brine, dried over $Na_2SO_4$, and concentrated to dryness. The remaining residue was purified by column chromatography on silica gel (eluted with DCM/MeOH=80:1) to afford 40-S10 (120 mg, 68.7% yield) as a yellow solid. LC/MS (ESI) m/z: 556 $(M+H)^+$.

Step 9: (1R,3S,5R)-2-(2-(3-Acetyl-7-((E)-S-methyl-N-(2,2,2-trifluoroacetyl)sulfinimidoyl)-1H-indazol-1-yl)acetyl)-N-(6-bromo-3-methylpyridin-2-yl)-5-methyl-2-azabicyclo[3.1.0]hexane-3-carboxamide (40-S11)

To a mixture of 40-S10 (120 mg, 0.215 mmol) and 2,2,2-trifluoroacetamide (36.6 mg, 0.324 mmol) in chloroform (10 mL) were added MgO (17.3 mg, 0.430 mmol), $PhI(OAc)_2$ (238 mg, 0.324 mmol), and $Rh_2(OAc)_4$ (0.22 mL, 0.022 mmol) at 0° C. The reaction mixture was stirred at room temperature overnight, quenched with sodium thiosulfate solution, and filtered. The filtrate was diluted with DCM, washed with water and brine, dried over $Na_2SO_4$, and concentrated to dryness. The remaining residue was purified by column chromatography on silica gel (eluted with DCM/MeOH=100:1) to afford 40-S11 (74 mg, 51.7% yield) as a yellow oil. LC/MS (ESI) m/z: 667 $(M+H)^+$.

Step 10: (1R,3S,5R)-2-(2-(3-Acetyl-7-(S-methylsulfinimidoyl)-1H-indazol-1-yl)acetyl)-N-(6-bromo-3-methylpyridin-2-yl)-5-methyl-2-azabicyclo[3.1.0]hexane-3-carboxamide (40) and (1R,3S,5R)-2-(2-(3-Acetyl-7-(S-methylsulfonimidoyl)-1H-indazol-1-yl)acetyl)-N-(6-bromo-3-methylpyridin-2-yl)-5-methyl-2-azabicyclo[3.1.0]hexane-3-carboxamide (41)

To a solution of 40-S11 (74 mg, 0.111 mmol) in MeOH/THF/$H_2O$ (7 mL/1 mL/5 mL) was added Oxone (116 mg, 0.189 mmol) and the mixture was adjusted to pH 10 with 10% aqueous LiCl solution at 0° C. The reaction mixture was stirred at room temperature overnight and filtered. The filtrate was diluted with DCM, washed with water and brine, dried over $Na_2SO_4$, and concentrated to dryness. The remaining residue was purified by preparative HPLC to afford 40 (3.2 mg, 5.0% yield) and 41 (8.0 mg, 12.2% yield) as white solids.

Compound 40: $^1H$ NMR (400 MHz, $CD_3OD$) δ 8.61 (d, J=7.3 Hz, 1H), 8.23 (d, J=7.0 Hz, 1H), 7.59 (t, J=7.9 Hz, 1H), 7.51 (d, J=7.9 Hz, 1H), 7.31 (d, J=7.9 Hz, 1H), 5.94 (dd, J=18.0, 18.0 Hz, 2H), 4.43 (dd, J=9.1, 5.7 Hz, 1H), 3.47 (dd, J=5.6, 2.4 Hz, 1H), 3.19 (s, 3H), 2.63-2.56 (m, 4H), 2.20-2.14 (m, 1H), 2.11 (s, 3H), 1.32 (s, 3H), 1.07 (t, J=5.8 Hz, 1H), 0.94 (dd, J=5.6, 2.4 Hz, 1H), 0.80-0.78 (m, 1H). LC/MS (ESI) m/z: 571 $(M+H)^+$.

Compound 41: $^1H$ NMR (400 MHz, $CD_3OD$) δ 8.75 (dd, J=8.1, 1.0 Hz, 1H), 8.27 (dd, J=7.6, 1.0 Hz, 1H), 7.55 (t, J=7.8 Hz, 2H), 7.37 (d, J=7.9 Hz, 1H), 6.42 (d, J=17.5 Hz, 1H), 6.00 (d, J=17.4 Hz, 1H), 4.48 (dd, J=9.1, 5.3 Hz, 1H), 3.46 (dd, J=5.4, 2.5 Hz, 1H), 3.39 (d, J=10.0 Hz, 3H), 2.69 (d, J=6.5 Hz, 3H), 2.66-2.58 (m, 1H), 2.28 (dd, J=14.2, 4.8 Hz, 1H), 2.10 (d, J=5.8 Hz, 3H), 1.40 (s, 3H), 1.13-1.05 (m, 2H), 0.91-0.88 (m, 1H). LC/MS (ESI) m/z: 587 $(M+H)^+$.

Scheme 20: Synthesis of (1R,3S,5R)-2-(3-Acetyl-7-methyl-1H-indazol-1-yl)acetyl)-N-(6-bromo-3-methylpyridin-2-yl)-5-((2,2-difluorocyclopentanecarboxamido)methyl)-2-azabicyclo[3.1.0]hexane-3-carboxamide (43)

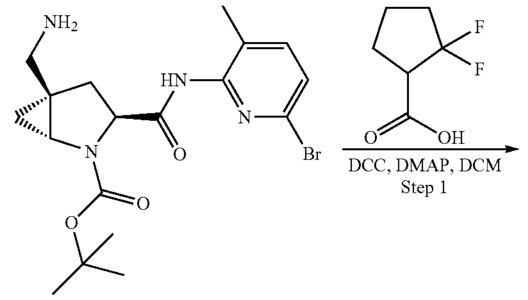

43-S1

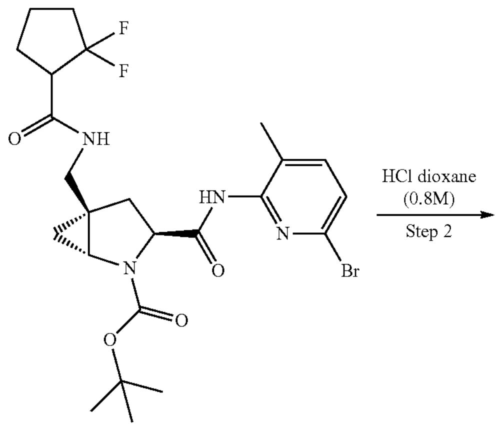

43-S2

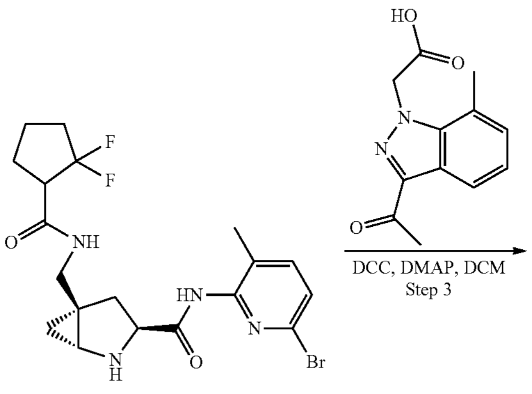

43-S3

-continued

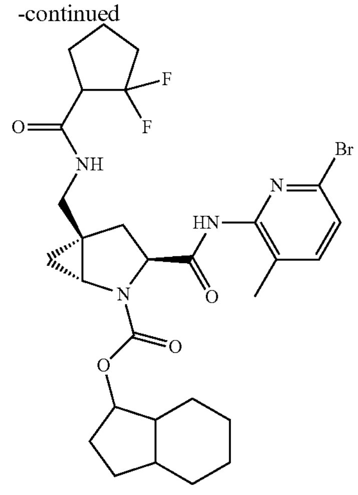

43

The above scheme and following detailed description depicts one non-limiting method for synthesizing compounds with amide $R^{201}$ groups on the C-Ring. The skilled artisan will recognize that 2,2-difluorocyclopentane-1-carboxylic acid can be replaced with other carboxylic acids to afford additional compounds of the present invention.

Step 1: (1R,3S,5R)-tert-Butyl 3-(6-bromo-3-methylpyridin-2-ylcarbamoyl)-5-((2,2-difluorocyclopentanecarboxamido)methyl)-2-azabicyclo[3.1.0]hexane-2-carboxylate (43-S2)

To a solution of 43-S1 (50 mg, 0.12 mmol) and 2,2-difluorocyclopentanecarboxylic acid (18 mg, 0.12 mmol) in DCM (3 mL) was added DCC (36 mg, 0.18 mmol) at 0° C. and DMAP (2 mg, 0.01 mmol). The reaction mixture was stirred at room temperature for 1 hour. The mixture was concentrated under reduced pressure and the remaining residue was purified by silica gel chromatography (eluted with DCM/MeOH=80:1) to afford 43-S2 (60 mg, 89.8% yield) as a white solid. LC/MS (ESI) m/z: 557 $(M+H)^+$.

Step 2: (1R,3S,5R)—N-(6-Bromo-3-methylpyridin-2-yl)-5-((2,2-difluorocyclopentanecarboxamido)methyl)-2-azabicyclo[3.1.0]hexane-3-carboxamide (43-S3)

To a solution of 43-S2 (60 mg, 0.11 mmol) in dioxane (1.5 mL) was added HCl/dioxane (2 M, 0.4 mL). The reaction mixture was stirred at room temperature for 1 hour and concentrated to afford 43-S3 (60 mg, 100% yield) as a white solid, which was carried forward in the next synthetic step without purification. LC/MS (ESI) m/z: 457 $(M+H)^+$.

Step 3: (1R,3S,5R)-2-(2-(3-Acetyl-7-methyl-1H-indazol-1-yl)acetyl)-N-(6-bromo-3-methylpyridin-2-yl)-5-((2,2-difluorocyclopentanecarboxamido)methyl)-2-azabicyclo[3.1.0]hexane-3-carboxamide (43)

To a solution of 43-S3 (30 mg, 0.08 mmol) and 2-(3-acetyl-7-methyl-1H-indazol-1-yl)acetic acid (21 mg, 0.08 mmol) in DCM (3 mL) was added DCC (25 mg, 0.12 mmol) at 0° C. followed by DMAP (2 mg, 0.01 mmol). The reaction mixture was stirred at room temperature for 1 hour. The mixture was concentrated to dryness and the remaining residue was purified by preparative HPLC to afford 43 (5.2 mg, 9.7% yield) as a white solid. $^1H$ NMR (400 MHz, $CD_3OD$) δ 8.14 (m, 1H), 7.57 (d, J=7.9 Hz, 1H), 7.41 (dd, J=7.9, 1.4 Hz, 1H), 7.21 (m, 2H), 5.93 (m, 1H), 5.79 (m, 1H), 4.71-4.54 (m, 1H), 3.78-3.39 (m, 3H), 3.07 (m, 1H), 2.69 (m, 6H), 2.55 (m, 2H), 2.24-2.06 (m, 6H), 2.03-1.84 (m, 2H), 1.75 (m, 1H), 1.34 (m, 1H), 1.07 (m, 1H). LC/MS (ESI) m/z: 671 $(M+H)^+$.

Scheme 21. Synthesis of (3-Acetyl-1-(2-((1R,3S,5R)-3-((3-chloro-2-fluorobenzyl)carbamoyl)-5-((4-methylpiperazin-1-yl)methyl)-2-azabicyclo[3.1.0]hexan-2-yl)-2-oxoethyl)-1H-indol-6-yl)phosphonic acid (44) and (3-Acetyl-1-(2-((1S,3S,5S)-3-((3-chloro-2-fluorobenzyl)carbamoyl)-5-((4-methylpiperazin-1-yl)methyl)-2-azabicyclo[3.1.0]hexan-2-yl)-2-oxoethyl)-1H-indol-6-yl)phosphonic acid (45)

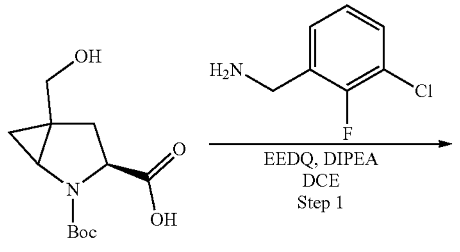

45-S1

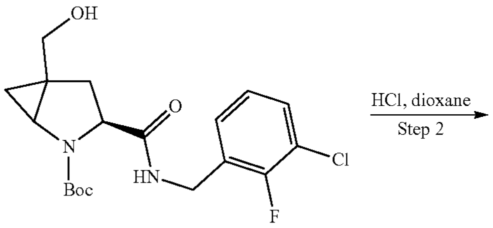

45-S2

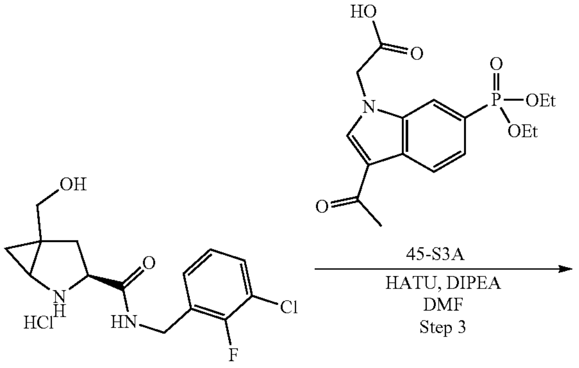

45-S3

-continued

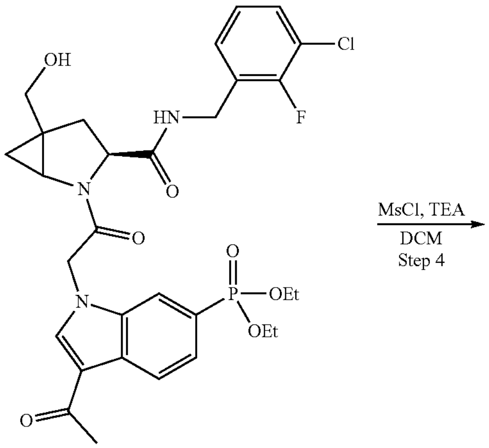

45-S4

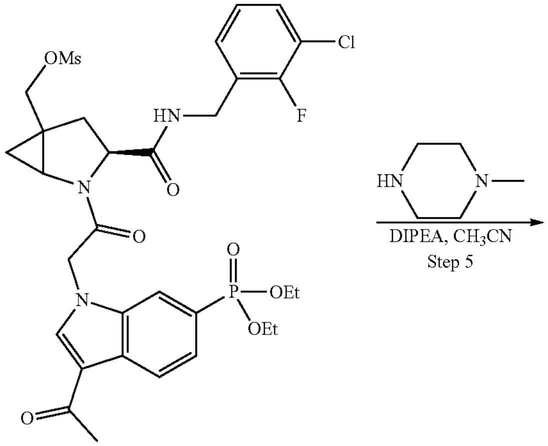

45-S5

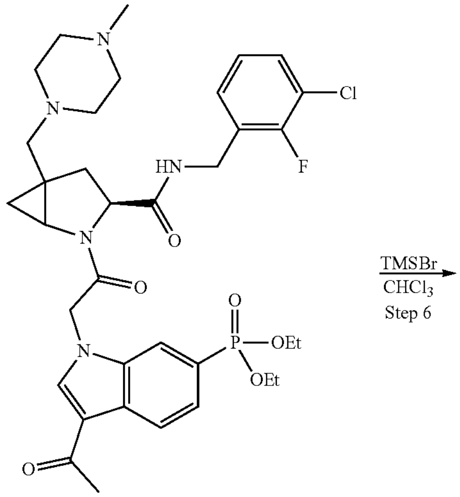

45-S6

-continued

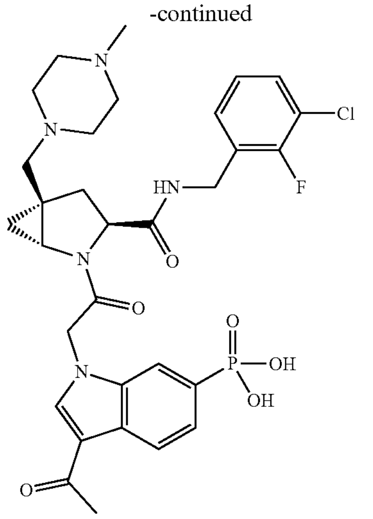

44

+

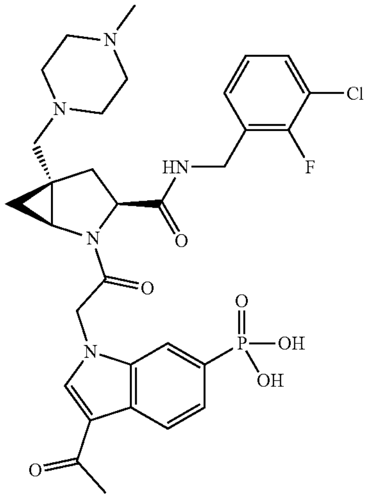

45

Step 1: (3S)-tert-Butyl 3-(3-chloro-2-fluorobenzyl-carbamoyl)-5-(hydroxymethyl)-2-azabicyclo[3.1.0] hexane-2-carboxylate (45-S2)

To a solution of 45-S1 (100 mg, 0.39 mmol) and (3-chloro-2-fluorophenyl)methanamine (0.053 mL, 0.42 mmol) in DCE (3 mL) was added DIPEA (0.25 mL, 1.55 mmol) and EEDQ (192 mg, 0.77 mmol). The reaction mixture was stirred at 90° C. overnight and evaporated to dryness under reduced pressure. The remaining residue was purified by column chromatography on silica gel (eluted with PE/EtOAc=2:1) to afford 45-S2 (120 mg, 77.4% yield) as a white solid. LC/MS (ESI) m/z: 399 $(M+H)^+$.

Step 2: (3S)—N-(3-Chloro-2-fluorobenzyl)-5-(hydroxymethyl)-2-azabicyclo[3.1.0]hexane-3-carboxamide (45-S3)

To a solution of 45-S2 (120 mg, 0.30 mmol) in dioxane (0.5 mL) was added HCl/dioxane (4 M, 2 mL). The reaction mixture was stirred at room temperature for 1 hour and concentrated to dryness to afford 45-S3 (89 mg, 100% yield) as a white solid, which was carried forward in the next synthetic step without purification. LC/MS (ESI) m/z: 299 $(M+H)^+$.

Step 3: Diethyl 3-acetyl-1-(2-((3S)-3-(3-chloro-2-fluorobenzylcarbamoyl)-5-(hydroxymethyl)-2-azabicyclo[3.1.0]hexan-2-yl)-2-oxoethyl)-1H-indol-6-ylphosphonate (45-S4)

To a mixture of 45-S3 (76 mg, 0.25 mmol), 2-(3-acetyl-6-(diethoxyphosphoryl)-1H-indol-1-yl)acetic acid (45-S3A, 100 mg, 0.28 mmol), and HATU (215 mg, 0.56 mmol) in DMF (3 mL) was added DIPEA (0.18 mL, 1.13 mmol). The reaction mixture was stirred at room temperature for 16 hours and partitioned with EtOAc and water. The organic layer was washed with brine, dried over anhydrous $Na_2SO_4$, and concentrated under reduced pressure. The remaining residue was purified by column chromatography on silica gel (eluted with DCM/MeOH=30:1) to afford 45-S4 (130 mg, 80.7% yield) as a yellow solid LC/MS (ESI) m/z: 634 $(M+H)^+$.

Step 4: ((3S)-2-(2-(3-Acetyl-6-(diethoxyphosphoryl)-1H-indol-1-yl)acetyl)-3-(3-chloro-2-fluorobenzylcarbamoyl)-2-azabicyclo[3.1.0]hexan-5-yl)methyl Methanesulfonate (45-S5)

To a solution of 45-S4 (130 mg, 0.20 mmol) in dry DCM (3 mL) was added $Et_3N$ (0.057 mL, 0.40 mmol) followed by methanesulfonyl chloride (0.023 mL, 0.30 mmol) at 0° C. The reaction mixture was stirred at 0° C. for 2 hours. The mixture was then diluted with water (20 mL) and extracted with DCM (4 mL×2). The combined organic phases were washed with brine, dried over anhydrous $Na_2SO_4$, filtered, and concentrated to afford 45-S5 (130 mg crude, 100% yield) as a yellow oil, which was carried forward in the next synthetic step without further purification. LC/MS (ESI) m/z: 712 $(M+H)^+$.

Step 5: Diethyl 3-acetyl-1-(2-((3S)-3-(3-chloro-2-fluorobenzylcarbamoyl)-5-((4-methylpiperazin-1-yl)methyl)-2-azabicyclo[3.1.0]hexan-2-yl)-2-oxoethyl)-1H-indol-6-ylphosphonate (45-S6)

To a solution of 45-S5 (130 mg crude, 0.18 mmol) in MeCN (3 mL) were added DIPEA (0.06 mL, 0.36 mmol), NaI (27 mg, 0.18 mmol), and 1-methylpiperazine (0.04 mL, 0.36 mmol). The reaction mixture was stirred at 30° C. overnight and partitioned with EtOAc and water. The organic layer was washed with brine, dried over anhydrous $Na_2SO_4$, and concentrated under reduced pressure. The remaining residue was purified by column chromatography on silica gel (eluted with DCM/MeOH=10:1) to afford 45-S6 (35 mg, 26.9% yield) as a white solid. LC/MS (ESI) m/z: 716 $(M+H)^+$.

Step 6: (3-Acetyl-1-(2-((1R,3S,5R)-3-((3-chloro-2-fluorobenzyl)carbamoyl)-5-((4-methylpiperazin-1-yl)methyl)-2-azabicyclo[3.1.0]hexan-2-yl)-2-oxoethyl)-1H-indol-6-yl)phosphonic acid (44) and (3-Acetyl-1-(2-((1S,3S,5S)-3-((3-chloro-2-fluorobenzyl)carbamoyl)-5-((4-methylpiperazin-1-yl)methyl)-2-azabicyclo[3.1.0]hexan-2-yl)-2-oxoethyl)-1H-indol-6-yl)phosphonic acid (45)

To a solution of diethyl 3-acetyl-1-(2-((3S)-3-(3-chloro-2-fluorobenzylcarbamoyl)-5-((4-methylpiperazin-1-yl)

methyl)-2-azabicyclo[3.1.0]hexan-2-yl)-2-oxoethyl)-1H-indol-6-ylphosphonate (45-S6, 35 mg, 0.05 mmol) in $CHCl_3$ (5 mL) was added TMSBr (1 mL) at 0° C. under an atmosphere of nitrogen. After the mixture was stirred at 50° C. for 1 hour, the reaction mixture was quenched with MeOH at 0° C. The mixture was concentrated to remove volatiles and the remaining residue was purified by preparative HPLC to afford 44 (8.0 mg, 24.8% yield) and 45 (2.1 mg, 6.5% yield) as white solids.

Compound 44: $^1$H NMR (400 MHz, $CD_3OD$) δ 8.18-8.28 (m, 2H), 7.82 (d, J=13.6 Hz, 1H), 7.73 (t, J=8.8 Hz, 1H), 7.30 (t, J=6.8 Hz, 1H), 7.18 (t, J=6.4 Hz, 1H), 7.00 (t, J=8.0 Hz, 1H), 5.31-5.35 (m, 1H), 5.14-5.18 (m, 1H), 4.35-4.39 (m, 2H), 4.20-4.24 (m, 1H), 3.43 (s, 1H), 3.29-3.31 (m, 6H), 3.18-3.22 (m, 2H), 2.78 (s, 3H), 2.59-2.62 (m, 1H), 2.48 (s, 3H), 2.25-2.36 (m, 3H), 0.99 (s, 2H). LC/MS (ESI) m/z: 660 $(M+H)^+$.

Compound 45: $^1$H NMR (400 MHz, $CD_3OD$) δ 8.29 (J=8.0 Hz, 1H), 8.13-8.18 (m, 1H), 7.69-7.75 (m, 2H), 7.31 (t, J=8.0 Hz, 1H), 7.16 (t, J=8.0 Hz, 1H), 7.02 (t, J=8.4 Hz, 1H), 4.72-4.96 (m, 3H), 4.34-4.35 (m, 2H), 3.21-3.32 (m, 5H), 2.65-2.87 (m, 9H), 2.51 (s, 3H), 2.21-2.29 (m, 1H), 1.86-1.90 (m, 1H), 1.35-1.36 (m, 1H), 0.84-0.87 (m, 1H). LC/MS (ESI) m/z: 660 $(M+H)^+$.

Scheme 22. Synthesis of (3-Acetyl-1-(2-((1R,3S,5R)-3-((3-chloro-2-fluorobenzyl)carbamoyl)-5-((dimethylamino)methyl)-2-azabicyclo[3.1.0]hexan-2-yl)-2-oxoethyl)-1H-indol-6-yl)phosphonic acid (46)

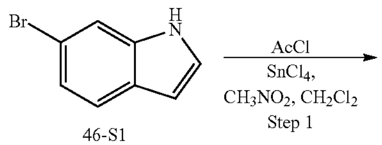

46-S1

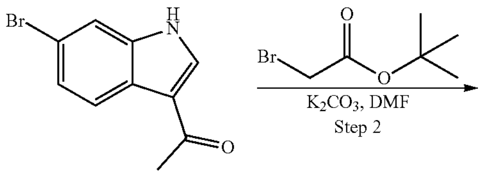

46-S2

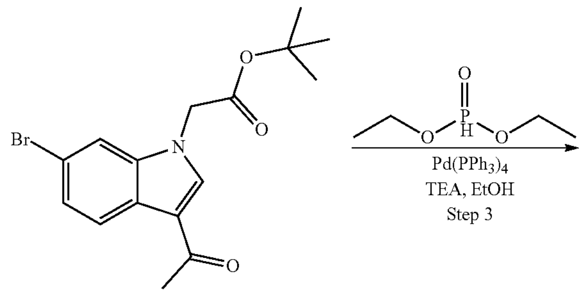

46-S3

-continued

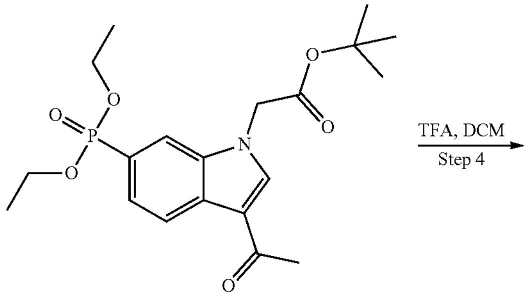

46-S4

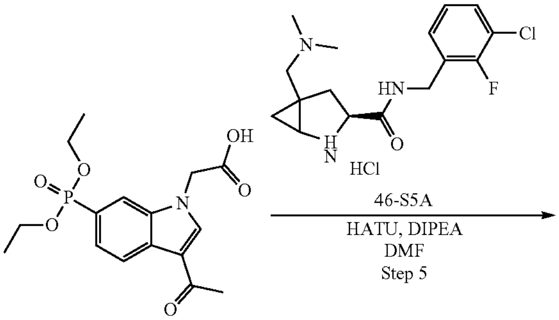

46-S5

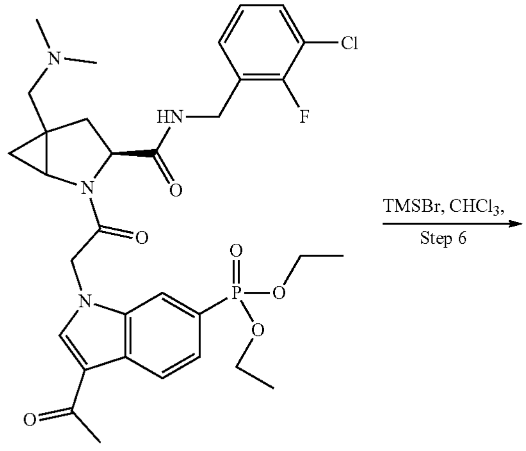

46-S6

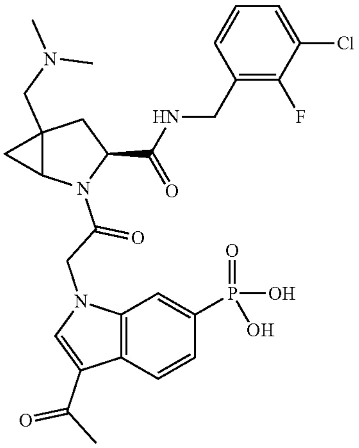

46

Step 1: 1-(6-Bromo-1H-indol-3-yl)ethanone (46-S2)

To a solution of 46-S1 (5 g, 25.5 mmol) in dry DCM (50 mL) was added $SnCl_4$ (5 mL) under an atmosphere of nitrogen at 0° C. The mixture was stirred at this temperature for 30 minutes and acetyl chloride (3.0 g, 38.3 mmol) was added dropwise to the reaction mixture, followed by nitromethane (30 mL). The reaction mixture was stirred at room temperature for 4 hours. The mixture was quenched with ice water and extracted with DCM twice. The combined organic layers were washed with water and brine, dried over anhydrous $Na_2SO_4$, filtered, and concentrated to dryness. The remaining residue was purified by column chromatography on silica gel (eluted with DCM/MeOH=100:1) to afford 46-S2 (669 mg, 11% yield) as a yellow solid. LC/MS (ESI) m/z: 238/240 $(M+H)^+$.

Step 2: tert-Butyl 2-(3-acetyl-6-bromo-1H-indol-1-yl)acetate (46-S3)

To a solution of 46-S2 (669 mg, 2.81 mmol) in DMF (10 mL) was added $K_2CO_3$ (776 mg, 5.62 mmol) and tert-butyl 2-bromoacetate (0.5 mL, 3.37 mmol) at 0° C. under an atmosphere of nitrogen. The reaction mixture was stirred at rt overnight. The mixture was diluted with EtOAc, washed with 10% aqueous LiCl solution and brine, dried over anhydrous $Na_2SO_4$, and concentrated to dryness. The remaining residue was purified by column chromatography on silica gel (eluted with PE/EtOAc=20:1 to 10:1) to afford 46-S3 (818 mg, 83% yield) as a white solid. 352/354 $(M+H)^+$.

Step 3: tert-Butyl 2-(3-acetyl-6-(ethoxy(methoxy)phosphoryl)-1H-indol-1-yl)acetate (46-S4)

To a mixture of 46-S3 (200 mg, 0.568 mmol), diethyl phosphonate (0.4 mL, 2.84 mmol), and $Et_3N$ (0.24 mL, 1.7 mmol) in EtOH (5 mL) was added $Pd(PPh_3)_4$ (66 mg, 0.0568 mmol). The mixture was purged with nitrogen and stirred at 90° C. under an atmosphere of nitrogen overnight. The mixture was concentrated to dryness and the remaining residue was purified by column chromatography on silica gel (eluted with PE/EtOAc=1:1) to afford 46-S4 (184 mg, 79.2% yield) as light a yellow solid. LC/MS (ESI) m/z: 410 $(M+H)^+$.

Step 4: 2-(3-Acetyl-6-(diethoxyphosphoryl)-1H-indol-1-yl)acetic acid (46-S5)

To a solution of 2-(3-acetyl-6-(diethoxyphosphoryl)-1H-indol-1-yl)acetic acid (46-S4) in DCM (3 mL) was added TFA (1 mL) at 0° C. After the reaction mixture was stirred at room temperature for 1 hour, the mixture was evaporated under reduced pressure to afford 46-S5 (180 mg, 100% yield), which was carried forward without further purification. LC/MS (ESI) m/z: 410 $(M+H)^+$.

Step 5: Diethyl-3-acetyl-1-(2-(3-(3-chloro-2-fluorobenzylcarbamoyl)-5-((dimethylamino)methyl)-2-azabicyclo[3.1.0]hexan-2-yl)-2-oxoethyl)-1H-indol-6-ylphosphonate (46-S6)

To a mixture of 46-S5 (49.72 mg, 0.14 mmol), N-(3-chloro-2-fluorobenzyl)-5-((dimethylamino)methyl)-2-azabicyclo[3.1.0]hexane-3-carboxamide (46-S5A, 50 mg, 0.12 mmol), and HATU (91.2 mg, 0.24 mmol) in DMF was added DIPEA (0.12 mL, 0.72 mmol) and the reaction mixture was stirred at room temperature overnight. The mixture was diluted with EtOAc, washed with 10% aqueous LiCi solution and brine, dried over $Na_2SO_4$, and concentrated to dryness. The remaining residue was purified by column chromatography on silica gel (DCM/MeOH=10:1 to 5:1) afford 46-S6 (67 mg, 72.4% yield) as a yellow powder. LC/MS (ESI) m/z: 661 $(M+H)^+$.

Step 6: 3-Acetyl-1-(2-(3-(3-chloro-2-fluorobenzylcarbamoyl)-5-((dimethylamino)methyl)-2-azabicyclo[3.1.0]hexan-2-yl)-2-oxoethyl)-1H-indol-6-ylphosphonic acid (46)

To a solution of 3-acetyl-1-(2-(3-(3-chloro-2-fluorobenzylcarbamoyl)-5-((dimethylamino)methyl)-2-azabicyclo[3.1.0]hexan-2-yl)-2-oxoethyl)-1H-indol-6-ylphosphonic acid (46-S6) in $CHCl_3$ (5 mL) was added TMSBr (1 mL) at 0° C. under an atmosphere of nitrogen. After the mixture was stirred at 50° C. for 1 hour, the reaction mixture was quenched with MeOH. The mixture was concentrated to dryness and the remaining residue was purified by preparative HPLC to afford 46 (3.2 mg, 12% yield) as a white solid. $^1H$ NMR (400 MHz, $CD_3OD$) δ 8.29 (d, J=12 Hz, 2H), 8.01 (s, 1H), 7.75 (t, J=14.8 Hz, 2H), 7.13 (s, 1H), 6.72-6.65 (m, 1H), 5.28 (s, 1H), 5.01 (d, J=12 Hz, 1H), 3.98-3.72 (m, 3H), 2.88-2.68 (m, 9H), 2.24 (s, 3H), 1.93-1.69 (m, 2H), 1.28 (m, 2H). LC/MS (ESI) m/z: 605 $(M+H)^+$.

Scheme 23. Synthesis of 3-Acetyl-1-(2-((1R,3S,5R)-3-((6-bromo-3-methylpyridin-2-yl)carbamoyl)-5-((dimethylamino)methyl)-2-azabicyclo[3.1.0]hexan-2-yl)-2-oxoethyl)-N-(cyclopropylsulfonyl)-1H-indazole-6-carboxamide (49) and 3-Acetyl-1-(2-((1S,3S,5S)-3-((6-bromo-3-methylpyridin-2-yl)carbamoyl)-5-((dimethylamino)methyl)-2-azabicyclo[3.1.0]hexan-2-yl)-2-oxoethyl)-N-(cyclopropylsulfonyl)-1H-indazole-6-carboxamide (50)

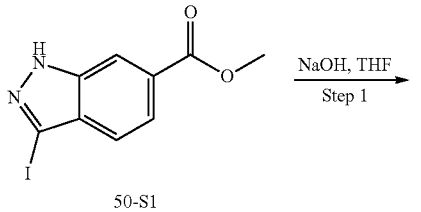

50-S1

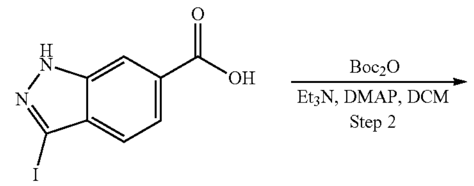

50-S2

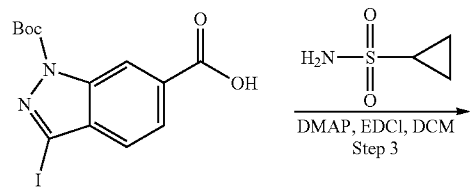

50-S3

-continued

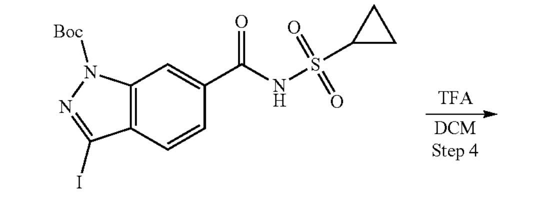

50-S4

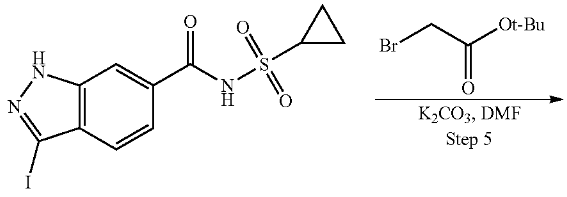

50-S5

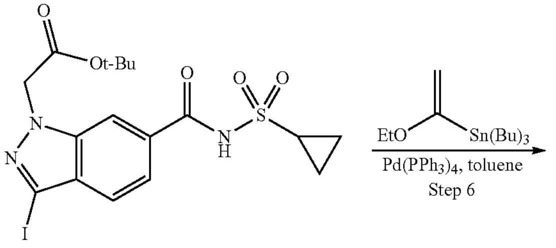

50-S6

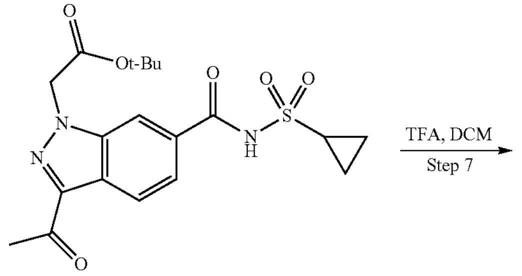

50-S7

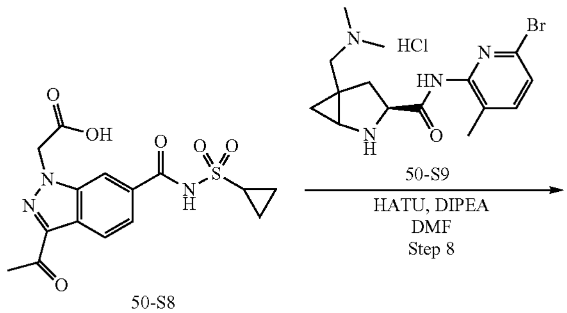

50-S8

-continued

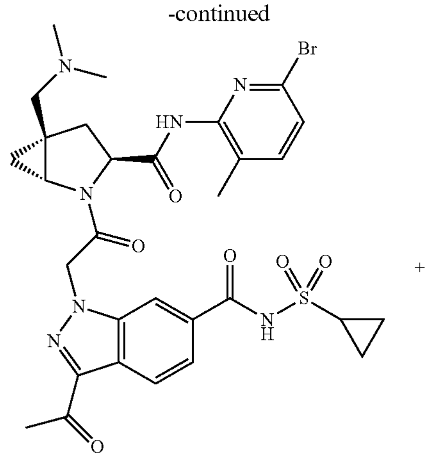

49

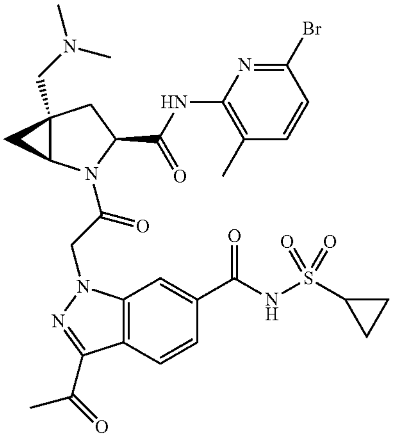

50

Step 1: 3-Iodo-1H-indazole-6-carboxylic acid (50-S2)

To a solution of 50-S1 (2.0 g, 6.6 mmol) in THF (20 mL) was added 1 M aqueous NaOH (13.2 mL, 13.2 mmol) and the reaction mixture was stirred at 50° C. overnight. The mixture was acidified with 1 N aqueous HCl (5 mL). The precipitated solid was collected by filtration and dried under vacuum to afford 50-S2 (1.9 g, 99.0% yield) as a white solid. LC/MS (ESI) m/z: 289 $(M+H)^+$.

Step 2: 1-(tert-Butoxycarbonyl)-3-iodo-1H-indazole-6-carboxylic acid (50-S3)

To a solution of 50-S2 (1.9 g, 6.6 mmol) in DCM (68 mL) were added $Et_3N$ (733 mg, 7.26 mmol), DMAP (80 mg, 0.66 mmol), and $Boc_2O$ (2.158 g, 9.9 mmol). The reaction mixture was stirred at room temperature overnight and concentrated to dryness. The remaining residue was diluted with water and washed with $Et_2O$ twice. The aqueous layer was acidified by addition of aqueous $KHSO_4$ (10% wt) solution and extracted with EtOAc twice. The combined organic layers were washed with brine, dried over anhydrous $Na_2SO_4$, filtered, and concentrated to dryness to afford 50-S3 (2.117 g, 82.7% yield) as a yellow oil. LC/MS (ESI) m/z: 389 $(M+H)^+$.

Step 3: tert-Butyl 6-((cyclopropylsulfonyl)carbamoyl)-3-iodo-1H-indazole-1-carboxylate (50-S4)

To a solution of 50-S3 (1.0 g, 2.58 mmol) in DCM (15 mL) were added DMAP (590 mg, 3.09 mmol) and EDCI (220 mg, 1.80 mmol). The mixture was stirred at room temperature under an atmosphere of nitrogen for 5 minutes followed by the addition of cyclopropanesulfonamide (623 mg, 5.15 mmol). The reaction mixture was stirred at room temperature under an atmosphere of nitrogen for 2 hours. The mixture was diluted with DCM, washed with water, washed with brine, dried over $Na_2SO_4$, filtered, and concentrated to dryness to afford 50-S4 (1.137 g, 89.9% yield) as a yellow oil. LC/MS (ESI) m/z: 492 $(M+H)^+$.

Step 4: N-(Cyclopropylsulfonyl)-3-iodo-1H-indazole-6-carboxamide (50-S5)

To a solution of 50-S4 (1.1 g, 2.23 mmol) in DCM (9 mL) was added TFA (3 mL) and the resulting reaction mixture was stirred at room temperature overnight. The mixture was concentrated to dryness and triturated with diethyl ether to afford 50-S5 (547 mg, 65.5% yield) as a yellow solid. LC/MS (ESI) m/z: 392 $(M+H)^+$.

Step 5: tert-Butyl 2-(6-((cyclopropylsulfonyl)carbamoyl)-3-iodo-1H-indazol-1-yl)acetate (50-S6)

To a solution of 50-S5 (547 mg, 1.40 mmol) in DMF (70 mL) were added $K_2CO_3$ (579 mg, 4.20 mmol) and tert-butyl 2-bromoacetate (0.2 mL, 1.40 mmol). The reaction mixture was stirred at room temperature under an atmosphere of nitrogen overnight and filtered. The filtrate was diluted with EtOAc, washed with aqueous LiCl (10%) solution and brine, dried over anhydrous $Na_2SO_4$, and concentrated to dryness. The remaining residue was purified by column chromatography on silica gel (eluted with PE/EtOAc=3:1) to afford 50-S6 (298 mg, 42.2% yield) as a light oil. LC/MS (ESI) m/z: 506 $(M+H)^+$.

Step 6: tert-Butyl 2-(3-acetyl-6-((cyclopropylsulfonyl)carbamoyl)-1H-indazol-1-yl)acetate (50-S7)

To a solution of 50-S6 (150 mg, 0.297 mmol) in toluene (5 mL) were added tributyl(1-ethoxyvinyl)stannane (160 mg, 0.446 mmol) and $Pd(PPh_3)_4$ (34 mg, 0.0297 mmol). The reaction mixture was stirred at 100° C. under an atmosphere of nitrogen overnight. The mixture was cooled to room temperature and 0.5 M aqueous HCl was added. The resulting mixture was stirred at room temperature for 30 minutes and diluted with EtOAc. The organic layer was washed with brine, dried over anhydrous $Na_2SO_4$, and concentrated to dryness. The remaining residue was purified by column chromatography on silica gel (eluted with PE/EtOAc=50:1) to afford 50-S7 (110 mg, 88.0% yield) as a light oil. LC/MS (ESI) m/z: 421 $(M+H)^+$.

Step 7: 2-(3-Acetyl-6-((cyclopropylsulfonyl)carbamoyl)-1H-indazol-1-yl)acetic acid (50-S8)

To a solution of 50-S7 (84 mg, 0.2 mmol) in DCM (3 mL) was added TFA (1 mL). The reaction mixture was stirred at room temperature overnight. The mixture was concentrated to dryness and the remaining residue was triturated with $Et_2O$ and dried under vacuum to afford 50-S8 (40 mg, 54.8% yield) as a white solid. LC/MS (ESI) m/z: 366 $(M+H)^+$.

Step 8: 3-Acetyl-1-(2-((1R,3S,5R)-3-((6-bromo-3-methylpyridin-2-yl)carbamoyl)-5-((dimethylamino)methyl)-2-azabicyclo[3.1.0]hexan-2-yl)-2-oxoethyl)-N-(cyclopropylsulfonyl)-1H-indazole-6-carboxamide (49) and 3-Acetyl-1-(2-((1S,3S,5S)-3-((6-bromo-3-methylpyridin-2-yl)carbamoyl)-5-((dimethylamino)methyl)-2-azabicyclo[3.1.0]hexan-2-yl)-2-oxoethyl)-N-(cyclopropylsulfonyl)-1H-indazole-6-carboxamide (50)

To a solution of 50-S8 (29 mg, 0.08 mmol), 50-S9 (31 mg, 0.08 mmol), and HATU (45.6 mg, 0.12 mmol) in DMF (3 mL) was added DIPEA (31 mg, 0.24 mmol). The reaction mixture was stirred at room temperature under an atmosphere of nitrogen for 1 hour. The mixture was basified by addition of aqueous $NaHCO_3$ solution and washed with EtOAc. The aqueous layer was acidified by addition of 0.5 M aqueous HCl and extracted with EtOAc twice. The combined organic layers were and washed with brine, dried over anhydrous $Na_2SO_4$, and concentrated to dryness. The remaining residue was purified by preparative HPLC to afford 49 (2.5 mg, 4.5% yield) and 50 (2.3 mg, 4.1% yield) as white solids.

Compound 49: $^1H$ NMR (400 MHz, DMSO-$d_6$) δ 10.36 (s, 1H), 8.22 (s, 1H), 8.12 (d, J=8.0 Hz, 1H), 7.97 (m, 1H), 7.61 (d, J=8.0 Hz, 1H), 7.44 (d, J=8.0 Hz, 1H), 5.89 (d, J=20.0 Hz, 1H), 5.62 (d, J=16.0 Hz, 1H), 4.49 (mi, 1H), 3.87 (s, 1H), 3.05-2.97 (m, 2H), 2.86-2.67 (m, 6H), 2.62 (s, 3H), 2.60 (s, 1H), 2.43-2.24 (m, 2H), 2.02 (d, J=12.0 Hz, 3H), 1.27 (d, J=24.0 Hz, 2H), 0.86 (d, J=4.0 Hz, 2H), 0.73 (d, J=8.0 Hz, 2H). LC/MS (ESI) m/z: 700 $(M+H)^+$.

Compound 50: $^1H$ NMR (400 MHz, DMSO-$d_6$) δ 10.41 (s, 1H), 8.20 (s, 1H), 8.11 (d, J=8.0 Hz, 1H), 7.97 (d, J=8.0 Hz, 1H), 7.60 (d, J=8.0 Hz, 1H), 7.42 (d, J=8.0 Hz, 1H), 6.04 (d, J=20 Hz, 1H), 5.53 (d, J=16.0 Hz, 1H), 5.01 (d, J=12.0 Hz, 1H), 3.92 (s, 1H), 3.06-2.94 (m, 2H), 2.81-2.64 (m, 6H), 2.61 (d, J=4.0 Hz, 3H), 2.25-2.11 (t, 2H), 2.01 (s, 3H), 1.59 (s, 1H), 1.18 (d, J=48.0 Hz, 2H), 0.86 (d, J=4.0 Hz, 2H), 0.73 (d, J=8.0 Hz, 2H). LC/MS (ESI) m/z: 700 $(M+H)^+$.

Scheme 24. Synthesis of (1R,3S,5R)-N-(6-Bromo-3-methylpyridin-2-yl)-5-methyl-2-{2-[3-(2-oxopyrrolidin-1-yl)pyrazolo[3,4-c]pyridin-1-yl]acetyl}-2-azabicyclo[3.1.0]hexane-3-carboxamide (51)

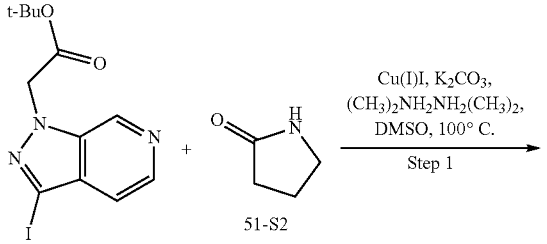

51-S1

51-S2

-continued

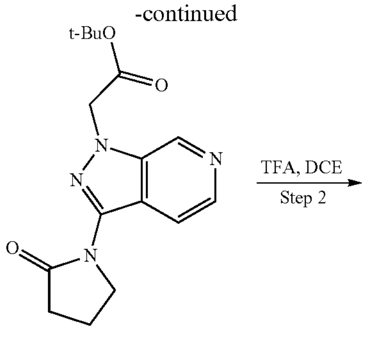

51-S3

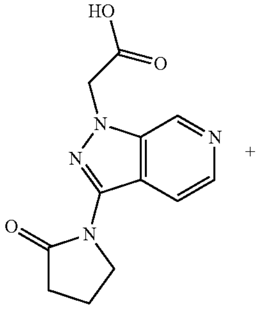

51-S4

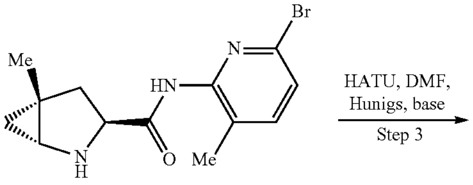

51-S5

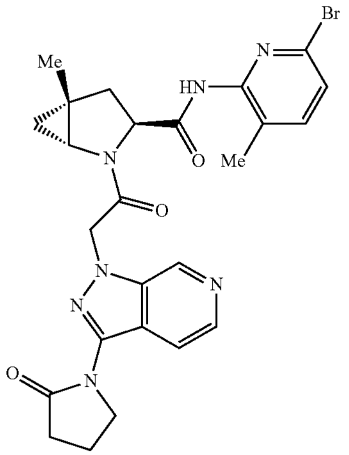

51

The above scheme and following detailed description depicts one non-limiting method for synthesizing compounds with heterocyclic $R^6$ groups on the A-Ring. The skilled artisan will recognize that pyrrolidinone can be replaced with other heterocyclic amines to afford additional compounds of the present invention.

Step 1: tert-Butyl 2-[3-(2-oxopyrrolidin-1-yl)pyrazolo[3,4-c]pyridin-1-yl]acetate (51-S3)

tert-Butyl 2-{3-iodopyrazolo[3,4-c]pyridin-1-yl}acetate (0.50 g, 1.4 mmol, 1 equiv.), potassium carbonate (0.385 g, 2.8 mmol, 2 equiv.), and copper(I) iodide (0.119 g, 0.63 mmol, 0.45 equiv.), were combined, degassed, and charged with argon gas (Ar). To the Ar blanketed mixture was added dimethyl sulfoxide (6.2 mL, 0.1 M, 52 Vols). To the dark heterogeneous mixture was added N,N'-Dimethylethylenediamine (0.067 mL, 0.63 mmol, 0.45 equiv.) and pyrrolidone (0.355 g, 4.2 mmol, 3 equiv.). The mixture was then heated to 100° C. and stirred at this temperature for three hours. LCMS showed conversion to the desired product. The mixture was cooled to room temperature, diluted with EtOAc and aqueous citric acid, and the layers were separated. The aqueous layer was extracted with EtOAc (2×15 mL). The combined organic extracts were washed with brine, dried over $Na_2SO_4$, filtered and concentrated to give dark orange oil. This oil was filtered on a column of silica gel (eluting with a 0-10% MeOH in DCM gradient over 10 CV) to give a brown oil containing tert-butyl 2-[3-(2-oxopyrrolidin-1-yl)pyrazolo[3,4-c]pyridin-1-yl]acetate.

Step 2: [3-(2-Oxopyrrolidin-1-yl)pyrazolo[3,4-c]pyridin-1-yl]acetic Acid (51-S4)

To a stirring solution of tert-butyl 2-[3-(2-oxopyrrolidin-1-yl)pyrazolo[3,4-c]pyridin-1-yl]acetate (0.32 g, 1.0 mmol, 1 equiv.) in 1,2-dichloroethane (10 mL, 0.1 M, 31 Vols) at room temperature was added trifluoroacetic acid (1.2 g, 0.77 mL, 10 mmol, 10 equiv.). The solution was stirred at room temperature overnight. LCMS showed a peak corresponding to the desired product [3-(2-oxopyrrolidin-1-yl)pyrazolo[3,4-c]pyridin-1-yl]acetic acid. The solution was concentrated in vacuo and was azeotroped with toluene (2×20 mL) and then DCM (2×20 mL). The mixture was then placed under vacuum for 24 h and then carried on without further manipulation.

Step 3: (1R,3S,5R)—N-(6-Bromo-3-methylpyridin-2-yl)-5-methyl-2-{2-[3-(2-oxopyrrolidin-1-yl)pyrazolo[3,4-c]pyridin-1-yl]acetyl}-2-azabicyclo[3.1.0]hexane-3-carboxamide (51)

To a stirring solution of [3-(2-oxopyrrolidin-1-yl)pyrazolo[3,4-c]pyridin-1-yl]acetic acid (50 mg, 0.19 mmol, 1 equiv.) and (1R,3S,5R)—N-(6-bromo-3-methylpyridin-2-yl)-5-methyl-2-azabicyclo[3.1.0]hexane-3-carboxamide (0.072 g, 0.23 mmol, 1.2 equiv.) in dimethylformamide (1.9 mL, 0.10 M, 38 Vols) was added successively (1R,3S,5R)—N-(6-bromo-3-methylpyridin-2-yl)-5-methyl-2-azabicyclo[3.1.0]hexane-3-carboxamide (0.072 g, 0.23 mmol, 1.2 equiv.) and then diisopropylethylamine (0.074 g, 0.58 mmol, 3.0 equiv.). The mixture was stirred at room temperature for 30 minutes. LCMS showed conversion to the desired product. The solution was then purified directly via reverse phase HPLC and concentrated to afford (1R,3S,5R)—N-(6-bromo-3-methylpyridin-2-yl)-5-methyl-2-{2-[3-(2-oxopyrrolidin-1-yl)pyrazolo[3,4-c]pyridin-1-yl]acetyl}-2-azabicyclo[3.1.0]hexane-3-carboxamide (51) as a white film. $^1H$ NMR (400 MHz, Methanol-d4) δ 9.49 (s, 1H), 8.91 (d, J=6.4 Hz, 1H), 8.32 (d, J=6.5 Hz, 1H), 7.57 (d, J=7.9 Hz, 1H), 7.40 (d, J=8.0 Hz, 1H), 5.91 (d, J=17.4 Hz, 1H), 5.70 (d, J=17.4 Hz, 1H), 4.54 (dd, J=9.3, 5.3 Hz, 1H), 4.14 (t, J=7.1 Hz, 2H), 3.52 (dd, J=5.7, 2.4 Hz, 1H), 2.71 (t, J=8.0 Hz, 2H), 2.65 (dd, J=13.4, 9.2 Hz, 1H), 2.40-2.26 (m, 3H), 2.14 (s, 3H), 1.42 (s, 3H), 1.13 (t, J=5.6 Hz, 1H), 1.04 (dd, J=5.6, 2.5 Hz, 1H).

Scheme 25. Synthesis of (1R,3S,5R)-2-(2-(3-(1H Tetrazol-5-yl)phenyl)acetyl)-N-(6-bromo-3-methylpyridin-2-yl)-5-methyl-2-azabicyclo[3.1.0]hexane-3-carboxamide (52)

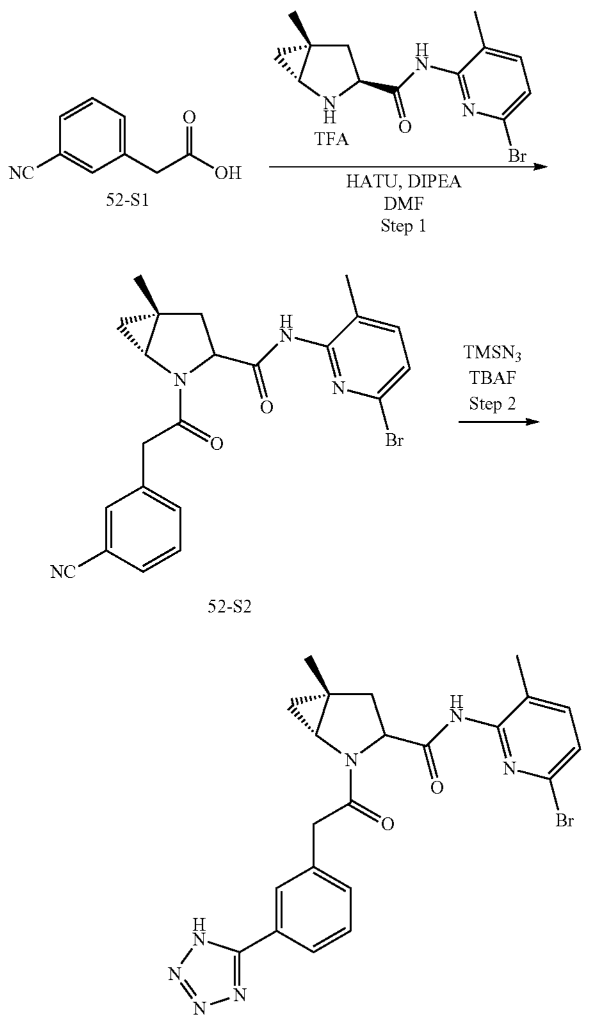

52-S1

52-S2

52

Step 1: (1R,3S,5R)—N-(6-bromo-3-methylpyridin-2-yl)-2-(2-(3-cyanophenyl)acetyl)-5-methyl-2-azabicyclo[3.1.0]hexane-3-carboxamide (52-S2)

To a mixture of compound 52-S1 (21 mg, 0.13 mmol) and (1R,3S,5R)—N-(6-bromo-3-methylpyridin-2-yl)-5-methyl-2-azabicyclo[3.1.0]hexane-3-carboxamide TFA salt (53 mg, 0.13 mmol) in DMF (2 mL) was added N-ethyldiisopropylamine (84 mg, 0.65 mmol) followed by HATU (76 mg, 0.2 mmol) at 0° C., and the reaction was stirred at room temperature for 1 hour. The mixture was diluted with water and extracted with EtOAc twice. The combined organic layers were washed with saturated aq. $NH_4Cl$ solution and brine, dried with anhydrous $Na_2SO_4$, and concentrated to dryness. The residue was purified by column chromatography on silica gel (eluted with PE:EtOAc=2:1) to give compound 52-S2 (45 mg, yield 76.3%) as a yellow solid. LC/MS (ESI) m/z: 453 $(M+H)^+$.

Step 2: (1R,3S,5R)-2-(2-(3-(1H-tetrazol-5-yl)phenyl)acetyl)-N-(6-bromo-3-methylpyridin-2-yl)-5-methyl-2-azabicyclo[3.1.0]hexane-3-carboxamide (52)

To a solution of compound 52-S2 (45 mg, 0.1 mmol) in trimethylsilyl azide (1 mL) was added 1 M TBAF-THF solution (3 drops), and the mixture was stirred at 85° C. for 16 hrs in a sealed tube. The reaction mixture was concentrated to dryness, and the residue was purified by preparatory H PLC to give 52 (3.3 mg, yield 6.64%) as a white solid. $^1H$-NMR (400 MHz, DMSO-$d_6$) δ 10.25 (s, 1H), 7.96 (s, 1H), 7.87-7.89 (d, J=8.0 Hz, 1H), 7.62-7.64 (d, J=8.4 Hz, 1H), 7.43-7.48 (m, 2H), 7.37-7.39 (d, J=7.6 Hz, 1H), 4.33-4.36 (m, 1H), 3.91-3.92 (m, 2H), 3.01-3.08 (m, 1H), 2.42-2.48 (m, 1H), 2.09 (s, 3H), 1.99 (m, 1H), 1.24 (s, 3H), 0.86 (m, 1H), 0.68 (m, 1H). LC/MS (ESI) m/z: 496 $(M+H)^+$.

Scheme 102: Synthesis of (1R,3S,5R)-2-(2-{3-acetyl-6-methyl[1,3]oxazolo[5,4-f]indazol-1-yl} acetyl)-N-(6-bromo-3-methylpyridin-2-yl)-5-methyl-2-azabicyclo[3.1.0]hexane-3-carboxamide (53)

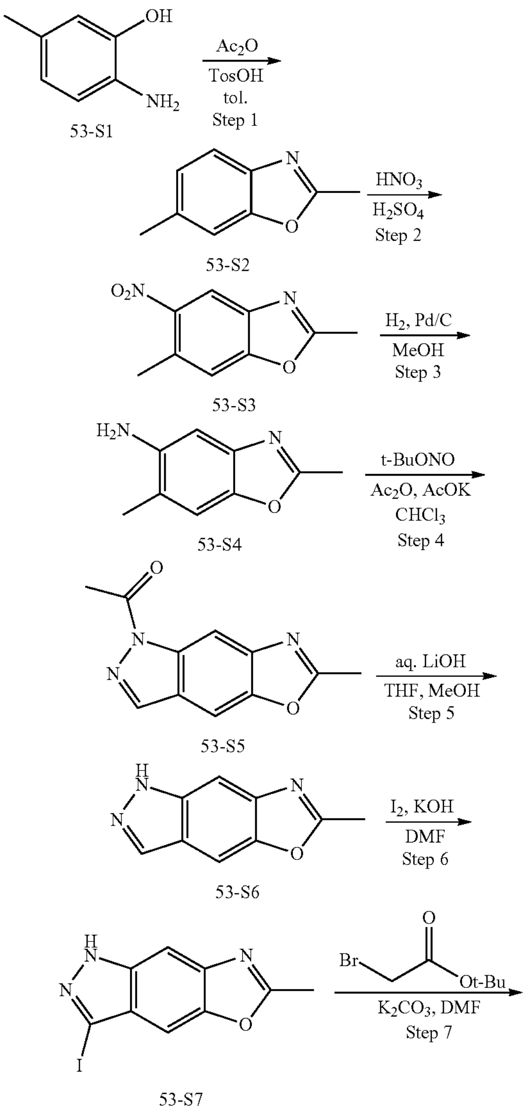

53-S1

53-S2

53-S3

53-S4

53-S5

53-S6

53-S7

-continued

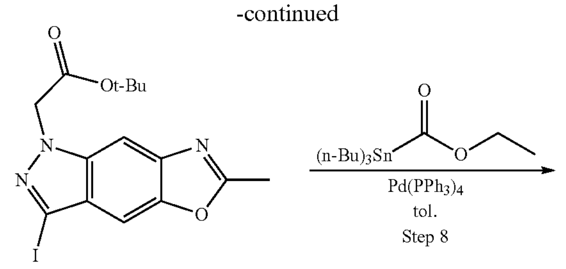

53-S8

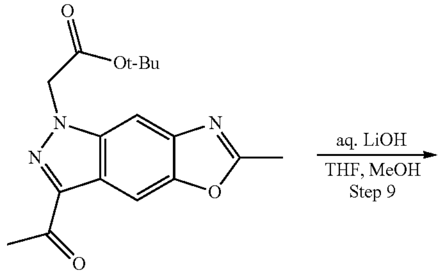

53-S9

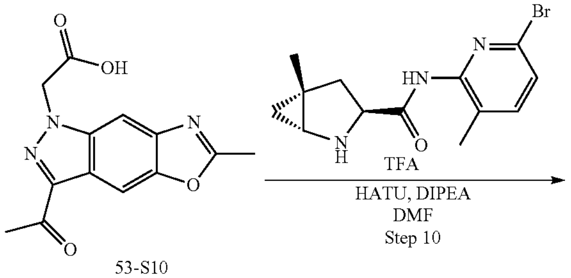

53-S10

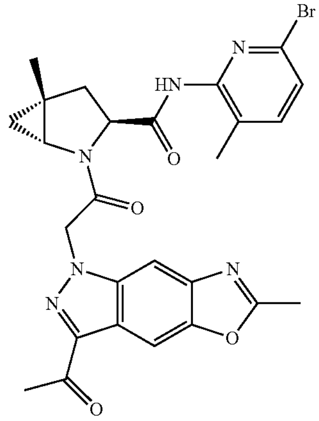

53

Step 1: 2,6-Dimethyl-1,3-benzoxazole (53-S2)

To a solution of 2-amino-5-methylphenol (4.95 g, 40.2 mmol) in toluene (25 mL) was added acetic anhydride (20.22 g, 198.2 mmol) and p-toluenesulfonic acid (0.69 g, 4.01 mmol), and the mixture was stirred at 50° C. for 1 hour. To a mixture was added p-toluenesulfonic acid (7.61 g, 44.21 mmol) and the mixture was stirred at 120° C. for 2 hours. The reaction mixture was quenched with ice water, diluted with EtOAc, washed with brine, dried over anhydrous $Na_2SO_4$, filtered, and concentrated to dryness. The residue was purified by column chromatography on silica gel (eluted with PE:EtOAc=5:1) to afford compound 53-2 (4.86 g, yield 82.2%) as a yellow solid. LC/MS (ESI) m/z: 148 $(M+H)^+$.

Step 2: 2,6-Dimethyl-5-nitro-1,3-benzoxazole (53-S3)

To a solution of compound 53-S2 (1.09 g, 7.40 mmol) in sulfuric acid (5 mL) was added a mixture of sulfuric acid (0.72 g, 7.40 mmol) and nitric acid (0.467 g, 7.40 mmol) at 0° C., and the mixture was stirred at 25° C. for 30 minutes. The reaction mixture was poured into the ice water and filtered, and the filter cake was washed with water and dried under vacuum to afford compound 53-S3 (1.06 g, yield 74.5%) as a yellow solid that was used directly in the next step. LC/MS (ESI) m/z: 193 $(M+H)^+$.

Step 3: 2,6-Dimethyl-1,3-benzoxazol-5-amine (53-S4)

To a solution of compound 53-S3 (1.06 g, 5.51 mmol) in methanol (10 mL) was added Pd/C (0.11 g, 10% wt), and the mixture was degassed under $N_2$ three times and stirred under a $H_2$ balloon at room temperature for 16 hours. The mixture was filtered, and the filtrate was concentrated to dryness to afford compound 53-S4 (0.67 g, yield 74.9%) as a yellow solid. LC/MS (ESI) m/z: 163 $(M+H)^+$.

Step 4: 1-{6-Methyl-[1,3]oxazolo[5,4-f]indazol-1-yl}ethanone (53-S5)

To a solution of compound 53-S4 (0.57 g, 3.51 mmol) in DCM (15 mL) was added potassium acetate (0.1 g, 1.01 mmol) and acetic anhydride (0.81 g, 0.75 mL, 7.97 mmol), and the mixture was stirred at 30° C. for 1 hour. To a mixture was added tert-butyl nitrite (0.77 g, 7.55 mmol), and the resulting mixture was stirred at 60° C. for 16 hours. The reaction mixture was quenched with ice-water and extracted with DCM twice. The combined organic layers were washed with brine, dried over anhydrous $Na_2SO_4$, filtered, and concentrated to dryness. The residue was purified by column chromatography on silica gel (eluted with DCM:MeOH=50:1) to afford compound 53-S5 (0.35 g, yield 46.3%) as a yellow solid. LC/MS (ESI) m/z: 148 $(M+H)^+$.

Step 5: 6-Methyl-1H-[1,3]oxazolo[5,4-f]indazole (53-S6)

To a solution of compound 53-S5 (0.35 g, 1.62 mmol) in MeOH (2 mL) and THF (1 mL) was added a solution of lithium hydroxide (39 mg, 1.63 mmol) in water (1 mL), and the mixture was stirred at room temperature for 1 hour. The mixture was concentrated to dryness, and the residue was diluted with water and extracted with EtOAc twice. The combined organic layers were washed with brine, dried with anhydrous $Na_2SO_4$, filtered, and concentrated to afford compound 53-S6 (0.31 g, yield 99.06%) as a yellow solid. LC/MS (ESI) m/z: 175 $(M+H)^+$.

Step 6: 3-Iodo-6-methyl-1H-[1,3]oxazolo[5,4-f]indazole (53-S7)

To a solution of compound 53-S6 (0.31 g, 1.79 mmol) in DMF (5 mL) was added potassium hydroxide (0.20 g, 3.58 mmol) and iodine (0.68 g, 2.68 mmol) at 0° C., and the mixture was stirred at room temperature for 2 hours. The reaction mixture was diluted with EtOAc, washed with saturated aqueous $Na_2S_2O_3$ solution and brine, dried over anhydrous $Na_2SO_4$, filtered, and concentrated to afford compound 53-S7 (0.52 g, yield 97.1%) as a yellow solid that was used directly in the next step. LC/MS (ESI) m/z: 300 $(M+H)^+$.

Step 7: tert-Butyl 2-{3-iodo-6-methyl-[1,3]oxazolo [5,4-f]indazol-1-yl}acetate (53-S8)

To a solution of 3-iodo-6-methyl-1H-[1,3]oxazolo[5,4-f] indazole (0.52 g, 1.74 mmol) in DMF (5 mL) was added tert-butyl 2-bromoacetate (0.407 g, 2.09 mmol) and potassium carbonate (0.481 g, 3.48 mmol), and the mixture was stirred at room temperature for 2 hours. The mixture was diluted with EtOAc, washed with saturated aqueous $NH_4Cl$ solution and brine successively, dried over anhydrous $Na_2SO_4$, and concentrated to dryness. The residue was purified by chromatography on silica gel (DCM: MeOH=100:1) to afford compound 53-S8 (0.32 g, yield 44.5%) as a yellow solid, which was used directly in the next step. LC/MS (ESI) m/z: 414 $(M+H)^+$.

Step 8: tert-Butyl 2-{3-acetyl-6-methyl-[1,3]oxazolo [5,4-f]indazol-1-yl}acetate (53-S9)

To a solution of compound 53-S8 (0.32 g, 0.77 mmol) in toluene (3 mL) was added tributyl(1-ethoxyethenyl)stannane (0.33 g, 0.92 mmol), and the mixture was degassed under $N_2$ atmosphere three times. $Pd(PPh_3)_4$ (0.089 g, 0.077 mmol) was added, and the resulting mixture was stirred at 100° C. under $N_2$ atmosphere for 16 hours. 1N aqueous HCl solution (5 mL) and THF (5 mL) were added, and the mixture was stirred at room temperature for 10 minutes. The mixture was extracted with EtOAc twice, and the combined organic layers were washed with brine, dried with anhydrous $Na_2SO_4$, and concentrated. The residue was purified by chromatography on silica gel (PE:EtOAc=100:1) to afford compound 53-S9 (0.33 g, yield 90.6%) as a yellow solid. LC/MS (ESI) m/z: 330 $(M+H)^+$.

Step 9: {3-Acetyl-6-methyl-[1,3]oxazolo[5,4-f]indazol-1-yl}acetic Acid (53-S10)

To a solution of compound 53-S9 (0.17 g, 0.51 mmol) in MeOH (2 mL) and THF (1 mL) was added a solution of lithium hydroxide (0.037 g, 1.54 mmol) in water (1 mL), and the mixture was stirred at room temperature for 1 hour. The mixture was concentrated to dryness, and the residue was diluted with water and washed with ether twice. The aqueous layer was acidified by 1 N aqueous HCl to a pH of approximately 3 and extracted with EtOAc twice. The combined organic layers were washed with brine, dried with anhydrous $Na_2SO_4$, filtered, and concentrated to afford compound 53-S10 (57 mg, yield 40.4%) as a yellow solid. LC/MS (ESI) m/z: 274 $(M+H)^+$.

Step 10: (1R,3S,5R)-2-(2-{3-Acetyl-6-methyl-[1,3] oxazolo[5,4-f]indazol-1-yl}acetyl)-N-(6-bromo-3-methylpyridin-2-yl)-5-methyl-2-azabicyclo[3.1.0] hexane-3-carboxamide (53)

To a solution of compound 53-S10 (31 mg, 0.11 mmol) in DMF (3 mL) was added (1R,3S,5R)—N-(6-bromo-3-methylpyridin-2-yl)-5-methyl-2-azabicyclo[3.1.0]hexane-3-carboxamide TFA salt (45 mg, 0.11 mmol), DIPEA (0.073 g, 0.56 mmol), and HATU (0.065 g, 0.17 mmol), and the mixture was stirred at 25° C. for 1 hour. The reaction mixture was diluted with EtOAc and washed with saturated aqueous $NH_4Cl$ solution and brine, dried over anhydrous $Na_2SO_4$, filtered, and concentrated to dryness. The residue was purified by preparatory HPLC to afford 53 (3 mg, yield 4.67%) as white solid. $^1H$-NMR (400 MHz, $CD_3OD$) δ 8.32 (s, 1H), 7.79 (s, 1H), 7.54 (d, J=6.9 Hz, 1H), 7.38 (d, J=6.8 Hz, 1H), 5.80 (d, J=17.1 Hz, 1H), 5.66 (d, J=17.2 Hz, 1H), 4.64-4.48 (m, 2H), 3.54 (s, 1H), 2.68 (s, 6H), 2.32 (s, 1H), 2.09 (s, 3H), 1.40 (s, 3H), 1.04 (m, 2H). LC/MS (ESI) m/z: 565 $(M+H)^+$.

Scheme 25. Synthesis of (S)-1-((1R,3S,5R)-3-((6-Bromo-3-methylpyridin-2-yl)carbamoyl)-2-(2-(3-carbamoyl-5-methyl-1H-thieno[3,2-c]pyrazol-1-yl)acetyl)-2-azabicyclo[3.1.0]hexan-5-yl)-24-carboxy-3,12,21,26-tetraoxo-5,8,14,17-tetraoxa-2,11,20,25-tetraazatritetracontan-43-oic Acid (54)

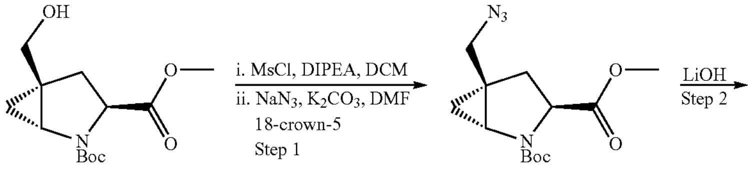

54-S1 54-S2

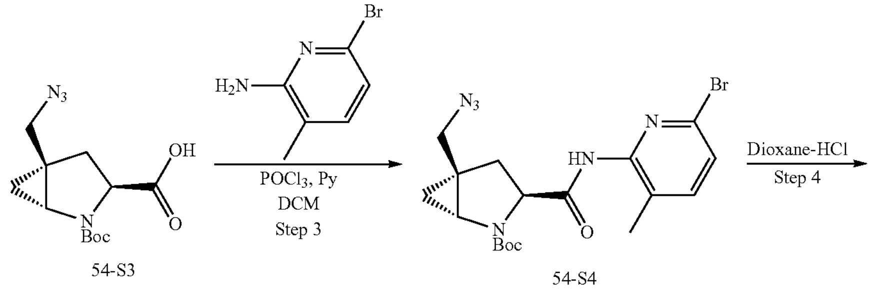

54-S3 54-S4

-continued
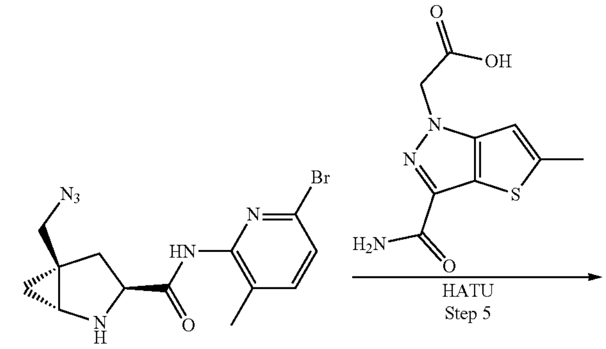
54-S5
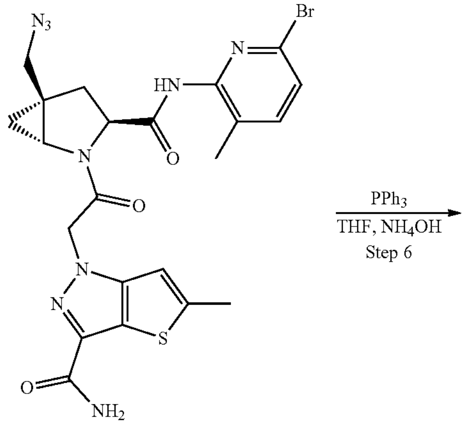
54-S6
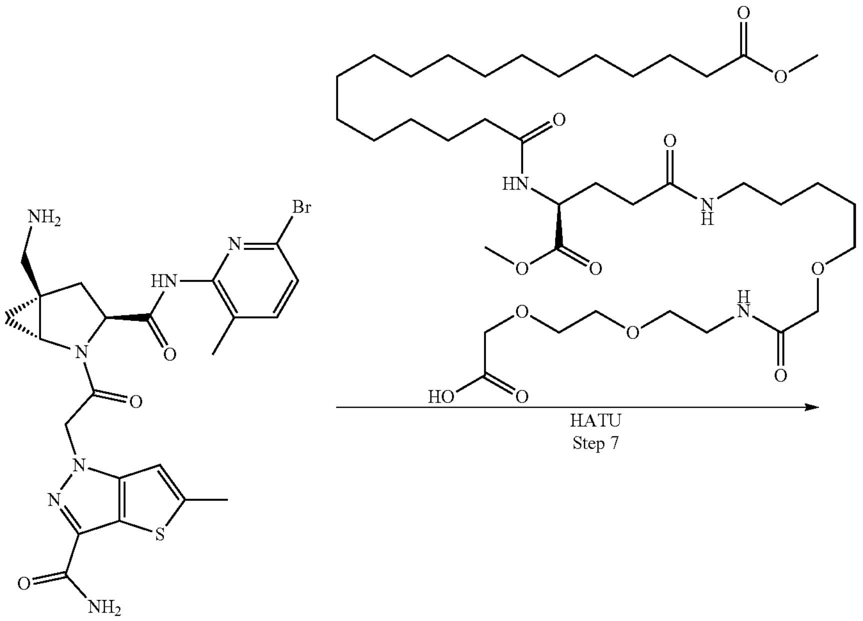
54-S7

-continued

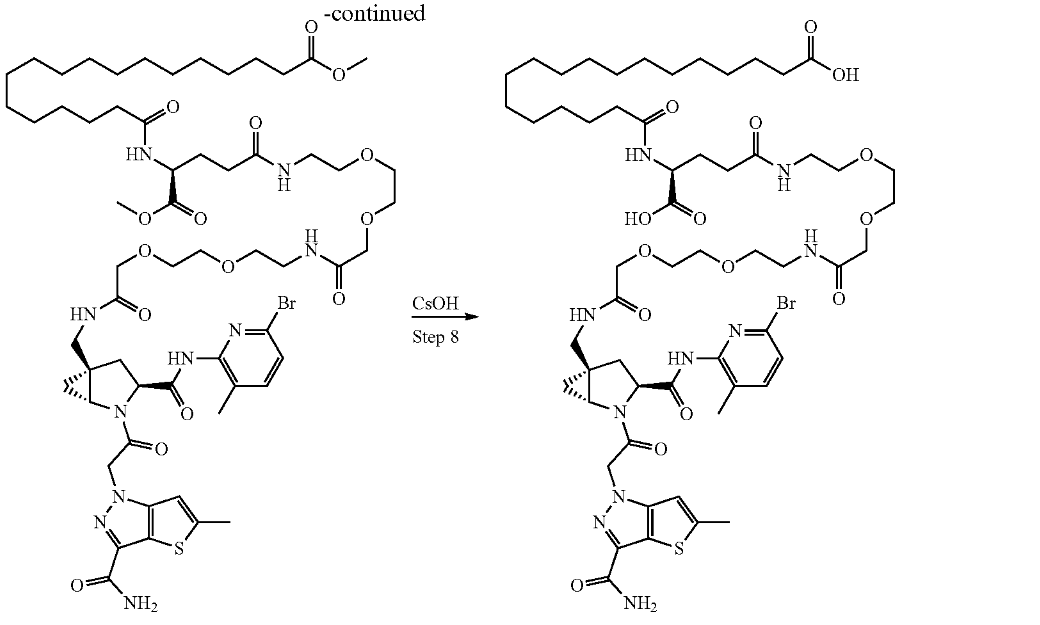

54-S8

54

Step 1: 2-(tert-Butyl) 3-Methyl (1R,3S,5R)-5-(Azidomethyl)-2-azabicyclo[3.1.0]hexane-2,3-dicarboxylate (54-S2)

To a solution of 2-(tert-butyl) 3-methyl (1R,3S,5S)-5-(hydroxymethyl)-2-azabicyclo[3.1.0]hexane-2,3-dicarboxylate (1 equiv) in DCM (20 vol) at 0° C. under nitrogen atmosphere was added DIPEA (2.5 equiv) and methanesulfonyl chloride (1.5 equiv). The reaction mixture was stirred at room temperature for 2 hours. After completion of the reaction, the reaction mixture was quenched with water. The resulting mixture was extracted with DCM. The organic layer was washed with brine, dried over anhydrous $Na_2SO_4$, filtered and then concentrated to give the mesylated intermediate.

To a solution of the above mesylated intermediate (1 equiv) in DMF (10 vol) at 0° C. under nitrogen atmosphere was added sodium azide (5.4 equiv), 18-crown-5 (0.4 equiv) and potassium carbonate (4.3 equiv). The reaction mixture was stirred at 80° C. for 8 hours. After completion of the reaction, the reaction mixture was quenched with water. The resulting mixture was extracted with ethyl acetate. The organic layer was washed with brine, dried over anhydrous $Na_2SO_4$, filtered and then concentrated. The residue was purified by column chromatography on silica gel using Hexane/EtOAc to give compound 54-S2.

Step 2: (1R,3S,5R)-5-(Azidomethyl)-2-(tert-butoxycarbonyl)-2-azabicyclo[3.1.0]hexane-3-carboxylic acid (54-S3)

To a solution of compound 54-S2 (1 equiv) in THF/water/MeOH (8:2:2) was added LiOH (3 equiv). The reaction mixture was stirred at room temperature for 2 hours and then quenched with 1 M citric acid. The resulting mixture was extracted with ethyl acetate. The organic layer was separated, dried over anhydrous $Na_2SO_4$, filtered and then concentrated to give compound 54-S3.

Step 3: tert-Butyl (1R,3S,5R)-5-(Azidomethyl)-3-((6-bromo-3-methylpyridin-2-yl)carbamoyl)-2-azabicyclo[3.1.0]hexane-2-carboxylate (54-S4)

To a solution of compound 54-3 (1 equiv) and 6-bromo-3-methylpyridin-2-amine (1.1 equiv) in DCM (10 vol) at 0° C. under nitrogen atmosphere was added pyridine (5 equiv) and $POCl_3$ (1 equiv). The reaction mixture was stirred at room temperature for 3 hours. After completion of the reaction, the reaction mixture was quenched with 10% $NaHCO_3$ solution. The resulting mixture was extracted with DCM. The organic layer was washed with brine, dried over anhydrous $Na_2SO_4$, filtered and then concentrated. The residue was purified by column chromatography on silica gel using Hexane/EtOAc to give compound 54-S4.

Step 4: (1R,3S,5R)-5-(Azidomethyl)-N-(6-bromo-3-methylpyridin-2-yl)-2-azabicyclo[3.1.0]hexane-3-carboxamide (54-S5)

To a solution of compound 54-S4 (I equiv) in 1,4-dioxane (2 vol) at 0° C. under nitrogen atmosphere was added 4 N HCl in 1,4-dioxane (10 vol) and stirred at room temperature for 3 hours. The volatiles are removed under reduced pressure to give compound 54-S5.

Step 5: 1-(2-((1R,3S,5R)-5-(Azidomethyl)-3-((6-bromo-3-methylpyridin-2-yl)carbamoyl)-2-azabicyclo[3.1.0]hexan-2-yl)-2-oxoethyl)-5-methyl-1H-thieno[3,2-c]pyrazole-3-carboxamide (54-S6)

To a solution of compound 54-S5 (1.2 equiv) in DMF (10 vol) at 0° C. under nitrogen atmosphere was added 2-(3-carbamoyl-5-methyl-1H-thieno[3,2-c]pyrazol-1-yl)acetic acid (1 equiv), HATU (1.5 equiv) and DIPEA (5 equiv). The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 54-S6.

Step 6: 1-(2-((1R,3S,5R)-5-(Aminomethyl)-3-((6-bromo-3-methylpyridin-2-yl)carbamoyl)-2-azabicyclo[3.1.0]hexan-2-yl)-2-oxoethyl)-5-methyl-1H-thieno[3,2-c]pyrazole-3-carboxamide (54-S7)

To a solution of compound 54-S6 (1 equiv) in THF (25 vol) was added triphenylphosphine (1.23 equiv) and ammonium hydroxide (10 vol). The reaction mixture is stirred at 60° C. for 2 hours then room temperature for 16 hours. After completion of the reaction, the solvent was removed under reduced pressure, and the residue was treated with HCl in dioxane to give compound 54-S7 as the HCl salt.

Step 7: Methyl (S)-1-((1R,3S,5R)-3-((6-Bromo-3-methylpyridin-2-yl)carbamoyl)-2-(2-(3-carbamoyl-5-methyl-1H-thieno[3,2-c]pyrazol-1-yl)acetyl)-2-azabicyclo[3.1.0]hexan-5-yl)-24-(methoxycarbonyl)-3,12,21,26-tetraoxo-5,8,14,17-tetraoxa-2,11,20,25-tetraazatritetracontan-43-oate (54-S8)

To a solution compound 54-S7 (1 equiv) in DMF (10 vol) at 0° C. under nitrogen atmosphere was added (S)-22-(methoxycarbonyl)-3,20,25,34-tetraoxo-2,29,32,38,41-pentaoxa-21,26,35-triazatritetracontan-43-oic acid (1.1 equiv), HATU (1.5 equiv) and DIPEA (5 equiv). The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and then concentrated. The residue was purified by preparative purification to give compound 54-S8.

Step 8: (S)-1-((1R,3S,5R)-3-((6-Bromo-3-methylpyridin-2-yl)carbamoyl)-2-(2-(3-carbamoyl-5-methyl-1H-thieno[3,2-c]pyrazol-1-yl)acetyl)-2-azabicyclo[3.1.0]hexan-5-yl)-24-carboxy-3,12,21,26-tetraoxo-5,8,14,17-tetraoxa-2,11,20,25-tetraazatritetracontan-43-oic Acid (54)

To a solution of compound 54-S8 (1 equiv) in THF/water (8:2) was added CsOH (2 equiv). The reaction mixture was stirred at room temperature for 2 hours and then quenched with 1 M citric acid. The resulting mixture was extracted with ethyl acetate. The organic layer was separated, dried over anhydrous $Na_2SO_4$, filtered and then concentrated. The residue was purified by preparative purification to give compound 54. $^1$H NMR (400 MHz, CD3OD) δ 7.58 (d, J=8.0 Hz, 1H), 7.41 (d, J=8.0 Hz, 1H), 6.83 (s, 1H), 5.46-5.43 (m, 2H), 4.65-4.64 (m, 1H), 4.44-4.43 (m, 1H), 4.11-4.10 (m, 4H), 3.73-3.33 (m, 19H), 2.51-2.49 (m, 5H), 2.32-2.29 (m, 7H), 2.11 (s, 3H), 1.98-1.97 (m, 1H), 1.57-1.55 (m, 4H), 1.30-1.23 (m, 24H), 1.28-1.27 (m, 1H), 0.98-0.97 (m, 1H).

Scheme 26. Synthesis of (S)-1-((1R,3S,5R)-3-((6-Bromo-3-methylpyridin-2-yl)carbamoyl)-2-(2-(3-carbamoyl-5-((5-fluoropyrimidin-2-yl)ethynyl)-1H-indazol-1-yl)acetyl)-2-azabicyclo[3.1.0]hexan-5-yl)-24-carboxy-3,12,21,26-tetraoxo-5,8,14,17-tetraoxa-2,11,20,25-tetraazatritetracontan-43-oic Acid (55)

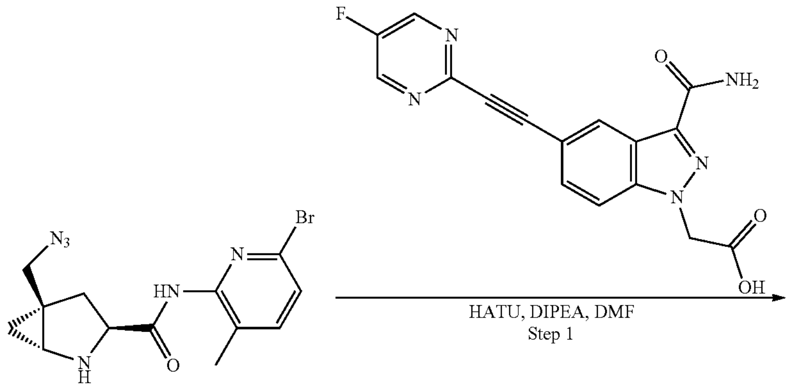

55-S1

-continued
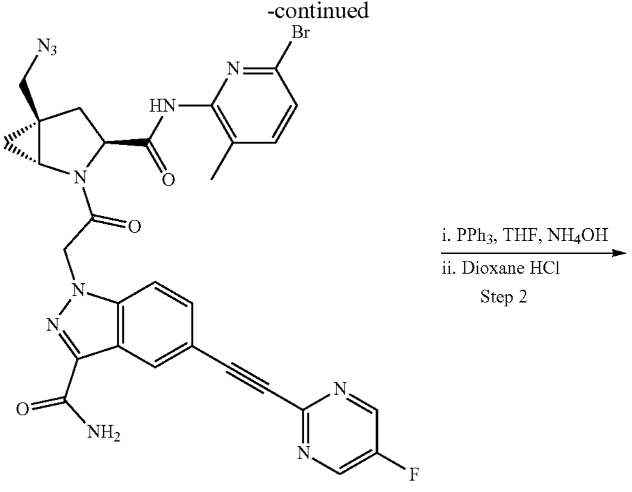
55-S2
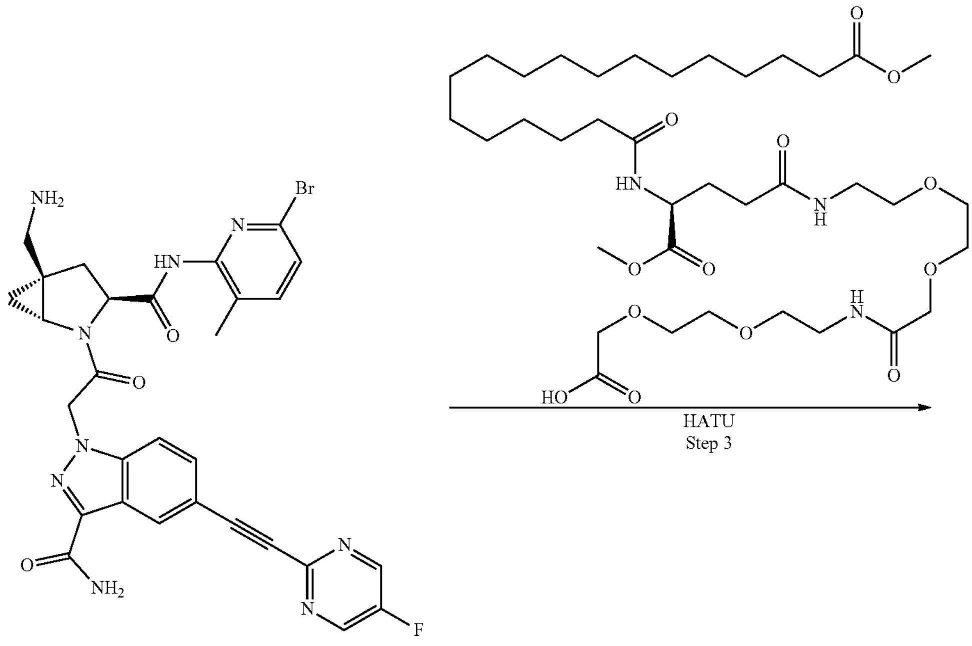
55-S3

-continued

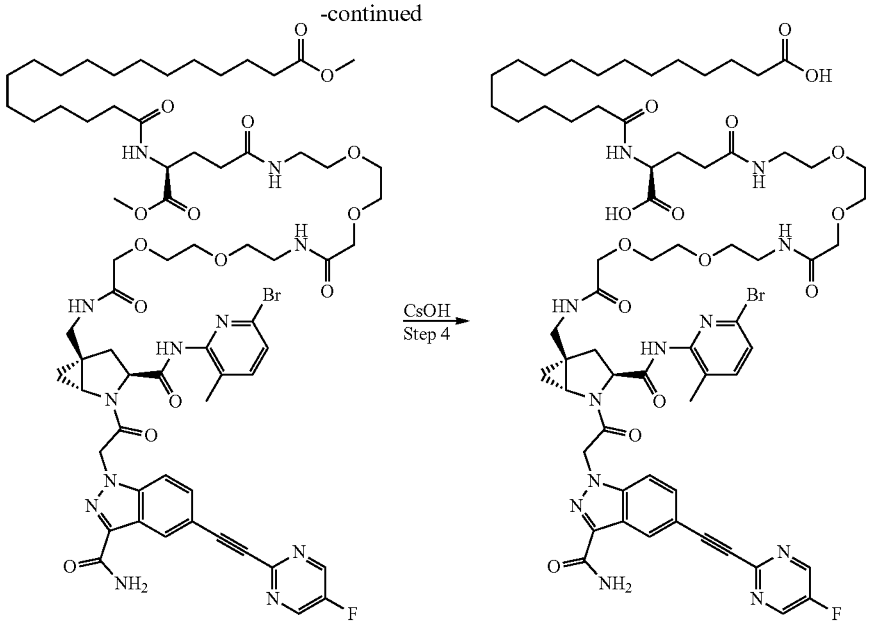

55-S4 55

Step 1: 1-(2-((1R,3S,5R)-5-(azidomethyl)-3-((6-bromo-3-methylpyridin-2-yl)carbamoyl)-2-azabicyclo[3.1.0]hexan-2-yl)-2-oxoethyl)-5-((5-fluoropyrimidin-2-yl)ethynyl)-1H-indazole-3-carboxamide (55-S2)

To a solution of (1R,3S,5R)-5-(azidomethyl)-N-(6-bromo-3-methylpyridin-2-yl)-2-azabicyclo[3.1.0]hexane-3-carboxamide hydrochloride (1.2 equiv) in DMF (10 vol) at 0° C. under nitrogen atmosphere was added 2-(3-carbamoyl-5-((5-fluoropyrimidin-2-yl)ethynyl)-1H-indazol-1-yl)acetic acid (1 equiv), HATU (1.5 equiv) and DIPEA (5 equiv). The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 55-S2.

Step 2: 1-(2-((1R,3S,5R)-5-(aminomethyl)-3-((6-bromo-3-methylpyridin-2-yl)carbamoyl)-2-azabicyclo[3.1.0]hexan-2-yl)-2-oxoethyl)-5-((5-fluoropyrimidin-2-yl)ethynyl)-1H-indazole-3-carboxamide (55-S3)

To a solution of compound 55-S2 (1 equiv) in THF (25 vol) was added triphenylphosphine (1.23 equiv) and ammonium hydroxide (10 vol). The reaction mixture was stirred at 60° C. for 2 hours then at room temperature for 16 hours. After completion of the reaction, the solvent was removed under reduced pressure, and the residue was treated with HCl in dioxane to give compound 55-S3 as HCl salt.

Step 3: methyl (S)-1-((1R,3S,5R)-3-((6-bromo-3-methylpyridin-2-yl)carbamoyl)-2-(2-(3-carbamoyl-5-((5-fluoropyrimidin-2-yl)ethynyl)-1H-indazol-1-yl)acetyl)-2-azabicyclo[3.1.0]hexan-5-yl)-24-(methoxycarbonyl)-3,12,21,26-tetraoxo-5,8,14,17-tetraoxa-2,11,20,25-tetraazatritetracontan-43-oate (55-S4)

To a solution compound 55-S3 (1 equiv) in DMF (10 vol) at 0° C. under nitrogen atmosphere was added (S)-22-(methoxycarbonyl)-3,20,25,34-tetraoxo-2,29,32,38,41-pentaoxa-21,26,35-triazatritetracontan-43-oic acid (1.1 equiv), HATU (1.5 equiv) and DIPEA (5 equiv). The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and then concentrated. The residue was purified by preparative purification to give compound 55-S4.

Step 4: (S)-1-((1R,3S,5R)-3-((6-bromo-3-methylpyridin-2-yl)carbamoyl)-2-(2-(3-carbamoyl-5-((5-fluoropyrimidin-2-yl)ethynyl)-1H-indazol-1-yl)acetyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid (55)

To a solution of compound 55-S4 (1 equiv) in THF/water (8:2) was added CsOH (2 equiv). The reaction mixture was stirred at room temperature for 2 hours and then quenched with 1 M citric acid. The resulting mixture was extracted with ethyl acetate. The organic layer was separated, dried over anhydrous $Na_2SO_4$, filtered and then concentrated. The residue was purified by preparative purification to give compound 55.

$^1H$ NMR (400 MHz, CD3OD) δ 8.80 (s, 2H), 8.58 (s, 1H), 7.70-7.68 (m, 2H), 7.62 (d, J=8.0 Hz, 1H), 7.48 (d, J=8.0 Hz, 1H), 5.79-5.85 (m, 2H), 4.62-4.60 (m, 1H), 4.44-4.43 (m, 1H), 4.00-3.98 (m, 4H), 3.75-3.33 (m, 20H), 2.58-2.57 (m, 2H), 2.42-2.11 (m, 13H), 1.35-1.32 (m, 25H), 1.11-1.10 (m, 1H), 0.98-0.97 (m, 1H).

Scheme 27. Synthesis of (S)-1-((1R,3S,5R)-3-((6-bromo-3-methylpyridin-2-yl)carbamoyl)-2-(2-(3-carbamoyl-6-((cyclopropylsulfonyl)carbamoyl)-1H-indazol-1-yl)acetyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid (56)
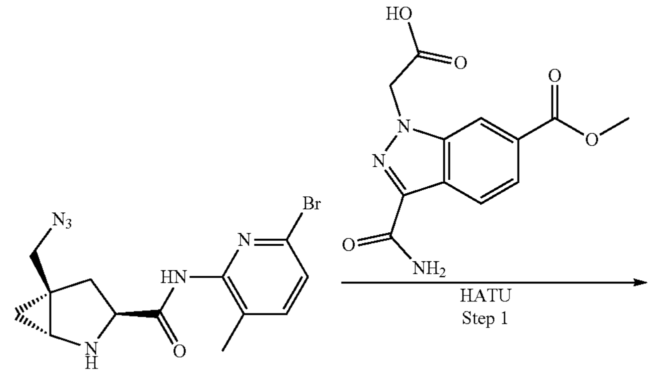
56-S1
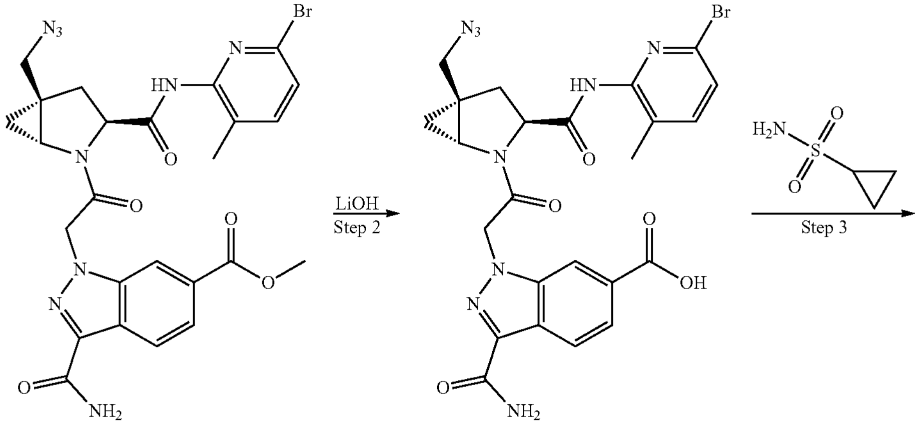
56-S2
56-S3
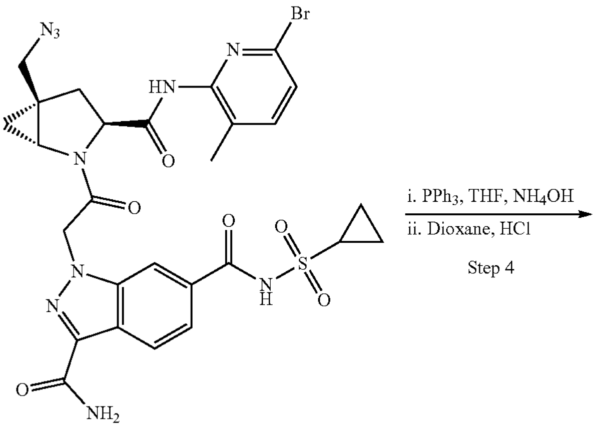
56-S4

-continued

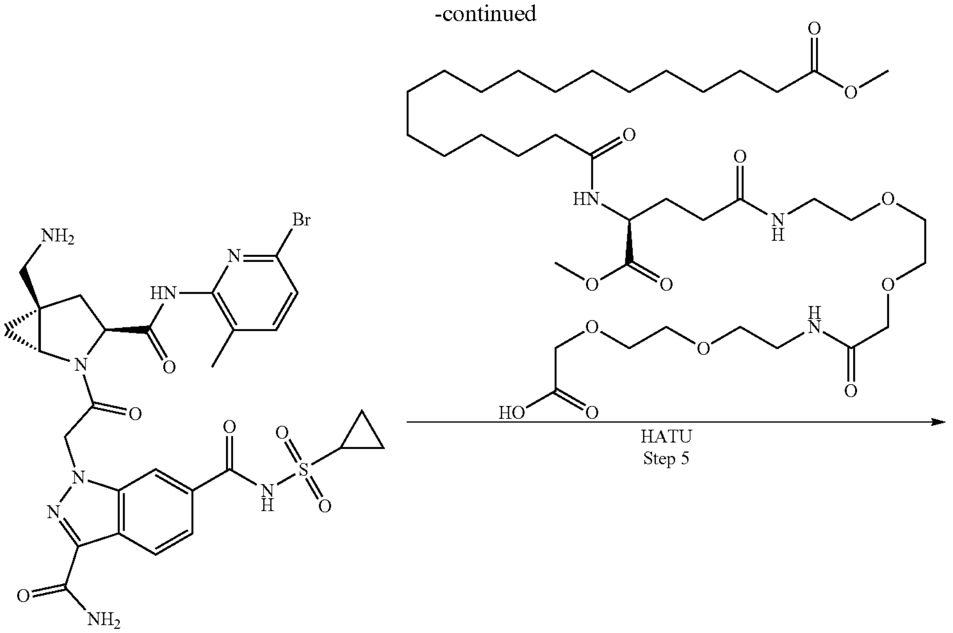

56-S5

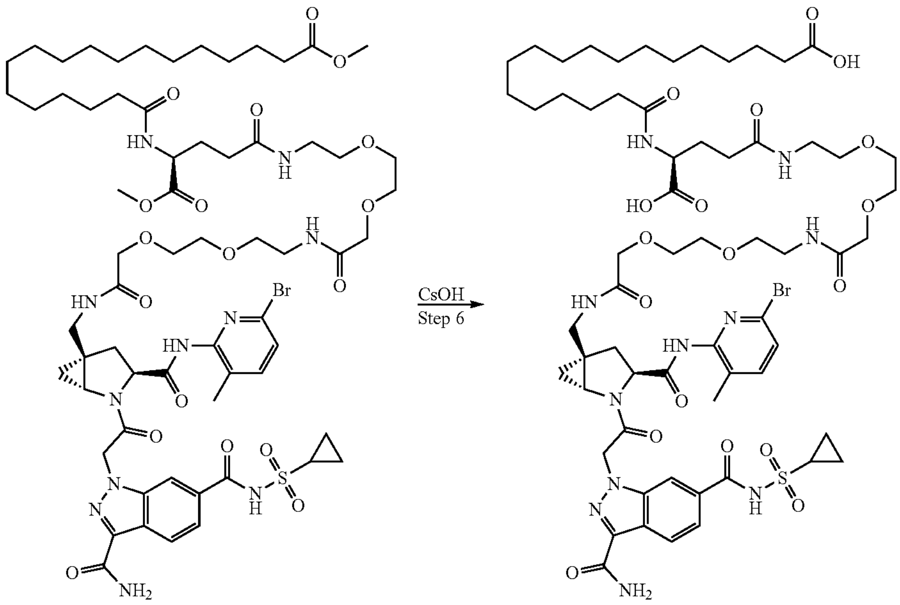

56-S6 56

Step 1: methyl 1-(2-((1R,3S,5R)-5-(azidomethyl)-3-((6-bromo-3-methylpyridin-2-yl)carbamoyl)-2-azabicyclo[3.1.0]hexan-2-yl)-2-oxoethyl)-3-carbamoyl-1H-indazole-6-carboxylate (56-S2)

To a solution of (1R,3S,5R)-5-(azidomethyl)-N-(6-bromo-3-methylpyridin-2-yl)-2-azabicyclo[3.1.0]hexane-3-carboxamide hydrochloride (1.2 equiv) in DMF (10 vol) at 0° C. under nitrogen atmosphere was added 2-(3-carbamoyl-6-(methoxycarbonyl)-1H-indazol-1-yl)acetic acid (1 equiv), HATU (1.5 equiv) and DIPEA (5 equiv). The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 56-S2.

Step 2: 1-(2-((1R,3S,5R)-5-(azidomethyl)-3-((6-bromo-3-methylpyridin-2-yl)carbamoyl)-2-azabicyclo[3.1.0]hexan-2-yl)-2-oxoethyl)-3-carbamoyl-1H-indazole-6-carboxylic acid (56-S3)

To a solution of compound 56-S2 (1 equiv) in THF/water (8:2) was added LiOH (4 equiv). The reaction mixture was stirred at room temperature for 4 hours and then quenched with 1 M citric acid. The resulting mixture was extracted with ethyl acetate. The organic layer was separated, dried over anhydrous $Na_2SO_4$, filtered and then concentrated to give compound 56-S3.

Step 3: 1-(2-((1R,3S,5R)-5-(azidomethyl)-3-((6-bromo-3-methylpyridin-2-yl)carbamoyl)-2-azabicyclo[3.1.0]hexan-2-yl)-2-oxoethyl)-N6-(cyclopropylsulfonyl)-1H-indazole-3,6-dicarboxamide (56-S4)

To a solution of compound 56-S3 (1 equiv) in DCM (10 vol) was added DMAP (3 equiv) and EDCI-HCl (3 equiv). The reaction mixture was stirred at room temperature for 15 minutes. DIPEA (5.8 equiv) and cyclopropylsulfonamide (3 equiv) were added, and the reaction mixture was stirred at room temperature for 16 hours. After completion of the reaction, the reaction mixture was quenched with water (30 vol). The resulting mixture was extracted with DCM. The organic layer was washed with brine, dried over anhydrous $Na_2SO_4$, filtered and then concentrated. The residue was purified by column chromatography on silica gel using DCM/MeOH to give compound 56-S4.

Step 4: 1-(2-((1R,3S,5R)-5-(aminomethyl)-3-((6-bromo-3-methylpyridin-2-yl)carbamoyl)-2-azabicyclo[3.1.0]hexan-2-yl)-2-oxoethyl)-N6-(cyclopropylsulfonyl)-1H-indazole-3,6-dicarboxamide (56-S5)

To a solution of compound 56-S4 (1 equiv) in THF (25 vol) was added triphenylphosphine (1.23 equiv) and ammonium hydroxide (10 vol). The reaction mixture was stirred at 60° C. for 2 hours then room temperature for 16 hours. After completion of the reaction, solvent was removed under reduced pressure, and the residue was treated with HCl in dioxane to give compound 56-S5 as HCl salt.

Step 5: methyl (S)-1-((1R,3S,5R)-3-((6-bromo-3-methylpyridin-2-yl)carbamoyl)-2-(2-(3-carbamoyl-6-((cyclopropylsulfonyl)carbamoyl)-1H-indazol-1-yl)acetyl)-2-azabicyclo[3.1.0]hexan-5-yl)-24-(methoxycarbonyl)-3,12,21,26-tetraoxo-5,8,14,17-tetraoxa-2,11,20,25-tetraazatritetracontan-43-oate (56-S6)

To a solution compound 56-S5 (1 equiv) in DMF (10 vol) at 0° C. under nitrogen atmosphere was added (S)-22-(methoxycarbonyl)-3,20,25,34-tetraoxo-2,29,32,38,41-pentaoxa-21,26,35-triazatritetracontan-43-oic acid (1.1 equiv), HATU (1.5 equiv) and DIPEA (5 equiv). The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and then concentrated. The residue was purified by preparative purification to give compound 56-S6.

Step 6: (S)-1-((1R,3S,5R)-3-((6-bromo-3-methylpyridin-2-yl)carbamoyl)-2-(2-(3-carbamoyl-6-((cyclopropylsulfonyl)carbamoyl)-1H-indazol-1-yl)acetyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid (56)

To a solution of compound 56-S6 (1 equiv) in THF/water (8:2) was added CsOH (2 equiv). The reaction mixture was stirred at room temperature for 2 hours and then quenched with 1 M citric acid. The resulting mixture was extracted with ethyl acetate. The organic layer was separated, dried over anhydrous $Na_2SO_4$, filtered and then concentrated. The residue was purified by preparative purification to give compound 56.

$^1$H NMR (400 MHz, CD3OD) δ 8.25-8.18 (m, 2H), 7.97-7.96 (m, 1H), 7.54 (d, J=8.0 Hz, 1H), 7.38 (d, J=8.0 Hz, 1H), 5.72-5.65 (m, 2H), 4.55-4.54 (m, 1H), 4.25-4.24 (m, 1H), 4.01-3.99 (m, 4H), 3.83-3.33 (m, 19H), 2.55-2.54 (m, 1H), 2.48-2.22 (m, 15H), 1.58-1.55 (m, 4H), 1.43-1.11 (m, 26H), 1.11-1.10 (m, 1H), 0.98-0.97 (m, 1H).

Scheme 28. Preperation of (S)-1-((1R,3S,5R)-2-(2-(3-acetyl-6-(diethoxyphosphoryl)-1H-indol-1-yl)acetyl)-3-((6-bromo-3-methylpyridin-2-yl)carbamoyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid (57)

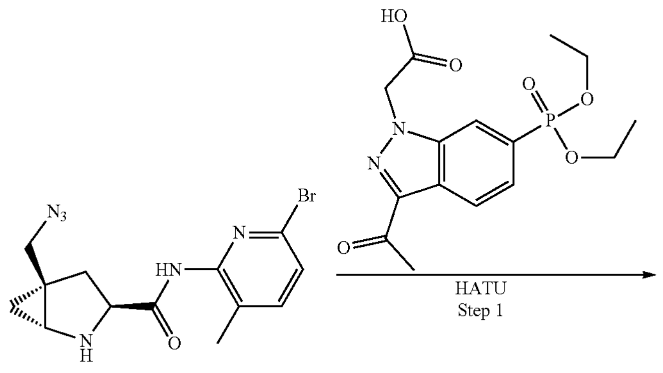

57-S1

-continued
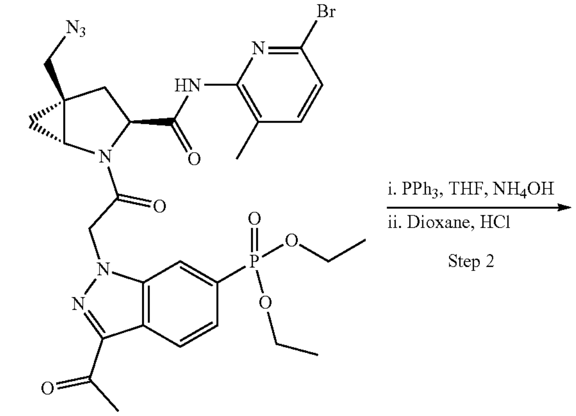
57-S2
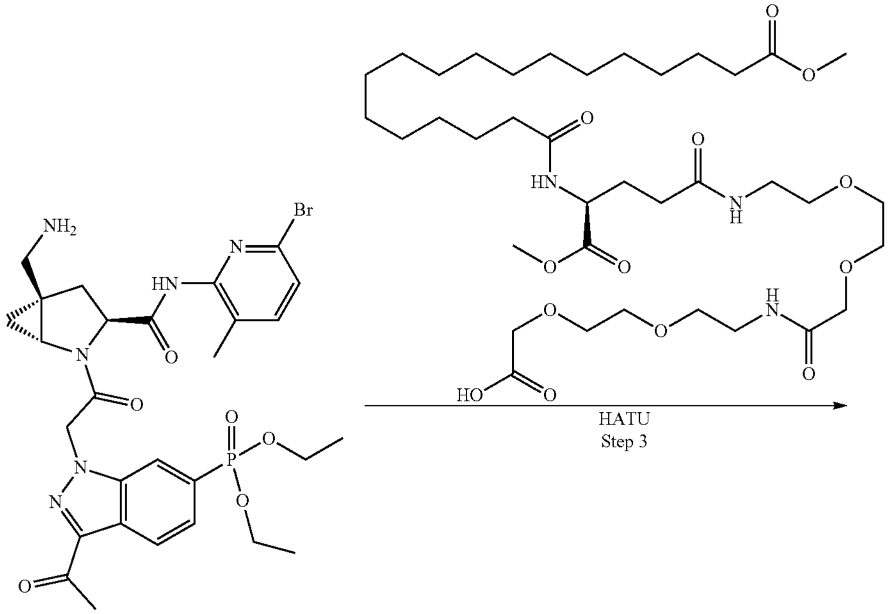
57-S3

-continued

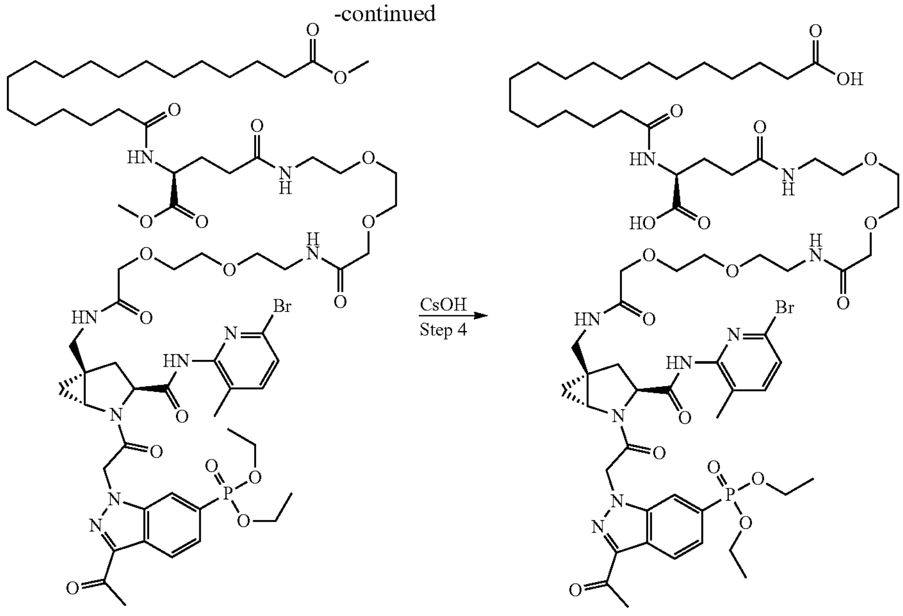

57-S4

57

Step 1: diethyl (3-acetyl-1-(2-((1R,3S,5R)-5-(azidomethyl)-3-((6-bromo-3-methylpyridin-2-yl)carbamoyl)-2-azabicyclo[3.1.0]hexan-2-yl)-2-oxoethyl)-1H-indol-6-yl)phosphonate (57-S2)

To a solution of (1R,3S,5R)-5-(azidomethyl)-N-(6-bromo-3-methylpyridin-2-yl)-2-azabicyclo[3.1.0]hexane-3-carboxamide hydrochloride (1.2 equiv) in DMF (10 vol) at 0° C. under nitrogen atmosphere was added 2-(3-acetyl-6-(diethoxyphosphoryl)-1H-indol-1-yl)acetic acid (1 equiv), HATU (1.5 equiv) and DIPEA (5 equiv). The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 57-S2.

Step 2: diethyl (3-acetyl-1-(2-((1R,3S,5R)-5-(aminomethyl)-3-((6-bromo-3-methylpyridin-2-yl)carbamoyl)-2-azabicyclo[3.1.0]hexan-2-yl)-2-oxoethyl)-1H-indol-6-yl)phosphonate (57-S3)

To a solution of compound 57-S2 (1 equiv) in TI-F (25 vol) was added triphenylphosphine (1.23 equiv) and ammonium hydroxide (10 vol). The reaction mixture was stirred at 60° C. for 2 hours then room temperature for 16 hours. After completion of the reaction, solvent was removed under reduced pressure, and the residue was treated with HCl in dioxane to give compound 57-S3 as HCl salt.

Step 3: methyl (S)-1-((1R,3S,5R)-2-(2-(3-acetyl-6-(diethoxyphosphoryl)-1H-indol-1-yl)acetyl)-3-((6-bromo-3-methylpyridin-2-yl)carbamoyl)-2-azabicyclo[3.1.0]hexan-5-yl)-24-(methoxycarbonyl)-3,12,21,26-tetraoxo-5,8,14,17-tetraoxa-2,11,20,25-tetraazatritetracontan-43-oate (57-S4)

To a solution compound 57-S3 (1 equiv) in DMF (10 vol) at 0° C. under nitrogen atmosphere was added (S)-22-(methoxycarbonyl)-3,20,25,34-tetraoxo-2,29,32,38,41-pentaoxa-21,26,35-triazatritetracontan-43-oic acid (1.1 equiv), HATU (1.5 equiv) and DIPEA (5 equiv). The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and then concentrated. The residue was purified by preparative purification to give compound 57-S4.

Step 4: (S)-1-((1R,3S,5R)-2-(2-(3-acetyl-6-(diethoxyphosphoryl)-1H-indol-1-yl)acetyl)-3-((6-bromo-3-methylpyridin-2-yl)carbamoyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid (57)

To a solution of compound 57-S4 (1 equiv) in THF/water (8:2) was added CsOH (2 equiv). The reaction mixture was stirred at room temperature for 2 hours and then quenched with 1 M citric acid. The resulting mixture was extracted with ethyl acetate. The organic layer was separated, dried over anhydrous $Na_2SO_4$, filtered and then concentrated. The residue was purified by preparative purification to give compound 57.

$^1$H NMR (400 MHz, CD3OD) δ 8.45-8.43 (m, 2H), 7.99-7.90 (m, 1H), 7.63-7.58 (m, 2H), 7.40 (d, J=7.8 Hz, 1H), 5.72-5.65 (m, 2H), 4.55-4.54 (m, 1H), 4.25-4.24 (m, 1H), 4.01-3.99 (m, 8H), 3.83-3.33 (m, 19H), 2.55-2.54 (m, 5H), 2.32-2.31 (m, 10H), 1.98-1.97 (m, 1H), 1.63-1.62 (m, 4H), 1.31-1.21 (m, 31H), 1.11-1.10 (m, 1H), 0.98-0.97 (m, 1H).

Scheme 29. Preperation of (S)-1-((1R,3S,5R)-2-(2-(3-acetyl-1H-indazol-1-yl)acetyl)-3-((6-bromo-3-methylpyridin-2-yl)carbamoyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid (58)
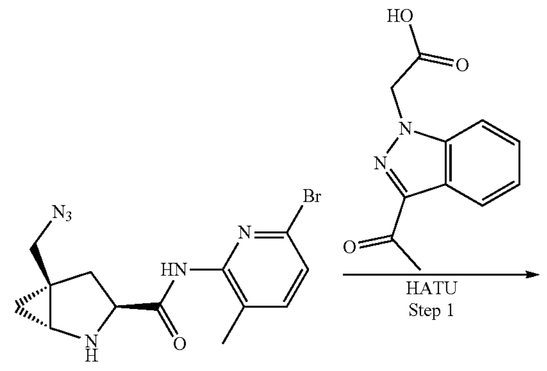
58-S1
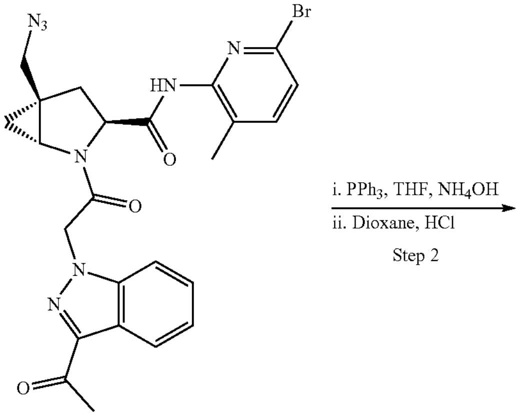
58-S2
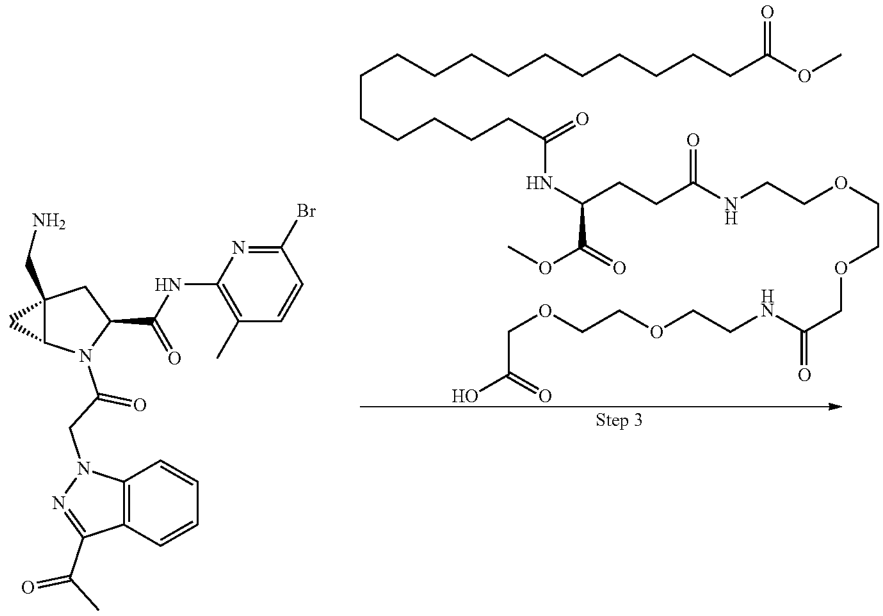
58-S3

-continued

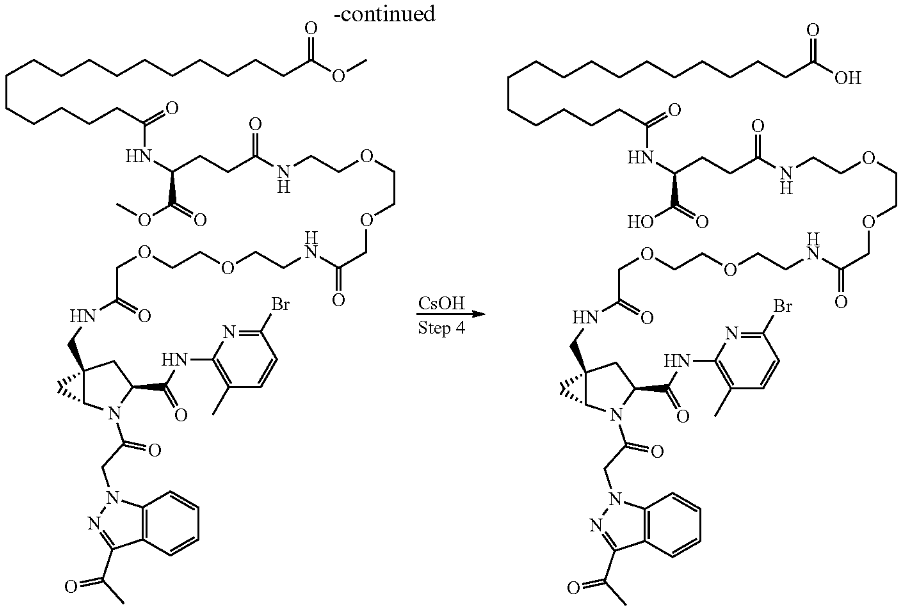

58-S4

58

Step 1: (1R,3S,5R)-2-(2-(3-acetyl-1H-indazol-1-yl)acetyl)-5-(azidomethyl)-N-(6-bromo-3-methylpyridin-2-yl)-2-azabicyclo[3.1.0]hexane-3-carboxamide (58-S2)

To a solution of (1R,3S,5R)-5-(azidomethyl)-N-(6-bromo-3-methylpyridin-2-yl)-2-azabicyclo[3.1.0]hexane-3-carboxamide hydrochloride (1.2 equiv) in DMF (10 vol) at 0° C. under nitrogen atmosphere was added 2-(3-acetyl-1H-indazol-1-yl)acetic acid (1 equiv), HATU (1.5 equiv) and DIPEA (5 equiv). The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 58-S2.

Step 2: (1R,3S,5R)-2-(2-(3-acetyl-1H-indazol-1-yl)acetyl)-5-(aminomethyl)-N-(6-bromo-3-methylpyridin-2-yl)-2-azabicyclo[3.1.0]hexane-3-carboxamide (58-S3)

To a solution of compound 58-S2 (1 equiv) in THF (25 vol) was added triphenylphosphine (1.23 equiv) and ammonium hydroxide (10 vol). The reaction mixture was stirred at 60° C. for 2 hours then room temperature for 16 hours. After completion of the reaction, solvent was removed under reduced pressure, and the residue was treated with HCl in dioxane to give compound 56-S3 as HCl salt.

Step 3: methyl (S)-1-((1R,3S,5R)-2-(2-(3-acetyl-1H-indazol-1-yl)acetyl)-3-((6-bromo-3-methylpyridin-2-yl)carbamoyl)-2-azabicyclo[3.1.0]hexan-5-yl)-24-(methoxycarbonyl)-3,12,21,26-tetraoxo-5,8,14,17-tetraoxa-2,11,20,25-tetraazatritetracontan-43-oate (58-S4)

To a solution compound 56-S3 (1 equiv) in DMF (10 vol) at 0° C. under nitrogen atmosphere was added (S)-22-(methoxycarbonyl)-3,20,25,34-tetraoxo-2,29,32,38,41-pentaoxa-21,26,35-triazatritetracontan-43-oic acid (1.1 equiv), HATU (1.5 equiv) and DIPEA (5 equiv). The reaction mixture was stirred at room temperature for 16 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by preparative purification to give compound 56-S4.

Step 4: (S)-1-((1R,3S,5R)-2-(2-(3-acetyl-1H-indazol-1-yl)acetyl)-3-((6-bromo-3-methylpyridin-2-yl)carbamoyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid (58)

To a solution of compound 56-S4 (1 equiv) in THF/water (8:2) was added CsOH (2 equiv). The reaction mixture was stirred at room temperature for 2 hours and then quenched with 1 M citric acid. The resulting mixture was extracted with ethyl acetate. The organic layer was separated, dried over anhydrous $Na_2SO_4$, filtered and then concentrated. The residue was purified by preparative purification to give compound 58.

$^1$H NMR (400 MHz, DMSO-d6) δ 8.19-8.17 (m, 2H), 8.00-7.99 (m, 1H), 7.77-7.75 (m, 2H), 7.61 (d, J=8.0 Hz, 1H), 7.52-7.31 (m, 4H), 5.86 (d, J=17.0 Hz, 1H), 5.54 (d, J=17.0 Hz, 1H), 4.44-4.43 (m, 1H), 4.00-3.98 (m, 5H), 3.75-3.13 (m, 19H), 2.69 (s, 3H), 2.35-2.34 (m, 2H), 2.10 (s, 3H), 2.08 (s, 3H), 1.81-1.73 (m, 6H), 1.31-1.11 (m, 27H), 1.10-0.98 (m, 1H), 0.97-0.96 (m, 1H).

Scheme 30. Synthesis of (S)-1-((1R,3S,5R)-3-((6-bromo-3-methylpyridin-2-yl)carbamoyl)-2-(2-(3-carbamoyl-5-(pyridin-3-ylamino-1H-indazol-1-yl)acetyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid (59)
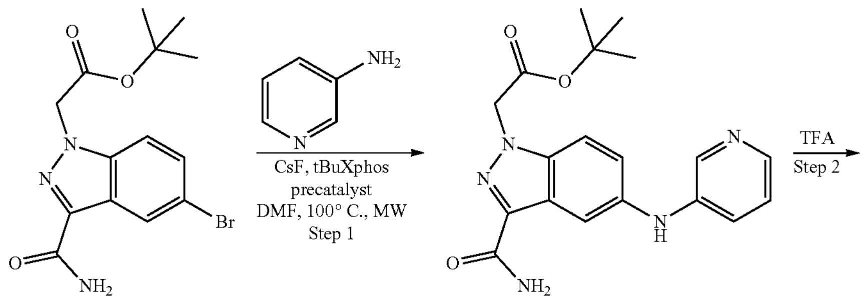
59-S1 59-S2
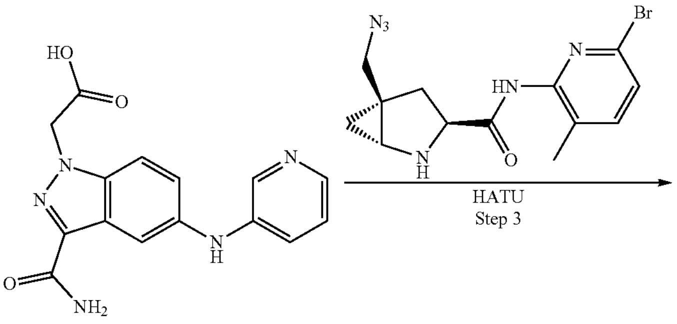
59-S3
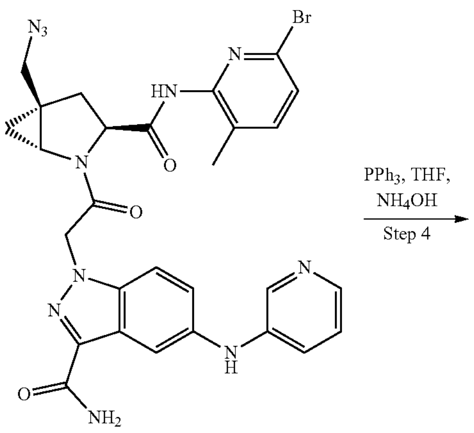
59-S4

-continued
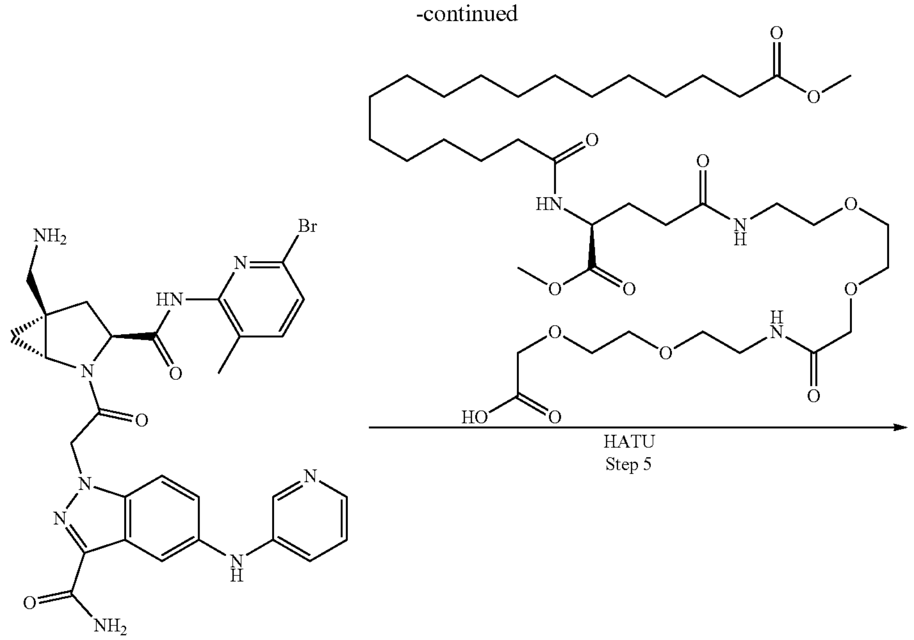
59-S5
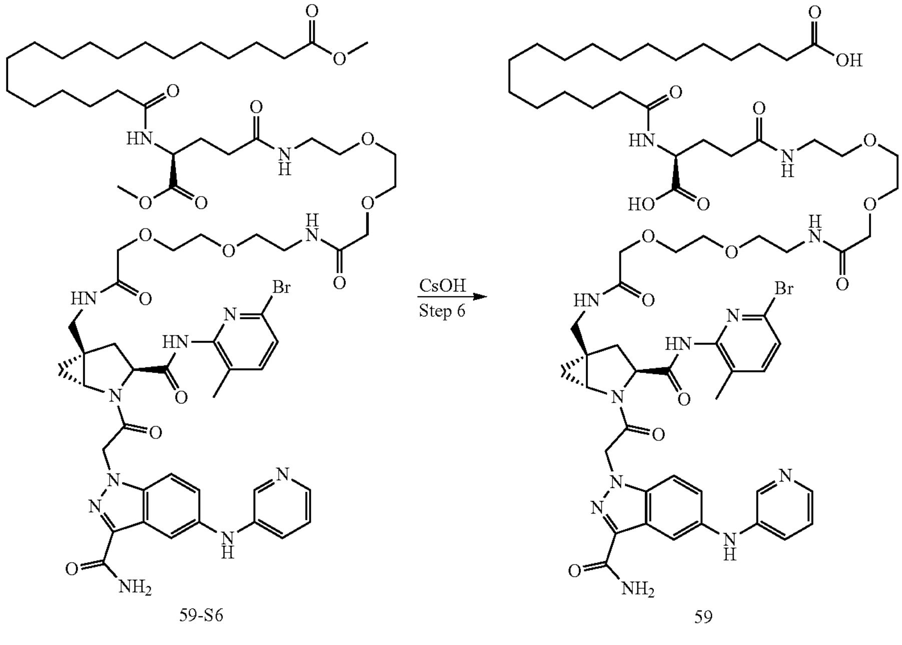
59-S6
59

Step-1: tert-butyl 2-(3-carbamoyl-5-(pyridin-3-ylamino)-1H-indazol-1-yl)acetate (59-S2)

A solution of tert-butyl 2-(5-bromo-3-carbamoyl-1H-indazol-1-yl)acetate (1 equiv), CsF (2.5 equiv), pyridin-3-amine (1.2 equiv) and tBuXPhos precatalyst (0.1 equiv) in DMF (10 vol) was bubbled with nitrogen and stirred at 100° C. for 3 hours in a sealed tube. After completion of the reaction, the reaction mixture was concentrated and the residue was purified by column chromatography on silica gel using DCM/MeOH to give compound 59-S2.

Step 2: 2-(3-carbamoyl-5-(pyridin-3-ylamino)-1H-indazol-1-yl)acetic acid (59-S3)

To a solution of compound 59-S2 (1 equiv) in DCM (10 vol) at 0° C. was added TFA (5 vol). The reaction mixture was stirred at 50° C. for 3 hours and then concentrated. The volatiles were removed under reduced pressure to give compound 59-S3.

Step 3: 1-(2-((1R,3S,5R)-5-(azidomethyl)-3-((6-bromo-3-methylpyridin-2-yl)carbamoyl)-2-azabicyclo[3.1.0]hexan-2-yl)-2-oxoethyl)-5-(pyridin-3-ylamino)-1H-indazole-3-carboxamide (59-S4)

To a solution of compound 59-S3 (1 equiv) in DMF (10 vol) at 0° C. under nitrogen atmosphere was added (1R,3S,5R)-5-(azidomethyl)-N-(6-bromo-3-methylpyridin-2-yl)-2-azabicyclo[3.1.0]hexane-3-carboxamide (1.2 equiv), HATU (1.5 equiv) and DIPEA (5 equiv). The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 59-S4.

Step 4: 1-(2-((1R,3S,5R)-5-(aminomethyl)-3-((6-bromo-3-methylpyridin-2-yl)carbamoyl)-2-azabicyclo[3.1.0]hexan-2-yl)-2-oxoethyl)-5-(pyridin-3-ylamino)-1H-indazole-3-carboxamide (59-S5)

To a solution of compound 59-S4 (1 equiv) in THF (25 vol) was added triphenylphosphine (1.23 equiv) and ammonium hydroxide (10 vol). The reaction mixture was stirred at 60° C. for 2 hours then room temperature for 16 hours. After completion of the reaction, solvent was removed under reduced pressure, and the residue was treated with HCl in dioxane to give compound 59-S5 as HCl salt.

Step 5: methyl (S)-1-((1R,3S,5R)-3-((6-bromo-3-methylpyridin-2-yl)carbamoyl)-2-(2-(3-carbamoyl-5-(pyridin-3-ylamino)-1H-indazol-1-yl)acetyl)-2-azabicyclo[3.1.0]hexan-5-yl)-24-(methoxycarbonyl)-3,12,21,26-tetraoxo-5,8,14,17-tetraoxa-2,11,20,25-tetraazatritetracontan-43-oate (59-S6)

To a solution compound 59-S5 (1 equiv) in DMF (10 vol) at 0° C. under nitrogen atmosphere was added (S)-22-(methoxycarbonyl)-3,20,25,34-tetraoxo-2,29,32,38,41-pentaoxa-21,26,35-triazatritetracontan-43-oic acid (1.1 equiv), HATU (1.5 equiv) and DIPEA (5 equiv). The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and then concentrated. The residue was purified by preparative purification to give compound 59-S6.

Step 6: (S)-1-((1R,3S,5R)-3-((6-bromo-3-methylpyridin-2-yl)carbamoyl)-2-(2-(3-carbamoyl-5-(pyridin-3-ylamino)-1H-indazol-1-yl)acetyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid (59)

To a solution of compound 59-S6 (1 equiv) in THF/water (8:2) was added CsOH (2 equiv). The reaction mixture was stirred at room temperature for 2 hours and then quenched with 1 M citric acid. The resulting mixture was extracted with ethyl acetate. The organic layer was separated, dried over anhydrous $Na_2SO_4$, filtered and then concentrated. The residue was purified by preparative purification to give compound 59.

$^1H$ NMR (400 MHz, CD3OD) δ 8.31 (s, 1H), 8.10 (s, 2H), 7.68 (d, J=8.0 Hz, 1H), 7.58-7.41 (m, 2H), 7.38 (d, J=8.0 Hz, 1H), 7.36-7.34 (m, 2H), 5.69 (d, J=17.0 Hz, 1H), 5.63 (d, J=17.0 Hz, 1H), 4.61-4.60 (m, 1H), 4.42-4.41 (m, 1H), 4.20-4.19 (m, 3H), 3.68-3.32 (m, 10H), 2.55-2.54 (m, 2H), 2.33-2.29 (m, 7H), 2.22-2.17 (m, 7H), 1.99-1.98 (m, 1H), 1.61-1.59 (m, 4H), 1.41-1.38 (m, 31H), 1.01-0.99 (m, 1H).

Scheme 31. Synthesis of (S)-1-((1R,3S,5R)-2-(2-(3-acetyl-6-phosphono-1H-indol-1-yl)acetyl)-3-((6-bromo-3-methylpyridin-2-yl)carbamoyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid (60)

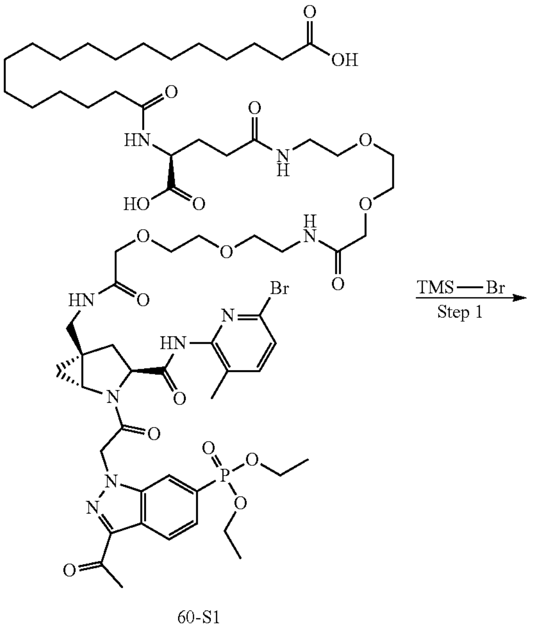

60-S1

-continued

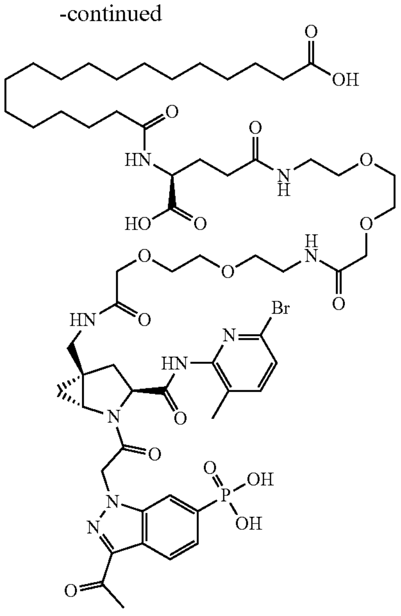

60

Step 1: (S)-1-((1R,3S,5R)-2-(2-(3-acetyl-6-phosphono-1H-indol-1-yl)acetyl)-3-((6-bromo-3-methylpyridin-2-yl)carbamoyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid (60)

To a solution of compound 60-S1 (1 equiv) in DCM (35 vol) at 0° C. under nitrogen atmosphere was added TMSBr (10 equiv). The reaction mixture was stirred at room temperature for 2 days. After completion of the reaction, the reaction mixture was quenched with water, and the resulting solid was filtered and dried. The residue was purified by preparative HPLC to give compound 60. $^{1}H$ NMR (400 MHz, CD3OD) δ 8.43-8.33 (m, 2H), 7.99-7.98 (m, 1H), 7.71-7.69 (m, 1H), 7.57 (d, J=7.9 Hz, 1H), 7.40 (d, J=7.9 Hz, 1H), 5.52-5.45 (m, 2H), 4.58-4.55 (m, 1H), 4.45-4.42 (m, 2H), 4.11-3.99 (m, 3H), 3.82-3.31 (m, 17H), 2.56-2.54 (m, 5H), 2.38-1.99 (m, 10H), 1.78-1.67 (m, 5H), 1.37-1.21 (m, 24H), 1.21-1.18 (m, 2H), 0.99-0.98 (m, 2H).

Scheme 32. Synthesis of (S)-1-((1R,3S,5R)-2-(2-(3-acetyl-6-(phosphonomethoxy)-1H-indol-1-yl)acetyl-3-((6-bromo-3-methylpyridin-2-yl)carbamoyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid (61)

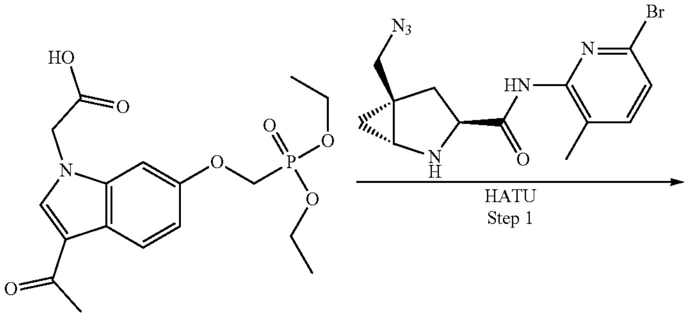

61-S1

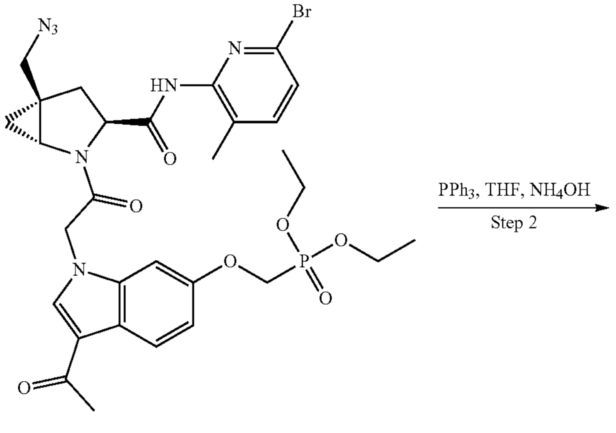

61-S2

-continued
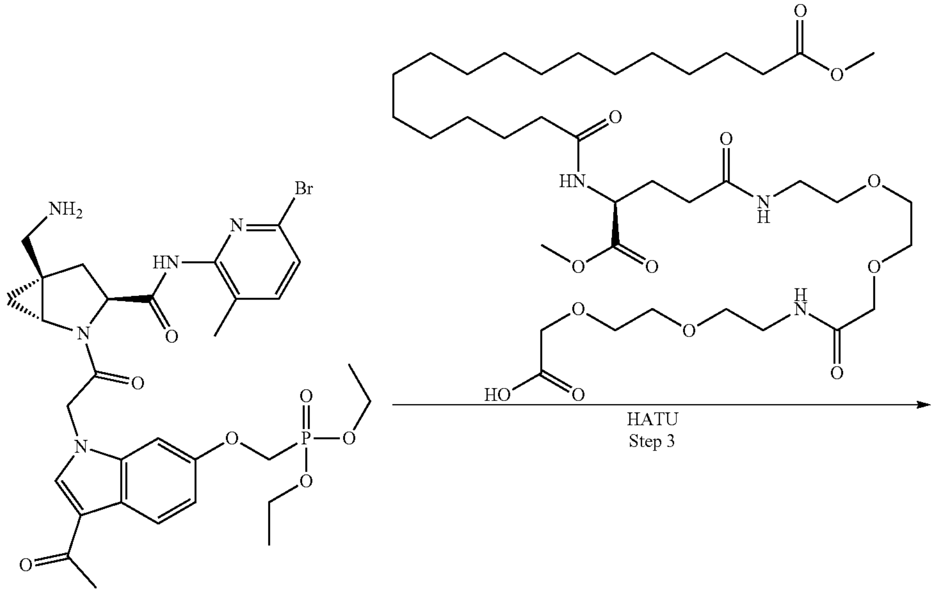
61-S3
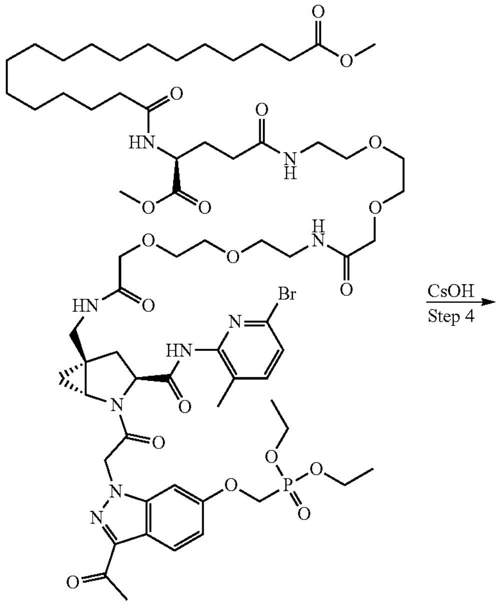
61-S4

-continued

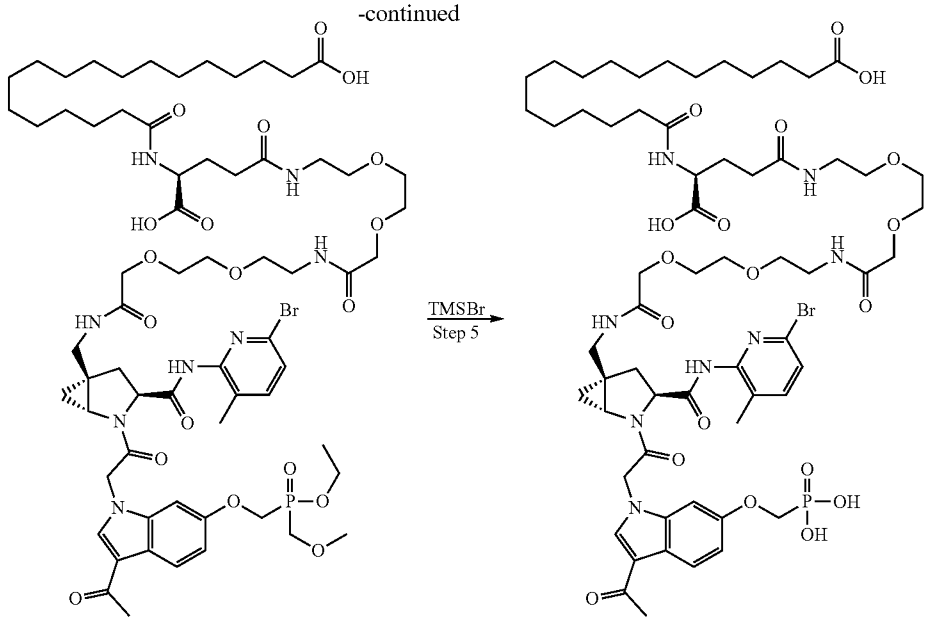

61-S5

61

Step 1: diethyl (((3-acetyl-1-(2-((1R,3S,5R)-5-(azidomethyl)-3-((6-bromo-3-methylpyridin-2-yl)carbamoyl)-2-azabicyclo[3.1.0]hexan-2-yl)-2-oxoethyl)-1H-indol-6-yl)oxy)methyl)phosphonate (61-S2)

To a solution of (1R,3S,5R)-5-(azidomethyl)-N-(6-bromo-3-methylpyridin-2-yl)-2-azabicyclo[3.1.0]hexane-3-carboxamide hydrochloride (1.2 equiv) in DMF (10 vol) at 0° C. under nitrogen atmosphere was added 2-(3-acetyl-6-((diethoxyphosphoryl)methoxy)-1H-indol-1-yl)acetic acid (1 equiv), HATU (1.5 equiv) and DIPEA (5 equiv). The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 61-S2.

Step 2: diethyl (((3-acetyl-1-(2-((1R,3S,5R)-5-(aminomethyl)-3-((6-bromo-3-methylpyridin-2-yl)carbamoyl)-2-azabicyclo[3.1.0]hexan-2-yl)-2-oxoethyl)-1H-indol-6-yl)oxy)methyl)phosphonate (61-S3)

To a solution of compound 61-S2 (1 equiv) in THF (25 vol) was added triphenylphosphine (1.23 equiv) and ammonium hydroxide (10 vol). The reaction mixture was stirred at 60° C. for 2 hours then room temperature for 16 hours. After completion of the reaction, solvent was removed under reduced pressure, and the residue was treated with HCl in dioxane to give compound 61-53 as HCl salt.

Step 3: methyl (S)-1-((1R,3S,5R)-2-(2-(3-acetyl-6-((diethoxyphosphoryl)methoxy)-1H-indol-1-yl)acetyl)-3-((6-bromo-3-methylpyridin-2-yl)carbamoyl)-2-azabicyclo[3.1.0]hexan-5-yl)-24-(methoxycarbonyl)-3,12,21,26-tetraoxo-5,8,14,17-tetraoxa-2,11,20,25-tetraazatritetracontan-43-oate (61-S4)

To a solution compound 61-S3 (1 equiv) in DMF (10 vol) at 0° C. under nitrogen atmosphere was added (S)-22-(methoxycarbonyl)-3,20,25,34-tetraoxo-2,29,32,38,41-pentaoxa-21,26,35-triazatritetracontan-43-oic acid (1.1 equiv), HATU (1.5 equiv) and DIPEA (5 equiv). The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and then concentrated. The residue was purified by preparative purification to give compound 61-S4.

Step 4: (S)-1-((1R,3S,5R)-2-(2-(3-acetyl-6-((diethoxyphosphoryl)methoxy)-1H-indol-1-yl)acetyl)-3-((6-bromo-3-methylpyridin-2-yl)carbamoyl)-2-azabicyclo[3.1.0]hexan-5-yl)-24-carboxy-3,12,21,26-tetraoxo-5,8,14,17-tetraoxa-2, 1,20,25-tetraazatritetracontan-43-oic acid (61-S5)

To a solution of compound 61-S4 (1 equiv) in THF/water (8:2) was added CsOH (2 equiv). The reaction mixture was stirred at room temperature for 2 hours and then quenched with 1 M citric acid. The resulting mixture was extracted with ethyl acetate. The organic layer was separated, dried over anhydrous $Na_2SO_4$, filtered and then concentrated. The residue was purified by preparative purification to give compound 61-S5.

Step 5: (S)-1-((1R,3S,5R)-2-(2-(3-acetyl-6-(phosphonomethoxy)-1H-indol-1-yl)acetyl)-3-((6-bromo-3-methylpyridin-2-yl)carbamoyl)-2-azabicyclo[3.1.0]hexan-5-yl)-24-carboxy-3,12,21,26-tetraoxo-5,8,14,17-tetraoxa-22,11,20,25-tetraazatritetracontan-43-oic acid (61)

To a solution of compound 61-S5 (1 equiv) in DCM (35 vol) at 0° C. under nitrogen atmosphere was added TMSBr (10 equiv). The reaction mixture was stirred at room temperature for 2 days. After completion of the reaction, the reaction mixture was quenched with water and the resulting solid is filtered and dried. The residue was purified by preparative HPLC to give compound 61. $^1$H NMR (400 MHz, CD3OD) δ 8.38-8.33 (m, 2H), 7.91-7.88 (m, 1H), 7.68-7.66 (m, 1H), 7.56 (d, J=8.0 Hz, 1H), 7.40 (d, J=8.0 Hz, 1H), 5.45-5.43 (m, 2H), 4.88-4.85 (m, 1H), 4.47-4.43 (m, 1H), 4.11-4.00 (m, 4H), 3.77-3.32 (m, 18H), 2.66-2.58 (m, 3H), 2.34-1.98 (m, 11H), 1.68-1.61 (m, 5H), 1.39-1.29 (m, 26H), 1.20-1.14 (m, 2H), 0.92-0.90 (m, 2H).

Scheme 33. Synthesis of 1-((1R,3S,5R)-2-(2-(3-acetyl-5-((cyclopropylcarbamoyl)oxy)-1H-indazol-1-yl)acetyl-3-((6-bromo-3-methylpyridin-2-yl)carbamoyl)-2-azabicyclo[3.1.0]hexan-5-yl)-3,12,21-trioxo-5,8,14,17-tetraoxa-2,11,20-triazaoctatriacontan-38-oic acid (62)

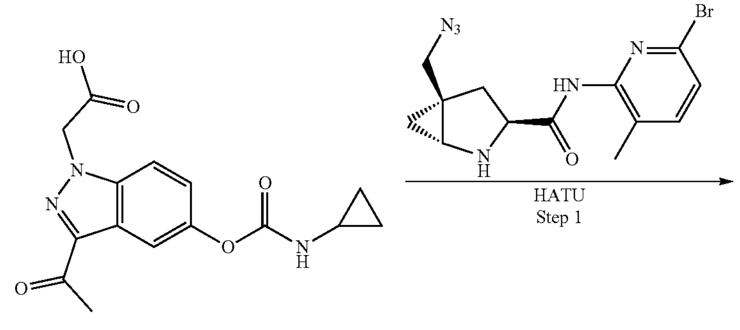

62-S1

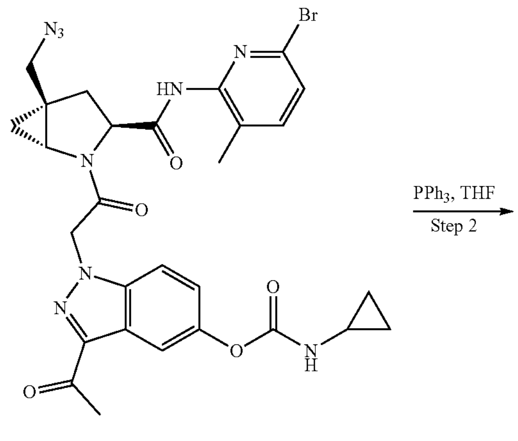

62-S2

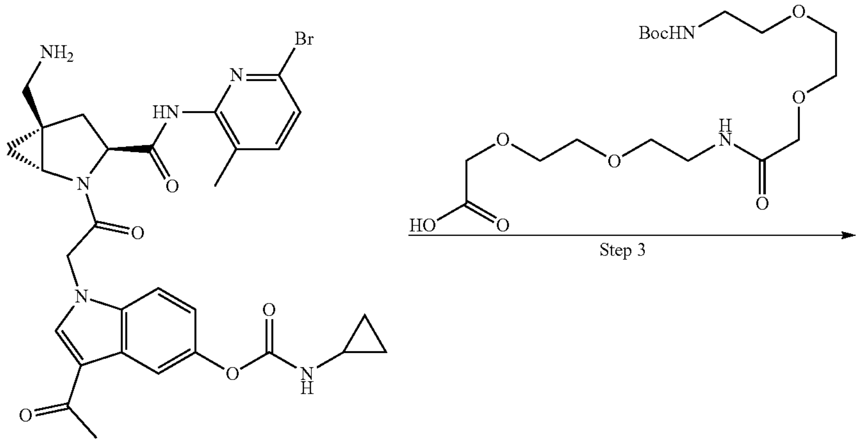

62-S3

-continued
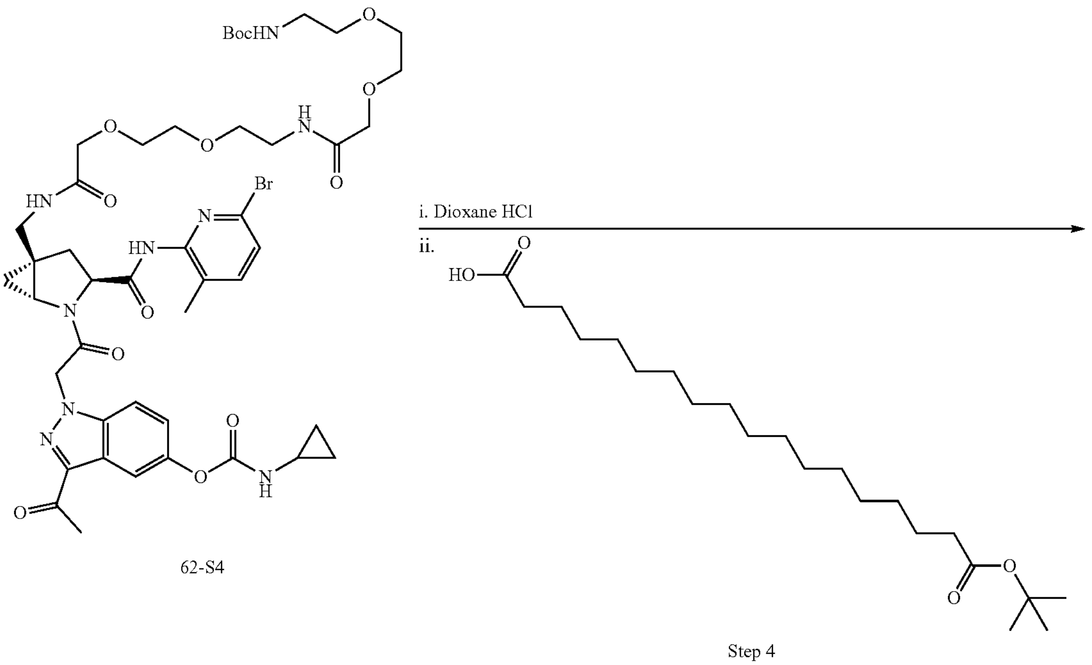
62-S4
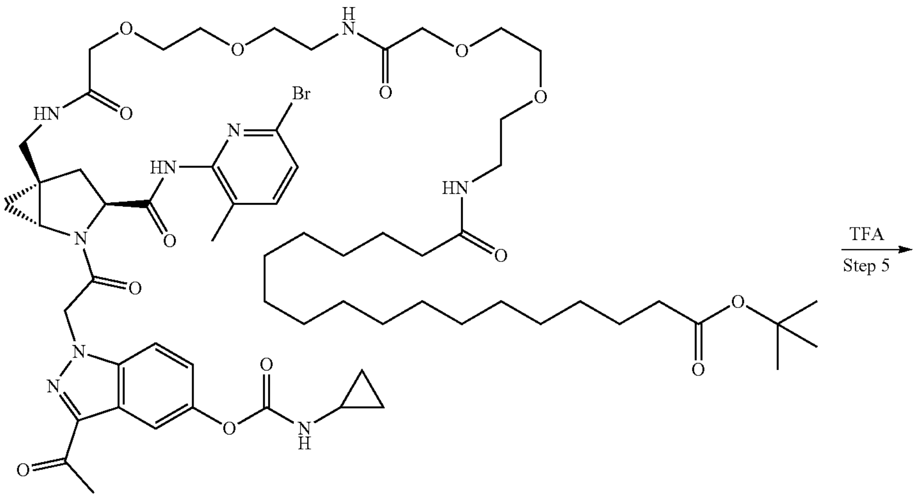
62-S5

-continued

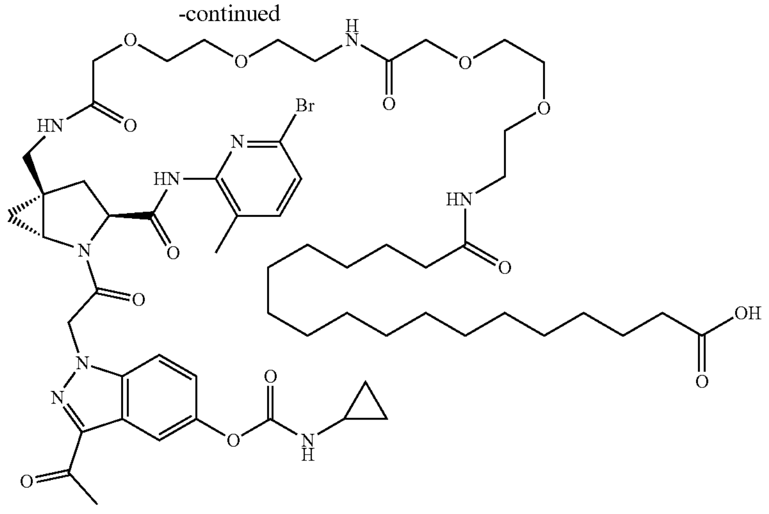

62

Step 1: 3-acetyl-1-(2-((1R,3S,5R)-5-(azidomethyl)-3-((6-bromo-3-methylpyridin-2-yl)carbamoyl)-2-azabicyclo[3.1.0]hexan-2-yl)-2-oxoethyl)-1H-indazol-5-yl cyclopropylcarbamate (62-S2)

To a solution of (1R,3S,5R)-5-(azidomethyl)-N-(6-bromo-3-methylpyridin-2-yl)-2-azabicyclo[3.1.0]hexane-3-carboxamide hydrochloride (1.2 equiv) in DMF (10 vol) at 0° C. under nitrogen atmosphere was added 2-(3-acetyl-5-((cyclopropylcarbamoyl)oxy)-1H-indazol-1-yl)acetic acid (1 equiv), HATU (1.5 equiv) and DIPEA (5 equiv). The reaction mixture was stirred at room temperature for 16 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 62-S2.

Step 2: 3-acetyl-1-(2-((1R,3S,5R)-5-(aminomethyl)-3-((6-bromo-3-methylpyridin-2-yl)carbamoyl)-2-azabicyclo[3.1.0]hexan-2-yl)-2-oxoethyl)-1H-indazol-5-yl cyclopropylcarbamate (62-S3)

To a solution of compound 62-S2 (1 equiv) in THF (25 vol) was added triphenylphosphine (1.23 equiv) and ammonium hydroxide (10 vol). The reaction mixture was stirred at 60° C. for 2 hours then room temperature for 16 hours. After completion of the reaction, solvent was removed under reduced pressure and the residue was treated with HCl in dioxane to give compound 62-S3 as HCl salt.

Step 3: tert-butyl (1-((1R,3S,5R)-2-(2-(3-acetyl-5-((cyclopropylcarbamoyl)oxy)-1H-indazol-1-yl)acetyl)-3-((6-bromo-3-methylpyridin-2-yl)carbamoyl)-2-azabicyclo[3.1.0]hexan-5-yl)-3,12-dioxo-5,8,14,17-tetraoxa-2,11-diazanonadecan-19-yl)carbamate (62-S4)

To a solution compound 62-S3 (1 equiv) in DMF (10 vol) at 0° C. under nitrogen atmosphere was added 2,2-dimethyl-4,13-dioxo-3,8,11,17,20-pentaoxa-5,14-diazadocosan-22-oic acid (1.1 equiv), HATU (1.5 equiv) and DIPEA (5 equiv). The reaction mixture was stirred at room temperature for 16 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by preparative purification to give compound 62-S4.

Step 4: tert-butyl 1-((1R,3S,5R)-2-(2-(3-acetyl-5-((cyclopropylcarbamoyl)oxy)-1H-indazol-1-yl)acetyl)-3-((6-bromo-3-methylpyridin-2-yl)carbamoyl)-2-azabicyclo[3.1.0]hexan-5-yl)-3,12,21-trioxo-5,8,14,17-tetraoxa-2,11,20-triazaoctatriacontan-38-oate (62-S5)

To a solution of compound 62-S4 (1 equiv) in 1,4-dioxane (3 vol) at 0° C. under nitrogen atmosphere was added 4 N HCl in 1,4-dioxane (10 vol) and stirred at room temperature for 3 h. The volatiles were removed under reduced pressure and the resulting residue was used as such for the next step.

To a solution of above residue in DMF (10 vol) at 0° C. under nitrogen atmosphere was added 18-(tert-butoxy)-18-oxooctadecanoic acid (1.1 equiv), HATU (1.5 equiv) and DIPEA (5 equiv). The reaction mixture was stirred at room temperature for 16 hours. After completion of the reaction, the reaction mixture was quenched with water. The resulting mixture was extracted with DCM. The organic layer was washed with brine, dried over anhydrous $Na_2SO_4$, filtered and then concentrated. The residue was purified by preparative purification to give compound 62-S5.

Step 5: 1-((1R,3S,5R)-2-(2-(3-acetyl-5-((cyclopropylcarbamoyl)oxy)-1H-indazol-1-yl)acetyl)-3-((6-bromo-3-methylpyridin-2-yl)carbamoyl)-2-azabicyclo[3.1.0]hexan-5-yl)-3,12,21-trioxo-5,8,14,17-tetraoxa-2,11,20-triazaoctatriacontan-38-oic acid (62)

To a solution of compound 62-S5 (1 equiv) in DCM (10 vol) at 0° C. was added TFA (5 vol). The reaction mixture was stirred at room temperature for 30 minutes. The volatiles were removed under reduced pressure, and the resulting residue was purified by preparative purification to give compound 62.

$^1H$ NMR (400 MHz, CD3OD) δ 7.94 (s, 1H), 7.62 (d, J=7.6 Hz, 1H), 7.56 (d, J=7.6 Hz, 1H), 7.39 (d, J=7.6 Hz, 1H), 7.24 (d, J=7.6 Hz, 1H), 5.74 (d, J=17.2 Hz, 1H), 5.62 (d, J=17.2 Hz, 1H), 4.63-4.61 (m, 1H), 4.10-4.00 (m, 4H), 3.75-3.36 (m, 17H), 2.66 (s, 6H), 2.54-2.29 (m, 12H), 1.87-1.80 (m, 5H), 1.67-1.63 (m, 21H), 0.98-0.79 (m, 5H).

Non-Limiting Examples of Compounds of the Present Invention

Table 5 and Table 6 show illustrative Factor D inhibitors with characterizing data. The HUMAN Factor D Assay was used to determine the $IC_{50}$'s of the compounds. Other standard factor D inhibition assays are also available. Three *s are used to denote compounds with an $IC_{50}$ less than 1 micromolar; two s indicate compound with an $IC_{50}$ between 1 micromolar and 10 micromolar, and one * denotes compounds with an $IC_{50}$ greater than 10 micromolar.

TABLE 5

Non-limiting Examples of Compounds of the Present Invention

| Cmp No. | Structure | Name | $IC_{50}$ (Stars) | RT min (Method A, B, C or D) | MS (M + 1) |
|---|---|---|---|---|---|
| T-1 | 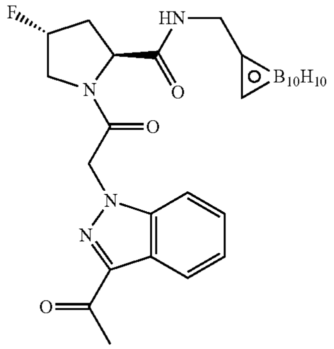 | | *** | 15.35 (C) | 487 (M − 1) |
| T-2 | 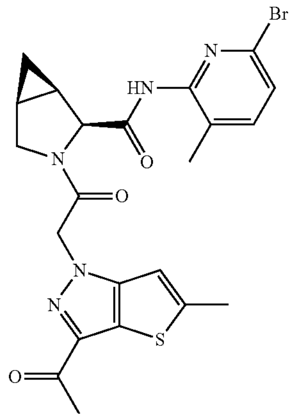 [SMILES: CC(=O)c1nn(CC(=O)N2C[C@H]3C[C@H]3[C@H]2C(=O)Nc2nc(Br)ccc2C)c2cc(C)sc12] | (1R,2S,5S)-3-(2-(3-acetyl-5-methyl-1H-thieno[3,2-c]pyrazol-1-yl)acetyl)-N-(6-bromo-3-methylpyridin-2-yl)-3-azabicyclo[3.10]hexane-2-carboxamide | *** | 2.94 (B) | 516 |
| T-3 | 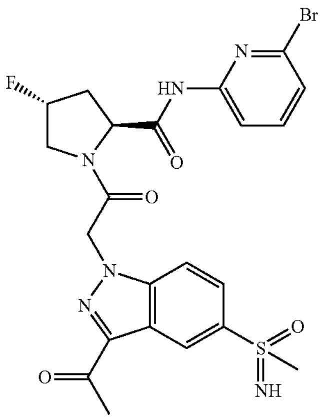 [SMILES: CC(=O)c1nn(CC(=O)N2C[C@H](F)C[C@H]2C(=O)Nc2cccc(Br)n2)c2ccc(S(C)(=N)=O)cc12] | (2S,4R)-1-(2-(3-acetyl-5-(S-methylsulfonimidoyl)-1H-indazol-1-yl)acetyl)-N-(6-bromopyridin-2-yl)-4-fluoropyrrolidine-2-carboxamide | *** | 2.17 (B) | 565 |

TABLE 5-continued

Non-limiting Examples of Compounds of the Present Invention

| Cmp No. | Structure | Name | $IC_{50}$ (Stars) | RT min (Method A, B, C or D) | MS (M + 1) |
|---|---|---|---|---|---|
| T-4 | 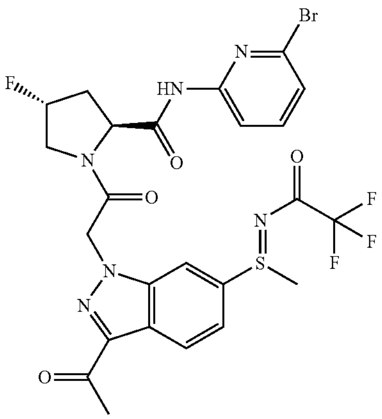 [SMILES: CC(=O)c1nn(CC(=O)N2C[C@H](F)C[C@H]2C(=O)Nc2cccc(Br)n2)c2cc(/S(C)=N/C(=O)C(F)(F)F)ccc12] | (2S,4R)-1-(2-(3-acetyl-6-((E)-S-methyl-N-(2,2,2-trifluoroacetyl) sulfinimidoyl)-1H-indazol-1-yl)acetyl)-N-(6-bromopyridin-2-yl)-4-fluoropyrrolidine-2-carboxamide | *** | 2.56 (B) | 645 |
| T-5 | 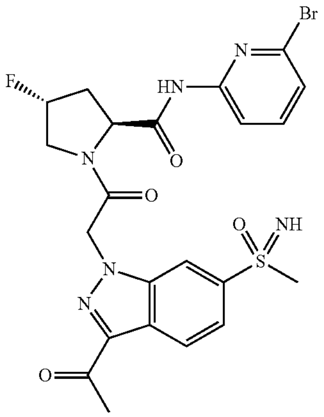 [SMILES: CC(=O)c1nn(CC(=O)N2C[C@H](F)C[C@H]2C(=O)Nc2cccc(Br)n2)c2cc(S(C)(=N)=O)ccc12] | (2S,4R)-1-(2-(3-acetyl-6-(S-methylsulfonimidoyl)-1H-indazol-1-yl)acetyl)-N-(6-bromopyridin-2-yl)-4-fluoropyrrolidine-2-carboxamide | *** | 2.62 (B) | 565 |
| T-6 | 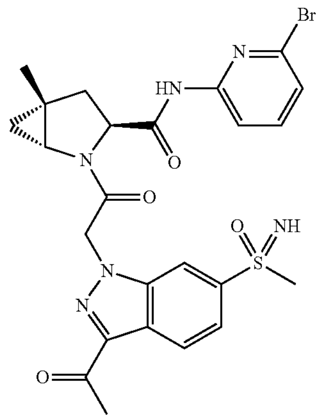 [SMILES: CC(=O)c1nn(CC(=O)N2[C@H](C(=O)Nc3cccc(Br)n3)C[C@@]3(C)C[C@@H]23)c2cc(S(C)(=N)=O)ccc12] | (1R,3S,5R)-2-(2-(3-acetyl-6-(S-methylsulfonimidoyl)-1H-indazol-1-yl)acetyl)-N-(6-bromopyridin-2-yl)-5-methyl-2-azabicyclo[3.1.0]hexane-3-carboxamide | *** | 3.06 (B) | 573 |

TABLE 5-continued

Non-limiting Examples of Compounds of the Present Invention

| Cmp No. | Structure | Name | $IC_{50}$ (Stars) | RT min (Method A, B, C or D) | MS (M + 1) |
|---|---|---|---|---|---|
| T-7 | 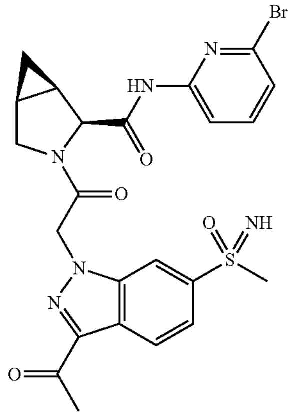 [SMILES: CC(=O)c1nn(CC(=O)N2C[C@H]3C[C@H]3[C@H]2C(=O)Nc2cccc(Br)n2)c2cc(S(C)(=N)=O)ccc12] | (1R,2S,5S)-3-(2-(3-acetyl-6-(S-methylsulfonimidoyl)-1H-indazol-1-yl)acetyl)-N-(6-bromopyridin-2-yl)-3-azabicyclo[3.1.0]hexane-2-carboxamide | *** | 2.71 (B) | 559 |
| T-8 | 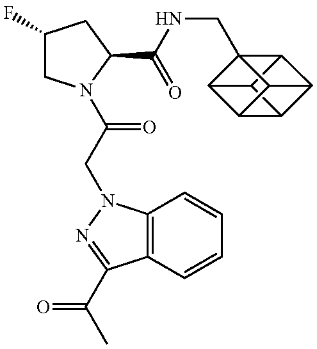 [SMILES: CC(=O)c1nn(CC(=O)N2C[C@H](F)C[C@H]2C(=O)NCC23C4C5C6C4C2C6C53)c2ccccc12] | (2S,4R)-1-(2-(3-acetyl-1H-indazol-1-yl)acetyl)-N-(cuban-1-ylmethyl)-4-fluoropyrrolidine-2-carboxamide | ** | 11.78 (D) | 449 |
| T-9 | 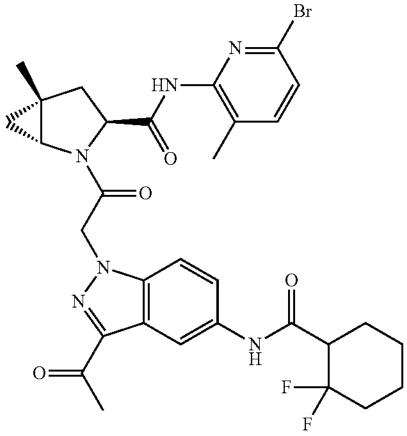 [SMILES: CC(=O)c1nn(CC(=O)N2[C@H](C(=O)Nc3nc(Br)ccc3C)C[C@@]3(C)C[C@@H]23)c2ccc(NC(=O)C3CCCCC3(F)F)cc12] | (1R,3S,5R)-2-(2-(3-acetyl-5-(2,2-difluorocyclohexane-1-carboxamido)-1H-indazol-1-yl)acetyl)-N-(6-bromo-3-methylpyridin-2-yl)-5-methyl-2-azabicyclo[3.10]hexane-3-carboxamide | *** | 13.87 (C) | 673 (M + 2) |

TABLE 5-continued
| Cmp No. | Structure | Name | $IC_{50}$ (Stars) | RT min (Method A, B, C or D) | MS (M + 1) |
|---|---|---|---|---|---|
| Non-limiting Examples of Compounds of the Present Invention | | | | | |
| T-10 | 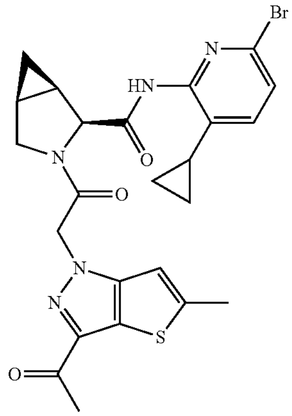 [SMILES: CC(=O)c1nn(CC(=O)N2C[C@H]3C[C@H]3[C@H]2C(=O)Nc2nc(Br)ccc2C2CC2)c2cc(C)sc12] | (1R,2S,5S)-3-(2-(3-acetyl-5-methyl-1H-thieno[3,2-c]pyrazol-1-yl)acetyl)-N-(6-bromo-3-cyclopropylpyridin-2-yl)-3-azabicyclo[3.1.0]hexane-2-carboxamide | *** | 3.15 (B) | 542 |
| T-11 | 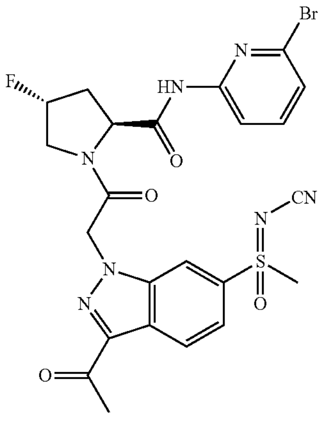 [SMILES: CC(=O)c1nn(CC(=O)N2C[C@H](F)C[C@H]2C(=O)Nc2cccc(Br)n2)c2cc(S(C)(=O)=NC#N)ccc12] | | *** | 2.34 (B) | 590 |
| T-12 | 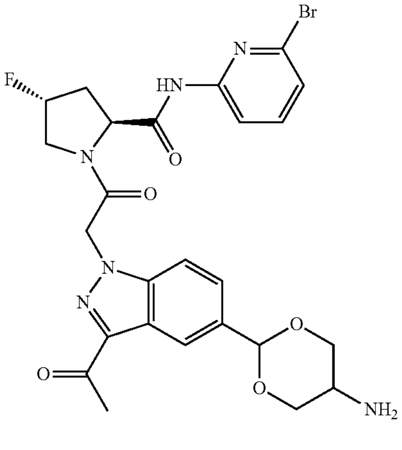 [SMILES: CC(=O)c1nn(CC(=O)N2C[C@H](F)C[C@H]2C(=O)Nc2cccc(Br)n2)c2ccc(C3OCC(N)CO3)cc12] | (2S,4R)-1-(2-(3-acetyl-5-(5-amino-1,3-dioxan-2-yl)-1H-indazol-1-yl)acetyl)-N-(6-bromopyridin-2-yl)-4-fluoropyrrolidine-2-carboxamide | *** | 8.52 (D) | 590 |

TABLE 5-continued

Non-limiting Examples of Compounds of the Present Invention

| Cmp No. | Structure | Name | $IC_{50}$ (Stars) | RT min (Method A, B, C or D) | MS (M + 1) |
|---|---|---|---|---|---|
| T-13 | 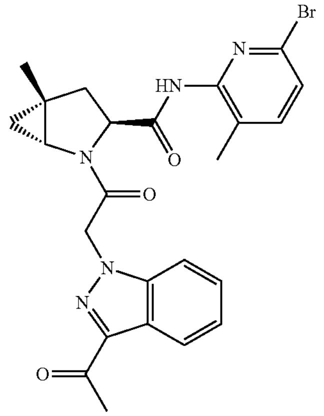 [SMILES: CC(=O)c1nn(CC(=O)N2[C@H](C(=O)Nc3nc(Br)ccc3C)C[C@@]3(C)C[C@@H]23)c2ccccc12] | (1R,3S,5R)-2-(2-(3-acetyl-1H-indazol-1-yl)acetyl)-N-(6-bromo-3-methylpyridin-2-yl)-5-methyl-2-azabicyclo[3.1.0]hexane-3-carboxamide | *** | 11.75 (D) | 512 (M + 2) |
| T-14 | 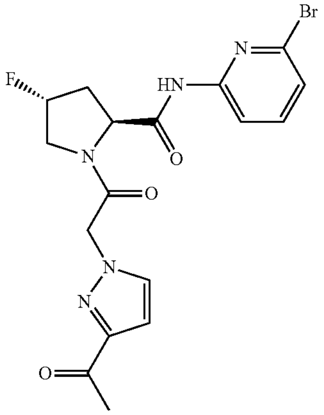 [SMILES: CC(=O)c1ccn(CC(=O)N2C[C@H](F)C[C@H]2C(=O)Nc2cccc(Br)n2)n1] | (2S,4R)-1-(2-(3-acetyl-1H-pyrazol-1-yl)acetyl)-N-(6-bromopyridin-2-yl)-4-fluoropyrrolidine-2-carboxamide | *** | 1.35 (A) | 438 |
| T-15 | 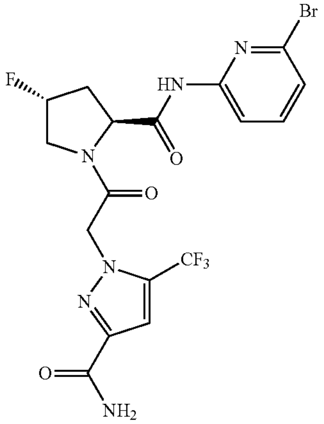 [SMILES: NC(=O)c1cc(C(F)(F)F)n(CC(=O)N2C[C@H](F)C[C@H]2C(=O)Nc2cccc(Br)n2)n1] | 1-(2-((2S,4R)-2-((6-bromopyridin-2-yl)carbamoyl)-4-fluoropyrrolidin-1-yl)-2-oxoethyl)-5-(trifluoromethyl)-1H-pyrazole-3-carboxamide | *** | 1.49 (A) | 507 |

TABLE 5-continued

Non-limiting Examples of Compounds of the Present Invention

| Cmp No. | Structure | Name | $IC_{50}$ (Stars) | RT min (Method A, B, C or D) | MS (M + 1) |
|---|---|---|---|---|---|
| T-16 | 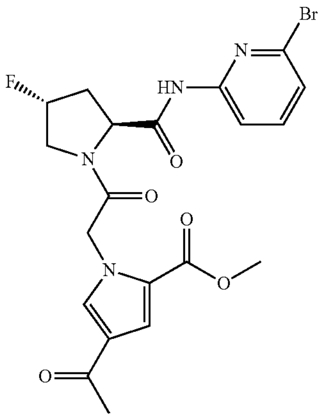 [SMILES: COC(=O)c1cc(C(C)=O)cn1CC(=O)N1C[C@H](F)C[C@H]1C(=O)Nc1cccc(Br)n1] | methyl 4-acetyl-1-(2-((2S,4R)-2-((6-bromopyridin-2-yl)carbamoyl)-4-fluoropyrrolidin-1-yl)-2-oxoethyl)-1H-pyrrole-2-carboxylate | ** | 1.63 (A) | 495 |
| T-17 | 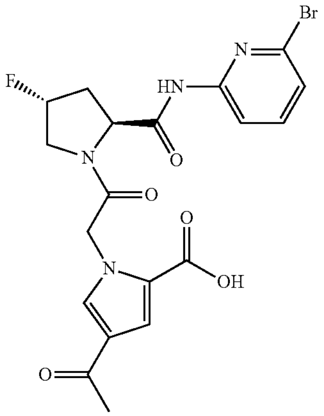 [SMILES: CC(=O)c1cc(C(=O)O)n(CC(=O)N2C[C@H](F)C[C@H]2C(=O)Nc2cccc(Br)n2)c1] | 4-acetyl-1-(2-((2S,4R)-2-((6-bromopyridin-2-yl)carbamoyl)-4-fluoropyrrolidin-1-yl)-2-oxoethyl)-1H-pyrrole-2-carboxylic acid | *** | 1.22 (A) | 481 |
| T-18 | 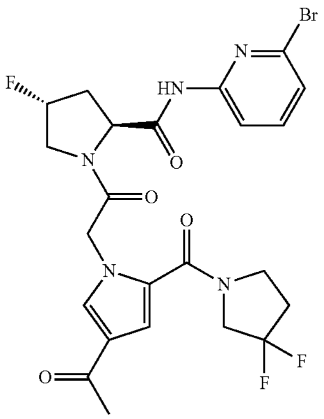 [SMILES: CC(=O)c1cc(C(=O)N2CCC(F)(F)C2)n(CC(=O)N2C[C@H](F)C[C@H]2C(=O)Nc2cccc(Br)n2)c1] | (2S,4R)-1-(2-(4-acetyl-2-(3,3-difluoropyrrolidine-1-carbonyl)-1H-pyrrol-1-yl)acetyl)-N-(6-bromopyridin-2-yl)-4-fluoropyrrolidine-2-carboxamide | * | 1.75 (A) | 570 |

TABLE 5-continued

Non-limiting Examples of Compounds of the Present Invention

| Cmp No. | Structure | Name | $IC_{50}$ (Stars) | RT min (Method A, B, C or D) | MS (M + 1) |
| --- | --- | --- | --- | --- | --- |
| T-19 | 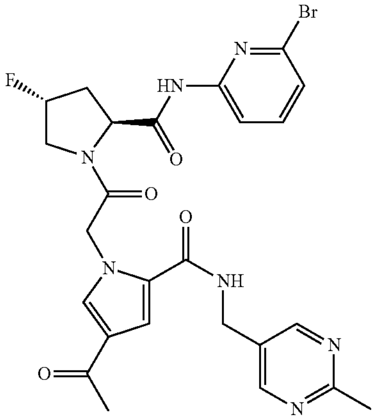 [SMILES: CC(=O)c1cc(C(=O)NCc2cnc(C)nc2)n(CC(=O)N2C[C@H](F)C[C@H]2C(=O)Nc2cccc(Br)n2)c1] | 4-acetyl-1-(2-((2S,4R)-2-((6-bromopyridin-2-yl)carbamoyl)-4-fluoropyrrolidin-1-yl)-2-oxoethyl)-N-((2-methylpyrimidin-5-yl)methyl)-1H-pyrrole-2-carboxamide | *** | 1.23 (A) | 586 |
| T-20 | 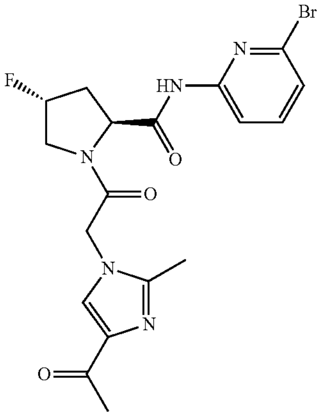 [SMILES: CC(=O)c1cn(CC(=O)N2C[C@H](F)C[C@H]2C(=O)Nc2cccc(Br)n2)c(C)n1] | (2S,4R)-1-(2-(4-acetyl-2-methyl-1H-imidazol-1-yl)acetyl)-N-(6-bromopyridin-2-yl)-4-fluoropyrrolidine-2-carboxamide | * | 0.77 (A) | 452 |
| T-21 | 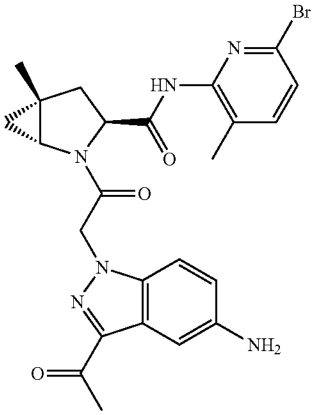 [SMILES: CC(=O)c1nn(CC(=O)N2[C@H](C(=O)Nc3nc(Br)ccc3C)C[C@@]3(C)C[C@@H]23)c2ccc(N)cc12] | (1R,3S,5R)-2-(2-(3-acetyl-5-amino-1H-indazol-1-yl)acetyl)-N-(6-bromo-3-methylpyridin-2-yl)-5-methyl-2-azabicyclo[3.10]hexane-3-carboxamide | *** | 10.12 (C) | 523 (M − 2) |

TABLE 5-continued

Non-limiting Examples of Compounds of the Present Invention

| Cmp No. | Structure | Name | $IC_{50}$ (Stars) | RT min (Method A, B, C or D) | MS (M + 1) |
|---|---|---|---|---|---|
| T-22 | 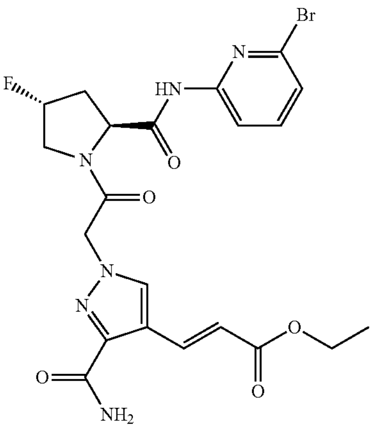 [SMILES: CCOC(=O)/C=C/c1cn(CC(=O)N2C[C@H](F)C[C@H]2C(=O)Nc2cccc(Br)n2)nc1C(N)=O] | (E)-ethyl 3-(1-(2-((2S,4R)-2-((6-bromopyridin-2-yl)carbamoyl)-4-fluoropyrrolidin-1-yl)-2-oxoethyl)-3-carbamoyl-1H-pyrazol-4-yl)acrylate | ** | 1.58 (A) | 537 |
| T-23 | 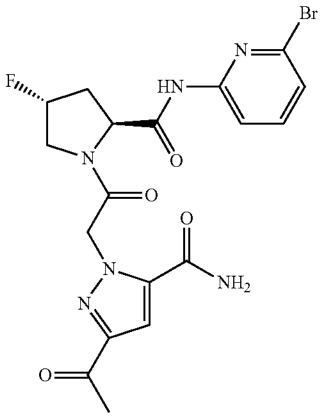 [SMILES: CC(=O)c1cc(C(N)=O)n(CC(=O)N2C[C@H](F)C[C@H]2C(=O)Nc2cccc(Br)n2)n1] | 3-acetyl-1-(2-((2S,4R)-2-((6-bromopyridin-2-yl)carbamoyl)-4-fluoropyrrolidin-1-yl)-2-oxoethyl)-1H-pyrazole-5-carboxamide | *** | 1.23 (A) | 481 |
| T-24 | 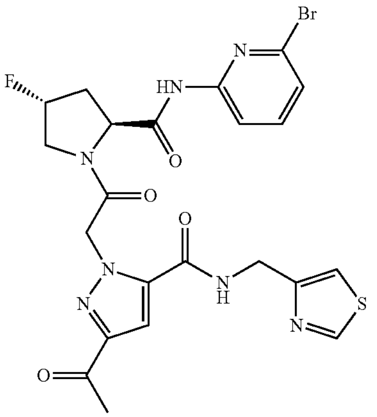 [SMILES: CC(=O)c1cc(C(=O)NCc2cscn2)n(CC(=O)N2C[C@H](F)C[C@H]2C(=O)Nc2cccc(Br)n2)n1] | 3-acetyl-1-(2-((2S,4R)-2-((6-bromopyridin-2-yl)carbamoyl)-4-fluoropyrrolidin-1-yl)-2-oxoethyl)-N-(thiazol-4-ylmethyl)-1H-pyrazole-5-carboxamide | *** | 1.50 (A) | 578 |

TABLE 5-continued

| Cmp No. | Structure | Name | $IC_{50}$ (Stars) | RT min (Method A, B, C or D) | MS (M + 1) |
|---|---|---|---|---|---|
| Non-limiting Examples of Compounds of the Present Invention | | | | | |
| T-25 | 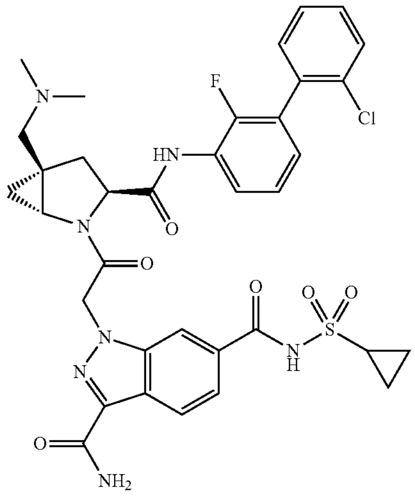 [SMILES: CN(C)C[C@@]12C[C@@H](C(=O)Nc3cccc(-c4ccccc4Cl)c3F)N(C(=O)Cn3nc(C(N)=O)c4ccc(C(=O)NS(=O)(=O)C5CC5)cc43)[C@@H]1C2] | 1-(2-((1R,3S,5R)-3-((2'-chloro-2-fluoro-[1,1'-biphenyl]-3-yl)carbamoyl)-5-((dimethylamino)methyl)-2-azabicyclo[3.10]hexan-2-yl)-2-oxoethyl)-N6-(cyclopropylsulfonyl)-1H-indazole-3,6-dicarboxamide | | 2.34 (B) | 736 |
| T-26 | 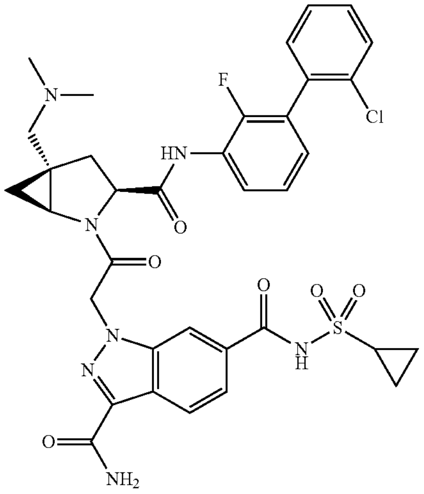 [SMILES: CN(C)C[C@@]12C[C@@H]1N(C(=O)Cn1nc(C(N)=O)c3ccc(C(=O)NS(=O)(=O)C4CC4)cc31)[C@H](C(=O)Nc1cccc(-c3ccccc3Cl)c1F)C2] | 1-(2-((1S,3S,5S)-3-((2'-chloro-2-fluoro-[1,1'-biphenyl]-3-yl)carbamoyl)-5-((dimethylamino)methyl)-2-azabicyclo[3.1.0]hexan-2-yl)-2-oxoethyl)-N6-(cyclopropylsulfonyl)-1H-indazole-3,6-dicarboxamide | | 2.33 (B) | 736 |
| T-27 | 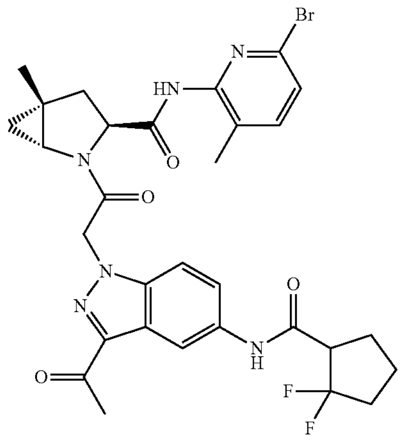 [SMILES: CC(=O)c1nn(CC(=O)N2[C@H](C(=O)Nc3nc(Br)ccc3C)C[C@@]3(C)C[C@@H]23)c2ccc(NC(=O)C3CCCC3(F)F)cc12] | (1R,3S,5R)-2-(2-(3-acetyl-5-(2,2-difluorocyclopentane-1-carboxamido)-1H-indazol-1-yl)acetyl)-N-(6-bromo-3-methylpyridin-2-yl)-5-methyl-2-azabicyclo[3.1.0]hexane-3-carboxamide | *** | 13.33 (C) | 659 (M + 2) |

TABLE 5-continued

| Non-limiting Examples of Compounds of the Present Invention | | | | | |
|---|---|---|---|---|---|
| Cmp No. | Structure | Name | $IC_{50}$ (Stars) | RT min (Method A, B, C or D) | MS (M + 1) |
| T-28 | 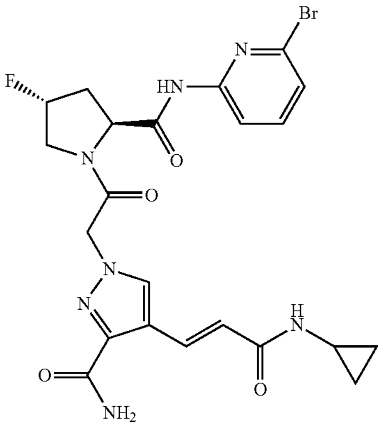 [SMILES: NC(=O)c1nn(CC(=O)N2C[C@H](F)C[C@H]2C(=O)Nc2cccc(Br)n2)cc1/C=C/C(=O)NC1CC1] | 1-(2-((2S,4R)-2-((6-bromopyridin-2-yl)carbamoyl)-4-fluoropyrrolidin-1-yl)-2-oxoethyl)-4-((E)-3-(cyclopropylamino)-3-oxoprop-1-en-1-yl)-1H-pyrazole-3-carboxamide | ** | 1.16 (A) | 548 |
| T-29 | 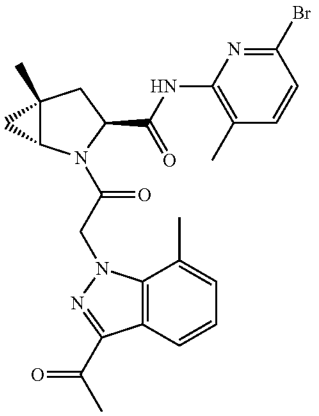 [SMILES: CC(=O)c1nn(CC(=O)N2[C@H](C(=O)Nc3nc(Br)ccc3C)C[C@@]3(C)C[C@@H]23)c2c(C)cccc12] | (1R,3S,5R)-2-(2-(3-acetyl-7-methyl-1H-indazol-1-yl)acetyl)-N-(6-bromo-3-methylpyridin-2-yl)-5-methyl-2-azabicyclo[3.1.0]hexane-3-carboxamide | *** | 14.13 (C) | 522 (M − 2) |
| T-30 | 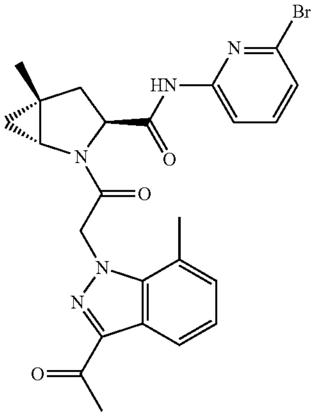 [SMILES: CC(=O)c1nn(CC(=O)N2[C@H](C(=O)Nc3cccc(Br)n3)C[C@@]3(C)C[C@@H]23)c2c(C)cccc12] | (1R,3S,5R)-2-(2-(3-acetyl-7-methyl-1H-indazol-1-yl)acetyl)-N-(6-bromopyridin-2-yl)-5-methyl-2-azabicyclo[3.1.0]hexane-3-carboxamide | *** | 15.16 (C) | 508 (M − 2) |

TABLE 5-continued

| Non-limiting Examples of Compounds of the Present Invention | | | | | |
|---|---|---|---|---|---|
| Cmp No. | Structure | Name | $IC_{50}$ (Stars) | RT min (Method A, B, C or D) | MS (M + 1) |
| T-31 | 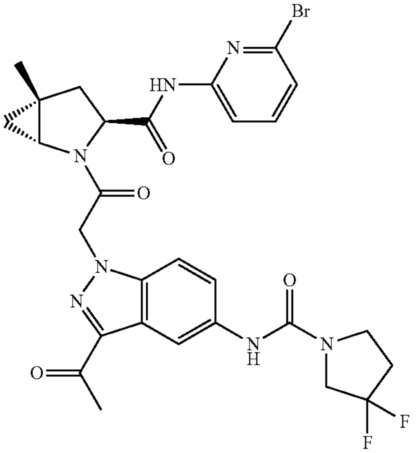 [SMILES: CC(=O)c1nn(CC(=O)N2[C@H](C(=O)Nc3cccc(Br)n3)C[C@@]3(C)C[C@@H]23)c2ccc(NC(=O)N3CCC(F)(F)C3)cc12] | (1R,3S,5R)-2-(2-(3-acetyl-5-(3,3-difluoropyrrolidine-1-carboxamido)-1H-indazol-1-yl)acetyl)-N-(6-bromopyridin-2-yl)-5-methyl-2-azabicyclo[3.1.0]hexane-3-carboxamide | *** | 12.34 (D) | 642 (M − 2) |
| T-32 | 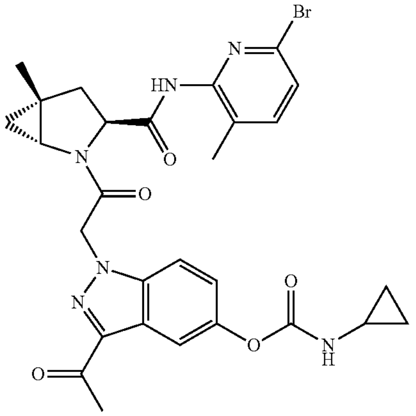 [SMILES: CC(=O)c1nn(CC(=O)N2[C@H](C(=O)Nc3nc(Br)ccc3C)C[C@@]3(C)C[C@@H]23)c2ccc(OC(=O)NC3CC3)cc12] | 3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-indazol-5-yl cyclopropylcarbamate | *** | 11.51 (D) | 611 (M + 2) |
| T-33 | 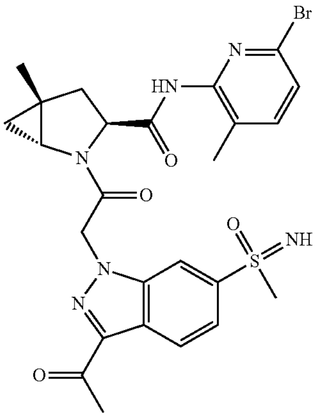 [SMILES: CC(=O)c1nn(CC(=O)N2[C@H](C(=O)Nc3nc(Br)ccc3C)C[C@@]3(C)C[C@@H]23)c2cc(S(C)(=N)=O)ccc12] | (1R,3S,5R)-2-(2-(3-acetyl-6-(S-methylsulfonimidoyl)-1H-indazol-1-yl)acetyl)-N-(6-bromo-3-methylpyridin-2-yl)-5-methyl-2-azabicyclo[3.1.0]hexane-3-carboxamide | *** | 2.62 (B) | 587 |

TABLE 5-continued

| Non-limiting Examples of Compounds of the Present Invention | | | | | |
|---|---|---|---|---|---|
| Cmp No. | Structure | Name | $IC_{50}$ (Stars) | RT min (Method A, B, C or D) | MS (M + 1) |
| T-34 | 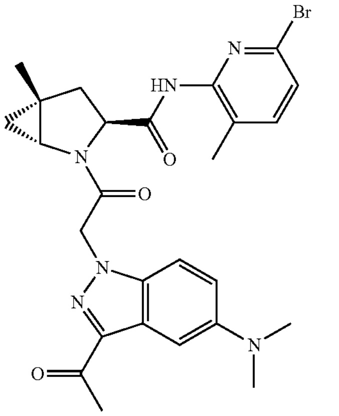 [SMILES: CC(=O)c1nn(CC(=O)N2[C@H](C(=O)Nc3nc(Br)ccc3C)C[C@@]3(C)C[C@@H]23)c2ccc(N(C)C)cc12] | (1R,3S,5R)-2-(2-(3-acetyl-5-(dimethylamino)-1H-indazol-1-yl)acetyl)-N-(6-bromo-3-methylpyridin-2-yl)-5-methyl-2-azabicyclo[3.1.0]hexane-3-carboxamide | *** | 7.76 (C) | 552 (M − 1) |
| T-35 | 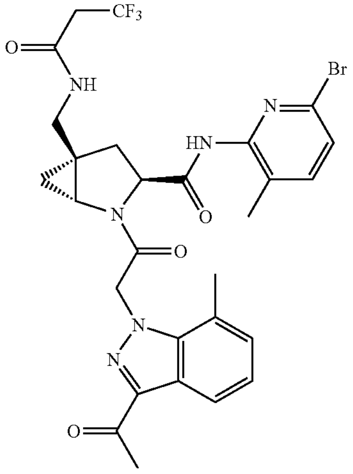 [SMILES: CC(=O)c1nn(CC(=O)N2[C@H](C(=O)Nc3nc(Br)ccc3C)C[C@@]3(CNC(=O)CC(F)(F)F)C[C@@H]23)c2c(C)cccc12] | (1R,3S,5R)-2-(2-(3-acetyl-7-methyl-1H-indazol-1-yl)acetyl)-N-(6-bromo-3-methylpyridin-2-yl)-5-((3,3,3-trifluoropropanamido) methyl)-2-azabicyclo[3.1.0]hexane-3-carboxamide | *** | 3.39 (B) | 649 |
| T-36 | 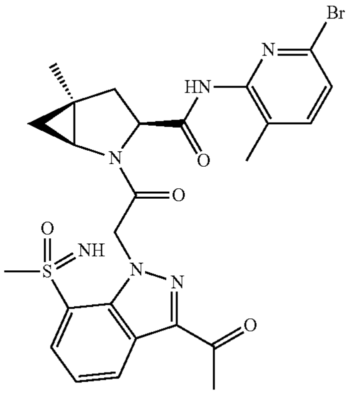 [SMILES: CC(=O)c1nn(CC(=O)N2[C@H]3C[C@@]3(C)C[C@H]2C(=O)Nc2nc(Br)ccc2C)c2c(S(C)(=N)=O)cccc12] | (1S,3S,5S)-2-(2-(3-acetyl-7-(S-methylsulfonimidoyl)-1H-indazol-1-yl)acetyl)-N-(6-bromo-3-methylpyridin-2-yl)-5-methyl-2-azabicyclo[3.1.0]hexane-3-carboxamide | * | 2.49 (B) | 587 |

TABLE 5-continued

Non-limiting Examples of Compounds of the Present Invention

| Cmp No. | Structure | Name | $IC_{50}$ (Stars) | RT min (Method A, B, C or D) | MS (M + 1) |
|---|---|---|---|---|---|
| T-37 | 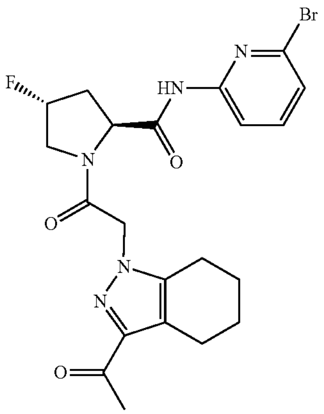 [SMILES: CC(=O)c1nn(CC(=O)N2C[C@H](F)C[C@H]2C(=O)Nc2cccc(Br)n2)c2c1CCCC2] | (2S,4R)-1-(2-(3-acetyl-4,5,6,7-tetrahydro-1H-indazol-1-yl)acetyl)-N-(6-bromopyridin-2-yl)-4-fluoropyrrolidine-2-carboxamide | ** | 1.84 (A) | 492 |
| T-38 | 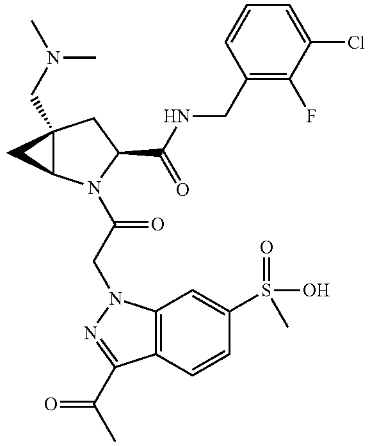 | (3-acetyl-1-(2-((1S,3S,5S)-3-((3-chloro-2-fluorobenzyl)carbamoyl)-5-((dimethylamino)methyl)-2-azabicyclo[3.1.0]hexan-2-yl)-2-oxoethyl)-1H-indazol-6-yl)(methyl)phosphinic acid | ** | 3.64 (B) | 604 |
| T-39 | 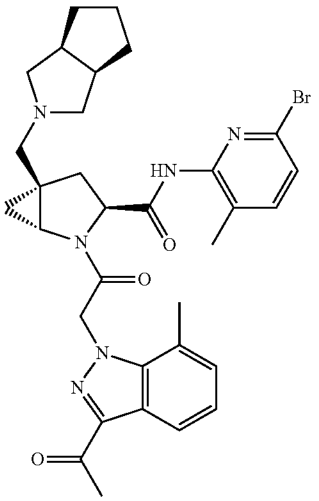 [SMILES: CC(=O)c1nn(CC(=O)N2[C@H](C(=O)Nc3nc(Br)ccc3C)C[C@@]3(CN4C[C@H]5CCC[C@H]5C4)C[C@@H]23)c2c(C)cccc12] | (1R,3S,5R)-2-(2-(3-acetyl-7-methyl-1H-indazol-1-yl)acetyl)-N-(6-bromo-3-methylpyridin-2-yl)-5-(((3aR,6aS)-hexahydrocyclopenta[c]pyrrol-2(1H)-yl)methyl)-2-azabicyclo[3.1.0]hexane-3-carboxamide | *** | 2.58 (B) | 633 |

TABLE 5-continued

| Non-limiting Examples of Compounds of the Present Invention | | | | | |
|---|---|---|---|---|---|
| Cmp No. | Structure | Name | $IC_{50}$ (Stars) | RT min (Method A, B, C or D) | MS (M + 1) |
| T-40 | 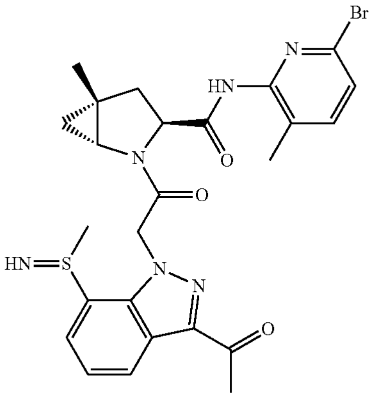 [SMILES: CC(=O)c1nn(CC(=O)N2[C@H](C(=O)Nc3nc(Br)ccc3C)C[C@@]3(C)C[C@@H]23)c2c(S(C)=N)cccc12] | (1R,3S,5R)-2-(2-(3-acetyl-7-(S-methylsulfinimidoyl)-1H-indazol-1-yl)acetyl)-N-(6-bromo-3-methylpyridin-2-yl)-5-methyl-2-azabicyclo[3.1.0]hexane-3-carboxamide | *** | 2.03 (B) | 571 |
| T-41 | 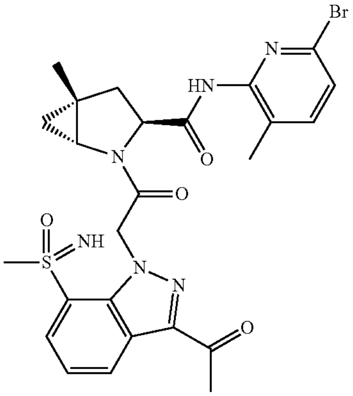 [SMILES: CC(=O)c1nn(CC(=O)N2[C@H](C(=O)Nc3nc(Br)ccc3C)C[C@@]3(C)C[C@@H]23)c2c(S(C)(=N)=O)cccc12] | (1R,3S,5R)-2-(2-(3-acetyl-7-(S-methylsulfonimidoyl)-1H-indazol-1-yl)acetyl)-N-(6-bromo-3-methylpyridin-2-yl)-5-methyl-2-azabicyclo[3.1.0]hexane-3-carboxamide | *** | 2.39 (B) | 587 |
| T-42 | 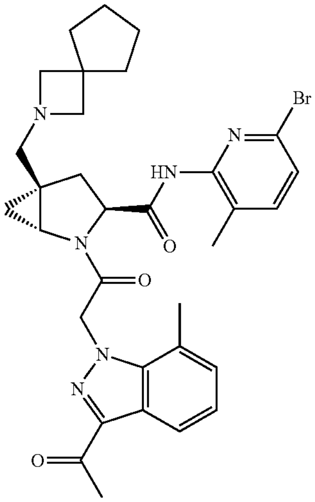 [SMILES: CC(=O)c1nn(CC(=O)N2[C@H](C(=O)Nc3nc(Br)ccc3C)C[C@@]3(CN4CC5(CCCC5)C4)C[C@@H]23)c2c(C)cccc12] | (1R,3S,5R)-5-(2-azaspiro[3,4]octan-2-ylmethyl)-2-(2-(3-acetyl-7-methyl-1H-indazol-1-yl)acetyl)-N-(6-bromo-3-methylpyridin-2-yl)-2-azabicyclo[3.1.0]hexane-3-carboxamide | *** | 3.09 (B) | 633 |

TABLE 5-continued

| Non-limiting Examples of Compounds of the Present Invention | | | | | |
|---|---|---|---|---|---|
| Cmp No. | Structure | Name | $IC_{50}$ (Stars) | RT min (Method A, B, C or D) | MS (M + 1) |
| T-43 | 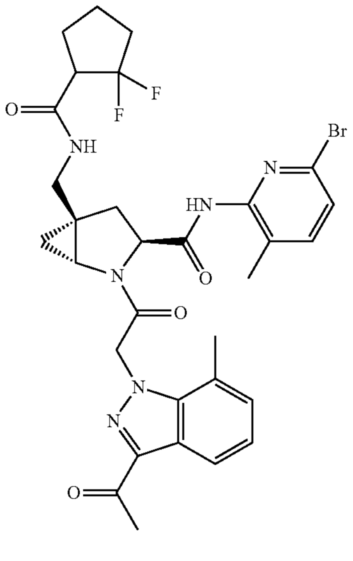 [SMILES: CC(=O)c1nn(CC(=O)N2[C@H](C(=O)Nc3nc(Br)ccc3C)C[C@@]3(CNC(=O)C4CCCC4(F)F)C[C@@H]23)c2c(C)cccc12] | (1R,3S,5R)-2-(2-(3-acetyl-7-methyl-1H-indazol-1-yl)acetyl)-N-(6-bromo-3-methylpyridin-2-yl)-5-((2,2-difluorocyclopentane-1-carboxamido)methyl)-2-azabicyclo[3.1.0]hexane-3-carboxamide | *** | 3.42 (B) | 671 |
| T-44 | 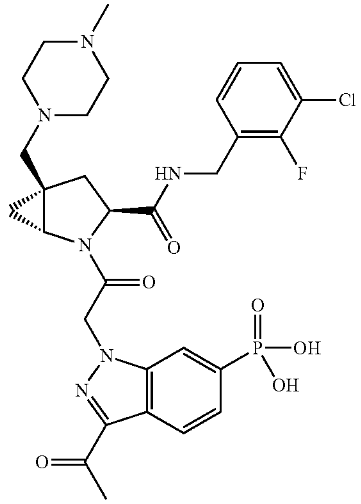 [SMILES: CC(=O)c1nn(CC(=O)N2[C@H](C(=O)NCc3cccc(Cl)c3F)C[C@@]3(CN4CCN(C)CC4)C[C@@H]23)c2cc(P(=O)(O)O)ccc12] | (3-acetyl-1-(2-((1R,3S,5R)-3-((3-chloro-2-fluorobenzyl)carbamoyl)-5-((4-methylpiperazin-1-yl)methyl)-2-azabicyclo[3.1.0]hexan-2-yl)-2-oxoethyl)-1H-indol-6-yl)phosphonic acid | *** | 1.26 (B) | 660 |

TABLE 5-continued

| Cmp No. | Structure | Name | $IC_{50}$ (Stars) | RT min (Method A, B, C or D) | MS (M + 1) |
|---|---|---|---|---|---|
| Non-limiting Examples of Compounds of the Present Invention | | | | | |
| T-45 | 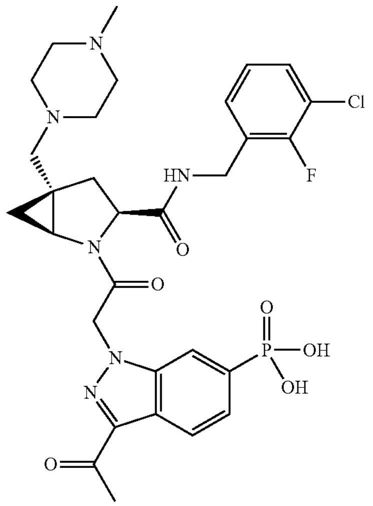 [SMILES: CC(=O)c1nn(CC(=O)N2[C@H]3C[C@@]3(CN3CCN(C)CC3)C[C@H]2C(=O)NCc2cccc(Cl)c2F)c2cc(P(=O)(O)O)ccc12] | (3-acetyl-1-(2-((1S,3S,5S)-3-((3-chloro-2-fluorobenzyl)carbamoyl)-5-((4-methylpiperazin-1-yl)methyl)-2-azabicyclo[3.1.0]hexan-2-yl)-2-oxoethyl)-1H-indol-6-yl)phosphonic acid | ** | 1.87 (B) | 660 |
| T-46 | 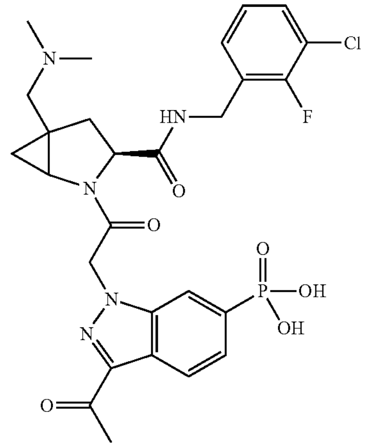 [SMILES: CC(=O)c1nn(CC(=O)N2C3CC3(CN(C)C)C[C@H]2C(=O)NCc2cccc(Cl)c2F)c2cc(P(=O)(O)O)ccc12] | (3-acetyl-1-(2-((3S)-3-((3-chloro-2-fluorobenzyl)carbamoyl)-5-((dimethylamino)methyl)-2-azabicyclo[3.1.0]hexan-2-yl)-2-oxoethyl)-1H-indol-6-yl)phosphonic acid | ** | 3.27 (B) | 605 |
| T-47 | 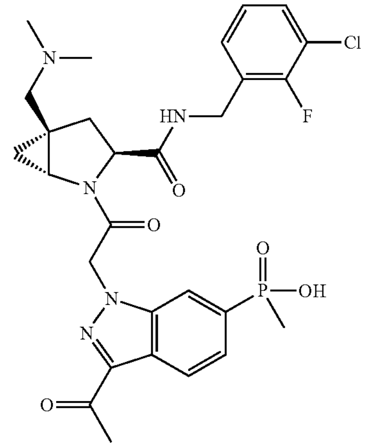 [SMILES: CC(=O)c1nn(CC(=O)N2[C@H](C(=O)NCc3cccc(Cl)c3F)C[C@@]3(CN(C)C)C[C@@H]23)c2cc(P(C)(=O)O)ccc12] | (3-acetyl-1-(2-((1R,3S,5R)-3-((3-chloro-2-fluorobenzyl)carbamoyl)-5-((dimethylamino)methyl)-2-azabicyclo[3.1.0]hexan-2-yl)-2-oxoethyl)-1H-indol-6-yl)(methyl)phosphinic acid | *** | 2.35 (B) | 603 |

TABLE 5-continued

| Non-limiting Examples of Compounds of the Present Invention | | | | | |
|---|---|---|---|---|---|
| Cmp No. | Structure | Name | $IC_{50}$ (Stars) | RT min (Method A, B, C or D) | MS (M + 1) |
| T-48 | 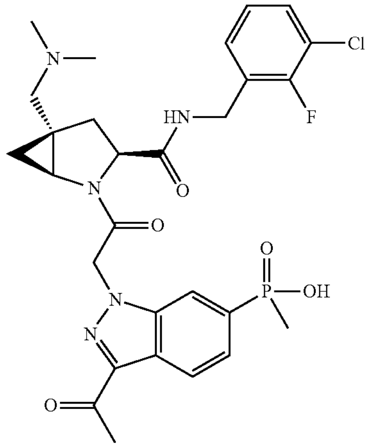 | (3-acetyl-1-(2-((1S,3S,5S)-3-((3-chloro-2-fluorobenzyl)carbamoyl)-5-((dimethylamino)methyl)-2-azabicyclo[3.1.0]hexan-2-yl)-2-oxoethyl)-1H-indol-6-yl)(methyl)phosphinic acid | ** | 2.43 (B) | 603 |
| T-49 | 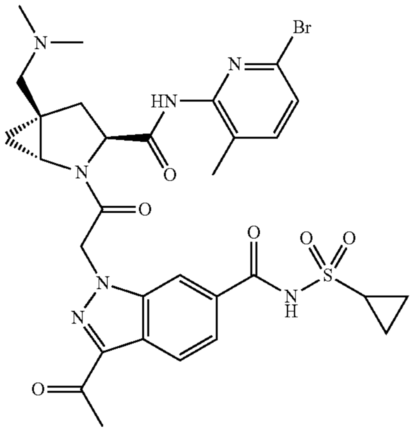 [SMILES: CC(=O)c1nn(CC(=O)N2[C@H](C(=O)Nc3nc(Br)ccc3C)C[C@@]3(CN(C)C)C[C@@H]23)c2cc(C(=O)NS(=O)(=O)C3CC3)ccc12] | 3-acetyl-1-(2-((1R,3S,5R)-3-((6-bromo-3-methylpyridin-2-yl)carbamoyl)-5-((dimethylamino)methyl)-2-azabicyclo[3.1.0]hexan-2-yl)-2-oxoethyl)-N-(cyclopropylsulfonyl)-1H-indazole-6-carboxamide | *** | 2.16 (B) | 700 |
| T-50 | 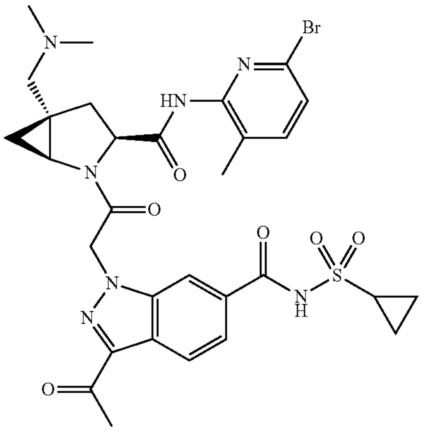 [SMILES: CC(=O)c1nn(CC(=O)N2[C@H]3C[C@@]3(CN(C)C)C[C@H]2C(=O)Nc2nc(Br)ccc2C)c2cc(C(=O)NS(=O)(=O)C3CC3)ccc12] | 3-acetyl-1-(2-((1S,3S,5S)-3-((6-bromo-3-methylpyridin-2-yl)carbamoyl)-5-((dimethylamino)methyl)-2-azabicyclo[3.1.0]hexan-2-yl)-2-oxoethyl)-N-(cyclopropylsulfonyl)-1H-indazole-6-carboxamide | ** | 2.21 (B) | 700 |

TABLE 6

Additional Non-limiting Examples of Compounds of the Present Invention

| Cmp No. | Structure | Name | $IC_5$ (Stars) | RT min (Method A, B, C or D) | MS (M + 1) |
|---|---|---|---|---|---|
| T-51 | 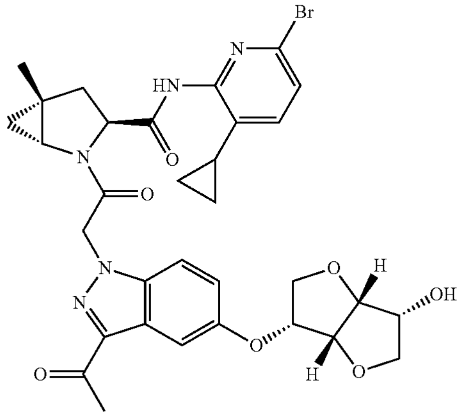 [SMILES: CC(=O)c1nn(CC(=O)N2[C@H](C(=O)Nc3nc(Br)ccc3C3CC3)C[C@@]3(C)C[C@@H]23)c2ccc(O[C@@H]3CO[C@H]4[C@@H]3OC[C@H]4O)cc12] | (1R,3S,5R)-2-(2-(3-acetyl-5-(((3R,3aR,6R,6aR)-6-hydroxy-hexahydrofuro[3,2-b]furan-3-yl)oxy)-1H-indazol-1-yl)acetyl)-N-(6-bromo-3-cyclopropyl-pyridin-2-yl)-5-methyl-2-azabicyclo[3.1.0]hexane-3-carboxamide | *** | 2.88 (B) | 681 |
| T-52 | 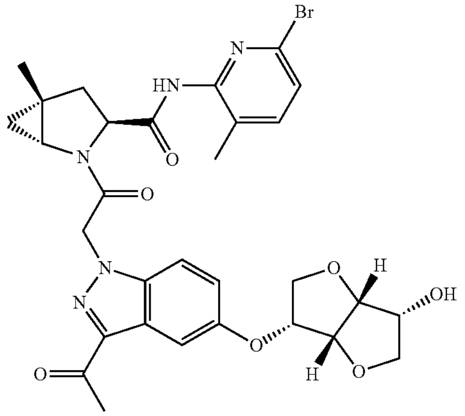 [SMILES: CC(=O)c1nn(CC(=O)N2[C@H](C(=O)Nc3nc(Br)ccc3C)C[C@@]3(C)C[C@@H]23)c2ccc(O[C@@H]3CO[C@H]4[C@@H]3OC[C@H]4O)cc12] | (1R,3S,5R)-2-(2-(3-acetyl-5-(((3R,3aR,6R,6aR)-6-hydroxy-hexahydrofuro[3,2-b]furan-3-yl)oxy)-1H-indazol-1-yl)acetyl)-N-(6-bromo-3-methylpyridin-2-yl)-5-methyl-2-azabicyclo[3.1.0]hexane-3-carboxamide | *** | 3.02 (B) | 655 |
| T-53 | 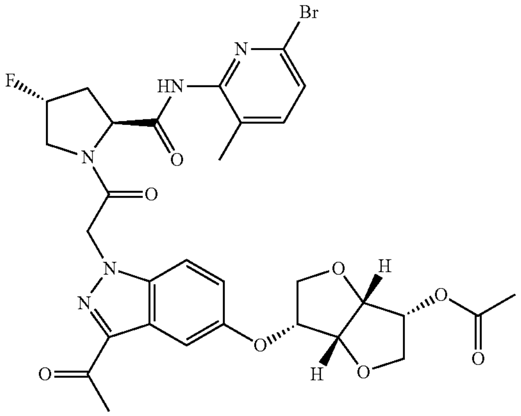 [SMILES: CC(=O)O[C@@H]1CO[C@H]2[C@@H]1OC[C@H]2Oc1ccc2c(c1)c(C(C)=O)nn2CC(=O)N1C[C@H](F)C[C@H]1C(=O)Nc1nc(Br)ccc1C] | (3R,3aR,6R,6aR)-6-((3-acetyl-1-(2-((2S,4R)-2-((6-bromo-3-methylpyridin-2-yl)carbamoyl)-4-fluoropyrrolidin-1-yl)-2-oxoethyl)-1H-indazol-5-yl)oxy)hexahydrofuro[3,2-b]furan-3-yl acetate | *** | 2.84 (B) | 688 |

TABLE 6-continued

Additional Non-limiting Examples of Compounds of the Present Invention

| Cmp No. | Structure | Name | IC5 (Stars) | RT min (Method A, B, C or D) | MS (M + 1) |
|---|---|---|---|---|---|
| T-54 | 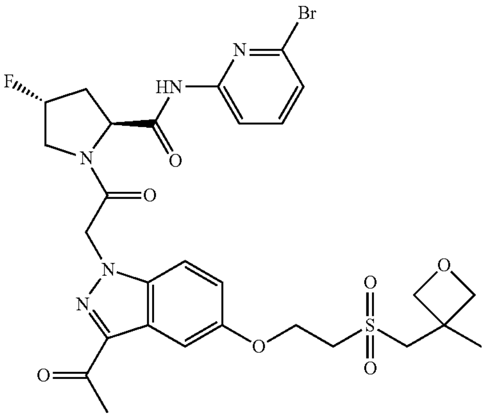 [SMILES: CC(=O)c1nn(CC(=O)N2C[C@H](F)C[C@H]2C(=O)Nc2cccc(Br)n2)c2ccc(OCCS(=O)(=O)CC3(C)COC3)cc12] | (2S,4R)-1-(2-(3-acetyl-5-(2-(((3-methyloxetan-3-yl)methyl)sulfonyl)ethoxy)-1H-indazol-1-yl)acetyl)-N-(6-bromopyridin-2-yl)-4-fluoro-pyrrolidine-2-carboxamide | *** | 2.93 (B) | 680 |
| T-55 | 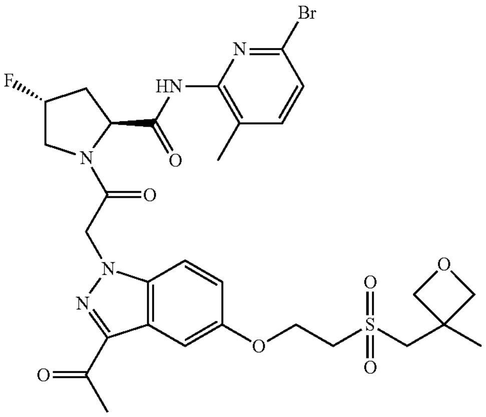 [SMILES: CC(=O)c1nn(CC(=O)N2C[C@H](F)C[C@H]2C(=O)Nc2nc(Br)ccc2C)c2ccc(OCCS(=O)(=O)CC3(C)COC3)cc12] | (2S,4R)-1-(2-(3-acetyl-5-(2-(((3-methyloxetan-3-yl)methyl)sulfonyl)ethoxy)-1H-indazol-1-yl)acetyl)-N-(6-bromo-3-methylpyridin-2-yl)-4-fluoro-pyrrolidine-2-carboxamide | *** | 2.57 (B) | 694 |
| T-56 | 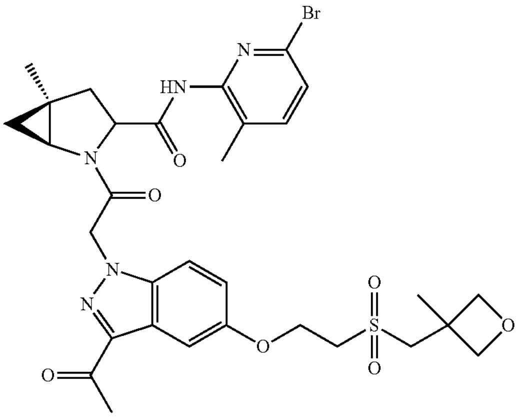 [SMILES: CC(=O)c1nn(CC(=O)N2C(C(=O)Nc3nc(Br)ccc3C)C[C@]3(C)C[C@H]23)c2ccc(OCCS(=O)(=O)CC3(C)COC3)cc12] | (1S,5S)-2-(2-(3-acetyl-5-(2-(((3-methyloxetan-3-yl)methyl)sulfonyl)ethoxy)-1H-indazol-1-yl)acetyl)-N-(6-bromo-3-methylpyridin-2-yl)-5-methyl-2-azabicyclo[3.1.0]hexane-3-carboxamide | ** | 3.13 (B) | 702 |

TABLE 6-continued

Additional Non-limiting Examples of Compounds of the Present Invention

| Cmp No. | Structure | Name | $IC_5$ (Stars) | RT min (Method A, B, C or D) | MS (M + 1) |
|---|---|---|---|---|---|
| T-57 | 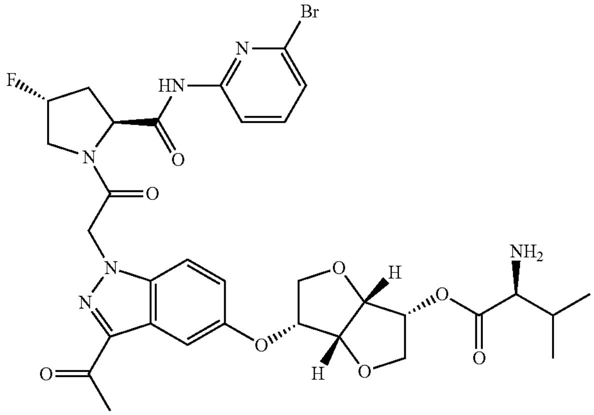 [SMILES: CC(=O)c1nn(CC(=O)N2C[C@H](F)C[C@H]2C(=O)Nc2cccc(Br)n2)c2ccc(O[C@@H]3CO[C@H]4[C@@H]3OC[C@H]4OC(=O)[C@@H](N)C(C)C)cc12] | (3R,3aR,6R, 6aR)-6-((3-acetyl-1-(2-((2S,4R)-2-((6-bromopyridin-2-yl)carbamoyl)-4-fluoropyrrolidin-1-yl)-2-oxoethyl)-1H-indazol-5-yl)oxy) hexahydrofuro [3,2-b]furan-3-yl L-valinate | *** | 2.67 (B) | 731 |
| T-58 | 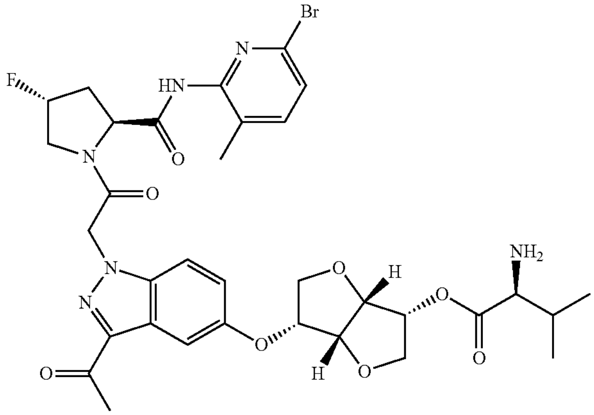 [SMILES: CC(=O)c1nn(CC(=O)N2C[C@H](F)C[C@H]2C(=O)Nc2nc(Br)ccc2C)c2ccc(O[C@@H]3CO[C@H]4[C@@H]3OC[C@H]4OC(=O)[C@@H](N)C(C)C)cc12] | (3R,3aR,6R, 6aR)-6-((3-acetyl-1-(2-((2S,4R)-2-((6-bromo-3-methylpyridin-2-yl)carbamoyl)-4-fluoropyrrolidin-1-yl)-2-oxoethyl)-lH-indazol-5-yl)oxy) hexahydrofuro [3,2-b]furan-3-yl L-valinate | *** | 2.36 (B) | 745 |
| T-59 | 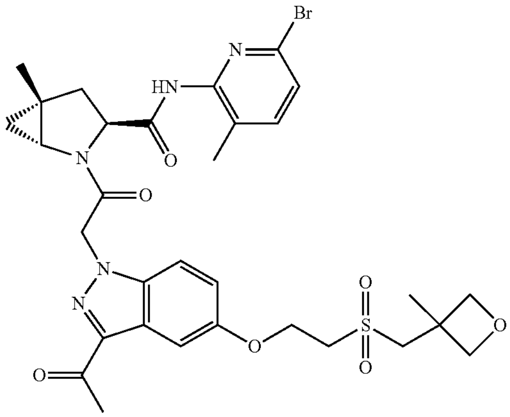 [SMILES: CC(=O)c1nn(CC(=O)N2[C@H](C(=O)Nc3nc(Br)ccc3C)C[C@@]3(C)C[C@@H]23)c2ccc(OCCS(=O)(=O)CC3(C)COC3)cc12] | (1R,5R)-2-(2-(3-acetyl-5-(2-(((3-methyloxetan-3-yl)methyl) sulfonyl) ethoxy)-1H-indazol-1-yl)acetyl)-N-(6-bromo-3-methylpyridin-2-yl)-5-methyl-2-azabicyclo [3.1.0]hexane-3-carboxamide | *** | 3.07 (B) | 702 |

TABLE 6-continued
Additional Non-limiting Examples of Compounds of the Present Invention
| Cmp No. | Structure | Name | $IC_5$ (Stars) | RT min (Method A, B, C or D) | MS (M + 1) |
|---|---|---|---|---|---|
| T-60 | 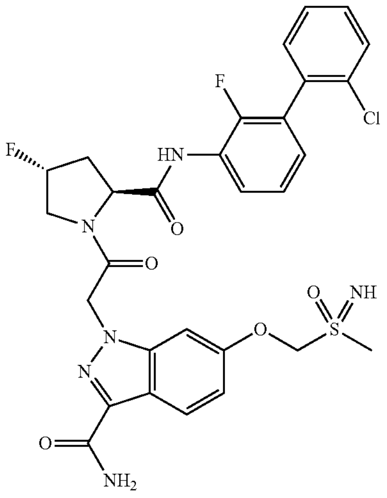 [SMILES: CS(=N)(=O)COc1ccc2c(C(N)=O)nn(CC(=O)N3C[C@H](F)C[C@H]3C(=O)Nc3cccc(-c4ccccc4Cl)c3F)c2c1] | 1-(2-((2S,4R)-2-((2'-chloro-2-fluoro-[1,1'-biphenyl]-3-yl)carbamoyl)-4-fluoropyrrolidin-1-yl)-2-oxoethyl)-6-((S-methyl sulfonimidoyl) methoxy)-1H-indazole-3-carboxamide | *** | 1.63 (A) | 644 |
| T-61 | 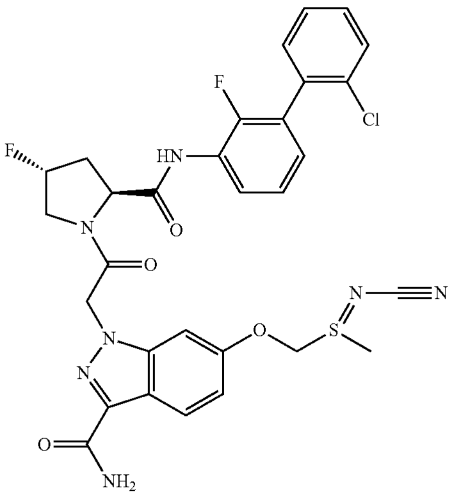 [SMILES: C/S(COc1ccc2c(C(N)=O)nn(CC(=O)N3C[C@H](F)C[C@H]3C(=O)Nc3cccc(-c4ccccc4Cl)c3F)c2c1)=N\C#N] | | *** | 1.68 (A) | 653 |

TABLE 6-continued
| Additional Non-limiting Examples of Compounds of the Present Invention | | | | | |
|---|---|---|---|---|---|
| Cmp No. | Structure | Name | $IC_5$ (Stars) | RT min (Method A, B, C or D) | MS (M + 1) |
| T-62 | 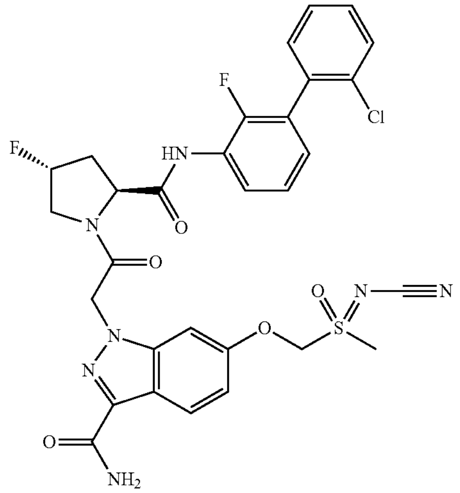 [SMILES: CS(=O)(COc1ccc2c(C(N)=O)nn(CC(=O)N3C[C@H](F)C[C@H]3C(=O)Nc3cccc(-c4ccccc4Cl)c3F)c2c1)=NC#N] | | *** | 1.86 (A) | 669 |
| T-63 | 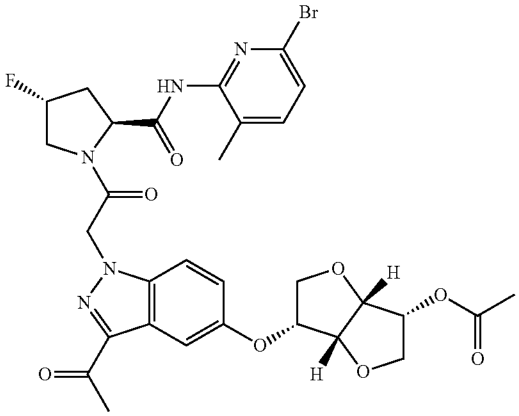 [SMILES: CC(=O)O[C@@H]1CO[C@H]2[C@@H]1OC[C@H]2Oc1ccc2c(c1)c(C(C)=O)nn2CC(=O)N1C[C@H](F)C[C@H]1C(=O)Nc1nc(Br)ccc1C] | (3R,3aR,6R, 6aR)-6-((3-acetyl-1-(2-((2S,4R)-2-((6-bromopyridin-2-yl)carbamoyl)-4-fluoropyrrolidin-1-yl)-2-oxoethyl)-1H-indazol-5-yl)oxy)hexa-hydrofuro[3,2-b]furan-3-yl acetate | *** | 2.51 (B) | 674 |

TABLE 7
| Cmp No. | Structure and Name | $IC_5$ (Stars) | RT min (Method A, B, C, or D) | MS (M + 1) |
|---|---|---|---|---|
| T-64 | 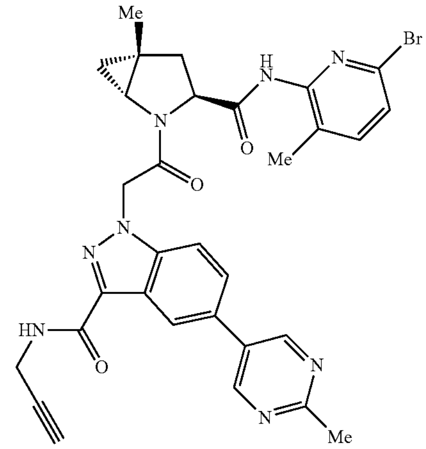 [SMILES: C#CCNC(=O)c1nn(CC(=O)N2[C@H](C(=O)Nc3nc(Br)ccc3C)C[C@@]3(C)C[C@@H]23)c2ccc(-c3cnc(C)nc3)cc12] 1-(2-((1R,3S,5R)-3-((6-bromo-3-methylpyridin-2-yl)carbamoyl)-5-methyl-2-azabicyclo[3.1.0]hexan-2-yl)-2-oxoethyl)-5-(2-methylpyrimidin-5-yl)-N-(prop-2-yn-1-yl)-1H-indazole-3-carboxamide | *** | 1.73 (A) | 640 |
| T-65 | 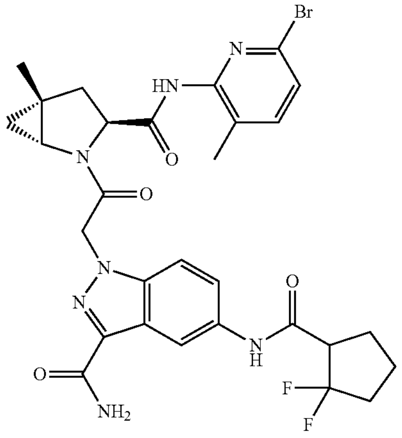 [SMILES: Cc1ccc(Br)nc1NC(=O)[C@@H]1C[C@@]2(C)C[C@H]2N1C(=O)Cn1nc(C(N)=O)c2cc(NC(=O)C3CCCC3(F)F)ccc21] 1-(2-((1R,3S,5R)-3-((6-bromo-3-methylpyridin-2-yl)carbamoyl)-5-methyl-2-azabicyclo[3.1.0]hexan-2-yl)-2-oxoethyl)-5-(2,2-difluorocyclopentane-1-carboxamido)-1H-indazole-3-carboxamide | *** | 10.20 (D) | 660 (M + 2) |
| T-66 | 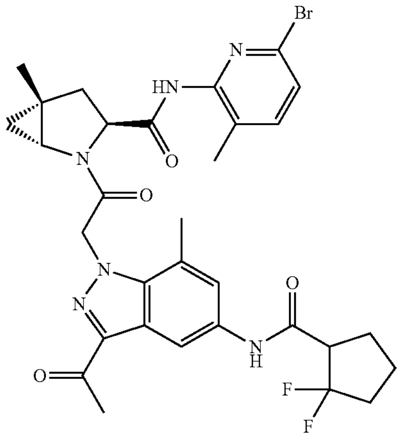 [SMILES: CC(=O)c1nn(CC(=O)N2[C@H](C(=O)Nc3nc(Br)ccc3C)C[C@@]3(C)C[C@@H]23)c2c(C)cc(NC(=O)C3CCCC3(F)F)cc12] | *** | 12.24 (D) | 669 (M − 2) |

TABLE 7-continued

| Cmp No. | Structure and Name | $IC_5$ (Stars) | RT min (Method A, B, C, or D) | MS (M + 1) |
|---|---|---|---|---|
| | (1R,3S,5R)-2-(2-(3-acetyl-5-(2,2-difluorocyclopentane-1-carboxamido)-7-methyl-1H-indazol-1-yl)acetyl)-N-(6-bromo-3-methylpyridin-2-yl)-5-methyl-2-azabicyclo[3.1.0]hexane-3-carboxamide | | | |
| T-67 | 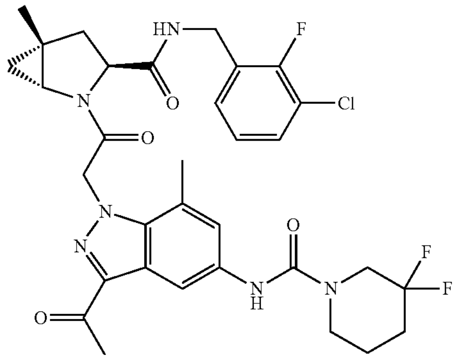 [SMILES: CC(=O)c1nn(CC(=O)N2[C@H](C(=O)NCc3cccc(Cl)c3F)C[C@@]3(C)C[C@@H]23)c2c(C)cc(NC(=O)N3CCCC(F)(F)C3)cc12] (1R,3S,5R)-2-(2-(3-acetyl-5-(3,3-difluoropiperidine-1-carboxamido)-7-methyl-1H-indazol-1-yl)acetyl)-N-(3-chloro-2-fluorobenzyl)-5-methyl-2-azabicyclo[3.1.0]hexane-3-carboxamide | *** | 11.89 (D) | 660 |
| T-68 | 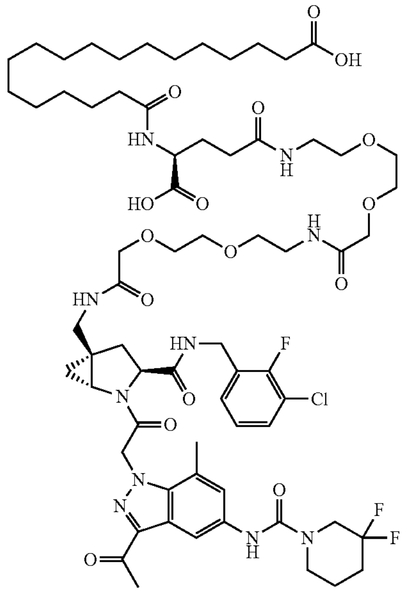 [SMILES: CC(=O)c1nn(CC(=O)N2[C@H](C(=O)NCc3cccc(Cl)c3F)C[C@@]3(CNC(=O)COCCOCCNC(=O)COCCOCCNC(=O)CC[C@H](NC(=O)CCCCCCCCCCCCCCCCC(=O)O)C(=O)O)C[C@@H]23)c2c(C)cc(NC(=O)N3CCCC(F)(F)C3)cc12] (S)-1-((1R,3S,5R)-2-(2-(3-acetyl-5-(3,3-difluoropiperidine-1-carboxamido)-7-methyl-1H-indazol-1-yl)acetyl)-3-((3-chloro-2-fluorobenzyl)carbamoyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid | *** | 8.87 (D) | 1392 (M + 2) |

TABLE 7-continued

| Cmp No. | Structure and Name | IC5 (Stars) | RT min (Method A, B, C, or D) | MS (M + 1) |
|---|---|---|---|---|
| T-69 | 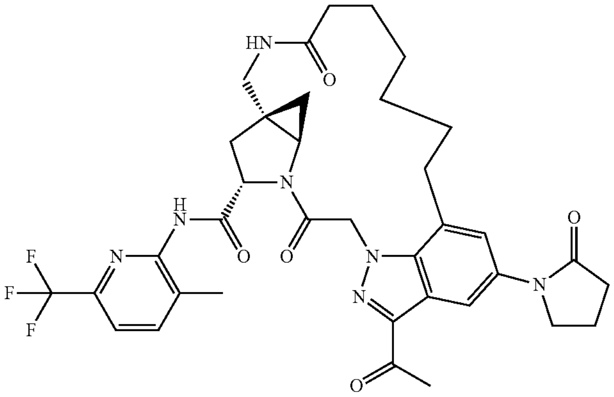 [SMILES: CC(=O)c1nn2c3c(cc(N4CCCC4=O)cc13)CCCCCCC(=O)NC[C@@]13C[C@@H](C(=O)Nc4nc(C(F)(F)F)ccc4C)N(C(=O)C2)[C@@H]1C3] (41R,43S,45R)-13-acetyl-N-(3-methyl-6-(trifluoromethyl)pyridin-2-yl)-3,7-dioxo-15-(2-oxopyrrolidin-1-yl)-11H-42,6-diaza-1(1,7)-indazola-4(2,5)-bicyclo[3.1.0]hexanacyclotridecaphane-43-carboxamide | ND | | |
| T-70 | 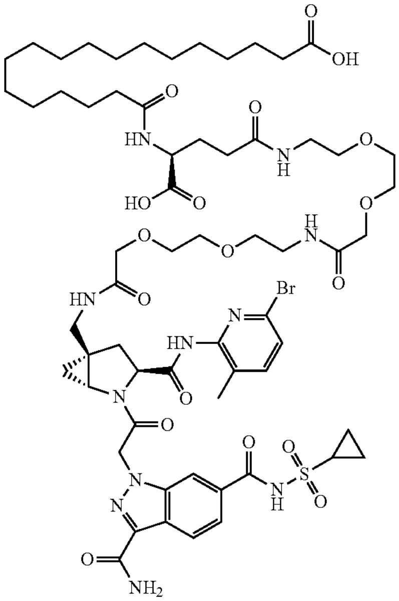 [SMILES: Cc1ccc(Br)nc1NC(=O)[C@@H]1C[C@@]2(CNC(=O)COCCOCCNC(=O)COCCOCCNC(=O)CC[C@H](NC(=O)CCCCCCCCCCCCCCCCC(=O)O)C(=O)O)C[C@H]2N1C(=O)Cn1nc(C(N)=O)c2ccc(C(=O)NS(=O)(=O)C3CC3)cc21] (S)-1-((1R,3S,5R)-3-((6-bromo-3-methylpyridin-2-yl)carbamoyl)-2-(2-(3-carbamoyl-6-((cyclopropylsulfonyl)carbamoyl)-1H-indazol-1-yl)acetyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid | *** | 7.10 (D) | 1391 (M + 2) |

TABLE 7-continued

| Cmp No. | Structure and Name | IC5 (Stars) | RT min (Method A, B, C, or D) | MS (M + 1) |
|---|---|---|---|---|
| T-71 | 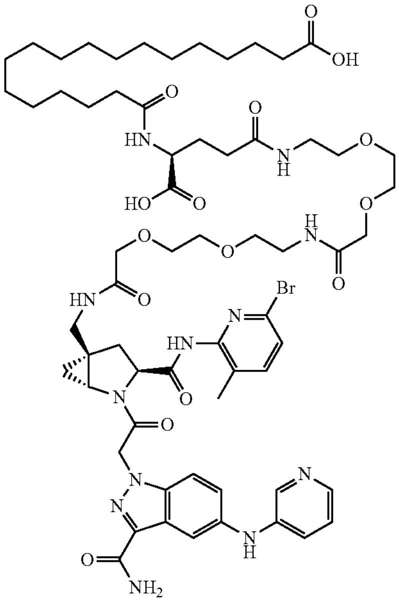 [SMILES: Cc1ccc(Br)nc1NC(=O)[C@@H]1C[C@@]2(CNC(=O)COCCOCCNC(=O)COCCOCCNC(=O)CC[C@H](NC(=O)CCCCCCCCCCCCCCCCC(=O)O)C(=O)O)C[C@H]2N1C(=O)Cn1nc(C(N)=O)c2cc(Nc3cccnc3)ccc21] (S)-1-((1R,3S,5R)-3-((6-bromo-3-methylpyridin-2-yl)carbamoyl)-2-(2-(3-carbamoyl-5-(pyridin-3-ylamino)-1H-indazol-1-yl)acetyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid | *** | | |
| T-72 | 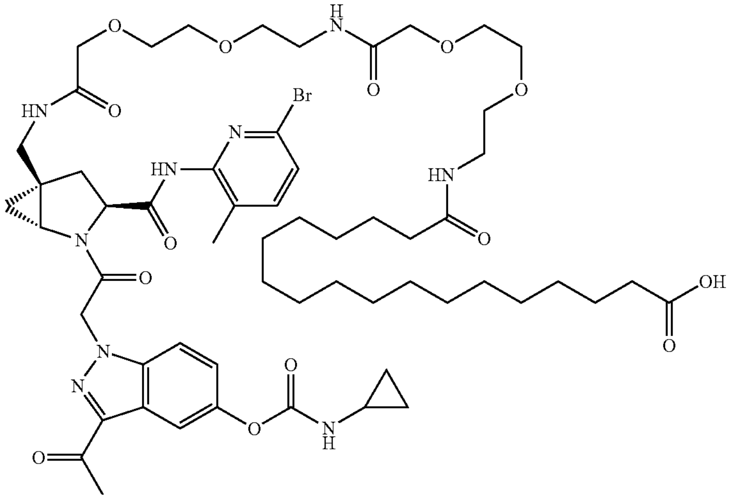 [SMILES: CC(=O)c1nn(CC(=O)N2[C@H](C(=O)Nc3nc(Br)ccc3C)C[C@@]3(CNC(=O)COCCOCCNC(=O)COCCOCCNC(=O)CCCCCCCCCCCCCCCCC(=O)O)C[C@@H]23)c2ccc(OC(=O)NC3CC3)cc12] 1-((1R,3S,5R)-2-(2-(3-acetyl-5-((cyclopropylcarbamoyl)oxy)-1H-indazol-1-yl)acetyl)-3-((6-bromo-3-methylpyridin-2-yl)carbamoyl)-2-azabicyclo[3.1.0]hexan-5-yl)-3,12,21-trioxo-5,8,14,17-tetraoxa-2,11,20-triazaoctatriacontan-38-oic acid | *** | | |

TABLE 7-continued

| Cmp No. | Structure and Name | $IC_5$ (Stars) | RT min (Method A, B, C, or D) | MS (M + 1) |
|---|---|---|---|---|
| T-73 | 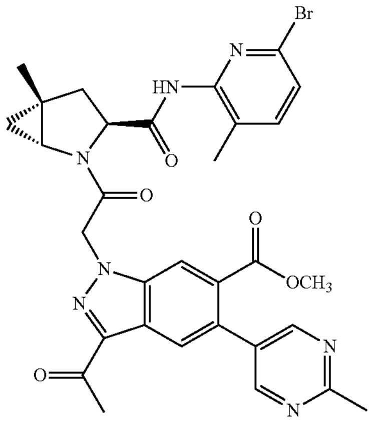 [SMILES: COC(=O)c1cc2c(cc1-c1cnc(C)nc1)c(C(C)=O)nn2CC(=O)N1[C@H](C(=O)Nc2nc(Br)ccc2C)C[C@@]2(C)C[C@@H]12] methyl 3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-5-(2-methylpyrimidin-5-yl)-1H-indazole-6-carboxylate | *** | 1.87 (A) | 660 |
| T-74 | 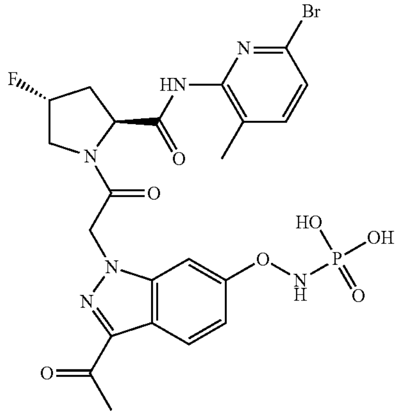 [SMILES: CC(=O)c1nn(CC(=O)N2C[C@H](F)C[C@H]2C(=O)Nc2nc(Br)ccc2C)c2cc(ONP(=O)(O)O)ccc12] (((3-acetyl-1-(2-((2S,4R)-2-((6-bromo-3-methylpyridin-2-yl)carbamoyl)-4-fluoropyrrolidin-1-yl)-2-oxoethyl)-1H-indazol-6-yl)oxy)methyl)phosphonic acid | *** | 9.35 (C) | 613 |
| T-75 | 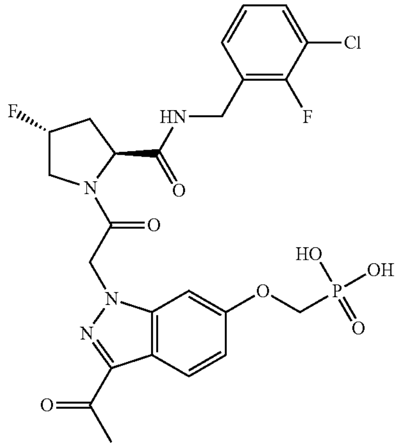 [SMILES: CC(=O)c1nn(CC(=O)N2C[C@H](F)C[C@H]2C(=O)NCc2cccc(Cl)c2F)c2cc(OCP(=O)(O)O)ccc12] (((3-acetyl-1-(2-((2S,4R)-2-((3-chloro-2-fluorobenzyl)carbamoyl)-4-fluoropyrrolidin-1-yl)-2-oxoethyl)-1H-indazol-6-yl)oxy)methyl)phosphonic acid | *** | 7.41 (D) | 587 (M + 2) |

TABLE 7-continued

| Cmp No. | Structure and Name | $IC_5$ (Stars) | RT min (Method A, B, C, or D) | MS (M + 1) |
|---|---|---|---|---|
| T-76 | 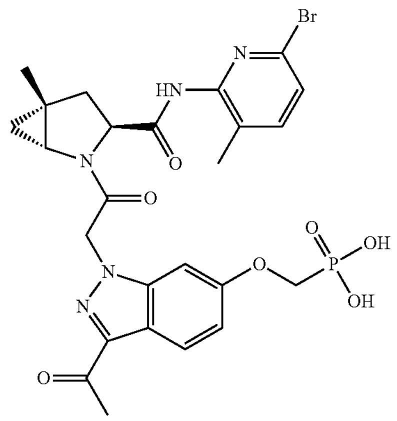 [SMILES: CC(=O)c1nn(CC(=O)N2[C@H](C(=O)Nc3nc(Br)ccc3C)C[C@@]3(C)C[C@@H]23)c2cc(OCP(=O)(O)O)ccc12] (((3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-indazol-6-yl)oxy)methyl)phosphonic acid | *** | 1.55 (A) | 619 |
| T-77 | 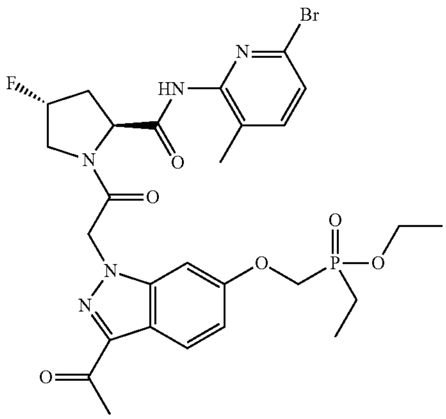 [SMILES: CCOP(=O)(CC)COc1ccc2c(C(C)=O)nn(CC(=O)N3C[C@H](F)C[C@H]3C(=O)Nc3nc(Br)ccc3C)c2c1] ethyl (((3-acetyl-1-(2-((2S,4R)-2-((6-bromo-3-methylpyridin-2-yl)carbamoyl)-4-fluoropyrrolidin-1-yl)-2-oxoethyl)-1H-indazol-6-yl)oxy)methyl)(ethyl)phosphinate | *** | 9.51 (D) | 653 (M + 1) |
| T-78 | 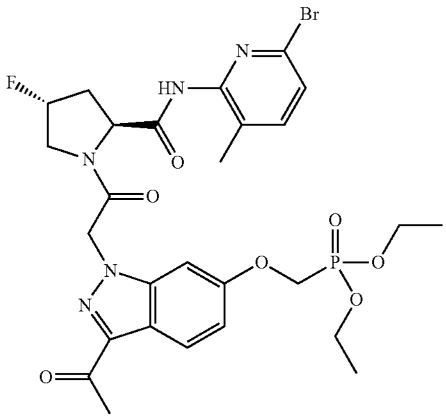 [SMILES: CCOP(=O)(COc1ccc2c(C(C)=O)nn(CC(=O)N3C[C@H](F)C[C@H]3C(=O)Nc3nc(Br)ccc3C)c2c1)OCC] diethyl (((3-acetyl-1-(2-((2S,4R)-2-((6-bromo-3-methylpyridin-2-yl)carbamoyl)-4-fluoropyrrolidin-1-yl)-2-oxoethyl)-1H-indazol-6-yl)oxy)methyl)phosphonate | *** | 10.04 (D) | 666 (M − 2) |

TABLE 7-continued

| Cmp No. | Structure and Name | IC5 (Stars) | RT min (Method A, B, C, or D) | MS (M + 1) |
|---|---|---|---|---|
| T-79 | 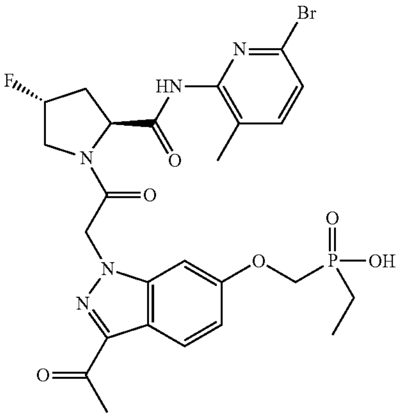 [SMILES: CCP(=O)(O)COc1ccc2c(C(C)=O)nn(CC(=O)N3C[C@H](F)C[C@H]3C(=O)Nc3nc(Br)ccc3C)c2c1] (((3-acetyl-1-(2-((2S,4R)-2-((6-bromo-3-methylpyridin-2-yl)carbamoyl)-4-fluoropyrrolidin-1-yl)-2-oxoethyl)-1H-indazol-6-yl)oxy)methyl)(ethyl)phosphinic acid | *** | 6.93 (D) | 626 (M + 2) |
| T-80 | 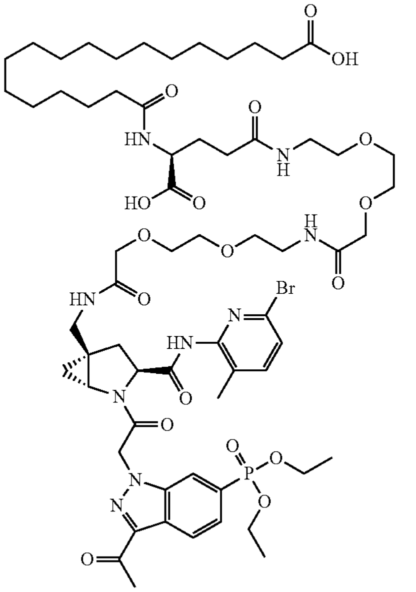 [SMILES: CCOP(=O)(OCC)c1ccc2c(C(C)=O)nn(CC(=O)N3[C@H](C(=O)Nc4nc(Br)ccc4C)C[C@@]4(CNC(=O)COCCOCCNC(=O)COCCOCCNC(=O)CC[C@H](NC(=O)CCCCCCCCCCCCCCCCC(=O)O)C(=O)O)C[C@@H]34)c2c1] (S)-1-((1R,3S,5R)-2-(2-(3-acetyl-6-(diethoxyphosphoryl)-1H-indol-1-yl)acetyl)-3-((6-bromo-3-methylpyridin-2-yl)carbamoyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid | *** | 12.84 (C) | 1378 (M + 2) |

TABLE 7-continued

| Cmp No. | Structure and Name | $IC_5$ (Stars) | RT min (Method A, B, C, or D) | MS (M + 1) |
|---|---|---|---|---|
| T-81 | 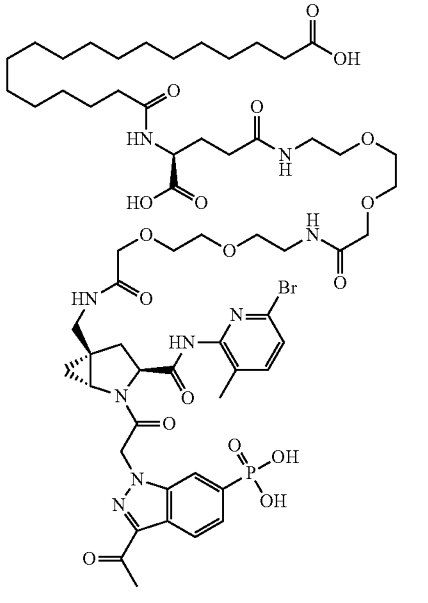 [SMILES: CC(=O)c1nn(CC(=O)N2[C@H](C(=O)Nc3nc(Br)ccc3C)C[C@@]3(CNC(=O)COCCOCCNC(=O)COCCOCCNC(=O)CC[C@H](NC(=O)CCCCCCCCCCCCCCCCC(=O)O)C(=O)O)C[C@@H]23)c2cc(P(=O)(O)O)ccc12] (S)-1-((1R,3S,5R)-2-(2-(3-acetyl-6-phosphono-1H-indol-1-yl)acetyl)-3-((6-bromo-3-methylpyridin-2-yl)carbamoyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid | *** | | |
| T-82 | 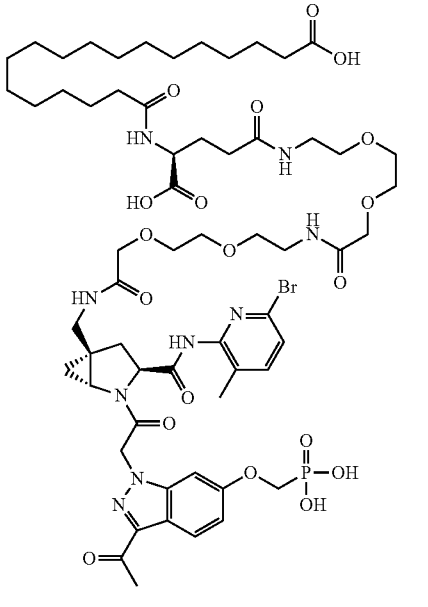 [SMILES: CC(=O)c1nn(CC(=O)N2[C@H](C(=O)Nc3nc(Br)ccc3C)C[C@@]3(CNC(=O)COCCOCCNC(=O)COCCOCCNC(=O)CC[C@H](NC(=O)CCCCCCCCCCCCCCCCC(=O)O)C(=O)O)C[C@@H]23)c2cc(OCP(=O)(O)O)ccc12] (S)-1-((1R,3S,5R)-2-(2-(3-acetyl-6-(phosphonomethoxy)-1H-indol-1-yl)acetyl)-3-((6-bromo-3-methylpyridin-2-yl)carbamoyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid | *** | | |

TABLE 7-continued
| Cmp No. | Structure and Name | $IC_5$ (Stars) | RT min (Method A, B, C, or D) | MS (M + 1) |
|---|---|---|---|---|
| T-83 | 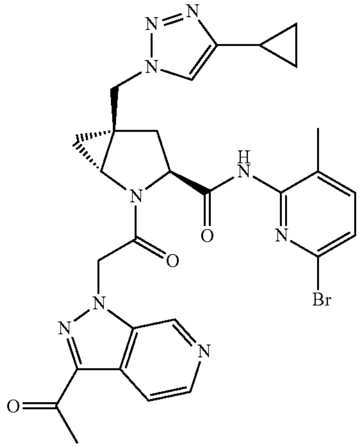 [SMILES: CC(=O)c1nn(CC(=O)N2[C@H](C(=O)Nc3nc(Br)ccc3C)C[C@@]3(Cn4cc(C5CC5)nn4)C[C@@H]23)c2cnccc12] (1R,3S,5R)-2-(2-(3-acetyl-1H-pyrazolo[3,4-c]pyridin-1-yl)acetyl)-N-(6-bromo-3-methylpyridin-2-yl)-5-((4-cyclopropyl-1H-1,2,3-triazol-1-yl)methyl)-2-azabicyclo[3.1.0]hexane-3-carboxamide | *** | 1.37 (A) | 618 |
| T-84 | 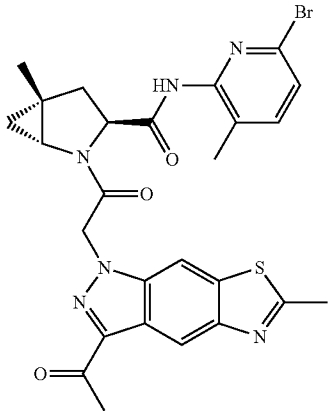 [SMILES: CC(=O)c1nn(CC(=O)N2[C@H](C(=O)Nc3nc(Br)ccc3C)C[C@@]3(C)C[C@@H]23)c2cc3sc(C)nc3cc12] (1R,3S,5R)-2-(2-(3-acetyl-6-methyl-1H-thiazolo[4,5-f]indazol-1-yl)acetyl)-N-(6-bromo-3-methylpyridin-2-yl)-5-methyl-2-azabicyclo[3.1.0]hexane-3-carboxamide | *** | 2.05 (A) | 581 |

TABLE 7-continued
| Cmp No. | Structure and Name | $IC_5$ (Stars) | RT min (Method A, B, C, or D) | MS (M + 1) |
|---|---|---|---|---|
| T-85 | 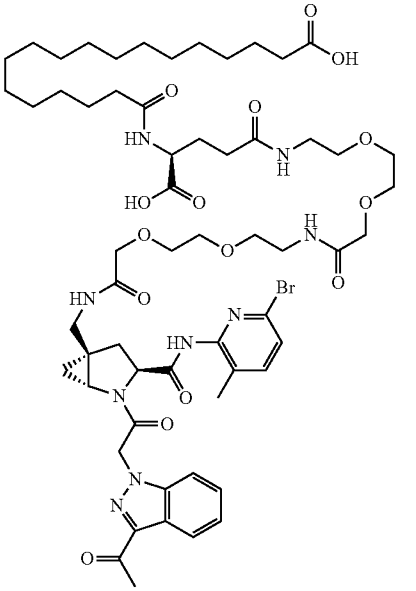 [SMILES: CC(=O)c1nn(CC(=O)N2[C@H](C(=O)Nc3nc(Br)ccc3C)C[C@@]3(CNC(=O)COCCOCCNC(=O)COCCOCCNC(=O)CC[C@H](NC(=O)CCCCCCCCCCCCCCCCC(=O)O)C(=O)O)C[C@@H]23)c2ccccc12] (S)-1-((1R,3S,5R)-2-(2-(3-acetyl-1H-indazol-1-yl)acetyl)-3-((6-bromo-3-methylpyridin-2-yl)carbamoyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid | *** | 13.15 (C) | 1243 (M + 2) |
| T-86 | 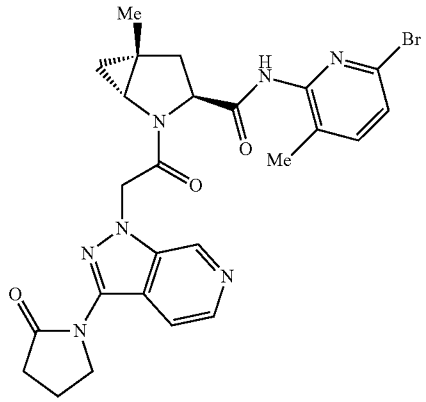 [SMILES: Cc1ccc(Br)nc1NC(=O)[C@@H]1C[C@@]2(C)C[C@H]2N1C(=O)Cn1nc(N2CCCC2=O)c2ccncc21] (1R,3S,5R)-N-(6-bromo-3-methylpyridin-2-yl)-5-methyl-2-(2-(3-(2-oxopyrrolidin-1-yl)-1H-pyrazolo[3,4-c]pyridin-1-yl)acetyl)-2-azabicyclo[3.1.0]hexane-3-carboxamide | * | 1.28 (A) | 552 |

TABLE 7-continued

| Cmp No. | Structure and Name | $IC_5$ (Stars) | RT min (Method A, B, C, or D) | MS (M + 1) |
|---|---|---|---|---|
| T-87 | 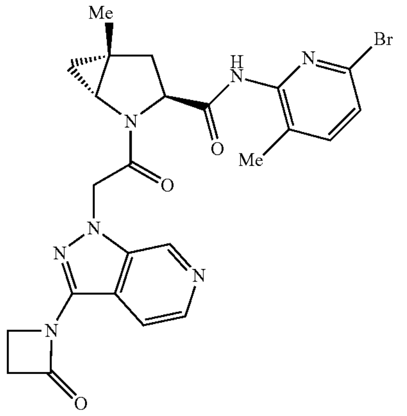 [SMILES: Cc1ccc(Br)nc1NC(=O)[C@@H]1C[C@@]2(C)C[C@H]2N1C(=O)Cn1nc(N2CCC2=O)c2ccncc21] (1R,3S,5R)-N-(6-bromo-3-methylpyridin-2-yl)-5-methyl-2-(2-(3-(2-oxoazetidin-1-yl)-1H-pyrazolo[3,4-c]pyridin-1-yl)acetyl)-2-azabicyclo[3.1.0]hexane-3-carboxamide | *** | 1.25 (A) | 537 |
| T-88 | 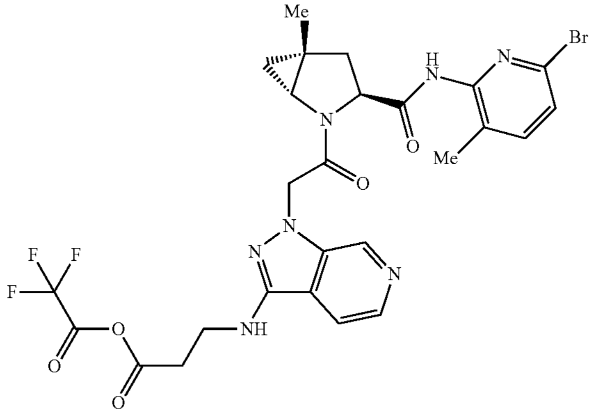 [SMILES: Cc1ccc(Br)nc1NC(=O)[C@@H]1C[C@@]2(C)C[C@H]2N1C(=O)Cn1nc(NCCC(=O)OC(=O)C(F)(F)F)c2ccncc21] 3-((1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-pyrazolo[3,4-c]pyridin-3-yl)amino)propanoic 2,2,2-trifluoroacetic anhydride | ND | | |
| T-89 | 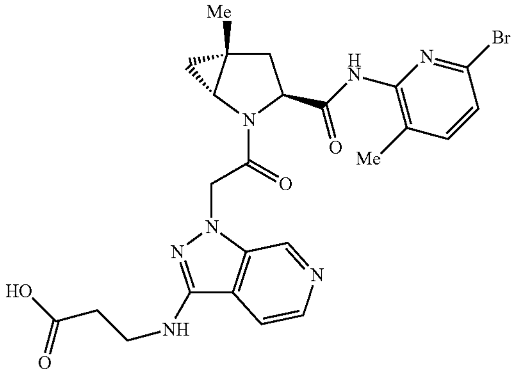 [SMILES: Cc1ccc(Br)nc1NC(=O)[C@@H]1C[C@@]2(C)C[C@H]2N1C(=O)Cn1nc(NCCC(=O)O)c2ccncc21] 3-((1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-pyrazolo[3,4-c]pyridin-3-yl)amino)propanoic acid | * | 0.93 (A) | 556 |

TABLE 7-continued

| Cmp No. | Structure and Name | IC5 (Stars) | RT min (Method A, B, C, or D) | MS (M + 1) |
|---|---|---|---|---|
| T-90 | 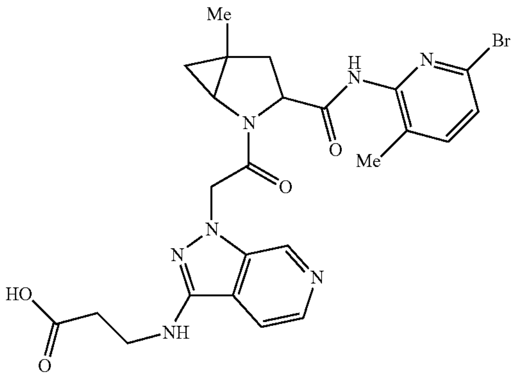 [SMILES: Cc1ccc(Br)nc1NC(=O)C1CC2(C)CC2N1C(=O)Cn1nc(NCCC(=O)O)c2ccncc21] 3-((1-(2-(3-((6-bromo-3-methylpyridin-2-yl)carbamoyl)-5-methyl-2-azabicyclo[3.1.0]hexan-2-yl)-2-oxoethyl)-1H-pyrazolo[3,4-c]pyridin-3-yl)amino)propanoic acid | * | 0.90 (A) | 556 |
| T-91 | 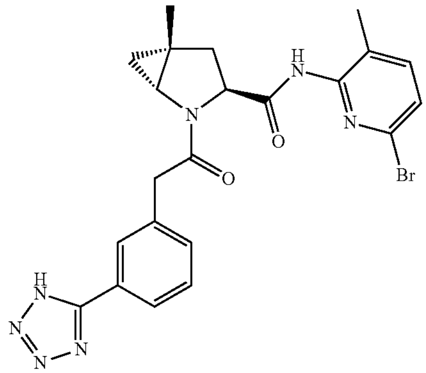 [SMILES: Cc1ccc(Br)nc1NC(=O)[C@@H]1C[C@@]2(C)C[C@H]2N1C(=O)Cc1cccc(-c2nnn[nH]2)c1] (1R,3S,5R)-2-(2-(3-(1H-tetrazol-5-yl)phenyl)acetyl)-N-(6-bromo-3-methylpyridin-2-yl)-5-methyl-2-azabicyclo[3.1.0]hexane-3-carboxamide | * | 2.29 (B) | 496 |
| T-92 | 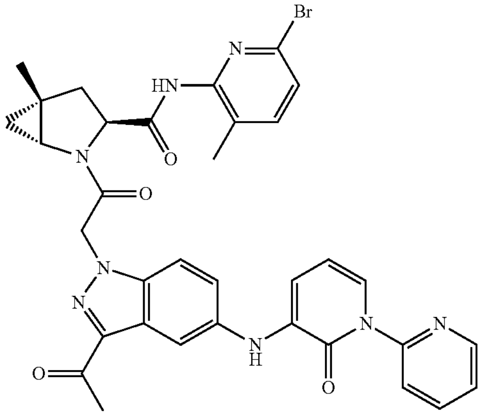 [SMILES: CC(=O)c1nn(CC(=O)N2[C@H](C(=O)Nc3nc(Br)ccc3C)C[C@@]3(C)C[C@@H]23)c2ccc(Nc3cccn(-c4ccccn4)c3=O)cc12] (1R,3S,5R)-2-(2-(3-acetyl-5-((2-oxo-2H-[1,2'-bipyridin]-3-yl)amino)-1H-indazol-1-yl)acetyl)-N-(6-bromo-3-methylpyridin-2-yl)-5-methyl-2-azabicyclo[3.1.0]hexane-3-carboxamide | *** | 3.52 (B) | 695 |

TABLE 7-continued

| Cmp No. | Structure and Name | $IC_5$ (Stars) | RT min (Method A, B, C, or D) | MS (M + 1) |
|---|---|---|---|---|
| T-93 | 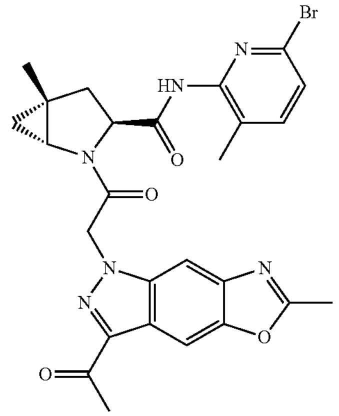 [SMILES: CC(=O)c1nn(CC(=O)N2[C@H](C(=O)Nc3nc(Br)ccc3C)C[C@@]3(C)C[C@@H]23)c2cc3nc(C)oc3cc12] (1R,3S,5R)-2-(2-(3-acetyl-6-methyl-1H-oxazolo[5,4-f]indazol-1-yl)acetyl)-N-(6-bromo-3-methylpyridin-2-yl)-5-methyl-2-azabicyclo[3.1.0]hexane-3-carboxamide | *** | 3.36 (B) | 565 |
| T-94 | 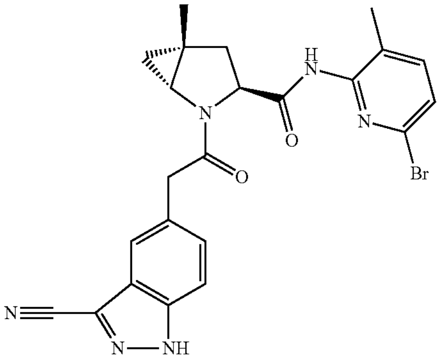 [SMILES: Cc1ccc(Br)nc1NC(=O)[C@@H]1C[C@@]2(C)C[C@H]2N1C(=O)Cc1ccc2[nH]nc(C#N)c2c1] (1R,3S,5R)-N-(6-bromo-3-methylpyridin-2-yl)-2-(2-(3-cyano-1H-indazol-5-yl)acetyl)-5-methyl-2-azabicyclo[3.1.0]hexane-3-carboxamide | * | 3.18 (B) | 493 |
| T-95 | 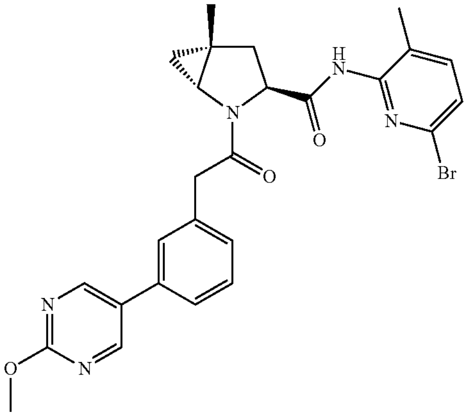 [SMILES: COc1ncc(-c2cccc(CC(=O)N3[C@H](C(=O)Nc4nc(Br)ccc4C)C[C@@]4(C)C[C@@H]34)c2)cn1] (1R,3S,5R)-N-(6-bromo-3-methylpyridin-2-yl)-2-(2-(3-(2-methoxypyrimidin-5-yl)phenyl)acetyl)-5-methyl-2-azabicyclo[3.1.0]hexane-3-carboxamide | * | 3.44 (B) | 536 |

TABLE 7-continued

| Cmp No. | Structure and Name | $IC_5$ (Stars) | RT min (Method A, B, C, or D) | MS (M + 1) |
|---|---|---|---|---|
| T-96 | 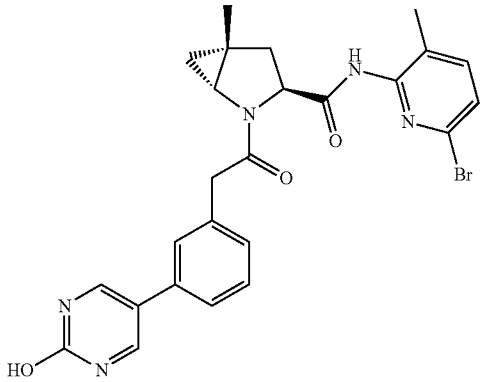 [SMILES: Cc1ccc(Br)nc1NC(=O)[C@@H]1C[C@@]2(C)C[C@H]2N1C(=O)Cc1cccc(-c2cnc(O)nc2)c1] (1R,3S,5R)-N-(6-bromo-3-methylpyridin-2-yl)-2-(2-(3-(2-hydroxypyrimidin-5-yl)phenyl)acetyl)-5-methyl-2-azabicyclo[3.1.0]hexane-3-carboxamide | * | 2.12 (B) | 522 |
| T-97 | 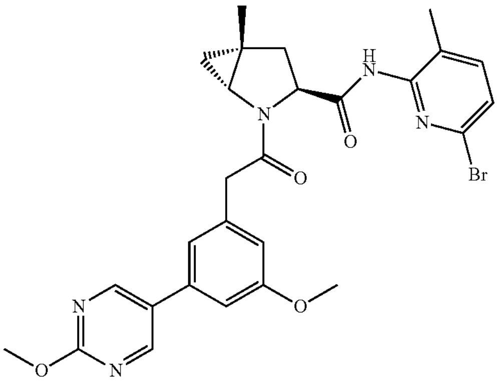 [SMILES: COc1cc(CC(=O)N2[C@H](C(=O)Nc3nc(Br)ccc3C)C[C@@]3(C)C[C@@H]23)cc(-c2cnc(OC)nc2)c1] (1R,3S,5R)-N-(6-bromo-3-methylpyridin-2-yl)-2-(2-(3-methoxy-5-(2-methoxypyrimidin-5-yl)phenyl)acetyl)-5-methyl-2-azabicyclo[3.1.0]hexane-3-carboxamide | ** | 3.13 (B) | 566 |
| T-98 | 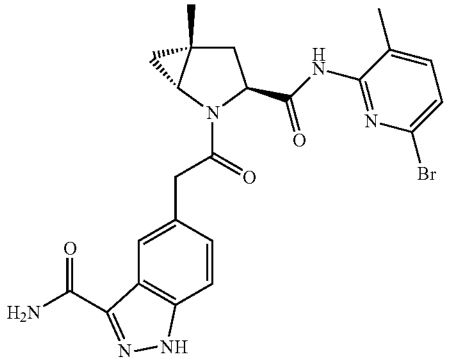 [SMILES: Cc1ccc(Br)nc1NC(=O)[C@@H]1C[C@@]2(C)C[C@H]2N1C(=O)Cc1ccc2[nH]nc(C(N)=O)c2c1] 5-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-indazole-3-carboxamide | * | 2.59 (B) | 511 |

TABLE 7-continued
| Cmp No. | Structure and Name | $IC_5$ (Stars) | RT min (Method A, B, C, or D) | MS (M + 1) |
|---|---|---|---|---|
| T-99 | 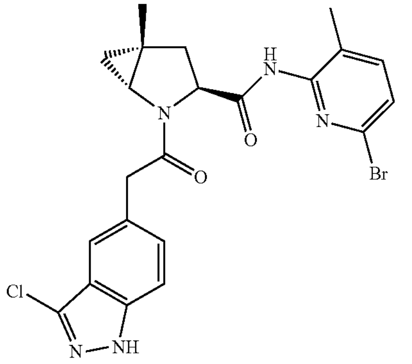 [SMILES: Cc1ccc(Br)nc1NC(=O)[C@@H]1C[C@@]2(C)C[C@H]2N1C(=O)Cc1ccc2[nH]nc(Cl)c2c1] (1R,3S,5R)-N-(6-bromo-3-methylpyridin-2-yl)-2-(2-(3-chloro-1H-indazol-5-yl)acetyl)-5-methyl-2-azabicyclo[3.1.0]hexane-3-carboxamide | ** | 2.86 (B) | 504 |
| T-100 | 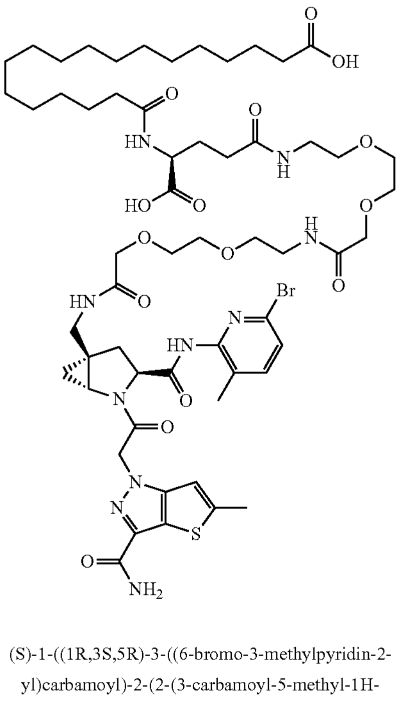 (S)-1-((1R,3S,5R)-3-((6-bromo-3-methylpyridin-2-yl)carbamoyl)-2-(2-(3-carbamoyl-5-methyl-1H-thieno[3,2-c]pyrazol-1-yl)acetyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid | *** | 8.00 (D) | 1264 (M + 2) |

TABLE 7-continued

| Cmp No. | Structure and Name | IC5 (Stars) | RT min (Method A, B, C, or D) | MS (M + 1) |
|---|---|---|---|---|
| T-101 | 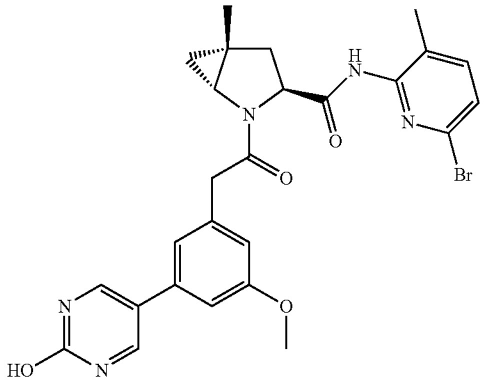 [SMILES: COc1cc(CC(=O)N2[C@H](C(=O)Nc3nc(Br)ccc3C)C[C@@]3(C)C[C@@H]23)cc(-c2cnc(O)nc2)c1] (1R,3S,5R)-N-(6-bromo-3-methylpyridin-2-yl)-2-(2-(3-(2-hydroxypyrimidin-5-yl)-5-methoxyphenyl)acetyl)-5-methyl-2-azabicyclo[3.1.0]hexane-3-carboxamide | *** | 2.27 (B) | 552 |
| T-102 | 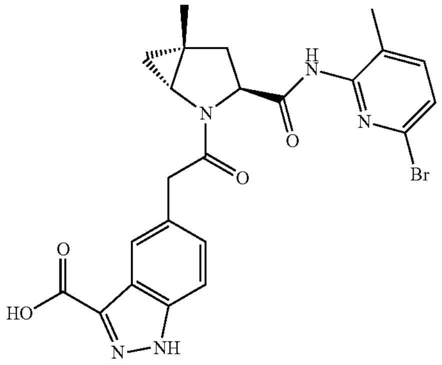 [SMILES: Cc1ccc(Br)nc1NC(=O)[C@@H]1C[C@@]2(C)C[C@H]2N1C(=O)Cc1ccc2[nH]nc(C(=O)O)c2c1] 5-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-indazole-3-carboxylic acid | ** | 2.45 (B) | 512 |
| T-103 | 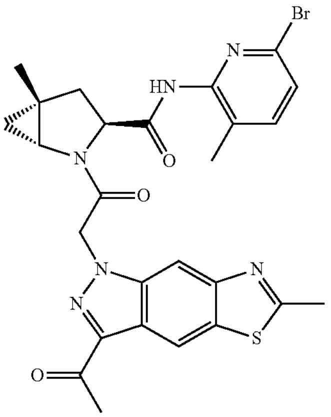 (1R,3S,5R)-2-(2-(3-acetyl-6-methyl-1H-thiazolo[5,4-f]indazol-1-yl)acetyl)-N-(6-bromo-3-methylpyridin-2-yl)-5-methyl-2-azabicyclo[3.1.0]hexane-3-carboxamide | *** | 2.05 (A) | 580 |

TABLE 7-continued

| Cmp No. | Structure and Name | $IC_5$ (Stars) | RT min (Method A, B, C, or D) | MS (M + 1) |
|---|---|---|---|---|
| T-104 | 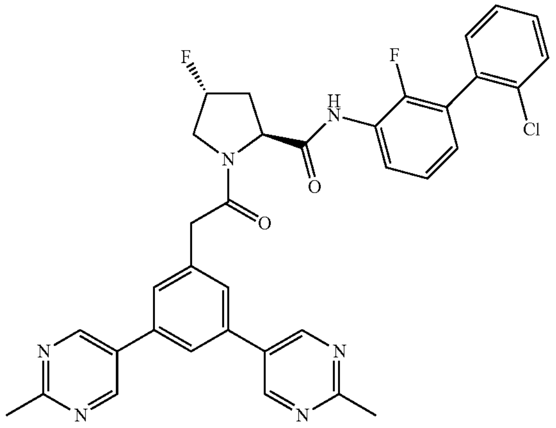 [SMILES: Cc1ncc(-c2cc(CC(=O)N3C[C@H](F)C[C@H]3C(=O)Nc3cccc(-c4ccccc4Cl)c3F)cc(-c3cnc(C)nc3)c2)cn1] (2S,4R)-1-(2-(3,5-bis(2-methylpyrimidin-5-yl)phenyl)acetyl)-N-(2'-chloro-2-fluoro-[1,1'-biphenyl]-3-yl)-4-fluoropyrrolidine-2-carboxamide | * | 2.01 (A) | 638 |
| T-105 | 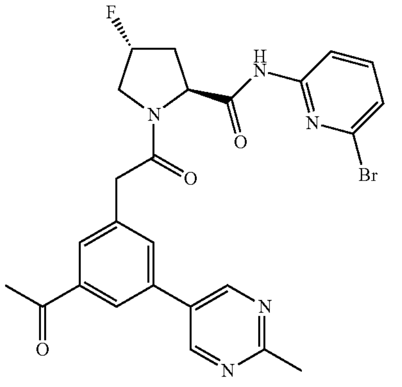 [SMILES: CC(=O)c1cc(CC(=O)N2C[C@H](F)C[C@H]2C(=O)Nc2cccc(Br)n2)cc(-c2cnc(C)nc2)c1] (2S,4R)-1-(2-(3-acetyl-5-(2-methylpyrimidin-5-yl)phenyl)acetyl)-N-(6-bromopyridin-2-yl)-4-fluoropyrrolidine-2-carboxamide | *** | 1.56 (A) | 539 |
| T-106 | 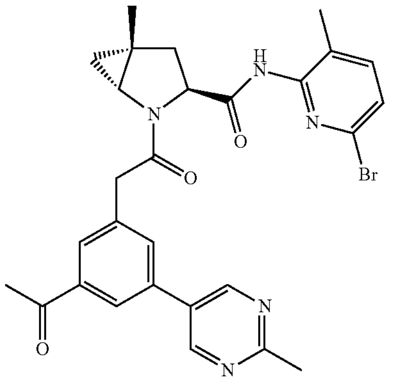 [SMILES: CC(=O)c1cc(CC(=O)N2[C@H](C(=O)Nc3nc(Br)ccc3C)C[C@@]3(C)C[C@@H]23)cc(-c2cnc(C)nc2)c1] (1R,3S,5R)-2-(2-(3-acetyl-5-(2-methylpyrimidin-5-yl)phenyl)acetyl)-N-(6-bromo-3-methylpyridin-2-yl)-5-methyl-2-azabicyclo[3.1.0]hexane-3-carboxamide | *** | 1.69 (A) | 561 |

TABLE 7-continued

| Cmp No. | Structure and Name | IC5 (Stars) | RT min (Method A, B, C, or D) | MS (M + 1) |
|---|---|---|---|---|
| T-107 | 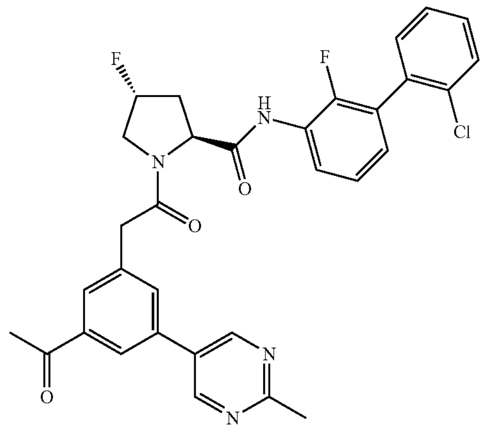 [SMILES: CC(=O)c1cc(CC(=O)N2C[C@H](F)C[C@H]2C(=O)Nc2cccc(-c3ccccc3Cl)c2F)cc(-c2cnc(C)nc2)c1] (2S,4R)-1-(2-(3-acetyl-5-(2-methylpyrimidin-5-yl)phenyl)acetyl)-N-(2'-chloro-2-fluoro-[1,1'-biphenyl]-3-yl)-4-fluoropyrrolidine-2-carboxamide | *** | 2.10 (A) | 588 |
| T-108 | 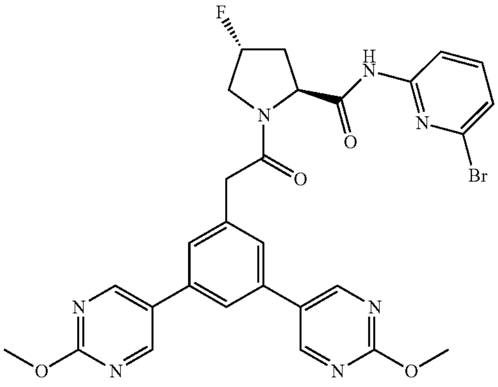 [SMILES: COc1ncc(-c2cc(CC(=O)N3C[C@H](F)C[C@H]3C(=O)Nc3cccc(Br)n3)cc(-c3cnc(OC)nc3)c2)cn1] (2S,4R)-1-(2-(3,5-bis(2-methoxypyrimidin-5-yl)phenyl)acetyl)-N-(6-bromopyridin-2-yl)-4-fluoropyrrolidine-2-carboxamide | * | 1.84 (A) | 621 |
| T-109 | 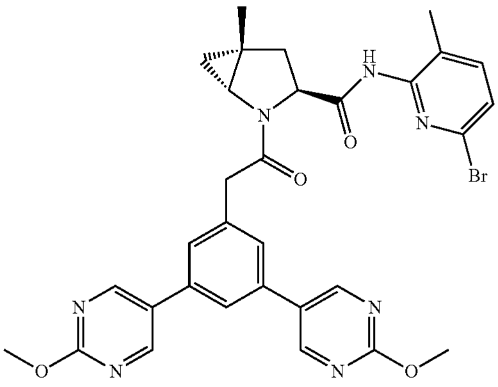 [SMILES: COc1ncc(-c2cc(CC(=O)N3[C@H](C(=O)Nc4nc(Br)ccc4C)C[C@@]4(C)C[C@@H]34)cc(-c3cnc(OC)nc3)c2)cn1] (1R,3S,5R)-2-(2-(3,5-bis(2-methoxypyrimidin-5-yl)phenyl)acetyl)-N-(6-bromo-3-methylpyridin-2-yl)-5-methyl-2-azabicyclo[3.1.0]hexane-3-carboxamide | * | 1.96 (A) | 643 |

TABLE 7-continued

| Cmp No. | Structure and Name | $IC_5$ (Stars) | RT min (Method A, B, C, or D) | MS (M + 1) |
|---|---|---|---|---|
| T-110 | 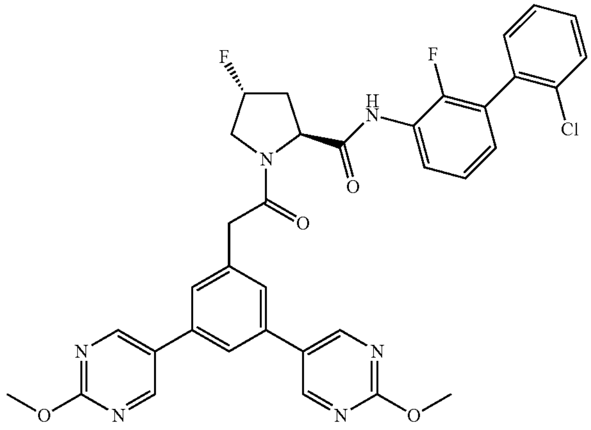 [SMILES: COc1ncc(-c2cc(CC(=O)N3C[C@H](F)C[C@H]3C(=O)Nc3cccc(-c4ccccc4Cl)c3F)cc(-c3cnc(OC)nc3)c2)cn1] (2S,4R)-1-(2-(3,5-bis(2-methoxypyrimidin-5-yl)phenyl)acetyl)-N-(2'-chloro-2-fluoro-[1,1'-biphenyl]-3-yl)-4-fluoropyrrolidine-2-carboxamide | * | 2.29 (A) | 670 |
| T-111 | 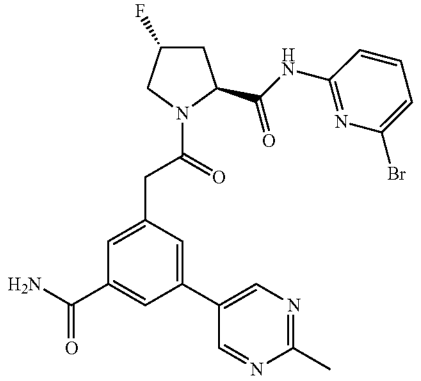 [SMILES: Cc1ncc(-c2cc(CC(=O)N3C[C@H](F)C[C@H]3C(=O)Nc3cccc(Br)n3)cc(C(N)=O)c2)cn1] (2S,4R)-N-(6-bromopyridin-2-yl)-1-(2-(3-carbamoyl-5-(2-methylpyrimidin-5-yl)phenyl)acetyl)-4-fluoropyrrolidine-2-carboxamide | ** | 1.18 (A) | 540 |
| T-112 | 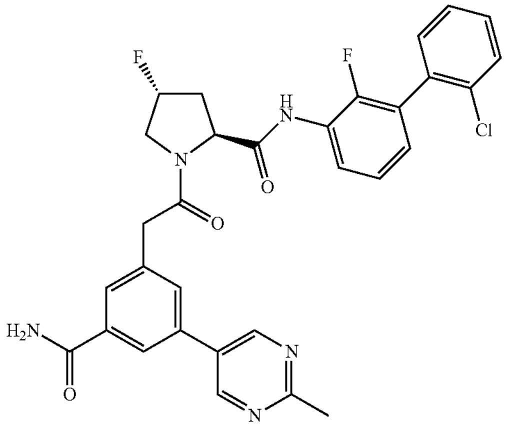 [SMILES: Cc1ncc(-c2cc(CC(=O)N3C[C@H](F)C[C@H]3C(=O)Nc3cccc(-c4ccccc4Cl)c3F)cc(C(N)=O)c2)cn1] (2S,4R)-1-(2-(3-carbamoyl-5-(2-methylpyrimidin-5-yl)phenyl)acetyl)-N-(2'-chloro-2-fluoro-[1,1'-biphenyl]-3-yl)-4-fluoropyrrolidine-2-carboxamide | *** | 1.77 (A) | 589 |

TABLE 7-continued

| Cmp No. | Structure and Name | $IC_5$ (Stars) | RT min (Method A, B, C, or D) | MS (M + 1) |
|---|---|---|---|---|
| T-113 | 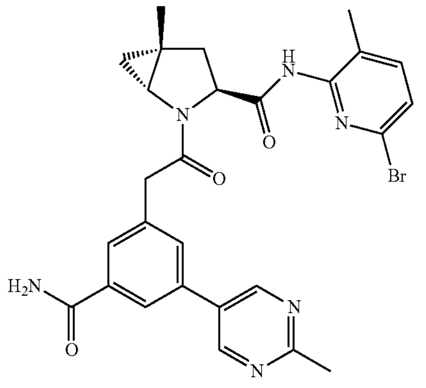 [SMILES: Cc1ncc(-c2cc(CC(=O)N3[C@H](C(=O)Nc4nc(Br)ccc4C)C[C@@]4(C)C[C@@H]34)cc(C(N)=O)c2)cn1] (1R,3S,5R)-N-(6-bromo-3-methylpyridin-2-yl)-2-(2-(3-carbamoyl-5-(2-methylpyrimidin-5-yl)phenyl)acetyl)-5-methyl-2-azabicyclo[3.1.0]hexane-3-carboxamide | ** | 1.33 (A) | 562 |
| T-114 | 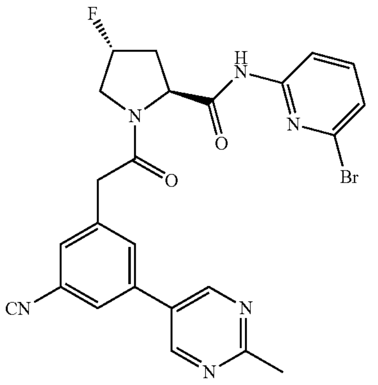 (2S,4R)-N-(6-bromopyridin-2-yl)-1-(2-(3-cyano-5-(2-methylpyrimidin-5-yl)phenyl)acetyl)-4-fluoropyrrolidine-2-carboxamide | ** | 1.65 (A) | 522 |
| T-115 | 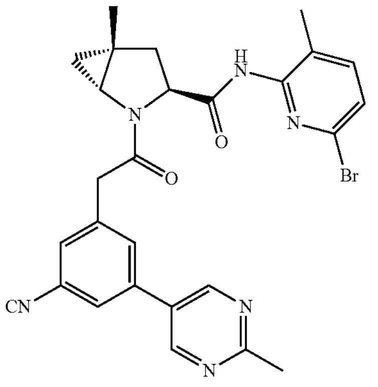 (1R,3S,5R)-N-(6-bromo-3-methylpyridin-2-yl)-2-(2-(3-cyano-5-(2-methylpyrimidin-5-yl)phenyl)acetyl)-5-methyl-2-azabicyclo[3.1.0]hexane-3-carboxamide | ** | 1.78 (A) | 544 |

TABLE 7-continued

| Cmp No. | Structure and Name | $IC_5$ (Stars) | RT min (Method A, B, C, or D) | MS (M + 1) |
|---|---|---|---|---|
| T-116 | 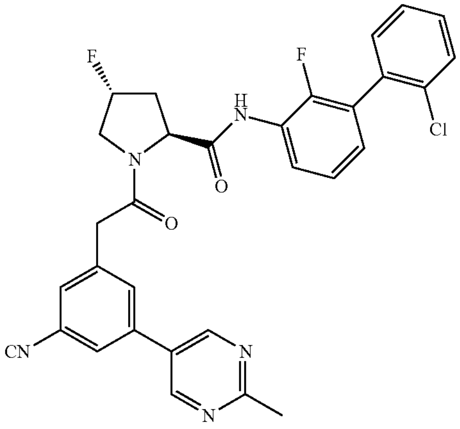 (2S,4R)-N-(2'-chloro-2-fluoro-[1,1'-biphenyl]-3-yl)-1-(2-(3-cyano-5-(2-methylpyrimidin-5-yl)phenyl)acetyl)-4-fluoropyrrolidine-2-carboxamide | *** | 2.30 (A) | 571 |
| T-117 | 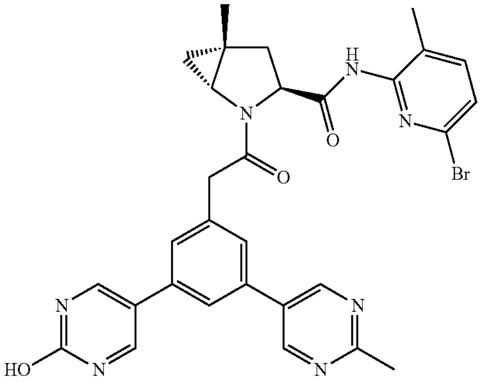 [SMILES: Cc1ncc(-c2cc(CC(=O)N3[C@H](C(=O)Nc4nc(Br)ccc4C)C[C@@]4(C)C[C@@H]34)cc(-c3cnc(O)nc3)c2)cn1] (1R,3S,5R)-N-(6-bromo-3-methylpyridin-2-yl)-2-(2-(3-(2-hydroxypyrimidin-5-yl)-5-(2-methylpyrimidin-5-yl)phenyl)acetyl)-5-methyl-2-azabicyclo[3.1.0]hexane-3-carboxamide | * | 1.31 (A) | 613 |
| T-118 | 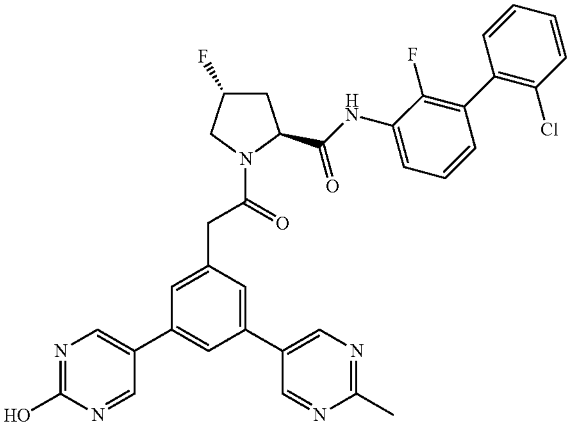 [SMILES: Cc1ncc(-c2cc(CC(=O)N3C[C@H](F)C[C@H]3C(=O)Nc3cccc(-c4ccccc4Cl)c3F)cc(-c3cnc(O)nc3)c2)cn1] (2S,4R)-N-(2'-chloro-2-fluoro-[1,1'-biphenyl]-3-yl)-4-fluoro-1-(2-(3-(2-hydroxypyrimidin-5-yl)-5-(2-methylpyrimidin-5-yl)phenyl)acetyl)pyrrolidine-2-carboxamide | * | 1.69 (A) | 640 |

TABLE 7-continued
| Cmp No. | Structure and Name | $IC_5$ (Stars) | RT min (Method A, B, C, or D) | MS (M + 1) |
|---|---|---|---|---|
| T-119 | 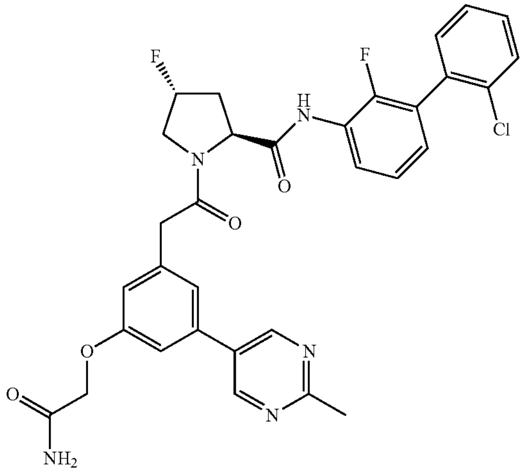 [SMILES: Cc1ncc(-c2cc(CC(=O)N3C[C@H](F)C[C@H]3C(=O)Nc3cccc(-c4ccccc4Cl)c3F)cc(OCC(N)=O)c2)cn1] (2S,4R)-1-(2-(3-(2-amino-2-oxoethoxy)-5-(2-methylpyrimidin-5-yl)phenyl)acetyl)-N-(2'-chloro-2-fluoro-[1,1'-biphenyl]-3-yl)-4-fluoropyrrolidine-2-carboxamide | ND | 1.81 (A) | 619 |
| T-120 | 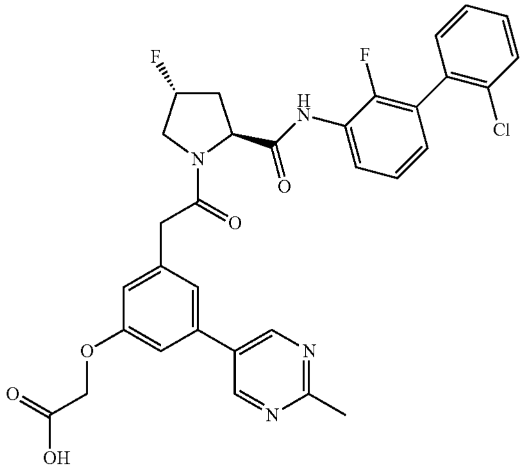 [SMILES: Cc1ncc(-c2cc(CC(=O)N3C[C@H](F)C[C@H]3C(=O)Nc3cccc(-c4ccccc4Cl)c3F)cc(OCC(=O)O)c2)cn1] 2-(3-(2-((2S,4R)-2-((2'-chloro-2-fluoro-[1,1'-biphenyl]-3-yl)carbamoyl)-4-fluoropyrrolidin-1-yl)-2-oxoethyl)-5-(2-methylpyrimidin-5-yl)phenoxy)acetic acid | ** | 1.95 (A) | 620 |

TABLE 7-continued
| Cmp No. | Structure and Name | $IC_5$ (Stars) | RT min (Method A, B, C, or D) | MS (M + 1) |
|---|---|---|---|---|
| T-121 | 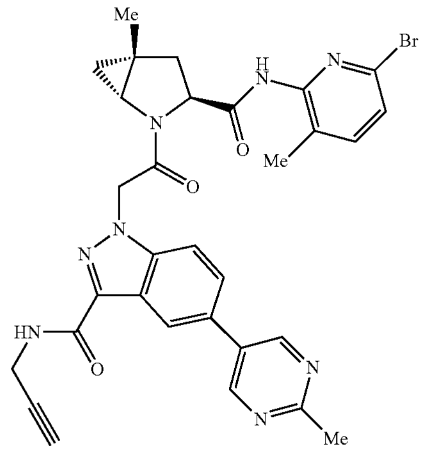 [SMILES: C#CCNC(=O)c1nn(CC(=O)N2[C@H](C(=O)Nc3nc(Br)ccc3C)C[C@@]3(C)C[C@@H]23)c2ccc(-c3cnc(C)nc3)cc12] 1-(2-((1R,3S,5R)-3-((6-bromo-3-methylpyridin-2-yl)carbamoyl)-5-methyl-2-azabicyclo[3.1.0]hexan-2-yl)-2-oxoethyl)-5-(2-methylpyrimidin-5-yl)-N-(prop-2-yn-1-yl)-1H-indazole-3-carboxamide | *** | 1.73 (A) | 640 |
| T-122 | 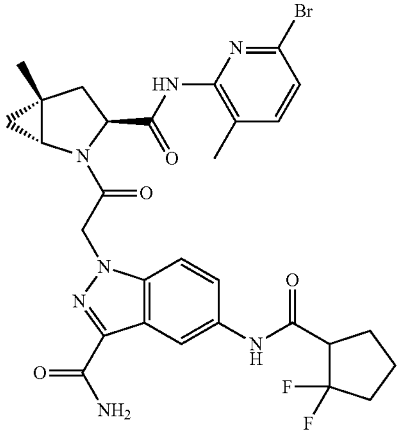 [SMILES: Cc1ccc(Br)nc1NC(=O)[C@@H]1C[C@@]2(C)C[C@H]2N1C(=O)Cn1nc(C(N)=O)c2cc(NC(=O)C3CCCC3(F)F)ccc21] 1-(2-((1R,3S,5R)-3-((6-bromo-3-methylpyridin-2-yl)carbamoyl)-5-methyl-2-azabicyclo[3.1.0]hexan-2-yl)-2-oxoethyl)-5-(2,2-difluorocyclopentane-1-carboxamido)-1H-indazole-3-carboxamide | *** | 10.20 (D) | 660 (M + 2) |
| T-123 | 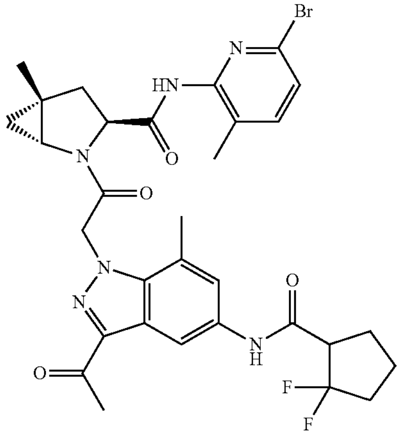 [SMILES: CC(=O)c1nn(CC(=O)N2[C@H](C(=O)Nc3nc(Br)ccc3C)C[C@@]3(C)C[C@@H]23)c2c(C)cc(NC(=O)C3CCCC3(F)F)cc12] | *** | 12.24 (D) | 669 (M − 2) |

TABLE 7-continued

| Cmp No. | Structure and Name | IC5 (Stars) | RT min (Method A, B, C, or D) | MS (M + 1) |
|---|---|---|---|---|
| | (1R,3S,5R)-2-(2-(3-acetyl-5-(2,2-difluorocyclopentane-1-carboxamido)-7-methyl-1H-indazol-1-yl)acetyl)-N-(6-bromo-3-methylpyridin-2-yl)-5-methyl-2-azabicyclo[3.1.0]hexane-3-carboxamide | | | |
| T-124 | 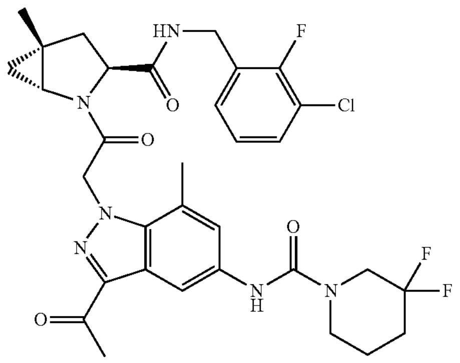 [SMILES: CC(=O)c1nn(CC(=O)N2[C@H](C(=O)NCc3cccc(Cl)c3F)C[C@@]3(C)C[C@@H]23)c2c(C)cc(NC(=O)N3CCCC(F)(F)C3)cc12] (1R,3S,5R)-2-(2-(3-acetyl-5-(3,3-difluoropiperidine-1-carboxamido)-7-methyl-1H-indazol-1-yl)acetyl)-N-(3-chloro-2-fluorobenzyl)-5-methyl-2-azabicyclo[3.1.0]hexane-3-catboxamide | *** | 11.89 (D) | 660 |
| T-125 | 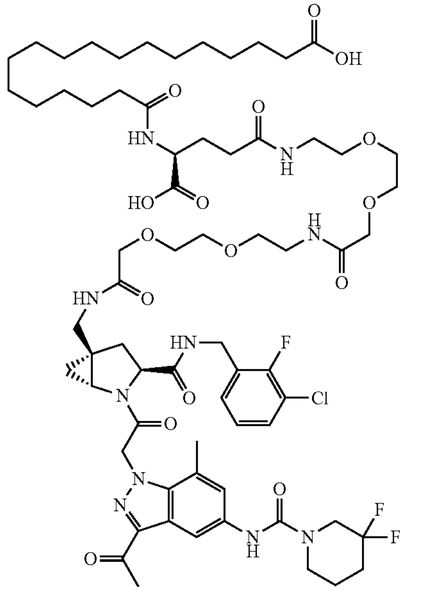 [SMILES: CC(=O)c1nn(CC(=O)N2[C@H](C(=O)NCc3cccc(Cl)c3F)C[C@@]3(CNC(=O)COCCOCCNC(=O)COCCOCCNC(=O)CC[C@H](NC(=O)CCCCCCCCCCCCCCCCC(=O)O)C(=O)O)C[C@@H]23)c2c(C)cc(NC(=O)N3CCCC(F)(F)C3)cc12] (S)-1-((1R,3S,5R)-2-(2-(3-acetyl-5-(3,3-difluoropiperidine-1-carboxamido)-7-methyl-1H-indazol-1-yl)acetyl)-3-((3-chloro-2-fluorobenzyl)carbamoyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid | *** | 8.87 (D) | 1392 (M + 2) |

TABLE 7-continued

| Cmp No. | Structure and Name | $IC_5$ (Stars) | RT min (Method A, B, C, or D) | MS (M + 1) |
| --- | --- | --- | --- | --- |
| T-126 | 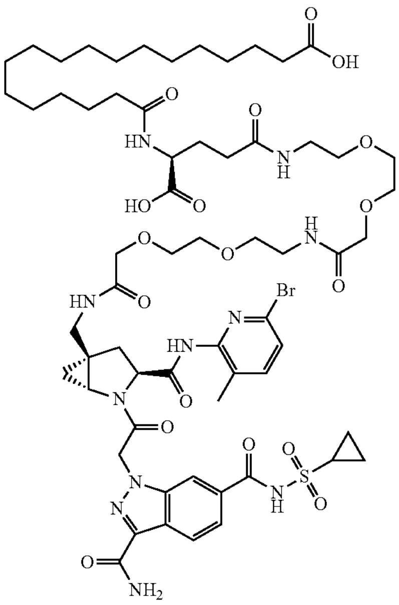 [SMILES: Cc1ccc(Br)nc1NC(=O)[C@@H]1C[C@@]2(CNC(=O)COCCOCCNC(=O)COCCOCCNC(=O)CC[C@H](NC(=O)CCCCCCCCCCCCCCCCC(=O)O)C(=O)O)C[C@H]2N1C(=O)Cn1nc(C(N)=O)c2ccc(C(=O)NS(=O)(=O)C3CC3)cc21] (S)-1-((1R,3S,5R)-3-((6-bromo-3-methylpyridin-2-yl)carbamoyl)-2-(2-(3-carbamoyl-6-((cyclopropylsulfonyl)carbamoyl)-1H-indazol-1-yl)acetyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid | *** | 7.10 (D) | 1391 (M + 2) |
| T-127 | 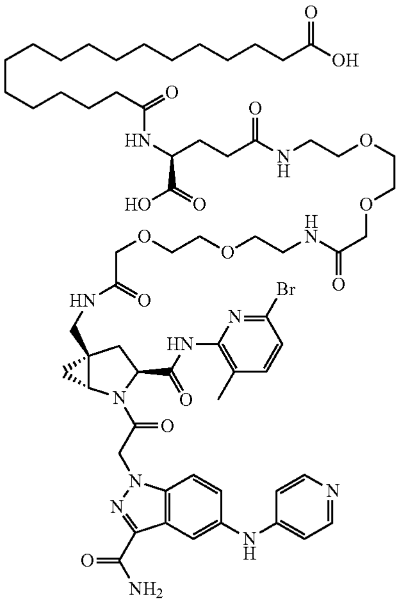 [SMILES: Cc1ccc(Br)nc1NC(=O)[C@@H]1C[C@@]2(CNC(=O)COCCOCCNC(=O)COCCOCCNC(=O)CC[C@H](NC(=O)CCCCCCCCCCCCCCCCC(=O)O)C(=O)O)C[C@H]2N1C(=O)Cn1nc(C(N)=O)c2cc(Nc3ccncc3)ccc21] (S)-1-((1R,3S,5R)-3-((6-bromo-3-methylpyridin-2-yl)carbamoyl)-2-(2-(3-carbamoyl-5-(pyridin-3-ylamino)-1H-indazol-1-yl)acetyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid | *** | | |

TABLE 7-continued

| Cmp No. | Structure and Name | $IC_5$ (Stars) | RT min (Method A, B, C, or D) | MS (M + 1) |
| --- | --- | --- | --- | --- |
| T-128 | 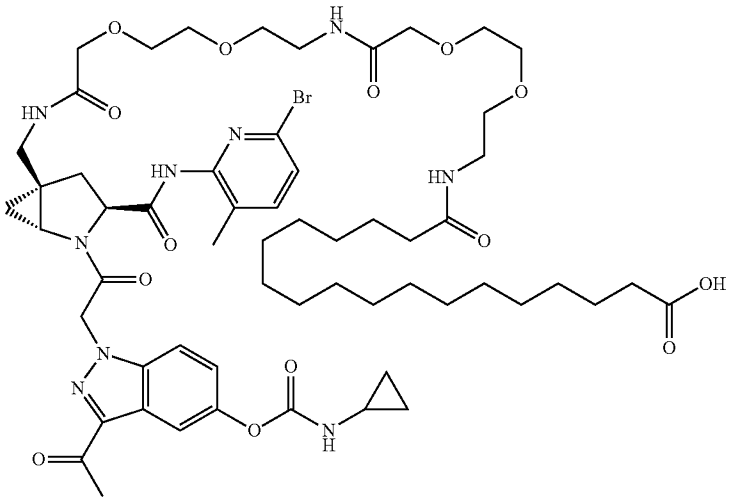 [SMILES: CC(=O)c1nn(CC(=O)N2[C@H](C(=O)Nc3nc(Br)ccc3C)C[C@@]3(CNC(=O)COCCOCCNC(=O)COCCOCCNC(=O)CCCCCCCCCCCCCCCCC(=O)O)C[C@@H]23)c2ccc(OC(=O)NC3CC3)cc12] 1-((1R,3S,5R)-2-(2-(3-acetyl-5-((cyclopropylcarbamoyl)oxy)-1H-indazol-1-yl)acetyl)-3-((6-bromo-3-methylpyridin-2-yl)carbamoyl)-2-azabicyclo[3.1.0]hexan-5-yl)-3,12,21-trioxo-5,8,14,17-tetraoxa-2,11,20-triazaoctatriacontan-38-oic acid | *** | | |
| T-129 | 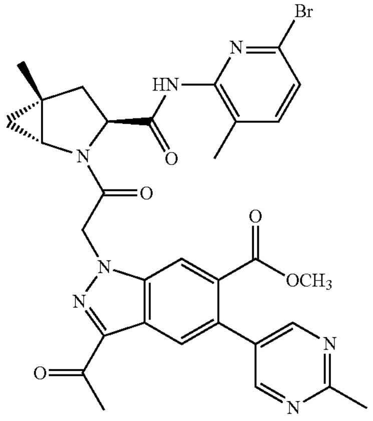 [SMILES: COC(=O)c1cc2c(cc1-c1cnc(C)nc1)c(C(C)=O)nn2CC(=O)N1[C@H](C(=O)Nc2nc(Br)ccc2C)C[C@@]2(C)C[C@@H]12] methyl 3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-5-(2-methylpyrimidin-5-yl)-1H-indazole-6-carboxylate | *** | 1.87 (A) | 660 |

TABLE 7-continued

| Cmp No. | Structure and Name | $IC_5$ (Stars) | RT min (Method A, B, C, or D) | MS (M + 1) |
|---|---|---|---|---|
| T-130 | 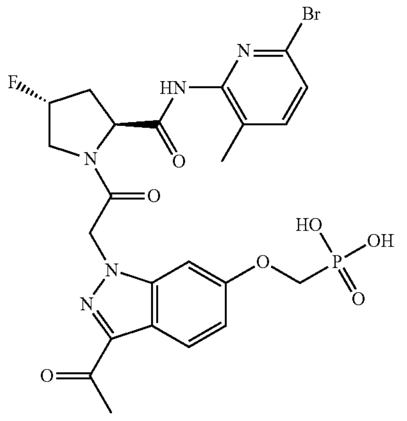 [SMILES: CC(=O)c1nn(CC(=O)N2C[C@H](F)C[C@H]2C(=O)Nc2nc(Br)ccc2C)c2cc(OCP(=O)(O)O)ccc12] (((3-acetyl-1-(2-((2S,4R)-2-((6-bromo-3-methylpyridin-2-yl)carbamoyl)-4-fluoropyrrolidin-1-yl)-2-oxoethyl)-1H-indazol-6-yl)oxy)methyl)phosphonic acid | *** | 9.35 (C) | 613 |
| T-131 | 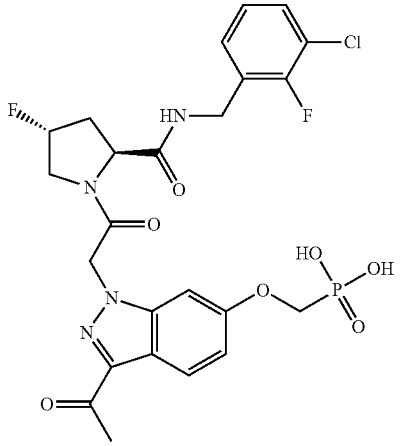 [SMILES: CC(=O)c1nn(CC(=O)N2C[C@H](F)C[C@H]2C(=O)NCc2cccc(Cl)c2F)c2cc(OCP(=O)(O)O)ccc12] (((3-acetyl-1-(2-((2S,4R)-2-((3-chloro-2-fluorobenzyl)carbamoyl)-4-fluoropyrrolidin-1-yl)-2-oxoethyl)-1H-indazol-6-yl)oxy)methyl)phosphonic acid | *** | 7.41 (D) | 587 (M + 2) |
| T-132 | 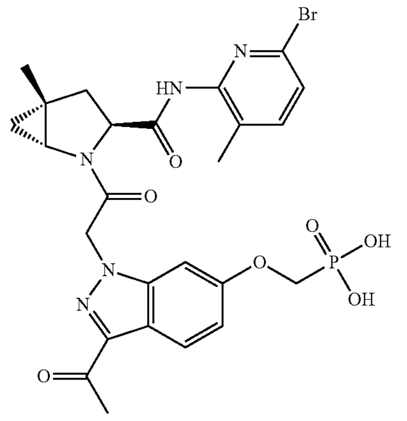 [SMILES: CC(=O)c1nn(CC(=O)N2[C@H](C(=O)Nc3nc(Br)ccc3C)C[C@@]3(C)C[C@@H]23)c2cc(OCP(=O)(O)O)ccc12] (((3-acetyl-1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-indazol-6-yl)oxy)methyl)phosphonic acid | *** | 1.55 (A) | 619 |

TABLE 7-continued

| Cmp No. | Structure and Name | $IC_5$ (Stars) | RT min (Method A, B, C, or D) | MS (M + 1) |
|---|---|---|---|---|
| T-133 | 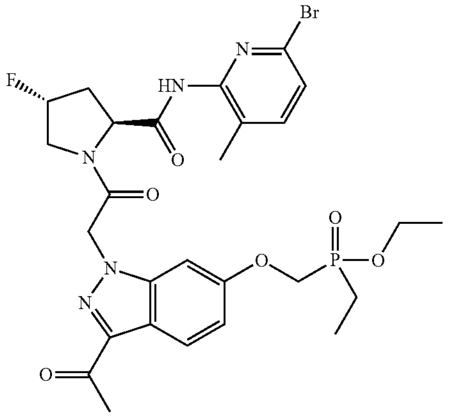 [SMILES: CCOP(=O)(CC)COc1ccc2c(C(C)=O)nn(CC(=O)N3C[C@H](F)C[C@H]3C(=O)Nc3nc(Br)ccc3C)c2c1] ethyl (((3-acetyl-1-(2-((2S,4R)-2-((6-bromo-3-methylpyridin-2-yl)carbamoyl)-4-fluoropyrrolidin-1-yl)-2-oxoethyl)-1H-indazol-6-yl)oxy)methyl)(ethyl)phosphinate | *** | 9.51 (D) | 653 (M + 1) |
| T-134 | 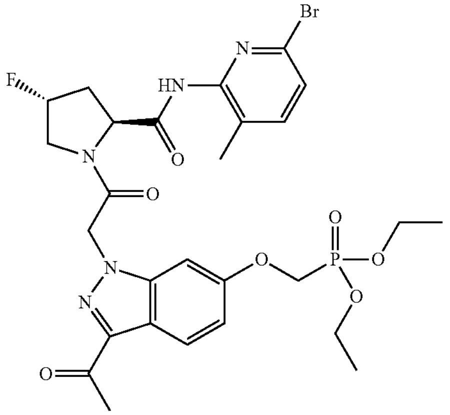 [SMILES: CCOP(=O)(COc1ccc2c(C(C)=O)nn(CC(=O)N3C[C@H](F)C[C@H]3C(=O)Nc3nc(Br)ccc3C)c2c1)OCC] diethyl (((3-acetyl-1-(2-((2S,4R)-2-((6-bromo-3-methylpyridin-2-yl)carbamoyl)-4-fluoropyrrolidin-1-yl)-2-oxoethyl)-1H-indazol-6-yl)oxy)methyl)phosphonate | *** | 10.04 (D) | 666 (M − 2) |
| T-135 | 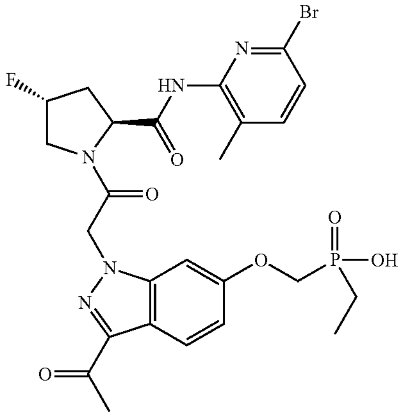 [SMILES: CCP(=O)(O)COc1ccc2c(C(C)=O)nn(CC(=O)N3C[C@H](F)C[C@H]3C(=O)Nc3nc(Br)ccc3C)c2c1] (((3-acetyl-1-(2-((2S,4R)-2-((6-bromo-3-methylpyridin-2-yl)carbamoyl)-4-fluoropyrrolidin-1-yl)-2-oxoethyl)-1H-indazol-6-yl)oxy)methyl)(ethyl)phosphinic acid | *** | 6.93 (D) | 626 (M + 2) |

TABLE 7-continued

| Cmp No. | Structure and Name | $IC_5$ (Stars) | RT min (Method A, B, C, or D) | MS (M + 1) |
|---|---|---|---|---|
| T-136 | 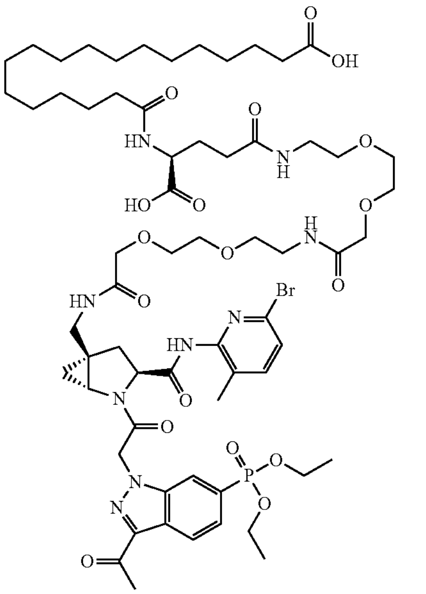 [SMILES: CCOP(=O)(OCC)c1ccc2c(C(C)=O)nn(CC(=O)N3[C@H](C(=O)Nc4nc(Br)ccc4C)C[C@@]4(CNC(=O)COCCOCCNC(=O)COCCOCCNC(=O)CC[C@H](NC(=O)CCCCCCCCCCCCCCCCC(=O)O)C(=O)O)C[C@@H]34)c2c1] (S)-1-((1R,3S,5R)-2-(2-(3-acetyl-6-(diethoxyphosphoryl)-1H-indol-1-yl)acetyl)-3-((6-bromo-3-methylpyridin-2-yl)carbamoyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid | *** | 12.84 (C) | 1378 (M + 2) |
| T-137 | 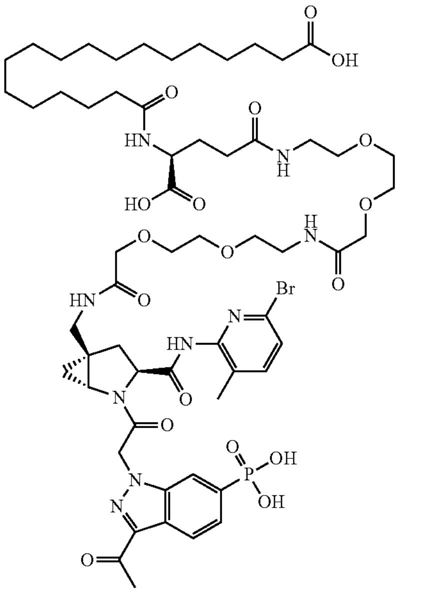 [SMILES: CC(=O)c1nn(CC(=O)N2[C@H](C(=O)Nc3nc(Br)ccc3C)C[C@@]3(CNC(=O)COCCOCCNC(=O)COCCOCCNC(=O)CC[C@H](NC(=O)CCCCCCCCCCCCCCCCC(=O)O)C(=O)O)C[C@@H]23)c2cc(P(=O)(O)O)ccc12] (S)-1-((1R,3S,5R)-2-(2-(3-acetyl-6-phosphono-1H-indol-1-yl)acetyl)-3-((6-bromo-3-methylpyridin-2-yl)carbamoyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid | *** | | |

TABLE 7-continued

| Cmp No. | Structure and Name | $IC_5$ (Stars) | RT min (Method A, B, C, or D) | MS (M + 1) |
|---|---|---|---|---|
| T-138 | 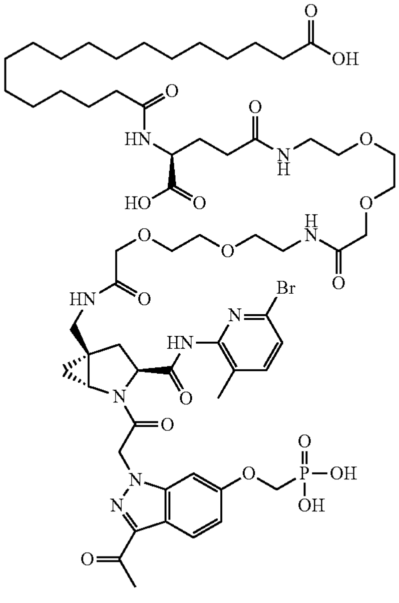 [SMILES: CC(=O)c1nn(CC(=O)N2[C@H](C(=O)Nc3nc(Br)ccc3C)C[C@@]3(CNC(=O)COCCOCCNC(=O)COCCOCCNC(=O)CC[C@H](NC(=O)CCCCCCCCCCCCCCCCC(=O)O)C(=O)O)C[C@@H]23)c2cc(OCP(=O)(O)O)ccc12] (S)-1-((1R,3S,5R)-2-(2-(3-acetyl-6-(phosphonomethoxy)-1H-indol-1-yl)acetyl)-3-((6-bromo-3-methylpyridin-2-yl)carbamoyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid | *** | | |
| T-139 | 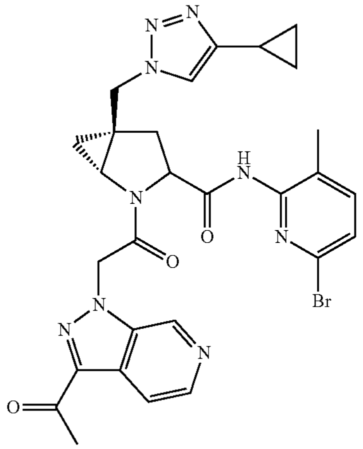 [SMILES: CC(=O)c1nn(CC(=O)N2C(C(=O)Nc3nc(Br)ccc3C)C[C@@]3(Cn4cc(C5CC5)nn4)C[C@@H]23)c2cnccc12] (1R,3S,5R)-2-(2-(3-acetyl-1H-pyrazolo[3,4-c]pyridin-1-yl)acetyl)-N-(6-bromo-3-methylpyridin-2-yl)-5-((4-cyclopropyl-1H-1,2,3-triazol-1-yl)methyl)-2-azabicyclo[3.1.0]hexane-3-carboxamide | *** | 1.37 (A) | 618 |

TABLE 7-continued
| Cmp No. | Structure and Name | $IC_5$ (Stars) | RT min (Method A, B, C, or D) | MS (M + 1) |
|---|---|---|---|---|
| T-140 | 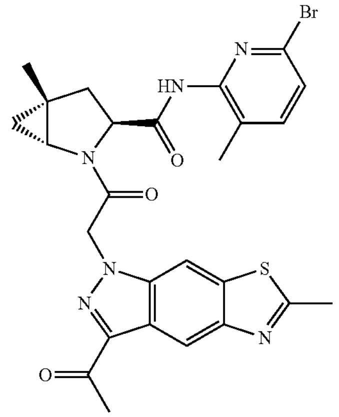 [SMILES: CC(=O)c1nn(CC(=O)N2[C@H](C(=O)Nc3nc(Br)ccc3C)C[C@@]3(C)C[C@@H]23)c2cc3sc(C)nc3cc12] (1R,3S,5R)-2-(2-(3-acetyl-6-methyl-1H-thiazolo[4,5-f]indazol-1-yl)acetyl)-N-(6-bromo-3-methylpyridin-2-yl)-5-methyl-2-azabicyclo[3.1.0]hexane-3-carboxamide | *** | 2.05 (A) | 581 |
| T-141 | 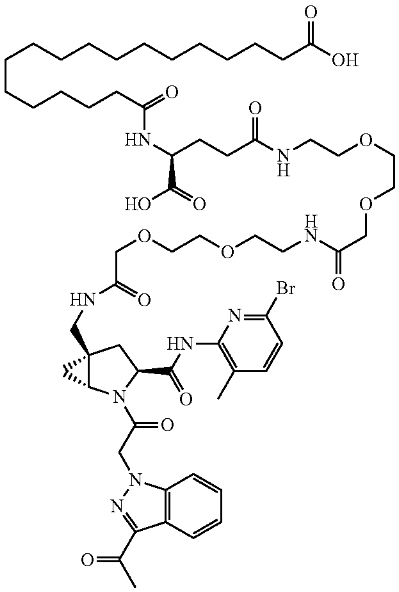 [SMILES: CC(=O)c1nn(CC(=O)N2[C@H](C(=O)Nc3nc(Br)ccc3C)C[C@@]3(CNC(=O)COCCOCCNC(=O)COCCOCCNC(=O)CC[C@H](NC(=O)CCCCCCCCCCCCCCCCC(=O)O)C(=O)O)C[C@@H]23)c2ccccc12] (S)-1-((1R,3S,5R)-2-(2-(3-acetyl-1H-indazol-1-yl)acetyl)-3-((6-bromo-3-methylpyridin-2-yl)carbamoyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid | *** | 13.15 (C) | 1243 (M + 2) |

TABLE 7-continued

| Cmp No. | Structure and Name | IC5 (Stars) | RT min (Method A, B, C, or D) | MS (M + 1) |
|---|---|---|---|---|
| T-142 | 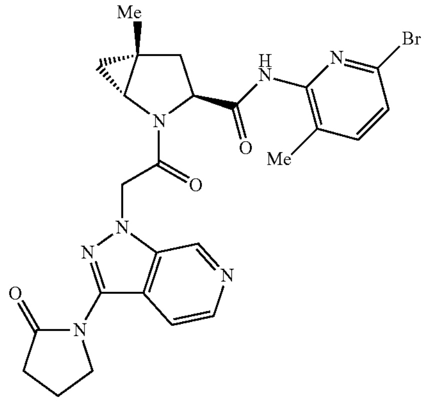 [SMILES: Cc1ccc(Br)nc1NC(=O)[C@@H]1C[C@@]2(C)C[C@H]2N1C(=O)Cn1nc(N2CCCC2=O)c2ccncc21] (1R,3S,5R)-N-(6-bromo-3-methylpyridin-2-yl)-5-methyl-2-(2-(3-(2-oxopyrrolidin-1-yl)-1H-pyrazolo[3,4-c]pyridin-1-yl)acetyl)-2-azabicyclo[3.1.0]hexane-3-carboxamide | * | 1.28 (A) | 552 |
| T-143 | 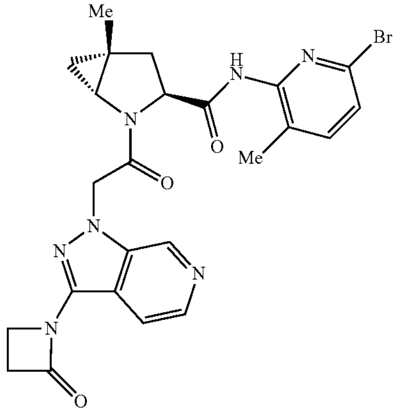 [SMILES: Cc1ccc(Br)nc1NC(=O)[C@@H]1C[C@@]2(C)C[C@H]2N1C(=O)Cn1nc(N2CCC2=O)c2ccncc21] (1R,3S,5R)-N-(6-bromo-3-methylpyridin-2-yl)-5-methyl-2-(2-(3-(2-oxoazetidin-1-yl)-1H-pyrazolo[3,4-c]pyridin-1-yl)acetyl)-2-azabicyclo[3.1.0]hexane-3-carboxamide | *** | 1.25 (A) | 537 |
| T-144 | 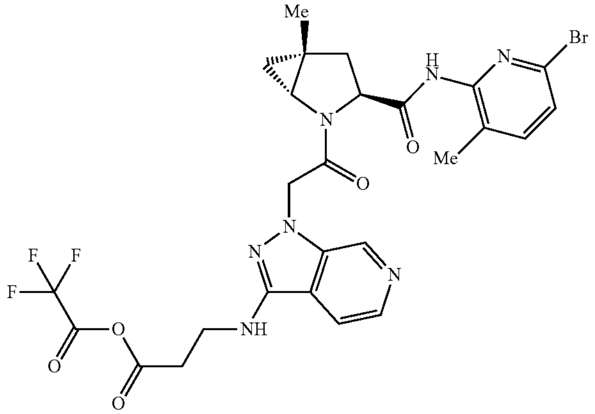 [SMILES: Cc1ccc(Br)nc1NC(=O)[C@@H]1C[C@@]2(C)C[C@H]2N1C(=O)Cn1nc(NCCC(=O)OC(=O)C(F)(F)F)c2ccncc21] 3-((1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-pyrazolo[3,4-c]pyridin-3-yl)amino)propanoic 2,2,2-trifluoroacetic anhydride | ND | | |

TABLE 7-continued

| Cmp No. | Structure and Name | $IC_5$ (Stars) | RT min (Method A, B, C, or D) | MS (M + 1) |
|---|---|---|---|---|
| T-145 | 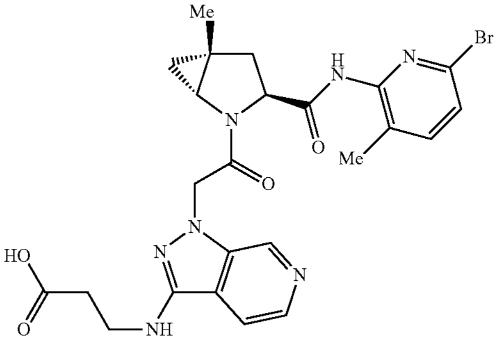 [SMILES: Cc1ccc(Br)nc1NC(=O)[C@@H]1C[C@@]2(C)C[C@H]2N1C(=O)Cn1nc(NCCC(=O)O)c2ccncc21] 3-((1-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-pyrazolo[3,4-c]pyridin-3-yl)amino)propanoic acid | * | 0.93 (A) | 556 |
| T-146 | 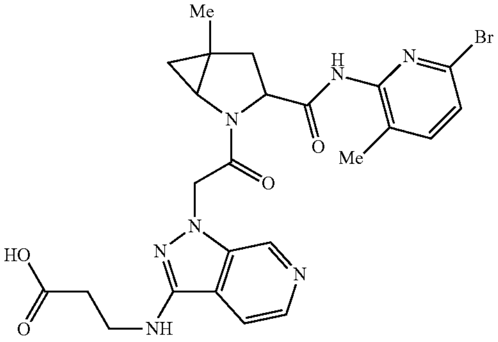 [SMILES: Cc1ccc(Br)nc1NC(=O)C1CC2(C)CC2N1C(=O)Cn1nc(NCCC(=O)O)c2ccncc21] 3-((1-(2-(3-((6-bromo-3-methylpyridin-2-yl)carbamoyl)-5-methyl-2-azabicyclo[3.1.0]hexan-2-yl)-2-oxoethyl)-1H-pyrazolo[3,4-c]pyridin-3-yl)amino)propanoic acid | * | 0.90 (A) | 556 |
| T-147 | 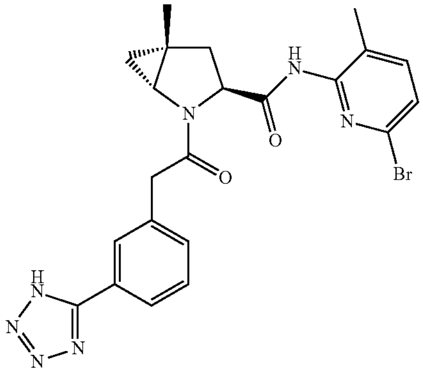 [SMILES: Cc1ccc(Br)nc1NC(=O)[C@@H]1C[C@@]2(C)C[C@H]2N1C(=O)Cc1cccc(-c2nnn[nH]2)c1] (1R,3S,5R)-2-(2-(3-(1H-tetrazol-5-yl)phenyl)acetyl)-N-(6-bromo-3-methylpyridin-2-yl)-5-methyl-2-azabicyclo[3.1.0]hexane-3-carboxamide | * | 2.29 (B) | 496 |

TABLE 7-continued

| Cmp No. | Structure and Name | $IC_5$ (Stars) | RT min (Method A, B, C, or D) | MS (M + 1) |
|---|---|---|---|---|
| T-148 | 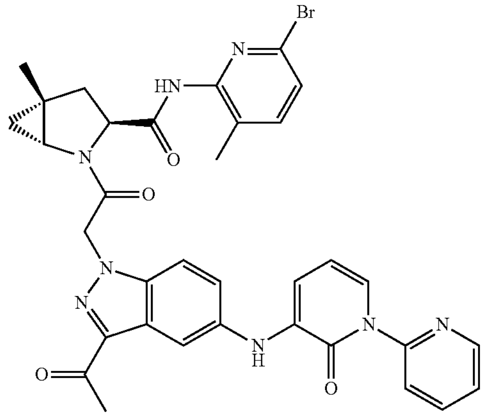 [SMILES: CC(=O)c1nn(CC(=O)N2[C@H](C(=O)Nc3nc(Br)ccc3C)C[C@@]3(C)C[C@@H]23)c2ccc(Nc3cccn(-c4ccccn4)c3=O)cc12] (1R,3S,5R)-2-(2-(3-acetyl-5-((2-oxo-2H-[1,2'-bipyridin]-3-yl)amino)-1H-indazol-1-yl)acetyl)-N-(6-bromo-3-methylpyridin-2-yl)-5-methyl-2-azabicyclo[3.1.0]hexane-3-carboxamide | *** | 3.52 (B) | 695 |
| T-149 | 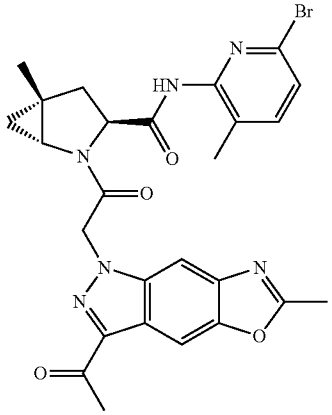 (1R,3S,5R)-2-(2-(3-acetyl-6-methyl-1H-oxazolo[5,4-f]indazol-1-yl)acetyl)-N-(6-bromo-3-methylpyridin-2-yl)-5-methyl-2-azabicyclo[3.1.0]hexane-3-carboxamide | *** | 3.36 (B) | 565 |
| T-150 | 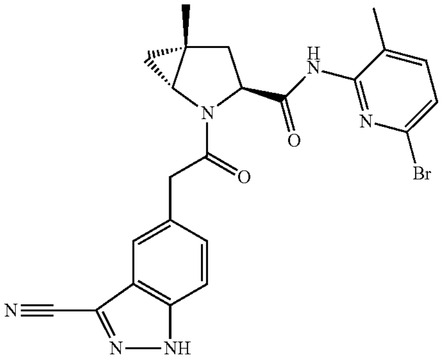 [SMILES: Cc1ccc(Br)nc1NC(=O)[C@@H]1C[C@@]2(C)C[C@H]2N1C(=O)Cc1ccc2[nH]nc(C#N)c2c1] (1R,3S,5R)-N-(6-bromo-3-methylpyridin-2-yl)-2-(2-(3-cyano-1H-indazol-5-yl)acetyl)-5-methyl-2-azabicyclo[3.1.0]hexane-3-carboxamide | * | 3.18 (B) | 493 |

TABLE 7-continued

| Cmp No. | Structure and Name | $IC_5$ (Stars) | RT min (Method A, B, C, or D) | MS (M + 1) |
|---|---|---|---|---|
| T-151 | 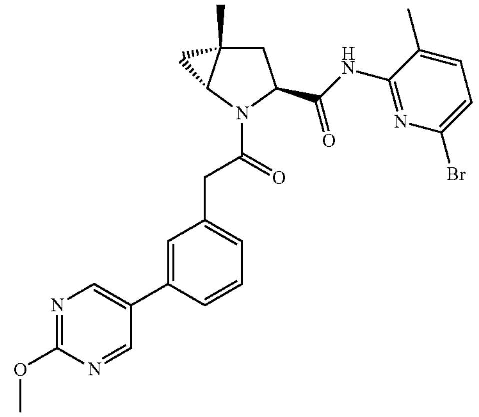 [SMILES: COc1ncc(-c2cccc(CC(=O)N3[C@H](C(=O)Nc4nc(Br)ccc4C)C[C@@]4(C)C[C@@H]34)c2)cn1] (1R,3S,5R)-N-(6-bromo-3-methylpyridin-2-yl)-2-(2-(3-(2-methoxypyrimidin-5-yl)phenyl)acetyl)-5-methyl-2-azabicyclo[3.1.0]hexane-3-carboxamide | * | 3.44 (B) | 536 |
| T-152 | 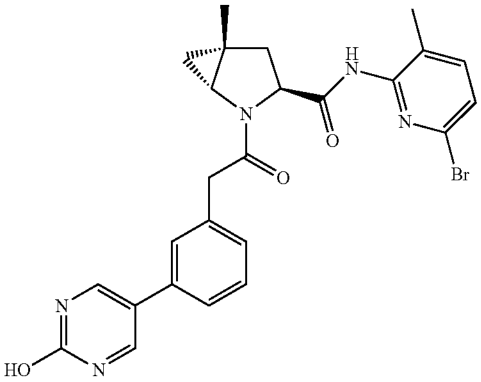 [SMILES: Cc1ccc(Br)nc1NC(=O)[C@@H]1C[C@@]2(C)C[C@H]2N1C(=O)Cc1cccc(-c2cnc(O)nc2)c1] (1R,3S,5R)-N-(6-bromo-3-methylpyridin-2-yl)-2-(2-(3-(2-hydroxypyrimidin-5-yl)phenyl)acetyl)-5-methyl-2-azabicyclo[3.1.0]hexane-3-carboxamide | * | 2.12 (B) | 522 |
| T-153 | 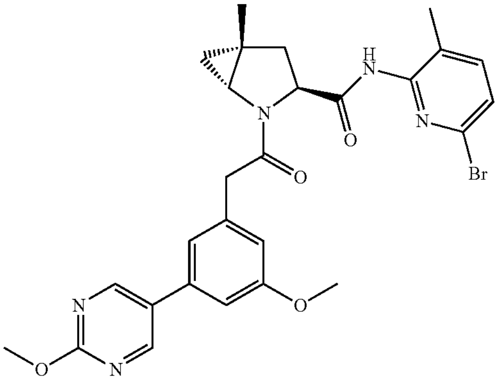 [SMILES: COc1cc(CC(=O)N2[C@H](C(=O)Nc3nc(Br)ccc3C)C[C@@]3(C)C[C@@H]23)cc(-c2cnc(OC)nc2)c1] (1R,3S,5R)-N-(6-bromo-3-methylpyridin-2-yl)-2-(2-(3-methoxy-5-(2-methoxypyrimidin-5-yl)phenyl)acetyl)-5-methyl-2-azabicyclo[3.1.0]hexane-3-carboxamide | ** | 3.13 (B) | 566 |

TABLE 7-continued
| Cmp No. | Structure and Name | IC$_5$ (Stars) | RT min (Method A, B, C, or D) | MS (M + 1) |
|---|---|---|---|---|
| T-154 | 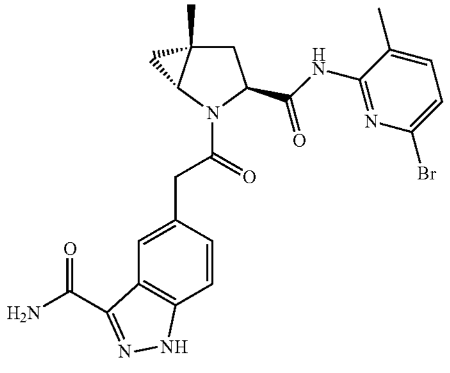 [SMILES: Cc1ccc(Br)nc1NC(=O)[C@@H]1C[C@@]2(C)C[C@H]2N1C(=O)Cc1ccc2[nH]nc(C(N)=O)c2c1] 5-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-indazole-3-carboxamide | * | 2.59 (B) | 511 |
| T-155 | 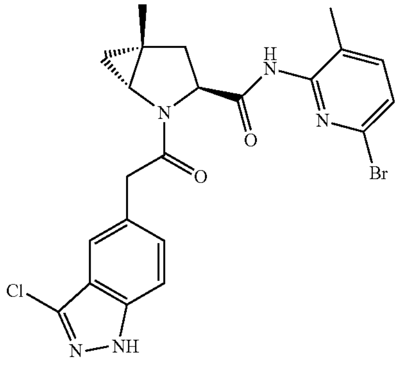 [SMILES: Cc1ccc(Br)nc1NC(=O)[C@@H]1C[C@@]2(C)C[C@H]2N1C(=O)Cc1ccc2[nH]nc(Cl)c2c1] (1R,3S,5R)-N-(6-bromo-3-methylpyridin-2-yl)-2-(2-(3-chloro-1H-indazol-5-yl)acetyl)-5-methyl-2-azabicyclo[3.1.0]hexane-3-carboxamide | ** | 2.86 (B) | 504 |
| T-156 | 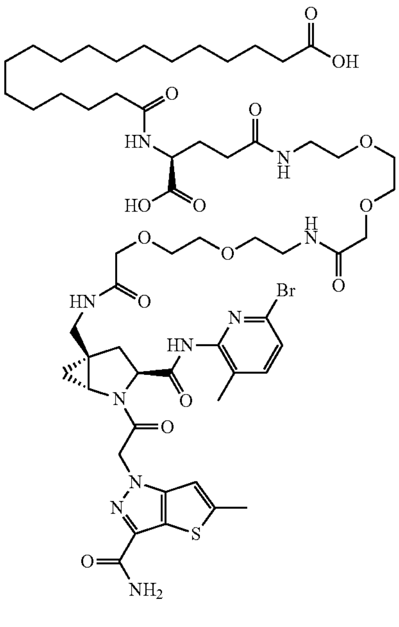 [SMILES: Cc1cc2c(s1)c(C(N)=O)nn2CC(=O)N1[C@H](C(=O)Nc2nc(Br)ccc2C)C[C@@]2(CNC(=O)COCCOCCNC(=O)COCCOCCNC(=O)CC[C@H](NC(=O)CCCCCCCCCCCCCCCCC(=O)O)C(=O)O)C[C@@H]12] (S)-1-((1R,3S,5R)-3-((6-bromo-3-methylpyridin-2-yl)carbamoyl)-2-(2-(3-carbamoyl-5-methyl-1H- | *** | 8.00 (D) | 1264 (M + 2) |

TABLE 7-continued

| Cmp No. | Structure and Name | $IC_5$ (Stars) | RT min (Method A, B, C, or D) | MS (M + 1) |
|---|---|---|---|---|
| | thieno[3,2-c]pyrazol-1-yl)acetyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid | | | |
| T-157 | 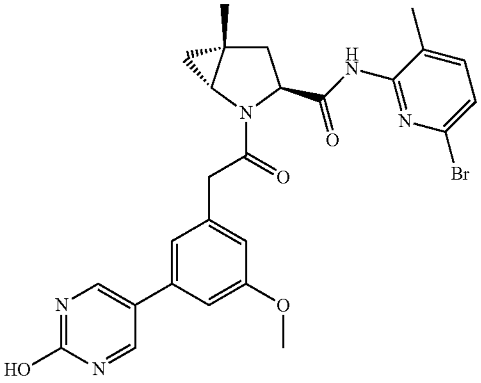 [SMILES: COc1cc(CC(=O)N2[C@H](C(=O)Nc3nc(Br)ccc3C)C[C@@]3(C)C[C@@H]23)cc(-c2cnc(O)nc2)c1] (1R,3S,5R)-N-(6-bromo-3-methylpyridin-2-yl)-2-(2-(3-(2-hydroxypyrimidin-5-yl)-5-methoxyphenyl)acetyl)-5-methyl-2-azabicyclo[3.1.0]hexane-3-carboxamide | *** | 2.27 (B) | 552 |
| T-158 | 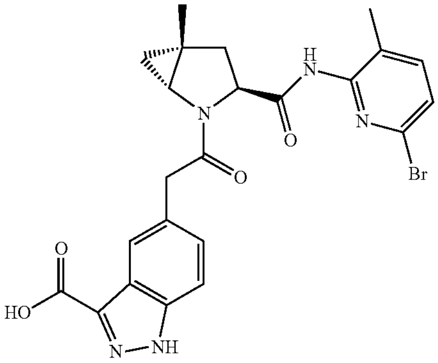 [SMILES: Cc1ccc(Br)nc1NC(=O)[C@@H]1C[C@@]2(C)C[C@H]2N1C(=O)Cc1ccc2[nH]nc(C(=O)O)c2c1] 5-(2-((1R,3S,5R)-3-((6-bromo-3-methylpyridin-2-yl)carbamoyl)-5-methyl-2-azabicyclo[3.1.0]hexan-2-yl)-2-oxoethyl)-1H-indazole-3-carboxylic acid | ** | 2.45 (B) | 512 |
| T-159 | 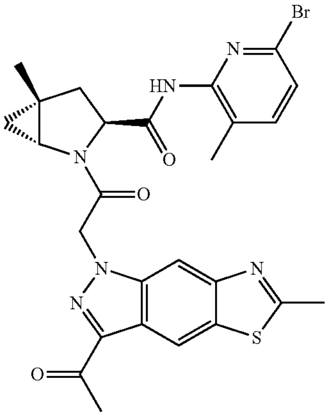 [SMILES: CC(=O)c1nn(CC(=O)N2[C@H](C(=O)Nc3nc(Br)ccc3C)C[C@@]3(C)C[C@@H]23)c2cc3nc(C)sc3cc12] (1R,3S,5R)-2-(2-(3-acetyl-6-methyl-1H-thiazolo[5,4-f]indazol-1-yl)acetyl)-N-(6-bromo-3-methylpyridin-2-yl)-5-methyl-2-azabicyclo[3.1.0]lhexane-3-carboxamide | *** | 2.05 (A) | 580 |

TABLE 7-continued

| Cmp No. | Structure and Name | $IC_5$ (Stars) | RT min (Method A, B, C, or D) | MS (M + 1) |
|---|---|---|---|---|
| T-160 | 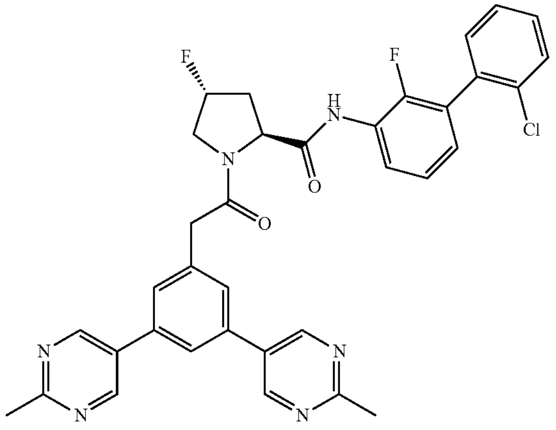 [SMILES: Cc1ncc(-c2cc(CC(=O)N3C[C@H](F)C[C@H]3C(=O)Nc3cccc(-c4ccccc4Cl)c3F)cc(-c3cnc(C)nc3)c2)cn1] (2S,4R)-1-(2-(3,5-bis(2-methylpyrimidin-5-yl)phenyl)acetyl)-N-(2'-chloro-2-fluoro-[1,1'-biphenyl]-3-yl)-4-fluoropyrrolidine-2-carboxamide | * | 2.01 (A) | 638 |
| T-161 | 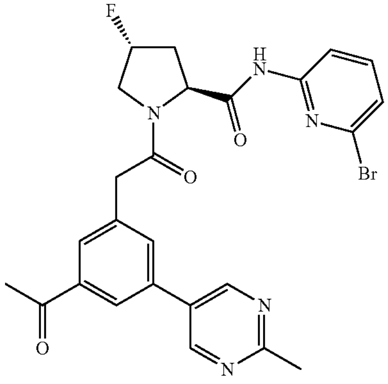 [SMILES: CC(=O)c1cc(CC(=O)N2C[C@H](F)C[C@H]2C(=O)Nc2cccc(Br)n2)cc(-c2cnc(C)nc2)c1] (2S,4R)-1-(2-(3-acetyl-5-(2-methylpyrimidin-5-yl)phenyl)acetyl)-N-(6-bromopyridin-2-yl)-4-fluoropyrrolidine-2-carboxamide | *** | 1.56 (A) | 539 |
| T-162 | 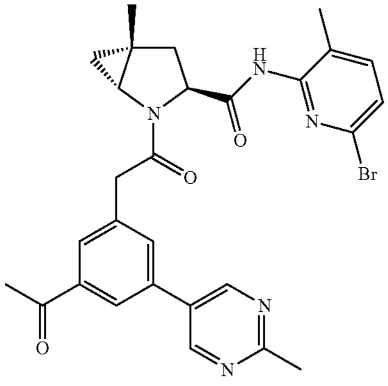 [SMILES: CC(=O)c1cc(CC(=O)N2[C@H](C(=O)Nc3nc(Br)ccc3C)C[C@@]3(C)C[C@@H]23)cc(-c2cnc(C)nc2)c1] (1R,3S,5R)-2-(2-(3-acetyl-5-(2-methylpyrimidin-5-yl)phenyl)acetyl)-N-(6-bromo-3-methylpyridin-2-yl)-5-methyl-2-azabicyclo[3.1.0]hexane-3-carboxamide | *** | 1.69 (A) | 561 |

TABLE 7-continued

| Cmp No. | Structure and Name | $IC_5$ (Stars) | RT min (Method A, B, C, or D) | MS (M + 1) |
| --- | --- | --- | --- | --- |
| T-163 | 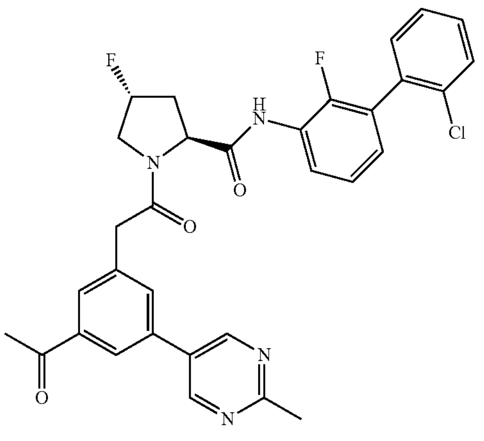 [SMILES: CC(=O)c1cc(CC(=O)N2C[C@H](F)C[C@H]2C(=O)Nc2cccc(-c3ccccc3Cl)c2F)cc(-c2cnc(C)nc2)c1] (2S,4R)-1-(2-(3-acetyl-5-(2-methylpyrimidin-5-yl)phenyl)acetyl)-N-(2'-chloro-2-fluoro-[1,1'-biphenyl]-3-yl)-4-fluoropyrrolidine-2-carboxamide | *** | 2.10 (A) | 588 |
| T-164 | 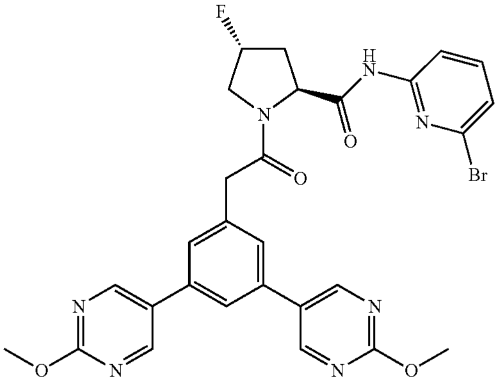 [SMILES: COc1ncc(-c2cc(CC(=O)N3C[C@H](F)C[C@H]3C(=O)Nc3cccc(Br)n3)cc(-c3cnc(OC)nc3)c2)cn1] (2S,4R)-1-(2-(3,5-bis(2-methoxypyrimidin-5-yl)phenyl)acetyl)-N-(6-bromopyridin-2-yl)-4-fluoropyrrolidine-2-carboxamide | * | 1.84 (A) | 621 |
| T-165 | 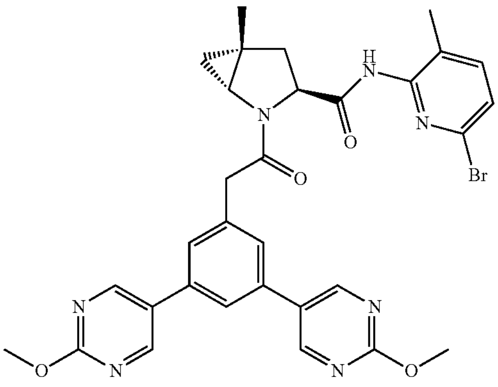 [SMILES: COc1ncc(-c2cc(CC(=O)N3[C@H](C(=O)Nc4nc(Br)ccc4C)C[C@@]4(C)C[C@@H]34)cc(-c3cnc(OC)nc3)c2)cn1] (1R,3S,5R)-2-(2-(3,5-bis(2-methoxypyrimidin-5-yl)phenyl)acetyl)-N-(6-bromo-3-methylpyridin-2-yl)-5-methyl-2-azabicyclo[3.1.0]hexane-3-carboxamide | * | 1.96 (A) | 643 |

TABLE 7-continued

| Cmp No. | Structure and Name | $IC_5$ (Stars) | RT min (Method A, B, C, or D) | MS (M + 1) |
|---|---|---|---|---|
| T-166 | 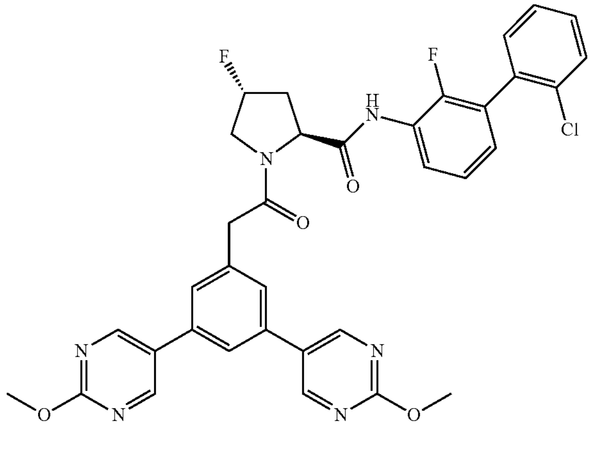 [SMILES: COc1ncc(-c2cc(CC(=O)N3C[C@H](F)C[C@H]3C(=O)Nc3cccc(-c4ccccc4Cl)c3F)cc(-c3cnc(OC)nc3)c2)cn1] (2S,4R)-1-(2-(3,5-bis(2-methoxypyrimidin-5-yl)phenyl)acetyl)-N-(2'-chloro-2-fluoro-[1,1'-biphenyl]-3-yl)-4-fluoropyrrolidine-2-carboxamide | * | 2.29 (A) | 670 |
| T-167 | 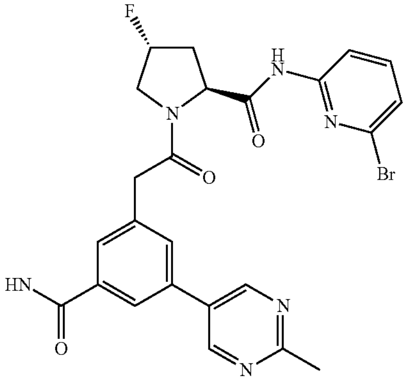 [SMILES: Cc1ncc(-c2cc(CC(=O)N3C[C@H](F)C[C@H]3C(=O)Nc3cccc(Br)n3)cc(C(N)=O)c2)cn1] (2S,4R)-N-(6-bromopyridin-2-yl)-1-(2-(3-carbamoyl-5-(2-methylpyrimidin-5-yl)phenyl)acetyl)-4-fluoropyrrolidine-2-carboxamide | ** | 1.18 (A) | 540 |
| T-168 | 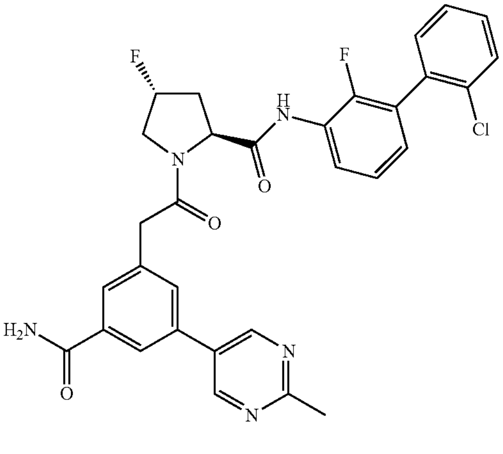 [SMILES: Cc1ncc(-c2cc(CC(=O)N3C[C@H](F)C[C@H]3C(=O)Nc3cccc(-c4ccccc4Cl)c3F)cc(C(N)=O)c2)cn1] (2S,4R)-1-(2-(3-carbamoyl-5-(2-methylpyrimidin-5-yl)phenyl)acetyl)-N-(2'-chloro-2-fluoro-[1,1'-biphenyl]-3-yl)-4-fluoropyrrolidine-2-carboxamide | *** | 1.77 (A) | 589 |

TABLE 7-continued

| Cmp No. | Structure and Name | $IC_5$ (Stars) | RT min (Method A, B, C, or D) | MS (M + 1) |
|---|---|---|---|---|
| T-169 | 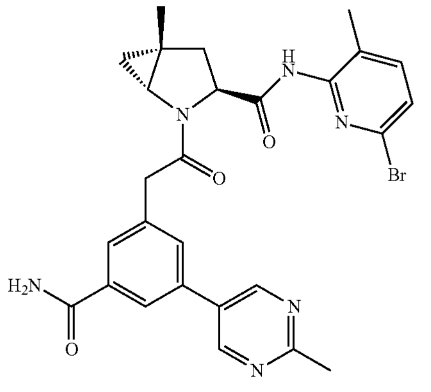 [SMILES: Cc1ncc(-c2cc(CC(=O)N3[C@H](C(=O)Nc4nc(Br)ccc4C)C[C@@]4(C)C[C@@H]34)cc(C(N)=O)c2)cn1] (1R,3S,5R)-N-(6-bromo-3-methylpyridin-2-yl)-2-(2-(3-carbamoyl-5-(2-methylpyrimidin-5-yl)phenyl)acetyl)-5-methyl-2-azabicyclo[3.1.0]hexane-3-carboxamide | ** | 1.33 (A) | 562 |
| T-170 | 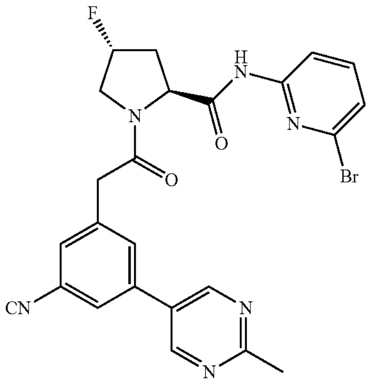 (2S,4R)-N-(6-bromopyridin-2-yl)-1-(2-(3-cyano-5-(2-methylpyrimidin-5-yl)phenyl)acetyl)-4-fluoropyrrolidine-2-carboxamide | ** | 1.65 (A) | 522 |
| T-171 | 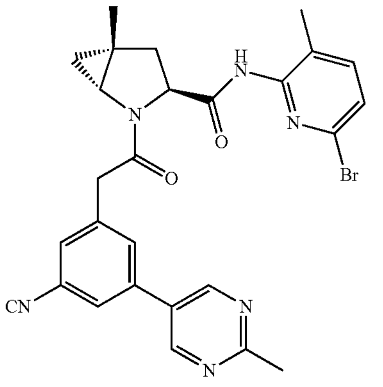 (1R,3S,5R)-N-(6-bromo-3-methylpyridin-2-yl)-2-(2-(3-cyano-5-(2-methylpyrimidin-5-yl)phenyl)acetyl)-5-methyl-2-azabicyclo[3.1.0]hexane-3-carboxamide | ** | 1.78 (A) | 544 |

TABLE 7-continued

| Cmp No. | Structure and Name | $IC_5$ (Stars) | RT min (Method A, B, C, or D) | MS (M + 1) |
|---|---|---|---|---|
| T-172 | 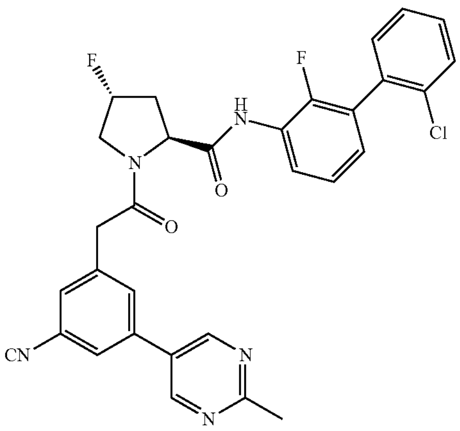 (2S,4R)-N-(2'-chloro-2-fluoro-[1,1'-biphenyl]-3-yl)-1-(2-(3-cyano-5-(2-methylpyrimidin-5-yl)phenyl)acetyl)-4-fluoropyrrolidine-2-carboxamide | *** | 2.30 (A) | 571 |
| T-173 | 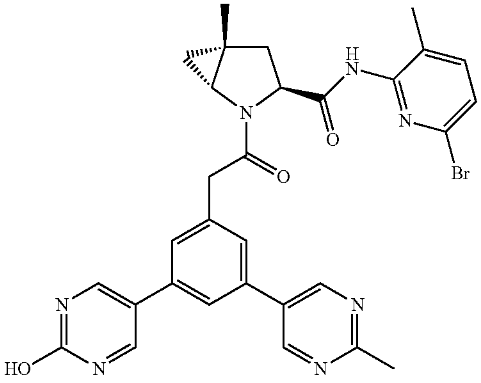 [SMILES: Cc1ncc(-c2cc(CC(=O)N3[C@H](C(=O)Nc4nc(Br)ccc4C)C[C@@]4(C)C[C@@H]34)cc(-c3cnc(O)nc3)c2)cn1] (1R,3S,5R)-N-(6-bromo-3-methylpyridin-2-yl)-2-(2-(3-(2-hydroxypyrimidin-5-yl)-5-(2-methylpyrimidin-5-yl)phenyl)acetyl)-5-methyl-2-azabicyclo[3.1.0]hexane-3-carboxamide | * | 1.31 (A) | 613 |
| T-174 | 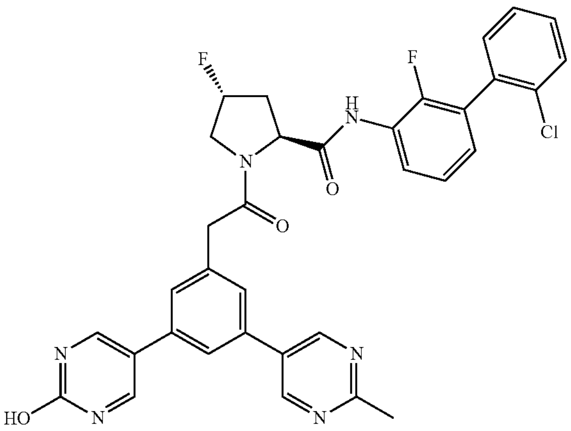 [SMILES: Cc1ncc(-c2cc(CC(=O)N3C[C@H](F)C[C@H]3C(=O)Nc3cccc(-c4ccccc4Cl)c3F)cc(-c3cnc(O)nc3)c2)cn1] (2S,4R)-N-(2'-chloro-2-fluoro-[1,1'-biphenyl]-3-yl)-4-fluoro-1-(2-(3-(2-hydroxypyrimidin-5-yl)-5-(2-methylpyrimidin-5-yl)phenyl)acetyl)pyrrolidine-2-carboxamide | * | 1.69 (A) | 640 |

TABLE 7-continued
| Cmp No. | Structure and Name | $IC_5$ (Stars) | RT min (Method A, B, C, or D) | MS (M + 1) |
|---|---|---|---|---|
| T-175 | 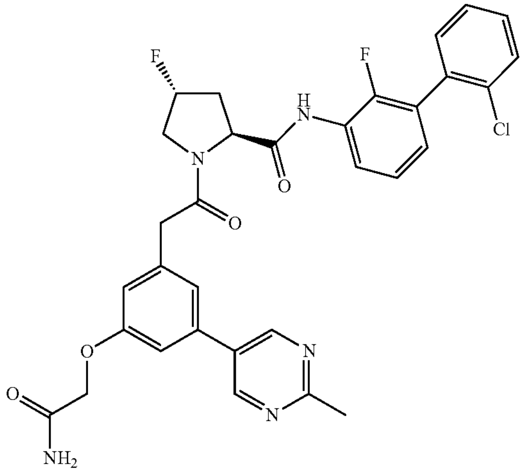 [SMILES: Cc1ncc(-c2cc(CC(=O)N3C[C@H](F)C[C@H]3C(=O)Nc3cccc(-c4ccccc4Cl)c3F)cc(OCC(N)=O)c2)cn1] (2S,4R)-1-(2-(3-(2-amino-2-oxoethoxy)-5-(2-methylpyrimidin-5-yl)phenyl)acetyl)-N-(2'-chloro-2-fluoro-[1,1'-biphenyl]-3-yl)-4-fluoropyrrolidine-2-carboxamide | ND | 1.81 (A) | 619 |
| T-176 | 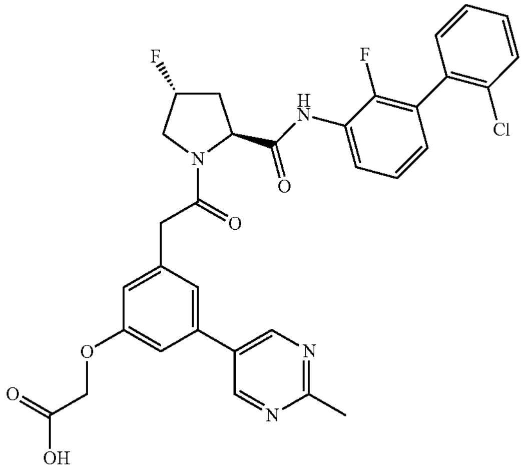 [SMILES: Cc1ncc(-c2cc(CC(=O)N3C[C@H](F)C[C@H]3C(=O)Nc3cccc(-c4ccccc4Cl)c3F)cc(OCC(=O)O)c2)cn1] 2-(3-(2-((2S,4R)-2-((2'-chloro-2-fluoro-[1,1'-biphenyl]-3-yl)carbamoyl)-4-fluoropyrrolidin-1-yl)-2-oxoethyl)-5-(2-methylpyrimidin-5-yl)phenoxy)acetic acid | ** | 1.95 (A) | 620 |

TABLE 7-continued

| Cmp No. | Structure and Name | $IC_5$ (Stars) | RT min (Method A, B, C, or D) | MS (M + 1) |
|---|---|---|---|---|
| T-177 | 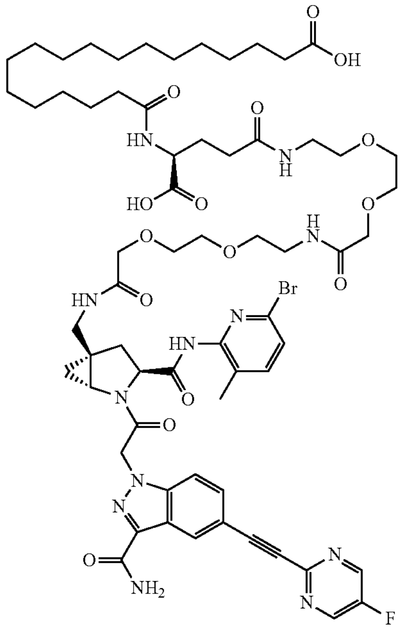 [SMILES: Cc1ccc(Br)nc1NC(=O)[C@@H]1C[C@@]2(CNC(=O)COCCOCCNC(=O)COCCOCCNC(=O)CC[C@H](NC(=O)CCCCCCCCCCCCCCCCC(=O)O)C(=O)O)C[C@H]2N1C(=O)Cn1nc(C(N)=O)c2cc(C#Cc3ncc(F)cn3)ccc21] (S)-1-((1R,3S,5R)-3-((6-bromo-3-methylpyridin-2-yl)carbamoyl)-2-(2-(3-carbamoyl-5-((5-fluoropyrimidin-2-yl)ethynyl)-1H-indazol-1-yl)acetyl)-2-azabicyclo[3.1.0]hexan-5-yl)-24-carboxy-3,12,21,26-tetraoxo-5,8,14,17-tetraoxa-2,11,20,25-tetraazatritetracontan-43-oic acid | *** | 12.35 (C) | 1354 (M + 2) |

Human Factor D Assay

Human Factor D (purified from human serum, Complement Technology, Inc.) at 80 nM final concentration is incubated with test compound at various concentrations for 5 min at room temperature in 50 mM Tris, 1M NaCl, pH 7.5. A synthetic substrate Z-L-Lys-SBzl and DTNB (Ellman's reagent) are added to final concentrations of 100 μM each. Absorbance at 405 nm ($A_{405}$) is recorded at 30 second intervals for 30 min using a microplate spectrophotometer. $IC_{50}$ values are calculated by nonlinear regression of Complement Factor D reaction rates as a function of test compound concentration.

Hemolysis Assay

The hemolysis assay was previously described by G. Ruiz-Gomez, et al., J. Med. Chem. (2009) 52: 6042-6052. Prior to the assay, the optimum concentration of Normal Human Serum (NHS) needed to achieve 100% lysis of rabbit erythrocytes (RE) is determined by titration. In the assay, NHS (Complement Technology) is diluted in $GVB^0$ Buffer (0.1% gelatin, 5 mM Veronal, 145 mM NaCl, 0.025% $NaN_3$, pH 7.3, Complement Technology) plus 10 mM Mg-EGTA and incubated with test compound at various concentrations for 15 min at 37° C. RE (Complement Technology) freshly suspended in $GVB^0$ plus 10 mM Mg-EGTA are added to a final concentration of $1\times10^8$ cells/mL and reactions are incubated for 30 min at 37° C. Positive control reactions (100% lysis) consist of $GVB^0$ plus 10 mM Mg-EGTA with NHS and RE but without test compound; negative control reactions (0% lysis) consist of $GVB^0$ plus 10 mM Mg-EGTA with RE only. Samples are centrifuged at 2000 g for 3 min and supernatants collected. Absorbance at 405 nm ($A_{405}$) is recorded using a microplate spectrophotometer. $IC_{50}$ values are calculated by nonlinear regression from the percentage of hemolysis as a function of test compound concentration.

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

We claim:

1. A compound of Formula:

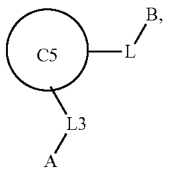

(II)

or a pharmaceutically acceptable salt thereof;

wherein:

A is selected from A1 and A3;

C5 is selected from:

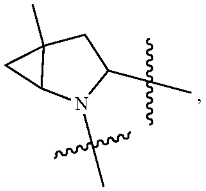,
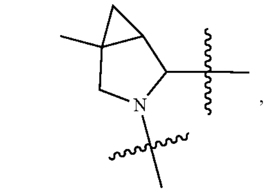,
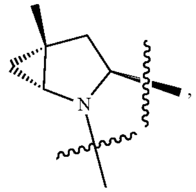,
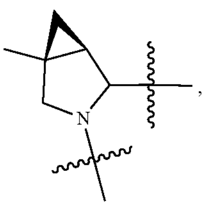, and
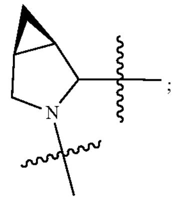;

L is

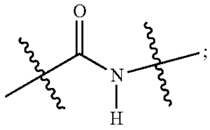 [SMILES: *NC(*)=O];

L3 is —C(O)—;

A1 is selected from:

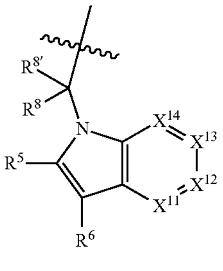 and 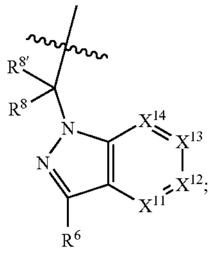;

A3 is selected from:

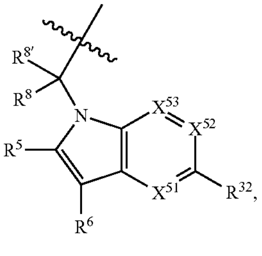,
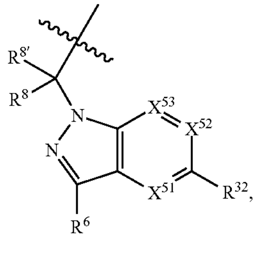,

-continued

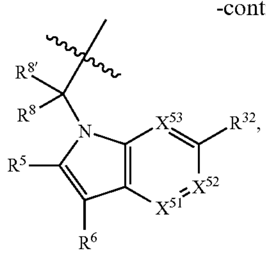,
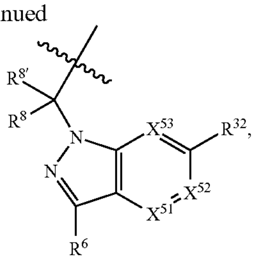,
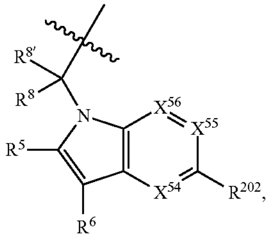,
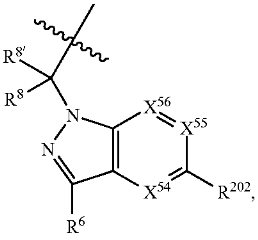,
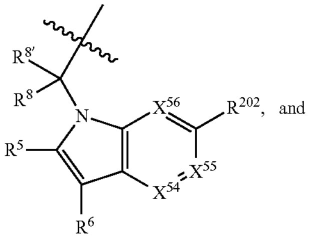, and
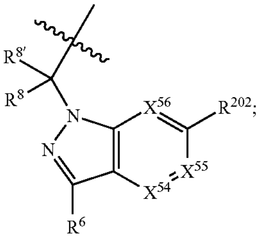;

$X^{51}$, $X^{52}$, and $X^{53}$ are independently selected from N, $CR^{31}$, and $CR^{201}$;

wherein at least one of $X^{51}$, $X^{52}$, and $X^{53}$ is selected from $CR^{201}$;

$X^{54}$, $X^{55}$, and $X^{56}$ are independently selected from N, $CR^{31}$, and $CR^{201}$;

$R^{201}$ is selected from aminoalkyl-, alkylaminoalkyl-, heterocycloalkyl-, hydroxyalkyl, -alkyl-O-alkyl, -alkyl-S-alkyl, -alkyl-N(alkyl)-alkyl, -alkyl-NH-alkyl, -aliphatic-O-aliphatic, -aliphatic-S-aliphatic, -aliphatic-N(aliphatic)-aliphatic, -aliphatic-NH-aliphatic, -aliphatic-O-heterocycle, -aliphatic-S-heterocycle, -aliphatic-N(aliphatic)-heterocycle, -aliphatic-NH-heterocycle, -alkyl-NHC(O)haloalkyl, -alkyl-$NR^9$C(O)haloalkyl, -alkyl-C(O)NHhaloalkyl, -alkyl-C(O)$NR^9$haloalkyl, -alkyl-NHC(O)haloalkyl, -alkyl-$NR^9$C(O)aliphatic, -alkyl-C(O)NHaliphatic, -alkyl-$NR^9$C(O)aliphatic, -alkyl-NHC(O)aliphatic, -substituted alkyl-N($R^9$)-substituted alkyl, alkyl-heteroaryl, -alkyl-O-haloalkyl, heteroaryl, heterocycle, alkyl-heterocycle, and —N(aliphatic)$_2$;

$R^{202}$ is selected from aryl and heteroaryl, wherein the aryl and heteroaryl groups are substituted with $R^{201}$;

$R^5$ and $R^6$ are independently selected from hydrogen, halogen, —CHO, —C(O)$NH_2$, —$C_2$-$C_6$alkanoyl, —C(O)NH($CH_3$), —COOH, —P(O)($OR^9$)$_2$, —OC(O)$R^9$, —C(O)$OR^9$, nitro, hydroxyl, phenyl, 5- to 6-membered heteroaryl, cyano, amino, and $C_1$-$C_6$alkyl;

$R^8$ and $R^{8'}$ are hydrogen;

$R^9$ and $R^{10}$ are independently selected from hydrogen, $C_1$-$C_6$alkyl, ($C_3$-$C_7$cycloalkyl)$C_0$-$C_4$alkyl, —$C_0$-$C_4$alkyl($C_3$-$C_7$cycloalkyl), and —O—$C_0$-$C_4$alkyl($C_3$-$C_7$cycloalkyl);

$X^{11}$ is N or $CR^{11}$;

$X^{12}$ is N or $CR^{12}$;

$X^{13}$ is N or $CR^{13}$;

$X^{14}$ is N or $CR^{14}$;

wherein no more than 2 of $X^{11}$, $X^{12}$, $X^{13}$, and $X^{14}$ are N;

wherein one of $R^{12}$ and $R^{13}$ is $R^{32}$ and the other is $R^{31}$ or $R^{32}$;

and wherein if there is no $R^{13}$ and no $R^{32}$ on the A ring then $R^{12}$ is $R^{32}$;

and wherein if there is no $R^{12}$ and no $R^{32}$ on the A ring then $R^{13}$ is $R^{32}$;

$R^{31}$ is independently selected from hydrogen, halogen, hydroxyl, nitro, cyano, amino, —COOH, $C_1$-$C_6$haloalkyl, $C_1$-$C_6$haloalkoxy, $C_1$-$C_6$alkyl, —$C_0$-$C_4$alkyl($C_3$-$C_7$cycloalkyl), $C_2$-$C_6$alkenyl, $C_2$-$C_6$alkanoyl, $C_1$-$C_6$alkoxy, $C_2$-$C_6$alkenyloxy, —C(O)$OR^9$, $C_1$-$C_6$thioalkyl, —$C_0$-$C_4$alkyl$NR^9R^{10}$, —C(O)$NR^9R^{10}$, —$SO_2R^9$, —$SO_2NR^9R^{10}$, —OC(O)$R^9$, and —C($NR^9$)$NR^9R^{10}$, each of which $R^{31}$ other than hydrogen, halogen, hydroxyl, nitro, cyano, $C_1$-$C_6$haloalkyl, and $C_1$-$C_6$haloalkoxy is optionally substituted with one or more substituents independently selected from halogen, hydroxyl, nitro, cyano, amino, —COOH, —C(O)$NR^9R^{10}$, $C_1$-$C_6$haloalkyl, $C_1$-$C_6$haloalkoxy, phenyl, and 4- to 7-membered heterocycle containing 1, 2, or 3 heteroatoms independently selected from N, O, and S; each of which phenyl or 4- to 7-membered heterocycle is optionally substituted with one or more substituents independently selected from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl)($C_3$-$C_7$cycloalkyl), $C_1$-$C_6$haloalkyl, and $C_1$-$C_6$haloalkoxy;

$R^{32}$ is selected from C(O)$NR^{21}R^{71}$, —C(O)$NR^9R^{71}$, —$NR^9$C(O)$OR^{10}$, —$NR^9$C(O)$OR^{23}$, —$NR^9$C(O)$R^{21}$, —$NR^9$C(O)$NR^9R^{10}$, and —$NR^9$C(O)$NR^{10}R^{23}$;

or $R^{32}$ is selected from $NR^{72}R^{73}$, $NR^9SO_2R^{73}$, and N($SO_2R^9$)$CH_2$C(O)$R^{74}$;

or $R^{32}$ is selected from —OC(O)$(CH_2)_{1-4}R^{21}$, —OC(O)$NR^{21}R^{22}$, —OC(O)($C_{1-6}$alkyl or $C_{3-6}$cycloalkyl)(aryl), —OC(O)($C_{1-6}$alkyl or $C_{3-6}$cycloalkyl)(heteroaryl), —OC(O)($C_{1-6}$alkyl or $C_{3-6}$cycloalkyl)(heterocycle), —OC(O)(heteroaryl), —OC(O)(aryl), —OC(O)($C_{1-6}$ alkyl or $C_{3-6}$cycloalkyl), —OC(O)$NR^9(CH_2)_{1-4}$P(O)($OR^{21}$)($OR^{22}$), —C(O)($C_{1-6}$alkyl or $C_{3-6}$cycloalkyl)(aryl), —C(O)($C_{1-6}$alkyl or $C_{3-6}$cycloalkyl)(heteroaryl), —C(O)($C_{1-6}$alkyl or $C_{3-6}$cycloalkyl)(heterocycle), —C(O)(heteroaryl), —C(O)(heterocycle), —C(O)(aryl), —C(O)($C_{1-6}$alkyl or $C_{3-6}$cycloalkyl), —C(O)($CH_2$)S(O)$R^{21}$, O-heteroalkyl, and O-heteroaliphatic;

or $R^{32}$ is selected from —$O(CH_2)_{1-4}R^{23a}$, —$OC_2$-$C_4$alkenyl$R^{23a}$, —$OC_2$-$C_4$alkynyl$R^{23}$, —$O(CH_2)_{1-4}$ paracyclophane, —$O(CH_2)_{1-4}$P(O)$R^{23b}R^{23b}$, —$O(CH_2)_{1-4}$S(O)$NR^{21}R^{22}$, —$O(CH_2)_{1-4}SO_2NR^{21}R^{22}$, —O($C_3$-$C_7$cycloalkyl), —O(aryl), —O(heteroaryl), and —O residue of a carbohydrate;

or $R^{32}$ is selected from $R^{48}$, S(O)═$NHR^{21}$, S(O)═N($R^{21}$)$R^{21}$, $SF_5$, S═$NHR^{21}$, S═N($R^{21}$)$R^{21}$, JC($R^9$)═$NR^{21}$, and $SO_2OR^{21}$;

or $R^{32}$ is selected from —$O(CH_2)_{1-4}$S(O)$NR^{24}R^{30}$ and —$O(CH_2)_{1-4}SO_2NR^{24}R^{30}$;

$R^{11}$ and $R^{14}$ are independently selected from hydrogen, halogen, hydroxyl, nitro, cyano, —O(PO)$(OR^9)_2$, —(PO)$(OR^9)_2$, $C_1$-$C_6$alkyl, $C_2$-$C_6$alkenyl, $C_2$-$C_6$alkynyl, $C_2$-$C_6$alkenyl(aryl), $C_2$-$C_6$alkenyl(cycloalkyl), $C_2$-$C_6$alkenyl(heterocycle), $C_2$-$C_6$alkenyl(heteroaryl), $C_2$-$C_6$alkynyl(aryl), $C_2$-$C_6$alkynyl(cycloalkyl), $C_2$-$C_6$alkynyl(heterocycle), $C_2$-$C_6$alkynyl(heteroaryl), $C_2$-$C_6$alkanoyl, $C_1$-$C_6$alkoxy, $C_1$-$C_6$thioalkyl, —$C_0$-$C_4$alkyl(mono- and di-$C_1$-$C_6$alkylamino), —$C_0$-$C_4$alkyl($C_3$-$C_7$cycloalkyl), —$C_0$-$C_4$alkoxy($C_3$-$C_7$cycloalkyl), $C_1$-$C_6$haloalkyl, and $C_1$-$C_6$haloalkoxy;

B is selected from:

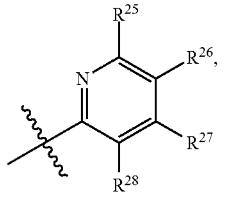

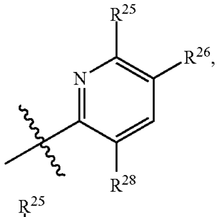

and

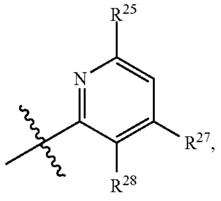

wherein $R^{25}$, $R^{26}$, and $R^{27}$ are independently selected from halogen and $C_1$-$C_6$alkyl optionally substituted with one or more halogen atoms; and $R^{28}$ is $C_1$-$C_6$alkyl or cyclopropyl; or B is

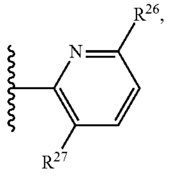

wherein $R^{26}$ is halogen or $C_1$-$C_6$alkyl optionally substituted with one or more halogen atoms, and $R^{27}$ is $C_1$-$C_6$alkyl or cyclopropyl;

J is independently selected from a covalent bond, $C_1$-$C_4$alkylene, —$OC_1$-$C_4$alkylene, $C_2$-$C_4$alkenylene, and $C_2$-$C_4$alkynylene;

$R^{21}$ and $R^{22}$ are independently selected from hydrogen, hydroxyl, cyano, amino, $C_1$-$C_6$alkyl, $C_1$-$C_6$haloalkyl, $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O)$OC_1$-$C_6$alkyl, —$C_1$-$C_4$alkylOC(O)$C_1$-$C_6$alkyl, —$C_1$-$C_4$alkylC(O)$OC_1$-$C_6$alkyl, (4- to 8-membered heterocycloalkyl)$C_0$-$C_4$alkyl having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S;

or $R^{21}$ and $R^{22}$ can be taken together to form a carbocyclic or heterocyclic ring;

$R^{23}$ is independently selected at each occurrence from $C_1$-$C_6$alkyl, $C_1$-$C_6$haloalkyl, (aryl)$C_0$-$C_4$alkyl, ($C_3$-$C_7$cycloalkyl)$C_0$-$C_4$alkyl, (phenyl)$C_0$-$C_4$alkyl, (4- to 8-membered heterocycle)$C_0$-$C_4$alkyl having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S;

$R^{23a}$ is independently selected at each occurrence from $C_3$-$C_7$cycloalkyl;

$R^{23b}$ is independently selected at each occurrence from hydroxyl, $C_1$-$C_6$alkoxy, $C_1$-$C_6$alkyl, ($C_3$-$C_7$cycloalkyl)$C_0$-$C_4$alkyl, (phenyl)$C_0$-$C_4$alkyl, —$O(CH_2)_{2-4}O(CH_2)_{8-18}$, —$OC(R^{23c})_2OC(O)OR^{23}$d, —$OC(R^{23c})_2OC(O)R^{23d}$, an N-linked amino acid, or an N-linked amino acid ester;

$R^{23c}$ is independently selected at each occurrence from hydrogen, $C_1$-$C_8$alkyl, $C_2$-$C_8$alkenyl, $C_2$-$C_8$alkynyl, (aryl)$C_0$-$C_4$alkyl, (aryl)$C_2$-$C_8$alkenyl- or (aryl)$C_2$-$C_8$alkynyl; or two $R^{23c}$ groups can be taken together with the carbon that they are bonded to form a 3-6 membered heterocycloalkyl having 1, 2, or 3 heteroatoms independently selected from N, O, and S, or a 3-6 membered carbocyclic ring;

$R^{23d}$ is independently selected at each occurrence from $C_1$-$C_8$alkyl, $C_2$-$C_8$alkenyl, $C_2$-$C_8$alkynyl, (aryl)$C_0$-$C_4$alkyl, (aryl)$C_2$-$C_8$alkenyl, or (aryl)$C_2$-$C_8$alkynyl;

$R^{24}$ and $R^{30}$ are taken together with the nitrogen to which they are attached to form a 4- to 7-membered monocyclic heterocycle, or a 6- to 10-membered bicyclic heterocycle group having fused, spiro, or bridged rings;

$R^{48}$ is selected from halogen, hydroxyl, nitro, cyano, amino, $C_1$-$C_6$haloalkyl, $C_2$-$C_6$alkenyl, $C_2$-$C_6$alkynyl, $C_1$-$C_6$thioalkyl, $C_1$-$C_6$alkoxy, -J$C_3$-$C_7$cycloalkyl, —$B(OH)_2$, -$JC(O)NR^9R^{23}$, -$JOSO_2OR^{21}$, —$C(O)(CH_2)_{1-4}S(O)R^{21}$, —$O(CH_2)_{1-4}S(O)NR^{21}R^{22}$, -$JOP(O)(OR^{21})(OR^{22})$, -$JP(O)(OR^{21})(OR^{22})$, -$JOP(O)(OR^{21})R^{22}$, -$JOP(O)R^{21}R^{22}$, -$JP(O)R^{21}R^{22}$, -$JSP(O)(OR^{21})(OR^{22})$, -$JSP(O)(OR^{21})(R^{22})$, -$JSP(O)(R^{21})(R^{22})$, -$JNR^9P(O)(NHR^{21})(NHR^{22})$, -$JNR^9P(O)(OR^{21})(NHR^{22})$, -$JNR^9P(O)(OR^{21})(OR^{22})$, -$JC(S)R^{21}$, -$JNR^{21}SO_2R^{22}$, -$JNR^9S(O)NR^{10}R^{22}$, -$JNR^9SO_2NR^1OR^{22}$, -$JSO_2NR^9COR^{22}$, -$JSO_2NR^9CONR^{21}R^{22}$, -$JNR^{21}SO_2R^{22}$, -$JC(O)NR^{21}SO_2R^{22}$, -$JC(NH_2)$$=NR^{22}$, -$JCH(NH_2)NR^9S(O)_2R^{22}$, -$JOC(O)NR^{21}R^{22}$, -$JNR^{21}C(O)OR^{22}$, -$JNR^{21}OC(O)R^{22}$, —$(CH_2)_{1-4}C(O)NR^{21}R^{22}$, -$JC(O)NR^{24}R^{30}$, -$JNR^9C(O)R^{21}$, -$JC(O)R^{21}$, -$JNR^9C(O)NR^{10}R^{22}$, —$CCR^{21}$, —$(CH_2)_{1-4}OC(O)R^{21}$, -$JC(O)OR^{23}$, and $R^{103}$; each of which $R^{48}$ may be optionally substituted with one or more substituents selected from halogen, hydroxyl, nitro, cyano, amino, oxo, —$B(OH)_2$, —$Si(CH_3)_3$, —COOH, —$CONR^9R^{10}$, —$P(O)(OH)_2$, $C_1$-$C_6$alkyl, —$C_0$-$C_4$alkyl($C_3$-$C_7$cycloalkyl), $C_1$-$C_6$alkoxy, —$C_0$-$C_4$alkyl(mono- and di-$C_1$-$C_4$alkyl$NR^9R^{10}$), $C_1$-$C_6$alkyl ester, $C_1$-$C_4$alkylamino, $C_1$-$C_4$hydroxylalkyl, —$OC(O)R^9$, —$NR^9C(O)R^{10}$, —$C(O)NR^9R^{10}$, —$OC(O)NR^9R^{10}$, —$NR^9C(O)OR^{10}$, $C_1$-$C_6$haloalkyl, $S(O)$=$NHR^{21}$, $SF_5$, $JC(R^9)$=$NR^{21}$, $SO_2OR^{21}$, and $C_1$-$C_6$haloalkoxy;

$R^{103}$ is $C_1$-$C_4$alkyl, $C_3$-$C_6$cycloalkyl, fluorine, chlorine, or bromine;

$R^{71}$ is independently selected at each occurrence from hydroxyl, $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O)O$C_1$-$C_6$alkyl, —$C_1$-$C_4$alkylOC(O)$C_1$-$C_6$alkyl, —$C_1$-$C_4$alkylC(O)O$C_1$-$C_6$alkyl, (4- to 7-membered heterocycloalkyl)$C_0$-$C_4$alkyl having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S;

$R^{72}$ is independently selected at each occurrence from aryl, heterocycle, alkynyl, hydroxyl, $C_1$-$C_6$alkoxy, ($C_3$-$C_7$cycloalkyl)$C_0$-$C_4$alkyl, (aryl)$C_0$-$C_4$alkyl, (heterocycle)$C_0$-$C_4$alkyl, (heteroaryl)$C_0$-$C_4$alkyl, —$C_1$-$C_6$alkylOC(O)O$C_1$-$C_6$alkyl, —$C_1$-$C_4$alkylOC(O)$C_1$-$C_6$alkyl, —$C_1$-$C_4$alkylC(O)O$C_1$-$C_6$alkyl, —S(O)(O)(alkyl), —S(O)(alkyl), —S(O)(O)(heteroalkyl), —S(O)(heteroalkyl), —S(O)(O)(aryl), —S(O)(aryl), —S(O)(O)(heteroaryl), and —S(O)(heteroaryl);

$R^{73}$ is independently selected at each occurrence from hydrogen, hydroxyl, cyano, amino, $C_1$-$C_6$alkyl, $C_1$-$C_6$haloalkyl, $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O)O$C_1$-$C_6$alkyl, —$C_1$-$C_4$alkylOC(O)$C_1$-$C_6$alkyl, —$C_1$-$C_4$alkylC(O)O$C_1$-$C_6$alkyl, (4- to 7-membered heterocycloalkyl)$C_0$-$C_4$alkyl having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S; and $R^{74}$ is proline substituted with a —$C(O)NR^9R^{10}$.

2. The compound of claim 1, wherein B1 is selected from:

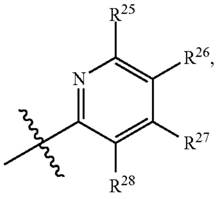

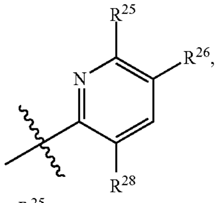

and

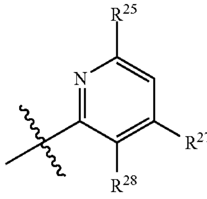

3. The compound of claim 1, wherein $R^{201}$ is selected from —$(CH_2)_m$—O-heterocycle, —$(CH_2)_m$—NH-heterocycle, and —$(CH_2)_m$—$NR^9$-heterocycle; and wherein m is 0, 1, 2, or 3.

4. The compound of claim 1, wherein C5 is selected from:

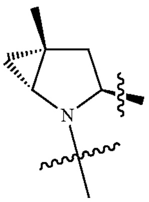

and

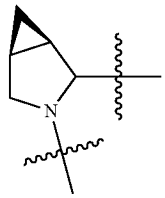

.

5. The compound of claim 1, wherein A is A3 and A3 is selected from:
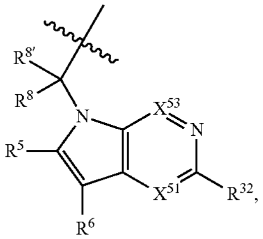
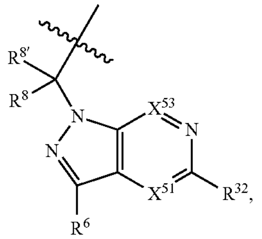
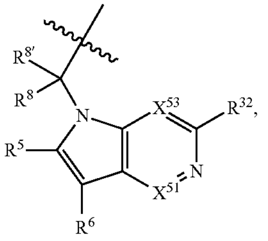
and
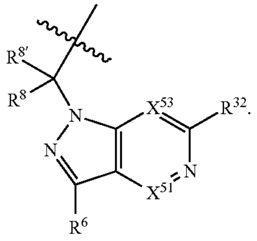
6. A pharmaceutical composition comprising a compound of claim 1 or a pharmaceutically acceptable salt thereof, and a pharmaceutically acceptable carrier.
7. The compound of claim 1, wherein the compound is
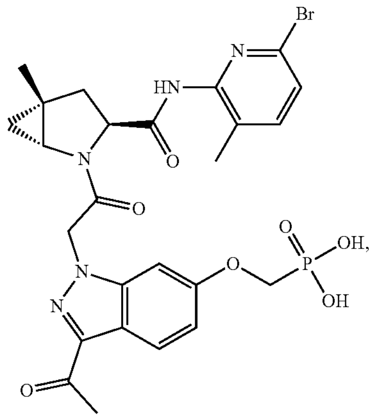 [SMILES: CC(=O)c1nn(CC(=O)N2[C@H](C(=O)Nc3nc(Br)ccc3C)C[C@@]3(C)C[C@@H]23)c2cc(OCP(=O)(O)O)ccc12]
or a pharmaceutically acceptable salt thereof.
8. The compound of claim 1, wherein B is
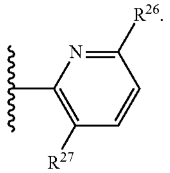
* * * * *